United States Patent
Takayama et al.

(10) Patent No.: US 9,422,240 B2
(45) Date of Patent: Aug. 23, 2016

(54) PARTIALLY SATURATED NITROGEN-CONTAINING HETEROCYCLIC COMPOUND

(71) Applicant: TAISHO PHARMACEUTICAL CO., LTD, Tokyo (JP)

(72) Inventors: Tetsuo Takayama, Tokyo (JP); Tsuyoshi Shibata, Tokyo (JP); Fumiyasu Shiozawa, Tokyo (JP); Kenichi Kawabe, Tokyo (JP); Yuki Shimizu, Tokyo (JP); Makoto Hamada, Tokyo (JP); Akira Hiratate, Tokyo (JP); Masato Takahashi, Tokyo (JP); Fumihito Ushiyama, Tokyo (JP); Takahiro Oi, Tokyo (JP); Yoshihisa Shirasaki, Tokyo (JP); Daisuke Matsuda, Tokyo (JP); Chie Koizumi, Tokyo (JP); Sota Kato, Tokyo (JP)

(73) Assignee: TAISHO PHARMACEUTICAL CO., LTD, Tokyo (JP)

( * ) Notice: Subject to any disclaimer, the term of this patent is extended or adjusted under 35 U.S.C. 154(b) by 0 days.

(21) Appl. No.: 14/417,387

(22) PCT Filed: Jul. 29, 2013

(86) PCT No.: PCT/JP2013/070522
§ 371 (c)(1),
(2) Date: Jan. 26, 2015

(87) PCT Pub. No.: WO2014/021281
PCT Pub. Date: Feb. 6, 2014

(65) Prior Publication Data
US 2015/0175541 A1 Jun. 25, 2015

(30) Foreign Application Priority Data
Jul. 30, 2012 (JP) .................. 2012-168828

(51) Int. Cl.
| | |
|---|---|
| *C07D 211/72* | (2006.01) |
| *C07D 211/90* | (2006.01) |
| *C07D 401/14* | (2006.01) |
| *C07D 215/56* | (2006.01) |
| *C07D 221/20* | (2006.01) |
| *C07D 401/06* | (2006.01) |
| *C07D 401/10* | (2006.01) |
| *C07D 401/12* | (2006.01) |
| *C07D 405/06* | (2006.01) |
| *C07D 409/06* | (2006.01) |
| *C07D 409/10* | (2006.01) |
| *C07D 413/06* | (2006.01) |
| *C07D 413/10* | (2006.01) |
| *C07D 413/12* | (2006.01) |
| *C07D 417/06* | (2006.01) |
| *C07D 417/10* | (2006.01) |
| *C07D 417/12* | (2006.01) |

(Continued)

(52) U.S. Cl.
CPC ............ *C07D 211/90* (2013.01); *C07D 207/36* (2013.01); *C07D 209/54* (2013.01); *C07D 215/56* (2013.01); *C07D 221/20* (2013.01); *C07D 401/06* (2013.01); *C07D 401/10* (2013.01); *C07D 401/12* (2013.01); *C07D 401/14* (2013.01); *C07D 405/06* (2013.01); *C07D 409/06* (2013.01); *C07D 409/10* (2013.01); *C07D 413/06* (2013.01); *C07D 413/10* (2013.01); *C07D 413/12* (2013.01); *C07D 417/06* (2013.01); *C07D 417/10* (2013.01); *C07D 417/12* (2013.01); *C07D 471/10* (2013.01); *C07D 491/107* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 2007/0299086 | A1 | 12/2007 | Kawamoto |
| 2009/0203694 | A1 | 8/2009 | Hurley et al. |

(Continued)

FOREIGN PATENT DOCUMENTS

| | | | |
|---|---|---|---|
| JP | 2009-544733 A | 12/2009 | |
| JP | 2012-500850 A | 1/2012 | |

(Continued)

OTHER PUBLICATIONS

International Search Report for PCT/JP2013/070522 dated Sep. 24, 2013.

(Continued)

*Primary Examiner* — Heidi Reese
(74) *Attorney, Agent, or Firm* — Sughrue Mion, PLLC

(57) ABSTRACT

There are provided compounds having a superior PHD2 inhibitory effect that are represented by general formula (I'):

[Formula 274]

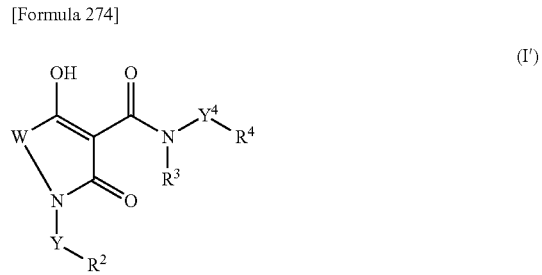

(I')

(in the above-mentioned general formula (I'), W, Y, $R^2$, $R^3$, $R^4$, and $Y^4$ are as described hereinabove), or pharmaceutically acceptable salts thereof.

16 Claims, No Drawings

(51) Int. Cl.
*C07D 471/10* (2006.01)
*C07D 491/107* (2006.01)
*C07D 207/36* (2006.01)
*C07D 498/04* (2006.01)
*C07D 209/54* (2006.01)

(56) References Cited

U.S. PATENT DOCUMENTS

2010/0035906 A1 2/2010 Flamme et al.
2010/0144737 A1 6/2010 Chow et al.
2011/0144167 A1 6/2011 Tedesco

FOREIGN PATENT DOCUMENTS

| WO | 2004/108681 A1 | 12/2004 |
| WO | 2006/114213 A1 | 11/2006 |
| WO | 2007/038571 A2 | 4/2007 |
| WO | 2007/150011 A2 | 12/2007 |
| WO | 2008002576 A2 | 1/2008 |
| WO | 2008/089051 A1 | 7/2008 |
| WO | 2008/089052 A2 | 7/2008 |
| WO | 2008/144266 A1 | 11/2008 |
| WO | 2009/049112 A1 | 4/2009 |
| WO | 2009/075822 A1 | 6/2009 |
| WO | 2009/108496 A1 | 9/2009 |
| WO | 2009/158315 A1 | 12/2009 |
| WO | 2010/025087 A1 | 3/2010 |

OTHER PUBLICATIONS

Alireza Khoshdel et al., "Potential roles of erythropoietin in the management of anaemia and other complications diabetes", Diabetes, Obesity and Metabolism, 2008, pp. 1-9, vol. 10.
Communication dated Nov. 25, 2015 from the European Patent Office in counterpart application No. 13825784.5.
Lin Yan et al.: "Prolyl hydroxylase domain-containing protein inhibitors as stabilizers of hypoxia-inducible factor: small molecule-based therapeutics for anemia", Expert Opinion on Therapeutic Patents, vol. 20, No. 9, 2010, pp. 1219-1245.

PARTIALLY SATURATED NITROGEN-CONTAINING HETEROCYCLIC COMPOUND

CROSS REFERENCE TO RELATED APPLICATIONS

This application is a National Stage of International Application No. PCT/JP2013/070522 filed Jul. 29, 2013, claiming priority based on Japanese Patent Application No. 2012-168828, filed Jul. 30, 2012, the contents of all of which are incorporated herein by reference in their entirety.

TECHNICAL FIELD

The present invention relates to novel prolyl hydroxylase (hereinafter also referred to as PHD) inhibitors, in particular, prolyl hydroxylase 2 (hereinafter also referred to as PHD2) inhibitors.

BACKGROUND ART

Erythrocytes in the blood are responsible for oxygen transport throughout the body and play an important role in maintaining oxygen levels constant in vivo. If, on account of bleeding due to certain kinds of disease, as well as to accidents or surgical operations, the erythrocyte counts or hemoglobins level in the blood decrease, a sense of fatigue, dizziness, shortness of breath and other anemic symptoms will develop. In anemia, the entire body will be exposed to oxygen deficiency and under such hypoxic conditions, the living body performs a compensatory reaction, in which the hematopoietic factor erythropoietin (hereinafter also referred to as EPO) which promotes the formation of erythrocytes is produced primarily from the kidney to increase the erythrocyte and hemoglobin levels in the blood, thus helping to ameliorate anemia. However, in certain kinds of disease, this erythropoietic action of erythropoietin is impaired and chronic anemia persists. For example, in patients with renal failure who have disorder in the kidney, it is known that the above-described mechanism for erythropoietin production under hypoxic conditions fails to work properly, causing them to present with a type of anemia (renal anemia) which is characterized by reduced erythrocyte counts and hemoglobin levels (see Non-Patent Documents 1 and 2).

The treatment of renal anemia and the anemia that accompanies cancer chemotherapy or medication of patients with HIV infection is currently carried out by erythropoiesis stimulating agents (ESA) such as genetically recombinant human erythropoietin preparations. The ESA greatly contributes to improving a patient's quality of life by increasing the erythrocyte counts and hemoglobin levels sufficiently to ameliorate the symptoms that accompany anemia. On the other hand, however, the currently available ESAs are all biologics in the form of expensive injections, so it is desired to develop an orally administrable pharmaceutical drug for the treatment of anemia.

A recent study has reported that erythropoietin also has an action for protecting tissues such as hearts and brains placed under the hypoxic conditions that accompany anemia. Therefore, orally administrable ESA preparations have the potential to find a wide range of applications covering not only renal and other types of anemia that result from various causes but also a diversity of ischemic diseases (see Non-Patent Document 3).

A substance that may be mentioned as a factor that increases the production of erythropoietin is a hypoxia-inducible factor (hereinafter also referred to as HIF). The HIF is a transcription factor including an α-subunit the degradation of which is regulated by changes in oxygen density and a β-subunit that is expressed constantly. Prolyl hydroxylases (PHD-1, -2 and -3) are known as factors that regulate the degradation of HIF's α-subunit (HIF-α). Under normal oxygen pressure conditions, the proline residues of HIF-α are hydroxylated by these prolyl hydroxylases and the HIF-α is rapidly degraded by proteasome. Under hypoxic conditions, on the other hand, the activity of prolyl hydroxylases is lowered, so the degradation of HIF-α is suppressed, thus promoting the transcription of the erythropoietin- and other HIF-responsive genes. Consequently, by inhibiting the prolyl hydroxylases, the stabilization of HIF-α is promoted, making it possible to increase the production of erythropoietin (see Non-Patent Documents 1, 2 and 4).

The compounds of the present invention provide means for inhibiting the activities of those prolyl hydroxylases to increase the amount of erythropoietin, thereby treating anemia. As another benefit, not only anemia but also various other ischemic diseases (e.g. brain stroke, myocardial infarction, and ischemic renal disorder) and diabetic complications (nephropathy, retinopathy, and neuropathy) can also be treated or prevented or improved or mitigated in symptoms by administering the compounds of the present invention (see Non-Patent Document 5).

Common PHD inhibitors reported to date include 4-hydroxyisoquinoline derivatives (see Patent Document 1), 5-hydroxy-3-oxo-2,3-dihydro-1H-pyrazole derivatives (see Patent Document 2), 4-hydroxy-2-oxo-1,2-dihydroquinoline derivatives (see Patent Document 3), 3-hydroxypyridine derivatives (see Patent Document 4), 2-oxo-2,3-dihydroindole derivatives (see Patent Document 5), etc. but compounds having the structures according to the present invention have not been disclosed. Also reported to date include are 6-hydroxy-2,4-dioxo-1,2,3,4-tetrahydropyrimidine derivatives (see Patent Document 6), 4-hydroxy-6-oxo-1,6-dihydropyrimidine derivatives (see Patent Document 7), 5-hydroxy-3-oxo-2,3-dihydropyridazine derivatives (see Patent Document 8), 6-hydroxy-4-oxo-4H-1,3-dioxin derivatives (see Patent Document 9), 4-hydroxy-2-oxo-1,2,5,7-tetrahydrofluoro[3,4-b]pyridine derivatives (see Patent Document 10), 4-hydroxy-2-oxo-1,2-dihydropyridine derivatives (see Patent Documents 11 and 12), etc. but compounds having the structures according to the present invention have not been disclosed.

CITATION LIST

Patent Documents

Patent Document 1: WO 2004/108681
Patent Document 2: WO 2006/114213
Patent Document 3: WO 2007/038571
Patent Document 4: US 2007/0299086
Patent Document 5: WO 2008/144266
Patent Document 6: WO 2007/150011
Patent Document 7: WO 2008/089051
Patent Document 8: WO 2008/089052
Patent Document 9: WO 2009/049112
Patent Document 10: WO 2009/108496
Patent Document 11: WO 2009/158315
Patent Document 12: WO 2010/025087

Non-Patent Documents

Non-Patent Document 1: American Journal of Physiology-Renal Physiology, 2010, 299, F1-13

Non-Patent Document 2: American Journal of Physiology-Renal Physiology, 2010, 298, F1287-1296

Non-Patent Document 3: The Journal of Physiology, 2011, 589, 1251-1258

Non-Patent Document 4: Expert Opinion on Therapeutic Patents, 2010, 20, 1219-1245

Non-Patent Document 5: Diabetes, Obesity and Metabolism, 2008, 10, 1-9

SUMMARY OF INVENTION

Technical Problem

An object of the present invention is to provide superior PHD 2 inhibitors.

Solution to Problem

The present inventors conducted intensive studies with a view to attaining the above-stated object and found as a result that compounds represented by the following general formula (I) or (I') have a superior PHD 2 inhibitory effect.

Briefly, the present invention is directed to:

(1) providing a compound represented by the following general formula (I')

[Formula 1]

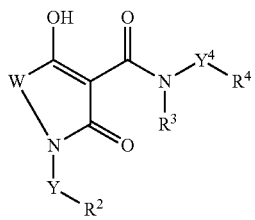

(wherein in formula (I'),

W represents the formula —$CR^{15}R^{16}$—, the formula —$CR^{11}R^{12}CR^{13}R^{14}$—, or the formula —$CH_2CR^{17}R^{18}CH_2$—;

$R^{15}$ represents a hydrogen atom, $C_{1-4}$ alkyl, or phenyl;

$R^{16}$ represents a hydrogen atom or $C_{1-4}$ alkyl;

provided that $R^{15}$ and $R^{16}$, together with the adjacent carbon atom, optionally form $C_{3-8}$ cycloalkane;

$R^{11}$ represents a hydrogen atom, a fluorine atom, $C_{1-4}$ alkyl, or phenyl;

$R^{12}$ represents a hydrogen atom, a fluorine atom, or $C_{1-4}$ alkyl;

provided that $R^{11}$ and $R^{12}$, together with the adjacent carbon atom, optionally form $C_{3-8}$ cycloalkane or a 4- to 8-membered saturated heterocycle containing an oxygen atom;

$R^{13}$ represents a hydrogen atom, carbamoyl, $C_{1-4}$ alkyl (the $C_{1-4}$ alkyl is optionally substituted by one group selected from the group consisting of hydroxy, $C_{1-3}$ alkoxy, and di-$C_{1-3}$ alkylamino), halo-$C_{1-4}$ alkyl, phenyl, pyridyl, benzyl, or phenethyl;

$R^{14}$ represents a hydrogen atom, $C_{1-4}$ alkyl, or halo-$C_{1-4}$ alkyl;

provided that $R^{13}$ and $R^{14}$, together with the adjacent carbon atom, optionally form $C_{3-8}$ cycloalkane, a 4- to 8-membered saturated heterocycle containing an oxygen atom, or a 4- to 8-membered saturated heterocycle containing a nitrogen atom (the 4- to 8-membered saturated heterocycle containing a nitrogen atom is optionally substituted by one or two groups which are the same or different and are selected from the group consisting of methyl, benzyl, phenylcarbonyl, and oxo);

provided that said $R^{12}$ and $R^{13}$, together with the adjacent carbon atoms, optionally form $C_{3-8}$ cycloalkane;

$R^{17}$ represents a hydrogen atom or $C_{1-4}$ alkyl;

$R^{18}$ represents a hydrogen atom or $C_{1-4}$ alkyl;

provided that $R^{17}$ and $R^{18}$, together with the adjacent carbon atom, optionally form $C_{3-8}$ cycloalkane;

Y represents a single bond or $C_{1-6}$ alkanediyl (the $C_{1-6}$ alkanediyl is optionally substituted by one hydroxy, and one of the carbon atoms in the $C_{1-6}$ alkanediyl is optionally substituted by $C_{3-6}$ cycloalkane-1,1-diyl);

$R^2$ represents a hydrogen atom, $C_{1-6}$ alkyl, $C_{3-8}$ cycloalkyl {the $C_{3-8}$ cycloalkyl is optionally substituted by one or two groups which are the same or different and are selected from the group consisting of $C_{1-6}$ alkyl (the $C_{1-6}$ alkyl is optionally substituted by one phenyl), phenyl (the phenyl is optionally substituted by one group selected from the group consisting of a halogen atom and halo-$C_{1-6}$ alkyl), $C_{1-6}$ alkoxy [the $C_{1-6}$ alkoxy is optionally substituted by one group selected from the group consisting of $C_{3-8}$ cycloalkyl, phenyl (the phenyl is optionally substituted by one group selected from the group consisting of a halogen atom and $C_{1-6}$ alkyl), and pyridyl (the pyridyl is optionally substituted by one halogen atom)], $C_{3-8}$ cycloalkoxy, phenoxy (the phenoxy is optionally substituted by one group selected from the group consisting of a halogen atom, $C_{1-6}$ alkyl, $C_{3-8}$ cycloalkyl, and halo-$C_{1-6}$ alkyl), and pyridyloxy (the pyridyloxy is optionally substituted by one group selected from the group consisting of a halogen atom, $C_{1-6}$ alkyl, $C_{3-8}$ cycloalkyl, and halo-$C_{1-6}$ alkyl)}, phenyl (the phenyl is optionally substituted by one to three groups which are the same or different and are selected from group α3 of substituents), naphthyl, indanyl, tetrahydronaphthyl, pyrazolyl, imidazolyl, isoxazolyl, oxazolyl [the pyrazolyl, imidazolyl, isoxazolyl, and oxazolyl are optionally substituted by one or two groups which are the same or different and are selected from the group consisting of $C_{1-6}$ alkyl and phenyl (the phenyl is optionally substituted by one group selected from the group consisting of a halogen atom and $C_{1-6}$ alkyl)], thiazoyl [the thiazoyl is optionally substituted by one or two groups which are the same or different and are selected from the group consisting of $C_{1-6}$ alkyl, phenyl (the phenyl is optionally substituted by one group selected from the group consisting of a halogen atom and $C_{1-6}$ alkyl), and morpholino], pyridyl (the pyridyl is optionally substituted by one or two groups which are the same or different and are selected from group α5 of substituents), pyridazinyl, pyrimidinyl, pyrazinyl [the pyridazinyl, pyrimidinyl, and pyrazinyl are optionally substituted by one group selected from the group consisting of $C_{1-6}$ alkyl, halo-$C_{1-6}$ alkyl, $C_{3-8}$ cycloalkyl, phenyl, $C_{1-6}$ alkoxy (the $C_{1-6}$ alkoxy is optionally substituted by one $C_{3-8}$ cycloalkyl), and phenoxy (the phenoxy is optionally substituted by one group selected from the group consisting of a halogen atom, $C_{1-6}$ alkyl, and $C_{3-8}$ cycloalkyl)], benzothiophenyl, quinolyl, methylenedioxyphenyl (the methylenedioxyphenyl is optionally substituted by one or two fluorine atoms), 4- to 8-membered saturated heterocyclyl containing a nitrogen atom [the 4- to 8-membered saturated heterocyclyl containing a nitrogen atom is optionally substituted by one group selected from the group consisting of pyrimidinyl, phenyl-$C_{1-3}$ alkyl, $C_{3-8}$ cycloalkyl-$C_{1-3}$ alkylcarbonyl, and phenyl-$C_{1-3}$ alkoxycarbonyl], or the following formula (I")

Formula 2

$$—CONR^5CH_2—R^6 \quad (I'')$$

[wherein in formula (I''), $R^5$ represents a hydrogen atom or $C_{1-3}$ alkyl, and $R^6$ represents phenyl (the phenyl is optionally substituted by one group selected from the group consisting of a halogen atom, $C_{1-6}$ alkyl, halo-$C_{1-6}$ alkyl, and phenyl)], group α3 of substituents consists of hydroxy, cyano, carboxy, a halogen atom, $C_{1-6}$ alkyl {the $C_{1-6}$ alkyl is optionally substituted by one group selected from the group consisting of $C_{3-8}$ cycloalkyl, phenyl, $C_{1-6}$ alkoxy [the $C_{1-6}$ alkoxy is optionally substituted by one $C_{3-8}$ cycloalkyl (the $C_{3-8}$ cycloalkyl is optionally substituted by one $C_{1-6}$ alkyl)], phenoxy (the phenoxy is optionally substituted by one $C_{1-6}$ alkyl), and pyridyloxy (the pyridyloxy is optionally substituted by one group selected from the group consisting of $C_{1-6}$ alkyl and halo-$C_{1-6}$ alkyl)}, halo-$C_{1-6}$ alkyl, $C_{3-8}$ cycloalkyl (the $C_{3-8}$ cycloalkyl is optionally substituted by one or two halogen atoms), $C_{3-8}$ cycloalkenyl (the $C_{3-8}$ cycloalkenyl is optionally substituted by one or two halogen atoms), phenyl (the phenyl is optionally substituted by one to three groups which are the same or different and are selected from group α4 of substituents), thienyl (the thienyl is optionally substituted by one $C_{1-6}$ alkyl), pyrazolyl (the pyrazolyl is optionally substituted by one $C_{1-6}$ alkyl), isoxazolyl, thiazoyl (the thiazoyl is optionally substituted by one or two groups which are the same or different and are selected from the group consisting of hydroxy, $C_{1-6}$ alkyl, and $C_{1-6}$ alkoxy), pyridyl (the pyridyl is optionally substituted by one group selected from the group consisting of carboxy, hydroxy, amino, a halogen atom, $C_{1-6}$ alkyl, halo-$C_{1-6}$ alkyl, $C_{3-8}$ cycloalkyl, $C_{1-6}$ alkoxy, halo-$C_{1-6}$ alkoxy, and $C_{1-6}$ alkylsulfonyl), pyrimidinyl (the pyrimidinyl is optionally substituted by one amino), quinolyl, $C_{1-6}$ alkoxy [the $C_{1-6}$ alkoxy is optionally substituted by one group selected from the group consisting of carboxy, hydroxy, carbamoyl, $C_{3-8}$ cycloalkyl (the $C_{3-8}$ cycloalkyl is optionally substituted by one $C_{1-6}$ alkyl), phenyl (the phenyl is optionally substituted by one group selected from the group consisting of hydroxy, a halogen atom, $C_{1-6}$ alkyl, halo-$C_{1-6}$ alkyl, $C_{1-6}$ alkoxy, hale-$C_{1-6}$ alkoxy, and di-$C_{1-6}$ alkylamino), pyridyl (the pyridyl is optionally substituted by one group selected from the group consisting of a halogen atom and $C_{1-6}$ alkyl), oxazolyl (the oxazolyl is optionally substituted by one or two $C_{1-6}$ alkyls), pyrazolyl (the pyrazolyl is optionally substituted by one or two $C_{1-6}$ alkyls), thiazoyl (the thiazoyl is optionally substituted by one $C_{1-6}$ alkyl), indazolyl (the indazolyl is optionally substituted by one $C_{1-6}$ alkyl), benzotriazolyl, imidazothiazoyl, and di-$C_{1-6}$ alkylamino], halo-$C_{1-6}$ alkoxy, $C_{2-6}$ alkenyloxy, $C_{3-8}$ cycloalkoxy, phenoxy (the phenoxy is optionally substituted by one or two groups which are the same or different and are selected from the group consisting of a halogen atom, $C_{1-6}$ alkyl, halo-$C_{1-6}$ alkyl, $C_{1-6}$ alkoxy, and halo-$C_{1-6}$ alkoxy), pyridyloxy (the pyridyloxy is optionally substituted by one group selected from the group consisting of a halogen atom, $C_{1-6}$ alkyl, halo-$C_{1-6}$ alkyl, and $C_{3-8}$ cycloalkyl), pyrimidinyloxy, piperazinyl (the piperazinyl is optionally substituted by one $C_{1-6}$ alkyl), mono-$C_{1-6}$ alkylaminocarbonyl (the $C_{1-6}$ alkyl in the mono-$C_{1-6}$ alkylaminocarbonyl is optionally substituted by one group selected from the group consisting of carboxy, hydroxy, di-$C_{1-6}$ alkylamino, pyridyl, phenyl, and 2-oxopyrrolidinyl), di-$C_{1-6}$ alkylaminocarbonyl (where the two $C_{1-6}$ alkyls in the di-$C_{1-6}$ alkylaminocarbonyl, together with the adjacent nitrogen atom, optionally form a 4- to 8-membered saturated heterocycle containing a nitrogen atom), $C_{1-6}$ alkylsulfanyl, and $C_{1-6}$ alkylsulfonyl;

group α4 of substituents consists of carboxy, cyano, hydroxy, sulfamoyl, a halogen atom, $C_{1-6}$ alkyl, halo-$C_{1-6}$ alkyl, $C_{3-8}$ cycloalkyl, phenyl, $C_{1-6}$ alkoxy, halo-$C_{1-6}$ alkoxy, $C_{1-6}$ alkylcarbonyl, di-$C_{1-6}$ alkylaminocarbonyl, $C_{1-6}$ alkylsulfonyl, mono-$C_{1-6}$ alkylaminosulfonyl (the $C_{1-6}$ alkyl in the mono-$C_{1-6}$ alkylaminosulfonyl is optionally substituted by one hydroxy), and di-$C_{1-6}$ alkylaminosulfonyl;

group α5 of substituents consists of a halogen atom, $C_{1-6}$ alkyl, halo-$C_{1-6}$ alkyl, $C_{1-6}$ alkoxy [the $C_{1-6}$ alkoxy is optionally substituted by one group selected from the group consisting of $C_{3-8}$ cycloalkyl (the $C_{3-8}$ cycloalkyl is optionally substituted by one $C_{1-6}$ alkyl) and phenyl (the phenyl is optionally substituted by one group selected from the group consisting of a halogen atom and $C_{1-6}$ alkyl)], halo-$C_{1-6}$ alkoxy, phenyl (the phenyl is optionally substituted by one group selected from group α6 of substituents), pyridyl, phenoxy [the phenoxy is optionally substituted by one or two groups which are the same or different and are selected from the group consisting of a halogen atom, cyano, $C_{1-6}$ alkyl, halo-$C_{1-6}$ alkyl, $C_{3-8}$ cycloalkyl, $C_{1-6}$ alkoxy (the $C_{1-6}$ alkoxy is optionally substituted by one phenyl), and halo-$C_{1-6}$ alkoxy], pyridyloxy (the pyridyloxy is optionally substituted by one $C_{1-6}$ alkyl), and phenylsulfanyl (the phenylsulfanyl is optionally substituted by one halogen atom); group α6 of substituents consists of a halogen atom, $C_{1-6}$ alkyl, halo-$C_{1-6}$ alkyl, $C_{3-8}$ cycloalkyl, $C_{1-6}$ alkoxy, and halo-$C_{1-6}$ alkoxy;

$Y^4$ represents $C_{1-4}$ alkanediyl;

$R^3$ represents a hydrogen atom or methyl;

$R^4$ represents —COOH, —CONHOH, or tetrazolyl);

or a pharmaceutically acceptable salt thereof.

(2) In another mode, the present invention is directed to providing the compound according to (1) wherein in the aforementioned general formula (I'), $Y^4$ is methanediyl, $R^3$ is a hydrogen atom, $R^4$ is —COOH, or a pharmaceutically acceptable salt thereof.

(3) In another mode, the present invention is directed to providing the compound according to (2) wherein in the aforementioned general formula (I'), W is the formula —$CR^{15}R^{16}$—, and the compound is represented by general formula (I'-1):

[Formula 3]

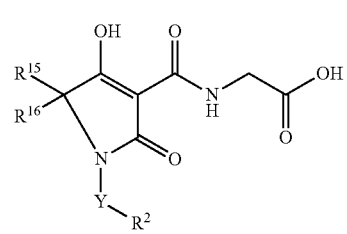

(wherein in formula (I'-1)

$R^{15}$ is a hydrogen atom, $C_{1-4}$ alkyl, or phenyl, $R^{16}$ is a hydrogen atom or $C_{1-4}$ alkyl, provided that $R^{15}$ and $R^{16}$, together with the adjacent carbon atom, optionally form $C_{3-8}$ cycloalkane), or a pharmaceutically acceptable salt thereof.

(4) In another mode, the present invention is directed to providing the compound according to (2) wherein in the aforementioned general formula (I'),
W is the formula —$CR^{11}R^{12}CR^{13}R^{14}$—, and the compound is represented by general formula (I'-2):

[Formula 4]

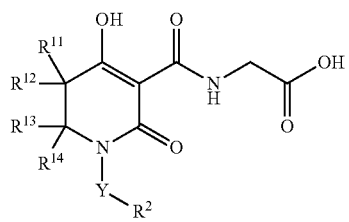

(I'-2)

(wherein in formula (I'-2),
$R^{11}$ is a hydrogen atom, a fluorine atom, $C_{1-4}$ alkyl, or phenyl,
$R^{12}$ is a hydrogen atom, a fluorine atom, or $C_{1-4}$ alkyl,
provided that $R^{11}$ and $R^{12}$, together with the adjacent carbon atom, optionally form $C_{3-8}$ cycloalkane or a 4- to 8-membered saturated heterocycle containing an oxygen atom;
$R^{13}$ is a hydrogen atom, carbamoyl, $C_{1-4}$ alkyl (the $C_{1-4}$ alkyl is optionally substituted by one group selected from the group consisting of hydroxy, $C_{1-3}$ alkoxy, and di-$C_{1-3}$ alkylamino), halo-$C_{1-4}$ alkyl, phenyl, pyridyl, benzyl, or phenethyl;
$R^{14}$ is a hydrogen atom, $C_{1-4}$ alkyl, or halo-$C_{1-4}$ alkyl,
provided that $R^{13}$ and $R^{14}$, together with the adjacent carbon atom, optionally form $C_{3-8}$ cycloalkane, a 4- to 8-membered saturated heterocycle containing an oxygen atom, or a 4- to 8-membered saturated heterocycle containing a nitrogen atom (the 4- to 8-membered saturated heterocycle containing a nitrogen atom is optionally substituted by one or two groups which are the same or different and are selected from the group consisting of methyl, benzyl, phenylcarbonyl, and oxo),
provided that the aforementioned $R^{12}$ and $R^{13}$, together with the adjacent carbon atoms, optionally form $C_{3-8}$ cycloalkane),
or a pharmaceutically acceptable salt thereof.

(5) In another mode, the present invention is directed to providing the compound according to (4) wherein in the aforementioned general formula (I'-2),
Y is a single bond or $C_{1-6}$ alkanediyl (one of the carbon atoms in the $C_{1-6}$ alkanediyl is optionally substituted by $C_{3-6}$ cycloalkane-1,1-diyl),
$R^2$ is $C_{3-8}$ cycloalkyl {the $C_{3-8}$ cycloalkyl is optionally substituted by one or two groups which are the same or different and are selected from the group consisting of $C_{1-6}$ alkyl (the $C_{1-6}$ alkyl is optionally substituted by one phenyl), phenyl (the phenyl is optionally substituted by one halo-$C_{1-6}$ alkyl), $C_{1-6}$ alkoxy [the $C_{1-6}$ alkoxy is optionally substituted by one group selected from the group consisting of $C_{3-8}$ cycloalkyl, phenyl (the phenyl is optionally substituted by one group consisting of a halogen atom and $C_{1-6}$ alkyl), and pyridyl (the pyridyl is optionally substituted by one halogen atom)], $C_{3-8}$ cycloalkoxy, phenoxy (the phenoxy is optionally substituted by one group selected from the group consisting of a halogen atom, $C_{1-6}$ alkyl, $C_{3-8}$ cycloalkyl, and halo-$C_{1-6}$ alkyl), and pyridyloxy (the pyridyloxy is optionally substituted by one group selected from the group consisting of a halogen atom, $C_{1-6}$ alkyl, $C_{3-8}$ cycloalkyl, and halo-$C_{1-6}$ alkyl)}, phenyl (the phenyl is optionally substituted by one to three groups which are the same or different and are selected from the aforementioned group α3 of substituents), naphthyl, indanyl, tetrahydronaphthyl, pyrazolyl [the pyrazolyl is optionally substituted by one or two groups which are the same or different and are selected from the group consisting of $C_{1-6}$ alkyl and phenyl (the phenyl is optionally substituted by one $C_{1-6}$ alkyl)], imidazolyl (the imidazolyl is optionally substituted by one group selected from the group consisting of $C_{1-6}$ alkyl and phenyl), isoxazolyl [the isoxazolyl is optionally substituted by one phenyl (the phenyl is optionally substituted by one halogen atom)], oxazolyl (the oxazolyl is optionally substituted by one or two groups which are the same or different and are selected from the group consisting of $C_{1-6}$ alkyl and phenyl), thiazoyl (the thiazoyl is optionally substituted by one group selected from the group consisting of $C_{1-6}$ alkyl, phenyl, and morpholino), pyridyl (the pyridyl is optionally substituted by one or two groups which are the same or different and are selected from the aforementioned group α5 of substituents), pyridazinyl [the pyridazinyl is optionally substituted by one $C_{1-6}$ alkoxy (the $C_{1-6}$ alkoxy is optionally substituted by one $C_{3-8}$ cycloalkyl)], pyrimidinyl [the pyrimidinyl is optionally substituted by one group selected from the group consisting of halo-$C_{1-6}$ alkyl, $C_{3-8}$ cycloalkyl, phenyl, and phenoxy (the phenoxy is optionally substituted by one $C_{1-6}$ alkyl)], pyrazinyl [the pyrazinyl is optionally substituted by one group selected from the group consisting of $C_{1-6}$ alkoxy (the $C_{1-6}$ alkoxy is optionally substituted by $C_{3-8}$ cycloalkyl) and phenoxy (the phenoxy is optionally substituted by one group selected from the group consisting of a halogen atom, $C_{1-6}$ alkyl, and $C_{3-8}$ cycloalkyl)], benzothiophenyl, quinolyl, or methylenedioxyphenyl (the methylenedioxyphenyl is optionally substituted by one or two fluorine atoms),
or a pharmaceutically acceptable salt thereof.

(6) In another mode, the present invention is directed to providing the compound according to (5) wherein in the aforementioned general formula (I'-2),
$R^{11}$ is a hydrogen atom,
$R^{12}$ is a hydrogen atom,
$R^{13}$ is a hydrogen atom,
$R^{14}$ is a hydrogen atom,
Y is methanediyl,
$R^2$ is
phenyl {the phenyl is substituted by one group selected from the group consisting of phenyl [the phenyl is optionally substituted by one or two groups which are the same or different and are selected from the group consisting of carboxy, cyano, hydroxy, sulfamoyl, a halogen atom, $C_{1-6}$ alkyl, halo-$C_{1-6}$ alkyl, $C_{3-8}$ cycloalkyl, phenyl, $C_{1-6}$ alkoxy, halo-$C_{1-6}$ alkoxy, $C_{1-6}$ alkylcarbonyl, di-$C_{1-6}$ alkylaminocarbonyl, $C_{1-6}$ alkylsulfonyl, mono-$C_{1-6}$ alkylaminosulfonyl (the $C_{1-6}$ alkyl in the mono-$C_{1-6}$ alkylaminosulfonyl is optionally substituted by one hydroxy), and di-$C_{1-6}$ alkylaminosulfonyl], pyridyl (the pyridyl is optionally substituted by one group selected from the group consisting of carboxy, hydroxy, amino, a halogen atom, $C_{1-6}$ alkyl, halo-$C_{1-6}$ alkyl, $C_{3-8}$ cycloalkyl, $C_{1-6}$ alkoxy, and $C_{1-6}$ alkylsulfonyl), phenoxy (the phenoxy is optionally substituted by one or two groups which are the same or different and are selected from the group consisting of a halogen atom, $C_{1-6}$ alkyl, $C_{1-6}$ alkoxy, and halo-$C_{1-6}$ alkoxy), and pyridyloxy (the pyridyloxy is optionally substituted by one group selected from the group consisting of a halogen atom, $C_{1-6}$ alkyl, halo-$C_{1-6}$ alkyl, and $C_{3-8}$ cycloalkyl), and may further be substituted by one halogen atom};

pyridyl {the pyridyl is substituted by one group selected from the group consisting of phenyl (the phenyl is optionally substituted by one group selected from the group consisting of a halogen atom, $C_{1-6}$ alkyl, halo-$C_{1-6}$ alkyl, $C_{3-8}$ cycloalkyl, $C_{1-6}$ alkoxy, and halo-$C_{1-6}$ alkoxy), pyridyl, phenoxy [the phenoxy is optionally substituted by one or two groups which are the same or different and are selected from the group consisting of a halogen atom, cyano, $C_{1-6}$ alkyl, halo-$C_{1-6}$ alkyl, $C_{3-8}$ cycloalkyl, $C_{1-6}$ alkoxy (the $C_{1-6}$ alkoxy is optionally substituted by one phenyl), and halo-$C_{1-6}$ alkoxy], and pyridyloxy (the pyridyloxy is optionally substituted by one $C_{1-6}$ alkyl), and may further be substituted by one group selected from the group consisting of a halogen atom and $C_{1-6}$ alkyl}; or pyrazinyl which is substituted by one phenoxy (the phenoxy is optionally substituted by one group selected from the group consisting of a halogen atom, $C_{1-6}$ alkyl, and $C_{3-8}$ cycloalkyl), or a pharmaceutically acceptable salt thereof.

(7) In another mode, the present invention is directed to providing the following compound according to (1):

N-{[4-hydroxy-2-oxo-1-(4-phenoxybenzyl)-1,2,5,6-tetrahydro-3-pyridinyl]carbonyl}glycine;

N-[(4-hydroxy-1-{[6-(4-methylphenoxy)-3-pyridinyl]methyl}-2-oxo-1,2,5,6-tetrahydro-3-pyridinyl)carbonyl]glycine;

N-({4-hydroxy-2-oxo-1-[(6-phenoxy-3-pyridinyl)methyl]-1,2,5,6-tetrahydro-3-pyridinyl}carbonyl)glycine;

N-({1-[4-(4-fluorophenoxy)benzyl]-4-hydroxy-2-oxo-1,2,5,6-tetrahydro-3-pyridinyl}carbonyl)glycine;

N-({4-hydroxy-1-[4-(4-methylphenoxyl)benzyl]-2-oxo-1,2,5,6-tetrahydro-3-pyridinyl}carbonyl)glycine;

N-[(1-{[6-(4-cyanophenoxy)-3-pyridinyl]methyl}-4-hydroxy-2-oxo-1,2,5,6-tetrahydro-3-pyridinyl)carbonyl]glycine;

N-(4-hydroxy-2-oxo-1-[4-(2-pyrimidinyloxy)benzyl]-1,2,5,6-tetrahydro-3-pyridinyl carbonyl)glycine;

N-[(1-{[6-(4-fluorophenoxy)-3-pyridinyl]methyl}-4-hydroxy-2-oxo-1,2,5,6-tetrahydro-3-pyridinyl)carbonyl]glycine;

N-[(1-{[6-(4-chlorophenoxy)-3-pyridinyl]methyl}-4-hydroxy-2-oxo-1,2,5,6-tetrahydro-3-pyridinyl)carbonyl]glycine;

N-{[4-hydroxy-2-oxo-1-({6-[4-(trifluoromethyl)phenoxy]-3-pyridinyl}methyl)-1,2,5,6-tetrahydro-3-pyridinyl]carbonyl}glycine;

N-[(4-hydroxy-1-{[6-(3-methylphenoxy)-3-pyridinyl]methyl}-2-oxo-1,2,5,6-tetrahydro-3-pyridinyl)carbonyl]glycine;

N-[(1-{[6-(3-fluorophenoxy)-3-pyridinyl]methyl}-4-hydroxy-2-oxo-1,2,5,6-tetrahydro-3-pyridinyl)carbonyl]glycine;

N-({4-hydroxy-1-[4-(3-methylphenoxyl)benzyl]-2-oxo-1,2,5,6-tetrahydro-3-pyridinyl}carbonyl)glycine;

N-({1-[4-(3-fluorophenoxy)benzyl]-4-hydroxy-2-oxo-1,2,5,6-tetrahydro-3-pyridinyl}carbonyl)glycine;

N-[(1-{[5-(4-fluorophenoxy)-2-pyridinyl]methyl}-4-hydroxy-2-oxo-1,2,5,6-tetrahydro-3-pyridinyl)carbonyl]glycine;

N-[(4-hydroxy-1-{[5-(4-methylphenoxy)-2-pyridinyl]methyl}-2-oxo-1,2,5,6-tetrahydro-3-pyridinyl)carbonyl]glycine;

N-({1-[4-(4-chlorophenoxyl)benzyl]-4-hydroxy-2-oxo-1,2,5,6-tetrahydro-3-pyridinyl}carbonyl)glycine;

N-[(4-hydroxy-1-{4-[(6-methyl-3-pyridinyl)oxy]benzyl}-2-oxo-1,2,5,6-tetrahydro-3-pyridinyl)carbonyl]glycine;

N-[(1-{[6-(2-fluorophenoxy)-3-pyridinyl]methyl}-4-hydroxy-2-oxo-1,2,5,6-tetrahydro-3-pyridinyl)carbonyl]glycine;

N-[(4-hydroxy-1-{[6-(2-methylphenoxy)-3-pyridinyl]methyl}-2-oxo-1,2,5,6-tetrahydro-3-pyridinyl)carbonyl]glycine;

N-({1-[4-(2-fluorophenoxy)benzyl]-4-hydroxy-2-oxo-1,2,5,6-tetrahydro-3-pyridinyl}carbonyl)glycine;

N-({4-hydroxy-1-[4-(2-methylphenoxyl)benzyl]-2-oxo-1,2,5,6-tetrahydro-3-pyridinyl}carbonyl)glycine;

N-[(1-{[6-(3-chlorophenoxy)-3-pyridinyl]methyl}-4-hydroxy-2-oxo-1,2,5,6-tetrahydro-3-pyridinyl)carbonyl]glycine;

N-{[4-hydroxy-2-oxo-1-({6-[3-(trifluoromethyl)phenoxy]-3-pyridinyl}methyl)-1,2,5,6-tetrahydro-3-pyridinyl]carbonyl}glycine;

N-({4-hydroxy-1-[4-(3-methoxyphenoxy)benzyl]-2-oxo-1,2,5,6-tetrahydro-3-pyridinyl}carbonyl)glycine;

N-{[4-hydroxy-2-oxo-1-({6-[3-(trifluoromethoxy)phenoxy]-3-pyridinyl}methyl)-1,2,5,6-tetrahydro-3-pyridinyl]carbonyl}glycine;

N-[(1-{4-[(5-fluoro-2-pyridinyl)oxy]benzyl}-4-hydroxy-2-oxo-1,2,5,6-tetrahydro-3-pyridinyl)carbonyl]glycine;

N-[(1-{4-[(5-chloro-2-pyridinyl)oxy]benzyl}-4-hydroxy-2-oxo-1,2,5,6-tetrahydro-3-pyridinyl)carbonyl]glycine;

N-[(1-{[6-(4-cyclopropylphenoxy)-3-pyridinyl]methyl}-4-hydroxy-2-oxo-1,2,5,6-tetrahydro-3-pyridinyl)carbonyl]glycine;

N-[(4-hydroxy-1-{4-[(5-methyl-2-pyridinyl)oxy]benzyl}-2-oxo-1,2,5,6-tetrahydro-3-pyridinyl)carbonyl]glycine;

N-{[4-hydroxy-2-oxo-1-(4-{[5-(trifluoromethyl)-2-pyridinyl]oxy}benzyl)-1,2,5,6-tetrahydro-3-pyridinyl]carbonyl}glycine;

N-{[4-hydroxy-1-({5-methyl-6-[(6-methyl-3-pyridinyl)oxy]-3-pyridinyl}methyl)-2-oxo-1,2,5,6-tetrahydro-3-pyridinyl]carbonyl}glycine;

N-[(1-{[5-(4-chlorophenoxy)-2-pyridinyl]methyl}-4-hydroxy-2-oxo-1,2,5,6-tetrahydro-3-pyridinyl)carbonyl]glycine;

N-[(4-hydroxy-1-{[6-(3-methoxyphenoxy)-3-pyridinyl]methyl}-2-oxo-1,2,5,6-tetrahydro-3-pyridinyl)carbonyl]glycine;

N-[(1-{4-[(6-chloro-3-pyridinyl)oxy]benzyl}-4-hydroxy-2-oxo-1,2,5,6-tetrahydro-3-pyridinyl)carbonyl]glycine;

N-{[4-hydroxy-2-oxo-1-({5-[4-(trifluoromethyl)phenoxy]-2-pyridinyl}methyl)-1,2,5,6-tetrahydro-3-pyridinyl]carbonyl}glycine;

N-[4-hydroxy-2-oxo-1-(4-{[6-(trifluoromethyl)-3-pyridinyl]oxy}benzyl)-1,2,5,6-tetrahydro-3-pyridinyl]carbonyl glycine;

N-[(1-{[6-(3-chloro-4-methylphenoxy)-3-pyridinyl]methyl}-4-hydroxy-2-oxo-1,2,5,6-tetrahydro-3-pyridinyl)carbonyl]glycine;

N-[(1-{[6-(3-fluoro-4-methylphenoxy)-3-pyridinyl]methyl}-4-hydroxy-2-oxo-1,2,5,6-tetrahydro-3-pyridinyl)carbonyl]glycine;

N-[(1-{[6-(4-fluoro-3-methylphenoxy)-3-pyridinyl]methyl}-4-hydroxy-2-oxo-1,2,5,6-tetrahydro-3-pyridinyl)carbonyl]glycine;

N-[(1-{[6-(4-ethylphenoxy)-3-pyridinyl]methyl}-4-hydroxy-2-oxo-1,2,5,6-tetrahydro-3-pyridinyl)carbonyl]glycine;

N-[(4-hydroxy-2-oxo-1-{[6-(4-propylphenoxy)-3-pyridinyl]methyl}-1,2,5,6-tetrahydro-3-pyridinyl)carbonyl]glycine;

N-[(4-hydroxy-1-{[6(4-isopropylphenoxy)-3-pyridinyl]methyl}-2-oxo-1,2,5,6-tetrahydro-3-pyridinyl)carbonyl]glycine;

N-[(4-hydroxy-1-{[5-(4-methylphenoxy)-2-pyrazinyl]methyl}-2-oxo-1,2,5,6-tetrahydro-3-pyridinyl)carbonyl]glycine;

N-({1-[4-(3,4-dimethylphenoxy)benzyl]-4-hydroxy-2-oxo-1,2,5,6-tetrahydro-3-pyridinyl}carbonyl)glycine;

N-[(1-{[5-chloro-6-(4-methylphenoxy)-3-pyridinyl]methyl}-4-hydroxy-2-oxo-1,2,5,6-tetrahydro-3-pyridinyl)carbonyl]glycine;

N-[(1-{[5-fluoro-6-(4-methylphenoxy)-3-pyridinyl]methyl}-4-hydroxy-2-oxo-1,2,5,6-tetrahydro-3-pyridinyl)carbonyl]glycine;

N-[(1-{4-[(5-cyclopropyl-2-pyridinyl)oxy]benzyl}-4-hydroxy-2-oxo-1,2,5,6-tetrahydro-3-pyridinyl)carbonyl]glycine;

N-[(4-hydroxy-1-{[2-(4-methylphenoxy)-5-pyrimidinyl]methyl}-2-oxo-1,2,5,6-tetrahydro-3-pyridinyl)carbonyl]glycine;

N-[(1-{[6-(4-chlorophenoxy)-5-methyl-3-pyridinyl]methyl}-4-hydroxy-2-oxo-1,2,5,6-tetrahydro-3-pyridinyl)carbonyl]glycine;

N-[(1-{[5-(4-chlorophenoxy)-2-pyrazinyl]methyl}-4-hydroxy-2-oxo-1,2,5,6-tetrahydro-3-pyridinyl)carbonyl]glycine; or N-[(1-{[5-(4-cyclopropylphenoxy)-2-pyrazinyl]methyl}-4-hydroxy-2-oxo-1,2,5,6-tetrahydro-3-pyridinyl)carbonyl]glycine, or a pharmaceutically acceptable salt thereof.

(8) In another mode, the present invention is directed to providing a compound having the aforementioned general formula (I'), wherein W is the formula $-CR^{11}R^{12}cR^{13}R^{14}$, and the compound is represented by general formula (I):

[Formula 5]

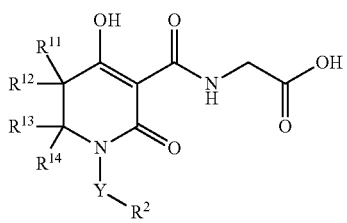

(wherein in formula (I), $R^{11}$ is a hydrogen atom, $C_{1-4}$ alkyl, or phenyl, $R^{12}$ is a hydrogen atom or $C_{1-4}$ alkyl, provided that $R^{11}$ and $R^{12}$, together with the adjacent carbon atom, optionally form $C_{3-8}$ cycloalkane or a 4- to 8-membered saturated heterocycle containing an oxygen atom;

$R^{13}$ is a hydrogen atom, $C_{1-4}$ alkyl, halo-$C_{1-4}$ alkyl, phenyl, benzyl, or phenethyl, $R^{14}$ is a hydrogen atom or $C_{1-4}$ alkyl, provided that $R^{13}$ and $R^{14}$, together with the adjacent carbon atom, optionally form $C_{3-8}$ cycloalkane or a 4- to 8-membered saturated heterocycle containing an oxygen atom, provided that the aforementioned $R^{12}$ and $R^{13}$, together with the adjacent carbon atoms, optionally form $C_{3-8}$ cycloalkane;

Y is a single bond or $C_{1-6}$ alkanediyl (one of the carbon atoms in the $C_{1-6}$ alkanediyl is optionally substituted by $C_{3-6}$ cycloalkane-1,1-diyl);

$R^2$ is $C_{3-8}$ cycloalkyl (the $C_{3-8}$ cycloalkyl is optionally substituted by one group selected from the group consisting of phenyl and benzyl), phenyl (the phenyl is optionally substituted by one to three groups which are the same or different and are selected from group α1 of substituents), naphthyl, indanyl, tetrahydronaphthyl, pyrazolyl [the pyrazolyl is substituted by one phenyl (the phenyl is optionally substituted by one $C_{1-6}$ alkyl) and may further be substituted by one $C_{1-6}$ alkyl], imidazolyl (the imidazolyl is substituted by one phenyl), isoxazolyl [the isoxazolyl is substituted by one phenyl (the phenyl is optionally substituted by one halogen atom)], oxazolyl (the oxazolyl is substituted by one phenyl and may further be substituted by one $C_{1-6}$ alkyl), thiazoyl (the thiazoyl is substituted by one phenyl), pyridyl [the pyridyl is substituted by one group selected from the group consisting of phenyl, phenoxy (the phenoxy is optionally substituted by one group selected from the group consisting of a halogen atom, cyano, $C_{1-6}$ alkyl, halo-$C_{1-6}$ alkyl, $C_{3-8}$ cycloalkyl, $C_{1-6}$ alkoxy, and halo-$C_{1-6}$ alkoxy), and phenylsulfanyl (the phenylsulfanyl is optionally substituted by one halogen atom)], pyrimidinyl (the pyrimidinyl is substituted by one group selected from the group consisting of cyclohexyl and phenyl), benzothiophenyl, quinolyl, or methylenedioxyphenyl (the methylenedioxyphenyl is optionally substituted by one or two fluorine atoms);

group α1 of substituents consists of a halogen atom, $C_{1-6}$ alkyl {the $C_{1-6}$ alkyl is optionally substituted by one group selected from the group consisting of $C_{3-8}$ cycloalkyl, phenyl, and $C_{1-6}$ alkoxy [the $C_{1-6}$ alkoxy is optionally substituted by one $C_{3-8}$ cycloalkyl (the $C_{3-8}$ cycloalkyl is optionally substituted by one $C_{1-6}$ alkyl)]}, halo-$C_{1-6}$ alkyl, $C_{3-8}$ cycloalkyl, phenyl (the phenyl is optionally substituted by one to three groups which are the same or different and are selected from group α2 of substituents), thienyl, pyrazolyl (the pyrazolyl is optionally substituted by one $C_{1-6}$ alkyl), isoxazolyl, thiazoyl (the thiazoyl is optionally substituted by one or two $C_{1-6}$ alkyls), pyridyl (the pyridyl is optionally substituted by one group selected from the group consisting of $C_{1-6}$ alkyl, halo-$C_{1-6}$ alkyl, $C_{1-6}$ alkoxy, and halo-$C_{1-6}$ alkoxy), quinolyl, $C_{1-6}$ alkoxy [the $C_{1-6}$ alkoxy is optionally substituted by one group selected from the group consisting of $C_{3-8}$ cycloalkyl and phenyl (the phenyl is optionally substituted by one group selected from the group consisting of a halogen atom and $C_{1-6}$ alkyl)], halo-$C_{1-6}$ alkoxy, $C_{2-6}$ alkenyloxy, $C_{3-8}$ cycloalkoxy, phenoxy (the phenoxy is optionally substituted by one group selected from the group consisting of a halogen atom, $C_{1-6}$ alkyl, halo-$C_{1-6}$ alkyl, $C_{1-6}$ alkoxy, and halo-$C_{1-6}$ alkoxy), pyridyloxy (the pyridyloxy is optionally substituted by one group selected from the group consisting of a halogen atom, $C_{1-6}$ alkyl, and halo-$C_{1-6}$ alkyl), and $C_{1-6}$ alkylsulfanyl;

group α2 of substituents consists of a halogen atom, cyano, hydroxy, $C_{1-6}$ alkyl, halo-$C_{1-6}$ alkyl, phenyl, $C_{1-6}$ alkoxy, halo-$C_{1-6}$ alkoxy, $C_{1-6}$ alkylcarbonyl, and di-$C_{1-6}$ alkylaminosulfonyl), or a pharmaceutically acceptable salt thereof.

(9) In another mode, the present invention is directed to providing a medicine comprising the compound according to any one of (1) to (8) or a pharmaceutically acceptable salt thereof as an active ingredient.

(10) In another mode, the present invention is directed to providing a PHD2 inhibitor comprising the compound according to any one of (1) to (8) or a pharmaceutically acceptable salt thereof as an active ingredient.

(11) In another mode, the present invention is directed to providing an EPO production promoter comprising the compound according to any one of (1) to (8) or a pharmaceutically acceptable salt thereof as an active ingredient.

(12) In another mode, the present invention is directed to providing a drug for preventing or treating anemia comprising the compound according to any one of (1) to (8) or a pharmaceutically acceptable salt thereof as an active ingredient.

Advantageous Effects of Invention

The present invention has made it possible to provide compounds having a superior PHD2 inhibitory effect.

DESCRIPTION OF EMBODIMENTS

The present invention provides compounds having a superior PHD2 inhibitory effect that are represented by general formula (I) or (I'), or pharmaceutically acceptable salts thereof.

On the following pages, the compounds of the present invention are described in greater detail but it should be understood that the present invention is by no means limited to the following illustrations.

As used herein, symbol "n" refers to normal, "s" or "sec", secondary, "t" or "tert", tertiary, "c", cyclo, "o", ortho, "m", meta, and "p", para.

The "halogen atom" refers to a fluorine atom, a chlorine atom, a bromine atom, and an iodine atom.

The "$C_{1-3}$ alkyl" refers to linear or branched alkyl having one to three carbon atoms. Specifically, methyl, ethyl, n-propyl, and isopropyl are referred to.

The "$C_{1-4}$ alkyl" refers to linear or branched alkyl having one to four carbon atoms. Specifically, methyl, ethyl, n-propyl, isopropyl, n-butyl, isobutyl, sec-butyl, and tert-butyl are referred to.

The "$C_{1-6}$ alkyl" refers to linear or branched alkyl having one to six carbon atoms, and examples include methyl, ethyl, n-propyl, isopropyl, n-butyl, isobutyl, sec-butyl, tert-butyl, n-pentyl, isopentyl, neopentyl, 2-methylbutyl, n-hexyl, isohexyl, etc.

The "halo-$C_{1-4}$ alkyl" refers to linear or branched alkyl having one to four carbon atoms, with substitution by a halogen atom. The number of substitutions by a halogen atom is preferably from one to three, and a preferred halogen atom is a fluorine atom. Examples include monofluoromethyl, difluoromethyl, trifluoromethyl, 1-fluoroethyl, 1,1-difluoroethyl, 2-fluoroethyl, 2-fluoro-2-methylpropyl, 2,2-difluoropropyl, 1-fluoro-2-methylpropan-2-yl, 1,1-difluoro-2-methylpropan-2-yl, etc.

The "halo-$C_{1-6}$ alkyl" refers to linear or branched alkyl having one to six carbon atoms, with substitution by a halogen atom. The number of substitutions by a halogen atom is preferably from one to five, and a preferred halogen atom is a fluorine atom. Examples include monofluoromethyl, difluoromethyl, trifluoromethyl, 1-fluoroethyl, 1,1-difluoroethyl, 1,1,2,2,2-pentafluoroethyl, 2-fluoroethyl, 2-fluoro-2-methylpropyl, 2,2-difluoropropyl, 1-fluoro-2-methylpropan-2-yl, 1,1-difluoro-2-methylpropan-2-yl, 1-fluoropentyl, 1-fluorohexyl, etc.

The "$C_{3-6}$ cycloalkane" refers to cyclic alkane having three to six carbon atoms. Examples include cyclopropane, cyclobutane, cyclopentane, and cyclohexane.

The "$C_{3-8}$ cycloalkane" refers to cyclic alkane having three to eight carbon atoms. Examples include cyclopropane, cyclobutane, cyclopentane, cyclohexane, cycloheptane, and cyclooctane.

The "$C_{3-8}$ cycloalkyl" refers to cyclic alkyl having three to eight carbon atoms. Examples include cyclopropyl, cyclobutyl, cyclopentyl, cyclohexyl, cycloheptyl, and cyclooctyl.

The "$C_{3-8}$ cycloalkenyl" refers to cyclic alkenyl having three to eight carbon atoms. Examples include cyclopropenyl, cyclobutenyl, cyclopentenyl, cyclohexenyl, cycloheptenyl, and cyclooctenyl.

The "4- to 8-membered saturated heterocycle containing an oxygen atom" refers to a 4- to 8-membered monocylic saturated heterocycle containing one oxygen atom in the ring. Examples include oxetane, tetrahydrofuran, tetrahydropyran, etc.

The "4- to 8-membered saturated heterocycle containing a nitrogen atom" refers to a 4to 8-membered monocylic saturated heterocycle containing one nitrogen atom in the ring. Examples include azetidine, pyrrolidine, piperidine, etc.

The "4- to 8-membered saturated heterocyclyl containing a nitrogen atom" refers to a 4to 8-membered monocytic saturated heterocyclic group containing one nitrogen atom in the ring. Examples include azetidinyl, pyrrolidinyl, piperidinyl, etc.

The "$C_{1-3}$ alkoxy" refers to linear or branched alkoxy having one to three carbon atoms. Specifically, methoxy, ethoxy, n-propoxy, and isopropoxy are referred to.

The "$C_{1-6}$ alkoxy" refers to linear or branched alkoxy having one to six carbon atoms. Examples include methoxy, ethoxy, n-propoxy, isopropoxy, n-butoxy, isobutoxy, sec-butoxy, tert-butoxy, n-pentyloxy, isopentyloxy, neopentyloxy, 2-methylbutoxy, n-hexyloxy, isohexyloxy, etc.

The "halo-$C_{1-6}$ alkoxy" refers to linear or branched alkoxy having one to six carbon atoms, with substitution by a halogen atom. The number of substitutions by a halogen atom is preferably from one to five, and a preferred halogen atom is a fluorine atom. Examples include monofluoromethoxy, difluoromethoxy, trifluoromethoxy, 1-fluoroethoxy, 1,1-difluoroethoxy, 1,1,2,2-tetrafluoroethoxy, 2-fluoroethoxy, 2,2,2-trifluoroethoxy, 3,3,3-trifluoropropoxy, 1,3-difluoropropan-2-yloxy, 2-fluoro-2-methylpropoxy, 2,2-difluoropropoxy, 1-fluoro-2-methylpropan-2-yloxy, 1,1-difluoro-2-methylpropan-2-yloxy, 4,4,4-trifluorobutoxy, etc.

The "$C_{1-6}$ alkenyloxy" refers to a group of such a structure that oxy is bound to linear or branched alkenyl having two to six carbon atoms. Examples include ethenyloxy, (E)-prop-1-en-1-yloxy, (Z)-prop-1-en-1-yloxy, prop-2-en-1-yloxy, (Z)-but-2-en-1-yloxy, (Z)-pent-3-en-1-yloxy, (Z)-hex-4-en-1-yloxy, (Z)-hept-5-en-1-yloxy, and (Z)-oct-6-en-1-yloxy, etc.

The "$C_{3-8}$ cycloalkoxy" refers to cyclic alkoxy having three to eight carbon atoms. Examples include cyclopropoxy, cyclobutoxy, cyclopentyloxy, cyclohexyloxy, cycloheptyloxy, and cyclooctyloxy.

The "di-$C_{1-3}$ alkylamino" refers to amino having the aforementioned "$C_{1-3}$ alkyl" as two substituents which are the same or different. Examples include dimethylamino, diethylamino, di(n-propyl)amino, di(isopropyl)amino, ethylmethylamino, methyl(n-propyl)amino, etc.

The "di-$C_{1-6}$ alkylamino" refers to amino having the aforementioned "$C_{1-6}$ alkyl" as two substituents which are the same or different. Examples include dimethylamino, diethylamino, di(n-propyl)amino, di(isopropyl)amino, ethylmethylamino, methyl(n-propyl)amino, etc.

The "$C_{1-6}$ alkylcarbonyl" refers to a group of such a structure that carbonyl is bound to the aforementioned "$C_{1-6}$ alkyl". Examples include methylcarbonyl, ethylcarbonyl, n-propylcarbonyl, isopropylcarbonyl, n-butylcarbonyl, isobutylcarbonyl, sec-butylcarbonyl, tert-butylcarbony, n-pentylcarbonyl, isopentylcarbonyl, neopentylcarbonyl, 2-methylbutylcarbonyl, n-hexylcarbonyl, isohexylcarbonyl, etc.

The "mono-$C_{1-6}$ alkylaminocarbonyl" refers to a group of such a structure that carbonyl is bound to amino having the aforementioned "$C_{1-6}$ alkyl" as a single substituent. Examples include methylaminocarbonyl, ethylaminocarbonyl, n-propylaminocarbonyl, isopropylaminocarbonyl, n-butylaminocarbonyl, isobutylaminocarbonyl, sec-butylaminocarbonyl, tert-butylaminocarbonyl, n-pentylaminocarbonyl, n-hexylaminocarbonyl, etc.

The "di-$C_{1-6}$ alkylaminocarbonyl" refers to a group of such a structure that carbonyl is bound to amino having the aforementioned "$C_{1-6}$ alkyl" as two substituents which are the same or different. Examples include dimethylaminocarbonyl, di(n-propyl)aminocarbonyl, di(isopropyl)aminocarbonyl, ethylmethylaminocarbonyl, methyl(n-propyl)aminocarbonyl, etc.

The two $C_{1-6}$ alkyls in the di-$C_{1-6}$ alkylaminocarbonyl, together with the adjacent nitrogen atom, may optionally form a 4- to 8-membered saturated heterocycle containing a nitrogen atom.

The "$C_{1-6}$ alkylsulfanyl" refers to a group of such a structure that sulfanyl is bound to the aforementioned "$C_{1-6}$ alkyl". Examples include methylsulfanyl, ethylsulfanyl, n-propylsulfanyl, isopropylsulfanyl, isobutylsulfanyl, n-hexylsulfanyl, etc.

The "$C_{1-6}$ alkylsulfonyl" is a group of such a structure that sulfonyl is bound to the aforementioned "$C_{1-6}$ alkyl". Examples include methylsulfonyl, ethylsulfonyl, n-propylsulfonyl, isopropylsulfonyl, isobutylsulfonyl, n-hexylsulfonyl, etc.

The "mono-$C_{1-6}$ alkylaminosulfonyl" refers to a group of such a structure that sulfonyl is bound to amino having the aforementioned "$C_{1-6}$ alkyl" as a single substituent. Examples include methylaminosulfonyl, ethylaminosulfonyl, n-propylaminosulfonyl, isopropylaminosulfonyl, n-butylaminosulfonyl, isobutylaminosulfonyl, sec-butylaminosulfonyl, tert-butylaminosulfonyl, n-pentylaminosulfonyl, n-hexylaminosulfonyl, etc.

The "di-$C_{1-6}$ alkylaminosulfonyl" refers to a group of such a structure that sulfonyl is bound to amino having the aforementioned "$C_{1-6}$ alkyl" as two substituents which are the same or different. Examples include dimethylaminosulfonyl, diethylaminosulfonyl, di(n-propyl)aminosulfonyl, di(isopropyl)aminosulfonyl, ethylmethylaminosulfonyl, methyl(n-propyl)aminosulfonyl, isopropyl(methyl)aminosulfonyl, etc.

The "$C_{1-4}$ alkanediyl" refers to a divalent hydrocarbon group of such a structure that one hydrogen atom has been removed from an alkyl group having one to four carbon atoms. Examples include methanediyl, ethane-1,1-diyl, ethane-1,2-diyl, propane-1,1-diyl, propane-1,2-diyl, propane-1,3-diyl, propane-2,2-diyl, butane-1,4-diyl, 2-methylpropane-1,2-diyl, etc. Among these, methanediyl, ethane-1,1-diyl, ethane-1,2-diyl, propane-1,1-diyl, propane-1,2-diyl, propane-1,3-diyl, and propane-2,2-diyl are $C_{1-3}$ alkanediyls.

The "$C_{1-6}$ alkanediyl" refers to a divalent hydrocarbon group of such a structure that one hydrogen atom has been removed from an alkyl group having one to six carbon atoms. Examples include methanediyl, ethane-1,1-diyl, ethane-1,2-diyl, propane-1,1-diyl, propane-1,2-diyl, propane-1,3-diyl, propane-2,2-diyl, butane-1,4-diyl, 2-methylpropane-1,2-diyl, pentane-1,5-diyl, hexane-1,6-diyl, etc.

The "$C_{3-6}$ cycloalkane-1,1-diyl" refers to a divalent cyclic hydrocarbon group of such a structure that one hydrogen atom has been removed from a cycloalkyl group having three to six carbon atoms. Examples include cyclopropane-1,1-diyl, cyclobutane-1,1-diyl, cyclopentane-1,1-diyl, and cyclohexane-1,1-diyl.

The "phenyl-$C_{1-3}$ alkyl" refers to the aforementioned "$C_{1-3}$ alkyl" having a phenyl group as a substituent. Examples include benzyl, phenethyl, and phenylpropyl.

The "$C_{3-8}$ cycloalkyl-$C_{1-3}$ alkylcarbonyl" refers to a group of such a structure that the aforementioned cycloalkyl group having three to eight carbon atoms binds a carbonyl group via the aforementioned $C_{1-3}$ alkyl. Examples include cyclopropylmethylcarbonyl, cyclopropylethylcarbonyl, cyclobutylmethylcarbonyl, cyclopentylmethylcarbonyl, cyclohexylmethylcarbonyl, etc.

The "phenyl-$C_{1-3}$ alkoxycarbonyl" refers to a group of such a structure that a phenyl group binds a carbonyl group via the aforementioned $C_{1-3}$ alkoxy. Examples include phenylmethoxycarbonyl, phenylethoxycarbonyl, and phenylpropoxycarbonyl.

Preferred modes of the compounds of the present invention are as follows.

A preferred case of W is the formula —$CR^{15}R^{16}$— or the formula —$CR^{11}R^{12}cR^{13}R^{14}$—.

When W represents the formula —$CR^{15}R^{16}$—,
one preferred case of $R^{15}$ is a hydrogen atom or $C_{1-4}$ alkyl, with a more preferred case of $R^{15}$ being a hydrogen atom or methyl, and an even more preferred case of $R^{15}$ being a hydrogen atom;
one preferred case of $R^{16}$ is a hydrogen atom or $C_{1-4}$ alkyl, with a more preferred case of $R^{16}$ being a hydrogen atom or methyl, and an even more preferred case of $R^{16}$ being a hydrogen atom;
another preferred case of $R^{15}$ and $R^{16}$ is such that the $R^{15}$ and $R^{16}$, together with the adjacent carbon atom, form $C_{3-8}$ cycloalkane, with a more preferred case of $R^{15}$ and $R^{16}$ being such that the $R^{15}$ and $R^{16}$, together with the adjacent carbon atom, form cyclobutane, cyclopentane, or cyclohexane.

When W represents the formula —$CR^{11}R^{12}cR^{13}R^{14}$—,
one preferred case of $R^{11}$ is a hydrogen atom or $C_{1-4}$ alkyl, with a more preferred case of $R^{11}$ being a hydrogen atom or methyl, and an even more preferred case of $R^{11}$ being a hydrogen atom;
one preferred case of R is a hydrogen atom or $C_{1-4}$ alkyl, with a more preferred case of $R^{12}$ being a hydrogen atom or methyl, and an even more preferred case of $R^{12}$ being a hydrogen atom;
another preferred case of $R^{11}$ and $R^{12}$ is such that the $R^{11}$ and $R^{12}$, together with the adjacent carbon atom, form $C_{3-8}$ cycloalkane or a 4- to 8-membered saturated heterocycle containing an oxygen atom, with a more preferred case of $R^{11}$ and $R^{12}$ being such that the $R^{11}$ and $R^{12}$, together with the adjacent carbon atom, form $C_{3-6}$ cycloalkane, and an even more preferred case of $R^{11}$ and $R^{12}$ being such that the $R^{11}$ and $R^{12}$, together with the adjacent carbon atom, form cyclopropane;
one preferred case of $R^{13}$ is a hydrogen atom, $C_{1-4}$ alkyl, or halo-$C_{1-4}$ alkyl, with a more preferred case of $R^{13}$ being a hydrogen atom or methyl, and an even more preferred case of $R^{13}$ being a hydrogen atom;
one preferred case of $R^{14}$ is a hydrogen atom or $C_{1-4}$ alkyl, with a more preferred case of $R^{14}$ being a hydrogen atom or methyl, and an even more preferred case of $R^{14}$ being a hydrogen atom;
another preferred case of $R^{13}$ and $R^{14}$ is such that the $R^{13}$ and $R^{14}$, together with the adjacent carbon atom, form $C_{3-8}$ cycloalkane, a 4- to 8-membered saturated heterocycle containing an oxygen atom, or a 4- to 8-membered saturated heterocycle containing a nitrogen atom (wherein the 4- to 8-membered saturated heterocycle containing a nitrogen atom is optionally substituted by one or two groups which are the same or different and are selected from the group consisting of methyl, benzyl, phenylcarbonyl, and oxo), with a more preferred case of $R^{13}$ and $R^{14}$ being such that the $R^{13}$ and $R^{14}$, together with the adjacent carbon atom, form $C_{3-6}$ cycloalkane, an even more preferred case of $R^{13}$ and $R^{14}$ being such that the $R^{13}$ and $R^{14}$, together with the adjacent carbon atom, form cyclopropane, cyclobutane, cyclopentane, or cyclohexane, and a particularly preferred case of $R^{13}$ and $R^{14}$ being such that the $R^{13}$ and $R^{14}$, together with the adjacent carbon atom, form cyclopropane.

A preferred case of Y is a single bond or $C_{1-6}$ alkanediyl (one of the carbon atoms in the $C_{1-6}$ alkanediyl is optionally substituted by $C_{3-6}$ cycloalkane-1,1-diyl), with a more preferred case of Y being a single bond, methanediyl, ethane-1,1-diyl, propane-1,1-diyl, propane-2,2-diyl, cyclopropane-1,1-diyl, or ethane-1,2-diyl, with an even more preferred case of Y being a single bond or methanediyl, and a particularly preferred case of Y being methanediyl.

Preferred modes of $R^2$ are described below under (1) to (4).

(1) A preferred case of $R^2$ is $C_{3-8}$ cycloalkyl{the $C_{3-8}$ cycloalkyl is optionally substituted by one or two groups which are the same or different and are selected from the group consisting of $C_{1-6}$ alkyl (the $C_{1-6}$ alkyl is optionally substituted by one phenyl), phenyl (the phenyl is optionally substituted by one halo-$C_{1-6}$ alkyl), $C_{1-6}$ alkoxy [the $C_{1-6}$ alkoxy is optionally substituted by one group selected from the group consisting of $C_{3-8}$ cycloalkyl, phenyl (the phenyl is optionally substituted by one group selected from the group consisting of a halogen atom and $C_{1-6}$ alkyl), and pyridyl (the pyridyl is optionally substituted by one halogen atom)], $C_{3-8}$ cycloalkoxy, phenoxy (the phenoxy is optionally substituted by one group selected from the group consisting of a halogen atom, $C_{1-6}$ alkyl, $C_{3-8}$ cycloalkyl, and halo-$C_{1-6}$ alkyl), and pyridyloxy (the pyridyloxy is optionally substituted by one group selected from the group consisting of a halogen atom, $C_{1-6}$ alkyl, $C_{3-8}$ cycloalkyl, and halo-$C_{1-6}$ alkyl)}, phenyl (the phenyl is optionally substituted by one to three groups which are the same or different and are selected from group α3 of substituents), indanyl, isoxazolyl [the isoxazolyl is optionally substituted by one phenyl (the phenyl is optionally substituted by one halogen atom)], oxazolyl (the oxazolyl is optionally substituted by one or two groups which are the same or different and are selected from the group consisting of $C_{1-6}$ alkyl and phenyl), thiazoyl (the thiazoyl is optionally substituted by one group selected from the group consisting of $C_{1-6}$ alkyl, phenyl, and morpholino), pyridyl (the pyridyl is optionally substituted by one or two groups which are the same or different and are selected from the aforementioned group α5 of substituents), pyrimidinyl [the pyrimidinyl is optionally substituted by one group selected from the group consisting of halo-$C_{1-6}$ alkyl, $C_{3-8}$ cycloalkyl, phenyl, and phenoxy (the phenoxy is optionally substituted by one $C_{1-6}$ alkyl)], pyrazinyl [the pyrazinyl is optionally substituted by one group selected from the group consisting of $C_{1-6}$ alkoxy (the $C_{1-6}$ alkoxy is optionally substituted by one $C_{3-8}$ cycloalkyl) and phenoxy (the phenoxy is optionally substituted by one group selected from the group consisting of a halogen atom, $C_{1-6}$ alkyl, and $C_{3-8}$ cycloalkyl)], or benzothiophenyl;

(2) A more preferred case of $R^2$ is $C_{3-8}$ cycloalkyl {the $C_{3-8}$ cycloalkyl is optionally substituted by one or two groups which are the same or different and are selected from the group consisting of phenyl (the phenyl is optionally substituted by one halo-$C_{1-6}$ alkyl), $C_{1-6}$ alkoxy [the $C_{1-6}$ alkoxy is optionally substituted by one group selected from the group consisting of $C_{3-8}$ cycloalkyl, phenyl (the phenyl is optionally substituted by one group selected from the group consisting of a halogen atom and $C_{1-6}$ alkyl), and pyridyl (the pyridyl is optionally substituted by one halogen atom)], phenoxy (the phenoxy is optionally substituted by one group selected from the group consisting of a halogen atom, $C_{1-6}$ alkyl, $C_{3-8}$ cycloalkyl, and halo-$C_{1-6}$ alkyl), and pyridyloxy (the pyridyloxy is optionally substituted by one group selected from the group consisting of a halogen atom, $C_{1-6}$ alkyl, $C_{3-8}$ cycloalkyl, and halo-$C_{1-6}$ alkyl)};

phenyl (the phenyl is optionally substituted by one to three groups which are the same or different and are selected from the group consisting of a halogen atom, $C_{1-6}$ alkyl {the $C_{1-6}$ alkyl is optionally substituted by one group selected from the group consisting of $C_{3-8}$ cycloalkyl, phenyl, $C_{1-6}$ alkoxy [the $C_{1-6}$ alkoxy is optionally substituted by one $C_{3-8}$ cycloalkyl (the $C_{3-8}$ cycloalkyl is optionally substituted by one $C_{1-6}$ alkyl)], phenoxy (the phenoxy is optionally substituted by one $C_{1-6}$ alkyl), and pyridyloxy (the pyridyloxy is optionally substituted by one group selected from the group consisting of $C_{1-6}$ alkyl and halo-$C_{1-6}$ alkyl)}, halo-$C_{1-6}$ alkyl, $C_{3-8}$ cycloalkyl (the $C_{3-8}$ cycloalkyl is optionally substituted by one or two halogen atoms), phenyl [the phenyl is optionally substituted by one to three groups which are the same or different and are selected from the group consisting of carboxy, cyano, hydroxy, sulfamoyl, a halogen atom, $C_{1-6}$ alkyl, halo-$C_{1-6}$ alkyl, $C_{3-8}$ cycloalkyl, phenyl, $C_{1-6}$ alkoxy, halo-$C_{1-6}$ alkoxy, $C_{1-6}$ alkylcarbonyl, di-$C_{1-6}$ alkylaminocarbonyl, $C_{1-6}$ alkylsulfonyl, mono-$C_{1-6}$ alkylaminosulfonyl (the $C_{1-6}$ alkyl of the mono-$C_{1-6}$ alkylaminosulfonyl is optionally substituted by one hydroxy), and di-$C_{1-6}$ alkylaminosulfonyl], thienyl (the thienyl is optionally substituted by one $C_{1-6}$ alkyl), pyrazolyl (the pyrazolyl is optionally substituted by one $C_{1-6}$ alkyl), isoxazolyl, thiazoyl (the thiazoyl is optionally substituted by one or two groups which are the same or different and are selected from the group consisting of hydroxy, $C_{1-6}$ alkyl, and $C_{1-6}$ alkoxy), pyridyl (the pyridyl is optionally substituted by one group selected from the group consisting of carboxy, hydroxy, amino, a halogen atom, $C_{1-6}$ alkyl, halo-$C_{1-6}$ alkyl, $C_{3-8}$ cycloalkyl, $C_{1-6}$ alkoxy, halo-$C_{1-6}$ alkoxy, and $C_{1-6}$ alkylsulfonyl), pyrimidinyl (the pyrimidinyl is optionally substituted by one amino), quinolyl, $C_{1-6}$ alkoxy [the $C_{1-6}$ alkoxy is optionally substituted by one group selected from the group consisting of $C_{3-8}$ cycloalkyl (the $C_{3-8}$ cycloalkyl is optionally substituted by one $C_{1-6}$ alkyl), phenyl (the phenyl is optionally substituted by one group selected from the group consisting of hydroxy, a halogen atom, $C_{1-6}$ alkyl, halo-$C_{1-6}$ alkyl, $C_{1-6}$ alkoxy, halo-$C_{1-6}$ alkoxy, and di-$C_{1-6}$ alkylamino), pyridyl (the pyridyl is optionally substituted by one group selected from the group consisting of a halogen atom and $C_{1-6}$ alkyl), oxazolyl (the oxazolyl is optionally substituted by one or two $C_{1-6}$ alkyls), pyrazolyl (the pyrazolyl is optionally substituted by one or two $C_{1-6}$ alkyls), thiazoyl (the thiazoyl is optionally substituted by one $C_{1-6}$ alkyl), indazolyl (the indazolyl is optionally substituted by one $C_{1-6}$ alkyl), benzotriazolyl, imidazothiazoyl, and di-$C_{1-6}$ alkylamino], halo-$C_{1-6}$ alkoxy, $C_{2-6}$ alkenyloxy, $C_{3-8}$ cycloalkoxy, phenoxy (the phenoxy is optionally substituted by one or two groups which are the same or different and are selected from the group consisting of a halogen atom, $C_{1-6}$ alkyl, halo-$C_{1-6}$ alkyl, $C_{1-6}$ alkoxy, and halo-$C_{1-6}$ alkoxy), pyridyloxy (the pyridyloxy is optionally substituted by one group selected from the group consisting of a halogen atom, $C_{1-6}$ alkyl, halo-$C_{1-6}$ alkyl, and $C_{3-8}$ cycloalkyl), $C_{1-6}$ alkylsulfanyl, and $C_{1-6}$ alkylsulfonyl);

pyridyl {the pyridyl is optionally substituted by one or two groups which are the same or different and are selected from the group consisting of a halogen atom, $C_{1-6}$ alkyl, $C_{1-6}$ alkoxy [the $C_{1-6}$ alkoxy is optionally substituted by one group selected from the group consisting of $C_{3-8}$ cycloalkyl (the $C_{3-8}$ cycloalkyl is optionally substituted by one $C_{1-6}$ alkyl), phenyl (the phenyl is optionally substituted by one group selected from the group consisting of a halogen atom and $C_{1-6}$ alkyl)], halo-$C_{1-6}$ alkoxy, phenyl (the phenyl is optionally substituted by one group selected from the group consisting of a halogen atom, $C_{1-6}$ alkyl, halo-$C_{1-6}$ alkyl, $C_{3-8}$ cycloalkyl, $C_{1-6}$ alkoxy, and halo-$C_{1-6}$ alkoxy), pyridyl, phenoxy [the phenoxy is optionally substituted by one or two groups which are the same or different and are selected from the group consisting of a halogen atom, cyano, $C_{1-6}$ alkyl, halo-$C_{1-6}$ alkyl, $C_{3-8}$ cycloalkyl, $C_{1-6}$ alkoxy (the $C_{1-6}$ alkoxy is optionally substituted by one phenyl), and halo-$C_{1-6}$ alkoxy], and pyridyloxy (the pyridyloxy is optionally substituted by one $C_{1-6}$ alkyl)}; or pyrazinyl [the pyrazinyl is optionally substituted by one group selected from the group consisting of $C_{1-6}$ alkoxy (the $C_{1-6}$ alkoxy is optionally substituted by one $C_{3-8}$ cycloalkyl) and phenoxy (the phenoxy is optionally substituted by one group selected from the group consisting of a halogen atom, $C_{1-6}$ alkyl, and $C_{3-8}$ cycloalkyl)];

(3) An even more preferred case of $R^2$ is phenyl {the phenyl is substituted by one group selected from the group consisting of phenyl [the phenyl is optionally substituted by one to three groups which are the same or different and are selected from the group consisting of carboxy, cyano, hydroxy, sulfamoyl, a halogen atom, $C_{1-6}$ alkyl, halo-$C_{1-6}$ alkyl, $C_{3-8}$ cycloalkyl, phenyl, $C_{1-6}$ alkoxy, halo-$C_{1-6}$ alkoxy, $C_{1-6}$ alkylcarbonyl, di-$C_{1-6}$ alkylaminocarbonyl, $C_{1-6}$ alkylsulfonyl, mono-$C_{1-6}$ alkylaminosulfonyl (the $C_{1-6}$ alkyl of the mono-$C_{1-6}$ alkylaminosulfonyl is optionally substituted by one hydroxy), and di-$C_{1-6}$ alkylaminosulfonyl], pyridyl (the pyridyl is optionally substituted by one group selected from the group consisting of carboxy, hydroxy, amino, a halogen atom, $C_{1-6}$ alkyl, halo-$C_{1-6}$ alkyl, $C_{3-8}$ cycloalkyl, $C_{1-6}$ alkoxy, halo-$C_{1-6}$ alkoxy, and $C_{1-6}$ alkylsulfonyl), $C_{1-6}$ alkoxy [the $C_{1-6}$ alkoxy is substituted by one group selected from the group consisting of $C_{3-8}$ cycloalkyl (the $C_{3-8}$ cycloalkyl is optionally substituted by one $C_{1-6}$ alkyl), phenyl (the phenyl is optionally substituted by one group selected from the group consisting of hydroxy, a halogen atom, $C_{1-6}$ alkyl, halo-$C_{1-6}$ alkyl, $C_{1-6}$ alkoxy, halo-$C_{1-6}$ alkoxy, and di-$C_{1-6}$ alkylamino), pyridyl (the pyridyl is optionally substituted by one group selected from the group consisting of a halogen atom and $C_{1-6}$ alkyl), oxazolyl (the oxazolyl is optionally substituted by one or two $C_{1-6}$ alkyls), pyrazolyl (the pyrazolyl is optionally substituted by one or two $C_{1-6}$ alkyls), thiazoyl (the thiazoyl is optionally substituted by one $C_{1-6}$ alkyl), indazolyl (the indazolyl is optionally substituted by one $C_{1-6}$ alkyl), benzotriazolyl, imidazothiazoyl, and di-$C_{16}$ alkylamino], halo-$C_{1-6}$ alkoxy, $C_{3-8}$ cycloalkoxy, phenoxy (the phenoxy is optionally substituted by one or two groups which are the same or different and are selected from the group consisting of a halogen atom, $C_{1-6}$ alkyl, halo-$C_{1-6}$ alkyl, $C_{1-6}$ alkoxy, and halo-$C_{1-6}$ alkoxy), pyridyloxy (the pyridyloxy is optionally substituted by one group selected from the group consisting of a halogen atom, $C_{1-6}$ alkyl, halo-$C_{1-6}$ alkyl, and $C_{3-8}$ cycloalkyl), $C_{1-6}$ alkylsulfanyl, and $C_{1-6}$ alkylsulfonyl and may further be substituted by one halogen atom};

pyridyl {the pyridyl is substituted by one group selected from the group consisting of $C_{1-6}$ alkoxy [the $C_{1-6}$ alkoxy is substituted by one group selected from the group consisting of $C_{3-8}$ cycloalkyl (the $C_{3-8}$ cycloalkyl is optionally substituted by one $C_{1-6}$ alkyl), phenyl (the phenyl is optionally substituted by one group selected from the group consisting of a halogen atom and $C_{1-6}$ alkyl)], halo-$C_{1-6}$ alkoxy, phenyl (the phenyl is optionally substituted by one group selected from the group consisting of a halogen atom, $C_{1-6}$ alkyl, halo-$C_{1-6}$ alkyl, $C_{3-8}$ cycloalkyl, $C_{1-6}$ alkoxy, and halo-$C_{1-6}$ alkoxy), pyridyl, phenoxy [the phenoxy is optionally substituted by one or two groups which are the same or different and are selected from the group consisting of a halogen atom, cyano, $C_{1-6}$ alkyl, halo-$C_{1-6}$ alkyl, $C_{3-8}$ cycloalkyl, $C_{1-6}$ alkoxy (the $C_{1-6}$ alkoxy is optionally substituted by one phenyl), and halo-$C_{1-6}$ alkoxy], and pyridyloxy (the pyridyloxy is optionally substituted by one $C_{1-6}$ alkyl) and may further be substituted by one group selected from the group consisting of a halogen atom and $C_{1-6}$ alkyl}; or pyrazinyl [the pyrazinyl is substituted by one group selected from the group consisting of $C_{1-6}$ alkoxy (the $C_{1-6}$ alkoxy is substituted by one $C_{3-8}$ cycloalkyl) and phenoxy (the phenoxy is optionally substituted by one group selected from the group consisting of a halogen atom, $C_{1-6}$ alkyl, and $C_{3-8}$ cycloalkyl)];

(4) A particularly preferred case of $R^2$ is phenyl [the phenyl is substituted by one group selected from the group consisting of phenoxy (the phenoxy is optionally substituted by one or two groups which are the same or different and are selected from the group consisting of a halogen atom, $C_{1-6}$ alkyl, $C_{1-6}$ alkoxy, and halo-$C_{1-6}$ alkoxy) and pyridyloxy (the pyridyloxy is optionally substituted by one group selected from the group consisting of a halogen atom, $C_{1-6}$ alkyl, halo-$C_{1-6}$ alkyl, and $C_{3-5}$ cycloalkyl) and may further be substituted by one halogen atom];

pyridyl {the pyridyl is substituted by one group selected from the group consisting of phenyl (the phenyl is optionally substituted by one group selected from the group consisting of a halogen atom, $C_{1-6}$ alkyl, halo-$C_{1-6}$ alkyl, $C_{3-8}$ cycloalkyl, $C_{1-6}$ alkoxy, and halo-$C_{1-6}$ alkoxy), pyridyl, phenoxy [the phenoxy is optionally substituted by one or two groups which are the same or different and are selected from the group consisting of a halogen atom, cyano, $C_{1-6}$ alkyl, halo-$C_{1-6}$ alkyl, $C_{3-8}$ cycloalkyl, $C_{1-6}$ alkoxy (the $C_{1-6}$ alkoxy is optionally substituted by one phenyl), and halo-$C_{1-6}$ alkoxy], and pyridyloxy (the pyridyloxy is optionally substituted by one $C_{1-6}$ alkyl) and may further be substituted by one group selected from the group consisting of a halogen atom and $C_{1-6}$ alkyl}; or pyrazinyl substituted by one phenoxy (the phenoxy is optionally substituted by one group selected from the group consisting of a halogen atom, $C_{1-6}$ alkyl, and $C_{3-8}$ cycloalkyl).

In the above case, preferred groups in group α3 of substituents are a halogen atom, $C_{1-6}$ alkyl {the $C_{1-6}$ alkyl is optionally substituted by one group selected from the group consisting of $C_{3-8}$ cycloalkyl, phenyl, $C_{1-6}$ alkoxy [the $C_{1-6}$ alkoxy is optionally substituted by one $C_{3-8}$ cycloalkyl (the $C_{3-8}$ cycloalkyl is optionally substituted by one $C_{1-6}$ alkyl)], phenoxy (the phenoxy is optionally substituted by one $C_{1-6}$ alkyl), and pyridyloxy (the pyridyloxy is optionally substituted by one group selected from the group consisting of $C_{1-6}$ alkyl and halo-$C_{1-6}$ alkyl)}, halo-$C_{1-6}$ alkyl, $C_{3-8}$ cycloalkyl (the $C_{3-8}$ cycloalkyl is optionally substituted by one or two halogen atoms), phenyl (the phenyl is optionally substituted by one to three groups which are the same or different and are selected from group α4 of substituents), thienyl (the thienyl is optionally substituted by one $C_{1-6}$ alkyl), pyrazolyl (the pyrazolyl is optionally substituted by one $C_{1-6}$ alkyl), isoxazolyl, thiazoyl (the thiazoyl is optionally substituted by one or two groups which are the same or different and are selected from the group consisting of hydroxy, $C_{1-6}$ alkyl, and $C_{1-6}$ alkoxy), pyridyl (the pyridyl is optionally substituted by one group selected from the group consisting of carboxy, hydroxy, amino, a halogen atom, $C_{1-6}$ alkyl, halo-$C_{1-6}$ alkyl, $C_{3-8}$ cycloalkyl, $C_{1-6}$ alkoxy, halo-$C_{1-6}$ alkoxy, and $C_{1-6}$ alkylsulfonyl), pyrimidinyl (the pyrimidinyl is optionally substituted by one amino), quinolyl, $C_{1-6}$ alkoxy [the $C_{1-6}$ alkoxy is optionally substituted by one group selected from the group consisting of carboxy, hydroxy, carbamoyl, $C_{3-8}$ cycloalkyl (the $C_{3-8}$ cycloalkyl is optionally substituted by one $C_{1-6}$ alkyl), phenyl (the phenyl is optionally substituted by one group selected from the group consisting of hydroxy, a halogen atom, $C_{1-6}$ alkyl, halo-$C_{1-6}$ alkyl, $C_{1-6}$ alkoxy, halo-$C_{1-6}$ alkoxy, and di-$C_{1-6}$ alkylamino), pyridyl (the pyridyl is optionally substituted by one group selected from the group consisting of a halogen atom and $C_{1-6}$ alkyl), oxazolyl (the oxazolyl is optionally substituted by one or two $C_{1-6}$ alkyls), pyrazolyl (the pyrazolyl is optionally substituted by one or two $C_{1-6}$ alkyls), thiazoyl (the thiazoyl is optionally substituted by one $C_{1-6}$ alkyl), indazolyl (the indazolyl is optionally substituted by one $C_{1-6}$ alkyl), benzotriazolyl, imidazothiazoyl, and di-$C_{1-6}$ alkylamino], halo-$C_{1-6}$ alkoxy, $C_{2-6}$ alkenyloxy, $C_{3-8}$ cycloalkoxy, phenoxy (the phenoxy is optionally substituted by one or two groups which are the same or different and are selected from the group consisting of a halogen atom, $C_{1-6}$ alkyl, halo-$C_{1-6}$ alkyl, $C_{1-6}$ alkoxy, and halo-$C_{1-6}$ alkoxy), pyridyloxy (the pyridyloxy is optionally substituted by one group selected from the group consisting of a halogen atom, $C_{1-6}$ alkyl, halo-$C_{1-6}$ alkyl, and $C_{3-8}$ cycloalkyl), $C_{1-6}$ alkylsulfanyl, and $C_{1-6}$ alkylsulfonyl;

in the above case, preferred groups in group α4 of substituents are carboxy, cyano, hydroxy, sulfamoyl, a halogen atom, $C_{1-6}$ alkyl, halo-$C_{1-6}$ alkyl, $C_{3-8}$ cycloalkyl, phenyl, $C_{1-6}$ alkoxy, halo-$C_{1-6}$ alkoxy, $C_{1-6}$ alkylcarbonyl, di-$C_{1-6}$ alkylaminocarbonyl, $C_{1-6}$ alkylsulfonyl, mono-$C_{1-6}$ alkylaminosulfonyl (the $C_{1-6}$ alkyl of the mono-$C_{1-6}$ alkylaminosulfonyl is optionally substituted by one hydroxy), and di-$C_{1-6}$ alkylaminosulfonyl;

Preferred groups in group α5 of substituents are a halogen atom, $C_{1-6}$ alkyl, $C_{1-6}$ alkoxy [the $C_{1-6}$ alkoxy is optionally substituted by one group selected from the group consisting of $C_{3-8}$ cycloalkyl (the $C_{3-8}$ cycloalkyl is optionally substituted by one $C_{1-6}$ alkyl), phenyl (the phenyl is optionally substituted by one group selected from the group consisting of a halogen atom and $C_{1-6}$ alkyl)], halo-$C_{1-6}$ alkoxy, phenyl (the phenyl is optionally substituted by one group selected from group α6 of substituents), pyridyl, phenoxy [the phenoxy is optionally substituted by one or two groups which are the same or different and are selected from the group consisting of a halogen atom, cyano, $C_{1-6}$ alkyl, halo-$C_{1-6}$ alkyl, $C_{3-8}$ cycloalkyl, $C_{1-6}$ alkoxy (the $C_{1-6}$ alkoxy is optionally substituted by one phenyl), and halo-$C_{1-6}$ alkoxy], pyridyloxy (the pyridyloxy is optionally substituted by one $C_{1-6}$ alkyl), and phenylsulfanyl (the phenylsulfanyl is optionally substituted by one halogen atom);

in this case, preferred groups in group α6 of substituents are a halogen atom, $C_{1-6}$ alkyl, halo-$C_{1-6}$ alkyl, $C_{3-8}$ cycloalkyl, $C_{1-6}$ alkoxy, and halo-$C_{1-6}$ alkoxy.

A preferred case of $Y^4$ is $C_{1-3}$ alkanediyl, with a more preferred case of $Y^4$ being methanediyl;

a preferred case of $R^3$ is a hydrogen atom; and
a preferred case of $R^4$ is —COOH.
One preferred mode of the compounds of the present invention is compounds represented by the below-mentioned formula (I-c) or pharmaceutically acceptable salts thereof:

[Formula 6]

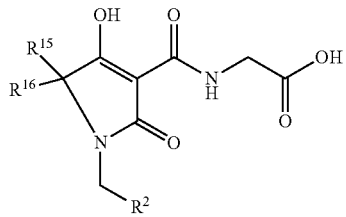

(I-c)

wherein preferred modes of $R^{15}$, $R^{16}$, and $R^2$ are as described above.

In this case, a more preferred mode is where $R^2$ is phenyl [the phenyl is substituted by one group selected from the group consisting of phenyl (the phenyl is optionally substituted by one group selected from the group consisting of a fluorine atom, a chlorine atom, and trifluoromethyl), $C_{1-6}$ alkoxy (the $C_{1-6}$ alkoxy is substituted by one $C_{3-8}$ cycloalkyl), and pyridyloxy (the pyridyloxy is optionally substituted by one trifluoromethyl)].

Another preferred mode of the compounds of the present invention is compounds represented by the below-mentioned formula (I-a) or pharmaceutically acceptable salts thereof.

[Formula 7]

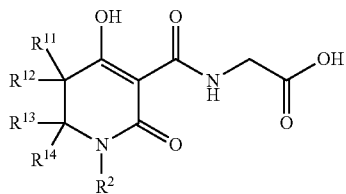

(I-a)

wherein preferred modes of $R^{11}$, $R^{12}$, $R^{13}$, $R^{14}$, and $R^2$ are as described above.

In this case, a more preferred mode is where $R^{11}$, $R^{12}$, $R^{13}$, and $R^{14}$ are all a hydrogen atom and where $R^2$ is $C_{3-8}$ cyclohexyl [the $C_{3-8}$ cycloalkyl is substituted by one $C_{1-6}$ alkyl (the $C_{1-6}$ alkyl is substituted by one phenyl)] or phenyl (the phenyl is substituted by one phenoxy).

Another preferred mode of the compound of the present invention is compounds represented by the below-mentioned formula (I-b) or pharmaceutically acceptable salts thereof.

[Formula 8]

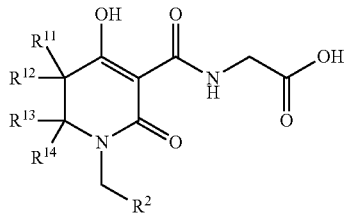

(I-b)

wherein preferred modes of $R^{11}$, $R^{12}$, $R^{13}$, $R^{14}$, and $R^2$ are as described above.

In this case, a more preferred mode is where $R^{11}$, $R^{12}$, $R^{13}$, and $R^{14}$ are all a hydrogen atom and where $R^2$ is phenyl {the phenyl is substituted by one group selected from the group consisting of phenyl [the phenyl is optionally substituted by one to three groups which are the same or different and are selected from the group consisting of carboxy, cyano, hydroxy, sulfamoyl, a halogen atom, $C_{1-6}$ alkyl, halo-$C_{1-6}$ alkyl, $C_{3-8}$ cycloalkyl, phenyl, $C_{1-6}$ alkoxy, halo-$C_{1-6}$ alkoxy, $C_{1-6}$ alkylcarbonyl, di-$C_{1-6}$ alkylaminocarbonyl, $C_{1-6}$ alkylsulfonyl, mono-$C_{1-6}$ alkylaminosulfonyl (the $C_{1-6}$ alkyl of the mono-$C_{1-6}$ alkylaminosulfonyl is optionally substituted by one hydroxy), and di-$C_{1-6}$ alkylaminosulfonyl], pyridyl (the pyridyl is optionally substituted by one group selected from the group consisting of carboxy, hydroxy, amino, a halogen atom, $C_{1-6}$ alkyl, halo-$C_{1-6}$ alkyl, $C_{3-8}$ cycloalkyl, $C_{1-6}$ alkoxy, halo-$C_{1-6}$ alkoxy, and $C_{1-6}$ alkylsulfonyl), $C_{1-6}$ alkoxy [the $C_{1-6}$ alkoxy is substituted by one group selected from the group consisting of $C_{3-8}$ cycloalkyl (the $C_{3-8}$ cycloalkyl is optionally substituted by one $C_{1-6}$ alkyl), phenyl (the phenyl is optionally substituted by one group selected from the group consisting of hydroxy, a halogen atom, $C_{1-6}$ alkyl, halo-$C_{1-6}$ alkyl, $C_{1-6}$ alkoxy, halo-$C_{1-6}$ alkoxy, and di-$C_{1-6}$ alkylamino), pyridyl (the pyridyl is optionally substituted by one group selected from the group consisting of a halogen atom and $C_{1-6}$ alkyl), oxazolyl (the oxazolyl is optionally substituted by one or two $C_{1-6}$ alkyls), pyrazolyl (the pyrazolyl is optionally substituted by one or two $C_{1-6}$ alkyls), thiazoyl (the thiazoyl is optionally substituted by one $C_{1-6}$ alkyl), indazolyl (the indazolyl is optionally substituted by one $C_{1-6}$ alkyl), benzotriazolyl, imidazothiazoyl, and di-$C_{1-6}$ alkylamino], halo-$C_{1-6}$ alkoxy, $C_{3-8}$ cycloalkoxy, phenoxy (the phenoxy is optionally substituted by one or two groups which are the same or different and are selected from the group consisting of a halogen atom, $C_{1-6}$ alkyl, halo-$C_{1-6}$ alkyl, $C_{1-6}$ alkoxy, and halo-$C_{1-6}$alkoxy), pyridyloxy (the pyridyloxy is optionally substituted by one group selected from the group consisting of a halogen atom, $C_{1-6}$ alkyl, halo-$C_{1-6}$ alkyl, and $C_{3-8}$ cycloalkyl), $C_{1-6}$ alkylsulfanyl, and $C_{1-6}$ alkylsulfonyl, and may further be substituted by one halogen atom};

pyridyl {the pyridyl is substituted by one group selected from the group consisting of $C_{1-6}$ alkoxy [the $C_{1-6}$alkoxy is substituted by one group selected from the group consisting of $C_{3-8}$ cycloalkyl (the $C_{3-8}$ cycloalkyl is optionally substituted by one $C_{1-6}$ alkyl) and phenyl (the phenyl is optionally substituted by one group selected from the group consisting of a halogen atom and $C_{1-6}$ alkyl)], halo-$C_{1-6}$ alkoxy, phenyl (the phenyl is optionally substituted by one group selected from the group consisting of a halogen atom, $C_{1-6}$ alkyl, halo-$C_{1-6}$ alkyl, $C_{3-8}$ cycloalkyl, $C_{1-6}$ alkoxy, and halo-$C_{1-6}$ alkoxy), pyridyl, phenoxy [the phenoxy is optionally substituted by one or two groups which are the same or different and are selected from the group consisting of a halogen atom, cyano, $C_{1-6}$ alkyl, halo-$C_{1-6}$ alkyl, $C_{3-8}$ cycloalkyl, $C_{1-6}$ alkoxy (the $C_{1-6}$ alkoxy is optionally substituted by one phenyl), and halo-$C_{1-6}$ alkoxy], and pyridyloxy (the pyridyloxy is optionally substituted by one $C_{1-6}$ alkyl) and may further be substituted by one group selected from the group consisting of a halogen atom and $C_{1-6}$ alkyl}; or pyrazinyl [the pyrazinyl is substituted by one group selected from the group consisting of $C_{1-6}$ alkoxy (the $C_{1-6}$ alkoxy is substituted by one $C_{3-8}$ cycloalkyl) and phenoxy (the phenoxy is optionally substituted by one group selected from the group consisting of a halogen atom, $C_{1-6}$ alkyl, and $C_{3-8}$ cycloalkyl)].

In the above case, an even more preferred mode is where $R^{11}$, $R^{12}$, $R^{13}$ and $R^{14}$ are all a hydrogen atom and where $R^2$ is phenyl [the phenyl is substituted by one group selected from the group consisting of phenoxy (the phenoxy is optionally substituted by one or two groups which are the same or different and are selected from the group consisting of a halogen atom, $C_{1-6}$ alkyl, $C_{1-6}$ alkoxy, and halo-$C_{1-6}$ alkoxy) and pyridyloxy (the pyridyloxy is optionally substituted by one group selected from the group consisting of a halogen atom, $C_{1-6}$ alkyl, halo-$C_{1-6}$ alkyl, and $C_{3-8}$ cycloalkyl) and may further be substituted by one halogen atom];

pyridyl {the pyridyl is substituted by one group selected from the group consisting of phenyl (the phenyl is optionally substituted by one group selected from the group consisting of a halogen atom, $C_{1-6}$ alkyl, halo-$C_{1-6}$ alkyl, $C_{3-8}$ cycloalkyl, $C_{1-6}$ alkoxy, and halo-$C_{1-6}$ alkoxy). pyridyl, phenoxy [the phenoxy is optionally substituted by one or two groups which are the same or different and are selected from the group consisting of a halogen atom, cyano, $C_{1-6}$ alkyl, halo-$C_{1-6}$ alkyl, $C_{3-8}$ cycloalkyl, $C_{1-6}$ alkoxy (the $C_{1-6}$ alkoxy is optionally substituted by one phenyl), and halo-$C_{1-6}$ alkoxy], and pyridyloxy (the pyridyloxy is optionally substituted by one $C_{1-6}$ alkyl) and may further be substituted by one group selected from the group consisting of a halogen atom and $C_{1-6}$ alkyl}; or pyrazinyl which is substituted by one phenoxy (the phenoxy is optionally substituted by one group selected from the group consisting of a halogen atom, $C_{1-6}$ alkyl, and $C_{3-8}$ cycloalkyl).

And other preferred modes of the compounds of the present invention are as described below (these modes also apply to the above-mentioned formulas (I-c), (I-a), and (I-b)).

One preferred case of $R^{11}$ is a hydrogen atom or $C_{1-4}$ alkyl, with a more preferred case of $R^{11}$ being a hydrogen atom or methyl.

One preferred case of $R^{12}$ is a hydrogen atom or $C_{1-4}$ alkyl, with a more preferred case of $R^{12}$ being a hydrogen atom or methyl.

Another preferred case of $R^{11}$ and $R^{12}$ is where the $R^{11}$ and $R^{12}$, together with the adjacent carbon atom, form $C_{3-8}$ cycloalkane or a 4- to 8-membered saturated heterocycle containing an oxygen atom, with a more preferred case of $R^{11}$ and $R^{12}$ being where the $R^{11}$ and $R^{12}$, together with the adjacent carbon atom, form $C_{3-6}$ cycloalkane.

One preferred case of $R^{13}$ is a hydrogen atom, $C_{1-4}$ alkyl, or halo-$C_{1-4}$ alkyl, with a more preferred case of $R^{13}$ being a hydrogen atom or methyl.

One preferred case of $R^{14}$ is a hydrogen atom or $C_{1-4}$ alkyl, with a more preferred case of $R^{14}$ being a hydrogen atom or methyl.

And another preferred case of $R^{13}$ and $R^{14}$ is where the $R^{13}$ and $R^{14}$, together with the adjacent carbon atom, form $C_{3-8}$ cycloalkane or a 4- to 8-membered saturated heterocycle containing an oxygen atom, with a more preferred case of $R^{13}$ and $R^{14}$ being where the $R^{13}$ and $R^{14}$, together with the adjacent carbon atom, form $C_{3-6}$ cycloalkane.

A preferred case of Y is a single bond or $C_{1-6}$ alkanediyl (one of the carbon atoms in the $C_{1-6}$ alkanediyl is optionally substituted by $C_{3-8}$ cycloalkane-1,1-diyl);

a more preferred case of Y is a single bond, methanediyl, ethane-1,1-diyl, propane-1,1-diyl, propane-2,2-diyl, cyclopropane-1,1-diyl, or ethane-1,2-diyl;

and an even more preferred case of Y is a single bond or methanediyl.

A preferred case of $R^2$ is $C_{3-8}$ cycloalkyl (the $C_{3-8}$ cycloalkyl is optionally substituted by one group selected from the group consisting of phenyl and benzyl), phenyl (the phenyl is optionally substituted by one to three groups which are the same or different and are selected from group α1 of substituents), naphthyl, indanyl, tetrahydronaphthyl, pyrazolyl [the pyrazolyl is substituted by one phenyl (the phenyl is optionally substituted by one $C_{1-6}$ alkyl) and may further be substituted by one $C_{1-6}$ alkyl], imidazolyl [the imidazolyl is substituted by one phenyl], isoxazolyl [the isoxazolyl is substituted by one phenyl (the phenyl is optionally substituted by one halogen atom)], oxazolyl (the oxazolyl is substituted by one phenyl and may further be substituted by one $C_{1-6}$ alkyl), thiazoyl (the thiazoyl is substituted by one phenyl), pyridyl [the pyridyl is substituted by one group selected from the group consisting of phenyl, phenoxy (the phenoxy is optionally substituted by one group selected from the group consisting of a halogen atom, cyano, $C_{1-6}$ alkyl, halo-$C_{1-6}$ alkyl, $C_{3-8}$ cycloalkyl, $C_{1-6}$ alkoxy, and halo-$C_{1-6}$ alkoxy), and phenylsulfanyl (the phenylsulfanyl is optionally substituted by one halogen atom)], pyrimidinyl (the pyrimidinyl is substituted by one group selected from the group consisting of cyclohexyl and phenyl), benzothiophenyl, quinolyl, or methylenedioxyphenyl (the methylenedioxyphenyl is optionally substituted by one or two fluorine atoms);

In this case, preferred groups in group α1 of substituents are a halogen atom, $C_{1-6}$ alkyl{the $C_{1-6}$ alkyl is optionally substituted by one group selected from the group consisting of $C_{3-8}$ cycloalkyl, phenyl, and $C_{1-6}$ alkoxy [the $C_{1-6}$ alkoxy is optionally substituted by one $C_{3-8}$ cycloalkyl (the $C_{3-8}$ cycloalkyl is optionally substituted by one $C_{1-6}$ alkyl)]}, halo-$C_{1-6}$ alkyl, $C_{3-8}$ cycloalkyl, phenyl (the phenyl is optionally substituted by one to three groups which are the same or different and are selected from group α2 of substituents), thienyl, pyrazolyl (the pyrazolyl is optionally substituted by one $C_{1-6}$ alkyl), isoxazolyl, thiazoyl (the thiazoyl is optionally substituted by one or two $C_{1-6}$ alkyls), pyridyl (the pyridyl is optionally substituted by one group selected from the group consisting of $C_{1-6}$ alkyl, halo-$C_{1-6}$ alkyl, $C_{1-6}$ alkoxy, and halo-$C_{1-6}$ alkoxy), quinolyl, $C_{1-6}$ alkoxy [the $C_{1-6}$ alkoxy is optionally substituted by one group selected from the group consisting of $C_{3-8}$ cycloalkyl and phenyl (the phenyl is optionally substituted by one group selected from the group consisting of a halogen atom and $C_{1-6}$ alkyl)], halo-$C_{1-6}$ alkoxy, $C_{2-6}$ alkenyloxy, $C_{3-8}$ cycloalkoxy, phenoxy (the phenoxy is optionally substituted by one group selected from the group consisting of a halogen atom, $C_{1-6}$ alkyl, halo-$C_{1-6}$ alkyl, $C_{1-6}$ alkoxy, and halo-$C_{1-6}$ alkoxy), pyridyloxy (the pyridyloxy is optionally substituted by one group selected from the group consisting of a halogen atom, $C_{1-6}$ alkyl, and halo-$C_{1-6}$ alkyl), and $C_{1-6}$ alkylsulfanyl;

in this case, preferred groups in group α2 of substituents are a halogen atom, cyano, hydroxy, $C_{1-6}$ alkyl, halo-$C_{1-6}$ alkyl, phenyl, $C_{1-6}$ alkoxy, halo-$C_{1-6}$ alkoxy, $C_{1-6}$ alkylcarbonyl, and di-$C_{1-6}$ alkylaminosulfonyl.

The compounds of the present invention are ones having partially saturated, nitrogen-containing heterocyclic structures and they may be in the form of their pharmaceutically acceptable salts (both types are hereinafter referred to as "compounds of the present invention" as appropriate).

Examples of the pharmaceutically acceptable salts include acid addition salts including mineral acid salts such as hydrochloride, hydrobromide, hydroiodide, phosphate, sulfate, and nitrate; sulfonic acid salts such as methanesulfonate, ethanesulfonate, benzenesulfonate, p-toluenesulfonate, and trifluoromethanesulfonate; organic acid salts such as oxalate, tartrate, citrate, maleate, succinate, acetate, trifluoroacetate, benzoate, mandelate, ascorbate, lactate, gluconate, and malate; amino acid salts such as glycine salt, lysine salt, arginine salt, ornithine salt, glutamate, and aspartate; inorganic salts such as lithium salt, sodium salt, potassium salt, calcium salt, and magnesium salt; and salts with organic bases such as ammonium salt, triethylamine salt, diisopropylamine salt, and cyclohexylamine salt. The term "salt(s)" as used herein encompass hydrate salt(s).

The compounds of the present invention have an asymmetric center or asymmetric centers in certain cases, where they give rise to a variety of optical isomers. Therefore, the compounds of the present invention can exist as separate optical isomers (R) and (S), or as a racemate or an (RS) mixture. In the case of compounds having two or more asymmetric centers, they give rise to diastereomers due to their respective optical isomerisms. The compounds of the present invention encompass mixtures that comprise all these types of isomer in any proportions. For example, diastereomers can be separated by methods well known to those skilled in the art, say, fractional crystallization, and optically active forms can be obtained by techniques in organic chemistry that are well known for this purpose. In addition, the compounds of the present invention sometimes give rise to geometrical isomers such as cis- and trans-forms. Further in addition, the compounds of the present invention may have tautomerism to give rise to a variety of tautomers. The compounds of the present invention encompass the-above mentioned isomers, as well as mixtures comprising those isomers in any proportions.

Furthermore, if the compounds of the present invention or salts thereof form hydrates or solvates, these are also included in the scope of the compounds of the present invention or salts thereof.

The compounds of the present invention may be administered either independently or together with pharmaceutically acceptable carriers or diluents.

In order to use the compounds of the present invention as medicines, they may assume any forms, i.e., as a solid composition, a liquid composition, or other compositions, with optimum forms being chosen depending on the need. The medicines of the present invention can be produced by incorporating pharmaceutically acceptable carriers for the compounds of the present invention. Stated specifically, commonly used excipients, fillers, binders, disintegrants, coating agents, sugar coating agents, pH modifiers, solubilizers, or aqueous or non-aqueous solvents, etc. may be added and commonly used pharmaceutical formulation techniques may be applied to prepare tablets, pills, capsules, granules, dusts, powders, liquids, emulsions, suspensions, injections, etc. Examples of the excipients and fillers include lactose, magnesium stearate, starch, talc, gelatin, agar, pectin, gum Arabic, olive oil, sesame oil, cocoa butter, ethylene glycol, and any other substances commonly used as excipients or fillers.

In addition, the compounds of the present invention may be formulated in pharmaceutical preparations by forming inclusion compounds with α, β or γ-cyclodextrin or methylated cyclodextrin, etc.

If the compounds of the present invention are used as PHD2 inhibitors and the like, they may be administered either orally or non-orally as such. Alternatively, the compounds of the present invention may be administered either orally or non-orally as agents that comprise them as the active ingredient. Example of non-oral administration include intravenous, transnasal, percutaneous, subcutaneous, intramuscular, and sublingual administrations.

The dosage of the compounds of the present invention varies with the subject of administration, the route of administration, the disease to be treated, the symptoms, and the like; for example, if they are to be administered orally to an adult patient presenting with anemia, a single dosage typically ranges from 0.1 mg to 1000 mg, preferably from 1 mg to 200 mg and this dosage is desirably administered once to three times a day, or once every two or three days.

It should be mentioned that the compounds of the present invention have properties desirable as pharmaceutical products. A property that can be given as an example is one that enables avoiding an excessive production of erythropoietin.

The PHD2 inhibitory effect of the compounds of the present invention can be evaluated by known techniques such as the methods described herein under the Tests.

Hereinafter, the processes for producing the compounds of the present invention are described in detail but are not particularly limited to the following illustrations. In addition, the solvents to be used in reactions may be of any types that will not interfere with the respective reactions and they are not particularly limited to the following description.

On the following pages, the processes for producing the compounds represented by formula (I) or (I')—hereinafter sometimes referred to as the compound (I) or the compound (I')—are described.

The compound (I) or (I') can be produced by methods known per se, for example, Processes 1 to 10 or modifications thereof. It should also be noted that in the respective production methods described below, the starting compounds may be used in the form of salts and examples of such salts include the aforementioned "pharmaceutically acceptable salts." In addition, the target compounds may also be obtained in the form of salts and examples of such salts include the aforementioned "pharmaceutically acceptable salts."

Further in addition, the obtained target compounds may be used in the next step in a yet-to-be purified state.

Compound (I-9) that belongs to the compound (I) or (I') of the present invention can be produced by, for example, the following Production Process 1 or modifications thereof.

Production Process 1:

[Formula 9]

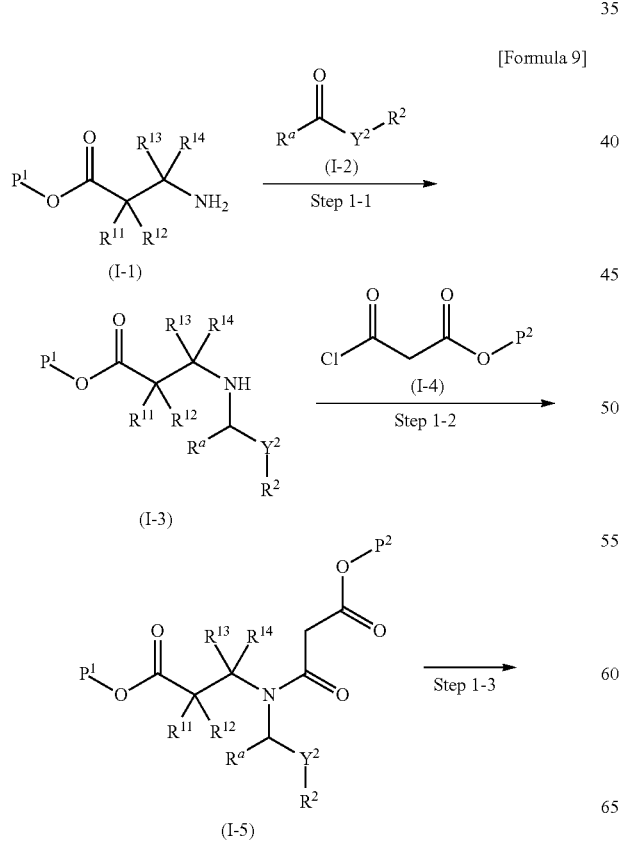

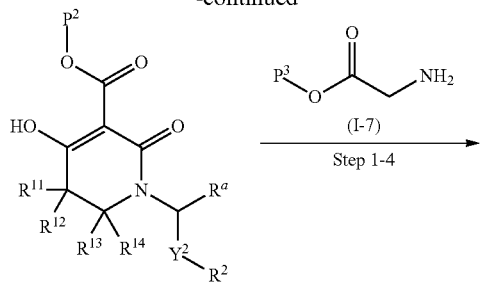

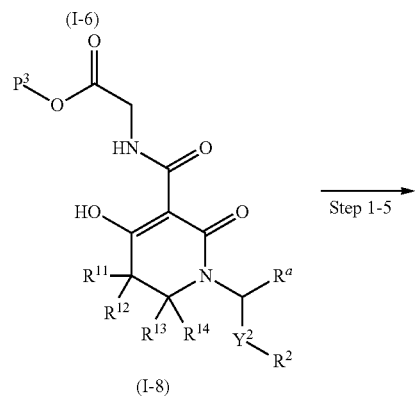

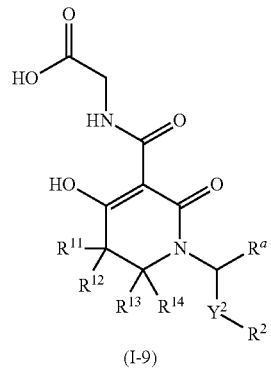

[wherein $R^{11}$, $R^{12}$, $R^{13}$, $R^{14}$, and $R^2$ have the same meanings as defined above; $R^a$ represents a hydrogen atom, methyl, or ethyl; $Y^2$ represents a single bond or $C_{1-5}$ alkanediyl; $P^1$, $P^2$, and $P^3$ represent common protective groups for carboxylic acids, as exemplified by the groups described in Protective Groups in Organic Synthesis (3$^{rd}$ Edition, 1999, edited by P. G. M. Wuts and T. W. Greene), etc. and specific examples are $C_{1-6}$ alkyl, benzyl, 4-methoxybenzyl, 2-(trimethylsilyl)ethyl, etc.]

[Step 1-1]

This step is a process for producing compound (I-3) by performing a reductive amination reaction using compound (I-1) and compound (I-2).

Reducing agents that can be used in the reaction include sodium triacetoxyborohydride, sodium borohydride, sodium cyanoborohydride, borane-2-picoline complex, etc. The amount of the reducing agents to be used ranges from one to three equivalents, preferably from one to two equivalents, relative to one equivalent of compound (I-1).

Solvents that can be used in the reaction include, for example, alcoholic solvents such as methanol and ethanol; ether-based solvents such as tetrahydrofuran and dioxane; halogenated hydrocarbon-based solvents such as methylene chloride and chloroform; aromatic hydrocarbon-based solvents such as toluene and xylene; and aprotic polar solvents such as N,N-dimethyformamide.

The reaction of interest can typically be carried out at between 0° C. and the reflux temperature.

The thus obtained compound (I-3) can be isolated and purified by known separation/purification means, such as concentrating, concentrating under reduced pressure, re-precipitation, extraction with solvent, crystallization, chromatography, etc.

[Step 1-2]

This step is a process for producing compound (I-5) by reacting compound (I-3) with compound (I-4) in the presence of a base.

Bases that can be used in the reaction typically include, for example, triethylamine, pyridine, etc. The amount of the bases to be used ranges from one to five equivalents, preferably from one to three equivalents, relative to one equivalent of compound (I-3).

Solvents that can be used in the reaction include, for example, ether-based solvents such as tetrahydrofuran and dioxane; halogenated hydrocarbon-based solvents such as methylene chloride and chloroform; aromatic hydrocarbon-based solvents such as toluene and xylene; and aprotic polar solvents such as ethyl acetate and N,N-dimethyformamide.

The reaction of interest can typically be carried out at between 0° C. and room temperature.

The thus obtained compound (I-5) can be isolated and purified by known separation/purification means, such as concentrating, concentrating under reduced pressure, re-precipitation, extraction with solvent, crystallization, chromatography, etc.

[Step 1-3]

This step is a process for producing compound (I-6) by cyclizing compound (I-5) in the presence of a base.

Bases that can be used in the reaction typically include, for example, sodium ethoxide, sodium methoxide, sodium hydride, potassium tert-butoxide, potassium carbonate, cesium carbonate, etc. The amount of the bases to be used typically ranges from one to five equivalents, preferably from two to three equivalents, relative to one equivalent of compound (I-5).

Solvents that can be used in the reaction include, for example, alcoholic solvents such as methanol, ethanol, and propanol; ether-based solvents such as tetrahydrofuran and dioxane; halogenated hydrocarbon-based solvents such as methylene chloride and chloroform; aromatic hydrocarbon-based solvents such as toluene and xylene; and aprotic polar solvents such as ethyl acetate and N,N-dimethyformamide.

The reaction of interest can typically be carried out at between 0° C. and the reflux temperature.

The thus obtained compound (I-6) can be isolated and purified by known separation/purification means, such as concentrating, concentrating under reduced pressure, re-precipitation, extraction with solvent, crystallization, chromatography, etc.

[Step 1-4]

This step is a process for producing compound (I-8) from compound (I-6) and compound (I-7).

Solvents that can be used in the reaction include, for example, ether-based solvents such as 1,2-dimethoxyethane, tetrahydrofuran, and dioxane; halogenated hydrocarbon-based solvents such as methylene chloride and chloroform; aromatic hydrocarbon-based solvents such as toluene and xylene; and aprotic polar solvents such as N,N-dimethyformamide.

The reaction of interest may employ a base as an additive. Examples of the base include triethylamine, N,N-diisopropylethylamine, etc.

This reaction can typically be carried out at between room temperature and the reflux temperature.

The thus obtained compound (I-8) can be isolated and purified by known separation/purification means, such as concentrating, concentrating under reduced pressure, re-precipitation, extraction with solvent, crystallization, chromatography, etc.

[Step 1-5]

This step is a process for producing compound (I-9) by deprotecting compound (I-8).

This reaction can be carried out by, for example, the method described in Protective Groups in Organic Synthesis ($3^{rd}$ Edition, 1999, edited by P. G. M. Wuts and T. W. Greene), etc. or modifications thereof. Specifically, if $P^3$ is tert-butyl, 4-methoxybenzyl or trimethylsilyl, compound (I-9) can be produced using a mineral acid such as hydrochloric acid or an organic acid such as acetic acid or trifluoroacetic acid in a solvent such as an ether-based solvent, say, tetrahydrofuran or dioxane, a halogenated hydrocarbon-based solvent, say, methylene chloride or chloroform, or an aromatic hydrocarbon-based solvent, say, toluene or xylene. If $P^3$ is benzyl or 4-methoxybenzyl, compound (I-9) can also be produced by hydrogenolysis in a solvent such as an alcoholic solvent, say, methanol or ethanol, an ether-based solvent, say, tetrahydrofuran or dioxane, a halogenated hydrocarbon-based solvent, say, methylene chloride or chloroform, or an aromatic hydrocarbon-based solvent, say, toluene or xylene in the presence of a catalyst such as palladium-carbon. If $P^3$ is 2-(trimethylsilyl)ethyl, trimethylsilyl, or tert-butyldimethylsilyl, it is also possible to produce compound (I-9) by treatment with potassium fluoride, tetrabutylammonium fluoride, etc. If $P^3$ is methyl, ethyl, or n-propyl, the solvent to be used may be an alcoholic solvent such as methanol or ethanol, an ether-based solvent such as tetrahydrofuran or dioxane, an aromatic hydrocarbon-based solvent such as toluene or xylene, an aprotic polar solvent such as acetonitrile or N,N-dimethylformamide, water, or the like; these solvents may be used in admixture at appropriate proportions and the treatment with a base such as lithium hydroxide, sodium hydroxide, potassium hydroxide, potassium carbonate, cesium carbonate, etc., can also produce compound (I-9).

The reaction of interest can typically be carried out at between room temperature and the reflux temperature.

The thus obtained compound (I-9) can be isolated and purified by known separation/purification means, such as concentrating, concentrating under reduced pressure, re-precipitation, extraction with solvent, crystallization, chromatography, etc.

Compound (II-6) that belongs to the compound (I) or (I') of the present invention can be produced by, for example, the following Production Process 2 or modifications thereof.

Production Process 2:

[Formula 10]

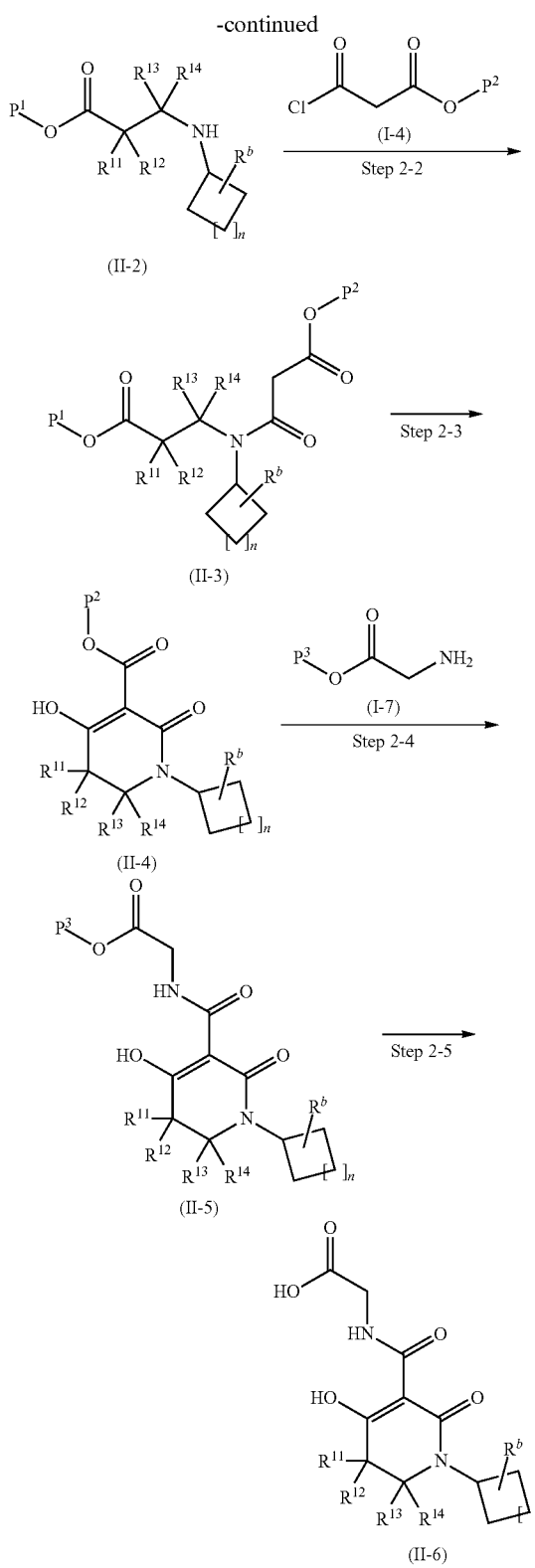

The reaction of interest can be carried out by a modification of the method described in Step 1-1 of Production Process 1.

The thus obtained compound (II-2) can be isolated and purified by known separation/purification means, such as concentrating, concentrating under reduced pressure, re-precipitation, extraction with solvent, crystallization, chromatography, etc.

[Step 2-2]

This step is a process for producing compound (II-3) from compound (II-2) and compound (I-4).

The reaction of interest can be carried out by a modification of the method described in Step 1-2 of Production Process 1.

The thus obtained compound (II-3) can be isolated and purified by known separation/purification means, such as concentrating, concentrating under reduced pressure, re-precipitation, extraction with solvent, crystallization, chromatography, etc.

[Step 2-3]

This step is a process for producing compound (II-4) from compound (II-3).

The reaction of interest can be carried out by a modification of the method described in Step 1-3 of Production Process 1.

The thus obtained compound (II-4) can be isolated and purified by known separation/purification means, such as concentrating, concentrating under reduced pressure, re-precipitation, extraction with solvent, crystallization, chromatography, etc.

[Step 2-4]

This step is a process for producing compound (II-5) from compound (II-4) and compound (I-7).

The reaction of interest can be carried out by a modification of the method described in Step 1-4 of Production Process 1.

The thus obtained compound (II-5) can be isolated and purified by known separation/purification means, such as concentrating, concentrating under reduced pressure, re-precipitation, extraction with solvent, crystallization, chromatography, etc.

[Step 2-5]

This step is a process for producing compound (II-6) from compound (II-5).

The reaction of interest can be carried out by a modification of the method described in Step 1-5 of Production Process 1.

The thus obtained compound (II-5) can be isolated and purified by known separation/purification means, such as concentrating, concentrating under reduced pressure, re-precipitation, extraction with solvent, crystallization, chromatography, etc.

Compound (III-6) that belongs to the compound (I) or (I') of the present invention can be produced by, for example, the following Production Process 3 or modifications thereof.

Production Process 3:

[wherein $R^{11}$, $R^{12}$, $R^{13}$, $R^{14}$, $P^1$, $P^2$, and $P^3$ have the same meanings as defined above; $R^b$ represents a hydrogen atom, phenyl, or benzyl; n represents an integer of 0 to 5].

[Step 2-1]

This step is a process for producing compound (II-2) from compound (I-1) and compound (II-1).

[Formula 11]

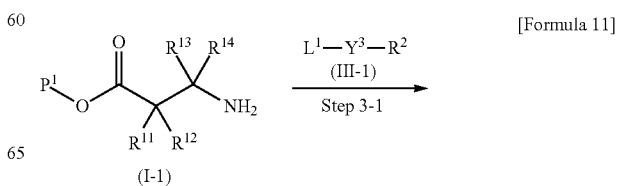

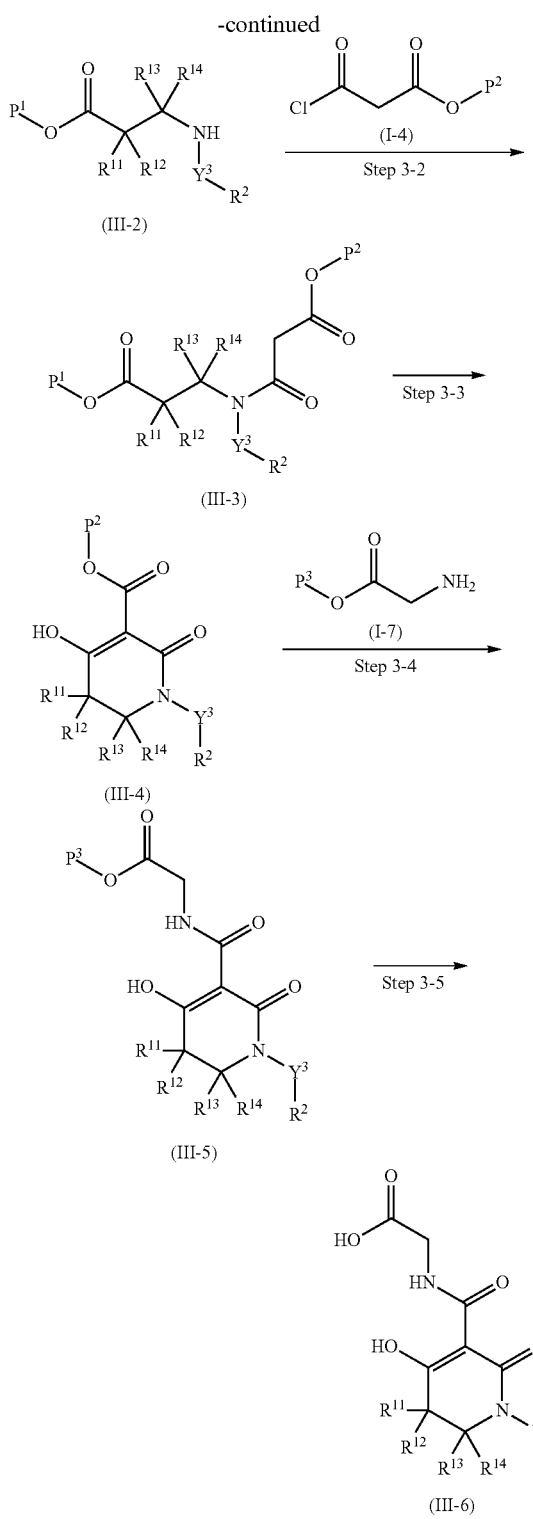

[wherein $R^{11}$, $R^{12}$, $R^{13}$, $R^{14}$, $R^2$, $P^1$, $P^2$, and $P^3$ have the same meanings as defined above; $L^1$ represents a common leaving group, say, a chlorine atom, a bromine atom, an iodine atom, methanesulfonyloxy, p-toluenesulfonyloxy, etc.; $Y^3$ represents $C_{1-6}$ alkanediyl].

[Step 3-1]

This step is a process for producing compound (III-2) by reacting compound (I-1) with compound (III-1) in the presence of a base.

Bases that can be used in the reaction include, for example, sodium hydroxide, potassium tert-butoxide, triethylamine, pyridine, cesium carbonate, potassium carbonate, sodium carbonate, sodium hydrogencarbonate, etc. The amount of the bases to be used ranges from one to three equivalents relative to one equivalent of compound (I-1).

Solvents that can be used in the reaction include, for example, alcoholic solvents such as methanol and ethanol; ether-based solvents such as tetrahydrofuran and dioxane; halogenated hydrocarbon-based solvents such as methylene chloride and chloroform; aromatic hydrocarbon-based solvents such as toluene and xylene; and aprotic polar solvents such as acetonitrile and N,N-dimethylformamide.

The reaction of interest can typically be carried out at between 0° C. and the reflux temperature.

The thus obtained compound (III-2) can be isolated and purified by known separation/purification means, such as concentrating, concentrating under reduced pressure, re-precipitation, extraction with solvent, crystallization, chromatography, etc.

[Step 3-2]

This step is a process for producing compound (III-3) from compound (III-2) and compound (I-4).

The reaction of interest can be carried out by a modification of the method described in Step 1-2 of Production Process 1.

The thus obtained compound (III-3) can be isolated and purified by known separation/purification means, such as concentrating, concentrating under reduced pressure, re-precipitation, extraction with solvent, crystallization, chromatography, etc.

[Step 3-3]

This step is a process for producing compound (III-4) from compound (III-3).

The reaction of interest can be carried out by a modification of the method described in Step 1-3 of Production Process 1.

The thus obtained compound (III-4) can be isolated and purified by known separation/purification means, such as concentrating, concentrating under reduced pressure, re-precipitation, extraction with solvent, crystallization, chromatography, etc.

[Step 3-4]

This step is a process for producing compound (III-5) from compound (III-4) and compound (I-7).

The reaction of interest can be carried out by a modification of the method described in Step 1-4 of Production Process 1.

The thus obtained compound (III-5) can be isolated and purified by known separation/purification means, such as concentrating, concentrating under reduced pressure, re-precipitation, extraction with solvent, crystallization, chromatography, etc.

[Step 3-5]

This step is a process for producing compound (III-6) from compound (III-5).

The reaction of interest can be carried out by a modification of the method described in Step 1-5 of Production Process 1.

The thus obtained compound (III-6) can be isolated and purified by known separation/purification means, such as concentrating, concentrating under reduced pressure, re-precipitation, extraction with solvent, crystallization, chromatography, etc.

Compound (IV-7) that belongs to the compound (I) or (I') of the present invention can be produced by, for example, the following Production Process 4 or modifications thereof.

Production Process 4:

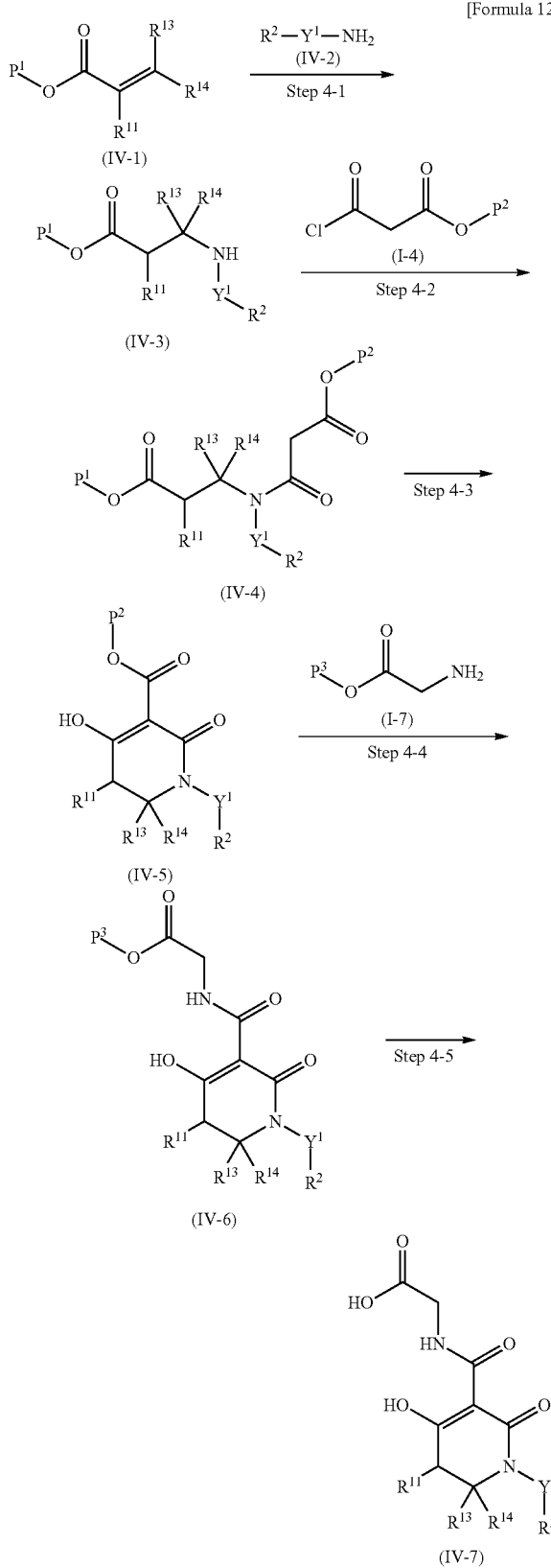

[wherein $R^{11}$, $R^{13}$, $R^{14}$, $R^2$, $P^1$, $P^2$, and $P^3$ have the same meanings as defined above; $Y^1$ represents a single bond or $C_{1-6}$ alkanediyl (one of the carbon atoms in the $C_{1-6}$ alkanediyl is optionally substituted by $C_{3-6}$ cycloalkane-1,1-diyl)].

[Step 4-1]

This step is a process for producing compound (IV-3) by reacting compound (IV-1) with compound (IV-2).

Solvents that can be used in the reaction include alcoholic solvents such as methanol and ethanol; ether-based solvents such as tetrahydrofuran and dioxane; halogenated hydrocarbon-based solvents such as methylene chloride and chloroform; aromatic hydrocarbon-based solvents such as toluene and xylene; aprotic polar solvents such as acetonitrile and N,N-dimethyformamide; water, etc; these solvents may be used in admixture at appropriate proportions.

In the reaction of interest, a base or an acid may be used as an additive. Examples of the base include sodium hydride, potassium tert-butoxide, triethylamine, pyridine, cesium carbonate, potassium carbonate, sodium carbonate, sodium hydrogencarbonate, etc. Examples of the acid include acetic acid, hydrochloric acid, sulfuric acid, etc.

The reaction of interest can typically be carried out at between 0° C. and the reflux temperature; it may even be carried out under irradiation with microwaves.

The thus obtained compound (IV-3) can be isolated and purified by known separation/purification means, such as concentrating, concentrating under reduced pressure, re-precipitation, extraction with solvent, crystallization, chromatography, etc.

[Step 4-2]

This step is a process for producing compound (IV-4) from compound (IV-3) and compound (I-4).

The reaction of interest may be carried out by a modification of the method described in Step 1-2 of Production Process 1.

The thus obtained compound (IV-4) can be isolated and purified by known separation/purification means, such as concentrating, concentrating under reduced pressure, re-precipitation, extraction with solvent, crystallization, chromatography, etc.

[Step 4-3]

This step is a process for producing compound (IV-5) from compound (IV-4).

The reaction of interest may be carried out by a modification of the method described in Step 1-3 of Production Process 1.

The thus obtained compound (IV-5) can be isolated and purified by known separation/purification means, such as concentrating, concentrating under reduced pressure, re-precipitation, extraction with solvent, crystallization, chromatography, etc.

[Step 4-4]

This step is a process for producing compound (IV-6) from compound (IV-5) and compound (I-7).

The reaction of interest may be carried out by a modification of the method described in Step 1-4 of Production Process 1.

The thus obtained compound (IV-6) can be isolated and purified by known separation/purification means, such as concentrating, concentrating under reduced pressure, re-precipitation, extraction with solvent, crystallization, chromatography, etc.

[Step 4-5]

This step is a process for producing compound (IV-7) from compound (IV-6).

The reaction of interest may be carried out by a modification of the method described in Step 1-5 of Production Process 1.

The thus obtained compound (IV-7) can be isolated and purified by known separation/purification means, such as concentrating, concentrating under reduced pressure, re-precipitation, extraction with solvent, crystallization, chromatography, etc.

Compound (V-4) that belongs to the compound (I) or (I') of the present invention can be produced by, for example, the following Production Process 5 or modifications thereof.

Production Process 5:

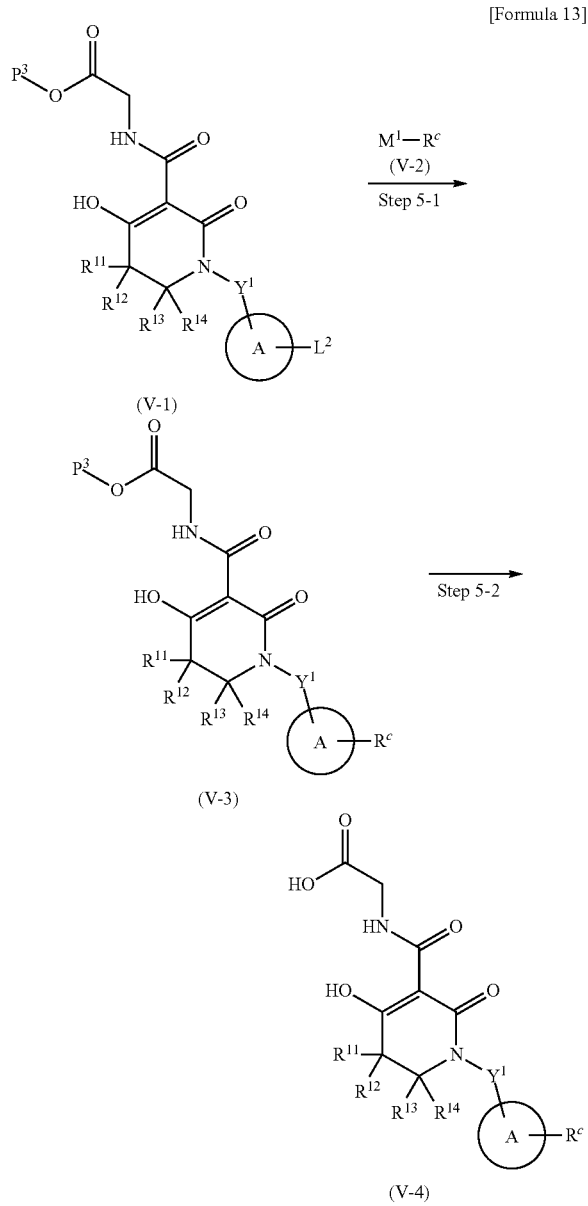

[Formula 13]

[wherein $R^{11}$, $R^{12}$, $R^{13}$, $R^{14}$, $Y^1$ and $P^3$ have the same meanings as defined above; ring A represents phenyl (the phenyl is optionally substituted by one to four groups which are the same or different and are selected from the group consisting of a halogen atom, $C_{1-6}$ alkyl, halo-$C_{1-6}$ alkyl, $C_{3-8}$ cycloalkyl, $C_{1-6}$ alkoxy, halo-$C_{1-6}$ alkoxy, and $C_{3-8}$ cycloalkoxy) or pyridyl (the pyridyl is optionally substituted by one to three groups which are the same or different and are selected from the group consisting of a halogen atom, $C_{1-6}$ alkyl, $C_{1-6}$ alkoxy, and halo-$C_{1-6}$ alkoxy); $L^2$ represents a common leaving group, say, a fluorine atom, a chlorine atom, a bromine atom, an iodine atom, trifluoromethanesulfonyloxy, etc.; $M^1$-$R^c$ represents a metal-containing organometallic compound, wherein $M^1$ represents boronic acid, a boronic acid ester, magnesium bromide, magnesium chloride, etc. and $R^c$ represents $C_{1-6}$ alkyl, halo-$C_{1-6}$ alkyl, $C_{3-8}$ cycloalkyl, phenyl (the phenyl is optionally substituted by one to three groups which are the same or different and are selected from group α2 of substituents), thienyl, pyrazolyl (the pyrazolyl is optionally substituted by one $C_{1-6}$ alkyl), isoxazolyl, thiazoyl (the thiazoyl is optionally substituted by one or two $C_{1-6}$ alkyls), pyridyl (the pyridyl is optionally substituted by one group selected from the group consisting of $C_{1-6}$ alkyl, halo-$C_{1-6}$ alkyl. $C_{1-6}$ alkoxy, and halo-$C_{1-6}$ alkoxy), quinolyl, etc.; compound (V-1) can be produced by implementing the procedures of the steps in Production Processes 1 to 4].

[Step 5-1]

This step is a process for producing compound (V-3) by performing a coupling reaction using compound (V-1) and organometallic compound (V-2).

If $M^1$ is boronic acid or a boronic acid ester, the reaction of interest is the so-called Suzuki-Miyaura coupling reaction and can be carried out by documented processes (Tetrahedron Letters, 1979, 20, 3437-3440; Chemical reviews, 1995, 95, 2457-2483) or modifications thereof in the presence of a palladium catalyst and a base. If $M^1$ is a Grignard reagent such as magnesium bromide or magnesium chloride, compound (V-3) can be produced in the presence of a palladium catalyst.

In this case, a metallic reagent such as indium chloride may be added as appropriate. The amount of compound (V-2) to be used in the step under consideration ranges from one to five equivalents, preferably from one to three equivalents, relative to one equivalent of compound (V-1).

Palladium catalysts that may be used in the coupling reaction include those which are known to skilled artisans, as exemplified by tetrakis(triphenylphosphine)palladium(0), bis(dibenzylideneacetone)palladium(0), bis(tri-tert-butylphosphine)palladium(0), bis(triphenylphosphine)palladium(II) dichloride, bis(triphenylphosphine)palladium(II) acetate and [1,1'-bis(diphenylphosphino)ferrocene]palladium(II) dichloride dichloromethane complex (1:1), etc. If desired, a palladium(0) catalyst, as generated in the system using palladium(II) acetate and a phosphine reagent such as triphenylphosphine or tri(2-methylphenyl)phosphine in the presence of a base, may be used for the reaction. The amount of the palladium catalyst to be used typically varies from 0.01 to 0.5 equivalents, preferably from 0.05 to 0.3 equivalents, relative to one equivalent of compound (V-1).

Bases that can be used include potassium carbonate, cesium carbonate, sodium carbonate, sodium hydrogencarbonate, tripotassium phosphate, potassium fluoride, cesium fluoride, triethylamine, etc. The amount of the bases to be used typically varies from one to five equivalents, preferably from one to three equivalents, relative to one equivalent of compound (V-1).

Solvents that can be used in the reaction include alcoholic solvents such as methanol, ethanol, and ethylene glycol; ether-based solvents such as tetrahydrofuran, dioxane, and 1,2-dimethoxyethane; aromatic hydrocarbon-based solvents such as toluene and xylene; aprotic polar solvents such as acetonitrile and N,N-dimethyformamide; water, etc; these solvents may be used in admixture at appropriate proportions.

In the reaction of interest, a copper compound may be used as an additive. Examples of the copper compound include copper(I) iodide, copper(II) acetate, etc.

The reaction of interest can typically be carried out at between room temperature and 180° C.; it may even be carried out under irradiation with microwaves.

The thus obtained compound (V-3) can be isolated and purified by known separation/purification means, such as concentrating, concentrating under reduced pressure, re-precipitation, extraction with solvent, crystallization, chromatography, etc.

[Step 5-2]

This step is a process for producing compound (V-4) from compound (V-3).

The reaction of interest can be carried out by a modification of the method described in Step 1-5 of Production Process 1.

The thus obtained compound (V-4) can be isolated and purified by known separation/purification means, such as concentrating, concentrating under reduced pressure, re-precipitation, extraction with solvent, crystallization, chromatography, etc.

Compound (VI-2) that belongs to the compound (I) or (I') of the present invention can be produced by, for example, the following Production Process 6 or modifications thereof Production Process 6:

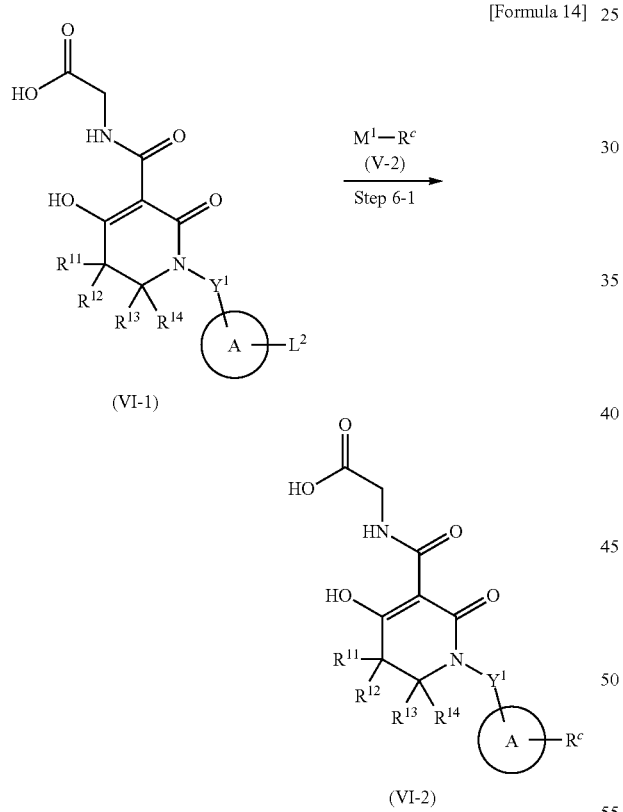

[Formula 14]

[wherein $R^{11}$, $R^{12}$, $R^{13}$, $R^{14}$, $Y^1$, ring A, $L^2$, $M^1$, and $R^c$ have the same meanings as defined above, and compound (VI-1) can be produced by implementing the procedures of the steps in Production Processes 1 to 4].

[Step 6-1]

This step is a process for producing compound (VI-2) from compound (VI-1) and organometallic compound (V-2).

The reaction of interest can be carried out by a modification of the method described in Step 5-1 of Production Process 5.

The thus obtained compound (VI-2) can be isolated and purified by known separation/purification means, such as concentrating, concentrating under reduced pressure, re-precipitation, extraction with solvent, crystallization, chromatography, etc.

Compound (VII-6) that belongs to the compound (I') of the present invention can be produced by, for example, the following Production Process 7 or modifications thereof.

Production Process 7:

[Formula 15]

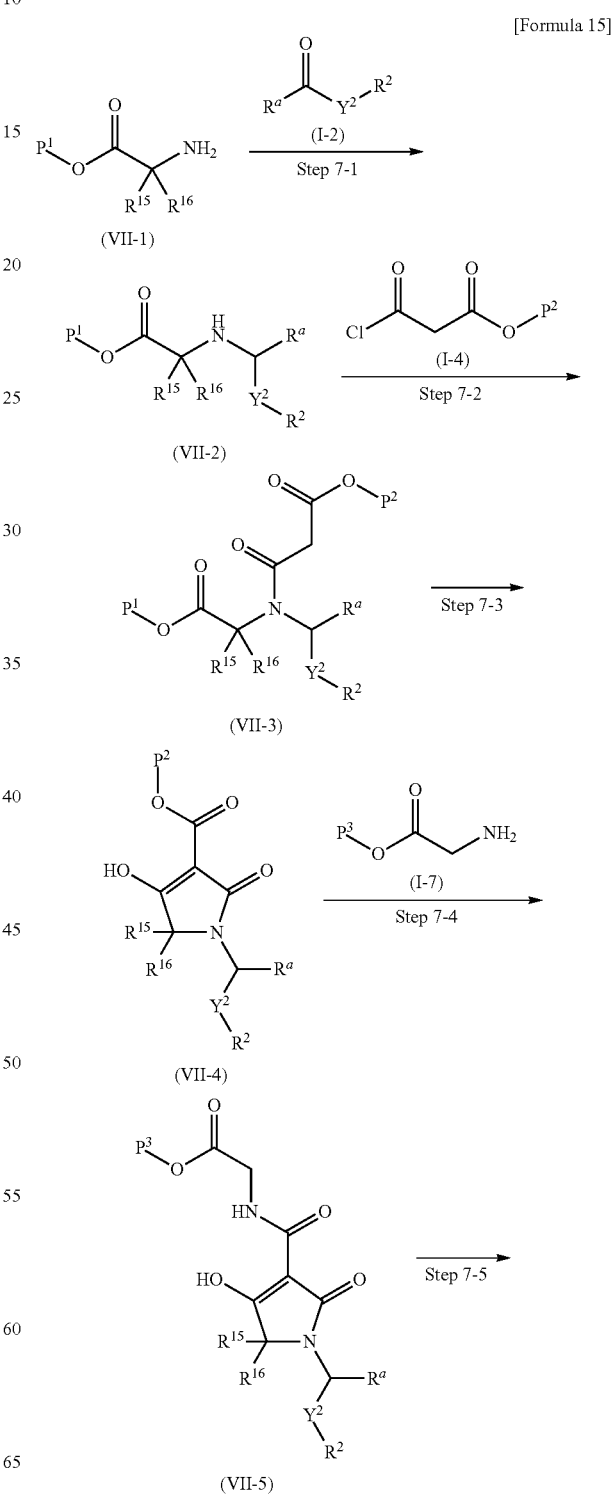

-continued

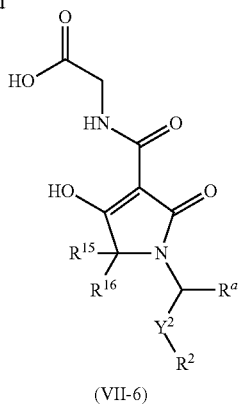

(VII-6)

[wherein $R^{15}$, $R^{16}$, $R^a$, $R^2$, $Y^2$, $P^1$, $P^2$, and $P^3$ have the same meanings as defined above].

[Step 7-1]

This step is a process for producing compound (VII-2) from compound (VII-1) and compound (I-2).

The reaction of interest can be carried out by a modification of the method described in Step 1-1 of Production Process 1.

The thus obtained compound (VII-2) can be isolated and purified by known separation/purification means, such as concentrating, concentrating under reduced pressure, re-precipitation, extraction with solvent, crystallization, chromatography, etc.

[Step 7-2]

This step is a process for producing compound (VII-3) from compound (VII-2) and compound (I-4).

The reaction of interest can be carried out by a modification of the method described in Step 1-2 of Production Process 1.

The thus obtained compound (VII-3) can be isolated and purified by known separation/purification means, such as concentrating, concentrating under reduced pressure, re-precipitation, extraction with solvent, crystallization, chromatography, etc.

[Step 7-3]

This step is a process for producing compound (VII-4) from compound (VII-3).

The reaction of interest can be carried out by a modification of the method described in Step 1-3 of Production Process 1.

The thus obtained compound (VII-4) can be isolated and purified by known separation/purification means, such as concentrating, concentrating under reduced pressure, re-precipitation, extraction with solvent, crystallization, chromatography, etc.

[Step 7-4]

This step is a process for producing compound (VII-5) from compound (VII-4) and compound (I-7).

The reaction of interest can be carried out by a modification of the method described in Step 1-4 of Production Process 1.

The thus obtained compound (VII-5) can be isolated and purified by known separation/purification means, such as concentrating, concentrating under reduced pressure, re-precipitation, extraction with solvent, crystallization, chromatography, etc.

[Step 7-5]

This step is a process for producing compound (VII-6) from compound (VII-5).

The reaction of interest can be carried out by a modification of the method described in Step 1-5 of Production Process 1.

The thus obtained compound (VII-6) can be isolated and purified by known separation/purification means, such as concentrating, concentrating under reduced pressure, re-precipitation, extraction with solvent, crystallization, chromatography, etc.

Compound (VIII-4) that belongs to the compound (I') of the present invention can be produced by, for example, the following Production Process 8 or modifications thereof.

Production Process 8:

[Formula 16]

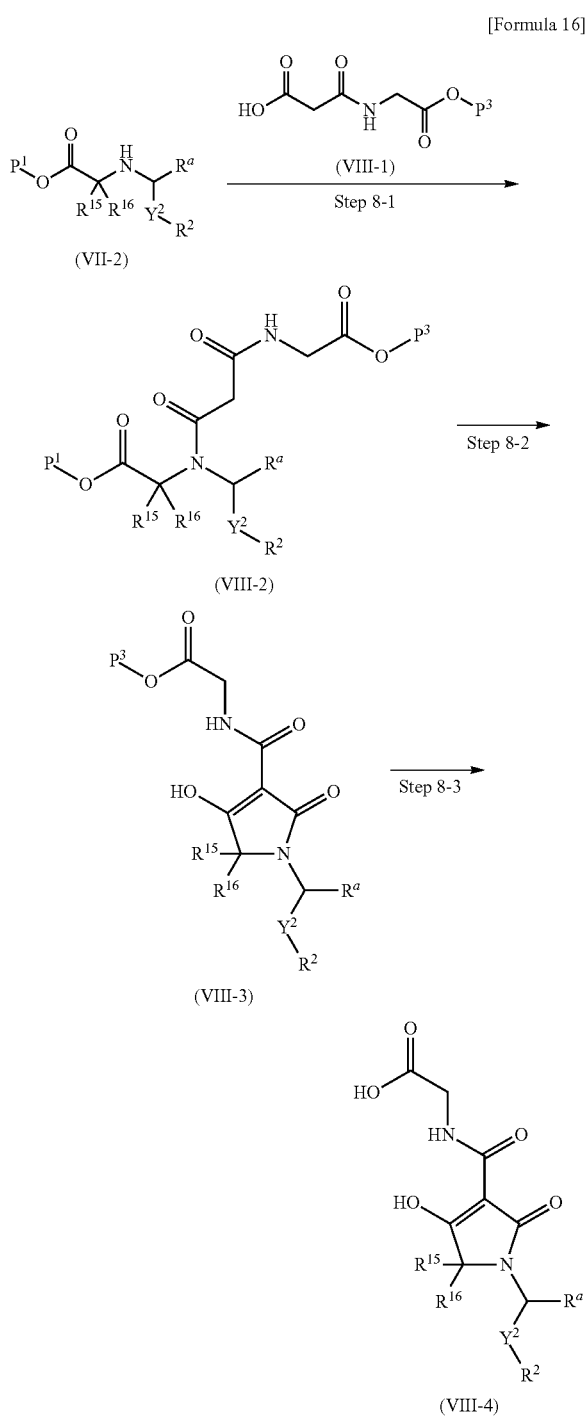

[wherein $R^{15}$, $R^{16}$, $R^a$, $R^2$, $Y^2$, $P^1$, and $P^3$ have the same meanings as defined above].

[Step 8-1]

This step is a process for producing compound (VIII-2) by performing a condensation reaction using compound (VII-2) and compound (VIII-1).

Reagents that can be used in the condensation reaction include the combination of 1-(3-dimethylaminopropyl)-3-ethylcarbodiimide and 1-hydroxybenzotriazole, as well as 1,1'-carbonyldiimidazole, propylphosphonic acid anhydride (cyclic trimer), etc. The amount of the condensation agent to be used varies from one to three equivalents, preferably from one to two equivalents, relative to one equivalent of compound (VII-2).

In the reaction of interest, a base can be used as an additive. Examples of the base include triethylamine and so forth.

Solvents that can be used in the reaction include, for example, alcoholic solvents such as methanol and ethanol; ether-based solvents such as tetrahydrofuran and dioxane; halogenated hydrocarbon-based solvents such as methylene chloride and chloroform; aromatic hydrocarbon-based solvents such as toluene and xylene; and aprotic polar solvents such as N,N-dimethylformamide.

The reaction of interest can typically be carried out at between 0° C. and the reflux temperature.

The thus obtained compound (VIII-2) can be isolated and purified by known separation/purification means, such as concentrating, concentrating under reduced pressure, re-precipitation, extraction with solvent, crystallization, chromatography, etc.

[Step 8-2]

This step is a process for producing compound (VIII-3) from compound (VIII-2).

The reaction of interest can be carried out by a modification of the method described in Step 1-3 of Production Process 1.

The thus obtained compound (VIII-3) can be isolated and purified by known separation/purification means, such as concentrating, concentrating under reduced pressure, re-precipitation, extraction with solvent, crystallization, chromatography, etc.

[Step 8-3]

This step is a process for producing compound (VIII-4) from compound (VIII-3).

The reaction of interest can be carried out by a modification of the method described in Step 1-5 of Production Process 1.

The thus obtained compound (VIII-4) can be isolated and purified by known separation/purification means, such as concentrating, concentrating under reduced pressure, re-precipitation, extraction with solvent, crystallization, chromatography, etc.

Compound (IX-4) that belongs to the compound (I) or (I') of the present invention can be produced by, for example, the following Production Process 9 or modifications thereof.

Production Process 9:

[Formula 17]

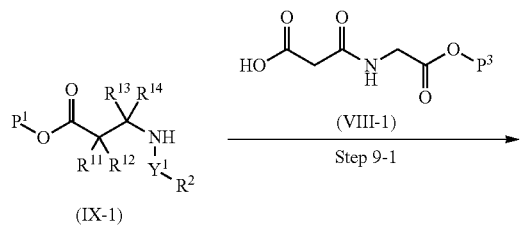

[wherein $R^{11}$, $R^{12}$, $R^{13}$, $R^{14}$, $R^2$, $Y^1$, $P^1$, and $P^3$ have the same meanings as defined above, and compound (IX-1) can be produced by implementing the procedures of Production Processes 1 to 4].

[Step 9-1]

This step is a process for producing compound (IX-2) by performing a condensation reaction using compound (IX-1) and compound (VIII-1).

The reaction of interest can be carried out by a modification of the method described in Step 8-1 of Production Process 8.

The thus obtained compound (IX-2) can be isolated and purified by known separation/purification means, such as concentrating, concentrating under reduced pressure, re-precipitation, extraction with solvent, crystallization, chromatography, etc.

[Step 9-2]

This step is a process for producing compound (IX-3) from compound (IX-2).

The reaction of interest can be carried out by a modification of the method described in Step 1-3 of Production Process 1.

The thus obtained compound (IX-3) can be isolated and purified by known separation/purification means, such as concentrating, concentrating under reduced pressure, re-precipitation, extraction with solvent, crystallization, chromatography, etc.

[Step 9-3]

This step is a process for producing compound (IX-4) from compound (IX-3).

The reaction of interest can be carried out by a modification of the method described in Step 1-5 of Production Process 1.

The thus obtained compound (IX-4) can be isolated and purified by known separation/purification means, such as concentrating, concentrating under reduced pressure, re-precipitation, extraction with solvent, crystallization, chromatography, etc.

Compound (X-4) that belongs to the compound (I') of the present invention can be produced by, for example, the following Production Process 10 or modifications thereof.

Production Process 10:

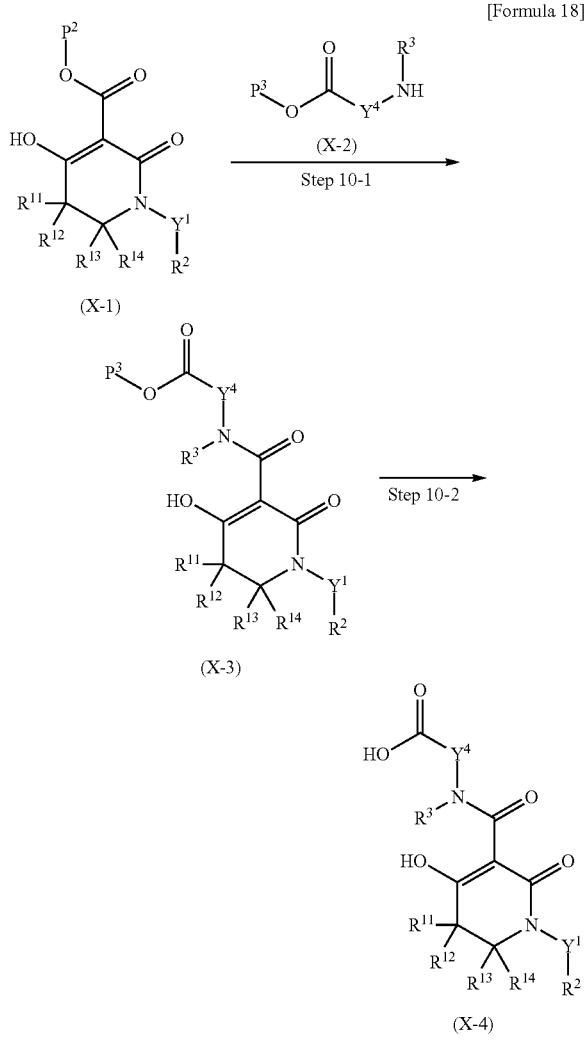

[Formula 18]

[wherein $R^{11}$, $R^{12}$, $R^{13}$, $R^{14}$, $R^2$, $R^3$, $Y^1$, $Y^4$, $P^2$, and $P^3$ have the same meanings as defined above, and compound (X-1) can be produced by implementing the procedures of Production Processes 1 to 4].

[Step 10-1]

This step is a process for producing compound (X-3) from compound (X-1) and compound (X-2).

The reaction of interest can be carried out by a modification of the method described in Step 1-4 of Production Process 0.1.

The thus obtained compound (X-3) can be isolated and purified by known separation/purification means, such as concentrating, concentrating under reduced pressure, re-precipitation, extraction with solvent, crystallization, chromatography, etc.

[Step 10-2]

This step is a process for producing compound (X-4) from compound (X-3).

The reaction of interest can be carried out by a modification of the method described in Step 1-5 of Production Process 1.

The thus obtained compound (X-4) can be isolated and purified by known separation/purification means, such as concentrating, concentrating under reduced pressure, re-precipitation, extraction with solvent, crystallization, chromatography, etc.

EXAMPLES

The present invention is described in greater detail by means of the following Reference Examples, Working Examples, and Tests but it should be understood that these are by no means intended to limit the present invention and may be changed to the extent that will not depart from the scope of the present invention.

The abbreviations used herein denote the following meanings.

s: singlet
d: doublet
t: triplet
q: quartet
quin: quintet
sept: septet
dd: double doublet
dt: double triplet
td: triplet doublet
m: multiplet
br: broad
J: coupling constant
Hz: Hertz
CHLOROFORM-d: deuterated chloroform
DMSO-$d_6$: deuterated dimethyl sulfoxide
METHANOL-$d_4$: deuterated methanol Proton nuclear magnetic resonance ($^1$H-NMR) spectrometry was implemented by the following Fourier transform NMR spectrometers.

200 MHz: Gemini 2000 (Agilent Technologies)
300 MHz: Inova 300 (Agilent Technologies)
600 MHz: JNM-ECA 600 (JEOL)

For analysis, ACD/SpecManager ver. 12.01 (product name), ACD/Spectrus Processor™, etc. were used. Very mild peaks derived from the protons of a hydroxy group, an amino group and other species are not reported.

Mass spectrometry (MS) was implemented by the following spectrometers.

Platform LC (Waters)
LCMS-2010EV (Shimadzu)
LCMS-IT-TOF (Shimadzu)
GCT (Micromass)
Agilent 6130 (Agilent)
LCQ Deca XP (ThermoFisher Scientific)

The ionization technique used was ESI (electrospray ionization), EI (electron ionization), or dual ionization employing ESI and APCI (atmospheric pressure chemical ionization). Found data are reported. Molecular ion peaks are usually observed but in the case of compounds having a hydroxy group (—OH), fragment peaks are sometimes observed with $H_2O$ eliminated. In the case of salts, molecular ion peaks or fragment ion peaks of their free forms are usually observed.

Purification by preparative high-performance liquid chromatography (preparative HPLC) was conducted under the following conditions. It should, however, be noted that in the case of compounds having basic functional groups, neutralization or other operations for obtaining their free forms may have to be performed when trifluoroacetic acid is used in the HPLC operation.
Apparatus: Gilson's preparative HPLC system
Column: Waters' SunFire™ Prep C18 OBD™ (5 μm, 30×50 mm)
Flow rate: 40 mL/min; Detection method: UV 254 nm
Solvent: Solution A, 0.1% trifluoroacetic acid containing water; Solution B, 0.1% trifluoroacetic acid containing acetonitrile
Gradient: 0 min (Solution A/Solution B=90/10), 2 min (Solution A/Solution B=90/10), 12 min (Solution A/Solution B=20/80), 13.5 min (Solution A/Solution B=5/95), 15 min (Solution A/Solution B=5/95)
Analysis by optical high-performance liquid chromatography (optical HPLC) was conducted under the following conditions.
Apparatus: Agilent 1100 (product of Agilent)
Column: DAICEL's CHIRALCEL OD-H (5 μm, 4.6×250 mm)
Flow rate: 0.5 mL/min; Detection method: UV 254 nm
Solvent: 0.1% trifluoroacetic acid containing acetonitrile
Purification by optical preparative high-performance liquid chromatography (optical preparative HPLC) was conducted under the following conditions.
Apparatus: Gilson's preparative HPLC system
Column: DAICEL's CHIRALCEL OD (10 μm, 20×250 mm)
Flow rate: 5 mL/min; Detection method: UV 254 nm
Solvent: 0.1% trifluoroacetic acid containing acetonitrile
For X-ray crystallography, XR-AXIS RAPID II (Rigaku) was used.
The optical purity of optically active forms was evaluated in terms of percent enantiomeric excess (%ee). This parameter was calculated from the following equation using the data obtained by optical HPLC.
{For (R)-form}

Percent enantiomeric excess(% ee)=100×[(R)−(S)]/[(R)+(S)]

[wherein (R) and (S) represent the absolute configurations of the respective enantiomers, as well as their peak areas in optical high-performance liquid chromatography (HPLC)].
Percent enantiomeric excess was similarly determined for the (S)-form.
The phase separator used was Biotage's ISOLUTE (registered trademark) Phase Separator.
The microwave reactor was Biotage's Initiator.
Compound names were assigned by means of ACD/Name (ACD/Labs 12.01, Advanced Chemistry Development Inc.)
Elemental analysis was conducted with the following apparatuses.
240011 (Perkin Elmer)
vario MICRO cube (elementar)
MT-6 (Yanaco Analytical Instruments Inc.)
Ion chromatographic analysis was conducted with the following apparatuses.
DX500 (Dionex)
XS 100 (Mitsubishi Chemical Corporation)
ICS3000 (Dionex)
Melting points were measured with the following apparatus.
MP-J3 (Yanaco Instrument Development Laboratory)
In the tables given in the Reference Examples and Working Examples, salt information is left blank for some compounds, indicating that they were obtained in the form of free forms.

Reference Example 1-1

Methyl (4-aminotetrahydro-2H-pyran-4-yl)acetate hydrochloride

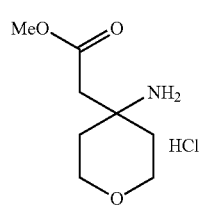

[Formula 19]

(1) Synthesis of methyl tetrahydro-4H-pyran-4-ylidene acetate

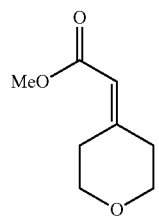

[Formula 20]

To a solution of tetrahydro-4H-pyran-4-one (10.0 g) in toluene (200 mL), methyl (triphenylphosphoranylidene)acetate was added at room temperature. After stirring at 100° C. for 15 hours, the mixture was cooled to room temperature. After concentrating under reduced pressure, ethyl acetate (200 mL) and n-hexane (200 mL) were added. After removing the precipitate by filtration, the filtrate was concentrated under reduced pressure. The resulting residue was purified by silica gel column chromatography (n-hexane:ethyl acetate=95:5-50:50) to give methyl tetrahydro-4H-pyran-4-ylidene acetate as a colorless oil (13.9 g).
$^1$H NMR (300 MHz, CHLOROFORM-d) δ ppm 2.30-2.37 (m, 2 H) 2.95-3.05 (m, 2 H) 3.70 (s, 3 H) 3.71-3.81 (m, 4 H) 5.69 (s, 1 H).
MS ESI/APCI Dual posi: 157 [M+H]$^+$, 179 [M+Na]$^+$.

(2) Synthesis of methyl (4-aminotetrahydro-2H-pyran-4-yl)acetate

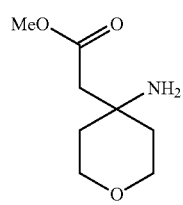

[Formula 21]

An 8 mol/L ammonia-methanol solution (100 mL) of the compound (13.6 g) obtained in step (1) above was stirred in a sealed tube at 90° C. for 4 days. After being cooled to room temperature, the mixture was concentrated under reduced pressure. The resulting residue was purified by silica gel column chromatography (chloroform:methanol=100:0-90:10) to give methyl (4-aminotetrahydro-2H-pyran-4-yl)acetate as a yellow oil (7.09 g).

¹H NMR (300 MHz, CHLOROFORM-d) δ ppm 1.44-1.56 (m, 2 H) 1.64-1.79 (m, 2 H) 2.45 (s, 2 H) 3.63-3.86 (m, 7 H).
MS ESI/APCI Dual posi: 174 [M+H]⁺, 196 [M+Na]⁺.

(3) Synthesis of the Titled Compound

To an ethyl acetate solution (100 mL) of the compound (7.09 g) in step (2) above, a 4 mol/L hydrogen chloride-ethyl acetate solution (10.2 mL) was added. Thereafter, n-hexane was added and the mixture was stirred at room temperature for 5 minutes. The precipitate was recovered by filtration to give the titled compound as a colorless solid (5.72 g).

¹H NMR (300 MHz, DMSO-d₆) δ ppm 1.76-1.85 (m, 4 H) 2.90 (s, 2 H) 3.49-3.61 (m, 2 H) 3.63-3.68 (m, 3 H) 3.70-3.83 (m, 2 H) 8.35 (br. s., 3 H).
MS ESI/APCI Dual posi: 174 [M+H]⁺.

Reference Example 1-2 tert-Butyl 4-amino-4-(2-methoxy-2-oxoethyl)piperidine-1-carboxylate

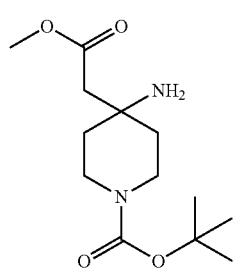

[Formula 22]

Instead of tetrahydro-4H-pyran-4-one, 1-(tert-butoxycarbonyl)-4-piperidone (5.00 g) was used and treated by the same techniques as in Reference Example 1-1(1) and (2) to give the titled compound as a colorless solid (4.65 g).

¹H NMR (600 MHz, CHLOROFORM-d) δ ppm 1.45 (s, 9 H) 1.49-1.52 (m, 2 H) 1.53-1.60 (m, 2 H) 2.41 (s, 2 H) 3.28-3.35 (m, 2 H) 3.58-3.68 (m, 2 H) 3.69 (s, 3 H).
MS ESI/APCI Dual posi: 273 [M+H]⁺.

Reference Example 1-3 tert-Butyl 3-amino-3-(2-methoxy-2-oxoethyl)azetidine-1-carboxylate

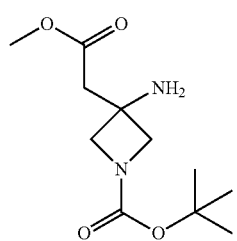

[Formula 23]

(1) Synthesis of tert-butyl 3-(2-methoxy-2-oxoethylidene)azetidine-1-carboxylate

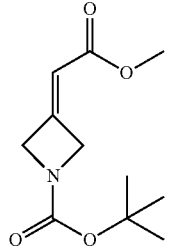

[Formula 24]

Instead of tetrahydro-4H-pyran-4-one, 1-(tert-butoxycarbonyl)-4-azetidinone (4.90 g) was used and treated by the same technique as in Reference Example 1-1(1) to give tert-butyl 3-(2-methoxy-2-oxoethylidene)azetidine-1-carboxylate as a colorless oil (6.21 g).

¹H NMR (200 MHz, DMSO-d₆) δ ppm 1.38-1.41 (m, 9 H) 3.61-3.67 (m, 3 H) 4.52-4.60 (m, 2 H) 4.66-4.73 (m, 2 H) 5.84-5.93 (m, 1 H)
MS ESI/APCI Dual nega: 226 [M−H]⁻.

(2) Synthesis of the Titled Compound

To a solution in ethanol (60 mL) of the compound (6.04 g) obtained in step (1) above, a solution of 28% ammonia in water was added and the mixture was stirred at 80° C. for 9 hours. After being cooled to room temperature, the reaction mixture was concentrated under reduced pressure to give the titled compound as a crude product (8.14 g). The titled compound was used in the next reaction as it remained the crude product.

Reference Example 2-1

Methyl (1-aminocyclobutyl)acetate

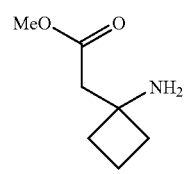

[Formula 25]

(1) Synthesis of 1-azaspiro[3.3]heptan-2-one

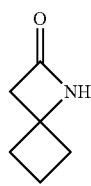

[Formula 26]

To a solution of methylenecyclobutane (2.35 g) in diethyl ether (34.9 mL), chlorosulfonyl isocyanate (4.88 g) was slowly added under cooling with ice and the mixture was stirred at room temperature for 30 minutes. After successively adding a solution of 20% sodium thiosulfate in water (43.0 mL) and a solution of 10% potassium hydroxide in water (43.0 mL) at 0° C., the mixture was stirred at that temperature for 2 hours. Following the confirmation that the interior of the reaction system was strongly basic, the mixture was extracted with diethyl ether nine times. The combined organic layers were dried over anhydrous magnesium sulfate and the desiccant was removed by filtration. The filtrate was concentrated under reduced pressure to give 1-azaspiro[3.3]heptan-2-one as a yellow oil (2.71 g).

$^1$H NMR (300 MHz, CHLOROFORM-d) δ ppm 1.63-1.82 (m, 2 H) 2.17-2.45 (m, 4 H) 2.96-2.99 (m, 2 H) 5.90-6.56 (m, 1 H).

MS ESI posi: 112 [M+H]$^+$, 134 [M+Na]$^+$.

(2) Synthesis of the Titled Compound

To a solution in methanol (60.0 mL) of the compound (2.67 g) obtained in step (1) above, conc. sulfuric acid was added slowly. After refluxing for an hour, the mixture was cooled to room temperature. After concentrating the mixture under reduced pressure, ethyl acetate was added and the mixture was extracted with 1 mol/L hydrochloric acid twice. To the combined aqueous layers, potassium carbonate was added at 0° C. until pH>10. After ten extractions with ethyl acetate, the combined organic layers were dried over added anhydrous magnesium sulfate. After removing the desiccant by filtration, the filtrate was concentrated under reduced pressure to give the titled compound as a pale yellow oil (2.82 g).

$^1$H NMR (300 MHz, CHLOROFORM-d) δ ppm 1.59-1.99 (m, 4 H) 2.03-2.16 (m, 2 H) 2.61 (s, 2 H) 3.69 (s, 3 H).

MS ESI posi: 144 [M+H]$^+$, 166 [M+Na]$^+$.

Reference Example 2-2

Methyl 3-amino-2,2,3-trimethylbutanoate hydrochloride

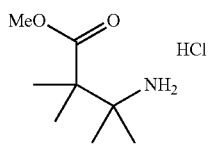

[Formula 27]

(1) Synthesis of 3,3,4,4-tetramethylazetidine-2-one

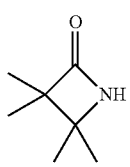

[Formula 28]

To a solution of 2,3-dimethyl-2-butene (5.76 g) in toluene (46.0 mL), chlorosulfonyl isocyanate (5.91 mL) was added at 0° C. After being stirred at that temperature for 10 minutes, the mixture was brought to room temperature. After being stirred for 45 minutes, the mixture was diluted with added toluene (69.0 mL). To a mixture of a solution of 25% sodium hydroxide in water (49.1 mL) and benzyltriethylammonium chloride (99.0 mg), the reaction mixture was added over a period of one hour. The resulting mixture was added dropwise to a solution of 25% sodium hydroxide in water and the mixture was stirred at 50° C. for an hour. After being cooled to room temperature, the mixture was extracted with toluene twice. The combined organic layers were washed with saturated brine and dried over added anhydrous magnesium sulfate. The desiccant was removed by filtration and the filtrate was concentrated under reduced pressure. The resulting residue was recrystallized with toluene to give 3,3,4,4-tetramethylazetidine-2-one as a colorless solid (5.52 g).

$^1$H NMR (300 MHz, CHLOROFORM-d) δ ppm 1.22 (s, 6 H) 1.33 (s, 6 H) 5.79 (br. s, 1 H).

MS ESI/APCI Dual posi: 128 [M+H]$^+$, 150 [M+Na]$^+$.

MS ESI/APCI Dual nega: 126 [M−H]$^−$.

(2) Synthesis of the Titled Compound

To the compound (5.52 g) obtained in step (1) above, a 2 mol/L hydrogen chloride-methanol solution (40.0 mL) was added and the mixture was refluxed for 5 hours. Further, a 2 mol/L hydrogen chloride-methanol solution (20.0 mL) was added and the mixture was refluxed for 6 hours. After cooling to room temperature, toluene (40.0 mL) was added and the mixture was concentrated under reduced pressure. After cooling the residue to 0° C., the precipitate was recovered by filtration and washed with toluene. The recovered precipitate was dried under reduced pressure to give the titled compound as a colorless solid (4.67 g).

$^1$H NMR (300 MHz, CHLOROFORM-d) δ ppm 1.36 (s, 6 H) 1.51 (s, 6 H) 3.73-3.83 (m, 3 H) 8.25-8.83 (m, 3 H).

MS ESI/APCI Dual posi: 160 [M+H]$^+$, 182 [M+Na]$^+$.

Reference Example 2-3

Methyl 3-amino3-ethylpentanoate hydrochloride

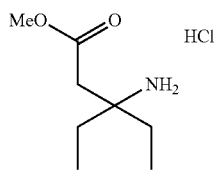

[Formula 29]

Instead of 2,3-dimethyl-2-butene, 2-ethyl-1-butene (10.0 g) was used and treated by the same technique as in Reference Example 2-2 to give the titled compound as a colorless amorphous mass (12.0 g).

$^1$H NMR (300 MHz, CHLOROFORM-d) δ ppm 1.06 (t, J=7.5 Hz, 6 H) 1.79-2.02 (m, 4 H) 2.80 (s, 2 H) 3.74 (s, 3 H) 8.52 (br. s., 3 H).

MS ESI/APCI Dual posi: 160 [M+H]$^+$, 182 [M+Na]$^+$.

Reference Example 3-1

Ethyl 3-amino-2,2-difluoropropanoate hydrochloride

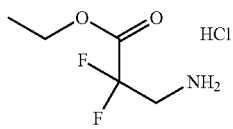

[Formula 30]

To ethanol (12.0 mL), thionyl chloride (0.587 mL) was added at 0° C. and the mixture was stirred at that temperature for 30 minutes. After adding 3-amino-2,2-difluoropropionic acid hydrochloride (950 mg) at 0° C., the mixture was refluxed for 4 hours. After being cooled to room temperature, the mixture was concentrated under reduced pressure. After adding ethyl acetate, the resulting precipitate was removed by filtration. The filtrate was concentrated under reduced pressure to give the titled compound as a pale brown oil (920 mg).

$^1$H NMR (300 MHz, CHLOROFORM-d) δ ppm 1.36 (t, J=7.0 Hz, 3 H) 3.84 (t, J=14.1 Hz, 2 H) 4.40 (q, J=7.0 Hz, 2 H) 8.70 (br. s., 3 H).

MS ESI/APCI Dual posi: 154 [M+H]$^+$.

In the following Reference Examples 3-2 and 3-3, a commercial grade of the corresponding β-alanine compounds was used as the starting material and treated by the method described in Reference Example 3-1 or a modification thereof to synthesize the intended compounds. The structures of the synthesized compounds and their NMR and MS data are shown in Table 1-1 below.

mL) was added and thereafter the mixture was stirred at 60° C. for 3 hours. The reaction mixture was concentrated under reduced pressure to give the titled compound as a pale yellow oil (1.42 g).

$^1$H NMR (300 MHz, DMSO-d$_6$) δ ppm 2.69 (d, J=6.5 Hz, 2 H) 3.34-3.60 (m, 2 H) 3.64 (s, 3 H) 4.27-4.57 (m, 1 H).

MS ESI/APCI Dual posi: 134 [M+H]$^+$.

Reference Example 3-5

Methyl (3S)-3-amino-4-hydroxybutanoate hydrochloride

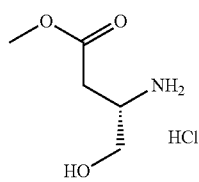

[Formula 32]

Instead of L-β-homoserine, D-β-homoserine (1.00 g) was used and treated by the same technique as in Reference Example 3-4 to give the titled compound as a pale yellow oil (1.42 g).

$^1$H NMR (300 MHz, DMSO-d$_6$) δ ppm 2.70 (d, J=6.7 Hz, 2 H) 3.35-3.60 (m, 2 H) 3.64 (s, 3 H) 4.29-4.55 (m, 1 H).

MS ESI/APCI Dual posi: 134 [M+H]$^+$.

TABLE 1-1

| Compound No. | Structure | Analytical Data | Salt information |
|---|---|---|---|
| Reference Example 3-2 | 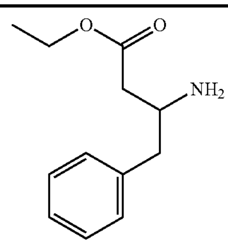 | $^1$H NMR (300 MHz, CHLOROFORM-d) δ ppm 1.18-1.28 (m, 3 H) 2.65-2.92 (m, 2 H) 2.96-3.11 (m, 1 H) 3.40-3.53 (m, 1 H) 3.74-3.91 (m, 1 H) 4.09-4.20 (m, 2 H) 7.21-7.38 (m, 5 H) 8.54-8.88 (m, 3 H). MS ESI/APCI Dual posi: 208[M + H]$^+$,230[M + Na]$^+$. | HCl |
| Reference Example 3-3 | 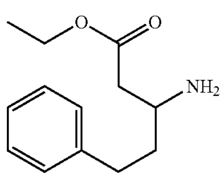 [SMILES: CCOC(=O)CC(N)CCc1ccccc1] | $^1$H NMR (300 MHz, CHLOROFORM-d) δ ppm 1.23 (t, J = 7.1 Hz, 3 H) 1.94-2.42 (m, 2 H) 2.66-2.99 (m, 4 H) 3.51-3.74 (m, 1 H) 4.09-4.20 (m, 2 H) 7.14-7.30 (m, 5 H) 8.66 (br. s., 3 H). MS ESI/APCI Dual posi: 222[M + H]$^+$, 244[M + Na]$^+$. | HCl |

Reference Example 3-4

Methyl (3R)-3-amino-4-hydroxybutanoate hydrochloride

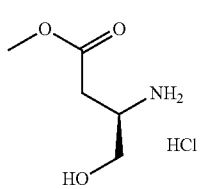

[Formula 31]

To a solution of L-β-homoserine (1.00 g) in methanol (8.4 mL), a 4 mol/L hydrogen chloride-1,4-dioxane solution (8.4

Reference Example 4-1

Ethyl (1-amino cyclopropyl)acetate hydrochloride

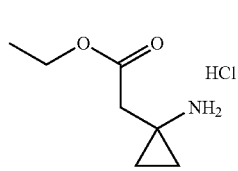

[Formula 33]

(1) Synthesis of 3-(benzyloxy)propanenitrile

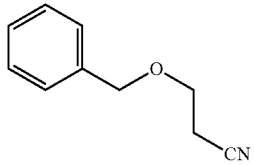

[Formula 57]

To a suspension of sodium hydride (60% dispersion in mineral oil; 14.6 g) in tetrahydrofuran (281 mL), ethylene cyanohydrin (21.0 mL) was added dropwise at 0° C. and the mixture was stirred at that temperature for 40 minutes. After adding benzyl bromide (44.4 mL) to the reaction mixture, the resulting mixture was stirred overnight as it was brought to room temperature. A saturated aqueous solution of ammonium chloride was added to the reaction mixture, which was then extracted with ethyl acetate three times. The combined organic layers were washed with saturated brine and dried over anhydrous magnesium sulfate. The desiccant was removed by filtration and the filtrate was concentrated under reduced pressure. The resulting residue was purified by NH silica gel column chromatography (n-hexane:ethyl acetate=100:0-70:30) to give 3-(benzyloxy)propanenitrile as a colorless oil (24.7 g).

$^1$H NMR (300 MHz, CHLOROFORM-d) δ ppm 2.63 (t, J=6.4 Hz, 2 H) 3.69 (t, J=6.4 Hz, 2 H) 4.59 (s, 2 H) 7.27-7.41 (m, 5 H).

(2) Synthesis of 1-[2-(benzyloxy)ethyl]cyclopropaneamine

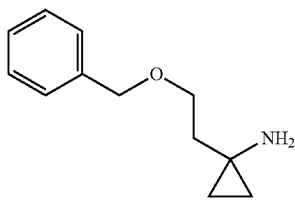

[Formula 35]

To a mixture of the compound (24.7 g) obtained in step (1) above, tetraisopropyl orthotitanate (49.4 mL) and methoxycyclopentane (306 mL), ethyl magnesium bromide (about 3 mol/L, solution in diethyl ether, 102 mL) was added at 0° C. and thereafter the mixture was stirred at room temperature for 3 hours. After adding boron trifluoride/diethylether complex (38.8 mL) at 0° C., the mixture was stirred at room temperature for 1.5 hours. After adding water at 0° C., pH was adjusted to 12 by adding a solution of 10% sodium hydroxide in water. The reaction mixture was extracted with chloroform three times. The combined organic layers were washed with saturated brine and then passed through a phase separator and concentrated under reduced pressure. The resulting residue was purified by NH silica gel column chromatography (n-hexane:ethyl acetate=100:0-5:95) and further purified by silica gel column chromatography (n-hexane:ethylacetate=90:10-5:95, then chloroform:methanol=100:0-90:10) to give 1-[2-(benzyloxy)ethyl]cyclopropaneamine as a pale yellow oil (12.5 g).

$^1$H NMR (300 MHz, CHLOROFORM-d) δ ppm 0.40-0.45 (m, 2 H) 0.53-0.59 (m, 2 H) 1.73 (t, J=6.4 Hz, 2 H) 3.69 (t, J=6.4 Hz, 2 H) 4.52-4.55 (m, 2 H) 7.27-7.37 (m, 5 H).

(3) Synthesis of tert-butyl {1-[2-(benzyloxy)ethyl]cyclopropyl}carbamate

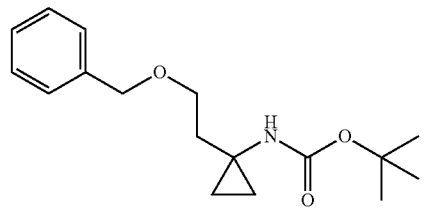

[Formula 36]

To a solution in tetrahydrofuran (130 mL) of the compound (12.5 g) obtained in step (2) above, an aqueous solution of sodium hydrogencarbonate (7.8%, 106 g) and di-tert-butyl dicarbonate (22.5 mL) were added successively and the mixture was stirred at room temperature for 14 hours. After adding saturated brine, the mixture was extracted with ethyl acetate three times. The combined organic layers were washed with saturated brine and then passed through a phase separator and concentrated under reduced pressure. The resulting residue was purified by silica gel column chromatography (n-hexane:ethyl acetate=100:0-50:50) to give tert-butyl {1-[2-(benzyloxy)ethyl]cyclopropyl}carbamate as a colorless solid (16.3 g).

$^1$H NMR (300 MHz, CHLOROFORM-d) δ ppm 0.61-0.80 (m, 4 H) 1.41 (s, 9 H) 1.84 (t, J=6.3 Hz, 2 H) 3.63 (t, J=6.3 Hz, 2 H) 4.51 (s, 2 H) 4.88 (br. s, 1 H) 7.27-7.39 (m, 5 H).

(4) Synthesis of tert-butyl[1-(2-hydroxyethyl)cyclopropyl]carbamate

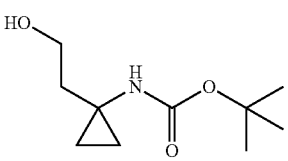

[Formula 37]

To a solution in ethanol (112 mL) of the compound (16.3 g) obtained in step (3) above, 20% palladium hydroxide/carbon (3.25 g) was added and the mixture was stirred at 60° C. for 23 hours in a hydrogen atmosphere. After being cooled to room temperature, the reaction mixture was filtered through Celite (registered trademark). The filtrate was concentrated under reduced pressure to give tert-butyl[1-(2-hydroxyethyl)cyclopropyl]carbamate as a colorless solid (11.1 g).

$^1$H NMR (300 MHz, CHLOROFORM-d) δ ppm 0.71-0.78 (m, 2 H) 0.79-0.87 (m, 2 H) 1.44 (s, 9 H) 1.60-1.66 (m, 2 H) 3.65-3.78 (m, 2 H) 4.83-4.99 (m, 1 H).

(5) Synthesis of {1-[(tert-butoxycarbonyl)amino]cyclopropyl}acetic acid

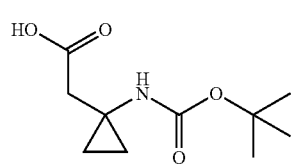

[Formula 38]

To a solution in acetonitrile (275 mL) of the compound (11.1 g) obtained in step (4) above and 2,2,6,6-tetramethylpiperidin-1-oxyl free radical (602 mg), a sodium phosphate buffer (0.67 mol/L, pH 6.7, 206 mL) was added. After heating to 35° C., an aqueous solution of sodium hypochlorite (0.265%, 32.6 mL) and an aqueous solution of sodium chlorite (14.7%, 110 mL) were added simultaneously over a period of 2 hours and the mixture was stirred at that temperature for 55 hours. The mixture was cooled to room temperature and after adding water (400 mL), it was rendered basic with a solution of 2 mol/L sodium hydroxide in water. The reaction mixture was poured into an aqueous solution of sodium thiosulfate (5.75%, 291 mL) at 0° C. After washing with diethyl ether (750 mL), the aqueous layer was added to 2 mol/L hydrochloric acid (140 mL) for pH adjustment to between 2 and 3. The mixture was extracted with diethyl ether and ethyl acetate and the combined organic layers were washed with saturated brine and dried over anhydrous magnesium sulfate. The desiccant was removed by filtration and the filtrate was concentrated under reduced pressure. The resulting residue was crystallized with a liquid mixture of n-hexane/ethyl acetate to give {1-[(tert-butoxycarbonyl)amino]cyclopropyl}acetic acid as a colorless solid (9.45 g).

$^{1}$H NMR (300 MHz, CHLOROFORM-d) δ ppm 0.73-0.83 (m, 2 H) 0.89-0.96 (m, 2 H) 1.45 (s, 9 H) 2.41-2.82 (m, 2 H) 5.09-5.49 (m, 1 H).

MS ESI/APCI Dual posi: 238 [M+Na]$^{+}$.
MS ESI/APCI Dual nega: 214 [M−H]$^{−}$.

(6) Synthesis of the Titled Compound

To ethanol (34.8 mL), thionyl chloride (1.51 mL) was added at 0° C. and the mixture was stirred at that temperature for 30 minutes. After adding the compound (1.50 g) obtained in step (5) above, the mixture was stirred at 75° C. for 4 hours. After being cooled to room temperature, the mixture was concentrated under reduced pressure to give the titled compound as a pale yellow oil (1.41 g).

$^{1}$H NMR (300 MHz, CHLOROFORM-d) δ ppm 0.73-0.81 (m, 2 H) 1.30 (t, J=7.2 Hz, 3 H) 1.44-1.51 (m, 2 H) 2.74 (s, 2 H) 4.23 (q, J=7.2 Hz, 2 H).

MS ESI/APCI Dual posi: 144 [M+H]$^{+}$.

Reference Example 5-1

Ethyl 1-(aminomethyl)cyclopropanecarboxylate

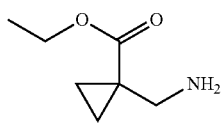

[Formula 39]

(1) Synthesis of ethyl 1-cyanocyclopropanecarboxylate

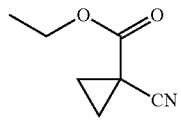

[Formula 40]

To a solution of ethyl cyanoacetate (11.8 g) in acetone (83.0 mL), potassium carbonate (43.1 g) and 1,2-dibromoethane (39.2 g) were added and the mixture was refluxed for 12 hours. After being cooled to room temperature, the reaction mixture was filtered through Celite (registered trademark). The filtrate was concentrated under reduced pressure and further dried under reduced pressure with heating to give ethyl 1-cyanocyclopropanecarboxylate as a red oil (14.2 g).

$^{1}$H NMR (300 MHz, DMSO-d$_{6}$) δ ppm 1.23 (t, J=7.1 Hz, 3 H) 1.57-1.62 (m, 2 H) 1.73-1.79 (m, 2 H) 4.19 (q, J=7.1 Hz, 2 H).

(2) Synthesis of the Titled Compound

To a solution in ethanol (127 mL) of the compound (14.0 g) obtained in step (1) above, a Raney nickel catalyst (about 2.8 g) was added. In a hydrogen atmosphere, the mixture was stirred at room temperature for 12 hours and further stirred at 40° C. for 12 hours. After being cooled to room temperature, the reaction mixture was filtered through Celite (registered trademark) and the filtrate was concentrated under reduced pressure. The resulting precipitate was recovered by filtration and washed with ethanol. The filtrate was concentrated to give the titled compound as a red oil (13.4 g).

$^{1}$H NMR (300 MHz, DMSO-d$_{6}$) δ ppm 0.82-0.88 (m, 2 H) 0.98-1.04 (m, 2 H) 1.13-1.21 (m, 3 H) 2.63-2.72 (m, 2 H) 4.00-4.10 (m, 2 H).

In the following Reference Examples 5-2 to 5-5, 1,2-dibromoethane was replaced by a commercial grade of the corresponding dihalogenated alkanes or dihalogenated alkyl ethers, which were treated by the method described in. Reference Example 5-1 or modifications thereof to synthesize the intended compounds. The structures of the synthesized compounds and their NMR and MS data are shown in Table 2-1 below.

TABLE 2-1

| Compound No. | Structure | Analytical Data | Salt information |
|---|---|---|---|
| Reference Example 5-2 | 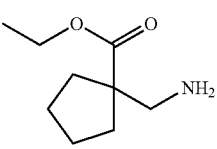 | $^{1}$H HMR (300 Mz, CHLOROFORM-d) δ ppm 1.22-1.31 (t, J = 7.0 Hz, 3 H) 1.46-2.39 (m, 8 H) 2.81 (s, 2 H) 4.16 (q, J = 7.0 Hz, 2 H). MS ESI/APCI Dual posi: 172[M + H]$^{+}$. | |

TABLE 2-1-continued

| Compound No. | Structure | Analytical Data | Salt information |
|---|---|---|---|
| Reference Example 5-3 | 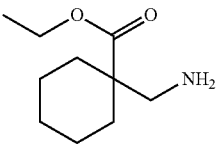 | $^1$H MR (300 MHz, CHLOROFORM-d) δ ppm 1.11-1.70 (m, 11 H) 1.99-2.13 (m, 2 H) 2.74 (s, 2 H) 4.18 (q, J = 7.1 Hz, 2 H). MS ESI/APCI Dual posi: 186[M + H]$^+$. | |
| Reference Example 5-4 | 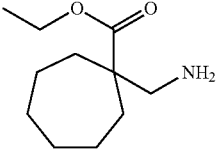 | $^1$H NMR (300 MHz, CHLOROFORM-d) δ ppm 1.20-1.32 (t, J = 7.1 Hz, 3 H) 1.38-1.87 (m, 10 H) 1.99-2.15 (m, 2 H) 2.73 (s, 2 H) 4.16 (q, J = 7.1 Hz, 2 H). MS ESI/APCI Dual posi: 200[M + H]$^+$, 222[M + Na]$^+$. | |
| Reference Example 5-5 | 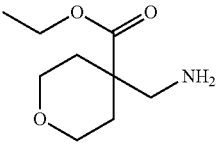 | $^1$H NMR (300 MHz, CHLOROFORM-d) δ ppm 1.26-1.32 (m, 3 H) 1.42-1.54 (m, 2 H) 2.00-2.14 (m, 2 H) 2.79 (s, 2 H) 3.41-3.55 (m, 2 H) 3.80-3.90 (m, 2 H) 4.23 (q, J = 7.1 Hz, 2 H). MS ESI/APCI Dual posi: 188[M + H]$^+$, 210[M + Na]$^+$. | |

Reference Example 6-1

4-Cyclobutylbenzaldehyde

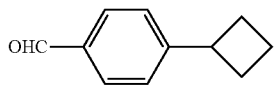

[Formula 41]

To a mixture of 4-iodobenzaldehyde (500 mg), bis(triphenylphosphine)palladium(II) dichloride (75.6 mg), copper(I) iodide (24.6 mg) and dehydrated tetrahydrofuran (10.0 mL), cyclobutylzinc bromide (0.5 mol/L, solution in tetrahydrofuran, 6.46 mL) was added and the mixture was stirred in a sealed tube at 60° C. for 14 hours. After cooling to room temperature, the precipitate was removed by filtration through Celite (registered trademark). The filtrate was concentrated under reduced pressure and thereafter purified by silica gel column chromatography (n-hexane:ethyl acetate=98:2-90:10) to give the titled compound as a colorless oil (225 mg).

$^1$H NMR (300 MHz, CHLOROFORM-d) δ ppm 1.79-2.28 (m, 4 H) 2.29-2.48 (m, 2 H) 3.54-3.73 (m, 1 H) 7.32-7.39 (m, 2 H) 7.74-7.87 (m, 2 H) 9.97 (s, 1 H).

MS ESI/APCI Dual posi: 161 [M+H]$^+$.

Reference Example 6-2

4'-(Trifluoromethyl)biphenyl-4-carbaldehyde

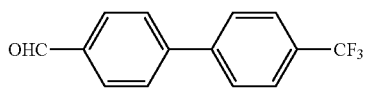

[Formula 42]

A mixture of 4-bromobenzotrifluoride (10.0 g), 4-formylphenylboronic acid (7.33 g), tetrakis(triphenylphosphine)palladium(0) (308 mg), potassium carbonate (30.7 g), tetrahydrofuran (300 mL) and water (100 mL) was stirred at 85° C. for 2 hours. After cooling the reaction mixture to room temperature, water was added to it, which was then extracted with ethyl acetate twice and the combined organic layers were washed with saturated brine. After adding anhydrous magnesium sulfate to the organic layers, the desiccant was removed by filtration and the filtrate was concentrated under reduced pressure. The resulting residue was dissolved in n-hexane (60 mL) with heating and thereafter cooled to 0° C. The resulting precipitate was recovered by filtration to give the titled compound as a gray solid (12.1 g).

$^1$H NMR (300 MHz, CHLOROFORM-d) δ ppm 7.71-7.80 (m, 6 H) 7.96-8.03 (m, 2 H) 10.09 (s, 1 H).

MS EI posi: 250 [M]

Reference Example 6-3

4'-Fluorobiphenyl-4-carbaldehyde

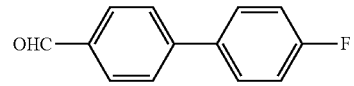

[Formula 43]

A mixture of 4-bromobenzaldehyde (10.0 g), 4-fluorophenylboronic acid (11.3 g), tetrakis(triphenylphosphine)palladium(0) (3.12 g), sodium carbonate (28.6 g), toluene (150 mL), ethanol (70.0 mL) and water (70.0 mL) was stirred at 100° C. for 12 hours. After cooling the reaction mixture to room temperature, water was added and extraction with toluene was conducted twice. The combined organic layers were washed with saturated brine and dried over anhydrous magnesium sulfate. The desiccant was removed by filtration and the filtrate was concentrated under reduced pressure. The concentrate was purified by silica gel column chromatography (n-hexane:ethyl acetate=90:10) and after adding n-hexane to the residue, the mixture was stirred. The precipitate was recovered by filtration and dried under reduced pressure to give the titled compound as a colorless solid (10.4 g).

$^1$H NMR (300 MHz, CHLOROFORM-d) δ ppm 7.12-7.22 (m, 2 H) 7.56-7.66 (m, 2 H) 7.68-7.75 (m, 2 H) 7.93-7.98 (m, 2 H) 10.06 (s, 1 H).

MS ESI/APCI Dual posi: 201 [M+H]$^+$.

Reference Example 6-4

4-Cyclopropyl-3-(trifluoromethyl)benzaldehyde

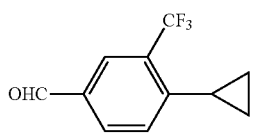
[Formula 44]

With 4-chloro-3-(trifluoromethyl)benzaldehyde (1.00 g) and cyclopropylboronic acid (1.24 g) being used as starting materials, the same technique as in Reference Example 6-3 was applied to give the titled compound as a pale yellow oil (900 mg).
$^1$H NMR (300 MHz, CHLOROFORM-d) δ ppm 0.85-0.95 (m, 2 H) 1.13-1.25 (m, 2 H) 2.23-2.37 (m, 1 H) 7.13 (d, J=8.1 Hz, 1 H) 7.94 (dd, J=8.1, 1.5 Hz, 1 H) 8.12 (d, J=1.5 Hz, 1 H) 10.00 (s, 1 H).
MS ESI/APCI Dual posi: 215 [M+H]$^+$.
MS ESI/APCI Dual nega: 213 [M−H]$^-$.

Reference Example 6-5

3,3'-Bipyridine-6-carbaldehyde

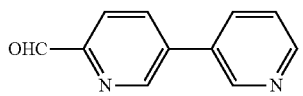
[Formula 45]

A mixture of 5-bromo-3-pyridinecarboxyaldehyde (1.00 g), 3-pyridylboronic acid (991 mg), [1,1'-bis(diphenylphosphino)ferrocene]palladium(II) dichloride dichloromethane adduct (220 mg), 2 mol/L sodium carbonate solution in water (5 mL), and N,N-dimethylformamide (20 mL) was stirred at 120° C. for 30 minutes under irradiation with microwaves.

After cooling the reaction mixture to room temperature, water was added to it and two extractions were conducted with ethyl acetate. The combined organic layers were washed with saturated brine and thereafter passed through a phase separator for concentrating under reduced pressure. The resulting residue was purified by silica gel column chromatography (chloroform:methanol=100:0-95:5) to give the titled compound as a pale yellow solid (944 mg).
$^1$H NMR (300 MHz, CHLOROFORM-d) δ ppm 7.44-7.54 (m, 1 H) 7.93-8.00 (m, 1 H) 8.09 (d, J=1.6 Hz, 2 H) 8.68-8.79 (m, 1 H) 8.90-8.97 (m, 1 H) 9.03 (t, J=1.6 Hz, 1 H) 10.08-10.19 (m, 1 H).

Reference Example 6-6

4-(6-Cyclopropyl-3-pyridinyl)benzaldehyde

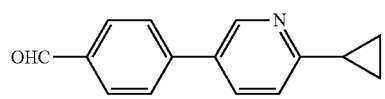
[Formula 46]

A mixture of 3-bromo-6-(cyclopropyl)pyridine (2.00 g), 4-formylphenylboronic acid (1.82 g), palladium(II) acetate (113 mg), tripotassium phosphate (4.50 g) and ethylene glycol (16.8 mL) was stirred at 80° C. for 3 hours. After cooling the reaction mixture to room temperature, water was added to it and two extractions were conducted with ethyl acetate. The combined organic layers were washed with saturated brine and thereafter the crude product was adsorbed on diatomaceous earth, with the solvent being distilled off under reduced pressure. The crude product adsorbed on the diatomaceous earth was purified by silica gel column chromatography (hexane:ethyl acetate=98:2-50:50) to give the titled compound as a colorless solid (1.81 g).
$^1$H NMR (300 MHz, CHLOROFORM-d) δ ppm 1.00-1.17 (m, 4 H) 2.03-2.16 (m, 1 H) 7.21-7.30 (m, 1 H) 7.66-7.83 (m, 3 H) 7.93-8.01 (m, 2 H) 8.68-8.76 (m, 1 H) 10.06 (s, 1 H).
MS ESI/APCI Dual posi: 224 [M+H]$^+$.

In the following Reference Examples 6-7 and 6-11, a commercial grade of the corresponding halogenated pyridines was used as the starting material and treated by the method described in Reference Example 6-6 or modifications thereof to synthesize the intended compounds. The structures of the synthesized compounds and their NMR and MS data are shown in Table 3-1 below.

TABLE 3-1

| Compound No. | Structure | Analytical Data | Salt information |
|---|---|---|---|
| Reference Example 6-7 | 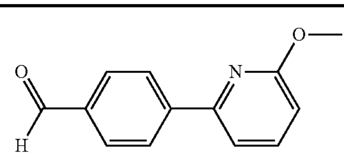 | $^1$H NMR (300 MHz, CHLOROFORM-d) δ ppm 4.06 (s, 3 H) 8.72-6.80 (m, 1 H) 7.38-7.47 (m, 1 H) 7.63-7.72 (m, 1 H) 7.92-8.00 (m, 2 H) 8.19-8.26 (m, 2 H) 10.03-10.12 (m, 1 H). MS ESI/APCI Dual posi: 214[M + H]$^+$. | |
| Reference Example 6-8 | 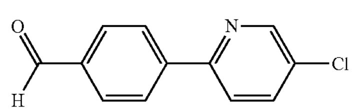 | $^1$H NMR (300 MHz, CHLOROFORM-d) δ ppm 7.74-7.82 (m, 1 H) 7.96-8.04 (m, 2 H) 8.10-8.20 (m, 2 H) 8.63-8.75 (m, 1 H) 10.09 (s, 1 H). MS ESI/APCI Dual posi: 218[M + H]$^+$. | |

TABLE 3-1-continued

| Compound No. | Structure | Analytical Data | Salt information |
|---|---|---|---|
| Reference Example 6-9 | 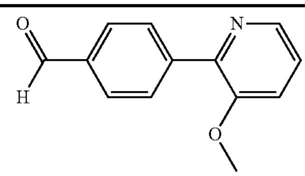 | $^1$H NMR (300 MHz, CHLOROFORM-d) δ ppm 3.93 (s, 3 H) 7.27-7.35 (m, 1 H) 7.73-7.80 (m, 1 H) 7.91-8.01 (m, 2 H) 8.08-8.17 (m, 2 H) 8.41-8.48 (m, 1 H) 10.07 (s, 1 H). MS ESI/APCI Dual posi: 214[M + H]$^+$. | |
| Reference Example 6-10 | 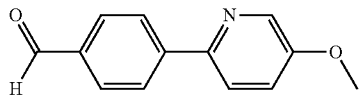 [SMILES: COc1ccc(-c2ccc(C=O)cc2)nc1] | $^1$H NMR (300 MHz, CHLOROFORM-d) δ ppm 3.90 (s, 3 H) 7.25-7.38 (m, 2 H) 7.92-7.99 (m, 2 H) 8.07-8.17 (m, 2 H) 8.31-8.39 (m, 1 H) 10.07 (s, 1 H). MS ESI/APCI Dual posi: 214[M + H]$^+$. | |
| Reference Example 6-11 | 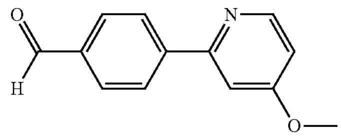 [SMILES: COc1ccnc(-c2ccc(C=O)cc2)c1] | $^1$H NMR (300 MHz, CHLOROFORM-d) δ ppm 3.93 (s, 3 H) 6.78-6.89 (m, 1 H) 7.28-7.33 (m, 1 H) 7.94-8.02 (m, 2 H) 8.10-8.18 (m, 2 H) 8.53-8.62 (m, 1H) 10.08 (s, 1 H). MS ESI/APCI Dual posi: 214[M + H]$^+$. | |

Reference Example 7-1

4-Phenylcyclohexanecarbaldehyde

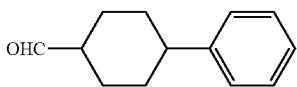

[Formula 47]

(1) Synthesis of [4-(methoxymethylidene)cyclohexyl]benzene

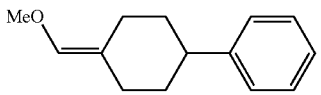

[Formula 48]

To a mixture of (methoxymethyl)triphenylphosphonium chloride (6.14 g) with tert-butyl methyl ether (30.0 mL), potassium tert-butoxide (2.32 g) was added, with the temperature in the system being held at −10° C. The mixture was stirred at −10° C. for 10 minutes and thereafter stirred at room temperature for an hour. A solution of 4-phenylcyclohexanone (2.4 0 g) in tetrahydrofuran (10.0 mL) was added, with the temperature in the system being held at −10° C. The mixture was stirred at −10° C. for 10 minutes and thereafter stirred at room temperature for two hours. After adding water, the mixture was extracted with ethyl acetate. The combined organic layers were passed through a phase separator and thereafter concentrated under reduced pressure. The resulting residue was purified by silica gel column chromatography (n-hexane:ethyl acetate=100:0-60:40) to give [4-(methoxymethylidene)cyclohexyl]benzene as a colorless oil (3.59 g).

$^1$H NMR (300 MHz, CHLOROFORM-d) δ ppm 1.36-1.53 (m, 2 H) 1.69-2.23 (m, 5 H) 2.56-2.70 (m, 1 H) 2.85-2.96 (m, 1 H) 3.57 (s, 3 H) 5.80-5.83 (m, 1 H) 7.12-7.34 (m, 5 H).

MS ESI/APCI Dual posi: 203 [M+H]$^+$.

(2) Synthesis of the Titled Compound

To a solution in tetrahydrofuran (10.0 mL) of the compound (3.59 g) obtained in step (1) above, 3 mol/L hydrochloric acid was added and the mixture was refluxed for 4 hours. After cooling the reaction mixture to room temperature, water was added to it and three extractions were conducted with ethyl acetate. The combined organic layers were washed with water and then concentrated under reduced pressure to give the titled compound as a colorless oil (2.75 g).

$^1$H NMR (300 MHz, CHLOROFORM-d) δ ppm 1.13-1.62 (m, 4 H) 1.63-2.19 (m, 4 H) 2.23-2.40 (m, 1 H) 2.42-2.60 (m, 1 H) 7.10-7.39 (m, 5 H) 9.65-9.82 (m, 1 H).

MS EI posi: 188 [M]$^+$.

Reference Example 8-1

4-(Cyclopropylmethoxy)benzaldehyde

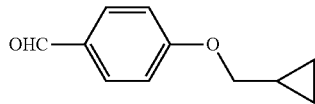

[Formula 49]

To a mixture of 4-hydroxybenzaldehyde (2.00 g), potassium carbonate (4.53 g) and acetone (50.0 mL), (bromomethyl)cyclopropane (3.32 g) was added and the mixture was refluxed for 9 hours. After cooling the reaction mixture to room temperature, the resulting precipitate was removed by filtration through Celite (registered trademark). The filtrate was concentrated under reduced pressure and, thereafter, the resulting residue was purified by silica gel column chromatography (n-hexane:ethyl acetate=90:10-50:50) to give the titled compound as a colorless oil (2.63 g).

$^1$H NMR (300 MHz, CHLOROFORM-d) δ ppm 0.34-0.42 (m, 2 H) 0.62-0.73 (m, 2 H) 1.21-1.37 (m, 1 H) 3.89 (d, J=7.0 Hz, 2 H) 6.96-7.04 (m, 2 H) 7.80-7.86 (m, 2 H) 9.88 (s, 1 H).

MS ESI/APCI Dual posi: 177 [M+H]$^+$, 199 [M+Na]$^+$.

In the following Reference Examples 8-2 to 8-5, a commercial grade each of the corresponding phenols and halogenated alkanes was used and treated by the method described in Reference Example 8-1 or modifications thereof to give the intended compounds. The structures of the synthesized compounds and their NMR and MS data are shown in Table 4-1.

TABLE 4-1

| Compound No. | Structure | Analytical Data | Salt information |
|---|---|---|---|
| Reference Example 8-2 | (structure: 4-(cyclopropylmethoxy)-3-fluorobenzaldehyde) | ¹H NMR (300 MHz, CHLOROFORM-d) δ ppm 0.36-0.45 (m, 2 H) 0.65-0.78 (m, 2 H) 1.27-1.42 (m, 1 H) 3.97 (d, J = 7.0 Hz, 2 H) 7.00-7.10 (m, 1 H) 7.56-7.68 (m, 2 H) 9.33-9.88 (m, 1 H). MS ESI/APCI Dual posi: 195[M + H]⁺. | |
| Reference Example 8-3 | (structure: 4-(cyclopropylmethoxy)-3-methylbenzaldehyde) | ¹H NMR (300 MHz, CHLOROFORM-d) δ ppm 0.35-0.43 (m, 2 H) 0.60-0.71 (m, 2 H) 1.20-1.39 (m, 1 H) 2.29 (s, 3 H) 3.92 (d, J = 6.7 Hz, 2 H) 6.83-6.91 (m, 1 H) 7.61-7.73 (m, 2 H) 9.84 (s, 1 H). MS ESI/APCI Dual posi: 191[M + H]⁺, 213[M + Na]⁺. | |
| Reference Example 8-4 | (structure: 4-((4-fluorobenzyl)oxy)benzaldehyde) | ¹H HMR (300 MHz, CHLOROFORM-d) δ ppm 5.11 (s, 2 H) 7.02-7.15 (m, 4 H) 7.37-7.46 (m, 2 H) 7.79-7.90 (m, 2 H) 9.90 (s, 1 H). MS ESI/APCI Dual posi: 231[M + H]⁺. MS ESI/APCI Dual nega: 229[M − H]⁻. | |
| Reference Example 8-5 | (structure: 4-((4-chlorobenzyl)oxy)benzaldehyde) | ¹H NMR: (300 MHz, CHLOROFORM-d) δ ppm 5.12 (s, 2 H) 7.02-7.10 (m, 2 H) 7.38 (s, 4 H) 7.81-7.89 (m, 2 H) 9.90 (s, 1 H). MS ESI/APCI Dual posi: 247[M + H]⁺. MS ESI/APCI Dual nega: 245[M − H]⁻. | |

Reference 9-1

4-(Cyclobutylmethoxy)benzaldehyde

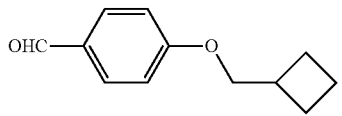

[Formula 50]

To a suspension of sodium hydride (60% dispersion in mineral oil, 0.328 g) in N,N-dimethylformamide (15.0 mL), a solution of 4-hydroxybenzaldehyde (1.00 g) in N,N-dimethylformamide (5.00 mL) was added at 0° C. and thereafter the mixture was stirred at room temperature for 30 minutes. After adding (bromomethyl)cyclobutane (1.22 g), the mixture was stirred at 70° C. for 24 hours. After cooling the reaction mixture to room temperature, 0.5 mol/L hydrochloric acid was added under cooling with ice and three extractions were conducted with ethyl acetate. The combined organic layers were passed through a phase separator and then concentrated under reduced pressure. The resulting residue was purified by silica gel column chromatography (n-hexane:ethyl acetate=95:5-40:60) to give the titled compound as a colorless oil (1.19 g).

¹H NMR (300 MHz, CHLOROFORM-d) δ ppm 1.79-2.04 (m, 4 H) 2.08-2.26 (m, 2 H) 2.72-2.91 (m, 1 H) 4.01 (d, J=6.7 Hz, 2 H) 6.88-7.07 (m, 2 H) 7.77-7.87 (m, 2 H) 9.88 (s, 1 H).

In the following Reference Examples 9-2 and 9-3, (bromomethyl)cyclobutane was replaced by a commercial grade of the corresponding halogenated alkane or halogenated cycloalkane and the method described in Reference Example 9-1 or a modification thereof was applied to synthesize the intended compounds. The structures of the synthesized compounds and their NMR and MS data are shown in Table 5-1 below.

TABLE 5-1

| Compound No. | Structure | Analytical Data | Salt information |
|---|---|---|---|
| Reference Example 9-2 | (structure: 4-(cyclopentylmethoxy)benzaldehyde) | ¹H NMR (300 MHz, CHLOROFORM-d) δ ppm 1.29-1.44 (m, 2 H) 1.50-1.74 (m, 4 H) 1.78-1.96 (m, 2 H) 2.30-2.48 (m, 1 H) 3.92 (d, J = 7.0 Hz, 2 H) 6.95-7.03 (m, 2 H) 7.79-7.86 (m, 2 H) 9.88 (s, 1 H). MS ESI/APCI Dual posi: 205[M + H]⁺. | |
| Reference Example 9-3 | (structure: 4-(cyclopentyloxy)benzaldehyde) | ¹H NMR (300 MHz, CHLOROFORM-d) δ ppm 1.54-2.06 (m, 8 H) 4.80-5.11 (m, 1 H) 6.93-7.00 (m, 2 H) 7.77-7.85 (m, 2 H) 9.87 (s, 1 H). MS ESI/APCI Dual posi: 191[M + H]⁺. | |

Reference Example 10-1

4-(Cyclopropoxy)benzaldehyde

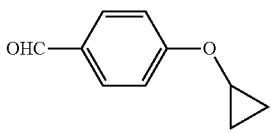

[Formula 51]

To a mixture of 4-hydroxybenzaldehyde (1.20 g), potassium carbonate (2.04 g), potassium iodide (49.0 mg) and N,N-dimethylformamide (9.80 mL), bromocyclopropane (1.02 mL) was added and the mixture was stirred at 200° C. for 3 hours under irradiation with microwaves. After being cooled to room temperature, the reaction mixture was poured into water and extracted with diethyl ether three times. The combined organic layers were washed with saturated brine and thereafter passed through a phase separator to be concentrated under reduced pressure. The resulting residue was purified by silica gel column chromatography (n-hexane:ethyl acetate=100:0-50:50) to give the titled compound as a colorless oil (510 mg).

$^1$H NMR (300 MHz, CHLOROFORM-d) δ ppm 0.76-0.91 (m, 4 H) 3.77-3.88 (m, 1 H) 7.12-7.19 (m, 2 H) 7.80-7.87 (m, 2 H) 9.90 (s, 1 H).

MS ESI/APCI Dual posi: 163 [M+H]$^+$, 185 [M+Na]$^+$.

In the following Reference Examples 10-2 to 10-5, bromo cyclopropane was replaced by a commercial grade of the corresponding halogenated alkanes and the method described in Reference Example 10-1 or a modification thereof was applied to synthesize the intended compounds. The structures of the synthesized compounds and their NMR and MS data are shown in Table 6-1 below.

Reference Example 11-1

4-(2-Cyclopropylethoxyl)benzaldehyde

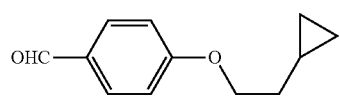

[Formula 52]

To a mixture of 4-hydroxybenzaldehyde (2.84 g), 2-cyclopropylethanol (2.00 g), triphenylphosphine (6.09 g) and tetrahydrofuran (100 mL), diethyl azodicarboxylate (2.2 mol/L, solution in toluene, 10.5 mL) was added and the mixture was stirred at room temperature for 4 days. After concentrating the reaction mixture under reduced pressure, ethyl acetate (7.50 mL) and n-hexane (143 mL) were added and the mixture was stirred at room temperature for 15 minutes. The precipitate was removed by filtration through Celite (registered trademark). The filtrate was concentrated under reduced pressure and, thereafter, the resulting residue was purified by silica gel column chromatography (n-hexane:ethyl acetate=95:5-50:50) to give the titled compound as a yellow oil (3.34 g).

$^1$H NMR (300 MHz, CHLOROFORM-d) δ ppm 0.10-0.18 (m, 2 H) 0.46-0.55 (m, 2 H) 0.78-0.95 (m, 1 H) 1.67-1.76 (m, 2 H) 4.12 (t, J=6.6 Hz, 2 H) 6.97-7.05 (m, 2 H) 7.80-7.87 (m, 2 H) 9.88 (s, 1 H).

MS ESI posi: 191 [M+H]$^+$.

In the following Reference Examples 11-2 to 11-11, a commercial grade of the corresponding hydroxybenzaldehydes and a commercial grade of the corresponding alcohols were used and treated by the method described in Reference Example 11-1 or modifications thereof to give the intended compounds. The structures of the synthesized compounds and their NMR and MS data are shown in Tables 7-1 and 7-2.

TABLE 6-1

| Compound No. | Structure | Analytical Data | Salt information |
|---|---|---|---|
| Reference Example 10-2 | 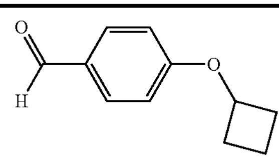 | $^1$H NMR (300 MHz, CHLOROFORM-d) δ ppm 1.63-1.82 (m, 1 H) 1.83-1.98 (m, 1 H) 2.11-2.30 (m, 2 H) 2.42-2.56 (m, 2 H) 4.73 (quin, J = 7.3 Hz, 1 H) 6.87-6.94 (m, 2 H) 7.77-7.85 (m, 2 H) 9.87 (s, 1 H). MS ESI/APCI Dual posi: 177[M + H]$^+$, 199[M + Na]$^+$. | |
| Reference Example 10-3 | 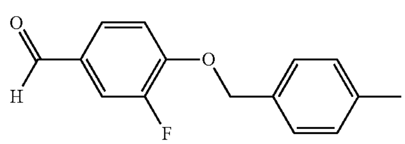 [SMILES: Cc1ccc(COc2ccc(C=O)cc2F)cc1] | $^1$H NMR (300 MHz, CHLOROFORM-d) δ ppm 2.37 (s, 3 H) 5.20 (s, 2 H) 7.08-7.15 (m, 1 H) 7.18-7.24 (m, 2 H) 7.30-7.36 (m, 2 H) 7.57-7.66 (m, 2 H) 9.85 (d, J = 2.2 Hz, 1 H). MS ESI/APCI Dual posi: 267[M + Na]$^+$. MS ESI/APCI Dual nega: 243[M − H]$^-$. | |
| Reference Example 10-4 | 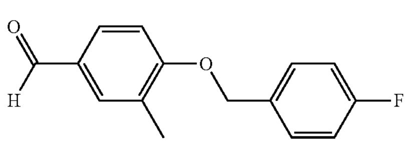 [SMILES: Cc1cc(C=O)ccc1OCc1ccc(F)cc1] | $^1$H NMR (300 MHz, CHLOROFORM-d) δ ppm 2.32 (s, 3 H) 5.14 (s, 2 H) 6.95-7.01 (m, 1 H) 7.05-7.15 (m, 2 H) 7.38-7.45 (m, 2 H) 7.67-7.73 (m, 2 H) 9.87 (s, 1 H). MS ESI/APCI Dual posi: 245[M + H]$^+$, 267[M + Na]$^+$. MS ESI/APCI Dual nega: 243[M − H]$^-$. | |
| Reference Example 10-5 | 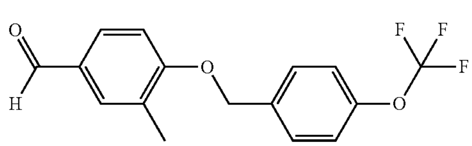 [SMILES: Cc1cc(C=O)ccc1OCc1ccc(OC(F)(F)F)cc1] | $^1$H NMR (300 MHz, CHLOROFORM-d) δ ppm 2.33 (s, 3 H) 5.17 (s, 2 H) 6.94-7.01 (m, 1 H) 7.22-7.31 (m, 2 H) 7.44-7.52 (m, 2 H) 7.68-7.76 (m, 2 H) 9.87 (s, 1 H). MS ESI/APCI Dual posi: 311[M + H]$^+$, 333[M + Na]$^+$. MS ESI/APCI Dual nega: 309[M − H]$^-$. | |

TABLE 7-1

| Compound No. | Structure | Analytical Data | Salt information |
|---|---|---|---|
| Reference Example 11-2 | 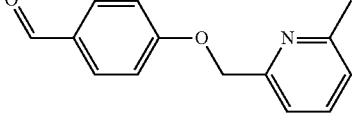 | ¹H NMR (300 MHz, CHLOROFORM-d) δ ppm 2.59 (s, 3 H) 5.25 (s, 2 H) 7.06-7.14 (m, 3 H) 7.29 (d, J = 7.8 Hz, 1 H) 7.62 (t, J = 7.8 Hz, 1 H) 7.81-7.88 (m, 2 H) 9.89 (s, 1 H). MS ESI/APCI Dual posi: 228[M + H]⁺, 250[M + Na]⁺, MS ESI/APCI Dual nega: 226[M − H]⁻. | |
| Reference Example 11-3 | 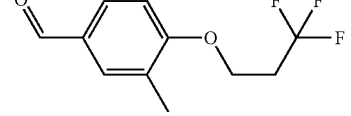 | ¹H NMR (300 MHz, CHLOROFORM-d ) δ ppm 2.27 (s, 3 H) 2.59-2.78 (m, 2 H) 4.30 (t, J = 6.3 Hz, 2 H) 6.91 (d, J = 8.9 Hz, 1 H) 7.66-7.77 (m, 2 H) 9.87 (s, 1 H). MS ESI/APCI Dual posi: 233[M + H]⁺. | |
| Reference Example 11-4 | 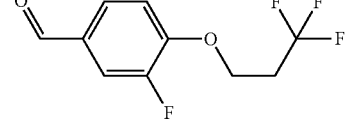 | ¹H NMR (300 MHz, CHLOROFORM-d ) δ ppm 2.59-2.85 (m, 2 H) 4.25-4.43 (m, 2 H) 7.00-7.15 (m, 1 H) 7.56-7.70 (m, 2 H) 9.82-9.96 (m, 1 H). | |
| Reference Example 11-5 | 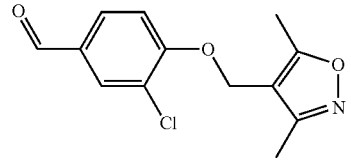 [SMILES: Cc1noc(C)c1COc1ccc(C=O)cc1Cl] | ¹H NMR (300 MHz, CHLOROFORM-d ) δ ppm 2.34 (s, 3 H) 2.46 (s, 3 H) 4.96 (s, 2 H) 7.11 (d, J = 8.4 Hz, 1 H) 7.80 (dd, J = 8.4, 2.0 Hz, 1 H) 7.94 (d, J = 2.0 Hz, 1 H) 9.88 (s, 1 H). MS ESI/APCI Dual posi: 266[M + H]⁺, 288[M + Na]⁺. MS ESI/APCI Dual nega: 264[M − H]⁻, 300[M + Cl]⁻. | |
| Reference Example 11-6 | 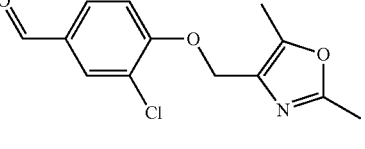 | ¹H NMR (300 MHz, CHLOROFORM-d ) δ ppm 2.36 (s, 3 H) 2.42 (s, 3 H) 5.08 (s, 2 H) 7.23 (d, J = 8.5 Hz, 1 H) 7.76 (dd, J = 8.5, 2.0 Hz, 1 H) 7.91 (d, J = 2.0 Hz, 1 H) 9.86 (s, 1 H). MS ESI/APCI Dual posi: 266[M + H]⁺, 288[M + Na]⁺. MS ESI/APCI Dual nega: 264[M − H]⁻. | |
| Reference Example 11-7 | 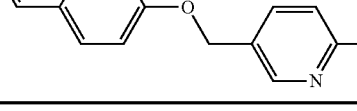 | ¹H NMR (300 MHz, CHLOROFORM-d ) δ ppm 2.59 (s, 3 H) 5.13 (s, 2 H) 7.05-7.11 (m, 2 H) 7.18-7.24 (m, 1 H) 7.69-7.72 (m, 1 H) 7.83-7.89 (m, 2 H) 8.55-8.59 (m, 1 H) 9.90 (s, 1 H). MS ESI/APCI Dual posi: 228[M + H]⁺. MS ESI/APCI Dual nega: 226[M − H]⁻. | |

TABLE 7-2

| Compound No. | Structure | Analytical Data | Salt information |
|---|---|---|---|
| Reference Example 11-8 | 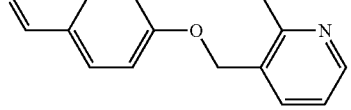 | ¹H NMR (300 MHz, CHLOROFORM-d ) δ ppm 2.61 (s, 3 H) 5.14 (s, 2 H) 7.06-7.13 (m, 2 H) 7.19 (dd, J = 7.7, 4.8 Hz, 1 H) 7.71-7.75 (m, 1 H) 7.85-7.91 (m, 2 H) 8.51 (dd, J = 4.8, 1.7 Hz, 1 H) 9.92 (s, 1 H). MS ESI/APCI Dual posi: 228[M + H]⁺. MS ESI/APCI Dual nega: 226[M − H]⁻. | |
| Reference Example 11-9 | 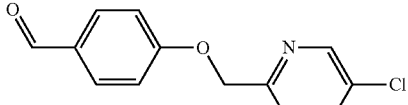 | ¹H NMR (300 MHz, CHLOROFORM-d ) δ ppm 5.26 (s, 2 H) 7.06-7.12 (m, 2 H) 7.45-7.50 (m, 1 H) 7.72 (dd, J = 8.5, 2.3 Hz, 1 H) 7.82-7.88 (m, 2 H) 8.58 (d, J = 2.3 Hz, 1 H) 9.90 (s, 1 H). MS ESI/APCI Dual posi: 248[M + H]⁺. | |
| Reference Example 11-10 | 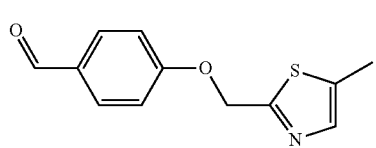 [SMILES: Cc1cnc(COc2ccc(C=O)cc2)s1] | ¹H NMR (300 MHz, CHLOROFORM-d ) δ ppm 2.46-2.50 (m, 3 H) 5.38 (s, 2 H) 7.09-7.15 (m, 2 H) 7.43-7.46 (m, 1 H) 7.82-7.88 (m, 2 H) 9.90 (s, 1 H). MS ESI/APCI Dual posi: 234[M + H]⁺. | |

TABLE 7-2-continued

| Compound No. | Structure | Analytical Data | Salt information |
|---|---|---|---|
| Reference Example 11-11 | 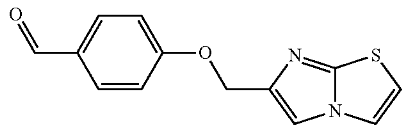 [SMILES: O=Cc1ccc(OCc2cn3ccsc3n2)cc1] | $^1$H NMR (300 MHz, CHLOROFORM-d) δ ppm 5.22 (s, 2 H) 6.86 (d, J = 4.5 Hz, 1 H) 7.11-7.17 (m, 2 H) 7.41 (d, J = 4.5 Hz, 1 H) 7.55 (s, 1 H) 7.81-7.88 (m, 2 H) 9.89 (s, 1 H). MS ESI/APCI Dual posi: 259[M + H]$^+$. | |

Reference Example 12-1

3-Fluoro-4-(2,2,2-trifluoroethoxyl)benzaldehyde

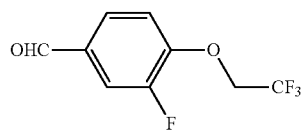

[Formula 53]

To a suspension of sodium hydride (60% dispersion in mineral oil, 0.844 g) in N,N-dimethylfounamide (30.0 mL), 2,2,2-trifluoroethanol (2.11 g) was added at 0° C. and thereafter the mixture was stirred at room temperature for 30 minutes. To the reaction mixture, a solution of 3,4-difluorobenzaldehyde (2.00 g) in N,N-dimethylformamide (10.0 mL) was added and thereafter the mixture was stirred at room temperature for 30 minutes. After adding 1 mol/L hydrochloric acid at 0° C., three extractions were conducted with ethyl acetate. The combined organic layers were passed through a phase separator and thereafter concentrated under reduced pressure. The resulting residue was purified by silica gel column chromatography (n-hexane:ethyl acetate=80:20-30:70) to give the titled compound as a colorless oil (2.50 g).

$^1$H NMR (300 MHz, CHLOROFORM-d) δ ppm 4.52 (q, J=7.9 Hz, 2 H) 7.11-7.19 (m, 1 H) 7.63-7.71 (m, 2 H) 9.89-9.91 (m, 1 H).

MS EI posi: 222 [M]$^+$.

In the following Reference Examples 12-2 to 12-9, a commercial grade of the corresponding fluorobenzaldehydes and a commercial grade of the corresponding alcohols were used and treated by the method described in Reference Example 12-1 or modifications thereof to give the intended compounds. The structures of the synthesized compounds and their NMR and MS data are shown in Tables 8-1 and 8-2.

TABLE 8-1

| Compound No. | Structure | Analytical Data | Salt information |
|---|---|---|---|
| Reference Example 12-2 | 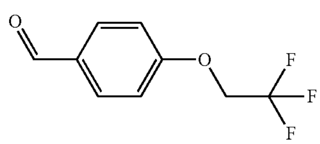 [SMILES: O=Cc1ccc(OCC(F)(F)F)cc1] | $^1$H NMR (300 MHz, CHLOROFORM-d) δ ppm 4.44 (q, J = 7.9 Hz, 2 H) 7.04-7.11 (m, 2 H) 7.86-7.92 (m, 2 H) 9.93 (s, 1 H). MS ESI/APCI Dual posi: 205[M + H]$^+$. | |
| Reference Example 12-3 | 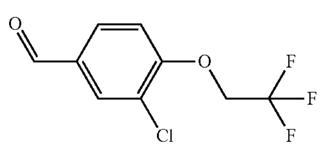 [SMILES: O=Cc1ccc(OCC(F)(F)F)c(Cl)c1] | $^1$H NMR (300 MHz, CHLOROFORM-d) δ ppm 4.51 (q, J = 7.8 Hz, 2 H) 7.03-7.09 (m, 1 H) 7.78-7.82 (m, 1 H) 7.94-7.98 (m, 1 H) 9.90 (s, 1 H). MS ESI/APCI Dual posi: 239[M + H]$^+$. | |
| Reference Example 12-4 | 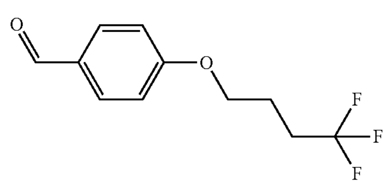 [SMILES: O=Cc1ccc(OCCCC(F)(F)F)cc1] | $^1$H NMR (300 MHz, CHLOROFORM-d) δ ppm 2.01-2.20 (m, 2 H), 2.23-2.46 (m, 2 H) 4.11 (t, J = 6.0 Hz, 2 H) 6.93-7.06 (m, 2 H) 7.79-7.91 (m, 2 H) 9.90 (s, 1 H). MS ESI/APCI Dual posi: 233[M + H]$^+$. | |
| Reference Example 12-5 | 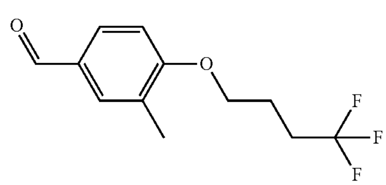 | $^1$H NMR (300 MHz, CHLOROFORM-d) δ ppm 2.06-2.20 (m, 2 H) 2.22-2.45 (m, 5 H) 4.13 (t, J = 6.0 Hz, 2 H) 6.87-6.93 (m, 1 H) 7.65-7.75 (m, 2 H) 9.86 (s, 1 H). MS ESI/APCI Dual posi: 247[M + H]$^+$. | |

TABLE 8-1-continued

| Compound No. | Structure | Analytical Data | Salt information |
|---|---|---|---|
| Reference Example 12-6 | 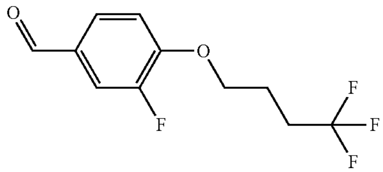 | $^1$H NMR (300 MHz, CHLOROFORM-d ) δ ppm 2.09-2.21 (m, 2 H) 2.27-2.46 (m, 2 H) 4.19 (t, J = 6.0 Hz, 2 H) 7.02-7.10 (m, 1 H) 7.59-7.67 (m, 2 H) 9.85-9.88 (m, 1 H). MS ESI/APCI Dual posi: 251[M + H]$^+$. | |
| Reference Example 12-7 | 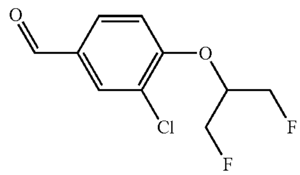 [SMILES: O=Cc1ccc(OC(CF)CF)c(Cl)c1] | $^1$H NMR (300 MHz, CHLOROFORM-d ) δ ppm 4.62-4.72 (m, 2 H) 4.75-4.98 (m, 3 H) 7.18 (d, J = 8.5 Hz, 1 H) 7.77 (d, J = 8.5, 2.1 Hz, 1 H) 7.94 (d, J = 2.1 Hz, 1 H) 9.88 (s, 1 H). MS ESI/APCI Dual posi: 235[M + H]$^+$. | |
| Reference Example 12-8 | 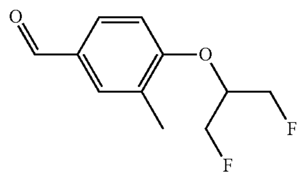 | $^1$H NMR (300 MHz, CHLOROFORM-d ) δ ppm 2.30 (s, 3 H) 4.59-4.67 (m, 2 H) 4.74-4.94 (m, 3 H) 6.98-7.04 (m, 1 H) 7.68-7.74 (m, 2 H) 9.88 (s, 1 H). MS ESI/APCI Dual posi: 215[M + H]$^+$. | |

TABLE 8-2

| Compound No. | Structure | Analytical Data | Salt information |
|---|---|---|---|
| Reference Example 12-9 | 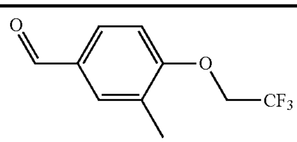 | $^1$H NMR (300 MHz, CHLOROFORM-d ) δ ppm 2.32 (s, 3 H) 4.45 (q, J = 7.9 Hz, 2 H) 6.83-6.97 (m, 1 H) 7.66-7.80 (m, 2 H) 9.90 (s, 1 H). MS ESI/APCI Dual posi: 219[M + H]$^+$. | |

Reference Example 13-1

6-[4-(Trifluoromethyl)phenoxy]pyridin-3-carbaldehyde

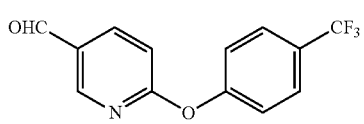

[Formula 54]

To a solution of 4-hydroxybenzotrifluoride (505 mg) in N,N-dimethylforamide (5.00 L), potassium carbonate (474 mg) was added and the mixture was stirred at room temperature for 10 minutes.

Subsequently, 6-bromo-3-pyridinecarboxyaldehyde (580 mg) was added and the mixture was stirred at 130° C. for 2 hours. After cooling the mixture to room temperature, water was added to the mixture, which was then extracted with ethyl acetate. The combined organic layers were washed with water and saturated brine successively and after passage through a phase separator, they were concentrated under reduced pressure. The resulting residue was purified by silica gel column chromatography (n-hexane:ethyl acetate=95:5-70:30) to give the titled compound as a colorless solid (605 mg).

$^1$H NMR (300 MHz, CHLOROFORM-d) δ ppm 7.09-7.15 (m, 1 H) 7.27-7.33 (m, 2 H) 7.66-7.75 (m, 2 H) 8.24 (dd, J=8.5, 2.3 Hz, 1 H) 8.62 (dd, J=2.3, 0.6 Hz, 1 H) 9.99-10.02 (m, 1 H).

MS ESI/APCI Dual posi: 268 [M+H]$^+$.

In the following Reference Examples 13-2 to 13-36, a commercial grade of the corresponding phenols or hydroxypyridines and a commercial grade of the corresponding halogenated benzaldehydes or halogenated pyridinecarboxyaldehydes were used and treated by the method described in Reference Example 13-1 or modifications thereof to give the intended compounds. The structures of the synthesized compounds and their NMR and MS data are shown in Tables 9-1 and 9-5.

TABLE 9-1

| Compound No. | Structure | Analytical Data | Salt information |
|---|---|---|---|
| Reference Example 13-2 | 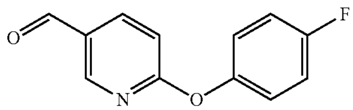 [SMILES: O=Cc1ccc(Oc2ccc(F)cc2)nc1] | ¹H NMR (300 MHz, CHLOROFORM-d) δ ppm 7.05 (dd, J = 8.5, 1.1 Hz, 1 H) 7.09-7.18 (m, 4 H) 8.20 (dd, J = 8.5, 2.3 Hz, 1 H) 8.61 (dd, J = 2.3, 0.6 Hz, 1 H) 9.99 (s, 1 H). MS ESI/APCI Dual posi: 218[M + H]⁺. MS ESI/APCI Dual nega: 216[M − H]⁻. | |
| Reference Example 13-3 | 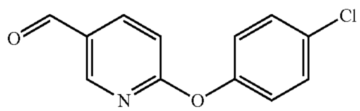 [SMILES: O=Cc1ccc(Oc2ccc(Cl)cc2)nc1] | ¹H NMR (300 MHz, CHLOROFORM-d) δ ppm 6.97-7.24 (m, 3 H) 7.33-7.45 (m, 2 H) 8.21 (dd, J = 8.6, 2.4 Hz, 1 H) 8.61 (d, J = 2.4 Hz, 1 H) 9.99 (d, J = 0.6 Hz, 1 H). MS ESI/APCI Dual posi: 234[M + H]⁺. MS ESI/APCI Dual nega: 232[M − H]⁻. | |
| Reference Example 13-4 | 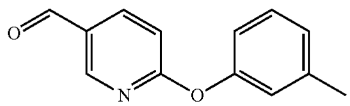 [SMILES: Cc1cccc(Oc2ccc(C=O)cn2)c1] | ¹H NMR (300 MHz, CHLOROFORM-d) δ ppm 2.39 (s, 3 H) 6.90-7.04 (m, 3 H) 7.09 (dd, J = 7.4, 0.9 Hz, 1 H) 7.27-7.39 (m, 1 H) 8.18 (dd, J = 8.6, 2.4 Hz, 1 H) 8.64 (d, J = 2.4 Hz, 1 H) 9.98 (s, 1 H). MS ESI/APCI Dual posi: 214[M + H]⁺. MS ESI/APCI Dual nega: 212[M − H]⁻. | |
| Reference Example 13-5 | 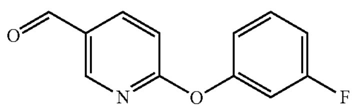 [SMILES: O=Cc1ccc(Oc2cccc(F)c2)nc1] | ¹H NMR (300 MHz, CHLOROFORM-d) δ ppm 6.85-7.13 (m, 4 H) 7.33-7.51 (m, 1 H) 8.22 (dd, J = 8.5, 2.3 Hz, 1 H) 8.58-8.70 (m, 1 H) 10.00 (d, J = 0.6 Hz, 1 H). MS ESI/APCI Dual posi: 218[M + H]⁺. MS ESI/APCI Dual nega: 216[M − H]⁻. | |
| Reference Example 13-6 | 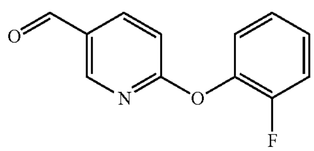 [SMILES: O=Cc1ccc(Oc2ccccc2F)nc1] | ¹H NMR (300 MHz, CHLOROFORM-d) δ ppm 7.13 (dt, J = 8.6, 0.7 Hz, 1 H) 7.17-7.32 (m, 4 H) 8.22 (dd, J = 8.6, 2.3 Hz, 1 H) 8.59 (dd, J = 2.3, 0.7 Hz, 1 H) 9.99 (d, J = 0.7 Hz, 1 H). MS ESI/APCI Dual posi: 218[M + H]⁺. | |
| Reference Example 13-7 | 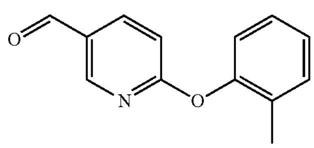 [SMILES: Cc1ccccc1Oc1ccc(C=O)cn1] | ¹H NMR (300 MHz, CHLOROFORM-d) δ ppm 2.16 (s, 3 H) 6.97-7.04 (m, 1 H) 7.05-7.11 (m, 1 H) 7.14-7.38 (m, 3 H) 8.18 (dd, J = 8.5, 2.3 Hz, 1 H) 8.61 (dd, J = 2.3, 0.6 Hz, 1 H) 9.97 (s, 1 H). MS ESI/APCI Dual posi: 214[M + H]⁺. | |
| Reference Example 13-8 | 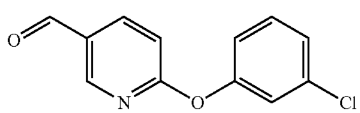 [SMILES: O=Cc1ccc(Oc2cccc(Cl)c2)nc1] | ¹H NMR (300 MHz, CHLOROFORM-d) δ ppm 7.03-7.11 (m, 2 H) 7.21 (t, J = 2.3 Hz, 1 H) 7.23-7.29 (m, 1 H) 7.34-7.41 (m, 1 H) 8.21 (dd, J = 8.5, 2.3 Hz, 1 H) 8.63 (dd, J = 2.3, 0.6 Hz, 1 H) 10.00 (d, J = 0.6 Hz, 1 H). MS ESI/APCI Dual posi: 234[M + H]⁺. MS ESI/APCI Dual nega: 232[M − H]⁻. | |

TABLE 9-2

| Compound No. | Structure | Analytical Data | Salt information |
|---|---|---|---|
| Reference Example 13-9 | 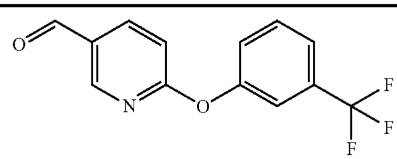 | ¹H NMR (300 MHz, CHLOROFORM-d) δ ppm 7.07-7.14 (m, 1 H) 7.30-7.42 (m, 1 H) 7.43-7.48 (m, 1 H) 7.50-7.63 (m, 2 H) 8.24 (dd, J = 8.5, 2.4 Hz, 1 H) 8.62 (dd, J = 2.4, 0.6 Hz, 1 H) 10.01 (d, J = 0.6 Hz, 1 H). MS ESI/APCI Dual posi: 268[M + H]⁺. | |
| Reference Example 13-10 | 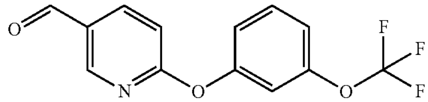 [SMILES: O=Cc1ccc(Oc2cccc(OC(F)(F)F)c2)nc1] | ¹H NMR (300 MHz, CHLOROFORM-d) δ ppm 7.04-7.18 (m, 4 H) 7.40-7.51 (m, 1 H) 8.23 (dd, J = 8.7, 2.3 Hz, 1 H) 8.63 (dd, J = 2.3, 0.6 Hz, 1 H) 10.00 (d, J = 0.6 Hz, 1 H). MS ESI/APCI Dual posi: 284[M + H]⁺. | |
| Reference Example 13-11 | 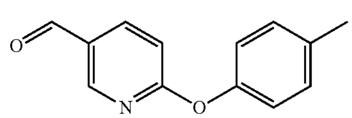 [SMILES: Cc1ccc(Oc2ccc(C=O)cn2)cc1] | ¹H NMR (300 MHz, CHLOROFORM-d) δ ppm 2.39 (s, 3 H) 6.94-7.10 (m, 3 H) 7.19-7.31 (m, 2 H) 8.17 (dd, J = 8.6, 2.4 Hz, 1 H) 8.62 (dd, J = 2.4, 0.6 Hz, 1 H) 9.97 (d, J = 0.6 Hz, 1 H). MS ESI/APCI Dual posi: 214[M + H]⁺. MS ESI/APCI Dual nega: 212[M − H]⁻. | |

TABLE 9-2-continued

| Compound No. | Structure | Analytical Data | Salt information |
|---|---|---|---|
| Reference Example 13-12 | 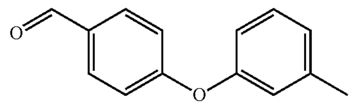 [SMILES: Cc1cccc(Oc2ccc(C=O)cc2)c1] | ¹H NMR (300 MHz, CHLOROFORM-d ) δ ppm 2.37 (s, 3 H) 6.82-6.94 (m, 2 H) 6.99-7.06 (m, 3 H) 7.24-7.33 (m, 1 H) 7.79-7.88 (m, 2 H) 9.92 (s, 1 H). MS ESI/APCI Dual posi: 213[M + H]⁺. MS ESI/APCI Dual nega: 211[M − H]⁻. | |
| Reference Example 13-13 | 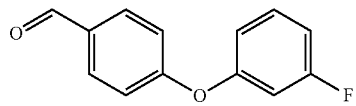 [SMILES: O=Cc1ccc(Oc2cccc(F)c2)cc1] | ¹H NMR (300 MHz, CHLOROFORM-d ) δ ppm 6.75-6.99 (m, 3 H) 7.05-7.15 (m, 2 H) 7.29-7.42 (m, 1 H) 7.83-7.91 (m, 2 H) 9.95 (s, 1 H). MS ESI/APCI Dual posi: 217[M + H]⁺. MS ESI/APCI Dual nega: 215[M − H]⁻. | |
| Reference Example 13-14 | 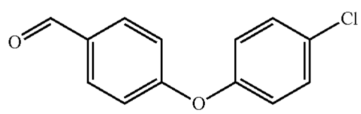 [SMILES: O=Cc1ccc(Oc2ccc(Cl)cc2)cc1] | ¹H NMR (300 MHz, CHLOROFORM-d ) δ ppm 6.96-7.12 (m, 4 H) 7.30-7.42 (m, 2 H) 7.80-7.90 (m, 2 H) 9.93 (s, 1 H). MS ESI/APCI Dual posi: 233[M + H]⁺. | |
| Reference Example 13-15 | 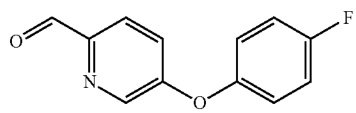 [SMILES: O=Cc1ccc(Oc2ccc(F)cc2)cn1] | ¹H NMR (300 MHz, CHLOROFORM-d ) δ ppm 7.04-7.19 (m, 4 H) 7.29 (ddd, J = 8.7, 2.8, 0.9 Hz, 1 H) 7.88-7.98 (m, 1 H) 8.49 (d, J = 2.8 Hz, 1 H) 10.02 (d, J = 0.9 Hz, 1 H). MS ESI/APCI Dual posi: 218[M + H]⁺, 240[M + Na]⁺. MS ESI/APCI Dual nega: 216[M − H]⁻. | |

TABLE 9-3

| Compound No. | Structure | Analytical Data | Salt information |
|---|---|---|---|
| Reference Example 13-16 | 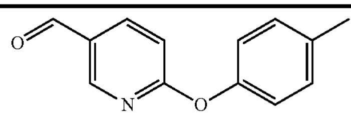 | ¹H NMR (300 MHz, CHLOROFORM-d ) δ ppm 2.38 (s, 3 H) 6.93-7.06 (m, 2 H) 7.17-7.23 (m, 3 H) 7.92 (dd, J = 8.7, 0.9 Hz, 1 H) 8.49 (d, J = 2.6 Hz, 1 H) 10.01 (d, J = 0.9 Hz, 1 H). MS ESI/APCI Dual posi: 214[M + H]⁺, 236[M + Na]⁺. | |
| Reference Example 13-17 | 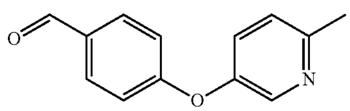 [SMILES: Cc1ccc(Oc2ccc(C=O)cc2)cn1] | ¹H NMR (300 MHz, CHLOROFORM-d ) δ ppm 2.59 (s, 3 H) 7.00-7.10 (m, 2 H) 7.17-7.24 (m, 1 H) 7.29-7.36 (m, 1 H) 7.81-7.92 (m, 2 H) 8.35 (d, J = 2.8 Hz, 1 H) 9.94 (s, 1 H). MS ESI/APCI Dual posi: 214[M + H]⁺. | |
| Reference Example 13-18 | 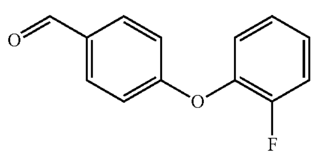 [SMILES: O=Cc1ccc(Oc2ccccc2F)cc1] | ¹H NMR (300 MHz, CHLOROFORM-d ) δ ppm 6.99-7.09 (m, 2 H) 7.13-7.20 (m, 4 H) 7.77-7.92 (m, 2 H) 9.93 (s, 1 H). MS ESI/APCI Dual posi: 217[M + H]⁺. MS ESI/APCI Dual nega: 215[M − H]⁻. | |
| Reference Example 13-19 | 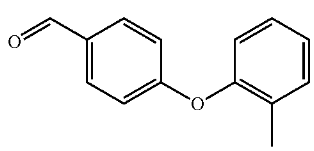 [SMILES: Cc1ccccc1Oc1ccc(C=O)cc1] | ¹H NMR (300 MHz, CHLOROFORM-d ) δ ppm 2.18 (s, 3 H) 6.99-7.04 (m, 3 H) 7.11-7.35 (m, 3 H) 7.77-7.88 (m, 2 H) 9.91 (s, 1 H). MS ESI/APCI Dual posi: 213[M + H]⁺. MS ESI/APCI Dual nega: 211[M − H]⁻. | |
| Reference Example 13-20 | 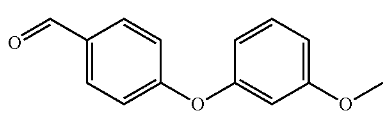 [SMILES: COc1cccc(Oc2ccc(C=O)cc2)c1] | ¹H NMR (300 MHz, CHLOROFORM-d ) δ ppm 3.80 (s, 3 H) 6.62-6.71 (m, 2 H) 6.77 (ddd, J = 8.3, 2.4, 0.9 Hz, 1 H) 7.04-7.11 (m, 2 H) 7.27-7.34 (m, 1 H) 7.80-7.92 (m, 2 H) 9.93 (s, 1 H). MS ESI/APCI Dual posi: 229[M + H]⁺. MS ESI/APCI Dual nega: 227[M − H]⁻. | |
| Reference Example 13-21 | 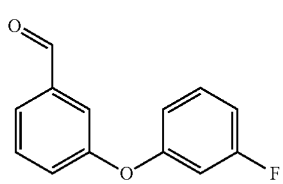 [SMILES: O=Cc1cccc(Oc2cccc(F)c2)c1] | ¹H NMR (300 MHz, CHLOROFORM-d ) δ ppm 6.84 (dd, J = 8.4, 0.8 Hz, 1 H) 7.00-7.23 (m, 5 H) 7.42-7.58 (m, 1 H) 7.93 (dd, J = 7.5, 1.6 Hz, 1 H) 10.53 (d, J = 0.8 Hz, 1 H). MS ESI/APCI Dual posi: 217[M + H]⁺, 239[M + Na]⁺. MS ESI/APCI Dual nega: 215[M − H]⁻. | |

TABLE 9-4

| Compound No. | Structure | Analytical Data | Salt information |
|---|---|---|---|
| Reference Example 13-22 | 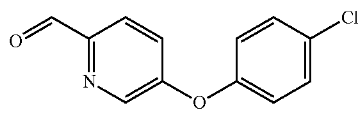 [SMILES: O=Cc1ccc(Oc2ccc(Cl)cc2)cn1] | ¹H NMR (300 MHz, CHLOROFORM-d) δ ppm 7.04 (d, J = 9.0 Hz, 2 H) 7.29-7.36 (m, 1 H) 7.37-7.45 (m, 2 H) 7.96 (dd, J = 9.0, 0.6 Hz, 1 H) 8.51 (dd, J = 2.6, 0.6 Hz, 1 H) 10.02 (d, J = 0.6 Hz, 1 H).<br>MS ESI/APCI Dual posi: 234[M + H]⁺, 256[M + Na]⁺.<br>MS ESI/APCI Dual nega: 232[M − H]⁻. | |
| Reference Example 13-23 | 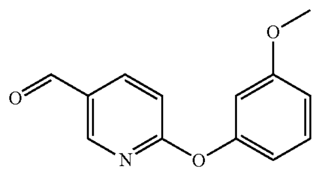 [SMILES: COc1cccc(Oc2ccc(C=O)cn2)c1] | ¹H NMR (300 MHz, CHLOROFORM-d) δ ppm 3.82 (s, 3 H) 6.70-6.79 (m, 2 H) 6.80-6.87 (m, 1 H) 7.03 (d, J = 8.5 Hz, 1 H) 7.34 (t, J = 8.5 Hz, 1 H) 8.18 (dd, J = 8.5, 2.4 Hz, 1 H) 8.65 (dd, J = 2.4, 0.7 Hz, 1 H) 9.98 (d, J = 0.7 Hz, 1 H).<br>MS ESI/APCI Dual posi: 230[M + H]⁺.<br>MS ESI/APCI Dual nega: 228[M − H]⁻. | |
| Reference Example 13-24 | 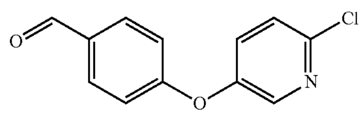 [SMILES: O=Cc1ccc(Oc2ccc(Cl)nc2)cc1] | ¹H NMR (300 MHz, CHLOROFORM-d) δ ppm 7.10 (d, J = 8.5 Hz, 2 H) 7.36-7.42 (m, 2 H) 7.86-7.96 (m, 2 H) 8.24 (dd, J = 2.4, 1.2 Hz, 1 H) 9.96 (s, 1 H).<br>MS ESI/APCI Dual posi: 234[M + H]⁺. | |
| Reference Example 13-25 | 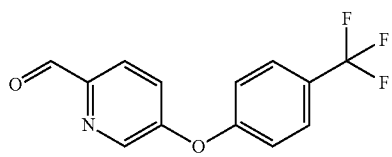 [SMILES: O=Cc1ccc(Oc2ccc(C(F)(F)F)cc2)cn1] | ¹H NMR (300 MHz, CHLOROFORM-d) δ ppm 7.19 (d, J = 8.5 Hz, 2 H) 7.36-7.48 (m, 1 H) 7.70 (d, J = 8.5 Hz, 2 H) 8.00 (d, J = 8.5 Hz, 1 H) 8.56 (d, J = 2.6 Hz, 1 H) 10.05 (d, J = 0.6 Hz, 1 H).<br>MS ESI/APCI Dual posi: 268[M + H]⁺, 290[M + Na]⁺. | |
| Reference Example 13-26 | 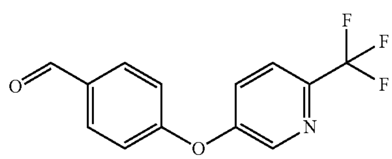 [SMILES: O=Cc1ccc(Oc2ccc(C(F)(F)F)nc2)cc1] | ¹H NMR (300 MHz, CHLOROFORM-d) δ ppm 7.11-7.23 (m, 2 H) 7.43-7.56 (m, 1 H) 7.67-7.80 (m, 1 H) 7.95 (d, J = 8.9 Hz, 2 H) 8.49-8.57 (m, 1 H) 9.99 (s, 1 H).<br>MS ESI/APCI Dual posi: 268[M + H]⁺. | |
| Reference Example 13-27 | 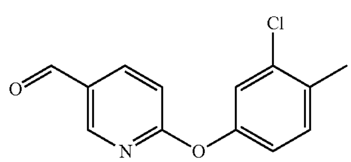 [SMILES: Cc1ccc(Oc2ccc(C=O)cn2)cc1Cl] | ¹H NMR (300 MHz, CHLOROFORM-d) δ ppm 2.39 (s, 3 H) 6.95-7.09 (m, 2 H) 7.18-7.21 (m, 1 H) 7.25-7.31 (m, 1 H) 8.20 (dd, J = 8.6, 2.4 Hz, 1 H) 8.62 (dd, J = 2.4, 0.6 Hz, 1 H) 9.98 (s, 1 H).<br>MS ESI/APCI Dual nega: 246[M − H]⁻. | |
| Reference Example 13-28 | 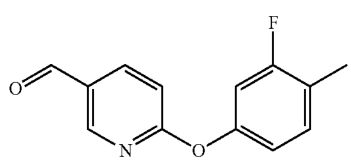 [SMILES: Cc1ccc(Oc2ccc(C=O)cn2)cc1F] | ¹H NMR (300 MHz, CHLOROFORM-d) δ ppm 2.29 (d, J = 2.0 Hz, 3 H) 6.80-6.92 (m, 2 H) 7.00-7.09 (m, 1 H) 7.17-7.30 (m, 1 H) 8.13-8.27 (m, 1 H) 8.56-8.68 (m, 1 H) 9.98 (s, 1 H).<br>MS EI posi: 231[M]. | |

TABLE 9-5

| Compound No. | Structure | Analytical Data | Salt information |
|---|---|---|---|
| Reference Example 13-29 | 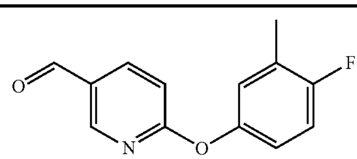 | ¹H NMR (300 MHz, CHLOROFORM-d) δ ppm 2.30 (d, J = 2.4 Hz, 3 H) 6.89-7.14 (m, 4 H) 8.19 (dd, J = 8.6, 2.4 Hz, 1 H) 8.62 (dd, J = 2.4, 0.6 Hz, 1 H) 9.98 (d, J = 0.6 Hz, 1 H).<br>MS ESI/APCI Dual nega: 230[M − H]⁻. | |
| Reference Example 13-30 | 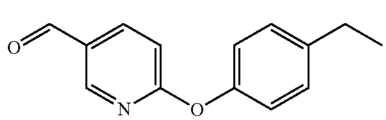 [SMILES: CCc1ccc(Oc2ccc(C=O)cn2)cc1] | ¹H NMR (300 MHz, CHLOROFORM-d) δ ppm 1.24-1.31 (m, 3 H) 2.63-2.75 (m, 2 H) 6.98-7.13 (m, 2 H) 7.23-7.32 (m, 2 H) 8.13-8.22 (m, 1 H) 8.60-8.86 (m, 1 H) 9.95-9.99 (m, 1 H).<br>MS ESI/APCI Dual posi: 228[M + H]⁺. | |

TABLE 9-5-continued

| Compound No. | Structure | Analytical Data | Salt information |
|---|---|---|---|
| Reference Example 13-31 | 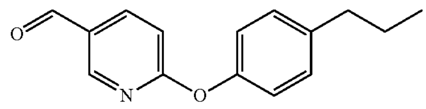 [SMILES: CCCc1ccc(Oc2ccc(C=O)cn2)cc1] | ¹H NMR (300 MHz, CHLOROFORM-d ) δ ppm 0.98 (t, J = 7.4 Hz, 3 H) 1.58-1.76 (m, 2 H) 2.56-2.68 (m, 2 H) 6.95-7.14 (m, 3 H) 7.17-7.35 (m, 2 H) 8.17 (dd, J = 8.6, 2.3 Hz, 1 H) 8.63 (dd, J = 2.3, 0.6 Hz, 1 H) 9.98 (s, 1 H). MS ESI/APCI Dual posi: 242[M + H]⁺. | |
| Reference Example 13-32 | 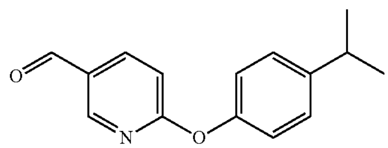 [SMILES: CC(C)c1ccc(Oc2ccc(C=O)cn2)cc1] | ¹H NMR (300 MHz, CHLOROFORM-d ) δ ppm 1.28 (d, J = 6.8 Hz, 6 H) 2.88-3.03 (m, 1 H) 6.99-7.04 (m, 1 H) 7.05-7.12 (m, 2 H) 7.21-7.37 (m, 2 H) 8.17 (dd, J = 8.6, 2.4 Hz, 1 H) 8.64 (dd, J = 2.4, 0.6 Hz, 1 H) 9.98 (s, 1 H). MS ESI/APCI Dual posi: 242[M + H]⁺. | |
| Reference Example 13-33 | 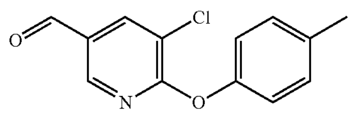 [SMILES: Cc1ccc(Oc2ncc(C=O)cc2Cl)cc1] | ¹H NMR (300 MHz, CHLOROFORM-d ) δ ppm 2.39 (s, 3 H) 7.01-7.09 (m, 2 H) 7.22-7.29 (m, 2 H) 8.20-8.27 (m, 1 H) 8.42-8.48 (m, 1 H) 9.94 (s, 1 H). MS ESI/APCI Dual posi: 248[M + H]⁺. | |
| Reference Example 13-34 | 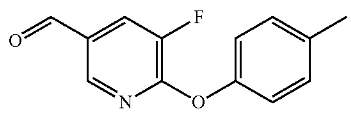 [SMILES: Cc1ccc(Oc2ncc(C=O)cc2F)cc1] | ¹H NMR (300 MHz, CHLOROFORM-d ) δ ppm 2.39 (s, 3 H) 7.00-7.07 (m, 2 H) 7.21-7.30 (m, 2 H) 7.91 (dd, J = 5.3, 1.9 Hz, 1 H) 8.36 (d, J = 1.9 Hz, 1 H) 9.97 (d, J = 2.6 Hz, 1 H). MS ESI/APCI Dual posi: 232[M + H]⁺. | |
| Reference Example 13-35 | 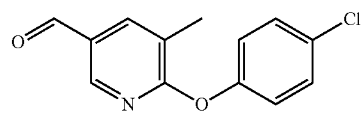 [SMILES: Cc1cc(C=O)cnc1Oc1ccc(Cl)cc1] | ¹H NMR (300 MHz, CHLOROFORM-d ) δ ppm 2.43 (s, 3 H) 7.07-7.14 (m, 2 H) 7.34-7.46 (m, 2 H) 8.03 (dd, J = 2.3, 0.9 Hz, 1 H) 8.40 (d, J = 2.3 Hz, 1 H) 9.94 (s, 1 H). MS ESI/APCI Dual posi: 248[M + H]⁺. | |
| Reference Example 13-36 | 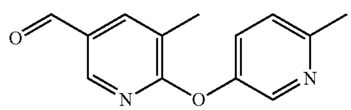 [SMILES: Cc1ccc(Oc2ncc(C=O)cc2C)cn1] | ¹H NMR (200 MHz, CHLOROFORM-d ) δ ppm 2.45 (s, 3 H) 2.60 (s,3 H) 7.21-7.26 (m, 1 H) 7.39-7.48 (m, 1 H) 8.01-8.06 (m, 1 H) 8.36-8.41 (m, 2 H) 9.95 (s, 1 H). MS ESI/APCI Dual posi: 229[M + H]⁺. | |

Reference Example 13-37

6-(4-Cyclopropylphenoxyl)pyridine-3-carbaldehyde

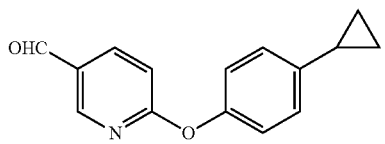

[Formula 55]

(1) Synthesis of 6-(4-bromophenoxy)pyridine-3-carbaldehyde

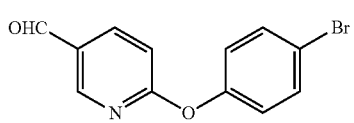

[Formula 56]

To a solution of 4-bromophenol (2.79 g) in N,N-dimethylfomamide (25.0 mL), potassium carbonate (2.45 g) was added and the mixture was stirred at room temperature for 10 minutes. Subsequently, 6-bromo-3-pyridinecarboxyaldehyde (3.00 g) was added and the mixture was stirred at 130° C. for 2.5 hours. After cooling the reaction mixture to room temperature, water was added to it and extraction was conducted with ethyl acetate. The combined organic layers were washed with water and saturated brine successively and after passage through a phase separator, they were concentrated under reduced pressure. The resulting residue was purified by silica gel column chromatography (n-hexane:ethyl acetate=100:0-50:50) to give 6-(4-bromophenoxy)pyridine-3-carbaldehyde as a pale yellow solid (3.23 g).

¹H NMR (300 MHz, CHLOROFORM-d) δ ppm 7.01-7.13 (m, 3 H) 7.51-7.61 (m, 2 H) 8.21 (dd, J=8.6, 2.4 Hz, 1 H) 8.61 (dd, J=2.4, 0.7 Hz, 1 H) 9.99 (d, J=0.7 Hz, 1 H).

MS ESI/APCI Dual posi: 278 [M+H]⁺.

(2) Synthesis of the Titled Compound

A mixture of the compound (3.22 g) obtained in step (1) above, 2-cyclopropyl-4,4,5,5-tetramethyl-1,3,2-dioxaborolane (3.89 g), tetrakis(triphenylphosphine)palladium(0) (669 mg), cesium carbonate (11.3 g), toluene (20.0 mL) and water (10.0 mL) was stirred at 100° C. for 6 hours. After cooling the reaction mixture to room temperature, the precipitate was removed by filtration through Celite (registered trademark). To the filtrate, water and ethyl acetate were added and extraction was conducted with ethyl acetate. The combined organic layers were washed with water and saturated brine successively and after passage through a phase separator, they were concentrated under reduced pressure. The resulting residue was purified by silica gel column chromatography (n-hexane: ethyl acetate=100:0-50:50) and further purified by preparative HPLC. A saturated aqueous solution of sodium hydrogencarbonate was then added and extraction was conducted with ethyl acetate. The combined organic layers were passed through a phase separator and thereafter concentrated under reduced pressure to give the titled compound as a colorless oil (614 mg).
$^1$H NMR (300 MHz, CHLOROFORM-d) δ ppm 0.65-0.76 (m, 2 H) 0.92-1.04 (m, 2 H) 1.84-1.98 (m, 1 H) 6.94-7.10 (m, 3 H) 7.11-7.20 (m, 2 H) 8.17 (dd, J=8.6, 2.4 Hz, 1 H) 8.60-8.67 (m, 1 H) 9.97 (d, J=0.6 Hz, 1 H).
MS ESI/APCI Dual posi: 240 [M+H]$^+$.
MS ESI/APCI Dual nega: 238 [M−H]$^−$.

Reference Example 14-1

4-[(5-Fuoropyridin-2-yl)oxy]benzaldehyde

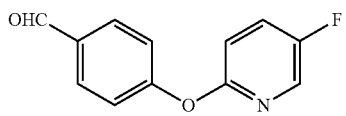

[Formula 57]

To a solution of 4-hydroxybenzaldehyde (5.00 g) in N,N-dimethylacetamide (60.0 L), potassium carbonate (6.23 g) was added and the mixture was stirred at room temperature for 10 minutes. Subsequently, 2,5-difluoropyridine (4.71 g) was added and the mixture was stirred at 150° C. for 64 hours. After cooling the reaction mixture to room temperature, water was added to it and extraction was conducted with ethyl acetate. The combined organic layers were washed with water and saturated brine successively and after passage through a phase separator, they were concentrated under reduced pressure. The resulting residue was purified by silica gel column chromatography (n-hexane:ethyl acetate=100:0-70:30) to give the titled compound as a colorless solid (3.24 g).
$^1$H NMR (300 MHz, CHLOROFORM-d) δ ppm 6.98-7.05 (m, 1 H) 7.21-7.29 (m, 2 H) 7.46-7.57 (m, 1 H) 7.89-7.96 (m, 2 H) 8.05-8.09 (m, 1 H) 9.98 (s, 1 H).
MS ESI/APCI Dual posi: 218 [M+H]$^+$.

In the following Reference Examples 14-2 to 14-4, a commercial grade of the corresponding halogenated pyridines was used and treated by the method described in Reference Example 14-1 or modifications thereof to give the intended compounds. The structures of the synthesized compounds and their NMR and MS data are shown in Table 10-1.

Reference 14-5

4-[(5-cyclopropylpyridin-2-yl)oxy]benzaldehyde

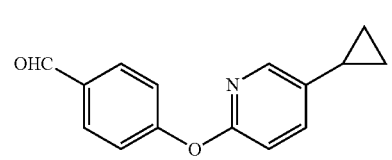

[Formula 58]

(1) Synthesis of 4-[(5-bromopyridin-2-yl)oxy]benzaldehyde

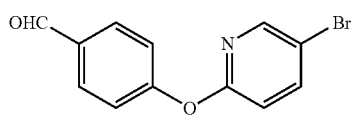

[Formula 59]

Instead of 2,5-difluoropyridine, 2,5-dibromopyridine (13.5 g) was used and treated by the same technique as in Reference 14-1 to give the titled compound as a pale yellow oil (12.4 g).
$^1$H NMR (300 MHz, CHLOROFORM-d) δ ppm 6.91-6.97 (m, 1 H) 7.24-7.32 (m, 2 H) 7.81-7.88 (m, 1 H) 7.90-7.98 (m, 2 H) 8.23-8.27 (m, 1 H) 9.99 (s, 1 H).
MS ESI/APCI Dual posi: 277 [M+H]$^+$.

(2) Synthesis of the Titled Compound

A mixture of the compound (5.00 g) obtained in step (1) above, cyclopropylboronic acid (2.01 g), palladium(II) acetate (201 mg), tripotassium phosphate (13.4 g), tricyclohexylphosphine (0.6 mol/L, solution in toluene, 30.0 mL), toluene (95.0 mL) and water (5.0 mL) was stirred at 100° C. for 3 hours. After cooling the reaction mixture to room temperature, water was added to it and two extractions were conducted with ethyl acetate. The combined organic layers were washed with saturated brine and thereafter the crude

TABLE 10-1

| Compound No. | Structure | Analytical Data | Salt information |
|---|---|---|---|
| Reference Example 14-2 | 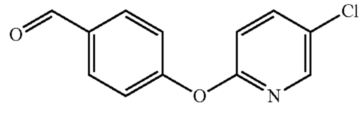 [SMILES: O=Cc1ccc(Oc2ccc(Cl)cn2)cc1] | $^1$H NMR (300 MHz, CHLOROFORM-d) δ ppm 6.93-7.03 (m, 1 H) 7.20-7.32 (m, 2 H) 7.66-7.78 (m, 1 H) 7.88-7.98 (m, 2 H) 8.14-8.19 (m, 1 H) 9.99 (s, 1 H). MS ESI/APCI Dual posi: 234[M + H]$^+$. | |
| Reference Example 14-3 | 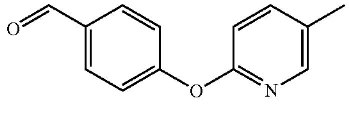 [SMILES: Cc1ccc(Oc2ccc(C=O)cc2)nc1] | $^1$H NMR (300 MHz, CHLOROFORM-d) δ ppm 2.32 (s, 3 H) 6.92 (d, J = 7.9 Hz, 1 H) 7.18-7.30 (m, 2 H) 7.54-7.62 (m, 1 H) 7.85-7.95 (m, 2 H) 8.06 (dt, J = 2.5, 0.7 Hz, 1 H) 9.96 (s, 1 H). MS ESI/APCI Dual posi: 214[M + H]$^+$, 236[M + Na]$^+$. | |
| Reference Example 14-4 | | $^1$H NMR (300 MHz, CHLOROFORM-d) δ ppm 7.12 (dt, J = 8.6, 0.7 Hz, 1 H) 7.29-7.35 (m, 2 H) 7.94-8.01 (m, 3 H) 8.41-8.49 (m, 1 H) 10.02 (s, 1 H), MS ESI/APCI Dual posi: 268[M + H]$^+$. | | product was adsorbed on diatomaceous earth, with the solvents being distilled off under reduced pressure. The crude product adsorbed on the diatomaceous earth was purified by silica gel column chromatography (hexane:ethyl acetate=95:5-63:37) to give the titled compound as a yellow oil (3.89 g).

$^1$H NMR (300 MHz, CHLOROFORM-d) δ ppm 0.64-0.74 (m, 2 H) 0.95-1.07 (m, 2 H) 1.82-1.97 (m, 1 H) 6.88-6.95 (m, 1 H) 7.19-7.26 (m, 2 H) 7.37-7.45 (m, 1 H) 7.86-7.94 (m, 2 H) 8.02-8.09 (m, 1 H) 9.96 (s, 1 H).

MS ESI/APCI Dual posi: 240 [M+H]$^+$.

Reference Example 15-1

4-(2-Cyclopropylethyl)benzaldehyde

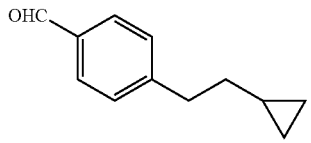

[Formula 60]

(1) Synthesis of 4-(cyclopropylethynyl)benzaldehyde

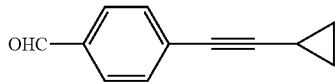

[Formula 61]

To a mixture of 4-bromobenzaldehyde (2.00 g), bis(triphenylphosphine)palladium(II) dichloride (228 mg), copper(I) iodide (20.6 mg), N,N-dimethylformamide (2.00 mL) and triethylamine (15.1 mL), cyclopropylacetylene was added and thereafter the mixture was stirred in a sealed tube at 110° C. for one minute under irradiation with microwaves. After being cooled to room temperature, the reaction mixture was poured into a saturated aqueous solution of ammonium chloride and extracted with a liquid mixture of n-hexane/ethyl acetate (1:1) three times. The combined organic layers were washed with saturated brine and dried over added anhydrous magnesium sulfate. The desiccant was removed by filtration and the filtrate was concentrated under reduced pressure. The resulting residue was purified by silica gel column chromatography (n-hexane:ethyl acetate=100:0-60:40) to give 4-(cyclopropylethynyl)benzaldehyde as a brown oil (1.79 g).

$^1$H NMR (300 MHz, CHLOROFORM-d) δ ppm 0.80-0.99 (m, 4 H) 1.42-1.54 (m, 1 H) 7.46-7.54 (m, 2 H) 7.75-7.82 (m, 2 H) 9.98 (s, 1 H).

MS ESI/APCI Dual posi: 171 [M+H]$^+$.

(2) Synthesis of the Titled Compound

To a solution in ethyl acetate (22.0 mL) of the compound (1.79 g) obtained in step (1) above, 10% palladium/carbon (179 mg) was added. The mixture was stirred at room temperature for 22 hours in a hydrogen atmosphere. More of 10% palladium/carbon (179 mg) was added and the mixture was stirred at room temperature for 3 hours in a hydrogen atmosphere. The insoluble matter was removed by filtration through Celite (registered trademark). After concentrating the filtrate under reduced pressure, the residue was purified by silica gel column chromatography (n-hexane:ethyl acetate=100:0-70:30) to give the titled compound as a crude product (1.23 g).

$^1$H NMR (300 MHz, CHLOROFORM-d) δ ppm 0.01-0.08 (m, 2 H) 0.39-0.48 (m, 2 H) 0.60-0.77 (m, 1 H) 1.50-1.59 (m, 2 H) 2.75-2.84 (m, 2 H) 7.30-7.39 (m, 2 H) 7.74-7.83 (m, 2 H) 9.97 (s, 1 H).

MS ESI/APCI Dual posi: 175 [M+H]$^+$.
MS ESI/APCI Dual nega: 173 [M−H]$^-$.

Reference Example 16-1

4-[(2,2-Dimethylpropoxy)methyl]benzaldehyde

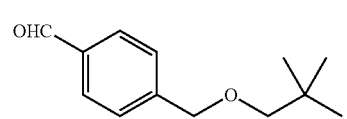

[Formula 62]

(1) Synthesis of 4-(chloromethyl)-N-methoxy-N-methylbenzamide

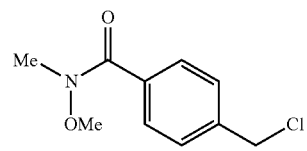

[Formula 63]

To a solution of 4-(bromomethyl)benzoic acid (10.7 g) in chloroform (200 mL), 1-(3-dimethylaminopropyl)-3-ethylcarbodiimide hydrochloride (10.5 g), 1-hydroxybenzotriazole monohydrate (8.38 g), N,O-dimethylhydroxylamine hydrochloride (4.85 g), and triethylamine (6.94 mL) were added. After stirring the mixture at room temperature for 53 hours, chloroform (200 mL) was added. The mixture was washed with a saturated aqueous solution of sodium hydrogencarbonate, a saturated aqueous solution of ammonium chloride, and saturated brine successively. After passage through a phase separator, the washed mixture was concentrated under reduced pressure. The resulting residue was purified by silica gel column chromatography (n-hexane:ethyl acetate=95:5-40:60) to give 4-(chloromethyl)-N-methoxy-N-methylbenzamide as a colorless oil (3.23 g).

$^1$H NMR (300 MHz, CHLOROFORM-d) δ ppm 3.37 (s, 3 H) 3.55 (s, 3 H) 4.61 (s, 2 H) 7.39-7.46 (m, 2 H) 7.65-7.72 (m, 2 H).

MS ESI/APCI Dual posi: 214 [M+H]$^+$, 236 [M+Na]$^+$.

(2) Synthesis of 4[(2,2-dimethylpropoxy)methyl]-N-methoxy-N-methylbenzamide

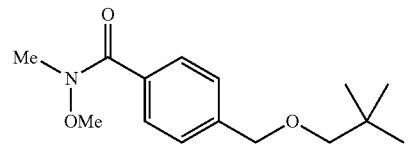

[Formula 64]

To a suspension of sodium hydride (60% dispersion in mineral oil, 286 mg) in N,N-dimethylformamide (23.4 mL), a solution of potassium iodide (70.2 mg) and 2,2-dimethyl- 1-propanol (618 mg) in N,N-dimethylformamide (5.00 mL) were added. After stirring the mixture at room temperature for an hour, a solution in tetrahydrofuran (5.00 mL) of the compound (1.00 g) obtained in step (1) above was added. After stirring the mixture at room temperature for 3 hours, a saturated aqueous solution of ammonium chloride was added. Two extractions were conducted with a liquid mixture of n-hexane/ethyl acetate (1:1) and the combined organic layers were washed with saturated brine. After drying over anhydrous magnesium sulfate, the desiccant was removed by filtration and the filtrate was concentrated under reduced pressure. The resulting residue was purified by silica gel column chromatography (n-hexane:ethyl acetate=100:0-65:35) to give 4-[(2,2-dimethylpropoxy)methyl]-N-methoxy-N-methylbenzamide as a colorless oil (304 mg).

¹H NMR (300 MHz, CHLOROFORM-d) δ ppm 0.93-0.97 (m, 9 H) 3.11-3.16 (m, 2 H) 3.36 (d, J=0.3 Hz, 3 H) 3.57 (s, 3 H) 4.56 (s, 2 H) 7.34-7.40 (m, 2 H) 7.63-7.69 (m, 2 H).

(3) Synthesis of the Titled Compound

To a solution in tetrahydrofuran (5.93 mL) of the compound (472 mg) obtained in step (2) above, diisobutylaluminum hydride (about 1.0 mol/L, solution in n-hexane, 2.64 mL) was added at −78° C. After stirring the mixture at −78° C. for 30 minutes, 1 mol/L hydrochloric acid (5.00 mL) was added at that temperature. After being stirred at room temperature for an hour, the reaction mixture was poured into 1 mol/L hydrochloric acid (20.0 mL). After three extractions with ethyl acetate, the combined organic layers were washed with saturated brine. The washed organic layers were passed through a phase separator and concentrated under reduced pressure. The resulting residue was purified by silica gel column chromatography (n-hexane:ethyl acetate=100:0-90:10) to give the titled compound as a colorless oil (302 mg).

¹H NMR (300 MHz, CHLOROFORM-d) δ ppm 0.93-0.99 (m, 9 H) 3.16 (s, 2 H) 4.60 (s, 2 H) 7.48-7.53 (m, 2 H) 7.82-7.90 (m, 2 H) 10.01 (s, 1 H).

Reference Example 16-2

4-{[(1-Methylcyclopropyl)methoxy]methyl}benzaldehyde

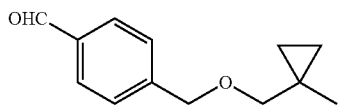

[Formula 65]

Instead of 2,2-dimethyl-1-propanol, 1-methylcyclopropanemethanol was used and treated by the same technique as in Reference Examples 16-1(2) and 16-1(3) to give the titled compound as a colorless oil.

¹H NMR (300 MHz, CHLOROFORM-d) δ ppm 0.32-0.45 (m, 4 H) 1.18 (s, 3 H) 3.30 (s, 2 H) 4.61 (s, 2 H) 7.48-7.54 (m, 2 H) 7.83-7.90 (m, 2 H) 10.01 (s, 1 H).

Reference Example 17-1

4-(1,1-Difluoroethyl)benzaldehyde

[Formula 66]

To a solution of 1-bromo-4-(1,1-difluoroethyl)benzene (1.00 g) in tetrahydrofuran (10.0 mL), n-butyl lithium (2.69 mol/L, solution in n-hexane, 1.68 mL) was added at −80° C. and the mixture was stirred at that temperature for 5 minutes. Subsequently, N,N-dimethylformamide (0.522 mL) was added at −80° C. and after stirring the mixture at that temperature for 20 minutes, 2 mol/L hydrochloric acid (2.50 mL) was added. After bringing the reaction mixture to room temperature, two extractions were conducted with ethyl acetate and the combined organic layers were washed with water. After drying over anhydrous magnesium sulfate and the desiccant was removed by filtration; the filtrate was then concentrated under reduced pressure. The resulting residue was purified by silica gel column chromatography (n-hexane:ethyl acetate=100:0-90:10) to give the titled compound as a colorless oil (510 mg).

¹H NMR (300 MHz, CHLOROFORM-d) δ ppm 1.95 (t, J=18.2 Hz, 3 H) 7.64-7.73 (m, 2 H) 7.92-7.98 (m, 2 H) 10.07 (s, 1 H).

MS EI posi: 170 [M]⁺.

Reference Example 18-1

4-(Difluoromethoxy)-3,5-dimethylbenzaldehyde

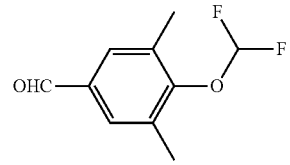

[Formula 67]

To a mixture of 4-hydroxy-3,5-dimethylbenzaldehyde (2.00 g), N,N-dimethylformamide (54.0 mL) and water (6.00 mL), sodium chlorodifluoroacetate (6.09 g) and potassium carbonate (3.68 g) were added and the mixture was stirred at 120° C. for 4.5 hours. After cooling the reaction mixture to room temperature, water was added to it and two extractions were conducted with ethyl acetate. The combined organic layers were washed with water four times and thereafter washed with saturated brine. After drying over anhydrous magnesium sulfate, the desiccant was removed by filtration and the filtrate was then concentrated under reduced pressure. The resulting residue was purified by silica gel column chromatography (n-hexane:ethyl acetate=97:3-88:12) to give the titled compound as a colorless solid (2.53 g).

¹H NMR (300 MHz, CHLOROFORM-d) δ ppm 2.35-2.41 (m, 6 H) 6.10-6.69 (m, 1 H) 7.59-7.64 (m, 2 H) 9.93 (s, 1 H).

MS ESI/APCI Dual posi: 201 [M+H]⁺.

Reference Example 19-1

[3-(Trifluoromethyl)phenyl]acetaldehyde

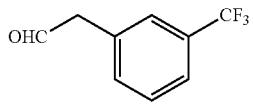

[Formula 68]

To a solution of 3-(trifluoromethyl)phenethyl alcohol (2.00 g) in chloroform (50.0 mL), Dess-Martin periodinane (4.70 g) was added under cooling with ice. After being brought to room temperature, the reaction mixture was stirred for an hour. Subsequently, a saturated aqueous solution of sodium hydrogencarbonate (25.0 mL) and a saturated aqueous solution of sodium thiosulfate (25.0 mL) were added and the mixture was vigorously stirred for an hour. After phase separation, the organic layer was dried over anhydrous magnesium sulfate, the desiccant was removed by filtration, and the filtrate was concentrated under reduced pressure. The resulting residue was purified by silica gel column chromatography (n-hexane:ethyl acetate=98:2-85:15) to give the titled compound as a pale yellow oil (1.19 g).

$^1$H NMR (300 MHz, CHLOROFORM-d) δ ppm 3.79 (s, 2 H) 7.36-7.62 (m, 4 H) 9.77-9.81 (m, 1 H).

MS ESI/APCI Dual nega: 187 [M−H]$^−$.

Reference Example 19-2

[4-(Trifluoromethyl)phenyl]acetaldehyde

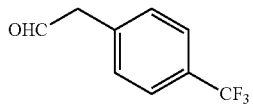

[Formula 69]

Instead of 3-(trifluoromethyl)phenethyl alcohol, 4-(trifluoromethyl)phenethyl alcohol was used and treated by the same technique as in Reference Example 19-1 to give the titled compound as a yellow oil.

$^1$H NMR (300 MHz, CHLOROFORM-d) δ ppm 3.79 (s, 2 H) 7.06-7.75 (m, 4 H) 9.77-9.80 (m, 1 H).

MS ESI/APCI Dual nega: 187 [M−H]$^−$.

Reference Example 20-1

3-Cyclopropyl-4-(trifluoromethyl)benzaldehyde

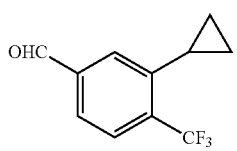

[Formula 70]

(1) Synthesis of methyl-3-cyclopropyl-4-(trifluoromethyl)benzoate

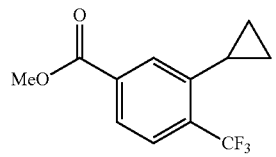

[Formula 71]

Instead of 6-(4-bromophenoxy)pyridine-3-carbaldehyde, methyl 4-(trifluoromethyl)-3-{[(trifluoromethyl)sulfonyl]oxy}benzoate (see WO 2007/129745) (2.21 g) was used and treated by the same technique as in Reference Example 13-37 (2) to give methyl 3-cyclopropyl-4-(trifluoromethyl)benzoate as a colorless oil (1.42 g).

$^1$H NMR (300 MHz, CHLOROFORM-d) δ ppm 0.81-0.90 (m, 2 H) 1.04-1.14 (m, 2 H) 2.16-2.30 (m, 1 H) 3.93 (s, 3 H) 7.65-7.72 (m, 2 H) 7.83-7.93 (m, 1 H).

MS ESI/APCI Dual posi: 245 [M+H]$^+$.

(2) Synthesis of [3-cyclopropyl-4-(trifluoromethyl)phenyl]methanol

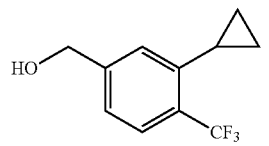

[Formula 72]

To a solution in dehydrated tetrahydrofuran (50.0 mL) of the compound (1.42 g) obtained in step (1) above, lithium borohydride (380 mg) was added and the mixture was stirred at 60° C. for 4 hours. Subsequently, 1 mol/L hydrochloric acid was added under cooling with ice. Following extraction with ethyl acetate, the organic layer was washed with saturated brine. After drying over anhydrous magnesium sulfate and removing the desiccant by filtration, the filtrate was concentrated under reduced pressure. The resulting residue was purified by silica gel column chromatography (n-hexane:ethyl acetate=98:2-75:25) to give [3-cyclopropyl-4-(trifluoromethyl)phenyl]methanol as a colorless oil (1.18 g).

$^1$H NMR (300 MHz, CHLOROFORM-d) δ ppm 0.72-0.83 (m, 2 H) 0.97-1.10 (m, 2 H) 1.70 (t, J=5.9 Hz, 1 H) 2.14-2.28 (m, 1 H) 4.71 (d, J=5.9 Hz, 2 H) 7.04 (s, 1 H) 7.23 (d, J=8.1 Hz, 1 H) 7.60 (d, J=8.1 Hz, 1 H).

MS ESI/APCI Dual nega: 215 [M−H]$^−$.

(3) Synthesis of the Titled Compound

The compound (1.18 g) obtained in step (2) above was used as the starting material and treated by the same technique as in Reference Example 19-1 to give the titled compound as a colorless oil (760 mg).

$^1$H NMR (600 MHz, CHLOROFORM-d) δ ppm 0.84-0.90 (m, 2 H) 1.08-1.15 (m, 2 H) 2.22-2.30 (m, 1 H) 7.54 (s, 1 H) 7.71-7.76 (m, 1 H) 7.77-7.82 (m, 1 H) 10.04 (s, 1 H).

MS EI posi: 214 [M]$^+$.

Reference Example 20-2

3-Methoxy-4-(trifluoromethyl)benzaldehyde

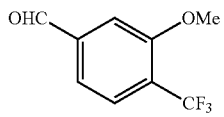

[Formula 73]

(1) Synthesis of methyl 3-methoxy-4-(trifluoromethyl)benzoate

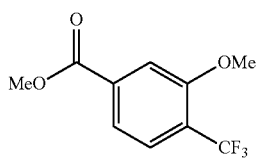

[Formula 74]

To a solution of methyl 3-hydroxy-4-(trifluoromethyl)benzoate (see WO 2007/129745) (2.00 g) in N,N-dimethylformamide (9.00 mL), sodium hydride (60% dispersion in mineral oil, 545 mg) was added in small portions under cooling with ice. After stirring the mixture at room temperature for 30 minutes, methyl iodide (0.849 mL) was added. After stirring the reaction mixture at room temperature for 2.5 hours, iced water was added and two extractions were conducted with ethyl acetate. The combined organic layers were washed with water three times and thereafter dried over anhydrous magnesium sulfate. After removing the desiccant by filtration, the filtrate was concentrated under reduced pressure. The resulting residue was purified by silica gel column chromatography (n-hexane:ethyl acetate=95:5-85:15) to give methyl 3-methoxy-4-(trifluoromethyl)benzoate as a colorless solid (2.11 g).

$^1$H NMR (300 MHz, CHLOROFORM-d) δ ppm 3.96 (s, 3 H) 3.97 (s, 3 H) 7.60-7.72 (m, 3 H).

MS EI posi: 234 [M]$^+$.

(2) Synthesis of the Titled Compound

The compound (2.11 g) obtained in step (1) above was used as the starting material and treated by the same techniques as in Reference Example 20-1(2) and Reference Example 19-1 to give the titled compound as a pale yellow oil (1.26 g).

$^1$H NMR (600 MHz, CHLOROFORM-d) δ ppm 3.97-4.01 (m, 3 H) 7.49-7.53 (m, 2 H) 7.74-7.79 (m, 1 H) 10.05 (s, 1 H).

MS EI posi: 204 [M]$^+$.

Reference Example 20-3

3-(Difluoromethoxy)-4-(trifluoromethyl)benzaldehyde

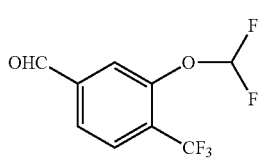

[Formula 75]

(1) Synthesis of methyl 3-(difluoromethoxy)-4-(trifluoromethyl)benzoate

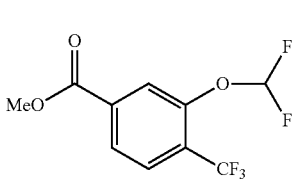

[Formula 76]

A suspension of methyl 3-hydroxy-4-(trifluoromethyl)benzoate (see WO 2007/129745) (2.00 g), sodium chlorodifluoroacetate (2.08 g) and potassium carbonate (2.51 g) in N,N-dimethylformamide (30.0 mL) was stirred at 100° C. for 6 hours. After cooling the reaction mixture to room temperature, water was added to it and two extractions were conducted with ethyl acetate. The combined organic layers were washed with water three times and thereafter dried over anhydrous magnesium sulfate. After removing the desiccant by filtration, the filtrate was concentrated under reduced pressure. The resulting residue was purified by silica gel column chromatography (n-hexane:ethyl acetate=98:2-85:15) to give methyl 3-(difluoromethoxy)-4-(trifluoromethyl)benzoate as a colorless oil (1.96 g).

$^1$H NMR (300 MHz, CHLOROFORM-d) δ ppm 3.93-4.01 (m, 3 H) 6.28-6.87 (m, 1 H) 7.72-7.80 (m, 1 H) 7.92-8.02 (m, 2 H).

MS EI posi: 270 [M]$^+$.

(2) Synthesis of the Titled Compound

The compound (1.96 g) obtained in step (1) above was used as the starting material and treated by the same techniques as in Reference Example 20-1(2) and Reference Example 19-1 to give the titled compound as a colorless oil (1.35 g).

$^1$H NMR (600 MHz, CHLOROFORM-d) δ ppm 6.50-6.79 (m, 1 H) 7.79-7.86 (m, 2 H) 7.88-7.91 (m, 1 H) 10.07 (s, 1 H).

MS EI posi: 240 [M]$^+$.

Reference Example 21-1

4-Cyclobutyl-3-(trifluoromethyl)benzaldehyde

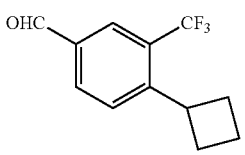

[Formula 77]

(1) Synthesis of 1[4-bromo-2-(trifluoromethyl)phenyl]cyclobutanol

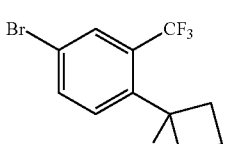

[Formula 78]

To a solution of 5-bromo-2-iodobenzotrifluoride (5.00 g) in dehydrated tetrahydrofuran (140 mL), n-butyl lithium (2.69 mol/L, solution in n-hexane, 5.30 mL) was added at −78° C. and the mixture was stirred at that temperature for 25 minutes. After adding a solution of cyclobutanone (999 mg) in tetrahydrofuran (5.00 mL), the mixture was brought to room temperature and stirred for 3 days. After adding a saturated aqueous solution of ammonium chloride under cooling with ice, two extractions were conducted with ethyl acetate. The combined organic layers were washed with water and thereafter dried over anhydrous magnesium sulfate. After removing the desiccant by filtration, the filtrate was concentrated under reduced pressure. The resulting residue was purified by silica gel column chromatography (n-hexane:ethyl acetate=98:2-80:20) to give 1-[4-bromo-2-(trifluoromethyl)phenyl]cyclobutanol as a pale yellow oil (3.00 g).

$^1$H NMR (300 MHz, CHLOROFORM-d) δ ppm 1.71-1.88 (m, 1 H) 2.20-2.49 (m, 3 H) 2.52-2.70 (m, 2 H) 7.29-7.35 (m, 1 H) 7.62-7.69 (m, 1 H) 7.78-7.84 (m, 1 H).

MS EI posi: 294 [M]$^+$.

(2) Synthesis of 4-bromo-1-cyclobutyl-2-(trifluoromethyl)benzene

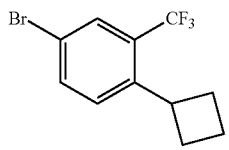

[Formula 79]

To a solution in chloroform (10.0 mL) of the compound (1.00 g) obtained in step (1) above and triethylsilane (406 mg), a solution of boron trifluoride/diethyl ether complex (601 mg) in chloroform (4.00 mL) was added at −65° C. After being brought to 0° C., the mixture was stirred at that temperature for 30 minutes. Subsequently, potassium carbonate (1.08 g) and water (10.0 mL) were added and the mixture was brought to room temperature. After phase separation, the organic layer was dried over anhydrous magnesium sulfate. After removing the desiccant by filtration, the filtrate was concentrated under reduced pressure. The resulting residue was purified by silica gel column chromatography (n-hexane:ethyl acetate=99:1-90:10) and further purified by NH silica gel column chromatography (n-hexane) to give 4-bromo-1-cyclobutyl-2-(trifluoromethyl)benzene as a colorless oil (490 mg).

$^1$H NMR (300 MHz, CHLOROFORM-d) δ ppm 1.78-1.91 (m, 1 H) 1.92-2.25 (m, 3 H) 2.27-2.42 (m, 2 H) 3.83 (quin, J=8.5 Hz, 1 H) 7.41-7.47 (m, 1 H) 7.59-7.67 (m, 1 H) 7.69-7.73 (m, 1 H).

MS EI posi: 278 [M]$^+$.

(3) Synthesis of the Titled Compound

The compound (480 mg) obtained in step (2) above was used as the starting material and treated by the same technique as in Reference Example 17-1 to give the titled compound as a colorless oil (300 mg).

$^1$H NMR (300 MHz, CHLOROFORM-d) δ ppm 1.82-1.97 (m, 1 H) 1.99-2.16 (m, 1 H) 2.16-2.33 (m, 2 H) 2.33-2.49 (m, 2 H) 3.96 (quin, J=8.6 Hz, 1 H) 7.74-7.81 (m, 1 H) 8.00-8.08 (m, 1 H) 8.09-8.13 (m, 1 H) 10.03 (s, 1 H).

MS EI posi: 228 [M]$^+$.

Reference Example 22-1

3-Cyclobutyl-4-(trifluoromethyl)benzaldehyde

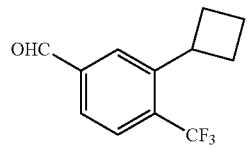

[Formula 80]

(1) Synthesis of 1-cyclobutyl-4-nitro-2-(trifluoromethyl)benzene

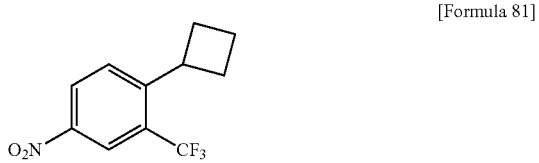 [SMILES: O=[N+]([O-])c1ccc(C2CCC2)c(C(F)(F)F)c1]

[Formula 81]

A mixture of 2-iodo-5-nitrobenzotrifluoride (4.62 g), cyclobutylboronic acid (4.15 g), [1,1'-bis(diphenylphosphino)ferrocene]palladium(II) dichloride (4.15 g), cesium carbonate (22.6 g), toluene (67.0 mL) and water (33.0 mL) was stirred in a sealed tube at 80° C. for 6 hours. After cooling the reaction mixture to room temperature, extraction was conducted with ethyl acetate. The combined organic layers were dried over anhydrous magnesium sulfate and after removing the desiccant by filtration, the filtrate was concentrated under reduced pressure. The resulting residue was purified by silica gel column chromatography (n-hexane:ethyl acetate=100:0-94:6) to give 1-cyclobutyl-4-nitro-2-(trifluoromethyl)benzene as a pale yellow oil (1.69 g).

$^1$H NMR (300 MHz, CHLOROFORM-d) δ ppm 1.84-1.99 (m, 1 H) 2.00-2.33 (m, 3 H) 2.35-2.52 (m, 2 H) 3.89-4.05 (m, 1 H) 7.74-7.81 (m, 1 H) 8.34-8.43 (m, 1 H) 8.45-8.50 (m, 1 H).

MS ESI/APCI Dual nega: 244 [M−H]$^−$.

(2) Synthesis of 4-cyclobutyl-3-(trifluoromethyl)aniline

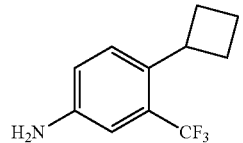

[Formula 82]

A mixture of the compound (1.69 g) obtained in step (1) above, an iron powder (2.14 g), ammonium chloride (442 mg), ethanol (26.0 mL) and water (13.0 mL) was stirred at 85° C. for an hour. After being cooled to room temperature, the reaction mixture was filtered through Celite (registered trademark). To the filtrate, a saturated aqueous solution of sodium hydrogencarbonate was added and three extractions were conducted with ethyl acetate. The combined organic layers were dried over anhydrous magnesium sulfate and after removing the desiccant by filtration, the filtrate was concentrated under reduced pressure. The resulting residue was purified by silica gel column chromatography (n-hexane:ethyl acetate=100:0-75:25) to give 4-cyclobutyl-3-(trifluoromethyl)aniline as a pale yellow oil (1.34 g).

$^1$H NMR (300 MHz, CHLOROFORM-d) δ ppm 1.72-1.87 (m, 1 H) 1.87-2.21 (m, 3 H) 2.21-2.36 (m, 2 H) 3.66-3.85 (m, 3 H) 6.78-6.86 (m, 1 H) 6.88-6.93 (m, 1 H) 7.31-7.37 (m, 1 H).
MS ESI posi: 216 [M+H]$^+$.

(3) Synthesis of
4-cyclobutyl-2-iodo-5-(trifluoromethyl)aniline

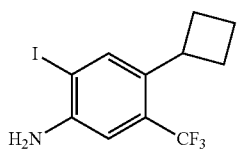

[Formula 83]

To a mixture of the compound (1.34 g) obtained in step (2) above, sodium hydrogencarbonate (628 mg), chloroform (32.0 mL) and methanol (8.00 mL), a solution of iodine monochloride (1.21 g) in chloroform (8.00 mL) was added dropwise at room temperature over a period of 30 minutes. The resulting mixture was stirred at room temperature for two hours. After adding a solution of 25% sodium metabisulfite in water (20.0 g) under cooling with ice, the mixture was stirred at room temperature for 30 minutes. The reaction mixture was extracted with chloroform and the combined organic layers were dried over anhydrous magnesium sulfate. After removing the desiccant by filtration, the filtrate was concentrated under reduced pressure to give 4-cyclobutyl-2-iodo-5-(trifluoromethyl)aniline as a brown oil (2.08 g).

$^1$H NMR (300 MHz, CHLOROFORM-d) δ ppm 1.71-1.89 (m, 1 H) 1.90-2.20 (m, 3 H) 2.20-2.37 (m, 2 H) 3.60-3.78 (m, 1 H) 4.12 (br. s, 2 H) 6.92 (s, 1 H) 7.76 (s, 1 H).
MS ESI posi: 342 [M+H]$^+$.

(4) Synthesis of
2-cyclobutyl-4-iodo-1-(trifluoromethyl)benzene

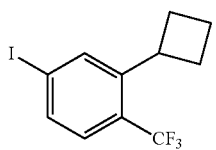

[Formula 84]

To a suspension in acetonitrile (60.0 mL) of the compound (2.08 g) obtained in step (3) above and sodium nitrite (2.10 g), conc. sulfuric acid (6.00 mL) was added at 0° C. over a period of 15 minutes. After stirring the mixture at that temperature for an hour, ethanol (24.0 mL) was added. After being stirred at 100° C. for two hours, the reaction mixture was stirred overnight at room temperature. The reaction mixture was poured into iced water and two extractions were conducted with chloroform. The combined organic layers were washed with a saturated aqueous solution of sodium hydrogencarbonate and thereafter dried over anhydrous magnesium sulfate.

After removing the desiccant by filtration, the filtrate was concentrated under reduced pressure and the residue was purified twice by NH silica gel column chromatography (with n-hexane only) to give 2-cyclobutyl-4-iodo-1-(trifluoromethyl)benzene as a colorless oil (1.25 g).

$^1$H NMR (300 MHz, CHLOROFORM-d) δ ppm 1.77-1.93 (m, 1 H) 1.95-2.26 (m, 3 H) 2.27-2.40 (m, 2 H) 3.81 (quin, J=8.8 Hz, 1 H) 7.26-7.31 (m, 1 H) 7.60-7.67 (m, 1 H) 7.88 (s, 1 H).

(5) Synthesis of the Titled Compound

The compound (1.25 g) obtained in step (4) above was used as the starting material and treated by the same technique as in Reference Example 17-1 to give the titled compound as a colorless oil (660 mg).

$^1$H NMR (300 MHz, CHLOROFORM-d) δ ppm 1.82-2.17 (m, 2 H) 2.17-2.49 (m, 4 H) 3.86-4.02 (m, 1 H) 7.73-7.83 (m, 2 H) 8.09 (s, 1 H) 10.11 (s, 1 H).
MS EI posi: 228 [M]$^+$.

Reference Example 23-1 cis-2-Phenylcyclopropanecarbaldehyde

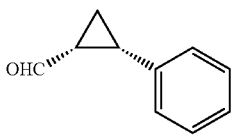

[Formula 85]

(1) Synthesis of ethyl
trans-2-phenylcyclopropanecarboxylate and ethyl
cis-2-phenylcyclopropanecarboxylate

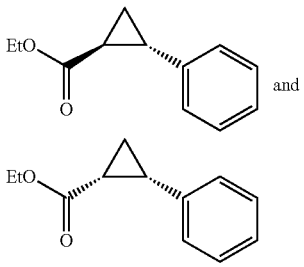

[Formula 86]

To a suspension of styrene (3.00 g) and rhodium(II) acetate dimer (40.0 mg) in 1,2-dichloroethane (29.0 mL), a solution of ethyl diazoacetate (3.03 mL) in 1,2-dichloroethane (29.0 mL) was added over a period of 4 hours and the mixture was stirred at room temperature for 19 hours. The reaction mixture was concentrated under reduced pressure and purified by silica gel column chromatography (n-hexane:diethyl ether=20:1) to give ethyl trans-2-phenylcyclopropanecarboxylate as a colorless oil (2.42 g) and ethyl cis-2-phenylcyclopropanecarboxylate as a colorless oil (1.51 g).

Ethyl trans-2-phenylcyclopropanecarboxylate $^1$H NMR (300 MHz, CHLOROFORM-d) δ ppm 1.24-1.36 (m, 4 H) 1.54-1.64 (m, 1 H) 1.86-1.95 (m, 1 H) 2.47-2.58 (m, 1 H) 4.17 (q, J=7.1 Hz, 2 H) 7.06-7.13 (m, 2 H) 7.16-7.32 (m, 3 H).
MS ESI/APCI Dual posi: 191 [M+H]$^+$, 213 [M+Na]$^+$.

Ethyl cis-2-phenylcyclopropanecarboxylate $^1$H NMR (300 MHz, CHLOROFORM-d) δ ppm 0.97 (t, J=7.1 Hz, 3 H) 1.28-1.37 (m, 1 H) 1.66-1.76 (m, 1 H) 2.02-2.14 (m, 1 H) 2.51-2.66 (m, 1 H) 3.87 (q, J=7.1 Hz, 2 H) 7.14-7.31 (m, 5 H).
MS ESI/APCI Dual posi: 191 [M+H]$^+$, 213 [M+Na]$^+$.

(2) Synthesis of (cis-2-phenylcyclopropyl)methanol

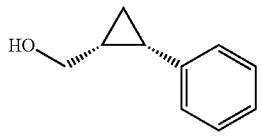

[Formula 87]

To a solution in diethyl ether (12.0 mL) of the ethyl cis-2-phenylcyclopropanecarboxylate (1.51 g) obtained in step (1) above, a suspension of aluminum lithium hydride (393 mg) in diethyl ether (12.0 mL) was added at 0° C. After being brought to room temperature, the mixture was stirred for 2 hours. After adding sodium sulfate decahydrate at 0° C., the reaction mixture was brought to room temperature and stirred for an hour. After removing the insoluble matter by filtration, the filtrate was concentrated under reduced pressure to give (cis-2-phenylcyclopropyl)methanol as a colorless oil (1.21 g).
$^1$H NMR (300 MHz, CHLOROFORM-d) δ ppm 0.84-0.94 (m, 1 H) 0.99-1.11 (m, 1 H) 1.42-1.58 (m, 1 H) 2.20-2.38 (m, 1 H) 3.18-3.34 (m, 1 H) 3.41-3.55 (m, 1 H) 7.11-7.35 (m, 5 H).
MS ESI/APCI Dual posi: 171 [M+Na]$^+$.

(3) Synthesis of the Titled Compound

The compound (1.21 g) obtained in step (2) above was used as the starting material and treated by the same technique as in Reference Example 19-1 to give the titled compound as a pale yellow oil (1.08 g).
$^1$H NMR (300 MHz, CHLOROFORM-d) δ ppm 1.53-1.65 (m, 1 H) 1.84-1.94 (m, 1 H) 2.08-2.20 (m, 1 H) 2.78-2.89 (m, 1 H) 7.19-7.37 (m, 5 H) 8.63-8.71 (m, 1 H).
MS ESI/APCI Dual posi: 147 [M+H]$^+$, 169 [M+Na]$^+$.

Reference Example 23-2 trans-2-Phenylcyclopropanecarbaldehyde

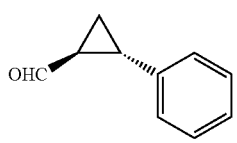

[Formula 88]

The ethyl trans-2-phenylcyclopropanecarboxylate (1.00 g) obtained in Reference Example 23-1(1) was used as the starting material and treated by the same techniques as in Reference Example 23-1(2) and Reference Example 19-1 to give a roughly purified product (620 mg) containing the titled compound.
$^1$H NMR (300 MHz, CHLOROFORM-d) δ ppm 1.49-1.59 (m, 1 H) 1.70-1.78 (m, 1 H) 2.13-2.23 (m, 1 H) 2.59-2.68 (m, 1 H) 7.08-7.16 (m, 2 H) 7.18-7.34 (m, 3 H) 9.30-9.35 (m, 1 H).
MS ESI/APCI Dual posi: 147 [M+H]$^+$.

Reference Example 23-3

2-(4-Fluorophenyl)cyclopropanecarbaldehyde

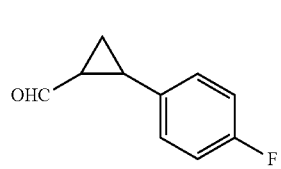

[Formula 89]

Instead of styrene, 4-fluorostyrene (10.0 g) was used and treated by the same techniques as in Reference Example 23-1(1) and (2) as well as Reference Example 19-1 to give the titled compound as a colorless oil (4.48 g).
$^1$H NMR (300 MHz, CHLOROFORM-d) δ ppm 1.31-1.55 (m, 1 H) 1.59-1.78 (m, 1 H) 1.80-2.19 (m, 1 H) 2.53-2.68 (m, 1 H) 6.91-7.16 (m, 4 H) 9.34 (d, J=4.5 Hz, 1 H).
MS ESI/APCI Dual posi: 165 [M+H]$^+$.

Reference Example 24-1 and Reference Example 24-2 trans-3-Phenylcyclobutanecarbaldehyde (Reference Example 24-1) and
cis-3-Phenylcyclobutanecarbaldehyde (Reference Example 24-2)

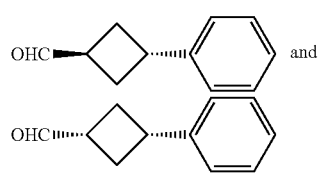

[Formula 90]

To a solution of diethyl isocyanomethylphosphonate (1.47 g) in tetrahydrofuran (45.0 mL), n-butyl lithium (2.69 mol/L, solution in n-hexane, 2.99 mL) was added at −78° C. and thereafter the mixture was stirred at that temperature for 80 minutes. After adding a solution of 3-phenylcyclobutanone (1.03 g) in tetrahydrofuran (15.0 mL) at −78° C. over a period of 30 minutes, the mixture was stirred at room temperature for 4 hours. After adding conc. hydrochloric acid (12.0 mL) at room temperature, the mixture was stirred at that temperature for 18 hours. Water was added to the reaction mixture which was then extracted with ethyl acetate twice. The combined organic layers were washed with saturated brine and thereafter dried over anhydrous magnesium sulfate. The insoluble matter was removed by filtration and the filtrate was concentrated under reduced pressure. The resulting residue was purified by silica gel column chromatography (n-hexane:ethyl acetate=99:1-96:4) to give the titled compound of Reference Example 24-1 as a colorless oil (160 mg) and the titled compound of Reference Example 24-2 as a colorless oil (390 mg).

trans-3-Phenylcyclobutanecarbaldehyde (Reference Example 24-1)

$^1$H NMR (300 MHz, CHLOROFORM-d) δ ppm 2.30-2.58 (m, 2 H) 2.65-2.83 (m, 2 H) 3.08-3.28 (m, 1 H) 3.47-3.68 (m, 1 H) 7.17-7.38 (m, 5 H) 9.94-9.97 (m, 1 H).

cis-3-Phenylcyclobutanecarbaldehyde (Reference Example 24-2)

$^1$H NMR (300 MHz, CHLOROFORM-d) δ ppm 2.30-2.49 (m, 2 H) 2.51-2.65 (m, 2 H) 3.13-3.29 (m, 1 H) 3.53-3.68 (m, 1 H) 7.17-7.37 (m, 5 H) 9.71-9.75 (m, 1 H).

Reference Example 24-3 trans-3-(4-Fluorophenyl)cyclobutanecarbaldehyde

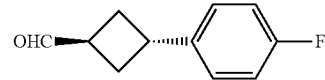

[Formula 91]

Instead of 3-phenylcyclobutanone, 3-(4-fluorophenyl)cyclobutanone (4.63 g) was used and treated by the same technique as in Reference Example 24-1 to give the titled compound as a colorless oil (720 mg).

$^1$H NMR (300 MHz, CHLOROFORM-d) δ ppm 2.26-2.45 (m, 2 H) 2.63-2.81 (m, 2 H) 3.09-3.24 (m, 1 H) 3.47-3.65 (m, 1 H) 6.94-7.07 (m, 2 H) 7.12-7.23 (m, 2 H) 9.95 (d, J=1.7 Hz, 1 H).

MS ESI/APCI Dual nega: 177 [M−H]$^-$.

Reference Example 25-1

4-Benzylcyclohexanone

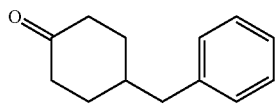

[Formula 92]

(1) Synthesis of 9-benzyl-3,3-dimethyl-1,5-dioxaspiro[5.5]undecan-9-ol

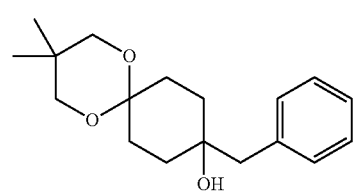

[Formula 93]

To a solution of 1,4-cyclohexanedione mono-2,2-dimethyltrimethylene ketal (3.76 g) and zinc chloride (about 1.0 mol/L, solution in diethyl ether, 1.90 mL) in tetrahydrofuran (63.0 mL), benzylmagnesium bromide (about 1.0 mol/L, solution in tetrahydrofuran, 24.7 mL) was added at 0° C. and thereafter the mixture was stirred at that temperature for 2.5 hours. To the reaction mixture, a saturated aqueous solution of ammonium chloride was added and three extractions were conducted with ethyl acetate. The combined organic layers were washed with saturated brine and thereafter dried over anhydrous magnesium sulfate. The desiccant was removed by filtration and the filtrate was concentrated under reduced pressure. The resulting residue was purified by silica gel column chromatography (n-hexane:ethyl acetate=95:5-60:40) to give 9-benzyl-3,3-dimethyl-1,5-dioxaspiro[5.5]undecan-9-ol as a colorless solid (1.28 g).

$^1$H NMR (300 MHz, CHLOROFORM-d) δ ppm 0.97 (s, 6 H) 1.43-1.89 (m, 6 H) 1.95-2.13 (m, 2 H) 2.76 (s, 2 H) 3.41-3.58 (m, 4 H) 7.16-7.36 (m, 5 H).

MS ESI/APCI Dual posi: 313 [M+Na]$^+$.

(2) Synthesis of the Titled Compound

To a solution in toluene (44.0 mL) of the compound (1.28 g) obtained in step (1) above, p-toluenesulfonic acid monohydrate (84.0 mg) was added and thereafter the mixture was refluxed for 3 hours with a Dean-Stark apparatus. After being cooled to room temperature, the reaction mixture was concentrated under reduced pressure. The resulting residue was purified by silica gel column chromatography (n-hexane:ethyl acetate=100:0-50:50). A suspension of the resulting purified product (935 mg) and 20% palladium hydroxide/carbon (93.5 mg) in methanol (11.3 mL) was stirred at room temperature for 5 hours in a hydrogen atmosphere. The reaction mixture was filtered through Celite (registered trademark). The filtrate was concentrated under reduced pressure. To a solution of the resulting residue (938 mg) in tetrahydrofuran (34.3 mL), 1 mol/L hydrochloric acid (9.30 mL) was added at 0° C. and the mixture was stirred at room temperature for 14.5 hours. After concentrating the stirred mixture under reduced pressure, three extractions were conducted with ethyl acetate. The combined organic layers were washed with saturated brine. After passage through a phase separator, the washed organic layers were concentrated under reduced pressure. The resulting residue was purified by silica gel column chromatography (n-hexane:ethyl acetate=90:10-50:50) to give the titled compound as a colorless oil (225 mg).

$^1$H NMR (300 MHz, CHLOROFORM-d) δ ppm 1.36-1.52 (m, 2 H) 1.95-2.10 (m, 3 H) 2.22-2.45 (m, 4 H) 2.62 (d, J=6.7 Hz, 2 H) 7.10-7.36 (m, 5 H).

MS ESI/APCI Dual posi: 189 [M+H]$^+$, 211 [M+Na]$^+$.

Reference Example 26-1

1-(Biphenyl-4-yl)propan-1-one

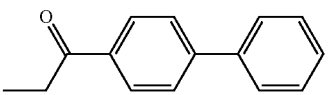

[Formula 94]

(1) Synthesis of 1-(biphenyl-4-yl)propan-1-ol

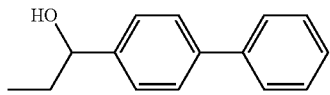

[Formula 95]

To a solution of 4-phenylbenzaldehyde (1.20 g) in diethyl ether (13.2 mL), ethylmagnesium bromide (about 3.0 mol/L, solution in diethyl ether, 3.29 mL) was added at 0° C. After stirring the mixture at room temperature for 3 hours, the precipitate was recovered by filtration. After dissolving the recovered precipitate in a liquid mixture of ethyl acetate and a saturated aqueous solution of ammonium chloride, three extractions were conducted with ethyl acetate. The combined organic layers were washed with saturated brine. After passage through a phase separator, the washed organic layers were concentrated under reduced pressure. The resulting residue was purified by silica gel column chromatography (n-hexane:ethyl acetate=100:0-70:30) to give 1-(biphenyl-4-yl)propan-1-ol as a colorless solid (1.27 g).

$^1$H NMR (300 MHz, CHLOROFORM-d) δ ppm 0.96 (t, J=7.4 Hz, 3 H) 1.72-1.98 (m, 2 H) 4.59-4.71 (m, 1 H) 7.29-7.48 (m, 5 H) 7.54-7.63 (m, 4 H).

MS EI posi: 212 [M]$^+$.

(2) Synthesis of the Titled Compound

To a solution in diethyl ether (30.0 mL) of the compound (1.27 g) obtained in step (1) above, manganese(IV) oxide (9.57 g) was added and the mixture was stirred at room temperature for 45 hours. After removing the insoluble matter by filtration, the filtrate was concentrated under reduced pressure. To a solution of the resulting residue in acetone (60.0 mL), a Jones' reagent {see Org. Synth., Coll. Vol. VI, 542 (1988)}(1.20 mL) was added until the color of the Jones' reagent was yet to disappear. The reaction mixture was concentrated under reduced pressure and ethyl acetate and water were added to the residue. Extraction with ethyl acetate was conducted three times and the combined organic layers were washed with saturated brine. After passage through a phase separator, the washed organic layers were concentrated under reduced pressure. The resulting residue was recrystallized with n-hexane to give the titled compound as a colorless solid (921 mg).

$^1$H NMR (300 MHz, CHLOROFORM-d) δ ppm 1.26 (t, J=7.3 Hz, 3 H) 3.04 (q, J=7.3 Hz, 2 H) 7.34-7.52 (m, 3 H) 7.58-7.73 (m, 4 H) 8.00-8.09 (m, 2 H).

MS ESI/APCI Dual posi: 211 [M+H]$^+$, 233 [M+Na]$^+$.

Reference Example 27-1

1-(Biphenyl-4-yl)cyclopropaneamine

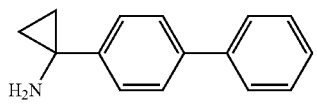

[Formula 96]

The compound 4-cyanobiphenyl (2.83 g) was used as the starting material and treated by the same technique as in Reference Example 4-1(2) to give the titled compound as a pale yellow solid (1.06 g).

$^1$H NMR (300 MHz, CHLOROFORM-d) δ ppm 0.99-1.07 (m, 2 H) 1.08-1.15 (m, 2 H) 7.28-7.49 (m, 5 H) 7.51-7.62 (m, 4 H).

MS ESI/APCI Dual posi: 210 [M+H]$^+$.

Reference Example 27-2

1-[4-(Trifluoromethyl)phenyl]cyclopropaneamine

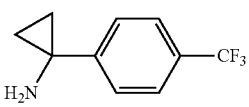

[Formula 97]

The compound 4-(trifluoromethyl)benzonitrile (5.18 g) was used as the starting material and treated by the same technique as in Reference Example 4-1(2) to give the titled compound as a pale yellow solid (2.92 g).

$^1$H NMR (300 MHz, CHLOROFORM-d) δ ppm 1.00-1.07 (m, 2 H) 1.11-1.19 (m, 2 H) 7.31-7.45 (m, 2 H) 7.49-7.64 (m, 2 H).

MS ESI/APCI Dual posi: 202 [M+H]$^+$.

Reference Example 27-3

2-[4-(Trifluoromethyl)phenyl]propane-2-amine

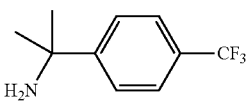

[Formula 98]

To a solution of 4-(trifluoromethyl)benzonitrile (3.01 g) in diethyl ether (88.0 mL), methylmagnesium bromide (about 3.0 mol/L, solution in diethyl ether, 17.6 mL) was added and the mixture was stirred at room temperature for 40 minutes. To the reaction mixture, tetraisopropyl orthotitanate (5.15 mL) was added slowly and thereafter the mixture was refluxed for 6 hours. After cooling the mixture to 0° C., an aqueous solution of 20% sodium hydroxide was added and the mixture was stirred at room temperature for an hour. After phase separation, the aqueous layer was extracted with diethyl ether twice. The combined organic layers were passed through a phase separator and thereafter concentrated under reduced pressure. The resulting residue was dissolved in 5% hydrochloric acid and washed with diethyl ether twice. The aqueous layer was rendered basic with an aqueous solution of 20% sodium hydroxide and extracted with diethyl ether three times. The combined organic layers were washed with saturated brine and thereafter passed through a phase separator to be concentrated under reduced pressure. The resulting residue was purified by silica gel column chromatography (n-hexane:ethyl acetate=95:5-10:90) to give the titled compound as a yellow oil (1.81 g).

$^1$H NMR (300 MHz, CHLOROFORM-d) δ ppm 1.51 (s, 6 H) 7.54-7.69 (m, 4 H).

MS ESI/APCI Dual posi: 204 [M+H]$^+$.

Reference Example 28-1

Methyl (3S)-3-amino-4-methoxybutanoate hydrochloride

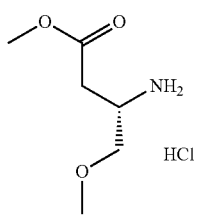

[Formula 99]

(1) Synthesis of tert-butyl [(2S)-1-cyano-3-hydroxypropan-2-yl]carbamate

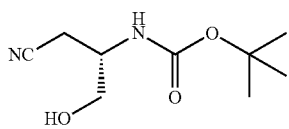

[Formula 100]

To a solution of N-α-(tert-butoxycarbonyl)-β-cyano-L-alanine (1.00 g) in tetrahydrofuran (13 mL), isobutyl chloroformate (674 μL) and triethylamine (716 μL) were added successively at 0° C. and the mixture was stirred at that temperature for 2 hours. After removing the precipitate by filtration, the filtrate was concentrated under reduced pressure. To a mixture of the resulting residue, tetrahydrofuran (13 mL) and water (4 mL), sodium borohydride (530 mg) were added and the mixture was stirred at room temperature for 30 minutes. After adding water, extraction was conducted with ethyl acetate. The combined organic layers were washed with saturated brine and thereafter passed through a phase separator to be concentrated under reduced pressure. The resulting residue was purified by silica gel column chromatography (n-hexane:ethyl acetate=80:20-40:60) to give tert-butyl [(2S)-1-cyano-3-hydroxypropan-2-yl]carbamate as a colorless oil (650 mg).

$^1$H NMR (300 MHz, CHLOROFORM-d) δ ppm 1.46 (s, 9 H) 2.10-2.18 (m, 1 H) 2.63-2.78 (m, 2 H) 3.69-3.88 (m, 2 H) 3.89-4.03 (m, 1 H) 5.02 (br. s., 1 H).
MS ESI/APCI Dual posi: 223 [M+Na]$^+$.

(2) Synthesis of tert-butyl [(2S)-1-cyano-3-methoxypropan-2-yl]carbamate

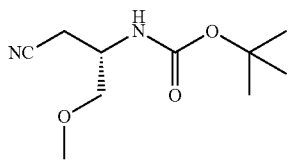

[Formula 101]

To a solution in tetrahydrofuran (10 mL) of the compound (650 mg) obtained in step (1) above, sodium hydride (60% dispersion in mineral oil, 143 mg) was added under cooling with ice. After stirring the mixture at the same temperature for 10 minutes, methyl iodide (603 μL) was added. After stirring the mixture at the same temperature for 30 minutes and then at room temperature for an hour, water was added and extraction was conducted with ethyl acetate. The combined organic layers were passed through a phase separator and concentrated under reduced pressure. The resulting residue was purified by silica gel column chromatography (n-hexane:ethyl acetate=90:10-60:40) to give tert-butyl [(2S)-1-cyano-3-methoxypropan-2-yl]carbamate as a colorless oil (247 mg).

$^1$H NMR (300 MHz, CHLOROFORM-d) δ ppm 1.45 (s, 9 H) 2.69 (d, J=6.2 Hz, 2 H) 3.39 (s, 3 H) 3.41-3.49 (m, 1 H) 3.53-3.61 (m, 1 H) 4.02 (br. s., 1 H) 4.96 (br. s., 1 H).
MS ESI/APCI Dual posi: 237 [M+Na]$^+$.
MS ESI/APCI Dual nega: 213 [M−H]$^-$.

(3) Synthesis of the Titled Compound

To a solution in 1,4-dioxane (2.0 mL) of the compound (247 mg) obtained in step (2) above, conc. hydrochloric acid (3.0 mL) was added and the mixture was stirred at 100° C. for an hour. After being cooled to room temperature, the reaction mixture was concentrated under reduced pressure. The resulting residue was used as the starting material and treated by the same technique as in Reference Example 3-4 to give the titled compound as a colorless solid (247 mg).

$^1$H NMR (300 MHz, DMSO-d$_6$) δ ppm 2.60-2.84 (m, 2 H) 3.30 (s, 3 H) 3.44-3.59 (m, 3 H) 3.64 (s, 3 H).
MS ESI/APCI Dual posi: 148 [M+H]$^+$.

Reference Example 28-2

Methyl (3 S)-3-amino-4-(dimethylamino)butanoate hydrochloride

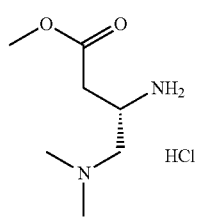

[Formula 102]

(1) Synthesis of (2S)-2-[(tert-butoxycarbonyl)amino]-3-cyanopropyl 4-methylbenzenesulfonate

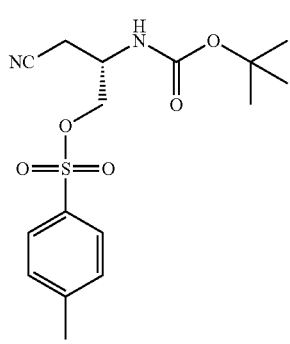

[Formula 103]

To a solution in chloroform (20 mL) of the compound (820 mg) obtained in Reference Example 28-1(1), p-toluenesulfonyl chloride (1.56 g) and triethylamine (1.14 mL) were added and the mixture was stirred at room temperature for 3 hours. After adding more p-toluenesulfonyl chloride (1.56 g) and triethylamine (1.14 mL), the mixture was stirred at room temperature for 30 minutes. Subsequently, a saturated aqueous solution of sodium hydrogencarbonate was added and extraction was conducted with chloroform. The combined organic layers were passed through a phase separator and thereafter concentrated under reduced pressure. The resulting residue was purified by silica gel column chromatography (n-hexane:ethyl acetate=80:20-40:60) to give (2S)-2-[(tert-butoxycarbonyl)amino]-3-cyanopropyl 4-methylbenzenesulfonate as a colorless solid (1.32 g).

$^1$H NMR (300 MHz, CHLOROFORM-d) δ ppm 1.43 (s, 9 H) 2.47 (s, 3 H) 2.63-2.71 (m, 2 H) 4.02-4.21 (m, 3 H) 4.86-5.01 (m, 1 H) 7.39 (d, J=8.5 Hz, 2 H) 7.81 (d, J=8.5 Hz, 2 H).

MS ESI/APCI Dual posi: 377 [M+Na]$^+$.

(2) Synthesis of tert-butyl [(2S)-1-cyano-3-(dimethylamino)propan-2-yl]carbamate

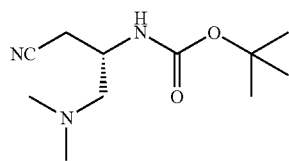

[Formula 104]

To a solution in ethanol (20 mL) of the compound (1.32 g) obtained in step (1) above, dimethylamine (about 50%, aqueous solution, 3.92 mL) and triethylamine (519 μL) were added and the mixture was stirred at 80° C. for an hour. After being cooled to room temperature, the reaction mixture was concentrated under reduced pressure. To the resulting residue, a saturated aqueous solution of sodium hydrogencarbonate was added and extraction was conducted with ethyl acetate. The combined organic layers were washed with saturated brine and after passage through a phase separator, they were concentrated under reduced pressure. The resulting residue was purified by silica gel column chromatography (chloroform:methanol=99:1-95:5) to give tert-butyl [(2S)-1-cyano-3-(dimethylamino)propan-2-yl]carbamate as a pale yellow oil (340 mg).

$^1$H NMR (300 MHz, CHLOROFORM-d) δ ppm 1.45 (s, 9 H) 2.25 (s, 6 H) 2.31-2.55 (m, 2 H) 2.62-2.76 (m, 1 H) 2.78-2.91 (m, 1 H) 3.74-3.90 (m, 1 H) 4.99 (br. s., 1 H).

MS ESI/APCI Dual posi: 228 [M+H]$^+$, 250 [M+Na]$^+$.

MS ESI/APCI Dual nega: 226 [M−H]$^−$.

(3) Synthesis of the Titled Compound

The compound (340 mg) obtained in step (2) above was used as the starting material and treated by the same technique as in Reference Example 28-1(3) to give the titled compound. Note that the titled compound was used in a subsequent reaction as it remained a crude product.

Reference Example 29-1

Methyl (3-amino-5-oxopyrrolidin-3-yl)acetate

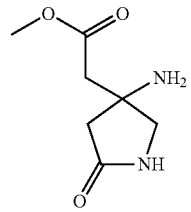

[Formula 105]

(1) Synthesis of 2-tert-butyl 1,3-dimethyl 2-cyanopropane-1,2,3-tricarboxylate

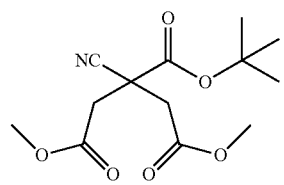

[Formula 106]

To a solution of tert-butyl cyanoacetate (10.0 g) in toluene (100 mL), sodium hydride (60% dispersion in mineral oil, 2.83 g) was added under cooling with ice. After being stirred at 80° C. for an hour, the mixture was cooled to 50° C. and methyl bromoacetate (6.51 mL) was added slowly. After adding tetrahydrofuran (15 mL), the mixture was stirred at 80° C. for two hours. The reaction mixture was cooled with ice and then sodium hydride (60% dispersion in mineral oil, 2.83 g) was added. After being stirred at 80° C. for an hour, the mixture was cooled to 50° C. and then methyl bromoacetate (6.51 mL) was added slowly. Subsequently, tetrahydrofuran (15 mL) was added and the mixture was stirred at 80° C. for two hours. After the reaction mixture to room temperature, a saturated aqueous solution of ammonium chloride and water were added and extraction was conducted with ethyl acetate. The combined organic layers were washed with water, a saturated aqueous solution of sodium hydrogen carbonate, and saturated brine successively and then dried over anhydrous magnesium sulfate. The desiccant was removed by filtration and the filtrate was concentrated under reduced pressure. The resulting residue was purified by silica gel column chromatography (n-hexane:ethyl acetate=100:0-40:60) to give 2-tert-butyl 1,3-dimethyl 2-cyanopropane-1,2,3-tricarboxylate as a pale yellow oil (17.8 g).

$^1$H NMR (300 MHz, CHLOROFORM-d) δ ppm 1.52 (s, 9 H) 2.96-3.12 (m, 4 H) 3.74 (s, 6 H).

MS ESI/APCI Dual posi: 286 [M+H]$^+$, 308 [M+Na]$^+$.

(2) Synthesis of tert-butyl 3-(2-methoxy-2-oxoethyl)-5-oxopyrrolidine-3-carboxylate

[Formula 107]

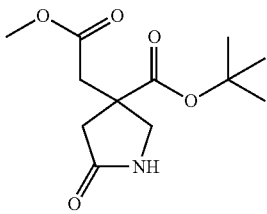

To a solution in methanol (70 mL) of the compound (5.00 g) obtained in step (1) above, a Raney nickel catalyst (about 7.5 g) was added. The mixture was stirred at 70° C. for 8 hours in a hydrogen atmosphere with 0.4 megapascals (MPa). After being cooled to room temperature, the reaction mixture was filtered through Celite (registered trademark) and the filtrate was concentrated under reduced pressure. To the resulting residue, diethyl ether (50 mL) and hexane (10 mL) were added and the mixture was stirred at room temperature for 15 minutes. The resulting precipitate was recovered by filtration to give tert-butyl 3-(2-methoxy-2-oxoethyl)-5-oxopyrrolidine-3-carboxylate as a colorless solid (1.75 g).

$^1$H NMR (300 MHz, CHLOROFORM-d) δ ppm 1.46 (s, 9 H) 2.33 (d, J=17.4 Hz, 1 H) 2.79-2.90 (m, 3 H) 3.35 (dd, J=10.3, 0.8 Hz, 1 H) 3.69 (s, 3 H) 3.84 (dd, J=10.3, 0.8 Hz, 1 H) 5.73 (br. s., 1 H).

MS ESI/APCI Dual posi: 258 [M+H]$^+$, 280 [M+Na]$^+$.

(3) Synthesis of methyl (3-{[(benzyloxy)carbonyl]amino}-5-oxopyrrolidin-3-yl)acetate

[Formula 108]

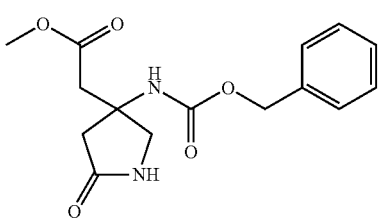

To the compound (3.41 g) obtained in step (2) above, trifluoroacetic acid (30 mL) was added and the mixture was stirred at room temperature for 4 hours. After concentrating under reduced pressure, chloroform was added to the resulting residue, which was concentrated again under reduced pressure. To a solution of the resulting residue in benzene (50 mL), there were successively added tetrahydrofuran (12 mL), triethylamine (3.71 mL), diphenylphosphoryl azide (3.73 mL) and benzyl alcohol (1.79 mL) and the mixture was stirred for 4 hours under reflux with heating. After cooling the reaction mixture to room temperature, ethyl acetate was added to it, which was then washed with water, an aqueous solution of 10% citric acid, a saturated aqueous solution of sodium hydrogen carbonate, and saturated brine successively and dried over anhydrous magnesium sulfate. The desiccant was removed by filtration and the filtrate was concentrated under reduced pressure. The resulting residue was purified by silica gel column chromatography (chloroform:methanol=100:0-85:15) to give methyl (3-{[(benzyloxy)carbonyl]amino}-5-oxopyrrolidin-3-yl)acetate as a colorless gum (1.91 g).

$^1$H NMR (300 MHz, CHLOROFORM-d) δ ppm 2.57 (d, J=17.2 Hz, 1 H) 2.78 (d, J=17.2 Hz, 1 H) 2.91 (d, J=16.2 Hz, 1 H) 3.01 (d, J=16.2 Hz, 1 H) 3.51 (dd, J=10.6, 0.8 Hz, 1 H) 3.67 (s, 3 H) 3.70-3.81 (m, 1 H) 5.08 (s, 2 H) 5.46 (br. s., 1 H) 5.69 (br. s., 1 H) 7.27-7.42 (m, 5 H).

MS ESI/APCI Dual posi: 307 [M+H]$^+$, 329 [M+Na]$^+$.
MS ESI/APCI Dual nega: 341 [M+Cl]$^-$.

(4) Synthesis of the Titled Compound

To a solution in methanol (30 mL) of the compound (1.91 g) obtained in step (3) above, 20% palladium hydroxide/carbon (191 mg) was added and the mixture was stirred at room temperature for an hour in a hydrogen atmosphere. The reaction mixture was filtered through Celite (registered trademark). The filtrate was concentrated under reduced pressure to give the titled compound as a colorless oil (1.12 g).

$^1$H NMR (300 MHz, CHLOROFORM-d) δ ppm 2.32 (d, J=16.7 Hz, 1 H) 2.47 (d, J=16.7 Hz, 1 H) 2.61-2.75 (m, 2 H) 3.33 (d, J=10.2 Hz, 1 H) 3.46 (d, J=10.2 Hz, 1 H) 3.72 (s, 3 H) 5.72 (br. s., 1 H).

MS ESI/APCI Dual posi: 173 [M+H]$^+$.

Reference Example 29-2

Methyl (3-amino-1-methyl-5-oxopyrrolidin-3-yl)acetate

[Formula 109]

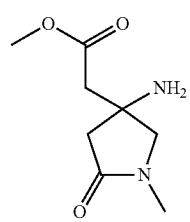

(1) Synthesis of tert-butyl 3-(2-methoxy-2-oxoethyl)-1-methyl-5-oxopyrrolidine-3-carboxylate

[Formula 110]

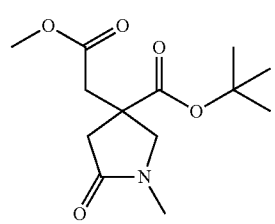

The compound (4.0 g) obtained in Reference Example 29-1(2) was used as the starting material and treated by the same technique as in Reference Example 28-1(2) to give tert-butyl 3-(2-methoxy-2-oxoethyl)-1-methyl-5-oxopyrrolidine-3-carboxylate as a pale yellow oil (3.74 g).

$^1$H NMR (300 MHz, CHLOROFORM-d) δ ppm 1.45 (s, 9 H) 2.39 (d, J=17.3 Hz, 1 H) 2.70 (d, J=16.6 Hz, 1 H) 2.79-2.90 (m, 5 H) 3.32 (d, J=10.6 Hz, 1 H) 3.69 (s, 3 H) 3.86 (d, J=10.6 Hz, 1 H).

MS ESI/APCI Dual posi: 272 [M+H]$^+$.

(2) Synthesis of the Titled Compound

The compound (3.74 g) obtained in step (1) above was used as the starting material and treated by the same techniques as in Reference Example 29-1(3) and (4) to give the titled compound.

$^1$H NMR (300 MHz, CHLOROFORM-d) δ ppm 2.36-2.45 (m, 1 H) 2.47-2.56 (m, 1 H) 2.59-2.72 (m, 2 H) 2.85-2.89 (m, 3 H) 3.33 (d, J=10.4 Hz, 1 H) 3.47 (d, J=10.4 Hz, 1 H) 3.72 (s, 3 H).

MS ESI/APCI Dual posi: 187 [M+H]$^+$. 209 [M+Na]$^+$.

Reference Example 30-1

Methyl L-α-asparaginate

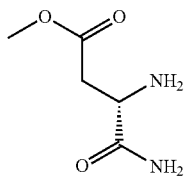

[Formula 111]

To a solution of N-α-(9-fluorenylmethoxycarbonyl)-L-aspartic α-amide (744 mg) in tetrahydrofuran (8 mL), trimethylsilyldiazomethane (2.0 mol/L, solution in diethyl ether, 1.20 mL) and methanol (808 μL) were added under cooling with ice. After being brought to room temperature, the mixture was stirred for 2.5 hours. The reaction mixture was then concentrated under reduced pressure. To a solution of the resulting residue in acetonitrile (14 mL), diethylamine (621 μL) was added and the mixture was stirred at room temperature for 3 hours. The reaction mixture was concentrated under reduced pressure and to the resulting residue, diethyl ether was added and the mixture was stirred. The resulting precipitate was recovered by filtration to give the titled compound as a colorless solid (274 mg).

$^1$H NMR (300 MHz, DMSO-d$_6$) δ ppm 2.37 (dd, J=15.6, 8.2 Hz, 1 H) 2.62 (dd, J=15.6, 5.1 Hz, 1 H) 3.46 (dd, J=8.2, 5.1 Hz, 1 H) 3.58 (s, 3 H).

MS ESI/APCI Dual posi: 169 [M+Na]$^+$.

Reference Example 30-2

Methyl D-α-asparaginate

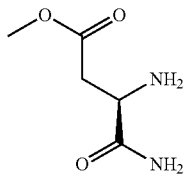

[Formula 112]

Instead of N-α-(9-fluorenylmethoxycarbonyl)-L-aspartic α-amide, N-α-(9-fluorenylmethoxycarbonyl)-D-aspartic α-amide was used and treated by the same technique as in Reference Example 30-1 to give the titled compound as a colorless oil. Note that the titled compound was used in a subsequent reaction as it remained a crude product.

Reference Example 31-1

6-[(1-Methylcyclopropyl)methoxy]pyridine-3-carbaldehyde

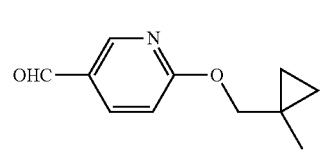

[Formula 113]

(1) Synthesis of 6-chloro-N-methoxy-N-methylpyridine-3-carboxamide

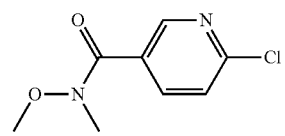

[Formula 114]

Instead of 4-(bromomethyl)benzoic acid, 6-chloronicotinic acid (6.50 g) was used and treated by the same technique as in Reference Example 16-1(1) to give 6-chloro-N-methoxy-N-methylpyridine-3-carboxamide as a colorless oil (7.55 g).

$^1$H NMR (300 MHz, CHLOROFORM-d) δ ppm 3.39 (s, 3 H) 3.56 (s, 3 H) 7.39 (dd, J=8.3, 0.7 Hz, 1 H) 8.03 (dd, J=8.3, 2.3 Hz, 1 H) 8.78 (dd, J=2.3, 0.7 Hz, 1 H).

MS ESI/APCI Dual posi: 201 [M+H]$^+$.

(2) Synthesis of N-methoxy-N-methyl-6-[(1-methylcyclopropyl)methoxy]pyridine-3-carboxamide

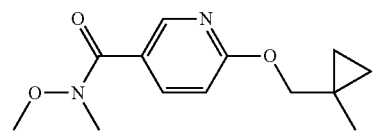

[Formula 115]

To a solution of potassium tert-butoxide (1.68 g) in tetrahydrofuran (30 mL), a solution of 1-methylcyclopropanemethanol (1.29 g) in tetrahydrofuran (5 mL) was added and the mixture was stirred at room temperature for 10 minutes. After the reaction mixture was cooled to 0° C., a solution in tetrahydrofuran (5 mL) of the compound (3.00 g) obtained in step (1) above was added and after being brought to room temperature, the reaction mixture was stirred for an hour. The reaction mixture was then concentrated under reduced pressure and the resulting residue was purified by silica gel column chromatography (n-hexane:ethyl acetate=95:5-50:50) to give N-methoxy-N-methyl-6-[(1-methylcyclopropyl)methoxy]pyridine-3-carboxamide as a colorless oil (2.02 g).

$^1$H NMR (300 MHz, CHLOROFORM-d) δ ppm 0.38-0.47 (m, 2 H) 0.52-0.60 (m, 2 H) 1.23 (s, 3 H) 3.37 (s, 3 H) 3.58 (s, 3 H) 4.15 (s, 2 H) 6.73-6.84 (m, 1 H) 8.00 (dd, J=8.7, 2.3 Hz, 1 H) 8.60 (dd, J=2.3, 0.7 Hz, 1 H).

MS ESI/APCI Dual posi: 251 [M+H]$^+$.

(3) Synthesis of the Titled Compound

The compound (2.00 g) obtained in step (2) above was used and treated by the same technique as in Reference Example 16-1(3) to give the titled compound as a colorless oil (1.51 g).

$^1$H NMR (300 MHz, CHLOROFORM-d) δ ppm 0.39-0.48 (m, 2 H) 0.53-0.62 (m, 2 H) 1.23 (s, 3 H) 4.20 (s, 2 H) 6.83-6.92 (m, 1 H) 8.02-8.11 (m, 1 H) 8.52-8.63 (m, 1 H) 9.91-9.97 (m, 1 H).

MS ESI/APCI Dual posi: 192 [M+H]$^+$.

Reference Example 31-2

6-(2-Cyclopropylethoxyl)pyridine-3-carbaldehyde

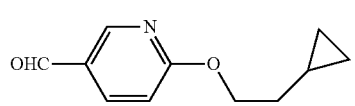

[Formula 116]

Instead of 1-methylcyclopropanemethanol, 2-cyclopropylethanol (1.29 g) was used and treated by the same technique as in Reference Example 31-1 to give the titled compound as a colorless oil (1.25 g).

$^1$H NMR (300 MHz, CHLOROFORM-d) δ ppm 0.08-0.18 (m, 2 H) 0.42-0.54 (m, 2 H) 0.75-0.89 (m, 1 H) 1.63-1.75 (m, 2 H) 4.48 (t, J=6.8 Hz, 2 H) 6.77-6.88 (m, 1 H) 8.01-8.10 (m, 1 H) 8.58-8.67 (m, 1 H) 9.92-9.98 (m, 1 H).

MS ESI/APCI Dual posi: 192 [M+H]$^+$.

Reference Example 32-1 trans-4-(4-Chlorophenoxyl)cyclohexanecarbaldehyde

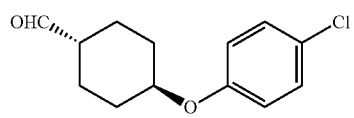

[Formula 117]

(1) Synthesis of cis-4-hydroxy-N-methoxy-N-methylcyclohexanecarboxamide

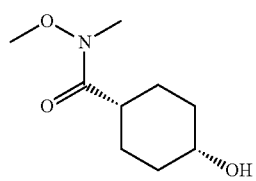

[Formula 118]

Instead of 4-(bromomethyl)benzoic acid, cis-4-hydroxycyclohexanecarboxylic acid (1.45 g) was used and treated by the same technique as in Reference Example 16-1(1) to give cis-4-hydroxy-N-methoxy-N-methylcyclohexanecarboxamide as a yellow oil (0.87 g).

$^1$H NMR (300 MHz, CHLOROFORM-d) δ ppm 1.49-1.74 (m, 4 H) 1.79-2.02 (m, 4 H) 2.65-2.79 (m, 1 H) 3.19 (s, 3 H) 3.70 (s, 3 H) 3.99-4.08 (m, 1 H).

MS ESI/APCI Dual posi: 188 [M+H]$^+$.

(2) Synthesis of trans-4-(4-chlorophenoxy)-N-methoxy-N-methylcyclohexanecarboxamide

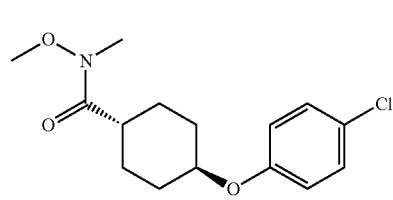

[Formula 119]

Instead of 2-cyclopropylethanol and 4-hydroxybenzaldehyde, the compound (850 mg) obtained in step (1) above and p-chlorophenol (700 mg) were respectively used and treated by the same technique as in Reference Example 11-1 to give trans-4-(4-chlorophenoxy)-N-methoxy-N-methylcyclohexanecarboxamide as a colorless solid (458 mg).

$^1$H NMR (300 MHz, CHLOROFORM-d) δ ppm 1.37-1.75 (m, 4 H) 1.86-1.98 (m, 2 H) 2.16-2.29 (m, 2 H) 2.65-2.79 (m, 1 H) 3.19 (s, 3 H) 3.72 (s, 3 H) 4.06-4.26 (m, 1 H) 6.78-6.88 (m, 2 H) 7.18-7.25 (m, 2 H).

MS ESI/APCI Dual posi: 298 [M+H]$^+$.

(3) Synthesis of the Titled Compound

The compound (455 mg) obtained in step (2) above was used and treated by the same technique as in Reference Example 23-1(2) to give the titled compound as a pale yellow solid (379 mg).

$^1$H NMR (300 MHz, CHLOROFORM-d) δ ppm 1.38-1.64 (m, 4 H) 2.01-2.21 (m, 4 H) 2.25-2.39 (m, 1 H) 4.03-4.27 (m, 1 H) 6.78-6.87 (m, 2 H) 7.18-7.26 (m, 2 H) 9.66-9.72 (m, 1 H).

MS ESI/APCI Dual nega: 237 [M−H]$^-$.

In the following Reference Examples 32-2 to 32-9, a commercial grade of the corresponding phenols and a commercial grade of the corresponding alcohols were used and treated by the method described in Reference Example 32-1 or modifications thereof to synthesize the intended compounds. The structures of the synthesized compounds and their NMR and MS data are shown in Table 11-1.

TABLE 11-1

| Compound No. | Structure | Analytical Data | Salt information |
|---|---|---|---|
| Reference Example 32-2 | 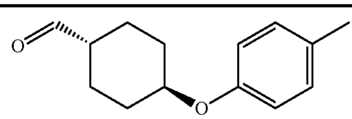 | $^1$H NMR (300 MHz, CHLOROFORM-d ) δ ppm 1.37-1.64 (m, 4 H) 2.02-2.21 (m, 4 H) 2.24-2.37 (m, 4 H) 4.06-4.24 (m, 1 H) 6.75-6.84 (m, 2 H) 7.02-7.12 (m, 2 H) 9.65-9.71 (m, 1H). | |
| Reference Example 32-3 | 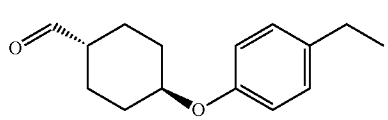 [SMILES: CCc1ccc(O[C@H]2CC[C@H](C=O)CC2)cc1] | $^1$H NMR (300 MHz, CHLOROFORM-d ) δ ppm 1.21 (t, J = 7.6 Hz, 3 H) 1.34-1.64 (m, 4 H) 2.00-2.39 (m, 5 H) 2.59 (q, J = 7.6 Hz, 2 H) 4.08-4.24 (m, 1 H) 6.73-6.89 (m, 2 H) 7.05-7.15 (m, 2 H) 9.63-9.74 (m, 1 H). | |

TABLE 11-1-continued

| Compound No. | Structure | Analytical Data | Salt information |
|---|---|---|---|
| Reference Example 32-4 | 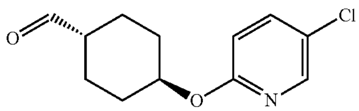 [SMILES: O=C[C@H]1CC[C@H](Oc2ccc(Cl)cn2)CC1] | ¹H NMR (300 MHz, CHLOROFORM-d ) δ ppm 1.34-1.66 (m, 4 H) 1.84-2.39 (m, 5 H) 4.84-5.03 (m, 1 H) 6.57-6.69 (m, 1 H) 7.43-7.55 (m, 1 H) 8.03-8.10 (m, 1 H) 9.62-9.72 (m, 1 H). | |
| Reference Example 32-5 | 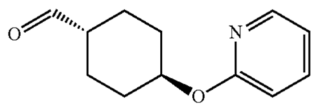 [SMILES: O=C[C@H]1CC[C@H](Oc2ccccn2)CC1] | ¹H NMR (300 MHz, CHLOROFORM-d ) δ ppm 1.34-1.76 (m, 4 H) 1.99-2.37 (m, 5 H) 4.92-5.09 (m, 1 H) 6.63-6.73 (m, 1 H) 6.79-6.89 (m, 1 H) 7.49-7.61 (m, 1 H) 8.08-8.17 (m, 1 H) 9.64-9.74 (m, 1 H). MS ESI/APCI Dual posi: 206[M + H]⁺. | |
| Reference Example 32-6 | 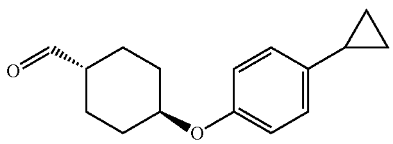 [SMILES: O=C[C@H]1CC[C@H](Oc2ccc(C3CC3)cc2)CC1] | ¹H NMR (300 MHz, CHLOROFORM-d ) δ ppm 0.56-0.66 (m, 2 H) 0.83-0.95 (m, 2 H) 1.35-1.67 (m, 4 H) 1.76-1.91 (m, 1 H) 2.03-2.38 (m, 5 H) 4.04-4.28 (m, 1 H) 6.76-6.84 (m, 2 H) 6.96-7.03 (m, 2 H) 9.66-9.72 (m, 1 H). | |
| Reference Example 32-7 | 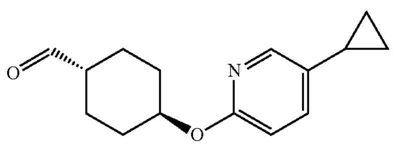 [SMILES: O=C[C@H]1CC[C@H](Oc2ccc(C3CC3)cn2)CC1] | ¹H NMR (300 MHz, CHLOROFORM-d ) δ ppm 0.52-0.69 (m, 2 H) 0.84-1.01 (m, 2 H) 1.33-1.65 (m, 4 H) 1.72-1.92 (m, 1 H) 1.99-2.36 (m, 5 H) 4.82-5.07 (m, 1 H) 6.55 -6.64 (m, 1 H) 7.17-7.28 (m, 1 H) 7.89-8.00 (m, 1 H) 9.60-9.72 (m, 1 H). MS ESI/APCI Dual posi: 246[M + H]⁺. | |
| Reference Example 32-8 | 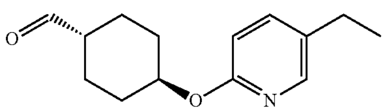 [SMILES: CCc1ccc(O[C@H]2CC[C@H](C=O)CC2)nc1] | ¹H NMR (200 MHz, CHLOROFORM-d ) δ ppm 1.21 (t, J = 7.7 Hz, 3 H) 1.37-1.68 (m, 4 H) 1.90-2.38 (m, 5 H) 2.45-2.66 (m, 2 H) 4.83-5.08 (m, 1 H) 6.56-6.70 (m, 1 H) 7.31-7.50 (m, 1 H) 7.89-8.01 (m, 1 H) 9.61-9.74 (m, 1 H). MS ESI/APCI Dual posi: 234[M + H]⁺. | |
| Reference Example 32-9 | 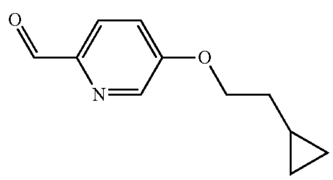 [SMILES: O=Cc1ccc(OCCC2CC2)cn1] | ¹H NMR (300 MHz, CHLOROFORM-d ) δ ppm 0.10-0.21 (m, 2 H) 0.48-0.57 (m, 2 H) 0.79-0.95 (m, 1 H) 1.74 (q, J = 6.6 Hz, 2 H) 4.18 (t, J = 6.6 Hz, 2 H) 7.28-7.35 (m, 1 H) 7.93-8.00 (m, 1 H) 8.41-8.46 (m, 1 H) 9.98-10.01 (m, 1 H). MS ESI/APCI Dual posi: 192[M + H]⁺, 214[M + Na]⁺. | |

Reference Example 33-1

5-Methyl-6-(2,2,2-trifluoroethoxy)pyridine-3-carbaldehyde

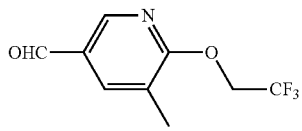

[Formula 120]

(1) Synthesis of 5-methyl-6-(2,2,2-trifluoroethoxy)pyridine-3-carboxylic acid

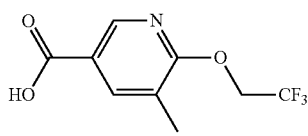

[Formula 121]

Instead of 3,4-difluorobenzaldehyde, 2-fluoro-3-methylpyridine-5-carboxylic acid (2.00 g) was used and treated by the same technique as in Reference Example 12-1 to give 5-methyl-6-(2,2,2-trifluoroethoxy)pyridine-3-carboxylic acid as a colorless solid (3.57 g).
¹H NMR (300 MHz, DMSO-d₆) δ ppm 2.23 (s, 3 H) 5.09 (q, J=9.0 Hz, 2 H) 8.02-8.17 (m, 1 H) 8.52-8.63 (m, 1 H) 13.11 (br. s, 1 H).
MS ESI/APCI Dual nega: 234 [M−H]⁻.

(2) Synthesis of N-methoxy-N,5-dimethyl-6-(2,2,2-trifluoroethoxy)pyridine-3-carboxamide

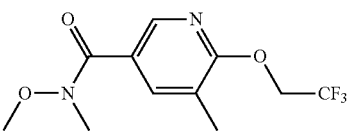

[Formula 122]

The compound (3.57 g) obtained in step (1) above was used and treated by the same technique as in Reference Example 16-1(1) to give N-methoxy-N,5-dimethyl-6-(2,2,2-trifluoroethoxy)pyridine-3-carboxamide as a colorless oil (2.98 g).
¹H NMR (300 MHz, CHLOROFORM-d) δ ppm 2.22-2.31 (m, 3 H) 3.37 (s, 3 H) 3.58 (s, 3 H) 4.81 (q, J=8.5 Hz, 2 H) 7.80-7.92 (m, 1 H) 8.37-8.49 (m, 1 H).
MS ESI/APCI Dual posi: 279 [M+H]⁺.

(3) Synthesis of the Titled Compound

The compound (2.66 g) obtained in step (2) above was used and treated by the same technique as in Reference Example 16-1(3) to give the titled compound as a colorless oil (2.10 g).

$^1$H NMR (300 MHz, CHLOROFORM-d) δ ppm 2.27-2.34 (m, 3 H) 4.76-4.96 (m, 2 H) 7.91-8.00 (m, 1 H) 8.41-8.51 (m, 1 H) 9.97 (s, 1 H).

MS ESI/APCI Dual posi: 220 [M+H]$^+$.

In the following Reference Examples 33-2 to 33-8, a commercial grade of the corresponding halogenated aryls and a commercial grade of the corresponding alcohols were used and treated by the method described in Reference Example 33-1 or modifications thereof to synthesize the intended compounds. The structures of the synthesized compounds and their NMR and MS data are shown in Table 12-1.

Reference Example 34-1

3-Phenylcyclopentanecarbaldehyde

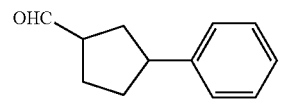

[Formula 123]

(1) Synthesis of (3-phenylcyclopentyl)methanol

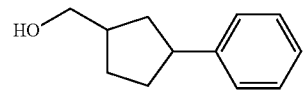

[Formula 124]

Instead of ethyl cis-2-phenylcyclopropanecarboxylate, 3-phenyl-cyclopentanecarboxylic acid methyl ester (1.76 g)

TABLE 12-1

| Compound No. | Structure | Analytical Data | Salt information |
|---|---|---|---|
| Reference Example 33-2 | 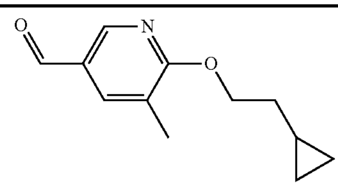 | $^1$H NMR (300 MHz, CHLOROFORM-d ) δ ppm 0.08-0.18 (m, 2 H) 0.44-0.54 (m, 2 H) 0.77-0.91 (m, 1 H) 1.65-1.77 (m, 2 H) 2.21-2.28 (m, 3 H) 4.50 (t, J = 6.6 Hz, 2 H) 7.83-7.90 (m, 1 H) 8.39-8.49 (m, 1 H) 9.92 (s, 1 H). MS ESI/APCI Dual posi: 206[M + H]$^+$. | |
| Reference Example 33-3 | 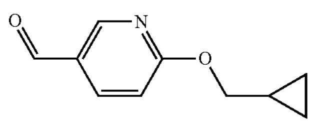 [SMILES: O=Cc1ccc(OCC2CC2)nc1] | $^1$H NMR (300 MHz, CHLOROFORM-d ) δ ppm 0.30-0.43 (m, 2 H) 0.57-0.69 (m, 2 H) 1.18-1.40 (m, 1 H) 4.25 (d, J = 7.3 Hz, 2 H) 6.80-6.92 (m, 1 H) 7.95-8.15 (m, 1 H) 8.60 (d, J = 2.3 Hz, 1 H) 9.94 (s, 1 H). MS ESI/APCI Dual posi: 178[M + H]$^+$. | |
| Reference Example 33-4 | 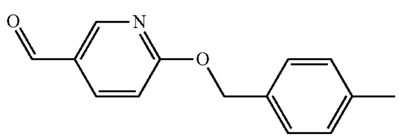 [SMILES: Cc1ccc(COc2ccc(C=O)cn2)cc1] | $^1$H NMR (300 MHz, CHLOROFORM-d ) δ ppm 2.37 (s, 3 H) 5.44 (s, 2 H) 6.85-6.91 (m, 1 H) 7.17-7.23 (m, 2 H) 7.33-7.39 (m, 2 H) 8.04-8.10 (m, 1 H) 8.63-8.66 (m, 1 H) 9.95-9.97 (m, 1 H). MS EI posi: 227[M]$^+$. | |
| Reference Example 33-5 | 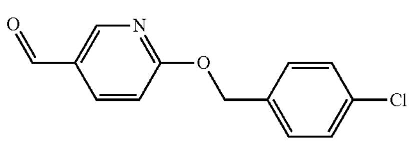 [SMILES: O=Cc1ccc(OCc2ccc(Cl)cc2)nc1] | $^1$H NMR (300 MHz, CHLOROFORM-d ) δ ppm 5.45 (s, 2 H) 6.87-6.92 (m, 1 H) 7.33-7.44 (m, 4 H) 8.06-8.12 (m, 1 H) 8.64 (d, J = 2.3 Hz, 1 H) 9.97 (s, 1 H). MS ESI/APCI Dual posi: 248 [M + H]$^+$. MS ESI/APCI Dual nega: 246[M − H]$^-$. | |
| Reference Example 33-6 | 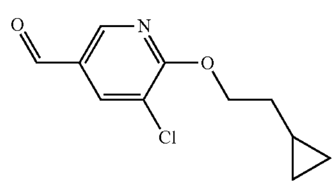 [SMILES: O=Cc1cnc(OCCC2CC2)c(Cl)c1] | $^1$H NMR (300 MHz, CHLOROFORM-d ) δ ppm 0.07-0.24 (m, 2 H) 0.40-0.57 (m, 2 H) 0.75-0.93 (m, 1 H) 1.66-1.82 (m, 2 H) 4.49-4.63 (m, 2 H) 8.11 (d, J = 2.2 Hz, 1 H) 8.51 (d, J = 2.2 Hz, 1 H) 9.93 (s, 1 H). MS ESI/APCI Dual posi: 226[M + H]$^+$. | |
| Reference Example 33-7 | 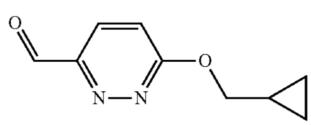 [SMILES: O=Cc1ccc(OCC2CC2)nn1] | $^1$H NMR (300 MHz, CHLOROFORM-d ) δ ppm 0.35-0.47 (m, 2 H) 0.61-0.73 (m, 2 H) 1.31-1.47 (m, 1 H) 4.49 (d, J = 7.4 Hz, 2 H) 7.10 (dd, J = 9.1, 0.9 Hz, 1 H) 7.95 (d, J = 9.1 Hz, 1 H) 10.24 (d, J = 0.9 Hz, 1 H). MS ESI/APCI Dual posi: 179[M + H]$^+$. | |
| Reference Example 33-8 | | $^1$H NMR (300 MHz, CHLOROFORM-d ) δ ppm 0.32-0.45 (m, 2 H) 0.58-0.73 (m, 2 H) 1.22-1.41 (m, 1 H) 4.28 (d, J = 7.1 Hz, 2 H) 8.32 (d, J = 1.4 Hz, 1 H) 8.72 (d, J = 1.4 Hz, 1 H) 10.05 (s, 1 H). MS ESI/APCI Dual posi: 179[M + H]$^+$. | | was used and treated by the same technique as in Reference Example 23-1(2) to give (3-phenylcyclopentyl)methanol as a colorless oil (1.31 g).

¹H NMR (300 MHz, CHLOROFORM-d) δ ppm 1.26-1.48 (m, 2 H) 1.54-2.19 (m, 5 H) 2.29-2.49 (m, 1 H) 2.97-3.16 (m, 1 H) 3.53-3.67 (m, 2 H) 7.12-7.35 (m, 5 H).

MS EI posi: 176 [M]⁺.

(2) Synthesis of the Titled Compound

The compound (0.90 g) obtained in step (1) above was used and treated by the same technique as in Reference Example 19-1 to give the titled compound as a yellow oil (0.90 g).

¹H NMR (300 MHz, CHLOROFORM-d) δ ppm 1.56-2.55 (m, 7 H) 2.90-3.19 (m, 1 H) 7.14-7.40 (m, 5 H) 9.65-9.78 (m, 1 H).

In the following Reference Examples 34-2 and 34-3, a commercial grade of the corresponding esters was used and treated by the method described in Reference Example 34-1 or a modification thereof to synthesize the intended compounds. The structures of the synthesized compounds and their NMR and MS data are shown in Table 13-1.

Reference Example 36-1 cis-4-[(4-Chlorobenzyl)oxy]cyclohexanecarbaldehyde

[Formula 126]

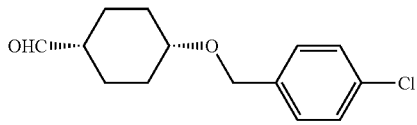

(1) Synthesis of ethyl cis-4-[(4-chlorobenzyl)oxy]cyclohexanecarboxylate and ethyl trans-4-[(4-chlorobenzyl)oxy]cyclohexanecarboxylate

[Formula 127]

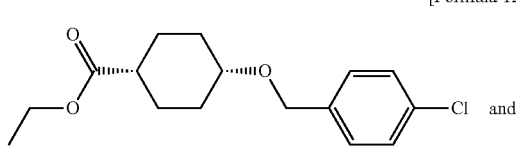
and

TABLE 13-1

| Compound No. | Structure | Analytical Data | Salt information |
|---|---|---|---|
| Reference Example 34-2 | 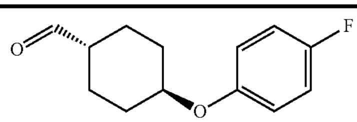 | ¹H NMR (300 MHz, CHLOROFORM-d) δ ppm 1.37-1.76 (m, 4 H) 2.00-2.38 (m, 5 H) 4.03-4.19 (m, 1 H) 6.78-7.02 (m, 4 H) 9.64-9.73 (m, 1 H). | |
| Reference Example 34-3 | 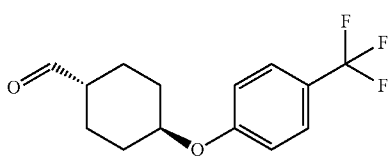 [SMILES: O=C[C@H]1CC[C@H](Oc2ccc(C(F)(F)F)cc2)CC1] | ¹H NMR (300 MHz, CHLOROFORM-d) δ ppm 1.41-1.85 (m, 4 H) 2.01-2.45 (m, 5 H) 4.19-4.38 (m, 1 H) 6.90-6.99 (m, 2 H) 7.46-7.58 (m, 2 H) 9.69 (s, 1 H). | |

Reference Example 35-1

4-{[(6-Methylpyridin-3-yl)oxy]methyl}benzaldehyde

[Formula 125]

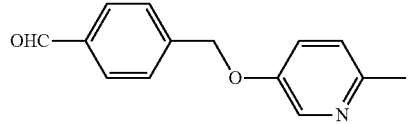

Instead of 4-hydroxybenzaldehyde and (bromomethyl)cyclobutane, 5-hydroxy-2-methylpyridine (767 mg) and 4-(chloromethyl)benzyl alcohol (1.00 g) were respectively used and treated by the same techniques as in Reference Examples 9-1 and 19-1 to give the titled compound as a pale yellow solid (1.65 g).

¹H NMR (300 MHz, CHLOROFORM-d) δ ppm 2.50 (s, 3 H) 5.17 (s, 2 H) 7.05-7.11 (m, 1 H) 7.14-7.20 (m, 1 H) 7.57-7.63 (m, 2 H) 7.89-7.94 (m, 2 H) 8.25-8.29 (m, 1 H) 10.03 (s, 1 H).

MS ESI/APCI Dual posi: 228 [M+H]⁺.

MS ESI/APCI Dual nega: 226 [M−H]⁻, 262 [M+Cl]⁻.

-continued

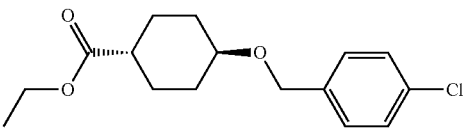

Instead of 4-hydroxybenzaldehyde and (bromomethyl)cyclobutane, ethyl 4-hydroxycyclohexanecarboxylate (2.00 g) and 4-chlorobenzylbromide (2.86 g) were respectively used and treated by the same technique as in Reference Example 9-1 to give ethyl cis-4-[(4-chlorobenzyl)oxy]cyclohexanecarboxylate as a colorless oil (0.33 g) and ethyl trans-4-[(4-chlorobenzyl)oxy]cyclohexanecarboxylate as a pale yellow oil (0.47 g).

Ethyl cis-4-[(4-chlorobenzyl)oxy]cyclohexanecarboxylate

¹H NMR (300 MHz, CHLOROFORM-d) δ ppm 1.29 (t, J=7.1 Hz, 3 H) 1.52-1.78 (m, 4 H) 1.83-2.06 (m, 4 H) 2.30-2.50 (m, 1 H) 3.54-3.66 (m, 1 H) 4.17 (q, J=7.1 Hz, 2 H) 4.51 (s, 2 H) 7.25-7.40 (m, 4 H).

Ethyl trans-4-[(4-chlorobenzyl)oxy]cyclohexanecarboxylate

¹H NMR (300 MHz, CHLOROFORM-d) δ ppm 1.17-1.57 (m, 7 H) 1.95-2.18 (m, 4 H) 2.20-2.35 (m, 1 H) 3.25-3.41 (m, 1 H) 4.11 (q, J=7.1 Hz, 2 H) 4.51 (s, 2 H) 7.21-7.37 (m, 4 H).

(2) Synthesis of {cis-4-[(4-chlorobenzyl)oxy]cyclohexyl}methanol

[Formula 128]

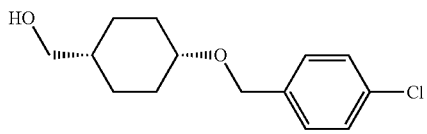

The compound cis-4-[(4-chlorobenzyl)oxy]cyclohexanecarboxylate (0.33 g) obtained in step (1) above was used and treated by the same technique as in Reference Example 23-1 (2) to give {cis-4-[(4-chlorobenzyl)oxy]cyclohexyl}methanol as a colorless oil (0.29 g).

¹H NMR (300 MHz, CHLOROFORM-d) δ ppm 1.20-1.67 (m, 8 H) 1.83-2.02 (m, 2 H) 3.49 (d, J=5.9 Hz, 2 H) 3.59-3.67 (m, 1 H) 4.46 (s, 2 H) 7.24-7.35 (m, 4 H).

(3) Synthesis of the Titled Compound

The compound (283 mg) obtained in step (2) above was used and treated by the same technique as in Reference Example 19-1 to give the titled compound as a yellow oil (257 mg).

¹H NMR (300 MHz, CHLOROFORM-d) δ ppm 1.49-1.99 (m, 8 H) 2.20-2.35 (m, 1 H) 3.51-3.65 (m, 1 H) 4.47 (s, 2 H) 7.22-7.35 (m, 4 H) 9.59-9.68 (m, 1 H).

MS ESI/APCI Dual posi: 275 [M+Na]⁺.

Reference Example 36-2 trans-4-[(4-Chlorobenzyl)oxy]cyclohexanecarbaldehyde

[Formula 129]

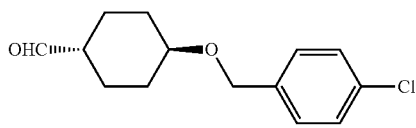

The ethyl trans-4-[(4-chlorobenzyl)oxy]cyclohexanecarboxylate (856 mg) obtained in Reference Example 36-1(1) was used and treated by the same techniques as in Reference Example 36-1(2) and (3) to give the titled compound as a yellow oil (388 mg).

¹H NMR (300 MHz, CHLOROFORM-d) δ ppm 1.23-1.50 (m, 4 H) 1.98-2.31 (m, 5 H) 3.26-3.41 (m, 1 H) 4.52 (s, 2 H) 7.22-7.36 (m, 4 H) 9.62-9.67 (m, 1 H).

Reference Example 36-3 trans-4-[(5-Chloro-2-pyridinyl)methoxy]cyclohexanecarbaldehyde

[Formula 130]

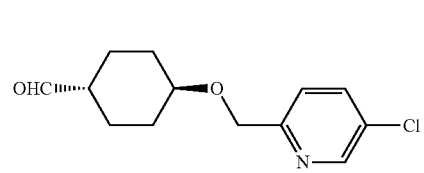

Instead of 4-chlorobenzylbromide, 2-(bromomethyl)-5-chloropyridine (5.23 g) was used and treated by the same technique as in Reference Example 36-1 to give the titled compound as a colorless oil (0.25 g).

¹H NMR (300 MHz, CHLOROFORM-d) δ ppm 1.28-1.67 (m, 4 H) 1.99-2.31 (m, 5 H) 3.33-3.52 (m, 1 H) 4.65 (s, 2 H) 7.39-7.48 (m, 1 H) 7.64-7.75 (m, 1 H) 8.48-8.54 (m, 1 H) 9.61-9.71 (m, 1 H).

Reference Example 37-1 trans-4-Phenoxycyclohexanecarbaldehyde

[Formula 131]

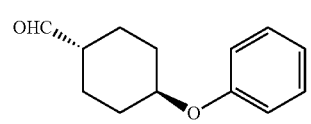

(1) Synthesis of methyl trans-4-phenoxycyclohexanecarboxylate

[Formula 132]

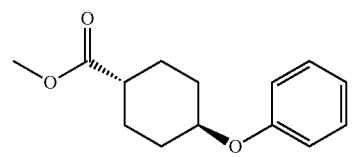

Instead of 4-hydroxybenzaldehyde and 2-cyclopropylethanol, phenol (1.43 g) and methyl cis-4-hydroxycyclohexanecarboxylate (2.00 g) were respectively used and treated by the same technique as in Reference Example 11-1 to give methyl trans-4-phenoxycyclohexanecarboxylate as a colorless oil (1.33 g).

¹H NMR (600 MHz, CHLOROFORM-d) δ ppm 1.43-1.65 (m, 4 H) 2.03-2.13 (m, 2 H) 2.15-2.23 (m, 2 H) 2.32-2.44 (m, 1 H) 3.68 (s, 3 H) 4.15-4.26 (m, 1 H) 6.86-6.97 (m, 3 H) 7.23-7.31 (m, 2 H).

MS ESI/APCI Dual posi: 235 [M+H]⁺.

(2) Synthesis of (trans-4-phenoxycyclohexyl)methanol

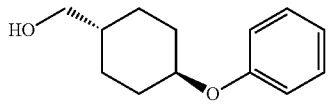

[Formula 133]

The compound (1.31 g) obtained in step (1) above was used and treated by the same technique as in Reference Example 23-1(2) to give (trans-4-phenoxycyclohexyl)methanol as a colorless oil (897 mg).

$^1$H NMR (200 MHz, CHLOROFORM-d) δ ppm 0.96-1.70 (m, 6 H) 1.81-2.01 (m, 2 H) 2.10-2.31 (m, 2 H) 3.50 (d, J=6.2 Hz, 2 H) 4.04-4.27 (m, 1 H) 6.82-7.00 (m, 3 H) 7.16-7.35 (m, 2 H).

MS ESI/APCI Dual posi: 207 [M+H]$^+$.

(3) Synthesis of the Titled Compound

The compound (897 mg) obtained in step (2) above was used and treated by the same technique as in Reference Example 19-1 to give the titled compound as a yellow oil (801 mg).

$^1$H NMR (600 MHz, CHLOROFORM-d) δ ppm 1.42-1.64 (m, 4 H) 2.04-2.22 (m, 4 H) 2.27-2.37 (m, 1 H) 4.16-4.28 (m, 1 H) 6.86-6.98 (m, 3 H) 7.23-7.33 (m, 2 H) 9.69 (s, 1 H).

In the following Reference Examples 37-2 to 37-8, a commercial grade of the corresponding phenols and a commercial grade of the corresponding alcohols were used and treated by the method described in Reference Example 37-1 or modifications thereof to synthesize the intended compounds. The structures of the synthesized compounds and their NMR and MS data are shown in Table 14-1.

TABLE 14-1

| Compound No. | Structure | Analytical Data | Salt information |
|---|---|---|---|
| Reference Example 37-2 | 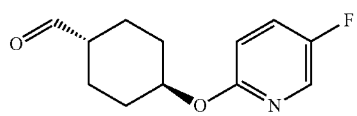 [SMILES: O=C[C@H]1CC[C@H](Oc2ccc(F)cn2)CC1] | $^1$H NMR (300 MHz, CHLOROFORM-d) δ ppm 1.39-1.83 (m, 4 H) 1.97-2.38 (m, 5 H) 4.83-5.02 (m, 1 H) 6.58-6.71 (m, 1 H) 7.23-7.40 (m, 1 H) 7.89-8.05 (m, 1 H) 9.64-9.72 (m, 1 H). | |
| Reference Example 37-3 | 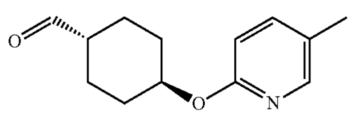 [SMILES: Cc1ccc(O[C@H]2CC[C@H](C=O)CC2)nc1] | $^1$H NMR (300 MHz, CHLOROFORM-d) δ ppm 1.42-1.65 (m, 4 H) 1.99-2.36 (m, 8 H) 4.88-5.04 (m, 1 H) 6.56-6.64 (m, 1 H) 7.33-7.43 (m, 1 H) 7.88-7.99 (m, 1 H) 9.61-9.72 (m, 1 H). | |
| Reference Example 37-4 | 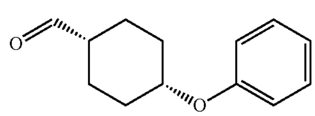 [SMILES: O=C[C@H]1CC[C@@H](Oc2ccccc2)CC1] | $^1$H NMR (600 MHz, CHLOROFORM-d) δ ppm 1.41-2.13 (m, 8 H) 2.26-2.37 (m, 1 H) 4.41-4.53 (m, 1 H) 6.84-6.96 (m, 3 H) 7.23-7.30 (m, 2 H) 9.63-9.70 (m, 1 H). | |
| Reference Example 37-5 | 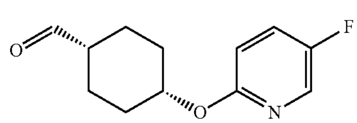 [SMILES: O=C[C@H]1CC[C@@H](Oc2ccc(F)cn2)CC1] | MS ESI/APCI Dual posi: 224[M + H]$^+$. | |
| Reference Example 37-6 | 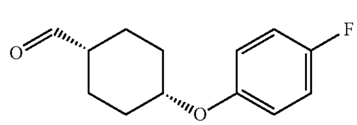 [SMILES: O=C[C@H]1CC[C@@H](Oc2ccc(F)cc2)CC1] | MS ESI/APCI Dual posi: 223[M + H]$^+$. | |
| Reference Example 37-7 | 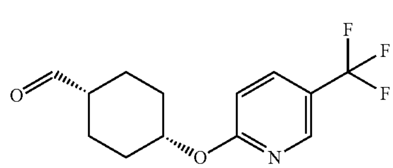 [SMILES: O=C[C@H]1CC[C@@H](Oc2ccc(C(F)(F)F)cn2)CC1] | MS ESI/APCI Dual posi: 274[M + H]$^+$. | |
| Reference Example 37-8 | 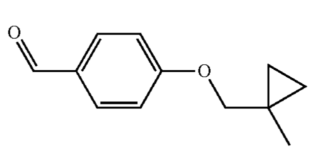 | $^1$H NMR (300 MHz, CHLOROFORM-d) δ ppm 0.43-0.51 (m, 2 H) 0.52-0.62 (m, 2 H) 1.24 (s, 3 H) 3.81 (s, 2 H) 6.95-7.03 (m, 2 H) 7.79-7.86 (m, 2 H) 9.88 (s, 1 H). MS ESI/APCI Dual posi: 191[M + H]$^+$. | |

Reference Example 38-1

4-({[6-(Trifluoromethyl)pyridin-3-yl]oxy}methyl)benzaldehyde

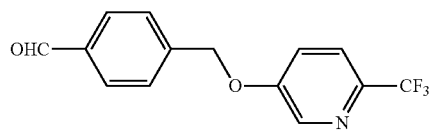
[Formula 134]

(1) Synthesis of 4-({[6-(trifluoromethyl)pyridin-3-yl]oxy}methyl)benzonitrile

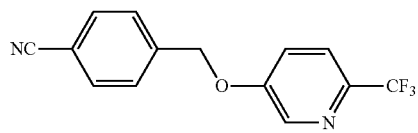
[Formula 135]

Instead of 4-hydroxybenzaldehyde and bromocyclopropane, 6-(trifluoromethyl)pyridin-3-ol (1.21 g) and 4-cyanobenzylbromide (1.45 g) were respectively used and treated by the same technique as in Reference Example 10-1 to give 4-({[6-(trifluoromethyl)pyridin-3-yl]oxy}methyl)benzonitrile as a pale brown solid (1.99 g).

¹H NMR (300 MHz, CHLOROFORM-d) δ ppm 5.23 (s, 2 H) 7.34 (dd, J=8.7, 2.8 Hz, 1 H) 7.52-7.59 (m, 2 H) 7.64 (d, J=8.7 Hz, 1 H) 7.69-7.77 (m, 2 H) 8.46 (d, J=2.8 Hz, 1 H).
MS ESI/APCI Dual posi: 279 [M+H]⁺.
MS ESI/APCI Dual nega: 277 [M−H]⁻.

(2) Synthesis of the Titled Compound

The compound (1.99 g) obtained in step (1) above was used and treated by the same technique as in Reference Example 16-1(3) to give the titled compound as a pale yellow solid (980 mg).

¹H NMR (300 MHz, CHLOROFORM-d) δ ppm 5.26 (s, 2 H) 7.35 (dd, J=8.8, 3.0 Hz, 1 H) 7.58-7.67 (m, 3 H) 7.91-7.98 (m, 2 H) 8.48 (d, J=3.0 Hz, 1 H) 10.05 (s, 1 H).
MS ESI/APCI Dual posi: 282 [M+H]⁺.

Reference Example 38-2

4-({[5-(Trifluoromethyl)pyridin-2-yl]oxy}methyl)benzaldehyde

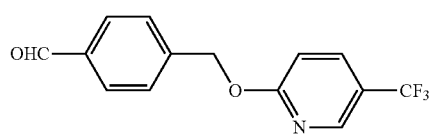
[Formula 136]

Instead of 6-(trifluoromethyl)pyridin-3-ol and 4-cyanobenzylbromide, 4-(hydroxymethyl)benzonitrile (1.87 g) and 2-fluoro-5-(trifluoromethyl)pyridine (1.55 g) were respectively used and treated by the same technique as in Reference Example 38-1 to give the titled compound as a pale yellow solid (1.49 g).

¹H NMR (300 MHz, CHLOROFORM-d) δ ppm 5.53 (s, 2 H) 6.90-6.97 (m, 1 H) 7.58-7.65 (m, 2 H) 7.82 (dd, J=8.9, 2.3 Hz, 1 H) 7.87-7.94 (m, 2 H) 8.40-8.47 (m, 1 H) 10.03 (s, 1 H).
MS ESI/APCI Dual posi: 282 [M+H]⁺.

Reference Example 39-1 trans-4-[(4-Fluorobenzyl)oxy]cyclohexanecarbaldehyde

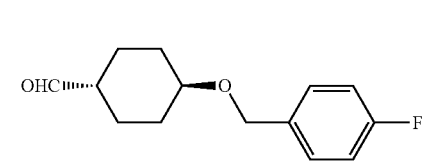
[Formula 137]

(1) Synthesis of trans-4-hydroxy-N-methoxy-N-methylcyclohexanecarboxamide

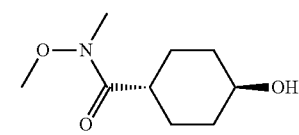
[Formula 138]

Instead of 4-(bromomethyl)benzoic acid, trans-4-hydroxycyclohexanecarboxylic acid (7.21 g) was used and treated by the same technique as in Reference Example 16-1(1) to give trans-4-hydroxy-N-methoxy-N-methylcyclohexanecarboxamide as a colorless oil (8.52 g).

¹H NMR (300 MHz, CHLOROFORM-d) δ ppm 1.21-1.40 (m, 2 H) 1.49-1.68 (m, 2 H) 1.78-1.90 (m, 2 H) 2.00-2.13 (m, 2 H) 2.54-2.73 (m, 2 H) 3.18 (s, 3 H) 3.57-3.74 (m, 4 H).

(2) Synthesis of trans-4-{[tert-butyl(dimethyl)silyl]oxy}-N-methoxy-N-methylcyclohexanecarboxamide

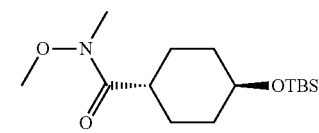
[Formula 139]

To a solution in N,N-dimethylformamide (91 mL) of the compound (8.52 g) obtained in step (1) above, imidazole (4.03 g) and tert-butyldimethylchlorosilane (6.86 g) were added and the mixture was stirred at room temperature for 1.5 hours. The reaction mixture was concentrated under reduced pressure and water was added to the resulting residue. After extraction with ethyl acetate, the combined organic layers were washed with water and saturated brine. The washed organic layers were dried over anhydrous magnesium sulfate and after removing the desiccant by filtration, the filtrate was concentrated under reduced pressure. The resulting residue was purified by silica gel column chromatography (n-hexane: ethyl acetate=100:0-75:25) to give the titled compound as a colorless oil (10.5 g).

¹H NMR (200 MHz, CHLOROFORM-d) δ ppm 0.06 (s, 6 H) 0.88 (s, 9 H) 1.15-1.69 (m, 4 H) 1.71-2.08 (m, 4 H) 2.50-2.73 (m, 1 H) 3.17 (s, 3 H) 3.48-3.75 (m, 4 H).

(3) Synthesis of trans-4-[(4-fluorobenzyl)oxy]-N-methoxy-N-methylcyclohexanecarboxamide

[Formula 140]

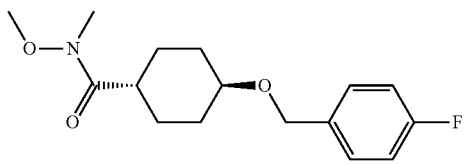

To a solution in acetonitrile (11 mL) of the compound (1.00 g) obtained in step (2) above, triethylsilane (579 mg) was added. Bismuth tribromide (104 mg) and 4-fluorobenzaldehyde (617 mg) were added under cooling with ice and the mixture was stirred at room temperature for two hours. To the reaction mixture, a saturated aqueous solution of sodium hydrogencarbonate and ethyl acetate were added and the insoluble matter was removed by filtration through Celite (registered trademark). The organic layer in the filtrate was separated and washed with saturated brine. The washed organic layer was dried over anhydrous magnesium sulfate and after removing the desiccant by filtration, the filtrate was concentrated under reduced pressure. The resulting residue was purified by silica gel column chromatography (n-hexane: ethyl acetate=100:0-50:50) to give the titled compound as a colorless oil (0.61 g).

¹H NMR (300 MHz, CHLOROFORM-d) δ ppm 1.23-1.43 (m, 2 H) 1.47-1.65 (m, 2 H) 1.79-1.93 (m, 2 H) 2.10-2.23 (m, 2 H) 2.57-2.74 (m, 1 H) 3.18 (s, 3 H) 3.29-3.43 (m, 1 H) 3.70 (s, 3 H) 4.52 (s, 2 H) 6.97-7.08 (m, 2 H) 7.25-7.36 (m, 2 H).

(4) Synthesis of the Titled Compound

The compound (0.59 g) obtained in step (3) above was used and treated by the same technique as in Reference Example 23-1(2) to give the titled compound as a yellow oil (0.46 g).

¹H NMR (300 MHz, CHLOROFORM-d) δ ppm 1.27-1.49 (m, 4 H) 1.97-2.34 (m, 5 H) 3.25-3.41 (m, 1 H) 4.52 (s, 2 H) 6.97-7.08 (m, 2 H) 7.25-7.36 (m, 2 H) 9.62-9.70 (m, 1 H).

In the following Reference Examples 39-2 to 39-7, a commercial grade of the corresponding aldehydes was used and treated by the method described in Reference Example 39-1 or modifications thereof to synthesize the intended compounds. The structures of the synthesized compounds and their NMR and MS data are shown in Table 15-1.

TABLE 15-1

| Compound No. | Structure | Analytical Data | Salt information |
|---|---|---|---|
| Reference Example 39-2 | 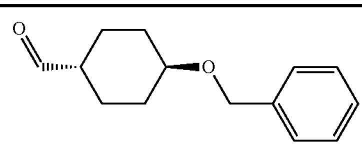 | ¹H NMR (300 MHz, CHLOROFORM-d ) δ ppm 1.22-1.49 (m, 4 H) 1.99-2.18 (m, 4 H) 2.18-2.31 (m, 1 H) 3.28-3.41 (m, 1 H) 4.56 (s, 2 H) 7.23-7.39 (m, 5 H) 9.61-9.69 (m, 1 H). | |
| Reference Example 39-3 | 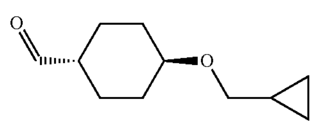 [SMILES: O=C[C@H]1CC[C@H](OCC2CC2)CC1] | ¹H NMR (300 MHz, CHLOROFORM-d ) δ ppm 0.14-0.24 (m, 2 H) 0.48-0.59 (m, 2 H) 0.96-1.13 (m, 1 H) 1.17-1.43 (m, 4 H) 1.93-2.30 (m, 5 H) 3.14-3.33 (m, 3 H) 9.62-9.67 (m, 1H). | |
| Reference Example 39-4 | 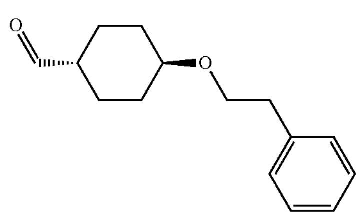 [SMILES: O=C[C@H]1CC[C@H](OCCc2ccccc2)CC1] | ¹H NMR (300 MHz, CHLOROFORM-d ) δ ppm 1.20-1.42 (m, 4 H) 1.92-2.29 (m, 5 H) 2.87 (t, J = 7.3 Hz, 2 H) 3.14-3.29 (m, 1 H) 3.67 (t, J = 7.3 Hz, 2 H) 7.15-7.36 (m, 5 H) 9.61-9.67 (m, 1 H). | |
| Reference Example 39-5 | 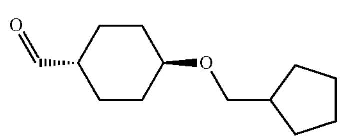 [SMILES: O=C[C@H]1CC[C@H](OCC2CCCC2)CC1] | ¹H NMR (300 MHz, CHLOROFORM-d ) δ ppm 1.13-1.40 (m, 6 H) 1.44-1.81 (m, 7 H) 1.85-2.30 (m, 5 H) 3.08-3.25 (m, 1 H) 3.32 (d, J = 7.1 Hz, 2 H) 9.62-9.69 (m, 1 H). | |
| Reference Example 39-6 | 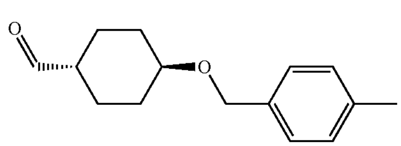 [SMILES: Cc1ccc(CO[C@H]2CC[C@H](C=O)CC2)cc1] | ¹H NMR (200 MHz, CHLOROFORM-d ) δ ppm 1.21-1.51 (m, 4 H) 1.93-2.31 (m, 5 H) 2.34 (s, 3 H) 3.20-3.43 (m, 1 H) 4.52 (s, 2 H) 7.09-7.28 (m, 4 H) 9.61-9.68 (m, 1 H). | |

| Compound No. | Structure | Analytical Data | Salt information |
|---|---|---|---|
| Reference Example 39-7 | 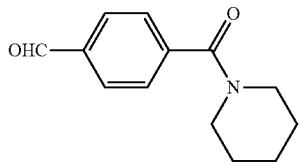 | $^1$H NMR (200 MHz, CHLOROFORM-d) δ ppm 1.17-1.77 (m, 6 H) 1.80-2.29 (m, 9 H) 3.11-3.33 (m, 1 H) 3.90-4.13 (m, 1 H) 9.59-9.68 (m, 1 H). | |

TABLE 15-1-continued

Reference Example 40-1

4-(Piperidin-1-ylcarbonyl)benzaldehyde

[Formula 141]

To a solution of 4-carboxybenzaldehyde (1.06 g) in chloroform (14.1 mL), 1-(3-dimethylaminopropyl)-3-ethylcarbodiimide hydrochloride (2.03 g), 1-hydroxybenzotriazole monohydrate (1.62 g) and piperdine (1.05 mL) were added. After stirring the mixture at room temperature for 15 hours, a saturated aqueous solution of ammonium chloride was added. After extraction with ethyl acetate, the combined organic layers were washed with saturated brine. The washed organic layers were dried over anhydrous magnesium sulfate and after removing the desiccant by filtration, the filtrate was concentrated under reduced pressure. The resulting residue was purified by silica gel column chromatography (n-hexane:ethyl acetate=85:15-30:70) to give the titled compound as a colorless oil (1.57 g).

$^1$H NMR (300 MHz, CHLOROFORM-d) δ ppm 1.50-1.53 (m, 2 H) 1.65-1.73 (m, 4 H) 3.24-3.35 (m, 2 H) 3.68-3.79 (m, 2 H) 7.52-7.57 (m, 2 H) 7.90-7.96 (m, 2 H) 10.05 (s, 1 H).

MS ESI/APCI Dual posi: 218 [M+H]$^+$.

MS ESI/APCI Dual nega: 232 [M+Cl]$^-$.

In the following Reference Examples 40-2 to 40-8, a commercial grade of the corresponding amines was used and treated by the method described in Reference Example 40-1 or modifications thereof to synthesize the intended compounds. The structures of the synthesized compounds and their NMR and MS data are shown in Table 16-1.

TABLE 16-1

| Compound No. | Structure | Analytical Data | Salt information |
|---|---|---|---|
| Reference Example 40-2 | 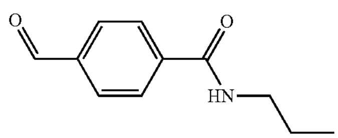 | $^1$H NMR (600 MHz, CHLOROFORM-d) δ ppm 1.00 (t, J = 7.4 Hz, 3 H) 1.66 (sxt, J = 7.4 Hz, 2 H) 3.42-3.47 (m, 2 H) 6.16 (br. s., 1 H) 7.88-7.92 (m, 2 H) 7.92-7.96 (m, 2 H) 10.07 (s, 1 H). MS ESI/APCI Dual posi: 192[M + H]$^+$. MS ESI/APCI Dual nega: 190[M − H]$^-$, 226[M + Cl]$^-$. | |
| Reference Example 40-3 | 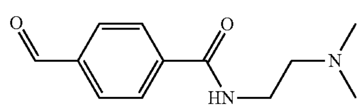 [SMILES: CN(C)CCNC(=O)c1ccc(C=O)cc1] | $^1$H NMR (300 MHz, DMSO-d$_6$) δ ppm 2.63 (br. s., 6 H) 3.03 (q, J = 7.2 Hz, 2 H) 3.61 (br. s., 2 H) 7.97 (d, J = 8.1 Hz, 2 H) 8.14 (d, J = 8.1 Hz, 2 H) 9.44-9.67 (m, 1 H) 10.08 (s, 1 H). MS ESI/APCI Dual posi: 221[M + H]$^+$. MS ESI/APCI Dual nega: 219[M − H]$^-$. | |
| Reference Example 40-4 | 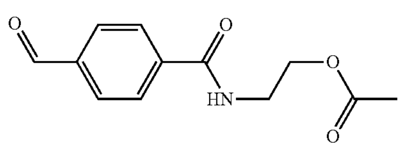 [SMILES: CC(=O)OCCNC(=O)c1ccc(C=O)cc1] | $^1$H NMR (300 MHz, CHLOROFORM-d) δ ppm 2.11 (s, 3 H) 3.71-3.81 (m, 2 H) 4.29-4.37 (m, 2 H) 6.71 (br. s., 1 H) 7.88-8.00 (m, 4 H) 10.09 (s, 1 H). MS ESI/APCI Dual posi: 258[M + Na]$^+$. MS ESI/APCI Dual nega: 234[M − H]$^-$. | |
| Reference Example 40-5 | 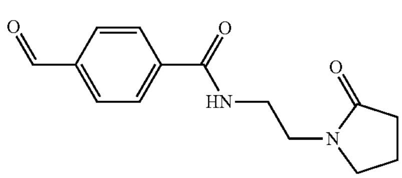 [SMILES: O=Cc1ccc(C(=O)NCCN2CCCC2=O)cc1] | $^1$H NMR (300 MHz, CHLOROFORM-d) δ ppm 2.01-2.20 (m, 2 H) 2.42 (t, J = 8.4 Hz, 2 H) 3.38-3.73 (m, 6 H) 7.57-7.77 (m, 1 H) 7.87-8.03 (m, 4 H) 10.07 (s, 1 H). MS ESI/APCI Dual posi: 283[M + Na]$^+$. MS ESI/APCI Dual nega: 259[M − H]$^-$. | |

TABLE 16-1-continued

| Compound No. | Structure | Analytical Data | Salt information |
|---|---|---|---|
| Reference Example 40-6 | ![structure] | ¹H NMR (300 MHz, CHLOROFORM-d) δ ppm 4.78 (d, J = 4.5 Hz, 2 H) 7.19-7.28 (m, 1 H) 7.29-7.39 (m, 1 H) 7.66-7.76 (m, 1 H) 7.77-7.85 (m, 1 H) 7.89-8.11 (m, 4 H) 8.52-8.64 (m, 1 H) 10.09 (s, 1 H). MS ESI/APCI Dual posi: 241[M+ H]⁺, 263[M + Na]⁺. MS ESI/APCI Dual nega: 239[M − H]⁻. | |
| Reference Example 40-7 | ![structure] | ¹H NMR (300 MHz, CHLOROFORM-d) δ ppm 3.07-3.17 (m, 2 H) 3.88 (dd, J = 6.5, 5.7 Hz, 2 H) 7.16-7.26 (m, 2 H) 7.58-7.73 (m, 1 H) 7.82-8.01 (m, 5 H) 8.47-8.67 (m, 1 H) 10.08 (s, 1 H). MS ESI/APCI Dual posi: 255[M + H]⁺, 277[M + Na]⁺. MS ESI/APCI Dual nesa: 253[M − H]⁻. | |
| Reference Example 40-8 | ![structure] | ¹H NMR (300 MHz, CHLOROFORM-d) δ ppm 1.52 (s, 9 H) 4.16 (d, J = 5.0 Hz, 2 H) 6.75 (br. s., 1 H) 7.96 (s, 4 H) 10.09 (s, 1 H). MS ESI/APCI Dual posi: -286[M + Na]⁺. MS ESI/APCI Dual nega: 262[M − H]⁻. | |

Reference Example 41-1

5-(4-Methylphenoxyl)pyrazine-2-carbaldehyde

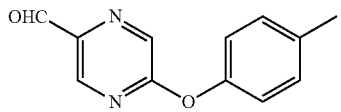

[Formula 142]

(1) Synthesis of methyl 5-(4-methylphenoxyl)pyrazine-2-carboxylate

[Formula 143]

Instead of 4-hydroxybenzotrifluoride and 6-bromo-3-pyridinecarboxyaldehyde, p-cresol (833 mg) and methyl 5-chloro-2-pyrazinecarboxylate (1.33 g) were respectively used and treated by the same technique as in Reference Example 13-1 to give methyl 5-(4-methylphenoxyl)pyrazine-2-carboxylate as a colorless solid (1.36 g).

¹H NMR (300 MHz, CHLOROFORM-d) δ ppm 2.39 (s, 3 H) 4.01 (s, 3 H) 7.03-7.09 (m, 2 H) 7.18-7.33 (m, 2 H) 8.48 (d, J=1.2 Hz, 1 H) 8.83 (d, J=1.2 Hz, 1 H).

MS ESI/APCI Dual posi: 245 [M+H]⁺.

(2) Synthesis of the Titled Compound

The compound (1.36 g) obtained in step (1) above was used and treated by the same technique as in Reference Example 16-1(3) to give the titled compound as a colorless solid (1.10 g).

¹H NMR (300 MHz, CHLOROFORM-d) δ ppm 2.40 (s, 3 H) 7.02-7.10 (m, 2 H) 7.22-7.31 (m, 2 H) 8.51 (d, J=1.2 Hz, 1 H) 8.71 (d, J=1.2 Hz, 1 H) 10.08 (s, 1 H).

MS ESI/APCI Dual posi: 215 [M+H]⁺.

Reference Example 41-2

5-(4-Chlorophenoxyl)pyrazine-2-carbaldehyde

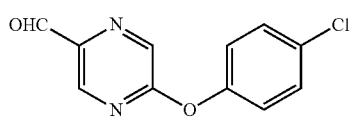

[Formula 144]

Instead of p-cresol, 4-chlorophenol (2.23 g) was used and treated by the same technique as in Reference Example 41-1 to give the titled compound as a pale yellow solid (0.45 g).

¹H NMR (300 MHz, CHLOROFORM-d) δ ppm 7.08-7.20 (m, 2 H) 7.36-7.49 (m, 2 H) 8.55 (d, J=1.4 Hz, 1 H) 8.67-8.72 (m, 1 H) 10.09 (s, 1 H).

MS ESI/APCI Dual posi: 235 [M+H]⁺.

Reference Example 41-3

5-(4-Cyclopropylphenoxyl)pyrazine-2-carbaldehyde

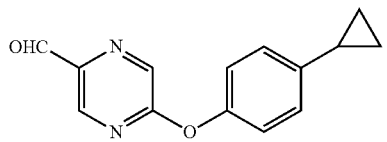 [SMILES: O=Cc1cnc(Oc2ccc(C3CC3)cc2)cn1]

(1) Synthesis of 5-(4-bromophenoxy)pyrazine-2-carbaldehyde

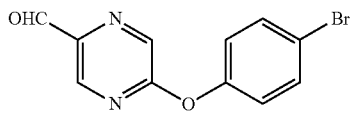

[Formula 146]

Instead of p-cresol, 4-bromophenol (5.01 g) was used and treated by the same technique as in Reference Example 41-1 to give 5-(4-bromophenoxy)pyrazine-2-carbaldehyde as a pale brown solid (1.88 g).

$^1$H NMR (300 MHz, CHLOROFORM-d) δ ppm 7.09 (d, J=9.0 Hz, 2 H) 7.58 (d, J=9.0 Hz, 2 H) 8.55 (d, 3=1.2 Hz, 1 H) 8.70 (s, 1 H) 10.09 (s, 1 H).

MS ESI/APCI Dual posi: 279 [M+H]$^+$.

(2) Synthesis of 2-(4-bromophenoxy)-5-(1,3-dioxolan-2-yl)pyrazine

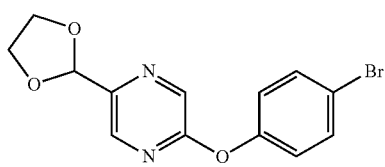

[Formula 147]

To a solution in toluene (20 mL) of the compound (1.66 g) obtained in step (1) above, ethylene glycol (1.11 g) and p-toluenesulfonic acid monohydrate (56.6 mg) were added and, thereafter, the mixture was stirred at 140° C. for an hour using a Dean-Stark apparatus. After cooling the reaction mixture to room temperature, a saturated aqueous solution of sodium hydrogencarbonate was added to it under cooling with ice and extraction was conducted with ethyl acetate. The combined organic layers were washed with saturated brine and dried over anhydrous magnesium sulfate. The desiccant was removed by filtration and the filtrate was concentrated under reduced pressure. Purification by silica gel column chromatography (n-hexane:ethyl acetate=100:0-60:40) gave 2-(4-bromophenoxy)-5-(1,3-dioxolan-2-yl)pyrazine as a colorless solid (1.78 g).

$^1$H NMR (300 MHz, CHLOROFORM-d) δ ppm 4.01-4.24 (m, 4 H) 5.92 (s, 1 H) 7.05 (d, J=9.0 Hz, 2 H) 7.48-7.59 (m, 2 H) 8.26-8.30 (m, 1 H) 8.40-8.44 (m, 1 H).

MS ESI/APCI Dual posi: 323 [M+H]$^+$.

(3) Synthesis of 2-(4-cyclopropylphenoxy)-5-(1,3-dioxolan-2-yl)pyrazine

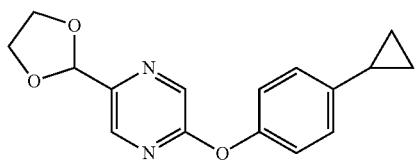

[Formula 148]

The compound (1.73 g) obtained in step (2) above was used and treated by the same technique as in Reference Example 14-5(2) to give 2-(4-cyclopropylphenoxy)-5-(1,3-dioxolan-2-yl)pyrazine as a brown oil (2.46 g).

$^1$H NMR (300 MHz, CHLOROFORM-d) δ ppm 0.65-0.74 (m, 2 H) 0.91-1.02 (m, 2 H) 1.84-1.98 (m, 1 H) 4.02-4.23 (m, 4 H) 5.91 (s, 1 H) 6.98-7.07 (m, 2 H) 7.09-7.16 (m, 2 H) 8.26-8.30 (m, 1 H) 8.35-8.42 (m, 1 H).

MS ESI/APCI Dual posi: 285 [M+H]$^+$.

(4) Synthesis of the Titled Compound

To a solution in acetone (107 mL) of the compound (2.46 g) obtained in step (3) above, p-toluenesulfonic acid monohydrate (2.04 g) was added and the mixture was stirred at 50° C. for two hours. After cooling the reaction mixture to room temperature, a saturated aqueous solution of sodium hydrogencarbonate was added to it under cooling with ice and two extractions were conducted with ethyl acetate. The combined organic layers were dried over anhydrous magnesium sulfate; thereafter, the desiccant was removed by filtration and the filtrate was concentrated under reduced pressure. The resulting residue was purified by silica gel column chromatography (n-hexane:ethyl acetate=100:0-80:20) to give the titled compound as a colorless solid (0.67 g).

$^1$H NMR (300 MHz, CHLOROFORM-d) δ ppm 0.66-0.78 (m, 2 H) 0.91-1.05 (m, 2 H) 1.87-2.00 (m, 1 H) 7.01-7.10 (m, 2 H) 7.12-7.20 (m, 2 H) 8.51 (s, 1 H) 8.71 (s, 1 H) 10.08 (s, 1 H).

MS ESI/APCI Dual posi: 241 [M+H]$^+$.

Reference Example 41-4

2-(4-Methylphenoxyl)pyrimidine-5-carbaldehyde

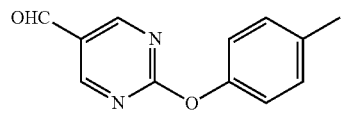

[Formula 149]

(1) Synthesis of 2-chloro-5-(1,3-dioxolan-2-yl)pyrimidine

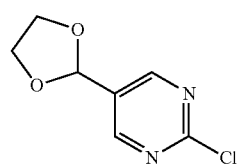

[Formula 150]

The compound 2-chloropyrimidine-5-carbaldehyde (1.00 g) was used and treated by the same technique as in Reference Example 41-3(2) to give 2-chloro-5-(1,3-dioxolan-2-yl)pyrimidine as a pale yellow oil (290 mg).

$^1$H NMR (300 MHz, CHLOROFORM-d) δ ppm 3.96-4.21 (m, 4 H) 5.89 (s, 1 H) 8.71 (s, 2 H).

MS ESI/APCI Dual posi: 187 [M+H]$^+$.

(2) Synthesis of 5-(1,3-dioxolan-2-yl)-2-(4-methylphenoxyl)pyrimidine

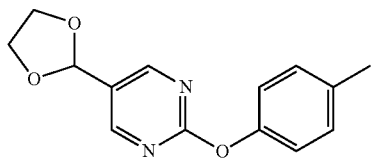

[Formula 151]

The compound (290 mg) obtained in step (1) above was used and treated by the same technique as in Reference Example 13-1 to give 5-(1,3-dioxolan-2-yl)-2-(4-methylphenoxyl)pyrimidine as a colorless solid (380 mg).

$^1$H NMR (300 MHz, CHLOROFORM-d) δ ppm 2.37 (s, 3 H) 3.97-4.19 (m, 4 H) 5.83 (s, 1 H) 7.04-7.10 (m, 2 H) 7.19-7.26 (m, 2 H) 8.61 (s 2 H).

MS ESI/APCI Dual posi: 259 [M+H]$^+$.

(3) Synthesis of the Titled Compound

The compound (380 mg) obtained in step (2) above was used and treated by the same technique as in Reference Example 41-3(4) to give the titled compound as a colorless solid (139 mg).

$^1$H NMR (300 MHz, CHLOROFORM-d) δ ppm 2.39 (s, 3 H) 7.09 (d, J=8.3 Hz, 2 H) 7.26 (d, J=8.3 Hz, 2 H) 9.01 (s, 2 H) 9.99-10.09 (m, 1 H).

MS ESI/APCI Dual posi: 215 [M+H]$^+$.

Reference Example 42-1

1-(Pyrimidin-2-yl)piperidine-4-carbaldehyde

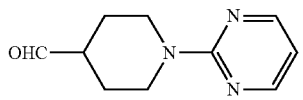

[Formula 152]

(1) Synthesis of [1-(pyrimidin-2-yl)piperidin-4-yl]methanol

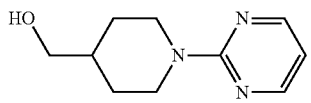

[Formula 153]

To a solution of 4-piperidinemethanol (1.00 g) in dimethyl sulfoxide (28.9 mL), 2-chloropyrimidine (994 mg) and potassium carbonate (2.40 g) were added and the mixture was stirred at 100° C. for three hours. After cooling the reaction mixture to room temperature, water was added to it and extraction was conducted with ethyl acetate. The combined organic layers were dried over anhydrous sodium sulfate and after removing the desiccant by filtration, the filtrate was concentrated under reduced pressure to give [1-([pyrimidin-2-yl)piperidin-4-yl]methanol as a colorless oil (1.50 g).

$^1$H NMR (300 MHz, CHLOROFORM-d) δ ppm 1.14-1.32 (m, 2 H) 1.72-1.89 (m, 3 H) 2.82-2.96 (m, 2 H) 3.53 (d, J=5.9 Hz, 2 H) 4.74-4.85 (m, 2 H) 6.41-6.47 (m, 1 H) 8.26-8.33 (m, 2 H).

MS ESI/APCI Dual posi: 194 [M+H]$^+$.

(2) Synthesis of the Titled Compound

The compound (1.50 g) obtained in step (1) above was used and treated by the same technique as in Reference Example 19-1 to give the titled compound as a yellow oil (1.21 g).

$^1$H NMR (300 MHz, CHLOROFORM-d) δ ppm 1.57-1.72 (m, 2 H) 1.94-2.05 (m, 2 H) 2.49-2.61 (m, 1 H) 3.12-3.24 (m, 2 H) 4.53-4.64 (m, 2 H) 6.48 (t, J=4.7 Hz, 1 H) 8.31 (d, J=4.7 Hz, 2 H) 9.70 (d, J=0.9 Hz, 1 H).

MS ESI/APCI Dual posi: 192 [M+H]$^+$.

Reference Example 42-2

1-(Cyclopropylacetyl)piperidine-4-carbaldehyde

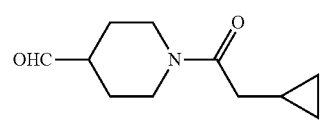

[Formula 154]

(1) Synthesis of 2-cyclopropyl-1-[4-(hydroxymethyl)piperidin-1-yl]ethanone

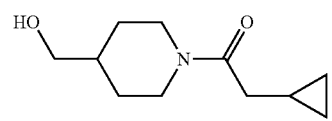

[Formula 155]

Instead of 4-(bromomethyl)benzoic acid and N,O-dimethylhydroxylamine hydrochloride, cyclopropylacetic acid (869 mg) and 4-piperidinemethanol (1.00 g) were respectively used and treated by the same technique as in Reference Example 16-1(1) to give the titled compound as a colorless oil (1.25 g).

$^1$H NMR (300 MHz, CHLOROFORM-d) δ ppm 0.12-0.23 (m, 2 H) 0.51-0.60 (m, 2 H) 0.96-1.30 (m, 3 H) 1.54-1.90 (m, 3 H) 2.28 (d, J=6.7 Hz, 2 H) 2.47-2.65 (m, 1 H) 2.95-3.10 (m, 1 H) 3.43-3.59 (m, 2 H) 3.80-3.94 (m, 1 H) 4.60-4.76 (m, 1 H).

MS ESI/APCI Dual posi: 198 [M+H]$^+$.

(2) Synthesis of the Titled Compound

The compound (1.25 g) obtained in step (1) above was used and treated by the same technique as in Reference Example 19-1 to give the titled compound as a yellow oil (800 mg).

$^1$H NMR (300 MHz, CHLOROFORM-d) δ ppm 0.13-0.22 (m, 2 H) 0.52-0.61 (m, 2 H) 0.96-1.10 (m, 1 H) 1.50-1.71 (m, 2 H) 1.88-2.03 (m, 2 H) 2.29 (d, J=6.8 Hz, 2 H) 2.45-2.59 (m, 1 H) 2.92-3.04 (m, 1 H) 3.11-3.25 (m, 1 H) 3.72-3.84 (m, 1 H) 4.29-4.41 (m, 1 H) 9.68 (s, 1 H).

MS ESI/APCI Dual posi: 196 [M+H]$^+$.

Reference Example 43-1

1-(Pyrimidin-2-yl)azetidine-3-carbaldehyde

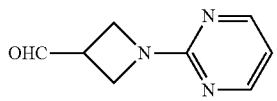

[Formula 156]

(1) Synthesis of tert-butyl 3-[methoxy(methyl)carbamoyl]azetidine-1-carboxylate

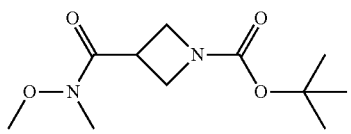

[Formula 157]

To a solution of 1-(tert-butoxycarbonyl)azetidine-3-carboxylic acid (5.00 g) in tetrahydrofuran (62.1 mL), 1,1'-carbonyldiimidazole (6.05 g) was added and the mixture was stirred at room temperature for an hour. To the reaction mixture, a solution of N,O-dimethylhydroxylamine hydrochloride (3.64 g) and triethylamine (4.02 g) in acetonitrile (62.1 mL) was added and the mixture was stirred at the same temperature for 15 hours. The reaction mixture was concentrated under reduced pressure and water was added to the resulting residue. Extraction was conducted with ethyl acetate and the combined organic layers were washed with an aqueous solution of 5% citric acid and saturated brine. The washed organic layers were dried over anhydrous sodium sulfate and after removing the desiccant by filtration, the filtrate was concentrated under reduced pressure to give tert-butyl 3-[methoxy(methyl)carbamoyl]azetidine-1-carboxylate as a pale yellow oil (7.30 g).

$^1$H NMR (300 MHz, CHLOROFORM-d) δ ppm 1.43 (s, 9 H) 3.21 (s, 3 H) 3.56-3.68 (m, 4 H) 4.00-4.09 (m, 2 H) 4.09-4.19 (m, 2 H).

(2) Synthesis of N-methoxy-N-methyl-1-(pyrimidin-2-yl)azetidine-3-carboxamide

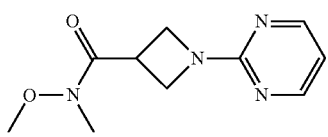

[Formula 158]

To a solution in chloroform (24.8 mL) of the compound (7.30 g) obtained in step (1) above, trifluoroacetic acid (12.4 mL) was added and the mixture was stirred at room temperature for 15 hours and then concentrated under reduced pressure. The resulting residue (6.29 g) was used and treated by the same technique as in Reference Example 42-1(1) to give N-methoxy-N-methyl-1-(pyrimidin-2-yl)azetidine-3-carboxamide as a colorless solid (810 mg).

$^1$H NMR (300 MHz, CHLOROFORM-d) δ ppm 3.23 (s, 3 H) 3.70 (s, 3 H) 3.80-3.96 (m, 1 H) 4.16-4.41 (m, 4 H) 6.51-6.59 (m, 1 H) 8.28-8.35 (m, 2 H).

MS ESI/APCI Dual posi: 223 [M+H]$^+$.

(3) Synthesis of the Titled Compound

The compound (810 mg) obtained in step (2) above was used and treated by the same technique as in Reference Example 16-1(3) to give the titled compound as a colorless oil (707 mg).

MS ESI/APCI Dual posi: 164 [M+H]$^+$.

Reference Example 44-1 tert-Butyl 4-formyl-2-methyl-1H-imidazole-1-carboxylate

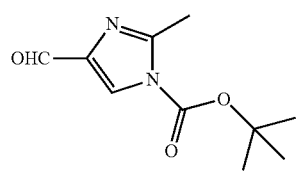

[Formula 159]

To a solution of 2-methyl-1H-imidazole-4-carbaldehyde (500 mg) in chloroform (15 mL), di-tert-butyl dicarbonate (1.19 g), triethylamine (949 μL), and 4-dimethylaminopyridine were added and the mixture was stirred at room temperature for 30 minutes. To the reaction mixture, a saturated aqueous solution of sodium hydrogencarbonate was added and extraction was conducted with chloroform. The combined organic layers were passed through a phase separator and thereafter concentrated under reduced pressure. The resulting residue was purified by silica gel column chromatography to give the titled compound as a colorless solid (883 mg).

$^1$H NMR (300 MHz, CHLOROFORM-d) δ ppm 1.64 (s, 9 H) 2.68 (s, 3 H) 7.98 (s, 1 H) 9.85 (s, 1 H).

MS ESI/APCI Dual posi: 233 [M+Na]$^+$.

MS ESI/APCI Dual nega: 209 [M−H]$^-$.

Reference Example 45-1

1-(4-Cyclohexyl-3-fluorophenyl)methaneamine hydrochloride

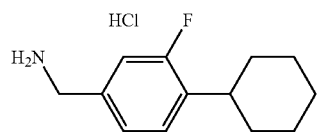

[Formula 160]

137

(1) Synthesis of 4-cyclohexen-1-yl-3-fluorobenzonitrile

[Formula 161]

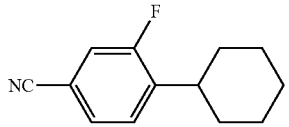

To a mixture of 3-fluoro-4-iodobenzonitrile (1.53 g), 1-cyclohexen-1-yl-boronic acid (938 mg), bis(triphenylphosphine)palladium(II) dichloride (435 mg) and ethanol (9.75 mL), sodium ethoxide (about 20%, solution in ethanol, 5.75 mL) was added and the mixture was stirred at 90° C. for 15 minutes under irradiation with microwaves. After being cooled to room temperature, the reaction mixture was poured into water and three extractions were conducted with chloroform. The combined organic layers were washed with saturated brine and passed through a phase separator to be concentrated under reduced pressure. The resulting residue was purified by silica gel column chromatography (n-hexane:ethyl acetate=100:0-75:25) to give the titled compound as a pale yellow oil (980 mg).

$^1$H NMR (300 MHz, CHLOROFORM-d) δ ppm 1.63-1.84 (m, 4 H) 2.18-2.29 (m, 2 H) 2.30-2.41 (m, 2 H) 6.01-6.10 (m, 1 H) 7.27-7.42 (m, 3 H).

MS ESI/APCI Dual posi: 224 [M+Na]$^+$.

MS ESI/APCI Dual nega: 236 [M+Cl]$^-$.

(2) Synthesis of the Titled Compound

To a solution in isopropyl alcohol (24 mL) of the compound (980 mg) obtained in step (1) above, a solution (3.7 mL) of 4 mol/L hydrogen chloride in 1,4-dioxane and 20% palladium hydroxide/carbon (98 mg) were added. The mixture was stirred at room temperature for 4 hours in a hydrogen atmosphere. The reaction mixture was filtered through Celite (registered trademark) and the filtrate was concentrated under reduced pressure. To a solution of the resulting residue in ethanol (10 mL), a solution (2.0 mL) of 2 mol/L hydrogen chloride in methanol and 20% palladium hydroxide/carbon (98 mg) were added. The mixture was stirred at room temperature for 26 hours in a hydrogen atmosphere. The reaction mixture was filtered through Celite (registered trademark) and the filtrate was concentrated under reduced pressure. To the resulting residue, ethanol (5 mL) and diethyl ether (50 mL) were added and the mixture was stirred for 15 minutes. The resulting precipitate was recovered by filtration to give the titled compound as a brown solid (1.06 g).

$^1$H NMR (300 MHz, DMSO-d$_6$) δ ppm 1.14-1.54 (m, 5 H) 1.63-1.86 (m, 5 H) 2.70-2.87 (m, 1 H) 3.99 (s, 2 H) 7.22-7.42 (m, 3 H) 8.43 (br. s., 2 H).

MS ESI/APCI Dual posi: 208 [M+H]$^+$.

Reference Example 45-2

1-[4-(Aminomethyl)phenyl]-4,4-difluorocyclohexanol hydrochloride

[Formula 162]

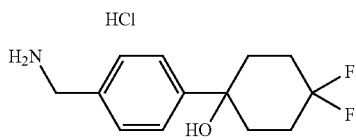

138

(1) Synthesis of 4-(4,4-difluoro-1-hydroxycyclohexyl)benzonitrile

[Formula 163]

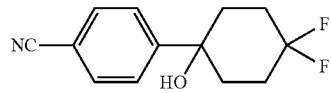

To a solution of 4-iodobenzonitrile (5.35 g) in tetrahydrofuran (100 mL), isopropylmagnesium bromide (about 1 mol/L, solution in tetrahydrofuran, 35 mL) was added dropwise at −40° C. in an argon atmosphere. After stirring the mixture at that temperature for an hour, a solution of 4,4-difluorocyclohexanone (4.70 g) in cyclopentyl methyl ether (10 mL) was added dropwise. The mixture was brought to room temperature over a period of 5.5 hours and a saturated aqueous solution of ammonium chloride was added. Three extractions were conducted with ethyl acetate and the combined organic layers were washed with saturated brine and thereafter dried over anhydrous magnesium sulfate. The insoluble matter was removed by filtration and the filtrate was concentrated under reduced pressure.

The resulting residue was purified by silica gel column chromatography (n-hexane:ethyl acetate=95:5-40:60) to give 4-(4,4-difluoro-1-hydroxycyclohexyl)benzonitrile as a colorless solid (2.19 g).

$^1$H NMR (300 MHz, CHLOROFORM-d) δ ppm 1.77-1.92 (m, 2 H) 2.00-2.45 (m, 6 H) 7.58-7.72 (m, 4 H).

MS EI posi: 237 [M]$^+$.

(2) Synthesis of the Titled Compound

The compound (2.19 g) obtained in step (1) above was used and treated by the same technique as in Reference Example 45-1(2) to give the titled compound as a colorless solid (1.51 g).

$^1$H NMR (300 MHz, DMSO-d$_6$) δ ppm 1.66-1.79 (m, 2 H) 1.85-2.04 (m, 4 H) 2.09-2.36 (m, 2 H) 3.99 (s, 2 H) 5.28 (s, 1 H) 7.40-7.48 (m, 2 H) 7.49-7.57 (m, 2 H) 8.32 (br. s., 3 H).

MS ESI/APCI Dual posi: 242 [M+H]$^+$.

MS ESI/APCI Dual nega: 276 [M+Cl]$^-$.

Reference Example 46-1

1-[trans-3-(4-Chlorophenoxyl)cyclobutyl]methaneamine

[Formula 164]

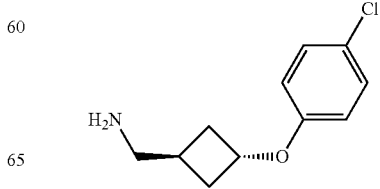

(1) Synthesis of N-benzyl-3-oxocyclobutanecarboxamide

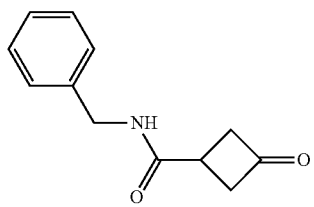

[Formula 165]

To a solution of 3-oxocyclobutanecarboxylic acid (13.5 g) in tetrahydrofuran (135 mL), 1,1'-carbonyldiimidazole (23.0 g) was added under cooling with ice. The mixture was brought to room temperature and stirred for 90 minutes. Benzylamine (15.5 mL) was added and the mixture was stirred at that temperature for 14 hours. The crude product was adsorbed on diatomaceous earth with the solvent being distilled off under reduced pressure. The crude product adsorbed on the diatomaceous earth was purified by silica gel column chromatography (chloroform:methanol=100:0-95:5) to give N-benzyl-3-oxocyclobutanecarboxamide as a colorless solid (16.9 g).

$^1$H NMR (300 MHz, CHLOROFORM-d) δ ppm 2.89-3.10 (m, 1 H) 3.11-3.32 (m, 2 H) 3.41-3.67 (m, 2 H) 4.50 (d, J=5.8 Hz, 2 H) 7.25-7.42 (m, 5 H).

MS ESI/APCI Dual posi: 204 [M+H]$^+$.

(2) Synthesis of cis-3-[(benzylamino)methyl]cyclobutanol

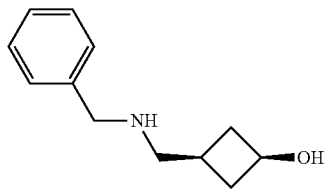

[Formula 166]

The compound (16.9 g) obtained in step (1) above was used and treated by the same technique as in Reference Example 23-1(2) to give cis-3-[(benzylamino)methyl]cyclobutanol as a pale yellow oil (16.2 g).

$^1$H NMR (300 MHz, DMSO-d$_6$) δ ppm 1.35-1.57 (m, 2 H) 1.66-1.93 (m, 2 H) 2.12-2.36 (m, 2 H) 2.42-2.53 (m, 2 H) 3.69 (s, 2 H) 3.78-4.00 (m, 1 H) 7.12-7.41 (m, 5 H).

MS ESI/APCI Dual posi: 192 [M+H]$^+$.

(3) Synthesis of cis-3-(aminomethyl)cyclobutanol

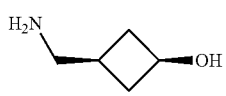

[Formula 167]

The compound (16.2 g) obtained in step (2) above was used and treated by the same technique as in Reference Example 29-1(4) to give cis-3-(aminomethyl)cyclobutanol as a colorless oil (10.4 g).

$^1$H NMR (300 MHz, DMSO-d$_6$) δ ppm 1.29-1.51 (m, 2 H) 1.53-1.70 (m, 1 H) 2.08-2.29 (m, 2 H) 2.41-2.51 (m, 2 H) 3.76-3.98 (m, 1 H).

(4) Synthesis of tert-butyl [(cis-3-hydroxycyclobutyl)methyl]carbamate

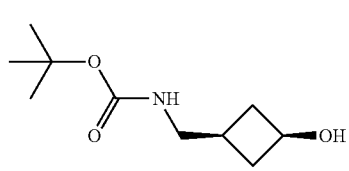

[Formula 168]

The compound (10.3 g) obtained in step (3) above was used and treated by the same technique as in Reference Example 44-1 to give tert-butyl [(cis-3-hydroxycyclobutyl)methyl]carbamate as a colorless solid (6.08 g).

$^1$H NMR (600 MHz, DMSO-d$_6$) δ ppm 1.37 (s, 9 H) 1.37-1.49 (m, 2 H) 1.66-1.79 (m, 1 H) 2.08-2.23 (m, 2 H) 2.87-2.91 (m, 2 H) 3.78-3.91 (m, 1 H) 4.82-4.94 (m, 1 H) 6.76 (t, J=5.4 Hz, 1 H).

MS ESI/APCI Dual posi: 224 [M+Na]$^+$.
MS ESI/APCI Dual nega: 200 [M−H]$^-$.

(5) Synthesis of tert-butyl {[trans-3-(4-chlorophenoxyl)cyclobutyl]methyl}carbamate

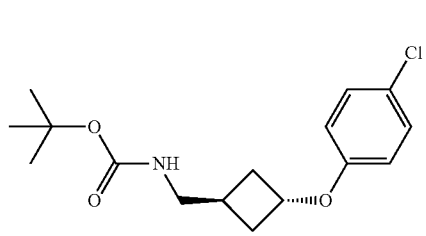

[Formula 169]

Instead of 4-hydroxybenzaldehyde and 2-cyclopropylethanol, 4-chlorophenol (767 mg) and the compound (1.00 g) obtained in step (4) above were respectively used and treated by the same technique as in Reference Example 11-1 to give tert-butyl {[trans-3-(4-chlorophenoxyl)cyclobutyl]methyl}carbamate as a colorless solid (1.05 g).

$^1$H NMR (600 MHz, CHLOROFORM-d) δ ppm 1.45 (s, 9 H) 2.15-2.37 (m, 4 H) 2.40-2.65 (m, 1 H) 3.12-3.35 (m, 2 H) 4.64-4.79 (m, 1 H) 6.63-6.76 (m, 2 H) 7.15-7.25 (m, 2 H).

(6) Synthesis of the Titled Compound

To a solution in 1,4-dioxane (30 mL) of the compound (0.98 g) obtained in step (5) above, a solution (25 mL) of 4 mol/L hydrogen chloride in 1,4-dioxane was added and the mixture was stirred at room temperature for 5 hours. After adding diethyl ether (120 mL), the mixture was stirred for another two hours and thereafter the precipitate was recovered by filtration. The recovered precipitate was dissolved in an aqueous solution of 1 mol/L sodium hydroxide and chloroform and two extractions were conducted with chloroform. The combined organic layers were dried over anhydrous magnesium sulfate and the desiccant was removed by filtration. The filtrate was concentrated under reduced pressure to give the titled compound as a colorless oil (660 mg).

$^1$H NMR (300 MHz, CHLOROFORM-d) δ ppm 2.12-2.48 (m, 5 H) 2.74-2.87 (m, 2 H) 4.61-4.77 (m, 1 H) 6.63-6.80 (m, 2 H) 7.12-7.27 (m, 2 H).

In the following Reference Examples 46-2 to 46-4, a commercial grade of the corresponding phenols was used and treated by the method described in Reference Example 46-1 or modifications thereof to synthesize the intended compounds. The structures of the synthesized compounds and their NMR and MS data are shown in Table 17-1.

respectively used and treated by the same technique as in Reference 9-1 to give tert-butyl ({cis-3-[(4-chlorobenzyl)oxy]cyclobutyl}methyl)carbamate as a colorless solid (750 mg).

TABLE 17-1

| Compound No. | Structure | Analytical Data | Salt information |
|---|---|---|---|
| Reference Example 46-2 | 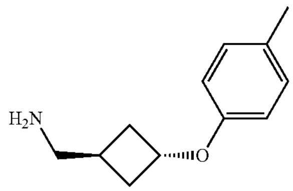 | $^1$H NMR (300 MHz, CHLOROFORM-d) δ ppm 2.17-2.39 (m, 8 H) 2.82 (d, J = 7.0 Hz, 2 H) 4.58-4.82 (m, 1 H) 6.61-6.77 (m, 2 H) 6.96-7.14 (m, 2 H). MS ESI/APCI Dual posi: 192[M + H]$^+$. | |
| Reference Example 46-3 | 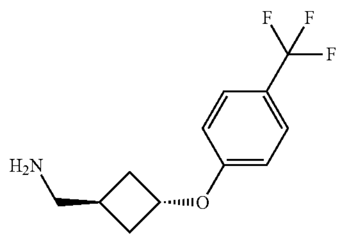 [SMILES: NC[C@H]1C[C@H](Oc2ccc(C(F)(F)F)cc2)C1] | $^1$H NMR (300 MHz, CHLOROFORM-d) δ ppm 2.21-2.55 (m, 5 H) 2.86 (d, J = 7.3 Hz, 2 H) 4.66-4.83 (m, 1 H) 6.74-6.91 (m, 2 H) 7.39-7.65 (m, 2 H). MS ESI/APCI Dual posi: 246[M + H]$^+$, 287[M + Na]$^+$. | |
| Reference Example 46-4 | 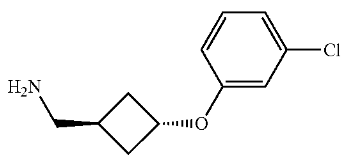 [SMILES: NC[C@H]1C[C@H](Oc2cccc(Cl)c2)C1] | $^1$H NMR (600 MHz, DMSO-d$_6$) δ ppm 2.15-2.22 (m, 2 H) 2.33-2.42 (m, 2 H) 2.47-2.57 (m, 1 H) 2.99 (d, J = 7.8 Hz, 2 H) 4.82-4.93 (m, 1 H) 6.78-6.84 (m, 1 H) 6.85-6.92 (m, 1 H) 6.97-7.02 (m, 1 H) 7.26-7.34 (m, 1 H) 7.73-8.00 (m, 3H). MS ESI/APCI Dual posi: 212[M + H]$^+$. | |

Reference Example 46-5

1-{cis-3-[(4-Chlorobenzyl)oxy]cyclobutyl}methaneamine

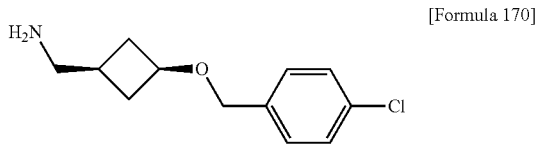 [SMILES: NC[C@H]1C[C@@H](OCc2ccc(Cl)cc2)C1]

[Formula 170]

(1) Synthesis of tert-butyl ({cis-3-[(4-chlorobenzyl)oxy]cyclobutyl}methyl)carbamate

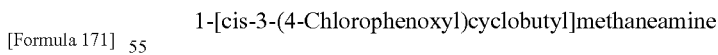

[Formula 171]

Instead of 4-hydroxybenzaldehyde and (bromomethyl)cyclobutane, the compound (1.00 g) obtained in Reference Example 46-1(4) and 4-chlorobenzyl bromide (1.02 g) were $^1$H NMR (300 MHz, CHLOROFORM-d) δ ppm 1.44 (s, 9 H) 1.58-1.71 (m, 2 H) 1.88-2.10 (m, 1 H) 2.25-2.43 (m, 2 H) 3.08-3.22 (m, 2 H) 3.81-3.95 (m, 1 H) 4.36 (s, 2 H) 7.20-7.37 (m, 4 H).

(2) Synthesis of the Titled Compound

The compound (750 mg) obtained in step (1) above was used and treated by the same technique as in Reference Example 46-1(6) to give the titled compound as a colorless oil (523 mg).

$^1$H NMR (300 MHz, CHLOROFORM-d) δ ppm 1.52-1.71 (m, 2 H) 1.77-1.95 (m, 1 H) 2.27-2.45 (m, 2 H) 2.72 (d, J=6.7 Hz, 2 H) 3.81-4.01 (m, 1 H) 4.38 (s, 2 H) 7.20-7.39 (m, 4 H). MS ESI/APCI Dual posi: 226 [M+H]$^+$.

Reference Example 46-6

1-[cis-3-(4-Chlorophenoxyl)cyclobutyl]methaneamine

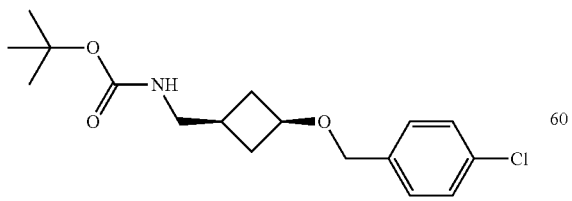

[Formula 172]

(1) Synthesis of trans-3-[({[(2-methyl-2-propanyl)oxy]carbonyl}amino)methyl]cyclobutyl 4-nitrobenzoate

[Formula 173]

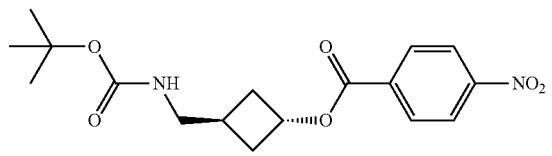

To a mixture of the compound (2.00 g) obtained in Reference Example 46-1(4), 4-nitrobenzoic acid (3.32 g), triphenylphosphine (5.21 g) and tetrahydrofuran (50 mL), diisopropyl azodicarboxylate (1.0 mol/L, solution in toluene, 10.5 mL) was added and the mixture was stirred at room temperature for 16 hours. After concentrating under reduced pressure, the resulting residue was purified by silica gel column chromatography (n-hexane:ethyl acetate=100:0-75:25) to give trans-3-[({[(2-methyl-2-propanyl)oxy]carbonyl}amino)methyl]cyclobutyl 4-nitrobenzoate as a colorless solid (3.88 g).

$^1$H NMR (300 MHz, CHLOROFORM-d) δ ppm 1.46 (s, 9 H) 2.24-2.45 (m, 4 H) 2.46-2.68 (m, 1 H) 3.21-3.33 (m, 2 H) 5.29-5.41 (m, 1 H) 8.18-8.25 (m, 2 H) 8.26-8.32 (m, 2 H).

(2) Synthesis of tert-butyl[(trans-3-hydroxycyclobutyl)methyl]carbamate

[Formula 174]

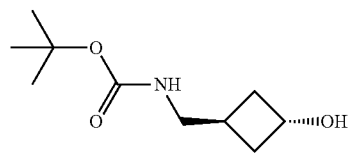

To a solution in tetrahydrofuran (100 mL) of the compound (3.88 g) obtained in step (1) above, an aqueous solution of 1 mol/L sodium hydroxide (19.9 mL) was added and the mixture was stirred at room temperature for 4 hours. Extraction was conducted with ethyl acetate and after drying the combined organic layers over anhydrous magnesium sulfate, the desiccant was removed by filtration. With the solvent being distilled off under reduced pressure, the crude product was adsorbed on diatomaceous earth. The crude product as adsorbed on the diatomaceous earth was purified by silica gel column chromatography (n-hexane:ethyl acetate=99:1-0:100, then chloroform:methanol=100:0-90:10) to give tert-butyl [(trans-3-hydroxycyclobutyl)methyl]carbamate as a colorless solid (1.87 g).

$^1$H NMR (300 MHz, DMSO-d$_6$) δ ppm 1.37 (s, 9 H) 1.72-2.00 (m, 4 H) 2.01-2.22 (m, 1 H) 2.85-3.02 (m, 2 H) 4.05-4.23 (m, 1 H) 4.81-4.95 (m, 1 H) 6.72-6.91 (m, 1 H).

(3) Synthesis of the Titled Compound

The compound (500 mg) obtained in step (2) above was used and treated by the same techniques as in Reference 46-1(5) and (6) to give the titled compound as a colorless oil (460 mg).

$^1$H NMR (300 MHz, CHLOROFORM-d) δ ppm 1.71-1.90 (m, 2 H) 1.95-2.13 (m, 1 H) 2.50-2.68 (m, 2 H) 2.77 (d, J=6.8 Hz, 2 H) 4.43-4.60 (m, 1 H) 6.66-6.80 (m, 2 H) 7.14-7.26 (m, 2 H).

MS ESI/APCI Dual posi: 212 [M+H]$^+$.

Reference Example 46-7

1-{trans-3-[(4-Chlorobenzyl)oxy]cyclobutyl}methaneamine

[Formula 175]

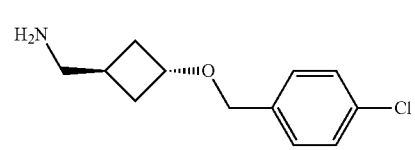

The compound (1.30 mg) obtained in Reference Example 46-6(2) was used and treated by the same technique as in Reference Example 46-5 to give the titled compound as a colorless oil (630 smg).

$^1$H NMR (300 MHz, CHLOROFORM-d) δ ppm 1.91-2.34 (m, 5 H) 2.72 (d, J=7.3 Hz, 2 H) 4.03-4.20 (m, 1 H) 4.36 (s, 2 H) 7.20-7.38 (m, 4 H).

MS ESI/APCI Dual posi: 226 [M+H]$^+$.

Reference Example 47-1

2-{[tert-Butyl(dimethyl)silyl]oxy}-1-(4-iodophenyl)ethaneamine

[Formula 176]

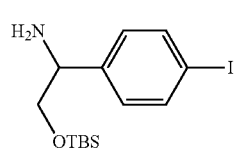

(1) Synthesis of amino(4-iodophenyl)acetonitrile

[Formula 177]

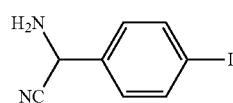

To a solution of 4-iodobenzaldehyde (10.4 g) in methanol (36 mL), tetraisopropyl orthotitanate (50.0 mL) and a solution (50 mL) of 8 mol/L ammonia in methanol were added and the mixture was stirred at room temperature for 3.5 hours. Trimethylsilyl cyanide (5.89 mL) was slowly added to the mixture, which was then stirred at the same temperature for 14 hours. Iced water was added to the reaction mixture, which was then filtered through Celite (registered trademark). The filtrate was concentrated under reduced pressure and the resulting residue was extracted with ethyl acetate. The combined organic layers were washed with water and dried over anhydrous magnesium sulfate. The desiccant was removed by filtration and the filtrate was concentrated under reduced pressure. The resulting residue was purified by silica gel column chromatography (n-hexane:ethyl acetate=99:1-25:75) to give amino(4-iodophenyl)acetonitrile as a pale yellow solid (5.05 g).

$^1$H NMR (300 MHz, CHLOROFORM-d) δ ppm 4.87 (s, 2 H) 7.27-7.33 (m, 2 H) 7.69-7.83 (m, 2 H).

(2) Synthesis of amino(4-iodophenyl)acetic acid hydrochloride

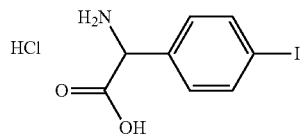

[Formula 178]

A suspension in 6 mol/L hydrochloric acid (65 mL) of the compound (5.05 g) obtained in Step (1) above was stirred at 105° C. for 14 hours. After being cooled to room temperature, the suspension was stirred at room temperature for an hour and then stirred for 30 minutes under cooling with ice. The resulting precipitate was recovered by filtration to give amino (4-iodophenyl)acetic acid hydrochloride as a colorless solid (4.32 g).

$^1$H NMR (300 MHz, DMSO-d$_6$) δ ppm 4.18 (s, 2 H) 7.08-7.30 (m, 2 H) 7.60-7.77 (m, 2 H).

MS ESI/APCI Dual posi: 278 [M+H]$^+$.
MS ESI/APCI Dual nega: 276 [M−H]$^−$.

(3) Synthesis of 2-amino-2-(4-iodophenyl)ethanol

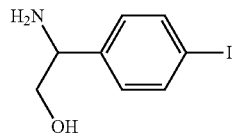

[Formula 179]

To a liquid mixture of lithium borohydride (2.0 mol/L, solution in tetrahydrofuran, 19.7 mL) and chlorotrimethylsilane (9.97 mL), the compound (4.95 g) obtained in step (2) above was added in small portions at room temperature and the mixture was stirred for 16 hours. Under cooling with ice, methanol (3.5 mL) was added to the mixture, which was then brought to room temperature and stirred for 15 minutes. To the stirred mixture, water (19.7 mL), ethyl acetate (39.4 mL), saturated brine (19.7 mL) and sodium hydroxide (1.87 g) were added successively and the mixture was stirred at the same temperature for 16 hours. The reaction mixture was extracted with ethyl acetate and the combined organic layers were dried over anhydrous magnesium sulfate. The desiccant was removed by filtration and the filtrate was concentrated under reduced pressure to give 2-amino-2-(4-iodophenyl)ethanol as a yellow solid (4.70 g).

$^1$H NMR (300 MHz, CHLOROFORM-d) δ ppm 3.43-3.59 (m, 1 H) 3.65-3.77 (m, 1 H) 3.94-4.10 (m, 1 H) 7.02-7.15 (m, 2 H) 7.62-7.75 (m, 2 H).

MS ESI/APCI Dual posi: 264[1\4+H]$^+$.

(4) Synthesis of the Titled Compound

To a mixture of the compound (4.70 g) obtained in step (3) above, 4-dimethylaminopyridine (48.2 mg), triethylamine (4.40 mL) and chloroform (63.2 mL), a solution of tert-butyldimethylchlorosilane (2.38 g) in chloroform (31.6 mL) was added dropwise under cooling with ice and the mixture was stirred at the same temperature for 30 minutes, and then at room temperature for three days. The reaction mixture was concentrated under reduced pressure and water and ethyl acetate were then added. Extraction was conducted with ethyl acetate and the combined organic layers were dried over anhydrous magnesium sulfate. The desiccant was removed by filtration and the filtrate was concentrated under reduced pressure. The resulting residue was purified by silica gel column chromatography (chloroform:methanol=100:0-98:2) to give the titled compound as a pale yellow oil (4.68 g).

$^1$H NMR (300 MHz, CHLOROFORM-d) δ ppm 0.02 (s, 6 H) 0.89 (s, 9 H) 3.40-3.56 (m, 1 H) 3.62-3.74 (m, 1 H) 3.97-4.07 (m, 1 H) 7.06-7.20 (m, 2 H) 7.56-7.72 (m, 2 H).

Reference Example A-1

Methyl[4-({[4'-(trifluoromethyl)biphenyl-4-yl]methyl}amino)tetrahydro-2H-pyran-4-yl]acetate

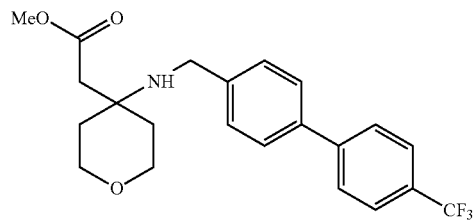

[Formula 180]

To a solution in chloroform (20 mL) of the compound (500 mg) obtained in Reference Example 1-1, the compound (627 mg) obtained in Reference Example 6-2 was added and the mixture was stirred at room temperature for 30 minutes. Sodium triacetoxyborohydride (654 mg) was added to the mixture which was further stirred at room temperature for 12 hours. Under cooling with ice, a saturated aqueous solution of sodium hydrogencarbonate was added to the mixture, which was then brought to room temperature. Three extractions were conducted with chloroform. The combined organic layers were passed through a phase separator and thereafter concentrated under reduced pressure. The resulting residue was purified by silica gel column chromatography (n-hexane:ethyl acetate=80:20-0:100) to give the titled compound as a colorless oil (784 mg).

$^1$H NMR (300 MHz, CHLOROFORM-d) δ ppm 1.66-1.76 (m, 4 H) 2.60 (s, 2 H) 3.60-3.78 (m, 7 H) 3.86-3.99 (m, 2 H) 4.77 (s, 1 H) 7.45-7.52 (m, 2 H) 7.54-7.63 (m, 2 H) 7.65-7.73 (m, 4 H).

MS ESI/APCI Dual posi: 408 [M+H]$^+$, 430 [M+Na]$^+$.

In the following Reference Examples A-2 to A-485, the compounds obtained in Reference Examples 1-1 to 5-5, Reference Examples 28-1 to 30-2, or commercial grades of the corresponding β-alanine esters, as well as the compounds obtained in Reference Examples 6-1 to 26-1, Reference Examples 31-1 to 44-1, or commercial grades of the corresponding aldehydes or ketones were used as starting materials and treated by the method described in Reference Example A-1 or modifications thereof to synthesize the intended compounds. The structures of the synthesized compounds and their NMR and MS data are shown in Tables 18-1 to 18-69.

TABLE 18-1

| Compound No. | Structure | Analytical Data | Salt information |
|---|---|---|---|
| Reference Example A-2 | 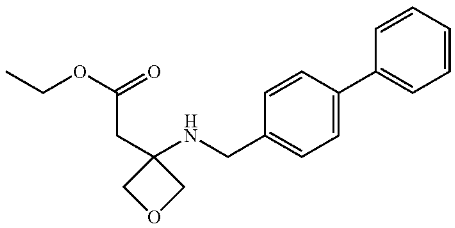 [SMILES: CCOC(=O)CC1(NCc2ccc(-c3ccccc3)cc2)COC1] | ¹H NMR (300 MHz, CHLOROFORM-d) δ ppm 1.27 (t, J = 7.1 Hz, 3 H) 2.98 (s, 2 H) 3.89 (s, 2 H) 4.17 (q, J = 7.1 Hz, 2 H) 4.56 (d, J = 6.7 Hz, 2 H) 4.71 (d, J = 6.7 Hz, 2 H) 7.29-7.38 (m, 1 H) 7.39-7.49 (m, 4 H) 7.51-7.63 (m, 4 H).<br>MS ESI/APCI Dual posi: 326[M + H]⁺. | |
| Reference Example A-3 | 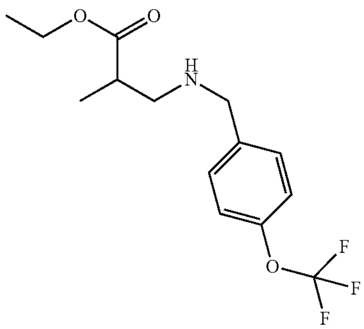 [SMILES: CCOC(=O)C(C)CNCc1ccc(OC(F)(F)F)cc1] | ¹H NMR (300 MHz, CHLOROFORM-d) δ ppm 1.17 (d, J = 6.8 Hz, 3 H) 1.25 (t, J = 7.1 Hz, 3 H) 2.57-2.71 (m, 2 H) 2.80-2.92 (m, 1 H) 3.79 (s, 2 H) 4.15 (q, J = 7.1 Hz, 2 H) 7.13-7.19 (m, 2 H) 7.32-7.36 (m, 2 H).<br>MS ESI/APCI Dual posi: 306[M + H]⁺, 328[M + Na]⁺. | |
| Reference Example A-4 | 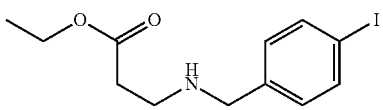 [SMILES: CCOC(=O)CCNCc1ccc(I)cc1] | ¹H NMR (300 MHz, CHLOROFORM-d) δ ppm 1.26 (t, J = 7.1 Hz, 3 H) 2.47-2.55 (m, 2 H) 2.82-2.91 (m, 2 H) 3.75 (s, 2 H) 4.14 (q, J = 7.1 Hz, 2 H) 7.01-7.13 (m, 2 H) 7.56-7.70 (m, 2 H).<br>MS ESI/APCI Dual posi: 334[M + H]⁺, 356[M + Na]⁺. | |
| Reference Example A-5 | 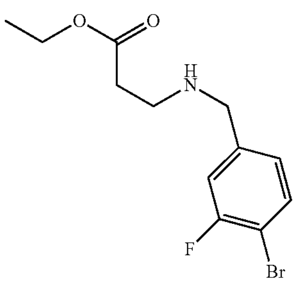 [SMILES: CCOC(=O)CCNCc1ccc(Br)c(F)c1] | ¹H NMR (300 MHz, CHLOROFORM-d) δ ppm 1.26 (t, J = 7.1 Hz, 3 H) 2.51 (t, J = 6.4 Hz, 2 H) 2.86 (t, J = 6.4 Hz, 2 H) 3.77 (s, 2 H) 4.15 (q, J = 7.1 Hz, 2 H) 6.96-7.02 (m, 1 H) 7.10-7.17 (m, 1 H) 7.44-7.51 (m, 1 H).<br>MS ESI/APCI Dual posi: 304[M + H]⁺, 326[M + Na]⁺. | |
| Reference Example A-6 | 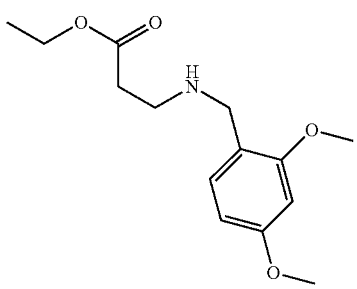 [SMILES: CCOC(=O)CCNCc1ccc(OC)cc1OC] | ¹H NMR (300 MHz, CHLOROFORM-d) δ ppm 1.25 (t, J = 7.1 Hz, 3 H) 2.51 (t, J = 6.7 Hz, 2 H) 2.85 (t, J = 6.7 Hz, 2 H) 3.73 (s, 2 H) 3.80 (s, 3 H) 3.81 (s, 3 H) 4.13 (q, J = 7.1 Hz, 2 H) 6.34-6.51 (m, 2 H) 7.13 (d, J = 7.9 Hz, 1 H).<br>MS ESI/APCI Dual posi: 268[M + H]⁺. | |
| Reference Example A-7 | 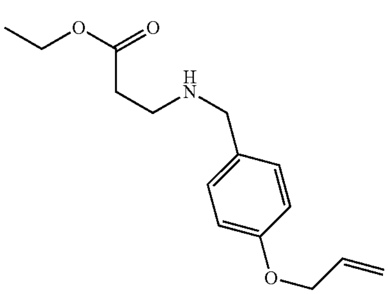 [SMILES: C=CCOc1ccc(CNCCC(=O)OCC)cc1] | ¹H NMR (300 MHz, CHLOROFORM-d) δ ppm 1.25 (t, J = 7.1 Hz, 3 H) 2.52 (t, J = 6.6 Hz, 2 H) 2.88 (t, J = 6.6 Hz, 2 H) 3.73 (s, 2 H) 4.14 (q, J = 7.1 Hz, 2 H) 4.52 (ddd, J = 5.3, 1.7, 1.4 Hz, 2 H) 5.28 (ddt, J = 10.5, 1.6, 1.4 Hz, 1 H) 5.41 (dtd, J = 17.3, 1.7, 1.6 Hz, 1 H) 6.06 (ddt, J = 17.3, 10.5, 5.3 Hz, 1 H) 6.84-6.90 (m, 2 H) 7.19-7.26 (m, 2 H).<br>MS ESI/APCI Dual posi: 264[M + H]⁺. | |

TABLE 18-1-continued

| Compound No. | Structure | Analytical Data | Salt information |
|---|---|---|---|
| Reference Example A-8 | 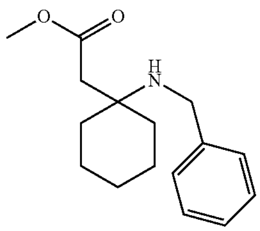 [SMILES: COC(=O)CC1(NCc2ccccc2)CCCCC1] | $^1$H NMR (300 MHz, CHLOROFORM-d) δ ppm 1.23-1.59 (m, 6 H) 1.59-1.76 (m, 4 H) 2.53 (s, 2 H) 3.67 (s, 3 H) 3.68 (s, 2 H) 7.19-7.26 (m, 1 H) 7.27-7.34 (m, 2 H) 7.35-7.41 (m, 2 H). MS ESI/APCI Dual posi: 262[M + H]$^+$. | |

TABLE 18-2

| Compound No. | Structure | Analytical Data | Salt information |
|---|---|---|---|
| Reference Example A-9 | 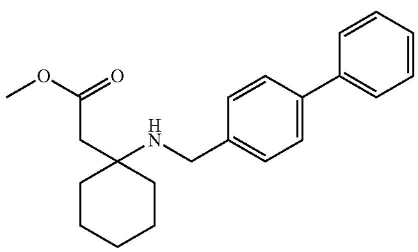 [SMILES: COC(=O)CC1(NCc2ccc(-c3ccccc3)cc2)CCCCC1] | $^1$H NMR (300 MHz, CHLOROFORM-d) δ ppm 1.29-1.59 (m, 6 H) 1.60-1.77 (m, 4 H) 2.55 (s, 2 H) 3.68 (s, 3 H) 3.72 (s, 2 H) 7.29-7.37 (m, 1 H) 7.39-7.49 (m, 4 H) 7.51-7.62 (m, 4 H). MS ESI/APCI Dual posi: 338[M + H]$^+$. | |
| Reference Example A-10 | 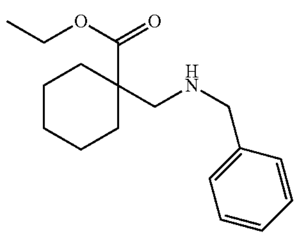 [SMILES: CCOC(=O)C1(CNCc2ccccc2)CCCCC1] | $^1$H NMR (300 MHz, CHLOROFORM-d) δ ppm 1.13-1.63 (m, 11 H) 1.95-2.12 (m, 2 H) 2.66 (s, 2 H) 3.76 (s, 2 H) 4.15 (q, J = 7.1 Hz, 2 H) 7.09-7.43 (m, 5 H). MS ESI/APCI Dual posi: 276[M + H]$^+$. | |
| Reference Example A-11 | 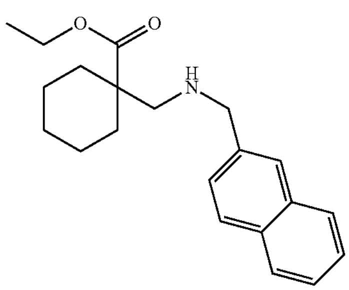 [SMILES: CCOC(=O)C1(CNCc2ccc3ccccc3c2)CCCCC1] | $^1$H NMR (300 MHz, CHLOROFORM-d) δ ppm 1.08-1.63 (m, 11 H) 1.93-2.15 (m, 2 H) 2.69 (s, 2 H) 3.92 (s, 2 H) 4.16 (q, J = 7.1 Hz, 2 H) 7.34-7.54 (m, 3 H) 7.71 (s, 1 H) 7.74-7.92 (m, 3 H). MS ESI/APCI Dual posi: 326[M + H]$^+$. | |
| Reference Example A-12 | 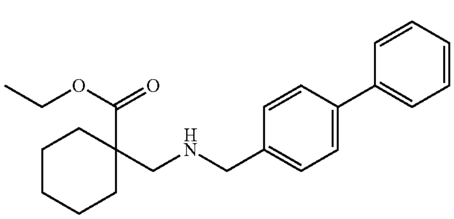 | $^1$H NMR (300 MHz, CHLOROFORM-d) δ ppm 1.15-1.64 (m, 11 H) 1.99-2.14 (m, 2 H) 2.70 (s, 2 H) 3.81 (s, 2 H) 4.17 (q, J = 7.1 Hz, 2 H) 7.29-7.49 (m, 5 H) 7.48-7.65 (m, 4 H). MS ESI/APCI Dual posi: 352[M + H]$^+$. | |

TABLE 18-2-continued

| Compound No. | Structure | Analytical Data | Salt information |
|---|---|---|---|
| Reference Example A-13 | 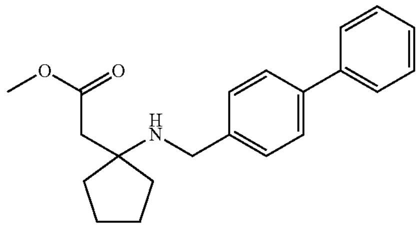 [SMILES: COC(=O)CC1(NCc2ccc(-c3ccccc3)cc2)CCCC1] | ¹H NMR (300 MHz, CHLOROFORM-d) δ ppm 1.51-1.90 (m, 8 H) 2.64 (s, 2 H) 3.70 (s, 3 H) 3.74 (s, 2 H) 7.28-7.37 (m, 1 H) 7.38-7.47 (m, 4 H) 7.49-7.62 (m, 4 H). MS ESI/APCI Dual posi: 324[M + H]⁺. | |
| Reference Example A-14 | 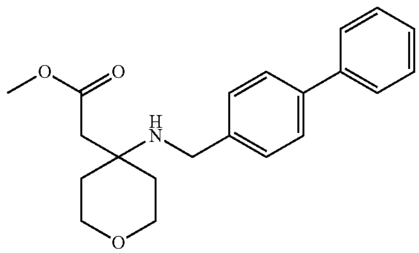 [SMILES: COC(=O)CC1(NCc2ccc(-c3ccccc3)cc2)CCOCC1] | ¹H NMR (600 MHz, CHLOROFORM-d) δ ppm 1.66-1.76 (m, 4 H) 2.59 (s, 2 H) 3.64-3.70 (m, 5 H) 3.72 (s, 2 H) 3.90-3.96 (m, 2 H) 7.31-7.35 (m, 1 H) 7.41-7.47 (m, 4 H) 7.54-7.60 (m, 4 H). MS ESI/APCI Dual posi: 340[M + H]⁺, 362[M + Na]⁺. | |
| Reference Example A-15 | 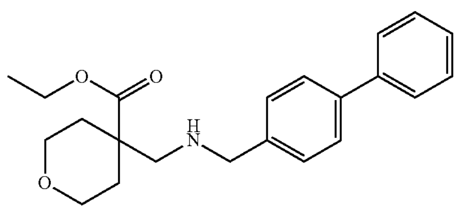 | ¹H NMR (600 MHz, CHLOROFORM-d) δ ppm 1.26 (t, J = 7.1 Hz, 3 H) 1.53-1.61 (m, 2 H) 2.07-2.13 (m, 2 H) 2.75 (s, 2 H) 3.50 (td, J = 11.5, 2.3 Hz, 2 H) 3.77-3.84 (m, 4 H) 4.21 (q, J = 7.1 Hz, 2 H) 7.31-7.37 (m, 3 H) 7.41-7.45 (m, 2 H) 7.52-7.56 (m, 2 H) 7.57-7.60 (m, 2 H). MS ESI/APCI Dual posi: 354[M + H]⁺. | |

TABLE 18-3

| Compound No. | Structure | Analytical Data | Salt information |
|---|---|---|---|
| Reference Example A-16 | 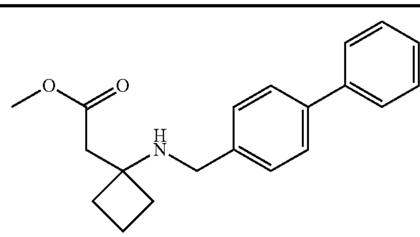 | ¹H NMR (300 MHz, CHLOROFORM-d) δ ppm 1.74-1.97 (m, 2 H) 1.97-2.19 (m, 4 H) 2.75 (s, 2 H) 3.70 (s, 3 H) 3.74 (s, 2 H) 7.29-7.37 (m, 1 H) 7.38-7.47 (m, 4 H) 7.51-7.61 (m, 4 H). MS ESI/APCI Dual posi: 310[M + H]⁺. | |
| Reference Example A-17 | 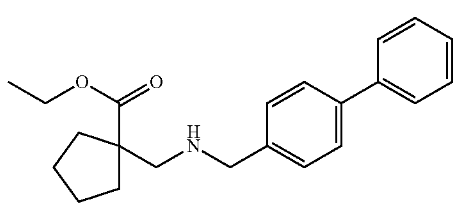 [SMILES: CCOC(=O)C1(CNCc2ccc(-c3ccccc3)cc2)CCCC1] | ¹H NMR (300 MHz, CHLOROFORM-d) δ ppm 1.24 (t, J = 7.1 Hz, 3 H) 1.50-1.74 (m, 6 H) 1.97-2.14 (m, 2 H) 2.74 (s, 2 H) 3.83 (s, 2 H) 4.14 (q, J = 7.1 Hz, 2 H) 7.28-7.48 (m, 5 H) 7.49-7.63 (m, 4 H). MS ESI/APCI Dual posi: 338[M + H]⁺. | |
| Reference Example A-18 | 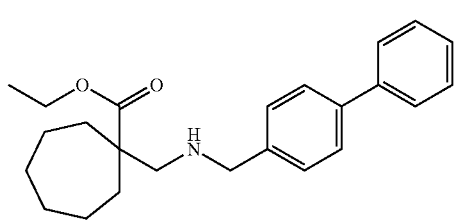 [SMILES: CCOC(=O)C1(CNCc2ccc(-c3ccccc3)cc2)CCCCCC1] | ¹H NMR (300 MHz, CHLOROFORM-d) δ ppm 1.24 (t, J = 7.1 Hz, 3 H) 1.41-1.63 (m, 10 H) 1.98-2.13 (m, 2 H) 2.68 (s, 2 H) 3.81 (s, 2 H) 4.15 (q, J = 7.1 Hz, 2 H) 7.28-7.48 (m, 5 H) 7.49-7.62 (m, 4 H). MS ESI/APCI Dual posi: 366[M + H]⁺. | |

TABLE 18-3-continued

| Compound No. | Structure | Analytical Data | Salt information |
|---|---|---|---|
| Reference Example A-19 | 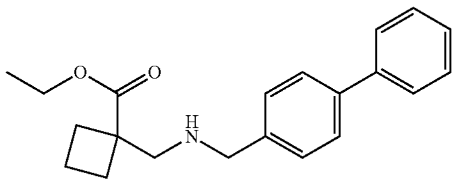 [SMILES: CCOC(=O)C1(CNCc2ccc(-c3ccccc3)cc2)CCC1] | $^1$H NMR (300 MHz, CHLOROFORM-d) δ ppm 1.27 (t, J = 7.1 Hz, 3 H) 1.82-2.03 (m, 4 H) 2.29-2.52 (m, 2 H) 2.94 (s, 2 H) 3.85 (s, 2 H) 4.17 (q, J = 7.1 Hz, 2 H) 7.29-7.48 (m, 5 H) 7.50-7.63 (m, 4 H).<br>MS ESI/APCI Dual posi: 324[M + H]$^+$. | |
| Reference Example A-20 | 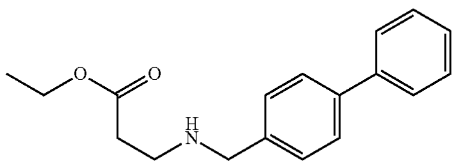 [SMILES: CCOC(=O)CCNCc1ccc(-c2ccccc2)cc1] | $^1$H NMR (200 MHz, CHLOROFORM-d) δ ppm 1.26 (t, J = 7.1 Hz, 3 H) 2.55 (t, J = 6.5 Hz, 2 H) 2.93 (t, J = 6.5 Hz, 2 H) 3.85 (s, 2 H) 4.15 (q, J = 7.1 Hz, 2 H) 7.31-7.49 (m, 5 H) 7.51-7.63 (m, 4 H).<br>MS ESI/APCI Dual posi: 284[M + H]$^+$. | |
| Reference Example A-21 | 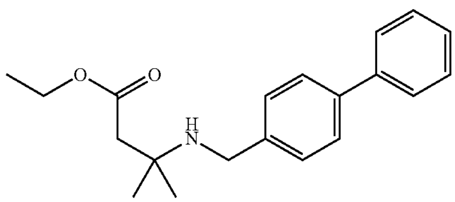 [SMILES: CCOC(=O)CC(C)(C)NCc1ccc(-c2ccccc2)cc1] | $^1$H NMR (300 MHz, CHLOROFORM-d) δ ppm 1.13-1.37 (m, 9 H) 2.53 (s, 2 H) 3.76 (s, 2 H) 4.15 (q, J = 7.2 Hz, 2 H) 7.27-7.48 (m, 5 H) 7.49-7.66 (m, 4 H).<br>MS ESI/APCI Dual posi: 312[M + H]$^+$, 334[M + Na]$^+$. | |
| Reference Example A-22 | 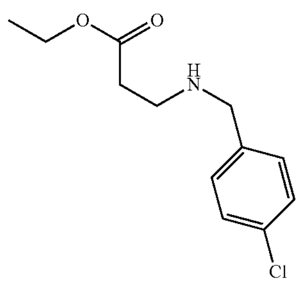 [SMILES: CCOC(=O)CCNCc1ccc(Cl)cc1] | $^1$H NMR (300 MHz, CHLOROFORM-d) δ ppm 1.26 (t, J = 7.1 Hz, 3 H) 2.52 (t, J = 6.4 Hz, 2 H) 2.87 (t, J = 6.4 Hz, 2 H) 3.77 (s, 2 H) 4.14 (q, J = 7.1 Hz, 2 H) 7.19-7.35 (m, 4 H).<br>MS ESI/APCI Dual posi: 242[M + H]$^+$. | |

TABLE 18-4

| Compound No. | Structure | Analytical Data | Salt information |
|---|---|---|---|
| Reference Example A-23 | 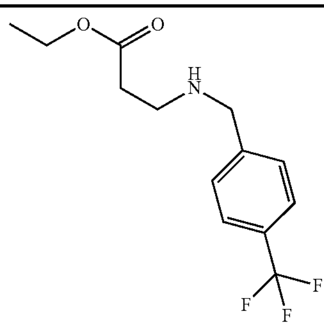 | $^1$H NMR (300 MHz, CHLOROFORM-d) δ ppm 1.26 (t, J = 7.1 Hz, 3 H) 2.53 (t, J = 6.4 Hz, 2 H) 2.89 (t, J = 6.4 Hz, 2 H) 3.87 (s, 2 H) 4.15 (q, J = 7.1 Hz, 2 H) 7.41-7.48 (m, 2 H) 7.55 -7.60 (m, 2 H).<br>MS ESI/APCI Dual posi: 276[M + H]$^+$. | |
| Reference Example A-24 | 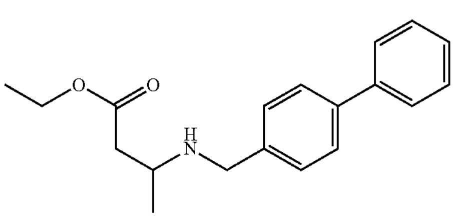 [SMILES: CCOC(=O)CC(C)NCc1ccc(-c2ccccc2)cc1] | $^1$H NMR (600 MHz, CHLOROFORM-d) δ ppm 1.18 (d, J = 6.2 Hz, 3 H) 1.26 (t, J = 7.1 Hz, 3 H) 2.40 (dd, J = 15.1, 6.0 Hz, 1 H) 2.46-2.58 (m, 1 H) 3.11-3.26 (m, 1 H) 3.81 (d, J = 12.9 Hz, 1 H) 3.88 (d, J = 12.9 Hz, 1 H) 4.14 (q, J = 7.1 Hz, 2 H) 7.29-7.39 (m, 1 H) 7.36-7.48 (m, 4 H) 7.49-7.64 (m, 4 H).<br>MS ESI/APCI Dual posi: 298[M + H]$^+$. | |

TABLE 18-4-continued

| Compound No. | Structure | Analytical Data | Salt information |
|---|---|---|---|
| Reference Example A-25 | 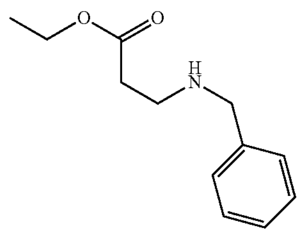 | $^1$H NMR (300 MHz, CHLOROFORM-d) δ ppm 1.25 (t, J = 7.1 Hz, 3 H) 2.53 (t, J = 6.4 Hz, 2 H) 2.90 (t, J = 6.4 Hz, 2 H) 3.81 (s, 2 H) 4.14 (q, J = 7.1 Hz, 2 H) 7.20-7.36 (m, 5 H). MS ESI/APCI Dual posi: 208[M + H]$^+$. | |
| Reference Example A-26 | 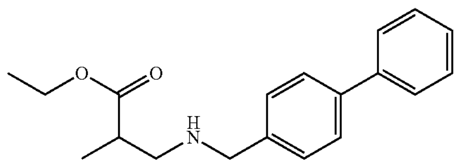 [SMILES: CCOC(=O)C(C)CNCc1ccc(-c2ccccc2)cc1] | $^1$H NMR (600 MHz, CHLOROFORM-d) δ ppm 1.18 (d, J = 7.0 Hz, 3 H) 1.26 (t, J = 7.1 Hz, 3 H) 2.63-2.73 (m, 2 H) 2.88-2.95 (m, 1 H) 3.79-3.88 (m, 2 H) 4.15 (q, J = 7.1 Hz, 2 H) 7.31-7.35 (m, 1 H) 7.36-7.40 (m, 2 H) 7.40-7.46 (m, 2 H) 7.52-7.57 (m, 2 H) 7.57-7.61 (m, 2 H). MS ESI/APCI Dual posi: 298[M + H]$^+$. | |
| Reference Example A-27 | 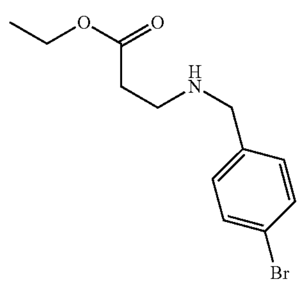 [SMILES: CCOC(=O)CCNCc1ccc(Br)cc1] | $^1$H NMR (300 MHz, CHLOROFORM-d) δ ppm 1.26 (t, J = 7.1 Hz, 3 H) 2.51 (t, J = 6.4 Hz, 2 H) 2.87 (t, J = 6.4 Hz, 2 H) 3.75 (s, 2 H) 4.14 (q, J = 7.1 Hz, 2 H) 7.15-7.24 (m, 2 H) 7.40-7.48 (m, 2 H). MS ESI/APCI Dual posi: 286[M + H]$^+$. | |
| Reference Example A-28 | 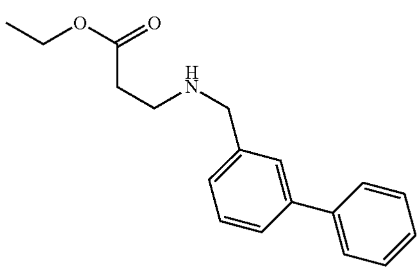 [SMILES: CCOC(=O)CCNCc1cccc(-c2ccccc2)c1] | $^1$H NMR (300 MHz, CHLOROFORM-d) δ ppm 1.25 (t, J = 7.1 Hz, 3 H) 2.54 (t, J = 6.5 Hz, 2 H) 2.93 (t, J = 6.5 Hz, 2 H) 3.87 (s, 2 H) 4.14 (q, J = 7.1 Hz, 2 H) 7.28-7.64 (m, 9 H). MS ESI/APCI Dual posi: 284[M + H]$^+$. | |
| Reference Example A-29 | 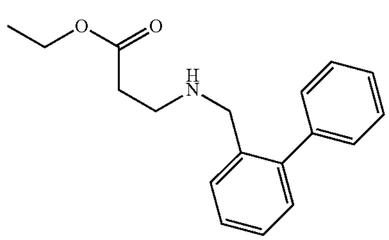 [SMILES: CCOC(=O)CCNCc1ccccc1-c1ccccc1] | $^1$H NMR (300 MHz, CHLOROFORM-d) δ ppm 1.24 (t, J = 7.1 Hz, 3 H) 2.40 (t, J = 6.6 Hz, 2 H) 2.76 (t, J = 6.6 Hz, 2 H) 3.73 (s, 2 H) 4.11 (q, J = 7.1 Hz, 2 H) 7.15-7.55 (m, 9 H). MS ESI/APCI Dual posi: 284[M + H]$^+$. | |

TABLE 18-5

| Compound No. | Structure | Analytical Data | Salt information |
|---|---|---|---|
| Reference Example A-30 | 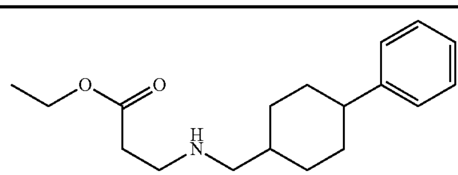 | $^1$H NMR (300 MHz, CHLOROFORM-d) δ ppm 0.95-1.19 (m, 2 H) 1.27 (t, J = 7.1 Hz, 3 H) 1.35-1.62 (m, 3 H) 1.82-2.00 (m, 4 H) 2.38-2.58 (m, 5 H) 2.89 (t, J = 6.5 Hz, 2 H) 4.15 (q, J = 7.1 Hz, 2 H) 7.12-7.23 (m, 3 H) 7.23-7.33 (m, 2 H). MS ESI/APCI Dual posi: 290[M + H]$^+$. | |

TABLE 18-5-continued

| Compound No. | Structure | Analytical Data | Salt information |
|---|---|---|---|
| Reference Example A-31 | 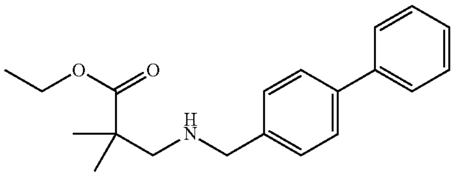 [SMILES: CCOC(=O)C(C)(C)CNCc1ccc(-c2ccccc2)cc1] | ¹H NMR (200 MHz, CHLOROFORM-d) δ ppm 1.09-1.35 (m, 9 H) 2.69 (s, 2 H) 3.84 (s, 2 H) 4.13 (q, J = 7.0 Hz, 2 H) 7.27-7.49 (m, 5 H) 7.50-7.63 (m, 4 H). MS ESI/APCI Dual posi: 312[M + H]⁺. | |
| Reference Example A-32 | 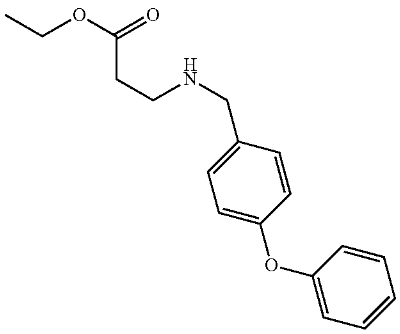 [SMILES: CCOC(=O)CCNCc1ccc(Oc2ccccc2)cc1] | ¹H NMR (600 MHz, CHLOROFORM-d) δ ppm 1.26 (t, J = 7.1 Hz, 3 H) 2.53 (t, J = 6.4 Hz, 2 H) 2.91 (t, J = 6.4 Hz, 2 H) 3.78 (s, 2 H) 4.14 (q, J = 7.1 Hz, 2 H) 6.94-7.02 (m, 4 H) 7.06-7.11 (m, 1 H) 7.27-7.35 (m, 4 H). MS ESI/APCI Dual posi: 300[M + H]⁺. | |
| Reference Example A-33 | 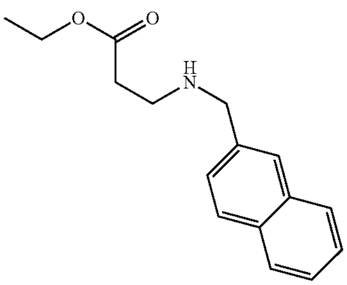 | ¹H NMR (600 MHz, CHLOROFORM-d) δ ppm 1.25 (t, J = 7.1 Hz, 3 H) 2.55 (t, J = 6.4 Hz, 2 H) 2.94 (t, J = 6.4 Hz, 2 H) 3.97 (s, 2 H) 4.14 (q, J = 7.1 Hz, 2 H) 7.41-7.48 (m, 3 H) 7.75 (s, 1 H) 7.78-7.84 (m, 3 H). MS ESI/APCI Dual posi: 258[M + H]⁺. | |
| Reference Example A-34 | 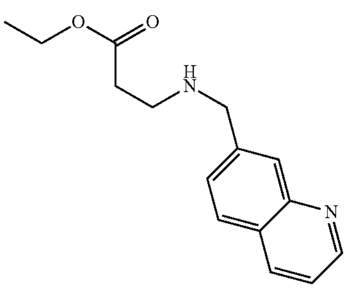 [SMILES: CCOC(=O)CCNCc1ccc2cccnc2c1] | ¹H NMR (600 MHz, CHLOROFORM-d) δ ppm 1.25 (t, J = 7.0 Hz, 3 H) 2.54 (t, J = 6.4 Hz, 2 H) 2.94 (t, J = 6.4 Hz, 2 H) 4.02 (s, 2 H) 4.14 (q, J = 7.0 Hz, 2 H) 7.37 (dd, J = 8.3, 4.1 Hz, 1 H) 7.56 (dd, J = 8.3, 1.7 Hz, 1 H) 7.79 (d, J = 8.3 Hz, 1 H) 7.95-8.05 (m, 1 H) 8.13 (dd, J = 8.3, 0.8 Hz, 1 H) 8.90 (dd, J = 4.1, 1.7 Hz, 1 H). MS ESI/APCI Dual posi: 259[M + H]⁺. | |
| Reference Example A-35 | 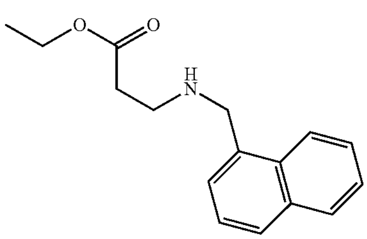 [SMILES: CCOC(=O)CCNCc1cccc2ccccc12] | ¹H NMR (600 MHz, CHLOROFORM-d) δ ppm 1.23 (t, J = 7.1 Hz, 3 H) 2.56 (t, J = 6.5 Hz, 2 H) 3.02 (t, J = 6.5 Hz, 2 H) 4.12 (q, J = 7.1 Hz, 2 H) 4.25 (s, 2 H) 7.39-7.43 (m, 1 H) 7.45-7.50 (m, 2 H) 7.50-7.55 (m, 1 H) 7.76 (d, J = 8.3 Hz, 1 H) 7.83-7.87 (m, 1 H) 8.12 (d, J = 8.3 Hz, 1 H). MS ESI/APCI Dual posi: 258[M + H]⁺. | |
| Reference Example A-36 | 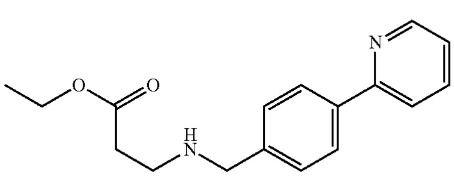 [SMILES: CCOC(=O)CCNCc1ccc(-c2ccccn2)cc1] | ¹H NMR (300 MHz, CHLOROFORM-d) δ ppm 1.26 (t, J = 7.1 Hz, 3 H) 2.54 (t, J = 6.5 Hz, 2 H) 2.92 (t, J = 6.5 Hz, 2 H) 3.87 (s, 2 H) 4.15 (q, J = 7.1 Hz, 2 H) 7.19-7.25 (m, 1 H) 7.43 (d, J = 8.1 Hz, 2 H) 7.68-7.77 (m, 2 H) 7.90-8.01 (m, 2 H) 8.69 (dt, J = 4.9, 1.4 Hz, 1 H). MS ESI/APCI Dual posi: 285[M + H]⁺. | |

TABLE 18-6

| Compound No. | Structure | Analytical Data | Salt information |
|---|---|---|---|
| Reference Example A-37 | 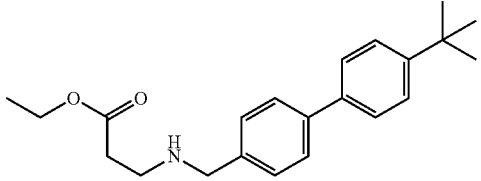 [SMILES: CCOC(=O)CCNCc1ccc(-c2ccc(C(C)(C)C)cc2)cc1] | $^1$H NMR (300 MHz, CHLOROFORM-d) δ ppm 1.26 (t, J = 7.1 Hz, 3 H) 1.36 (s, 9 H) 2.55 (t, J = 6.5 Hz, 2 H) 2.93 (t, J = 6.5 Hz, 2 H) 3.84 (s, 2 H) 4.15 (q, J = 7.1 Hz, 2 H) 7.34-7.40 (m, 2 H) 7.43-7.48 (m, 2 H) 7.50-7.57 (m, 4 H).<br>MS ESI/APCI Dual posi: 340[M + H]$^+$. | |
| Reference Example A-38 | 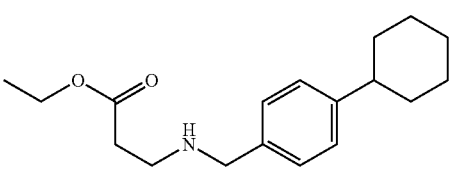 [SMILES: CCOC(=O)CCNCc1ccc(C2CCCCC2)cc1] | $^1$H NMR (300 MHz, CHLOROFORM-d) δ 1.20-1.50 (m, 8 H) 1.69-1.94 (m, 5 H) 2.38-2.59 (m, 3 H) 2.90 (t, J = 6.5 Hz, 2 H) 3.76 (s, 2 H) 4.14 (q, J = 7.1 Hz, 2 H) 7.13-7.18 (m, 2 H) 7.20-7.26 (m, 2 H).<br>MS ESI/APCI Dual posi: 290[M + H]$^+$. | |
| Reference Example A-39 | 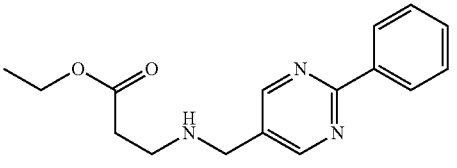 [SMILES: CCOC(=O)CCNCc1cnc(-c2ccccc2)nc1] | $^1$H NMR (300 MHz, CHLOROFORM-d) δ ppm 1.26 (t, J = 7.1 Hz, 3 H) 2.54 (t, J = 6.3 Hz, 2 H) 2.92 (t, J = 6.3 Hz, 2 H) 3.85 (s, 2 H) 4.15 (q, J = 7.1 Hz, 2 H) 7.42-7.54 (m, 3 H) 8.35-8.49 (m, 2 H) 8.77 (s, 2 H).<br>MS ESI/APCI Dual posi: 286[M + H]$^+$. | |
| Reference Example A-40 | 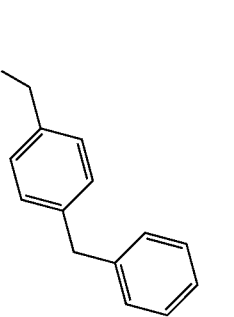 | $^1$H NMR (300 MHz, CHLOROFORM-d) δ ppm 1.25 (t, J = 7.1 Hz, 3 H) 2.51 (t, J = 6.5 Hz, 2 H) 2.88 (t, J = 6.5 Hz, 2 H) 3.76 (s, 2 H) 3.96 (s, 2 H) 4.13 (q, J = 7.1 Hz, 2 H) 7.08-7.35 (m, 9 H).<br>MS ESI/APCI Dual posi: 298[M + H]$^+$. | |
| Reference Example A-41 | 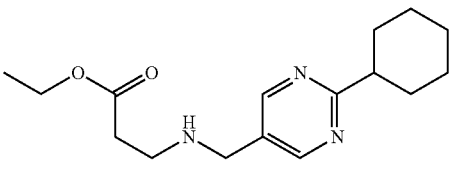 | $^1$H NMR (300 MHz, CHLOROFORM-d) δ ppm 1.26 (t, J = 7.1 Hz, 3 H) 1.30-1.51 (m, 2 H) 1.54-1.79 (m, 4 H) 1.80-1.93 (m, 2 H) 1.93-2.06 (m, 2 H) 2.52 (t, J = 6.4 Hz, 2 H) 2.78-2.96 (m, 3 H) 3.77 (s, 2 H) 4.14 (q, J = 7.1 Hz, 2 H) 8.62 (s, 2 H).<br>MS ESI/APCI Dual posi: 292[M + H]$^+$. | |
| Reference Example A-42 | 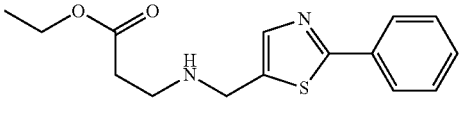 | $^1$H NMR (600 MHz, CHLOROFORM-d) δ ppm 1.26 (t, J = 7.1 Hz, 3 H) 2.54 (t, J = 6.4 Hz, 2 H) 2.94 (t, J = 6.4 Hz, 2 H) 4.04 (s, 2 H) 4.15 (q, J = 7.1 Hz, 2 H) 7.37-7.45 (m, 3 H) 7.65 (s, 1 H) 7.89-7.93 (m, 2 H).<br>MS ESI/APCI Dual posi: 291[M + H]$^+$. | |
| Reference Example A-43 | 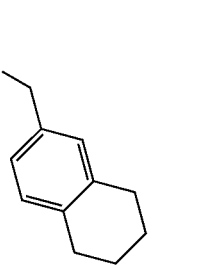 | $^1$H NMR (600 MHz, CHLOROFORM-d) δ ppm 1.25 (t, J = 7.1 Hz, 3 H) 1.75-1.80 (m, 4 H) 2.52 (t, J = 6.5 Hz, 2 H) 2.71-2.77 (m, 4 H) 2.90 (t, J = 6.5 Hz, 2 H) 3.72 (s, 2 H) 4.14 (q, J = 7.1 Hz, 2 H) 6.91-7.05 (m, 3 H).<br>MS ESI/APCI Dual posi: 262[M + H]$^+$. | |

TABLE 18-7

| Compound No. | Structure | Analytical Data | Salt information |
|---|---|---|---|
| Reference Example A-44 | 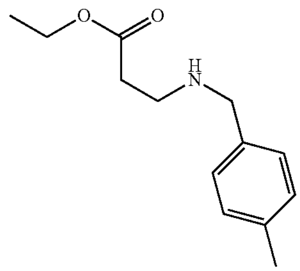 [SMILES: CCOC(=O)CCNCc1ccc(C)cc1] | ¹H NMR (200 MHz, CHLOROFORM-d) δ ppm 1.25 (t, J = 7.2 Hz, 3 H) 2.33 (s, 3 H) 2.52 (t, J = 6.5 Hz, 2 H) 2.89 (t, J = 6.5 Hz, 2 H) 3.76 (s, 2 H) 4.14 (q, J = 7.2 Hz, 2 H) 7.09-7.17 (m, 2 H) 7.17-7.24 (m, 2 H). MS ESI/APCI Dual posi: 222[M + H]⁺. | |
| Reference Example A-45 | 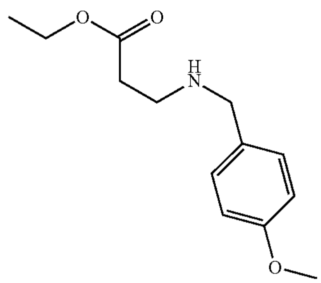 [SMILES: CCOC(=O)CCNCc1ccc(OC)cc1] | ¹H NMR (200 MHz, CHLOROFORM-d) δ ppm 1.25 (t, J = 7.0 Hz, 3 H) 2.52 (t, J = 6.5 Hz, 2 H) 2.88 (t, J = 6.5 Hz, 2 H) 3.74 (s, 2 H) 3.80 (s, 3 H) 4.14 (q, J = 7.0 Hz, 2 H) 6.79-6.91 (m, 2 H) 7.17-7.30 (m, 2 H). MS ESI/APCI Dual posi: 238[M + H]⁺. | |
| Reference Example A-46 | 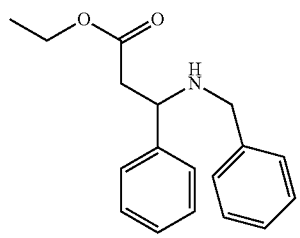 [SMILES: CCOC(=O)CC(NCc1ccccc1)c1ccccc1] | ¹H NMR (300 MHz, CHLOROFORM-d) δ ppm 1.19 (t, J = 7.1 Hz, 3 H) 2.61 (dd, J = 15.6, 5.3 Hz, 1 H) 2.72 (dd, J = 15.6, 8.8 Hz, 1 H) 3.54 (d, J = 13.1 Hz, 1 H) 3.66 (d, J = 13.1 Hz, 1 H) 4.01-4.18 (m, 3 H) 7.13-7.44 (m, 10 H). MS ESI/APCI Dual posi: 284[M + H]⁺. | |
| Reference Example A-47 | 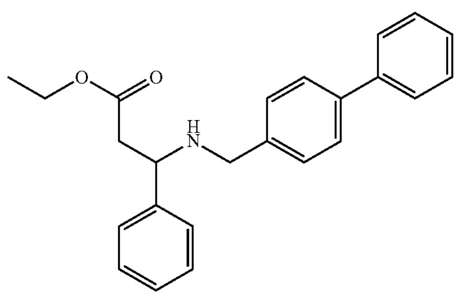 [SMILES: CCOC(=O)CC(NCc1ccc(-c2ccccc2)cc1)c1ccccc1] | ¹H NMR (300 MHz, CHLOROFORM-d) δ ppm 1.20 (t, J = 7.1 Hz, 3 H) 2.63 (dd, J = 15.5, 5.3 Hz, 1 H) 2.74 (dd, J = 15.5, 8.8 Hz, 1 H) 3.59 (d, J = 13.5 Hz, 1 H) 3.70 (d, J = 13.5 Hz, 1 H) 4.02-4.21 (m, 3 H) 7.25-7.48 (m, 10 H) 7.48-7.64 (m, 4 H). MS ESI/APCI Dual posi: 360[M + H]⁺. | |
| Reference Example A-48 | 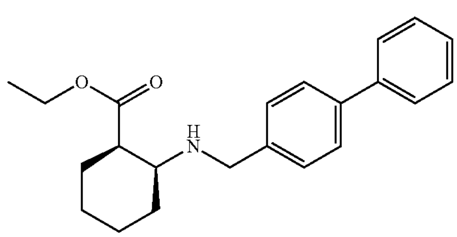 [SMILES: CCOC(=O)[C@@H]1CCCC[C@@H]1NCc1ccc(-c2ccccc2)cc1] | ¹H NMR (200 MHz, CHLOROFORM-d) δ ppm 1.24 (t, J = 7.0 Hz, 3 H) 1.28-1.71 (m, 6 H) 1.77-2.03 (m, 2 H) 2.61-2.76 (m, 1 H) 3.03 (dt, J = 6.7, 3.5 Hz, 1 H) 3.76 (d, J = 13.3 Hz, 1 H) 3.89 (d, J = 13.3 Hz, 1 H) 4.02-4.23 (m, 2 H) 7.27-7.49 (m, 5 H) 7.49-7.64 (m, 4 H). MS ESI/APCI Dual posi: 338[M + H]⁺. | |
| Reference Example A-49 | 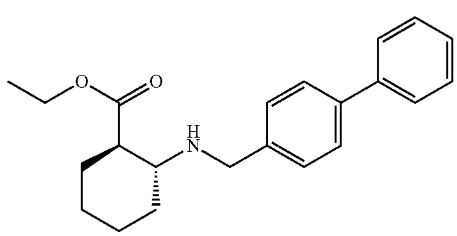 [SMILES: CCOC(=O)[C@@H]1CCCC[C@H]1NCc1ccc(-c2ccccc2)cc1] | ¹H NMR (200 MHz, CHLOROFORM-d) δ ppm 1.01-1.61 (m, 7 H) 1.62-1.86 (m, 2 H) 1.86-2.02 (m, 1 H) 2.08-2.36 (m, 2 H) 2.69-2.93 (m, 1 H) 3.75 (d, J = 13.3 Hz, 1 H) 3.92 (d, J = 13.3 Hz, 1 H) 4.15 (q, J = 7.1 Hz, 2 H) 7.26-7.48 (m, 5 H) 7.49-7.63 (m, 4 H). MS ESI/APCI Dual posi: 338[M + H]⁺. | |

TABLE 18-7-continued

| Compound No. | Structure | Analytical Data | Salt information |
|---|---|---|---|
| Reference Example A-50 | 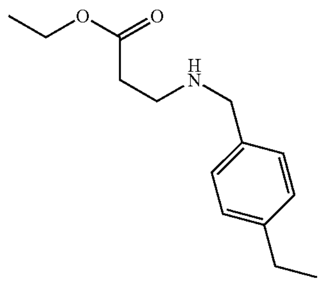 [SMILES: CCOC(=O)CCNCc1ccc(CC)cc1] | ¹H NMR (200 MHz, CHLOROFORM-d) δ ppm 1.14-1.35 (m, 6 H) 2.44-2.72 (m, 4 H) 2.83-2.97 (m, 2 H) 3.77 (s, 2 H) 4.14 (q, J = 7.0 Hz, 2 H) 7.09-7.30 (m, 4 H). MS ESI/APCI Dual posi: 236[M + H]⁺. | |

TABLE 18-8

| Compound No. | Structure | Analytical Data | Salt information |
|---|---|---|---|
| Reference Example A-51 | 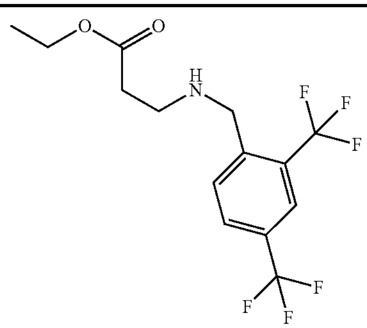 | ¹H NMR (200 MHz, CHLOROFORM-d) δ ppm 1.27 (t, J = 7.1 Hz, 3 H) 2.55 (t, J = 6.4 Hz, 2 H) 2.92 (t, J = 6.4 Hz, 2 H) 4.03 (s, 2 H) 4.16 (q, J = 7.1 Hz, 2 H) 7.73-7.84 (m, 1 H) 7.84-7.97 (m, 2 H). MS ESI/APCI Dual posi: 344[M + H]⁺. | |
| Reference Example A-52 | 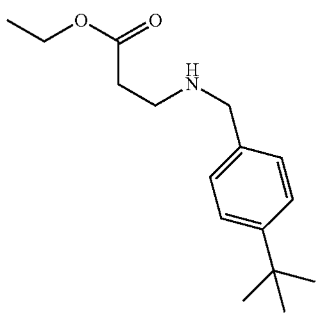 [SMILES: CCOC(=O)CCNCc1ccc(C(C)(C)C)cc1] | ¹H NMR (300 MHz, CHLOROFORM-d) δ ppm 1.25 (t, J = 7.1 Hz, 3 H) 1.31 (s, 9 H) 2.53 (t, J = 6.5 Hz, 2 H) 2.91 (t, J = 6.5 Hz, 2 H) 3.77 (s, 2 H) 4.14 (q, J = 7.1 Hz, 2 H) 7.21-7.29 (m, 2 H) 7.30-7.39 (m, 2 H). MS ESI/APCI Dual posi: 264[M + H]⁺. | |
| Reference Example A-53 | 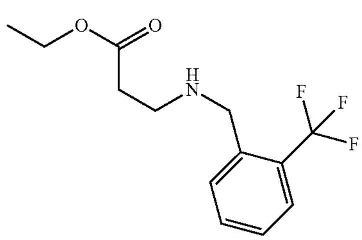 [SMILES: CCOC(=O)CCNCc1ccccc1C(F)(F)F] | ¹H NMR (300 MHz, CHLOROFORM-d) δ ppm 1.26 (t, J = 7.1 Hz, 3 H) 2.54 (t, J = 6.5 Hz, 2 H) 2.93 (t, J = 6.5 Hz, 2 H) 3.97 (s, 2 H) 4.15 (q, J = 7.1 Hz, 2 H) 7.30-7.38 (m, 1 H) 7.49-7.57 (m, 1 H) 7.60-7.68 (m, 2 H). MS ESI/APCI Dual posi: 276[M + H]⁺. | |
| Reference Example A-54 | 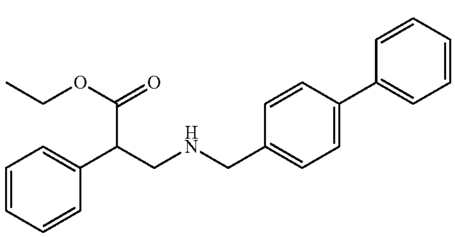 [SMILES: CCOC(=O)C(CNCc1ccc(-c2ccccc2)cc1)c1ccccc1] | ¹H NMR (300 MHz, CHLOROFORM-d) δ ppm 1.21 (t, J = 7.1 Hz, 3 H) 2.95 (dd, J = 12.0, 6.5 Hz, 1 H) 3.31 (dd, J = 12.0, 8.6 Hz, 1 H) 3.74-3.92 (m, 3 H) 4.02-4.27 (m, 2 H) 7.22-7.38 (m, 8 H) 7.39-7.47 (m, 2 H) 7.50-7.61 (m, 4 H). MS ESI/APCI Dual posi: 360[M + H]⁺. | |

TABLE 18-8-continued

| Compound No. | Structure | Analytical Data | Salt information |
|---|---|---|---|
| Reference Example A-55 | [structure: ethyl 3-{[3-(trifluoromethyl)benzyl]amino}propanoate] | ¹H NMR (300 MHz, CHLOROFORM-d) δ ppm 1.26 (t, J = 7.1 Hz, 3 H) 2.53 (t, J = 6.4 Hz, 2 H) 2.90 (t, J = 6.4, Hz, 2 H) 3.86 (s, 2 H) 4.15 (q, J = 7.1 Hz, 2 H) 7.39-7.47 (m, 1 H) 7.47-7.56 (m, 2 H) 7.60 (s, 1 H). MS ESI/APCI Dual posi: 276[M + H]⁺. | |
| Reference Example A-56 | [structure: ethyl 3-{[3,5-bis(trifluoromethyl)benzyl]amino}propanoate] | ¹H NMR (300 MHz, CHLOROFORM-d) δ ppm 1.27 (t, J = 7.1 Hz, 3 H) 2.54 (t, J = 6.3 Hz, 2 H) 2.90 (t, J = 6.3 Hz, 2 H) 3.93 (s, 2 H) 4.16 (q, J = 7.1 Hz, 2 H) 7.76 (s, 1 H) 7.82 (s, 2 H). MS ESI/APCI Dual posi: 344[M + H]⁺. | |
| Reference Example A-57 | [structure: ethyl 3-{[(2,4-dimethylbenzyl)amino}propanoate] | ¹H NMR (300 MHz, CHLOROFORM-d) δ ppm 1.25 (t, J = 7.1 Hz, 3 H) 2.22-2.36 (m, 6 H) 2.53 (t, J = 6.5 Hz, 2 H) 2.92 (t, J = 6.5 Hz, 2 H) 3.74 (s, 2 H) 4.13 (q, J = 7.1 Hz, 2 H) 6.91-7.01 (m, 2 H) 7.16 (d, J = 8.4 Hz, 1 H). MS ESI/APCI Dual posi: 236[M + H]⁺. | |

TABLE 18-9

| Compound No. | Structure | Analytical Data | Salt information |
|---|---|---|---|
| Reference Example A-58 | [structure: ethyl 3-{[(3-methoxybenzyl)amino}propanoate] | ¹H NMR (300 MHz, CHLOROFORM-d) δ ppm 1.26 (t, J = 7.1 Hz, 3 H) 2.52 (t, J = 6.5 Hz, 2 H) 2.89 (t, J = 6.5 Hz, 2 H) 3.78 (s, 2 H) 3.81 (s, 2 H) 4.14 (q, J = 7.1 Hz, 2 H) 6.76-6.82 (m, 1 H) 6.87-6.93 (m, 2 H) 7.19-7.25 (m, 1 H). MS ESI/APCI Dual posi: 238[M + H]⁺. | |
| Reference Example A-59 | [structure: ethyl 3-{[(4-methoxy-2-methylbenzyl)amino}propanoate] | ¹H NMR (300 MHz, CHLOROFORM-d) δ ppm 1.25 (t, J = 7.1 Hz, 3 H) 2.33 (s, 3 H) 2.53 (t, J = 6.5 Hz, 2 H) 2.91 (t, J = 6.5 Hz, 2 H) 3.71 (s, 2 H) 3.78 (s, 3 H) 4.13 (q, J = 7.1 Hz, 2 H) 6.63-6.76 (m, 2 H) 7.18 (d, J = 8.4 Hz, 1 H). MS ESI/APCI Dual posi: 252[M + H]⁺. | |

TABLE 18-9-continued

| Compound No. | Structure | Analytical Data | Salt information |
|---|---|---|---|
| Reference Example A-60 | 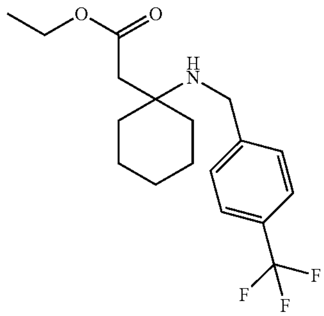 [SMILES: CCOC(=O)CC1(NCc2ccc(C(F)(F)F)cc2)CCCCC1] | ¹H NMR (300 MHz, CHLOROFORM-d) δ ppm 1.24 (t, J = 7.1 Hz, 3 H) 1.29-1.75 (m, 10 H) 2.50 (s, 2 H) 3.74 (s, 2 H) 4.13 (q, J = 7.1 Hz, 2 H) 7.42-7.64 (m, 4 H).<br>MS ESI/APCI Dual posi: 344[M + H]⁺. | |
| Reference Example A-61 | 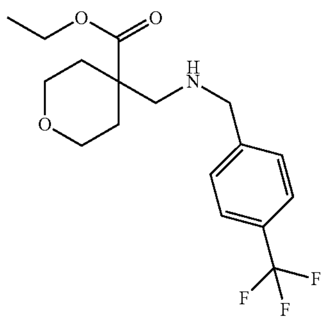 [SMILES: CCOC(=O)C1(CNCc2ccc(C(F)(F)F)cc2)CCOCC1] | ¹H NMR (300 MHz, CHLOROFORM-d) δ ppm 1.25 (t, J = 7.1 Hz, 3 H) 1.55 (ddd, J = 13.7, 10.9, 4.4 Hz, 2 H) 2.00-2.18 (m, 2 H) 2.70 (s, 2 H) 3.49 (ddd, J = 11.8, 10.9, 2.4 Hz, 2 H) 3.73-3.87 (m, 4 H) 4.19 (q, J = 7.1 Hz, 2 H) 7.41 (2, J = 8.1 Hz, 2 H) 7.56 (d, J = 8.1 Hz, 2 H).<br>MS ESI/APCI Dual posi: 346[M + H]⁺. | |
| Reference Example A-62 | 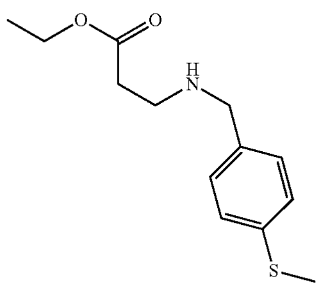 | ¹H NMR (300 MHz, CHLOROFORM-d) δ ppm 1.25 (t, J = 7.1 Hz, 3 H) 2.40-2.57 (m, 5 H) 2.88 (t, J = 6.5 Hz, 2 H) 3.76 (s, 2 H) 4.14 (q, J = 7.1 Hz, 2 H) 7.16-7.30 (m, 4 H).<br>MS ESI/APCI Dual posi: 254[M + H]⁺. | |
| Reference Example A-63 | 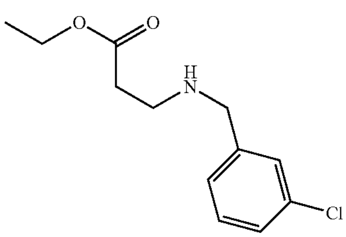 [SMILES: CCOC(=O)CCNCc1cccc(Cl)c1] | ¹H NMR (200 MHz, CHLOROFORM-d) δ ppm 1.26 (t, J = 7.1 Hz, 3 H) 2.52 (t, J = 6.5 Hz, 2 H) 2.88 (t, J = 6.5 Hz, 2 H) 3.78 (s, 2 H) 4.15 (q, J = 7.1 Hz, 2 H) 7.18-7.25 (m, 3 H) 7.33 (s, 1 H).<br>MS ESI/APCI Dual posi: 242[M + H]⁺. | |
| Reference Example A-64 | 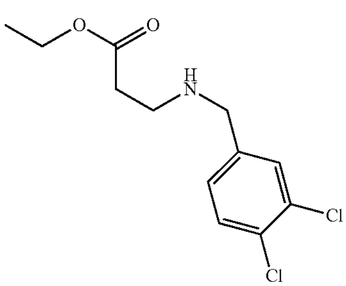 [SMILES: CCOC(=O)CCNCc1ccc(Cl)c(Cl)c1] | ¹H NMR (200 MHz, CHLOROFORM-d) δ ppm 1.26 (t, J = 7.1 Hz, 3 H) 2.51 (t, J = 6.5 Hz, 2 H) 2.86 (t, J = 6.5 Hz, 2 H) 3.76 (s, 2 H) 4.15 (q, J = 7.1 Hz, 2 H) 7.16 (dd, J = 8.4, 2.2 Hz, 1 H) 7.38 (d, J = 8.4 Hz, 1 H) 7.44 (d, J = 2.2 Hz, 1 H).<br>MS ESI/APCI Dual posi: 276[M + H]⁺. | |

TABLE 18-10

| Compound No. | Structure | Analytical Data | Salt information |
|---|---|---|---|
| Reference Example A-65 | 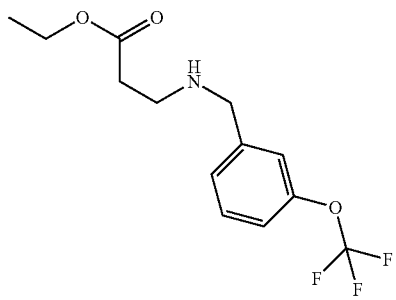 [SMILES: CCOC(=O)CCNCc1cccc(OC(F)(F)F)c1] | $^1$H NMR (300 MHz, CHLOROFORM-d) δ ppm 1.26 (t, J = 7.1 Hz, 3 H) 2.53 (t, J = 6.3 Hz, 2 H) 2.89 (t, J = 6.3 Hz, 2 H) 3.82 (s, 2 H) 4.15 (q, J = 7.1 Hz, 2 H) 7.06-7.14 (m, 1 H) 7.18-7.35 (m, 3 H). MS ESI/APCI Dual posi: 292[M + H]$^+$. | |
| Reference Example A-66 | 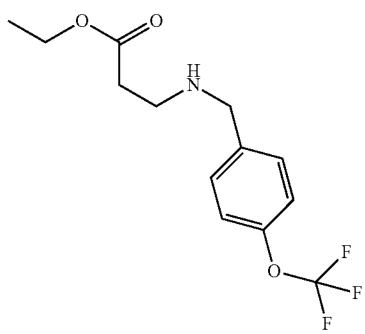 [SMILES: CCOC(=O)CCNCc1ccc(OC(F)(F)F)cc1] | $^1$H NMR (300 MHz, CHLOROFORM-d) δ ppm 1.26 (t, J = 7.1 Hz, 3 H) 2.53 (t, J = 6.4 Hz, 2 H) 2.89 (t, J = 6.4 Hz, 2 H) 3.80 (s, 2 H) 4.15 (q, J = 7.1 Hz, 2 H) 7.13-7.19 (m, 2 H) 7.32-7.37 (m, 2 H). MS ESI/APCI Dual posi: 292[M + H]$^+$. | |
| Reference Example A-67 | 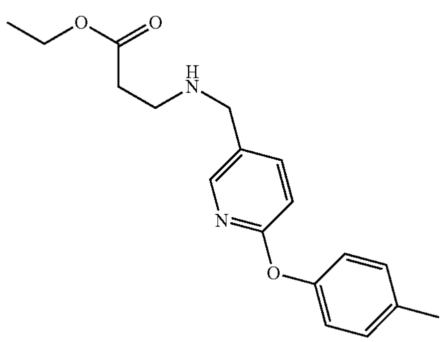 [SMILES: CCOC(=O)CCNCc1ccc(Oc2ccc(C)cc2)nc1] | $^1$H NMR (300 MHz, CHLOROFORM-d) δ ppm 1.25 (t, J = 7.1 Hz, 3 H) 2.35 (s, 3 H) 2.51 (t, J = 6.5 Hz, 2 H) 2.88 (t, J = 6.5 Hz, 2 H) 3.74 (s, 2 H) 4.14 (q, J = 7.1 Hz, 2 H) 6.84 (d, J = 8.5 Hz, 1 H) 6.97-7.04 (m, 2 H) 7.19 (d, J = 8.1 Hz, 2 H) 7.67 (dd, J = 8.5, 2.4 Hz, 1 H) 8.09 (d, J = 2.4 Hz, 1 H). MS ESI/APCI Dual posi: 315[M + H]$^+$. | |
| Reference Example A-68 | 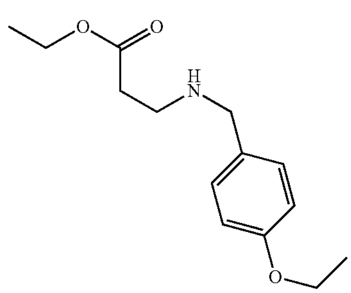 [SMILES: CCOC(=O)CCNCc1ccc(OCC)cc1] | $^1$H NMR (300 MHz, CHLOROFORM-d) δ ppm 1.25 (t, J = 7.1 Hz, 3 H) 1.40 (t, J = 7.0 Hz, 3 H) 2.52 (t, J = 6.5 Hz, 2 H) 2.88 (t, J = 6.5 Hz, 2 H) 3.73 (s, 2 H) 4.02 (q, J = 7.0 Hz, 2 H) 4.14 (q, J = 7.1 Hz, 2 H) 6.82-6.88 (m, 2 H) 7.19-7.24 (m, 2 H). MS ESI/APCI Dual posi: 252[M + H]$^+$. | |

TABLE 18-10-continued

| Compound No. | Structure | Analytical Data | Salt information |
|---|---|---|---|
| Reference Example A-69 | 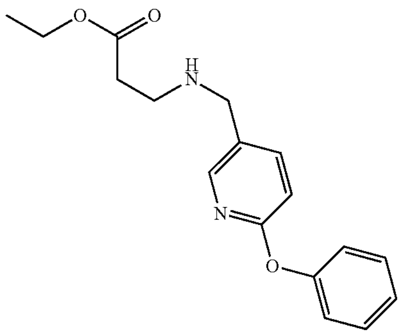 [SMILES: CCOC(=O)CCNCc1ccc(Oc2ccccc2)nc1] | $^1$H NMR (300 MHz, CHLOROFORM-d) δ ppm 1.26 (t, J = 7.1 Hz, 3 H) 2.52 (t, J = 6.4 Hz, 2 H) 2.88 (t, J = 6.4 Hz, 2 H) 3.76 (s, 2 H) 4.14 (q, J = 7.1 Hz, 2 H) 6.87 (d, J = 8.3 Hz, 1 H) 7.08-7.23 (m, 3 H) 7.35-7.43 (m, 2 H) 7.69 (dd, J = 8.3, 2.5 Hz, 1 H) 8.11 (d, J = 2.5 Hz, 1 H).<br>MS ESI/APCI Dual posi: 301[M + H]$^+$. | |
| Reference Example A-70 | 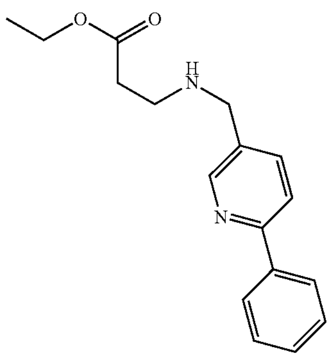 [SMILES: CCOC(=O)CCNCc1ccc(-c2ccccc2)nc1] | $^1$H NMR (300 MHz, CHLOROFORM-d) δ ppm 1.26 (t, J = 7.2 Hz, 3 H) 2.54 (t, J = 6.4 Hz, 2 H) 2.93 (t, J = 6.4 Hz, 2 H) 3.86 (s, 2 H) 4.15 (q, J = 7.2 Hz, 2 H) 7.36-7.51 (m, 3 H) 7.67-7.79 (m, 2 H) 7.91-8.04 (m, 2 H) 8.62 (s, 1 H).<br>MS ESI/APCI Dual posi: 285[M + H]$^+$. | |
| Reference Example A-71 | 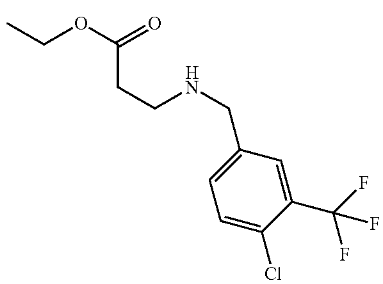 [SMILES: CCOC(=O)CCNCc1ccc(Cl)c(C(F)(F)F)c1] | $^1$H NMR (300 MHz, CHLOROFORM-d) δ ppm 1.26 (t, J = 7.1 Hz, 3 H) 2.52 (t, J = 6.3 Hz, 2 H) 2.88 (t, J = 6.3 Hz, 2 H) 3.82 (s, 2 H) 4.15 (q, J = 7.1 Hz, 2 H) 7.42-7.46 (m, 2 H) 7.67 (s, 1 H).<br>MS ESI/APCI Dual posi: 310[M + H]$^+$. | |

TABLE 18-11

| Compound No. | Structure | Analytical Data | Salt information |
|---|---|---|---|
| Reference Example A-72 | 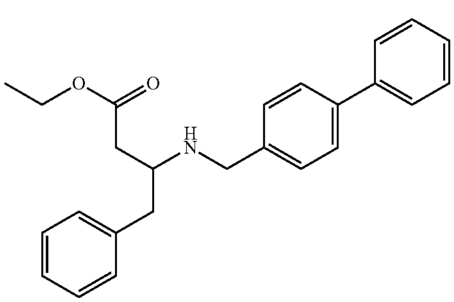 [SMILES: CCOC(=O)CC(Cc1ccccc1)NCc1ccc(-c2ccccc2)cc1] | $^1$H NMR (300 MHz, CHLOROFORM-d) δ ppm 1.25 (t, J = 7.1 Hz, 3 H) 2.44 (d, J = 6.4 Hz, 2 H) 2.78 (dd, J = 13.5, 6.8 Hz, 1 H) 2.89 (dd, J = 13.5, 6.5 Hz, 1 H) 3.20-3.40 (m, 1 H) 3.86 (s, 2 H) 4.01-4.22 (m, 2 H) 7.13-7.37 (m, 7 H) 7.38-7.64 (m, 7 H).<br>MS ESI/APCI Dual posi: 374 [M + H]$^+$, 396 [M + Na]$^+$. | |

TABLE 18-11-continued

| Compound No. | Structure | Analytical Data | Salt information |
|---|---|---|---|
| Reference Example A-73 | 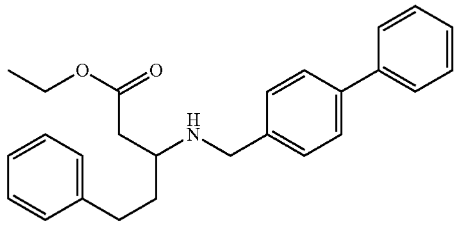 [SMILES: CCOC(=O)CC(CCc1ccccc1)NCc1ccc(-c2ccccc2)cc1] | ¹H NMR (300 MHz, CHLOROFORM-d) δ ppm 1.25 (t, J = 7.1 Hz, 3 H) 1.70-1.96 (m, 2 H) 2.53 (d, J = 6.2 Hz, 2 H) 2.72 (t, J = 7.9 Hz, 2 H) 3.00-3.18 (m, 1 H) 3.70-3.93 (m, 2 H) 4.14 (q, J = 7.2 Hz, 2 H) 7.08-7.68 (m, 14 H). MS ESI/APCI Dual posi: 388 [M + H]⁺, 410 [M + Na]⁺. | |
| Reference Example A-74 | 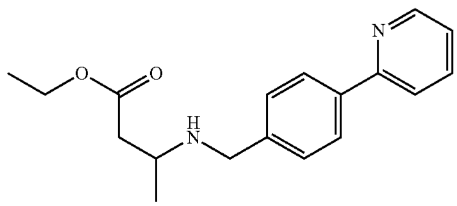 | ¹H NMR (300 MHz, CHLOROFORM-d) δ ppm 1.17 (d, J = 6.4 Hz, 3 H) 1.26 (t, J = 7.1 Hz, 3 H) 2.39 (dd, J = 15.2, 6.0 Hz, 1 H) 2.51 (dd, J = 15.2, 6.8 Hz, 1 H) 3.09-3.27 (m, 1 H) 3.74-3.96 (m, 2 H) 4.14 (q, J = 7.1 Hz, 2 H) 7.21 (ddd, J = 6.2, 4.9, 2.4 Hz, 1 H) 7.44 (d, J = 8.1 Hz, 2 H) 7.68-7.76 (m, 2 H) 7.91-7.99 (m, 2 H) 8.68 (dt, J = 4.9, 1.3 Hz, 1 H). MS ESI/APCI Dual posi: 299 [M + H]⁺, 321 [M + Na]⁺. | |
| Reference Example A-75 | 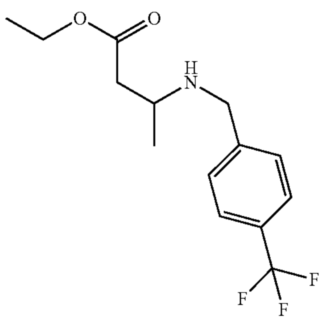 [SMILES: CCOC(=O)CC(C)NCc1ccc(C(F)(F)F)cc1] | ¹H NMR (300 MHz, CHLOROFORM-d) δ ppm 1.16 (d, J = 6.4 Hz, 3 H) 1.25 (t, J = 7.1 Hz, 3 H) 2.31-2.55 (m, 2 H) 3.04-3.23 (m, 1 H) 3.82-3.90 (m, 2 H) 4.14 (q, J = 7.1 Hz, 2 H) 7.38-7.50 (m, 2 H) 7.52-7.65 (m, 2 H). MS ESI/APCI Dual posi: 290 [M + H]⁺. MS ESI/APCI Dual nega: 324 [m + Cl]⁻. | |
| Reference Example A-76 | 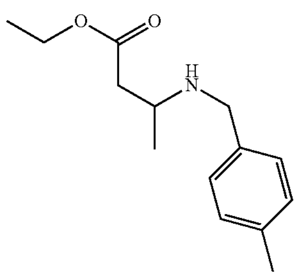 [SMILES: CCOC(=O)CC(C)NCc1ccc(C)cc1] | ¹H NMR (300 MHz, CHLOROFORM-d) δ ppm 1.15 (d, J = 6.4 Hz, 3 H) 1.25 (t, J = 7.1 Hz, 3 H) 2.29-2.42 (m, 4 H) 2.49 (dd, J = 15.0, 6.7 Hz, 1 H) 3.04-3.24 (m, 1 H) 3.64-3.86 (m, 2 H) 4.13 (q, J = 7.1 Hz, 2 H) 7.07-7.16 (m, 2 H) 7.17-7.25 (m, 2 H). MS ESI/APCI Dual posi: 236 [M + H]⁺, 258 [M + Na]⁺. | |
| Reference Example A-77 | 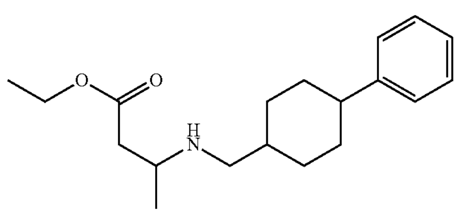 [SMILES: CCOC(=O)CC(C)NCC1CCC(c2ccccc2)CC1] | ¹H NMR (300 MHz, CHLOROFORM-d) δ ppm 0.99-1.20 (m, 5 H) 1.27 (t, J = 7.1 Hz, 3 H) 1.38-1.76 (m, 5 H) 1.83-1.99 (m, 3 H) 2.25-2.40 (m, 1 H) 2.40-2.59 (m, 4 H) 2.99-3.14 (m, 1 H) 4.15 (q, J = 7.1 Hz, 2 H) 7.14-7.33 (m, 5 H). MS ESI/APCI Dual posi: 304 [M + H]⁺. | |
| Reference Example A-78 | 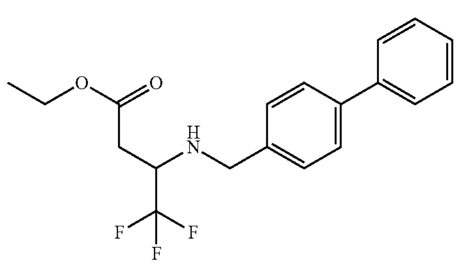 [SMILES: CCOC(=O)CC(NCc1ccc(-c2ccccc2)cc1)C(F)(F)F] | ¹H NMR (300 MHz, CHLOROFORM-d) δ ppm 1.25 (t, J = 7.1 Hz, 3 H) 2.51 (dd, J = 15.5, 9.6 Hz, 1 H) 2.71 (dd, J = 15.5, 4.0 Hz, 1 H) 3.56-3.76 (m, 1 H) 3.92 (d, J = 13.0 Hz, 1 H) 3.98-4.27 (m, 3 H) 7.28-7.49 (m, 5 H) 7.49-7.66 (m, 4 H). MS ESI/APCI Dual posi: 352 [M + H]⁺. | |

TABLE 18-12

| Compound No. | Structure | Analytical Data | Salt information |
|---|---|---|---|
| Reference Example A-79 | 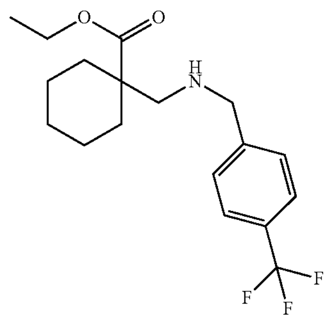 | $^1$H NMR (300 MHz, CHLOROFORM-d) δ ppm 1.14-1.81 (m, 11 H) 1.98-2.12 (m, 2 H) 2.65 (s, 2 H) 3.82 (s, 2 H) 4.15 (q, J = 7.1 Hz. 2 H) 7.41 (d, J = 8.1 Hz, 2 H) 7.56 (d, J = 8.1 Hz, 2 H). MS ESI/APCI Dual posi: 344[M + H]$^+$, 366[M + Na]$^+$. | |
| Reference Example A-80 | 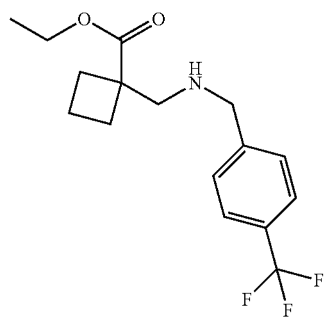 [SMILES: CCOC(=O)C1(CNCc2ccc(C(F)(F)F)cc2)CCC1] | $^1$H NMR (300 MHz, CHLOROFORM-d) δ ppm 1.26 (t, J = 7.1 Hz, 3 H) 1.86-2.00 (m, 4 H) 2.34-2.50 (m, 2 H) 2.89 (s, 2 H) 3.86 (s, 2 H) 4.17 (q, J = 7.1 Hz, 2 H) 7.44 (d, J = 8.1 Hz, 2H) 7.57 (d, J = 8.1 Hz, 2H). MS ESI/APCI Dual posi: 316[M + H]$^+$, 338[M + Na]$^+$. | |
| Reference Example A-81 | 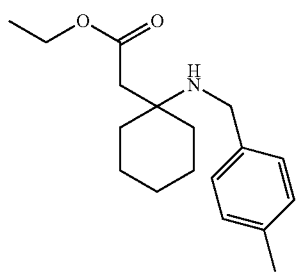 [SMILES: CCOC(=O)CC1(NCc2ccc(C)cc2)CCCCC1] | $^1$H NMR (300 MHz, CHLOROFORM-d) δ ppm 1.25 (t, J = 7.1 Hz, 3 H) 1.29-1.52 (m, 6 H) 1.58-1.73 (m, 4 H) 2.33 (s, 3 H) 2.51 (s, 2 H) 3.63 (s, 2 H) 4.13 (q, J = 7.1 Hz, 2 H) 7.12 (d, J = 7.9 Hz, 2 H) 7.18-7.38 (m, 2 H). MS ESI/APCI Dual posi: 290[M + H]$^+$. | |
| Reference Example A-82 | 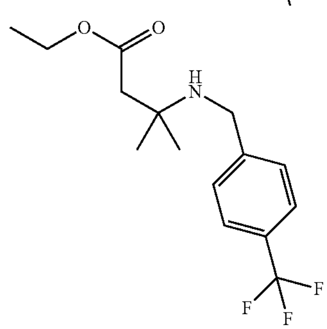 | $^1$H NMR (300 MHz, CHLOROFORM-d) δ ppm 1.21-1.29 (m, 9 H) 2.50 (s, 2 H) 3.78 (s, 2 H) 4.14 (q, J = 7.1 Hz, 2 H) 7.45-7.59 (m, 4 H). MS ESI/APCI Dual posi: 304[M + H]$^+$. | |
| Reference Example A-83 | 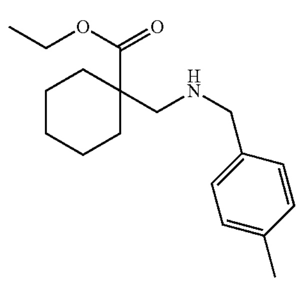 [SMILES: CCOC(=O)C1(CNCc2ccc(C)cc2)CCCCC1] | $^1$H NMR (300 MHz, CHLOROFORM-d) δ ppm 1.13-1.62 (m, 11 H) 1.96-2.12 (m, 2 H) 2.33 (s, 3 H) 2.64 (s, 2 H) 3.72 (s, 2 H) 4.15 (q, J = 7.0 Hz, 2 H) 7.08-7.14 (m, 2 H) 7.14-7.20 (m, 2 H). MS ESI/APCI Dual posi: 290[M + H]$^+$, 312[M + Na]$^+$. | |

TABLE 18-12-continued

| Compound No. | Structure | Analytical Data | Salt information |
|---|---|---|---|
| Reference Example A-84 | 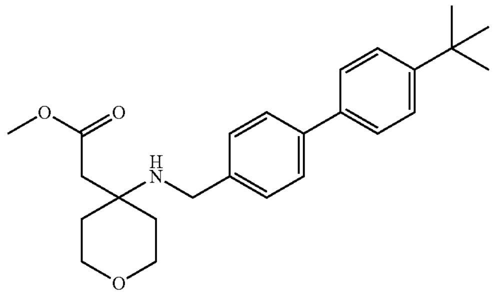 [SMILES: COC(=O)CC1(NCc2ccc(-c3ccc(C(C)(C)C)cc3)cc2)CCOCC1] | ¹H NMR (300 MHz, CHLOROFORM-d) δ ppm 1.37 (s, 8 H) 1.71 (dd, J = 6.2, 4.2 Hz, 4 H) 2.59 (s, 2 H) 3.60-3.77 (m, 7 H) 3.84-4.01 (m, 2 H) 7.38-7.65 (m, 8 H), MS ESI/APCI Dual posi: 396[M + H]⁺, 418[M + Na]⁺. | |
| Reference Example A-85 | 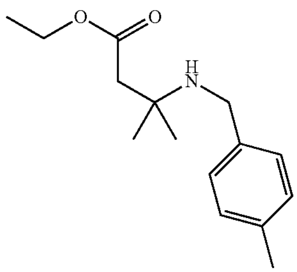 [SMILES: CCOC(=O)CC(C)(C)NCc1ccc(C)cc1] | ¹H NMR (300 MHz, CHLOROFORM-d) δ ppm 1.15-1.31 (m, 9 H) 2.32 (s, 3 H) 2.50 (s, 2 H) 3.67 (s, 2 H) 4.14 (q, J = 7.1 Hz, 2 H) 7.11 (d, J = 7.8 Hz, 2 H) 7.23 (d, J = 7.8 Hz, 2 H). MS ESI/APCI Dual posi: 250[M + H]⁺. | |

TABLE 18-13

| Compound No | Structure | Analytical Data | Salt information |
|---|---|---|---|
| Reference Example A-86 | 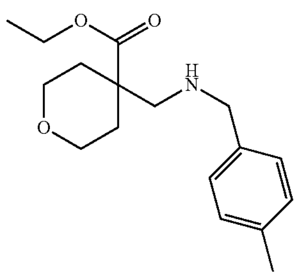 [SMILES: CCOC(=O)C1(CNCc2ccc(C)cc2)CCOCC1] | ¹H NMR (300 MHz, CHLOROFORM-d) δ ppm 1.25 (t, J = 7.1 Hz, 3 H) 1.46-1.62 (m, 2 H) 1.98-2.14 (m, 2 H) 2.33 (s, 3 H) 2.70 (s, 2 H) 3.48 (ddd, J = 11.9, 10.7, 2.3 Hz, 2 H) 3.72 (s, 2 H) 3.79 (dt, J = 11.9, 4.0 Hz, 2 H) 4.19 (q, J = 7.1 Hz, 2 H) 7.06-7.21 (m, 4 H). MS ESI/APCI Dual posi: 292[M + H]⁺, 314[M + Na]⁺. | |
| Reference Example A-87 | 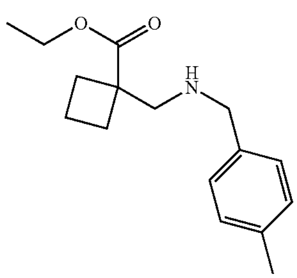 [SMILES: CCOC(=O)C1(CNCc2ccc(C)cc2)CCC1] | ¹H NMR (300 MHz, CHLOROFORM-d) δ ppm 1.26 (t, J = 7.1 Hz, 3 H) 1.85-1.99 (m, 4 H) 2.33 (s, 3 H) 2.35-2.47 (m, 2 H) 2.89 (s, 2 H) 3.76 (s, 2 H) 4.16 (q, J = 7.1 Hz, 2 H) 7.09-7.15 (m, 2 H) 7.16-7.22 (m, 2 H). MS ESI/APCI Dual posi: 262[M + H]⁺, 284[M + Na]⁺. | |
| Reference Example A-88 | 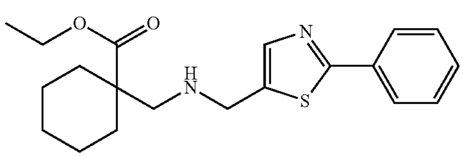 [SMILES: CCOC(=O)C1(CNCc2cnc(-c3ccccc3)s2)CCCCC1] | ¹H NMR (300 MHz, CHLOROFORM-d) δ ppm 1.12-1.62 (m, 11 H) 1.95-2.12 (m, 2 H) 2.71 (s, 2 H) 3.99 (s, 2 H) 4.17 (q, J = 6.9 Hz, 2 H) 7.36-7.50 (m, 3 H) 7.55-7.68 (m, 1 H) 7.84-8.02 (m, 2 H). MS ESI/APCI Dual posi: 359[M + H]⁺, 381[M + Na]⁺. | |

TABLE 18-13-continued

| Compound No | Structure | Analytical Data | Salt information |
|---|---|---|---|
| Reference Example A-89 | 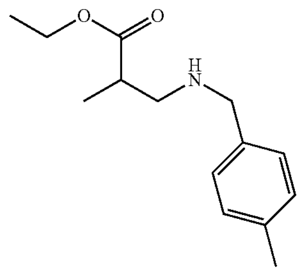 [SMILES: CCOC(=O)C(C)CNCc1ccc(C)cc1] | $^1$H NMR (300 MHz. CHLOROFORM-d) δ ppm 1.16 (d, J = 7.0 Hz, 3 H) 1.25 (t, J = 7.1 Hz, 3 H) 2.33 (s, 3 H) 2.55-2.75 (m, 2 H) 2.79-2.95 (m, 1 H) 3.75 (s, 2 H) 4.14 (q, J = 7.1 Hz, 2 H) 7.10-7.22 (m, 4 H). MS ESI/APCI Dual posi: 236[M + H]$^+$, 258[M + Na]$^+$. | |
| Reference Example A-90 | 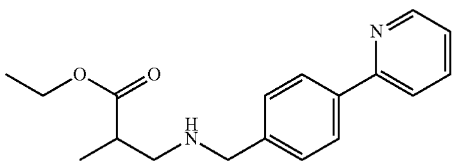 | $^1$H NMR (300 MHz, CHLOROFORM-d) δ ppm 1.17 (d, J = 6.8 Hz, 3 H) 1.26 (t, J = 7.1 Hz, 3 H) 2.54-2.77 (m, 2 H) 2.82-2.98 (m, 1 H) 3.86 (s, 2 H) 4.15 (q, J = 7.1 Hz, 2 H) 7.22 (ddd, J = 6.3, 4.9, 2.3 Hz, 1 H) 7.42 (d, J = 8.4 Hz, 2 H) 7.69-7.76 (m, 2 H) 7.95 (d, J = 8.4 Hz, 2 H) 8.64-8.72 (m, 1 H). MS ESI/APCI Dual posi: 299[M + H]$^+$, 321[M + Na]$^+$. | |
| Reference Example A-91 | 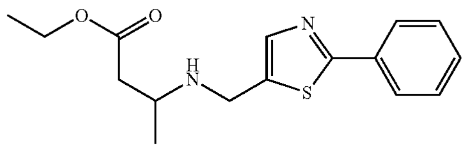 [SMILES: CCOC(=O)CC(C)NCc1cnc(-c2ccccc2)s1] | $^1$H NMR (300 MHz, CHLOROFORM-d) δ ppm 1.17 (d, J = 6.4 Hz, 3 H) 1.25 (t, J = 7.1 Hz, 3 H) 2.30-2.54 (m, 2 H) 3.11-3.29 (m, 1 H) 3.96-4.20 (m, 4 H) 7.37-7.44 (m, 3 H) 7.64 (s, 1 H) 7.87-7.94 (m, 2 H). MS ESI/APCI Dual posi: 305[M + H]$^+$, 327[M + Na]$^+$. MS ESI/APCI Dual nega: 303[M − H]$^−$. | |
| Reference Example A-92 | 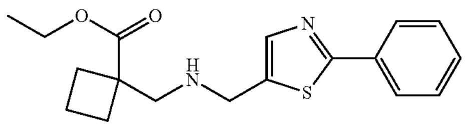 [SMILES: CCOC(=O)C1(CNCc2cnc(-c3ccccc3)s2)CCC1] | $^1$H NMR (300 MHz, CHLOROFORM-d) δ ppm 1.27 (t, J = 7.1 Hz, 3 H) 1.83-2.01 (m, 4 H) 2.33-2.52 (m, 2 H) 2.95 (s, 2 H) 4.04 (d, J = 0.9 Hz, 2 H) 4.17 (q, J = 7.1 Hz, 2 H) 7.36-7.52 (m, 3 H) 7.62-7.66 (m, 1 H) 7.86-7.98 (m, 2 H). MS ESI/APCI Dual Posi: 331[M + H]$^+$, 353[M + Na]$^+$. | |

TABLE 18-14

| Compound No. | Structure | Analytical Data | Salt information |
|---|---|---|---|
| Reference Example A-93 | 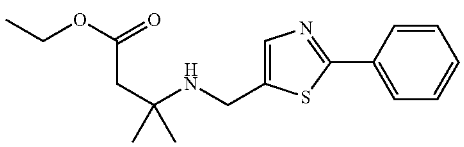 [SMILES: CCOC(=O)CC(C)(C)NCc1cnc(-c2ccccc2)s1] | $^1$H NMR (300 MHz, CHLOROFORM-d) δ ppm 1.18-1.34 (m, 9 H) 2.49 (s, 2 H) 3.98 (d, J = 0.9 Hz, 2 H) 4.16 (q, J = 7.0 Hz, 2 H) 7.38-7.47 (m, 3 H) 7.66 (s, 1 H) 7.86-7.95 (m, 2 H). MS ESI/APCI Dual posi: 319[M + H]$^+$, 341[M + Na]$^+$. | |
| Reference Example A-94 | 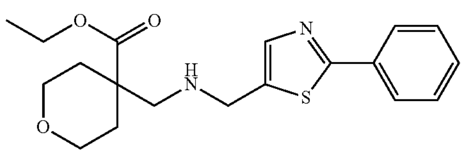 | $^1$H NMR (300 MHz, CHLOROFORM-d) δ ppm 1.26 (t, J = 7.1 Hz, 3 H) 1.49-1.62 (m, 2 H) 2.03-2.13 (m, 2 H) 2.76 (s, 2 H) 3.49 (ddd, J = 11.8, 11.0, 2.4 Hz, 2 H) 3.80 (dt, J = 11.8, 4.2 Hz, 2 H) 4.00 (d, J = 0.8 Hz, 2 H) 4.21 (q, J = 7.1 Hz, 2 H) 7.36-7.50 (m, 3 H) 7.62 (s, 1 H) 7.82-7.97 (m, 2 H). MS ESI/APCI Dual Posi: 361[M + H]$^+$, 383[M + Na]$^+$. | |
| Reference Example A-95 | 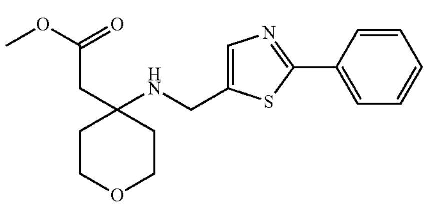 [SMILES: COC(=O)CC1(NCc2cnc(-c3ccccc3)s2)CCOCC1] | $^1$H NMR (300 MHz, CHLOROFORM-d) δ ppm 1.64-1.76 (m, 4 H) 2.56 (s, 2 H) 3.55-3.78 (m, 5 H) 3.83-3.98 (m, 4 H) 7.35-7.50 (m, 3 H) 7.67 (s, 1 H) 7.86-8.00 (m, 2 H). MS ESI/APCI Dual posi: 347[M + H]$^+$, 369[M + Na]$^+$. | |

TABLE 18-14-continued

| Compound No. | Structure | Analytical Data | Salt information |
|---|---|---|---|
| Reference Example A-96 | 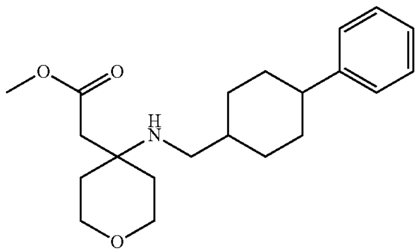 [SMILES: COC(=O)CC1(NCC2CCC(c3ccccc3)CC2)CCOCC1] | $^1$H NMR (300 MHz, CHLOROFORM-d) δ ppm 1.01-1.21 (m, 2 H) 1.38-1.57 (m, 3 H) 1.62 (dd, J = 6.2, 4.4 Hz, 4 H) 1.87-2.03 (m, 4 H) 2.36 (d, J = 6.2 Hz, 2 H) 2.41-2.61 (m, 3 H) 3.48-3.75 (m, 5 H) 3.77-3.99 (m, 2 H) 7.09-7.37 (m, 5 H). MS ESI/APCI Dual posi: 346[M + H]$^+$, 368[M + Na]$^+$. | |
| Reference Example A-97 | 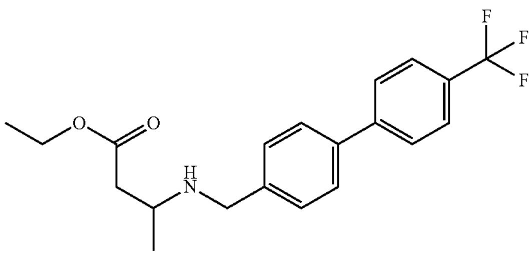 [SMILES: CCOC(=O)CC(C)NCc1ccc(-c2ccc(C(F)(F)F)cc2)cc1] | $^1$H NMR (300 MHz, CHLOROFORM-d) δ ppm 1.18 (d, J = 6.4 Hz, 3 H) 1.26 (t, J = 7.1 Hz, 3 H) 2.35-2.58 (m, 2 H) 3.13-3.26 (m, 1 H) 3.65-3.95 (m, 2 H) 4.15 (q, J = 7.1 Hz, 2 H) 7.41-7.47 (m, 2 H) 7.53-7.58 (m, 2 H) 7.63-7.77 (m, 4 H). MS ESI/APCI Dual posi: 366[M + H]$^+$, 388[M + Na]$^+$. | |
| Reference Example A-98 | 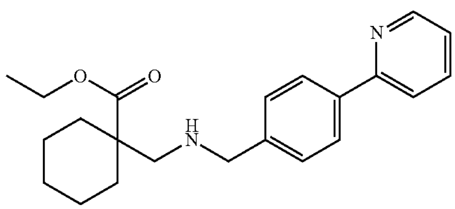 | $^1$H NMR (300 MHz, CHLOROFORM-d) δ ppm 1.11-1.62 (m, 11 H) 1.96-2.21 (m, 2 H) 2.67 (s, 2 H) 3.82 (s, 2 H) 4.17 (q, J = 7.1 Hz, 2 H) 7.18-7.25 (m, 1 H) 7.39 (d, J = 8.5 Hz, 2 H) 7.68-7.74 (m, 2 H) 7.94 (d, J = 8.4 Hz, 2 H) 8.62-8.74 (m, 1 H). MS ESI/APCI Dual posi: 353[M + H]$^+$, 375[M + Na]$^+$. | |
| Reference Example A-99 | 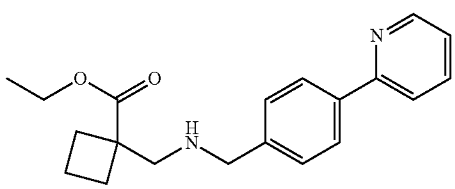 | $^1$H NMR (300 MHz, CHLOROFORM-d) δ ppm 1.11-1.62 (m, 11 H) 1.96-2.21 (m, 2 H) 2.67 (s, 2 H) 3.82 (s, 2 H) 4.17 (q, J = 7.1 Hz, 2 H) 7.18-7.25 (m, 1 H) 7.39 (d, J = 8.5 Hz, 2 H) 7.68-7.74 (m, 2 H) 7.94 (d, J = 8.4 Hz, 2 H) 8.62-8.74 (m, 1 H). MS ESI/APCI Dual posi: 353[M+ H]$^+$, 375[M + Na]$^+$. | |

TABLE 18-15

| Compound No. | Structure | Analytical Data | Salt information |
|---|---|---|---|
| Reference Example A-100 | 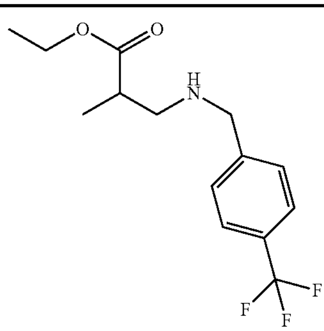 | $^1$H NMR (300 MHz, CHLOROFORM-d) δ ppm 1.17 (d, J = 6.7 Hz, 3 H) 1.26 (t, J = 7.1 Hz, 3 H) 2.53-2.76 (m, 2 H) 2.80-2.96 (m, 1 H) 3.86 (s, 2 H) 4.15 (q, J = 7.1 Hz, 2 H) 7.41-7.46 (m, 2 H) 7.54-7.60 (m, 2 H). MS ESI/APCI Dual posi: 290[M + H]$^+$, 312[M + Na]$^+$. | |
| Reference Example A-101 | 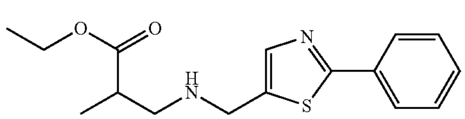 [SMILES: CCOC(=O)C(C)CNCc1cnc(-c2ccccc2)s1] | $^1$H NMR (300 MHz, CHLOROFORM-d) δ ppm 1.18 (d, J = 7.0 Hz, 3 H) 1.26 (t, J = 7.1 Hz, 3 H) 2.56-2.79 (m, 2 H) 2.81-3.01 (m, 1 H) 3.97-4.06 (m, 2 H) 4.16 (q, J = 7.1 Hz, 2 H) 7.39-7.48 (m, 3 H) 7.64 (s, 1 H) 7.89-7.94 (m, 2 H). MS ESI/APCI Dual posi: 305[M + H]$^+$, 327[M + Na]$^+$. | |

TABLE 18-15-continued

| Compound No. | Structure | Analytical Data | Salt information |
|---|---|---|---|
| Reference Example A-102 | 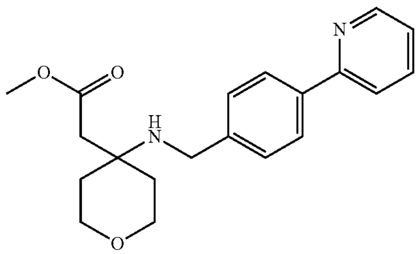 [SMILES: COC(=O)CC1(NCc2ccc(-c3ccccn3)cc2)CCOCC1] | ¹H NMR (300 MHz, CHLOROFORM-d) δ ppm 1.63-1.78 (m, 4 H) 2.59 (s, 2 H) 3.62-3.71 (m, 5 H) 3.75 (s, 2 H) 3.93 (dt, J = 11.9, 6.2 Hz, 2 H) 7.18-7.25 (m, 1 H) 7.49 (d, J = 8.2 Hz, 2 H) 7.65-7.81 (m, 2 H) 7.96 (d, J = 8.2 Hz, 2 H) 8.63-8.73 (m, 1 H). MS ESI/APCI Dual posi: 341[M + H]⁺, 363[M + Na]⁺. | |
| Reference Example A-103 | 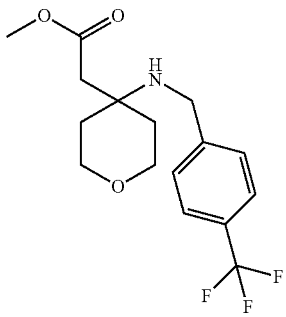 [SMILES: COC(=O)CC1(NCc2ccc(C(F)(F)F)cc2)CCOCC1] | ¹H NMR (300 MHz, CHLOROFORM-d) δ ppm 1.61-1.77 (m, 4 H) 2.57 (s, 2 H) 3.61-3.71 (m, 5 H) 3.74 (s, 2 H) 3.82-3.99 (m, 2 H) 7.48-7.54 (m, 2 H) 7.55-7.61 (m, 2 H). MS ESI/APCI Dual posi: 332[M + H]⁺, 354[M + Na]⁺. | |
| Reference Example A-104 | 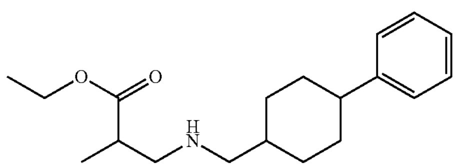 [SMILES: CCOC(=O)C(C)CNCC1CCC(c2ccccc2)CC1] | ¹H NMR (300 MHz, CHLOROFORM-d) δ ppm 0.99-2.40 (m, 15 H) 2.39-2.97 (m, 6 H) 4.09-4.22 (m, 2 H) 7.11-7.35 (m, 5 H). MS ESI/APCI Dual posi: 304[M + H]⁺. | |
| Reference Example A-105 | 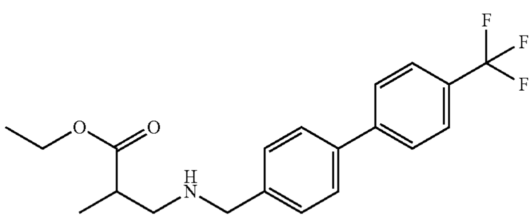 [SMILES: CCOC(=O)C(C)CNCc1ccc(-c2ccc(C(F)(F)F)cc2)cc1] | ¹H NMR (300 MHz, CHLOROFORM-d) δ ppm 1.19 (d, J = 6.8 Hz, 3 H) 1.26 (t, J = 7.1 Hz, 3 H) 2.56-2.76 (m, 2 H) 2.83-3.00 (m, 1 H) 3.85 (s, 2 H) 4.16 (q, J = 7.1 Hz, 2 H) 7.37-7.46 (m, 2 H) 7.52-7.59 (m, 2 H) 7.64-7.72 (m, 4 H). MS ESI/APCI Dual posi: 366[M + H]⁺, 388[M + Na]⁺. | |
| Reference Example A-106 | 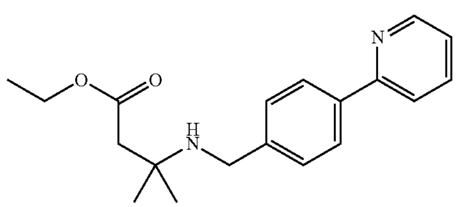 [SMILES: CCOC(=O)CC(C)(C)NCc1ccc(-c2ccccn2)cc1] | ¹H NMR (300 MHz, CHLOROFORM-d) δ ppm 1.22-1.29 (m, 9 H) 2.53 (s, 2 H) 3.78 (s, 2 H) 4.15 (q, j = 7.1 Hz, 2 H) 7.18-7.25 (m, 1 H) 7.43-7.48 (m, 2 H) 7.68-7.75 (m, 2 H) 7.94 (d, J = 8.2 Hz, 2 H) 8.64-8.71 (m, 1 H). MS ESI/APCI Dual posi: 313[M + H]⁺, 335[M + Na]⁺. | |

TABLE 18-16

| Compound No. | Structure | Analytical Data | Salt information |
|---|---|---|---|
| Reference Example A-107 | 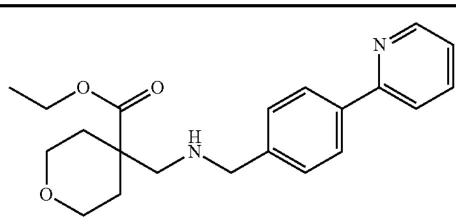 | ¹H NMR (300 MHz, CHLOROFORM-d) δ ppm 1.26 (t, J = 7.1 Hz, 3 H) 1.44-1.64 (m, 2 H) 1.99-2.16 (m, 2 H) 2.72 (s, 2 H) 3.49 (ddd, J = 11.8, 10.9, 2.4 Hz, 2 H) 3.74-3.86 (m, 4 H) 4.21 (q, J = 7.1 Hz, 2 H) 7.19-7.25 (m, 1 H) 7.39 (d, J = 8.3 Hz, 2 H) 7.66-7.81 (m, 2 H) 7.94 (d, J = 8.3 Hz, 2 H) 8.63-8.72 (m, 1 H). MS ESI/APCI Dual posi: 355[M + H]⁺, 377[M + Na]⁺. | |

TABLE 18-16-continued

| Compound No. | Structure | Analytical Data | Salt information |
|---|---|---|---|
| Reference Example A-108 | 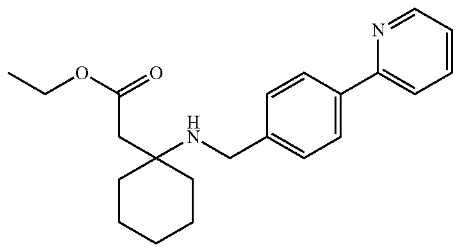 [SMILES: CCOC(=O)CC1(NCc2ccc(-c3ccccn3)cc2)CCCCC1] | ¹H NMR (300 MHz, CHLOROFORM-d) δ ppm 1.12-1.77 (m, 13 H) 2.53 (s, 2 H) 3.75 (s, 2 H) 4.14 (q, J = 7.2 Hz, 2 H) 7.21 (ddd, J = 6.1, 4.8. 2.4 Hz, 1 H) 7.49 (d, J = 8.5 Hz, 2 H) 7.65-7.79 (m, 2 H) 7.86-8.00 (m, 2 H) 8.60-8.72 (m, 1 H). MS ESI/APCI Dual posi: 353[M + H]⁺, 375[M + Na]⁺. | |
| Reference Example A-109 | 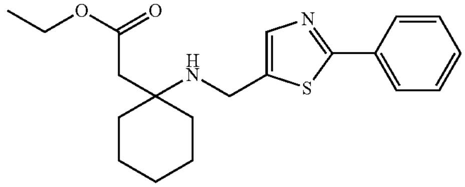 [SMILES: CCOC(=O)CC1(NCc2cnc(-c3ccccc3)s2)CCCCC1] | ¹H NMR (300 MHz, CHLOROFORM-d) δ ppm 1.20-1.76 (m, 13 H) 2.48 (s, 2 H) 3.94 (s, 2 H) 4.15 (q, J = 7.1 Hz. 2 H) 7.32-7.50 (m, 3 H) 7.66 (s, 1 H) 7.85-7.96 (m, 2 H). MS ESI/APCI Dual posi: 359[M + H]⁺, 381[M + Na]⁺. MS ESI/APCI Dual nega: 357[M − H]⁻. | |
| Reference Example A-110 | 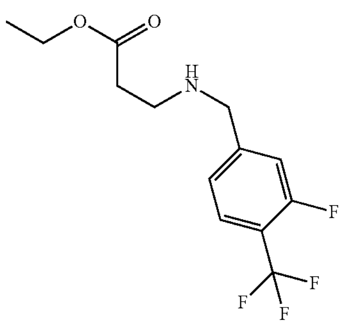 [SMILES: CCOC(=O)CCNCc1ccc(C(F)(F)F)c(F)c1] | ¹H NMR (300 MHz, CHLOROFORM-d) δ ppm 1.27 (t, J = 7.1 Hz, 3 H) 2.53 (t, J = 6.3 Hz, 2 H) 2.88 (t, J = 6.3 Hz, 2 H) 3.86 (s, 2 H) 4.15 (q, J = 7.1 Hz, 2 H) 7.16-7.25 (m, 2 H) 7.50-7.58 (m, 1 H). MS ESI/APCI Dual posi : 294[M + H]⁺, 316[M + Na]⁺. | |
| Reference Example A-111 | 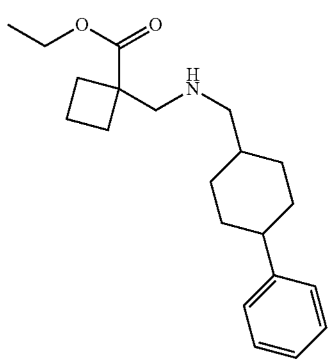 [SMILES: CCOC(=O)C1(CNCC2CCC(c3ccccc3)CC2)CCC1] | ¹H NMR (300 MHz, CHLOROFORM-d) δ ppm 0.92-1.17 (m, 2 H) 1.28 (t, J = 7.1 Hz, 3 H) 1.33-1.77 (m, 3 H) 1.79-2.05 (m, 8 H) 2.31-2.56 (m, 5 H) 2.92 (s, 2 H) 4.17 (q, J = 7.1 Hz, 2 H) 7.09-7.38 (m, 5 H). MS ESI/APCI Dual posi: 330[M + H]⁺. | |
| Reference Example A-112 | 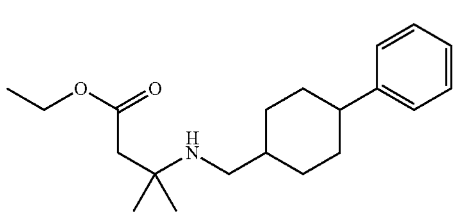 [SMILES: CCOC(=O)CC(C)(C)NCC1CCC(c2ccccc2)CC1] | ¹H NMR (300 MHz, CHLOROF0RM-d) δ ppm 1.02-1.19 (m, 8 H) 1.27 (t, J = 7.1 Hz, 3 H) 1.38-1.64 (m, 3 H) 1.84-2.03 (m, 4 H) 2.33-2.57 (m, 5 H) 4.14 (q, J = 7.1 Hz, 2 H) 7.11-7.37 (m, 5 H). MS ESI/APCI Dual posi: 318[M + H]⁺. | |

TABLE 18-16-continued

| Compound No. | Structure | Analytical Data | Salt information |
|---|---|---|---|
| Reference Example A-113 | 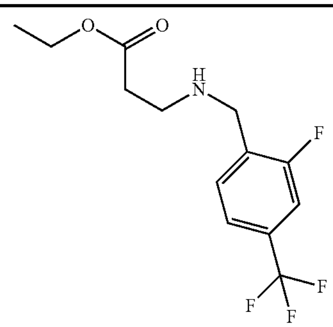 | ¹H NMR (300 MHz, CHLOROFORM-d) δ ppm 1.26 (t, J = 7.1Hz, 3 H) 2.53 (t, J = 6.3 Hz, 2 H) 2.89 (d, J = 6.3 Hz, 2 H) 3.90 (s, 2 H) 4.15 (q, J = 7.1 Hz, 2 H) 7.30 (d, J = 9.8 Hz, 1 H) 7.39 (d, J = 7.5 Hz, 1 H) 7.49-7.57 (m, 1 H). MS ESI/APCI Dual posi: 294[M + H]⁺, 316[M + Na]⁺. | |

TABLE 18-17

| Compound No. | Structure | Analytical Data | Salt information |
|---|---|---|---|
| Reference Example A-114 | 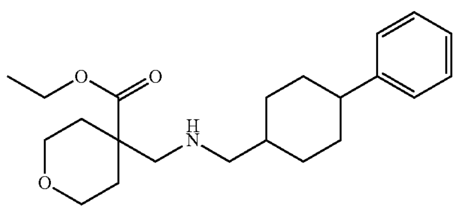 [SMILES: CCOC(=O)C1(CNCC2CCC(c3ccccc3)CC2)CCOCC1] | ¹H NMR (300 MHz, CHLOROFORM-d) δ ppm 0.92-1.16 (m, 2 H) 1.20-1.33 (m, 3 H) 1.35-1.71 (m, 3 H) 1.79-1.97 (m, 4 H) 1.97-2.18 (m, 4 H) 2.38-2.55 (m, 3 H) 2.67-2.79 (m, 2 H) 3 38-3.58 (m, 2 H) 3.73-3.89 (m, 2 H) 4-06-4.29 (m, 2 H) 7.09-7.38 (m, 5 H). MS ESI/APCI Dual posi: 360[M + H]⁺, 382[M + Na]⁺. | |
| Reference Example A-115 | 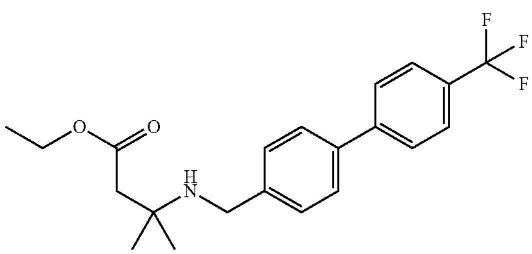 [SMILES: CCOC(=O)CC(C)(C)NCc1ccc(-c2ccc(C(F)(F)F)cc2)cc1] | ¹H NMR (300 MHz, CHLOROFORM-d) δ ppm 1.24-1.30 (m, 9 H) 2.53 (s, 2 H) 3.78 (s, 2 H) 4.16 (q, J = 7.0 Hz, 2 H) 7.43-7.50 (m, 2 H) 7.52-7.57 (m, 2 H) 7.66-7.68 (m, 4 H). MS ESI/APCI Dual posi: 380[M + H]⁺, 402[M + Na]⁺. | |
| Reference Example A-116 | 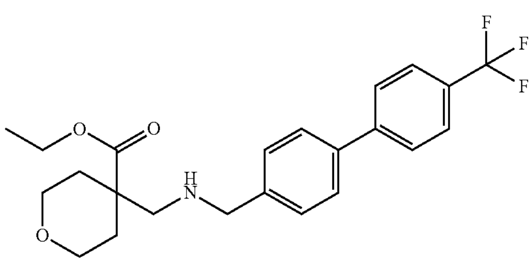 [SMILES: CCOC(=O)C1(CNCc2ccc(-c3ccc(C(F)(F)F)cc3)cc2)CCOCC1] | ¹H NMR (300 MHz, CHLOROFORM-d) δ ppm 1.27 (t, J = 7.1 Hz, 3 H) 1.43-1.66 (m, 2 H) 2.00-2.18 (m, 2 H) 2.75 (s, 2 H) 3.42- 3.56 (m, 2 H) 3.75-3.86 (m, 4 H) 4.21 (q, J = 7.1 Hz, 2 H) 7.39 (d, J = 8.3 Hz, 2 H) 7.55 (d, J = 8.3 Hz, 2 H) 7.60-7.77 (m, 4 H). MS ESI/APCI Dual posi: 422[M + H]⁺, 444[M + Na]⁺. | |
| Reference Example A-117 | 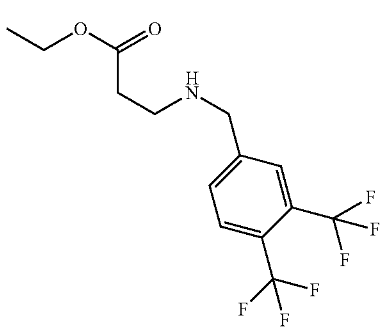 [SMILES: CCOC(=O)CCNCc1ccc(C(F)(F)F)c(C(F)(F)F)c1] | ¹H NMR (300 MHz, CHLOROFORM-d δ ppm 1.27 (t, J = 7.1 Hz, 3 H) 2.54 (t, J = 6.1 Hz, 2 H) 2.89 (t, J = 6.1 Hz, 2 H) 3.92 (s, 2 H); 4.16 (q, J = 7.1 Hz, 2 H) 7.66 (d, J = 7.8 Hz, 1 H) 7.75-7.89 (m, 2 H). MS ESI/APCI Dual posi: 344[M + H]⁺, 366[M + Na]⁺. MS ESI/APCI Dual nega: 378[M + Cl]⁻. | |

TABLE 18-17-continued

| Compound No. | Structure | Analytical Data | Salt information |
|---|---|---|---|
| Reference Example A-118 | 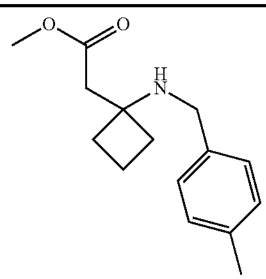 | $^1$H NMR (300 MHz, CHLOROFORM-d) δ ppm 1.72-1.95 (m, 2 H) 1.95-2.16 (m, 4 H) 2.32 (s, 3 H) 2.72 (s, 2 H) 3.65 (s, 2 H) 3.68 (s, 3 H) 7.07-7.15 (m, 2 H) 7.19-7.25 (m, 2 H). MS ESI/APCI Dual posi: 248[M + H]$^+$, 270[M + Na]$^+$. | |
| Reference Example A-119 | 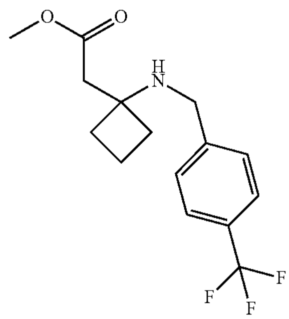 [SMILES: COC(=O)CC1(NCc2ccc(C(F)(F)F)cc2)CCC1] | $^1$H NMR (300 MHz, CHLOROFORM-d) δ ppm 1.74-1.96 (m, 2 H) 1.96-2.15 (m, 4 H) 2.73 (s, 2 H) 3.68 (s, 3 H) 3.76 (s, 2 H) 7.40-7.52 (m, 2 H) 7.52-7.62 (m, 2 H). MS ESI/APCI Dual posi: 302[M + H]$^+$, 324[M + Na]$^+$. | |
| Reference Example A-120 | 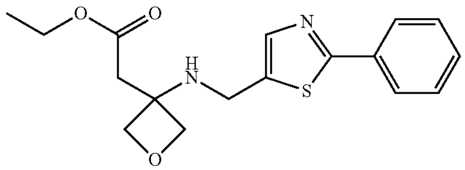 [SMILES: CCOC(=O)CC1(NCc2cnc(-c3ccccc3)s2)COC1] | $^1$H NMR (300 MHz, CHLOROFORM-d) δ ppm 1.27 (t, J = 7.1 Hz, 3 H) 2.97 (s, 2 H) 4.09-4.13 (m, 2 H) 4.18 (q, J = 7.1 Hz, 2 H) 4.55 (d, J = 6.9 Hz, 2 H) 4.69 (d, J = 6.9 Hz, 2 H) 7.35-7.49 (m, 3 H) 7.68 (s, 1 H) 7.84-7.97 (m, 2 H). MS ESI/APCI Dual posi: 333[M + H]$^+$, 355[M + Na]$^+$. MS ESI/APCI Dual nega: 331[M −H]$^-$. | |

TABLE 18-18

| Compound No. | Structure | Analytical Data | Salt information |
|---|---|---|---|
| Reference Example A-121 | 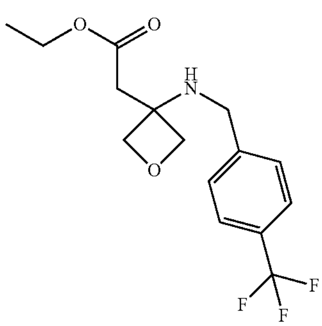 [SMILES: CCOC(=O)CC1(NCc2ccc(C(F)(F)F)cc2)COC1] | $^1$H NMR (300 MHz, CHLOROFORM-d) δ ppm 1.26 (t, J = 7.1 Hz, 3 H) 2.96 (s, 2 H) 3.92 (s, 2 H) 4.16 (q, J = 7.1 Hz, 2 H) 4.54 (d, J = 6.9 Hz, 2 H) 4.68 (d, J = 6.9 Hz, 2 H) 7.43-7.52 (m, 2 H) 7.53-7.65 (m, 2 H). MS ESI/APCI Dual posi: 318[M + H]$^+$. | |
| Reference Example A-122 | 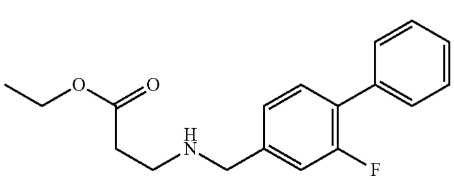 [SMILES: CCOC(=O)CCNCc1ccc(-c2ccccc2)c(F)c1] | $^1$H NMR (300 MHz, CHLOROFORM-d) δ ppm 1.27 (t, J = 7.1 Hz, 3 H) 2.55 (t, J = 6.4 Hz, 2 H) 2.92 (t, J = 6.4 Hz, 2 H) 3.84 (s, 2 H) 4.16 (q, J = 7.1 Hz, 2 H) 7.10-7.20 (m, 2 H) 7.34-7.49 (m, 4 H) 7.49-7.62 (m, 2 H). MS ESI/APCI Dual posi: 302[M + H]$^+$, 324[M + Na]$^+$. | |

TABLE 18-18-continued

| Compound No. | Structure | Analytical Data | Salt information |
|---|---|---|---|
| Reference Example A-123 | 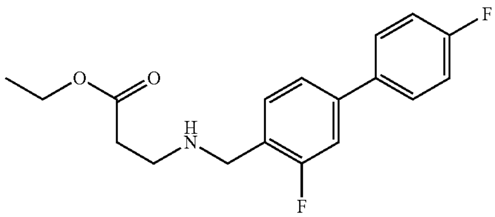 [SMILES: CCOC(=O)CCNCc1ccc(-c2ccc(F)cc2)cc1F] | $^1$H NMR (300 MHz, CHLOROFORM-d) δ ppm 1.26 (t, J = 7.1 Hz, 3 H) 2.55 (t, J = 6.5 Hz, 2 H) 2.92 (t, J = 6.5 Hz, 2 H) 3.89 (s, 2 H) 4.15 (q, J = 7.1 Hz, 2 H) 7.08-7.17 (m, 2 H) 7.19-7.32 (m, 2 H) 7.34-7.46 (m, 1 H) 7.46-7.58 (m, 2 H). MS ESI/APCI Dual posi: 320[M + H]$^+$, 342[M + Na]$^+$. | |
| Reference Example A-124 | 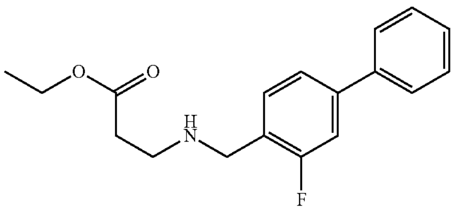 [SMILES: CCOC(=O)CCNCc1ccc(-c2ccccc2)cc1F] | $^1$H NMR (300 MHz, CHLOROFORM-d) δ ppm 1.26 (t, J = 7.1 Hz, 3 H) 2.55 (t, J = 6.5 Hz, 2 H) 2.92 (t, J = 6.5 Hz, 2 H) 3.89 (s, 2 H) 4.15 (q, J = 7.1 Hz, 2 H) 7.23-7.48 (m, 6 H) 7.53-7.60 (m, 2 H). MS ESI/APCI Dual posi: 302[M + H]$^+$, 324[M + Na]$^+$. | |
| Reference Example A-125 | 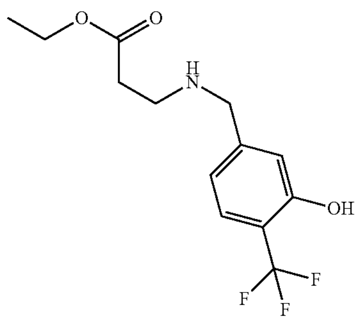 | $^1$H NMR (300 MHz, CHLOROFORM-d) δ ppm 1.27 (t, J = 7.1 Hz, 3 H) 2.53 (t, J = 6.3 Hz, 2 H) 2.88 (t, J = 6.3 Hz, 2 H) 3.84 (s, 2 H) 4.16 (q, J = 7.1 Hz, 2 H) 7.29-7.36 (m, 1 H) 7.51 (s, 1 H) 7.63 (d, J = 7.9 Hz, 1H). MS ESI/APCI Dual posi: 310[M + H]$^+$, 332[M +Na]$^+$. | |
| Reference Example A-126 | 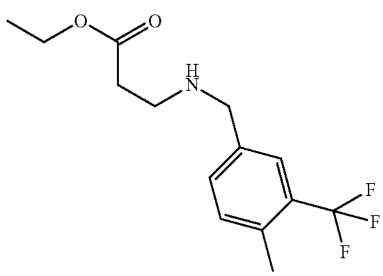 [SMILES: CCOC(=O)CCNCc1ccc(C)c(C(F)(F)F)c1] | $^1$H NMR (300 MHz, CHLOROFORM-d) δ ppm 1.26 (t, J = 7.1Hz, 3 H) 2.46 (s, 3 H) 2.53 (t, J = 6.5 Hz, 2 H) 2.88 (t, J = 6.5 Hz, 2H) 3.81 (s, 2 H) 4.14 (q, J = 7.1 Hz, 2 H) 7.23 (d, J = 7.6 Hz, 1 H) 7.38 (d, J = 7.6 Hz, 1 H) 7.56 (s, 1 H). MS ESI/APCI Dual posi: 290[M + H]$^+$, 312[M + Na]$^+$. | |
| Reference Example A-127 | 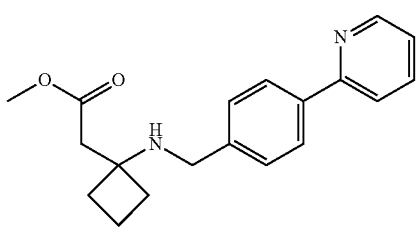 [SMILES: COC(=O)CC1(NCc2ccc(-c3ccccn3)cc2)CCC1] | $^1$H NMR (300 MHz, CHLOROFORM-d) δ ppm 1.77-1.97 (m, 2 H) 1.98-2.18 (m, 4 H) 2.75 (s, 2 H) 3.70 (s, 3 H) 3.76 (s, 2 H) 7.21 (ddd, J = 6.3, 4.8, 2.4 Hz, 1 H) 7.40-7.51 (m, 2 H) 7.67-7.80 (m, 2 H) 7.89-7.99 (m, 2 H) 8.63-8.73 (m, 1 H). MS ESI/APCI Dual posi: 311[M + H]$^+$. | |

TABLE 18-19

| Compound No. | Structure | Analytical Data | Salt information |
|---|---|---|---|
| Reference Example A-128 | 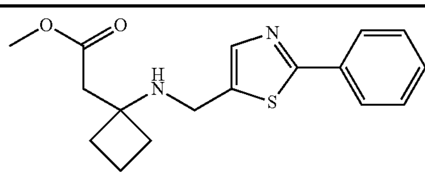 | $^1$H NMR (300 MHz, CHLOROFORM-d) δ ppm 1.78-1.94 (m, 2 H) 1.96-2.18 (m, 4 H) 2.72 (s, 2 H) 3.71 (s, 3 H) 3.88-4.00 (m, 2 H) 7.34-7.49 (m, 3 H) 7.62-7.69 (m, 1 H) 7.85-7.97 (m, 2H). MS ESI/APCI Dual posi: 317[M + H]$^+$, 339[M + Na]$^+$. MS ESI/APCI Dual nega: 315[M − H]$^-$. | |

TABLE 18-19-continued

| Compound No. | Structure | Analytical Data | Salt information |
|---|---|---|---|
| Reference Example A-129 | 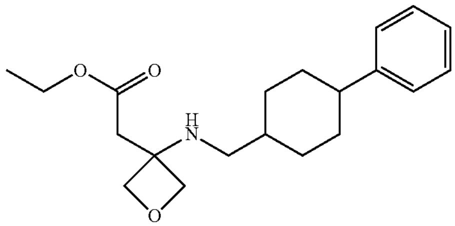 [SMILES: CCOC(=O)CC1(NCC2CCC(c3ccccc3)CC2)COC1] | $^1$H NMR (300 MHz. CHLOROFORM-d) δ ppm 1.04-1.20 (m, 2 H) 1.27 (t, J = 7.1 Hz, 3 H) 1.37-1.59 (m, 3 H) 1.85-2.00 (m, 4 H) 2.38-2.56 (m, 3 H) 2.90 (s, 2 H) 4.16 (q, J = 7.1 Hz, 2 H) 4.51 (d, J = 6.8 Hz, 2 H) 4.63 (d, J = 6.8 Hz, 2 H) 7.15-7.23 (m, 3 H) 7.23-7.33 (m, 2 H). MS ESI/APCI Dual posi: 332[M + H]$^+$. | |
| Reference Example A-130 | 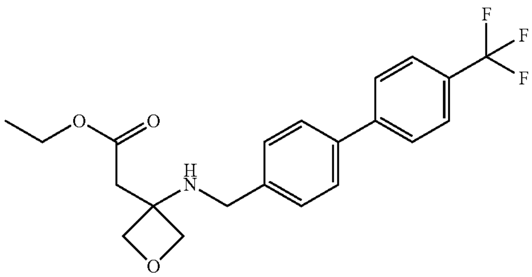 [SMILES: CCOC(=O)CC1(NCc2ccc(-c3ccc(C(F)(F)F)cc3)cc2)COC1] | $^1$H NMR (300 MHz, CHLOROFORM-d) δ ppm 1.27 (t, J = 7.1 Hz, 3 H) 2.99 (s, 2 H) 3.91 (s, 2 H) 4.17 (q, J = 7.7 Hz, 2 H) 4.56 (d, J = 6.7 Hz, 2 H) 4.71 (d, J = 6.7 Hz, 2 H) 7.42-7.51 (m, 2 H) 7.50-7.60 (m, 2 H) 7.68 (s, 4 H). MS ESI/APCI Dual posi: 394[M + H]$^+$. | |
| Reference Example A-131 | 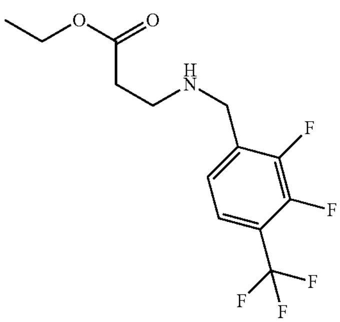 [SMILES: CCOC(=O)CCNCc1ccc(C(F)(F)F)c(F)c1F] | $^1$H NMR (300 MHz, CHLOROFORM-d) δ ppm 1.26 (t, J = 7.1 Hz, 3 H) 2.53 (t, J = 6.3 Hz, 2 H) 2.89 (t, J = 6.3 Hz, 2 H) 3.93 (s, 2 H) 4.15 (q, J = 7.1 Hz, 2 H) 7.15-7.41 (m, 2 H). MS ESI/APCI Dual posi: 312[M + H]$^+$, 334[M + Na]$^+$. MS ESI/APCI Dual nega: 346[M + Cl]$^-$. | |
| Reference Example A-132 | 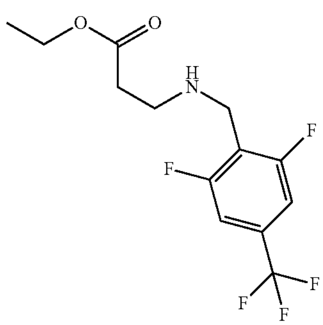 [SMILES: CCOC(=O)CCNCc1c(F)cc(C(F)(F)F)cc1F] | $^1$H NMR (300 MHz, CHLOROFORM-d) δ ppm 1.24 (t, J = 7.1 Hz, 3 H) 2.52 (t, J = 6.4 Hz, 2 H) 2.88 (t, J = 6.4 Hz, 2 H) 3.94 (s, 2 H) 4.13 (q, J = 7.1 Hz, 2 H) 7.11-7.23 (m, 2 H). MS ESI/APCI Dual posi: 312[M + H]$^+$, 334[M + Na]$^+$. | |
| Reference Example A-133 | 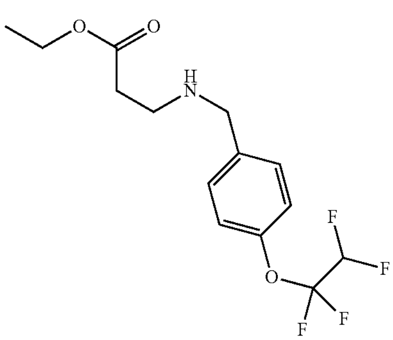 [SMILES: CCOC(=O)CCNCc1ccc(OC(F)(F)C(F)F)cc1] | $^1$H NMR (300 MHz, CHLOROFORM-d) δ ppm 1.26 (t, J = 7.1 Hz, 3 H) 2.53 (t, J = 6.4 Hz, 2 H) 2.89 (t, J = 6.4 Hz, 2 H) 3.80 (s, 2 H) 4.14 (q, J = 7.1 Hz, 2 H) 5.67-6.12 (m, 1 H) 7.12-7.22 (m, 2 H) 7.30-7.41 (m, 2 H). MS ESI/APCI Dual posi: 324[M + H]$^+$, 346[M + Na]$^+$. | |

TABLE 18-19-continued

| Compound No. | Structure | Analytical Data | Salt information |
|---|---|---|---|
| Reference Example A-134 | 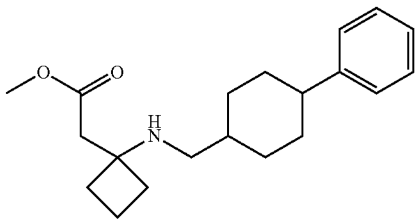 [SMILES: COC(=O)CC1(NCC2CCC(c3ccccc3)CC2)CCC1] | $^1$H NMR (300 MHz, CHLOROFORM-d) δ ppm 1.01-1.18 (m, 2 H) 1.36-1.57 (m, 3 H) 1.71-2.10 (m, 10 H) 2.38 (d, J = 6.4 Hz, 2 H) 2.40-2.55 (m, 1 H) 2.65 (s, 2 H) 3.68 (s, 3 H) 7.13-7.23 (m, 3 H) 7.24-7.32 (m, 2 R). MS ESI/APCI Dual posi: 316[M + H]$^+$. | |

TABLE 18-20

| Compound No. | Structure | Analytical Data | Salt information |
|---|---|---|---|
| Reference Example A-135 | 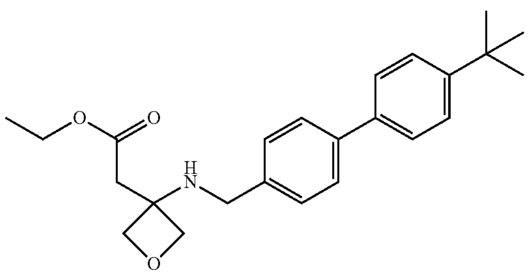 [SMILES: CCOC(=O)CC1(NCc2ccc(-c3ccc(C(C)(C)C)cc3)cc2)COC1] | $^1$H NMR (300 MHz, CHLOROFORM-d) δ ppm 1.27 (t, J = 7.1 Hz, 3 H) 1.36 (s, 9 H) 2.98 (s, 2 H) 3.88 (s, 2 H) 4.17 (q, J = 7.1 Hz, 2 H) 4.55 (d, J = 6.7 Hz, 2 H) 4.70 (d, J = 6.7 Hz, 2 H) 7.37-7.49 (m, 4 H) 7.48-7.59 (m, 4 H). MS ESI/APCI Dual posi: 382[M + H]$^+$ 404[M + Na]$^+$. | |
| Reference Example A-136 | 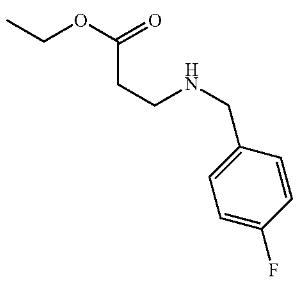 [SMILES: CCOC(=O)CCNCc1ccc(F)cc1] | $^1$H NMR (600 MHz, CHLOROFORM-d) δ ppm 1.25 (t, J = 7.0 Hz, 3 H) 2.56 (t, J = 6.4 Hz, 2 H) 2.91 (t, J = 6.4 Hz, 2 H) 3.81 (s, 2 H) 4.14 (q, J = 7.0 Hz, 2 H) 6.98-7.04 (m, 2 H) 7.27-7.32 (m, 2 H). MS ESI/APCI Dual posi: 226[M + H]$^+$, 248[M + Na]$^+$. | |
| Reference Example A-137 | 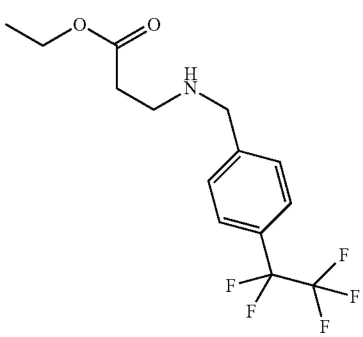 [SMILES: CCOC(=O)CCNCc1ccc(C(F)(F)C(F)(F)F)cc1] | $^1$H NMR (600 MHz. CHLOROFORM-d) δ ppm 1.25 (t, J = 7.1 Hz, 3 H) 2.53 (t, J = 6.4 Hz, 2 H) 2.89 (t, J = 6.4 Hz, 2 H) 3.87 (s, 2 H) 4.14 (q, J = 7.1 Hz, 2 H) 7.43-7.51 (m, 2 H) 7.52-7.60 (m, 2 H). MS ESI/APCI Dual posi: 326[M + H]$^+$, 348[M + Na]$^+$. | |
| Reference Example A-138 | 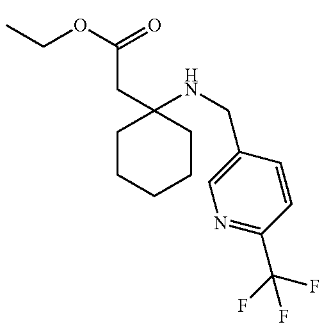 | $^1$H NMR (600 MHz, CHLOROFORM-d) δ ppm 1.25 (t, J = 7.2 Hz, 3 H) 1.29-1.70 (m, 10 H) 2.50 (s, 2 H) 3.79 (s, 2 H) 4.13 (q, J = 7.2 Hz, 2 H) 7.63 (d, J = 8.3 Hz, 1 H) 7.89-7.99 (m, 1 H) 8.72 (s, 1 H). MS ESI/APCI Dual posi: 346[M + H]$^+$, 367[M + Na]$^+$. MS ESI/APCI Dual nega: 379[M + Cl]$^-$. | |

TABLE 18-20-continued

| Compound No. | Structure | Analytical Data | Salt information |
|---|---|---|---|
| Reference Example A-139 | 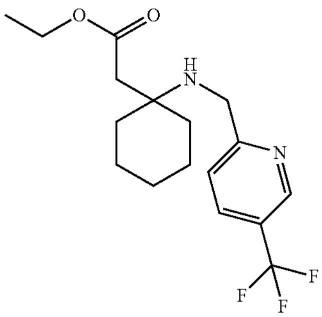 [SMILES: CCOC(=O)CC1(NCc2ccc(C(F)(F)F)cn2)CCCCC1] | $^1$H NMR (600 MHz, CHLOROFORM-d) δ ppm 1.22 (t, J = 7.0 Hz, 3 H) 1.30-1.79 (m, 10 H) 2.51 (s, 2 H) 3.95 (s, 2 H) 4.12 (q, J = 7.0 Hz, 2 H) 7.62 (d, J = 8.3 Hz, 1 H) 7.87 (dd, J = 8.3, 2.1 Hz, 1 H) 8.79 (d, J = 2.1 Hz, 1 H). MS ESI/APCI Dual posi: 345[M + H]$^+$, 367[M + Na]$^+$. | |
| Reference Example A-140 | 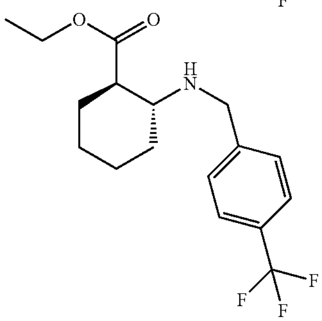 | $^1$H NMR (600 MHz, CHLOROFORM-d) δ ppm 1.14-1.34 (m, 5 H) 1.41-1.55 (m, 2 H) 1.67-1.81 (m, 2 H) 1.89-1.99 (m, 1 H) 2.07-2.16 (m, 1 H) 2.18-2.29 (m, 1 H) 2.75 (td, J = 10.7, 3.7 Hz, 1 H) 3.78 (d, J = 13.6 Hz, 1 H) 3.93 (d, J = 13.6 Hz, 1 H) 4.09 - 4.17 (m, 2 H) 7.42 (d, J=7.8 Hz, 2 H) 7.55 (d, J=7.8 Hz, 2 H). MS ESI/APCI Dual posi: 330[M + H]$^+$, 352[M + Na]+. | |
| Reference Example A-141 | 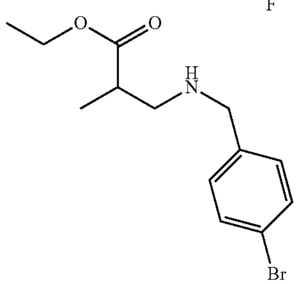 | $^1$H NMR (300 MHz, CHLOROFORM-d) δ ppm 1.16 (d, J = 6.5 Hz, 3 H) 1.25 (t, J = 7.1 Hz, 3 H) 2.54-2.73 (m, 2 H) 2.78-2.93 (m, 1 H) 3.74 (s, 2 H) 4.14 (q, J = 7.1 Hz, 2 H) 7.16-7.22 (m, 2 H) 7.41-7.46 (m, 2 H). MS ESI/APCI Dual posi: 300[M + H]$^+$, 322[M + Na]$^+$. | |

TABLE 18-21

| Compound No. | Structure | Analytical Data | Salt information |
|---|---|---|---|
| Reference Example A-142 | 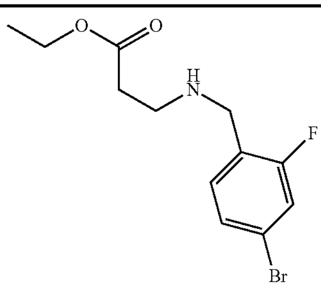 | $^1$H NMR (300 MHz, CHLOROFORM-d) δ ppm 1.25 (t, J = 7.1 Hz, 3 H) 2.54 (t, J = 6.4 Hz, 2 H) 2.88 (t, J = 6.4 Hz, 2 H) 3.82 (d, J = 0.9 Hz, 2 H) 4.14 (q, J = 7.1 Hz, 2 H) 7.06-7.44 (m, 3 H). MS ESI/APCI Dual posi: 304 [M + H]$^+$, 326[M + Na]$^+$. MS ESI/APCI Dual nega: 338[M + Cl]$^-$. | |
| Reference Example A-143 | 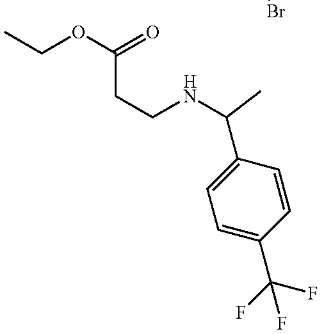 | $^1$H NMR (300 MHz, CHLOROFORM-d) δ ppm 1.26 (t, J = 7.1 Hz, 3 H) 1.34 (d, J = 6.7 Hz, 3 H) 2.42-2.50 (m, 2 H) 2.59-2.70 (m, 1 H) 2.70-2.82 (m, 1 H) 3.84 (q, J = 6.7 Hz, 1 H) 4.14 (q, J = 7.1 Hz, 2 H) 7.44 (d, J = 8.1 Hz. 2 H) 7.68 (d, J = 8.1 Hz, 2H). MS ESI/APCI Dual posi: 290[M + H]$^+$, 312[M + Na]$^+$. | |

TABLE 18-21-continued

| Compound No. | Structure | Analytical Data | Salt information |
|---|---|---|---|
| Reference Example A-144 | 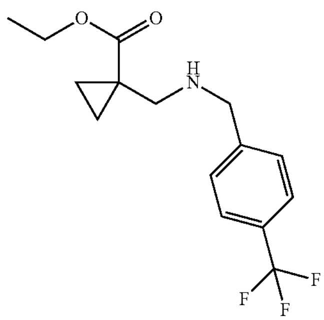 [SMILES: CCOC(=O)C1(CNCc2ccc(C(F)(F)F)cc2)CC1] | ¹H NMR (300 MHz, CHLOROFORM-d) δ ppm 0.70-0.83 (m, 2 H) 1.13-1.37 (m, 5 H) 2.69 (s, 2 H) 3.87 (s, 2 H) 4.12 (q, J = 7.0 Hz, 2 H) 7.39-7.43 (m, 2 H) 7.52-7.62 (m, 2 H). MS ESI/APCI Dual posi: 302[M + H]⁺. | |
| Reference Example A-145 | 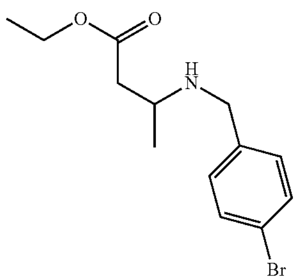 [SMILES: CCOC(=O)CC(C)NCc1ccc(Br)cc1] | ¹H NMR (300 MHz, CHLOROFORM-d) δ ppm 1.15 (d, J = 6.4 Hz. 3 H) 1.25 (t, J = 7.1 Hz, 3 H) 2.37 (dd, J = 15.2, 5.9 Hz, 1 H) 2.46 (dd, J = 15.2, 7.0 Hz, 1 H) 3.02-3.23 (m, 1 H) 3.71 (d, J = 13.5 Hz, 1H) 3.79 (d. J = 13.5 Hz, 1 H) 4.13 (q, J = 7.1 Hz, 2 H) 7.15-7.25 (m, 2 H) 7.36-7.48 (m, 2 H). | |
| Reference Example A-146 | 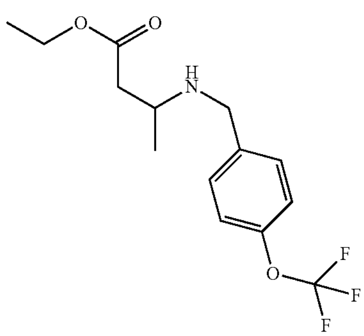 [SMILES: CCOC(=O)CC(C)NCc1ccc(OC(F)(F)F)cc1] | ¹H NMR (300 MHz, CHLOROFORM-d) δ ppm 1.16 (d, J = 6.4 Hz, 3 H) 1.25 (t, J = 7.1 Hz, 3 H) 2.39 (dd, J = 15.2, 5.8 Hz, 1 H) 2.47 (dd, J = 15.2, 7.0 Hz, 1 H) 3.04-3.23 (m, 1 H) 3.76 (d, J = 13.2 Hz, 1 H) 3.84 (d, J = 13.2 Hz, 1 H) 4.14 (q, J = 7.1 Hz, 2 H) 7.10-7.21 (m, 2 H) 7.30-7.42 (m, 2 H). MS ESI/APCI Dual posi: 306[M + H]⁺. | |
| Reference Example A-147 | 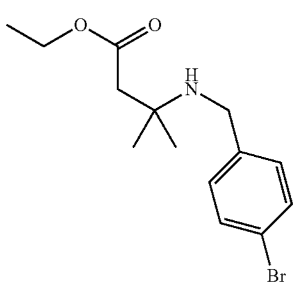 [SMILES: CCOC(=O)CC(C)(C)NCc1ccc(Br)cc1] | ¹H NMR (300 MHz, CHLOROFORM-d) δ ppm 1.12-1.35 (m, 9 H) 2.49 (s, 2 H) 3.67 (s, 2 H) 4.14 (q, J = 7.1 Hz, 2 H) 7.18-7.28 (m, 2 H) 7.38-7.48 (m, 2 H). MS ESI/APCI Dual posi: 314[M + H]⁺. | |
| Reference Example A-148 | 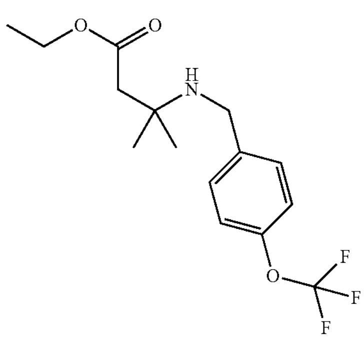 [SMILES: CCOC(=O)CC(C)(C)NCc1ccc(OC(F)(F)F)cc1] | ¹H NMR (300 MHz, CHLOROFORM-d) δ ppm 1.14-1.34 (m, 9 H) 2.50 (s, 2 H) 3.72 (s, 2 H) 4.14 (q, J = 7.1 Hz, 2 H) 7.10-7.20 (m, 2 H) 7.32-7.45 (m, 2 H). MS ESI/APCI Dual posi: 320[M + H]⁺. | |

TABLE 18-22

| Compound No. | Structure | Analytical Data | Salt information |
|---|---|---|---|
| Reference Example A-149 | 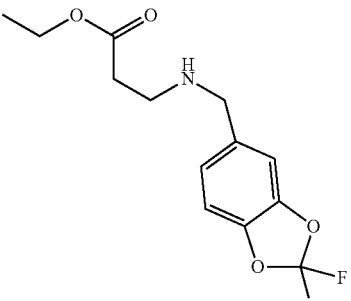 | ¹H NMR (300 MHz, CHLOROFORM-d) δ ppm 1.26 (t, J = 7.1 Hz, 3 H) 2.54 (t, J = 6.3 Hz, 2 H) 2.88 (t, J = 6.3 Hz, 2 H) 3.80 (s, 2 H) 4.15 (q, J = 7.1 Hz, 2 H) 6.96-7.05 (m, 2 H) 7.10 (d, J = 0.9 Hz, 1 H). MS ESI/APCI Dual posi: 288[M + H]⁺, 310[M + Na]⁺. | |
| Reference Example A-150 | 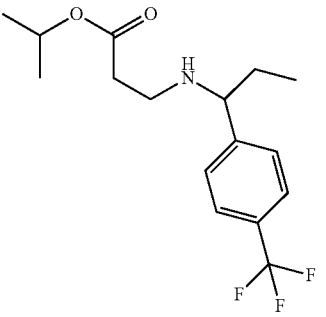 [SMILES: CCC(NCCC(=O)OC(C)C)c1ccc(C(F)(F)F)cc1] | ¹H NMR (300 MHz, CHLOROFORM-d) δ ppm 0.82 (t, J = 7.5 Hz, 3 H) 1.23 (d, J = 6.3 Hz, 6 H) 1.52-1.81 (m, 2 H) 2.34-2.49 (m, 2 H) 2.53-2.78 (m, 2 H) 3.57 (t, J = 6.8 Hz, 1 H) 5.01 (spt, J = 6.3 Hz, 1 H) 7.41 (d, J = 8.1 Hz, 2 H) 7.57 (d, J = 8.1 Hz, 2 H). MS ESI/APCI Dual posi: 318[M + H]⁺, 340[M + Na]⁺. | |
| Reference Example A-151 | 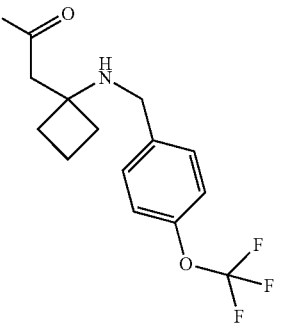 | ¹H NMR (300 MHz, CHLOROFORM-d) δ ppm 1.70-1.95 (m, 2 H) 1.95-2.18 (m, 4 H) 2.72 (s, 2 H) 3.65-3.76 (m, 5 H) 7.15 (d, J = 8.4 Hz, 2 H) 7.37 (d, J = 8.4 Hz, 2 H). MS ESI/APCI Dual posi: 313[M + H]⁺, 340[M + Na]⁺. | |
| Reference Example A-152 | 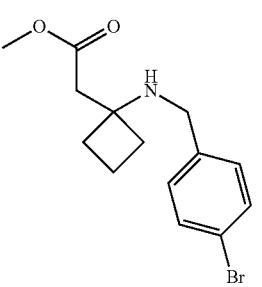 [SMILES: COC(=O)CC1(NCc2ccc(Br)cc2)CCC1] | ¹H NMR (300 MHz. CHLOROFORH-d) δ ppm 1.74-1.94 (m, 2 H) 1.95-2.14 (m, 4 H) 2.71 (s, 2 H) 3.65 (s, 2 H) 3.68 (s, 3 H) 7.20-7.25 (m, 2 H) 7.40-7.45 (m, 2 H). MS ESI/APCI Dual posi: 312[M + H]⁺, 334[M + Na]⁺. | |
| Reference Example A-153 | 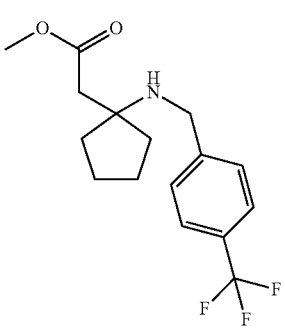 [SMILES: COC(=O)CC1(NCc2ccc(C(F)(F)F)cc2)CCCC1] | ¹H NMR (300 MHz, CHLOROFORM-d) δ ppm 1.53-1.89 (m, 8 H) 2.62 (s, 2 H) 3.68 (s, 3 H) 3.76 (s, 2 H) 7.41-7.53 (m, 2 H) 7.51-7.60 (m, 2 H). MS ESI/APCI Dual posi: 316[M + H]⁺, 338[M + Na]⁺. | |

TABLE 18-22-continued

| Compound No. | Structure | Analytical Data | Salt information |
|---|---|---|---|
| Reference Example A-154 | 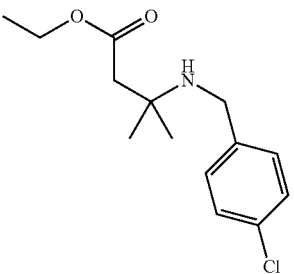 [SMILES: CCOC(=O)CC(C)(C)NCc1ccc(Cl)cc1] | ¹H NMR (300 MHz, CHLOROFORM) δ ppm 1.13-1.34 (m, 9 H) 2.50 (s, 2 H) 3.69 (s, 2 H) 4.14 (q, J = 7.1 Hz, 2 H) 7.20-7.33 (m, 4 H). | |
| Reference Example A-155 | 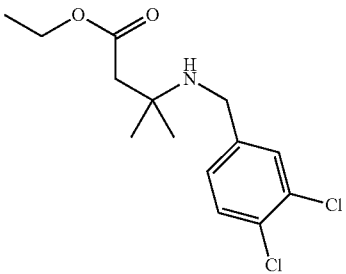 [SMILES: CCOC(=O)CC(C)(C)NCc1ccc(Cl)c(Cl)c1] | ¹H NMR (300 MHz, CHLOROFORM-d) δ ppm 1.22 (s, 6 H) 1.26 (t, J = 7.1 Hz, 3 H) 2.48 (s, 2 H) 3.68 (s, 2 H) 4.15 (q, J = 7.1 Hz, 2 H) 7.19 (dd, J = 8.2, 2.1 Hz, 1 H) 7.36 (d, J = 8.2 Hz, 1 H) 7.48 (d, J = 2.1 Hz, 1 H). MS ESI/APCI Dual posi: 304[M + H]⁺. | |

TABLE 18-23

| Compound No. | Structure | Analytical Data | Salt information |
|---|---|---|---|
| Reference Example A-156 | 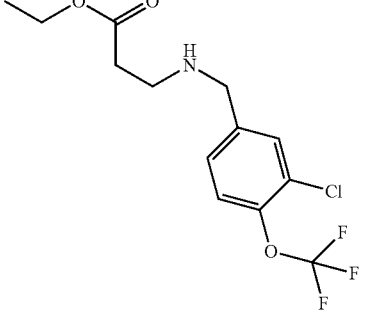 | ¹H NMR (300 MHz, CHLOROFORM-d) δ ppm 1.26 (t, J = 7.1 Hz, 3 H) 2.53 (t, J = 6.4 Hz, 2 H) 2.88 (t, J = 6.4 Hz, 2 H) 3.79 (s, 2 H) 4.15 (q, J = 7.1 Hz, 2 H) 7.19-7.30 (m, 2 H) 7.47 (s, 1 H). MS ESI/APCI Dual posi: 326[M + H]⁺, 348[M + Na]⁺. | |
| Reference Example A-157 | 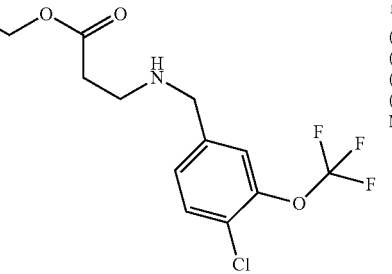 | ¹H NMR (300 MHz, CHLOROFORM-d) δ ppm 1.26 (t, J = 7.1 Hz, 3 H) 2.52 (t, J = 6.3 Hz, 2 H) 2.87 (t, J = 6.3 Hz, 2 H) 3.80 (s, 2 H) 4.15 (q, J = 7.1 Hz, 2 H) 7.19-7.24 (m, 1 H) 7.30-7.34 (m, 1 H) 7.41 (d, J = 8.2 Hz. 1 H). MS ESI/APCI Dual posi: 326[M + H]⁺, 348[M + Na]⁺. | |

TABLE 18-23-continued

| Compound No. | Structure | Analytical Data | Salt information |
|---|---|---|---|
| Reference Example A-158 | 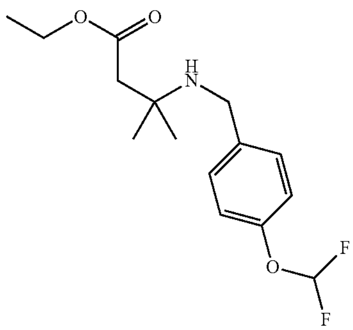 [SMILES: CCOC(=O)CC(C)(C)NCc1ccc(OC(F)F)cc1] | $^1$H NMR (300 MHz, CHLOROFORM-d) δ ppm 1.06-1.39 (m, 9 H) 2.50 (s, 2 H) 3.70 (s, 2 H) 4.14 (q, J = 7.0 Hz, 2 H) 6.14-6.78 (m, 1 H) 7.03-7.15 (m, 2 H) 7.33-7.37 (m, 2 H). MS ESI/APCI Dual posi: 302[M + H]$^+$, 324[M + Na]$^+$. | |
| Reference Example A-159 | 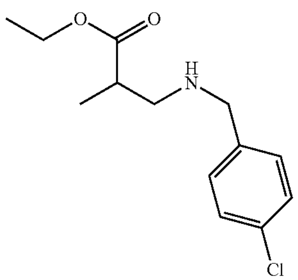 [SMILES: CCOC(=O)C(C)CNCc1ccc(Cl)cc1] | $^1$H NMR (300 MHz, CHLOROFORM-d) δ ppm 1.16 (d, J = 6.5 Hz, 3 H) 1.25 (t, J = 7.1 Hz, 3 H) 2.53-2.74 (m, 2 H) 2.75-2.95 (m, 1 H) 3.75 (s, 2 H) 4.14 (q, J = 7.1 Hz, 2 H) 7.22-7.31 (m, 4 H). MS ESI/APCI Dual posi: 256[M + H]$^+$, 278[M + Na]$^+$. | |
| Reference Example A-160 | 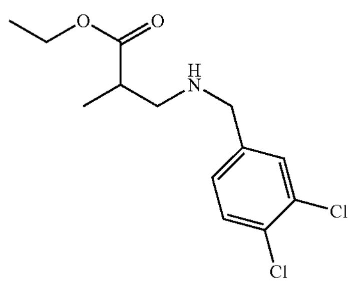 [SMILES: CCOC(=O)C(C)CNCc1ccc(Cl)c(Cl)c1] | $^1$H NMR (300 MHz, CHLOROFORM-d) δ ppm 1.17 (d, J = 6.8 Hz, 3 H) 1.26 (t, J = 7.1 Hz, 3 H) 2.55-2.71 (m, 2 H) 2.77-2.92 (m, 1 H) 3.74 (s, 2 H) 4.15 (q, J = 7.1 Hz, 2 H) 7.15 (dd, J = 8.1, 2.1 Hz, 1 H) 7.38 (d, J = 8.1 Hz, 1 H) 7.43 (d, J = 2.1 Hz, 1 H). MS ESI/APCI Dual posi : 290[M + H]$^+$, 312[M + Na]$^+$. | |
| Reference Example A-161 | 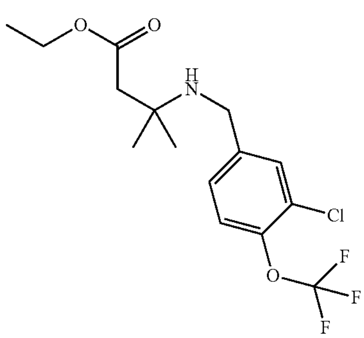 [SMILES: CCOC(=O)CC(C)(C)NCc1ccc(OC(F)(F)F)c(Cl)c1] | $^1$H NMR (300 MHz, CHLOROFORM-d) δ ppm 1.22 (s, 6 H) 1.26 (t, J = 7.1 Hz, 3 H) 2.49 (s, 2 H) 3.70 (s, 2 H) 4.15 (q, J = 7.1 Hz, 2 H) 7.19-7.32 (m, 2 H) 7.48-7.55 (m, 1 H). MS ESI/APCI Dual posi; 354[M + H]$^+$. | |
| Reference Example A-162 | 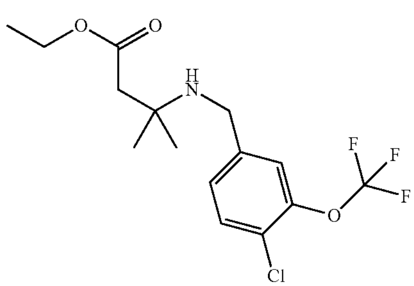 [SMILES: CCOC(=O)CC(C)(C)NCc1ccc(Cl)c(OC(F)(F)F)c1] | $^1$H NMR (300 MHz, CHLOROFORM-d) δ ppm 1.21 (s, 6 H) 1.25 (t, J = 7.1 Hz, 3 H) 2.48 (s, 2 H) 3.72 (s, 2 H) 4.14 (q, J = 7.1 Hz, 2 H) 7.22-7.28 (m, 1 H) 7.34-7.42 (m, 2 H). MS ESI/APCI Dual posi: 354[M + H]$^+$. | |

TABLE 18-24

| Compound No. | Structure | Analytical Data | Salt information |
|---|---|---|---|
| Reference Example A-163 | 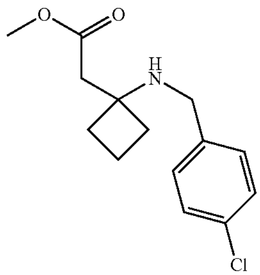 [SMILES: COC(=O)CC1(NCc2ccc(Cl)cc2)CCC1] | ¹H NMR (300 MHz, CHLOROFORM-d) δ ppm 1.76-1.94 (m, 2 H) 1.95-2.16 (m, 4 H) 2.72 (s, 2 H) 3.66 (s, 2 H) 3.68 (s, 3 H) 7.27-7.29 (m, 4 H). MS ESI/APCI Dual posi: 268[M + H]⁺, 290[M + Na]⁺. | |
| Reference Example A-164 | 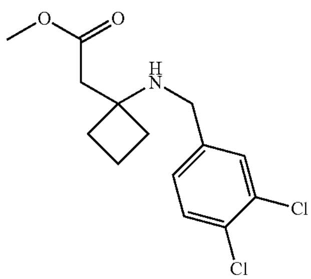 [SMILES: COC(=O)CC1(NCc2ccc(Cl)c(Cl)c2)CCC1] | ¹H NMR (300 MHz, CHLOROFORM-d) δ ppm 1.72-1.92 (m, 2 H) 1.94-2.14 (m, 4 H) 2.71 (s, 2 H) 3.66 (s, 2 H) 3.69 (s, 3 H) 7.18 (dd, J = 8.2, 2.0 Hz, 1 H) 7.37 (d, J = 8.2 Hz, 1 H) 7.47 (d, J = 2.0 Hz, 1 H). MS ESI/APCI Dual posi: 302[M + H]⁺, 324[M + Na]⁺. | |
| Reference Example A-165 | 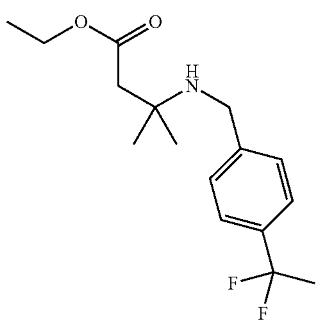 [SMILES: CCOC(=O)CC(C)(C)NCc1ccc(C(C)(F)F)cc1] | ¹H NMR (600 MHz, CHLOROFORM-d) δ ppm 1.24 (s, 6 H) 1.26 (t, J = 7.0 Hz, 3 H) 1.65-1.83 (m, 3 H) 2.51 (s, 2 H) 3.74 (s, 2 H) 4.14 (q, J = 7.0 Hz, 2 H) 7.39-7.46 (m, 4 H). MS ESI/APCI Dual posi: 300[M + H]⁺, 322[M + Na]⁺. | |
| Reference Example A-166 | 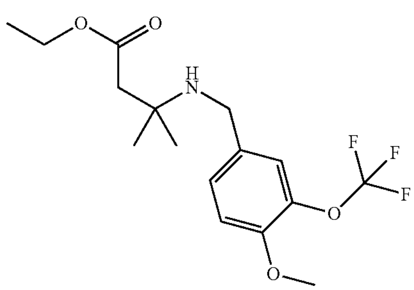 [SMILES: CCOC(=O)CC(C)(C)NCc1ccc(OC)c(OC(F)(F)F)c1] | ¹H NMR (600 MHz, CHLOROFORM-d) δ ppm 1.22 (s, 6 H) 1.26 (t, J = 7.0 Hz, 3 H) 2.49 (s, 2 H) 3.67 (s, 2 H) 3.86 (s, 3 H) 4.14 (q, J = 7.0 Hz, 2 H) 6.93 (d, J = 8.7 Hz, 1 H) 7.22-7.26 (m, 2 H). MS ESI/APCI Dual posi: 350[M + H]⁺, 372[M + Na]⁺. | |
| Reference Example A-167 | 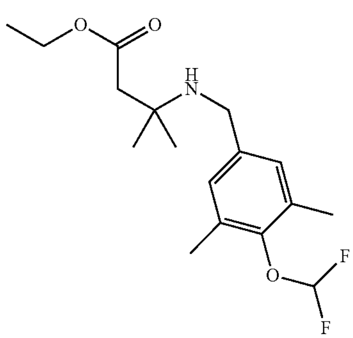 [SMILES: CCOC(=O)CC(C)(C)NCc1cc(C)c(OC(F)F)c(C)c1] | ¹H NMR (600 MHz, CHLOROFORM-d) δ ppm 1.23 (s, 6 H) 1.26 (t, J = 7.0 Hz, 3 H) 2.28 (s, 6 H) 2.50 (s, 2 H) 3.62 (s, 2 H) 4.15 (q, J = 7.0 Hz, 2 H) 6.14-6.42 (m, 1 H) 7.04 (s, 2 H). MS ESI/APCI Dual posi: 330[M + H]⁺, 352[M + Na]⁺. | |

TABLE 18-24-continued

| Compound No. | Structure | Analytical Data | Salt information |
|---|---|---|---|
| Reference Example A-168 | 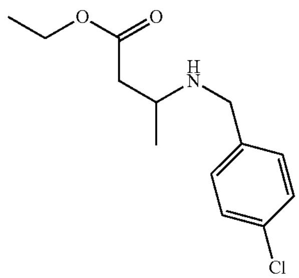 [SMILES: CCOC(=O)CC(C)NCc1ccc(Cl)cc1] | $^1$H NMR (300 MHz, CHLOROFORM-d) δ ppm 1.14 (d, J = 6.4 Hz, 3 H) 1.25 (t, J = 7.1 Hz, 3 H) 2.37 (dd, J = 15.2, 5.8 Hz, 1 H) 2.46 (dd, J = 15.2, 7.0 Hz, 1 H) 3.04-3.20 (m, 1 H) 3.72 (d, J = 13.2 Hz, 1 H) 3.80 (d, J = 13.2 Hz, 1 H) 4.13 (q, J = 7.1 Hz, 2 H) 7.17-7.37 (m, 4 H). MS ESI/APCI Dual posi: 256[M + H]$^+$. | |
| Reference Example A-169 | 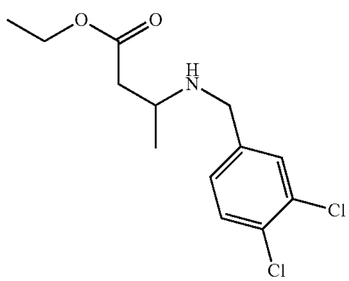 [SMILES: CCOC(=O)CC(C)NCc1ccc(Cl)c(Cl)c1] | $^1$H NMR (300 MHz, CHLOROFORM-d) δ ppm 1.14 (d, J = 6.4 Hz, 3 H) 1.26 (t, J = 7.1 Hz, 3 H) 2.31-2.52 (m, 2 H) 3.05-3.15 (m, 1 H) 3.71 (d, J = 13.6 Hz, 1 H) 3.79 (d, J = 13.6 Hz, 1 H) 4.14 (q, J = 7.2 Hz, 2 H) 7.17 (dd, J = 8.2, 2.0 Hz, 1 H) 7.37 (d, J = 8.2 Hz, 1 H) 7.45 (d, J = 2.0 Hz, 1 H). MS ESI/APCI Dual posi: 290[M + H]$^+$. | |

TABLE 18-25

| Compound No. | Structure | Analytical Data | Salt information |
|---|---|---|---|
| Reference Example A-170 | 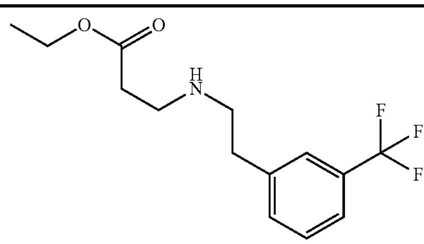 | $^1$H NMR 300 MHz, CHLOROFORM-d) δ ppm 1.11-1.31 (m, 3 H) 2.50 (t, J = 6.4 Hz, 2 H) 2.76-2.98 (m, 6 H) 4.02-4.21 (m, 2 H) 7.36-7.52 (m, 4 H). MS ESI/APCI Dual posi: 290[M + H]$^+$, 312[M + Na]$^+$. | |
| Reference Example A-171 | 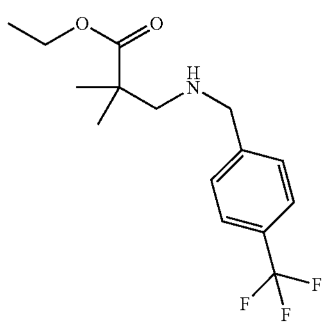 [SMILES: CCOC(=O)C(C)(C)CNCc1ccc(C(F)(F)F)cc1] | $^1$H NMR (300 MHz, CHLOROFORM-d) δ ppm 1.06-1.31 (m, 9 H) 2.64 (s, 2 H) 3.85 (s, 2 H) 4.13 (q, J = 7.1 Hz, 2 H) 7.35-7.50 (m, 2 H) 7.49-7.64 (m, 2 H). MS ESI/APCI Dual Posi: 304[M + H]$^+$, 326[M + Na]$^+$. | |
| Reference Example A-172 | 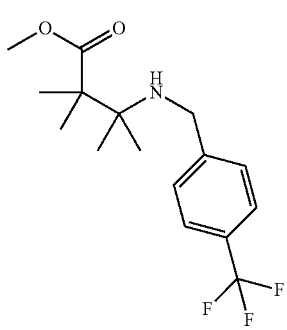 [SMILES: COC(=O)C(C)(C)C(C)(C)NCc1ccc(C(F)(F)F)cc1] | $^1$H NMR (300 MHz, CHLOROFORM-d) δ ppm 1.11-1.15 (m, 6 H) 1.23-1.28 (m, 6 H) 3.59-3.73 (m, 3 H) 3.30 (s, 2 H) 7.44-7.51 (m, 2 H) 7.51-7.58 (m, 2 H). MS ESI/APCI Dual posi: 318[M + H]$^+$, 340[M + Na]$^+$. | |

TABLE 18-25-continued

| Compound No. | Structure | Analytical Data | Salt information |
|---|---|---|---|
| Reference Example A-173 | 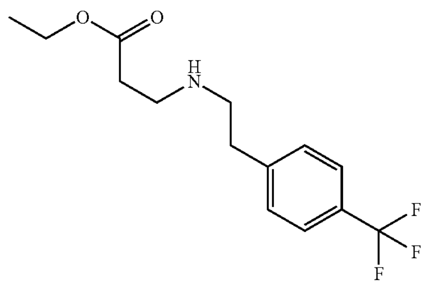 [SMILES: CCOC(=O)CCNCCc1ccc(C(F)(F)F)cc1] | $^1$H NMR (300 Mz, CHLOROFORM-d) δ ppm 1.23 (t, J = 7.1 Hz, 3 H) 3.04 (t, J = 7.0 Hz, 2 H) 3.18-3.44 (m, 6 H) 4.16 (q, J = 7.1 Hz, 2 H) 7.39 (d, J = 7.9 Hz, 2 H) 7.59 (d, J = 7.9 Hz, 2 H). MS ESI/APCI Dual posi: 290[M + H]$^+$. MS ESI/APCI Dual nesa: 324[M + Cl]$^-$. | |
| Reference Example A-174 | 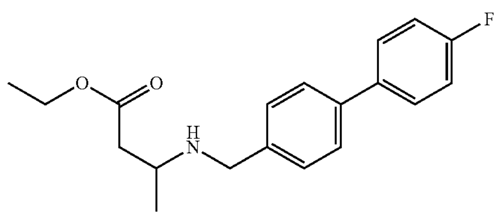 [SMILES: CCOC(=O)CC(C)NCc1ccc(-c2ccc(F)cc2)cc1] | $^1$H NMR (300 MHz, CHLOROFORM-d) δ ppm 1.18 (d, J = 6.4 Hz, 3 H) 1.26 (t, J = 7.1 Hz, 3 H) 2.40 (dd, J = 15.2, 5.8 Hz, 1 H) 2.50 (dd, J = 15.2, 7.0 Hz, 1 H) 3.10-3.28 (m, 1H) 3.75-3.94 (m, 2 H) 4.14 (q, J = 7.1 Hz, 2 H) 7.07-7.16 (m, 2 H) 7.36-7.42 (m, 2 H) 7.46-7.57 (m, 4 H). MS ESI/APCI Dual posi: 316[M + H]$^+$, 338[M + Na]$^+$. | |
| Reference Example A-175 | 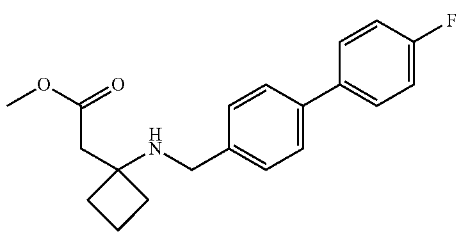 [SMILES: COC(=O)CC1(NCc2ccc(-c3ccc(F)cc3)cc2)CCC1] | $^1$H NMR (300 MHz, CHLOROFORM-d) δ ppm 1.72-1.98 (m, 2 H) 1.98-2.20 (m, 4 H) 2.75 (s, 2 H) 3.70 (s, 3 H) 3.74 (s, 2 H) 7.02-7.18 (m, 2 H) 7.35-7.45 (m, 2 H) 7.45-7.60 (m, 4 H). MS ESI/APCI Dual Posi: 328[M + H]$^+$, 350[M + Na]$^+$. | |
| Reference Example A-176 | 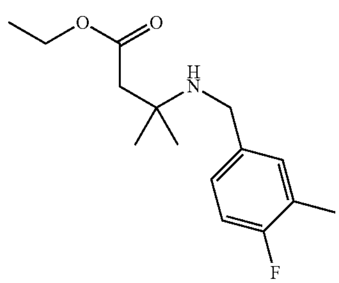 [SMILES: CCOC(=O)CC(C)(C)NCc1ccc(F)c(C)c1] | $^1$H NMR (300 MHz, CHLOROFORM-d) δ ppm 1.15-1.35 (m, 9 H) 2.24-2.31 (m, 3 H) 2.51 (s, 2 H) 3.65 (s, 2 H) 4.15 (q, J = 6.9 Hz, 2 H) 6.85-7.06 (m, 1 H) 7.06-7.24 (m, 2 H). MS ESI/APCI Dual posi: 268[M + H]$^+$. | |

TABLE 18-26

| Compound No. | Structure | Analytical Data | Salt information |
|---|---|---|---|
| Reference Example A-177 | 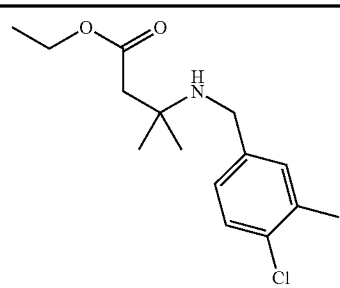 | $^1$H NMR (300 MHz, CHLOROFORM-d) δ ppm 1.17-1.32 (m, 9 H) 2.35 (s, 3 H) 2.50 (s, 2 H) 3.66 (s, 2 H) 4.14 (q, J = 7.1 Hz, 2 H) 7.08-7.17 (m, 1 H) 7.20-7.36 (m, 2 H). MS ESI/APCI Dual posi: 284[M + H]$^+$, 306[M + Na]$^+$. | |

TABLE 18-26-continued

| Compound No. | Structure | Analytical Data | Salt information |
|---|---|---|---|
| Reference Example A-178 | 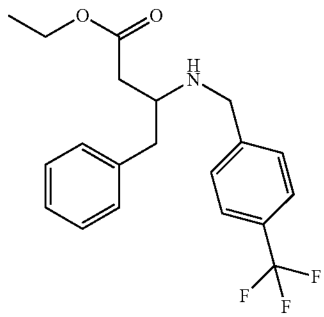 [SMILES: CCOC(=O)CC(Cc1ccccc1)NCc1ccc(C(F)(F)F)cc1] | $^1$H NMR (300 MHz, CHLOROFORM-d) δ ppm 1.24 (t, J = 7.1 Hz, 3 H) 2.35-2.47 (m, 2 H) 2.69-2.95 (m, 2 H) 3.18-3.35 (m, 1 H) 3.86 (s, 2 H) 4.02-4.21 (m, 2 H) 7.13-7.19 (m, 2 H) 7.21-7.38 (m, 5 H) 7.48-7.58 (m, 2 H). MS ESI/APCI Dual posi: 366[M + H]$^+$. | |
| Reference Example A-179 | 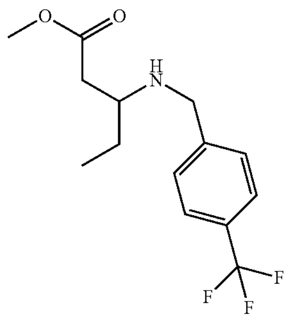 [SMILES: CCC(CC(=O)OC)NCc1ccc(C(F)(F)F)cc1] | $^1$H NMR (300 MHz, CHLOROFORM-d) δ ppm 0.93 (t, J = 7.4 Hz, 3 H) 1.42-1.65 (m, 2 H) 2.35-2.56 (m, 2 H) 2.88-3.04 (m, 1 H) 3.67 (s, 3 H) 3.85 (s, 2 H) 7.43-7.49 (m, 2 H) 7.54-7.60 (m, 2 H). MS ESI/APCI Dual posi: 290[M + H]$^+$, 312[M + Na]$^+$. | |
| Reference Example A-180 | 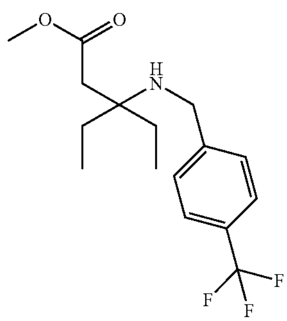 [SMILES: CCC(CC)(CC(=O)OC)NCc1ccc(C(F)(F)F)cc1] | $^1$H NMR (300 MHz, CHLOROFORM-d) δ ppm 0.89 (t, J = 7.5 Hz, 6 H) 1.35-1.65 (m, 4 H) 2.47 (s, 2 H) 3.64-3.74 (m, 5 H) 7.38-7.65 (m, 4 H). MS ESI/APCI Dual posi: 318[M + H]$^+$, 340[M + Na]$^+$. | |
| Reference Example A-181 | 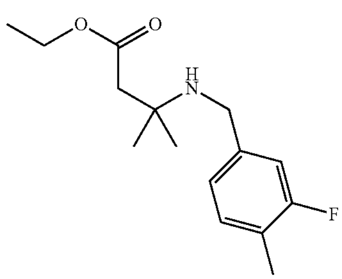 [SMILES: CCOC(=O)CC(C)(C)NCc1ccc(C)c(F)c1] | $^1$H NMR (300 MHz, CHLOROFORM-d) δ ppm 1.22 (s, 6 H) 1.26 (t, J = 7.1 Hz, 3 H) 2.22-2.25 (m, 3 H) 2.49 (s, 2 H) 3.67 (s, 2 H) 4.14 (q, J = 7.1 Hz, 2 H) 6.97-7.13 (m, 3 H). MS ESI/APCI Dual posi: 268[M + H]$^+$. | |
| Reference Example A-182 | 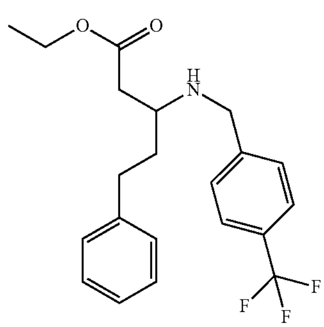 [SMILES: CCOC(=O)CC(CCc1ccccc1)NCc1ccc(C(F)(F)F)cc1] | $^1$H NMR (300 MHz, CHLOROFORM-d) δ ppm 1.24 (t, J = 7.1 Hz, 3 H) 1.68-1.94 (m, 2 H) 2.42-2.60 (m, 2 H) 2.70 (t, J = 8.0 Hz, 2 H) 2.95-3.13 (m, 1 H) 3.80-3.87 (m, 2 H) 4.13 (q, J = 7.1 Hz, 2 H) 7.11-7.22 (m, 3 H) 7.23-7.31 (m, 2 H) 7.40-7.46 (m, 2 H) 7.53-7.59 (m, 2 H). MS ESI/APCI Dual posi: 380[M + H]$^+$, 402[M + Na]$^+$. | |

TABLE 18-26-continued

| Compound No. | Structure | Analytical Data | Salt information |
|---|---|---|---|
| Reference Example A-183 | 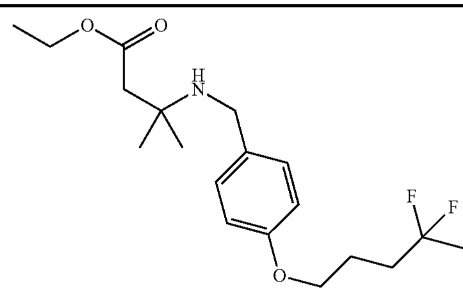 | $^1$H NMR (300 MHz, CHLOROFORM-d) δ ppm 1.20-1.30 (m, 9 H) 1.96-2.12 (m, 2 H) 2.21-2.42 (m, 2 H) 2.50 (s, 2 H) 3.65 (s, 2 H) 3.93-4.06 (m, 2 H) 4.14 (q, J = 7.1 Hz, 2 H) 6.80-6.86 (m, 2 H) 7.23-7.29 (m, 2 H). MS ESI/APCI Dual posi: 362[M + H]$^+$. | |

TABLE 18-27

| Compound No. | Structure | Analytical Data | Salt information |
|---|---|---|---|
| Reference Example A-184 | 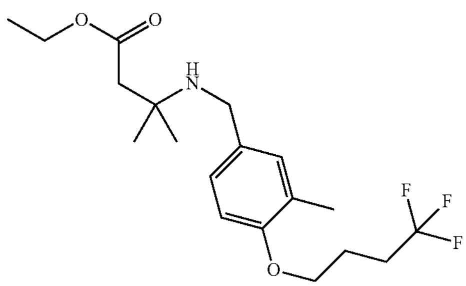 | $^1$H NMR (300 MHz, CHLOROFORM-d) δ ppm 1.13-1.35 (m, 9 H) 1.95-2.13 (m, 2 H) 2.14-2.44 (m, 5 H) 2.51 (s, 2 H) 3.62 (s, 2 H) 3.91-4.07 (m, 2 H) 4.14 (q, J = 7.2 Hz, 2 H) 6.63-6.83 (m, 1 H) 7.01-7.20 (m, 2 H). MS ESI/APCI Dual posi: 376[M + H]$^+$. | |
| Reference Example A-185 | 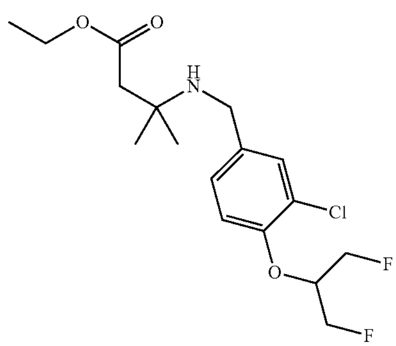 [SMILES: CCOC(=O)CC(C)(C)NCc1ccc(OC(CF)CF)c(Cl)c1] | $^1$H NMR (300 MHz, CHLOROFORM-d) δ ppm 1.12-1.36 (m, 9 H) 2.49 (s, 2 H) 3.65 (s, 2 H) 4.15 (q, J = 7.3 Hz, 2 H) 4.48-4.68 (m, 5 H) 6.99-7.10 (m, 1 H) 7.17-7.25 (m, 1 H) 7.39-7.45 (m, 1 H). MS ESI/APCI Dual posi: 364[M + H]$^+$, 386[M + Na]$^+$. | |
| Reference Example A-186 | 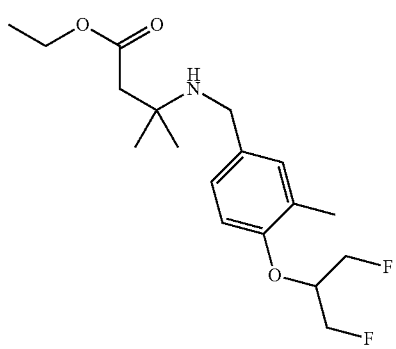 [SMILES: CCOC(=O)CC(C)(C)NCc1ccc(OC(CF)CF)c(C)c1] | $^1$H NMR (300 MHz, CHLOROFORM-d) δ ppm 1.15-1.35 (m, 9 H) 2.22 (s, 3 H) 2.51 (s, 2 H) 3.63 (s, 2 H) 4.15 (q, J = 7.1 Hz, 2 H) 4.50-4.68 (m, 5 H) 6.80-6.85 (m, 1 H) 7.09-7.18 (m, 2 H). MS ESI/APCI Dual posi: 344[M + H]$^+$, 366[M + Na]$^+$. MS ESI/APCI Dual nega: 342[M − H]$^-$, 378[M + Cl]$^-$. | |

TABLE 18-27-continued

| Compound No. | Structure | Analytical Data | Salt information |
|---|---|---|---|
| Reference Example A-187 | 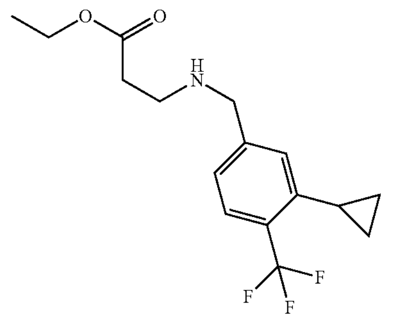 [SMILES: CCOC(=O)CCNCc1ccc(C(F)(F)F)c(C2CC2)c1] | $^1$H NMR (600 MHz, CHLOROFORM-d) δ ppm 0.70-0.83 (m, 2 H) 0.96-1.07 (m, 2 H) 1.26 (t, J = 7.1 Hz, 3 H) 2.10-2.27 (m, 1 H) 2.52 (t, J = 6.4 Hz, 2 H) 2.87 (t, J = 6.4 Hz, 2 H) 3.79 (s, 2 H) 4.15 (q, J = 7.1 Hz, 2 H) 6.99 (s, 1 H) 7.17-7.21 (m, 1 H) 7.55 (d, J = 7.8 Hz, 1 H). MS ESI/APCI Dual posi: 316[M +H]$^+$, 338[M + Na]$^+$. | |
| Reference Example A-188 | 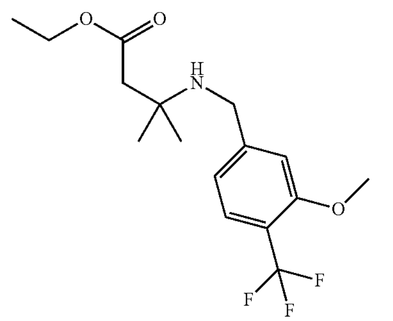 [SMILES: CCOC(=O)CC(C)(C)NCc1ccc(C(F)(F)F)c(OC)c1] | $^1$H NMR (600 MHz, CHLOROFORM-d) δ ppm 1.11-1.34 (m, 9 H) 2.50 (s, 2 H) 3.76 (s. 2 H) 3.91 (s, 3 H) 4.14 (q, J =7.3 Hz, 2 H) 6.98 (d, J = 7.8Hz, 1 H) 7.06 (s, 1 H) 7.43-7.51 (m, 1 H). MS ESI/APCI Dual posi: 334[M + H]$^+$, 356[M + Na]$^+$. MS ESI/APCI Dual nega: 368[M + Cl]$^-$. | |
| Reference Example A-189 | 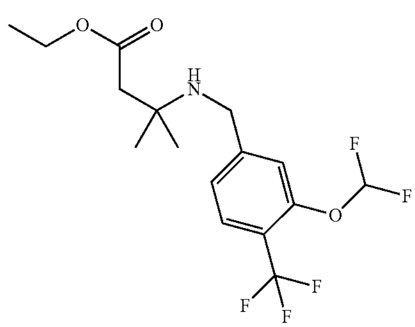 [SMILES: CCOC(=O)CC(C)(C)NCc1ccc(C(F)(F)F)c(OC(F)F)c1] | $^1$H NMR (600 MHz, CHLOROFORM-d) δ ppm 1.06-1.34 (m, 9 H) 2.49 (s, 2 H) 3.78 (s, 2 H) 4.15 (q, J = 7.3 Hz, 2 H) 6.34-6.74 (m, 1 H) 7.29-7.32 (m, 1 H) 7.34 (s, 1 H) 7.59 (d, J = 8.3 Hz, 1 H). MS ESI/APCI Dual posi: 370[M + H]$^+$. | |
| Reference Example A-190 | 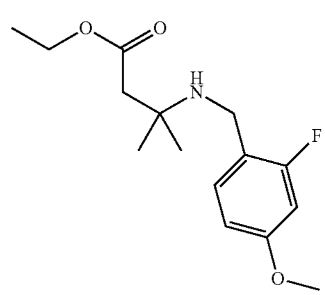 [SMILES: CCOC(=O)CC(C)(C)NCc1ccc(OC)cc1F] | $^1$H NMR (300 MHz, CHLOROFORM-d) δ ppm 1.17-1.32 (m, 9 H) 2.50 (s, 2 H) 3.70 (s, 2 H) 3.78 (s, 3 H) 4.14 (q, J = 7.1 Hz, 2 H) 6.52-6.75 (m, 3 H). MS ESI/APCI Dual posi: 284[M + H]$^+$, 306[M + Na]$^+$. | |

TABLE 18-28

| Compound No. | Structure | Analytical Data | Salt information |
|---|---|---|---|
| Reference Example A-191 | | $^1$H NMR (300 MHz, CHLOROFORM-d) δ ppm 1.20-1.30 (m, 9 H) 2.49 (s, 2 H) 3.65 (s, 2 H) 3.87 (s, 3 H) 4.15 (q, J = 7.3 Hz, 2 H) 6.85-6.92 (m, 1 H) 7.01-7.15 (m, 2 H). MS ESI/APCI Dual posi: 284[M + H]$^+$, [M + Na]$^+$. | |
| Reference Example A-192 | | $^1$H NMR (300 MHz, CHLOROFORM-d) δ ppm 1.13-1.33 (m, 9 H) 2.49 (s, 2 H) 3.64 (s, 2 H) 3.88 (s, 3 H) 4.15 (q, J = 7.1 Hz, 2 H) 6.87 (d, J = 8.4 Hz, 1 H) 7.17-7.23 (m, 1 H) 7.38 (d, J = 2.2 Hz, 1 H). MS ESI/APCI Dual posi: 300[M + H]$^+$, 322[M + Na]$^+$. | |
| Reference Example A-193 | | $^1$H NMR (300 MHz, CHLOROFORM-d) δ ppm 1.16-1.32 (m, 9 H) 2.20 (s, 3 H) 2.51 (s, 2 H) 3.62 (s, 2 H) 3.81 (s, 3 H) 4.14 (q, J = 7.3 Hz, 2 H) 6.73-6.79 (m, 1 H) 7.09-7.19 (m, 2 H). MS ESI/APCI Dual posi: 280[M + H]$^+$. | |
| Reference Example A-194 | | $^1$H NMR (300 MHz, CHLOROFORM-d) δ ppm 0.82-1.00 (m, 6 H) 1.27 (t, J = 7.1 Hz, 3 H) 1.87-2.02 (m, 1 H) 2.26-2.44 (m, 1 H) 2.71 (dd, J = 11.8, 4.0 Hz, 1 H) 2.90 (dd, J = 11.8, 10.0 Hz, 1 H) 3.74-3.94 (m, 2 H) 4.11-4.23 (m, 2 H) 7.38-7.47 (m, 2 H) 7.52-7.61 (m, 2 H). MS ESI/APCI Dual posi: 318[M + H]$^+$. | |
| Reference Example A-195 | | $^1$H NMR (300 MHz, CHLOROFORM-d) δ ppm 0.29-0.38 (m, 2 H) 0.58-0.69 (m, 2 H) 1.19-1.31 (m, 10 H) 2.50 (s, 2 H) 3.65 (s, 2 H) 3.78 (d, J = 7.1 Hz, 2 H) 4.14 (q, J = 7.1 Hz, 2 H) 6.82-6.87 (m, 2 H) 7.22-7.27 (m, 2 H). MS ESI/APCI Dual posi : 306[M + H]$^+$. | |

TABLE 18-28-continued

| Compound No. | Structure | Analytical Data | Salt information |
|---|---|---|---|
| Reference Example A-196 | 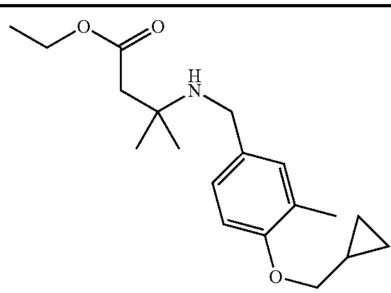 | $^1$H NMR (300 MHz, CHLOROFORM-d) δ ppm 0.26-0.41 (m, 2 H) 0.53-0.68 (m, 2 H) 1.14-1.34 (m, 10 H) 2.23 (s, 3 H) 2.51 (s, 2 H) 3.62 (s, 2 H) 3.79 (d, J = 6.7 Hz, 2 H) 4.14 (q, J = 7.1 Hz, 2 H) 6.73 (d, J = 8.1 Hz, 1 H) 7.04-7.13 (m, 2 H) MS ESI/APCI Dual posi: 320[M + H]$^+$. | |
| Reference Example A-197 | 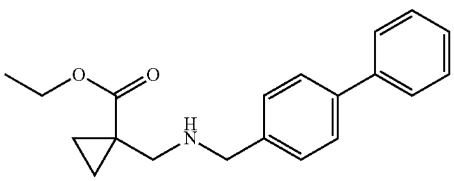 [SMILES: CCOC(=O)C1(CNCc2ccc(-c3ccccc3)cc2)CC1] | $^1$H NMR (300 MHz, CHLOROFORM-d) δ ppm 0.74-0.87 (m, 2 H) 1.13-1.34 (m, 5 H) 2.74 (s, 2 H) 3.86 (s, 2 H) 4.13 (q, J = 7.1 Hz, 2 H) 7.29-7.37 (m, 1 H) 7.37-7.47 (m, 4 H) 7.52-7.62 (m, 4 H). MS ESI/APCI Dual posi: 310[M + H]$^+$, 332[M + Na]$^+$. | |

TABLE 18-29

| Compound No. | Structure | Analytical Data | Salt information |
|---|---|---|---|
| Reference Example A-198 | 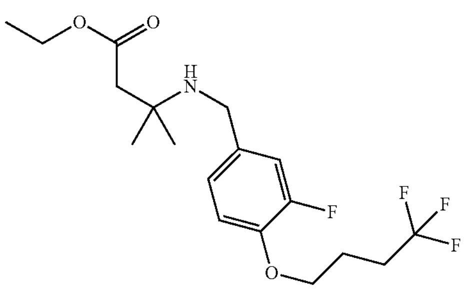 [SMILES: CCOC(=O)CC(C)(C)NCc1ccc(OCCCC(F)(F)F)c(F)c1] | $^1$H NMR (300 MHz, CHLOROFORM-d) δ ppm 1.22 (s, 6 H) 1.26 (t, j = 7.1 Hz, 3 H) 1.99-2.11 (m, 2 H) 2.24-2.44 (m, 2 H) 2.49 (s, 2 H) 3.65 (s, 2 H) 4.06 (t, J = 6.1 Hz, 2 H) 4.14 (q, J = 7.1 Hz, 2 H) 6.83-6.92 (m, 1 H) 6.99-7.06 (m, 1 H) 7.12 (dd, J = 12.1, 2.0 Hz, 1 H). MS ESI/APCI Dual posi: 380[M + H]$^+$, 402[M + Na]$^+$. | |
| Reference Example A-199 | 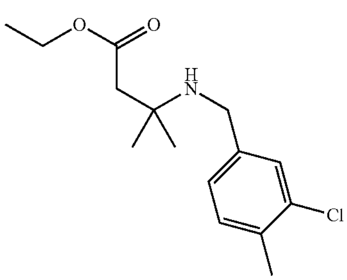 [SMILES: CCOC(=O)CC(C)(C)NCc1ccc(C)c(Cl)c1] | $^1$H NMR (300 MHz, CHLOROFORM) δ ppm 1.22 (s, 6 H) 1.26 (t, J = 7.1 Hz, 3 H) 2.34 (s, 3 H) 2.49 (s, 2 H) 3.66 (s, 2 H) 4.14 (q, = 7.1 Hz, 2 H) 7.05-7.23 (m, 2 H) 7.34 (d, J = 1.1 Hz, 1 H). MS ESI/APCI Dual posi: 284[M + H]$^+$. 306[M + Na]$^+$. | |
| Reference Example A-200 | 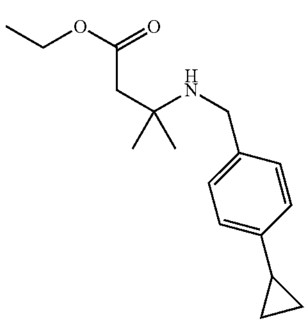 [SMILES: CCOC(=O)CC(C)(C)NCc1ccc(C2CC2)cc1] | $^1$H NMR (300 MHz, CHLOROFORM-d) δ ppm 0.58-0.73 (m, 2 H) 0.86-1.00 (m, 2 H) 1.18-1.29 (m, 9 H) 1.81-1.97 (m, 1 H) 2.50 (s, 2 H) 3.66 (s, 2 H) 4.14 (q, J = 7.1 Hz, 2 H) 6.95-7.10 (m, 2 H) 7.19-7.25 (m, 2 H). MS ESI/APCI Dual posi: 276[M + H]$^+$. | |

TABLE 18-29-continued

| Compound No. | Structure | Analytical Data | Salt information |
|---|---|---|---|
| Reference Example A-201 | 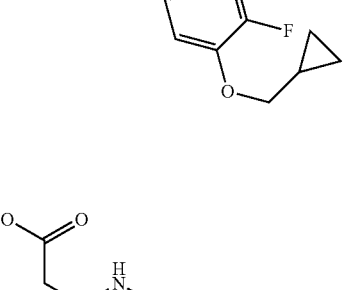 | $^1$H NMR (300 MHz, CHLOROFORM-d) δ ppm 0.28-0.40 (m, 2 H) 0.55-0.71 (m, 2 H) 1.13-1.34 (m, 10 H) 2.49 (s, 2 H) 3.64 (s, 2 H) 3.85 (d, J = 7.0 Hz, 2 H) 4.14 (q, j = 7.1 Hz, 2 H) 6.82-6.92 (m, 1 H) 6.95-7.05 (m, 1 H) 7.06-7.15 (m, 1 H). MS ESI/APCI Dual posi: 324[M + H]$^+$. | |
| Reference Example A-202 | 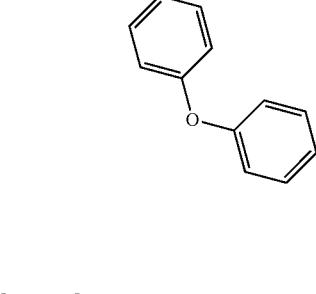 | $^1$H NMR (300 MHz, CHLOROFORM-d) δ ppm 1.26 (t, J = 7.0 Hz, 3 H) 2.53 (t, J = 6.5 Hz, 2 H) 2.90 (t, J = 6.5 Hz, 2 H) 3.77 (s, 2 H) 4.14 (q, J = 7.0 Hz, 2 H) 6.85-7.09 (m, 6 H) 7.21-7.35 (m, 2 H). MS ESI/APCI Dual posi: 318[M + H]$^+$, 340[M + Na]$^+$. MS ESI/APCI Dual nega: 316[M − H]$^-$. | |
| Reference Example A-203 | 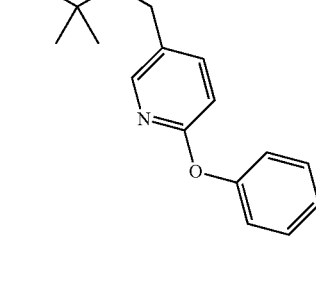 | $^1$H NMR (300 MHz, CHLOROFORM-d) δ ppm 1.11-1.34 (m, 9 H) 2.35 (s, 3 H) 2.49 (s, 2 H) 3.66 (s, 2 H) 4.14 (q, J = 7.1 Hz, 2 H) 6.83 (d, J = 8.4 Hz, 1 H) 7.00 (d, J = 8.3 Hz, 2 H) 7.18 (d, J = 8.3 Hz, 2 H) 7.71 (dd, J = 8.4, 2.4 Hz, 1 H) 8.12 (d, J = 2.4 Hz, 1 H). MS ESI/APCI Dual posi: 343[M + H]$^+$, 365[M + Na]$^+$. MS ESI/APCI Dual nega: 341[M − H]$^-$. | |
| Reference Example A-204 | 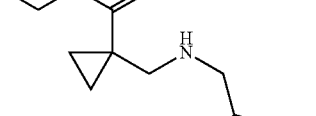 | $^1$H NMR (300 MHz, CHLOROFORM-d) δ ppm 0.73-0.79 (m, 2 H) 1.19-1.29 (m, 5 H) 2.67 (s, 2 H) 3.76 (s, 2 H) 4.12 (q, J = 7.1 Hz, 2 H) 7.17-7.24 (m, 2 H) 7.38-7.50 (m, 2 H). MS ESI/APCI Dual posi: 312[M + H]$^+$. | |

TABLE 18-30

| Compound No. | Structure | Analytical Data | Salt information |
|---|---|---|---|
| Reference Example A-205 | 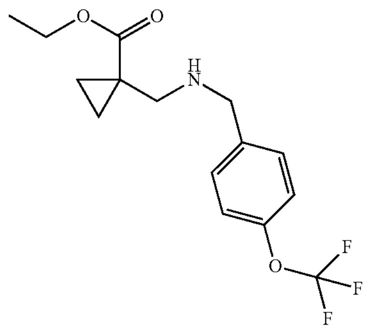 [SMILES: CCOC(=O)C1(CNCc2ccc(OC(F)(F)F)cc2)CC1] | ¹H NMR (300 MHz, CHLOROFORM-d) δ ppm 0.71-0.82 (m, 2 H) 1.16-1.32 (m, 5 H) 2.70 (s, 2 H) 3.81 (s, 2 H) 4.12 (q, J = 7.1 Hz, 2 H) 7.07-7.23 (m, 2 H) 7.31-7.43 (m, 2H). MS ESI/APCI Dual posi: 318[M + H]⁺. | |
| Reference Example A-206 | 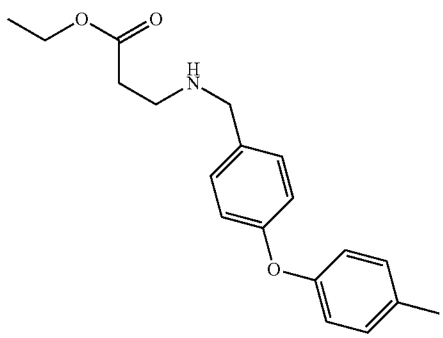 [SMILES: CCOC(=O)CCNCc1ccc(Oc2ccc(C)cc2)cc1] | ¹H NMR (300 MHz, CHLOROFORM-d) δ ppm 1.26 (t, J = 7.1 Hz, 3 H) 2.33 (s, 3 H) 2.53 (t, J = 6.5 Hz, 2 H) 2.90 (t, J = 6.5 Hz, 2 H) 3.77 (s, 2 H) 4.14 (q, J = 7.1 Hz, 2 H) 6.87-6.96 (m, 4 H) 7.09-7.16 (m, 2 H) 7.22-7.29 (m, 2 H). MS ESI/APCI Dual posi: 314[M + H]⁺, 336[M + Na]⁺. MS ESI/APCI Dual nega: 312[M − H]⁻. | |
| Reference Example A-207 | 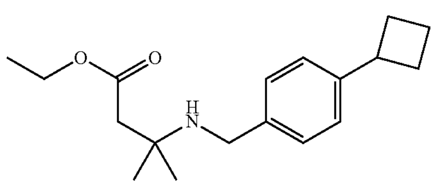 [SMILES: CCOC(=O)CC(C)(C)NCc1ccc(C2CCC2)cc1] | ¹H NMR (300 MHz, CHLOROFORM-d) δ ppm 1.14-1.35 (m, 9 H) 1.75-1.90 (m, 1 H) 1.90-2.22 (m, 3 H) 2.25-2.38 (m, 2 H) 2.51 (s, 2 H) 3.43-3.60 (m, 1 H) 3.68 (s, 2 H) 4.14 (q, J = 7.0 Hz, 2 H) 7.13-7.19 (m, 2 H) 7.24-7.30 (m, 2 H). MS ESI/APCI Dual posi: 290[M + H]⁺, 312[M + Na]⁺. | |
| Reference Example A-208 | 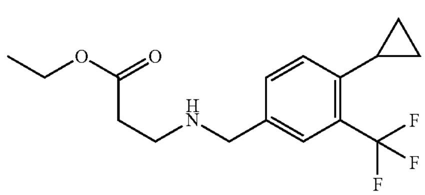 [SMILES: CCOC(=O)CCNCc1ccc(C2CC2)c(C(F)(F)F)c1] | ¹H NMR (300 MHz, CHLOROFORM-d) δ ppm 0.65-0.82 (m, 2 H) 0.94-1.06 (m, 2 H) 1.25 (t, J = 7.1 Hz, 3 H) 2.11- 2.27 (m, 1 H) 2.52 (t, J = 6.4 Hz, 2 H) 2.88 (t, J = 6.4 Hz, 2 H) 3.79 (s, 2 H) 4.14 (q, J = 7.1 Hz, 2 H) 6.99 (d, J = 7.9 Hz, 1 H) 7.35-7.42 (m, 1 H) 7.52-7.58 (m, 1 H). MS ESI posi: 316[M + H]⁺. | |
| Reference Example A-209 | 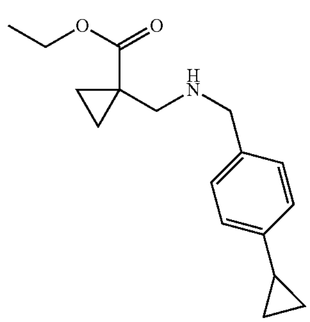 [SMILES: CCOC(=O)C1(CNCc2ccc(C3CC3)cc2)CC1] | ¹H NMR (300 MHz, CHLOROFORM-d) δ ppm 0.58-0.73 (m, 2 H) 0.73-0.83 (m, 2 H) 0.87-0.99 (m, 2 H) 1.15-1.31 (m, 5 H) 1.75-1.93 (m, 1 H) 2.69 (s, 2 H) 3.77 (s, 2 H) 4.11 (q, J = 7.1 Hz, 2 H) 6.96-7.06 (m, 2 H) 7.18-7.25 (m, 2 H). MS ESI/APCI Dual posi: 274[M + H]⁺. | |

TABLE 18-30-continued

| Compound No. | Structure | Analytical Data | Salt information |
|---|---|---|---|
| Reference Example A-210 | 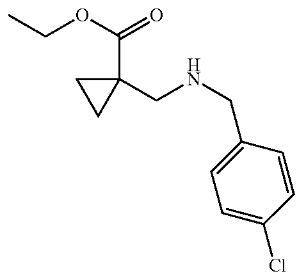 [SMILES: CCOC(=O)C1(CNCc2ccc(Cl)cc2)CC1] | ¹H NMR (300 MHz, CHLOROFORM-d) δ ppm 0.70-0.82 (m, 2 H) 1.17-1.31 (m, 5 H) 2.68 (s, 2 H) 3.78 (s, 2 H) 4.12 (q, J = 7.1 Hz, 2 H) 7.22-7.34 (m, 4 H). MS ESI/APCI Dual posi: 268[M + H]⁺. | |
| Reference Example A-211 | 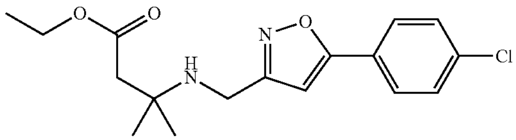 [SMILES: CCOC(=O)CC(C)(C)NCc1cc(-c2ccc(Cl)cc2)on1] | ¹H NMR (300 MHz, CHLOROFORM-d) δ ppm 1.13-1.34 (m, 9 H) 2.49 (s, 2 H) 3,86 (s, 2 H) 4.15 (q, J = 7.1 Hz, 2H) 6.57 (s, 1 H) 7.37-7.48 (m, 2 H) 7.65-7.76 (m, 2 H). MS ESI posi: 337[M + H]⁺, 359[M + Na]⁺. | |

TABLE 18-31

| Compound No. | Structure | Analytical Data | Salt information |
|---|---|---|---|
| Reference Example A-212 | 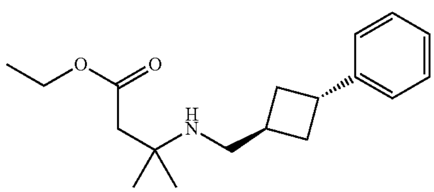 [SMILES: CCOC(=O)CC(C)(C)NC[C@H]1C[C@H](c2ccccc2)C1] | ¹H NMR (300 MHz, CHLOROFORM-d) δ ppm 1.20 (s, 6 H) 1.27 (t, J = 7.1 Hz, 3 H) 2.09-2.23 (m, 2 H) 2.23-2.52 (m, 5 H) 2.76 (d, J = 7.3 Hz, 2 H) 3.45-3.71 (m, 1 H) 4.15 (q, J = 7.1 Hz, 2 H) 7.13-7.21 (m, 1 H) 7.22-7.36 (m, 4 H). MS ESI posi: 290[M + H]⁺. | |
| Reference Example A-213 | 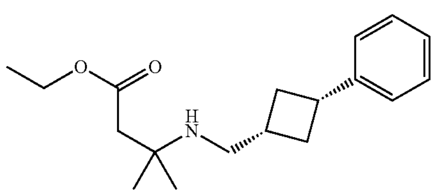 [SMILES: CCOC(=O)CC(C)(C)NC[C@H]1C[C@@H](c2ccccc2)C1] | ¹H NMR (300 MHz, CHLOROFORM-d) δ ppm 1.15 (s, 6 H) 1.25 (t, J = 7.1 Hz, 3 H) 1.69-1.85 (m, 2 H) 2.29-2.65 (m, 7 H) 3.28-3.51 (m, 1 H) 4.13 (q, J = 7.1 Hz, 2 H) 7.13-7.23 (m, 3 H) 7.26-7.33 (m, 2 H). MS ESI posi: 290[M + H]⁺. | |
| Reference Example A-214 | 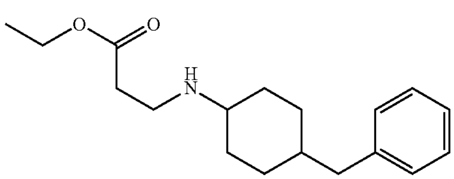 [SMILES: CCOC(=O)CCNC1CCC(Cc2ccccc2)CC1] | ¹H NMR (300 MHz, CHLOROFORM-d) δ ppm 0.91-1.10 (m, 2 H) 1.27 (t, J = 7.1 Hz, 3 H) 1.32-1.79 (m, 6 H) 1.82-1.99 (m, 1 H) 2.44-2.61 (m, 4 H) 2.64-2.74 (m, 1 H) 2.82-2.90 (m, 2 H) 4.16 (q, J = 7.1 Hz, 2 H) 6.99-7.35 (m, 5 H). MS ESI/APCI Dual posi: 290[M + H]⁺. | |
| Reference Example A-215 | 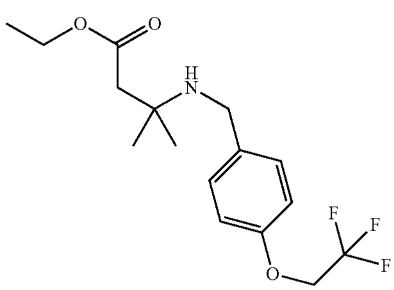 [SMILES: CCOC(=O)CC(C)(C)NCc1ccc(OCC(F)(F)F)cc1] | ¹H NMR (300 MHz, CHLOROFORM-d) δ ppm 1.14-1.33 (m, 9 H) 2.50 (s, 2 H) 3.67 (s, 2 H) 4.14 (q, J = 7.1 Hz, 2 H) 4.27-4.38 (m, 2 H) 6.86-6.91 (m, 2 H) 7.28-7.33 (m, 2 H). MS ESI/APCI Dual posi: 334[M + H]⁺. | |

TABLE 18-31-continued

| Compound No. | Structure | Analytical Data | Salt information |
|---|---|---|---|
| Reference Example A-216 | 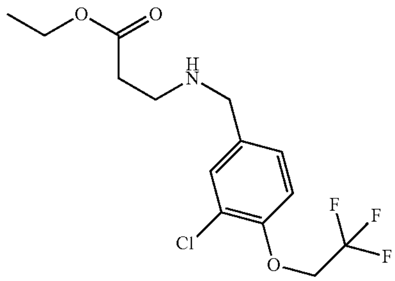 [SMILES: CCOC(=O)CCNCc1ccc(OCC(F)(F)F)c(Cl)c1] | ¹H NMR (300 MHz, CHLOROFORM-d) δ ppm 1.26 (t, J = 7.1 Hz, 3 H) 2.52 (t, J = 6.4 Hz, 2 H) 2.87 (t, J = 6.4 Hz, 2 H) 3.74 (s, 2 H) 4.15 (q, j = 7.1 Hz, 2 H) 4.39 (q, J = 8.1 Hz, 2 H) 6.93 (d, J = 8.4 Hz, 1 H) 7.19 (dd, J = 8.4, 2.2 Hz, 1 H) 7.39 (d, J = 2.2 Hz, 1 H). MS ESI/APCI Dual posi: 340[M + H]⁺. | |
| Reference Example A-217 | 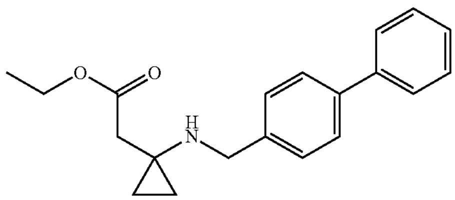 [SMILES: CCOC(=O)CC1(NCc2ccc(-c3ccccc3)cc2)CC1] | ¹H NMR (300 MHz, CHLOROFORM-d) δ ppm 0.44-0.62 (m, 2 H) 0.71-0.83 (m, 2 H) 1.28 (t, J = 7.1 Hz, 3 H) 2.52 (s, 2 H) 3.86 (s, 2 H) 4.18 (q, J = 7.1 Hz, 2 H) 7.29-7.47 (m, 5 H) 7.49-7.61 (m, 4 H). MS ESI/APCI Dual posi: 310[M + H]⁺, 332[M + Na]⁺. MS ESI/APCI Dual nega: 344[M + Cl]⁻. | |
| Reference Example A-218 | 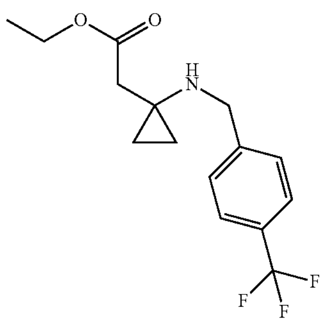 [SMILES: CCOC(=O)CC1(NCc2ccc(C(F)(F)F)cc2)CC1] | ¹H NMR (300 MHz, CHLOROFORM-d) δ ppm 0.45-0.57 (m, 2 H) 0.68-0.82 (m, 2 H) 1.27 (t, J = 7.1 Hz, 3 H) 2.49 (s, 2 H) 3.88 (s, 2 H) 4.17 (q, J = 7.1 Hz, 2 H) 7.34-7.49 (m, 2 H) 7.48-7.61 (m, 2 H). MS ESI/APCI Dual posi: 302[M + H]⁺, 324[M + Na]⁺. MS ESI/APCI Dual nega: 300[M − H]⁻. | |

TABLE 18-32

| Compound No. | Structure | Analytical Data | Salt information |
|---|---|---|---|
| Reference Example A-219 | 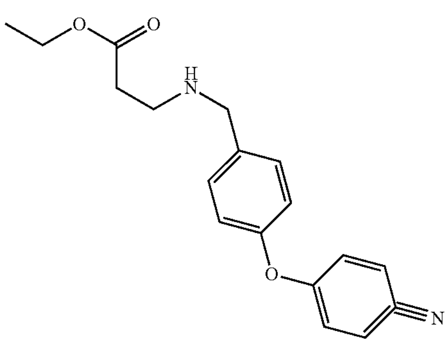 | ¹H NMR (300 MHz, CHLOROFORM-d) δ ppm 1.18-1.31 (m, 3 H) 2.47-2.57 (m, 2 H) 2.89 (t, J = 6.3 Hz, 2 H) 3.79 (s, 2 H) 4.08-4.19 (m, 2 H) 6.98 (d, J = 8.4 Hz, 1 H) 7.16-7.25 (m, 2 H) 7.63-7.71 (m, 2 H) 7.78 (dd, J = 8.4, 2.5 Hz, 1 H) 8.13 (dd, J = 2.5, 0.6 Hz, 1 H). MS ESI/APCI Dual posi: 326[M + H]⁺, 348[M + Na]⁺. MS ESI/APCI Dual nega: 324[M − H]⁻. | |

TABLE 18-32-continued

| Compound No. | Structure | Analytical Data | Salt information |
|---|---|---|---|
| Reference Example A-220 | 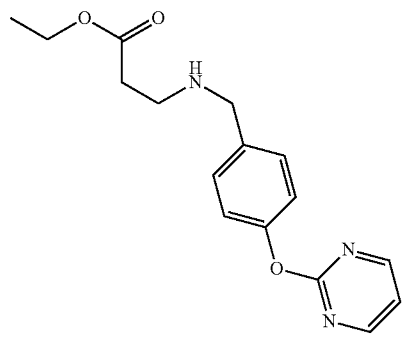 [SMILES: CCOC(=O)CCNCc1ccc(Oc2ncccn2)cc1] | $^1$H NMR (300 MHz, CHLOROFORM-d) δ ppm 1.26 (t, J = 7.1 Hz, 3 H) 2.54 (t, J = 6.5 Hz, 2 H) 2.93 (t, J = 6.5 Hz, 2 H) 3.83 (s, 2 H) 4.15 (q, J = 7.1 Hz, 2 H) 7.03 (t, J = 4.8 Hz, 1 H) 7.10-7.19 (m, 2 H) 7.34-7.43 (m, 2 H) 8.51-8.59 (m, 2 H). MS ESI/APCI Dual posi: 302[M + H]$^+$, 324[M + Na]$^+$. | |
| Reference Example A-221 | 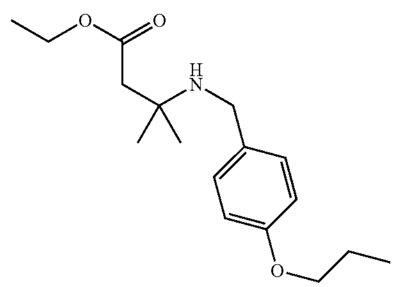 [SMILES: CCCOc1ccc(CNC(C)(C)CC(=O)OCC)cc1] | $^1$H NMR (300 MHz, CHLOROFORM-d) δ ppm 0.99-1.07 (m, 3 H) 1.20-1.29 (m, 9 H) 1.74-1.86 (m, 2 H) 2.50 (s, 2 H) 3.65 (s, 2 H) 3.86-3.96 (m, 2 H) 4.10-4.19 (m, 2 H) 6.79-6.87 (m, 2 H) 7.22-7.28 (m, 2 H). MS ESI posi: 294[M + H]$^+$. | |
| Reference Example A-222 | 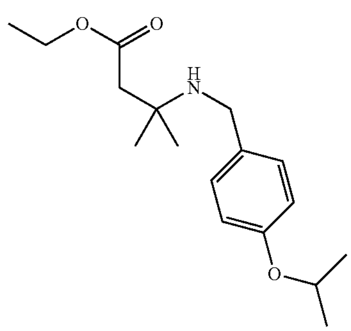 [SMILES: CCOC(=O)CC(C)(C)NCc1ccc(OC(C)C)cc1] | $^1$H NMR (300 MHz, CHLOROFORM-d) δ ppm 1.20-1.36 (m, 15 H) 2.50 (s, 2 H) 3.64 (s, 2 H) 4.14 (q, J = 7.1 Hz, 2 H) 4.46-4.58 (m, 1 H) 6.79-6.86 (m, 2 H) 7.20-7.28 (m, 2 H). MS ESI posi: 294[M + H]$^+$. | |
| Reference Example A-223 | 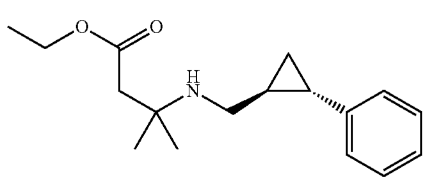 [SMILES: CCOC(=O)CC(C)(C)NC[C@H]1C[C@@H]1c1ccccc1] | $^1$H NMR (300 MHz, CHLOROFORM-d) δ ppm 0.80-0.97 (m, 2 H) 1.13-1.19 (m, 6 H) 1.26 (t, J = 7.1 Hz, 3 H) 1.30-1.41 (m, 1 H) 1.74 (dt, J = 8.9, 4.7 Hz, 1 H) 2.42 (s, 2 H) 2.47 (dd, J = 11.0, 7.1 Hz, 1 H) 2.70 (dd, J = 11.0, 6.4 Hz, 1 H) 4.14 (q, J = 7.1 Hz, 2 H) 7.02-7.08 (m, 2 H) 7.09-7.16 (m, 1 H) 7.20-7.28 (m, 2 H). MS ESI posi: 276[M + H]$^+$. | |
| Reference Example A-224 | 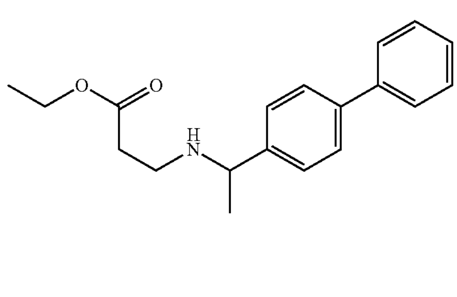 [SMILES: CCOC(=O)CCNC(C)c1ccc(-c2ccccc2)cc1] | $^1$H NMR (300 MHz, CHLOROFORM-d) δ ppm 1.26 (t, J = 7.1 Hz, 3 H) 1.39 (d, J = 6.7 Hz, 3 H) 2.41-2.54 (m, 2 H) 2.64-2.86 (m, 2 H) 3.74-3.92 (m, 1 H) 4.14 (q, J = 7.1 Hz, 2 H) 7.29-7.48 (m, 5 H) 7.50-7.67 (m, 4 H). | |

TABLE 18-32-continued

| Compound No. | Structure | Analytical Data | Salt information |
|---|---|---|---|
| Reference Example A-225 | 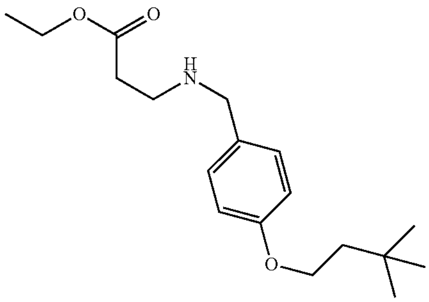 [SMILES: CCOC(=O)CCNCc1ccc(OCCC(C)(C)C)cc1] | ¹H NMR (300 MHz, CHLOROFORM-d) δ ppm 0.93 (s, 9 H) 1.25 (t, J = 7.1 Hz, 3 H) 2.53 (t, J = 6.5 Hz, 2 H) 2.90 (t, J = 6.5 Hz, 2 H) 3.10 (s, 2 H) 3.80 (s, 2 H) 4.14 (q, J = 7.1 Hz, 2 H) 4.50 (s, 2 H) 7.28-7.30 (m, 4 H). MS ESI/APCI Dual posi: 308[M + H]⁺, 330[M + Na]⁺. | |

TABLE 18-33

| Compound No. | Structure | Analytical Data | Salt information |
|---|---|---|---|
| Reference Example A-226 | 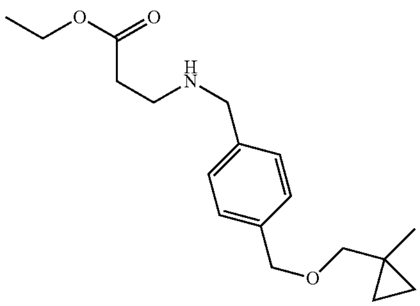 [SMILES: CCOC(=O)CCNCc1ccc(COCC2(C)CC2)cc1] | ¹H NMR (300 MHz, CHLOROFORM-d) δ ppm 0.29-0.35 (m, 2 H) 0.36-0.42 (m, 2 H) 1.15 (s, 3 H) 1.25 (t, J = 7.1 Hz, 3 H) 2.52 (t, J = 6.5 Hz, 2 H) 2.89 (t, J = 6.5 Hz, 2 H) 3.24 (s, 2 H) 3.79 (s, 2 H) 4.14 (q, J = 7.1 Hz, 2 H) 4.51 (s, 2 H) 7.28-7.31 (m, 4 H). MS ESI/APCI Dual posi: 306[M + H]⁺, 328[M + Na]⁺. | |
| Reference Example A-227 | 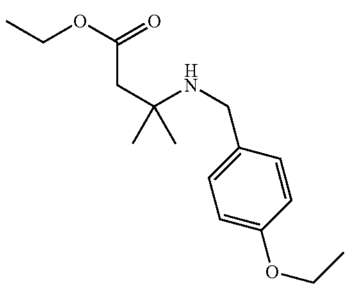 [SMILES: CCOC(=O)CC(C)(C)NCc1ccc(OCC)cc1] | ¹H NMR(300 MHz, CHLOROFORM-d) δ ppm 1.21-1.29 (m, 9 H) 1.40 (t, J = 7.0 Hz, 3 H) 2.50 (s, 2 H) 3.65 (s, 2 H) 4.01 (q, J = 7.0 Hz, 2 H) 4.14 (q, J = 7.0 Hz, 2 H) 6.81-6.86 (m, 2 H) 7.21-7.27 (m, 2 H). MS ESI/APCI Dual posi: 280[M + H]⁺. | |
| Reference Example A-228 | 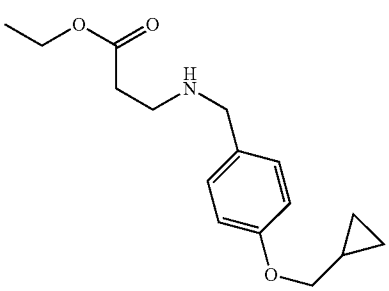 [SMILES: CCOC(=O)CCNCc1ccc(OCC2CC2)cc1] | ¹H NMR (300 MHz, CHLOROFORM-d) δ ppm 0.25-0.41 (m, 2 H) 0.54-0.69 (m, 2 H) 1.15-1.35 (m, 4 H) 2.52 (t, J = 6.5 Hz, 2 H) 2.88 (t, J = 6.5 Hz, 2 H) 3.73 (s, 2 H) 3.78 (d, J = 7.0 Hz, 2 H) 4.13 (q, J = 7.1 Hz, 2 H) 6.82-6.89 (m, 2 H) 7.18-7.24 (m, 2 H). MS ESI/APCI Dual posi: 278[M + H]⁺. | |

TABLE 18-33-continued

| Compound No. | Structure | Analytical Data | Salt information |
|---|---|---|---|
| Reference Example A-229 | 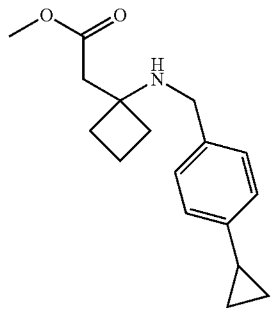 [SMILES: COC(=O)CC1(NCc2ccc(C3CC3)cc2)CCC1] | ¹H NMR (300 MHz, CHLOROFORM-d) δ ppm 0.60-0.75 (m, 2 H) 0.88-1.01 (m, 2 H) 1.72-1.95 (m, 3 H) 1.95-2.17 (m, 4 H) 2.72 (s, 2 H) 3.64 (s, 2 H) 3.68 (s, 3 H) 6.99-7.04 (m, 2 H) 7.19-7.24 (m, 2 H). MS ESI/APCI Dual posi: 274[M +H]⁺, 296[M + Na]⁺. | |
| Reference Example A-230 | 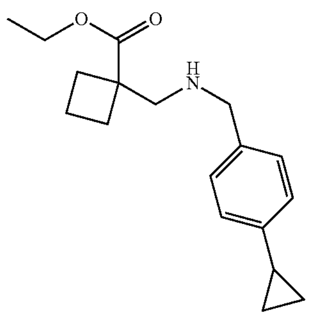 [SMILES: CCOC(=O)C1(CNCc2ccc(C3CC3)cc2)CCC1] | ¹H NMR (300 MHz, CHLOROFORM-d) δ ppm 0.63-0.71 (m, 2 H) 0.90-0.98 (m, 2 H) 1.25 (t, J = 7.1 Hz, 3 H) 1.82-1.99 (m, 5 H) 2.32-2.48 (m, 2 H) 2.89 (s, 2 H) 3.75 (s, 2 H) 4.15 (q, J = 7.1 Hz, 2 H) 6.95-7.07 (m, 2 H) 7.13-7.24 (m, 2 H). MS ESI/APCI Dual posi.: 288[M + H]⁺, 310[M + Na]⁺. | |
| Reference Example A-231 | 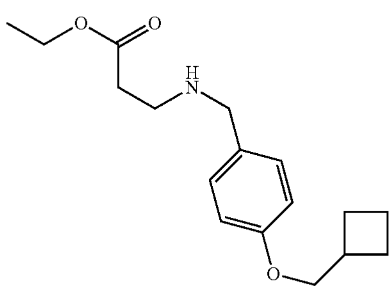 [SMILES: CCOC(=O)CCNCc1ccc(OCC2CCC2)cc1] | ¹H NMR (300 MHz, CHLOROFORM-d) δ ppm 1.25 (t, J = 7.1 Hz, 3 H) 1.78-2.03 (m, 4 H) 2.05-2.21 (m, 2 H) 2.52 (t, J = 6.5 Hz, 2 H) 2.68-2.82 (m, 1 H) 2.88 (t J = 6.5 Hz, 2 H) 3.73 (s, 2 H) 3.91 (d, J = 6.7 Hz, 2 H) 4.14 (q, J = 7.1 Hz, 2 H) 6.82-6.89 (m, 2 H) 7.17-7.25 (m, 2 H). MS ESI/APCI Dual posi: 292[M + H]⁺. | |
| Reference Example A-232 | 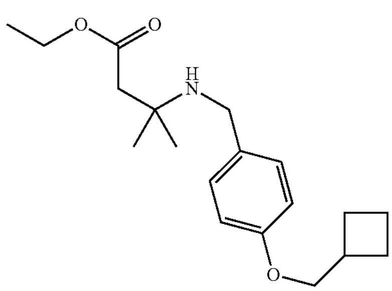 [SMILES: CCOC(=O)CC(C)(C)NCc1ccc(OCC2CCC2)cc1] | ¹H NMR (300 MHz, CHLOROFORM-d) δ ppm 1.13-1.36 (m, 9 H) 1.80-2.03 (m, 4 H) 2.03-2.22 (m, 2 H) 2.50 (s, 2 H) 2.70-2.88 (m, 1 H) 3.65 (s, 2 H) 3.90 (d, J = 6.7 Hz, 2 H) 4.14 (q, J = 7.1 Hz, 2 H) 6.80-6.88 (m, 2 H) 7.19-7.30 (m, 2 H). MS ESI/APCI Dual posi: 320[M + H]⁺. | |

TABLE 18-34

| Compound No. | Structure | Analytical Data | Salt information |
|---|---|---|---|
| Reference Example A-233 | 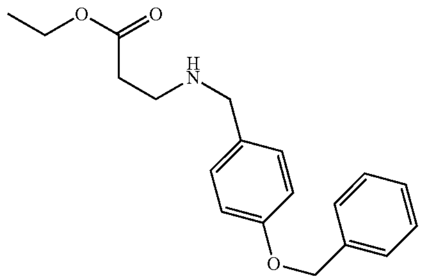 [SMILES: CCOC(=O)CCNCc1ccc(OCc2ccccc2)cc1] | $^1$H NMR (300 MHz, CHLOROFORM-d) δ ppm 1.25 (t, J = 7.1 Hz, 3 H) 2.52 (t, J = 6.5 Hz, 2 H) 2.88 (t, J = 6.5 Hz, 2 H) 3.74 (s, 2 H) 4.14 (q, J = 7.1 Hz, 2 H) 5.06 (s, 2 H) 6.93 (d, J = 8.7 Hz, 2 H) 7.20-7.25 (m, 3 H) 7.30-7.46 (m, 4 H).<br>MS ESI/APCI Dual posi: 314[M + H]$^+$, 336[M + Na]$^+$.<br>MS ESI/APCI Dual nega: 312[M − H]$^−$. | |
| Reference Example A-234 | 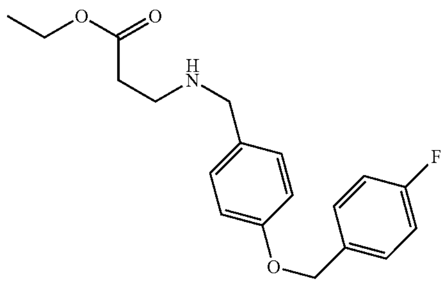 [SMILES: CCOC(=O)CCNCc1ccc(OCc2ccc(F)cc2)cc1] | $^1$H NMR (300 MHz, CHLOROFORM-d) δ ppm 1.25 (t, J = 7.1 Hz, 3 H) 2.52 (t, J = 6.5 Hz, 2 H) 2.89 (t, J = 6.5 Hz, 2 H) 3.74 (s, 2 H) 4.14 (q, J = 7.1 Hz, 2 H) 5.01 (s, 2 H) 6.88-6.94 (m, 2 H) 7.02-7.11 (m, 2 H) 7.21-7.26 (m, 2 H) 7.36-7.43 (m, 2 H).<br>MS ESI/APCI Dual posi: 332[M + H]$^+$, 354[M + Na]$^+$.<br>MS ESI/APCI Dual nega: 330[M − H]$^−$. | |
| Reference Example A-235 | 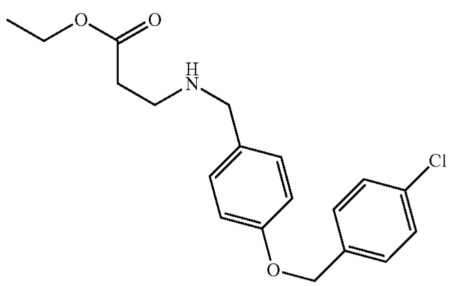 [SMILES: CCOC(=O)CCNCc1ccc(OCc2ccc(Cl)cc2)cc1] | $^1$H NMR (300 MHz, CHLOROFORM-d) δ ppm 1.25 (t, J = 7.1 Hz, 3 H) 2.52 (t, J = 6.5 Hz, 2 H) 2.88 (t, J = 6.5 Hz, 2 H) 3.74 (s, 2 H) 4.14 (q, J = 7.1 Hz, 2 H) 5.02 (s, 2 H) 6.87-6.94 (m, 2 H) 7.20-7.26 (m, 2 H) 7.35 (s, 4 H).<br>MS ESI/APCI Dual posi: 348[M + H]$^+$, 370[M + Na]$^+$.<br>MS ESI/APCI Dual nega: 346[M − H]$^−$, 382[M + Cl]$^−$. | |
| Reference Example A-236 | 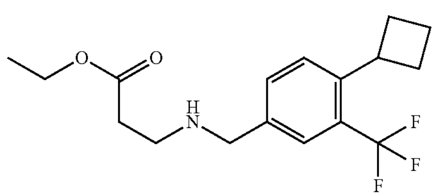 [SMILES: CCOC(=O)CCNCc1ccc(C2CCC2)c(C(F)(F)F)c1] | $^1$H NMR (300 MHz, CHLOROFORM-d) δ ppm 1.26 (t, J = 7.1 Hz, 3 H) 1.76-1.92 (m, 1H) 1.95-2.10 (m, 1 H) 2.10-2.27 (m, 2 H) 2.27-2.43 (m, 2 H) 2.53 (t, J = 6.5 Hz, 2 H) 2.89 (t, J = 6.5 Hz, 2 H) 3.69-4.00 (m, 3 H) 4.14 (q, J = 7.1 Hz, 2 H) 7.41-7.63 (m, 3 H).<br>MS ESI/APCI Dual posi: 330[M + H]$^+$. | |
| Reference Example A-237 | 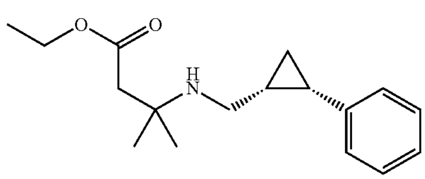 [SMILES: CCOC(=O)CC(C)(C)NC[C@@H]1C[C@@H]1c1ccccc1] | $^1$H NMR (300 MHz, CHLOROFORM-d) δ ppm 0.83 (q, J = 5.5 Hz, 1 H) 0.91 (s, 3 H) 0.93 (s, 3 H) 1.02 (td, J = 8.4, 5.5 Hz, 1 H) 1.24 (t, J = 7.1 Hz, 3 H) 1.27-1.41 (m, 1 H) 2.06 (d, J = 14.0 Hz, 1 H) 2.14-2.28 (m, 3 H) 2.32 (dd, J = 11.2, 6.8 Hz, 1 H) 4.08 (q, J = 7.1 Hz, 2 H) 7.07-7.39 (m, 5 H).<br>MS ESI/APCI Dual posi: 276[M + H]$^+$. | |
| Reference Example A-238 | 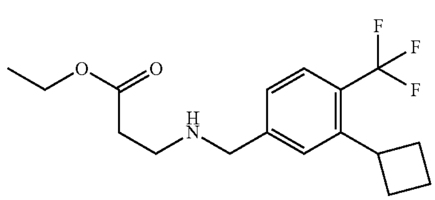 [SMILES: CCOC(=O)CCNCc1ccc(C(F)(F)F)c(C2CCC2)c1] | $^1$H NMR (300 MHz, CHLOROFORM-d) δ ppm 1.26 (t, J = 7.1 Hz, 3 H) 1.81-1.93 (m, 1 H) 1.95-2.12 (m, 1 H) 2.13-2.26 (m, 2 H) 2.26-2.41 (m, 2 H) 2.55 (t, J = 6.4 Hz, 2 H) 2.91 (t, J = 6.4 Hz, 2 H) 3.77-3.98 (m, 3 H) 4.15 (q, J = 7.1 Hz, 2 H) 7.14-7.28 (m, 1 H) 7.48-7.60 (m, 2 H).<br>MS ESI/APCI Dual posi : 330[M + H]$^+$. | |

TABLE 18-34-continued

| Compound No. | Structure | Analytical Data | Salt information |
|---|---|---|---|
| Reference Example A-239 | 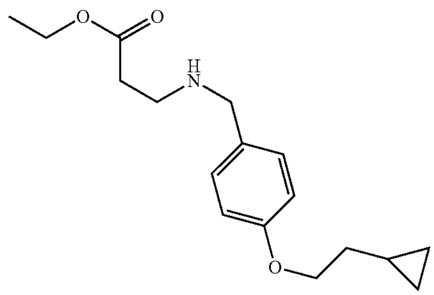 [SMILES: CCOC(=O)CCNCc1ccc(OCCC2CC2)cc1] | ¹H NMR (300 MHz, CHLOROFORM-d) δ ppm 0.05-0.21 (m, 2 H) 0.37-0.58 (m, 2 H) 0.74-0.95 (m, 1 H) 1.25 (t, J = 7.1 Hz, 3 H) 1.67 (q, J = 6.7 Hz, 2 H) 2.52 (t, J = 6.5 Hz, 2 H) 2.88 (t, J = 6.5 Hz, 2 H) 3.73 (s, 2 H) 4.02 (t, J = 6.8 Hz, 2 H) 4.14 (q, J = 7.1 Hz, 2 H) 6.81-6.90 (m, 2 H) 7.18-7.25 (m, 2 H). MS ESI/APCI Dual posi: 292[M + H]⁺. | |

TABLE 18-35

| Compound No. | Structure | Analytical Data | Salt information |
|---|---|---|---|
| Reference Example A-240 | 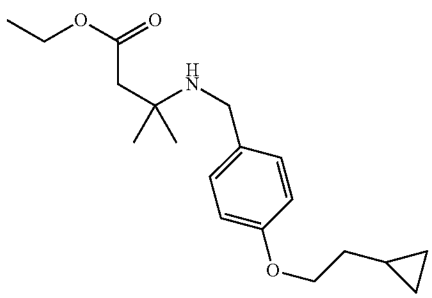 [SMILES: CCOC(=O)CC(C)(C)NCc1ccc(OCCC2CC2)cc1] | ¹H NMR (300 MHz, CHLOROFORM-d) δ ppm 0.05-0.20 (m, 2 H) 0.40-0.54 (m, 2 H) 0.75-0.92 (m, 1 H) 1.14-1.34 (m, 9 H) 1.64-1.72 (m, 2 H) 2.51 (s, 2 H) 3.65 (s, 2 H) 4.03 (q, J = 6.8 Hz, 2 H) 4.14 (q, J = 7.1 Hz, 2 H) 6.82-6.88 (m, 2 H) 7.22-7.28 (m, 2 H). MS ESI/APCI Dual posi: 320[M + H]⁺. | |
| Reference Example A-241 | 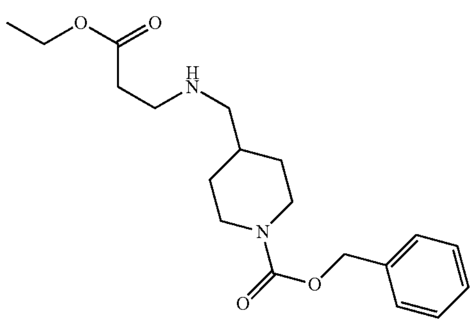 [SMILES: CCOC(=O)CCNCC1CCN(C(=O)OCc2ccccc2)CC1] | ¹H NMR (300 MHz, CHLOROFORM-d) δ ppm 1.02-1.86 (m, 8 H) 2.43-2.57 (m, 4 H) 2.60-2.94 (m, 6 H) 4.14 (q, J = 7.1 Hz, 2 H) 5.12 (s, 2 H) 7.20-7.46 (m, 5 H). MS ESI/APCI Dual posi: 349[M + H]⁺. | |
| Reference Example A-242 | 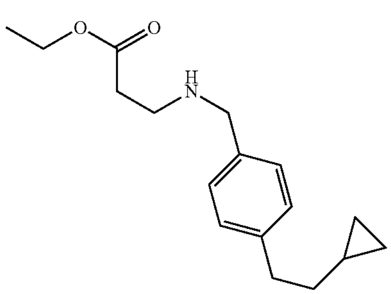 [SMILES: CCOC(=O)CCNCc1ccc(CCC2CC2)cc1] | ¹H NMR (300 MHz, CHLOROFORM-d) δ ppm −0.11-0.10 (m, 2 H) 0.34-0.48 (m, 2 H) 0.59-0.79 (m, 1 H) 1.25 (t, J = 7.1 Hz, 3 H) 1.44-1.54 (m, 2 H) 2.52 (t, J = 6.5 Hz, 2 H) 2.64-2.73 (m, 2 H) 2.89 (t, J = 6.5 Hz, 2 H) 3.77 (s, 2 H) 4.14 (q, J = 7.1 Hz, 2 H) 7.11-7.18 (m, 2 H) 7.18-7.25 (m, 2 H). MS ESI/APCI Dual posi: 276[M + H]⁺, 298[M + Na]⁺. | |

TABLE 18-35-continued

| Compound No. | Structure | Analytical Data | Salt information |
|---|---|---|---|
| Reference Example A-243 | 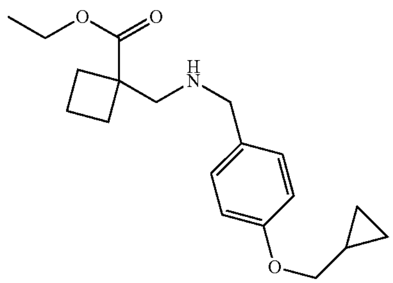 [SMILES: CCOC(=O)C1(CNCc2ccc(OCC3CC3)cc2)CCC1] | $^1$H NMR (300 MHz, CHLOROFORM-d) δ ppm 0.25-0.41 (m, 2 H) 0.58-0.69 (m, 2 H) 1.25 (t, J = 7.1 Hz, 3 H) 1.83-1.99 (m, 5 H) 2.31-2.47 (m, 2 H) 2.88 (s, 2 H) 3.73 (s, 2 H) 3.79 (d, J = 6.8 Hz, 2 H; 4.15 (q, J = 7.1 Hz, 2 H) 6.82-6.88 (m, 2 H) 7.18-7.24 (m, 2 H). MS ESI/APCI Dual posi: 318[M + H]$^+$. | |
| Reference Example A-244 | 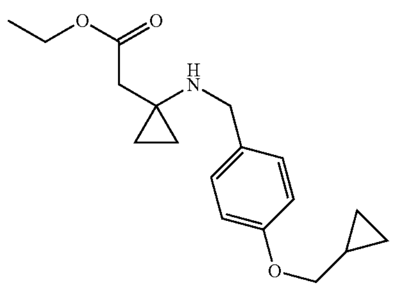 [SMILES: CCOC(=O)CC1(NCc2ccc(OCC3CC3)cc2)CC1] | $^1$H NMR (300 MHz, CHLOROFORM-d) δ ppm 0.29-0.37 (m, 2H) 0.47-0.53 (m, 2 H) 0.59-0.68 (m. 2 H) 0.69-0.76 (m, 2 H) 1.24-1.31 (m, 4 H) 2.49 (s, 2 H) 3.74 (s, 2 H) 3.77 (d, J = 7.0 Hz, 2 H) 4.17 (q, J= 7.1 Hz, 2 H) 6.80-6.87 (m, 2 H) 7.16-7.23 (m, 2 H). MS ESI/APCI Dual posi: 304[M + H]$^+$. | |
| Reference Example A-245 | 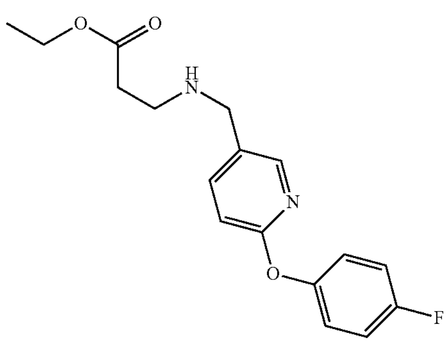 [SMILES: CCOC(=O)CCNCc1ccc(Oc2ccc(F)cc2)nc1] | $^1$H NMR (300 MHz, CHLOROFORM-d) δ ppm 1.20-1.31 (m, 3 H) 2.43-2.58 (m, 2 H) 2.82-2.92 (m, 2 H) 3.75 (s, 2 H) 4.07- 4.19 (m, 2 H) 6.87 (d, J = 8.4 Hz, 1 H) 7.01-7.15 (m, 4 H) 7.65-7.72 (m, 1 H) 8.04-8.10 (m, 1 H). MS ESI/APCI Dual posi: 319[M + H]$^+$, 341[M + Na]$^+$. MS ESI/APCI Dual nega: 317[M − H]$^-$. | |
| Reference Example A-246 | 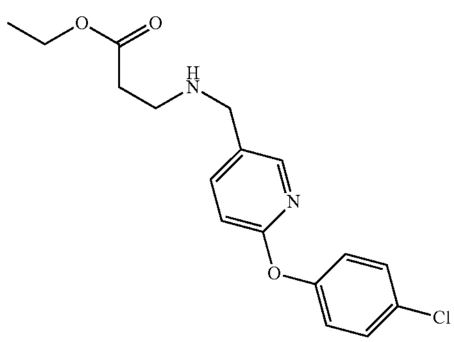 [SMILES: CCOC(=O)CCNCc1ccc(Oc2ccc(Cl)cc2)nc1] | $^1$H NMR (300 MHz, CHLOROFORM-d) δ ppm 1.21-1.30 (m, 3 H) 2.47-2.57 (m, 2 H) 2.82-2.92 (m, 2 H) 3.76 (s, 2 H) 4.07- 4.20 (m, 2 H) 6.89 (dd, J = 8.4, 0.8 Hz, 1 H) 7.01-7.10 (m, 2 H) 7.29-7.38 (m, 2 H) 7.71 (dd, J = 8.5, 2.4 Hz, 1 H) 8.09 (dd, J = 2.4, 0.8 Hz, 1 H). MS ESI/APCI Dual posi: 335[M + H]$^+$, 357[M + Na]$^+$. MS ESI/APCI Dual nega: 333 [M − H]$^-$. | |

TABLE 18-36

| Compound No. | Structure | Analytical Data | Salt information |
|---|---|---|---|
| Reference Example A-247 | (structure) | ¹H NMR (300 MHz, CHLOROFORM-d) δ ppm 1.19-1.29 (m, 3 H) 2.48-2.58 (m, 2 H) 2.85-2.94 (m, 2 H) 3.78 (s, 2 H) 4.07-4.22 (m, 2 H) 6.95 (d, J = 8.4 Hz, 1 H) 7.19-7.29 (m, 2 H) 7.58-7.69 (m, 2 H) 7.76 (dd, J = 8.4, 2.5 Hz, 1 H) 8.12 (d, J = 2.5 Hz, 1 H). MS ESI/APCI Dual posi: 369[M + H]⁺, 381[M + Na]⁺. | |
| Reference Example A-248 | (structure) | ¹H NMR (300 MHz, CHLOROFORM-d) δ 1.20-1.29 (m, 3 H) 2.36 (s, 3 H) 2.49-2.57 (m, 2 H) 2.89 (t, J = 6.4 Hz, 2 H) 3.76 (s, 2 H) 4.08-4.19 (m, 2 H) 6.80-8.85 (m, 3 H) 6.97-7.05 (m, 1 H) 7.20-7.33 (m, 1 H) 7.68 (dd, J = 8.5, 2.5 Hz, 1 H) 8.12 (dd, J = 2.5, 0.6 Hz, 1 H). MS ESI/APCI Dual posi : 315[M + H]⁺, 337[M + Na]⁺. MS ESI/APCI Dual nega: 313[M − H]⁻. | |
| Reference Example A-249 | (structure) | ¹H NMR (300 MHz, CHLOROFORM-d) δ ppm 1.18-1.32 (m, 3 H) 2.46-2.57 (m, 2 H) 2.83-2.93 (m, 2 H) 3.77 (s, 2 H) 4.07-4.18 (m, 2 H) 6.79-7.01 (m, 4 H) 7.28-7.40 (m, 1 H) 7.67-7.75 (m, 1 H) 8.13 (dd, J = 2.5, 0.6 Hz, 1 H). MS ESI/APCI Dual posi: 318[M + H]⁺, 341[M + Na]⁺. MS ESI/APCI Dual nega: 317[M − H]⁻. | |
| Reference Example A-250 | (structure) | ¹H NMR (300 MHz, CHLOROFORM-d) δ ppm 1.21-1.31 (m, 3 H) 2.32 (s, 3 H) 2.54 (t, J = 6.5 Hz, 2 H) 2.91 (t, J = 6.5 Hz, 2 H) 3.78 (s, 2 H) 4.14 (q, J = 7.1 Hz, 2 H) 6.73-6.84 (m, 2 H) 6.86-7.00 (m, 3 H) 7.20 (t, J = 7.9 Hz, 1 H) 7.23-7.31 (m, 2 H). MS ESI/APCI Dual posi: 314[M + H]⁺, 336 [M + Na]⁺. MS ESI/APCI Dual nega: 312[M −H]⁻. | |

TABLE 18-36-continued

| Compound No. | Structure | Analytical Data | Salt information |
|---|---|---|---|
| Reference Example A-251 | 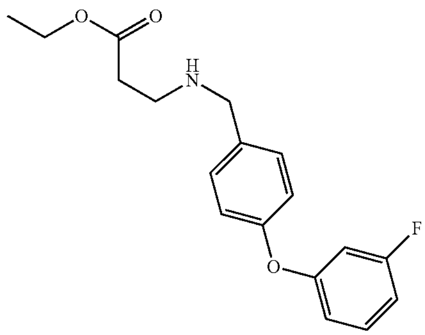 [SMILES: CCOC(=O)CCNCc1ccc(Oc2cccc(F)c2)cc1] | $^1$H NMR (300 MHz, CHLOROFORM-d) δ ppm 1.26 (t, J = 7.1 Hz, 3 H) 2.54 (t, J = 6.5 Hz, 2 H) 2.91 (t, J = 6.5 Hz, 2 H) 3.79 (s, 2 H) 4.15 (q, J = 7.1 Hz, 2 H) 6.62-6.72 (m, 1 H) 6.73-6.82 (m, 2 H) 6.93-7.05 (m, 2 H) 7.16-7.36 (m, 3 H). MS ESI/APCI Dual posi: 318[M + H]$^+$, 340[M + Na]$^+$. MS ESI/APCI Dual nega: 316[M − H]$^−$. | r |
| Reference Example A-252 | 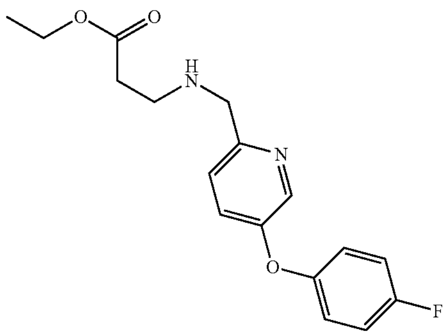 [SMILES: CCOC(=O)CCNCc1ccc(Oc2ccc(F)cc2)cn1] | $^1$H NMR (300 MHz, CHLOROFORM-d) δ ppm 1.20-1.31 (m, 3H) 2.55 (t, J = 6.5 Hz, 2 H) 2.94 (t, J = 6.5 Hz, 2 H) 3.91 (s, 2 H) 4.07-4.22 (m, 2 H) 6.87-7.11 (m, 4 H) 7.17-7.33 (m, 2 H) 8.32 (d, J = 2.8 Hz, 1H). MS ESI/APCI Dual posi: 319[M + H]$^+$, 341[M + Na]$^+$. MS ESI/APCI Dual nega: 317[M − H]$^−$. | |
| Reference Example A-253 | 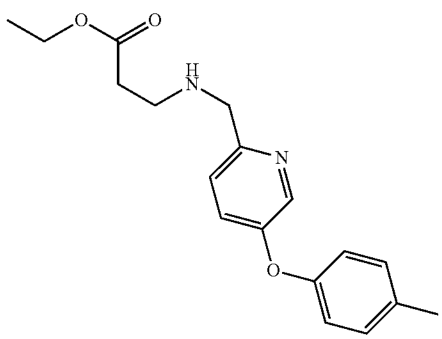 | $^1$H NMR (300 MHz, CHLOROFORM-d) δ ppm 1.18-1.33 (m, 3 H) 2.34 (s, 3 H) 2.46-2.62 (m, 2 H) 2.94 (t, J = 6.6 Hz, 2 H) 3.90 (s, 2 H) 4.06-4.21 (m, 2 H) 6.79-7.00 (m, 2 H) 7.10-7.18 (m, 2 H) 7.19-7.30 (m, 2 H) 8.32 (dd, J = 2.6, 0.9 Hz, 1 H). MS ESI/APCI Dual posi: 315[M + H]$^+$, 337[M + Na]$^+$. MS ESI/APCI Dual nega: 313[M − H]$^−$. | |

TABLE 18-37

| Compound No. | Structure | Analytical Data | Salt information |
|---|---|---|---|
| Reference Example A-254 | 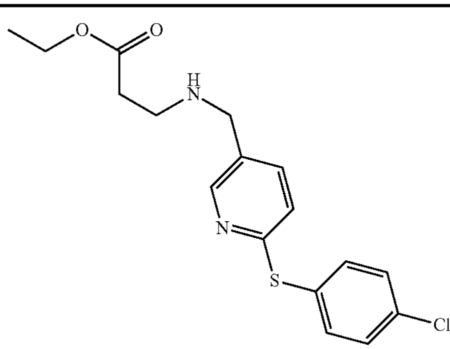 | $^1$H NMR (300 MHz, CHLOROFORM-d) δ ppm 1.25 (t, J = 7.1 Hz, 3 H) 2.50 (t, J = 6.4 Hz, 2 H) 2.86 (t, J = 6.4 Hz, 2 H) 3.75 (s, 2 H) 4.13 (q, J = 7.1 Hz, 2 H) 6.94 (d, J = 8.1 Hz, 1 H) 7.31-7.44 (m, 2 H) 7.44-7.59 (m, 3 H) 8.37 (d, J = 1.7 Hz, 1 H). MS ESI/APCI Dual posi: 351[M + H]$^+$. | |

TABLE 18-37-continued

| Compound No. | Structure | Analytical Data | Salt information |
|---|---|---|---|
| Reference Example A-255 | 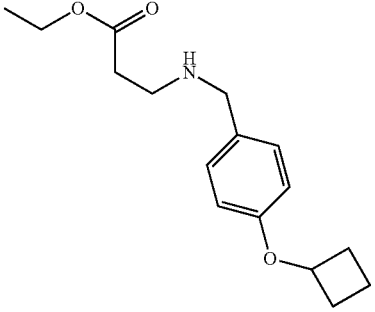 [SMILES: CCOC(=O)CCNCc1ccc(OC2CCC2)cc1] | $^1$H NMR (300 MHz, CHLOROFORM-d) δ ppm 1.25 (t, J = 7.1 Hz, 3 H) 1.61-1.77 (m, 1 H) 1.78-1.93 (m, 1 H) 2.07-2.24 (m, 2 H) 2.37-2.49 (m, 2 H) 2.52 (t, J = 6.5 Hz, 2 H) 2.88 (t, J = 6.5 Hz, 2 H) 3.72 (s, 2 H) 4.13 (q, J = 7.1 Hz, 2 H) 4.52-4.72 (m, 1 H) 6.69-6.83 (m, 2 H) 7.16-7.23 (m, 2 H). MS ESI/APCI Dual posi: 278[M + H]$^+$, 300[M + Na]$^+$. | |
| Reference Example A-256 | 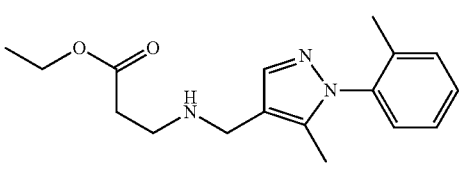 [SMILES: CCOC(=O)CCNCc1cnn(-c2ccccc2C)c1C] | $^1$H NMR (300 MHz, CHLOROFORM-d) δ ppm 1.27 (t, J = 7.1 Hz, 3 H) 2.03 (s, 3H) 2.07 (s, 3 H) 2.56 (t, J = 6.5 Hz, 2 H) 2.95 (t, J = 6.5 Hz, 2 H) 3.70 (s, 2 H) 4.15 (q, J = 7.1 Hz, 2 H) 7.13-7.41 (m, 4 H) 7.58 (s, 1H). MS ESI/APCI Dual posi: 302[M + H]$^+$, 324[M + Na]$^+$. MS ESI/APCI Dual nega: 300[M − H]$^-$, 336[M + Cl]$^-$. | |
| Reference Example A-257 | 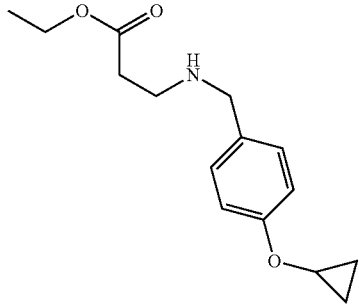 [SMILES: CCOC(=O)CCNCc1ccc(OC2CC2)cc1] | $^1$H NMR (300 MHz, CHLOROFORM-d) δ ppm 0.70-0.82 (m, 4 H) 1.25 (t, J = 7.1 Hz, 3 H) 2.52 (t, J = 6.5 Hz, 2 H) 2.89 (t, J = 6.5 Hz, 2 H) 3.64-3.78 (m, 3 H) 4.14 (q, J = 7.1 Hz, 2 H) 6.97-7.03 (m, 2 H) 7.20-7.25 (m, 2 H). MS ESI/APCI Dual posi: 264[M + H]$^+$, 286[M + Na]$^+$. MS ESI/APCI Dual nega: 262[M − H]$^-$. I | |
| Reference Example A-258 | 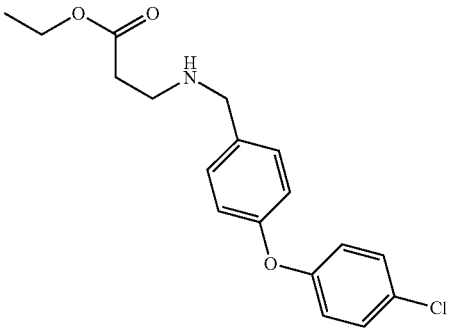 [SMILES: CCOC(=O)CCNCc1ccc(Oc2ccc(Cl)cc2)cc1] | $^1$H NMR (300 MHz, CHLOROFORM-d) δ ppm 1.18-1.33 (m, 3 H) 2.54 (t, J = 6.5 Hz, 2 H) 2.91 (t, J = 6.5 Hz, 2 H) 3.78 (s, 2 H) 4.15 (q, J = 7.1 Hz, 2 H) 6.83-7.02 (m, 4 H) 7.20-7.35 (m, 4 H). [MS ESI/APCI Dual posi: 334[M + H]$^+$, 356[M + Na]$^+$. MS ESI/APCI Dual nega: 332[M − H]$^-$. | |
| Reference Example A-259 | 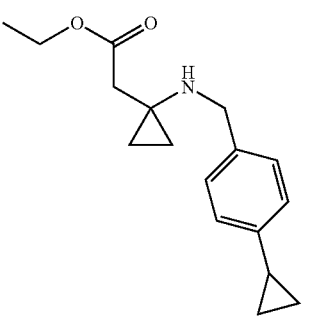 [SMILES: CCOC(=O)CC1(NCc2ccc(C3CC3)cc2)CC1] | $^1$H NMR (300 MHz, CHLOROFORM-d) δ ppm 0.44-0.55 (m, 2 H) 0.30-0.69 (m, 2 H) 0.69-0.77 (m, 2 H) 0.86-0.99 (m, 2 H) 1.27 (t, J = 7.1 Hz, 3 H) 1.86 (tt, J = 8.5, 5.1 Hz, 1 H) 2.49 (s, 2 H) 3.76 (s, 2 H) 4.16 (q, J = 7.1 Hz, 2 H) 6.95-7.05 (m, 2 H) 7.12-7.22 (m, 2 H). MS ESI/APCI Dual posi: 274[M + H]$^+$. | |

TABLE 18-37-continued

| Comd-poun No. | Structure | Analytical Data | Salt information |
|---|---|---|---|
| Reference Example A-260 | 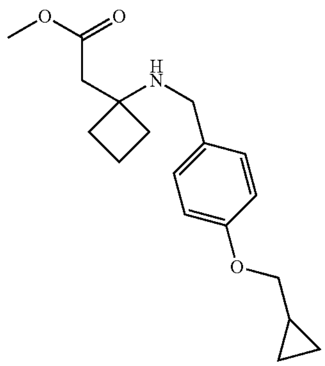 [SMILES: COC(=O)CC1(NCc2ccc(OCC3CC3)cc2)CCC1] | ¹H NMR (300 MHz, CHLOROFORM-d) δ ppm 0.29-0.39 (m, 2 H) 0.57-0.69 (m, 2 H) 1.17-1.34 (m, 1 H) 1.71-1.94 (m, 2 H) 1.95-2.16 (m, 4 H) 2.72 (s, 2 H) 3.62 (s, 2 H) 3.68 (s, 3 H) 3.75-3.80 (m, 2 H) 6.81-6.87 (m, 2 H) 7.21-7.26 (m, 2 H). MS ESI/APCI Dual posi: 304[M + H]⁺. | |

TABLE 18-38

| Compound No. | Structure | Analytical Data | Salt information |
|---|---|---|---|
| Reference Example A-261 | 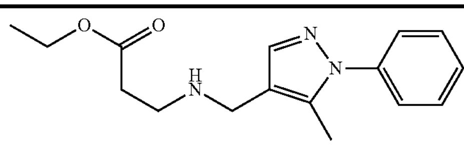 | ¹H NMR (300 MHz, CHLOROFORM-d) δ ppm 1.26 (t, J = 7.1 Hz, 3 H) 2.31 (s. 3 H) 2.56 (t, J = 6.5 Hz, 2 H) 2.95 (t, J = 6.5 Hz, 2 H) 3.70 (s, 2 H) 4.15 (q, J = 7.1 Hz, 2 H) 7.32-7.52 (m, 5 H) 7.59 (s, 1 H). MS-ESI/APCI Dual posi: 283[M + H]⁺, 310[M + Na]⁺. | |
| Reference Example A-262 | 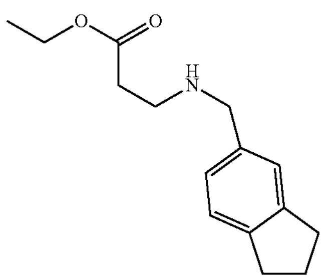 [SMILES: CCOC(=O)CCNCc1ccc2c(c1)CCC2] | ¹H NMR (300 MHz, CHLOROFORM-d) δ ppm 1.25 (t, J = 7.1 Hz, 3H) 2.06 (quin, J = 7.4 Hz, 2 H) 2.53 (t, J = 6.5 Hz, 2 H) 2.81-2.96 (m, 6 H) 3.76 (s, 2 H) 4.14 (q, J = 7.1 Hz, 2 H) 7.04-7.10 (m, 1 H) 7.14-7.20 (m, 2 H). MS ESI/APCI Dual posi: 248[M + H]⁺, 270[M + Na]⁺. | |
| Reference Example A-263 | 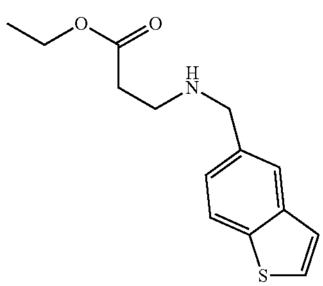 [SMILES: CCOC(=O)CCNCc1ccc2sccc2c1] | ¹H NMR (300 MHz, CHLOROFORM-d) δ ppm 1.25 (t, J = 7.1 Hz, 3 H) 2.54 (t, J = 6.5 Hz, 2 H) 2.92 (t, J = 6.5 Hz, 2 H) 3.93 (s, 2 H) 4.14 (q, J = 7.1 Hz, 2 H) 7.28-7.35 (m, 2 H) 7.43 (dd, J = 5.4, 0.5 Hz, 1 H) 7.75-7.79 (m, 1 H) 7.83 (d, J = 8.4 Hz, 1 H). MS ESI/APCI Dual posi: 264[M + H]⁺, 286[M + Na]⁺. | |
| Reference Example A-264 | 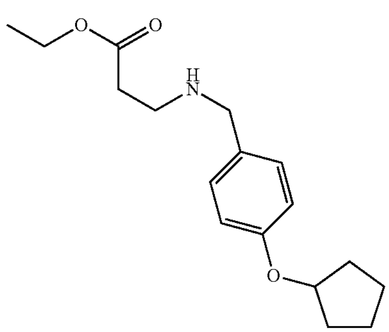 [SMILES: CCOC(=O)CCNCc1ccc(OC2CCCC2)cc1] | ¹H NMR (300 MHz, CHLOROFORM-d) δ ppm 1.25 (t, J = 7.1 Hz, 3 H) 1.49-1.71 (m, 2 H) 1.71-1.99 (m, 6 H) 2.52 (t, J = 6.5 Hz, 2 H) 2.89 (t, J = 6.5 Hz, 2 H) 3.72 (s, 2 H) 4.13 (q, J = 7.1 Hz, 2 H) 4.66-4.80 (m, 1 H) 6.74-6.89 (m, 2 H) 7.14-7.24 (m, 2 H). MS ESI/APCI Dual posi: 292[M + H]⁺. | |

TABLE 18-38-continued

| Compound No. | Structure | Analytical Data | Salt information |
|---|---|---|---|
| Reference Example A-265 | 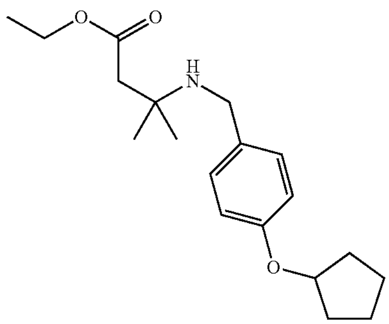 [SMILES: CCOC(=O)CC(C)(C)NCc1ccc(OC2CCCC2)cc1] | ¹H NMR (300 MHz, CHLOROFORM-d) δ ppm 1.07-1.37 (m, 9 H) 1.51-1.94 (m, 8 H) 2.50 (s, 2 H) 3.64 (s, 2 H) 4.14 (q, J = 7.1 Hz, 2 H) 4.68-4.80 (m, 1 H) 6.77-6.84 (m, 2 H) 7.19-7.26 (m, 2 H). MS ESI/APCI Dual posi: 320[M + H]⁺. | |
| Reference Example A-266 | 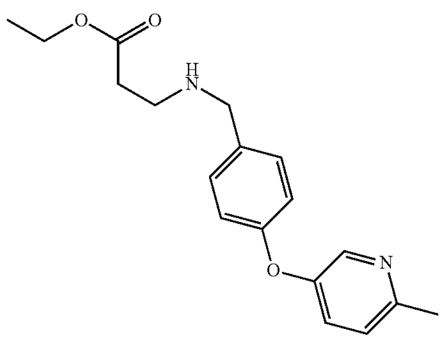 [SMILES: CCOC(=O)CCNCc1ccc(Oc2ccc(C)nc2)cc1] | ¹H NMR (300 MHz, CHLOROFORM-d) δ ppm 1.19-1.31 (m, 3 H) 2.45-2.58 (m, 5 H) 2.83-2.95 (m, 2 H) 3.78 (s, 2 H) 4.06-4.22 (m, 2 H) 6.90-6.98 (m, 2 H) 7.07-7.13 (m, 1 H) 7.16-7.23 (m, 1 H) 7.27-7.34 (m, 2 H) 8.29 (d, J = 2.8 Hz, 1 H). MS ESI/APCI Dual posi: 315[M + H]⁺. | |
| Reference Example A-267 | 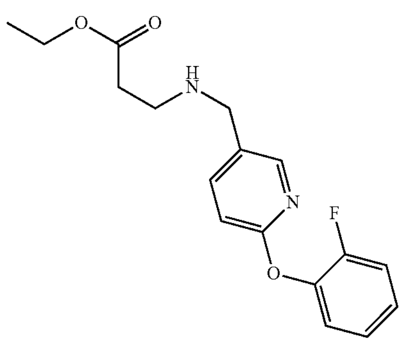 [SMILES: CCOC(=O)CCNCc1ccc(Oc2ccccc2F)nc1] | ¹H NMR (300 MHz, CHLOROFORM-d) δ ppm 1.25 (t, J = 7.1 Hz, 3 H) 2.44-2.56 (m, 2 H) 2.81-2.91 (m, 2 H) 3.75 (s, 2 H) 4.14 (q, J = 7.1 Hz, 2 H) 6.91-6.97 (m, 1 H) 7.10-7.25 (m, 4 H) 7.67-7.75 (m, 1 H) 8.05 (dd, J = 2.5, 0.6 Hz, 1 H). MS ESI/APCI Dual posi: 319[M + H]⁺, 341[M + Na]⁺. | |

TABLE 18-39

| Compound No. | Structure | Analytical Data | Salt information |
|---|---|---|---|
| Reference Example A-268 | 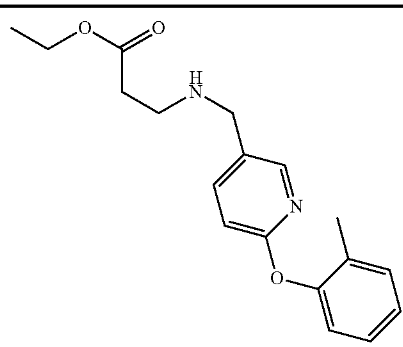 | ¹H NMR (300 MHz, CHLOROFORM-d) δ ppm 1.18-1.33 (m, 3 H) 2.18 (s, 3 H) 2.44-2.56 (m, 2 H) 2.82-2.93 (m, 2 H) 3.74 (s, 2 H) 4.14 (q, J = 7.1 Hz, 2 H) 6.81 (dd, J = 8.5, 0.7 Hz, 1 H) 6.98-7.07 (m, 1 H) 7.08-7.30 (m, 3 H) 7.67 (dd, J = 8.5, 2.5 Hz, 1 H) 8.08 (dd, J = 2.5, 0.7 Hz, 1 H). MS ESI/APCI Dual pos: 315[M + H]⁺, 337[M + Na]⁺. | |

TABLE 18-39-continued

| Compound No. | Structure | Analytical Data | Salt information |
|---|---|---|---|
| Reference Example A-269 | 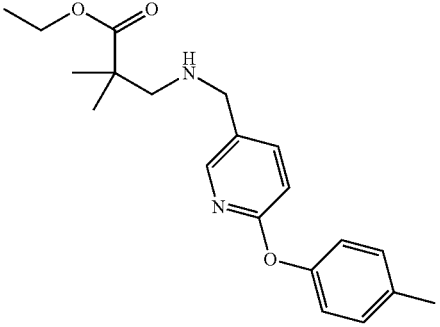 [SMILES: CCOC(=O)C(C)(C)CNCc1ccc(Oc2ccc(C)cc2)nc1] | $^1$H NMR (300 MHz, CHLOROFORM-d) δ ppm 1.17 (s, 6 H) 1.23 (t, J = 7.1 Hz, 3 H) 2.35 (s, 3 H) 2.63 (s, 2 H) 3.72 (s, 2 H) 4.11 (q, J = 7.1 Hz, 2 H) 6.84 (d, J = 8.5 Hz, 1 H) 6.96-7.08 (m, 2 H) 7.12-7.23 (m, 2 H) 7.66 (dd, J = 8.5, 2.4 Hz, 1 H) 8.08 (d, J = 2.4 Hz, 1 H). MS ESI/APCI Dual posi: 343[M + H]$^+$. | |
| Reference Example A-270 | 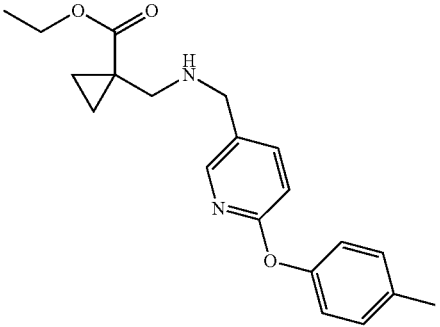 [SMILES: CCOC(=O)C1(CNCc2ccc(Oc3ccc(C)cc3)nc2)CC1] | $^1$H NMR (300 MHz, CHLOROFORM-d) δ ppm 0.68-0.84 (m, 2 H) 1.11-1.34 (m, 5 H) 2.35 (s, 3 H) 2.69 (s, 2 H) 3.75 (s, 2 H) 4.11 (q, J = 6.9 Hz, 2 H) 6.85 (d, J = 8.4 Hz, 1 H) 6.97-7.05 (m, 2 H) 7.15-7.22 (m, 2 H) 7.69 (dd, J = 8.4, 2.4 Hz, 1 H), 8.09 (d, J = 2.4 Hz, 1 H). MS ESI/APCI Dual posi: 341[M + H]$^+$. | |
| Reference Example A-271 | 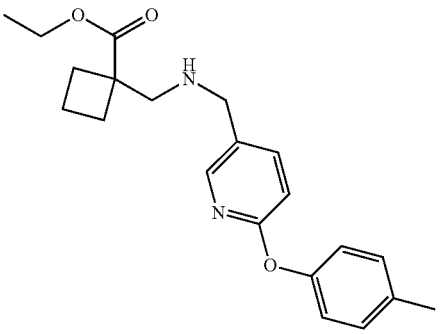 [SMILES: CCOC(=O)C1(CNCc2ccc(Oc3ccc(C)cc3)nc2)CCC1] | $^1$H NMR (300 MHz, CHLOROFORM-d) δ ppm 1.25 (t, J = 7.1 Hz, 3 H) 1.79-2.00 (m, 4 H) 2.25-2.51 (m, 5 H) 2.88 (s, 2 H) 3.74 (s, 2 H) 4.15 (q, J = 7.1 Hz, 2 H) 6.84 (d, J = 8.4 Hz, 1 H) 6.98-7.05 (m, 2 H) 7.15-7.22 (m, 2 H) 7.66 (dd, J = 8.4, 2.5 Hz, 1 H) 8.08 (d, J = 2.5 Hz, 1 H). MS ESI/APCI Dual posi: 355[M + H]$^+$. | |
| Reference Example A-272 | 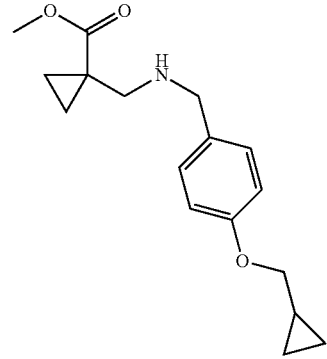 | $^1$H NMR (300 MHz, CHLOROFORM-d) δ ppm 0.30-0.39 (m, 2 H) 0.58-0.69 (m, 2 H) 0.84-0.92 (m, 2 H) 1.22 (t, J = 7.1 Hz, 3 H) 1.25-1.34 (m, 3 H) 2.78 (s, 2 H) 3.79 (d, J = 7.0 Hz, 2 H) 3.84 (s, 2 H) 4.11 (q, J = 7.1 Hz, 2 H) 6.83-6.91 (m, 2 H) 7.22-7.29 (m, 2 H). MS ESI/APCI Dual posi: 304[M + H]$^+$. | |

TABLE 18-39-continued

| Compound No. | Structure | Analytical Data | Salt information |
|---|---|---|---|
| Reference Example A-273 | 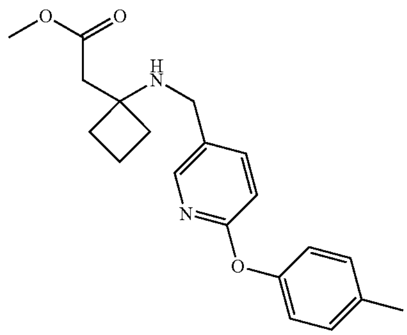 | ¹H NMR (300 MHz, CHLOROFORM-d) δ ppm 1.72-1.95 (m, 2 H) 1.96-2.16 (m, 4 H) 2.34 (s, 3 H) H) 3.68 (s, 3H) 6.84 (d, J = 8.5 Hz, 1 H) 6.97-7.04 (m, 2 H) 7.14-7.21 (m, 2 H) 7.69 (dd, J = 8.5, 2.5 Hz, 1 H) 8.11 (d, J = 2.5 Hz, 1 H). MS ESI/APCI Dual posi: 341[M + H]⁺. | |
| Reference Example A-274 | 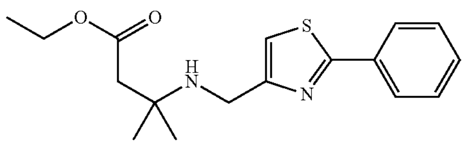 | ¹H NMR (300 MHz, CHLOROFORM-d) δ ppm 1.07-1.37 (m, 9 H) 2.53 (s, 2 H) 3.87-4.04 (m, 2 H) 4.15 (q, J = 7.1 Hz, 2 H) 7.15 (s, 1 H) 7.38-7.47 (m, 3 H) 7.90-7.97 (m, 2 H). MS ESI/APCI Dual posi: 319[M + H]⁺, 341[M + Na]⁺. | |

TABLE 18-40

| Compound No. | Structure | Analytical Data | Salt information |
|---|---|---|---|
| Reference Example A-275 | 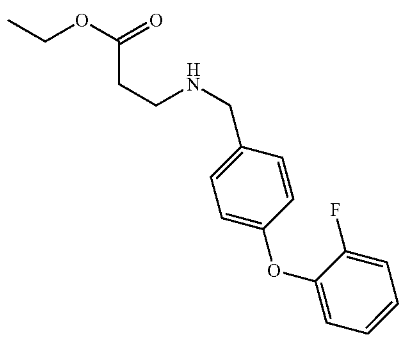 [SMILES: CCOC(=O)CCNCc1ccc(Oc2ccccc2F)cc1] | ¹H NMR (300 MHz, CHLOROFORM-d) δ ppm 1.15-1.32 (m, 3 H) 2.46-2.58 (m, 2 H) 2.83-2.94 (m, 2 H) 3.77 (s, 2 H) 4.14 (q, J = 7.1 Hz, 2 H) 6.89-6.97 (m, 2 H) 6.98-7.22 (m, 4 H) 7.27-7.30 (m, 2 H). MS ESI/APCI Dual posi: 318[M + H]⁺, 340[M + Na]⁺. MS ESI/APCI Dual nega: 316[M − H]⁻. | |
| Reference Example A-276 | 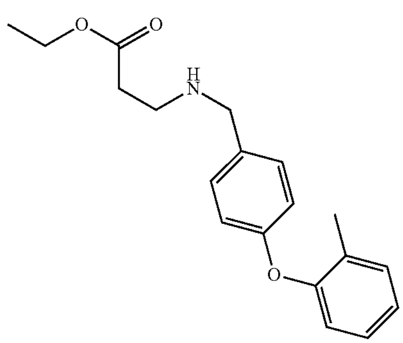 [SMILES: CCOC(=O)CCNCc1ccc(Oc2ccccc2C)cc1] | ¹H NMR (300 MHz, CHLOROFORM- d) δ ppm 1.26 (t, J = 7.1 Hz, 3 H) 2.24 (s, 3 H) 2.47-2.57 (m, 2 H) 2.86-2.93 (m, 2 H) 3.76 (s, 2 H) 4.14 (q, J = 7.1 Hz, 2 H) 6.79-6.92 (m, 3 H) 7.01-7.09 (m, 1 H) 7.11-7.19 (m, 1 H) 7.21-7.28 (m, 3 H). MS ESI/APCI Dual posi: 314[M + H]⁺, 336[M + Na]⁺. MS ESI/APCI Dual nega: 312[M − H]⁻. | |

| Compound No. | Structure | Analytical Data | Salt information |
|---|---|---|---|
| Reference Example A-277 | 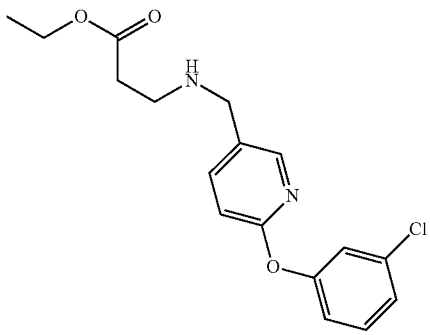 [SMILES: CCOC(=O)CCNCc1ccc(Oc2cccc(Cl)c2)nc1] | ¹H NMR (300 MHz, CHLOROFORM-d) δ ppm 1.20-1.31 (m, 3 H) 2.52 (t, J = 6.4 Hz, 2 H) 2.83-2.93 (m, 2 H) 3.77 (s, 2 H) 4.14 (q, J = 7.1 Hz, 2 H) 6.90 (d, J = 8.4 Hz, 1 H) 6.98-7.07 (m, 1 H) 7.10-7.21 (m, 2 H) 7.27-7.35 (m, 1 H) 7.67-7.75 (m, 1 H) 8.12 (dd, J = 2.5, 0.6 Hz, 1 H) MS ESI/APCI Dual posi: 335[M + H]⁺, 357[M + Na]⁺. | |
| Reference Example A-278 | 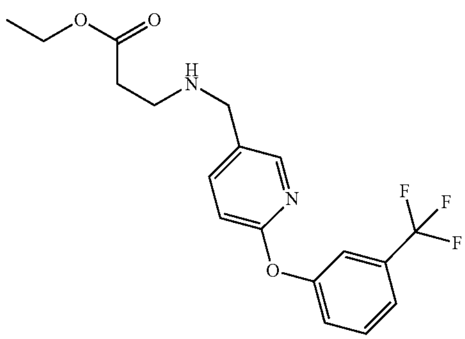 [SMILES: CCOC(=O)CCNCc1ccc(Oc2cccc(C(F)(F)F)c2)nc1] | ¹H NMR (300 MHz, CHLOROFORM-d) δ ppm 1.20-1.30 (m, 3 H) 2.47-2.57 (m, 2 H) 2.84-2.93 (m, 2 H) 3.78 (s, 2 H) 4.15 (q, J = 7.0 Hz, 2 H) 6.88-6.97 (m, 1 H) 7.28-7.36 (m, 1 H) 7.37-7.56 (m, 3 H) 7.75 (dd, J = 8.4. 2.5 Hz, 1 H) 8.11 (dd, J = 2.5, 0.6 Hz, 1 H). MS ESI/APCI Dual posi: 369[M + H]⁺, 391[M + Na]⁺. | |
| Reference Example A-279 | 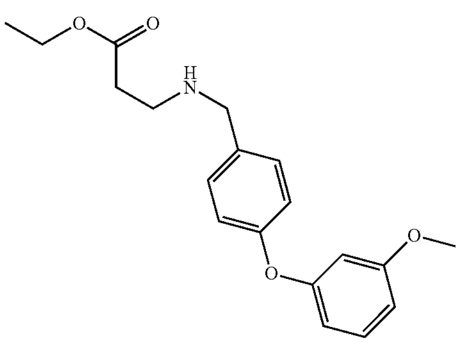 [SMILES: CCOC(=O)CCNCc1ccc(Oc2cccc(OC)c2)cc1] | ¹H NMR (300 MHz, CHLOROFORM-d) δ ppm 1.26 (t, J = 7.1 Hz, 3H) 2.47-2.58 (m, 2 H) 2.85-2.96 (m, 2 H) 3.74-3.80 (m, 5 H) 4.15 (q, J = 7.1 Hz, 2 H) 6.52-6.60 (m, 2 H) 6.64 (ddd, J = 8.3, 2.4, 1.0 Hz, 1 H) 6.93-7.03 (m, 2 H) 7.16-7.32 (m, 3 H). MS ESI/APCI Dual posi: 330[M + H]⁺, 352[M + Na]⁺, MS ESI/APCI Dual nega: 328[M − H]⁻. | |
| Reference Example A-280 | 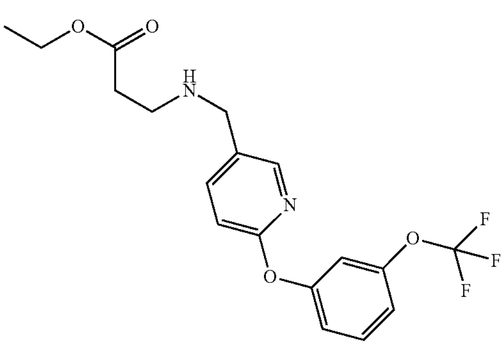 [SMILES: CCOC(=O)CCNCc1ccc(Oc2cccc(OC(F)(F)F)c2)nc1] | ¹H NMR (300 MHz, CHLOROFORH-d) δ ppm 1.20-1.31 (m, 3 H) 2.53 (t, J = 6.4 Hz, 2 H) 2.84-2.93 (m, 2 H) 3.77 (s, 2 H) 4.08-4.25 (m, 2 H) 6.86-6.95 (m, 1 H) 7.00-7.12 (m, 3 H) 7.33-7.44 (m, 1 H) 7.74 (dd J = 8.4, 2.3 Hz, 1 H) 8.06-8.08 (m, 1 H). MS ESI/APCI Dual posi: 385[M + H]⁺, 407[M + Na]⁺. | |

TABLE 18-40-continued

| Compound No. | Structure | Analytical Data | Salt information |
|---|---|---|---|
| Reference Example A-281 | (ethyl 3-{[4-(5-fluoropyridin-2-yloxy)benzyl]amino}propanoate) | ¹H NMR (300 MHz, CHLOROFORM-d) δ ppm 1.20-1.31 (m, 3 H) 2.46-2.58 (m, 2 H) 2.92 (t, J = 6.5 Hz, 2 H) 3.81 (s, 2 H) 4.05-4.24 (m, 2 H) 6.79-6.93 (m, 1 H) 7.01-7.12 (m, 2 H) 7.30-7.48 (m, 3 H) 8.02 (d, J = 3.1 Hz, 1 H). MS ESI/APCI Dual posi: 319[M + H]⁺, 341 [M + Na]⁺. | |

TABLE 18-41

| Compound No. | Structure | Analytical Data | Salt information |
|---|---|---|---|
| Reference Example A-282 | (ethyl 3-{[4-(5-chloropyridin-2-yloxy)benzyl]amino}propanoate) | ¹H NMR (300 MHz, CHLOROFORM-d) δ ppm 1.26 (t, J = 7.1 Hz, 3 H) 2.54 (t, J = 6.5 Hz, 2 H) 2.92 (t, J = 6.5 Hz, 2 H) 3.81 (s, 2 H) 4.15 (q, J = 7.1 Hz, 2 H) 6.73-6.92 (m, 1 H) 7.00-7.13 (m, 2 H) 7.31-7.42 (m, 2 H) 7.56-7.70 (m, 1 H) 8.12 (dd, J = 2.6, 0.6 Hz, 1 H). MS ESI/APCI Dual posi: 335[M + H]⁺, 357[M + Na]⁺. MS ESI/APCI Dual nega: 333[M − H]⁻. | |
| Reference Example A-283 | (ethyl 3-{[2-(4-fluorophenoxy)benzyl]amino}propanoate) | ¹H NMR (300 MHz, CHLOROFORM-d) δ ppm 1.10-1.32 (m, 3 H) 2.40-2.61 (m, 2 H) 2.77-2.96 (m, 2 H) 3.84 (s, 2 H) 4.02-4.21 (m, 2 H) 6.81 (dd, J = 8.1, 1.2 Hz, 1 H) 6.83-7.14 (m, 5 H) 7.16-7.24 (m, 1 H) 7.40 (dd, J = 7.5, 1.9 Hz, 1 H). MS ESI/APCI Dual posi: 318[M + H]⁺, 340[M + Na]⁺. | |
| Reference Example A-284 | (ethyl 3-{[4-(2,2,2-trifluoroethoxy)benzyl]amino}propanoate) | ¹H NMR (300 MHz, CHLOROFORM-d) δ ppm 1.25 (t, J = 7.1 Hz, 3 H) 2.52 (t, J = 6.3 Hz, 2 H) 2.88 (t, J = 6.3 Hz, 2 H) 3.76 (s, 2 H) 4.14 (q, J = 7.1 Hz, 2 H) 4.34 (q, J = 8.1 Hz, 2 H) 6.80-6.95 (m, 2 H) 7.17-7.35 (m, 2 H). MS ESI/APCI Dual posi: 306[K + H]⁺. | |

TABLE 18-41-continued

| Compound No. | Structure | Analytical Data | Salt information |
|---|---|---|---|
| Reference Example A-285 | (structure) | $^1$H NMR (300 MHz, CHLOROFORM-d) δ ppm 1.26 (t, J = 7.1 Hz, 3 H) 2.52 (t, J = 6.4 Hz, 2 H) 2.87 (t, J = 6,4 Hz, 2 H) 3.75 (s, 2 H) 4.15 (q, J = 7.1 Hz, 2 H) 4.40 (q, J = 8.2 Hz. 2 H) 6.94-7.05 (m, 2 H) 7.13 (dd, J = 11.8, 1.7 Hz, 1 H). MS ESI/APCI Dual posi: 324[M + H]$^+$. | |
| Reference Example A-286 | (structure) | $^1$H NMR (300 MHz, CHLOROFORM-d) δ ppm 1.21-1.35 (m, 9 H) 2.54 (s, 2H) 3.84 (s, 2 H) 4.19 (q, J = 7.1 Hz, 2 H) 6.98 (s, 1 H) 7.29-7.37 (m, 1 H) 7.39-7.46 (m, 2 H) 7.80-7.89 (m, 2 H). MS ESI/APCI Dual posi: 302[M + H]$^+$, 324[M + Na]$^+$. MS ESI/APCI Dual nega: 300[M − H]$^-$, 336[M + Cl]$^-$. | |
| Reference Example A-287 | (structure) | $^1$H NMR (300 MHz, CHLOROFORM-d) δ ppm 1.19-1.32 (m, 9 H) 2.50 (s, 2 H) 4.07-4.23 (m, 4 H) 7.30-7.35 (m, 1 H) 7.37-7.45 (m, 3 H) 7.87 (dd, J = 8.3, 1.3 Hz, 2 H). [MS ESI/APCI Dual posi: 319[M + H]$^+$, 341[M + Na]$^+$. | |
| Reference Example A-288 | (structure) | $^1$H NMR (300 MHz, CHLOROFORM-d) δ ppm 1.18-1.35 (m, 9 H) 2.52 (s, 2 H) 3.73-3.81 (m, 2 H) 4.15 (q, J = 7.1 Hz, 2 H) 7.38-7.51 (m, 3 H) 7.60 (s, 1 H) 7.97-8.10 (m, 2 H). MS ESI/APCI Dual posi: 303[M + H]$^+$, 325[M + Na]$^+$. | |

TABLE 18-42

| Compound No. | Structure | Analytical Data | Salt information |
|---|---|---|---|
| Reference Example A-289 | 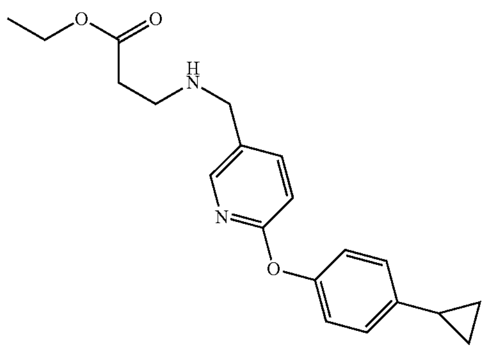 [SMILES: CCOC(=O)CCNCc1ccc(Oc2ccc(C3CC3)cc2)nc1] | $^1$H NMR (300 MHz, CHLOROFORM-d) δ ppm 0.59-0.74 (m, 2 H) 0.86-1.02 (m, 2 H) 1.25 (t, J = 7.0 Hz, 3 H) 1.80-2.01 (m, 1 H) 2.51 (t, J = 6.5 Hz, 2 H) 2.88 (t, J = 6.5 Hz, 2 H) 3.74 (s, 2 H) 4.14 (q, J = 7.0 Hz, 2 H) 6.84 (d, J = 8.4 Hz, 1 H) 6.98-7.04 (m, 2 H) 7.04-7.12 (m, 2 H) 7.66 (dd, J = 8.4, 2.3 Hz, 1 H) 8.10 (d, J = 2.3 Hz, 1 H).<br>MS ESI/APCI Dual posi: 341[M + H]$^+$, 363[M + Na]$^+$.<br>MS ESI/APCI Dual nega: 339[M − H]$^-$. | |
| Reference Example A-290 | 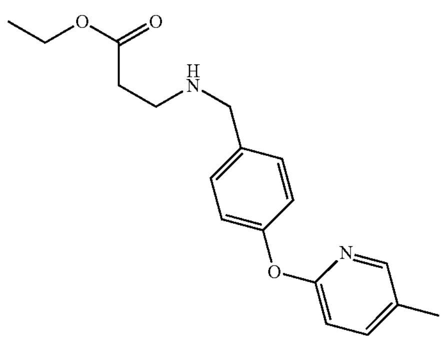 [SMILES: CCOC(=O)CCNCc1ccc(Oc2ccc(C)cn2)cc1] | $^1$H NMR (300 MHz, CHLOROFORM-d) δ ppm 1.26 (t, J = 7.1 Hz, 3 H) 2.27 (s, 3 H) 2.53 (t, J = 6.5 Hz, 2 H) 2.92 (t, J = 6.5 Hz, 2 H) 3.80 (s, 2 H) 4.15 (q, J = 7.1 Hz, 2 H) 6.73-6.84 (m, 1 H) 7.03-7.09 (m, 2 H) 7.30-7.36 (m, 2 H) 7.45-7.54 (m, 1 H) 7.96-8.05 (m, 1 H).<br>MS ESI/APCI Dual posi: 315[M + H]$^+$, 337[M + Na]$^+$.<br>MS ESI/APCI Dual nega: 313[M − H]$^-$. | |
| Reference Example A-291 | 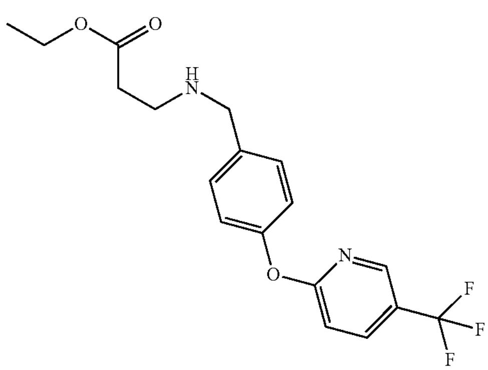 [SMILES: CCOC(=O)CCNCc1ccc(Oc2ccc(C(F)(F)F)cn2)cc1] | $^1$H NMR (300 MHz, CHLOROFORM-d) δ ppm 1.27 (t, J = 7.1 Hz, 3 H) 2.55 (t, J = 6.5 Hz, 2 H) 2.93 (t, J = 6.5 Hz, 2 H) 3.83 (s, 2 H) 4.15 (q, J = 7.1 Hz, 2 H) 6.96-7.03 (m, 1 H) 7.06-7.14 (m, 2 H) 7.35-7.43 (m, 2 H) 7.84-7.92 (m, 1 H) 8.40-8.47 (m, 1 H).<br>MS ESI/APCI Dual posi: 369[M + H]$^+$, 391[M + Na]$^+$.<br>MS ESI/APCI Dual nega: 367[M − H]$^-$, 403[M + Cl]$^-$. | |
| Reference Example A-292 | 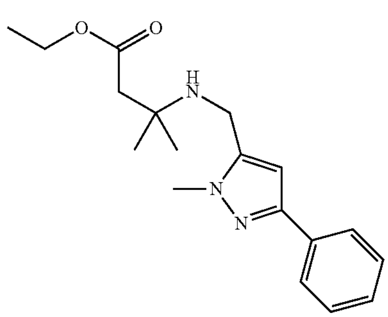 [SMILES: CCOC(=O)CC(C)(C)NCc1cc(-c2ccccc2)nn1C] | $^1$H NMR (300 MHz, CHLOROFORM-d) δ ppm 1.18-1.32 (m, 9 H) 2.49 (s, 2 H) 3.77 (s, 2 H) 3.93 (s, 3 H) 4.14 (q, J = 7.0 Hz, 2 H) 6.46 (s, 1 H) 7.23-7.30 (m, 1 H) 7.33-7.40 (m, 2 H) 7.72-7.79 (m, 2 H).<br>MS ESI/APCI Dual posi: 316[M + H]$^+$, 338[M + Na]$^+$. | |

TABLE 18-42-continued

| Compound No. | Structure | Analytical Data | Salt information |
|---|---|---|---|
| Reference Example A-293 | 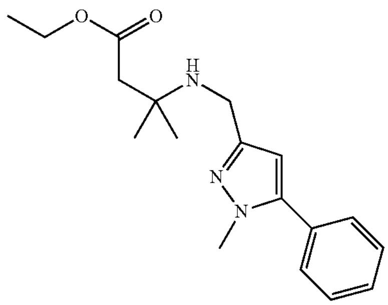 [SMILES: CCOC(=O)CC(C)(C)NCc1cc(-c2ccccc2)n(C)n1] | ¹H NMR (300 MHz, CHLOROFORM-d) δ ppm 1.20-1.33 (m, 9 H) 2.52 (s, 2 H) 3.78 (s, 2 H) 3.83 (s, 3 H) 4.14 (q, J = 7.1 Hz, 2 H) 6.27 (s, 1 H) 7.33-7.50 (m, 5 H). MS ESI/APCI Dual posi: 316[M + H]⁺, 338[M + Na]⁺. | |
| Reference Example A-294 | 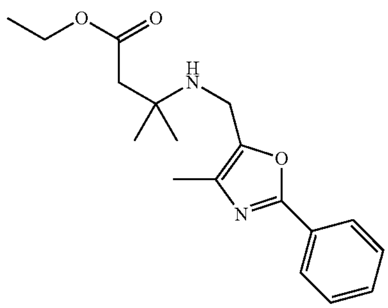 [SMILES: CCOC(=O)CC(C)(C)NCc1oc(-c2ccccc2)nc1C] | ¹H NMR (300 MHz, CHLOROFORM-d) δ ppm 1.15-1.34 (m, 9 H) 2.23 (s, 3 H) 2.50 (s, 2 H) 3.81 (s, 2 H) 4.15 (q, J = 7.1 Hz, 2 H) 7.36-7.48 (m, 3 H) 7.94-8.06 (m, 2 H). MS ESI/APCI Dual posi: 317[M + H]⁺, 339[M + Na]⁺. | |
| Reference Example A-295 | 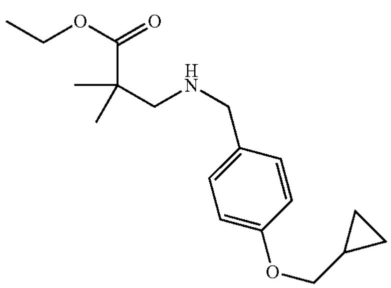 [SMILES: CCOC(=O)C(C)(C)CNCc1ccc(OCC2CC2)cc1] | ¹H NMR (300 MHz, CHLOROFORM-d) δ ppm 0.26-0.41 (m, 2 H) 0.57-0.70 (m, 2 H) 1.17 (s, 6 H) 1.20-1.26 (m, 4 H) 2.63 (s, 2 H) 3.71 (s, 2 H) 3.78 (d, J = 6.8 Hz, 2 H) 4.12 (q, J = 7.1 Hz, 2 H) 6.81-6.87 (m, 2 H) 7.17-7.22 (m, 2 H). MS ESI/APCI Dual posi: 306[M + H]⁺. | |

TABLE 18-43

| Compound No. | Structure | Analytical Data | Salt information |
|---|---|---|---|
| Reference Example A-296 | 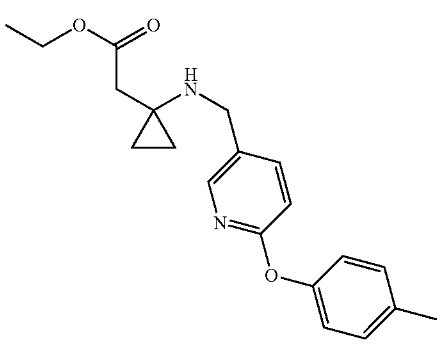 [SMILES: CCOC(=O)CC1(NCc2ccc(Oc3ccc(C)cc3)nc2)CC1] | ¹H NMR (300 MHz, CHLOROFORM-d) δ ppm 0.46-0.56 (m, 2 H) 0.66-0.76 (m, 2 H) 1.27 (t, J = 7.1 Hz, 3 H) 2.35 (s, 3 H) 2.49 (s, 2 H) 3.76 (s, 2 H) 4.17 (q, J = 7.0 Hz, 2 H) 6.82 (d, J = 8.4 Hz, 1 H) 6.95-7.03 (m, 2 H) 7.14-7.21 (m, 2 H) 7.63 (dd, J = 8.4, 2.5 Hz, 1 H) 8.08 (d, J = 2.5 Hz, 1 H). MS ESI/APCI Dual posi: 341[M + H]⁺. | |

TABLE 18-43-continued

| Compound No. | Structure | Analytical Data | Salt information |
|---|---|---|---|
| Reference Example A-297 | 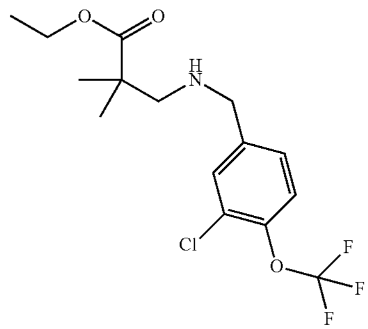 [SMILES: CCOC(=O)C(C)(C)CNCc1ccc(OC(F)(F)F)c(Cl)c1] | $^1$H NMR (300 MHz, CHLOROFORM-d) δ ppm 1.20 (s, 6 H) 1.24 (t, J = 7.1 Hz, 3 H) 2.63 (s, 2 H) 3.77 (s, 2 H) 4.13 (q, J = 7.1 Hz, 2 H) 7.23-7.25 (m, 2 H) 7.44-7.46 (m, 1 H). MS ESI/APCI Dual posi: 354[M + H]$^+$. | |
| Reference Example A-298 | 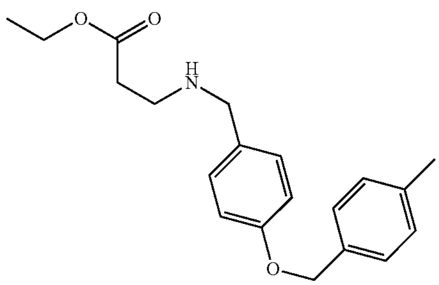 [SMILES: CCOC(=O)CCNCc1ccc(OCc2ccc(C)cc2)cc1] | $^1$H NMR (300 MHz, CHLOROFORM-d) δ ppm 1.25 (t, J = 7.1 Hz, 3 H) 2.36 (s, 3 H) 2.52 (t, J = 6.5 Hz, 2 H) 2.88 (t, J = 6.5 Hz, 2 H) 3.73 (s, 2 H) 4.13 (q, J = 7.1 Hz, 2 H) 5.01 (s, 2 H) 6.88-6.95 (m, 2 H) 7.16-7.24 (m, 4 H) 7.29-7.35 (m, 2 H). MS ESI/APCI Dual posi: 328[M + H]$^+$, 350[M + Na]$^+$. MS ESI/APCI Dual nega: 326[M − H]$^-$. | |
| Reference Example A-299 | 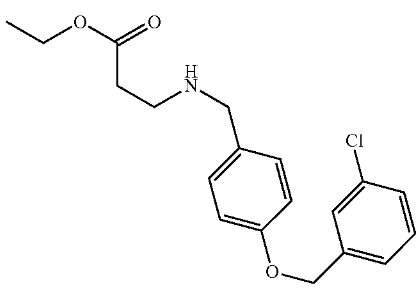 [SMILES: CCOC(=O)CCNCc1ccc(OCc2cccc(Cl)c2)cc1] | $^1$H NMR (300 MHz, CHLOROFORM-d) δ ppm 1.25 (t, J = 7.1 Hz, 3 H) 2.52 (t, J = 6.5 Hz, 2 H) 2.89 (t, J = 6.5 Hz, 2 H) 3.74 (s, 2 H) 4.14 (q, J = 7.1 Hz, 2 H) 5.03 (s, 2 H) 6.83-6.95 (m, 2 H) 7.22-7.26 (m, 2 H) 7.28-7.32 (m, 3 H) 7.42-7.45 (m, 1 H). MS ESI/APCI Dual posi: 348[M + H]$^+$, 370[M + Na]$^+$. MS ESI/APCI Dual nega: 346[M − H]$^-$, 382[M + Cl]$^-$. | |
| Reference Example A-300 | 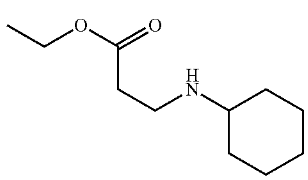 | $^1$H NMR (300 MHz, CHLOROFORM-d) δ ppm 0.96-1.34 (m, 8 H) 1.58-1.65 (m, 1 H) 1.67-1.79 (m, 2 H) 1.80-1.94 (m, 2 H) 2.36-2.54 (m, 3 H) 2.90 (t, J = 6.6 Hz, 2 H) 4.14 (q, J = 7.0 Hz, 2 H). MS ESI/APCI Dual posi: 200[M + H]$^+$. | |

TABLE 18-44

| Compound No. | Structure | Analytical Data | Salt information |
|---|---|---|---|
| Reference Example A-301 | 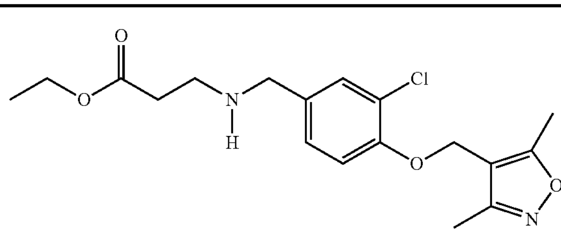 | $^1$H NMR (300 MHz, CHLOROFORM-d) δ ppm 1.26 (t, J = 7.1 Hz, 3 H) 2.32 (s, 3 H) 2.40 (s, 3 H) 2.48-2.56 (m, 2 H) 2.84-2.91 (m, 2 H) 3.73 (s, 2 H) 4.15 (q, J = 7.1 Hz, 2 H) 4.85 (s, 2 H) 6.92 (d, J = 8.2 Hz, 1 H) 7.18 (dd, J = 8.2, 2.2 Hz, 1 H) 7.36 (d, J = 2.2 Hz, 1 H). MS ESI/APCI Dual posi: 367[M + H]$^+$, 389[M + Na]$^+$. MS ESI/APCI Dual nega: 365[M − H]$^-$. | |

TABLE 18-44-continued

| Compound No. | Structure | Analytical Data | Salt information |
|---|---|---|---|
| Reference Example A-302 | 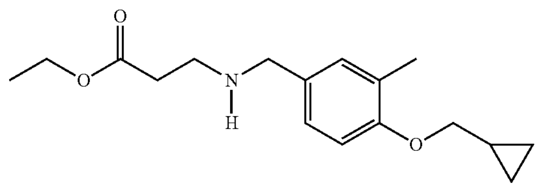 [SMILES: CCOC(=O)CCNCc1ccc(OCC2CC2)c(C)c1] | $^1$H NMR (300 MHz, CHLOROFORM-d) δ ppm 0.27-0.41 (m, 2 H) 0.54-0.66 (m, 2 H) 1.15-1.33 (m, 4 H) 2.24 (s, 3 H) 2.44-2.58 (m, 2 H) 2.82-2.97 (m, 2 H) 3.70 (s, 2 H) 3.80 (d, J = 6.7 Hz, 2 H) 4.13 (q, J = 7.1 Hz, 2 H) 6.73 (d, J = 8.1 Hz, 1 H) 6.98-7.13 (m, 2 H). MS ESI/APCI Dual posi: 292[M + H]$^+$. | |
| Reference Example A-303 | 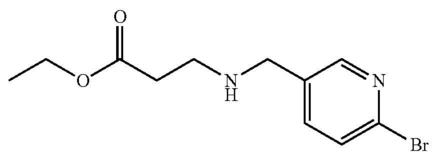 [SMILES: CCOC(=O)CCNCc1ccc(Br)nc1] | $^1$H NMR (300 MHz, CHLOROFORM-d) δ ppm 1.26 (t, J = 7.1 Hz, 3 H) 2.52 (t, J = 6.3 Hz, 2 H) 2.87 (t, J = 6.3 Hz, 2 H) 3.78 (s, 2 H) 4.15 (q, J = 7.1 Hz, 2 H) 7.40-7.47 (m, 1 H) 7.53-7.60 (m, 1 H) 8.31 (d, J = 2.3 Hz, 1 H). MS ESI/APCI Dual posi: 287[M + H]$^+$. | |
| Reference Example A-304 | 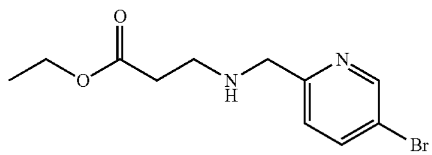 [SMILES: CCOC(=O)CCNCc1ccc(Br)cn1] | $^1$H NMR (300 MHz, CHLOROFORM-d) δ ppm 1.22-1.32 (m, 3 H) 2.54 (t, J = 6.5 Hz, 2 H) 2.92 (t, J = 6.5 Hz, 2 H) 3.89 (s, 2 H) 4.08-4.21 (m, 2 H) 7.22-7.29 (m, 1 H) 7.77 (dd, J = 8.2, 2.3 Hz, 1 H) 8.61 (d, J = 2.3 Hz, 1 H). MS ESI/APCI Dual posi: 287[M + H]$^+$. | |
| Reference Example A-305 | 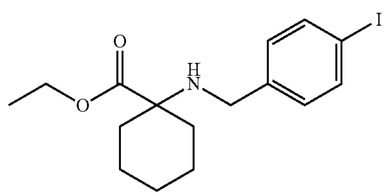 [SMILES: CCOC(=O)C1(NCc2ccc(I)cc2)CCCCC1] | $^1$H NMR (300 MHz, CHLOROFORM-d) δ ppm 1.16-2.00 (m, 13 H) 3.52 (s, 2 H) 4.05-4.26 (m, 2 H) 7.10 (d, J = 8.4 Hz, 2 H) 7.63 (d, J = 8.4 Hz, 2 H). MS ESI/APCI Dual posi: 388[M + H]$^+$. | |
| Reference Example A-306 | 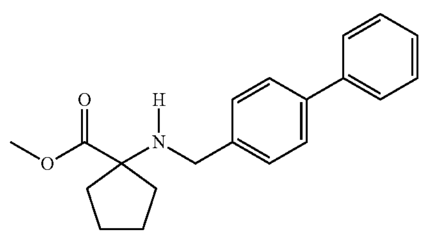 [SMILES: COC(=O)C1(NCc2ccc(-c3ccccc3)cc2)CCCC1] | $^1$H NMR (600 MHz, CHLOROFORM-d) δ ppm 1.67-1.81 (m, 4 H) 1.81-1.90 (m, 2 H) 2.04-2.12 (m, 2 H) 3.65 (s, 2 H) 3.74 (s, 3 H) 7.30-7.35 (m, 1 H) 7.38-7.45 (m, 4 H) 7.51-7.60 (m, 4 H). MS ESI posi: 310[M + H]$^+$. | |
| Reference Example A-307 | 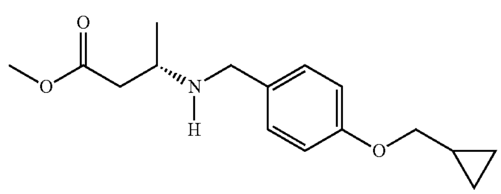 [SMILES: COC(=O)C[C@H](C)NCc1ccc(OCC2CC2)cc1] | $^1$H NMR (300 MHz, CHLOROFORM-d) δ ppm 0.30-0.38 (m, 2 H) 0.59-0.68 (m, 2 H) 1.15 (d, J = 6.4 Hz, 3 H) 1.19-1.35 (m, 1 H) 2.33-2.55 (m, 2 H) 3.08-3.21 (m, 1 H) 3.67 (s, 3 H) 3.65-3.82 (m, 2 H) 3.78 (d, J = 7.0 Hz, 2 H) 6.82-6.89 (m, 2 H) 7.18-7.25 (m, 2 H). MS ESI/APCI Dual posi: 278[M + H]$^+$. | |

TABLE 18-45

| Compound No. | Structure | Analytical Data | Salt information |
|---|---|---|---|
| Reference Example A-308 | 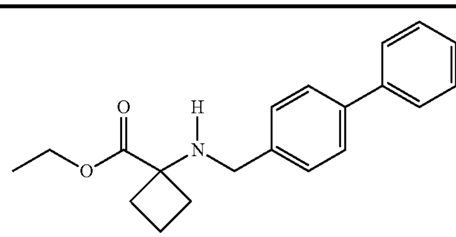 | $^1$H NMR (600 MHz, CHLOROFORM-d) δ ppm 1.31 (t, J = 7.2 Hz, 3 H) 1.90-2.13 (m, 4 H) 2.41-2.49 (m, 2 H) 3.63 (s, 2 H) 4.21 (q, J = 7.2 Hz, 2 H) 7.30-7.36 (m, 1 H) 7.39-7.46 (m, 4 H) 7.52-7.60 (m, 4 H). MS ESI posi: 310[M + H]$^+$. | |

TABLE 18-45-continued

| Compound No. | Structure | Analytical Data | Salt information |
|---|---|---|---|
| Reference Example A-309 | 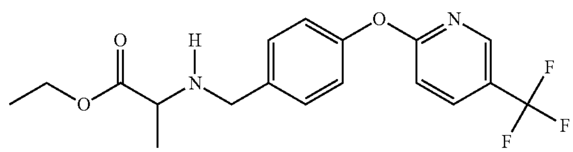 [SMILES: CCOC(=O)C(C)NCc1ccc(Oc2ccc(C(F)(F)F)cn2)cc1] | $^1$H NMR (300 MHz, CHLOROFORM-d) δ ppm 1.19-1.39 (m, 6 H) 3.40 (q, J = 7.1 Hz, 1 H) 3.69 (d, J = 12.9 Hz, 1 H) 3.79-3.87 (m, 1 H) 4.21 (q, J = 7.1 Hz, 2 H) 7.00 (d, J = 8.7 Hz, 1 H) 7.06-7.14 (m, 2 H) 7.40 (d, J = 8.7 Hz, 2 H) 7.83-7.93 (m, 1 H) 8.40-8.48 (m, 1 H). MS ESI/APCI Dual posi: 369[M + H]$^+$, 391[M + Na]$^+$ MS ESI/APCI Dual nega: 367[M − H]$^-$ | |
| Reference Example A-310 | 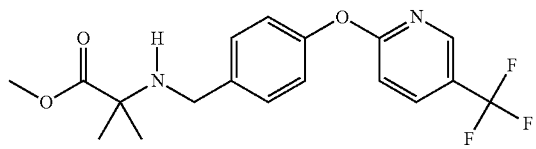 [SMILES: COC(=O)C(C)(C)NCc1ccc(Oc2ccc(C(F)(F)F)cn2)cc1] | $^1$H NMR (300 MHz, CHLOROFORM-d) δ ppm 1.39 (s, 6 H) 3.65 (s, 2 H) 3.75 (s, 3 H) 6.94-7.02 (m, 1 H) 7.10 (d, J = 8.5 Hz, 2 H) 7.41 (d, J = 8.7 Hz, 2 H) 7.81-7.93 (m, 1 H) 8.37-8.50 (m, 1 H). MS ESI/APCI Dual posi: 369[M + H]$^+$, 391[M + Na]$^+$. MS ESI/APCI Dual nega: 367[M − H]$^-$. | |
| Reference Example A-311 | 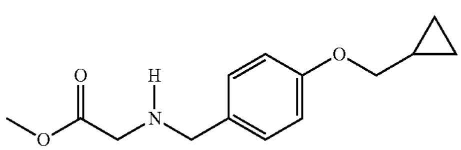 [SMILES: COC(=O)CNCc1ccc(OCC2CC2)cc1] | $^1$H NMR (300 MHz, CHLOROFORM-d) δ ppm 0.26-0.40 (m, 2 H) 0.56-0.70 (m, 2 H) 1.17-1.35 (m, 1 H) 3.41 (s, 2 H) 3.62-3.88 (m, 7 H) 6.86 (d, J = 8.5 Hz, 2 H) 7.15-7.30 (m, 2 H). MS ESI/APCI Dual posi: 250[M + H]$^+$, 272[M + Na]$^+$. | |
| Reference Example A-312 | 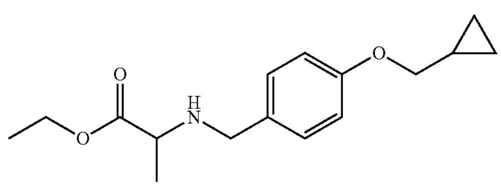 [SMILES: CCOC(=O)C(C)NCc1ccc(OCC2CC2)cc1] | $^1$H NMR (300 MHz, CHLOROFORM-d) δ ppm 0.27-0.42 (m, 2 H) 0.54-0.73 (m, 2 H) 1.15-1.36 (m, 7 H) 3.24-3.43 (m, 1 H) 3.54-3.65 (m, 1 H) 3.66-3.84 (m, 3 H) 4.19 (d, J = 7.1 Hz, 2 H) 6.82-6.91 (m, 2 H) 7.22 (d, J = 8.4 Hz, 2 H). MS ESI/APCI Dual posi: 278[M + H]$^+$, 300[M + Na]$^+$. | |
| Reference Example A-313 | 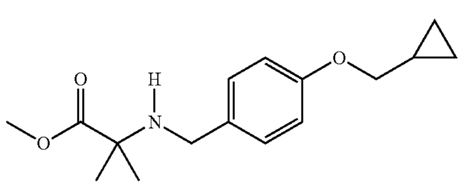 [SMILES: COC(=O)C(C)(C)NCc1ccc(OCC2CC2)cc1] | $^1$H NMR (300 MHz, CHLOROFORM-d) δ ppm 0.29-0.37 (m, 2 H) 0.60-0.66 (m, 2 H) 1.18-1.33 (m, 1 H) 1.36 (s, 6 H) 3.54 (s, 2 H) 3.74 (s, 3 H) 3.78 (d, J = 7.0 Hz, 2 H) 6.85 (d, J = 8.5 Hz, 2 H) 7.23 (d, J = 8.5 Hz, 2 H). MS ESI/APCI Dual posi: 278[M + H]$^+$, 300[M + Na]$^+$. | |
| Reference Example A-314 | 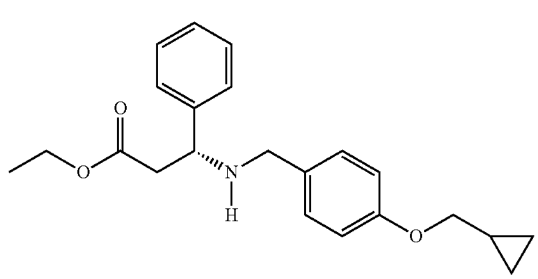 [SMILES: CCOC(=O)C[C@@H](NCc1ccc(OCC2CC2)cc1)c1ccccc1] | $^1$H NMR (300 MHz, CHLOROFORM-d) δ ppm 0.26-0.44 (m, 2 H) 0.56-0.69 (m, 2 H) 1.06-1.32 (m, 4 H) 2.46-2.78 (m, 2 H) 3.37-3.51 (m, 1 H) 3.53-3.63 (m, 1 H) 3.78 (d, J = 6.8 Hz, 2 H) 3.97-4.19 (m, 3 H) 6.80-6.87 (m, 2 H) 7.12-7.19 (m, 2 H) 7.23-7.37 (m, 5 H). MS ESI/APCI Dual posi: 354[M + H]$^+$, 376[M + Na]$^+$. MS ESI/APCI Dual nega: 352[M − H]$^-$. | |

TABLE 18-46

| Compound No. | Structure | Analytical Data | Salt information |
|---|---|---|---|
| Reference Example A-315 | (structure) | ¹H NMR (300 MHz, CHLOROFORM-d) δ ppm 0.24-0.40 (m, 2 H) 0.57-0.69 (m, 2 H) 1.18 (t, J = 7.1 Hz, 3 H) 1.22-1.35 (m, 1 H) 2.51-2.79 (m, 2 H) 3.38-3.51 (m, 1 H) 3.54-3.63 (m, 1 H) 3.78 (d, J = 7.1 Hz, 2 H) 4.02-4.17 (m, 3 H) 6.76-6.92 (m, 2 H) 7.16 (d, J = 8.7 Hz, 2 H) 7.23-7.42 (m, 5 H). MS ESI/APCI Dual posi: 354[M + H]⁺, 376[M + Na]⁺. MS ESI/APCI Dual nega: 352[M − H]⁻. | |
| Reference Example A-316 | (structure) | ¹H NMR (300 MHz, CHLOROFORM-d) δ ppm 0.30-0.38 (m, 2 H) 0.59-0.68 (m, 2 H) 1.15 (d, J = 6.4 Hz, 3 H) 1.19-1.35 (m, 1 H) 2.33-2.55 (m, 2 H) 3.08-3.21 (m, 1 H) 3.67 (s, 3 H) 3.65-3.82 (m, 2 H) 3.78 (d, J = 7.0 Hz, 2 H) 6.82-6.89 (m, 2 H) 7.18-7.25 (m, 2 H). MS ESI/APCI Dual posi: 278[M + H]⁺. | |
| Reference Example A-317 | (structure) | ¹H NMR (300 MHz, CHLOROFORM-d) δ ppm 0.30-0.38 (m, 2 H) 0.59-0.68 (m, 2 H) 1.20-1.34 (m, 1 H) 1.64-1.71 (m, 4 H) 2.57 (s, 2 H) 3.58-3.70 (m, 7 H) 3.79 (d, J = 7.0 Hz, 2 H) 3.85-3.95 (m, 2 H) 6.83-6.90 (m, 2 H) 7.24-7.31 (m, 2 H). MS ESI/APCI Dual posi: 334[M + H]⁺. | |
| Reference Example A-318 | (structure) | ¹H NMR (300 MHz, CHLOROFORM-d) δ ppm 0.31-0.38 (m, 2 H) 0.60-0.68 (m, 2 H) 1.19-1.35 (m, 4 H) 2.96 (s, 2 H) 3.74-3.81 (m, 4 H) 4.11-4.21 (m, 2 H) 4.53 (d, J = 6.8 Hz, 2 H) 4.66 (d, J = 6.8 Hz, 2 H) 6.82-6.90 (m, 2 H) 7.20-7.28 (m, 2 H). MS ESI/APCI Dual posi: 320[M + H]⁺. | |
| Reference Example A-319 | (structure) | ¹H NMR (300 MHz, CHLOROFORM-d) δ ppm 0.29-0.40 (m, 2 H) 0.60-0.70 (m, 2 H) 1.17-1.34 (m, 1 H) 2.76-2.82 (m, 2 H) 3.48 (dd, J = 6.8, 4.9 Hz, 1 H) 3.69 (s, 3 H) 3.73 (d, J = 2.8 Hz, 2 H) 3.79 (d, J = 6.8 Hz, 2 H) 5.36-5.53 (m, 1 H) 6.87 (d, J = 8.7 Hz, 2 H) 7.14-7.24 (m, 2 H). MS ESI/APCI Dual posi: 307[M + H]⁺, 329[M + Na]⁺. | |
| Reference Example A-320 | (structure) | ¹H NMR (300 MHz, CHLOROFORM-d) δ ppm 0.29-0.40 (m, 2 H) 0.58-0.70 (m, 2 H) 1.17-1.35 (m, 1 H) 2.76-2.84 (m, 2 H) 3.43-3.54 (m, 1 H) 3.69 (s, 3 H) 3.73 (d, J = 2.6 Hz, 2 H) 3.79 (d, J = 7.0 Hz, 2 H) 5.42 (br. s., 1 H) 6.80-6.94 (m, 2 H) 7.21 (d, J = 8.7 Hz, 2 H). MS ESI/APCI Dual posi: 307[M + H]⁺, 329[M + Na]⁺. | |
| Reference Example A-321 | (structure) | ¹H NMR (300 MHz, CHLOROFORM-d) δ ppm 1.10-1.30 (m, 10 H) 1.57-1.78 (m, 1 H) 1.80-1.91 (m, 2 H) 2.38-2.47 (m, 4 H) 2.80-2.93 (m, 2 H) 4.08-4.18 (m, 2 H) 4.70-4.81 (m, 2 H) 6.42 (t, J = 4.8 Hz, 1 H) 8.28 (d, J = 4.8 Hz, 2 H). MS ESI/APCI Dual posi: 321[M + H]⁺. | |

TABLE 18-47

| Compound No. | Structure | Analytical Data | Salt information |
|---|---|---|---|
| Reference Example A-322 | 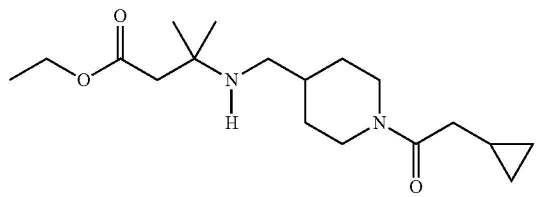 [SMILES: CCOC(=O)CC(C)(C)NCC1CCN(C(=O)CC2CC2)CC1] | ¹H NMR (300 MHz, CHLOROFORM-d) δ ppm 0.13-0.21 (m, 2 H) 0.51-0.59 (m, 2 H) 0.97-1.31 (m, 12 H) 1.53-1.69 (m, 1 H) 1.77-1.89 (m, 2 H) 2.24-2.29 (m, 2 H) 2.37-2.46 (m, 4 H) 2.48-2.62 (m, 1 H) 2.94-3.06 (m, 1 H) 3.78-3.89 (m, 1 H) 4.07-4.20 (m, 2 H) 4.59-4.70 (m, 1 H). MS ESI/APCI Dual posi: 325[M + H]⁺. | |
| Reference Example A-323 | 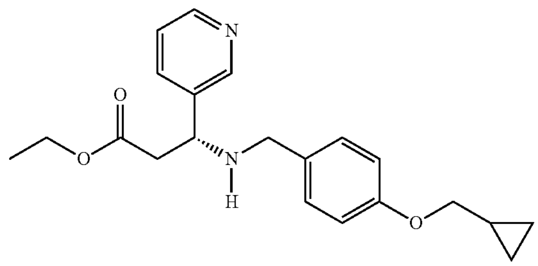 [SMILES: CCOC(=O)C[C@@H](NCc1ccc(OCC2CC2)cc1)c1cccnc1] | ¹H NMR (300 MHz, CHLOROFORM-d) δ ppm 0.28-0.43 (m, 2 H) 0.57-0.74 (m, 2 H) 1.12-1.33 (m, 4 H) 2.47-2.85 (m, 2 H) 3.40-3.52 (m, 1 H) 3.54-3.63 (m, 1 H) 3.78 (d, J = 7.0 Hz, 2 H) 3.98-4.19 (m, 3 H) 6.76-6.89 (m, 2 H) 7.08-7.19 (m, 2 H) 7.29 (ddd, J = 7.8, 4.8, 0.8 Hz, 1 H) 7.73 (dt, J = 7.8 2.0 Hz, 1 H) 8.48-8.62 (m, 2 H). MS ESI/APCI Dual posi: 355 M + H]⁺, 377[M + Na]⁺. | |
| Reference Example A-324 | 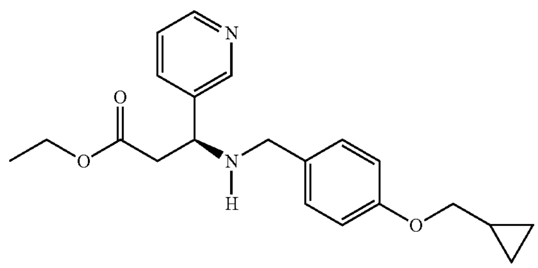 [SMILES: CCOC(=O)C[C@H](NCc1ccc(OCC2CC2)cc1)c1cccnc1] | ¹H NMR (300 MHz, CHLOROFORM-d) δppm 0.28-0.43 (m, 2 H) 0.57-0.70 (m, 2 H) 1.13-1.33 (m, 4 H) 2.53-2.81 (m, 2 H) 3.41-3.52 (m, 1 H) 3.53-3.64 (m, 1 H) 3.78 (d, J = 6.8 Hz, 2 H) 4.02-4.18 (m, 3 H) 6.78-6.92 (m, 2 H) 7.14 (d, J = 8.7 Hz, 2 H) 7.26-7.34 (m, 1 H) 7.73 (dt, J = 7.9, 1.9 Hz, 1 H) 8.48-8.63 (m, 2 H). MS ESI/APCI Dual posi: 355[M + H]⁺, 377[M + Na]⁺. | |
| Reference Example A-325 | 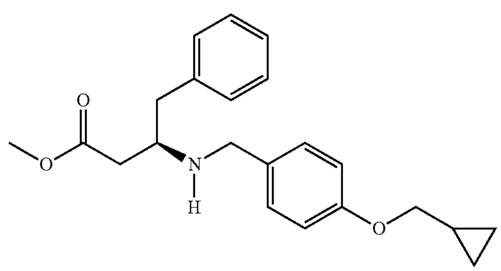 [SMILES: COC(=O)C[C@@H](Cc1ccccc1)NCc1ccc(OCC2CC2)cc1] | ¹H NMR (300 MHz, CHLOROFORM-d) δ ppm 0.30-0.39 (m, 2 H) 0.58-0.68 (m, 2 H) 1.19-1.34 (m, 1 H) 2.42 (d, J = 6.4 Hz, 2 H) 2.68-2.91 (m, 2 H) 3.21-3.32 (m, 1 H) 3.65 (s, 3 H) 3.71-3.81 (m, 4 H) 6.78-6.86 (m, 2 H) 7.09-7.34 (m, 7 H). MS ESI/APCI Dual posi: 354 [M + H]⁺. | |
| Reference Example A-326 | 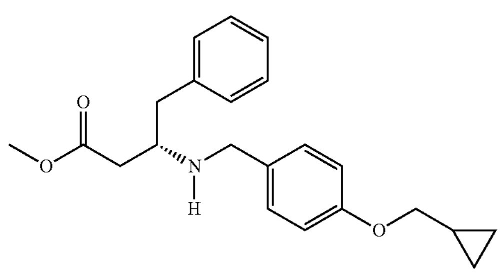 [SMILES: COC(=O)C[C@H](Cc1ccccc1)NCc1ccc(OCC2CC2)cc1] | ¹H NMR (300 MHz, CHLOROFORM-d) δ ppm 0.30-0.39 (m, 2 H) 0.58-0.68 (m, 2 H) 1.19-1.34 (m, 1 H) 2.42 (d, J = 6.4 Hz, 2 H) 2.68-2.91 (m, 2 H) 3.21-3.32 (m, 1 H) 3.65 (s, 3 H) 3.71-3.81 (m, 4 H) 6.78-6.86 (m, 2 H) 7.09-7.34 (m, 7 H). MS ESI/APCI Dual posi: 354 [M + H]⁺. | |
| Reference Example A-327 | 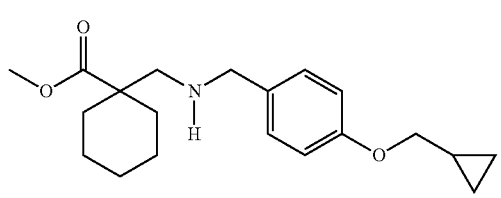 [SMILES: COC(=O)C1(CNCc2ccc(OCC3CC3)cc2)CCCCC1] | ¹H NMR (300 MHz, CHLOROFORM-d) δ ppm 0.20-0.49 (m, 2 H) 0.56-0.72 (m, 2 H) 1.10-1.63 (m, 9 H) 1.91-2.18 (m, 2 H) 2.64 (s, 2 H) 3.68 (s, 5 H) 3.74-3.84 (m, 2 H) 6.84 (d, J = 8.7 Hz, 2 H) 7.18 (d, J = 8.7 Hz, 2 H). MS ESI/APCI Dual posi: 332[M + H]⁺, 354[M + Na]⁺. | |

TABLE 18-47-continued

| Compound No. | Structure | Analytical Data | Salt information |
|---|---|---|---|
| Reference Example A-328 | 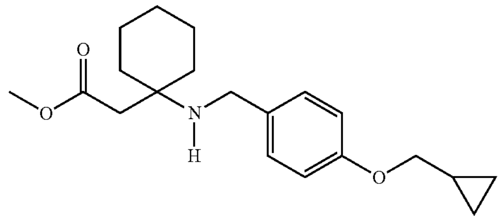 [SMILES: COC(=O)CC1(NCc2ccc(OCC3CC3)cc2)CCCCC1] | ¹H NMR (300 MHz, CHLOROFORM-d) δ ppm 0.25-0.40 (m, 2 H) 0.56-0.69 (m, 2 H) 1.17-1.76 (m, 11 H) 2.52 (s, 2 H) 3.60 (s, 2 H) 3.67 (s, 3 H) 3.78 (d, J = 6.8 Hz, 2 H) 6.85 (d, J = 8.7 Hz, 2 H). MS ESI/APCI Dual posi: 332[M + H]⁺, 354[M + Na]⁺. | |

TABLE 18-48

| Compound No. | Structure | Analytical Data | Salt information |
|---|---|---|---|
| Reference Example A-329 | 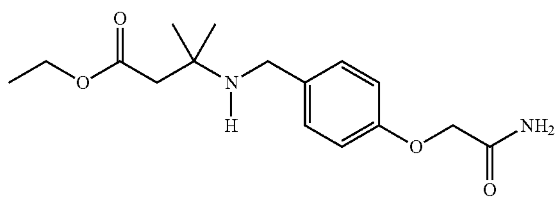 [SMILES: CCOC(=O)CC(C)(C)NCc1ccc(OCC(N)=O)cc1] | ¹H NMR (300 MHz, CHLOROFORM-d) δ ppm ppm 1.18-1.33 (m, 9 H) 2.50 (s, 2 H) 3.67 (s, 2 H) 4.14 (q, J = 7.1 Hz, 2 H) 4.48 (s, 2 H) 6.87 (d, J = 8.7 Hz, 2 H) 7.31 (d, J = 8.7 Hz, 2 H). MS ESI/APCI Dual posi: 309[M + H]⁺, 331[M + Na]⁺. MS ESI/APCI Dual nega: 307[M − H]⁻. | |
| Reference Example A-330 | 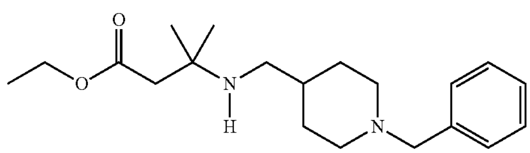 [SMILES: CCOC(=O)CC(C)(C)NCC1CCN(Cc2ccccc2)CC1] | ¹H NMR (300 MHz, CHLOROFORM-d) δ ppm 1.14 (s, 6 H) 1.18-1.45 (m, 4 H) 1.59-1.79 (m, 4 H) 1.88-2.01 (m, 2 H) 2.35-2.44 (m, 4 H) 2.82-2.94 (m, 2 H) 3.48 (s, 2 H) 4.12 (q, J = 7.2 Hz, 2 H) 7.18-7.36 (m, 5 H). MS ESI/APCI Dual posi: 333[M + H]⁺. | |
| Reference Example A-331 | 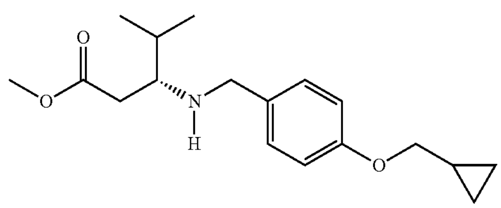 [SMILES: COC(=O)C[C@@H](NCc1ccc(OCC2CC2)cc1)C(C)C] | ¹H NMR (300 MHz, CHLOROFORM-d) δ ppm 0.29-0.39 (m, 2 H) 0.58-0.67 (m, 2 H) 0.88-0.92 (m, 6 H) 1.19-1.34 (m, 1 H) 1.79-1.95 (m, 1 H) 2.27-2.50 (m, 2 H) 2.80-2.92 (m, 1 H) 3.67 (s, 3 H) 3.70 (s, 2 H) 3.75-3.82 (m, 2 H) 6.84 (d, J = 8.7 Hz, 2 H) 7.18-7.26 (m, 2 H). MS ESI/APCI Dual posi: 306[M + H]⁺, 328[M + Na]⁺. | |
| Reference Example A-332 | 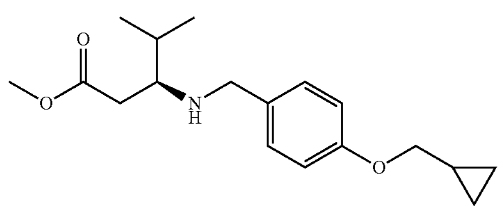 [SMILES: COC(=O)C[C@H](NCc1ccc(OCC2CC2)cc1)C(C)C] | ¹H NMR (300 MHz, CHLOROFORM-d) δ ppm 0.29-0.39 (m, 2 H) 0.59-0.69 (m, 2 H) 0.85-1.00 (m, 6 H) 1.18-1.35 (m, 1 H) 1.79-1.95 (m, 1 H) 2.26-2.50 (m, 2 H) 2.81-2.95 (m, 1 H) 3.67 (s, 3 H) 3.70 (s, 2 H) 3.78 (d, J = 6.8 Hz, 2 H) 6.85 (d, J = 8.4 Hz, 2 H) 7.22 (d, J = 8.4 Hz, 2 H). MS ESI/APCI Dual posi: 306[M + H]⁺, 328[M + Na]⁺. | |
| Reference Example A-333 | 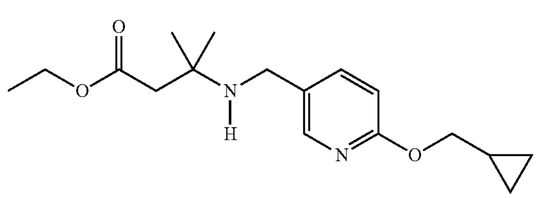 [SMILES: CCOC(=O)CC(C)(C)NCc1ccc(OCC2CC2)nc1] | ¹H NMR (300 MHz, CHLOROFORM-d) δ ppm 0.28-0.39 (m, 2 H) 0.56-0.63 (m, 2 H) 1.19-1.36 (m, 10 H) 2.50 (s, 2 H) 3.63 (s, 2 H) 4.02-4.20 (m, 4 H) 6.73 (d, J = 8.5 Hz, 1 H) 7.61 (dd, J = 8.5, 2.4 Hz, 1 H) 8.02-8.07 (m, 1 H). MS ESI/APCI Dual posi: 307[M + H]⁺, 329[M + Na]⁺. | |

TABLE 18-48-continued

| Compound No. | Structure | Analytical Data | Salt information |
|---|---|---|---|
| Reference Example A-334 | 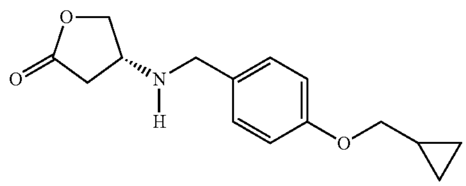 [SMILES: O=C1C[C@@H](NCc2ccc(OCC3CC3)cc2)CO1] | $^1$H NMR (300 MHz, CHLOROFORM-d) δ ppm 0.29-0.38 (m, 2 H) 0.59-0.69 (m, 2 H) 1.15-1.35 (m, 1 H) 2.29-2.45 (m, 1 H) 2.62-2.75 (m, 1 H) 3.57-3.70 (m, 1 H) 3.70-3.74 (m, 2 H) 3.79 (d, J = 6.8 Hz, 2 H) 4.05-4.17 (m, 1 H) 4.29-4.40 (m, 1 H) 6.87 (d, J = 8.9 Hz, 2 H) 7.20 (d, 8.9 Hz, 2 H). MS ESI/APCI Dual posi: 284[M + Na]$^+$. MS ESI/APCI Dual nega: 260[M − H]$^−$. | |
| Reference Example A-335 | 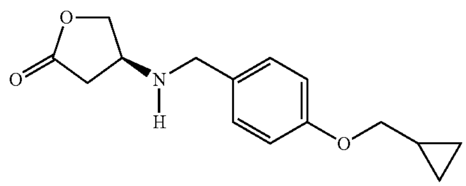 [SMILES: O=C1C[C@H](NCc2ccc(OCC3CC3)cc2)CO1] | $^1$H NMR (300 MHz, CHLOROFORM-d) δ ppm 0.28-0.39 (m, 2 H) 0.58-0.69 (m, 2 H) 1.17-1.35 (m, 1 H) 2.38 (dd, J = 17.5, 4.7 Hz, 1 H) 2.65-2.73 (m, 1 H) 3.62-3.70 (m, 1 H) 3.73 (d, J = 1.4 Hz, 2 H) 3.79 (d, J = 7.0 Hz, 2 H) 4.10 (dd, J = 9.5, 4.1 Hz, 1 H) 4.36 (dd, J = 9.5, 6.1 Hz, 1 H) 6.81-6.92 (m, 2 H) 7.15-7.24 (m, 2 H). MS ESI/APCI Dual posi: 284[M + Na]$^+$. MS ESI/APCI Dual nega: 260[M − Na]$^−$. | |
| Reference Example A-336 | 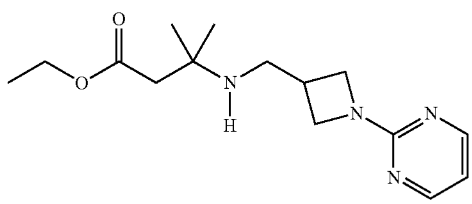 [SMILES: CCOC(=O)CC(C)(C)NCC1CN(c2ncccn2)C1] | $^1$H NMR (300 MHz, CHLOROFORM-d) δ ppm 1.17 (s, 6 H) 1.22-1.31 (m, 3 H) 2.42 (s, 2 H) 2.71-2.81 (m, 1 H) 3.79-3.86 (m, 2 H) 4.07-4.27 (m, 6 H) 6.47-6.52 (m, 1 H) 8.28-8.32 (m, 2 H). MS ESI/APCI Dual posi: 293[M + H]$^+$. | |

TABLE 18-49

| Compound No. | Structure | Analytical Data | Salt information |
|---|---|---|---|
| Reference Example A-337 | 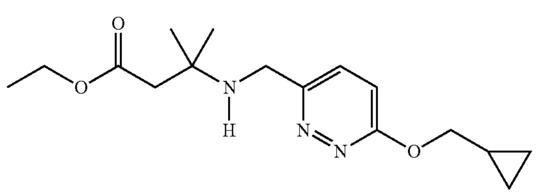 [SMILES: CCOC(=O)CC(C)(C)NCc1ccc(OCC2CC2)nn1] | $^1$H NMR (300 MHz, CHLOROFORM-d) δ ppm 0.34-0.42 (m, 2 H) 0.59-0.67 (m, 2 H) 1.19-1.28 (m, 9 H) 1.28-1.41 (m, 1 H) 2.49 (s, 2 H) 3.98 (s, 2 H) 4.14 (q, J = 7.1 Hz, 2 H) 4.32 (d, J = 7.2 Hz, 2 H) 6.94 (d, J = 9.0 Hz, 1 H) 7.50 (d, J = 9.0 Hz, 1 H). MS ESI/APCI Dual posi: 308[M + H]$^+$. | |
| Reference Example A-338 | 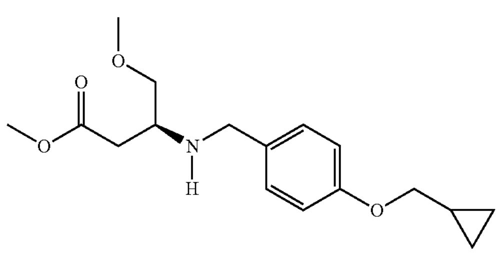 [SMILES: COC[C@H](CC(=O)OC)NCc1ccc(OCC2CC2)cc1] | $^1$H NMR (300 MHz, CHLOROFORM-d) δ ppm 0.29-0.38 (m, 2 H) 0.59-0.68 (m, 2 H) 1.18-1.33 (m, 1 H) 2.48-2.51 (m, 2 H) 3.14-3.27 (m, 1 H) 3.32 (s, 3 H) 3.34-3.47 (m, 2 H) 3.67 (s, 3 H) 3.70-3.82 (m, 4 H) 6.79-6.92 (m, 2 H) 7.17-7.28 (m, 2 H). MS ESI/APCI Dual posi: 308[M + H]$^+$, 330[M + Na]$^+$. MS ESI/APCI Dual nega: 306[M − H]$^−$. | |
| Reference Example A-339 | 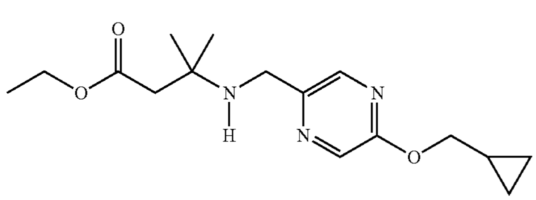 [SMILES: CCOC(=O)CC(C)(C)NCc1cnc(OCC2CC2)cn1] | $^1$H NMR (300 MHz, CHLOROFORM-d) δ ppm 0.31-0.40 (m, 2 H) 0.57-0.67 (m, 2 H) 1.19-1.36 (m, 10 H) 2.51 (s, 2 H) 3.82 (s, 2 H) 4.10-4.17 (m, 4 H) 8.08 (d, J = 1.4 Hz, 1 H) 8.19 (d, J = 1.4 Hz, 1 H). MS ESI/APCI Dual posi: 308[M + H]$^+$. | |

TABLE 18-49-continued

| Compound No. | Structure | Analytical Data | Salt information |
|---|---|---|---|
| Reference Example A-340 | 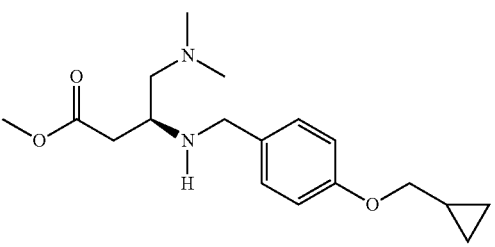 [SMILES: COC(=O)C[C@@H](CN(C)C)NCc1ccc(OCC2CC2)cc1] | ¹H NMR (300 MHz, CHLOROFORM-d) δ ppm 0.27-0.39 (m, 2 H) 0.58-0.68 (m, 2 H) 1.18-1.35 (m, 1 H) 2.15 (s, 6 H) 2.16-2.28 (m, 2 H) 2.31-2.45 (m, 2 H) 2.49-2.56 (m, 1 H) 3.03-3.17 (m, 1 H) 3.67 (s, 3 H) 3.74-3.83 (m, 3 H) 6.85 (d, J = 8.7 Hz, 2 H) 7.16-7.24 (m, 2 H). MS ESI/APCI Dual posi: 321[M + H]⁺. | |
| Reference Example A-341 | 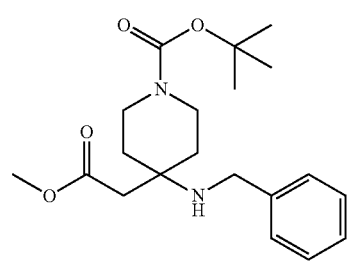 [SMILES: COC(=O)CC1(NCc2ccccc2)CCN(C(=O)OC(C)(C)C)CC1] | ¹H NMR (600 MHz, CHLOROFORM-d) δ ppm 1.46 (s, 9 H) 1.49-1.57 (m, 2 H) 1.64-1.76 (m, 2 H) 2.49-2.57 (m, 2 H) 3.27-3.40 (m, 2 H) 3.61-3.78 (m, 7 H) 7.22-7.26 (m, 1 H) 7.29-7.34 (m, 2 H) 7.35-7.39 (m, 2 H). MS ESI/APCI Dual posi: 363[M + H]⁺, 385[M + Na]⁺. | |
| Reference Example A-342 | 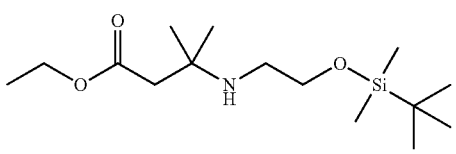 [SMILES: CCOC(=O)CC(C)(C)NCCO[Si](C)(C)C(C)(C)C] | ¹H NMR (300 MHz, CHLOROFORM-d) δ ppm 0.06 (s, 6 H) 0.90 (s, 9 H) 1.18 (s, 6 H) 1.26 (t, J = 7.1 Hz, 3 H) 2.42 (s, 2 H) 2.66 (t, J = 5.8 Hz, 2 H) 3.70 (t, J = 5.8 Hz, 2 H) 4.13 (q, J = 7.1 Hz, 2 H). | |
| Reference Example A-343 | 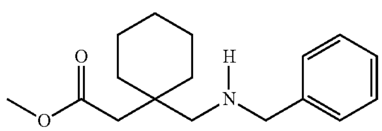 [SMILES: COC(=O)CC1(CNCc2ccccc2)CCCCC1] | ¹H NMR (300 MHz, DMSO-d₆) δ ppm 1.31-1.46 (m, 10 H) 2.56 (s, 2 H) 2.86-2.96 (m, 2 H) 3.42 (s, 3 H) 4.12-4.19 (m, 2 H) 7.41-7.47 (m, 3 H) 7.59-7.66 (m, 2 H) 9.12 (br. s, 2 H). MS ESI/APCI Dual posi: 276[M + H]⁺. | HCl |

TABLE 18-50

| Compound No. | Structure | Analytical Data | Salt information |
|---|---|---|---|
| Reference Example A-344 | 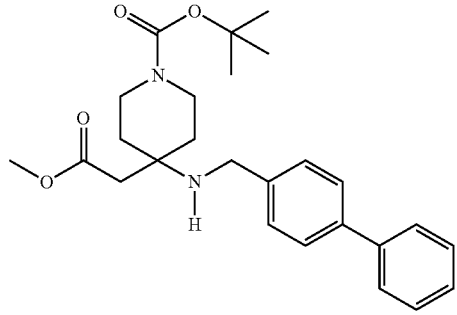 [SMILES: COC(=O)CC1(NCc2ccc(-c3ccccc3)cc2)CCN(C(=O)OC(C)(C)C)CC1] | ¹H NMR (600 MHz, CHLOROFORM-d) δ ppm 1.46 (s, 9 H) 1.51-1.60 (m, 2 H) 1.67-1.78 (m, 2 H) 2.52-2.60 (m, 2 H) 3.31-3.42 (m, 2 H) 3.64-3.79 (m, 7 H) 7.32-7.36 (m, 1 H) 7.41-7.47 (m, 4 H) 7.53-7.62 (m, 4 H). MS ESI/APCI Dual posi: 439[M + H]⁺. | |
| Reference Example A-345 | 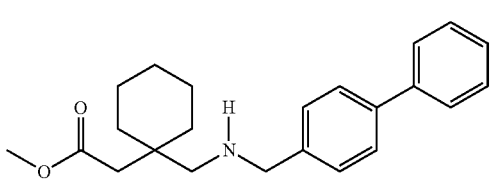 [SMILES: COC(=O)CC1(CNCc2ccc(-c3ccccc3)cc2)CCCCC1] | ¹H NMR (300 MHz, METHANOL-d₄) δ ppm 1.32-1.61 (m, 10 H) 2.61 (s, 2 H) 3.14 (s, 2 H) 3.64 (s, 3 H) 4.33 (s, 2 H) 7.32-7.41 (m, 1 H) 7.42-7.51 (m, 2 H) 7.61-7.68 (m, 4 H) 7.71-7.77 (m, 2 H). MS ESI/APCI Dual posi: 352[M + H]⁺. | HCl |

TABLE 18-50-continued

| Compound No. | Structure | Analytical Data | Salt information |
|---|---|---|---|
| Reference Example A-346 | 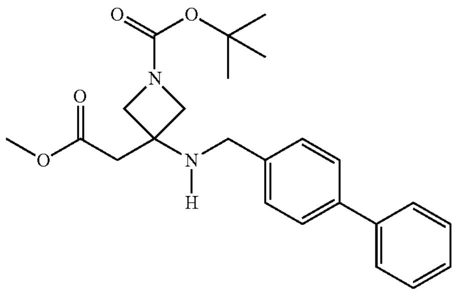 | $^1$H NMR (600 MHz, CHLOROFORM-d) δ ppm 1.27 (t, J = 7.2 Hz, 3 H) 1.45 (s, 9 H) 3.79 (s, 2 H) 3.85 (d, J = 9.1 Hz, 2 H) 3.94 (d, J = 9.1 Hz, 2 H) 4.17 (q, J = 7.2 Hz, 2 H) 7.32-7.37 (m, 1 H) 7.39-7.47 (m, 4 H) 7.53-7.62 (m, 4 H). MS ESI/APCI Dual posi: 425[M + H]$^+$, 447[M + Na]$^+$. MS ESI/APCI Dual nega: 459[M + Cl]$^-$. | |
| Reference Example A-347 | 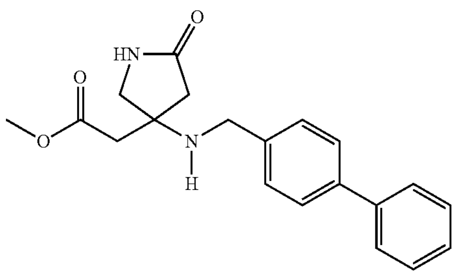 [SMILES: COC(=O)CC1(NCc2ccc(-c3ccccc3)cc2)CNC(=O)C1] | $^1$H NMR (300 MHz, CHLOROFORM-d) δ ppm 2.02-2.08 (m, 1 H) 2.39-2.48 (m, 1 H) 2.55-2.64 (m, 1 H) 2.72-2.91 (m, 2 H) 3.45-3.50 (m, 2 H) 3.72 (s, 3 H) 3.75-3.80 (m, 2 H) 5.63 (br. s., 1 H) 7.35-7.47 (m, 5 H) 7.52-7.61 (m, 4 H). MS ESI/APCI Dual posi: 339[M + H]$^+$, 361[M + Na]$^+$. MS ESI/APCI Dual nega: 373[M + Cl]$^-$. | |
| Reference Example A-348 | 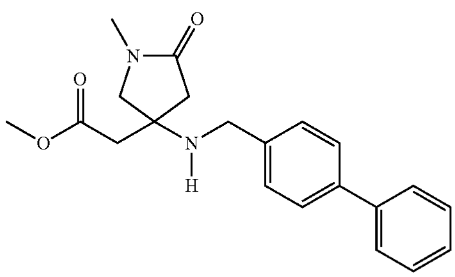 [SMILES: COC(=O)CC1(NCc2ccc(-c3ccccc3)cc2)CC(=O)N(C)C1] | $^1$H NMR (300 MHz, CHLOROFORM-d) δ ppm 2.43-2.53 (m, 1 H) 2.62-2.70 (m, 1 H) 2.74-2.90 (m, 5 H) 3.41-3.52 (m, 2 H) 3.68-3.77 (m, 5 H) 7.32-7.47 (m, 5 H) 7.52-7.61 (m, 4 H). MS ESI/APCI Dual posi: 353[M + H]$^+$, 375[M + Na]$^+$. | |
| Reference Example A-349 | 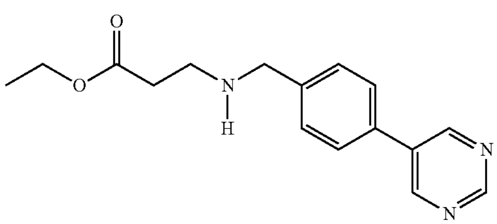 [SMILES: CCOC(=O)CCNCc1ccc(-c2cncnc2)cc1] | $^1$H NMR (300 MHz, CHLOROFORM-d) δ ppm 1.27 (t, J = 7.1 Hz, 3 H) 2.55 (t, J = 6.4 Hz, 2 H) 2.93 (t, J = 6.4 Hz, 2 H) 3.88 (s, 2 H) 4.16 (q, J = 7.1 Hz, 2 H) 7.47-7.51 (m, 2 H) 7.53-7.57 (m, 2 H) 8.95 (s, 2 H) 9.20 (s, 1 H). MS ESI/APCI Dual posi: 286[M + H]. | |
| Reference Example A-350 | 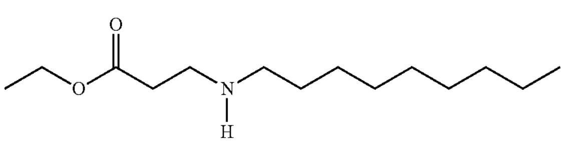 [SMILES: CCCCCCCCCNCCC(=O)OCC] | $^1$H NMR (300 MHz, CHLOROFORM-d) δ ppm 0.84-0.91 (m, 3 H) 1.21-1.34 (m, 15 H) 1.42-1.57 (m, 2 H) 2.54 (t, J = 6.5 Hz, 2 H) 2.63 (t, J = 7.1 Hz, 2 H) 2.90 (t, J = 6.5 Hz, 2 H) 4.15 (q, J = 7.1 Hz, 2 H). MS ESI/APCI Dual posi: 244[M + H]$^+$. | |

TABLE 18-51

| Compound No. | Structure | Analytical Data | Salt information |
|---|---|---|---|
| Reference Example A-351 | 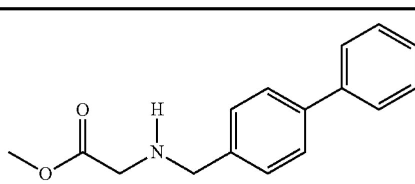 | $^1$H NMR (200 MHz, CHLOROFORM-d) δ ppm 3.46 (s, 2 H) 3.74 (s, 3 H) 3.85 (s, 2 H) 7.28-7.49 (m, 5 H) 7.52-7.63 (m, 4 H). MS ESI/APCI Dual posi: 256[M + H]$^+$. | |

TABLE 18-51-continued

| Compound No. | Structure | Analytical Data | Salt information |
|---|---|---|---|
| Reference Example A-352 | 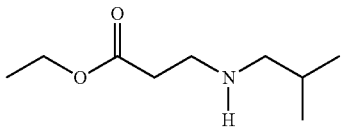 | ¹H NMR (300 MHz, CHLOROFORM-d) δ ppm 0.90 (d, J = 6.7 Hz, 6 H) 1.26 (t, J = 7.1 Hz, 3 H) 1.66-1.82 (m, 1 H) 2.42 (d, J = 6.8 Hz, 2 H) 2.48-2.54 (m, 2 H) 2.83-2.89 (m, 2 H) 4.14 (q, J = 7.1 Hz, 2 H). MS ESI/APCI Dual posi: 174[M + H]$^+$. | |
| Reference Example A-353 | 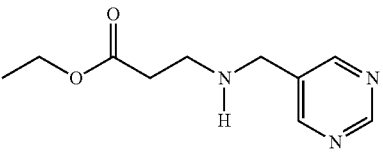 | ¹H NMR (600 MHz, CHLOROFORM-d) δ ppm 1.26 (t, J = 7.2 Hz, 3 H) 2.53 (t, J = 6.4 Hz, 2 H) 2.90 (t, J = 6.4 Hz, 2 H) 3.83 (s, 2 H) 4.15 (q, J = 7.2 Hz, 2 H) 8.72 (s, 2 H) 9.13 (s, 1 H). MS ESI/APCI Dual posi: 210[M + H]$^+$. | |
| Reference Example A-354 | 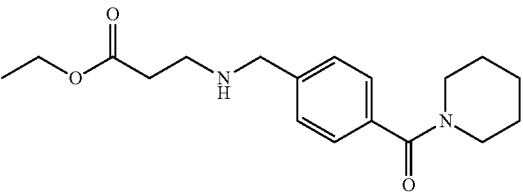 [SMILES: CCOC(=O)CCNCc1ccc(C(=O)N2CCCCC2)cc1] | ¹H NMR (600 MHz, CHLOROFORM-d) δ ppm 1.26 (t, J = 7.2 Hz, 3 H) 1.46-1.65 (m, 6 H) 2.53 (t, J = 6.4 Hz, 2 H) 2.89 (t, J = 6.4 Hz, 2 H) 3.29-3.39 (m, 2 H) 3.66-3.75 (m, 2 H) 3.82 (s, 2 H) 4.15 (q, J = 7.2 Hz, 2 H) 7.33-7.37 (m, 4 H). MS ESI/APCI Dual posi: 319[M + H]$^+$, 341[M + Na]$^+$. | |
| Reference Example A-355 | 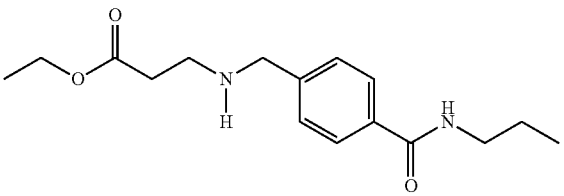 [SMILES: CCCNC(=O)c1ccc(CNCCC(=O)OCC)cc1] | ¹H NMR (600 MHz, CHLOROFORM-d) δ ppm 0.98 (t, J = 7.4 Hz, 3 H) 1.25 (t, J = 7.2 Hz, 3 H) 1.60-1.67 (m, 2 H) 2.51 (t, J = 6.4 Hz, 2 H) 2.87 (t, J = 6.4 Hz 2 H) 3.39-3.44 (m, 2 H) 3.83 (s, 2 H) 4.13 (q, J = 7.2 Hz, 2 H) 6.03-6.11 (m, 1 H) 7.36-7.39 (m, 2 H) 7.66-7.76 (m, 2 H). MS ESI/APCI Dual posi: 293[M + H]$^+$, 315[M + Na]$^+$. | |
| Reference Example A-356 | 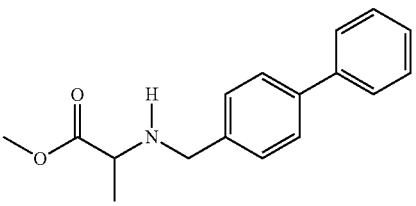 [SMILES: COC(=O)C(C)NCc1ccc(-c2ccccc2)cc1] | ¹H NMR (500 MHz, CHLOROFORM-d) δ ppm 1.34 (d, J = 6.9 Hz, 3 H) 3.39-3.47 (m, 1 H) 3.67-3.77 (m, 4 H) 3.81-3.88 (m, 1 H) 7.31-7.37 (m, 1 H) 7.38-7.47 (m, 4 H) 7.52-7.61 (m, 4 H). MS ESI/APCI Dual posi: 270[M + H]$^+$, 292[M + Na]$^+$. | |
| Reference Example A-357 | 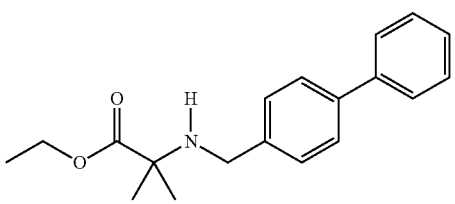 [SMILES: CCOC(=O)C(C)(C)NCc1ccc(-c2ccccc2)cc1] | ¹H NMR (500 MHz, CHLOROFORM-d) δ ppm 1.31 (m, 3 H) 1.38 (s, 6 H) 3.67 (s, 2 H) 4.18-4.24 (m, 2 H) 7.30-7.36 (m, 1 H) 7.39-7.46 (m, 4 H) 7.52-7.60 (m, 4 H). MS ESI/APCI Dual posi: 298[M + H]$^+$, 320[M + Na]$^+$. | |

TABLE 18-52

| Compound No. | Structure | Analytical Data | Salt information |
|---|---|---|---|
| Reference Example A-358 | 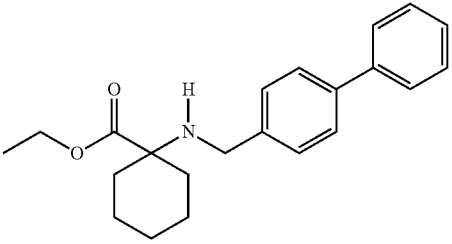 [SMILES: CCOC(=O)C1(NCc2ccc(-c3ccccc3)cc2)CCCCC1] | ¹H NMR (600 MHz, CHLOROFORM-d) δ ppm 1.31 (t, J = 7.0 Hz, 3 H) 1.37-1.53 (m, 4 H) 1.60-1.68 (m, 2 H) 1.71-1.81 (m, 2 H) 1.90-1.99 (m, 2 H) 3.63 (s, 2 H) 4.21 (q, J = 7.0 Hz, 2 H) 7.31-7.36 (m, 1 H) 7.38-7.46 (m, 4 H) 7.52-7.60 (m, 4 H). MS ESI/APCI Dual posi: 338[M + H]$^+$. | |

TABLE 18-52-continued

| Compound No. | Structure | Analytical Data | Salt information |
|---|---|---|---|
| Reference Example A-359 | 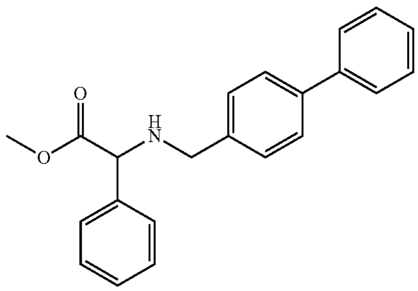 [SMILES: COC(=O)C(NCc1ccc(-c2ccccc2)cc1)c1ccccc1] | $^1$H NMR (300 MHz, CHLOROFORM-d) δ ppm 3.70 (s, 3 H) 3.77 (s, 2 H) 4.43 (s, 1 H) 7.28-7.49 (m, 10 H) 7.51-7.62 (m, 4 H). MS ESI/APCI Dual posi: 332[M + H]$^+$, 354[M + Na]$^+$. | |
| Reference Example A-360 | 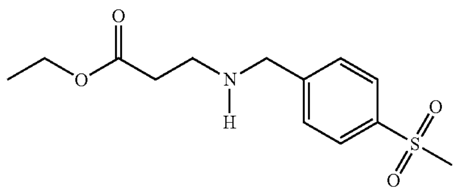 [SMILES: CCOC(=O)CCNCc1ccc(S(C)(=O)=O)cc1] | $^1$H NMR (300 MHz, CHLOROFORM-d) δ ppm 1.27 (t, J = 7.1 Hz, 3 H) 2.53 (t, J = 6.3 Hz, 2 H) 2.89 (t, J = 6.3 Hz, 2 H) 3.04 (s, 3 H) 3.90 (s, 2 H) 4.15 (q, J = 7.1 Hz, 2 H) 7.55 (d, J = 8.4 Hz, 2 H) 7.90 (d, J = 8.4 Hz, 2 H). MS ESI/APCI Dual posi: 286[M + H]$^+$. | |
| Reference Example A-361 | 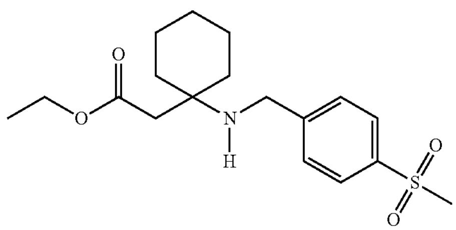 [SMILES: CCOC(=O)CC1(NCc2ccc(S(C)(=O)=O)cc2)CCCCC1] | $^1$H NMR (300 MHz, CHLOROFORM-d) δ ppm 1.20-1.27 (m, 3 H) 1.31-1.74 (m, 10 H) 2.50 (s, 2 H) 3.04 (s, 3 H) 3.78 (s, 2 H) 4.05-4.19 (m, 2 H) 7.61 (d, J = 8.4 Hz, 2 H) 7.88 (d, J = 8.4 Hz, 2 H). MS ESI/APCI Dual posi: 354[M + H]$^+$. | |
| Reference Example A-362 | 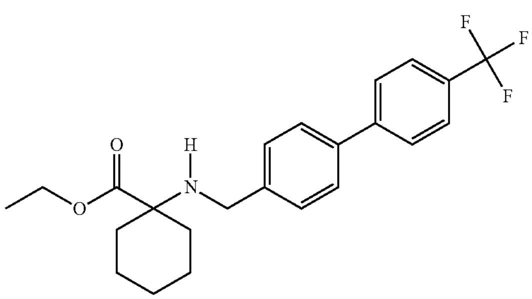 [SMILES: CCOC(=O)C1(NCc2ccc(-c3ccc(C(F)(F)F)cc3)cc2)CCCCC1] | $^1$H NMR (300 MHz, CHLOROFORM-d) δ ppm 1.32 (t, J = 7.1 Hz, 3 H) 1.36-2.03 (m, 10 H) 3.65 (s, 2 H) 4.22 (q, J = 7.1 Hz, 2 H) 7.41-7.50 (m, 2 H) 7.51-7.60 (m, 2 H) 7.63-7.74 (m, 4 H). MS ESI/APCI Dual posi: 406[M + H]$^+$, 428[M + Na]$^+$. | |
| Reference Example A-363 | 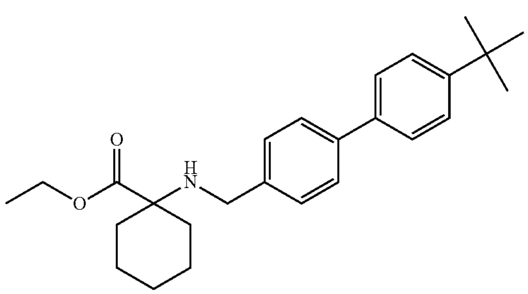 [SMILES: CCOC(=O)C1(NCc2ccc(-c3ccc(C(C)(C)C)cc3)cc2)CCCCC1] | $^1$H NMR (300 MHz, CHLOROFORM-d) δ ppm 1.17-2.03 (m, 22 H) 3.62 (s, 2 H) 4.21 (q, J = 7.3 Hz, 2 H) 7.33-7.62 (m, 8 H). MS ESI/APCI Dual posi: 394[M + H]$^+$, 416[M + Na]$^+$. | |
| Reference Example A-364 | 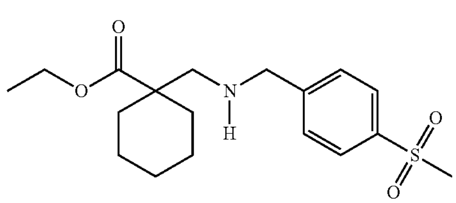 [SMILES: CCOC(=O)C1(CNCc2ccc(S(C)(=O)=O)cc2)CCCCC1] | $^1$H NMR (300 MHz, CHLOROFORM-d) δ ppm 1.17-1.34 (m, 7 H) 1.35-1.58 (m, 4 H) 2.01-2.10 (m, 2 H) 2.65 (s, 2 H) 3.05 (s, 3 H) 3.86 (s, 2 H) 4.17 (q, J = 7.0 Hz, 2 H) 7.51 (d, J = 8.4 Hz, 2 H) 7.88 (d, J = 8.4 Hz, 2 H). MS ESI/APCI Dual posi: 354[M + H]$^+$, 376[M + Na]$^+$. | |

TABLE 18-53

| Compound No. | Structure | Analytical Data | Salt information |
|---|---|---|---|
| Reference Example A-365 | 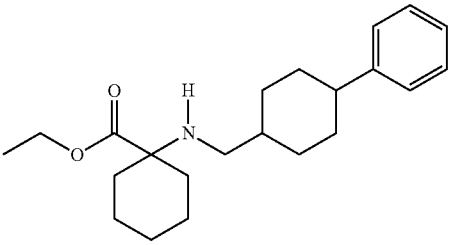 [SMILES: CCOC(=O)C1(NCC2CCC(c3ccccc3)CC2)CCCCC1] | $^1$H NMR (300 MHz, CHLOROFORM-d) δ ppm 1.00-1.18 (m, 1 H) 1.20-1.80 (m, 16 H) 1.81-2.01 (m, 4 H) 2.24-2.35 (m, 1 H) 2.38-2.56 (m, 1 H) 4.18 (q, J = 7.0 Hz, 2 H) 7.08-7.37 (m, 5 H). MS ESI/APCI Dual posi: 344[M + H]$^+$, 366[M + Na]$^+$. | |
| Reference Example A-366 | 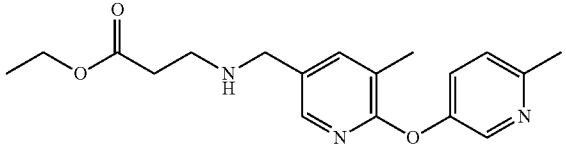 [SMILES: CCOC(=O)CCNCc1cnc(Oc2ccc(C)nc2)c(C)c1] | $^1$H NMR (300 MHz, CHLOROFORM-d) δ ppm 1.26 (t, J = 7.1 Hz, 3 H) 2.35 (s, 3 H) 2.52 (t, J = 6.4 Hz, 2 H) 2.56 (s, 3 H) 2.88 (t, J = 6.4 Hz, 2 H) 3.72 (s, 2 H) 4.14 (q, J = 7.1 Hz, 2 H) 7.17 (d, J = 8.4 Hz, 1 H) 7.37 (dd, J = 8.4, 2.8 Hz, 1 H) 7.54-7.57 (m, 1 H) 7.84-7.87 (m, 1 H) 8.34 (d, J = 2.8 Hz, 1 H). MS ESI/APCI Dual posi: 330[M + H]$^+$, 352[M + Na]$^+$. | |
| Reference Example A-367 | 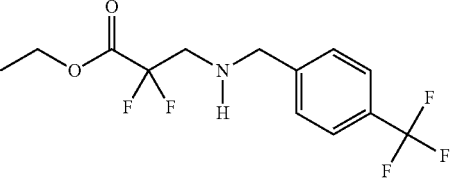 [SMILES: CCOC(=O)C(F)(F)CNCc1ccc(C(F)(F)F)cc1] | $^1$H NMR (300 MHz, CHLOROFORM-d) δ ppm 1.23-1.41 (m, 3 H) 3.21 (t, J = 13.3 Hz, 2 H) 3.87-3.97 (m, 2 H) 4.33 (q, J = 7.1 Hz, 2 H) 7.42 (d, J = 7.9 Hz, 2 H) 7.59 (d, J = 7.9 Hz, 2 H). MS ESI/APCI Dual posi: 312[M + H]$^+$, 334[M + Na]$^+$. | |
| Reference Example A-368 | 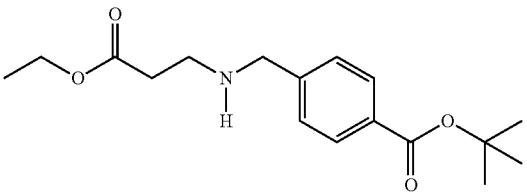 [SMILES: CCOC(=O)CCNCc1ccc(C(=O)OC(C)(C)C)cc1] | $^1$H NMR (300 MHz, CHLOROFORM-d) δ ppm 1.26 (t, J = 7.1 Hz, 3 H) 1.59 (s, 9 H) 2.44-2.58 (m, 2 H) 2.82-2.94 (m, 2 H) 3.86 (s, 2 H) 4.09-4.21 (m, 2 H) 7.31-7.42 (m, 2 H) 7.90-7.98 (m, 2 H). MS ESI/APCI Dual posi: 308[M + H]$^+$, 330[M + Na]$^+$. | |
| Reference Example A-369 | 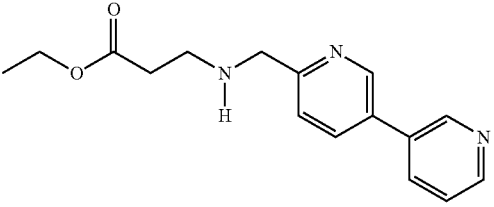 [SMILES: CCOC(=O)CCNCc1ccc(-c2cccnc2)cn1] | $^1$H NMR (300 MHz, CHLOROFORM-d) δ ppm 1.27 (t, J = 7.1 Hz, 3 H) 2.58 (t, J = 6.5 Hz, 2 H) 2.98 (t, J = 6.5 Hz, 2 H) 4.01 (s, 2 H) 4.16 (q, J = 7.1 Hz, 2 H) 7.35-7.50 (m, 2 H) 7.81-7.95 (m, 2 H) 8.61-8.70 (m, 1 H) 8.73-8.89 (m, 2 H). MS ESI/APCI Dual posi: 286[M + H]$^+$, 308[M + Na]$^+$. | |
| Reference Example A-370 | 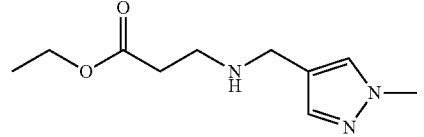 | $^1$H NMR (300 MHz, CHLOROFORM-d) δ ppm 1.26 (t, J = 7.1 Hz, 3 H) 2.52 (t, J = 6.5 Hz, 2 H) 2.84-2.96 (m, 2 H) 3.68 (s, 2 H) 3.87 (s, 3 H) 4.14 (q, J = 7.1 Hz, 2 H) 7.31 (s, 1 H) 7.41 (s, 1 H). MS ESI/APCI Dual posi: 212[M + H]$^+$, 234[M + Na]$^+$. | |
| Reference Example A-371 | 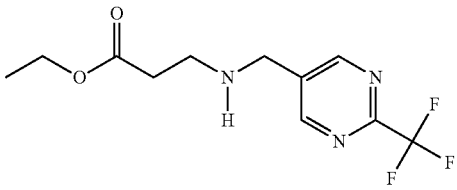 [SMILES: CCOC(=O)CCNCc1cnc(C(F)(F)F)nc1] | $^1$H NMR (300 MHz, CHLOROFORM-d) δ ppm 1.27 (t, J = 7.1 Hz, 3 H) 2.54 (t, J = 6.2 Hz, 2 H) 2.90 (t, J = 6.2 Hz, 2 H) 3.93 (d, J = 0.6 Hz, 2 H) 4.16 (q, J = 7.1 Hz, 2 H) 8.88 (s, 2 H). MS ESI/APCI Dual posi: 278[M + H]$^+$, 300[M + Na]$^+$. | |

TABLE 18-54

| Compound No. | Structure | Analytical Data | Salt information |
|---|---|---|---|
| Reference Example A-372 | 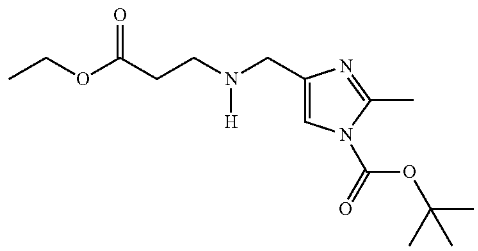 [SMILES: CCOC(=O)CCNCc1cn(C(=O)OC(C)(C)C)c(C)n1] | $^1$H NMR (300 MHz, CHLOROFORM-d) δ ppm 1.26 (t, J = 7.1 Hz, 3 H) 1.60 (s, 9 H) 2.47-2.57 (m, 2 H) 2.59 (s, 3 H) 2.92 (t, J = 6.7 Hz, 2 H) 3.67 (d, J = 0.9 Hz, 2 H) 4.14 (q, J = 7.1 Hz, 2 H) 7.18 (s, 1 H). MS ESI/APCI Dual posi: 312[M + H]$^+$, 334[M + Na]$^+$. MS ESI/APCI Dual nega: 310[M − H]$^-$. | |
| Reference Example A-373 | 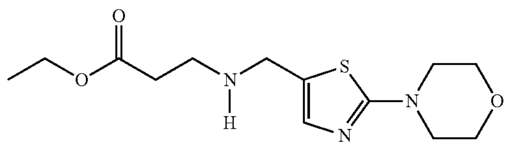 [SMILES: CCOC(=O)CCNCc1cnc(N2CCOCC2)s1] | $^1$H NMR (300 MHz, CHLOROFORM-d) δ ppm 1.26 (t, J = 7.1 Hz, 3 H) 2.51 (t, J = 6.5 Hz, 2 H) 2.89 (t, J = 6.5 Hz, 2 H) 3.39-3.46 (m, 4 H) 3.76-3.83 (m, 4 H) 3.85 (d, J = 0.9 Hz, 2 H) 4.14 (q, J = 7.1 Hz, 2 H) 7.00 (t, J = 0.9 Hz, 1 H). MS ESI/APCI Dual posi: 300[M + H]$^+$, 322[M + Na]$^+$. | |
| Reference Example A-374 | 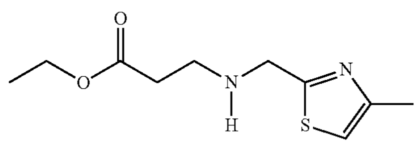 | $^1$H NMR (300 MHz, CHLOROFORM-d) δ ppm 1.19-1.32 (m, 3 H) 2.38-2.45 (m, 3 H) 2.49-2.58 (m, 2 H) 2.98 (t, J = 6.5 Hz, 2 H) 3.98-4.10 (m, 2 H) 4.10-4.21 (m, 2 H) 6.75-6.88 (m, 1 H). MS ESI/APCI Dual posi: 229[M + H]$^+$, 251[M + Na]$^+$. | |
| Reference Example A-375 | 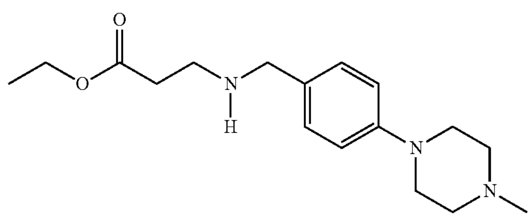 [SMILES: CCOC(=O)CCNCc1ccc(N2CCN(C)CC2)cc1] | $^1$H NMR (300 MHz, CHLOROFORM-d) δ ppm 1.16-1.31 (m, 3 H) 2.35 (s, 3 H) 2.46-2.64 (m, 6 H) 2.88 (t, J = 6.5 Hz, 2 H) 3.11-3.26 (m, 4 H) 3.72 (s, 2 H) 4.07-4.19 (m, 2 H) 6.80-6.97 (m, 2 H) 7.13-7.25 (m, 2 H). MS ESI/APCI Dual posi: 328[M + Na]$^+$. | |
| Reference Example A-376 | 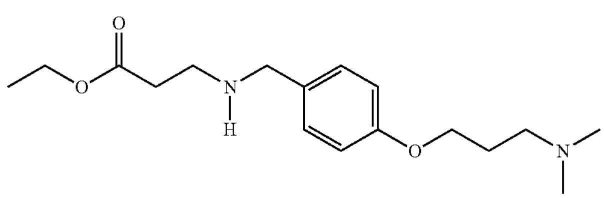 [SMILES: CCOC(=O)CCNCc1ccc(OCCCN(C)C)cc1] | $^1$H NMR (300 MHz, CHLOROFORM-d) δ ppm 1.25 (t, J = 7.1 Hz, 3 H) 1.88-2.01 (m, 2 H) 2.26 (s, 6 H) 2.39-2.58 (m, 4 H) 2.88 (t, J = 6.5 Hz, 2 H) 3.73 (s, 2 H) 4.00 (t, J = 6.5 Hz, 2 H) 4.13 (q, J = 7.1 Hz, 2 H) 6.80-6.90 (m, 2 H) 7.17-7.25 (m, 2 H) MS ESI/APCI Dual posi: 309[M + H]$^+$, 331[M + Na]$^+$. | |
| Reference Example A-377 | 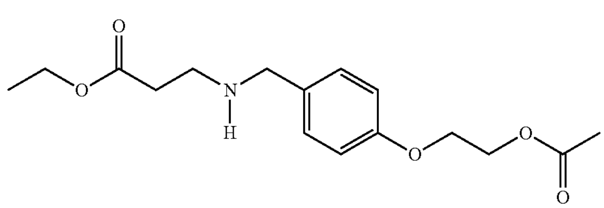 [SMILES: CCOC(=O)CCNCc1ccc(OCCOC(C)=O)cc1] | $^1$H NMR (300 MHz, CHLOROFORM-d) δ ppm 1.19-1.30 (m, 3 H) 2.10 (s, 3 H) 2.45-2.56 (m, 2 H) 2.83-2.92 (m, 2 H) 3.74 (s, 2 H) 4.03-4.20 (m, 4 H) 4.37-4.48 (m, 2 H) 6.87 (d, J = 8.7 Hz, 2 H) 7.24 (d, J = 8.7 Hz, 2 H). MS ESI/APCI Dual posi: 310[M + H]$^+$. | |
| Reference Example A-378 | 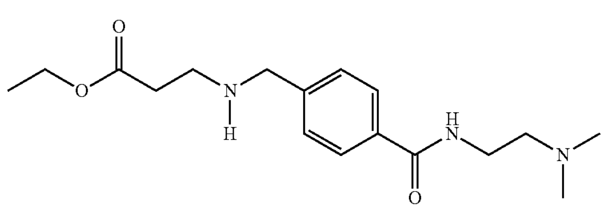 [SMILES: CCOC(=O)CCNCc1ccc(C(=O)NCCN(C)C)cc1] | $^1$H NMR (300 MHz, CHLOROFORM-d) δ ppm 1.26 (t, J = 7.1 Hz, 3 H) 2.34 (s, 6 H) 2.53-2.67 (m, 4 H) 2.82-2.93 (m, 2 H) 3.51-3.63 (m, 2 H) 3.85 (s, 2 H) 4.14 (q, J = 7.1 Hz, 2 H) 7.38 (d, J = 8.5 Hz, 2 H) 7.78 (d, J = 8.5 Hz, 2 H). MS ESI/APCI Dual posi: 322[M + H]$^+$, 344[M + Na]$^+$. MS ESI/APCI Dual nega: 320[M − H]$^-$. | |

TABLE 18-55

| Compound No. | Structure | Analytical Data | Salt information |
|---|---|---|---|
| Reference Example A-379 | 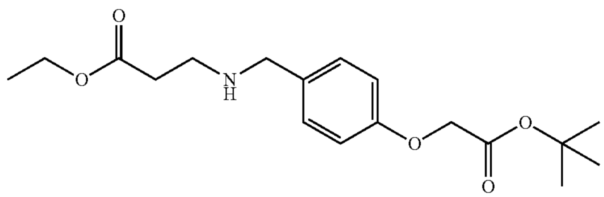 [SMILES: CCOC(=O)CCNCc1ccc(OCC(=O)OC(C)(C)C)cc1] | ¹H NMR (300 MHz, CHLOROFORM-d) δ ppm 1.25 (t, J = 7.1 Hz, 3 H) 1.49 (s, 9 H) 2.47-2.57 (m, 2 H) 2.88 (t, J = 6.5 Hz, 2 H) 3.74 (s, 2 H) 4.14 (q, J = 7.1 Hz, 2 H) 4.50 (s, 2 H) 6.80-6.91 (m, 2 H) 7.18-7.25 (m, 2 H). MS ESI/APCI Dual posi: 338[M + H]⁺, 360[M + Na]⁺. MS ESI/APCI Dual nega: 336[M − H]⁻. | |
| Reference Example A-380 | 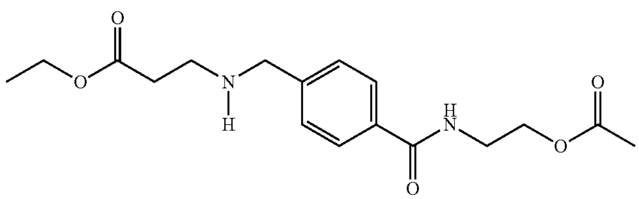 [SMILES: CCOC(=O)CCNCc1ccc(C(=O)NCCOC(C)=O)cc1] | ¹H NMR (300 MHz, CHLOROFORM-d) δ ppm 1.26 (t, J = 7.1 Hz, 3 H) 2.10 (s, 3 H) 2.45-2.61 (m, 2 H) 2.83-2.94 (m, 2 H) 3.73 (q, J = 5.5 Hz, 2 H) 3.85 (s, 2 H) 4.14 (q, J = 7.1 Hz, 2 H) 4.25-4.35 (m, 2 H) 6.43-6.60 (m, 1 H) 7.40 (d, J = 8.5 Hz, 2 H) 7.73 (d, J = 8.5 Hz, 2 H). MS ESI/APCI Dual posi: 337[M + H]⁺, 359[M + Na]⁺. | |
| Reference Example A-381 | 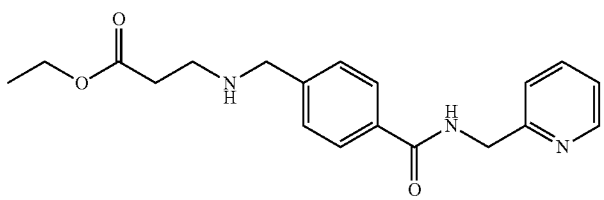 [SMILES: CCOC(=O)CCNCc1ccc(C(=O)NCc2ccccn2)cc1] | ¹H NMR (300 MHz, CHLOROFORM-d) δ ppm 1.26 (t, J = 7.1 Hz, 3 H) 2.50-2.56 (m, 2 H) 2.89 (t, J = 6.4 Hz, 2 H) 3.86 (s, 2 H) 4.15 (q, J = 7.1 Hz, 2 H) 4.76 (d, J = 4.8 Hz, 2 H) 7.16-7.25 (m, 1 H) 7.33 (d, J = 7.8 Hz, 1 H) 7.41 (d, J = 8.4 Hz, 2 H) 7.56 (br. s., 1 H) 7.64-7.75 (m, 1 H) 7.79-7.87 (m, 2 H) 8.57 (dt, J = 5.0, 0.9 Hz, 1 H). MS ESI/APCI Dual posi: 342[M + H]⁺, 364[M + Na]⁺. MS ESI/APCI Dual nega: 340[M − H]⁻. | |
| Reference Example A-382 | 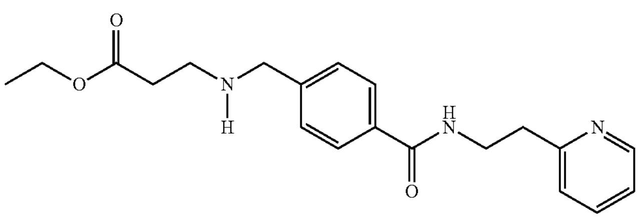 [SMILES: CCOC(=O)CCNCc1ccc(C(=O)NCCc2ccccn2)cc1] | ¹H NMR (300 MHz, CHLOROFORM-d) δ ppm 1.26 (t, J = 7.1 Hz, 3 H) 2.52 (t, J = 6.4 Hz, 2 H) 2.85-2.93 (m, 2 H) 3.10 (t, J = 6.4 Hz, 2 H) 3.79-3.95 (m, 4 H) 4.06-4.23 (m, 2 H) 7.11-7.24 (m, 2 H) 7.33-7.41 (m, 2 H) 7.45-7.56 (m, 1 H) 7.58-7.67 (m, 1 H) 7.68-7.77 (m, 2 H) 8.51-8.60 (m, 1 H). MS ESI/APCI Dual posi: 356[M + H]⁺, 378[M + Na]⁺. MS ESI/APCI Dual nega: 354[M − H]⁻. | |
| Reference Example A-383 | 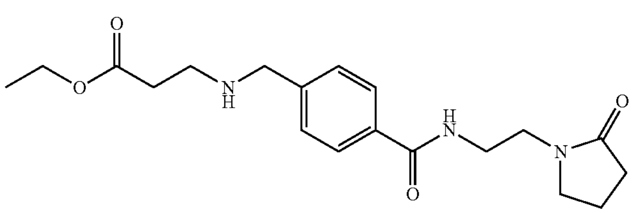 [SMILES: CCOC(=O)CCNCc1ccc(C(=O)NCCN2CCCC2=O)cc1] | ¹H NMR (300 MHz, CHLOROFORM-d) δ ppm 1.26 (t, J = 7.1 Hz, 3 H) 1.98-2.14 (m, 2 H) 2.34-2.43 (m, 2 H) 2.52 (t, J = 6.5 Hz, 2 H) 2.83-2.92 (m, 2 H) 3.44-3.68 (m, 6 H) 3.84 (s, 2 H) 4.14 (q, J = 7.1 Hz, 2 H) 7.16-7.25 (m, 1 H) 7.33-7.41 (m, 2 H) 7.69-7.81 (m, 2 H). MS ESI/APCI Dual posi: 362[M + H]⁺, 384[M + Na]⁺. MS ESI/APCI Dual nega: 360[M − H]⁻. | |
| Reference Example A-384 | 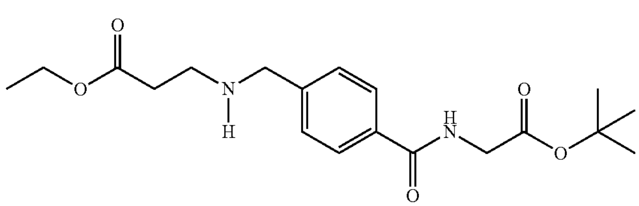 [SMILES: CCOC(=O)CCNCc1ccc(C(=O)NCC(=O)OC(C)(C)C)cc1] | ¹H NMR (300 MHz, CHLOROFORM-d) δ ppm 1.26 (t, J = 7.1 Hz, 3 H) 1.51 (s, 9 H) 2.53 (t, J = 6.4 Hz, 2 H) 2.89 (t, J = 6.4 Hz, 2 H) 3.85 (s, 2 H) 4.08-4.21 (m, 4 H) 6.59-6.67 (m, 1 H) 7.36-7.43 (m, 2 H) 7.74-7.80 (m, 2 H). MS ESI/APCI Dual posi: 365[M + H]⁺, 387[M + Na]⁺. MS ESI/APCI Dual nega: 363[M − H]⁻. | |
| Reference Example A-385 | 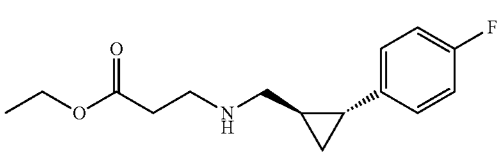 [SMILES: CCOC(=O)CCNC[C@@H]1C[C@H]1c1ccc(F)cc1] | ¹H NMR (300 MHz, CHLOROFORM-d) δ ppm 0.76-0.92 (m, 2 H) 1.15-1.37 (m, 4 H) 1.66-1.76 (m, 1 H) 2.52 (t, J = 6.5 Hz, 2 H) 2.58-2.74 (m, 2 H) 2.84-3.00 (m, 2 H) 4.14 (q, J = 7.1 Hz, 2 H) 6.83-7.09 (m, 4 H). MS ESI/APCI Dual posi: 266[M + H]⁺. | |

TABLE 18-56

| Compound No. | Structure | Analytical Data | Salt information |
|---|---|---|---|
| Reference Example A-386 | 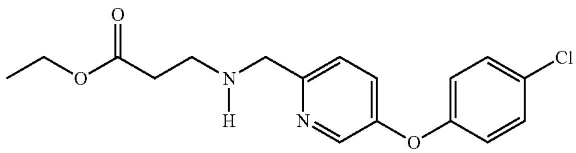 [SMILES: CCOC(=O)CCNCc1ccc(Oc2ccc(Cl)cc2)cn1] | ¹H NMR (300 MHz, CHLOROFORM-d) δ ppm 1.26 (t, J = 7.1 Hz, 3 H) 2.56 (t, J = 6.6 Hz, 2 H) 2.91-2.98 (m, 2 H) 3.92 (s, 2 H) 4.15 (d, J = 7.1 Hz, 2 H) 6.94 (d, J = 9.0 Hz, 2 H) 7.22-7.35 (m, 4 H) 8.31-8.36 (m, 1 H). MS ESI/APCI Dual posi: 335[M + H]⁺, 357[M + Na]⁺. MS ESI/APCI Dual nega: 333[M − H]⁻. | |
| Reference Example A-387 | 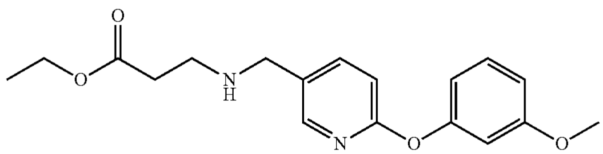 [SMILES: CCOC(=O)CCNCc1ccc(Oc2cccc(OC)c2)nc1] | ¹H NMR (300 MHz, CHLOROFORM-d) δ ppm 1.26 (t, J = 7.1 Hz, 3 H) 2.48-2.55 (m, 2 H) 2.84-2.93 (m, 2 H) 3.76 (s, 2 H) 3.79 (s, 3 H) 4.14 (q, J = 7.1 Hz, 2 H) 6.64-6.78 (m, 3 H) 6.83-6.90 (m, 1 H) 7.25-7.33 (m, 1 H) 7.62-7.76 (m, 1 H) 8.07-8.19 (m, 1 H). MS ESI/APCI Dual posi: 331[M + H]⁺, 353[M + Na]⁺. MS ESI/APCI Dual nega: 329[M − H]⁻. | |
| Reference Example A-388 | 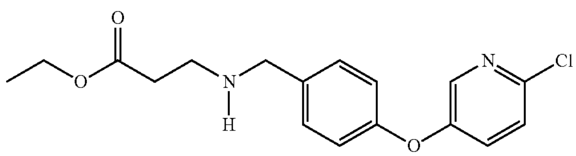 [SMILES: CCOC(=O)CCNCc1ccc(Oc2ccc(Cl)nc2)cc1] | ¹H NMR (300 MHz, CHLOROFORM-d) δ ppm 1.26 (t, J = 7.1 Hz, 3 H) 2.54 (t, J = 6.5 Hz, 2 H) 2.91 (t, J = 6.5 Hz, 2 H) 3.80 (s, 2 H) 4.15 (q, J = 7.1 Hz, 2 H) 6.92-7.03 (m, 2 H) 7.20-7.28 (m, 2 H) 7.31-7.38 (m, 2 H) 8.10-8.19 (m, 1 H). MS ESI/APCI Dual posi: 335[M + H]⁺, 357[M + Na]⁺. MS ESI/APCI Dual nega: 333[M − H]⁻. | |
| Reference Example A-389 | 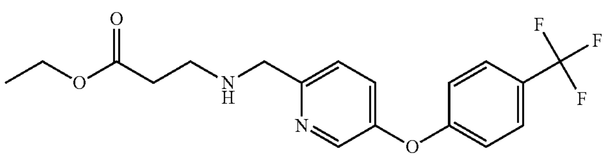 [SMILES: CCOC(=O)CCNCc1ccc(Oc2ccc(C(F)(F)F)cc2)cn1] | ¹H NMR (300 MHz, CHLOROFORM-d) δ ppm 1.27 (t, J = 7.1 Hz, 3 H) 2.57 (t, J = 6.5 Hz, 2 H) 2.96 (t, J = 6.5 Hz, 2 H) 3.94 (s, 2 H) 4.16 (q, J = 7.1 Hz, 2 H) 6.98-7.10 (m, 2 H) 7.30-7.41 (m, 2 H) 7.60 (d, J = 8.5 Hz, 2 H) 8.35-8.43 (m, 1 H). MS ESI/APCI Dual posi: 369[M + H]⁺, 391[M + Na]⁺. MS ESI/APCI Dual nega: 367[M − H]⁻. | |
| Reference Example A-390 | 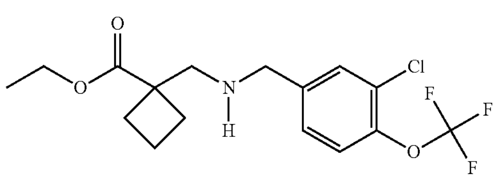 [SMILES: CCOC(=O)C1(CNCc2ccc(OC(F)(F)F)c(Cl)c2)CCC1] | ¹H NMR (300 MHz, CHLOROFORM-d) δ ppm 1.26 (t, J = 7.1 Hz, 3 H) 1.82-2.03 (m, 4 H) 2.33-2.51 (m, 2 H) 2.89 (s, 2 H) 3.78 (s, 2 H) 4.12-4.25 (m, 2 H) 7.22-7.30 (m, 2 H) 7.42-7.49 (m, 1 H). MS ESI/APCI Dual posi: 366[M + H]⁺. | |
| Reference Example A-391 | 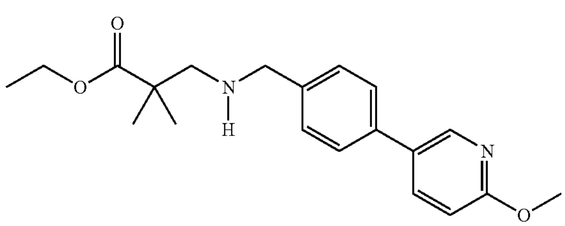 [SMILES: CCOC(=O)C(C)(C)CNCc1ccc(-c2ccc(OC)nc2)cc1] | ¹H NMR (300 MHz, CHLOROFORM-d) δ ppm 1.16-1.31 (m, 9 H) 2.68 (s, 2 H) 3.83 (s, 2 H) 3.93-4.02 (m, 3 H) 4.08-4.19 (m, 2 H) 6.78-6.85 (m, 1 H) 7.35-7.51 (m, 4 H) 7.74-7.82 (m, 1 H) 8.35-8.42 (m, 1 H). MS ESI/APCI Dual posi: 343[M + H]⁺, 365[M + Na]⁺. | |
| Reference Example A-392 | 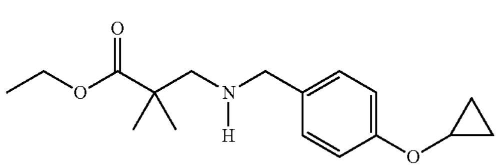 [SMILES: CCOC(=O)C(C)(C)CNCc1ccc(OC2CC2)cc1] | ¹H NMR (300 MHz, CHLOROFORM-d) δ ppm 0.73-0.81 (m, 4 H) 1.18 (s, 6 H) 1.20-1.27 (m, 3 H) 2.62-2.67 (m, 2 H) 3.67-3.77 (m, 3 H) 4.07-4.17 (m, 2 H) 6.95-7.02 (m, 2 H) 7.18-7.25 (m, 2 H). MS ESI/APCI Dual posi: 292[M + H]⁺. MS ESI/APCI Dual nega: 290[M − H]⁻. | |

TABLE 18-57

| Compound No. | Structure | Analytical Data | Salt information |
|---|---|---|---|
| Reference Example A-393 | 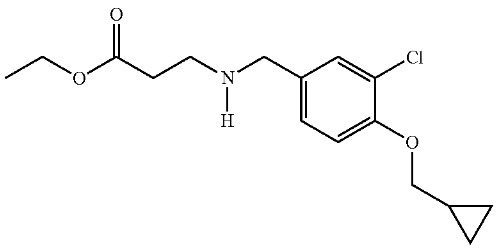 [SMILES: CCOC(=O)CCNCc1ccc(OCC2CC2)c(Cl)c1] | $^1$H HMR (300 MHz, CHLOROFORM-d) δ ppm 0.33-0.42 (m, 2 H) 0.57-0.70 (m, 2 H) 1.26 (t, J = 7.1 Hz, 3 H) 1.26-1.39 (m, 1 H) 2.47-2.56 (m, 2 H) 2.81-2.92 (m, 2 H) 3.71 (s, 2 H) 3.87 (d, J = 6.7 Hz, 2 H) 4.14 (q, J = 7.1 Hz, 2 H) 6.86 (d, J = 8.4 Hz, 1 H) 7.13 (dd, J = 8.4, 2.1 Hz, 1 H) 7.33 (d, J = 2.1 Hz. 1 H). MS ESI/APCI Dual posi: 312[M + H]$^+$. | |
| Reference Example A-394 | 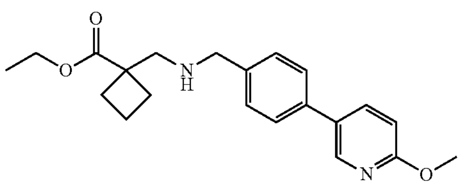 [SMILES: CCOC(=O)C1(CNCc2ccc(-c3ccc(OC)nc3)cc2)CCC1] | $^1$H NMR (300 MHz, CHLOROFORM-d) δ ppm 1.17-1.30 (m, 3 H) 1.85-2.03 (m, 4 H) 2.30-2.50 (m, 2 H) 2.93 (s, 2 H) 3.97 (s, 3 H) 4.08-4.22 (m, 2 H) 4.75 (s, 2 H) 6.78-6.85 (m, 1 H) 7.35-7.52 (m, 4 H) 7.75-7.83 (m, 1 H) 8.35-8.41 (m, 1 H). MS ESI/APCI Dual posi: 355[M + H]$^+$. | |
| Reference Example A-395 | 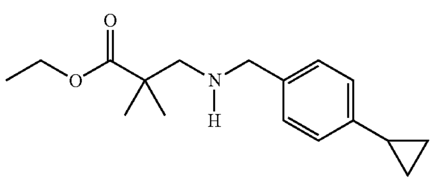 [SMILES: CCOC(=O)C(C)(C)CNCc1ccc(C2CC2)cc1] | $^1$H NMR (300 MHz, CHLOROFORM-d) δ ppm 0.62-0.72 (m, 2 H) 0.89-0.98 (m, 2 H) 1.18 (s, 6 H) 1.23 (t, J = 7.1 Hz, 3 H) 1.81-1.94 (m, 1 H) 2.64 (s, 2 H) 3.74 (s, 2 H) 4.06-4.17 (m, 2 H) 6.98-7.05 (m, 2 H) 7.15-7.22 (m, 2 H). MS ESI/APCI Dual posi: 276[M + H]$^+$. | |
| Reference Example A-396 | 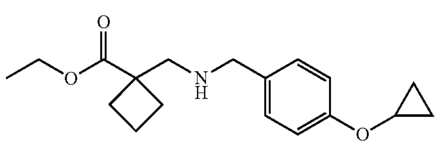 [SMILES: CCOC(=O)C1(CNCc2ccc(OC3CC3)cc2)CCC1] | $^1$H NMR (300 MHz, CHLOROFORM-d) δ ppm 0.71-0.82 (m, 4 H) 1.21-1.29 (m, 3 H) 1.81-2.03 (m, 4 H) 2.30-2.49 (m, 2 H) 2.89 (s, 2 H) 3.65-3.79 (m, 3 H) 4.16 (q, J = 7.0 Hz, 2 H) 6.95-7.02 (m, 2 H) 7.18-7.25 (m, 2 H). MS ESI/APCI Dual posi: 304[M + H]$^+$, 326[M + Na]$^+$. | |
| Reference Example A-397 | 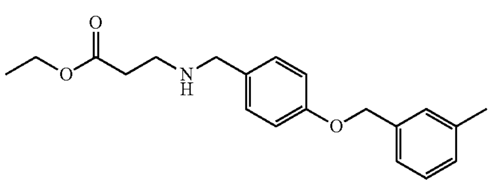 [SMILES: CCOC(=O)CCNCc1ccc(OCc2cccc(C)c2)cc1] | $^1$H NMR (300 MHz, CHLOROFORM-d) δ ppm 1.25 (t, J = 7.1 Hz, 3 H) 2.37 (s, 3 H) 2.52 (t, J = 6.5 Hz, 2 H) 2.89 (t, J = 6.5 Hz, 2 H) 3.74 (s, 2 H) 4.14 (q, J = 7.1 Hz, 2 H) 5.01 (s, 2 H) 6.90-6.96 (m, 2 H) 7.10-7.16 (m, 1 H) 7.19-7.28 (m, 5 H). MS ESI/APCI Dual posi: 328[M + H]$^+$, 350[M + Na]$^+$. MS ESI/APCI Dual nega: 326[M − H]$^-$. | |
| Reference Example A-398 | 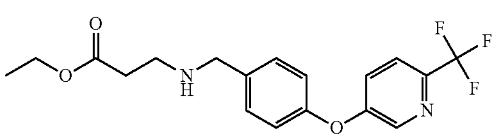 [SMILES: CCOC(=O)CCNCc1ccc(Oc2ccc(C(F)(F)F)nc2)cc1] | $^1$H NMR (300 MHz, CHLOROFORM-d) δ ppm 1.27 (t, J = 7.1 Hz, 3 H) 2.55 (t, J = 6.4 Hz, 2 H) 2.87-2.97 (m, 2 H) 3.82 (s, 2 H) 4.15 (q, J = 7.1 Hz, 2 H) 6.99-7.08 (m, 2 H) 7.27-7.43 (m, 3 H) 7.61 (d, J = 8.5 Hz, 1 H) 8.42-8.50 (m, 1 H). MS ESI/APCI Dual posi: 369[M + H]$^+$, 391[M + Na]$^+$. MS ESI/APCI Dual nega: 367[M − H]$^-$. | |
| Reference Example A-399 | 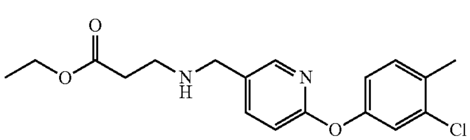 [SMILES: CCOC(=O)CCNCc1ccc(Oc2ccc(C)c(Cl)c2)nc1] | $^1$H NMR (300-MHz, CHLOROFORM-d) δ ppm 1.26 (t, J = 7.1 Hz, 3 H) 2.36 (s, 3 H) 2.48-2.56 (m, 2 H) 2.83-2.92 (m, 2 H) 3.75 (s, 2 H) 4.14 (q, J = 7.1 Hz, 2 H) 6.82-6.99 (m, 2 H) 7.10-7.27 (m, 2 H) 7.70 (dd, J = 8.4, 2.5 Hz, 1 H) 8.10 (dd, J = 2.5, 0.6 Hz, 1 H). MS ESI/APCI Dual posi: 349[M + H]$^+$, 371[M + Na]$^+$. MS.ESI/APCI Dual nega: 347[M − H]$^-$. | |

TABLE 18-58

| Compound No. | Structure | Analytical Data | Salt information |
|---|---|---|---|
| Reference Example A-400 | 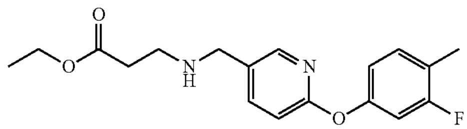 [SMILES: CCOC(=O)CCNCc1ccc(Oc2ccc(C)c(F)c2)nc1] | $^1$H HMR (300 MHz, CHLOROFORM-d) δ ppm 1.26 (t, J = 7.1 Hz, 3 H) 2 26 (d, J = 1.9 Hz, 3 H) 2.46-2.57 (m, 2 H) 2.83-2.92 (m, 2 H) 3.76 (s, 2 H) 4.14 (q, J = 7.1 Hz, 2 H) 6.76-6.94 (m, 3 H) 7.11-7.22 (m, 1 H) 7.70 (dd, J = 8.4, 2.5 Hz, 1 H) 8.10 (dd, J = 2.5, 0.6 Hz, 1 H). MS ESI/APCI Dual posi: 333[M + H]$^+$, 355[M + Na]$^+$. MS ESI/APCI Dual nega: 331[M − H]$^-$. | |
| Reference Example A-401 | 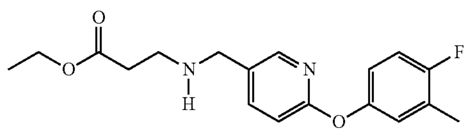 [SMILES: CCOC(=O)CCNCc1ccc(Oc2ccc(F)c(C)c2)nc1] | $^1$H NMR (300 MHz, CHLOROFORM-d) δ ppm 1.20-1.31 (m, 3 H) 2.27 (d, J = 2.0 Hz, 3 H) 2.46-2.57 (m, 2 H) 2.83-2.92 (m, 2 H) 3.75 (s, 2 H) 4.14 (q, J = 7.1 Hz, 2 H) 6.78-7.08 (m, 4 H) 7.69 (dd, J = 8.4, 2.5 Hz, 1 H) 8.04-8.12 (m, 1 H). MS ESI/APCI Dual posi: 333[M + H]$^+$, 355[M + Na]$^+$. MS ESI/APCI Dual nega: 331[M − H]$^-$. | |
| Reference Example A-402 | 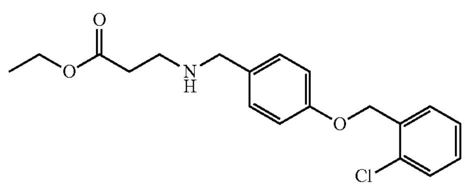 [SMILES: CCOC(=O)CCNCc1ccc(OCc2ccccc2Cl)cc1] | $^1$H NMR (300 MHz, CHLOROFORM-d) δ ppm 1.25 (t, J = 7.1 Hz, 3 H) 2 52 (t, J = 6.5 Hz, 2 H) 2.89 (t, J = 6.5 Hz, 2 H) 3.74 (s, 2 H) 4.14 (q, J = 7.1 Hz, 2 H) 5.16 (s, 2 H) 6.92-6.97 (m, 2 H) 7.23-7.30 (m, 4 H) 7.37-7.42 (m, 1 H) 7.53-7.58 (m, 1 H). MS ESI/APCI Dual posi: 348[M + H]$^+$, 370[M + Na]$^+$. MS ESI/APCI Dual nega: 346[M − H]$^-$. | |
| Reference Example A-403 | 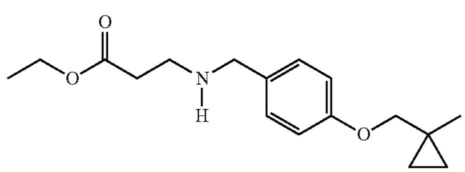 [SMILES: CCOC(=O)CCNCc1ccc(OCC2(C)CC2)cc1] | $^1$H HMR (300 MHz, CHLOROFORM-d) δ ppm 0.38-0.45 (m, 2 H) 0.49-0.58 (m, 2 H) 1.20-1.30 (m, 6 H) 1.61-1.71 (m, 1 H) 2.51 (t, J = 6.5 Hz, 2 H) 2.88 (t, J = 6.5 Hz, 2 H) 3.68-3.75 (m, 4 H) 4.13 (q, J = 7.0 Hz, 2 H) 6.81-6.89 (m, 2 H) 7.15-7.24 (m, 2 H). MS ESI/APCI Dual posi: 292[M + H]$^+$. | |
| Reference Example A-404 | 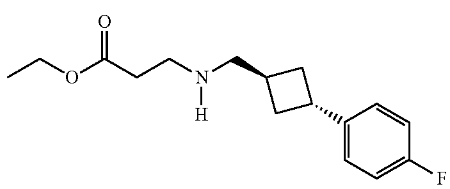 [SMILES: CCOC(=O)CCNC[C@H]1C[C@H](c2ccc(F)cc2)C1] | $^1$H NMR (300 MHz, CHLOROFORM-d) δ ppm 1.21-1.31 (m, 3 H) 2.05-2.32 (m, 4 H) 2.35-2.62 (m, 3 H) 2.83 (d, J = 7.6 Hz, 2 H) 2.88-2.96 (m, 2 H) 3.42-3.67 (m, 1 H) 4.04-4.24 (m, 2 H) 6.89-7.05 (m, 2 H) 7.09-7.25 (m, 2 H). MS ESI/APCI Dual posi: 280[M + H]$^+$. | |
| Reference Example A-405 | 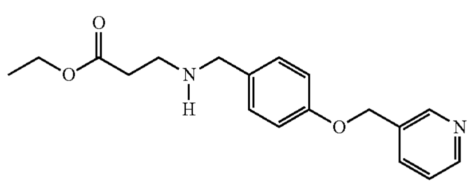 [SMILES: CCOC(=O)CCNCc1ccc(OCc2cccnc2)cc1] | $^1$H NMR (300 MHz, CHLOROFORM-d) δ ppm 1.26 (t, J = 7.1 Hz, 3 H) 2.53 (t, J = 6.5 Hz, 2 H) 2.89 (t, J = 6.5 Hz, 2 H) 3.75 (s, 2 H) 4.14 (q, J = 7.1 Hz, 2 H) 5.07 (s, 2 H) 6.89-6.96 (m, 2 H) 7.22-7.28 (m, 2 H) 7.29-7.36 (m, 1 H) 7.75-7.81 (m, 1 H) 8.58 (dd, J = 4.8, 1.6 Hz, 1 H) 8.68 (d, J = 1.6 Hz, 1 H). MS ESI/APCI Dual posi: 315[M + H]$^+$, 337[M + Na]$^+$. MS ESI/APCI Dual nega: 313[M − H]$^-$, 349[M + Cl]$^-$. | |
| Reference Example A-406 | 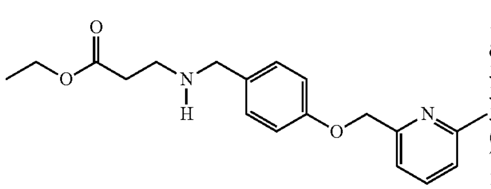 [SMILES: CCOC(=O)CCNCc1ccc(OCc2cccc(C)n2)cc1] | $^1$H NMR (300 MHz, CHLOROFORM-d) δ ppm 1.25 (t, J = 7.1 Hz, 3 H) 2.52 (t, J = 6.5 Hz, 2 H) 2.57 (s, 3 H) 2.88 (t, J = 6.5 Hz, 2 H) 3.74 (s, 2 H) 4.13 (q, J = 7.1 Hz, 2 H) 5.16 (s, 2 H) 6.89-6.97 (m, 2 H) 7.07 (d, J = 7.8 Hz, 1 H) 7.20-7.25 (m, 2 H) 7.32 (d, J = 7.8 Hz, 1 H) 7.59 (t, J = 7.8 Hz, 1 H). MS ESI/APCI Dual posi: 329[M + H]$^+$, 351[M + Na]$^+$. | |

TABLE 18-59

| Compound No. | Structure | Analytical Data | Salt information |
|---|---|---|---|
| Reference Example A-407 | 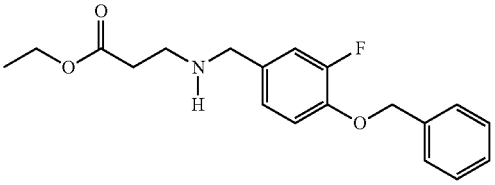 | ¹H NMR (300 MHz, CHLOROFORM-d) δ ppm 1.26 (t, J = 7.1 Hz, 3 H) 2.51 (t, J = 6.5 Hz, 2 H) 2.87 (t, J = 6.5 Hz, 2 H) 3.72 (s, 2 H) 4.14 (q, J = 7.1 Hz, 2 H) 5.13 (s, 2 H) 6.89-6.97 (m, 2 H) 7.05-7.12 (m, 1 H) 7.32-7.46 (m, 4 H). MS ESI/APCI Dual posi: 332[M + H]⁺, 354[M + Na]⁺. MS ESI/APCI Dual nega: 330[M − H]⁻. | |
| Reference Example A-408 | 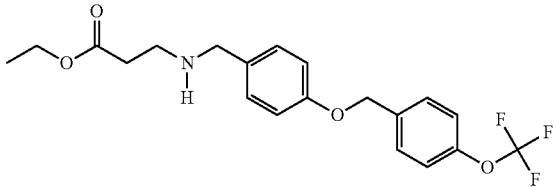 [SMILES: CCOC(=O)CCNCc1ccc(OCc2ccc(OC(F)(F)F)cc2)cc1] | ¹H NMR (300 MHz, CHLOROFORM-d) δ ppm 1.25 (t, J = 7.1 Hz, 3 H) 2.52 (t, J = 6.5 Hz, 2 H) 2.89 (t, J = 6.5 Hz, 2 H) 3.74 (s, 2 H) 4.14 (q, J = 7.1 Hz, 2 H) 5.05 (s, 2 H) 6.89-6.95 (m, 2 H) 7.20-7.26 (m, 4 H) 7.43-7.49 (m, 2 H). MS ESI/APCI Dual posi: 398[M + H]⁺, 420[M + Na]⁺. MS ESI/APCI Dual nega: 396[M − H]⁻, 432[M + Cl]⁻. | |
| Reference Example A-409 | 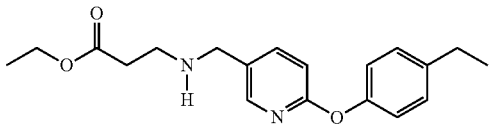 [SMILES: CCOC(=O)CCNCc1ccc(Oc2ccc(CC)cc2)nc1] | ¹H HMR (300 MHz, CHLOROFORM-d) δ ppm 1.19-1.32 (m, 6 H) 2.43-2.57 (m, 2 H) 2.66 (q, J = 7.6 Hz, 2 H) 2.79-2.96 (m, 2 H) 3.75 (s, 2 H) 4.14 (q, J = 7.1 Hz, 2 H) 6.85 (d, J = 8.4 Hz, 1 H) 6.99-7.09 (m, 2 H) 7.17-7.25 (m, 2 H) 7.67 (dd, J = 8.4, 2.5 Hz, 1 H) 8.10 (dd, J = 2.5, 0.6 Hz, 1 H). MS ESI/APCI Dual posi: 329[M + H]⁺. | |
| Reference Example A-410 | 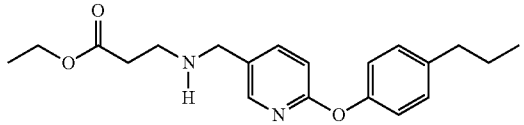 [SMILES: CCCc1ccc(Oc2ccc(CNCCC(=O)OCC)cn2)cc1] | ¹H NMR (300 MHz, CHLOROFORM-d) δ ppm 0.96 (t, J = 7.4 Hz, 3 H) 1.19-1.32 (m, 3 H) 1.60-1.74 (m, 2 H) 2.44-2.66 (m, 4 H) 2.79-2.96 (m, 2 H) 3.75 (s, 2 H) 4.05-4.22 (m, 2 H) 6.84 (d, J = 8.4 Hz, 1 H) 6.96-7.10 (m, 2 H) 7.12-7.28 (m, 2 H) 7.67 (dd, J = 8.4, 2.5 Hz, 1 H) 8.00-8.19 (m, 1 H). MS ESI/APCI Dual posi: 343[M + H]⁺. | |
| Reference Example A-411 | 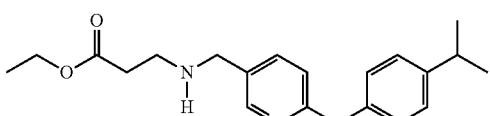 | ¹H NMR (300 MHz, CHLOROFORM-d) δ ppm 1.22-1.30 (m, 9 H) 2.46-2.57 (m, 2 H) 2.79-2.99 (m, 3 H) 3.75 (s, 2 H) 4.08-4.20 (m, 2 H) 6.85 (d, J = 8.4 Hz, 1 H) 7.04 (d, J = 8.4 Hz, 2 H) 7.14-7.34 (m, 2 H) 7.67 (dd, J = 8.4, 2.5 Hz, 1 H) 8.11 (d, J = 2.5 Hz, 1 H). MS ESI/APCI Dual posi: 343[M + H]⁺. | |
| Reference Example A-412 | 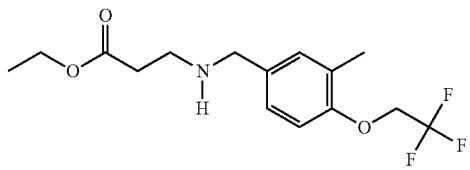 [SMILES: CCOC(=O)CCNCc1ccc(OCC(F)(F)F)c(C)c1] | ¹H NMR (300 MHz, CHLOROFORM-d) δ ppm 1.18-1.33 (m, 3 H) 2.25 (s, 3 H) 2.47-2.59 (m, 2 H) 2.82-2.93 (m, 2 H) 3.72 (s, 2 H) 4.05-4.20 (m, 2 H) 4.33 (q, J = 8.1 Hz, 2 H) 6.74 (d, J = 8.1 Hz, 1 H) 7.04-7.18 (m, 2 H). MS EPI/APCI Dual posi: 320[M + H]⁺. | |
| Reference Example A-413 | 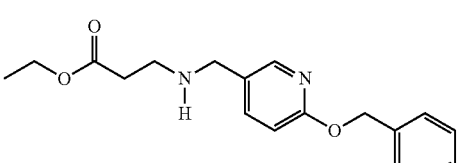 | ¹H NMR (300 MHz, CHLOROFORM-d) δ ppm 1.26 (t, J = 7.1 Hz, 3 H) 2.52 (t, J = 6.4 Hz, 2 H) 2.88 (t, J = 6.4 Hz, 2 H) 3.73 (s, 2 H) 4.14 (q, J = 7.1 Hz, 2 H) 5.37 (s, 2 H) 6.78 (d, J = 8.7 Hz, 1 H) 7.30-7.41 (m, 3 H) 7.43-7.49 (m, 2 H) 7.59 (dd, J = 8.7, 2.5 Hz, 1 H) 8.08 (d, J = 2.5 Hz, 1 H). MS ESI/APCI Dual posi: 315[M + H]⁺, 337[M + Na]⁺. | |

TABLE 18-60

| Compound No. | Structure | Analytical Data | Salt information |
|---|---|---|---|
| Reference Example A-414 | 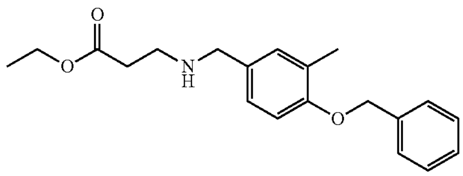 [SMILES: CCOC(=O)CCNCc1ccc(OCc2ccccc2)c(C)c1] | $^1$H NMR (300 MHz, CHLOROFORM-d) δ ppm 1.25 (t, J = 7.1 Hz, 3 H) 2.27 (s, 3 H) 2.52 (t, J = 6.5 Hz, 2 H) 2.89 (t, J = 6.5 Hz, 2 H) 3.71 (s, 2 H) 4.14 (q, J = 7.1 Hz, 2 H) 5.07 (s, 2 H) 6.83 (d, J = 8.2 Hz, 1 H) 7.04-7.14 (m, 2 H) 7.28-7.47 (m, 5 H). MS ESI/APCI Dual posi: 328[M + H]$^+$, 350[M + Na]$^+$. MS ESI/APCI Dual nega: 326[M − H]$^-$. | |
| Reference Example A-415 | 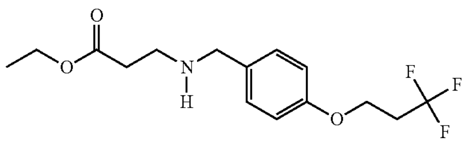 [SMILES: CCOC(=O)CCNCc1ccc(OCCC(F)(F)F)cc1] | $^1$H NMR (300 MHz, CHLOROFORM-d) δ ppm 1.25 (t, J = 7.1 Hz, 3 H) 2.48-2.55 (m, 2 H) 2.56-2.70 (m, 2 H) 2.88 (t, J = 6.5 Hz, 2 H) 3.74 (s, 2 H) 4.07-4.23 (m, 4 H) 6.82-6.89 (m, 2 H) 7.20-7.28 (m, 2 H). MS ESI/APCI Dual posi: 320[M + H]$^+$. | |
| Reference Example A-416 | 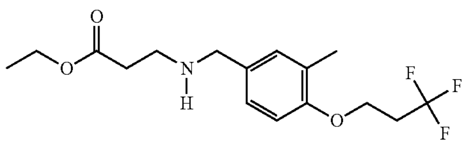 [SMILES: CCOC(=O)CCNCc1ccc(OCCC(F)(F)F)c(C)c1] | $^1$H NMR (300 MHz, CHLOROFORM-d) δ ppm 1.20-1.29 (m, 3 H) 2.20 (s, 3 H) 2.48-2.55 (m, 2 H) 2.56-2.72 (m, 2 H) 2.88 (t, J = 6.5 Hz, 2 H) 3.71 (s, 2 H) 4.08-4.23 (m, 4 H) 6.69-6.78 (m, 1 H) 7.04-7.14 (m, 2 H). MS ESI/APCI Dual posi: 334[M + H]$^+$. | |
| Reference Example A-417 | 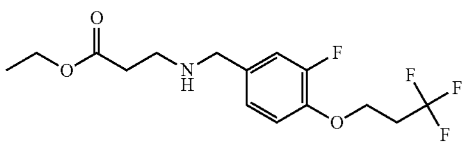 [SMILES: CCOC(=O)CCNCc1ccc(OCCC(F)(F)F)c(F)c1] | $^1$H NMR (300 MHz, CHLOROFORM-d) δ ppm 1.26 (t, J = 7.1 Hz, 3 H) 2.46-2.57 (m, 2 H) 2.59-2.74 (m, 2 H) 2.82-2.90 (m, 2 H) 3.73 (s, 2 H) 4.15 (q, J = 7.1 Hz, 2 H) 4.25 (t, J = 6.8 Hz, 2 H) 6.86-6.96 (m, 1 H) 6.98-7.15 (m, 2 H). MS ESI/APCI Dual posi: 338[M + H]$^+$. | |
| Reference Example A-418 | 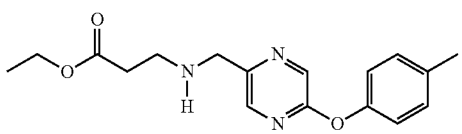 [SMILES: CCOC(=O)CCNCc1cnc(Oc2ccc(C)cc2)cn1] | $^1$H NMR (300 MHz, CHLOROFORM-d) δ ppm 1.26 (t, J = 7.1 Hz, 3 H) 2.37 (s, 3 H) 2.54 (t, J = 6.5 Hz, 2 H) 2.93 (t, J = 6.5 Hz, 2 H) 3.90 (s, 2 H) 4.14 (q, J = 7.0 Hz, 2 H) 6.98-7.07 (m, 2 H) 7.18-7.25 (m, 2 H) 7.93-8.19 (m, 1 H) 8.34 (d, J = 1.2 Hz, 1 H). MS ESI/APCI Dual posi: 316[M + H]$^+$. | |
| Reference Example A-419 | 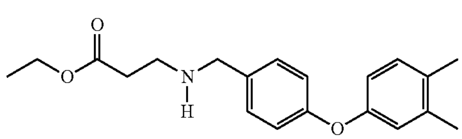 [SMILES: CCOC(=O)CCNCc1ccc(Oc2ccc(C)c(C)c2)cc1] | $^1$H HMR (300 MHz, CHLOROFORM-d) δ ppm 1.26 (t, J = 7.1 Hz, 3 H) 2.23 (s, 6 H) 2.38-2.70 (m, 2 H) 2.91 (t, J = 6.5 Hz, 2 H) 3.77 (s, 2 H) 4.01-4.25 (m, 2 H) 6.70-6.77 (m, 1 H) 6.78-6.84 (m, 1 H) 6.87-6.99 (m, 2 H) 7.07 (d, J = 8.2 Hz, 1 H) 7.17-7.34 (m, 2 H). MS ESI/APCI Dual posi: 328[M + H]$^+$. | |
| Reference Example A-420 | 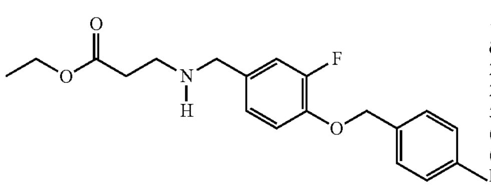 [SMILES: CCOC(=O)CCNCc1ccc(OCc2ccc(C)cc2)c(F)c1] | $^1$H NMR (300 MHz, CHLOROFORM-d) δ ppm 1.26 (t, J = 7.1 Kz, 3 H) 2.35 (s, 3 H) 2.51 (t, J = 6.4 Hz, 2 H) 2.86 (t, J = 6.4 Hz, 2 H) 3.71 (s, 2 H) 4.14 (q, J = 7.1 Hz, 2 H) 5.08 (s, 2 H) 6.89-6.99 (m, 2 H) 7.04-7.11 (m, 1 H) 7.18 (d, J = 8.0 Hz, 2 H) 7.32 (d, J = 8.0 Hz, 2 H). MS ESI/APCI Dual posi: 346[M + H]$^+$, 368[M + Na]$^+$. MS ESI/APCI Dual nega: 344[M − H]$^-$. | |

TABLE 18-61

| Compound No. | Structure | Analytical Data | Salt information |
|---|---|---|---|
| Reference Example A-421 | 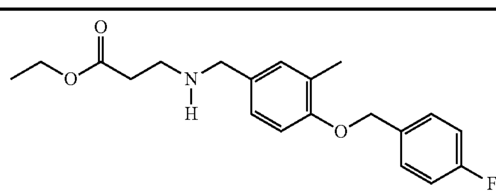 | $^1$H NMR (300 MHz, CHLOROFORM-d) δ ppm 1.25 (t, J = 7.1 Hz, 3 H) 2.26 (s, 3 H) 2.52 (t, J = 6.5 Hz, 2 H) 2.89 (t, J = 6.5 Hz, 2 H) 3.71 (s, 2 H) 4.14 (q, J = 7.1 Hz, 2 H) 5.02 (s, 2 H) 6.81 (d, J = 8.2 Hz, 1 H) 7.02-7.14 (m, 4 H) 7.36-7.44 (m, 2 H). MS ESI/APCI Dual posi: 346[M + H]$^+$, 368[M + Na]$^+$. MS ESI/APCI Dual nega: 344[M − H]$^-$. | |

TABLE 18-61-continued

| Compound No. | Structure | Analytical Data | Salt information |
|---|---|---|---|
| Reference Example A-422 | 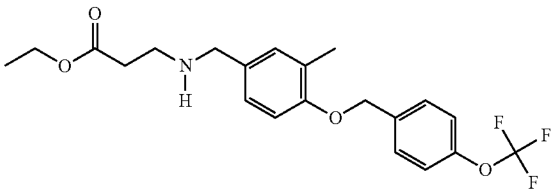 [SMILES: CCOC(=O)CCNCc1ccc(OCc2ccc(OC(F)(F)F)cc2)c(C)c1] | ¹H NMR (300 MHz, CHLOROFORM-d) δ ppm 1.25 (t, J = 7.1 Hz, 3 H) 2.27 (s, 3 H) 2.53 (t, J = 6.5 Hz, 2 H) 2.89 (t, J = 6.5 Hz, 2 H) 3.71 (s, 2 H) 4.14 (q, J = 7.1 Hz, 2 H) 5.06 (s, 2 H) 6.80 (d, J = 8.2 Hz, 1 H) 7.06-7.15 (m, 2 H) 7.20-7.26 (m, 2 H) 7.44-7.50 (m, 2 H). MS ESI/APCI Dual posi: 412[M + H]⁺, 434[M + Na]⁺. MS ESI/APCI Dual nega: 410[M − H]⁻, 446[M + Cl]⁻. | |
| Reference Example A-423 | 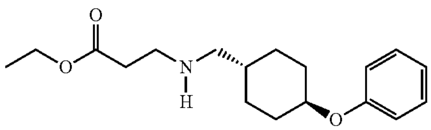 [SMILES: CCOC(=O)CCNC[C@H]1CC[C@H](Oc2ccccc2)CC1] | ¹H NMR (600 MHz, CHLOROFORM-d) δ ppm 1.00-1.10 (m, 2 H) 1.26 (t, J = 7.2 Hz, 3 H) 1.37-1.56 (m, 3 H) 1.86-1.94 (m, 2 H) 2.14-2.23 (m, 2 H) 2.46-2.56 (m, 4 H) 2.37 (t, J = 6.4 Hz, 2 H) 4.10-4.20 (m, 3 H) 6.86-6.95 (m, 3 H) 7.22-7.29 (m, 2 H). MS ESI/APCI Dual posi: 306[M + H]⁺. | |
| Reference Example A-424 | 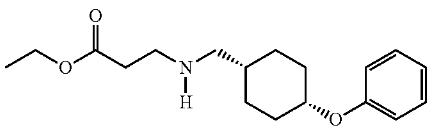 [SMILES: CCOC(=O)CCNC[C@H]1CC[C@@H](Oc2ccccc2)CC1] | ¹H NMR (200 MHz, CHLOROFORM-d) δ ppm 1.19-1.33 (m, 3 H) 1.34-1.71 (m, 7 H) 1.93-2.10 (m, 2 H) 2.44-2.58 (m, 4 H) 2.80-2.96 (m, 2 H) 4.04-4.23 (m, 2 H) 4.47-4.59 (m, 1 H) 6.83-6.99 (m, 3 H) 7.17-7.34 (m, 2 H). MS ESI/APCI Dual posi: 306[M + H]⁺. | |
| Reference Example A-425 | 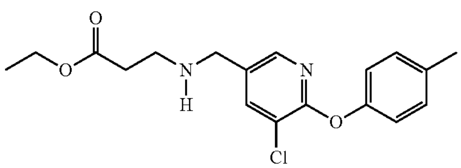 [SMILES: CCOC(=O)CCNCc1cnc(Oc2ccc(C)cc2)c(Cl)c1] | ¹H NMR (300 MHz, CHLOROFORM-d) δ ppm 1.26 (t, J = 7.1 Hz, 3 H) 2.36 (s, 3 H) 2.51 (t, J = 6.4 Hz, 2 H) 2.87 (t, J = 6.4 Hz, 2 H) 3.73 (s, 2 H) 4.15 (q, J = 7.1 Hz, 2 H) 6.97-7.08 (m, 2 H) 7.14-7.25 (m, 2 H) 7.78 (d, J = 2.2 Hz, 1 H) 7.92 (d, J = 2.2 Hz, 1 H). MS ESI/APCI Dual posi: 349[M + H]⁺. | |
| Reference Example A-426 | 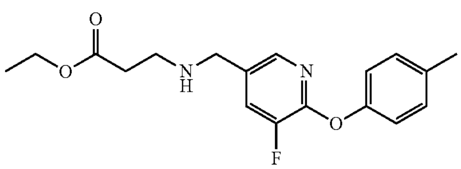 [SMILES: CCOC(=O)CCNCc1cnc(Oc2ccc(C)cc2)c(F)c1] | ¹H NMR (300 MHz, CHLOROFORM-d) δ ppm 1.26 (t, J = 7.1 Hz, 3 H) 2.36 (s, 3 H) 2.52 (t, J = 6.3 Hz, 2 H) 2.87 (t, J = 6.3 Hz, 2 H) 3.76 (s, 2 H) 4.15 (q, J = 7.1 Hz, 2 H) 6.99-7.09 (m, 2 H) 7.15-7.25 (m, 2 H) 7.47-7.56 (m, 1 H) 7.82 (d, J = 2.0 Hz, 1 H). MS ESI/APCI Dual posi: 333[M + H]⁺. | |
| Reference Example A427 | 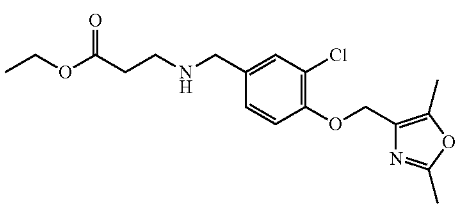 [SMILES: CCOC(=O)CCNCc1ccc(OCc2nc(C)oc2C)c(Cl)c1] | ¹H HMR (300 MHz, CHLOROFORM-d) δ ppm 1.26 (t, J = 7.1 Hz, 3 H) 2.32 (s, 3 H) 2.40 (s, 3 H) 2.52 (t, J = 6.4 Hz, 2 H) 2.87 (t, J = 6.4 Hz, 2 H) 3.72 (s, 2 H) 4.14 (q, J = 7.1 Hz, 2 H) 4.95 (s, 2 H) 7.01 (d, J = 8.4 Hz, 1 H) 7.15 (dd, J = 8.4, 2.2 Hz, 1 H) 7.34 (d, J = 2.2 Hz, 1 H). MS ESI/APCI Dual posi: 367[M + H]⁺. 389[M + Na]⁺. MS ESI/APCI Dual nega: 365[M − H]⁻. | |

TABLE 18-62

| Compound No. | Structure | Analytical Data | Salt information |
|---|---|---|---|
| Reference Example A-428 | 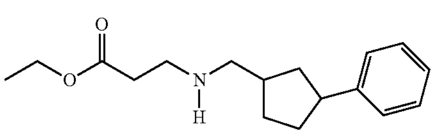 [SMILES: CCOC(=O)CCNCC1CCC(c2ccccc2)C1] | ¹H NMR (300 MHz, CHLOROFORM-d) δ ppm 1.17-1.40 (m, 4 H) 1.58-1.92 (m, 3 H) 1.94-2.40 (m, 3 H) 2.46-2.57 (m, 2 H) 2.58-2.67 (m, 2 H) 2.83-2.96 (m, 2 H) 3.00-3.17 (m, 1 H) 4.15 (q, J = 7.1 Hz, 2 H) 7.12-7.33 (m, 5 H). MS ESI/APCI Dual posi: 276[M + H]⁺. | |

TABLE 18-62-continued

| Compound No. | Structure | Analytical Data | Salt information |
|---|---|---|---|
| Reference Example A-429 | 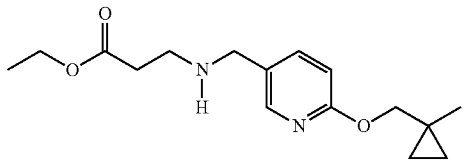 [SMILES: CCOC(=O)CCNCc1ccc(OCC2(C)CC2)nc1] | ¹H NMR (300 MHz, CHLOROFORM-d) δ ppm 0.36-0.43 (m, 2 H) 0.51-0.59 (m, 2 H) 1.19-1.29 (m, 6 H) 2.51 (t, J = 6.4 Hz, 2 H) 2.87 (t, J = 6.4 Hz, 2 H) 3.71 (s, 2 H) 4.06 (s, 2 H) 4.09-4.18 (m, 2 H) 6.75 (d, J = 8.4 Hz, 1 H) 7.57 (dd (J = 8.4, 2.5 Hz, 1 H) 8.02 (d, J = 2.5 Hz, 1 H). MS ESI/APCI Dual posi: 293[M + H]⁺. | |
| Reference Example A-430 | 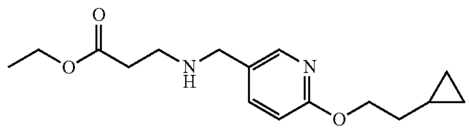 [SMILES: CCOC(=O)CCNCc1ccc(OCCC2CC2)nc1] | ¹H NMR (300 MHz, CHLOROFORM-d) δ ppm 0.06-0.16 (m, 2 H) 0.39-0.52 (m, 2 H) 0.73-0.90 (m, 1 H) 1.20-1.32 (m, 3 H) 1.61-1.71 (m, 2 H) 2.44-2.57 (m, 2 H) 2.82-2.93 (m, 2 H) 3.72 (s, 2 H) 4.06-4.20 (m, 2 H) 4.34 (t, J = 6.8 Hz, 2 H) 6.70 (d, J = 8.4 Hz, 1 H) 7.57 (dd, J = 8.4, 2.5 Hz, 1 H) 8.01-8.09 (m, 1 H). MS ESI/APCI Dual posi: 293[M + H]⁺. | |
| Reference Example A-431 | 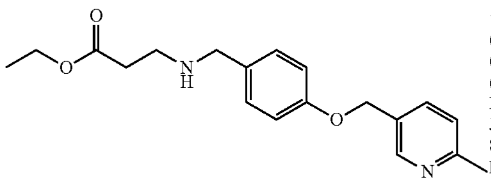 [SMILES: CCOC(=O)CCNCc1ccc(OCc2ccc(C)nc2)cc1] | ¹H NMR (300 MHz, DMSO-d₆) δ ppm 1.17 (t, J = 7.1 Hz, 3 H) 2.38-2.44 (m, 2 H) 2.46 (s, 3 H) 2.64-2.71 (m, 2 H) 3.60 (s, 2 H) 4.04 (q, J = 7.1 Hz, 2 H) 5.07 (s, 2 H) 6.94 (d, J = 8.7 Hz, 2 H) 7.21 (d, J = 8.7 Hz, 2 H) 7.27 (d, J = 7.9 Hz, 1 H) 7.73 (dd, J = 7.9, 2.2 Hz, 1 H) 8.51 (d, J = 2.2 Hz, 1 H). MS ESI/APCI Dual posi: 329[M + H]⁺, 351[M + Na]⁺. MS ESI/APCI Dual nega: 327[M − H]⁻. | |
| Reference Example A-432 | 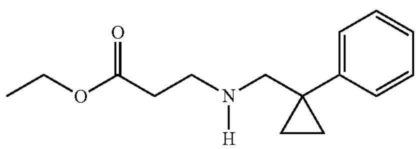 [SMILES: CCOC(=O)CCNCC1(c2ccccc2)CC1] | ¹H NMR (300 MHz, CHLOROFORM-d) δ ppm 0.73-0.81 (m, 2 H) 0.82-0.89 (m, 2 H) 1.20 (t, J = 7.1 Hz, 3 H) 2.43 (t, J = 6.7 Hz, 2 H) 2.78 (s, 2 H) 2.86 (t, J = 6.7 Hz, 2 H) 4.08 (q, J = 7.1 Hz, 2 H) 7.14-7.24 (m, 1 H) 7.25-7.38 (m, 4 H). MS ESI/APCI Dual posi: 248[M + H]⁺. | |
| Reference Example A-433 | 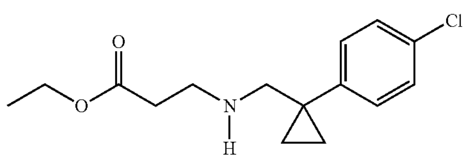 [SMILES: CCOC(=O)CCNCC1(c2ccc(Cl)cc2)CC1] | ¹H NMR (300 MHz, CHLOROFORM-d) δ ppm 0.73-0.86 (m, 4 H) 1.21 (t, J =7.1 Hz, 3 H) 2.43 (t, J = 6.5 Hz, 2 H) 2.76 (s, 2 H) 2.85 (t, J = 6.5 Hz, 2 H) 4.09 (q, J = 7.1 Hz, 2 H) 7.19-7.33 (m, 4 H). MS ESI/APCI Dual posi: 282[M + H]⁺. | |
| Reference Example A-443 | 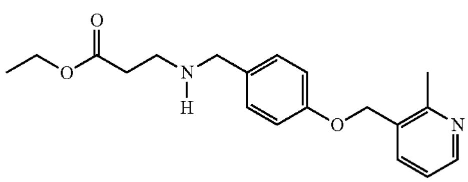 [SMILES: CCOC(=O)CCNCc1ccc(OCc2cccnc2C)cc1] | ¹H NMR (300 MHz, DMSO-d₆) δ ppm 1.17 (t, J = 7.1 Hz, 3 H) 2.38-2.44 (m, 2 H) 2.64-2.72 (m, 2 H) 3.61 (s, 2 H) 4.04 (q, J = 7.1 Hz, 2 H) 5.10 (s, 2 H) 6.95-7.02 (m, 2 H) 7.20-7.27 (m, 3 H) 7.77 (dd, J = 7.7, 1.8 Hz, 1 H) 8.40 (dd, J = 4.9, 1.8 Hz, 1 H). MS ESI/APCI Dual posi: 329[M + H]⁺, 351[M + Na]⁺. MS ESI/APCI Dual nega: 327[M − H]⁻. | |

TABLE 18-63

| Compound No. | Structure | Analytical Data | Salt information |
|---|---|---|---|
| Reference Example A-435 | 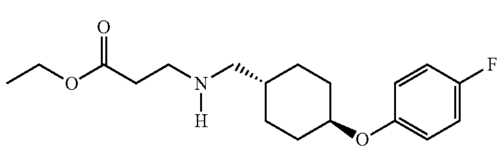 [SMILES: CCOC(=O)CCNC[C@H]1CC[C@H](Oc2ccc(F)cc2)CC1] | ¹H HMR (300 MHz, CHLOROFORM-d) δ ppm 0.94-1.13 (m, 2 H) 1.26 (t, J = 7.1 Hz, 3 H) 1.32-1.62 (m, 3 H) 1.83-1.95 (m, 2 H) 2.06-2.21 (m, 2 H) 2.43-2.57 (m, 4 H) 2.82-2.92 (m, 2 H) 3.98- 4.10 (m, 1 H) 4.10-4.20 (m, 2 H) 6.79-6.87 (m, 2 H) 6.90-6.99 (m, 2 H). MS ESI/APCI Dual posi: 324[M + H]⁺. | |

TABLE 18-63-continued

| Compound No. | Structure | Analytical Data | Salt information |
| --- | --- | --- | --- |
| Reference Example A-436 | 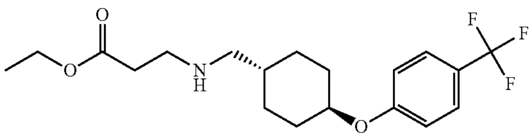 [SMILES: CCOC(=O)CCNC[C@H]1CC[C@H](Oc2ccc(C(F)(F)F)cc2)CC1] | ¹H HMR (300 MHz, CHLOROFORM-d) δ ppm 0.96-1.17 (m, 2 H) 1.27 (t, J = 7.1 Hz, 3 H) 1.37-1.67 (m, 3 H) 1.85-1.99 (m, 2 H) 2.10-2.25 (m, 2 H) 2.46-2.59 (m, 4 H) 2.88 (t, J = 6.5 Hz, 2 H) 4.05-4.30 (m, 3 H) 6.87-6.99 (m, 2 H) 7.45-7.58 (m, 2 H). MS ESI/APCI Dual pcsi: 374[M + H]⁺. | |
| Reference Example A-437 | 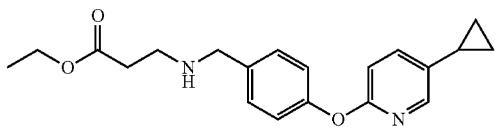 [SMILES: CCOC(=O)CCNCc1ccc(Oc2ccc(C3CC3)cn2)cc1] | ¹H NMR (300 MHz, CHLOROFORM-d) δ ppm 0.58-0.71 (m, 2 H) 0.90-1.02 (m, 2 H) 1.26 (t, J = 7.1 Hz, 3 H) 1.78-1.93 (m, 1 H) 2.53 (t, J = 6.5 Hz, 2 H) 2.92 (t, J = 6.5 Hz, 2 H) 3.80 (s, 2 H) 4.15 (q, J = 7.1 Hz, 2 H) 6.75-6.83 (m, 1 H) 7.00-7.10 (m, 2 H) 7.28-7.39 (m, 3 H) 7.97-8.08 (m, 1 H). MS ESI/APCI Dual posi: 341[M + H]⁺. | |
| Reference Example A-438 | 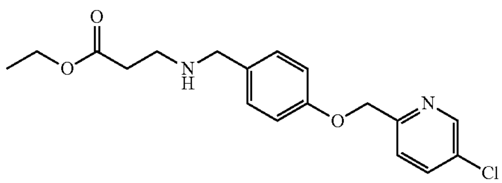 [SMILES: CCOC(=O)CCNCc1ccc(OCc2ccc(Cl)cn2)cc1] | ¹H NMR (300 MHz, CHLOROFORM-d) δ ppm 1.25 (t, J = 7.1 Hz, 3 H) 2.52 (t, J = 6.5 Hz, 2 H) 2.88 (t, J = 6.5 Hz, 2 H) 3.74 (s, 2 H) 4.13 (q, J = 7.1 Hz, 2 H) 5.17 (s, 2 H) 6.89-6.95 (m, 2 H) 7.21-7.26 (m, 2 H) 7.48 (dd, J = 8.4, 0.7 Hz, 1 H) 7.69 (dd, J = 3.4, 2.4 Hz, 1 H) 8.55 (dd, J = 2.4, 0.7 Hz, 1 H). MS ESI/APCI Dual posi: 349[M + H]⁺, 371[M + Na]⁺. MS ESI/APCI Dual nega: 347[M − H]⁻, 383[M + Cl]⁻. | |
| Reference Example A-439 | 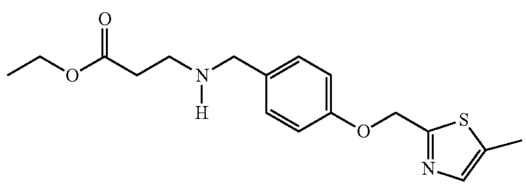 [SMILES: CCOC(=O)CCNCc1ccc(OCc2ncc(C)s2)cc1] | ¹H NMR (300 MHz, CHLOROFORM-d) δ ppm 1.25 (t, J = 7.1 Hz, 3 H) 2.46 (d, J = 1.1 Hz, 3 H) 2.52 (t, J = 6.5 Hz, 2 H) 2.88 (t, J = 6.5 Hz, 2 H) 3.74 (s, 2 H) 4.14 (q, J = 7.1 Hz, 2 H) 5.28 (s, 2 H) 6.93-6.98 (m, 2 H) 7.21-7.26 (m, 2 H) 7.41 (q, J = 1.1 Hz, 1 H). MS ESI/APCI Dual posi: 335[M + H]⁺, 357[M + Na]⁺. MS ESI/APCI Dual nega: 333[M − H]⁻. | |
| Reference Example A-440 | 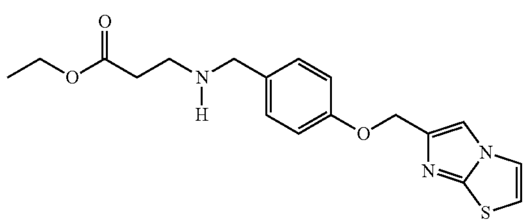 [SMILES: CCOC(=O)CCNCc1ccc(OCc2cn3ccsc3n2)cc1] | ¹H NMR (300 MHz, CHLOROFORM-d) δ ppm 1.25 (t, J = 7.1 Hz, 3 H) 2.52 (t, J = 6.5 Hz, 2 H) 2.89 (t, J = 6.5 Hz, 2 H) 3.74 (s, 2 H) 4.14 (q, J = 7.1 Hz, 2 H) 5.13 (s, 2 H) 6.83 (d, J = 4.5 Hz, 1 H) 6.96-7.00 (m, 2 H) 7.20-7.30 (m, 2 H) 7.39 (d, J = 4.5 Hz, 1 H) 7.51 (s, 1 H). MS ESI/APCI Dual posi: 360[M + H]⁺, 332[M + Na]⁺. MS ESI/APCI Dual nega: 358[M − H]⁻. | |
| Reference Example A-441 | 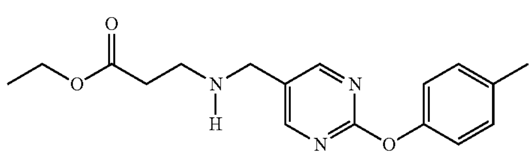 [SMILES: CCOC(=O)CCNCc1cnc(Oc2ccc(C)cc2)nc1] | ¹H NMR (300 MHz, CHLOROFORM-d) δ ppm 1.20-1.30 (m, 3 H) 2.37 (s, 3 H) 2.44-2.60 (m, 2 H) 2.88 (t, J = 6.3 Hz, 2 H) 3.76 (s, 2 H) 4.08-4.20 (m, 2 H) 7.03-7.12 (m, 2 H) 7.18-7.26 (m, 2 H) 8.49 (s, 2 H). MS ESI/APCI Dual posi: 316[M + H]⁺. | |

TABLE 18-64

| Compound No. | Structure | Analytical Data | Salt information |
| --- | --- | --- | --- |
| Reference Example A-442 | 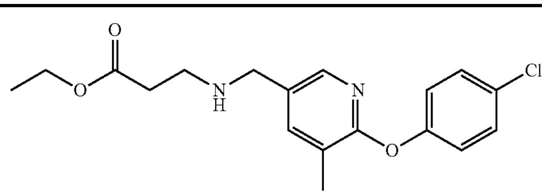 | ¹H NMR (300 MHz, CHLOROFORM-d) δ ppm 1.19 -1.32 (m, 3 H) 2.05 (s, 2 H) 2.33 (s, 3 H) 2.55 (t, J = 6.4 Hz, 2 H) 2.82-2.98 (m, 2 H) 3.67-3.79 (m, 5 H) 4.06-4.22 (m, 2 H) 7.00-7.09 (m, 2 H) 7.30-7.37 (m, 2 H) 7.56 (d, J = 1.9 Hz, 1 H) 7.89 (d, J = 1.9 Hz, 1 H). MS ESI/APCI Dual posi: 349[M + H]⁺. | |

TABLE 18-64-continued

| Compound No. | Structure | Analytical Data | Salt information |
|---|---|---|---|
| Reference Example A-443 | 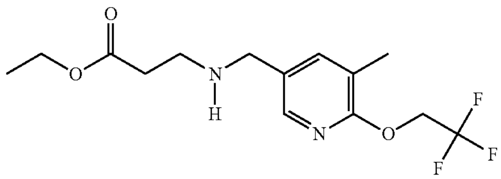 [SMILES: CCOC(=O)CCNCc1cnc(OCC(F)(F)F)c(C)c1] | $^1$H NMR (300 MHz, CHLOROFORM-d) δ ppm 1.26 (t, J = 7.1 Hz, 3 H) 2.22 (s, 3 H) 2.45-2.56 (m, 2 H) 2.83-2.94 (m, 2 H) 3.71 (s, 2 H) 4.14 (q, J = 7.1 Hz, 2 H) 4.75 (q, J = 8.7 Hz, 2 H) 7.41-7.49 (m, 1 H) 7.83-7.91 (m, 1 H). MS ESI/APCI Dual posi: 321[M + H]$^+$. | |
| Reference Example A-444 | 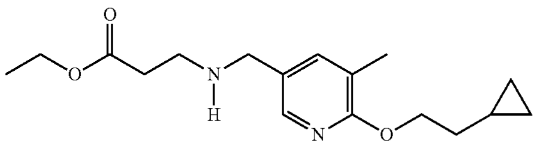 [SMILES: CCOC(=O)CCNCc1cnc(OCCC2CC2)c(C)c1] | $^1$H NMR (300 MHz, CHLOROFORM-d) δ ppm 0.06-0.17 (m, 2 H) 0.39-0.51 (m, 2 H) 0.75-0.91 (m, 1 H) 1.18-1.30 (m, 3 H) 1.61-1.74 (m, 2 H) 2.15-2.22 (m, 3 H) 2.47-2.58 (m, 2 H) 2.81-2.94 (m, 2 H) 3.68 (s, 2 H) 4.06-4.20 (m, 2 H) 4.36 (t, J = 6.6 Hz, 2 H) 7.35-7.41 (m, 1 H) 7.80-7.90 (m, 1 H). MS ESI/APCI Dual posi: 307[M + H]$^+$. | |
| Reference Example A-445 | 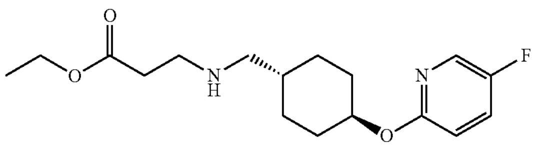 [SMILES: CCOC(=O)CCNC[C@H]1CC[C@H](Oc2ccc(F)cn2)CC1] | $^1$H NMR (300 MHz, CHLOROFORM-d) δ ppm 0.99-1.21 (m, 2 H) 1.26 (t, J = 7.1 Hz, 3 H) 1.33-1.62 (m, 3 H) 1.81-1.94 (m, 2 H) 2.09-2.24 (m, 2 H) 2.42-2.60 (m, 4 H) 2.87 (t, J = 6.5 Hz, 2 H) 4.15 (q, J = 7.1 Hz, 2 H) 4.79-4.95 (m, 1 H) 6.56-6.70 (m, 1 H) 7.22-7.37 (m, 1 H) 7.92-8.01 (m, 1 H). MS ESI/APCI Dual posi: 325[M + H]$^+$. | |
| Reference Example A-446 | 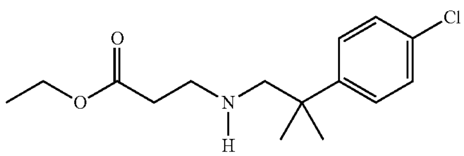 [SMILES: CCOC(=O)CCNCC(C)(C)c1ccc(Cl)cc1] | $^1$H NMR (300 MHz, CHLOROFORM-d) δ ppm 1.20 (t, J = 7.1 Hz, 3 H) 1.31 (s, 6 H) 2.40 (t, J = 6.5 Hz, 2 H) 2.71 (s, 2 H) 2.80 (t, J = 6.5 Hz, 2 H) 4.07 (q, J = 7.1 Hz, 2 H) 7.24-7.34 (m, 2 H) 7.37-7.46 (m, 2H). MS ESI/APCI Dual posi: 284[M + H]$^+$. | |
| Reference Example A-447 | 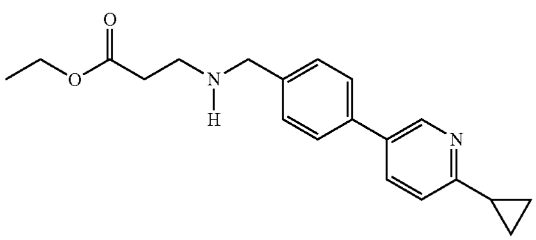 [SMILES: CCOC(=O)CCNCc1ccc(-c2ccc(C3CC3)nc2)cc1] | $^1$H NMR (300 MHz, CHLOROFORM-d) δ ppm 0.97-1.11 (m, 4 H) 1.26 (t, J = 7.1 Hz, 3 H) 2.01-2.16 (m, 1 H) 2.54 (t, J = 6.5 Hz, 2 H) 2.92 (t, J = 6.5 Hz, 2 H) 3.85 (s, 2 H) 4.15 (q, J = 7.1 Hz, 2 H) 7.14-7.23 (m, 1 H) 7.37-7.44 (m, 2 H) 7.47-7.55 (m, 2 H) 7.67-7.77 (m, 1 H) 8.61-8.73 (m, 1 H). MS ESI/APCI Dual posi: 324[M + H]$^+$. | |
| Reference Example A-448 | 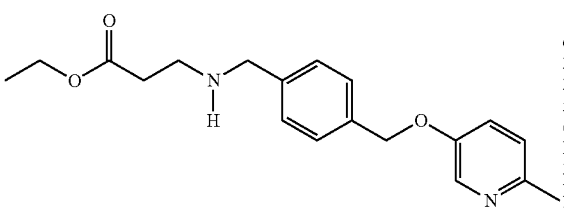 [SMILES: CCOC(=O)CCNCc1ccc(COc2ccc(C)nc2)cc1] | $^1$H NMR (300 MHz, CHLOROFORM-d) δ ppm 1.26 (t, J = 7.1 Hz, 3 H) 2.49 (s, 3 H) 2.53 (t, J = 6.4 Hz, 2 H) 2.90 (t, J = 6.4 Hz, 2 H) 3.81 (s, 2 H) 4.14 (q, J = 7.1 Hz, 2 H) 5.06 (s, 2 H) 7.03-7.07 (m, 1 H) 7.13-7.19 (m, 1 H) 7.32-7.41 (m, 4 H) 8.24-8.27 (m, 1 H). MS ESI/APCI Dual posi: 329[M + H]$^+$, 351[M + Na]$^+$. MS ESI/APCI Dual nega: 327[M − H]$^-$, 363[M + Cl]$^-$. | |

TABLE 18-65

| Compound No. | Structure | Analytical Data | Salt information |
|---|---|---|---|
| Reference Example A-449 | 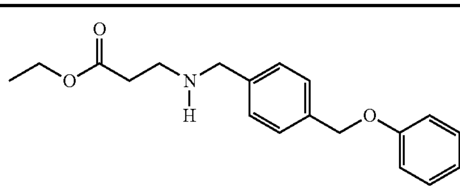 | $^1$H NMR (300 MHz, CHLOROFORM-d) δ ppm 1.26 (t, J = 7.1 Hz, 3 H) 2.53 (t, J = 6.5 Hz, 2 H) 2.90 (t, J = 6.5 Hz, 2 H) 3.81 (s, 2 H) 4.14 (q, J = 7.1 Hz, 2 H) 5.05 (s, 2 H) 6.94-7.01 (m, 3 H) 7.27-7.42 (m, 6 H). MS ESI/APCI Dual posi: 314[M + H]$^+$, 338[M + Na]$^+$. MS ESI/APCI Dual nega: 312[M − H]$^-$, 348[M + Cl]$^-$. | |

TABLE 18-65-continued

| Compound No. | Structure | Analytical Data | Salt information |
|---|---|---|---|
| Reference Example A-450 | 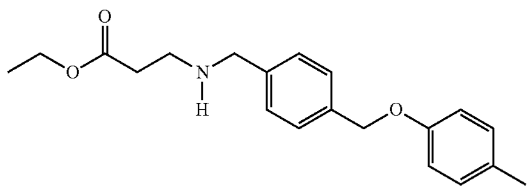 [SMILES: CCOC(=O)CCNCc1ccc(COc2ccc(C)cc2)cc1] | ¹H NMR (300 MHz, CHLOROFORM-d) δ ppm 1.26 (t, J = 7.1 Hz, 3 H) 2.28 (s, 3 H) 2.52 (t, J = 6.5 Hz, 2 H) 2.89 (t, J = 6.5 Hz, 2 H) 3.81 (s, 2 H) 4.14 (q, J = 7.1 Hz, 2 H) 5.02 (s, 2 H) 6.84-6.90 (m, 2 H) 7.05-7.11 (m, 2 H) 7.30-7.41 (m, 4 H). MS ESI/APCI Dual posi: 328[M + H]⁺, 350[M + Na]⁺. MS ESI/APCI Dual nega: 326[M − H]⁻, 362[M + Cl]⁻. | |
| Reference Example A-451 | 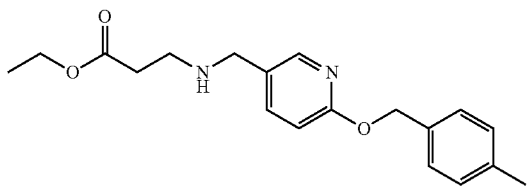 [SMILES: CCOC(=O)CCNCc1ccc(OCc2ccc(C)cc2)nc1] | ¹H NMR (300 MHz, CHLOROFORM-d) δ ppm 1.26 (t, J = 7.1 Hz, 3 H) 2.35 (s, 3 H) 2.52 (t, J = 6.5 Hz, 2 H) 2.88 (t, J = 6.5 Hz, 2 H) 3.73 (s, 2 H) 4.14 (q, J = 7.1 Hz, 2 H) 5.32 (s, 2 H) 6.76 (dd, J = 8.5, 0.5 Hz, 1 H) 7.18 (d, J = 8.0 Hz, 2 H) 7.35 (d, J = 8.0 Hz, 2 H) 7.58 (dd, J = 8.5, 2.4 Hz, 1 H) 8.08 (dd, J = 2.4, 0.5 Hz, 1 H). MS ESI/APCI Dual posi: 329[M + H]⁺, 351[M + Na]⁺. | |
| Reference Example A-452 | 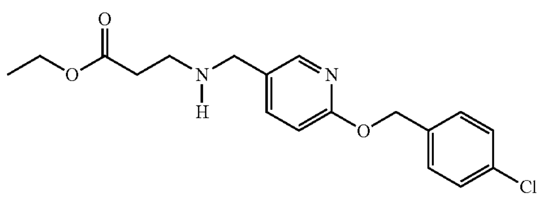 [SMILES: CCOC(=O)CCNCc1ccc(OCc2ccc(Cl)cc2)nc1] | ¹H NMR (300 MHz, CHLOROFORM-d) δ ppm 1.26 (t, J = 7.1 Hz, 3 H) 2.52 (t, J = 6.4 Hz, 2 H) 2.88 (t, J = 6.4 Hz, 2 H) 3.73 (s, 2 H) 4.14 (q, J = 7.1 Hz, 2 H) 5.33 (s, 2 H) 6.77 (dd, J = 8.5, 0.5 Hz, 1 H) 7.31-7.36 (m, 2 H) 7.36-7.42 (m, 2 H) 7.60 (dd, J = 8.5, 2.5 Hz, 1 H) 8.06 (dd, J = 2.5, 0.5 Hz, 1 H). MS ESI/APCI Dual posi: 349[M + H]⁺, 371[M + Na]⁺. MS ESI/APCI Dual nega: 347[M − H]⁻, 383[M + Cl]⁻. | |
| Reference Example A-453 | 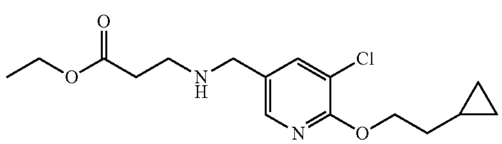 [SMILES: CCOC(=O)CCNCc1cnc(OCCC2CC2)c(Cl)c1] | ¹H NMR (300 MHz, CHLOROFORM-d) δ ppm 0.08-0.17 (m, 2 H) 0.41-0.53 (m, 2 H) 0.76-0.93 (m, 1 H) 1.26 (t, J = 7.1 Hz, 3 H) 1.66-1.76 (m, 2 H) 2.44-2.57 (m, 2 H) 2.77-2.94 (m, 2 H) 3.71 (s, 2 H) 4.15 (q, J = 7.1 Hz, 2 H) 4.39-4.47 (m, 2 H) 7.66 (d, J = 2.2 Hz, 1 H) 7.94 (d, J = 2.2 Hz, 1 H) MS ESI/APCI Dual posi: 327[M + H]⁺. | |
| Reference Example A-454 | 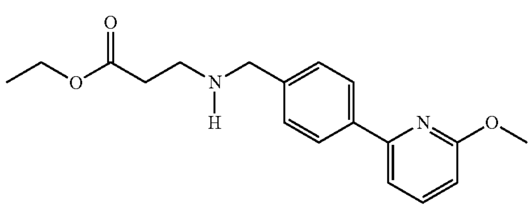 [SMILES: CCOC(=O)CCNCc1ccc(-c2cccc(OC)n2)cc1] | ¹H NMR (300 MHz, CHLOROFORM-d) δ ppm 1.26 (t, J = 7.1 Hz, 3 H) 2.54 (t, J = 6.5 Hz, 2 H) 2.92 (t, J = 8.5 Hz, 2 H) 3.86 (s, 2 H) 4.04 (s, 3 H) 4.15 (q, J = 7.1 Hz, 2 H) 6.65-6.71 (m, 1 H) 7.30-7.36 (m, 1 H) 7.37-7.44 (m, 2 H) 7.57-7.68 (m, 1 H) 7.96-8.05 (m, 2 H). MS ESI/APCI Dual posi: 315[M + H]⁺. | |
| Reference Example A-455 | 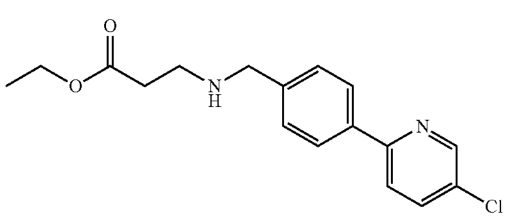 [SMILES: CCOC(=O)CCNCc1ccc(-c2ccc(Cl)cn2)cc1] | ¹H NMR (300 MHz, CHLOROFORM-d) δ ppm 1.26 (t, J = 7.1 Hz, 3 H) 2.54 (t, J = 6.5 Hz, 2 H) 2.91 (t, J = 6.5 Hz, 2 H) 3.87 (s, 2 H) 4.15 (q, J = 7.1 Hz, 2 H) 7.39-7.47 (m, 2 H) 7.63-7.77 (m, 2 H) 7.89-7.96 (m, 2 H) 8.60-8.68 (m, 1 H). MS ESI/APCI Dual posi: 319[M + H]⁺. | |

TABLE 18-66

| Compound No. | Structure | Analytical Data | Salt information |
|---|---|---|---|
| Reference Example A-456 | 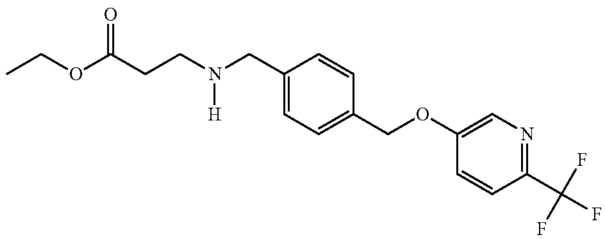 [SMILES: CCOC(=O)CCNCc1ccc(COc2ccc(C(F)(F)F)nc2)cc1] | ¹H NMR (300 MHz, CHLOROFORM-d) δ ppm 1.26 (t, J = 7.1 Hz, 3 H) 2.53 (t, J = 6.4 Hz, 2 H) 2.90 (t, J = 6.4 Hz, 2 H) 3.82 (s, 2 H) 4.14 (q, J = 7.1 Hz, 2 H) 5.15 (s, 2 H) 7.29-7.40 (m, 5 H) 7.56-7.64 (m, 1 H) 8.43-8.48 (m, 1 H). MS ESI/APCI Dual posi: 383[M + H]⁺, 405 [M + Na]⁺. MS ESI/APCI Dual nega: 381[M − H]⁻. | |
| Reference Example A-457 | 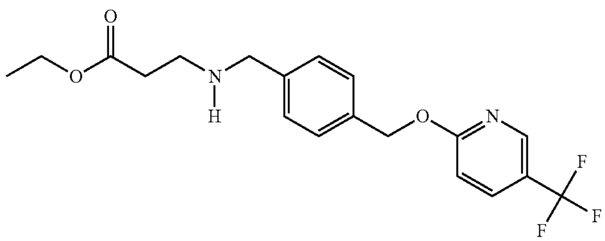 [SMILES: CCOC(=O)CCNCc1ccc(COc2ccc(C(F)(F)F)cn2)cc1] | ¹H NMR (300 MHz, CHLOROFORM-d) δ ppm 1.25 (t, J = 7.1 Hz, 3 H) 2.53 (t, J = 6.5 Hz, 2 H) 2.90 (t, J = 6.5 Hz, 2 H) 3.82 (s, 2 H) 4.14 (q, J = 7.1 Hz, 2 H) 5.41 (s, 2 H) 6.84-6.89 (m, 1 H) 7.31-7.37 (m, 2 H) 7.39-7.45 (m, 2 H) 7.74-7.80 (m, 1 H) 8.43-8.47 (m, 1 H). MS ESI/APCI Dual posi: 383[M + H]⁺, 405 [M + Na]⁺. MS ESI/APCI Dual nega: 381[M − H]⁻. | |
| Reference Example A-458 | 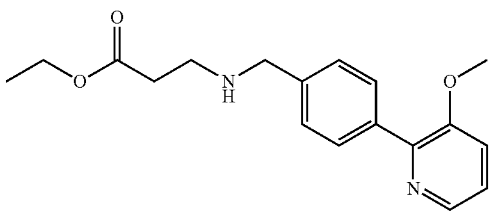 [SMILES: CCOC(=O)CCNCc1ccc(-c2ncccc2OC)cc1] | ¹H NMR (300 MHz, CHLOROFORM-d) δ ppm 1.26 (t, J = 7.1 Hz, 3 H) 2.54 (t, J = 6.5 Hz, 2 H) 2.92 (t, J = 6.5 Hz, 2 H) 3.83-3.87 (m, 2 H) 3.90 (s, 3 H) 4.15 (q, J = 7.1 Hz, 2 H) 7.21-7.30 (m, 1 H) 7.37-7.45 (m, 2 H) 7.62-7.71 (m, 1 H) 7.85-7.93 (m, 2 H) 8.36-8.42 (m, 1 H). MS ESI/APCI Dual posi: 315[M + H]⁺. | |
| Reference Example A-459 | 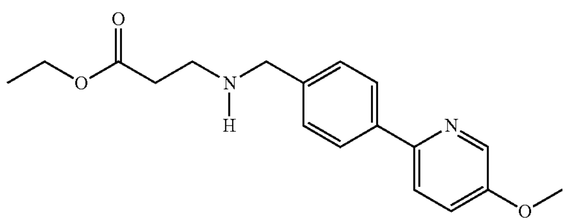 [SMILES: CCOC(=O)CCNCc1ccc(-c2ccc(OC)cn2)cc1] | ¹H NMR (300 MHz, CHLOROFORM-d) δ ppm 1.24 (t, J = 7.1 Hz, 3 H) 2.63-2.76 (m, 2 H) 2.95-3.08 (m, 2 H) 3.85 (s, 3 H) 3.98 (s, 2 H) 4.13 (q, J = 7.1 Hz, 2 H) 7.19-7.54 (m, 4 H) 7.85-7.96 (m, 2 H) 8.28-8.34 (m, 1 H). MS ESI/APCI Dual posi: 315[M + H]⁺. | |
| Reference Example A-460 | 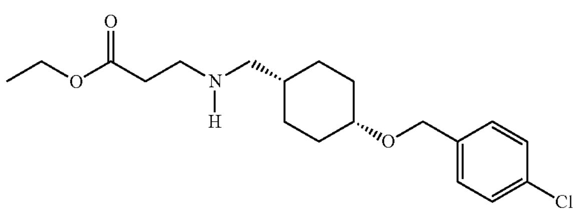 [SMILES: CCOC(=O)CCNC[C@H]1CC[C@@H](OCc2ccc(Cl)cc2)CC1] | ¹H NMR (300 MHz, CHLOROFORM-d) δ ppm 1.26 (t, J = 7.1 Hz, 3 H) 1.31-1.60 (m, 5 H) 1.79-1.96 (m, 4 H) 2.47-2.57 (m, 4 H) 2.83-2.92 (m, 2 H) 3.57-3.65 (m, 1 H) 4.14 (q, J = 7.1 Hz, 2 H) 4.45 (s, 2 H) 7.26-7.31 (m, 4 H). MS ESI/APCI Dual posi: 354[M + H]⁺. | |
| Reference Example A-461 | 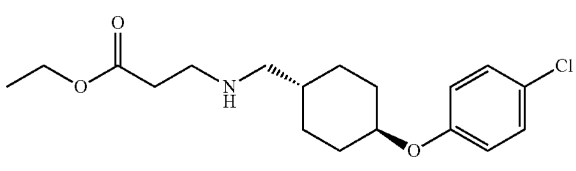 [SMILES: CCOC(=O)CCNC[C@H]1CC[C@H](Oc2ccc(Cl)cc2)CC1] | ¹H NMR (300 MHz, CHLOROFORM-d) δ ppm 0.94-1.15 (m, 2 H) 1.19-1.64 (m, 4 H) 1.83-1.96 (m, 2 H) 2.08-2.21 (m, 2 H) 2.44-2.57 (m, 4 H) 2.80-2.92 (m, 2 H) 4.02-4.27 (m, 4 H) 6.76-6.86 (m, 2 H) 7.16-7.24 (m, 2 H). MS ESI/APCI Dual posi: 340[M + H]⁺. | |
| Reference Example A-462 | 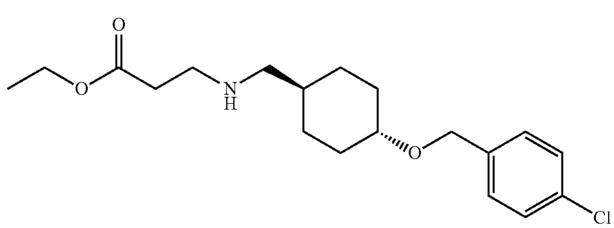 [SMILES: CCOC(=O)CCNC[C@H]1CC[C@H](OCc2ccc(Cl)cc2)CC1] | ¹H NMR (300 MHz, CHLOROFORM-d) δ ppm 0.85-1.04 (m, 2 H) 1.20-1.58 (m, 6 H) 1.77-1.91 (m, 2 H) 2.03-2.16 (m, 2 H) 2.42-2.58 (m, 4 H) 2.86 (t, J = 6.4 Hz, 2 H) 3.20-3.35 (m, 1 H) 4.14 (q, J = 7.1 Hz, 2 H) 4.51 (s, 2 H) 7.25-7.35 (m, 4 H). MS ESI/APCI Dual posi: 354[M + H]⁺. | |

TABLE 18-67

| Compound No. | Structure | Analytical Data | Salt information |
|---|---|---|---|
| Reference Example A-463 | 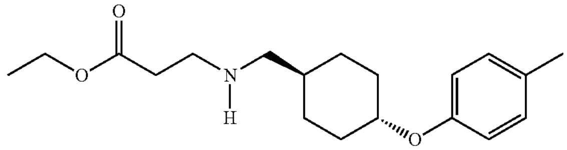 [SMILES: CCOC(=O)CCNC[C@H]1CC[C@H](Oc2ccc(C)cc2)CC1] | $^1$H NMR (300 MHz, CHLOROFORM-d) δ ppm 0.93-1.13 (m, 2 H) 1.26 (t, J = 7.1 Hz, 3 H) 1.32-1.59 (m, 3 H) 1.81-1.95 (m, 2 H) 2.09-2.22 (m, 2 H) 2.27 (s, 3 H) 2.44-2.56 (m, 4 H) 2.81-2.92 (m, 2 H) 4.01-4.22 (m, 3 H) 6.74-6.85 (m, 2 H) 7.01-7.11 (m, 2 H). MS ESI/APCI Dual posi: 320[M + H]$^+$. | |
| Reference Example A-464 | 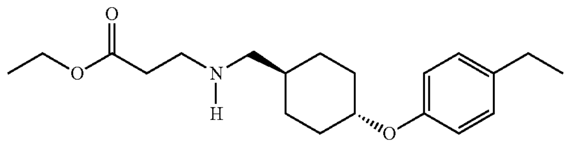 [SMILES: CCOC(=O)CCNC[C@H]1CC[C@H](Oc2ccc(CC)cc2)CC1] | $^1$H NMR (300 MHz, CHLOROFORM-d) δ ppm 0.95-1.13 (m, 2 H) 1.15-1.31 (m, 6 H) 1.33-1.62 (m, 3 H) 1.81-1.95 (m, 2 H) 2.10-2.24 (m, 2 H) 2.44-2.65 (m, 6 H) 2.82-2.92 (m, 2 H) 4.03-4.22 (m, 3 H) 6.77-6.86 (m, 2 H) 7.05-7.13 (m, 2 H). MS ESI/APCI Dual posi: 334[M + H]$^+$. | |
| Reference Example A-465 | 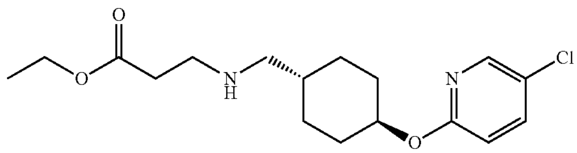 [SMILES: CCOC(=O)CCNC[C@H]1CC[C@H](Oc2ccc(Cl)cn2)CC1] | $^1$H NMR (300 MHz, CHLOROFORM-d) δ ppm 1.00-1.19 (m, 2 H) 1.27 (t, J = 7.1 Hz, 3 H) 1.32-1.62 (m, 3 H) 1.80-1.94 (m, 2 H) 2.07-2.23 (m, 2 H) 2.42-2.60 (m, 4 H) 2.87 (t, J = 6.5 Hz, 2 H) 4.15 (q, J = 7.1 Hz, 2 H) 4.80-4.99 (m, 1 H) 6.57-6.68 (m, 1 H) 7.40-7.55 (m, 1 H) 8.00-8.11 (m, 1 H). MS ESI/APCI Dual posi: 341[M + H]$^+$. | |
| Reference Example A-466 | 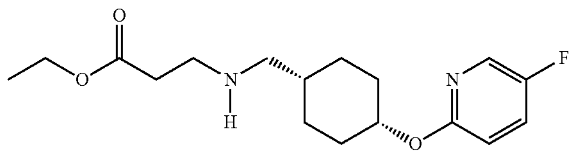 [SMILES: CCOC(=O)CCNC[C@H]1CC[C@@H](Oc2ccc(F)cn2)CC1] | MS ESI/APCI Dual posi: 325[M + H]$^+$. | |
| Reference Example A-467 | 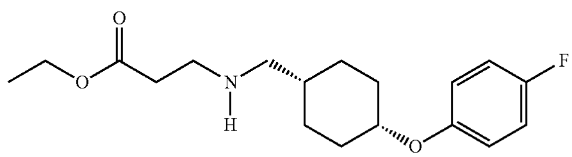 [SMILES: CCOC(=O)CCNC[C@H]1CC[C@@H](Oc2ccc(F)cc2)CC1] | MS ESI/APCI Dual posi: 324[M + H]$^+$. | |
| Reference Example A-468 | 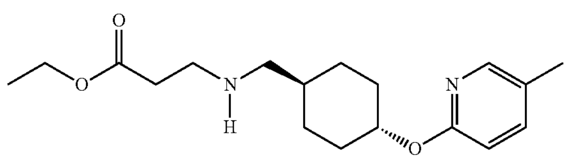 [SMILES: CCOC(=O)CCNC[C@H]1CC[C@H](Oc2ccc(C)cn2)CC1] | $^1$H NMR (300 MHz, CHLOROFORM-d) δ ppm 1.02-1.20 (m, 2 H) 1.26 (t, J = 7.1 Hz, 3 H) 1.33-1.60 (m, 3 H) 1.81-1.94 (m, 2 H) 2.10-2.27 (m, 5 H) 2.43-2.58 (m, 4 H) 2.82-2.92 (m, 2 H) 4.15 (q, J = 7.1 Hz, 2 H) 4.82-4.99 (m, 1 H) 6.53-6.64 (m, 1 H) 7.30-7.41 (m, 1 H) 7.88-7.98 (m, 1 H). MS ESI/APCI Dual posi: 321[M + H]$^+$. | |
| Reference Example A-469 | 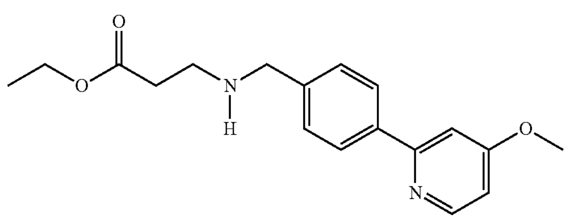 [SMILES: CCOC(=O)CCNCc1ccc(-c2cc(OC)ccn2)cc1] | $^1$H NMR (300 MHz, CHLOROFORM-d) δ ppm 1.26 (t, J = 7.1 Hz, 3 H) 2.54 (t, J = 6.5 Hz, 2 H) 2.91 (t, J = 6.5 Hz, 2 H) 3.86 (s, 2 H) 3.91 (s, 3 H) 4.15 (q, J = 7.1 Hz, 2 H) 6.72-6.80 (m, 1 H) 7.18-7.25 (m, 1 H) 7.36-7.47 (m, 2 H) 7.87-7.98 (m, 2 H) 8.46-8.55 (m, 1 H). MS ESI/APCI Dual posi: 315[M + H]$^+$. | |

TABLE 18-68

| Compound No. | Structure | Analytical Data | Salt information |
|---|---|---|---|
| Reference Example A-470 | 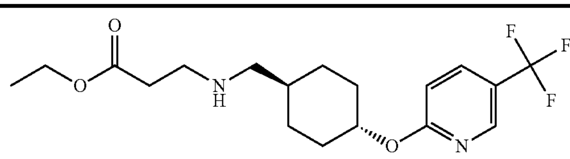 | $^1$H NMR (300 MHz, CHLOROFORM-d) δ ppm 1.04-1.21 (m, 2 H) 1.27 (t, J = 7.1 Hz, 3 H) 1.35-1.62 (m, 3 H) 1.82-1.97 (m, 2 H) 2.10-2.26 (m, 2 H) 2.43-2.58 (m, 4 H) 2.82-2.93 (m, 2 H) 4.15 (q, J = 7.1 Hz, 2 H) 4.93-5.10 (m, 1 H) 6.70-6.79 (m, 1 H) 7.68-7.79 (m, 1 H) 8.36-8.45 (m, 1 H). MS ESI/APCI Dual posi: 375[M + H]$^+$. | |

TABLE 18-68-continued

| Compound No. | Structure | Analytical Data | Salt information |
|---|---|---|---|
| Reference Example A-4711 | 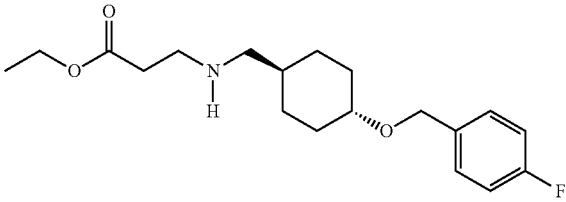 [SMILES: CCOC(=O)CCNC[C@H]1CC[C@H](OCc2ccc(F)cc2)CC1] | $^1$H NMR (300 MHz, CHLOROFORM-d) δ ppm 0.84-1.04 (m, 2 H) 1.20-1.54 (m, 6 H) 1.77-1.91 (m, 2 H) 2.04-2.16 (m, 2 H) 2.41-2.55 (m, 4 H) 2.81-2.89 (m, 2 H) 3.21-3.35 (m, 1 H) 4.14 (q, J = 7.1 Hz, 2 H) 4.51 (s, 2 H) 6.96-7.07 (m, 2 H) 7.25-7.36 (m, 2 H). MS ESI/APCI Dual posi: 338[M + H]$^+$. | |
| Reference Example A-472 | 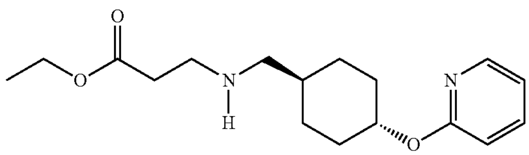 [SMILES: CCOC(=O)CCNC[C@H]1CC[C@H](Oc2ccccn2)CC1] | $^1$H NMR (300 MHz, CHLOROFORM-d) δ ppm 1.02-1.21 (m, 2 H) 1.26 (t, J = 7.1 Hz, 3 H) 1.35-1.66 (m, 3 H) 1.74-1.95 (m, 3 H) 2.11-2.25 (m, 2 H) 2.44-2.60 (m, 4 H) 2.80-2.94 (m, 2 H) 4.15 (q, J = 7.1 Hz, 2 H) 4.89-5.04 (m, 1 H) 6.63-6.71 (m, 1 H) 6.76-6.86 (m, 1 H) 7.49-7.59 (m, 1 H) 8.08-8.18 (m, 1 H). MS ESI/APCI Dual posi: 307[M + H]$^+$. | |
| Reference Example A-473 | 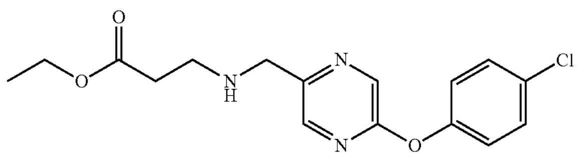 [SMILES: CCOC(=O)CCNCc1cnc(Oc2ccc(Cl)cc2)cn1] | $^1$H NMR (300 MHz, CHLOROFORM-d) δ ppm 1.22-1.29 (m, 3 H) 2.52-2.60 (m, 2 H) 2.94 (t, J = 6.5 Hz, 2 H) 3.92 (s, 2 H) 4.09-4.21 (m, 2 H) 7.10 (d, J = 9.0 Hz, 2 H) 7.38 (d, J = 9.0 Hz, 2 H) 8.07-8.11 (m, 1 H) 8.38 (d, J = 1.4 Hz, 1 H). MS ESI/APCI Dual posi: 336[M + H]$^+$. | |
| Reference Example A-474 | 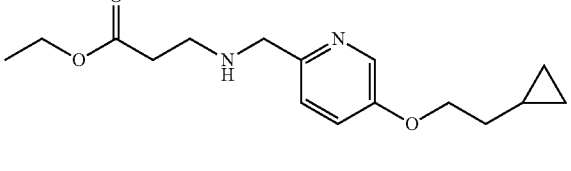 | $^1$H NMR (300 MHz, CHLOROFORM-d) δ ppm 0.09-0.17 (m, 2 H) 0.46-0.54 (m, 2 H) 0.77-0.93 (m, 1 H) 1.26 (t, J = 7.1 Hz, 3 H) 1.69 (q, J = 6.7 Hz, 2 H) 2.56 (t, J = 6.6 Hz, 2 H) 2.93 (t, J = 6.6 Hz, 2 H) 3.87 (s, 2 H) 4.06 (t, J = 6.7 Hz, 2 H) 4.15 (q, J = 7.1 Hz, 2 H) 7.14-7.19 (m, 1 H) 7.21-7.25 (m, 1 H) 8.25 (dd, J = 2.8, 0.6 Hz, 1 H). MS ESI/APCI Dual posi: 293[M + H]$^+$, 315 [M + Na]$^+$. | |
| Reference Example A-475 | 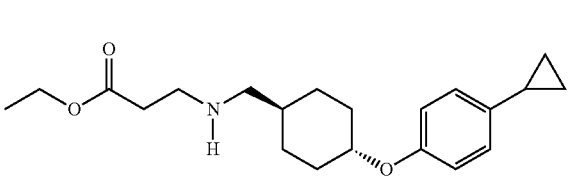 [SMILES: CCOC(=O)CCNC[C@H]1CC[C@H](Oc2ccc(C3CC3)cc2)CC1] | $^1$H NMR (300 MHz, CHLOROFORM-d) δ ppm 0.54-0.66 (m, 2 H) 0.84-0.93 (m, 2 H) 0.95-1.14 (m, 2 H) 1.21-1.31 (m, 3 H) 1.33-1.61 (m, 3 H) 1.78-1.95 (m, 3 H) 2.08-2.24 (m, 2 H) 2.43-2.57 (m, 4 H) 2.82-2.92 (m, 2 H) 4.01-4.22 (m, 3 H) 6.75-6.83 (m, 2 H) 6.94-7.01 (m, 2 H). MS ESI/APCI Dual posi: 346[M + H]$^+$. | |
| Reference Example A-476 | 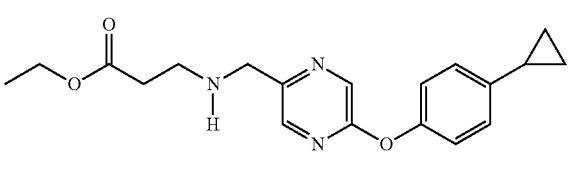 [SMILES: CCOC(=O)CCNCc1cnc(Oc2ccc(C3CC3)cc2)cn1] | $^1$H NMR (300 MHz, CHLOROFORM-d) δ ppm 0.63-0.75 (m, 2 H) 0.90-1.01 (m, 2 H) 1.26 (t, J = 7.1 Hz, 3 H) 1.85-1.97 (m, 1 H) 2.49-2.59 (M, 2 H) 2.88-2.97 (m, 2 H) 3.90 (s, 2 H) 4.08-4.21 (m, 2 H) 6.98-7.07 (m, 2 H) 7.08-7.16 (m, 2 H) 7.98-8.19 (m, 1 H) 8.34 (d, J = 1.4 Hz, 1 H). MS ESI/APCI Dual posi: 342[M + H]$^+$. | |

TABLE 18-69

| Compound No. | Structure | Analytical Data | Salt information |
|---|---|---|---|
| Reference Example A-477 | 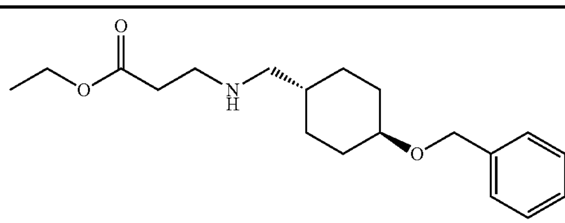 | $^1$H NMR (300 MHz, CHLOROFORM-d) δ ppm 0.84-1.02 (m, 2 H) 1.20-1.54 (m, 6 H) 1.78-1.89 (m, 2 H) 2.06-2.18 (m, 2 H) 2.40-2.58 (m, 4 H) 2.81-2.89 (m, 2 H) 3.21-3.37 (m, 1 H) 4.14 (q, J = 7.1 Hz, 2 H) 4.56 (s, 2 H) 7.24-7.37 (m, 5 H). MS ESI/APCI Dual posi: 320[M + H]$^+$. | |

TABLE 18-69-continued

| Compound No. | Structure | Analytical Data | Salt information |
|---|---|---|---|
| Reference Example A-478 | 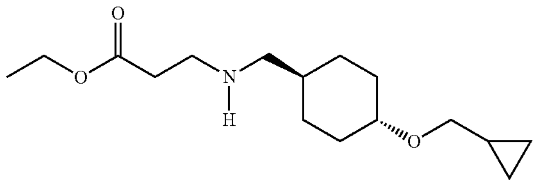 [SMILES: CCOC(=O)CCNC[C@H]1CC[C@H](OCC2CC2)CC1] | ¹H NMR (300 MHz, CHLOROFORM-d) δ ppm 0.13-0.24 (m, 2 H) 0.43-0.59 (m, 2 H) 0.82-1.12 (m, 3 H) 1.15-1.32 (m, 5 H) 1.34-1.53 (m, 1 H) 1.75-1.89 (m, 2 H) 1.98-2.11 (m, 2 H) 2.40-2.56 (m, 4 H) 2.81-2.90 (m, 2 H) 3.12-3.24 (m, 1 H) 3.29 (d, J = 6.8 Hz, 2 H) 4.14 (q, J = 7.1 Hz, 2 H). MS ESI/APCI Dual posi: 284[M + H]⁺, 306 [M + Na]⁺. | |
| Reference Example A-479 | 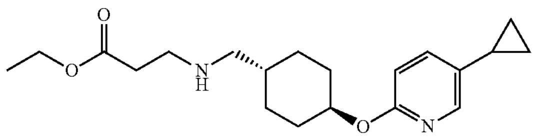 [SMILES: CCOC(=O)CCNC[C@H]1CC[C@H](Oc2ccc(C3CC3)cn2)CC1] | ¹H NMR (300 MHz, CHLOROFORM-d) δ ppm 0.52-0.66 (m, 2 H) 0.85-0.98 (m, 2 H) 1.02-1.56 (m, 8 H) 1.75-1.94 (m, 3 H) 2.09-2.25 (m, 2 H) 2.42-2.62 (m, 4 H) 2.79-2.95 (m, 2 H) 4.06-4.24 (m, 2 H) 4.82-4.99 (m, 1 H) 6.54-6.63 (m, 1 H) 7.18-7.26 (m, 1 H) 7.91-7.98 (m, 1 H). MS ESI/APCI Dual posi: 347[M + H]⁺. | |
| Reference Example A-480 | 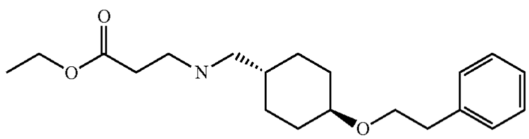 [SMILES: CCOC(=O)CCNC[C@H]1CC[C@H](OCCc2ccccc2)CC1] | ¹H NMR (300 MHz, CHLOROFORM-d) δ ppm 0.82-1.02 (m, 2 H) 1.12-1.31 (m, 5 H) 1.33-1.53 (m, 1 H) 1.71-1.87 (m, 2 H) 1.98-2.10 (m, 2 H) 2.39-2.57 (m, 4 H) 2.79-2.92 (m, 4 H) 3.11-3.25 (m, 1 H) 3.66 (t, J = 7.5 Hz, 2 H) 4.14 (q, J = 7.1 Hz, 2 H) 7.15-7.33 (m, 5 H). MS ESI/APCI Dual posi: 334[M + H]⁺. | |
| Reference Example A-481 | 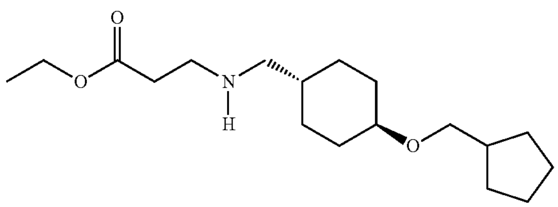 [SMILES: CCOC(=O)CCNC[C@H]1CC[C@H](OCC2CCCC2)CC1] | ¹H NMR (300 MHz, CHLOROFORM-d) δ ppm 0.80-1.04 (m, 2 H) 1.12-1.30 (m, 6 H) 1.35-1.63 (m, 6 H) 1.64-1.87 (m, 4 H) 1.97-2.19 (m, 3 H) 2.40-2.56 (m, 4 H) 2.79-2.91 (m, 2 H) 3.07-3.21 (m, 1 H) 3.31 (d, J = 7.3 Hz, 2 H) 4.14 (q, J = 7.0 Hz, 2 H). MS ESI/APCI Dual posi: 312[M + H]⁺, 334 [M + Na]⁺. | |
| Reference Example A-482 | 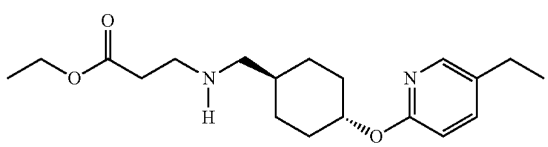 [SMILES: CCOC(=O)CCNC[C@H]1CC[C@H](Oc2ccc(CC)cn2)CC1] | ¹H NMR (200 MHz, CHLOROFORM-d) δ ppm 0.94-1.60 (m, 11 H) 1.77-1.95 (m, 2 H) 2.07-2.27 (m, 2 H) 2.40-2.65 (m, 6 H) 2.76-2.95 (m, 2 H) 4.15 (q, J = 7.3 Hz, 2 H) 4.81-5.04 (m, 1 H) 6.54-6.67 (m, 1 H) 7.31-7.44 (m, 1 H) 7.89-8.00 (m, 1 H). MS ESI/APCI Dual posi: 335[M + H]⁺. | |
| Reference Example A-483 | 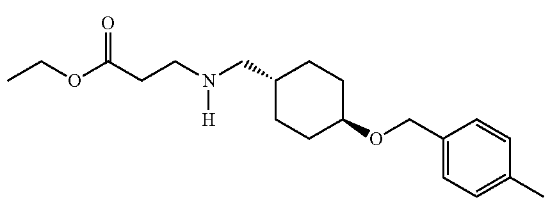 [SMILES: CCOC(=O)CCNC[C@H]1CC[C@H](OCc2ccc(C)cc2)CC1] | ¹H NMR (200 MHz, CHLOROFORM-d) δ ppm 0.78-1.06 (m, 2 H) 1.14-1.57 (m, 6 H) 1.74-1.90 (m, 2 H) 2.00-2.19 (m, 2 H) 2.33 (s, 3 H) 2.40-2.56 (m, 4 H) 2.79-2.91 (m, 2 H) 3.16-3.38 (m, 1 H) 4.14 (q, J = 7.0 Hz, 2 H) 4.51 (s, 2 H) 7.08-7.28 (m, 4 H). MS ESI/APCI Dual posi: 334[M + H]⁺. | |
| Reference Example A-484 | 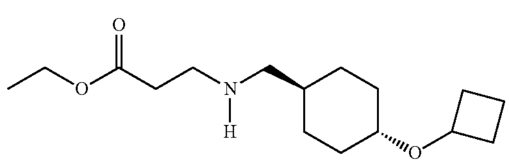 [SMILES: CCOC(=O)CCNC[C@H]1CC[C@H](OC2CCC2)CC1] | ¹H NMR (200 MHz, CHLOROFORM-d) δ ppm 0.77-1.05 (m, 2 H) 1.09-2.06 (m, 15 H) 2.08-2.29 (m, 2 H) 2.38-2.59 (m, 4 H) 2.79-2.92 (m, 2 H) 3.07-3.29 (m, 1 H) 3.92-4.24 (m, 3 H). MS ESI/APCI Dual posi: 284[M + H]⁺, 306 [M + Na]⁺. | |
| Reference Example A-485 | 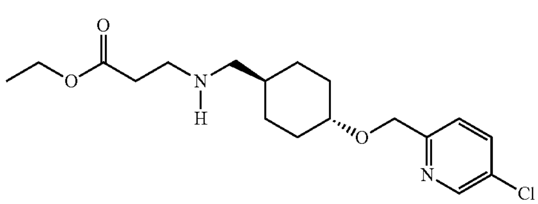 [SMILES: CCOC(=O)CCNC[C@H]1CC[C@H](OCc2ccc(Cl)cn2)CC1] | ¹H NMR (300 MHz, CHLOROFORM-d) δ ppm 0.86-1.06 (m, 2 H) 1.19-1.57 (m, 6 H) 1.78-1.92 (m, 2 H) 2.04-2.21 (m, 2 H) 2.44-2.58 (m, 4 H) 2.88 (t, J = 6.4 Hz, 2 H) 3.24-3.45 (m, 1 H) 4.15 (q, J = 7.0 Hz, 2 H) 4.64 (s, 2 H) 7.44 (d, J = 8.4 Hz, 1 H) 7.66 (dd, J = 8.4, 2.3 Hz, 1 H) 8.49 (d, J = 2.3 Hz, 1 H). MS ESI/APCI Dual posi: 355[M + H]⁺. | |

323
Reference Example A-486

Ethyl N-[1-(4-chlorophenyl)-2-propanyl]-β-alaninate

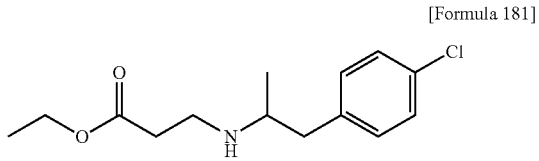 [SMILES: CCOC(=O)CCNC(C)Cc1ccc(Cl)cc1]

[Formula 181]

To a solution of β-alanine ethyl ester hydrochloride (1.00 g) in ethanol (13.5 mL), triethylamine (907 μL), 4-chlorophenylacetone (1.32 g), acetic acid (1.5 mL) and borane-2-picoline complex (1.39 g) were added successively and the mixture was stirred at 60° C. for 30 minutes. After being cooled to room temperature, the mixture was concentrated under reduced pressure. To the resulting residue, a saturated aqueous solution of sodium hydrogencarbonate was added and the mixture was extracted with chloroform twice. The combined organic layers were washed with saturated brine and dried over anhydrous sodium sulfate. The desiccant was removed by filtration and the filtrate was concentrated under reduced pressure. The resulting residue was purified by silica gel column chromatography (chloroform:methanol=100:0-95:5) to give the titled compound as a yellow oil (1.70 g).

$^1$H NMR (300 MHz, CHLOROFORM-d) δ ppm 1.03 (d, J=6.2 Hz, 3 H) 1.22 (t, J=7.1 Hz, 3 H) 2.40-2.49 (m, 2 H) 2.51-2.61 (m, 1 H) 2.65-2.76 (m, 1 H) 2.79-2.99 (m, 3 H) 4.10 (q, J=7.1 Hz, 2 H) 7.06-7.15 (m, 2 H) 7.21-7.29 (m, 2 H).

MS ESI/APCI Dual posi: 270 [M+H]$^+$.

324
Reference Example B-1

Ethyl N-{2-[4-(trifluoromethyl)phenyl]propan-2-yl}-β-alaninate

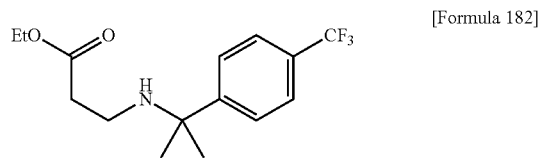 [SMILES: CCOC(=O)CCNC(C)(C)c1ccc(C(F)(F)F)cc1]

[Formula 182]

To a mixture of the compound (1.11 g) obtained in Reference Example 27-3, methanol (6.00 mL) and water (3.00 mL), ethyl acrylate (0.594 mL) was added and the resulting mixture was stirred at 90° C. for an hour under irradiation with microwaves. After being cooled to room temperature, the reaction mixture was poured into water and extracted with ethyl acetate three times. The combined organic layers were washed with saturated brine and thereafter passed through a phase separator for concentrating under reduced pressure. The resulting residue was purified by silica gel column chromatography (n-hexane:ethyl acetate=95:5-10:90) to give the titled compound as a pale yellow oil (957 mg).

$^1$H NMR (300 MHz, CHLOROFORM-d) δ ppm 1.26 (t, J=7.1 Hz, 3 H) 1.47 (s, 6 H) 2.39-2.49 (m, 2 H) 2.53-2.61 (m, 2 H) 4.14 (q, J=7.1 Hz, 2 H) 7.58 (s, 4 H).

MS ESI/APCI Dual posi: 304 [M+H]$^+$.

In the following Reference Examples B-2 to B-19, the compounds obtained in Reference Examples 27-1 to 27-3, Reference Examples 45-1 to 47-1, or commercial grades of the corresponding amines, as well as commercial grades of the corresponding acrylic acid esters or crotonic acid esters were used as starting materials and treated by the method described in Reference Example B-1 or modifications thereof to synthesize the intended compounds. The structures of the synthesized compounds and their NMR and MS data are shown in Tables 19-1 and 19-2.

TABLE 19-1

| Compound No. | Structure | Analytical Data | Salt information |
|---|---|---|---|
| Reference Example B-2 | 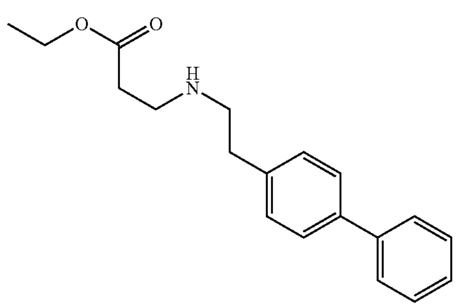 [SMILES: CCOC(=O)CCNCCc1ccc(-c2ccccc2)cc1] | $^1$H NMR (600 MHz, CHLOROFORM-d) δ ppm 1.23 (t, J = 7.2 Hz, 3 H) 2.51 (t, J = 6.6 Hz, 2 H) 2.84 (t, J = 7.1 Hz, 2 H) 2.90-2.96 (m, 4 H) 4.12 (q, J = 7.2 Hz, 2 H) 7.26-7.30 (m, 2 H) 7.31-7.35 (m, 1 H) 7.41-7.46 (m, 2 H) 7.51-7.54 (m, 2 H) 7.56-7.60 (m, 2 H).<br>MS ESI/APCI Dual posi: 298[M + H]$^+$. | |
| Reference Example B-3 | 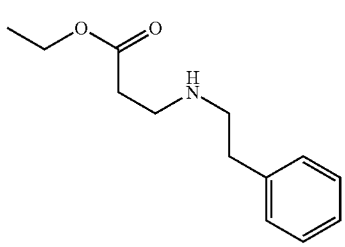 [SMILES: CCOC(=O)CCNCCc1ccccc1] | $^1$H NMR (200 MHz, CHLOROFORM-d) δ ppm 1.14-1.33 (m, 3 H) 2.34-2.56 (m, 2 H) 2.64-2.97 (m, 6 H) 4.00-4.23 (m, 2 H) 7.08-7.38 (m, 5 H).<br>MS ESI/APCI Dual posi: 222[M + H]$^+$. | |

TABLE 19-1-continued

| Compound No. | Structure | Analytical Data | Salt information |
|---|---|---|---|
| Reference Example B-4 | 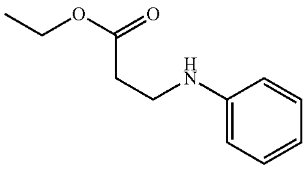 | ¹H NMR (300 MHz, CHLOROFORM-d) δ ppm 1.26 (t, J = 7.1 Hz, 3 H) 2.61 (t, J = 6.4 Hz, 2 H) 3.45 (t, J = 6.4 Hz, 2 H) 4.16 (q, J = 7.1 Hz, 2 H) 6.58-6.66 (m, 2 H) 6.72 (m, 1 H) 7.13-7.22 (m, 2 H). MS ESI/APCI Dual posi: 194[M + H]⁺. | |
| Reference Example B-5 | 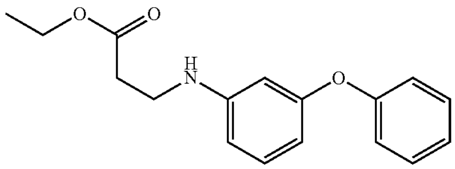 [SMILES: CCOC(=O)CCNc1cccc(Oc2ccccc2)c1] | ¹H NMR (300 MHz, CHLOROFORM-d) δ ppm 1.26 (t, J = 7.1 Hz, 3 H) 2.59 (t, J = 6.3 Hz, 2 H) 3.41 (t, J = 6.3 Hz, 2 H) 4.15 (q, J = 7.1 Hz, 2 H) 6.19-6.44 (m, 3 H) 6.93-7.18 (m, 4 H) 7.28-7.38 (m, 2 H). MS ESI/APCI Dual posi: 286[M + H]⁺. | |
| Reference Example B-6 | 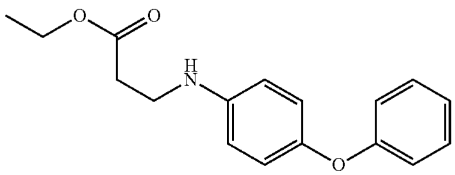 [SMILES: CCOC(=O)CCNc1ccc(Oc2ccccc2)cc1] | ¹H NMR (300 MHz, CHLOROFORM-d) δ ppm 1.27 (t, J = 7.1 Hz, 3 H) 2.62 (t, J = 6.3 Hz, 2 H) 3.44 (t, J = 6.3 Hz, 2 H) 4.17 (q, J = 7.1 Hz, 2 H) 6.59-6.65 (m, 2 H) 6.87-6.95 (m, 4 H) 6.97-7.04 (m, 1 H) 7.23-7.32 (m, 2 H). MS ESI/APCI Dual posi: 286[M + H]⁺. | |
| Reference Example B-7 | 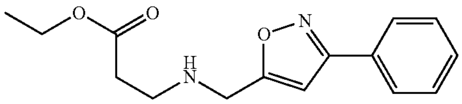 [SMILES: CCOC(=O)CCNCc1cc(-c2ccccc2)no1] | ¹H NMR (600 MHz, CHLOROFORM-d) δ ppm 1.27 (t, J = 7.0 Hz, 3 H) 2.55 (t, J = 6.3 Hz, 2 H) 2.97 (t, J = 6.3 Hz, 2 H) 3.99 (s, 2 H) 4.16 (q, J = 7.0 Hz, 2 H) 6.50 (t, J = 0.8 Hz, 1 H) 7.38-7.50 (m, 3 H) 7.76-7.85 (m, 2 H). MS ESI/APCI Dual posi: 275[M + H]⁺. | |
| Reference Example B-8 | 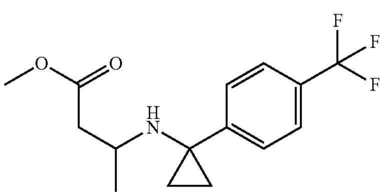 [SMILES: COC(=O)CC(C)NC1(c2ccc(C(F)(F)F)cc2)CC1] | ¹H NMR (300 MHz, CHLOROFORM-d) δ ppm 0.76-0.90 (m, 1 H) 0.92-1.18 (m, 6 H) 2.18-2.33 (m, 1 H) 2.33-2.51 (m, 1 H) 2.95-3.14 (m, 1 H) 3.64 (s, 3 H) 7.43-7.54 (m, 2 H) 7.52-7.63 (m, 2 H). MS ESI/APCI Dual posi: 302[M + H]⁺, 324[M + Na]⁺. | |
| Reference Example B-9 | 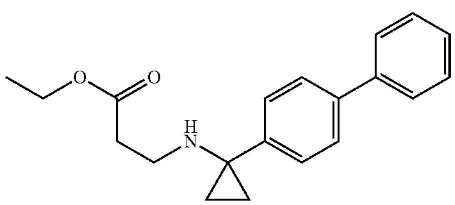 [SMILES: CCOC(=O)CCNC1(c2ccc(-c3ccccc3)cc2)CC1] | ¹H NMR (300 MHz, CHLOROFORM-d) δ ppm 0.93-1.00 (m, 2 H) 1.00-1.07 (m, 2 H) 1.25 (t, J = 7.1 Hz, 3 H) 2.46 (t, J = 6.5 Hz, 2 H) 2.85 (t, J = 6.5 Hz, 2 H) 4.13 (q, J = 7.1 Hz, 2 H) 7.32-7.47 (m, 5 H) 7.52-7.62 (m, 4 H). MS ESI/APCI Dual posi: 310[M + H]⁺, 332[M + Na]⁺. | |

Formula 19-2

| Compound No. | Structure | Analytical Data | Salt information |
|---|---|---|---|
| Reference Example B-10 | 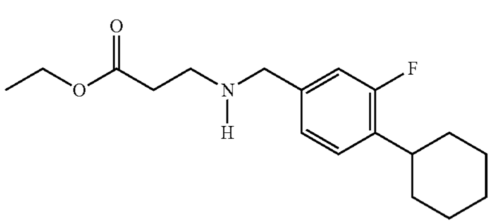 [SMILES: CCOC(=O)CCNCc1ccc(C2CCCCC2)c(F)c1] | ¹H NMR (300 MHz, CHLOROFORM-d) δ ppm 1.26 (t, J = 7.1 Hz, 3 H) 1.32-1.52 (m, 4 H) 1.69-1.91 (m, 5 H) 2.48-2.56 (m, 2 H) 2.76-2.85 (m, 1 H) 2.85-2.93 (m, 2 H) 3.75 (s, 2 H) 4.14 (t, J = 7.1 Hz, 2 H) 6.93-7.06 (m, 2 H) 7.12-7.20 (m, 1 H). MS ESI/APCI Dual posi: 308[M + H]⁺, 330 [M + Na]⁺. | |

| Compound No. | Structure | Analytical Data | Salt information |
|---|---|---|---|
| Reference Example B-11 | (structure) | ¹H NMR (300 MHz, CHLOROFORM-d) δ ppm 1.27 (t, J = 7.1 Hz, 3 H) 2.15-2.37 (m, 4 H) 2.41-2.57 (m, 3 H) 2.70-2.77 (m, 2 H) 2.84-2.96 (m, 2 H) 4.15 (q, J = 7.1 Hz, 2 H) 4.63-4.76 (m, 1 H) 6.67-6.74 (m, 2 H) 7.16-7.24 (m, 2 H). | |
| Reference Example B-12 | (structure) | ¹H NMR (300 MHz, CHLOROFORM-d) δ ppm 1.26 (t, J = 7.1 Hz, 3 H) 1.52-1.72 (m, 2 H) 1.87-2.04 (m, 1 H) 2.32-2.45 (m, 2 H) 2.45-2.54 (m, 2 H) 2.62-2.70 (m, 2 H) 2.81-2.90 (m, 2 H) 3.80-3.98 (m, 1 H) 4.14 (q, J = 7.1 Hz, 2 H) 4.37 (s, 2 H) 7.23-7.34 (m, 4 H). MS ESI/APCI Dual posi: 326[M + H]⁺. | |
| Reference Example B-13 | (structure) | ¹H NMR (300 MHz, CHLOROFORM-d) δ ppm 1.26 (t, J = 7.1 Hz, 3 H) 1.73-1.89 (m, 2 H) 2.03-2.24 (m, 1 H) 2.50 (t, J = 6.5 Hz, 2 H) 2.55-2.67 (m, 2 H) 2.68-2.76 (m, 2 H) 2.81-2.94 (m, 2 H) 4.14 (q, J = 7.1 Hz, 2 H) 4.41-4.59 (m, 1 H) 6.65-6.79 (m, 2 H) 7.13-7.25 (m, 2 H). MS ESI/APCI Dual posi: 312[M + H]⁺. | |
| Reference Example B-14 | (structure) | ¹H NMR (300 MHz, CHLOROFORM-d) δ ppm 1.26 (t, J = 7.1 Hz, 3 H) 1.93-2.23 (m, 4 H) 2.28-2.56 (m, 3 H) 2.67 (d, J = 7.6 Hz, 2 H) 2.77-3.01 (m, 2 H) 4.03-4.23 (m, 3 H) 4.38 (s, 2 H) 7.21-7.35 (m, 4 H). | |
| Reference Example B-15 | (structure) | ¹H NMR (300 MHz, CHLOROFORM-d) δ ppm 1.27 (t, J = 7.1 Hz, 3 H) 2.16-2.37 (m, 7 H) 2.41-2.61 (m, 3 H) 2.74 (d, J = 7.5 Hz, 2 H) 2.91 (t, J = 6.5 Hz, 2 H) 4.15 (q, J = 7.1 Hz, 2 H) 4.56-4.86 (m, 1 H) 6.57-6.82 (m, 2 H) 6.94-7.15 (m, 2 H). MS ESI/APCI Dual posi: 292[M + H]⁺. | |
| Reference Example B-16 | (structure) | ¹H NMR (300 MHz, CHLOROFORM-d) δ ppm 1.22-1.31 (m, 3 H) 2.17-2.42 (m, 4 H) 2.44-2.60 (m, 3 H) 2.75 (d, J = 7.5 Hz, 2 H) 2.91 (t, J = 6.5 Hz, 2 H) 4.05-4.22 (m, 2 H) 4.64-4.89 (m, 1 H) 6.83 (d, J = 8.5 Hz, 2 H) 7.51 (d, J = 8.5 Hz, 2 H). MS ESI/APCI Dual posi: 346[M + H]⁺. | |
| Reference Example B-17 | (structure) | ¹H NMR (600 MHz, CHLOROFORM-d) δ ppm 1.23-1.31 (m, 3 H) 2.20-2.34 (m, 4 H) 2.47-2.54 (m, 3 H) 2.74 (d, J = 7.4 Hz, 2 H) 2.90 (t, J = 6.6 Hz, 2 H) 4.15 (q, J = 7.2 Hz, 2 H) 4.68-4.73 (m, 1 H) 6.67 (dd, J = 8.3, 2.5 Hz, 1 H) 6.73-6.79 (m, 1 H) 6.88-6.93 (m, 1 H) 7.13-7.19 (m, 1 H). MS ESI/APCI Dual posi: 312[M + H]⁺. | |
| Reference Example B-18 | (structure) | ¹H NMR (300 MHz, CHLOROFORM-d) δ ppm 1.26 (t, J = 7.1 Hz, 3 H) 1.81-1.94 (m, 2 H) 1.97-2.42 (m, 6 H) 2.53 (t, J = 6.4 Hz, 2 H) 2.90 (t, J = 6.4 Hz, 2 H) 3.80 (s, 2 H) 4.14 (q, J = 7.1 Hz, 2 H) 7.29-7.36 (m, 2 H) 7.42-7.47 (m, 2 H). MS ESI/APCI Dual posi: 342[M + H]⁺, 364 [M + Na]⁺. MS ESI/APCI Dual nega: 340[M − H]⁻, 376 [M + Cl]⁻. | |

Formula 19-2

| Compound No. | Structure | Analytical Data | Salt information |
|---|---|---|---|
| Reference Example B-19 | (structure shown) | $^1$H NMR (300 MHz, CHLOROFORM-d) δ ppm 0.02 (s, 6 H) 0.88 (s, 9 H) 1.25 (t, J = 7.1 Hz, 3 H) 2.38-2.50 (m, 2 H) 2.61-2.81 (m, 2 H) 3.40-3.51 (m, 1 H) 3.55-3.64 (m, 1 H) 3.67-3.76 (m, 1 H) 4.13 (q, J = 7.1 Hz, 2 H) 7.11 (d, J = 8.1 Hz, 2 H) 7.64 (d, J = 8.1 Hz, 2 H). MS ESI/APCI Dual posi: 478[M + H]$^+$. | |

Reference Example C-1

Ethyl N-(5-phenylpentyl)-β-alaninate

[Formula 183]

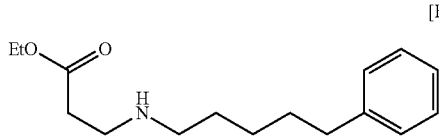

To a solution of β-alanine ethyl hydrochloride (2.00 g) in N,N-dimethylformamide (65.0 mL), sodium hydride (60% dispersion in mineral oil, 1.15 g) was added and the mixture was stirred at room temperature for an hour. After adding (5-bromopentyl)benzene (2.52 mL), the mixture was stirred at 80° C. for 4 hours. After being cooled to room temperature, the reaction mixture was diluted with ethyl acetate and washed with saturated brine. The organic layer was separated off and dried over anhydrous magnesium sulfate; after removing the desiccant by filtration, the filtrate was concentrated under reduced pressure. The resulting residue was purified by silica gel column chromatography (chloroform:methanol=100:0-85:15) to give the titled compound as a pale yellow oil (480 mg).

$^1$H NMR (300 MHz, CHLOROFORM-d) δ ppm 1.19-1.30 (m, 3 H) 1.31-1.70 (m, 6 H) 2.42-2.54 (m, 2 H) 2.56-2.67 (m, 4 H) 2.81-2.92 (m, 2 H) 4.14 (q, J=7.1 Hz, 2 H) 7.10-7.22 (m, 3 H) 7.23-7.32 (m, 2 H).

MS ESI/APCI Dual posi: 264 [M+H]$^+$.

Reference Example D-1

Ethyl 3-({[3-(4-chlorophenyl)-isoxazol-5-yl]methyl}amino)-3-methylbutanoate

[Formula 184]

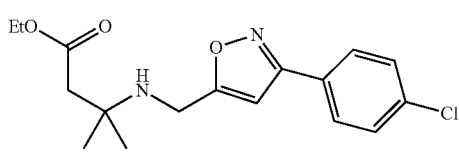

(1) Synthesis of 1-(4-chlorophenyl)-N-hydroxymethaneimine

[Formula 185]

To a solution of 4-chlorobenzaldehyde (10.0 g) in chloroform (350 mL), hydroxylamine hydrochloride (10.2 g) was added and the mixture was stirred at room temperature for 18 hours in an argon atmosphere. After adding 2 mol/L hydrochloric acid (200 mL), three extractions were conducted with chloroform. The combined organic layers were washed with saturated brine and thereafter dried over anhydrous magnesium sulfate. After removing the desiccant by filtration, the filtrate was concentrated under reduced pressure. The resulting residue was crystallized with a liquid mixture of n-hexane and chloroform to give 1-(4-chlorophenyl)-N-hydroxymethaneimine as a colorless solid (9.27 g).

$^1$H NMR (300 MHz, CHLOROFORM-d) δ ppm 7.34-7.39 (m, 2 H) 7.48-7.54 (m, 2 H) 8.10 (s, 1 H).

MS ESI/APCI Dual posi: 156 [M+H]$^+$.
MS ESI/APCI Dual nega: 154 [M−H]$^-$.

(2) Synthesis of 5-(bromomethyl)-3-(4-chlorophenyl)-isoxazole

[Formula 186]

To a solution in chloroform (28.5 mL) of the compound (1.85 g) obtained in step (1) above, propargyl bromide (1.07 mL) and triethylamine (1.99 mL) were added and then 5% sodium hypochlorite in aqueous solution (57.0 mL) was added dropwise at 0° C. over a period of 30 minutes. The reaction mixture was brought to room temperature and stirred for 5 hours. After separating the aqueous layer, two extractions were conducted with chloroform. The combined organic layers were washed with saturated brine and dried over anhydrous magnesium sulfate. After removing the desiccant by filtration, the filtrate was concentrated under reduced pressure. The resulting residue was purified by silica gel column chromatography (n-hexane:ethyl acetate=99:1-85:15) and reduced to powder with n-hexane, thus giving 5-(bromomethyl)-3-(4-chlorophenyl)-isoxazole as a colorless solid (1.01 g).

$^1$H NMR (300 MHz, CHLOROFORM-d) δ ppm 4.51 (s, 2 H) 6.58-6.64 (m, 1 H) 7.38-7.52 (m, 2 H) 7.68-7.79 (m, 2 H).

MS ESI/APCI Dual posi: 271 [M+H]$^+$.

(3) Synthesis of the Titled Compound

To a solution of ethyl 3-amino-3-methylbutyrate hydrochloride (333 mg) in tetrahydrofuran (4.00 mL), a solution in tetrahydrofuran (2.00 mL) of the compound (100 mg) obtained in step (2) above and potassium carbonate (406 mg) were added and the mixture was stirred at 60° C. for three days. After passing the reaction mixture through Celite (registered trademark), the filtrate was concentrated under reduced pressure and the resulting residue was roughly purified by preparative HPLC. To the resulting roughly purified product, a saturated aqueous solution of sodium hydrogencarbonate was added and extraction was conducted with chloroform. The combined organic layers were dried over anhydrous magnesium sulfate and after removing the desiccant by filtration, the filtrate was concentrated under reduced pressure. The resulting residue was purified by silica gel column chromatography (n-hexane:ethyl acetate=98:2-50:50) to give the titled compound as a colorless amorphous mass.

$^1$H NMR (300 MHz, CHLOROFORM-d) δ ppm 1.20-1.32 (m, 9 H) 2.48 (s, 2 H) 3.92 (d, J=0.9 Hz, 2 H) 4.15 (q, J=7.1 Hz, 2 H) 6.48 (t, J=0.9 Hz, 1 H) 7.37-7.45 (m, 2 H) 7.69-7.77 (m, 2 H).

MS ESI posi: 337 [M+H]$^+$.
MS ESI nega: 335 [M−H]$^−$.

Reference Example E-1

2-(Trimethylsilyl)ethyl glycinate

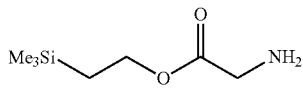

[Formula 187]

(1) Synthesis of 2-(trimethylsilyl)ethyl N-[(benzyloxy)carbonyl]glycinate

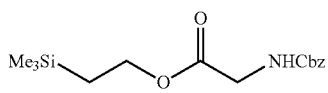

[Formula 188]

To a mixture of N-[(benzyloxy)carbonyl]glycine (5.33 g), 1-(3-dimethylaminopropyl)-3-ethylcarbodiimide hydrochloride (5.86 g), 1-hydroxybenzotriazole monohydrate (4.68 g) and chloroform (51.0 mL), 2-(trimethylsilyl)ethanol (4.36 mL) was added and the mixture was stirred at room temperature for 8 hours. To the reaction mixture, 2-(trimethylsilyl)ethanol (3.00 mL), 1-(3-dimethylaminopropyl)-3-ethylcarbodiimide hydrochloride (2.93 g) and 4-dimethylaminopyridine (312 mg) were added and the mixture was stirred at room temperature for 65 hours. After pouring the reaction mixture into a saturated aqueous solution of ammonium chloride, three extractions were conducted with ethyl acetate. The combined organic layers were washed with saturated brine and dried over anhydrous magnesium sulfate. After removing the desiccant by filtration, the filtrate was concentrated under reduced pressure and purified by silica gel column chromatography (n-hexane:ethyl acetate=95:5-80:20) to give 2-(trimethylsilyl)ethyl N-[(benzyloxy)carbonyl] glycinate as a colorless oil (6.64 g).

$^1$H NMR (300 MHz, CHLOROFORM-d) δ ppm 0.04 (s, 9 H) 0.96-1.06 (m, 2 H) 3.96 (d, J=5.6 Hz, 2 H) 4.20-4.30 (m, 2 H) 5.13 (s, 2 H) 5.19-5.28 (m, 1 H) 7.28-7.41 (m, 5 H).

(2) Synthesis of the Titled Compound

To a solution in ethyl acetate (20.0 mL) of the compound (634 mg) obtained in step (1) above, 20% palladium hydroxide/carbon (63.0 mg) was added. The mixture was stirred at room temperature for an hour in a hydrogen atmosphere. After passing the reaction mixture through Celite (registered trademark), the filtrate was concentrated under reduced pressure to give the titled compound as a pale yellow oil (320 mg).

$^1$H NMR (300 MHz, CHLOROFORM-d) δ ppm 0.05 (s, 9 H) 0.89-1.07 (m, 2 H) 3.40 (s, 2 H) 4.13-4.29 (m, 2 H).

Reference Example F-1

Ethyl N-[4-(1 H-benzotriazol-1-ylmethoxy)benzyl]-β-alaninate

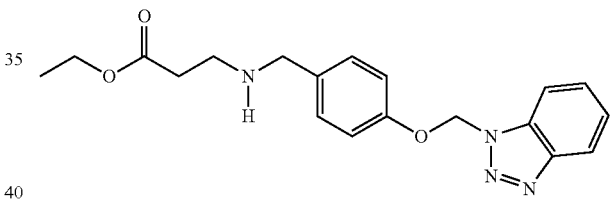

[Formula 189]

To a mixture of 1 H-benzotriazole-1-methanol (1.22 g), 4-hydroxybenzaldehyde (1.00 g), triphenylphosphine (2.26 g) and chloroform (27 mL), diisopropyl azodicarboxylate (1.9 mol/L, solution in toluene, 4.53 mL) was added under cooling with ice. After being brought to room temperature, the mixture was stirred for 2.5 hours. Following the addition of triphenylphosphine (1.13 g) and diisopropyl azodicarboxylate (1.9 mol/L, solution in toluene, 2.27 mL), the mixture was stirred for an additional 40 minutes. To the reaction mixture, methanol (165 μL) and acetic acid (750 μL) were added and the resulting mixture was stirred at the same temperature for 20 minutes. To the reaction mixture, β-alanine ethyl hydrochloride (1.38 g), triethylamine (1.26 μL) and sodium triacetoxyborohydride (2.60 g) were added and the mixture was stirred at room temperature for 1.5 hours. After adding 1 mol/L hydrochloric acid, the mixture was washed with diethyl ether. To the aqueous layer, an aqueous solution of 2 mol/L sodium hydroxide was added to provide a basic pH. Following extraction with chloroform, the combined organic layers were washed with saturated brine and thereafter passed through a phase separator for concentrating under reduced pressure. The resulting residue was purified by silica gel column chromatography (n-hexane:ethyl acetate=100:0-50:50) to give the titled compound as a colorless oil (1.13 g).

$^1$H NMR (300 MHz, CHLOROFORM-d) δ ppm 1.24 (t, J=7.1 Hz, 3 H) 2.47-2.52 (m, 2 H) 2.81-2.87 (m, 2 H) 3.71 (s, 2 H) 4.12 (q, J=7.1 Hz, 2 H) 6.54 (s, 2 H) 6.99-7.06 (m, 2 H)

7.19-7.25 (m, 2 H) 7.40 (ddd, J=8.3, 7.0, 1.0 Hz, 1 H) 7.53 (ddd, J=8.3, 7.0, 1.0 Hz, 1 H) 7.70 (dt, J=8.3, 1.0 Hz, 1 H) 8.07 (dt, J=8.3, 1.0 Hz, 1 H).
MS ESI/APCI Dual posi: 355 [M+H]$^+$, 377 [M+Na]$^+$.
MS ESI/APCI Dual nega: 353 [M−H]$^−$, 389 [M+O]$^−$.

In the following Reference Examples F-2 and F-3, a commercial grade of the corresponding alcohols was used as the starting material and treated by the method descried in Reference Example F-1 or a modification thereof to synthesize the intended compounds. The structures of the synthesized compounds and their NMR and MS data are shown in Table 20-1.

ride (2.07 g), triethylamine (3.13 g) and propylphosphonic acid anhydride (cyclic trimer) (48%, solution in N,N-dimethylformamide, 8.22 g) were added and the mixture was stirred at room temperature for an hour. To the reaction mixture, water was added and extraction was conducted with ethyl acetate. The combined organic layers were dried over anhydrous sodium sulfate. The desiccant was removed by filtration and the filtrate was concentrated under reduced pressure. The resulting residue was purified by silica gel column chromatography (n-hexane:ethyl acetate=67:33-50:50) to give benzyl 3-({2-[(2-methyl-2-propanyl)oxy]-2-oxoethyl}amino)-3-oxopropanoate as a colorless oil (1.46 g).

TABLE 20-1

| Compound No. | Structure | Analytical Data | Salt information |
|---|---|---|---|
| Reference Example F-2 | 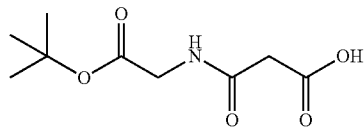 | $^1$H NMR (300 MHz, CHLOROFORM-d) δ ppm 1.25 (t, J = 7.1 Hz, 3 H) 2.23 (s, 3 H) 2.26-2.29 (m, 3 H) 2.51 (t, J = 6.5 Hz, 2 H) 2.87 (t, J = 6.5 Hz, 2 H) 3.73 (s, 2 H) 4.13 (q, J = 7.1 Hz, 2 H) 5.83 (s, 2 H) 5.86 (s, 1 H) 6.97-7.03 (m, 2 H) 7.19-7.26 (m, 2 H). MS ESI/APCI Dual posi: 332[M + H]$^+$, 354 [M + Na]$^+$. MS ESI/APCI Dual nega: 330[M − H]$^−$. | |
| Reference Example F-3 | 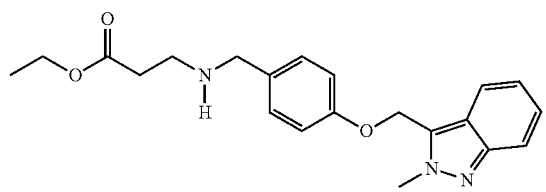 [SMILES: CCOC(=O)CCNCc1ccc(OCc2c3ccccc3nn2C)cc1] | $^1$H NMR (300 MHz, CHLOROFORM-d) δ ppm 1.26 (t, J = 7.1 Hz, 3 H) 2.52 (t, J = 6.5 Hz, 2 H) 2.88 (t, J = 6.5 Hz, 2 H) 3.75 (s, 2 H) 4.14 (q, J = 7.1 Hz, 2 H) 4.24 (s, 3 H) 5.39 (s, 2 H) 6.95-7.01 (m, 2 H) 7.12 (ddd, J = 8.4, 6.6, 0.9 Hz, 1 H) 7.24-7.34 (m, 3 H) 7.64 (dt, J = 8.4, 1.1 Hz, 1 H) 7.69 (dt, J = 8.8, 0.9 Hz, 1 H). MS ESI/APCI Dual posi: 368[M + H]$^+$, 390 [M + Na]$^+$. MS ESI/APCI Dual nega: 366[M − H]$^−$, 402 [M + Cl]$^−$. | |

Reference Example G-1

3-({2-[(2-Methyl-2-propanyl)oxy]-2-oxoethyl}amino)-3-oxopropanoic acid

[Formula 190]

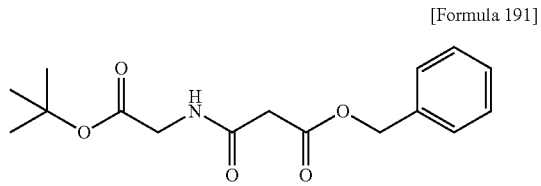 [SMILES: CC(C)(C)OC(=O)CNC(=O)CC(=O)OCc1ccccc1]

(1) Synthesis of benzyl 3-({2-[(2-methyl-2-propanyl)oxy]-2-oxoethyl}amino)-3-oxopropanoate

[Formula 191]

To a solution of monobenzyl malonate (2.00 g) in N,N-dimethylformamide (51.5 mL), glycine tert-butyl hydrochlo- $^1$H NMR (600 MHz, CHLOROFORM-d) δ ppm 1.48 (s, 9 H) 3.40 (s, 2 H) 3.97 (d, J=5.0 Hz, 2 H) 5.19 (s, 2 H) 7.31-7.40 (m, 5 H) 7.47-7.57 (m, 1 H).
MS ESI posi: 330 [M+Na]$^+$.
MS ESI nega: 306 [M−H]$^−$.

(2) Synthesis of the Titled Compound

The compound (1.46 g) obtained in step (1) above was used and treated by the same technique as in Reference Example E-1(2) to give the titled compound as a colorless oil (1.03 g).
$^1$H NMR (600 MHz, CHLOROFORM-d) δ ppm 1.48 (s, 9 H) 3.40 (s, 2 H) 3.99 (d, J=5.0 Hz, 2 H) 7.28-7.41 (m, 1 H).
MS ESI posi: 240 [M+Na]$^+$.
MS ESI nega: 216 [M−H]$^−$.

Reference Example G-2

3-({3-[(2-Methyl-2-propanyl)oxy]-3-oxopropyl}amino)-3-oxopropanoic acid

[Formula 192]

Instead of glycine tert-butyl hydrochloride, β-alanine tert-butyl hydrochloride (1.82 g) was used and treated by the same technique as in Reference Example G-1 to give the titled compound as a colorless solid (1.03 g).

$^1$H NMR (300 MHz, CHLOROFORM-d) δ ppm 1.46 (s, 9 H) 2.43-2.54 (m, 2 H) 3.32 (s, 2 H) 3.55 (q, J=6.1 Hz, 2 H) 7.02-7.18 (m, 1 H).

MS ESI/APCI Dual posi: 254 [M+Na]$^+$.
MS ESI/APCI Dual nega: 230 [M–H]$^-$.

Reference Example G-3

3-[(2-Ethoxy2-oxoethyl)amino]-3-oxopropanoic acid

[Formula 193]

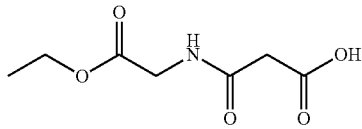

To a solution of Meldrum's acid (10.0 g) in acetonitrile (231 mL), glycine ethyl hydrochloride (14.5 g) and triethylamine (14.1 g) were added and the mixture was stirred at 60° C. for 5 hours. After cooling the mixture to room temperature, ethyl acetate was added and extraction was conducted with a saturated aqueous solution of sodium hydrogencarbonate. To the combined aqueous layers, 1 mol/L hydrochloric acid was added and extraction was conducted with ethyl acetate. The combined organic layers were dried over anhydrous sodium sulfate. After removing the desiccant by filtration, the filtrate was concentrated under reduced pressure to give the titled compound as a colorless solid (7.95 g).

$^1$H NMR (300 MHz, CHLOROFORM-d) δ ppm 1.30 (t, J=7.2 Hz, 3 H) 3.44 (s, 2 H) 4.10 (d, J=5.3 Hz, 2 H) 4.25 (q, J=7.2 Hz, 2 H).

MS ESI/APCI Dual posi: 190 [M+H]$^+$.
MS ESI/APCI Dual nega: 188 [M–H]$^-$.

Example 1-1

N-[(4-Hydroxy-2-oxo-1-{[4'-(trifluoromethyl)biphenyl-4-yl]methyl}-9-oxa-1-azaspiro[5.5]undec-3-en-3-yl)carbonyl]glycine

[Formula 194]

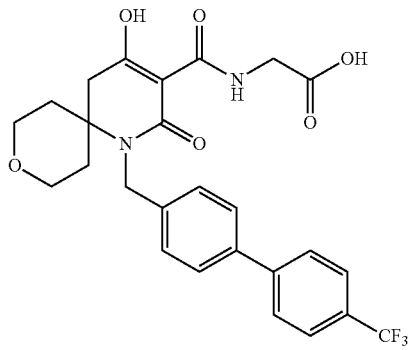

(1) Synthesis of ethyl 3-([4-(2-ethoxy-2-oxoethyl) tetrahydro-2H-pyran-4-yl]{[4'-(trifluoromethyl)biphenyl-4-yl]methyl}amino)-3-oxopropanoate

[Formula 195]

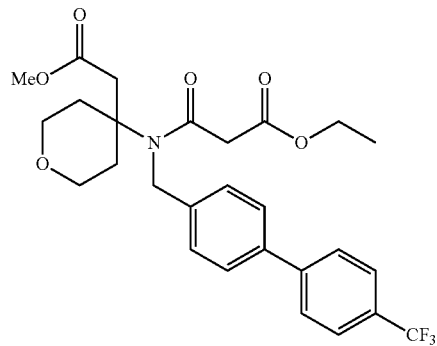

To a solution in ethyl acetate (11.6 mL) of the compound (770 mg) obtained in Reference Example A-1 and triethylamine (287 mg), ethyl malonyl chloride (341 mg) was added at 0° C. and the mixture was stirred at room temperature for 30 minutes. More of triethylamine (95.7 mg) was added and following the addition of ethyl malonyl chloride (114 mg) at 0° C., the mixture was stirred at room temperature for 30 minutes. After adding 1 mol/L hydrochloric acid, two extractions were conducted with ethyl acetate. The combined organic layers were passed through a phase separator and thereafter concentrated under reduced pressure to give a mixture (1.44 g) comprising ethyl 3-([4-(2-ethoxy-2-oxoethyl) tetrahydro-2H-pyran-4-yl]{[4'-(trifluoromethyl)biphenyl-4-yl]methyl}amino)-3-oxopropanoate.

MS ESI/APCI Dual posi: 522 [M+H]$^+$, 544 [M+Na]$^+$.

(2) Synthesis of sodium 3-(ethoxycarbonyl)-2-oxo-1-{[4'-(trifluoromethyl)biphenyl-4-yl]methyl}-9-oxa-1-azaspiro[5.5]undec-3-en-4-olate

[Formula 196]

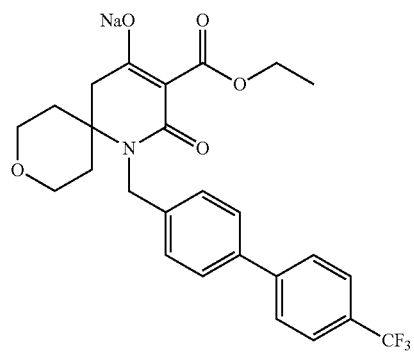

To a solution in ethanol (24.7 mL) of the mixture (1.43 g) obtained in step (1) above, sodium ethoxide (about 20%, solution in ethanol, 1.30 mL) was added and the resulting mixture was stirred at an external temperature of 90° C. for 4 hours. After cooling the reaction mixture to room temperature, the precipitate was recovered by filtration to give sodium 3-(ethoxycarbonyl)-2-oxo-1-{[4'-(trifluoromethyl)biphenyl-4-yl]methyl}-9-oxa-1-azaspiro[5.5]undec-3-en-4-olate as a brown solid (534 mg).

$^1$H NMR (300 MHz, DMSO-d$_6$) δ ppm 1.14 (t, J=7.1 Hz, 3 H) 1.40-1.55 (m, 2 H) 1.74-1.92 (m, 2 H) 2.42 (s, 2 H) 3.37-3.46 (m, 2 H) 3.61-3.71 (m, 2 H) 3.94 (q, J=6.9 Hz, 2 H) 4.70 (br. s., 2 H) 7.40 (d, J=7.9 Hz, 2 H) 7.65 (d, J=8.1 Hz, 2 H) 7.75-7.82 (m, 2 H) 7.84-7.92 (m, 2 H).

MS ESI/APCI Dual posi: 512 [M+Na]$^+$.
MS ESI/APCI Dual nega: 488 [M−H]$^−$.

(3) Synthesis of tert-butyl N-[(4-hydroxy-2-oxo-1-{[4'-(trifluoromethyl)biphenyl-4-yl]methyl}-9-oxa-1-azaspiro[5.5]undec-3-en-3-yl)carbonyl]glycinate

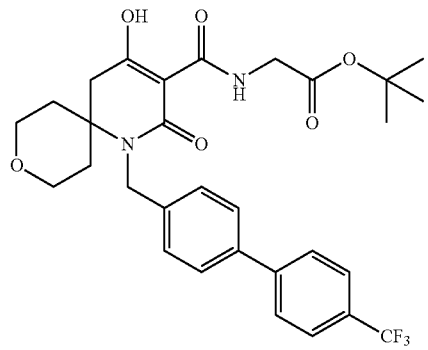

[Formula 197]

To a solution in 1,2-dimethoxyethane (10.2 mL) of the compound (508 mg) obtained in step (2) above, triethylamine (100 mg) and glycine tert-butyl hydrochloride (200 mg) were added and the mixture was stirred at an external temperature of 90° C. for two hours. After being cooled to room temperature, the reaction mixture was concentrated under reduced pressure. The resulting residue was purified by silica gel column chromatography (n-hexane:ethyl acetate=85:15-20:80) to give tert-butyl N-[(4-hydroxy-2-oxo-1-{[4'-(trifluoromethyl)biphenyl-4-yl]methyl}-9-oxa-1-azaspiro[5.5]undec-3-en-3-yl)carbonyl]glycinate as a colorless amorphous mass (329 mg).

$^1$H NMR (300 MHz, CHLOROFORM-d) δ ppm 1.47-1.53 (m, 9 H) 1.59-1.68 (m, 2 H) 1.99-2.16 (m, 2 H) 2.83-2.98 (m, 2 H) 3.44-3.60 (m, 2 H) 3.79-3.93 (m, 2 H) 3.99-4.08 (m, 2 H) 4.84 (br. s., 2 H) 7.31-7.41 (m, 2 H) 7.50-7.59 (m, 2 H) 7.62-7.72 (m, 4 H) 10.12-10.45 (m, 1 H).

MS ESI/APCI Dual posi: 575 [M+H]$^+$.
MS ESI/APCI Dual nega: 573 [M−H]$^−$.

(4) Synthesis of the Titled Compound

To the compound (319 mg) obtained in step (3) above, a solution (6.4 mL) of 4 mol/L hydrogen chloride in 1,4-dioxane was added and the mixture was stirred at room temperature for 18 hours. After concentrating under reduced pressure, ethyl acetate (5.00 mL) was added to the residue and with continued stirring, n-hexane (5.00 mL) was added. After stirring the reaction mixture at room temperature for 30 minutes, the precipitate was recovered by filtration to give the titled compound as a colorless solid (245 mg).

$^1$H NMR (300 MHz, DMSO-d$_6$) δ ppm 1.46-1.61 (m, 2 H) 1.89-2.10 (m, 2 H) 2.89-3.14 (m, 2 H) 3.41-3.56 (m, 2 H) 3.65-3.78 (m, 2 H) 3.96-4.16 (m, 2 H) 4.74-4.93 (m, 2 H) 7.40-7.51 (m, 2 H) 7.63-7.74 (m, 2 H) 7.75-7.93 (m, 4 H) 9.93-10.27 (m, 1 H) 12.76-12.95 (m, 1 H).

MS ESI/APCI Dual posi: 519 [M+H]$^+$, 541 [M+Na]$^+$.
MS ESI/APCI Dual nega: 517 [M−H]$^−$.

Example 1-2

N-{[5-(Biphenyl-4-ylmethyl)-8-hydroxy-6-oxo-2-oxa-5-azaspiro[3.5]non-7-en-7-yl]carbonyl}glycine

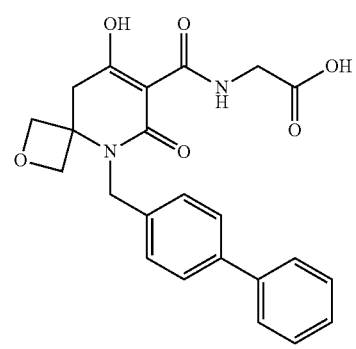

[Formula 198]

(1) Synthesis of tert-butyl N-{[5-(biphenyl-4-ylmethyl)-8-hydroxy-6-oxo-2-oxa-5-azaspiro[3.5]non-7-en-7-yl]carbonyl}glycinate

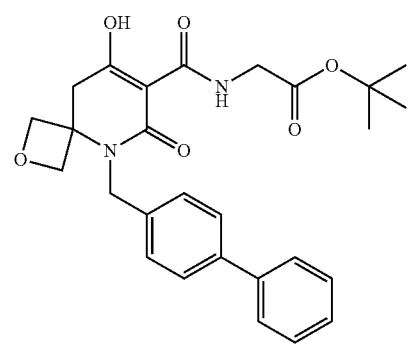

[Formula 199]

Instead of the compound obtained in Reference Example A-1, the compound (1.90 g) obtained in Reference Example A-2 was used and treated by the same techniques as in Example 1-1(1) to (3) to give tert-butyl N-{[5-(biphenyl-4-ylmethyl)-8-hydroxy-6-oxo-2-oxa-5-azaspiro[3.5]non-7-en-7-yl]carbonyl}glycinate as a pale brown solid (2.67 g).

$^1$H NMR (200 MHz, CHLOROFORM-d) δ ppm 1.43-1.52 (m, 9 H) 3.01-3.23 (m, 2 H) 3.94-4.11 (m, 2 H) 4.37-4.62 (m, 2 H) 4.74-4.93 (m, 2 H) 5.06-5.21 (m, 2 H) 7.24-7.50 (m, 5 H) 7.51-7.62 (m, 4 H) 9.95-10.57 (m, 1 H).

MS ESI/APCI Dual posi: 501 [M+Na]$^+$.

(2) Synthesis of the Titled Compound

To a solution in chloroform (20.0 mL) of the compound (2.60 g) obtained in step (1) above, trifluoroacetic acid (8.00 mL) was added and the mixture was stirred at room temperature for 12 hours. After concentrating under reduced pressure, ethyl acetate was added to the residue. With continued stirring, n-hexane was added and the precipitate was recovered by filtration to give the titled compound as a pale brown solid (2.18 g).

$^1$H NMR (300 MHz, DMSO-d$_6$) δ ppm 3.08-3.28 (m, 2 H) 3.93-4.12 (m, 2 H) 4.45 (d, J=7.1 Hz, 2 H) 4.74 (d, J=7.1 Hz, 2 H) 5.01-5.18 (m, 2 H) 7.26-7.52 (m, 5 H) 7.57-7.71 (m, 4 H) 9.80-10.34 (m, 1 H) 12.89 (br. s., 1 H).

MS ESI/APCI Dual posi: 423 [M+H]$^+$.

Example 1-3

N-({4-Hydroxy-5-methyl-2-oxo-1-[4-(trifluoromethoxy)benzyl]-1,2,5,6-tetrahydropyridin-3-yl}carbonyl)glycine sodium salt

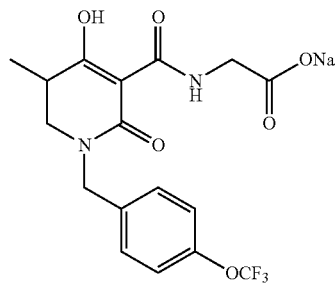

[Formula 200]

(1) Synthesis of tert-butyl N-({4-hydroxy-5-methyl-2-oxo-1-[4-(trifluoromethoxy)benzyl]-1,2,5,6-tetrahydropyridin-3-yl}carbonyl)glylcinate

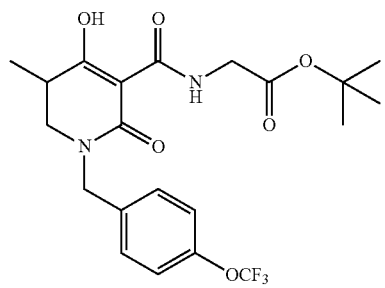

[Formula 201]

Instead of the compound obtained in Reference Example A-1, the compound (1.12 g) obtained in Reference Example A-3 was used and treated by the same techniques as in Example 1-1(1) to (3) to give tert-butyl N-({4-hydroxy-5-methyl-2-oxo-1-[4-(trifluoromethoxy)benzyl]-1,2,5,6-tetrahydropyridin-3-yl}carbonyl)glycinate as a colorless solid (704 mg).

$^1$H NMR (300 MHz, CHLOROFORM-d) δ ppm 1.04-1.16 (m, 3 H) 1.42-1.56 (m, 9 H) 2.61-2.76 (m, 1 H) 2.93-3.07 (m, 1 H) 3.26-3.38 (m, 1 H) 3.97-4.04 (m, 2 H) 4.50-4.68 (m, 2 H) 7.11-7.33 (m, 4 H) 10.13-10.57 (m, 1 H).

MS ESI/APCI Dual posi: 481 [M+Na]$^+$.

MS ESI/APCI Dual nega: 457 [M−H]$^-$.

(2) Synthesis of N-({4-hydroxy-5-methyl-2-oxo-1-[4-(trifluoromethoxy)benzyl]-1,2,5,6-tetrahydropyridin-3-yl}carbonyl)glycine

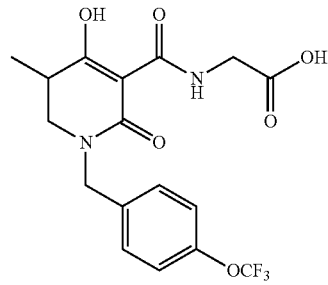

[Formula 202]

To the compound (1.12 g) obtained in step (1) above, a solution (10.0 mL) of 4 mol/L hydrochloride in 1,4-dioxane was added and the mixture was stirred at room temperature for 16 hours. After being concentrated under reduced pressure, the reaction mixture was purified by preparative HPLC to give N-({4-hydroxy-5-methyl-2-oxo-1-[4-(trifluoromethoxy)benzyl]-1,2,5,6-tetrahydropyridin-3-yl}carbonyl)glycine as a colorless amorphous mass (482 mg).

$^1$H NMR (600 MHz, CHLOROFORM-d) δ ppm 1.07-1.19 (m, 3 H) 2.53-2.78 (m, 1 H) 2.98-3.10 (m, 1 H) 3.33-3.41 (m, 1 H) 4.15-4.23 (m, 2 H) 4.56-4.70 (m, 2 H) 7.15-7.23 (m, 2 H) 7.27-7.34 (m, 2 H) 10.13-10.50 (m, 1 H).

MS ESI/APCI Dual posi: 403 [M+H]$^+$, 425 [M+Na]$^+$.

MS ESI/APCI Dual nega: 401[M−H]$^-$.

(3) Synthesis of the Titled Compound

To a solution in methanol (3.00 mL) of the compound (321 mg) obtained in step (2) above, 1 mol/L sodium hydroxide in aqueous solution (0.798 mL) was added and the mixture was stirred at room temperature for 30 minutes. The reaction mixture was concentrated under reduced pressure. To the resulting residue, isopropyl alcohol was added and thereafter the mixture was stirred overnight at room temperature. The precipitate was recovered by filtration to give the titled compound as a pale yellow solid (205 mg).

$^1$H NMR (300 MHz, METHANOL-d$_4$) δ ppm 1.10 (d, J=7.0 Hz, 3 H) 2.56-2.73 (m, 1 H) 3.06 (dd, J=12.6, 7.9 Hz, 1 H) 3.44 (dd, J=12.6, 5.7 Hz, 1 H) 3.89 (s, 2 H) 4.58 (d, J=14.9 Hz, 1 H) 4.70 (d, J=14.9 Hz, 1 H) 7.16-7.30 (m, 2 H) 7.36-7.47 (m, 2 H).

MS ESI/APCI Dual posi: 425 [M+Na]$^+$.

Example 1-4 sodium N-[(1-{[6-(4-Chlorophenoxy)-3-pyridinyl]methyl}-4-hydroxy-2-oxo-1,2,5,6-tetrahydro-3-pyridinyl)carbonyl]glycinate

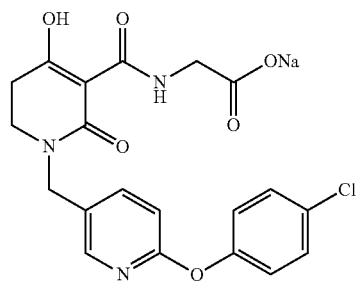

[Formula 203]

(1) Synthesis of 2-methyl-2-propanyl N-[(1-{[6-(4-chlorophenoxy)-3-pyridinyl]methyl}-4-hydroxy-2-oxo-1,2,5,6-tetrahydro-3-pyridinyl)carbonyl]glycinate

[Formula 204]

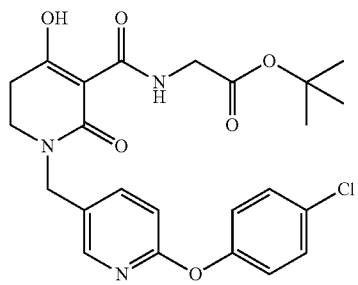

Instead of the compound obtained in Reference Example A-1, the compound (1.15 g) obtained in Reference Example A-246 was used and treated by the same techniques as in Example 1-1(1) to (3) to give 2-methyl-2-propanyl N-[(1-{[6-(4-chlorophenoxy)-3-pyridinyl]methyl}-4-hydroxy-2-oxo-1,2,5,6-tetrahydro-3-pyridinyl)carbonyl]glycinate as a pale yellow gum (1.02 g).

$^1$H NMR (300 MHz, CHLOROFORM-d) δ ppm 1.49 (s, 9 H) 2.50-2.67 (m, 2 H) 3.27-3.38 (m, 2 H) 3.95-4.07 (m, 2 H) 4.56 (s, 2 H) 6.88-6.94 (m, 1 H) 7.04-7.14 (m, 2 H) 7.31-7.41 (m, 2 H) 7.63-7.74 (m, 1 H) 8.04-8.09 (m, 1 H) 10.07-10.51 (m, 1 H).
MS ESI/APCI Dual posi: 510 [M+Na]$^+$.
MS ESI/APCI Dual nega: 486 [M−H]$^−$.

(2) Synthesis of N-[(1-{[6-(4-chlorophenoxy)-3-pyridinyl]methyl}-4-hydroxy-2-oxo-1,2,5,6-tetrahydro-3-pyridinyl)carbonyl]glycine To the compound (1.02 g) obtained in step (1) above, a solution (10.0 mL) of 4 mol/L hydrogen chloride in 1,4-dioxane was added and the mixture was stirred overnight at room temperature. The resulting precipitate was recovered by filtration and the solid obtained was heated upon addition of ethyl acetate. After adding acetonitrile, the mixture was cooled to room temperature and stirred at that temperature. The resulting precipitate was recovered by filtration to give a colorless solid (645 mg).

$^1$H NMR (300 MHz, DMSO-d$_6$) δ ppm 2.50-2.74 (m, 2 H) 3.37-3.49 (m, 2 H) 3.96-4.08 (m, 2 H) 4.48-4.62 (m, 2 H) 7.05 (d, J=8.4 Hz, 1 H) 7.14-7.20 (m, 2 H) 7.42-7.49 (m, 2 H) 7.79 (dd, J=8.4, 2.5 Hz, 1 H) 8.07-8.14 (m, 1 H) 9.94-10.26 (m, 1 H) 12.87 (br. s., 1 H).
MS ESI/APCI Dual posi: 432 [M+H]$^+$.
MS ESI/APCI Dual nega: 430 [M−H]$^−$.

(3) Crystallization of N-[(1-{[6-(4-chlorophenoxy)-3-pyridinyl]methyl}-4-hydroxy-2-oxo-1,2,5,6-tetrahydro-3-pyridinyl)carbonyl]glycine To the compound (30 mg) obtained in step (2) above, a liquid mixture of water and ethanol (5:4) was added and the resulting mixture was heated on a hot water bath with 80° C. until it turned to solution, which was thereafter left to stand overnight at room temperature. The solvent was distilled off under a nitrogen stream to give a colorless solid (30 mg). m.p.: 191° C.

(4) Synthesis of the Titled Compound

To a solution in acetone of the compound (645 mg) obtained in step (2) above, 1 mol/L sodium hydroxide in aqueous solution (1.50 mL) was added and the mixture was stirred at room temperature for 30 minutes. The resulting precipitate was recovered by filtration to give the titled compound as a colorless solid (543 mg).

$^1$H NMR (300 MHz, DMSO-d$_6$) δ ppm 2.53-2.59 (m, 2 H) 3.34 (t, J=7.1 Hz, 2 H) 3.48-3.60 (m, 2 H) 4.52 (s, 2 H) 7.04 (d, J=8.4 Hz, 1 H) 7.12-7.21 (m, 2 H) 7.36-7.50 (m, 2 H) 7.79 (dd, J=8.4, 2.5 Hz, 1 H) 8.09 (d, J=2.5 Hz, 1 H) 10.08 (br. s., 1 H).
MS ESI posi: 432 [M+H]$^+$.
MS ESI nega: 430 [M−H]$^−$.

In the following Examples 1-5 to 1-464, the compounds obtained in Reference Examples A-8 to A-245, A-247 to A-300, A-343 to A-486, Reference Examples B-1 to B-17, Reference Example C-1, Reference Example D-1, Reference Examples F-1 to F-3, or commercial grades of the corresponding amines were used as starting materials and treated by the methods described in Examples 1-1 to 1-4 or modifications thereof to synthesize the intended compounds. The structures of the synthesized compounds and their NMR and MS data are shown in Tables 21-1 to 21-67.

TABLE 21-1

| Compound No. | Structure | Analytical Data | Salt information |
|---|---|---|---|
| Example 1-5 | (structure shown) | $^1$H NMR (600 MHz, DMSO-d$_6$) δ ppm 1.08-1.78 (m, 10 H) 2.74-2.90 (m, 2 H) 3.98-4.09 (m, 2 H) 4.66-4.89 (m, 2 H) 7.30-7.49 (m, 5 H) 7.55-7.68 (m, 4 H) 9.95-10.24 (m, 1 H) 12.84 (br. s., 1 H). MS ESI/APCI Dual posi: 449[M + H]$^+$, 471[M + Na]$^+$. MS ESI/APCI Dual nega: 447[M − H]$^−$. | |

TABLE 21-1-continued

| Compound No. | Structure | Analytical Data | Salt information |
|---|---|---|---|
| Example 1-6 | 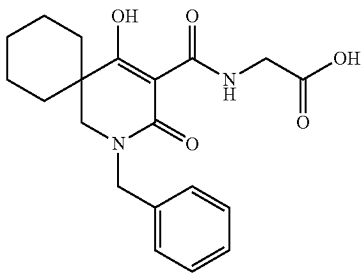 [SMILES: O=C(O)CNC(=O)C1=C(O)C2(CCCCC2)CN(Cc2ccccc2)C1=O] | ¹H NMR (300 MHz, DMSO-d₆) δ ppm 0.92-1.73 (m, 10 H) 3.31 (s, 2 H) 3.93-4.08 (m, 2 H) 4.52-4.67 (m, 2 H) 7.20-7.44 (m, 5 H) 10.11-10.40 (m, 1 H) 12.70-12.99 (m, 1 H). MS ESI/APCI Dual posi: 373[M + H]⁺, 395[M + Na]⁺. MS ESI/APCI Dual nega: 371[M − H]⁻. | |
| Example 1-7 | 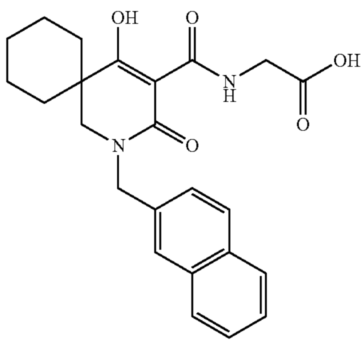 [SMILES: O=C(O)CNC(=O)C1=C(O)C2(CCCCC2)CN(Cc2ccc3ccccc3c2)C1=O] | ¹H NMR (300 MHz, DMSO-d₆) δ ppm 0.93-1.76 (m, 10 H) 3.35-3.41 (m, 2 H) 3.99-4.11 (m, 2 H) 4.70-4.85 (m, 2 H) 7.41-7.56 (m, 3 H) 7.83-7.96 (m, 4 H) 10.15-10.44 (m, 1 H) 12.75-13.01 (m, 1 H). MS ESI/APCI Dual posi: 423[M + H]⁺, 445[M + Na]⁺. MS ESI/APCI Dual nega: 421[M − H]⁻. | |
| Example 1-8 | 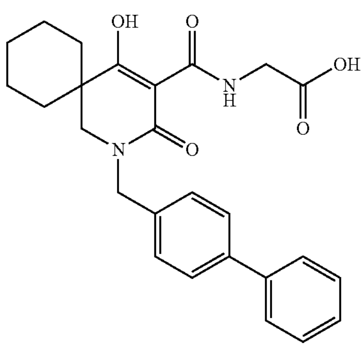 [SMILES: O=C(O)CNC(=O)C1=C(O)C2(CCCCC2)CN(Cc2ccc(-c3ccccc3)cc2)C1=O] | ¹H NMR (300 MHz, DMSO-d₆) δ ppm 1.00-1.74 (m, 10 H) 3.34-3.39 (m, 2 H) 3.96-4.09 (m, 2 H) 4.58-4.71 (m, 2 H) 7.28-7.54 (m, 5 H) 7.59-7.75 (m, 4 H) 10.13-10.42 (m, 1 H) 12.61-13.17 (M, 1 H). MS ESI/APCI Dual posi: 449[M + H]⁺, 471[M + Na]⁺. MS ESI/APCI Dual nega: 447[M − H]⁻. | |
| Example 1-9 | 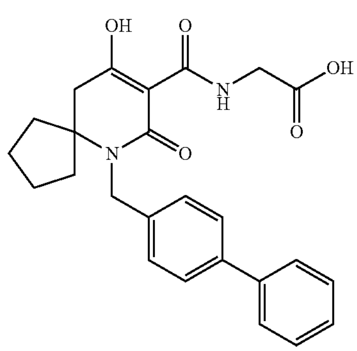 [SMILES: O=C(O)CNC(=O)C1=C(O)CC2(CCCC2)N(Cc2ccc(-c3ccccc3)cc2)C1=O] | ¹H NMR (300 MHz, DMSO-d₆) δ ppm 1.48-1.94 (m, 8 H) 2.59-2.84 (m, 2 H) 3.93-4.11 (m, 2 H) 4.53-4.78 (m, 2 H) 7.29-7.51 (m, 5 H) 7.55-7.68 (m, 4 H) 9.93-10.25 (m, 1 H) 12.67-13.15 (m, 1 H). MS ESI/APCI Dual posi: 435[M + H]⁺, 457[M + Na]⁺. MS ESI/APCI Dual nega: 433[M − H]⁻. | |

TABLE 21-1-continued

| Compound No. | Structure | Analytical Data | Salt information |
|---|---|---|---|
| Example 1-10 | 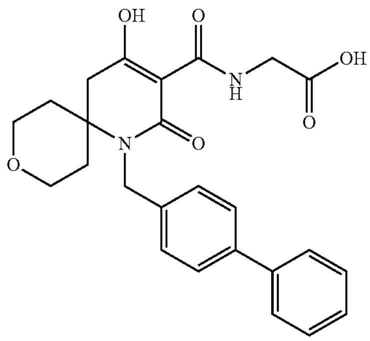 | $^1$H NMR (600 MHz, DMSO-$d_6$) δ ppm 1.47-1.60 (m, 2 H) 1.92-2.05 (m, 2 H) 2.86-3.12 (m, 2 H) 3.42-3.55 (m, 2 H) 3.63-3.76 (m, 2 H) 3.96-4.08 (m, 2 H) 4.69-4.90 (m, 2 H) 7.30-7.49 (m, 5 H) 7.53-7.70 (m, 4 H) 9.95-10.26 (m, 1 H). MS ESI/APCI Dual posi: 451[M + H]$^+$. MS ESI/APCI Dual nega: 449[M − H]$^−$. | |

TABLE 21-2

| Compound No. | Structure | Analytical Data | Salt information |
|---|---|---|---|
| Example 1-11 | 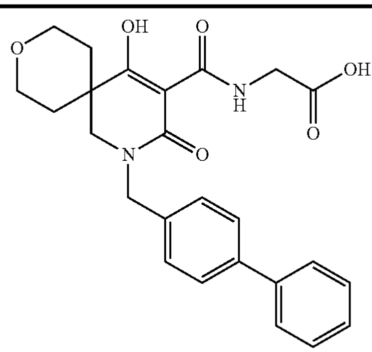 | $^1$H NMR (600 MHz, DMSO-$d_6$) δ ppm 1.19-1.40 (m, 2 H) 1.72-1.89 (m, 2 H) 3.29-3.38 (m, 2 H) 3.43-3.51 (m, 2 H) 3.56-3.65 (m, 2 H) 3.97-4.07 (m, 2 H) 4.58-4.75 (m, 2 H) 7.32-7.50 (m, 5 H) 7.62-7.70 (m, 4 H) 10.14-10.33 (m, 1 H). MS ESI/APCI Dual posi: 451[M + H]$^+$, 473[M + Na]$^+$. MS ESI/APCI Dual nega: 449[M − H]$^−$. | |
| Example 1-12 | 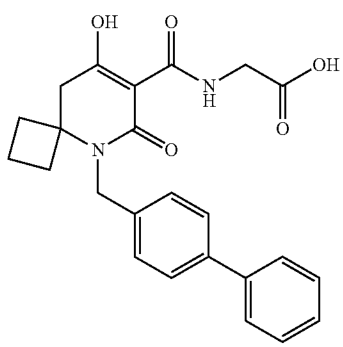 | $^1$H NMR (300 MHz, DMSO-$d_6$) δ ppm 1.58-1.95 (m, 4 H) 2.28-2.47 (m, 2 H) 2.76-3.08 (m, 2 H) 3.95-4.12 (m, 2 H) 4.78-5.03 (m, 2 H) 7.29-7.51 (m, 5 H) 7.57-7.68 (m, 4 H) 9.87-10.29 (m, 1 H) 12.69-13.02 (m, 1 H). MS ESI/APCI Dual posi: 421[M + H]$^+$. | |
| Example 1-13 | 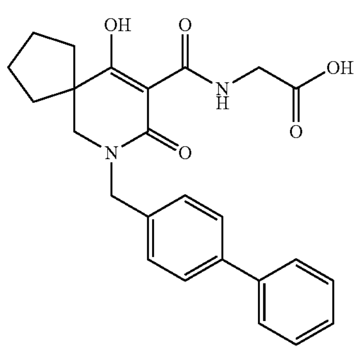 [SMILES: O=C(O)CNC(=O)C1=C(O)C2(CCCC2)CN(Cc2ccc(-c3ccccc3)cc2)C1=O] | $^1$H NMR (300 MHz, DMSO-$d_6$) δ ppm 1.23-1.94 (m, 8 H) 3.15-3.28 (m, 2 H) 3.97-4.09 (m, 2 H) 4.56-4.71 (m, 2 H) 7.29-7.53 (m, 5 H) 7.60-7.74 (m, 4 H) 10.13-10.41 (m, 1 H). MS ESI/APCI Dual posi: 435[M + H]$^+$, 457[M + Na]$^+$. | |

TABLE 21-2-continued

| Compound No. | Structure | Analytical Data | Salt information |
|---|---|---|---|
| Example 1-14 | (structure) | $^1$H NMR (300 MHz, DMSO-d$_6$) δ ppm 1.12-1.60 (m, 10 H) 1.62-1.82 (m, 2 H) 3.11-3.24 (m, 2 H) 3.96-4.07 (m, 2 H) 4.54-4.73 (m, 2 H) 7.30-7.52 (m, 5 H) 7.58-7.73 (m, 4 H) 10.12-10.42 (m, 1 H).<br>MS ESI/APCI Dual posi: 463[M + H]$^+$, 485[M + Na]$^+$.<br>MS ESI/APCI Dual nega: 461[M − H]$^−$. | |
| Example 1-15 | (structure) | $^1$H NMR (300 MHz, DMSO-d$_6$) δ ppm 1.50-2.02 (m, 4 H) 2.12-2.41 (m, 2 H) 3.49 (s, 2 H) 3.93-4.17 (m, 2 H) 4.56-4.78 (m, 2 H) 7.28-7.54 (m, 5 H) 7.57-7.74 (m, 4 H) 10.00-10.44 (m, 1 H) 12.77-13.03 (m, 1 H).<br>MS ESI/APCI Dual posi: 421[M + H]$^+$, 443[M + Na]$^+$.<br>MS ESI/APCI Dual nega: 419[M − H]$^−$. | |
| Example 1-16 | (structure) | $^1$H NMR (600 MHz, DMSO-d$_6$) δ ppm 2.64-2.73 (m, 2 H) 3.36-3.49 (m, 2 H) 3.97-4.10 (m, 2 H) 4.55-4.71 (m, 2 H) 7.26-7.51 (m, 5 H) 7.59-7.70 (m, 4 H) 10.01-10.30 (m, 1 H) 12.67-13.04 (m, 1 H).<br>MS ESI/APCI Dual posi: 381[M + H]$^+$, 403[M + Na]$^+$.<br>MS ESI/APCI Dual nega: 379[M − H]$^−$. | |
| Example 1-17 | (structure) | $^1$H NMR (600 MHz, DMSO-d$_6$) δ ppm 1.24 (s, 6 H) 3.16 (s, 2 H) 3.91-4.14 (m, 2 H) 4.59-4.81 (m, 2 H) 7.27-7.49 (m, 5 H) 7.56-7.67 (m, 4 H) 9.96-10.27 (m, 1 H).<br>MS ESI/APCI Dual posi: 409[M + H]$^+$, 431[M + Na]$^+$.<br>MS ESI/APCI Dual nega: 407[M − H]$^−$. | |

TABLE 21-3

| Compound No. | Structure | Analytical Data | Salt information |
|---|---|---|---|
| Example 1-18 | 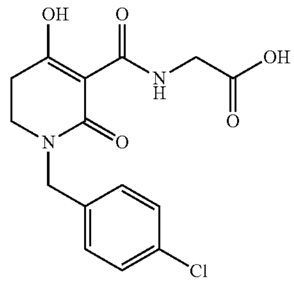 [SMILES: O=C(O)CNC(=O)C1=C(O)CCN(Cc2ccc(Cl)cc2)C1=O] | ¹H NMR (300 MHz, CHLOROFORM-d) δ ppm 2.47-2.73 (m, 2 H) 3.24-3.41 (m, 2 H) 4.12-4.27 (m, 2 H) 4.52-4.65 (m, 2 H) 7.17-7.25 (m, 2 H) 7.28-7.36 (m, 2 H) 10.07-10.50 (m, 1 H). MS ESI/APCI Dual posi: 339[M + H]⁺, 361[M + Na]⁺. MS ESI/APCI Dual nega: 337[M − H]. | |
| Example 1-19 | 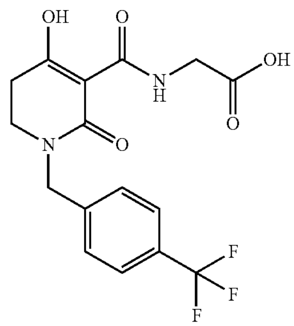 [SMILES: O=C(O)CNC(=O)C1=C(O)CCN(Cc2ccc(C(F)(F)F)cc2)C1=O] | ¹H NMR (300 MHz, CHLOROFORM-d) δ ppm 2.57-2.70 (m, 2 H) 3.31-3.42 (m, 2 H) 4.17-4.23 (m, 2 H) 4.59-4.74 (m, 2 H) 7.32-7.47 (m, 2 H) 7.53-7.70 (m, 2 H) 10.06-10.48 (m, 1 H). MS ESI/APCI Dual posi: 373[M + H]⁺, 395[M + Na]⁺. MS ESI/APCI Dual nega: 371[M − H]⁻. | |
| Example 1-20 | 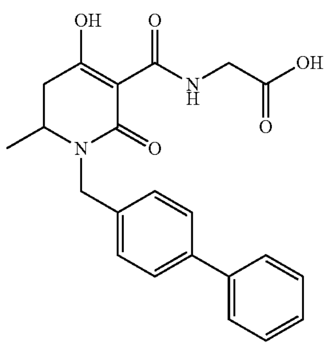 | ¹H NMR (600 MHz, DMSO-d₆) δ ppm 1.16 (d, J = 6.6 Hz, 3 H) 2.15-2.38 (m, 1 H) 3.02-3.14 (m, 1 H) 3.61-3.77 (m, 1 H) 3.95-4.07 (m, 2 H) 4.13-4.38 (m, 1 H) 4.96-5.10 (m, 1 H) 7.32-7.49 (m, 5 H) 7.58-7.68 (m, 4 H) 9.91-10.24 (m, 1 H). MS ESI/APCI Dual posi: 395[M + H]⁺, 417[M + Na]⁺. MS ESI/APCI Dual nega: 393[M − H]⁻. | |
| Example 1-21 | 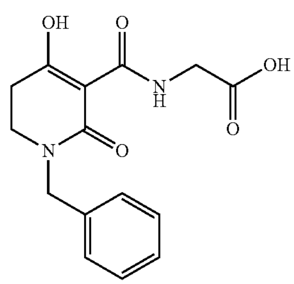 [SMILES: O=C(O)CNC(=O)C1=C(O)CCN(Cc2ccccc2)C1=O] | ¹H NMR (300 MHz, CHLOROFORM-d) δ ppm 2.45-2.71 (m, 2 H) 3.20-3.47 (m, 2 H) 4.17-4.22 (m, 2 H) 4.64 (s, 2 H) 7.13-7.48 (m, 5 H) 10.15-10.47 (m, 1 H). MS ESI/APCI Dual posi: 305[M + H]⁺, 327[M + Na]⁺. MS ESI/APCI Dual nega: 303[M − H]⁻. | |
| Example 1-22 | 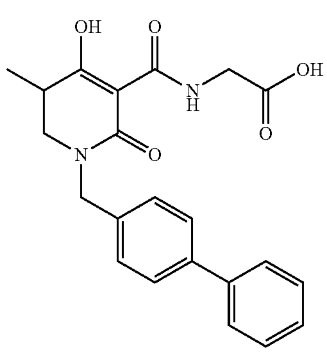 [SMILES: CC1CN(Cc2ccc(-c3ccccc3)cc2)C(=O)C(C(=O)NCC(=O)O)=C1O] | ¹H HMR (600 MHz, DMSO-d₆) δ ppm 1.09 (d, J = 7.0 Hz, 3 H) 2.78-2.90 (m, 1 H) 3.05-3.20 (m, 1 H) 3.43-3.56 (m, 1 H) 3.98-4.09 (m, 2 H) 4.51-4.80 (m, 2 H) 7.32-7.50 (m, 5 H) 7.59-7.70 (m, 4 H) 9.99-10.38 (m, 1 H). MS ESI/APCI Dual posi: 395[M + H]⁺, 417[M + Na]⁺. MS ESI/APCI Dual nega: 393[M − H]⁻. | |

TABLE 21-3-continued

| Compound No. | Structure | Analytical Data | Salt information |
|---|---|---|---|
| Example 1-23 | (4-bromobenzyl substituted pyridinone glycine amide) | ¹H NMR (600 MHz, CHLOROFORM-d) δ ppm 2.60-2.67 (m, 2 H) 3.29-3.37 (m, 2 H) 4.16-4.23 (m, 2 H) 4.54-4.60 (m, 2 H) 7.12-7.19 (m, 2 H) 7.43-7.52 (m, 2 H) 10.12-10.50 (m, 1 H).<br>MS ESI/APCI Dual posi: 383[M + H]⁺, 405[M + Na]⁺.<br>MS ESI/APCI Dual nega: 381[M − H]⁻. | |
| Example 1-24 | (3-biphenylmethyl substituted pyridinone glycine amide) | ¹H NMR (300 MHz, DMSO-d₆) δ ppm 2.42-2.77 (m, 2 H) 3.23-3.51 (m, 2 H) 3.93-4.14 (m, 2 H) 4.58-4.84 (m, 2 H) 7.23-7.33 (m, 1 H) 7.33-7.51 (m, 4 H) 7.52-7.60 (m, 2 H) 7.61-7.69 (m, 2 H) 9.90-10.31 (m, 1 H) 12.85 (br. s., 1 H).<br>MS ESI/APCI Dual posi: 381[M + H]⁺.<br>MS ESI/APCI Dual nega: 379[M − H]⁻. | |

TABLE 21-4

| Compound No. | Structure | Analytical Data | Salt information |
|---|---|---|---|
| Example 1-25 | (2-biphenylmethyl substituted pyridinone glycine amide) | ¹H NMR (300 MHz, DMSO-d₆) δ ppm 2.63-2.78 (m, 2 H) 3.36-3.53 (m, 2 H) 3.93-4.09 (m, 2 H) 4.58-4.76 (m, 2 H) 7.21-7.74 (m, 9 H) 9.96-10.31 (m, 1 H) 12.67-12.98 (m, 1 H).<br>MS ESI/APCI Dual posi: 381[M + H]⁺, 403[M + Na]⁺.<br>MS ESI/APCI Dual nega: 379[M − H]⁻. | |
| Example 1-26 | (4-phenylcyclohexylmethyl substituted pyridinone glycine amide) | ¹H NMR (300 MHz, DMSO-d₆) δ ppm 0.97-1.24 (m, 2 H) 1.31-1.56 (m, 2 H) 1.63-1.93 (m, 5 H) 2.41-3.36 (m, 5 H) 3.37-3.54 (m, 2 H) 3.94-4.08 (m, 2 H) 7.09-7.35 (m, 5 H) 10.02-10.21 (m, 1 H) 12.67-12.96 (m, 1 H).<br>MS ESI/APCI Dual posi: 387[M + H]⁺, 409[M + Na]⁺.<br>MS ESI/APCI Dual nega: 385[M − H]⁻. | |

TABLE 21-4-continued

| Compound No. | Structure | Analytical Data | Salt information |
|---|---|---|---|
| Example 1-27 | 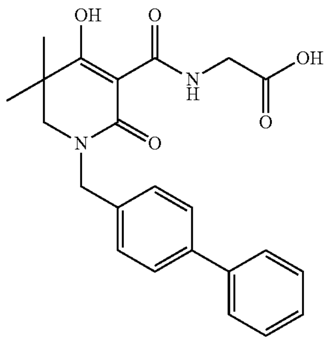 [SMILES: CC1(C)CN(Cc2ccc(-c3ccccc3)cc2)C(=O)C(C(=O)NCC(=O)O)=C1O] | $^1$H NMR (600 MHz, DMSO-d$_6$) δ ppm 0.94-1.10 (m, 6 H) 3.17-3.24 (m, 2 H) 3.98-4.06 (m, 2 H) 4.59-4.70 (m, 2 H) 7.31-7.48 (m, 5 H) 7.59-7.69 (m, 4 H) 10.09-10.37 (m, 1 H). MS ESI/APCI Dual posi: 409[M + H]$^+$, 431[M + Na]$^+$. MS ESI/APCI Dual nega: 407[M − H]$^-$. | |
| Example 1-28 | 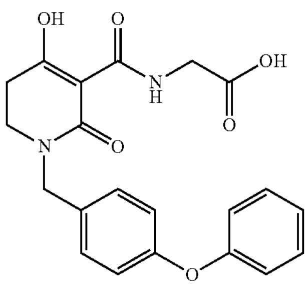 [SMILES: O=C(O)CNC(=O)C1=C(O)CCN(Cc2ccc(Oc3ccccc3)cc2)C1=O] | $^1$H NMR (600 MHz, DMSO-d$_6$) δ ppm 2.44-2.71 (m, 2 H) 3.34-3.45 (m, 2 H) 3.97-4.07 (m, 2 H) 4.49-4.64 (m, 2 H) 6.93-7.04 (m, 4 H) 7.09-7.17 (m, 1 H) 7.25-7.42 (m, 4 H) 9.96-10.27 (m, 1 H) 12.65-12.98 (m, 1 H). MS ESI/APCI Dual posi: 397[M + H]$^+$, 419[M + Na]$^+$. MS ESI/APCI Dual nega: 395[M − H]$^-$. | |
| Example 1-29 | 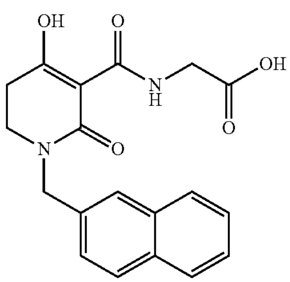 [SMILES: O=C(O)CNC(=O)C1=C(O)CCN(Cc2ccc3ccccc3c2)C1=O] | $^1$H NMR (600 MHz, DMSO-d$_6$) δ ppm 2.51-2.75 (m, 2 H) 3.37-3.48 (m, 2 H) 3.95-4.12 (m, 2 H) 4.64-4.85 (m, 2 H) 7.40-7.45 (m, 1 H) 7.47-7.54 (m, 2 H) 7.81 (s, 1 H) 7.86-7.96 (m, 3 H) 10.02-10.31 (m, 1 H). MS ESI/APCI Dual posi: 355[M + H]$^+$, 377[M + Na]$^+$. MS ESI/APCI Dual nega: 353[M − H]$^-$. | |
| Example 1-30 | 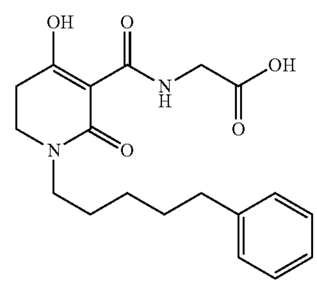 [SMILES: O=C(O)CNC(=O)C1=C(O)CCN(CCCCCc2ccccc2)C1=O] | $^1$H NMR (300 MHz, CHLOROFORM-d) δ ppm 1.23-1.46 (m, 2 H) 1.49-1.86 (m, 4 H) 2.42-2.73 (m, 4 H) 3.24-3.54 (m, 4 H) 4.08-4.22 (m, 2 H) 7.13-7.22 (m, 3 H) 7.23-7.31 (m, 2 H) 10.11-10.43 (m, 1 H). MS ESI/APCI Dual posi: 361[M + H]$^+$, 383[M + Na]$^+$. MS ESI/APCI Dual nega: 359[M − H]$^-$. | |
| Example 1-31 | 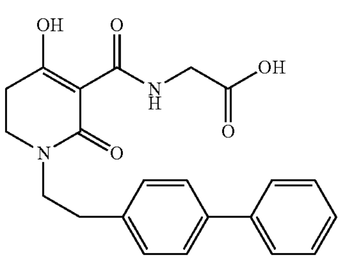 [SMILES: O=C(O)CNC(=O)C1=C(O)CCN(CCc2ccc(-c3ccccc3)cc2)C1=O] | $^1$H NMR (600 MHz, DMSO-d$_6$) δ ppm 2.56-2.64 (m, 2 H) 2.79-2.92 (m, 2 H) 3.36-3.47 (m, 2 H) 3.53-3.69 (m, 2 H) 3.96-4.06 (m, 2 H) 7.31-7.38 (m, 3 H) 7.42-7.48 (m, 2 H) 7.58-7.63 (m, 2 H) 7.64-7.67 (m, 2 H) 9.97-10.20 (m, 1 H). MS ESI/APCI Dual posi: 395[M + H]$^+$, 417[M + Na]$^+$. MS ESI/APCI Dual nega: 393[M − H]$^-$. | |

TABLE 21-5

| Compound No. | Structure | Analytical Data | Salt information |
|---|---|---|---|
| Example 1-32 | (structure) | ¹H NMR (600 MHz, DMSO-d₆) δ ppm 2.79 (t, J = 6.8 Hz, 2 H) 3.52 (t, J = 7.0 Hz, 2 H) 3.96-4.12 (m, 2 H) 4.82-4.97 (m, 2 H) 7.80 (d, J = 8.7 Hz, 1 H) 7.89-7.99 (m, 1 H) 8.14 (s, 1 H) 8.26 (d, J = 8.7 Hz, 1 H) 8.91-9.03 (m, 1 H) 9.20 (d, J = 4.5 Hz, 1 H) 9.98 (br. s., 1 H).<br>MS ESI/APCI Dual posi: 356[M + H]⁺.<br>MS ESI/APCI Dual nega: 354[M − H]⁻. | HCl |
| Example 1-33 | (structure) | ¹H NMR (600 MHz, DMSO-d₆) δ ppm 2.42-2.65 (m, 2 H) 3.34-3.45 (m, 2 H) 4.00-4.10 (m, 2 H) 5.00-5.13 (m, 2 H) 7.39-7.64 (m, 4 H) 7.84-7.92 (m, 1 H) 7.94-8.01 (m, 1 H) 8.07-8.16 (m, 1 H) 9.99-10.34 (m, 1 H) 12.65-13.04 (m, 1 H).<br>MS ESI/APCI Dual posi: 355[M + H]⁺, 377[M + Na]⁺.<br>MS ESI/APCI Dual nega: 353[M − H]⁻. | |
| Example 1-34 | (structure) | ¹H NMR (600 MHz, CHLOROFORM-d) δ ppm 2.36-2.56 (m, 2 H) 2.79-2.94 (m, 2 H) 3.12-3.26 (m, 2 H) 3.55-3.70 (m, 2 H) 4.04-4.20 (m, 2 H) 7.15-7.36 (m, 5 H) 10.01-10.39 (m, 1 H).<br>MS ESI/APCI Dual posi: 341[M + Na]⁺.<br>MS ESI/APCI Dual nega: 317[M − H]⁻. | |
| Example 1-35 | (structure) | ¹H NMR (300 MHz, DMSO-d₆) δ ppm 2.53-2.82 (m, 2 H) 3.44 (t, J = 6.8 Hz, 2 H) 3.93-4.12 (m, 2 H) 4.67 (s, 2 H) 7.49 (d, J = 8.4 Hz, 2 H) 7.61-7.70 (m, 1 H) 8.07 (d, J = 8.4 Hz, 2 H) 8.13-8.29 (m, 2 H) 8.77 (d, J = 4.7 Hz, 1 H) 9.90-10.27 (m, 1 H).<br>MS ESI/APCI Dual posi: 382[M + H]⁺, 404[M + Na]⁺.<br>MS ESI/APCI Dual nega: 380[M − H]⁻. | HCl |

TABLE 21-5-continued

| Compound No. | Structure | Analytical Data | Salt information |
|---|---|---|---|
| Example 1-36 | (structure) | $^1$H NMR (300 MHz, CHLOROFORM-d) δ ppm 1.36 (s, 9 H) 2.53-2.71 (m, 2 H) 3.33-3.44 (m, 2 H) 4.17-4.24 (m, 2 H) 4.63-4.70 (m, 2 H) 7.29-7.37 (m, 2 H) 7.42-7.61 (m, 6 H) 10.20-10.46 (m, 1 H). MS ESI/APCI Dual posi: 437[M + H]$^+$, 459[M + Na]$^+$. MS ESI/APCI Dual nega: 435[M − H]$^-$. | |
| Example 1-37 | (structure) | $^1$H NMR (300 MHz, CHLOROFORM-d) δ ppm 1.18-1.51 (m, 5 H) 1.68-1.96 (m, 5 H) 2.41-2.68 (m, 3 H) 3.29-3.41 (m, 2 H) 4.14-4.23 (m, 2 H) 4.56-4.62 (m, 2 H) 7.14-7.21 (m, 4 H) 10.21-10.43 (m, 1 H). MS ESI/APCI Dual posi: 387[M + H]$^+$, 409[M + Na]$^+$. MS ESI/APCI Dual nega: 385[M − H]$^-$. | |
| Example 1-38 | (structure) | $^1$H NMR (300 MHz, DMSO-d$_6$) δ ppm 2.59-2.91 (m, 2 H) 3.72-3.89 (m, 2 H) 3.97-4.10 (m, 2 H) 7.17-7.52 (m, 5 H) 9.80-10.39 (m, 1 H) 12.57-13.07 (m, 1 H). MS ESI/APCI Dual posi: 291[M + H]$^+$, 313[M + Na]$^+$. MS ESI/APCI Dual nega: 289[M − H]$^-$. | |

TABLE 21-6

| Compound No. | Structure | Analytical Data | Salt information |
|---|---|---|---|
| Example 1-39 | (structure) | $^1$H NMR (300 MHz, DMSO-d$_6$) δ ppm 2.56-2.87 (m, 2 H) 3.76-3.88 (m, 2 H) 3.96-4.09 (m, 2 H) 6.82-6.95 (m, 1 H) 6.97-7.21 (m, 5 H) 7.34-7.47 (m, 3 H) 9.77-10.40 (m, 1 H) 12.73-12.98 (m, 1 H). MS ESI/APCI Dual posi: 383[M + H]$^+$, 405[M + Na]$^+$. MS ESI/APCI Dual nega: 381[M − H]$^-$. | |

TABLE 21-6-continued

| Compound No. | Structure | Analytical Data | Salt information |
|---|---|---|---|
| Example 1-40 | 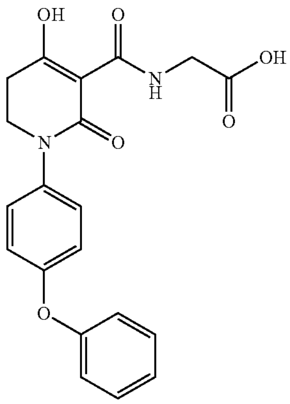 [SMILES: O=C(O)CNC(=O)C1=C(O)CCN(c2ccc(Oc3ccccc3)cc2)C1=O] | ¹H NMR (300 MHz, DMSO-d₆) δ ppm 2.60-2.90 (m, 2 H) 3.72-3.87 (m, 2 H) 3.94-4.12 (m, 2 H) 6.97-7.23 (m, 5 H) 7.25-7.50 (m, 4 H) 9.83-10.38 (m, 1 H) 12.72-13.05 (m, 1 H). MS ESI/APCI Dual posi: 383[M + H]⁺, 405[M + Na]⁺. MS ESI/APCI Dual nega: 381[M − H]⁻. | |
| Example 1-41 | 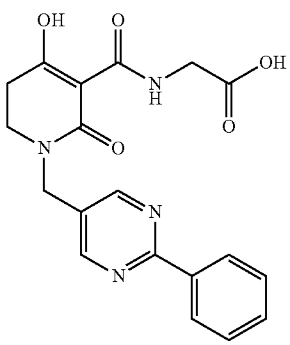 [SMILES: O=C(O)CNC(=O)C1=C(O)CCN(Cc2cnc(-c3ccccc3)nc2)C1=O] | ¹H NMR (300 MHz, DMSO-d₆) δ ppm 2.67-2.82 (m, 2 H) 3.46-3.61 (m, 2 H) 3.96-4.07 (m, 2 H) 4.62 (s, 2 H) 7.28-7.71 (m, 3 H) 8.24-8.55 (m, 2 H) 8.86 (s, 2 H) 9.78-10.08 (m, 1 H). MS ESI/APCI Dual posi: 383[M + H]⁺, 405[M + Na]⁺. | |
| Example 1-42 | 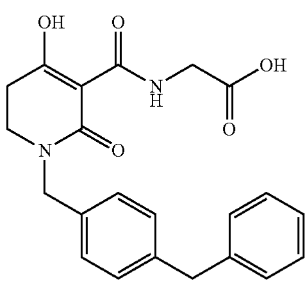 [SMILES: O=C(O)CNC(=O)C1=C(O)CCN(Cc2ccc(Cc3ccccc3)cc2)C1=O] | ¹H NMR (300 MHz, CHLOROFORM-d) δ ppm 2.50-2.67 (m, 2 H) 3.25-3.39 (m, 2 H) 3.96 (s, 2 H) 4.15-4.22 (m, 2 H) 4.50-4.63 (m, 2 H) 7.12-7.33 (m, 9 H) 10.11-10.50 (m, 1 H). MS ESI/APCI Dual posi: 395[M + H]⁺, 417[M + Na]⁺. MS ESI/APCI Dual nega: 393[M − H]⁻. | |
| Example 1-43 | 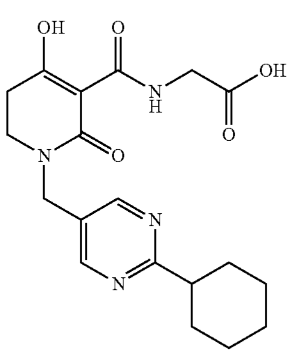 [SMILES: O=C(O)CNC(=O)C1=C(O)CCN(Cc2cnc(C3CCCCC3)nc2)C1=O] | ¹H NMR (300 MHz, DMSO-d₆) δ ppm 1.17-2.00 (m, 10 H) 2.61-2.92 (m, 3 H) 3.50 (t, J = 7.2 Hz, 2 H) 4.01 (d, J = 5.4 Hz, 2 H) 4.55 (s, 2 H) 8.71 (s, 2 H) 9.93 (br. s., 1 H). MS ESI/APCI Dual posi: 389[M + H]⁺, 411[M + Na]⁺. MS ESI/APCI Dual nega: 387[M − H]⁻. | HCl |

TABLE 21-6-continued

| Compound No. | Structure | Analytical Data | Salt information |
|---|---|---|---|
| Example 1-44 | 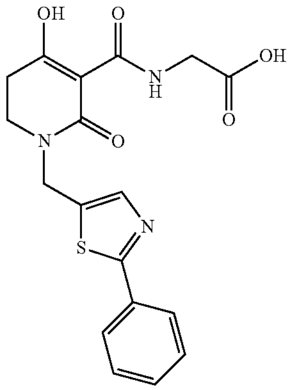 [SMILES: O=C(O)CNC(=O)C1=C(O)CCN(Cc2cnc(-c3ccccc3)s2)C1=O] | $^1$H NMR (600 MHz, DMSO-d$_6$) δ ppm 2.67-2.77 (m, 2 H) 3.41-3.52 (m, 2 H) 3.96-4.11 (m, 2 H) 4.72-4.91 (m, 2 H) 7.33-7.57 (m, 3 H) 7.79-7.98 (m, 3 H) 9.87-10.05 (m, 1 H). MS ESI/APCI Dual posi: 388[M + H]$^+$. MS ESI/APCI Dual nega: 386[M − H]$^-$. | HCl |
| Example 1-45 | 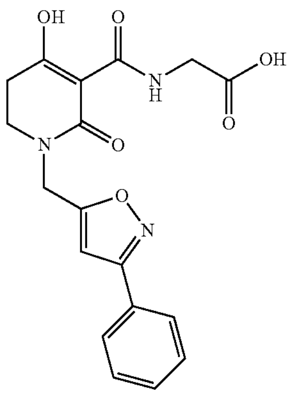 [SMILES: O=C(O)CNC(=O)C1=C(O)CCN(Cc2cc(-c3ccccc3)no2)C1=O] | $^1$H NMR (500 MHz, CHLOROFORM-d) δ ppm 2.74 (t, J = 7.3 Hz, 2 H) 3.58 (t, J = 7.3 Hz, 2 H) 4.15-4.23 (m, 2 H) 4.70-4.80 (m, 2 H) 6.52-6.57 (m, 1 H) 7.41-7.51 (m, 3 H) 7.74-7.83 (m, 2 H) 9.97-10.52 (m, 1 H). MS ESI/APCI Dual posi: 372[M + H]$^+$, 394[M + Na]$^+$. MS ESI/APCI Dual nega: 370[M − H]$^-$. | |

TABLE 21-7

| Compound No. | Structure | Analytical Data | Salt information |
|---|---|---|---|
| Example 1-46 | 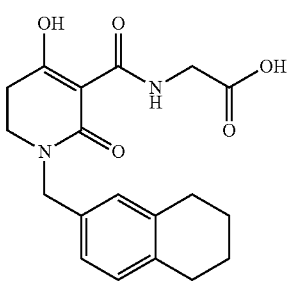 [SMILES: O=C(O)CNC(=O)C1=C(O)CCN(Cc2ccc3c(c2)CCCC3)C1=O] | $^1$H NMR (600 MHz, DMSO-d$_6$) δ ppm 1.67-1.76 (m, 4 H) 2.56-2.75 (m, 6 H) 3.25-3.40 (m, 2 H) 3.97-4.07 (m, 2 H) 4.44-4.55 (m, 2 H) 6.90-7.11 (m, 3 H) 9.98-10.27 (m, 1 H). MS ESI/APCI Dual posi: 359[M + H]$^+$, 381[M + Na]$^+$. MS ESI/APCI Dual nega: 357[M − H]$^-$. | |
| Example 1-47 | 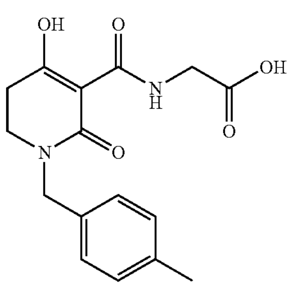 [SMILES: Cc1ccc(CN2CCC(O)=C(C(=O)NCC(=O)O)C2=O)cc1] | $^1$H NMR (300 MHz, DMSO-d$_6$) δ ppm 2.28 (s, 3 H) 2.48-2.69 (m, 2 H) 3.06-3.61 (m, 2 H) 3.88-4.14 (m, 2 H) 4.36-4.73 (m, 2 H) 7.12-7.28 (m, 4 H) 9.79-10.41 (m, 1 H) 12.81 (br. s, 1 H). MS ESI/APCI Dual posi: 319[M + H]$^+$, 341[M + Na]$^+$. MS ESI/APCI Dual nega: 317[M − H]$^-$. | |

TABLE 21-7-continued

| Compound No. | Structure | Analytical Data | Salt information |
|---|---|---|---|
| Example 1-48 | 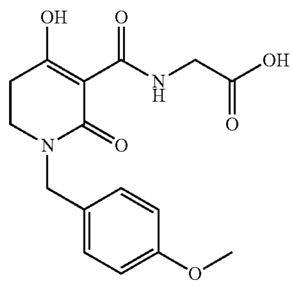 [SMILES: COc1ccc(CN2CCC(O)=C(C(=O)NCC(=O)O)C2=O)cc1] | $^1$H NMR (300 MHz, DMSO-d$_6$) δ ppm 2.43-2.64 (m, 2 H) 3.25-3.42 (m, 2 H) 3.73 (s, 3 H) 3.94-4.08 (m, 2 H) 4.44-4.58 (m, 2 H) 6.75-7.04 (m, 2 H) 7.08-7.40 (m, 2 H) 9.94-10.31 (m, 1 H) 12.86 (br. s, 1 H).<br>MS ESI/APCI Dual posi: 335[M + H]$^+$, 357[M + Na]$^+$.<br>MS ESI/APCI Dual nega: 333[M − H]$^−$. | |
| Example 1-49 | 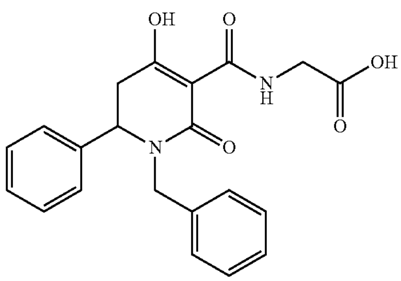 [SMILES: O=C(O)CNC(=O)C1=C(O)CC(c2ccccc2)N(Cc2ccccc2)C1=O] | $^1$H NMR (600 MHz, CHLOROFORM-d) δ ppm 2.61-2.70 (m, 1 H) 3.01-3.24 (m, 1 H) 3.51-3.73 (m, 1 H) 4.11-4.31 (m, 2 H) 4.53-4.59 (m, 1 H) 5.44-5.63 (m, 1 H) 7.11-7.17 (m, 2 H) 7.19-7.24 (m, 2 H) 7.26-7.39 (m, 6 H) 10.24-10.39 (m, 1 H).<br>MS ESI/APCI Dual posi: 381[M + H]$^+$, 403[M + Na]$^+$.<br>MS ESI/APCI Dual nega: 379[M − H]$^−$. | |
| Example 1-50 | 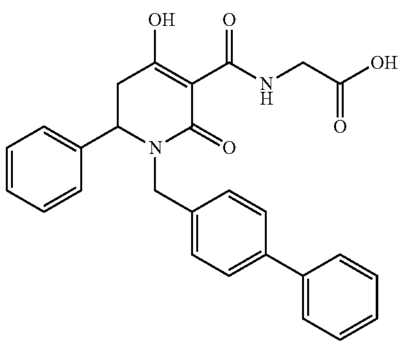 [SMILES: O=C(O)CNC(=O)C1=C(O)CC(c2ccccc2)N(Cc2ccc(-c3ccccc3)cc2)C1=O] | $^1$H NMR (600 MHz, CHLOROFORM-d) δ ppm 2.64-2.71 (m, 1 H) 3.05-3.28 (m, 1 H) 3.59-3.79 (m, 1 H) 4.13-4.32 (m, 2 H) 4.59-4.64 (m, 1 H) 5.47-5.67 (m, 1 H) 7.13-7.20 (m, 2 H) 7.27-7.40 (m, 5 H) 7.41-7.47 (m, 2 H) 7.53-7.60 (m, 4 H) 10.28-10.42 (m, 1 H).<br>MS ESI/APCI Dual posi: 457[M + H]$^+$, 479[M + Na]$^+$.<br>MS ESI/APCI Dual nega: 455[M − H]$^−$. | |
| Example 1-51 | 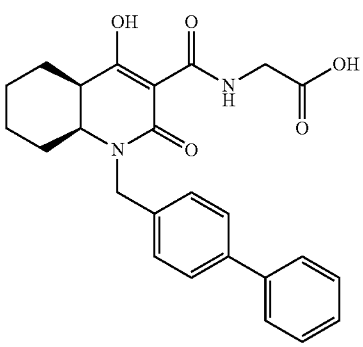 [SMILES: O=C(O)CNC(=O)C1=C(O)[C@@H]2CCCC[C@@H]2N(Cc2ccc(-c3ccccc3)cc2)C1=O] | $^1$H NMR (300 MHz, CHLOROFORM-d) δ ppm 1.07-1.43 (m, 3 H) 1.44-1.66 (m, 2 H) 1.68-1.88 (m, 2 H) 2.35-2.65 (m, 1 H) 2.76-3.09 (m, 1 H) 3.25-3.45 (m, 1 H) 3.89-4.32 (m, 3 H) 5.22-5.44 (m, 1 H) 7.29-7.49 (m, 5 H) 7.51-7.62 (m, 4 H) 10.21-10.57 (m, 1 H).<br>MS ESI/APCI Dual posi: 435[M + H]$^+$, 457[M + Na]$^+$.<br>MS ESI/APCI Dual nega: 433[M − H]$^−$. | |
| Example 1-52 | 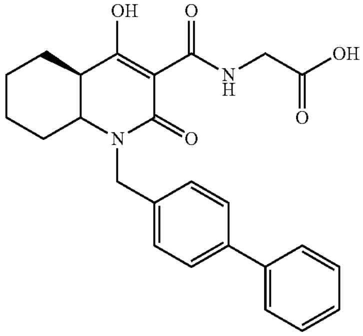 | $^1$H NMR (300 MHz, DMSO-d$_6$) δ ppm 0.92-1.46 (m, 4 H) 1.60-1.81 (m, 2 H) 2.05-2.78 (m, 3 H) 3.22-3.39 (m, 1 H) 3.98-4.12 (m, 2 H) 4.45-4.69 (m, 1 H) 4.93-5.11 (m, 1 H) 7.24-7.51 (m, 5 H) 7.58-7.70 (m, 4 H) 10.09-10.42 (m, 1 H) 12.74-12.98 (m, 1 H).<br>MS ESI/APCI Dual posi: 457[M + Na]$^+$.<br>MS ESI/APCI Dual nega: 433[M − H]$^−$. | |

TABLE 21-8

| Compound No. | Structure | Analytical Data | Salt information |
|---|---|---|---|
| Example 1-53 | 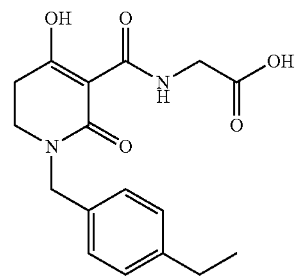 [SMILES: CCc1ccc(CN2CCC(O)=C(C(=O)NCC(=O)O)C2=O)cc1] | ¹H NMR (300 MHz, CHLOROFORM-d) δ ppm 1.23 (t, J = 7.5 Hz, 3 H) 2.50-2.72 (m, 4 H) 3.27-3.40 (m, 2 H) 4.13-4.22 (m, 2 H) 4.55-4.63 (m, 2 H) 7.15-7.21 (m, 4 H) 10.14-10.46 (m, 1 H). MS ESI/APCI Dual posi: 333[M + H]⁺, 355[M + Na]⁺. MS ESI/APCI Dual nega: 331[M − H]⁻. | |
| Example 1-54 | 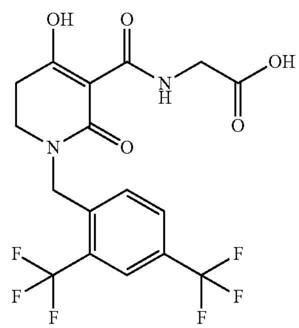 [SMILES: O=C(O)CNC(=O)C1=C(O)CCN(Cc2ccc(C(F)(F)F)cc2C(F)(F)F)C1=O] | ¹H NMR (300 MHz, CHLOROFORM-d) δ ppm 2.59-2.76 (m, 2 H) 3.34-3.45 (m, 2 H) 4.15-4.25 (m, 2 H) 4.83-4.93 (m, 2 H) 7.55 (d, J = 8.2 Hz, 1 H) 7.76-7.86 (m, 1 H) 7.93 (s, 1 H) 9.91-10.67 (m, 1 H). MS ESI/APCI Dual posi: 441[M + H]⁺, 463[M + Na]⁺. MS ESI/APCI Dual nega: 439[M − H]⁻. | |
| Example 1-55 | 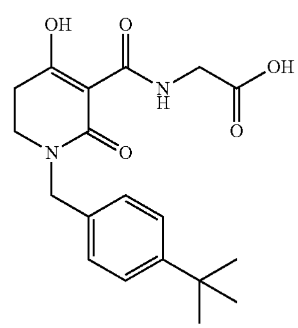 [SMILES: CC(C)(C)c1ccc(CN2CCC(O)=C(C(=O)NCC(=O)O)C2=O)cc1] | ¹H NMR (300 MHz, CHLOROFORM-d) δ ppm 1.29-1.33 (m, 9 H) 2.52-2.67 (m, 2 H) 3.30-3.41 (m, 2 H) 4.15-4.23 (m, 2 H) 4.56-4.63 (m, 2 H) 7.19 (d, J = 8.5 Hz, 2 H) 7.32-7.40 (m, 2 H) 10.21-10.43 (m, 1 H). MS ESI/APCI Dual posi: 361[M + H]⁺, 383[M + Na]⁺. MS ESI/APCI Dual nega: 359[M − H]⁻. | |
| Example 1-56 | 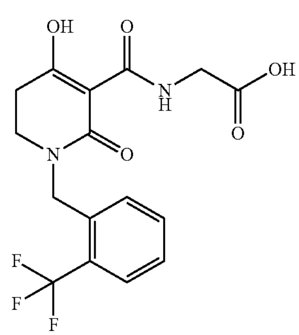 [SMILES: O=C(O)CNC(=O)C1=C(O)CCN(Cc2ccccc2C(F)(F)F)C1=O] | ¹H NMR (300 MHz, CHLOROFORM-d) δ ppm 2.65-2.74 (m, 2 H) 3.29-3.43 (m, 2 H) 4.13-4.26 (m, 2 H) 4.77-4.90 (m, 2 H) 7.34-7.45 (m, 2 H) 7.55 (t, J = 7.5 Hz, 1 H) 7.61-7.76 (m, 1 H) 10.13-10.51 (m, 1 H). MS ESI/APCI Dual posi: 373[M + H]⁺, 395[M + Na]⁺. MS ESI/APCI Dual nega: 371[M − H]⁻. | |

TABLE 21-8-continued

| Compound No. | Structure | Analytical Data | Salt information |
|---|---|---|---|
| Example 1-57 | 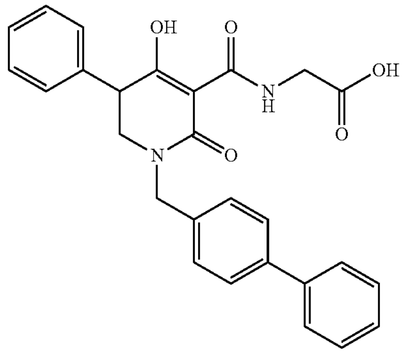 [SMILES: O=C(O)CNC(=O)C1=C(O)C(c2ccccc2)CN(Cc2ccc(-c3ccccc3)cc2)C1=O] | $^1$H NMR (300 MHz, CHLOROFORM-d) δ ppm 3.36-3.88 (m, 3 H) 4.09-4.33 (m, 2 H) 4.54-4.71 (m, 2 H) 7.08-7.60 (m, 14 H) 10.29-10.56 (m, 1 H). MS ESI/APCI Dual posi: 457[M + H]$^+$, 479[M + Na]$^+$. MS ESI/APCI Dual nega: 455[M − H]$^-$. | |
| Example 1-58 | 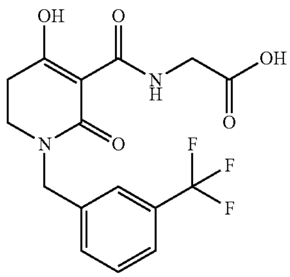 [SMILES: O=C(O)CNC(=O)C1=C(O)CCN(Cc2cccc(C(F)(F)F)c2)C1=O] | $^1$H NMR (300 MHz, CHLOROFORM-d) δ ppm 2.54-2.70 (m, 2 H) 3.28-3.43 (m, 2 H) 4.13-4.24 (m, 2 H) 4.60-4.71 (m, 2 H) 7.42-7.64 (m, 4 H) 10.09-10.53 (m, 1 H). MS ESI/APCI Dual posi: 373[M + H]$^+$, 395[M + Na]$^+$. MS ESI/APCI Dual nega: 371[M − H]$^-$. | |
| Example 1-59 | 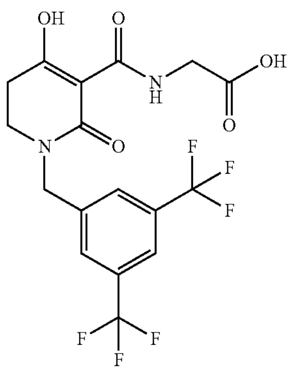 [SMILES: O=C(O)CNC(=O)C1=C(O)CCN(Cc2cc(C(F)(F)F)cc(C(F)(F)F)c2)C1=O] | $^1$H NMR (300 MHz, CHLOROFORM-d) δ ppm 2.57-2.75 (m, 2 H) 3.33-3.46 (m, 2 H) 4.15-4.27 (m, 2 H) 4.67-4.77 (m, 2 H) 7.73 (s, 2 H) 7.79-7.86 (m, 1 H) 10.00-10.65 (m, 1 H). MS ESI/APCI Dual posi: 441[M + H]$^+$, 463[M + Na]$^+$. MS ESI/APCI Dual nega: 439[M − H]$^-$. | |

TABLE 21-9

| Compound No. | Structure | Analytical Data | Salt information |
|---|---|---|---|
| Example 1-60 | 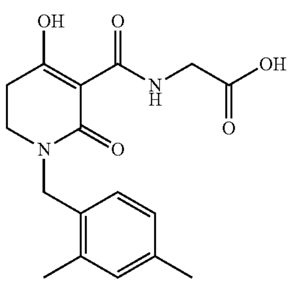 [SMILES: Cc1ccc(CN2CCC(O)=C(C(=O)NCC(=O)O)C2=O)c(C)c1] | $^1$H NMR (300 MHz, CHLOROFORM-d) δ ppm 2.21-2.35 (m, 6 H) 2.45-2.70 (m, 2 H) 3.17-3.38 (m, 2 H) 4.05-4.29 (m, 2 H) 4.47-4.74 (m, 2 H) 6.84-7.12 (m, 3 H) 10.16-10.49 (m, 1 H). MS ESI/APCI Dual posi: 333[M + H]$^+$, 355[M + Na]$^+$. MS ESI/APCI Dual nega: 331[M − H]$^-$. | |

TABLE 21-9-continued

| Compound No. | Structure | Analytical Data | Salt information |
|---|---|---|---|
| Example 1-61 | 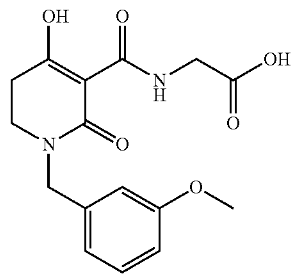 [SMILES: COc1cccc(CN2CCC(O)=C(C(=O)NCC(=O)O)C2=O)c1] | ¹H NMR (300 MHz, CHLOROFORM-d) δ ppm 2.51-2.68 (m, 2 H) 3.28-3.41 (m, 2 H) 3.74-3.86 (m, 3 H) 4.09-4.28 (m, 2 H) 4.59 (s, 2 H) 6.77-6.89 (m, 3 H) 7.20-7.32 (m, 1 H) 10.11-10.49 (m, 1 H). MS ESI/APCI Dual posi: 335[M + H]⁺, 357[M + Na]⁺. MS ESI/APCI Dual nega: 333[M − H]⁻. | |
| Example 1-62 | 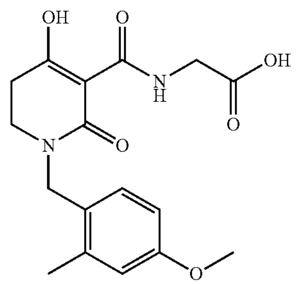 [SMILES: COc1ccc(CN2CCC(O)=C(C(=O)NCC(=O)O)C2=O)c(C)c1] | ¹H NMR (300 MHz, CHLOROFORM-d) δ ppm 2.19-2.35 (m, 3 H) 2.44-2.66 (m, 2 H) 3.13-3.37 (m, 2 H) 3.60-3.94 (m, 3 H) 4.12-4.28 (m, 2 H) 4.50-4.63 (m, 2 H) 6.65-6.81 (m, 2 H) 7.00-7.13 (m, 1 H) 10.14-10.47 (m, 1 H). MS ESI/APCI Dual posi: 349[M + H]⁺, 371[M + Na]⁺. MS ESI/APCI Dual nega: 347[M − H]⁻. | |
| Example 1-63 | 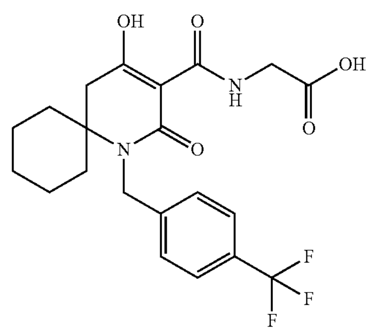 [SMILES: O=C(O)CNC(=O)C1=C(O)CC2(CCCCC2)N(Cc2ccc(C(F)(F)F)cc2)C1=O] | ¹H NMR (600 MHz, DMSO-d₆) δ ppm 1.02-1.73 (m, 10 H) 2.70-2.96 (m, 2 H) 3.94-4.07 (m, 2 H) 4.73-4.91 (m, 2 H) 7.45-7.56 (m, 2 H) 7.61-7.70 (m, 2 H) 9.91-10.22 (m, 1 H) 12.76-12.93 (m, 1 H). MS ESI/APCI Dual posi: 441[M + H]⁺, 463[M + Na]⁺. MS ESI/APCI Dual nega: 439[M − H]⁻. | |
| Example 1-64 | 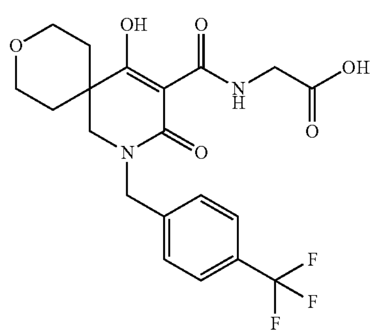 [SMILES: O=C(O)CNC(=O)C1=C(O)C2(CCOCC2)CN(Cc2ccc(C(F)(F)F)cc2)C1=O] | ¹H NMR (600 MHz, DMSO-d₆) δ ppm 1.16-1.38 (m, 2 H) 1.71-1.90 (m, 2 H) 3.33-3.41 (m, 2 H) 3.44-3.52 (m, 2 H) 3.58-3.65 (m, 2 H) 3.99-4.09 (m, 2 H) 4.66-4.76 (m, 2 H) 7.50-7.61 (m, 2 H) 7.66-7.76 (m, 2 H) 10.08-10.35 (m, 1 H) 12.71-13.00 (m, 1 H). MS ESI/APCI Dual posi: 443[M + H]⁺, 465[M + Na]⁺. MS ESI/APCI Dual nega: 441[M − H]⁻. | |
| Example 1-65 | 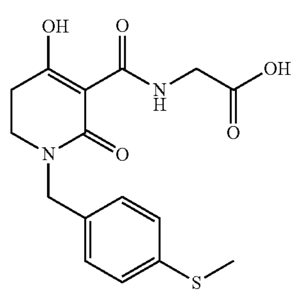 [SMILES: CSc1ccc(CN2CCC(O)=C(C(=O)NCC(=O)O)C2=O)cc1] | ¹H NMR (600 MHz, DMSO-d₆) δ ppm 2.46 (s, 3 H) 2.59-2.69 (m, 2 H) 3.32-3.40 (m, 2 H) 3.95-4.05 (m, 2 H) 4.42-4.64 (m, 2 H) 7.16-7.29 (m, 4 H) 10.00-10.24 (m, 1 H) 12.87 (br. s., 1 H). MS ESI/APCI Dual posi: 351[M + H]⁺, 373[M + Na]⁺. MS ESI/APCI Dual nega: 349[M − H]⁻. | |

TABLE 21-9-continued

| Compound No. | Structure | Analytical Data | Salt information |
|---|---|---|---|
| Example 1-66 | 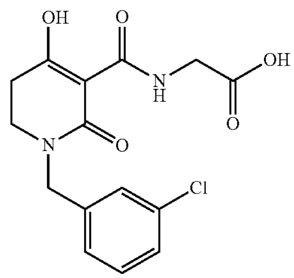 [SMILES: O=C(O)CNC(=O)C1=C(O)CCN(Cc2cccc(Cl)c2)C1=O] | $^1$H NMR (300 MHz, CHLOROFORM-d) δ ppm 2.53-2.72 (m, 2 H) 3.28-3.43 (m, 2 H) 4.11-4.26 (m, 2 H) 4.51- 4.67 (m, 2 H) 7.12-7.19 (m, 1 H) 7.20-7.36 (m, 3 H) 10.07-10.50 (m, 1 H). <br>MS ESI/APCI Dual posi: 339[M + H]$^+$, 361[M + Na]$^+$. <br>MS ESI/APCI Dual nega: 337[M − H]$^−$. | |

TABLE 21-10

| Compound No. | Structure | Analytical Data | Salt information |
|---|---|---|---|
| Example 1-67 | 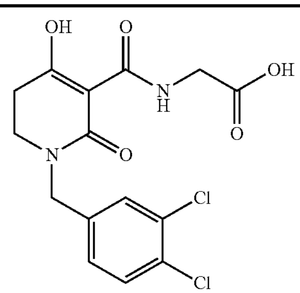 | $^1$H NMR (300 MHz, CHLOROFORM-d) δ ppm 2.50-2.73 (m, 2 H) 3.26-3.42 (m, 2 H) 4.07-4.28 (m, 2 H) 4.47-4.64 (m, 2 H) 7.03-7.17 (m, 1 H) 7.30-7.53 (m, 2 H) 10.03-10.53 (m, 1 H). <br>MS ESI/APCI Dual posi: 373[M + H]$^+$, 395[M + Na]$^+$. <br>MS ESI/APCI Dual nega: 371[M − H]$^−$. | |
| Example 1-68 | 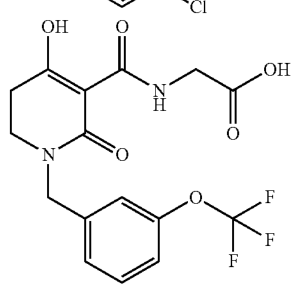 | $^1$H NMR (300 MHz, CHLOROFORM-d) δ ppm 2.51-2.77 (m, 2 H) 3.22-3.48 (m, 2 H) 4.09-4.27 (m, 2 H) 4.63 (s, 2 H) 7.08-7.24 (m, 3 H) 7.32-7.44 (m, 1 H) 10.11-10.49 (m, 1 H). <br>MS ESI/APCI Dual posi: 389[M + H]$^+$, 411[M + Na]$^+$. <br>MS ESI/APCI Dual nega: 387[M − H]$^−$. | |
| Example 1-69 | 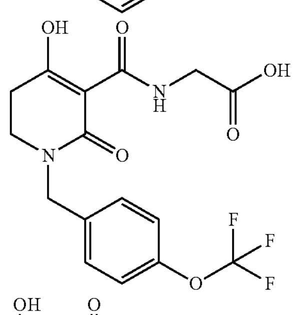 | $^1$H NMR (300 MHz, CHLOROFORM-d) δ ppm 2.54-2.70 (m, 2 H) 3.30-3.41 (m, 2 H) 4.15-4.23 (m, 2 H) 4.58-4.66 (m, 2 H) 7.15-7.24 (m, 2 H) 7.27-7.34 (m, 2 H) 10.06-10.50 (m, 1 H). <br>MS ESI/APCI Dual posi: 389[M + H]$^+$, 411[M + Na]$^+$. <br>MS ESI/APCI Dual nega: 387[M − H]$^−$. | |
| Example 1-70 | 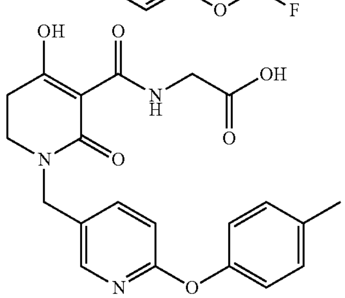 | $^1$H NMR (600 MHz, CHLOROFORM-d) δ ppm 2.36 (s, 3 H) 2.54-2.67 (m, 2 H) 3.32-3.38 (m, 2 H) 4.15-4.21 (m, 2 H) 4.52-4.58 (m, 2 H) 6.84-6.90 (m, 1 H) 6.99-7.04 (m, 2 H) 7.17-7.22 (m, 2 H) 7.62-7.67 (m, 1 H) 8.10 (d, J = 2.1 Hz, 1 H) 10.14-10.47 (m, 1 H). <br>MS ESI/APCI Dual posi: 412[ M + H]$^+$. <br>MS ESI/APCI Dual nega: 410[M − H]$^−$. | |

TABLE 21-10-continued

| Compound No. | Structure | Analytical Data | Salt information |
|---|---|---|---|
| Example 1-71 | 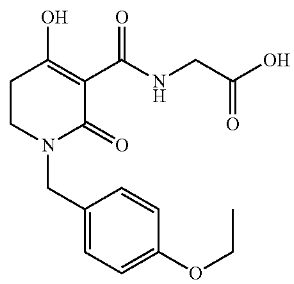 [SMILES: CCOc1ccc(CN2CCC(O)=C(C(=O)NCC(=O)O)C2=O)cc1] | ¹H NMR (600 MHz, CHLOROFORM-d) δ ppm 1.37-1.45 (m, 3 H) 2.47-2.64 (m, 2 H) 3.26-3.38 (m, 2 H) 3.97-4.06 (m, 2 H) 4.15-4.23 (m, 2 H) 4.50-4.61 (m, 2 H) 6.83-6.89 (m, 2 H) 7.14-7.21 (m, 2 H) 10.24-10.43 (m, 1 H).<br>MS ESI/APCI Dual posi: 349[M + H]⁺, 371[M + Na]⁺.<br>MS ESI/APCI Dual nega: 347[M − H]⁻. | |
| Example 1-72 | 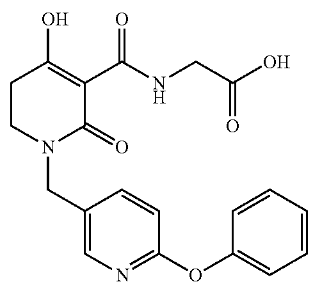 [SMILES: O=C(O)CNC(=O)C1=C(O)CCN(Cc2ccc(Oc3ccccc3)nc2)C1=O] | ¹H NMR (300 MHz, CHLOROFORM-d) δ ppm 2.48-2.75 (m, 2 H) 3.25-3.48 (m, 2 H) 4.08-4.25 (m, 2 H) 4.45-4.65 (m, 2 H) 6.84-6.95 (m, 1 H) 7.10-7.16 (m, 2 H) 7.18-7.25 (m, 1 H) 7.36-7.45 (m, 2 H) 7.58-7.75 (m, 1 H) 8.03-8.22 (m, 1 H) 10.10-10.50 (m, 1 H).<br>MS ESI/APCI Dual Posi: 398[M + H]⁺, 420[M + Na]⁺.<br>MS ESI/APCI Dual nega: 396[M − H]⁻. | |
| Example 1-73 | 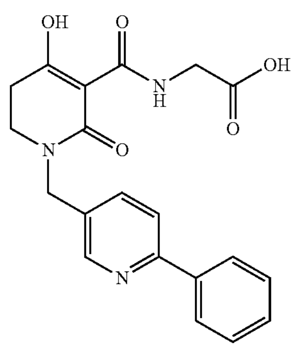 [SMILES: O=C(O)CNC(=O)C1=C(O)CCN(Cc2ccc(-c3ccccc3)nc2)C1=O] | ¹H NMR (300 MHz, DMSO-d₆) δ ppm 2.38-2.83 (m, 2 H) 3.50 (t, J = 7.1 Hz, 2 H) 4.03 (d, J = 5.1 Hz, 2 H) 4.60-4.76 (m, 2 H) 7.44-7.61 (m, 3 H) 7.94-8.15 (m, 4 H) 8.69 (s, 1 H) 9.87-10.08 (m, 1 H).<br>MS ESI/APCI Dual posi: 382[M + H]⁺, 404[M + Na]⁺.<br>MS ESI/APCI Dual nega: 380[M − H]⁻. | |

TABLE 21-11

| Compound No. | Structure | Analytical Data | Salt information |
|---|---|---|---|
| Example 1-74 | 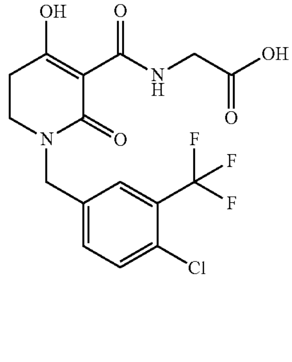 [SMILES: O=C(O)CNC(=O)C1=C(O)CCN(Cc2ccc(Cl)c(C(F)(F)F)c2)C1=O] | ¹H NMR (300 MHz, CHLOROFORM-d) δ ppm 2.54-2.72 (m, 2 H) 3.29-3.43 (m, 2 H) 4.13-4.24 (m, 2 H) 4.55-4.68 (m, 2 H) 7.37-7.45 (m, 1 H) 7.45-7.51 (m, 1 H) 7.56-7.61 (m, 1 H) 10.03-10.56 (m, 1 H).<br>MS ESI/APCI Dual posi: 407[M + H]⁺, 429[M + Na]⁺.<br>MS ESI/APCI Dual nega: 405[M − H]⁻. | |

TABLE 21-11-continued

| Compound No. | Structure | Analytical Data | Salt information |
|---|---|---|---|
| Example 1-75 | 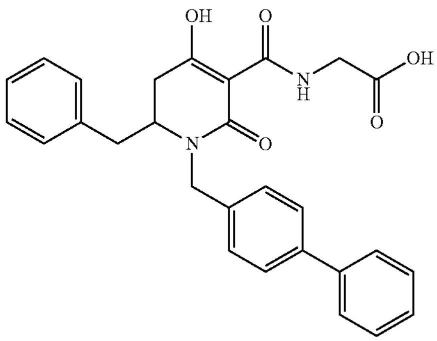 [SMILES: O=C(O)CNC(=O)C1=C(O)CC(Cc2ccccc2)N(Cc2ccc(-c3ccccc3)cc2)C1=O] | $^1$H NMR (300 MHz, DMSO-d$_6$) δ ppm 2.03-2.29 (m, 1 H) 2.65-3.08 (m, 3 H) 3.67-3.88 (m, 1 H) 3.96-4.22 (m, 3 H) 4.96-5.16 (m, 1 H) 7.07-7.52 (m, 10 H) 7.58-7.70 (m, 4 H) 9.90-10.22 (m, 1 H) 12.76-12.98 (m, 1 H).<br>MS ESI/APCI Dual posi: 471[M + H]$^+$, 493[M + Na]$^+$.<br>MS ESI/APCI Dual nega: 469[M − H]$^−$. | |
| Example 1-76 | 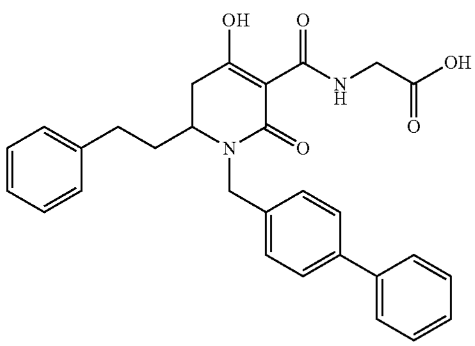 [SMILES: O=C(O)CNC(=O)C1=C(O)CC(CCc2ccccc2)N(Cc2ccc(-c3ccccc3)cc2)C1=O] | $^1$H NMR (300 MHz, DMSO-d$_6$) δ ppm 1.77-1.95 (m, 2 H) 2.51-2.75 (m, 3 H) 3.07 (dd, J = 17.4, 7.0 Hz, 1 H) 3.50 (m, 1 H) 3.98-4.32 (m, 3 H) 4.98-5.12 (m, 1 H) 7.12-7.40 (m, 8 H) 7.42-7.51 (m, 2 H) 7.54-7.69 (m, 4 H) 9.90-10.20 (m, 1 H) 12.73-12.92 (m, 1 H).<br>MS ESI/APCI Dual posi: 485[M + H]$^+$, 507[M + Na]$^+$.<br>MS ESI/APCI Dual nega: 483[M − H]$^−$. | |
| Example 1-77 | 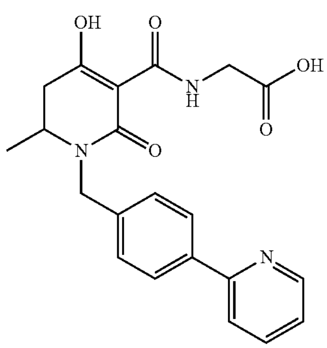 [SMILES: CC1CC(O)=C(C(=O)NCC(=O)O)C(=O)N1Cc1ccc(-c2ccccn2)cc1] | $^1$H NMR (600 MHz, DMSO-d$_6$) δ ppm 1.17 (d, J = 6.2 Hz, 3 H) 2.37 (d, J = 17.3 Hz, 1 H) 3.04-3.19 (m, 1 H) 3.65-3.78 (m, 1 H) 3.95-4.09 (m, 2 H) 4.25 (d, J = 15.7 Hz, 1 H) 5.07 (d, J = 15.7 Hz, 1 H) 7.51 (d, J = 7.8 Hz, 2 H) 7.64 (br. s., 1 H) 7.89-8.36 (m, 4 H) 8.76 (d, J = 4.5 Hz, 1 H) 9.84-10.30 (m, 1 H).<br>MS ESI/APCI Dual posi: 396[M + H]$^+$.<br>MS ESI/APCI Dual nega: 394[M − H]$^−$. | HCl |
| Example 1-78 | 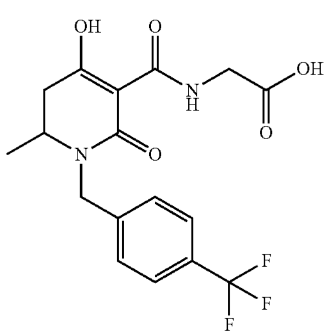 [SMILES: CC1CC(O)=C(C(=O)NCC(=O)O)C(=O)N1Cc1ccc(C(F)(F)F)cc1] | $^1$H NMR (300 MHz, CHLOROFORM-d) δ ppm 1.15-1.31 (m, 3 H) 2.26-2.41 (m, 1 H) 2.75-3.01 (m, 1 H) 3.49-3.63 (m, 1 H) 3.92-4.25 (m, 3 H) 5.17-5.40 (m, 1 H) 7.31-7.45 (m, 2 H) 7.54-7.67 (m, 2 H) 10.05-10.41 (m, 1 H).<br>MS ESI/APCI Dual posi: 387[M + H]$^+$, 409[M + Na]$^+$.<br>MS ESI/APCI Dual nega: 385[M − H]$^−$. | |

TABLE 21-11-continued

| Compound No. | Structure | Analytical Data | Salt information |
|---|---|---|---|
| Example 1-79 | 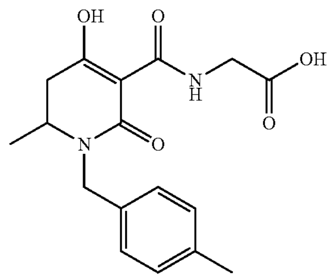 [SMILES: Cc1ccc(CN2C(=O)C(C(=O)NCC(=O)O)=C(O)CC2C)cc1] | $^1$H NMR (300 MHz, CHLOROFORM-d) δ ppm 1.16-1.24 (m, 3 H) 2.20-2.38 (m, 4 H) 2.70-2.96 (m, 1 H) 3.49-3.64 (m, 1 H) 3.81-4.04 (m, 1 H) 4.15-4.23 (m, 2 H) 5.11-5.35 (m, 1 H) 7.09-7.20 (m, 4 H) 10.17-10.39 (m, 1 H).<br>MS ESI/APCI Dual Posi: 333[M + H]$^+$, 355[M + Na]$^+$.<br>MS ESI/APCI Dual nega: 331[M − H]$^−$. | |
| Example 1-80 | 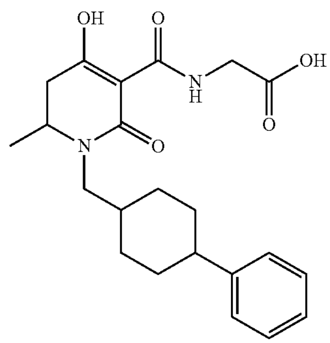 [SMILES: CC1CC(O)=C(C(=O)NCC(=O)O)C(=O)N1CC1CCC(c2ccccc2)CC1] | $^1$H NMR (300 MHz, CHLOROFORM-d) δ ppm 1.03-1.34 (m, 5 H) 1.36-2.01 (m, 7 H) 2.26-2.75 (m, 3 H) 2.87-3.11 (m, 1 H) 3.54-3.70 (m, 1 H) 3.84-4.02 (m, 1 H) 4.08-4.21 (m, 2 H) 7.13-7.35 (m, 5 H) 10.15-10.35 (m, 1 H).<br>MS ESI/APCI Dual posi: 401[M + H]$^+$, 423[M + Na]$^+$.<br>MS ESI/APCI Dual nega: 399[M − H]$^−$. | |

TABLE 21-12

| Compound No. | Structure | Analytical Data | Salt information |
|---|---|---|---|
| Example 1-81 | 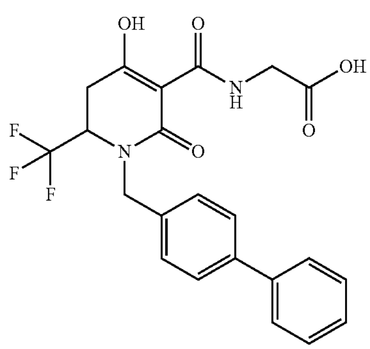 [SMILES: O=C(O)CNC(=O)C1=C(O)CC(C(F)(F)F)N(Cc2ccc(-c3ccccc3)cc2)C1=O] | $^1$H NMR (300 MHz, CHLOROFORM-d) δ ppm 2.62-3.05 (m, 2 H) 3.58-4.36 (m, 4 H) 5.64-5.81 (m, 1 H) 7.27-7.49 (m, 5 H) 7.51-7.64 (m, 4 H) 9.88-10.45 (m,1 H).<br>MS ESI/APCI Dual posi: 449[M + H]$^+$, 471[M + Na]$^+$.<br>MS ESI/APCI Dual nega: 447[M − H]$^−$. | |
| Example 1-82 | 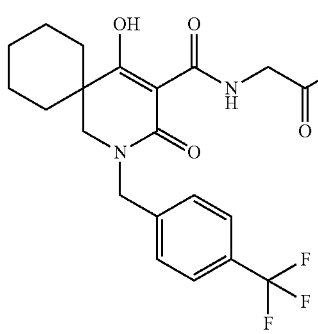 | $^1$H NMR (300 MHz, CHLOROFORM-d) δ ppm 0.90-1.11 (m, 2 H) 1.16-1.26 (m, 1 H) 1.36-1.61 (m, 5 H) 1.67-1.86 (m, 2 H) 3.22 (s, 2 H) 4.13-4.23 (m, 2 H) 4.60-4.73 (m, 2 H) 7.37-7.47 (m, 2 H) 7.53-7.74 (m, 2 H) 9.99-10.52 (m, 1 H).<br>MS ESI/APCI Dual posi: 441[M + H]$^+$, 463[M + Na]$^+$.<br>MS ESI/APCI Dual nega: 4.39[M − H]$^−$. | |

TABLE 21-12-continued

| Compound No. | Structure | Analytical Data | Salt information |
|---|---|---|---|
| Example 1-83 | 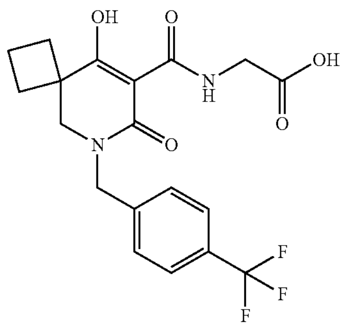 [SMILES: O=C(O)CNC(=O)C1=C(O)C2(CCC2)CN(Cc2ccc(C(F)(F)F)cc2)C1=O] | ¹H NMR (300 MHz, CHLOROFORM-d) δ ppm 1.61-1.78 (m, 2 H) 1.79-2.04 (m, 2 H) 2.38-2.57 (m, 2 H) 3.28-3.37 (m, 2 H) 4.13-4.22 (m, 2 H) 4.64-4.72 (m, 2 H) 7.36-7.44 (m, 2 H) 7.57-7.66 (m, 2 H) 10.19-10.30 (m, 1 H). MS ESI/APCI Dual posi: 413[M + H]⁺, 435[M + Na]⁺. MS ESI/APCI Dual nega: 411[M − H]⁻. | |
| Example 1-84 | 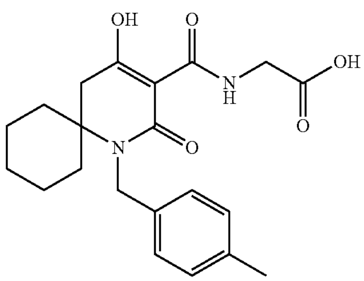 [SMILES: Cc1ccc(CN2C(=O)C(C(=O)NCC(=O)O)=C(O)CC23CCCCC3)cc1] | ¹H NMR (300 MHz, DMSO-d₆) δ ppm 1.03-1.81 (m, 10 H) 2.73-2.99 (m, 2 H) 3.19 (s, 3 H) 3.96-4.09 (m, 2 H) 4.76-4.95 (m, 2 H) 7.49-7.62 (m, 2 H) 7.79-7.92 (m, 2 H) 9.88-10.26 (m, 1H) 12.73-13.02 (m, 1 H). MS ESI/APCI Dual posi: 409[ M + Na]⁺. MS ESI/APCI Dual nega: 385[M − H]⁻. | |
| Example 1-85 | 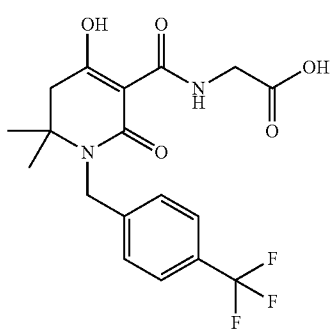 [SMILES: CC1(C)CC(O)=C(C(=O)NCC(=O)O)C(=O)N1Cc1ccc(C(F)(F)F)cc1] | ¹H NMR (300 MHz, CHLOROFORM-d) δ ppm 1.16-1.37 (m, 6 H) 2.49-2.70 (m, 2 H) 4.09-4.26 (m, 2 H) 4.62-4.79 (m, 2 H) 7.34-7.43 (m, 2 H) 7.49-7.66 (m, 2 H) 10.09-10.47 (m, 1 H). MS ESI/APCI Dual posi: 401[M + H]⁺, 423[Na + H]⁺. MS ESI/APCI Dual nega: 399[M − H]⁻. | |
| Example 1-86 | 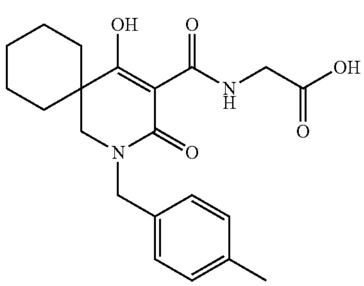 [SMILES: Cc1ccc(CN2CC3(CCCCC3)C(O)=C(C(=O)NCC(=O)O)C2=O)cc1] | ¹H NMR (300 MHz, CHLOROFORM-d) δ ppm 0.86-1.08 (m, 2 H) 1.08-1.57 (m, 6 H) 1.61-1.82 (m, 2 H) 2.26-2.41 (m, 3 H) 3.09-3.25 (m, 2 H) 4.10-4.23 (m, 2 H) 4.49-4.66 (m, 2 H) 7.11-7.21 (m, 4 H) 10.31-10.66 (m, 1 H). MS ESI/APCI Dual Posi: 387[M + H]⁺, 409[M + Na]⁺. MS ESI/APCI Dual nega: 385[M − H]⁻. | |

TABLE 21-12-continued

| Compound No. | Structure | Analytical Data | Salt information |
|---|---|---|---|
| Example 1-87 | 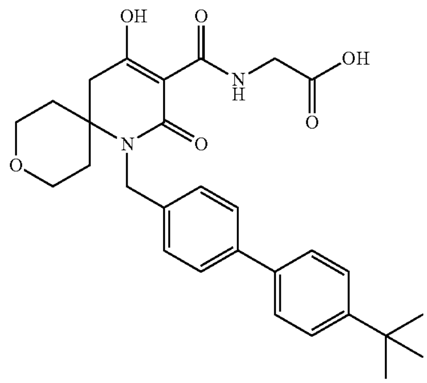 [SMILES: CC(C)(C)c1ccc(-c2ccc(CN3C(=O)C(C(=O)NCC(=O)O)=C(O)CC34CCOCC4)cc2)cc1] | ¹H NMR (300 MHz, DMSO-d₆) δ ppm 1.31 (s, 9 H)1.47-1.60 (m, 2 H) 1.89-2.06 (m, 2 H) 2.88-3.13 (m, 2 H) 3.42-3.57 (m, 2 H) 3.66-3.78 (m, 2 H) 3.97-4.11 (m, 2 H) 4.70-4.88 (m, 2 H) 7.33-7.51 (m, 4 H) 7.52-7.65 (m, 4 H) 9.95-10.27 (m, 1 H) 12.74-12.97 (m, 1 H).<br>MS ESI/APCI Dual posi: 507[M + H]⁺, 529[M + Na]⁺.<br>MS ESI/APCI Dual nega: 505[M − H]⁻. | |

TABLE 21-13

| Compound No. | Structure | Analytical Data | Salt information |
|---|---|---|---|
| Example 1-88 | 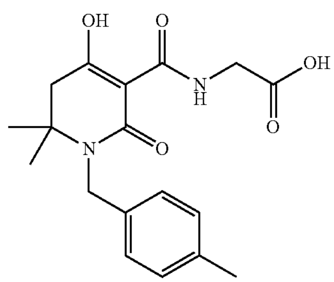 [SMILES: Cc1ccc(CN2C(=O)C(C(=O)NCC(=O)O)=C(O)CC2(C)C)cc1] | ¹H NMR (300 MHz, CHLOROFORM-d) δ 1.18-1.35 (m, 6 H) 2.23-2.37 (m, 3 H) 2.46-2.67 (m, 2 H) 4.10-4.25 (m, 2 H) 4.57-4.71 (m, 2 H) 7.06-7.18 (m, 4 H) 10.21-10.46 (m, 1 H).<br>MS ESI/APCI Dual posi: 347[M + H]⁺, 369[M + Na]⁺.<br>MS ESI/APCI Dual nega: 345[M − H]⁻. | |
| Example 1-89 | 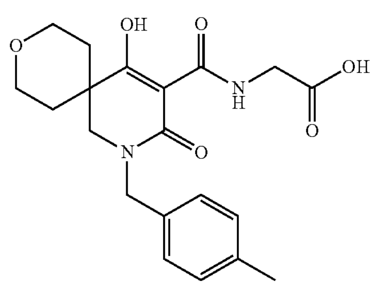 [SMILES: Cc1ccc(CN2CC3(CCOCC3)C(O)=C(C(=O)NCC(=O)O)C2=O)cc1] | ¹H NMR (300 MHz, CHLOROFORM-d) δ ppm 1.18-1.37 (m, 2 H) 1.94-2.07 (m, 2 H) 2.30-2.38 (m, 3 H) 3.17-3.30 (m, 4 H) 3.64-3.76 (m, 2 H) 4.19 (d, J = 5.6 Hz, 2 H) 4.54-4.61 (m, 2 H) 7.12-7.19 (m, 4 H) 10.30-10.55 (m, 1 H).<br>MS ESI/APCI Dual posi: 389[M + H]⁺, 411[M + Na]⁺.<br>MS ESI/APCI Dual nega: 387[M − H]⁻. | |
| Example 1-90 | 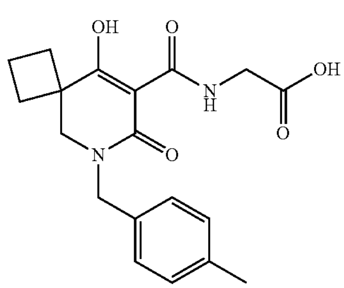 [SMILES: Cc1ccc(CN2CC3(CCC3)C(O)=C(C(=O)NCC(=O)O)C2=O)cc1] | ¹H NMR (300 MHz, DMSO-d₆) δ ppm 1.49-1.68 (m, 2 H) 1.69-1.89 (m, 2 H) 2.16-2.31 (m, 5 H) 2.45-2.55 (m, 2 H) 3.44 (d, J = 4.0 Hz, 2 H) 4.48-4.57 (m, 2 H) 7.09-7.23 (m, 4 H).<br>MS ESI/APCI Dual nega: 357[M − H]⁻. | Na |

TABLE 21-13-continued

| Compound No. | Structure | Analytical Data | Salt information |
|---|---|---|---|
| Example 1-91 | 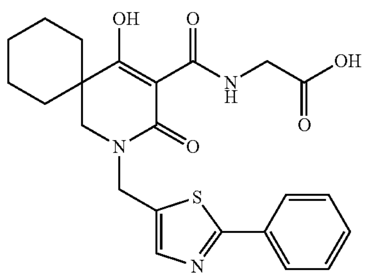 [SMILES: O=C(O)CNC(=O)C1=C(O)C2(CCCCC2)CN(Cc2cnc(-c3ccccc3)s2)C1=O] | ¹H NMR (300 MHz, DMSO-d₆) δ ppm 1.05-1.73 (m, 10 H) 3.35-3.50 (m, 2 H) 3.94-4.11 (m, 2 H) 4.76-4.94 (m, 2 H) 7.39-7.55 (m, 3 H) 7.81-8.02 (m, 3 H) 9.98-10.43 (m, 1 H).<br>MS ESI/APCI Dual nega: 454[M − H]⁻. | HCl |
| Example 1-92 | 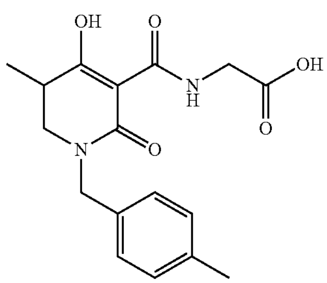 [SMILES: Cc1ccc(CN2CC(C)C(O)=C(C(=O)NCC(=O)O)C2=O)cc1] | ¹H NMR (300 MHz, DMSO-d₆) δ ppm 0.90-1.06 (m, 3 H) 2.28 (s, 3 H) 2.86-3.02 (m, 1 H) 3.21-3.58 (m, 4 H) 4.38-4.64 (m, 2 H) 7.07-7.22 (m, 4 H) 10.07-10.30 (m, 1 H).<br>MS ESI/APCI Dual posi: 355[M + Na]⁺.<br>MS ESI/APCI Dual nega: 331[M − H]⁻. | Na |
| Example 1-93 | 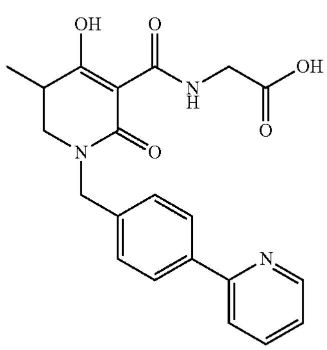 [SMILES: CC1CN(Cc2ccc(-c3ccccn3)cc2)C(=O)C(C(=O)NCC(=O)O)=C1O] | ¹H NMR (300 MHz, DMSO-d₆) δ ppm 0.95-1.17 (m, 3 H) 2.76-2.95 (m, 1 H) 3.08-3.23 (m, 1 H) 3.45-3.59 (m, 1 H) 3.96-4.11 (m, 2 H) 4.54-4.83 (m, 2 H) 7.43-7.56 (m, 2 H) 7.62-7.74 (m, 1 H) 8.00-8.13 (m, 2 H) 8.14-8.33 (m, 2 H) 8.73-8.82 (m, 1 H) 9.99-10.39 (m, 1 H).<br>MS ESI/APCI Dual posi: 396[M + H]⁺, 418[M + Na]⁺.<br>MS ESI/APCI Dual nega: 394[M − H]⁻. | HCl |
| Example 1-94 | 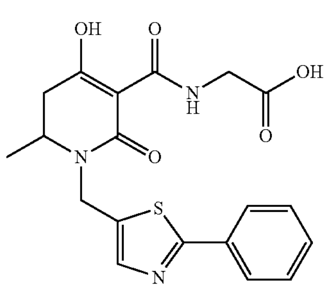 [SMILES: CC1CC(O)=C(C(=O)NCC(=O)O)C(=O)N1Cc1cnc(-c2ccccc2)s1] | ¹H NMR (300 MHz, DMSO-d₆) δ ppm 1.16 (d, J = 6.4 Hz, 3 H) 2.26-2.45 (m, 1 H) 2.94-3.15 (m, 1 H) 3.75- 3.89 (m, 1 H) 3.99-4.09 (m, 2 H) 4.45-4.60 (m, 1 H) 4.98-5.12 (m, 1 H) 7.43-7.54 (m, 3 H) 7.85-7.98 (m, 3 H) 9.94 (br. s., 1 H).<br>MS ESI/APCI Dual posi: 402[M + H]⁺.<br>MS ESI/APCI Dual nega: 400[M − H]⁻. | HCl |

TABLE 21-14

| Compound No. | Structure | Analytical Data | Salt information |
|---|---|---|---|
| Example 1-95 | 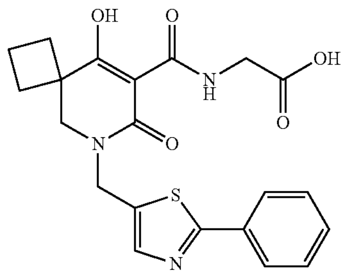 [SMILES: O=C(O)CNC(=O)C1=C(O)C2(CCC2)CN(Cc2cnc(-c3ccccc3)s2)C1=O] | ¹H NMR (300 MHz, CHLOROFORM-d) δ ppm 1.71-1.83 (m, 2 H) 1.87-2.04 (m, 2 H) 2.41-2.57 (m, 2 H) 3.42 (s, 2 H) 4.14-4.24 (m, 2 H) 4.75-4.86 (m, 2 H) 7.39-7.46 (m, 3 H) 7.78 (s, 1 H) 7.83-7.97 (m, 2 H) 10.10-10.27 (m, 1 H).<br>MS ESI/APCI Dual posi: 428[M + H]⁺, 450[M + Na]⁺.<br>MS ESI/APCI Dual nega: 426[M − H]⁻. | |
| Example 1-96 | 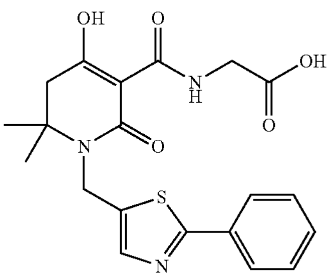 [SMILES: CC1(C)CC(O)=C(C(=O)NCC(=O)O)C(=O)N1Cc1cnc(-c2ccccc2)s1] | ¹H NMR (300 MHz, CHLOROFORM-d) δ ppm 1.28-1.45 (m, 6 H) 2.47-2.63 (m, 2 H) 4.12-4.26 (m, 2 H) 4.71-4.90 (m, 2 H) 7.34-7.51 (m, 3 H) 7.74 (s, 1 H) 7.82-7.98 (m, 2 H) 10.11-10.51 (m, 1 H).<br>MS ESI/APCI Dual posi: 416[M + H]⁺, 438[M + Na]⁺.<br>MS ESI/APCI Dual nega: 414[M − H]⁻. | |
| Example 1-97 | 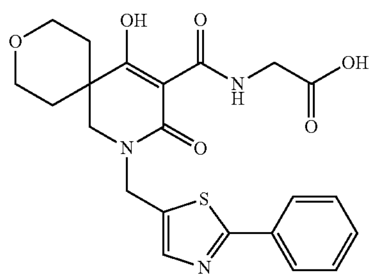 [SMILES: O=C(O)CNC(=O)C1=C(O)C2(CCOCC2)CN(Cc2cnc(-c3ccccc3)s2)C1=O] | ¹H NMR (300 MHz, CHLOROFORM-d) δ ppm 1.23-1.52 (m, 2 H) 1.90-2.15 (m, 2 H) 3.29-3.39 (m, 2 H) 3.44-3.58 (m, 2 H) 3.76-3.90 (m, 2 H) 4.15-4.25 (m, 2 H) 4.77-4.86 (m, 2 H) 7.40-7.47 (m, 3 H) 7.79 (s, 1 H) 7.84-7.95 (m, 2 H) 10.14-10.66 (m, 1 H).<br>MS ESI/APCI Dual posi: 458[M + H]⁺, 480[M + Na]⁺.<br>MS ESI/APCI Dual nega: 456[M − H]⁻. | |
| Example 1-98 | 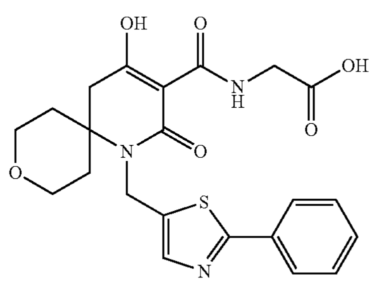 [SMILES: O=C(O)CNC(=O)C1=C(O)CC2(CCOCC2)N(Cc2cnc(-c3ccccc3)s2)C1=O] | ¹H NMR (300 MHz, DMSO-d₆) δ ppm 1.48-1.67 (m, 2 H) 1.98-2.17 (m, 2 H) 2.81-3.09 (m, 2 H) 3.41-3.59 (m, 2 H) 3.68-3.81 (m, 2 H) 3.99-4.13 (m, 2 H) 4.85-5.03 (m, 2 H) 7.39-7.54 (m, 3 H) 7.81-7.99 (m, 3 H) 9.85-10.25 (m, 1H) 12.78-13.01 (m, 1 H).<br>MS ESI/APCI Dual posi: 458[M + H]⁺. | |
| Example 1-99 | 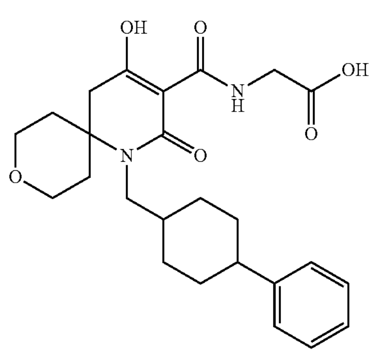 [SMILES: O=C(O)CNC(=O)C1=C(O)CC2(CCOCC2)N(CC2CCC(c3ccccc3)CC2)C1=O] | ¹H NMR (300 MHz, DMSO-d₆) δ ppm 0.99-1.49 (m, 4 H) 1.51-1.70 (m, 3 H) 1.72-2.09 (m, 6 H) 2.39-2.47 (m, 1 H) 2.78-3.05 (m, 2 H) 3.32-3.43 (m, 2 H) 3.44-3.61 (m, 2 H) 3.70-3.87 (m, 2 H) 3.92-4.10 (m, 2 H) 7.05-7.35 (m, 5 H) 10.03-10.21 (m, 1 H) 12.75-12.92 (m, 1 H).<br>MS ESI/APCI Dual posi: 457[M + H]⁺. | |

TABLE 21-14-continued

| Compound No. | Structure | Analytical Data | Salt information |
|---|---|---|---|
| Example 1-100 | 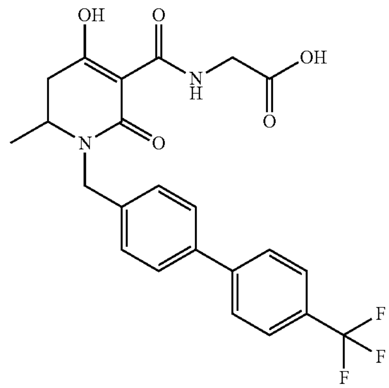 [SMILES: CC1CC(O)=C(C(=O)NCC(=O)O)C(=O)N1Cc1ccc(-c2ccc(C(F)(F)F)cc2)cc1] | $^1$H NMR (300 MHz, CHLOROFORM-d) δ ppm 1.20-1.32 (m, 3 H) 2.33 (dd, J = 17.2, 2.1 Hz, 1 H) 2.76-3.04 (m, 1 H) 3.56-3.70 (m, 1 H) 3.92-4.15 (m, 1 H) 4.16-4.25 (m, 2 H) 5.21-5.42 (m, 1 H) 7.32-7.43 (m, 2 H) 7.52-7.62 (m, 2 H) 7.63-7.74 (m, 4 H) 10.10-10.41 (m, 1 H).<br>MS ESI/APCI Dual Posi: 463[M + H]$^+$, 485[M + Na]$^+$.<br>MS ESI/APCI Dual nega: 461[M − H]$^−$. | |
| Example 1-101 | 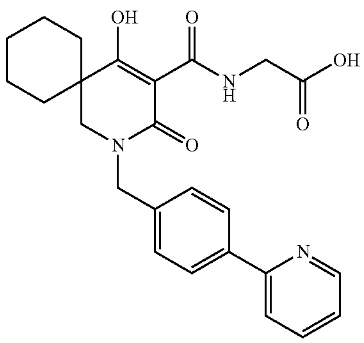 [SMILES: O=C(O)CNC(=O)C1=C(O)C2(CCCCC2)CN(Cc2ccc(-c3ccccn3)cc2)C1=O] | $^1$H NMR (300 MHz, DMSO-d$_6$) δ ppm 1.02-1.77 (m, 10 H) 3.29-3.60 (m, 2 H) 3.98-4.11 (m, 2 H) 4.57-4.80 (m, 2 H) 7.38-7.57 (m, 3 H) 7.96-8.15 (m, 4 H) 8.63-8.76 (m, 1 H) 10.08-10.42 (m, 1 H).<br>MS ESI/APCI Dual posi: 472[M + Na]$^+$.<br>MS ESI/APCI Dual nega: 448[M − H]$^−$. | HCl |

TABLE 21-15

| Compound No. | Structure | Analytical Data | Salt information |
|---|---|---|---|
| Example 1-102 | 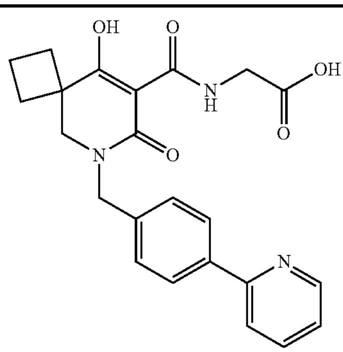 | $^1$H NMR (300 MHz, CHLOROFORM-d) δ ppm 1.66-1.81 (m, 2 H) 1.82-2.01 (m, 2 H) 2.42-2.55 (m, 2 H) 3.38 (s, 2 H) 4.14-4.20 (m, 2 H) 4.62-4.78 (m, 2 H) 7.39-7.54 (m, 2 H) 7.60-7.74 (m, 1 H) 7.79-8.04 (m, 3 H) 8.14-8.30 (m, 1 H) 8.93-9.07 (m, 1 H) 10.13-10.62 (m, 1 H).<br>MS ESI/APCI Dual posi: 422[M + H]$^+$, 444[M + Na]$^+$.<br>MS ESI/APCI Dual nega: 420[M − H]$^−$. | TFA |
| Example 1-103 | 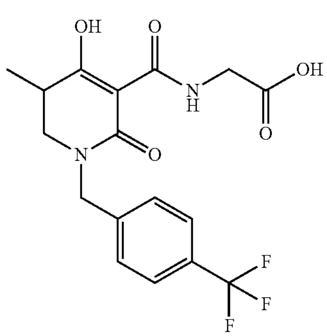 [SMILES: CC1CN(Cc2ccc(C(F)(F)F)cc2)C(=O)C(C(=O)NCC(=O)O)=C1O] | $^1$H NMR (300 MHz, DMSO-d$_6$) δ ppm 0.95-1.07 (m, 3 H) 2.48-2.78 (m, 1 H) 2.97-3.10 (m, 1 H) 3.36-3.45 (m, 1 H) 3.49-3.57 (m, 2 H) 4.56-4.75 (m, 2 H) 7.50 (d, J = 8.2 Hz, 2 H) 7.70 (d, J = 8.2 Hz, 2 H) 10.16 (br. s., 1 H).<br>MS ESI posi: 387[M + H]$^+$. | Na |

TABLE 21-15-continued

| Compound No. | Structure | Analytical Data | Salt information |
|---|---|---|---|
| Example 1-104 | 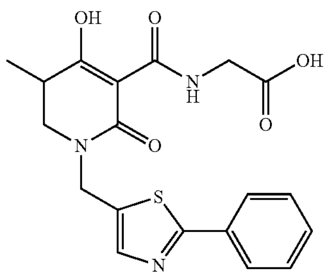 [SMILES: CC1CN(Cc2cnc(-c3ccccc3)s2)C(=O)C(C(=O)NCC(=O)O)=C1O] | ¹H NMR (300 MHz, DMSO-d₆) δ ppm 0.96-1.15 (m, 3 H) 2.63-2.95 (m, 1 H) 3.11-3.24 (m, 1 H) 3.47-3.62 (m, 1 H) 3.95-4.14 (m, 2 H) 4.65-4.97 (m, 2 H) 7.37-7.56 (m, 3 H) 7.82-7.99 (m, 3 H) 9.90-10.39 (m, 1 H). MS ESI posi: 402[M + H]⁺. | HCl |
| Example 1-105 | 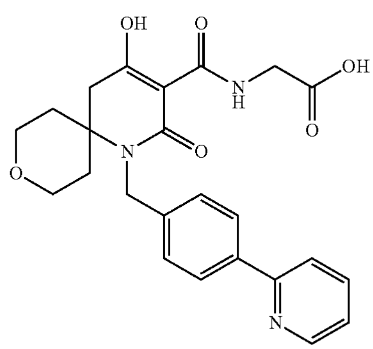 [SMILES: O=C(O)CNC(=O)C1=C(O)CC2(CCOCC2)N(Cc2ccc(-c3ccccn3)cc2)C1=O] | ¹H NMR (300 MHz, DMSO-d₆) δ ppm 1.45-1.59 (m, 2 H) 1.88-2.05 (m, 2 H) 2.87-3.17 (m, 2 H) 3.42-3.58 (m, 2 H) 3.63-3.79 (m, 2 H) 3.95-4.11 (m, 2 H) 4.74-4.97 (m, 2 H) 7.45-7.57 (m, 2 H) 7.63-7.71 (m, 1 H) 7.97-8.08 (m, 2 H) 8.13-8.32 (m, 2 H) 8.72-8.81 (m, 1 H) 9.92-10.29 (m, 1 H). MS ESI/APCI Dual posi: 452[M + H]⁺. | HCl |
| Example 1-106 | 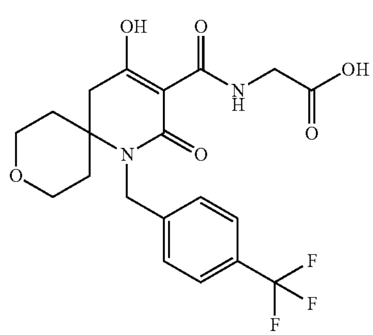 [SMILES: O=C(O)CNC(=O)C1=C(O)CC2(CCOCC2)N(Cc2ccc(C(F)(F)F)cc2)C1=O] | ¹H NMR (300 MHz, DMSO-d₆) δ ppm 1.41-1.65 (m, 2 H) 1.82-2.04 (m, 2 H) 2.85-3.17 (m, 2 H) 3.41-3.59 (m, 2 H) 3.63-3.80 (m, 2 H) 3.94-4.13 (m, 2 H) 4.75-4.97 (m, 2 H) 7.46-7.60 (m, 2 H) 7.61-7.76 (m, 2 H) 9.91-10.29 (m, 1 H) 12.63-13.13 (m, 1 H). MS ESI/APCI Dual posi: 443[M + H]⁺. MS ESI/APCI Dual nega: 441[M − H]⁻. | |
| Example 1-107 | 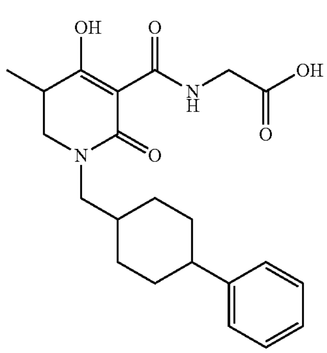 [SMILES: CC1CN(CC2CCC(c3ccccc3)CC2)C(=O)C(C(=O)NCC(=O)O)=C1O] | ¹H NMR (300 MHz, CHLOROFORM-d) δ ppm 0.99-2.12 (m, 12 H) 2.34-2.89 (m, 2 H) 3.02-3.57 (m, 4 H) 4.01-4.30 (m, 2 H) 6.94-7.48 (m, 5 H) 10.12-10.52 (m, 1 H). MS ESI/APCI Dual posi: 401[M + H]⁺, 423[M + Na]⁺. MS ESI/APCI Dual nega: 399[M − H]⁻. | |

TABLE 21-15-continued

| Compound No. | Structure | Analytical Data | Salt information |
|---|---|---|---|
| Example 1-108 | (structure) | $^1$H NMR (300 MHz, CHLOROFORM-d) δ ppm 1.03-1.21 (m, 3 H) 2.52-2.82 (m, 1 H) 3.07 (dd, J = 12.5, 8.0 Hz, 1 H) 3.40 (dd, J = 12.5, 5.8 Hz, 1 H) 4.15-4.24 (m, 2 H) 4.59-4.74 (m, 2 H) 7.32-7.43 (m, 2 H) 7.52-7.62 (m, 2 H) 7.60-7.75 (m, 4 H) 10.11-10.53 (m, 1 H).<br>MS ESI/APCI Dual posi: 463[M + H]$^+$, 485[M + Na]$^+$.<br>MS ESI/APCI Dual nega: 461[M − H]$^-$. | |

TABLE 21-16

| Compound No. | Structure | Analytical Data | Salt information |
|---|---|---|---|
| Example 1-109 | (structure) | $^1$H NMR (300 MHz, DMSO-d$_6$) δ ppm 1.25 (s, 6 H) 2.55-2.80(m, 2H) 3.95-4.13 (m, 2 H) 4.64-4.84 (m, 2 H) 7.42-7.63 (m, 3 H) 7.97-8.21 (m, 4 H) 8.70-8.77 (m, 1 H) 10.01-10.28 (m, 1 H).<br>MS ESI/APCI Dual posi: 410[M + H]$^+$, 432[M + Na]$^+$.<br>MS ESI/APCI Dual nega: 408[M − H]$^-$. | HCl |
| Example 1-110 | (structure) | $^1$H NMR (300 MHz, DMSO-d$_6$) δ ppm 1.17-1.41 (m, 2 H) 1.70-1.94 (m, 2 H) 3.35 (t, J = 11.0 Hz, 2 H) 3.45-3.54 (m, 2 H) 3.55-3.66 (m, 2 H) 3.97-4.12 (m, 2 H) 4.60-4.78 (m, 2 H) 7.44-7.66 (m, 3 H) 7.98-8.21 (m, 4 H) 8.74 (d, J = 4.8 Hz, 1 H) 10.08-10.37 (m, 1 H).<br>MS ESI/APCI Dual posi: 452[M + H]$^+$.<br>MS ESI/APCI Dual nega: 450[M − H]$^-$. | HCl |
| Example 1-111 | (structure) | $^1$H NMR (300 MHz, DMSO-d$_6$) δ ppm 1.06-1.80 (m, 10 H) 2.70-3.03 (m, 2 H) 3.93-4.14 (m, 2 H) 4.72-4.98 (m, 2 H) 7.43-7.59 (m, 2 H) 7.67-7.80 (m, 1 H) 7.96-8.13 (m, 2 H) 8.16-8.39 (m, 2 H) 8.73-8.84 (m, 1 H) 9.88-10.28 (m, 1 H)<br>MS ESI/APCI Dual posi: 450[M + H]$^+$. | HCl |

TABLE 21-16-continued

| Compound No. | Structure | Analytical Data | Salt information |
|---|---|---|---|
| Example 1-112 | 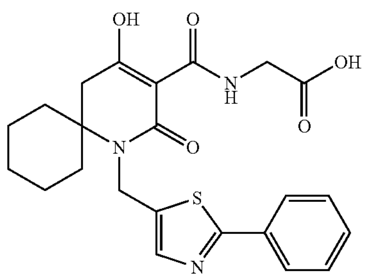 [SMILES: O=C(O)CNC(=O)C1=C(O)CC2(CCCCC2)N(Cc2cnc(-c3ccccc3)s2)C1=O] | ¹H NMR (300 MHz, DMSO-d₆) δ ppm 1.08-1.89 (m, 10 H) 2.83 (m, 2 H) 3.98-4.10 (m, 2 H) 4.75-5.02 (m, 2 H) 7.40-7.53 (m, 3 H) 7.81-7.97 (m, 3 H) 9.85-10.13 (m, 1 H). MS ESI/APCI Dual posi: 456[M + H]⁺. | HCl |
| Example 1-113 | 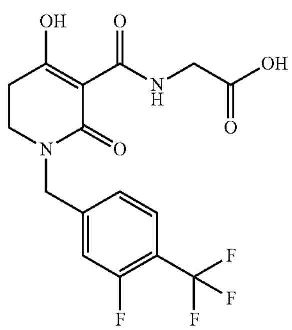 [SMILES: O=C(O)CNC(=O)C1=C(O)CCN(Cc2ccc(C(F)(F)F)c(F)c2)C1=O] | ¹H NMR (300 MHz, CHLOROFORM-d) δ ppm 2.52-2.79 (m, 2 H) 3.38 (t, J = 7.1 Hz, 2 H) 4.08-4.29 (m, 2 H) 4.65 (s, 2 H) 7.00-7.22 (m, 2 H) 7.47-7.67 (m, 1H) 9.87-10.41 (m, 1 H). MS ESI/APCI Dual posi: 391[M + H]⁺, 413[M + Na]⁺. MS ESI/APCI Dual nega: 389[M − H]⁻. | |
| Example 1-114 | 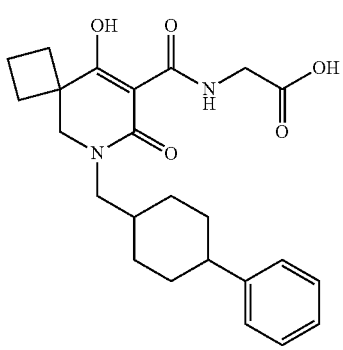 [SMILES: O=C(O)CNC(=O)C1=C(O)C2(CCC2)CN(CC2CCC(c3ccccc3)CC2)C1=O] | ¹H NMR (300 MHz, CHLOROFORM-d) δ ppm 1.06-1.34 (m, 2 H) 1.33-1.58 (m, 2 H) 1.58-2.14 (m, 9 H) 2.39-2.65 (m, 3 H) 3.21-3.60 (m, 4 H) 4.08-4.25 (m, 2 H) 7.14-7.23 (m, 3 H) 7.23-7.33 (m, 2 H) 10.16-10.54 (m, 1 H). MS ESI/APCI Dual posi: 427[M + H]⁺, 449[M + Na]⁺. MS ESI/APCI Dual nega: 425[M − H]⁻. | |
| Example 1-115 | 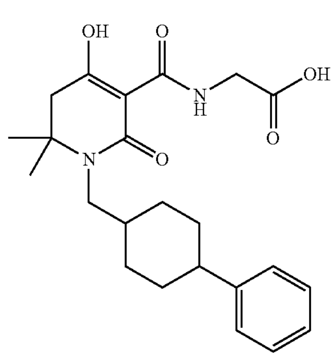 [SMILES: CC1(C)CC(O)=C(C(=O)NCC(=O)O)C(=O)N1CC1CCC(c2ccccc2)CC1] | ¹H NMR (300 MHz, CHLOROFORM-d) δ ppm 1.08-1.53 (m, 10 H) 1.61-2.02 (m, 5 H) 2.41-2.61 (m, 3 H) 3.29 (dd, J = 17.2, 7.4 Hz, 2 H) 4.10-4.23 (m, 2 H) 7.13-7.22 (m, 3 H) 7.23-7.33 (m, 2 H) 10.18-10.46 (m, 1 H). MS ESI/APCI Dual posi: 415[M + H]⁺, 437[M + Na]⁺. MS ESI/APCI Dual nega: 413[M − H]⁻. | |

TABLE 21-17

| Compound No. | Structure | Analytical Data | Salt information |
|---|---|---|---|
| Example 1-116 | 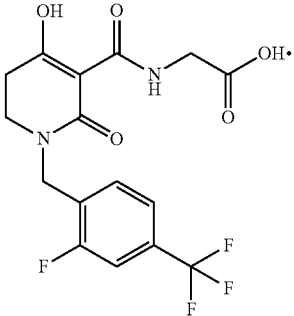 | ¹H NMR (300 MHz, DMSO-$d_6$) δ ppm 2.54-2.64 (m, 2 H) 3.36-3.54 (m, 4 H) 4.67 (s, 2 H) 7.45-7.61 (m, 2 H) 7.67 (d, J = 10.4 Hz, 1 H) 10.00 (br. s., 1 H). MS ESI/APCI Dual nega: 389[M − H]⁻. | Na |
| Example 1-117 | 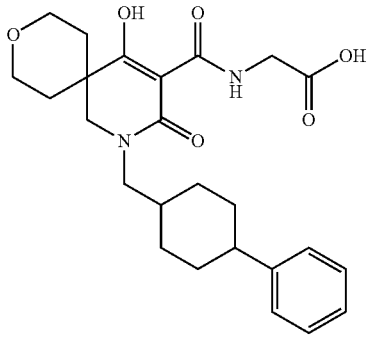 [SMILES: O=C(O)CNC(=O)C1=C(O)C2(CCOCC2)CN(CC2CCC(c3ccccc3)CC2)C1=O] | ¹H NMR (300 MHz, DMSO-$d_6$) δ ppm 1.02-1.23 (m, 2 H) 1.26-1.54 (m, 4 H) 1.62-1.99 (m, 8 H) 3.22-3.41 (m, 2 H) 3.51 (s, 2 H) 3.56-3.81 (m, 4 H) 3.96-4.05 (m, 2 H) 7.05-7.36 (m, 5 H) 10.19-10.31 (m, 1 H). MS ESI/APCI Dual posi: 479[M + Na]⁺. MS ESI/APCI Dual nega: 455[M − H]⁻. | |
| Example 1-118 | 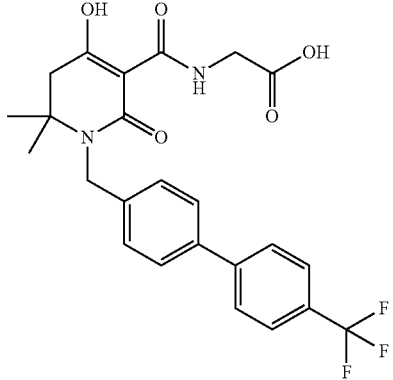 [SMILES: CC1(C)CC(O)=C(C(=O)NCC(=O)O)C(=O)N1Cc1ccc(-c2ccc(C(F)(F)F)cc2)cc1] | ¹H NMR (300 MHz, DMSO-$d_6$) δ ppm 1.25 (s, 6 H) 2.68-2.79 (m, 2 H) 3.95-4.08 (m, 2 H) 4.63-4.80 (m, 2 H) 7.39-7.48 (m, 2 H) 7.64-7.74 (m, 2 H) 7.76-7.84 (m, 2 H) 7.84-7.92 (m, 2 H) 9.98-10.29 (m, 1 H). MS ESI/APCI Dual posi: 497[M + Na]⁺. MS ESI/APCI Dual nega: 475[M − H]⁻. | |
| Example 1-119 | 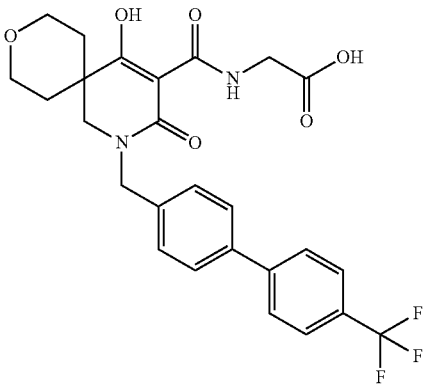 [SMILES: O=C(O)CNC(=O)C1=C(O)C2(CCOCC2)CN(Cc2ccc(-c3ccc(C(F)(F)F)cc3)cc2)C1=O] | ¹H NMR (300 MHz, DMSO-$d_6$) δ ppm 1.17-1.43 (m, 2 H) 1.65-1.94 (m, 2 H) 3.27-3.42 (m, 2 H) 3.44-3.54 (m, 2 H) 3.54-3.69 (m, 2 H) 3.98-4.08 (m, 2 H) 4.61-4.75 (m, 2 H) 7.44-7.53 (m, 2 H) 7.70-7.78 (m, 2 H) 7.78-7.85 (m, 2 H) 7.85-7.93 (m, 2 H) 10.05-10.39 (m, 1 H). MS ESI/APCI Dual posi: 541[M + Na]⁺. MS ESI/APCI Dual nega: 517[M − H]⁻. | |

TABLE 21-17-continued

| Compound No. | Structure | Analytical Data | Salt information |
|---|---|---|---|
| Example 1-120 | 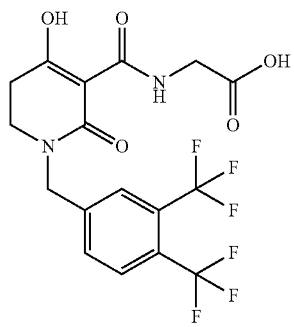 [SMILES: O=C(O)CNC(=O)C1=C(O)CCN(Cc2ccc(C(F)(F)F)c(C(F)(F)F)c2)C1=O] | ¹H NMR (300 MHz, CHLOROFORM-d) δ ppm 2.53-2.80 (m, 2 H) 3.30-3.48 (m, 2 H) 4.09-4.30 (m, 2 H) 4.72 (s, 2 H) 7.60 (d, J = 7.9 Hz, 1 H) 7.74 (s, 1 H) 7.78-7.93 (m, 1 H) 9.75-10.65 (m, 1 H). MS ESI/APCI Dual posi: 463[M + Na]⁺. MS ESI/APCI Dual nega: 439[M − H]⁻. | |
| Example 1-121 | 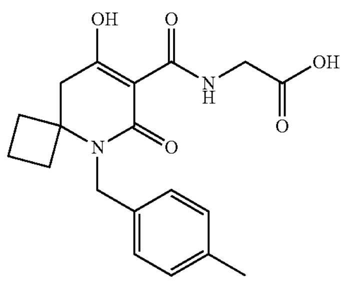 [SMILES: Cc1ccc(CN2C(=O)C(C(=O)NCC(=O)O)=C(O)CC23CCC3)cc1] | ¹H NMR (300 MHz, DMSO-d₆) δ ppm 1.57-1.90 (m, 4 H) 2.21-2.45 (m, 5 H) 2.74-3.01 (m, 2 H) 3.95-4.09 (m, 2 H) 4.73-4.88 (m, 2 H) 7.08-7.23 (m, 4 H) 9.92-10.24 (m, 1 H) 12.78-12.97 (m, 1 H). MS ESI/APCI Dual posi: 359[M + H]⁺, 381[M + Na]⁺. | |
| Example 1-122 | 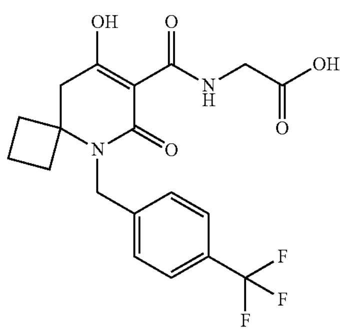 [SMILES: O=C(O)CNC(=O)C1=C(O)CC2(CCC2)N(Cc2ccc(C(F)(F)F)cc2)C1=O] | ¹H NMR (300 MHz, DEUTERIUM OXIDE) δ ppm 1.60-2.09 (m, 4 H) 2.25-2.50 (m, 2 H) 2.82-3.02 (m, 2 H) 3.85-4.01 (m, 2 H) 4.81-5.04 (m, 2 H) 7.38-7.58 (m, 2 H) 7.63-7.82 (m, 2 H). MS ESI/APCI Dual posi: 413[M + H]⁺. | Na |

TABLE 21-18

| Compound No. | Structure | Analytical Data | Salt information |
|---|---|---|---|
| Example 1-123 | 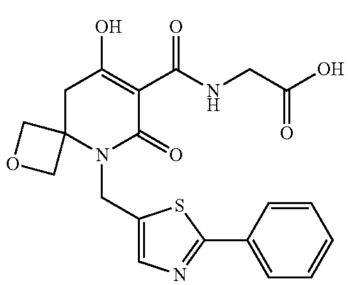 [SMILES: O=C(O)CNC(=O)C1=C(O)CC2(COC2)N(Cc2cnc(-c3ccccc3)s2)C1=O] | ¹H NMR (300 MHz, DMSO-d₆) δ ppm 3.16-3.28 (m, 2 H) 3.95-4.12 (m, 2 H) 4.35-4.57 (m, 2 H) 4.78-4.93 (m, 2 H) 5.19 (s, 2 H) 7.38-7.56 (m, 3 H) 7.81-8.02 (m, 3 H) 9.68-9.93 (m, 1 H). MS ESI/APCI Dual posi: 430[M + H]⁺, 452[M + Na]⁺. | |

TABLE 21-18-continued

| Compound No. | Structure | Analytical Data | Salt information |
|---|---|---|---|
| Example 1-124 | 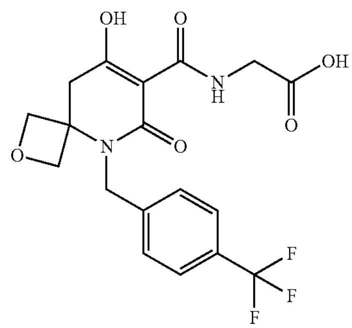 [SMILES: O=C(O)CNC(=O)C1=C(O)CC2(COC2)N(Cc2ccc(C(F)(F)F)cc2)C1=O] | ¹H NMR (300 MHz, DMSO-d₆) δ ppm 3.01-3.32 (m, 2 H) 3.92-4.11 (m, 2 H) 4.36-4.52 (m, 2 H) 4.62-4.74 (m, 2 H) 5.06-5.21 (m, 2 H) 7.41-7.75 (m, 4 H) 9.72-10.36 (m, 1 H). MS ESI/APCI Dual posi: 415[M + H]⁺. MS ESI/APCI Dual nega: 413[M − H]⁻. | |
| Example 1-125 | 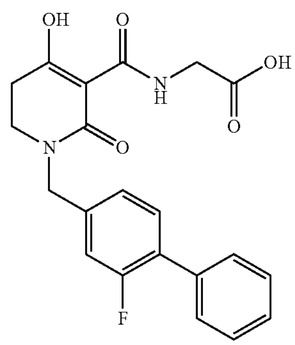 [SMILES: O=C(O)CNC(=O)C1=C(O)CCN(Cc2ccc(-c3ccccc3)c(F)c2)C1=O] | ¹H NMR (300 MHz, CHLOROFORM-d) δ ppm 2.56-2.73 (m, 2 H) 3.34-3.46 (m, 2 H) 4.14-4.26 (m, 2 H) 4.59-4.69 (m, 2 H) 7.04-7.15 (m, 2 H) 7.33-7.48 (m, 4 H) 7.49-7.56 (m, 2 H) 10.11-10.50 (m, 1 H). MS ESI/APCI Dual posi: 421[M + Na]⁺. MS ESI/APCI Dual nega: 397[M − H]⁻. | |
| Example 1-126 | 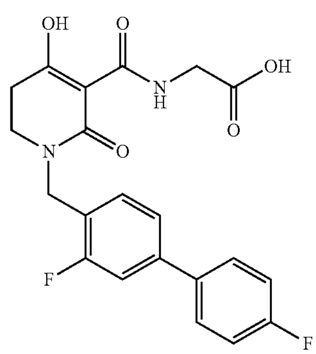 [SMILES: O=C(O)CNC(=O)C1=C(O)CCN(Cc2ccc(-c3ccc(F)cc3)cc2F)C1=O] | ¹H NMR (300 MHz, CHLOROFORM-d) δ ppm 2.53-2.75 (m, 2 H) 3.37-3.53 (m, 2 H) 4.09-4.23 (m, 2 H) 4.63-4.77 (m, 2 H) 7.08-7.17 (m, 2 H) 7.20-7.34 (m, 2 H) 7.37-7.44 (m, 1 H) 7.47-7.55 (m, 2 H) 10.10-10.47 (m, 1 H). MS ESI/APCI Dual posi: 417[M + H]⁺, 439[M + Na]⁺. MS ESI/APCI Dual nega: 415[M − H]⁻. | |
| Example 1-127 | 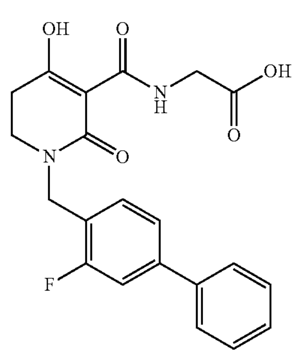 [SMILES: O=C(O)CNC(=O)C1=C(O)CCN(Cc2ccc(-c3ccccc3)cc2F)C1=O] | ¹H NMR (300 MHz, CHLOROFORM-d) δ ppm 2.56-2.71 (m, 2 H) 3.41-3.52 (m, 2 H) 4.13-4.23 (m, 2 H) 4.66-4.74 (m, 2 H) 7.23-7.49 (m, 6 H) 7.51-7.58 (m, 2 H) 10.12-10.45 (m, 1 H). MS ESI/APCI Dual posi: 399[M + H]⁺, 421[M + Na]⁺. MS ESI/APCI Dual nega: 397[M − H]⁻. | |

TABLE 21-18-continued

| Compound No. | Structure | Analytical Data | Salt information |
|---|---|---|---|
| Example 1-128 | (structure) | ¹H NMR (300 MHz, CHLOROFORM-d) δ ppm 2.45-2.84 (m, 2H) 3.25-3.50 (m, 2 H) 4.10-4.28 (m, 2 H) 4.63 (s, 2 H) 7.10-7.35 (m, 1 H) 7.41 (s, 1 H) 7.57-7.81 (m, 1 H) 9.84-10.63 (m, 1 H).<br>MS ESI/APCI Dual posi: 407[M + H]⁺, 429[M + Na]⁺.<br>MS ESI/APCI Dual nega: 405[M − H]⁻. | |
| Example 1-129 | (structure) | ¹H NMR (300 MHz, CHLOROFORM-d) δ ppm 2.47 (s, 3 H) 2.53-2.73 (m, 2 H) 3.27-3.42 (m, 2 H) 4.09-4.26 (m, 2 H) 4.62 (s, 2 H) 7.18-7.39 (m, 2 H) 7.48 (s, 1 H) 9.95-10.56 (m, 1 H).<br>MS ESI/APCI Dual posi: 387[M + H]⁺, 409[M + Na]⁺.<br>MS ESI?APCI Dual nega: 385[M − H]⁻. | |

TABLE 21-19

| Compound No. | Structure | Analytical Data | Salt information |
|---|---|---|---|
| Example 1-130 | (structure) | ¹H NMR (300 MHz, DMSO-d₆) δ ppm 1.58-1.94 (m, 4 H) 2.29-2.46 (m, 2 H) 2.79-3.06 (m, 2 H) 3.95-4.12 (m, 2 H) 4.85-5.01 (m, 2 H) 7.30-7.46 (m, 3 H) 7.82-8.11 (m, 4 H) 8.62-8.70 (m, 1 H) 9.90-10.26 (m, 1 H).<br>MS ESI/APCI Dual posi: 422[M + H]⁺, 444 [M + Na]⁺.<br>MS ESI/APCI Dual nega: 420[M − H]⁻. | |
| Example 1-131 | (structure) | ¹H NMR (300 MHz, DMSO-d₆) δ ppm 1.63-2.02 (m, 4 H) 2.21-2.50 (m, 2 H) 2.74-3.03 (m, 2 H) 3.93-4.11 (m, 2 H) 4.95-5.10 (m, 2 H) 7.42-7.53 (m, 3 H) 7.82-7.99 (m, 3 H) 9.79-10.28 (m, 1 H).<br>MS ESI/APCI Dual posi: 428[M + H]⁺, 450 [M + Na]⁺. | |

TABLE 21-19-continued

| Compound No. | Structure | Analytical Data | Salt information |
|---|---|---|---|
| Example 1-132 | 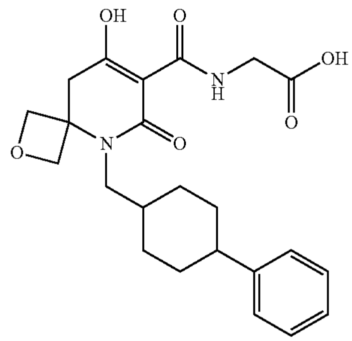 [SMILES: O=C(O)CNC(=O)C1=C(O)CC2(COC2)N(CC2CCC(c3ccccc3)CC2)C1=O] | ¹H NMR (300 MHz, DMSO-d₆) δ ppm 1.00-1.68 (m, 5 H) 1.73-1.93 (m, 4 H) 2.38-2.49 (m, 1 H) 2.96-3.27 (m, 2 H) 3.52-3.74 (m, 2 H) 3.92-4.11 (m, 2 H) 4.33-4.53 (m, 2 H) 4.68-4.94 (m, 2 H) 7.06-7.33 (m, 5 H) 9.89-10.24 (m, 1 H) 12.67-13.09 (m, 1 H).<br>MS ESI/APCI Dual posi: 429[M + H]⁺, 451 [M + Na]⁺.<br>MS ESI/APCI Dual nega: 427[M − H]⁻. | |
| Example 1-133 | 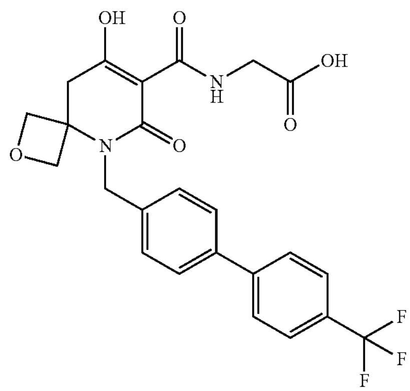 [SMILES: O=C(O)CNC(=O)C1=C(O)CC2(COC2)N(Cc2ccc(-c3ccc(C(F)(F)F)cc3)cc2)C1=O] | ¹H NMR (300 MHz, DMSO-d₆) δ ppm 3.06-3.42 (m, 2 H) 3.95-4.10 (m, 2H) 4.38-4.51 (m, 2 H) 4.68-4.81 (m, 2 H) 5.04-5.19 (m, 2 H) 7.39-7.49 (m, 2 H) 7.66-7.76 (m, 2 H) 7.77-7.92 (m, 4 H) 9.79-10.33 (m, 1 H).<br>MS ESI/APCI Dual posi: 491[M + H]⁺. | |
| Example 1-134 | 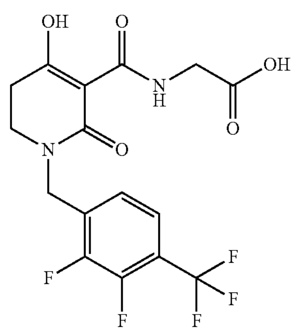 [SMILES: O=C(O)CNC(=O)C1=C(O)CCN(Cc2ccc(C(F)(F)F)c(F)c2F)C1=O] | ¹H NMR (600 MHz, CHLOROFORM-d) δ ppm 2.56-2.74 (m, 2 H) 3.45 (t, J = 7.2 Hz, 2 H) 4.13-4.23 (m, 2 H) 4.65-4.78 (m, 2 H) 7.19-7.30 (m, 1 H) 7.31-7.40 (m, 1 H) 9.85-10.57 (m, 1 H).<br>MS ESI/APCI Dual posi: 431[M + Na]⁺.<br>MS ESI/APCI Dual nega: 407[M − H]⁻. | |
| Example 1-135 | 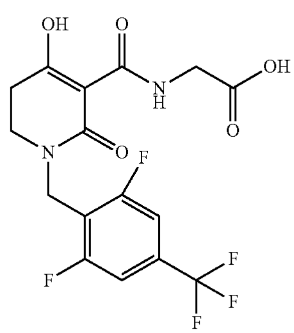 [SMILES: O=C(O)CNC(=O)C1=C(O)CCN(Cc2c(F)cc(C(F)(F)F)cc2F)C1=O] | ¹H NMR (600 MHz, CHLOROFORM-d) δ ppm 2.53-2.68 (m, 2 H) 3.46 (t, J = 7.0 Hz, 2 H) 4.11-4.19 (m, 2 H) 4.68-4.76 (m, 2 H) 7.16-7.23 (m, 2 H) 9.90-10.52 (m, 1 H).<br>MS ESI/APCI Dual posi: 431[M + Na]⁺.<br>MS ESI/APCI Dual nega: 407[M − H]⁻. | |

TABLE 21-19-continued

| Compound No. | Structure | Analytical Data | Salt information |
|---|---|---|---|
| Example 1-136 | 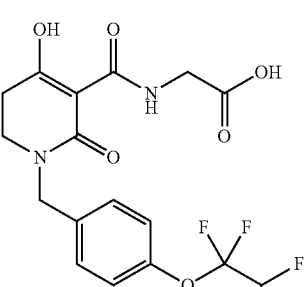 | ¹H NMR (600 MHz, METHANOL-d₄) δ ppm 2.56-2.63 (m, 2 H) 3.37 (t, J = 7.2 Hz, 2 H) 3.89 (s, 2 H) 4.64 (s, 2 H) 6.14-6.42 (m, 1 H) 7.15-7.25 (m, 2 H) 7.33-7.42 (m, 2 H).<br>MS ESI/APCI Dual posi: 443[M + Na]⁺.<br>MS ESI/APCI Dual nega: 419[M − H]⁻. | Na |

TABLE 21-20

| Compound No. | Structure | Analytical Data | Salt information |
|---|---|---|---|
| Example 1-137 | 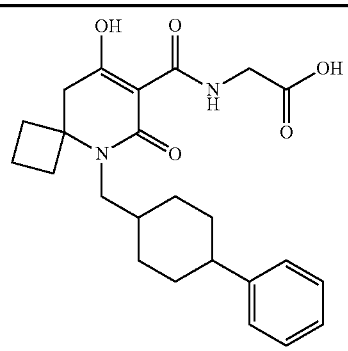 | ¹H NMR (300 MHz, DMSO-d₆) δ ppm 1.01-1.62 (m, 5 H) 1.64-2.02 (m, 8 H) 2.28-2.48 (m, 3 H) 2.66-2.98 (m, 2 H) 3.35-3.54 (m, 2 H) 3.91-4.08 (m, 2 H) 7.06-7.34 (m, 5 H) 9.99-10.18 (m, 1 H) 12.66-13.03 (m, 1 H).<br>MS ESI/APCI Dual posi: 427[M + H]⁺, 449[M + Na]⁺. | |
| Example 1-138 | 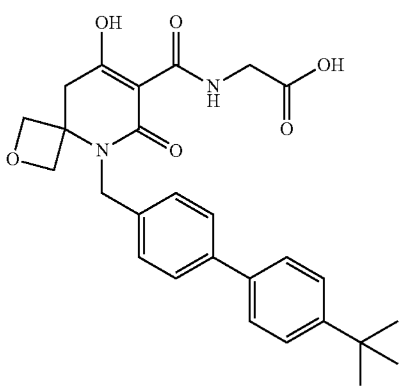 [SMILES: CC(C)(C)c1ccc(-c2ccc(CN3C(=O)C(C(=O)NCC(=O)O)=C(O)CC34COC4)cc2)cc1] | ¹H NMR (300 MHz, DMSO-d₆) δ ppm 1.31 (s, 9 H) 3.29-3.34 (m, 2 H) 3.95-4.11 (m, 2 H) 4.36-4.49 (m, 2 H) 4.69-4.81 (m, 2 H) 5.00-5.15 (m, 2 H) 7.30-7.42 (m, 2 H) 7.43-7.50 (m, 2 H) 7.51-7.66 (m, 4 H) 9.84-10.33 (m, 1 H).<br>MS ESI/APCI Dual posi: 479[M + H]⁺, 501[M + Na]⁺. | |
| Example 1-139 | 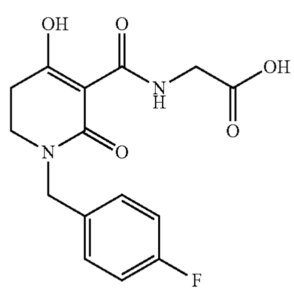 [SMILES: O=C(O)CNC(=O)C1=C(O)CCN(Cc2ccc(F)cc2)C1=O] | ¹H NMR (600 MHz, CHLOROFORM-d) δ ppm 2.51-2.68 (m, 2 H) 3.27-3.38 (m, 2 H) 4.14-4.22 (m, 2 H) 4.53-4.65 (m, 2 H) 6.98-7.08 (m, 2 H) 7.18-7.31 (m, 2 H) 10.08-10.53 (m, 1 H).<br>MS ESI/APCI Dual posi: 345[M + Na]⁺.<br>MS ESI/APCI Dual nega: 321[M − H]⁻. | |

TABLE 21-20-continued

| Compound No. | Structure | Analytical Data | Salt information |
|---|---|---|---|
| Example 1-140 | 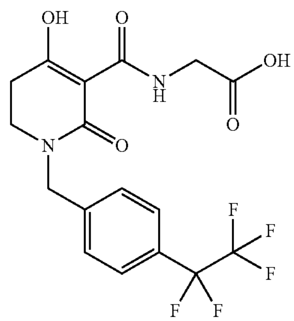 [SMILES: O=C(O)CNC(=O)C1=C(O)CCN(Cc2ccc(C(F)(F)C(F)(F)F)cc2)C1=O] | ¹H NMR (600 MHz, DMSO-d₆) δ ppm 2.46-2.63 (m, 2 H) 3.31-3.40 (m, 2H) 3.43-3.54 (m, 2 H) 4.66 (s, 2 H) 7.52 (d, J = 8.3 Hz, 2 H) 7.66 (d, J = 8.3 Hz, 2 H). MS ESI/APCI Dual nega: 421[M − H]⁻. | Na |
| Example 1-141 | 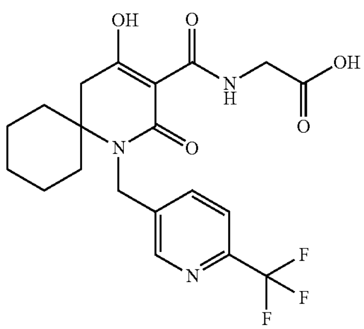 [SMILES: O=C(O)CNC(=O)C1=C(O)CC2(CCCCC2)N(Cc2ccc(C(F)(F)F)nc2)C1=O] | ¹H NMR (600 MHz, DMSO-d₆) δ ppm 1.07-1.21 (m, 1 H) 1.29-1.43 (m, 2 H) 1.48-1.61 (m, 5 H) 1.61-1.71 (m, 2 H) 2.79 (br. s., 2 H) 3.42-3.53 (m, 2 H) 4.84 (br. s., 2 H) 7.82 (d, J = 7.8 Hz, 1 H) 7.95 (d, J = 7.8 Hz, 1 H) 8.71 (s, 1 H). MS ESI/APCI Dual nega: 440[M − H]⁻. | Na |
| Example 1-142 | 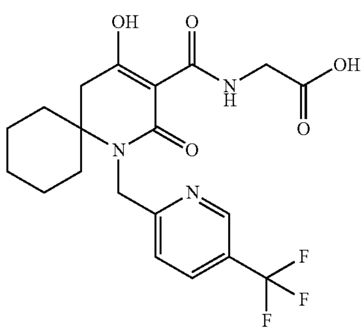 [SMILES: O=C(O)CNC(=O)C1=C(O)CC2(CCCCC2)N(Cc2ccc(C(F)(F)F)cn2)C1=O] | ¹H NMR (600 MHz, DMSO-d₆) δ ppm 1.08-1.21 (m, 1 H) 1.31-1.45 (m, 2 H) 1.48-1.63 (m, 5 H) 1.64-1.75 (m, 2 H) 2.66-3.09 (m, 2 H) 3.95-4.08 (m, 2 H) 4.84-4.96 (m, 2 H) 7.39-7.73 (m, 1 H) 7.98-8.22 (m, 1 H) 8.89 (s, 1 H) 9.79-10.27 (m, 1 H). MS ESI/APCI Dual nega: 440[M − H]⁻. | Na |
| Example 1-143 | cis-trans mixture | ¹H NMR (600 MHz, METHANOL-d₄) δ ppm 1.05-1.86 (m, 7 H) 2.03-2.46 (m, 2 H) 3.36-3.44 (m, 1 H) 3.78-3.84 (m, 2 H) 4.15-4.30 (m, 1 H) 5.14-5.26 (m, 1 H) 7.32-7.73 (m, 4 H). MS ESI/APCI Dual posi: 449[M + Na]⁺. MS ESI/APCI Dual nega: 425[M − H]⁻. | Na |

TABLE 21-21

| Compound No. | Structure | Analytical Data | Salt information |
|---|---|---|---|
| Example 1-144 | 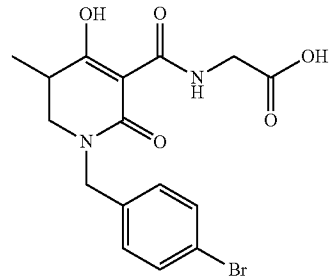 [SMILES: CC1CN(Cc2ccc(Br)cc2)C(=O)C(C(=O)NCC(=O)O)=C1O] | ¹H NMR (600 MHz, METHANOL-d₄) δ ppm 1.09 (d, J = 7.0 Hz, 3 H) 2.55-2.69 (m, 1 H) 3.04 (dd, J = 12.6, 8.1 Hz, 1 H) 3.41 (dd, J = 12.6, 5.6 Hz, 1 H) 3.89 (s, 2 H) 4.52 (d, J = 15.1 Hz, 1 H) 4.64 (d, J = 15.1 Hz, 1 H) 7.24 (d, J = 8.5 Hz, 2 H) 7.48 (d, J = 8.5 Hz, 2 H).<br>MS ESI/APCI Dual posi: 419[M + H]⁺.<br>MS ESI/APCI Dual nega: 395[M − H]⁻. | Na |
| Example 1-145 | 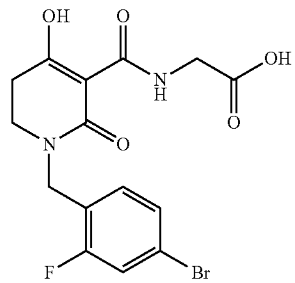 [SMILES: O=C(O)CNC(=O)C1=C(O)CCN(Cc2ccc(Br)cc2F)C1=O] | ¹H NMR (600 MHz, DMSO-d₆) δ ppm 2.49-2.64 (m, 2 H) 3.30-3.41 (m, 2 H) 3.49 (d, J = 4.5 Hz, 2 H) 4.55 (s, 2 H) 7.28 (t, J = 8.1 Hz, 1 H) 7.39 (dd, J = 8.1, 1.7 Hz, 1 H) 7.54 (dd, J = 9.5, 1.7 Hz, 1 H).<br>MS ESI/APCI Dual nega: 399[M − H]⁻. | Na |
| Example 1-146 | 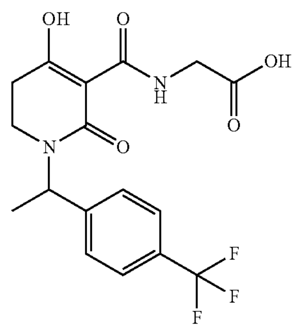 [SMILES: CC(c1ccc(C(F)(F)F)cc1)N1CCC(O)=C(C(=O)NCC(=O)O)C1=O] | ¹H NMR (600 MHz, CHLOROFORM-d) δ ppm 1.52-1.64 (m, 3 H) 2.43-2.58 (m, 2 H) 2.91-3.01 (m, 1 H) 3.23-3.35 (m, 1 H) 4.15-4.25 (m, 2 H) 5.83-6.09 (m, 1 H) 7.38-7.51 (m, 2 H) 7.56-7.67 (m, 2 H) 10.08-10.52 (m, 1 H).<br>MS ESI/APCI Dual posi: 409[M + Na]⁺.<br>MS ESI/APCI Dual nega: 385[M − H]⁻. | |
| Example 1-147 | 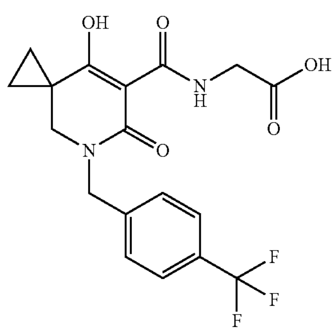 [SMILES: O=C(O)CNC(=O)C1=C(O)C2(CC2)CN(Cc2ccc(C(F)(F)F)cc2)C1=O] | ¹H NMR (300 MHz, DMSO-d₆) δ ppm 0.62-0.96 (m, 2 H) 1.03-1.31 (m, 2H) 3.32-3.40 (m, 2 H) 3.98-4.08 (m, 2 H) 4.62-4.76 (m, 2 H) 7.45-7.56 (m, 2 H) 7.68-7.80 (m, 2 H) 10.01-10.42 (m, 1 H).<br>MS ESI/APCI Dual posi: 399[M + H]⁺, 421 [M + Na]⁺.<br>MS ESI/APCI Dual nega: 397[M − H]⁻. | |
| Example 1-148 | 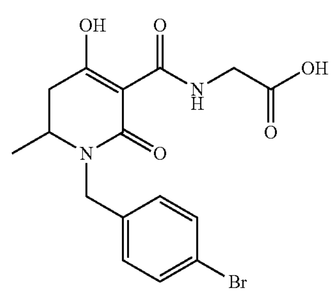 [SMILES: CC1CC(O)=C(C(=O)NCC(=O)O)C(=O)N1Cc1ccc(Br)cc1] | ¹H NMR (300 MHz, DMSO-d₆) δ ppm 1.03-1.16 (m, 3 H) 2.13-2.28 (m, 1 H) 2.77-2.97 (m, 1 H) 3.45-3.64 (m, 3 H) 4.03-4.18 (m, 1 H) 4.88-5.01 (m, 1 H) 7.22-7.31 (m, 2 H) 7.45-7.57 (m, 2 H) 9.90-10.19 (m, 1 H).<br>MS ESI/APCI Dual posi: 397[M + H]⁺, 419[M + Na]⁺. | Na |

TABLE 21-21-continued

| Compound No. | Structure | Analytical Data | Salt information |
|---|---|---|---|
| Example 1-149 | 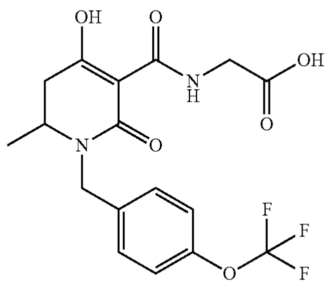 [SMILES: CC1CC(O)=C(C(=O)NCC(=O)O)C(=O)N1Cc1ccc(OC(F)(F)F)cc1] | $^1$H NMR (300 MHz, DMSO-d$_6$) δ ppm 1.07-1.16 (m, 3 H) 2.15-2.30 (m, 1 H) 2.84-3.04 (m, 1 H) 3.52-3.68 (m, 3 H) 4.17 (d, J = 15.5 Hz, 1 H) 5.00 (d, J = 15.5 Hz, 1 H) 7.26-7.37 (m, 2 H) 7.38-7.48 (m, 2 H) 9.96-10.15 (m, 1 H). MS ESI/APCI Dual posi: 403[M + H]$^+$. | Na |
| Example 1-150 | 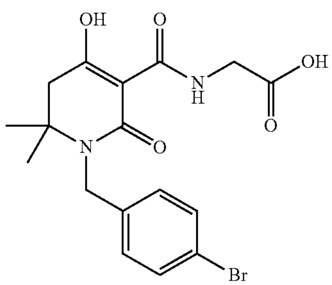 [SMILES: CC1(C)CC(O)=C(C(=O)NCC(=O)O)C(=O)N1Cc1ccc(Br)cc1] | $^1$H NMR (300 MHz, DMSO-d$_6$) δ ppm 1.21 (s, 6 H) 2.52-2.77 (m, 2 H) 3.94-4.11 (m, 2 H) 4.54-4.71 (m, 2 H) 7.20-7.33 (m, 2 H) 7.42-7.58 (m, 2 H) 9.96-10.27 (m, 1 H). MS ESI/APCI Dual posi: 411[M + H]$^+$. | |

TABLE 21-22

| Compound No. | Structure | Analytical Data | Salt information |
|---|---|---|---|
| Example 1-151 | 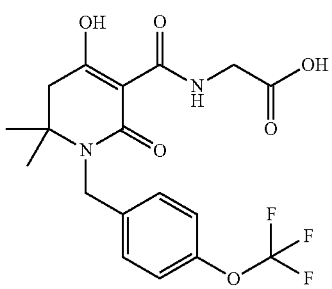 [SMILES: CC1(C)CC(O)=C(C(=O)NCC(=O)O)C(=O)N1Cc1ccc(OC(F)(F)F)cc1] | $^1$H NMR (300 MHz, DMSO-d$_6$) δ ppm 1.22 (s, 6 H) 2.54-2.78 (m, 2 H) 3.92-4.09 (m, 2 H) 4.59-4.77 (m, 2 H) 7.23-7.36 (m, 2 H) 7.36-7.48 (m, 2 H) 9.95-10.27 (m, 1 H). MS ESI/APCI Dual posi: 417[M + H]$^+$. | |
| Example 1-152 | 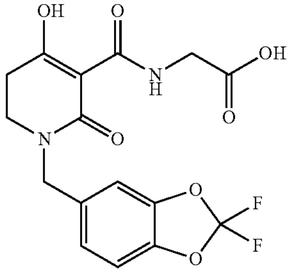 [SMILES: O=C(O)CNC(=O)C1=C(O)CCN(Cc2ccc3c(c2)OC(F)(F)O3)C1=O] | $^1$H NMR (300 MHz, DMSO-d$_6$) δ ppm 2.49-2.60 (m, 2 H) 3.27-3.33 (m, 2 H) 3.50 (d, J = 4.5 Hz, 2 H) 4.56 (s, 2 H) 7.05-7.22 (m, 1 H) 7.26-7.46 (m, 2 H) 9.91-10.24 (m, 1 H). MS ESI/APCI Dual posi: 385[M + H]$^+$. MS ESI/APCI Dual nega: 383[M − H]$^-$. | Na |

TABLE 21-22-continued

| Compound No. | Structure | Analytical Data | Salt information |
|---|---|---|---|
| Example 1-153 | 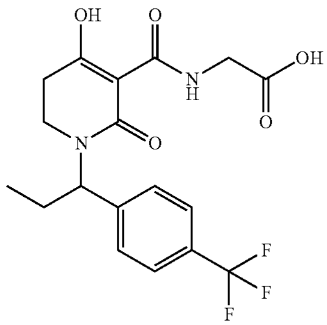 [SMILES: CCC(c1ccc(C(F)(F)F)cc1)N1CCC(O)=C(C(=O)NCC(=O)O)C1=O] | $^1$H NMR (300 MHz, DMSO-d$_6$) δ ppm 0.91 (t, J = 7.2 Hz, 3 H) 1.82-2.16 (m, 2 H) 2.22-2.47 (m, 1 H) 2.79-2.95 (m, 1 H) 3.14-3.35 (m, 2 H) 3.49 (d, J = 4.5 Hz, 2 H) 5.67 (dd, J = 10.1, 5.9 Hz, 1 H) 7.55 (d, J = 8.2 Hz, 2 H) 7.70 (d, J = 8.2 Hz, 2 H) 10.10 (br. s., 1 H). MS ESI/APCI Dual nega: 399[M − H]$^-$. | Na |
| Example 1-154 | 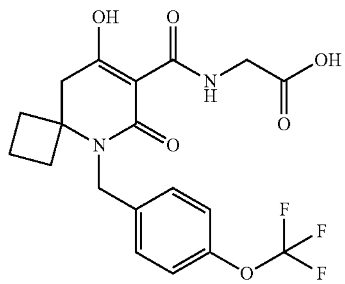 [SMILES: O=C(O)CNC(=O)C1=C(O)CC2(CCC2)N(Cc2ccc(OC(F)(F)F)cc2)C1=O] | $^1$H NMR (300 MHz, CHLOROFORM-d) δ ppm 1.63-1.87 (m, 2 H) 1.88-2.07 (m, 2 H) 2.24-2.46 (m, 2 H) 2.76-2.98 (m, 2 H) 4.10-4.26 (m, 2 H) 4.78-4.91 (m, 2 H) 7.13-7.22 (m, 2 H) 7.23-7.32 (m, 2 H) 10.02-10.44 (m, 1 H). MS ESI/APCI Dual posi: 451[M + Na]$^+$. MS ESI/APCI Dual nega: 427[M − H]$^-$. | |
| Example 1-155 | 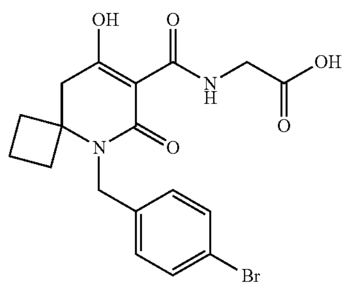 | $^1$H NMR (300 MHz, CHLOROFORM-d) δ ppm 1.61-1.82 (m, 2 H) 1.87-2.02 (m, 2 H) 2.24-2.44 (m, 2 H) 2.77-2.91 (m, 2 H) 4.14-4.21 (m, 2 H) 4.74-4.86 (m, 2 H) 7.04-7.20 (m, 2 H) 7.38-7.50 (m, 2 H) 10.04-10.42 (m, 1 H). MS ESI/APCI Dual posi: 445[M + Na]$^+$. MS ESI/APCI Dual nega: 421[M − H]$^-$. | |
| Example 1-156 | 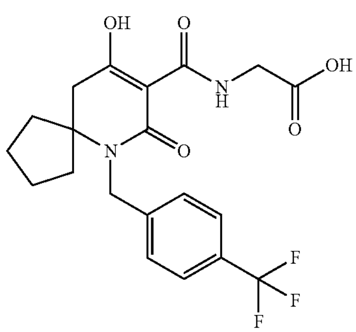 [SMILES: O=C(O)CNC(=O)C1=C(O)CC2(CCCC2)N(Cc2ccc(C(F)(F)F)cc2)C1=O] | $^1$H NMR (300 MHz, CHLOROFORM-d) δ ppm 1.53-1.93 (m, 8 H) 2.59-2.75 (m, 2 H) 4.08-4.27 (m, 2 H) 4.58-4.75 (m, 2 H) 7.31-7.40 (m, 2 H) 7.54-7.63 (m, 2 H) 9.98-10.49 (m, 1 H). MS ESI/APCI Dual posi: 449[M + Na]$^+$. MS ESI/APCI Dual nega: 425[M − H]$^-$. | |
| Example 1-157 | 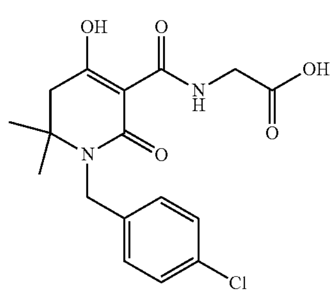 [SMILES: CC1(C)CC(O)=C(C(=O)NCC(=O)O)C(=O)N1Cc1ccc(Cl)cc1] | $^1$H NMR (300 MHz, DMSO-d$_6$) δ ppm 1.21 (s, 6 H) 2.52-2.76 (m, 2 H) 3.95-4.10 (m, 2 H) 4.56-4.74 (m, 2 H) 7.25-7.43 (m, 4 H) 9.98-10.27 (m, 1 H) 12.86 (br. s., 1 H). MS ESI/APCI Dual posi: 367[M + H]$^+$. MS ESI/APCI Dual nega: 365[M − H]$^-$. | |

TABLE 21-23

| Compound No. | Structure | Analytical Data | Salt information |
|---|---|---|---|
| Example 1-158 | 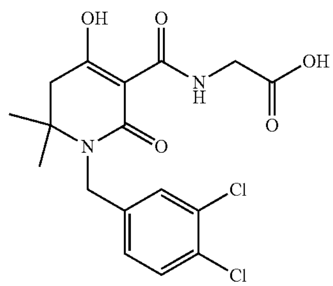 [SMILES: CC1(C)CC(O)=C(C(=O)NCC(=O)O)C(=O)N1Cc1ccc(Cl)c(Cl)c1] | $^1$H NMR (300 MHz, DMSO-d$_6$) δ ppm 1.18 (s, 6 H) 2.50-2.68 (m, 2 H) 3.48-3.58 (m, 2 H) 4.61 (s, 2 H) 7.24-7.33 (m, 1 H) 7.49-7.60 (m, 2 H) 9.92-10.24 (m, 1 H).<br>MS ESI/APCI Dual posi: 401[M + H]$^+$.<br>MS ESI/APCI Dual nega: 399[M − H]$^−$. | Na |
| Example 1-159 | 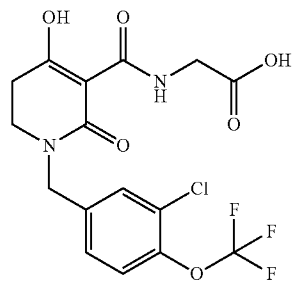 [SMILES: O=C(O)CNC(=O)C1=C(O)CCN(Cc2ccc(OC(F)(F)F)c(Cl)c2)C1=O] | $^1$H NMR (600 MHz, CHLOROFORM-d) δ ppm 2.57-2.7 (m, 2 H) 3.34-3.41 (m, 2 H) 4.15-4.23 (m, 2 H) 4.57-4.63 (m, 2 H) 7.18-7.24 (m, 1 H) 7.27-7.33 (m, 1 H) 7.37-7.41 (m, 1 H) 10.01-10.58 (m, 1 H).<br>MS ESI/APCI Dual posi: 445[M + Na]$^+$.<br>MS ESI/APCI Dual nega: 421[M − H]$^−$. | |
| Example 1-160 | 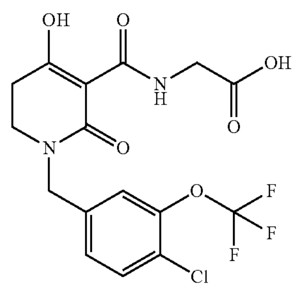 [SMILES: O=C(O)CNC(=O)C1=C(O)CCN(Cc2ccc(Cl)c(OC(F)(F)F)c2)C1=O] | $^1$H NMR (600 MHz, CHLOROFORM-d) δ ppm 2.55-2.69 (m, 2 H) 3.32-3.40 (m, 2 H) 4.15-4.22 (m, 2 H) 4.57-4.63 (m, 2 H) 7.15-7.21 (m, 1 H) 7.21-7.28 (m, 1 H) 7.40-7.50 (m, 1 H) 9.92-10.55 (m, 1 H).<br>MS ESI/APCI Dual posi: 455[M + Na]$^+$.<br>MS ESI/APCI Dual nega: 421[M − H]$^−$. | |
| Example 1-161 | 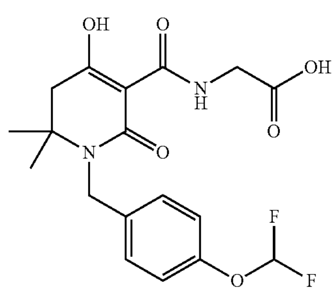 [SMILES: CC1(C)CC(O)=C(C(=O)NCC(=O)O)C(=O)N1Cc1ccc(OC(F)F)cc1] | $^1$H NMR (600 MHz, DMSO-d$_6$) δ ppm 1.17 (s, 6 H) 3.29-3.36 (m, 2 H) 3.46 (d, J = 4.1 Hz, 2 H) 4.60 (br. s., 2 H) 7.00-7.40 (m, 5 H).<br>MS ESI/APCI Dual posi: 421[M + Na]$^+$.<br>MS ESI/APCI Dual nega: 397[M − H]$^−$. | Na |
| Example 1-162 | 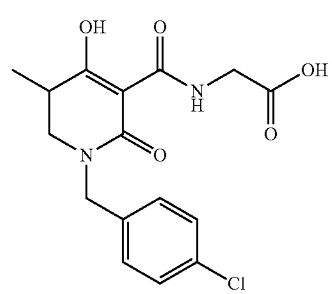 [SMILES: CC1CN(Cc2ccc(Cl)cc2)C(=O)C(C(=O)NCC(=O)O)=C1O] | $^1$H NMR (600 MHz, METHANOL-d$_4$) δ ppm 1.03-1.18 (m, 3 H) 2.58-2.69 (m, 1 H) 3.00-3.07 (m, 1 H) 3.38-3.44 (m, 1 H) 3.88 (s, 2 H) 4.53 (d, J = 15.1Hz, 1 H) 4.66 (d, J = 15.1 Hz, 1 H) 7.25-7.38 (m, 4 H).<br>MS ESI/APCI Dual posi: 375[M + Na]$^+$.<br>MS ESI/APCI Dual nega: 351[M − H]$^−$. | Na |

TABLE 21-23-continued

| Compound No. | Structure | Analytical Data | Salt information |
|---|---|---|---|
| Example 1-163 | 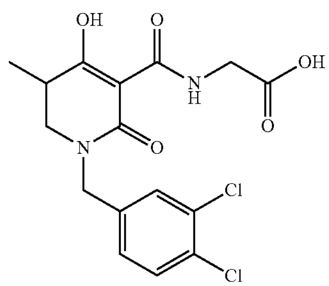 [SMILES: CC1CN(Cc2ccc(Cl)c(Cl)c2)C(=O)C(C(=O)NCC(=O)O)=C1O] | $^1$H NMR (600 MHz, METHANOL-d$_4$) δ ppm 1.05-1.18 (m, 3 H) 2.60-2.68 (m, 1 H) 3.06 (dd, J = 12.6, 7.6 Hz, 1 H) 3.44 (dd, J = 12.6, 5.4 Hz, 1 H) 3.89 (s, 2 H) 4.50-4.58 (m, 1 H) 4.61-4.68 (m, 1 H) 7.26 (dd, J = 8.3, 2.1 Hz, 1 H) 7.44-7.52 (m, 2 H). MS ESI/APCI Dual posi: 409[M + Na]$^+$. MS ESI/APCI Dual nega: 385[M − H]$^-$. | Na |
| Example 1-164 | 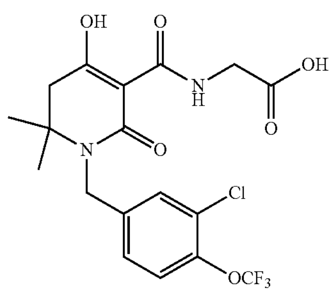 [SMILES: CC1(C)CC(O)=C(C(=O)NCC(=O)O)C(=O)N1Cc1ccc(OC(F)(F)F)c(Cl)c1] | $^1$H NMR (300 MHz, DMSO-d$_6$) δ ppm 1.18 (s, 6 H) 2.53-2.61 (m, 2 H) 3.47-3.55 (m, 2 H) 4.63 (s, 2 H) 7.38 (dd, J = 8.5, 2.0 Hz, 1 H) 7.46-7.52 (m, 1 H) 7.56 (d, J = 2.0 Hz, 1 H) 9.99-10.19 (m, 1 H). MS ESI/APCI Dual posi: 451[M + H]$^+$. MS ESI/APCI Dual nega: 449[M − H]$^-$. | Na |

TABLE 21-24

| Compound No. | Structure | Analytical Data | Salt information |
|---|---|---|---|
| Example 1-165 | 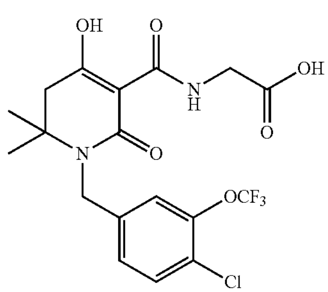 [SMILES: CC1(C)CC(O)=C(C(=O)NCC(=O)O)C(=O)N1Cc1ccc(Cl)c(OC(F)(F)F)c1] | $^1$H NMR (300 MHz, DMSO-d$_6$) δ ppm 1.17 (s, 6 H) 2.50-2.59 (m, 2 H) 3.46-3.56 (m, 2 H) 4.66 (s, 2 H) 7.37 (dd, J = 8.4, 1.9 Hz, 1 H) 7.43-7.50 (m, 1 H) 7.61 (d, J = 8.4 Hz, 1 H) 10.07 (br. s., 1 H). MS ESI/APCI Dual posi: 451 [M + H]$^+$. MS ESI/APCI Dual nega: 449 [M − H]$^-$. | Na |
| Example 1-166 | 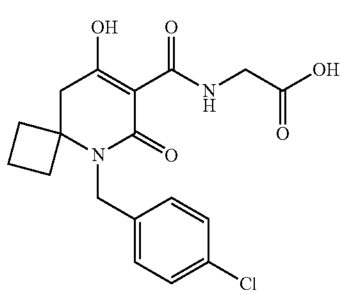 [SMILES: O=C(O)CNC(=O)C1=C(O)CC2(CCC2)N(Cc2ccc(Cl)cc2)C1=O] | $^1$H NMR (300 MHz, METHANOL-d$_4$) δ ppm 1.59-1.77 (m, 2 H) 1.78-1.94 (m, 2 H) 2.22-2.39 (m, 2 H) 2.56-2.76 (m, 2 H) 3.87 (s, 2 H) 4.85 (s, 2 H) 7.28 (s, 4 H). MS ESI/APCI Dual posi: 401 [M + Na]$^+$. MS ESI/APCI Dual nega: 377 [M − H]$^-$. | Na |

TABLE 21-24-continued

| Compound No. | Structure | Analytical Data | Salt information |
|---|---|---|---|
| Example 1-167 | 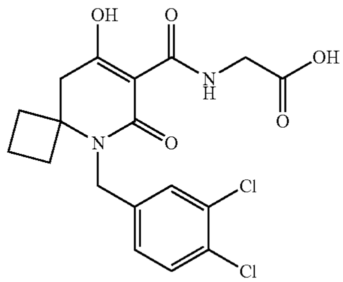 [SMILES: O=C(O)CNC(=O)C1=C(O)CC2(CCC2)N(Cc2ccc(Cl)c(Cl)c2)C1=O] | $^1$H NMR (300 MHz, METHANOL-d$_4$) δ ppm 1.66-1.83 (m, 2 H) 1.83-1.99 (m, 2 H) 2.29-2.46 (m, 2 H) 2.86 (s, 2 H) 3.88 (s, 2 H) 4.86 (s, 2 H) 7.23 (dd, J = 8.2, 2.2 Hz, 1 H) 7.40-7.49 (m, 2H). MS ESI/APCI Dual posi: 435 [M + Na]$^+$. MS ESI/APCI Dual nega: 411 [M − H]$^−$. | Na |
| Example 1-168 | 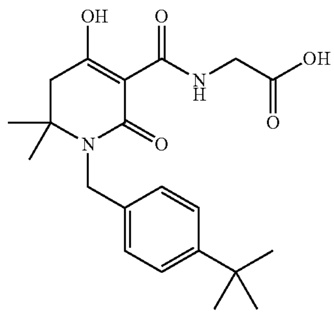 [SMILES: CC(C)(C)c1ccc(CN2C(=O)C(C(=O)NCC(=O)O)=C(O)CC2(C)C)cc1] | $^1$H NMR (600 MHz, CHLOROFORM-d) δ ppm 1.22-1.32 (m, 6 H) 1.84-1.96 (m, 3 H) 2.51-2.66 (m, 2 H) 4.14-4.22 (m, 2 H) 4.64-4.77 (m, 2 H) 7.27-7.36 (m, 2 H) 7.41-7.50 (m, 2 H) 10.12-10.50 (m, 1 H). MS ESI/APCI Dual posi: 397 [M + H]$^+$, 419 [M + Na]$^+$. MS ESI/APCI Dual nega: 395 [M − H]$^−$. | |
| Example 1-169 | 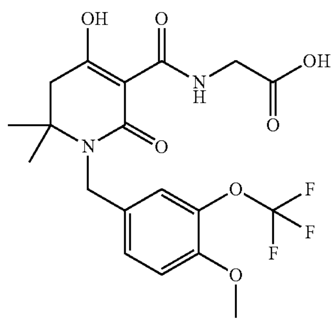 [SMILES: COc1ccc(CN2C(=O)C(C(=O)NCC(=O)O)=C(O)CC2(C)C)cc1OC(F)(F)F] | $^1$H NMR (600 MHz, CHLOROFORM-d) δ ppm 1.20-1.31 (m, 6 H) 2.48-2.64 (m, 2 H) 3.82-3.89 (m, 3 H) 4.14-4.23 (m, 2 H) 4.55-4.68 (m, 2 H) 6.90-6.98 (m, 1 H) 7.11-7.22 (m, 2 H) 10.12-10.50 (m, 1 H). MS ESI/APCI Dual posi: 447 [M + H]$^+$, 469 [M + Na]$^+$. MS ESI/APCI Dual nega: 445 [M − H]$^−$. | |
| Example 1-170 | 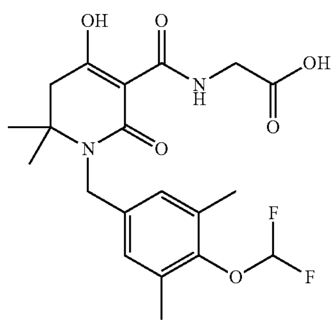 [SMILES: Cc1cc(CN2C(=O)C(C(=O)NCC(=O)O)=C(O)CC2(C)C)cc(C)c1OC(F)F] | $^1$H NMR (600 MHz, CHLOROFORM-d) δ ppm 1.19-1.37 (m, 6 H) 2.17-2.35 (m, 6 H) 2.48-2.69 (m, 2 H) 4.07-4.25 (m, 2 H) 4.48-4.67 (m, 2 H) 6.09-6.48 (m, 1 H) 6.84-7.00 (m, 2 H) 10.11-10.48 (m, 1 H). MS ESI/APCI Dual posi: 427 [M + H]$^+$, 449 [M + Na]$^+$. MS ESI/APCI Dual nega: 425 [M − H]$^−$. | |
| Example 1-171 | 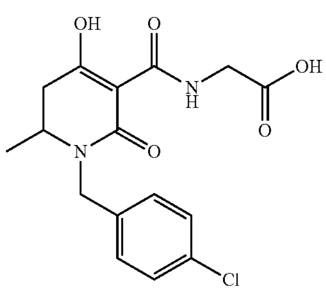 [SMILES: CC1CC(O)=C(C(=O)NCC(=O)O)C(=O)N1Cc1ccc(Cl)cc1] | $^1$H NMR (300 MHz, DMSO-d$_6$) δ ppm 1.06-1.14 (m, 3 H) 2.13-2.25 (m, 1 H) 2.80-2.98 (m, 1 H) 3.47-3.63 (m, 3 H) 4.05-4.21 (m, 1 H) 4.92-5.01 (m, 1 H) 7.27-7.43 (m, 4 H) 10.05 (br. s., 1 H). MS ESI/APCI Dual posi: 353 [M + H]$^+$. | Na |

TABLE 21-25

| Compound No. | Structure | Analytical Data | Salt information |
|---|---|---|---|
| Example 1-172 | 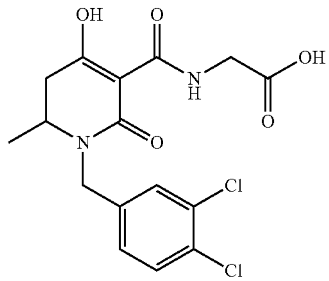 [SMILES: CC1CC(O)=C(C(=O)NCC(=O)O)C(=O)N1Cc1ccc(Cl)c(Cl)c1] | ¹H NMR (300 MHz, CHLOROFORM-d) δ ppm 1.15-1.30 (m, 3 H) 2.09-2.44 (m, 1 H) 2.76-3.01 (m, 1 H) 3.46-3.66 (m, 1 H) 3.82-4.05 (m, 1 H) 4.07-4.25 (m, 2 H) 5.04-5.26 (m, 1 H) 7.04-7.20 (m, 1 H) 7.31-7.49 (m, 2 H) 9.97-10.33 (m, 1 H).<br>MS ESI/APCI Dual posi: 387 [M + H]⁺.<br>MS ESI/APCI Dual nega: 385 [M − H]⁻. | |
| Example 1-173 | 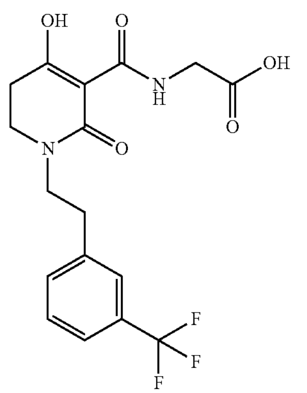 [SMILES: O=C(O)CNC(=O)C1=C(O)CCN(CCc2cccc(C(F)(F)F)c2)C1=O] | ¹H NMR (600 MHz, DMSO-d₆) δ ppm 2.29-2.50 (m, 2 H) 2.90 (t, J = 6.8 Hz, 2 H) 3.29-3.35 (m, 2 H) 3.45 (d, J = 4.5 Hz, 2 H) 3.57 (br. s., 2 H) 7.46-7.70 (m, 4 H).<br>MS ESI/APCI Dual posi: 387 [M + H]⁺, 409 [M + Na]⁺.<br>MS ESI/APCI Dual nega: 385 [M − H]⁻. | Na |
| Example 1-174 | 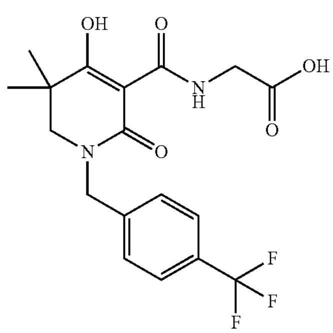 [SMILES: CC1(C)CN(Cc2ccc(C(F)(F)F)cc2)C(=O)C(C(=O)NCC(=O)O)=C1O] | ¹H NMR (300 MHz, CHLOROFORM-d) δ ppm 0.99-1.22 (m, 6 H) 2.98-3.12 (m, 2 H) 4.13-4.25 (m, 2 H) 4.60-4.73 (m, 2 H) 7.33-7.50 (m, 2 H) 7.54-7.68 (m, 2 H) 10.19-10.65 (m, 1 H).<br>MS ESI/APCI Dual posi: 401 [M + H]⁺, 423 [M + Na]⁺.<br>MS ESI/APCI Dual nega: 399 [M − H]⁻. | |
| Example 1-175 | 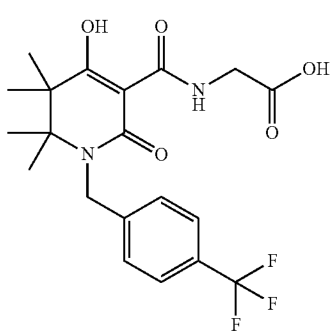 [SMILES: CC1(C)C(O)=C(C(=O)NCC(=O)O)C(=O)N(Cc2ccc(C(F)(F)F)cc2)C1(C)C] | ¹H NMR (300 MHz, METHANOL-d₄) δ ppm 1.02-1.27 (m, 12 H) 3.82-3.93 (m, 2 H) 4.80-4.87 (m, 2 H) 7.43-7.67 (m, 4 H).<br>MS ESI/APCI Dual posi: 429 [M + H]⁺, 451 [M + Na]⁺.<br>MS ESI/APCI Dual nega: 427 [M − H]⁻. | Na |

TABLE 21-25-continued

| Compound No. | Structure | Analytical Data | Salt information |
|---|---|---|---|
| Example 1-176 | 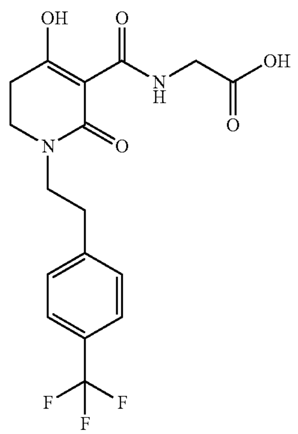 [SMILES: O=C(O)CNC(=O)C1=C(O)CCN(CCc2ccc(C(F)(F)F)cc2)C1=O] | $^1$H NMR (600 MHz, DMSO-d$_6$) δ ppm 2.41-2.53 (m, 2 H) 2.84-2.97 (m, 2 H) 3.29-3.36 (m, 2 H) 3.44 (d, J = 4.1 Hz, 2 H) 3.57 (br. s., 2 H) 7.50 (d, J = 8.0 Hz, 2 H) 7.66 (d, J = 8.0 Hz, 2 H). MS ESI/APCI Dual nega: 385 [M − H]$^-$. | Na |
| Example 1-177 | 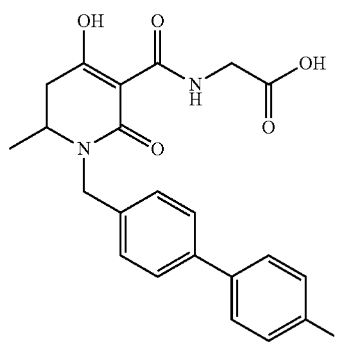 | $^1$H NMR (600 MHz, DMSO-d$_6$) δ ppm 1.13 (d, J = 6.6 Hz, 3 H) 2.10-2.34 (m, 1 H) 2.76-3.03 (m, 1 H) 3.51 (d, J = 4.5 Hz, 2 H) 3.62 (d, J = 5.0 Hz, 1 H) 4.00-4.28 (m, 1 H) 5.05 (d, J = 15.3 Hz, 1 H) 7.24-7.32 (m, 2 H) 7.39 (d, J = 7.8 Hz, 2 H) 7.61 (d, J = 8.3 Hz, 2 H) 7.66-7.73 (m, 2 H). MS ESI/APCI Dual posi: 413 [M + H]$^+$. MS ESI/APCI Dual nega: 411 [M − H]$^-$. | Na |
| Example 1-178 | 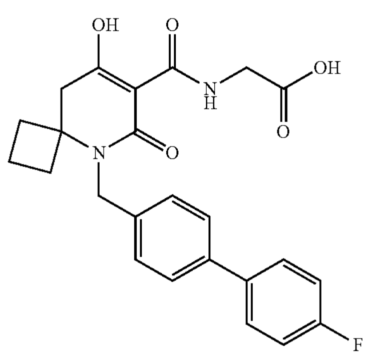 [SMILES: O=C(O)CNC(=O)C1=C(O)CC2(CCC2)N(Cc2ccc(-c3ccc(F)cc3)cc2)C1=O] | $^1$H NMR (600 MHz, CHLOROFORM-d) δ ppm 1.70-1.82 (m, 2 H) 1.93-2.01 (m, 2 H) 2.36-2.46 (m, 2 H) 2.82-2.94 (m, 2 H) 4.14-4.22 (m, 2 H) 4,81-4.97 (m, 2 H) 7.08-7.15 (m, 2 H) 7.27-7.34 (m, 2 H) 7.46-7.55 (m, 4 H) 10.03-10.46 (m, 1 H). MS ESI/APCI Dual posi: 439 [M + H]$^+$, 461 [M + Na]$^+$. MS ESI/APCI Dual nega: 437 [M − H]$^-$. | |

TABLE 21-26

| Compound No. | Structure | Analytical Data | Salt information |
|---|---|---|---|
| Example 1-179 | 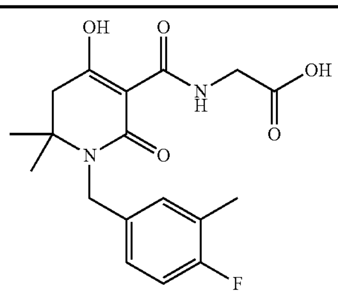 | $^1$H NMR (300 MHz, CHLOROFORM-d) δ ppm 1.17-1.39 (m, 6 H) 2.12-2.33 (m, 3 H) 2.48-2.68 (m, 2 H) 4.10-4.25 (m, 2 H) 4.50-4.67 (m, 2 H) 6.88-7.12 (m, 3 H) 10.17-10.44 (m, 1 H). MS ESI/APCI Dual posi: 365 [M + H]$^+$, 387 [M + Na]$^+$. MS ESI/APCI Dual nega: 363 [M − H]$^-$. | |

TABLE 21-26-continued

| Compound No. | Structure | Analytical Data | Salt information |
|---|---|---|---|
| Example 1-180 | 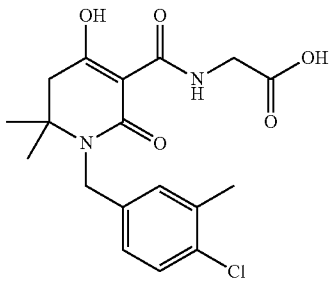 [SMILES: Cc1cc(CN2C(=O)C(C(=O)NCC(=O)O)=C(O)CC2(C)C)ccc1Cl] | $^1$H NMR (300 MHz, DMSO-$d_6$) δ ppm 1.18 (s, 6 H) 2.31 (s, 3 H) 2.39-2.62 (m, 2 H) 3.47 (d, J = 4.4 Hz, 2 H) 4.58 (br. s., 2 H) 7.13 (d, J = 8.2 Hz, 1 H) 7.25 (s, 1 H) 7.32 (d, J = 8.2 Hz, 1 H) 10.02 (br. s., 1 H).<br>MS ESI/APCI Dual posi: 403 [M + Na]$^+$.<br>MS ESI/APCI Dual nega: 379 [M − H]$^−$. | Na |
| Example 1-181 | 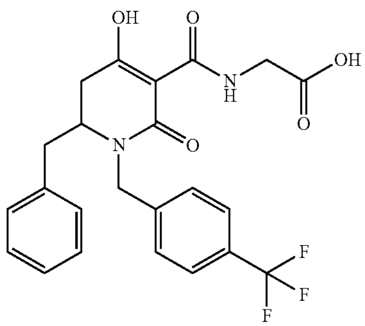 [SMILES: O=C(O)CNC(=O)C1=C(O)CC(Cc2ccccc2)N(Cc2ccc(C(F)(F)F)cc2)C1=O] | $^1$H NMR (300 MHz, CHLOROFORM-d) δ ppm 2.33-2.48 (m, 1 H) 2.60-2.87 (m, 2 H) 2.91-3.04 (m, 1 H) 3.46-3.61 (m, 1 H) 3.62-3.77 (m, 1 H) 4.18-4.26 (m, 2 H) 5.16-5.45 (m, 1 H) 7.02-7.16 (m, 2 H) 7.27-7.40 (m, 5 H) 7.55-7.64 (m, 2 H) 9.98-10.47 (m, 1 H).<br>MS ESI/APCI Dual posi: 463 [M + H]$^+$, 485 [M + Na]$^+$.<br>MS ESI/APCI Dual nega: 461 [M − H]$^−$. | |
| Example 1-182 | 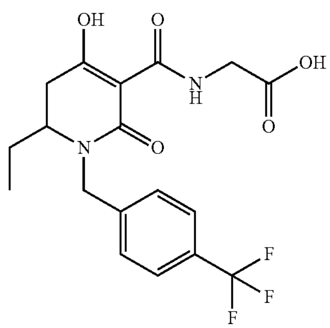 [SMILES: CCC1CC(O)=C(C(=O)NCC(=O)O)C(=O)N1Cc1ccc(C(F)(F)F)cc1] | $^1$H NMR (300 MHz, CHLOROFORM-d) δ ppm 0.92 (t, J = 7.5 Hz, 3 H) 1.62-1.75 (m, 2 H) 2.42-2.54 (m, 1 H) 2.74-2.94 (m, 1 H) 3.22-3.33 (m, 1 H) 3.90-4.10 (m, 1 H) 4.14-4.25 (m, 2 H) 5.28-5.47 (m, 1 H) 7.35-7.43 (m, 2 H) 7.56-7.65 (m, 2 H) 10.01-10.38 (m, 1 H).<br>MS ESI/APCI Dual posi: 401 [M + H]$^+$, 423 [M + Na]$^+$.<br>MS ESI/APCI Dual nega: 399 [M − H]$^−$. | |
| Example 1-183 | 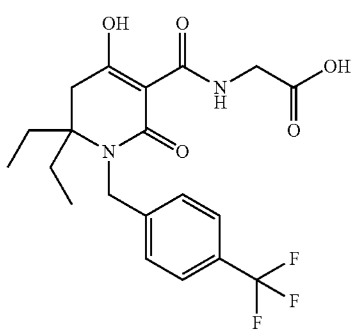 [SMILES: CCC1(CC)CC(O)=C(C(=O)NCC(=O)O)C(=O)N1Cc1ccc(C(F)(F)F)cc1] | $^1$H NMR (300 MHz, CHLOROFORM-d) δ ppm 0.74-0.94 (m, 6 H) 1.57-1.81 (m, 4 H) 2.56-2.72 (m, 2 H) 4.10-4.24 (m, 2 H) 4.64-4.79 (m, 2 H) 7.30-7.44 (m, 2 H) 7.49-7.67 (m, 2 H) 10.09-10.34 (m, 1 H).<br>MS ESI/APCI Dual posi: 429 [M + H]$^+$, 451 [M + Na]$^+$.<br>MS ESI/APCI Dual nega: 427 [M − H]$^−$. | |
| Example 1-184 | 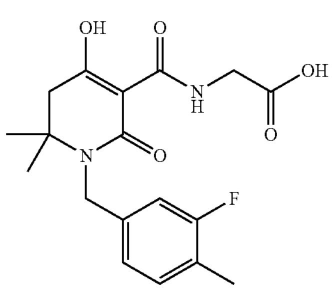 [SMILES: Cc1ccc(CN2C(=O)C(C(=O)NCC(=O)O)=C(O)CC2(C)C)cc1F] | $^1$H NMR (300 MHz, DMSO-$d_6$) δ ppm 1.17 (s, 6 H) 2.16-2.22 (m, 3 H) 2.49-2.59 (m, 2 H) 3.43-3.53 (m, 2 H) 4.59 (s, 2 H) 6.98-7.07 (m, 2 H) 7.15-7.25 (m, 1 H) 9.97-10.24 (m, 1 H).<br>MS ESI/APCI Dual posi: 365 [M + H]$^+$.<br>MS ESI/APCI Dual nega: 363 [M − H]$^−$. | Na |

TABLE 21-26-continued

| Compound No. | Structure | Analytical Data | Salt information |
|---|---|---|---|
| Example 1-185 | 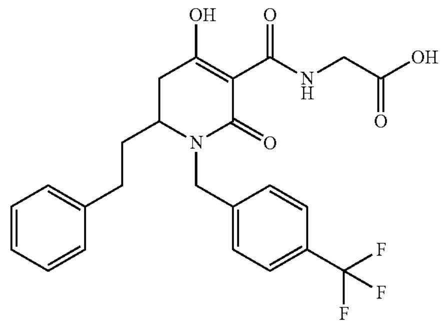 [SMILES: O=C(O)CNC(=O)C1=C(O)CC(CCc2ccccc2)N(Cc2ccc(C(F)(F)F)cc2)C1=O] | $^1$H NMR (300 MHz, CHLOROFORM-d) δ ppm 1.79-2.13 (m, 2 H) 2.39-2.56 (m, 2 H) 2.68-2.92 (m, 2 H), 3.21-3.35 (m, 1 H) 3.71-3.93 (m, 1 H) 4.15-4.25 (m, 2 H) 5.17-5.37 (m, 1 H) 7.06-7.35 (m, 7 H) 7.48-7.57 (m, 2 H) 10.05-10.13 (m, 1 H).<br>MS ESI/APCI Dual posi: 477 [M + H]$^+$, 499 [M + Na]$^+$.<br>MS ESI/APCI Dual nega: 475 [M − H]$^−$. | |

TABLE 21-27

| Compound No. | Structure | Analytical Data | Salt information |
|---|---|---|---|
| Example 1-186 | 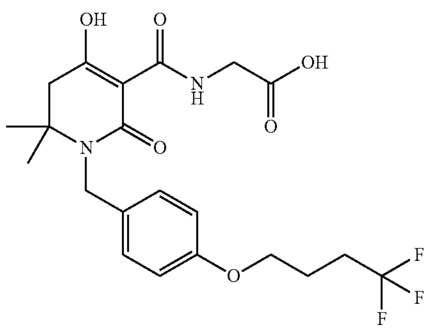 [SMILES: CC1(C)CC(O)=C(C(=O)NCC(=O)O)C(=O)N1Cc1ccc(OCCCC(F)(F)F)cc1] | $^1$H NMR (300 MHz, CHLOROFORM-d) δ ppm 1.22-1.30 (m, 6 H) 1.95-2.11 (m, 2 H) 2.20-2.42 (m, 2 H) 2.45-2.63 (m, 2 H) 3.90-4.08 (m, 2 H) 4.12-4.26 (m, 2 H) 4.55-4.71 (m, 2 H) 6.78-6.88 (m, 2 H) 7.15-7.24 (m, 2 H) 10.21-10.47 (m, 1 H).<br>MS ESI/APCI Dual posi: 481 [M + Na]$^+$.<br>MS ESI/APCI Dual nega: 457 [M − H]$^−$. | |
| Example 1-187 | 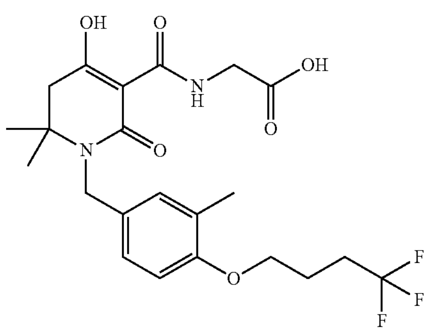 [SMILES: Cc1cc(CN2C(=O)C(C(=O)NCC(=O)O)=C(O)CC2(C)C)ccc1OCCCC(F)(F)F] | $^1$H NMR (300 MHz, CHLOROFORM-d) δ ppm 1.21-1.35 (m, 6 H) 1.97-2.13 (m, 2 H) 2.17-2.24 (m, 3 H) 2.23-2.44 (m, 2 H) 2.49-2.64 (m, 2 H) 3.92-4.07 (m, 2 H) 4.14-4.24 (m, 2 H) 4.53-4.65 (m, 2 H) 6.65-6.77 (m, 1 H) 6.96-7.10 (m, 2 H) 10.25-10.42 (m, 1 H).<br>MS ESI/APCI Dual posi: 495 [M + Na]$^+$.<br>MS ESI/APCI Dual nega: 471 [M − H]$^−$. | |
| Example 1-188 | 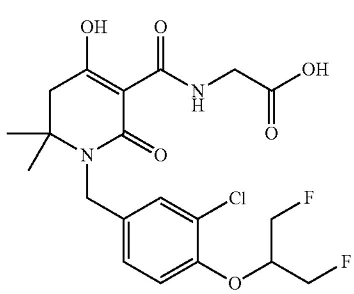 [SMILES: CC1(C)CC(O)=C(C(=O)NCC(=O)O)C(=O)N1Cc1ccc(OC(CF)CF)c(Cl)c1] | $^1$H NMR (300 MHz, CHLOROFORM-d) δ ppm 1.26-1.30 (m, 6 H) 2.52-2.68 (m, 2 H) 4.15-4.24 (m, 2 H) 4.51-4.68 (m, 5 H) 4.75-4.80 (m, 2 H) 7.00-7.07 (m, 1 H) 7.09-7.17 (m, 1 H) 7.27-7.33 (m, 1 H) 10.10-10.36 (m, 1 H).<br>MS ESI/APCI Dual posi: 483 [M + Na]$^+$.<br>MS ESI/APCI Dual nega: 459 [M − H]$^−$. | |

TABLE 21-27-continued

| Compound No. | Structure | Analytical Data | Salt information |
|---|---|---|---|
| Example 1-189 | 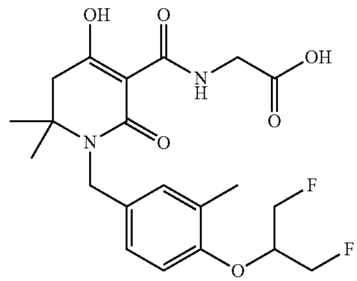 [SMILES: Cc1cc(CN2C(=O)C(C(=O)NCC(=O)O)=C(O)CC2(C)C)ccc1OC(CF)CF] | $^1$H NMR (300 MHz, DMSO-d$_6$) δ ppm 1.07 (s, 6 H) 2.10-2.21 (m, 5 H) 3.43 (d, J = 4.4 Hz, 2 H) 4.40-4.87 (m, 7 H) 6.86-6.99 (m, 1 H) 6.99-7.11 (m, 2 H) 10.07-10.20 (m, 1 H). MS ESI/APCI Dual posi: 463 [M + Na]$^+$. MS ESI/APCI Dual nega: 439 [M − H]$^−$. | Na |
| Example 1-190 | 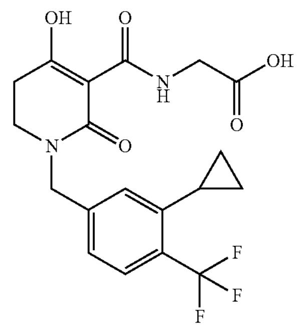 [SMILES: O=C(O)CNC(=O)C1=C(O)CCN(Cc2ccc(C(F)(F)F)c(C3CC3)c2)C1=O] | $^1$H NMR (600 MHz, CHLOROFORM-d) δ ppm 0.68-0.81 (m, 2 H) 0.98-1.09 (m, 2 H) 2.15-2.25 (m, 1 H) 2.54-2.68 (m, 2 H) 3.26-3.38 (m, 2 H) 4.15-4.25 (m, 2 H) 4.55-4.65 (m, 2 H) 6.92 (s, 1 H) 7.09-7.17 (m, 1 H) 7.45-7.74 (m, 1 H) 9.98-10.64 (m, 1 H). MS ESI/APCI Dual posi: 413 [M + H]$^+$. MS ESI/APCI Dual nega: 411 [M − H]$^−$. | |
| Example 1-191 | 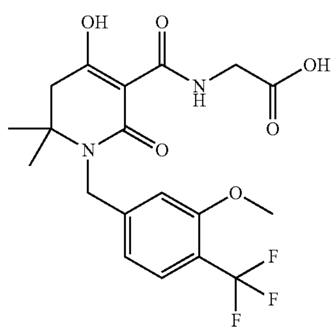 [SMILES: COc1cc(CN2C(=O)C(C(=O)NCC(=O)O)=C(O)CC2(C)C)ccc1C(F)(F)F] | $^1$H NMR (600 MHz, CHLOROFORM-d) δ ppm 1.21-1.34 (m, 6 H) 2.54-2.67 (m, 2 H) 3.83-3.92 (m, 3 H) 4.08-4.23 (m, 2 H) 4.61-4.76 (m, 2 H) 3.83-3.92 (m, 3 H) 4.08-4.23 (m, 2 H) 4.61-4.76 (m, 2 H) 6.84-6.95 (m, 2 H) 7.45-7.54 (m, 1 H) 9.99-10.45 (m, 1 H). MS ESI/APCI Dual posi: 431 [M + H]$^+$, 453 [M + Na]$^+$. MS ESI/APCI Dual nega: 429 [M − H]$^−$. | |
| Example 1-192 | 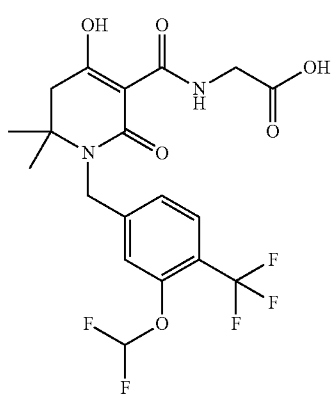 [SMILES: CC1(C)CC(O)=C(C(=O)NCC(=O)O)C(=O)N1Cc1ccc(C(F)(F)F)c(OC(F)F)c1] | $^1$H NMR (600 MHz, CHLOROFORM-d) δ ppm 1.24-1.34 (m, 6 H) 2.55-2.69 (m, 2 H) 4.15-4.23 (m, 2 H) 4.62-4.77 (m, 2 H) 6.36-6.69 (m, 1 H) 7.16-7.29 (m, 2 H) 7.58-7.67 (m, 1 H) 9.91-10.55 (m, 1 H). MS ESI/APCI Dual posi: 467 [M + H]$^+$, 489 [M + Na]$^+$. MS ESI/APCI Dual nega: 465 [M − H]$^−$. | |

TABLE 21-28

| Compound No. | Structure | Analytical Data | Salt information |
| --- | --- | --- | --- |
| Example 1-193 | 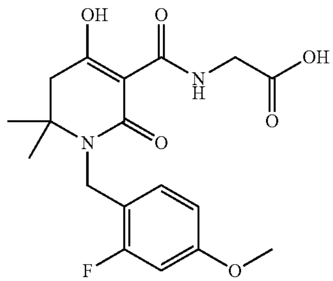 [SMILES: COc1ccc(CN2C(=O)C(C(=O)NCC(=O)O)=C(O)CC2(C)C)c(F)c1] | ¹H NMR (300 MHz, CHLOROFORM-d) δ ppm 1.23-1.30 (m, 6 H) 2.47-2.65 (m, 2 H) 3.71-3.83 (m, 3 H) 4.09-4.25 (m, 2 H) 4.59-4.72 (m, 2 H) 6.54-6.71 (m, 2 H) 7.18-7.24 (m, 1 H) 10.17-10.43 (m, 1 H).<br>MS ESI/APCI Dual posi: 403 [M + Na]⁺.<br>MS ESI/APCI Dual nega: 379 [M − H]⁻. | |
| Example 1-194 | 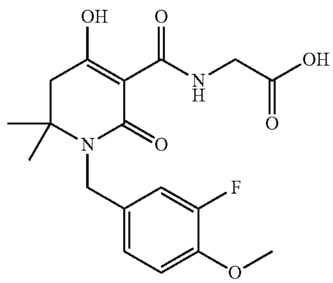 [SMILES: COc1ccc(CN2C(=O)C(C(=O)NCC(=O)O)=C(O)CC2(C)C)cc1F] | ¹H NMR (300 MHz, CHLOROFORM-d) δ ppm 1.19-1.33 (m, 6 H) 2.49-2.64 (m, 2 H) 3.82-3.91 (m, 3 H) 4.12-4.25 (m, 2 H) 4.52-4.65 (m, 2 H) 6.82-7.12 (m, 3 H) 10.17-10.44 (m, 1 H).<br>MS ESI/APCI Dual posi: 403 [M + Na]⁺.<br>MS ESI/APCI Dual nega: 379 [M − H]⁻. | |
| Example 1-195 | 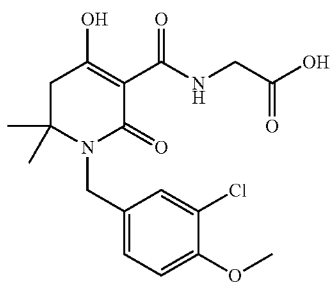 [SMILES: COc1ccc(CN2C(=O)C(C(=O)NCC(=O)O)=C(O)CC2(C)C)cc1Cl] | ¹H NMR (300 MHz, CHLOROFORM-d) δ ppm 1.17-1.36 (m, 6 H) 2.48-2.64 (m, 2 H) 3.82-3.93 (m, 3 H) 4.14-4.26 (m, 2 H) 4.52-4.64 (m, 2 H) 6.84-6.92 (m, 1 H) 7.10-7.19 (m, 1 H) 7.25-7.32 (m, 1 H) 10.18-10.45 (m, 1 H).<br>MS ESI/APCI Dual posi: 419 [M + Na]⁺.<br>MS ESI/APCI Dual nega: 395 [M − H]⁻. | |
| Example 1-196 | 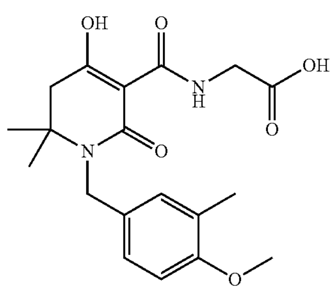 [SMILES: COc1ccc(CN2C(=O)C(C(=O)NCC(=O)O)=C(O)CC2(C)C)cc1C] | ¹H NMR (300 MHz, DMSO-d₆) δ ppm 1.17 (s, 6 H) 2.12 (s, 3 H) 2.40-2.60 (m, 2 H) 3.45 (d, J = 4.2 Hz, 2 H) 3.75 (s, 3H) 4.53 (br. s., 2 H) 6.84 (d, J = 7.9 Hz, 1 H) 7.01-7.12 (m, 2 H).<br>MS ESI/APCI Dual posi: 399 [M + Na]⁺.<br>MS ESI/APCI Dual nega: 375 [M − H]⁻. | Na |
| Example 1-197 | 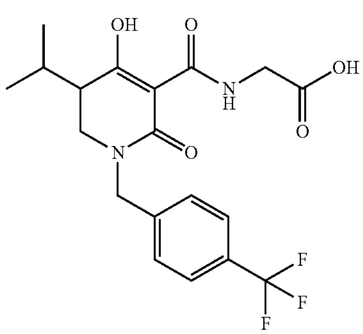 [SMILES: CC(C)C1CN(Cc2ccc(C(F)(F)F)cc2)C(=O)C(C(=O)NCC(=O)O)=C1O] | ¹H NMR (600 MHz, CHLOROFORM-d) δ ppm 0.73-0.80 (m, 3 H) 0.89-0.98 (m, 3 H) 1.97-2.14 (m, 1 H) 2.15-2.28 (m, 1 H) 3.17-3.29 (m, 1 H) 3.36-3.46 (m, 1 H) 4.12-4.27 (m, 2 H) 4.55-4.75 (m, 2 H) 7.37-7.44 (m, 2 H) 7.57-7.64 (m, 2 H) 10.11-10.61 (m, 1 H).<br>MS ESI/APCI Dual posi: 415 [M + H]⁺.<br>MS ESI/APCI Dual nega: 413 [M − H]⁻. | |

TABLE 21-28-continued

| Compound No. | Structure | Analytical Data | Salt information |
|---|---|---|---|
| Example 1-198 | 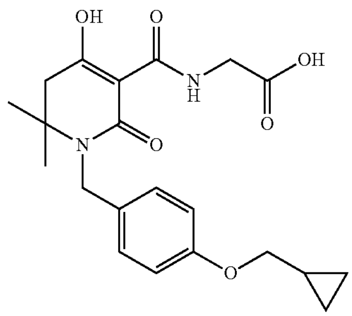 [SMILES: CC1(C)CC(O)=C(C(=O)NCC(=O)O)C(=O)N1Cc1ccc(OCC2CC2)cc1] | $^1$H NMR (300 MHz, CHLOROFORM-d) δ ppm 0.29-0.38 (m, 2 H) 0.58-0.69 (m, 2 H) 1.18-1.32 (m, 7 H) 2.48-2.62 (m, 2 H) 3.73-3.82 (m, 2 H) 4.12-4.23 (m, 2 H) 4.57-4.68 (m, 2 H) 6.80-6.89 (m, 2 H) 7.12-7.23 (m, 2 H) 10.24-10.41 (m, 1 H).<br>MS ESI/APCI Dual posi: 403 [M + H]$^+$.<br>MS ESI/APCI Dual nega: 401 [M − H]$^-$. | |
| Example 1-199 | 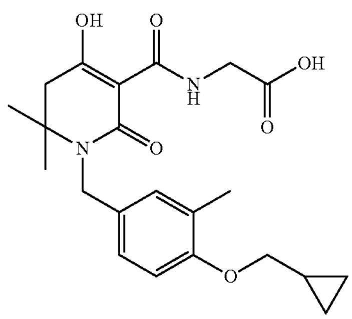 [SMILES: Cc1cc(CN2C(=O)C(C(=O)NCC(=O)O)=C(O)CC2(C)C)ccc1OCC1CC1] | $^1$H NMR (300 MHz, DMSO-d$_6$) δ ppm 0.27-0.37 (m, 2 H) 0.49-0.60 (m, 2 H) 1.09-1.29 (m, 7 H) 2.14 (s, 3 H) 2.41-2.64 (m, 2 H) 3.45-3.53 (m, 2 H) 3.74-3.83 (m, 2 H) 4.52 (s, 2 H) 6.74-6.86 (m, 1 H) 6.96-7.10 (m, 2 H) 9.94-10.38 (m, 1 H).<br>MS ESI/APCI Dual posi: 417 [M + H]$^+$.<br>MS ESI/APCI Dual nega: 415 [M − H]$^-$. | Na |

TABLE 21-29

| Compound No. | Structure | Analytical Data | Salt information |
|---|---|---|---|
| Example 1-200 | 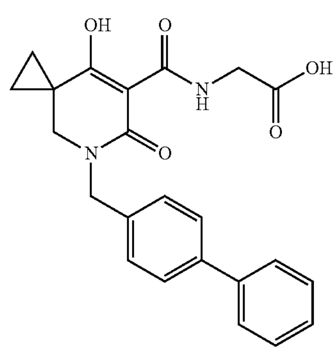 [SMILES: O=C(O)CNC(=O)C1=C(O)C2(CC2)CN(Cc2ccc(-c3ccccc3)cc2)C1=O] | $^1$H NMR (300 MHz, DMSO-d$_6$) δ ppm 0.65-0.77 (m, 2 H) 1.06-1.15 (m, 2 H) 3.23 (s, 2 H) 3.52-3.59 (m, 2 H) 4.61 (s, 2 H) 7.31-7.40 (m, 3 H) 7.41-7.51 (m, 2 H) 7.60-7.69 (m, 4 H) 10.27 (br. s., 1 H).<br>MS ESI/APCI Dual posi: 407 [M + H]$^+$.<br>MS ESI/APCI Dual nega: 405 [M − H]$^-$. | Na |
| Example 1-201 | 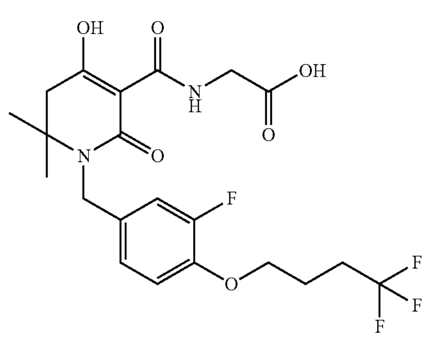 [SMILES: CC1(C)CC(O)=C(C(=O)NCC(=O)O)C(=O)N1Cc1ccc(OCCCC(F)(F)F)c(F)c1] | $^1$H NMR (300 MHz, CHLOROFORM-d) δ ppm 1.22-1.34 (m, 6 H) 1.96-2.15 (m, 2 H) 2.23-2.45 (m, 2 H) 2.49-2.68 (m, 2 H) 3.98-4.11 (m, 2 H) 4.14-4.27 (m, 2 H) 4.52-4.66 (m, 2 H) 6.79-7.11 (m, 3 H) 10.17-10.45 (m, 1 H).<br>MS ESI/APCI Dual posi: 477 [M + H]$^+$.<br>MS ESI/APCI Dual nega: 475 [M − H]$^-$. | |

TABLE 21-29-continued

| Compound No. | Structure | Analytical Data | Salt information |
|---|---|---|---|
| Example 1-202 | 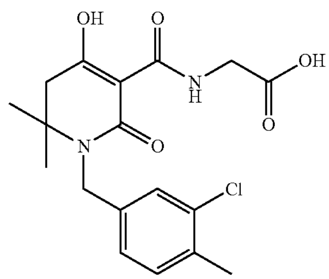 [SMILES: Cc1ccc(CN2C(=O)C(C(=O)NCC(=O)O)=C(O)CC2(C)C)cc1Cl] | ¹H NMR (300 MHz, CHLOROFORM-d) δ ppm 1.21-1.33 (m, 6 H) 2.23-2.42 (m, 3 H) 2.45-2.68 (m, 2 H) 4.12-4.23 (m, 2 H) 4.54-4.67 (m, 2 H) 6.98-7.25 (m, 3 H) 10.17-10.44 (m, 1 H).<br>MS ESI/APCI Dual posi: 381 [M + H]⁺, 403 [M + Na]⁺.<br>MS ESI/APCI Dual nega: 379 [M − H]⁻. | |
| Example 1-203 | 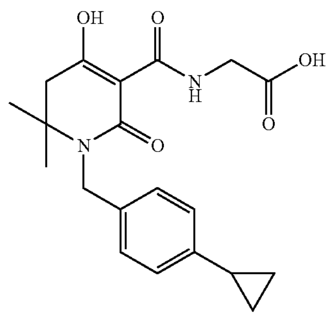 [SMILES: CC1(C)CC(O)=C(C(=O)NCC(=O)O)C(=O)N1Cc1ccc(C2CC2)cc1] | ¹H NMR (300 MHz, CHLOROFORM-d) δ ppm 0.55-0.74 (m, 2 H) 0.85-1.01 (m, 2 H) 1.21-1.33 (m, 6 H) 1.76-1.94 (m, 1 H) 2.45-2.66 (m, 2 H) 4.08-4.25 (m, 2 H) 4.54-4.73 (m, 2 H) 6.95-7.06 (m, 2 H) 7.09-7.20 (m, 2 H) 10.21-10.42 (m, 1 H).<br>MS ESI/APCI Dual posi: 373 [M + H]⁺, 395 [M + Na]⁺.<br>MS ESI/APCI Dual nega: 371 [M − H]⁻. | |
| Example 1-204 | 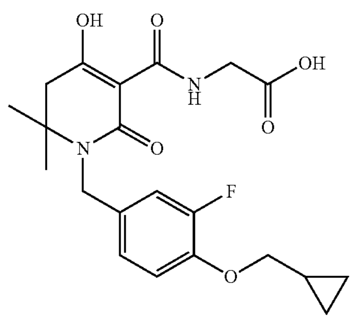 [SMILES: CC1(C)CC(O)=C(C(=O)NCC(=O)O)C(=O)N1Cc1ccc(OCC2CC2)c(F)c1] | ¹H NMR (600 MHz, CHLOROFORM-d) δ ppm 0.28-0.40 (m, 2 H) 0.57-0.70 (m, 2 H) 1.17-1.35 (m, 7 H) 2.50-2.64 (m, 2 H) 3.81-3.89 (m, 2 H) 4.10-4.23 (m, 2 H) 4.53-4.65 (m, 2 H) 6.80-7.10 (m, 3 H) 10.15-10.43 (m, 1 H).<br>MS ESI/APCI Dual posi: 421 [M + H]⁺.<br>MS ESI/APCI Dual nega: 419 [M − H]⁻. | |
| Example 1-205 | 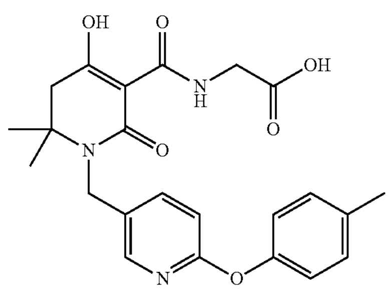 | ¹H NMR (300 MHz, CHLOROFORM-d) δ ppm 2.53-2.68 (m, 2 H) 3.31-3.42 (m, 2 H) 4.15-4.22 (m, 2 H) 4.55-4.62 (m, 2 H) 6.88-7.08 (m, 6 H) 7.19-7.26 (m, 2 H) 10.17-10.44 (m, 1 H).<br>MS ESI/APCI Dual posi: 415 [M + H]⁺, 437 [M + Na]⁺.<br>MS ESI/APCI Dual nega: 413 [M − H]⁻. | |
| Example 1-206 | 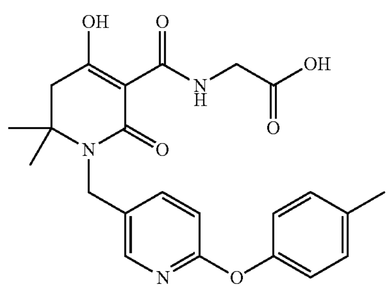 | ¹H NMR (300 MHz, CHLOROFORM-d) δ ppm 1.23-1.34 (m, 6 H) 2.35 (s, 3 H) 2.50-2.62 (m, 2 H) 4.13-4.22 (m, 2 H) 4.56-4.65 (m, 2 H) 6.80-6.90 (m, 1 H) 6.95-7.06 (m, 2 H) 7.17-7.22 (m, 2 H) 7.60-7.72 (m, 1 H) 8.08-8.17 (m, 1 H) 10.16-10.48 (m, 1 H).<br>MS ESI/APCI Dual posi: 440 [M + H]⁺, 462 [M + Na]⁺.<br>MS ESI/APCI Dual nega: 438 [M − H]⁻. | |

TABLE 21-30

| Compound No. | Structure | Analytical Data | Salt information |
|---|---|---|---|
| Example 1-207 | 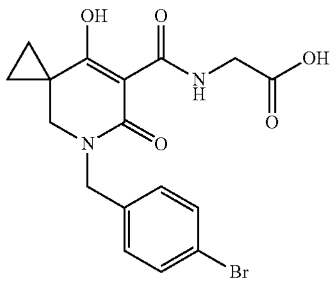 [SMILES: O=C(O)CNC(=O)C1=C(O)C2(CC2)CN(Cc2ccc(Br)cc2)C1=O] | ¹H NMR (300 MHz, CHLOROFORM-d) δ ppm 0.50-0.75 (m, 2 H) 1.23-1.45 (m, 2 H) 3.07-3.17 (m, 2 H) 4.14-4.23 (m, 2 H) 4.54-4.60 (m, 2 H) 7.10-7.19 (m, 2 H) 7.42-7.52 (m, 2 H) 10.17-10.56 (m, 1 H).<br>MS ESI/APCI Dual posi: 411 [M + H]⁺.<br>MS ESI/APCI Dual nega: 409 [M − H]⁻. | |
| Example 1-208 | 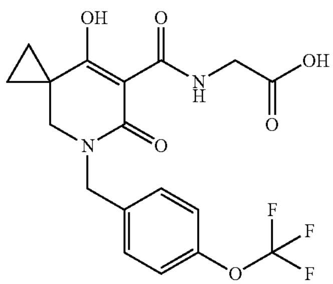 [SMILES: O=C(O)CNC(=O)C1=C(O)C2(CC2)CN(Cc2ccc(OC(F)(F)F)cc2)C1=O] | ¹H NMR (300 MHz, CHLOROFORM-d) δ ppm 0.52-0.78 (m, 2 H) 1.27-1.47 (m, 2 H) 3.09-3.21 (m, 2 H) 4.15-4.24 (m, 2 H) 4.58-4.66 (m, 2 H) 7.11-7.40 (m, 4 H) 10.17-10.63 (m, 1 H).<br>MS ESI/APCI Dual posi: 415 [M + H]⁺.<br>MS ESI/APCI Dual nega: 413 [M − H]⁻. | |
| Example 1-209 | 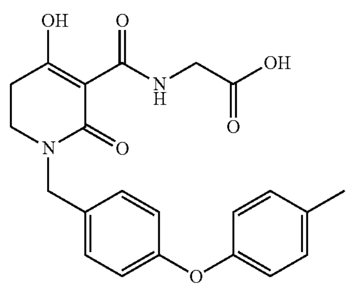 | ¹H NMR (300 MHz, DMSO-d₆) δ ppm 2.28 (s, 3 H) 2.62-2.77 (m, 2 H) 3.27-3.47 (m, 2 H) 3.95-4.10 (m, 2 H) 4.46-4.64 (m, 2 H) 6.85-7.00 (m, 4 H) 7.12-7.21 (m, 2 H) 7.24-7.34 (m, 2 H) 9.97-10.28 (m, 1 H) 12.85 (br. s., 1 H).<br>MS ESI/APCI Dual posi: 411 [M + H]⁺, 433 [M + Na]⁺.<br>MS ESI/APCI Dual nega: 409 [M − H]⁻. | |
| Example 1-210 | 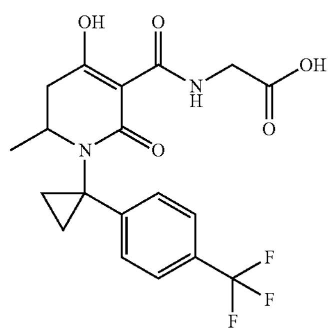 [SMILES: CC1CC(O)=C(C(=O)NCC(=O)O)C(=O)N1C1(c2ccc(C(F)(F)F)cc2)CC1] | ¹H NMR (300 MHz, CHLOROFORM-d) δ ppm 1.07-1.20 (m, 3 H) 1.20-1.41 (m, 2 H) 1.49-1.72 (m, 2 H) 2.23-2.40 (m, 1 H) 2.75-3.03 (m, 1 H) 3.83-4.00 (m, 1 H) 4.07-4.25 (m, 2 H) 7.37-7.49 (m, 2 H) 7.49-7.60 (m, 2 H) 10.03-10.40 (m, 1 H).<br>MS ESI/APCI Dual posi: 413 [M + H]⁺.<br>MS ESI/APCI Dual nega: 411 [M − H]⁻. | |
| Example 1-211 | 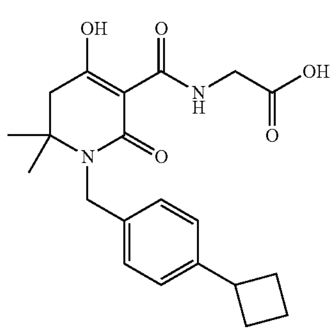 [SMILES: CC1(C)CC(O)=C(C(=O)NCC(=O)O)C(=O)N1Cc1ccc(C2CCC2)cc1] | ¹H NMR (600 MHz, CHLOROFORM-d) δ ppm 1.23-1.31 (m, 6 H) 1.79-1.89 (m, 1 H) 1.95-2.06 (m, 1 H) 2.07-2.17 (m, 2 H) 2.26-2.37 (m, 2 H) 2.51-2.63 (m, 2 H) 3.46-3.56 (m, 1 H) 4.14-4.23 (m, 2 H) 4.60-4.70 (m, 2 H) 7.12-7.22 (m, 4 H) 10.25-10.41 (m, 1 H).<br>MS ESI/APCI Dual posi: 387 [M + H]⁺, 409 [M + Na]⁺.<br>MS ESI/APCI Dual nega: 358 [M − H]⁻. | |

TABLE 21-30-continued

| Compound No. | Structure | Analytical Data | Salt information |
|---|---|---|---|
| Example 1-212 | (structure) | $^1$H NMR (600 MHz, CHLOROFORM-d) δ ppm 0.70-0.80 (m, 2 H) 0.99-1.09 (m, 2 H) 2.13-2.24 (m, 1 H) 2.53-2.68 (m, 2 H) 3.29-3.39 (m, 2 H) 4.16-4.24 (m, 2 H) 4.55-4.64 (m, 2 H) 7.01 (d, J = 8.3 Hz, 1 H) 7.34 (d, J = 6.6 Hz, 1 H) 7.45-7.52 (m, 1 H) 10.06-10.54 (m, 1 H).<br>MS ESI/APCI Dual posi: 413 [M + H]$^+$.<br>MS ESI/APCI Dual nega: 411 [M − H]$^-$. | |
| Example 1-213 | (structure) | $^1$H NMR (600 MHz, CHLOROFORM-d) δ ppm 1.33-1.43 (m, 6 H) 2.51-2.71 (m, 2 H) 4.13-4.25 (m, 2 H) 4.67-4.81 (m, 2 H) 6.45-6.61 (m, 1 H) 7.36-7.48 (m, 2 H) 7.67-7.79 (m, 2 H) 9.95-10.55 (m, 1 H).<br>MS ESI/APCI Dual posi: 434 [M + H]$^+$, 456 [M + Na]$^+$.<br>MS ESI/APCI Dual nega: 432 [M − H]$^-$. | |

TABLE 21-31

| Compound No. | Structure | Analytical Data | Salt information |
|---|---|---|---|
| Example 1-214 | (structure) | $^1$H NMR (300 MHz, CHLOROFORM-d) δ ppm 0.49-1.02 (m, 6 H) 1.25-1.42 (m, 2 H) 1.82-1.94 (m, 1 H) 3.07-3.16 (m, 2 H) 4.16-4.21 (m, 2 H) 4.55-4.61 (m, 2 H) 6.99-7.08 (m, 2 H) 7.10-7.19 (m, 2 H) 10.27-10.55 (m, 1 H).<br>MS ESI/APCI Dual posi: 371 [M + H]$^+$.<br>MS ESI/APCI Dual nega: 369 [M − H]$^-$. | |
| Example 1-215 | (structure) | $^1$H NMR (300 MHz, CHLOROFORM-d) δ ppm 0.51-0.76 (m, 2 H) 1.27-1.45 (m, 2 H) 3.09-3.17 (m, 2 H) 4.17-4.23 (m, 2 H) 4.56-4.63 (m, 2 H) 7.15-7.38 (m, 4 H) 10.20-10.59 (m, 1 H).<br>MS ESI/APCI Dual posi: 365 [M + H]$^+$.<br>MS ESI/APCI Dual nega: 363 [M − H]$^-$. | |

TABLE 21-31-continued

| Compound No. | Structure | Analytical Data | Salt information |
|---|---|---|---|
| Example 1-216 | 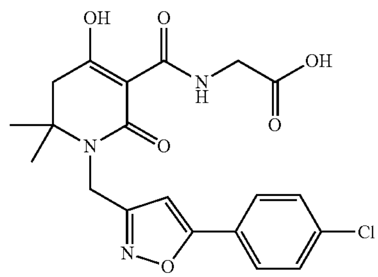 [SMILES: CC1(C)CC(O)=C(C(=O)NCC(=O)O)C(=O)N1Cc1cc(-c2ccc(Cl)cc2)on1] | ¹H NMR (600 MHz, CHLOROFORM-d) δ ppm 1.30-1.43 (m, 6 H) 2.47-2.68 (m, 2 H) 4.04-4.29 (m, 2 H), 4.66-4.84 (m, 2 H) 6.46-6.65 (m, 1 H) 7.37-7.48 (m, 2 H) 7.62-7.77 (m, 2 H) 10.06-10.54 (m, 1 H).<br>MS ESI/APCI Dual posi: 434 [M + H]⁺, 456 [M + Na]⁺.<br>MS ESI/APCI Dual nega: 432 [M − H]⁻. | |
| Example 1-217 | 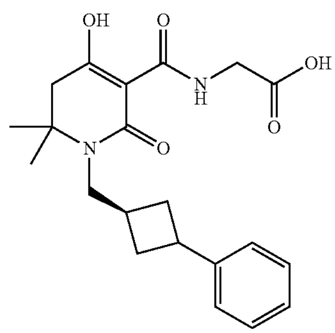 | ¹H NMR (600 MHz, CHLOROFORM-d) δ ppm 1.30-1.38 (m, 6 H) 2.21-2.31 (m, 4 H) 2.47-2.57 (m, 2 H) 2.57-2.69 (m, 1 H) 3.63-3.74 (m, 3 H) 4.14-4.21 (m, 2 H) 7.15-7.22 (m, 1 H) 7.22-7.27 (m, 2 H) 7.28-7.34 (m, 2 H) 10.33 (br. s., 1 H).<br>MS ESI/APCI Dual posi: 387 [M + H]⁺, 409 [M + Na]⁺.<br>MS ESI/APCI Dual nega: 385 [M − H]⁻. | |
| Example 1-218 | 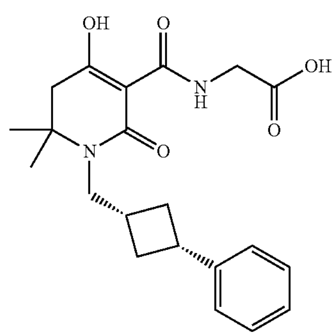 [SMILES: CC1(C)CC(O)=C(C(=O)NCC(=O)O)C(=O)N1C[C@H]1C[C@@H](c2ccccc2)C1] | ¹H NMR (600 MHz, CHLOROFORM-d) δ ppm 1.29-1.36 (m, 6 H) 1.83-1.97 (m, 2 H) 2.45-2.58 (m, 5 H) 3.24-3.38 (m, 1 H) 3.39-3.49 (m, 2 H) 4.17 (dd, J = 10.1, 5.6 Hz, 2 H) 7.15-7.23 (m, 3 H) 7.27-7.33 (m, 2 H) 10.17-10.37 (m, 1 H).<br>MS ESI/APCI Dual posi: 387 [M + H]⁺, 409 [M + Na]⁺.<br>MS ESI/APCI Dual nega: 385 [M − H]⁻. | |
| Example 1-219 | 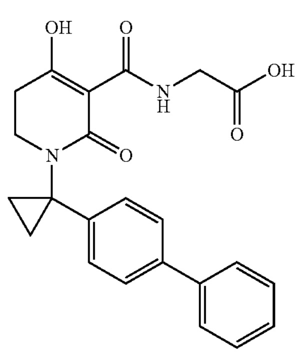 [SMILES: O=C(O)CNC(=O)C1=C(O)CCN(C2(c3ccc(-c4ccccc4)cc3)CC2)C1=O] | ¹H NMR (300 MHz, CHLOROFORM-d) δ ppm 1.32-1.51 (m, 4 H) 2.53-2.76 (m, 2 H) 3.51-3.69 (m, 2 H) 4.04-4.24 (m, 2 H) 7.23-7.37 (m, 3 H) 7.38-7.47 (m, 2 H) 7.49-7.58 (m, 4 H) 10.11-10.46 (m, 1 H).<br>MS ESI/APCI Dual posi: 407 [M + H]⁺.<br>MS ESI/APCI Dual nega: 405 [M − H]⁻. | |

TABLE 21-31-continued

| Compound No. | Structure | Analytical Data | Salt information |
|---|---|---|---|
| Example 1-220 | 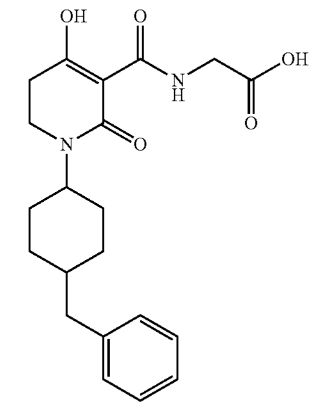 [SMILES: O=C(O)CNC(=O)C1=C(O)CCN(C2CCC(Cc3ccccc3)CC2)C1=O] | $^1$H NMR (300 MHz, METHANOL-d$_4$) δ ppm 1.06-1.27 (m, 1 H) 1.35-2.11 (m, 8 H) 2.44-2.63 (m, 3 H) 2.73 (d, J = 8.1 Hz, 1 H) 3.30-3.54 (m, 2 H) 3.82-3.91 (m, 2 H) 4.22-4.45 (m, 1 H) 7.08-7.33 (m, 5 H). MS ESI/APCI Dual posi: 387 [M + H]$^+$, 409 [M + Na]$^+$. MS ESI/APCI Dual nega: 385 [M − H]$^-$. | Na |

TABLE 21-32

| Compound No. | Structure | Analytical Data | Salt information |
|---|---|---|---|
| Example 1-221 | 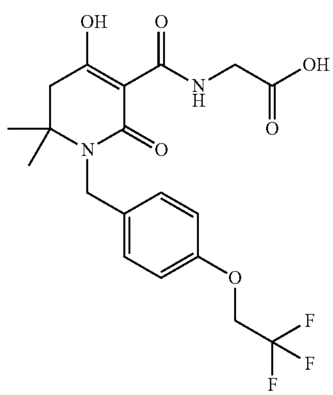 [SMILES: CC1(C)CC(O)=C(C(=O)NCC(=O)O)C(=O)N1Cc1ccc(OCC(F)(F)F)cc1] | $^1$H NMR (300 MHz, CHLOROFORM-d) δ ppm 1.17-1.33 (m, 6 H) 2.47-2.65 (m, 2 H) 4.10-4.25 (m, 2 H) 4.25-4.40 (m, 2 H) 4.57-4.70 (m, 2 H) 6.85-6.94 (m, 2 H) 7.19-7.25 (m, 2 H) 10.21-10.44 (m, 1 H). MS ESI/APCI Dual posi: 431 [M + H]$^+$, 453 [M + Na]$^+$. MS ESI/APCI Dual nega: 429 [M − H]$^-$. | |
| Example 1-222 | 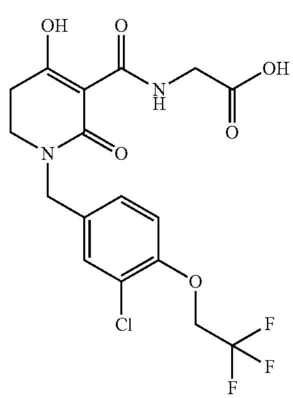 [SMILES: O=C(O)CNC(=O)C1=C(O)CCN(Cc2ccc(OCC(F)(F)F)c(Cl)c2)C1=O] | $^1$H NMR (300 MHz, METHANOL-d$_4$) δ ppm 2.51-2.66 (m, 2 H) 3.30-3.40 (m, 2 H) 3.89 (s, 2 H) 4.50-4.65 (m, 4 H) 7.07-7.16 (m, 1 H) 7.20-7.32 (m, 1 H) 7.34-7.44 (m, 1 H). MS ESI/APCI Dual posi: 437 [M + H]$^+$, 459 [M + Na]$^+$. | Na |

TABLE 21-32-continued

| Compound No. | Structure | Analytical Data | Salt information |
|---|---|---|---|
| Example 1-223 | 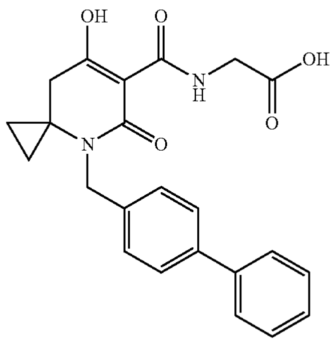 [SMILES: O=C(O)CNC(=O)C1=C(O)CC2(CC2)N(Cc2ccc(-c3ccccc3)cc2)C1=O] | ¹H NMR (300 MHz, DMSO-d₆) δ ppm 0.56-0.84 (m, 2 H) 0.84-1.04 (m, 2 H) 2.41-2.69 (m, 2 H) 3.97-4.13 (m, 2 H) 4.46-4.60 (m, 2 H) 7.31-7.42 (m, 3 H) 7.42-7.51 (m, 2 H) 7.58-7.69 (m, 4 H) 9.88-10.34 (m, 1 H) 12.89 (br. s., 1 H). MS ESI/APCI Dual posi: 407 [M + H]⁺. | |
| Example 1-224 | 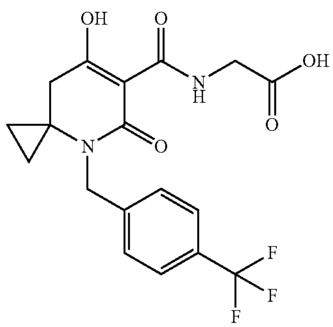 [SMILES: O=C(O)CNC(=O)C1=C(O)CC2(CC2)N(Cc2ccc(C(F)(F)F)cc2)C1=O] | ¹H NMR (300 MHz, CHLOROFORM-d) δ ppm 0.57-0.77 (m, 2 H) 0.85-1.00 (m, 2 H) 2.40-2.64 (m, 2 H) 4.12-4.29 (m, 2 H) 4.57 (s, 2 H) 7.30-7.40 (m, 2 H) 7.55-7.63 (m, 2 H) 10.00-10.15 (m, 1 H). MS ESI/APCI Dual posi: 399 [M + H]⁺, 421 [M + Na]⁺. | |
| Example 1-225 | 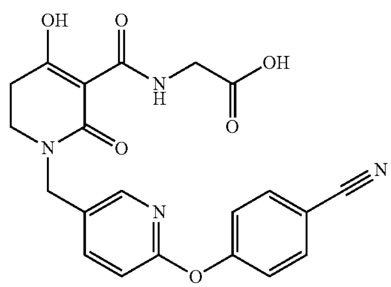 [SMILES: N#Cc1ccc(Oc2ccc(CN3CCC(O)=C(C(=O)NCC(=O)O)C3=O)cn2)cc1] | ¹H NMR (300 MHz, CHLOROFORM-d) δ ppm 2.54-2.74 (m, 2 H) 3.31-3.46 (m, 2 H) 4.13-4.25 (m, 2 H) 4.54-4.65 (m, 2 H) 7.00 (d, J = 8.5 Hz, 1 H) 7.17-7.30 (m, 2 H) 7.62-7.73 (m, 2 H) 7.79 (dd, J = 8.5, 2.5 Hz, 1 H) 8.16 (d, J = 2.5 Hz, 1 H) 10.11 (m, 1 H). MS ESI/APCI Dual posi: 423 [M + H]⁺. MS ESI/APCI Dual nega: 421 [M − H]⁻. | HCl |
| Example 1-226 | 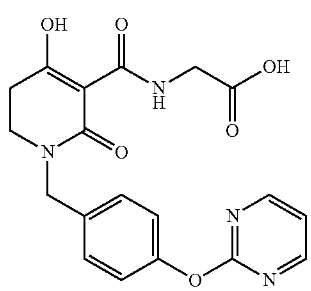 [SMILES: O=C(O)CNC(=O)C1=C(O)CCN(Cc2ccc(Oc3ncccn3)cc2)C1=O] | ¹H NMR (300 MHz, DMSO-d₆) δ ppm 2.58-2.72 (m, 2 H) 3.40 (t, J = 7.1 Hz, 2 H) 3.73 (d, J = 4.8 Hz, 2 H) 4.59 (s, 2 H) 7.11-7.20 (m, 2 H) 7.26 (t, J = 4.8 Hz, 1 H) 7.35 (d, J = 8.5 Hz, 2 H) 8.64 (d, J = 4.8 Hz, 2 H) 9.97-10.14 (m, 1 H). MS ESI/APCI Dual posi: 399 [M + H]⁺. MS ESI/APCI Dual nega: 397 [M − H]⁻. | Na |
| Example 1-227 | 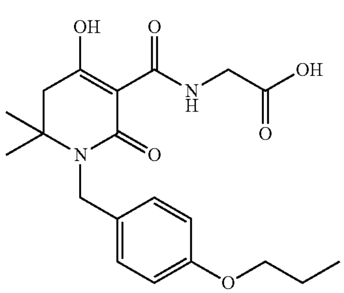 [SMILES: CCCOc1ccc(CN2C(=O)C(C(=O)NCC(=O)O)=C(O)CC2(C)C)cc1] | ¹H NMR (300 MHz, CHLOROFORM-d) δ ppm 0.98-1.07 (m, 3 H) 1.22-1.29 (m, 6 H) 1.71-1.88 (m, 2 H) 2.50-2.61 (m, 2 H) 3.85-3.94 (m, 2 H) 4.10-4.22 (m, 2 H) 4.58-4.66 (m, 2 H) 6.79-6.88 (m, 2 H) 7.13-7.23 (m, 2 H) 10.22-10.38 (m, 1 H). MS ESI/APCI Dual posi: 391 [M + H]⁺, 413 [M + Na]⁺. MS ESI/APCI Dual nega: 389 [M − H]⁻. | |

TABLE 21-33

| Compound No. | Structure | Analytical Data | Salt information |
|---|---|---|---|
| Example 1-228 | 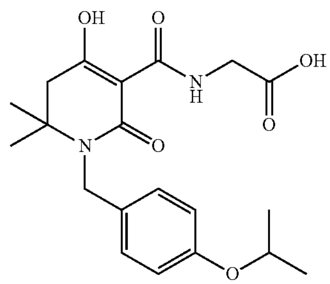 [SMILES: CC(C)Oc1ccc(CN2C(=O)C(C(=O)NCC(=O)O)=C(O)CC2(C)C)cc1] | ¹H NMR (300 MHz, CHLOROFORM-d) δ ppm 1.23-1.29 (m, 6 H) 1.29-1.35 (m, 6 H) 2.51-2.62 (m, 2 H) 4.12-4.22 (m, 2 H) 4.44-4.57 (m, 1 H) 4.58-4.67 (m, 2 H) 6.76-6.88 (m, 2 H) 7.10-7.24 (m, 2 H) 10.23-10.40 (m, 1 H). MS ESI/APCI Dual posi: 391 [M + H]⁺, 413 [M + Na]⁺. MS ESI/APCI Dual nega: 389 [M − H]⁻. | |
| Example 1-229 | 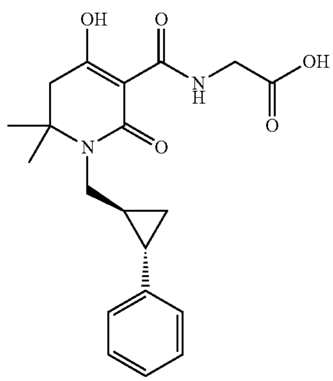 [SMILES: CC1(C)CC(O)=C(C(=O)NCC(=O)O)C(=O)N1C[C@H]1C[C@@H]1c1ccccc1] | ¹H NMR (300 MHz, DMSO-d₆) δ ppm 0.86-1.07 (m, 2 H) 1.24-1.31 (m, 6 H) 1.29-1.37 (m, 1 H) 1.89-1.99 (m, 1 H) 2.43-2.54 (m, 2 H) 3.37-3.46 (m, 2 H) 3.46-3.53 (m, 2 H) 6.97-7.14 (m, 3 H) 7.16-7.27 (m, 2 H) 10.11 (br. s., 1 H). MS ESI/APCI Dual posi: 373 [M + H]⁺. MS ESI/APCI Dual nega: 371 [M − H]⁻. | |
| Example 1-230 | 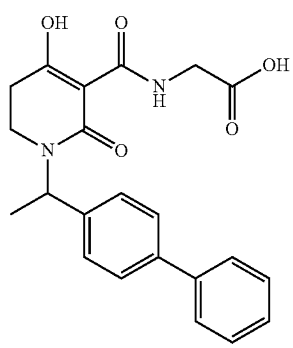 [SMILES: CC(c1ccc(-c2ccccc2)cc1)N1CCC(O)=C(C(=O)NCC(=O)O)C1=O] | ¹H NMR (300 MHz, CHLOROFORM-d) δ ppm 1.45-1.68 (m, 3 H) 2.41-2.62 (m, 2 H) 2.96-3.11 (m, 1 H) 3.21-3.37 (m, 1 H) 4.17-4.25 (m, 2 H) 5.84-6.13 (m, 1 H) 7.30-7.49 (m, 5 H) 7.52-7.64 (m, 4 H) 10.19-10.50 (m, 1 H). MS ESI/APCI Dual posi: 395 [M + H]⁺, 417 [M + Na]⁺. MS ESI/APCI Dual nega: 393 [M − H]⁻. | |
| Example 1-231 | 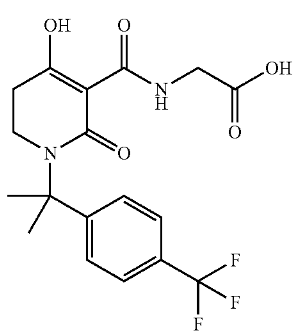 [SMILES: CC(C)(c1ccc(C(F)(F)F)cc1)N1CCC(O)=C(C(=O)NCC(=O)O)C1=O] | ¹H NMR (300 MHz, CHLOROFORM-d) δ ppm 1.60-1.79 (m, 6 H) 2.55-2.79 (m, 2 H) 3.50-3.65 (m, 2 H) 3.96-4.16 (m, 2 H) 7.41 (d, J = 8.1 Hz, 2 H) 7.51-7.65 (m, 2 H) 9.77-10.51 (m, 1 H). MS ESI/APCI Dual posi: 401 [M + H]⁺, 423 [M + Na]⁺. MS ESI/APCI Dual nega: 399 [M − H]⁻. | |

TABLE 21-33-continued

| Compound No. | Structure | Analytical Data | Salt information |
|---|---|---|---|
| Example 1-232 | 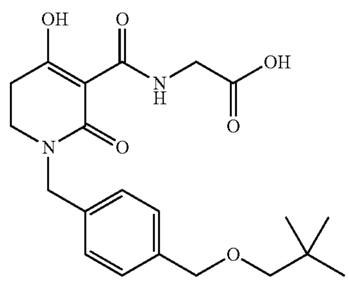 [SMILES: CC(C)(C)COCc1ccc(CN2CCC(O)=C(C(=O)NCC(=O)O)C2=O)cc1] | ¹H NMR (300 MHz, CHLOROFORM-d) δ ppm 0.93 (s, 9 H) 2.47-2.68 (m, 2 H) 3.06-3.17 (m, 2 H) 3.27-3.43 (m, 2 H) 4.15-4.25 (m, 2 H) 4.51 (s, 2 H) 4.56-4.66 (m, 2 H) 7.21-7.27 (m, 2 H) 7.28-7.35 (m, 2 H) 10.19-10.46 (m, 1 H).<br>MS ESI/APCI Dual posi: 405 [M + H]⁺, 427 [M + Na]⁺.<br>MS ESI/APCI Dual nega: 403 [M − H]⁻. | |
| Example 1-233 | 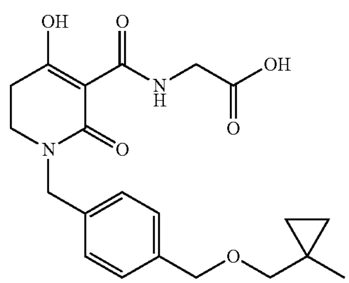 [SMILES: CC1(COCc2ccc(CN3CCC(O)=C(C(=O)NCC(=O)O)C3=O)cc2)CC1] | ¹H NMR (300 MHz, METHANOL-d₄) δ ppm 0.27-0.34 (m, 2 H) 0.35-0.42 (m, 2 H) 1.13 (s, 3 H) 2.50-2.61 (m, 2 H) 3.23-3.27 (m, 2 H) 3.33-3.38 (m, 2 H) 3.89 (s, 2 H) 4.49 (s, 2 H) 4.62 (s, 2 H) 7.24-7.35 (m, 4 H).<br>MS ESI/APCI Dual posi: 403 [M + H]⁺, 425 [M + Na]⁺.<br>MS ESI/APCI Dual nega: 401 [M − H]⁻. | Na |
| Example 1-234 | 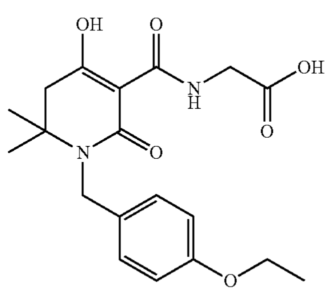 [SMILES: CCOc1ccc(CN2C(=O)C(C(=O)NCC(=O)O)=C(O)CC2(C)C)cc1] | ¹H NMR (300 MHz, CHLOROFORM-d) δ ppm 1.20-1.29 (m, 6 H) 1.35-1.44 (m, 3 H) 2.47-2.63 (m, 2 H) 3.96-4.06 (m, 2 H) 4.13-4.23 (m, 2 H) 4.58-4.67 (m, 2 H) 6.78-6.88 (m, 2 H) 7.12-7.24 (m, 2 H) 10.24-10.38 (m, 1 H).<br>MS ESI/APCI Dual posi: 377 [M + H]⁺.<br>MS ESI/APCI Dual nega: 375 [M − H]⁻. | |

TABLE 21-34

| Compound No. | Structure | Analytical Data | Salt information |
|---|---|---|---|
| Example 1-235 | 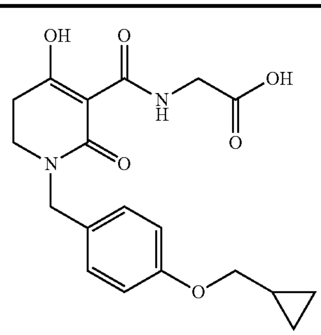 | ¹H NMR (300 MHz, CHLOROFORM-d) δ ppm 0.30-0.38 (m, 2 H) 0.58-0.70 (m, 2 H) 1.16-1.35 (m, 1 H) 2.49-2.64 (m, 2 H) 3.25-3.37 (m, 2 H) 3.74-3.82 (m, 2 H) 4.14-4.22 (m, 2 H) 4.50-4.59 (m, 2 H) 6.81-6.91 (m, 2 H) 7.15-7.21 (m, 2 H) 10.16-10.42 (m, 1 H).<br>MS ESI/APCI Dual posi: 375 [M + H]⁺.<br>MS ESI/APCI Dual nega: 373 [M − H]⁻. | |

TABLE 21-34-continued

| Compound No. | Structure | Analytical Data | Salt information |
|---|---|---|---|
| Example 1-236 | 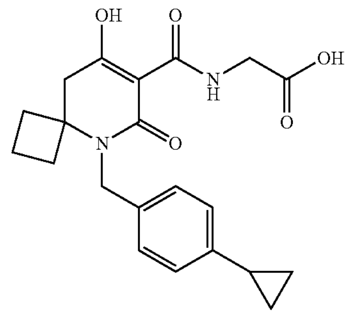 [SMILES: O=C(O)CNC(=O)C1=C(O)CC2(CCC2)N(Cc2ccc(C3CC3)cc2)C1=O] | ¹H NMR (300 MHz, CHLOROFORM-d) δ ppm 0.60-0.71 (m, 2 H) 0.85-1.01 (m, 2 H) 1.62-2.02 (m, 5 H) 2.27-2.49 (m, 2 H) 2.77-2.92 (m, 2 H) 4.10-4.22 (m, 2 H) 4.74-4.86 (m, 2 H) 6.96-7.07 (m, 2 H) 7.07-7.16 (m, 2 H) 10.12-10.40 (m, 1 H). MS ESI/APCI Dual posi: 385 [M + H]⁺. MS ESI/APCI Dual nega: 383 [M − H]⁻. | |
| Example 1-237 | 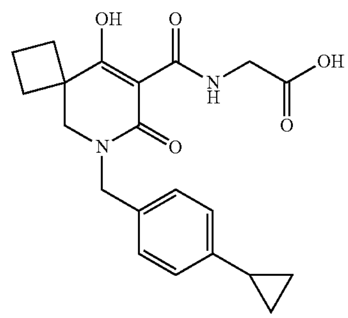 [SMILES: O=C(O)CNC(=O)C1=C(O)C2(CCC2)CN(Cc2ccc(C3CC3)cc2)C1=O] | ¹H NMR (300 MHz, CHLOROFORM-d) δ ppm 0.64-0.72 (m, 2 H) 0.91-1.02 (m, 2 H) 1.51-2.02 (m, 5 H) 2.34-2.54 (m, 2 H) 3.27-3.34 (m, 2 H) 4.15-4.23 (m, 2 H) 4.55-4.60 (m, 2 H) 7.00-7.09 (m, 2 H) 7.12-7.20 (m, 2 H) 10.29-10.58 (m, 1 H). MS ESI/APCI Dual posi: 385 [M + H]⁺. MS ESI/APCI Dual nega: 383 [M − H]⁻. | |
| Example 1-238 | 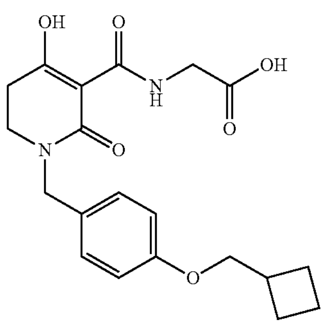 [SMILES: O=C(O)CNC(=O)C1=C(O)CCN(Cc2ccc(OCC3CCC3)cc2)C1=O] | ¹H NMR (300 MHz, CHLOROFORM-d) δ ppm 1.77-2.22 (m, 6 H) 2.47-2.66 (m, 2 H) 2.69-2.84 (m, 1 H) 3.26-3.38 (m, 2 H) 3.86-3.96 (m, 2 H) 4.15-4.22 (m, 2 H) 4.56 (s, 2 H) 6.83-6.92 (m, 2 H) 7.13-7.23 (m, 2 H) 10.18-10.43 (m, 1 H). MS ESI/APCI Dual posi: 389 [M + H]⁺. MS ESI/APCI Dual nega: 387 [M − H]⁻. | |
| Example 1-239 | 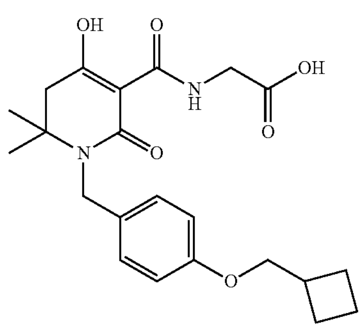 [SMILES: CC1(C)CC(O)=C(C(=O)NCC(=O)O)C(=O)N1Cc1ccc(OCC2CCC2)cc1] | ¹H NMR (300 MHz, CHLOROFORM-d) δ ppm 1.22-1.29 (m, 6 H) 1.76-2.03 (m, 4 H) 2.04-2.21 (m, 2 H) 2.47-2.62 (m, 2 H) 2.68-2.83 (m, 1 H) 3.86-3.93 (m, 2 H) 4.13-4.23 (m, 2 H) 4.53-4.68 (m, 2 H) 6.78-6.90 (m, 2 H) 7.12-7.24 (m, 2 H) 10.27-10.42 (m, 1 H). MS ESI/APCI Dual posi: 417 [M + H]⁺. MS ESI/APCI Dual nega: 415 [M − H]⁻. | |

TABLE 21-34-continued

| Compound No. | Structure | Analytical Data | Salt information |
|---|---|---|---|
| Example 1-240 | 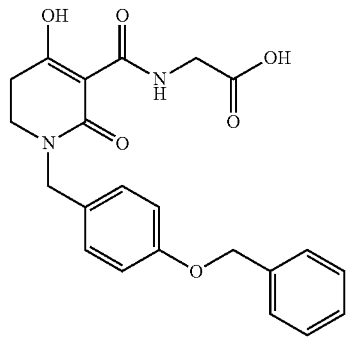 | $^1$H NMR (300 MHz, CHLOROFORM-d) δ ppm 2.46-2.68 (m, 2 H) 3.24-3.40 (m, 2 H) 4.09-4.26 (m, 2H) 4.49-4.63 (m, 2 H) 5.05 (s, 2 H) 6.90-6.98 (m, 2 H) 7.15-7.23 (m, 2 H) 7.28-7.46 (m, 5 H) 10.21-10.45 (m, 1 H). MS ESI/APCI Dual posi: 411 [M + H]$^+$, 433 [M + Na]$^+$. MS ESI/APCI Dual nega: 409 [M − H]$^-$. | |
| Example 1-241 | 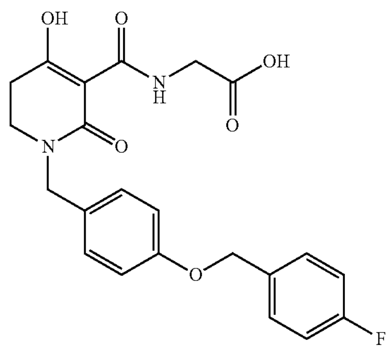 | $^1$H NMR (300 MHz, DMSO-d$_6$) δ ppm 2.40-2.69 (m, 2 H) 3.23-3.40 (m, 2 H) 3.93-4.07 (m, 2 H) 4.43-4.58 (m, 2 H) 5.06 (s, 2 H) 6.89-7.04 (m, 2 H) 7.14-7.29 (m, 4 H) 7.42-7.56 (m, 2 H) 100-10.26 (m, 1 H). MS ESI/APCI Dual posi: 429 [M + H]$^+$, 451 [M + Na]$^+$. MS ESI/APCI Dual nega: 427 [M − H]$^-$. | |

TABLE 21-35

| Compound No. | Structure | Analytical Data | Salt information |
|---|---|---|---|
| Example 1-242 | 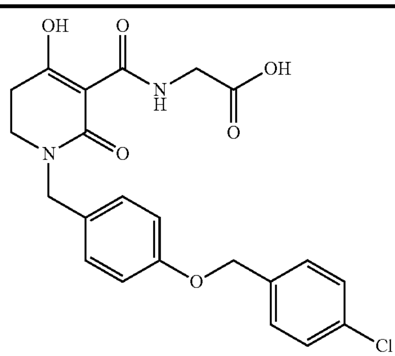 | $^1$H NMR (300 MHz, CHLOROFORM-d) δ ppm 2.49-2.68 (m, 2 H) 3.25-3.40 (m, 2 H) 4.12-4.24 (m, 2 H) 4.50-4.60 (m, 2 H) 4.97-5.06 (m, 2 H) 6.88-6.96 (m, 2 H) 7.15-7.23 (m, 2 H) 7.36 (s, 4 H) 10.21-10.44 (m, 1 H). MS ESI/APCI Dual posi: 445 [M + H]$^+$, 467 [M + Na]$^+$. MS ESI/APCI Dual nega: 443 [M − H]$^-$. | |
| Example 1-243 | 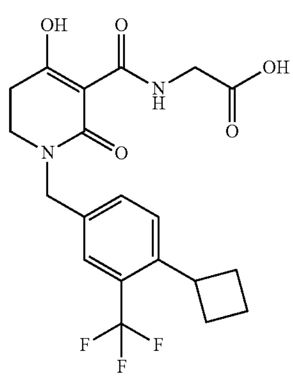 [SMILES: O=C(O)CNC(=O)C1=C(O)CCN(Cc2ccc(C3CCC3)c(C(F)(F)F)c2)C1=O] | $^1$H NMR (300 MHz, CHLOROFORM-d) δ ppm 1.74-2.45 (m, 6 H) 2.64 (t, J = 7.1 Hz, 2 H) 3.34 (t, J = 7.1 Hz, 2 H) 3.77-3.98 (m, 1 H) 4.14-4.27 (m, 2 H) 4.56-4.68 (m, 2 H) 7.37-7.50 (m, 2 H) 7.50-7.64 (m, 1 H) 10.06-10.55 (m, 1 H). MS ESI/APCI Dual posi: 427 [M + H]$^+$. MS ESI/APCI Dual nega: 425 [M − H]$^-$. | |

TABLE 21-35-continued

| Compound No. | Structure | Analytical Data | Salt information |
|---|---|---|---|
| Example 1-244 | (structure) | $^1$H NMR (300 MHz, DMSO-d$_6$) δ ppm 0.92-1.26 (m, 8 H) 1.27-1.46 (m, 1 H) 2.13-2.28 (m, 1 H) 2.30-2.49 (m, 2 H) 2.83-3.00 (m, 1 H) 3.08-3.25 (m, 1 H) 3.54 (d, J = 4.4 Hz, 2 H) 7.13-7.41 (m, 5 H) 10.15 (br. s., 1 H).<br>MS ESI/APCI Dual posi: 373 [M + H]$^+$.<br>MS ESI/APCI Dual nega: 371 [M − H]$^-$. | Na |
| Example 1-245 | (structure) | $^1$H NMR (300 MHz, DMSO-d$_6$) δ ppm 1.69-2.37 (m, 6 H) 2.48-2.53 (m, 2 H) 3.32 (t, J = 6.9 Hz, 2 H) 3.54 (d, J = 4.4 Hz, 2 H) 3.78 (quin, J = 8.5 Hz, 1 H) 4.59-4.74 (m, 2 H) 7.27 (d, J = 8.1 Hz, 1 H) 7.46-7.75 (m, 2 H) 10.11 (br. s., 1 H).<br>MS ESI/APCI Dual posi: 427 [M + H]$^+$.<br>MS ESI/APCI Dual nega: 425 [M − H]$^-$. | Na |
| Example 1-246 | (structure) | $^1$H NMR (300 MHz, DMSO-d$_6$) δ ppm 0.06-0.16 (m, 2 H) 0.37-0.47 (m, 2 H) 0.74-0.92 (m, 1 H) 1.55-1.67 (m, 2 H) 2.43-2.55 (m, 2 H) 3.20-3.31 (m, 2 H) 3.49-3.57 (m, 2 H) 3.93-4.05 (m, 2 H) 4.48 (s, 2 H) 6.83-6.94 (m, 2 H) 7.11-7.25 (m, 2 H) 10.11 (br. s., 1 H).<br>MS ESI/APCI Dual posi: 389 [M + H]$^+$.<br>MS ESI/APCI Dual nega: 387 [M − H]$^-$. | Na |
| Example 1-247 | (structure) | $^1$H NMR (300 MHz, DMSO-d$_6$) δ ppm 0.06-0.15 (m, 2 H) 0.36-0.48 (m, 2 H) 0.73-0.91 (m, 1 H) 1.16 (s, 6 H) 1.52-1.67 (m, 2 H) 2.43-2.59 (m, 2 H) 3.43-3.54 (m, 2 H) 3.92-4.03 (m, 2 H) 4.56 (s, 2 H) 6.79-6.93 (m, 2 H) 7.14-7.27 (m, 2 H) 9.95-10.26 (m, 1 H).<br>MS ESI/APCI Dual posi: 417 [M + H]$^+$.<br>MS ESI/APCI Dual nega: 415 [M − H]$^-$. | Na |

TABLE 21-35-continued

| Compound No. | Structure | Analytical Data | Salt information |
|---|---|---|---|
| Example 1-248 | 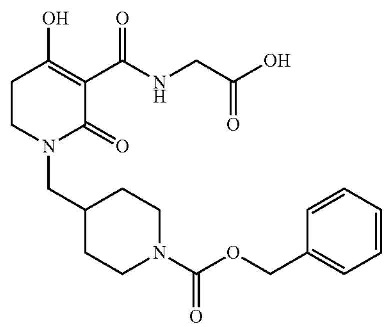 [SMILES: O=C(O)CNC(=O)C1=C(O)CCN(CC2CCN(C(=O)OCc3ccccc3)CC2)C1=O] | $^1$H NMR (300 MHz, METHANOL-d$_4$) δ ppm 1.06-1.26 (m, 2 H) 1.61-1.75 (m, 2 H) 1.81-2.00 (m, 1 H) 2.61 (t, J = 7.2 Hz, 2 H) 2.72-2.94 (m, 2 H) 3.30-3.34 (m, 2 H) 3.45 (t, J = 7.1 Hz, 2 H) 3.94 (s, 2 H) 4.08-4.21 (m, 2 H) 5.10 (s, 2 H) 7.24-7.38 (m, 5 H).<br>MS ESI/APCI Dual posi: 446 [M + H]$^+$, 468 [M + Na]$^+$.<br>MS ESI/APCI Dual nega: 444 [M − H]$^-$. | Na |

TABLE 21-36

| Compound No. | Structure | Analytical Data | Salt information |
|---|---|---|---|
| Example 1-249 | 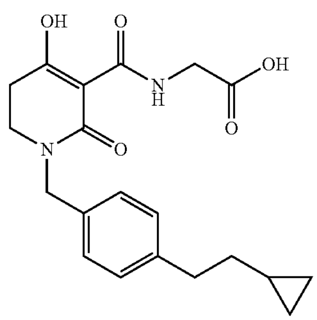 [SMILES: O=C(O)CNC(=O)C1=C(O)CCN(Cc2ccc(CCC3CC3)cc2)C1=O] | $^1$H NMR (300 MHz, METHANOL-d$_4$) δ ppm −0.02-0.06 (m, 2 H) 0.38-0.44 (m, 2 H) 0.59-0.79 (m, 1 H) 1.39-1.54 (m, 2 H) 2.55 (t, J = 7.2 Hz, 2 H) 2.62-2.74 (m, 2 H) 3.31-3.35 (m, 2 H) 3.89 (s, 2 H) 4.58 (s, 2 H) 7.11-7.24 (m, 4 H).<br>MS ESI/APCI Dual posi: 373 [M + H]$^+$.<br>MS ESI/APCI Dual nega: 371 [M − H]$^-$. | Na |
| Example 1-250 | 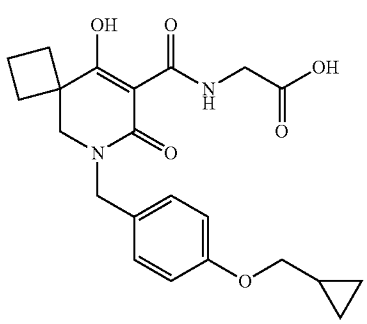 [SMILES: O=C(O)CNC(=O)C1=C(O)C2(CCC2)CN(Cc2ccc(OCC3CC3)cc2)C1=O] | $^1$H NMR (300 MHz, DMSO-d$_6$) δ ppm 0.26-0.36 (m, 2 H) 0.48-0.61 (m, 2 H) 1.11-1.32 (m, 1 H) 1.48-1.95 (m, 4 H) 2.18-2.34 (m, 2 H) 3.32 (s, 2 H) 3.47-3.55 (m, 2 H) 3.73-3.82 (m, 2 H) 4.50 (s, 2 H) 6.89 (d, J = 8.7 Hz, 2 H) 7.21 (d, J = 8.7 Hz, 2 H).<br>MS ESI/APCI Dual posi: 415 [M + H]$^+$.<br>MS ESI/APCI Dual nega: 413 [M − H]$^-$. | Na |
| Example 1-251 | 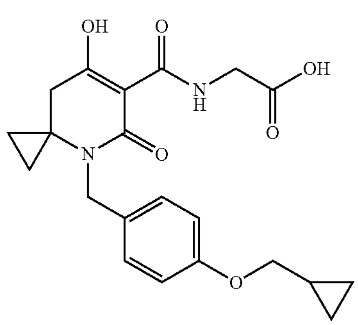 [SMILES: O=C(O)CNC(=O)C1=C(O)CC2(CC2)N(Cc2ccc(OCC3CC3)cc2)C1=O] | $^1$H NMR (300 MHz, DMSO-d$_6$) δ ppm 0.27-0.34 (m, 2 H) 0.51-0.63 (m, 4 H) 0.81-0.92 (m, 2 H) 1.12-1.27 (m, 1 H) 2.39-2.58 (m, 2 H) 3.42-3.49 (m, 2 H) 3.73-3.81 (m, 2 H) 4.39 (s, 2 H) 6.81-6.88 (m, 2 H) 7.12-7.20 (m, 2 H).<br>MS ESI/APCI Dual posi: 401 [M + H]$^+$.<br>MS ESI/APCI Dual nega: 399 [M − H]$^-$. | Na |

TABLE 21-36-continued

| Compound No. | Structure | Analytical Data | Salt information |
|---|---|---|---|
| Example 1-252 | 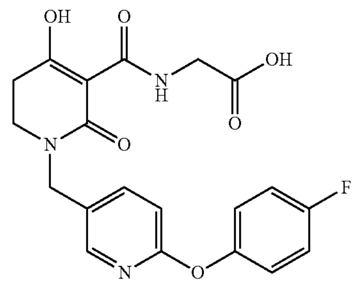 [SMILES: O=C(O)CNC(=O)C1=C(O)CCN(Cc2ccc(Oc3ccc(F)cc3)nc2)C1=O] | $^1$H NMR (300 MHz, DMSO-d$_6$) δ ppm 2.59-2.74 (m, 2 H) 3.41 (t, J = 7.1 Hz, 2 H) 4.02 (d, J = 5.8 Hz, 2 H) 4.54 (s, 2 H) 7.02 (d, J = 8.5 Hz, 1 H) 7.12-7.30 (m, 4 H) 7.78 (dd, J = 8.5, 2.3 Hz, 1 H) 8.09 (d, J = 2.3 Hz, 1 H) 10.00 (br. s., 1 H).<br>MS ESI/APCI Dual posi: 416 [M + H]$^+$.<br>MS ESI/APCI Dual nega: 414 [M − H]$^-$. | HCl |
| Example 1-253 | 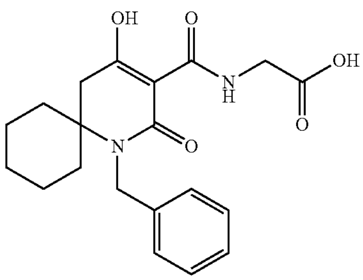 [SMILES: O=C(O)CNC(=O)C1=C(O)CC2(CCCCC2)N(Cc2ccccc2)C1=O] | $^1$H NMR (300 MHz, DMSO-d$_6$) δ ppm 0.95-1.81 (m, 10 H) 2.69-2.83 (m, 2 H) 4.09-4.24 (m, 2 H) 4.70-4.82 (m, 2 H) 7.14-7.38 (m, 5 H) 10.17-10.38 (m, 1 H).<br>MS ESI/APCI Dual posi: 373 [M + H]$^+$, 395 [M + Na]$^+$.<br>MS ESI/APCI Dual nega: 371 [M − H]$^-$. | |
| Example 1-254 | 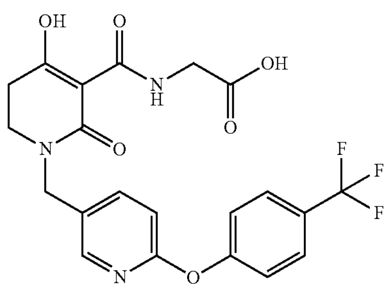 [SMILES: O=C(O)CNC(=O)C1=C(O)CCN(Cc2ccc(Oc3ccc(C(F)(F)F)cc3)nc2)C1=O] | $^1$H NMR (300 MHz, DMSO-d$_6$) δ ppm 2.36-2.48 (m, 2 H) 3.20-3.37 (m, 2 H) 3.51 (d, J = 4.4 Hz, 2 H) 4.53 (s, 2 H) 7.11 (d, J = 8.4 Hz, 1 H) 7.33 (d, J = 8.5 Hz, 2 H) 7.67-7.90 (m, 3 H) 8.13 (d, J = 2.2 Hz, 1 H) 10.11 (br. s., 1 H).<br>MS ESI/APCI Dual posi: 466 [M + H]$^+$.<br>MS ESI/APCI Dual nega: 464 [M − H]$^-$. | Na |
| Example 1-255 | 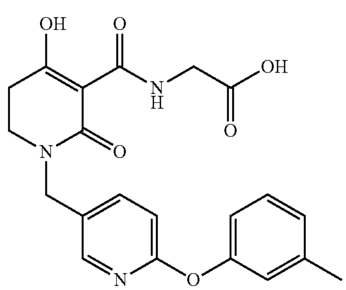 [SMILES: Cc1cccc(Oc2ccc(CN3CCC(O)=C(C(=O)NCC(=O)O)C3=O)cn2)c1] | $^1$H NMR (300 MHz, DMSO-d$_6$) δ ppm 2.31 (s, 3 H) 2.60-2.78 (m, 2 H) 3.42 (t, J = 7.1 Hz, 2 H) 4.02 (d, J = 5.6 Hz, 2 H) 4.54 (s, 2 H) 6.77-7.07 (m, 4 H) 7.19-7.35 (m, 1 H) 7.77 (dd, J = 8.5, 2.5 Hz, 1 H) 8.11 (d, J = 2.5 Hz, 1 H) 10.00 (br. s., 1 H).<br>MS ESI/APCI Dual posi: 412 [M + H]$^+$.<br>MS ESI/APCI Dual nega: 410 [M − H]$^-$. | HCl |

TABLE 21-37

| Compound No. | Structure | Analytical Data | Salt information |
|---|---|---|---|
| Example 1-256 | 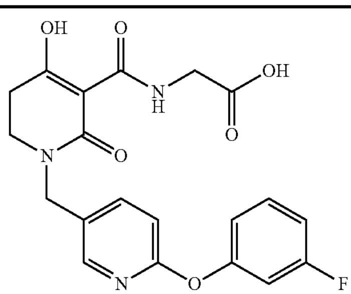 | $^1$H NMR (300 MHz, DMSO-d$_6$) δ ppm 2.41-2.63 (m, 2 H) 3.34 (t, J = 7.1 Hz, 2 H) 3.49 (d, J = 4.4 Hz, 2 H) 4.53 (s, 2 H) 6.89-7.13 (m, 4 H) 7.34-7.54 (m, 1 H) 7.80 (dd, J = 8.5, 2.4 Hz, 1 H) 8.12 (d, J = 2.4 Hz, 1 H) 10.05 (br. s., 1 H).<br>MS ESI/APCI Dual posi: 416 [M + H]$^+$.<br>MS ESI/APCI Dual nega: 414 [M − H]$^-$. | Na |

TABLE 21-37-continued

| Compound No. | Structure | Analytical Data | Salt information |
|---|---|---|---|
| Example 1-257 | 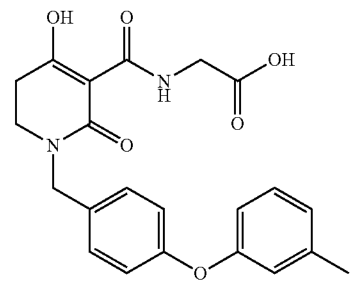 [SMILES: Cc1cccc(Oc2ccc(CN3CCC(O)=C(C(=O)NCC(=O)O)C3=O)cc2)c1] | $^1$H NMR (300 MHz, DMSO-$d_6$) δ ppm 2.28 (s, 3 H) 2.53-2.56 (m, 2 H) 3.31 (t, J = 6.9 Hz, 2 H) 3.50 (d, J = 4.4 Hz, 2 H) 4.54 (s, 2 H) 6.70-6.85 (m, 2 H) 6.88-7.02 (m, 3 H) 7.17-7.36 (m, 3 H) 10.09 (br. s., 1 H). MS ESI/APCI Dual posi: 411 [M + H]$^+$. MS ESI/APCI Dual nega: 409 [M − H]$^-$. | Na |
| Example 1-258 | 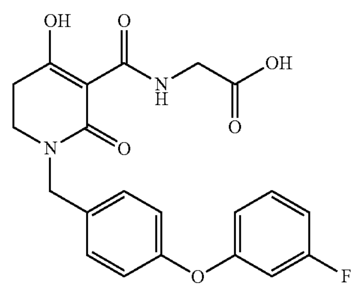 [SMILES: O=C(O)CNC(=O)C1=C(O)CCN(Cc2ccc(Oc3cccc(F)c3)cc2)C1=O] | $^1$H NMR (300 MHz, DMSO-$d_6$) δ ppm 2.50-2.57 (m, 2 H) 3.25-3.35 (m, 2 H) 3.47 (d, J = 4.5 Hz, 2 H) 4.56 (s, 2 H) 6.77- 7.00 (m, 3 H) 7.01-7.07 (m, 2 H) 7.27-7.47 (m, 3 H) 10.08 (br. s., 1 H). MS ESI/APCI Dual posi: 415 [M + H]$^+$. MS ESI/APCI Dual nega: 413 [M − H]$^-$. | Na |
| Example 1-259 | 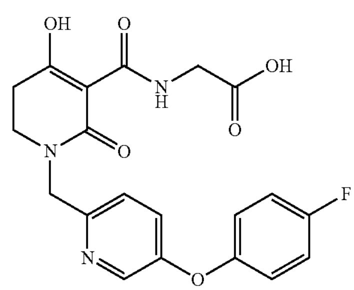 [SMILES: O=C(O)CNC(=O)C1=C(O)CCN(Cc2ccc(Oc3ccc(F)cc3)cn2)C1=O] | $^1$H NMR (300 MHz, DMSO-$d_6$) δ ppm 2.50-2.57 (m, 2 H) 3.36-3.54 (m, 4 H) 4.63 (s, 2 H) 7.07-7.16 (m, 2 H) 7.20-7.43 (m, 4 H) 8.30 (d, J = 2.8 Hz, 1 H) 10.04 (br. s., 1 H). MS ESI/APCI Dual posi: 416 [M + H]$^+$. MS ESI/APCI Dual nega: 414 [M − H]$^-$. | Na |
| Example 1-260 | 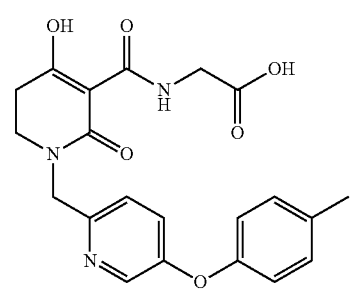 [SMILES: Cc1ccc(Oc2ccc(CN3CCC(O)=C(C(=O)NCC(=O)O)C3=O)nc2)cc1] | $^1$H NMR (300 MHz, DMSO-$d_6$) δ ppm 2.29 (s, 3 H) 2.54-2.57 (m, 2 H) 3.28-3.49 (m, 4 H) 4.62 (s, 2 H) 6.88-7.01 (m, 2 H) 7.21 (dd, J = 8.7, 0.6 Hz, 2 H) 7.24-7.39 (m, 2 H) 8.27 (d, J = 2.8 Hz, 1 H) 10.03 (br. s., 1 H). MS ESI/APCI Dual posi: 412 [M + H]$^+$. MS ESI/APCI Dual nega: 410 [M − H]$^-$. | Na |
| Example 1-261 | 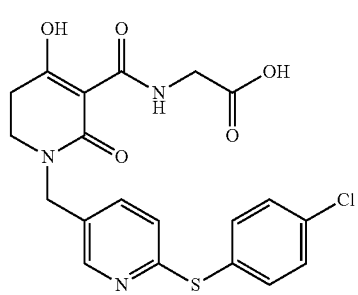 [SMILES: O=C(O)CNC(=O)C1=C(O)CCN(Cc2ccc(Sc3ccc(Cl)cc3)nc2)C1=O] | $^1$H NMR (300 MHz, DMSO-$d_6$) δ ppm 2.47-2.54 (m, 2 H) 3.27-3.35 (m, 2 H) 3.42 (d, J = 4.2 Hz, 2 H) 4.51 (s, 2 H) 7.05 (d, J = 8.2 Hz, 1 H) 7.50-7.63 (m, 5 H) 8.32-8.39 (m, 1 H). MS ESI/APCI Dual posi: 448 [M + H]$^+$. MS ESI/APCI Dual nega: 446 [M − H]$^-$. | Na |

TABLE 21-37-continued

| Compound No. | Structure | Analytical Data | Salt information |
|---|---|---|---|
| Example 1-262 | 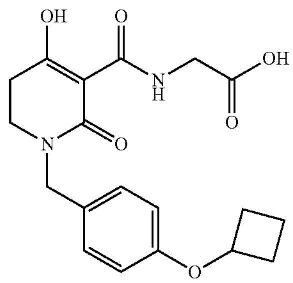 [SMILES: O=C(O)CNC(=O)C1=C(O)CCN(Cc2ccc(OC3CCC3)cc2)C1=O] | ¹H NMR (300 MHz, DMSO-d₆) δ ppm 1.52-1.82 (m, 2 H) 1.90-2.11 (m, 2 H) 2.34-2.50 (m, 4 H) 3.17-3.47 (m, 4 H) 4.47 (s, 2 H) 4.58-4.73 (m, 1 H) 6.71-6.84 (m, 2 H) 7.10-7.25 (m, 2 H). MS ESI/APCI Dual posi: 375 [M + H]⁺. MS ESI/APCI Dual nega: 373 [M − H]⁻. | Na |

TABLE 21-38

| Compound No. | Structure | Analytical Data | Salt information |
|---|---|---|---|
| Example 1-263 | 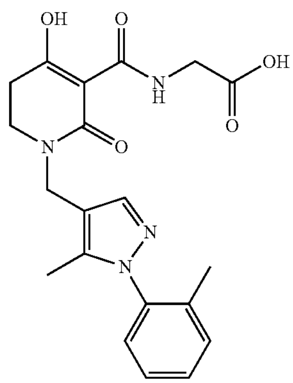 [SMILES: Cc1ccccc1-n1ncc(CN2CCC(O)=C(C(=O)NCC(=O)O)C2=O)c1C] | ¹H NMR (300 MHz, DMSO-d₆) δ ppm 1.93 (s, 3 H) 2.03 (s, 3 H) 2.49-2.52 (m, 2 H) 3.29-3.36 (m, 2 H) 3.45 (d, J = 4.2 Hz, 2 H) 4.45 (s, 2 H) 7.23-7.45 (m, 4 H) 7.57 (s, 1 H). MS ESI/APCI Dual posi: 399 [M + H]⁺. MS ESI/APCI Dual nega: 397 [M − H]⁻. | Na |
| Example 1-264 | 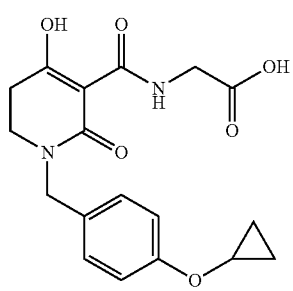 [SMILES: O=C(O)CNC(=O)C1=C(O)CCN(Cc2ccc(OC3CC3)cc2)C1=O] | ¹H NMR (300 MHz, METHANOL-d₄) δ ppm 0.62-0.71 (m, 2 H) 0.71-0.81 (m, 2 H) 2.55 (t, J = 7.3 Hz, 2 H) 3.31-3.35 (m, 2 H) 3.72-3.80 (m, 1 H) 3.89 (s, 2 H) 4.55 (s, 2 H) 6.95-7.06 (m, 2 H) 7.17-7.28 (m, 2 H). MS ESI/APCI Dual posi: 361 [M + H]⁺. MS ESI/APCI Dual nega: 359 [M − H]⁻. | Na |
| Example 1-265 | 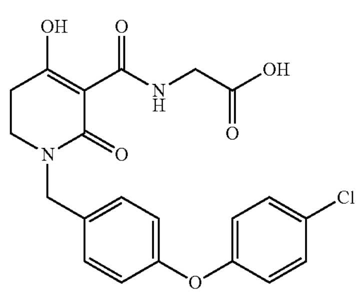 [SMILES: O=C(O)CNC(=O)C1=C(O)CCN(Cc2ccc(Oc3ccc(Cl)cc3)cc2)C1=O] | ¹H NMR (300 MHz, DMSO-d₆) δ ppm 2.53-2.57 (m, 2 H) 3.31 (t, J = 7.1 Hz, 2 H) 3.50 (d, J = 4.5 Hz, 2 H) 4.55 (s, 2 H) 6.96-7.06 (m, 4 H) 7.27-7.34 (m, 2 H) 7.37-7.45 (m, 2 H) 10.09 (br. s., 1 H). MS ESI/APCI Dual posi: 431 [M + H]⁺. MS ESI/APCI Dual nega: 429 [M − H]⁻. | Na |

TABLE 21-38-continued

| Compound No. | Structure | Analytical Data | Salt information |
|---|---|---|---|
| Example 1-266 | 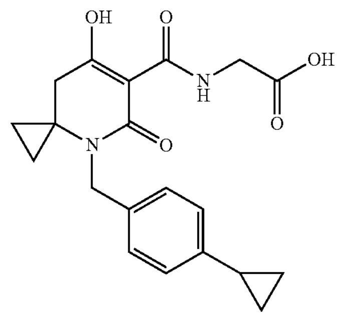 [SMILES: O=C(O)CNC(=O)C1=C(O)CC2(CC2)N(Cc2ccc(C3CC3)cc2)C1=O] | $^1$H NMR (300 MHz, DMSO-d$_6$) δ ppm 0.53-0.70 (m, 4 H) 0.80-0.98 (m, 4 H) 1.81-1.94 (m, 1 H) 2.38-2.47 (m, 2 H) 3.42-3.50 (m, 2 H) 4.41 (s, 2 H) 6.95-7.06 (m, 2 H) 7.08-7.17 (m, 2 H). <br> MS ESI/APCI Dual posi: 371 [M + H]$^+$. <br> MS ESI/APCI Dual nega: 369 [M − H]$^−$. | Na |
| Example 1-267 | 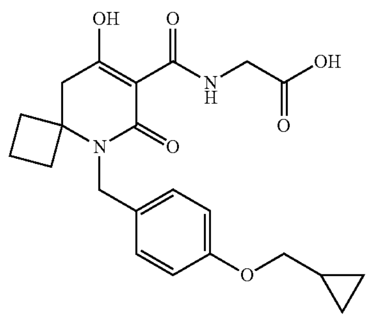 [SMILES: O=C(O)CNC(=O)C1=C(O)CC2(CCC2)N(Cc2ccc(OCC3CC3)cc2)C1=O] | $^1$H NMR (300 MHz, DMSO-d$_6$) δ ppm 0.25-0.34 (m, 2 H) 0.48-0.60 (m, 2 H) 1.12-1.29 (m, 1 H) 1.53-1.86 (m, 4 H) 2.21-2.39 (m, 2 H) 2.72-2.82 (m, 2 H) 3.38-3.47 (m, 2 H) 3.77 (d, J = 7.0 Hz, 2 H) 4.73 (s, 2 H) 6.85 (d, J = 8.9 Hz, 2 H) 7.17 (d, J = 8.9 Hz, 2 H). <br> MS ESI/APCI Dual posi: 415 [M + H]$^+$. <br> MS ESI/APCI Dual nega: 413 [M − H]$^−$. | Na |
| Example 1-268 | 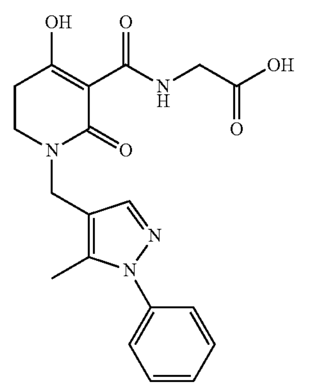 [SMILES: Cc1c(CN2CCC(O)=C(C(=O)NCC(=O)O)C2=O)cnn1-c1ccccc1] | $^1$H NMR (300 MHz, DMSO-d$_6$) δ ppm 2.31 (s, 3 H) 2.49-2.51 (m, 2 H) 3.31-3.37 (m, 2 H) 3.46 (d, J = 4.5 Hz, 2 H) 4.44 (s, 2 H) 7.39-7.45 (m, 1 H) 7.48-7.53 (m, 4 H) 7.59 (s, 1 H). <br> MS ESI/APCI Dual posi: 385 [M + H]$^+$. <br> MS ESI/APCI Dual nega: 383 [M − H]$^−$. | Na |
| Example 1-269 | 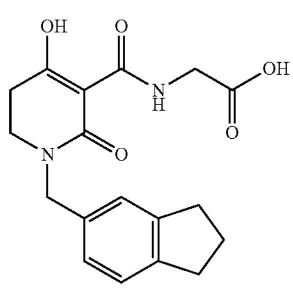 [SMILES: O=C(O)CNC(=O)C1=C(O)CCN(Cc2ccc3c(c2)CCC3)C1=O] | $^1$H NMR (300 MHz, METHANOL-d$_4$) δ ppm 2.05 (quin, J = 7.5 Hz, 2 H) 2.45-2.60 (m, 2 H) 2.84-2.92 (m, 4 H) 3.30-3.31 (m, 2 H) 3.89 (s, 2 H) 4.57 (s, 2 H) 6.98-7.08 (m, 1 H) 7.10-7.21 (m, 2 H). <br> MS ESI/APCI Dual posi: 345 [M + H]$^+$. <br> MS ESI/APCI Dual nega: 343 [M − H]$^−$. | Na |

TABLE 21-39

| Compound No. | Structure | Analytical Data | Salt information |
|---|---|---|---|
| Example 1-270 | 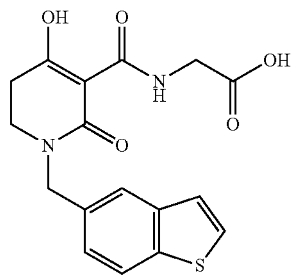 [SMILES: O=C(O)CNC(=O)C1=C(O)CCN(Cc2ccc3sccc3c2)C1=O] | $^1$H NMR (300 MHz, METHANOL-d$_6$) δ ppm 2.43-2.63 (m, 2 H) 3.32-3.40 (m, 2 H) 3.90 (s, 2 H) 4.74 (s, 2 H) 7.27-7.37 (m, 2 H) 7.52-7.58 (m, 1 H) 7.75-7.79 (m, 1 H) 7.82-7.99 (m, 1 H).<br>MS ESI/APCI Dual posi: 361[M + H]$^+$.<br>MS ESI/APCI Dual nega: 359[M − H]$^−$. | Na |
| Example 1-271 | 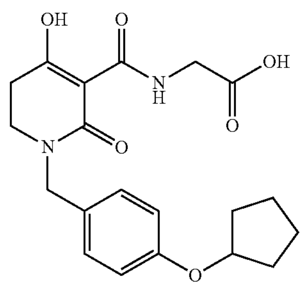 [SMILES: O=C(O)CNC(=O)C1=C(O)CCN(Cc2ccc(OC3CCCC3)cc2)C1=O] | $^1$H NMR (300 MHz, DMSO-d$_6$) δ ppm 1.47-1.76 (m, 6 H) 1.80-1.98 (m, 2 H) 2.44-2.51 (m, 2 H) 3.20-3.31 (m, 2 H) 3.46-3.54 (m, 2 H) 4.47 (s, 2 H) 4.71-4.83 (m, 1 H) 6.80-6.89 (m, 2 H) 7.11-7.23 (m, 2 H) 10.11 (br. s., 1 H).<br>MS ESI/APCI Dual posi: 389[M + H]$^+$.<br>MS ESI/APCI Dual nega: 387[M − H]$^−$. | Na |
| Example 1-272 | 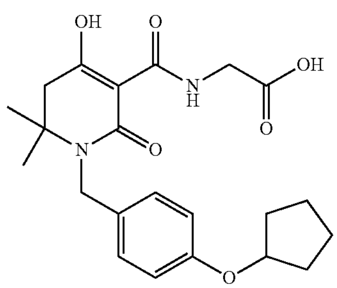 [SMILES: CC1(C)CC(O)=C(C(=O)NCC(=O)O)C(=O)N1Cc1ccc(OC2CCCC2)cc1] | $^1$H NMR (300 MHz, DMSO-d$_6$) δ ppm 1.17 (s, 6 H) 1.48-1.76 (m, 6 H) 1.80-1.97 (m, 2 H) 2.43-2.62 (m, 2 H) 3.43-3.52 (m, 2 H) 4.55 (s, 2 H) 4.72-4.80 (m, 1 H) 6.77-6.88 (m, 2 H) 7.14-7.23 (m, 2 H).<br>MS ESI/APCI Dual posi: 417[M + H]$^+$.<br>MS ESI/APCI Dual nega: 415[M − H]$^−$. | Na |
| Example 1-273 | 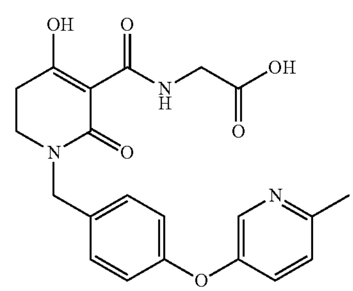 [SMILES: Cc1ccc(Oc2ccc(CN3CCC(O)=C(C(=O)NCC(=O)O)C3=O)cc2)cn1] | $^1$H NMR (300 MHz, DMSO-d$_6$) δ ppm 2.45 (s, 3 H) 2.56-2.71 (m, 2 H) 3.31-3.50 (m, 2 H) 3.95 (d, J = 5.4 Hz, 2 H) 4.56 (s, 2 H) 6.99 (d, J = 8.7 Hz, 2 H) 7.19-7.41 (m, 4 H) 8.24 (d, J = 2.8 Hz, 1 H) 10.08 (br. s., 1 H).<br>MS ESI/APCI Dual posi: 412[M + H]$^+$.<br>MS ESI/APCI Dual nega: 410[M − H]$^−$. | Na |
| Example 1-274 | 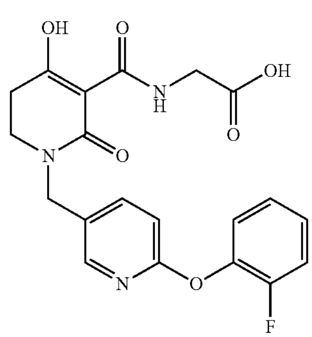 [SMILES: O=C(O)CNC(=O)C1=C(O)CCN(Cc2ccc(Oc3ccccc3F)nc2)C1=O] | $^1$H NMR (300 MHz, DMSO-d$_6$) δ ppm 2.50-2.59 (m, 2 H) 3.27-3.38 (m, 2 H) 3.48 (d, J = 4.5 Hz, 2 H) 4.51 (s, 2 H) 7.10 (dd, J = 8.5, 0.6 Hz, 1 H) 7.18-7.42 (m, 4 H) 7.79 (dd, J = 8.5, 2.5 Hz, 1 H) 8.03 (d, J = 2.5 Hz, 1 H) 10.03 (br. s., 1 H).<br>MS ESI/APCI Dual posi: 416[M + H]$^+$.<br>MS ESI/APCI Dual nega: 414[M − H]$^−$. Na | |

TABLE 21-39-continued

| Compound No. | Structure | Analytical Data | Salt information |
|---|---|---|---|
| Example 1-275 | 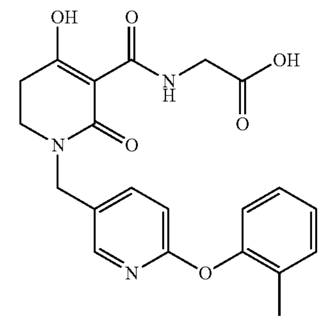 [SMILES: Cc1ccccc1Oc1ccc(CN2CCC(O)=C(C(=O)NCC(=O)O)C2=O)cn1] | $^1$H NMR (300 MHz, DMSO-$d_6$) δ ppm 2.08 (s, 3 H) 2.53-2.59 (m, 2 H) 3.28-3.38 (m, 2 H) 3.51 (d, J = 4.5 Hz, 2 H) 4.51 (s, 2 H) 6.99 (dd, J = 16.6, 8.5 Hz, 2 H) 7.08-7.38 (m, 3 H) 7.75 (dd, J = 8.5, 2.4 Hz, 1 H) 8.04 (d, J = 2.4 Hz, 1 H) 10.08 (br. s., 1 H). MS ESI/APCI Dual posi: 412[M + H]$^+$. MS ESI/APCI Dual nega: 410[M − H]$^−$. | Na |
| Example 1-276 | 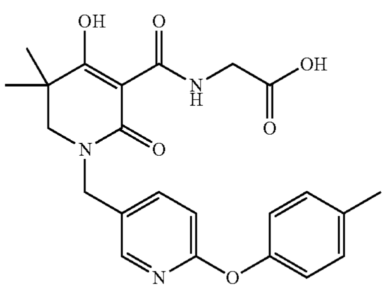 | $^1$H NMR (300 MHz, DMSO-$d_6$) δ ppm 1.05 (s, 6 H) 2.31 (s, 3 H) 3.10 (s, 2 H) 3.41-3.48 (m, 2 H) 4.52 (s, 2 H) 6.80-7.05 (m, 3 H) 7.20 (d, J = 8.1 Hz, 2 H) 7.77 (dd, J = 8.4, 2.6 Hz, 1 H) 8.09 (d, J = 2.6 Hz, 1 H). MS ESI/APCI Dual posi: 440[M + H]$^+$. MS ESI/APCI Dual nega: 438[M − H]$^−$. | Na |

TABLE 21-40

| Compound No. | Structure | Analytical Data | Salt information |
|---|---|---|---|
| Example 1-277 | 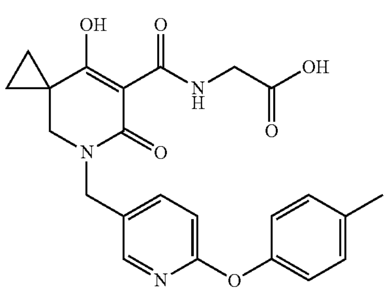 [SMILES: Cc1ccc(Oc2ccc(CN3CC4(CC4)C(O)=C(C(=O)NCC(=O)O)C3=O)cn2)cc1] | $^1$H NMR (300 MHz, DMSO-$d_6$) δ ppm 0.58-0.78 (m, 2 H) 0.99-1.15 (m, 2 H) 2.31 (s, 3 H) 3.20 (s, 2 H) 3.49 (s, 2 H) 4.51 (s, 2 H) 6.87-7.06 (m, 3 H) 7.20 (d, J = 8.2 Hz, 2 H) 7.73 (dd, J = 8.6, 2.4 Hz, 1 H) 8.05 (d, J = 2.4 Hz, 1 H) 10.08-10.35 (m, 1 H). MS ESI/APCI Dual posi: 438[M + H]$^+$. MS ESI/APCI Dual nega: 436[M − H]$^−$. | Na |
| Example 1-278 | 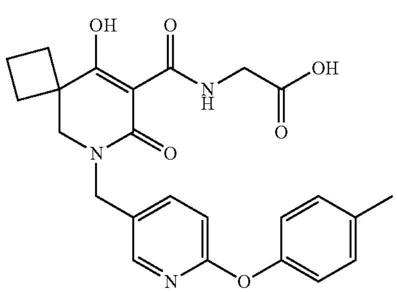 [SMILES: Cc1ccc(Oc2ccc(CN3CC4(CCC4)C(O)=C(C(=O)NCC(=O)O)C3=O)cn2)cc1] | $^1$H NMR (300 MHz, DMSO-$d_6$) δ ppm 1.46-1.64 (m, 2 H) 1.69-1.97 (m, 2 H) 2.14-2.38 (m, 5 H) 3.20-3.40 (m, 2 H) 3.42-3.53 (m, 2 H) 4.53 (s, 2 H) 6.89-7.03 (m, 3 H) 7.14-7.25 (m, 2 H) 7.76 (dd, J = 8.4, 2.2 Hz, 1 H) 8.10 (d, J = 2.2 Hz, 1 H) 10.13-10.33 (m, 1 H). MS ESI/APCI Dual posi: 452[M + H]$^+$. MS ESI/APCI Dual nega: 450[M − H]$^−$. | Na |

TABLE 21-40-continued

| Compound No. | Structure | Analytical Data | Salt information |
|---|---|---|---|
| Example 1-279 | 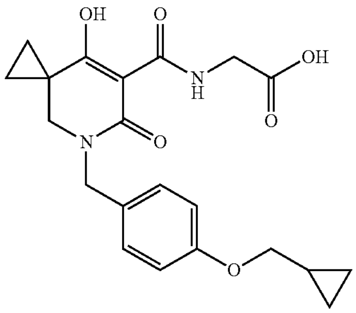 [SMILES: O=C(O)CNC(=O)C1=C(O)C2(CC2)CN(Cc2ccc(OCC3CC3)cc2)C1=O] | ¹H NMR (300 MHz, DMSO-d₆) δ ppm 0.24-0.36 (m, 2 H) 0.49-0.75 (m, 4 H) 1.02-1.12 (m, 2 H) 1.13-1.29 (m, 1 H) 3.13 (s, 2 H) 3.51 (d, J = 4.5 Hz, 2 H) 3.78 (d, J = 7.0 Hz, 2 H) 4.48 (s, 2 H) 6.81-6.93 (m, 2 H) 7.12-7.23 (m, 2 H) 10.12-10.34 (m, 1 H).<br>MS ESI/APCI Dual posi: 401[M + H]⁺.<br>MS ESI/APCI Dual nega: 399[M − H]⁻. | Na |
| Example 1-280 | 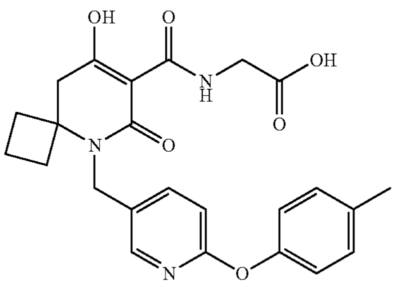 [SMILES: Cc1ccc(Oc2ccc(CN3C(=O)C(C(=O)NCC(=O)O)=C(O)CC34CCC4)cn2)cc1] | ¹H NMR (300 MHz, DMSO-d₆) δ ppm 1.59-1.90 (m, 4 H) 2.19-2.37 (m, 5 H) 2.70 (s, 2 H) 3.46 (d, J = 4.2 Hz, 2 H) 4.76 (s, 2 H) 6.85-7.04 (m, 3 H) 7.15-7.24 (m, 2 H) 7.71 (dd, J = 8.4, 2.5 Hz, 1 H) 8.05 (d, J = 2.5 Hz, 1 H) 9.93-10.07 (m, 1 H).<br>MS ESI/APCI Dual posi: 452[M + H]⁺.<br>MS ESI/APCI Dual nega: 450[M − H]⁻. | |
| Example 1-281 | 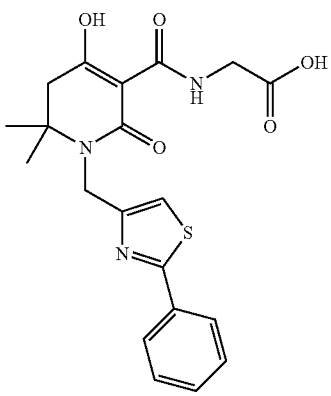 [SMILES: CC1(C)CC(O)=C(C(=O)NCC(=O)O)C(=O)N1Cc1csc(-c2ccccc2)n1] | ¹H NMR (300 MHz, METHANOL-d₆) δ ppm 1.37 (s, 6 H) 2.64 (s, 2 H) 3.89 (s, 2 H) 4.82 (s, 2 H) 7.38 (s, 1 H) 7.41-7.50 (m, 3 H) 7.88-7.98 (m, 2 H).<br>MS ESI/APCI Dual posi: 416[M + H]⁺.<br>MS ESI/APCI Dual nega: 414[M − H]⁻. | Na |
| Example 1-282 | 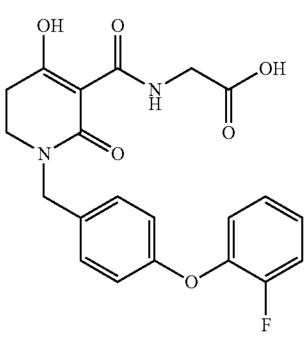 [SMILES: O=C(O)CNC(=O)C1=C(O)CCN(Cc2ccc(Oc3ccccc3F)cc2)C1=O] | ¹H NMR (300 MHz, DMSO-d₆) δ ppm 2.53-2.58 (m, 2 H) 3.30 (t, J = 7.1 Hz, 2 H) 3.51 (d, J = 4.5 Hz, 2 H) 4.53 (s, 2 H) 6.90-6.98 (m, 2 H) 7.11-7.32 (m, 5 H) 7.33-7.43 (m, 1 H) 10.09 (br. s., 1 H).<br>MS ESI/APCI Dual posi: 415[M + H]⁺.<br>MS ESI/APCI Dual nega: 413[M − H]⁻. | Na |

TABLE 21-40-continued

| Compound No. | Structure | Analytical Data | Salt information |
|---|---|---|---|
| Example 1-283 | 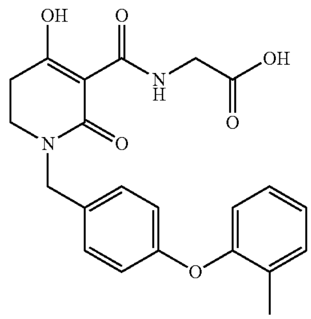 [SMILES: Cc1ccccc1Oc1ccc(CN2CCC(O)=C(C(=O)NCC(=O)O)C2=O)cc1] | $^1$H NMR (300 MHz, DMSO-$d_6$) δ ppm 2.17 (s, 3 H) 2.53-2.57 (m, 2 H) 3.26-3.34 (m, 2 H) 3.50 (d, J = 4.4 Hz, 2 H) 4.52 (s, 2 H) 6.81-6.93 (m, 3 H) 7.05-7.13 (m, 1 H) 7.16-7.34 (m, 4 H) 10.09 (br. s., 1 H). MS ESI/APCI Dual posi: 411[M + H]$^+$. MS ESI/APCI Dual nega: 409[M − H]$^-$. | Na |

TABLE 21-41

| Compound No. | Structure | Analytical Data | Salt information |
|---|---|---|---|
| Example 1-284 | 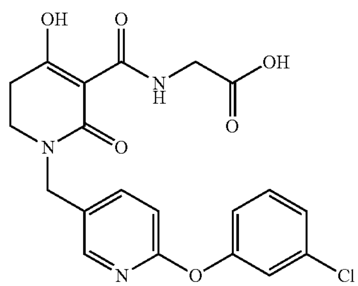 [SMILES: O=C(O)CNC(=O)C1=C(O)CCN(Cc2ccc(Oc3cccc(Cl)c3)nc2)C1=O] | $^1$H NMR (300 MHz, DMSO-$d_6$) δ ppm 2.53-2.60 (m, 2 H) 3.35 (t, J = 6.9 Hz, 2 H) 3.51 (d, J = 4.5 Hz, 2 H) 4.53 (s, 2 H) 6.98-7.17 (m, 2 H) 7.23-7.32 (m, 2 H) 7.36-7.50 (m, 1 H) 7.80 (dd, J = 8.4, 2.4 Hz, 1 H) 8.07-8.17 (m, 1 H) 10.07 (br. s., 1 H). MS ESI/APCI Dual posi: 432[M + H]$^+$. MS ESI/APCI Dual nega: 430[M − H]$^-$. | Na |
| Example 1-285 | 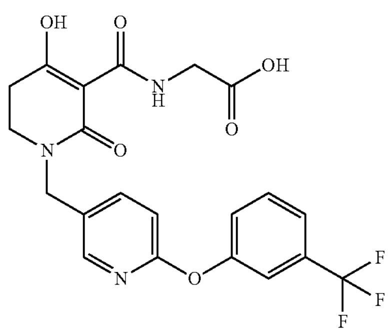 [SMILES: O=C(O)CNC(=O)C1=C(O)CCN(Cc2ccc(Oc3cccc(C(F)(F)F)c3)nc2)C1=O] | $^1$H NMR (300 MHz, DMSO-$d_6$) δ ppm 2.54-2.64 (m, 2 H) 3.37 (t, J = 7.1 Hz, 2 H) 3.63 (d, J = 4.8 Hz, 2 H) 4.54 (s, 2 H) 7.11 (dd, J = 8.4, 0.6 Hz, 1 H) 7.38-7.71 (m, 4 H) 7.76-7.89 (m, 1 H) 8.11 (d, J = 1.9 Hz, 1 H) 10.06 (br. s., 1 H). MS ESI/APCI Dual posi: 466[M + H]$^+$. MS ESI/APCI Dual nega: 464[M − H]$^-$. | Na |
| Example 1-286 | 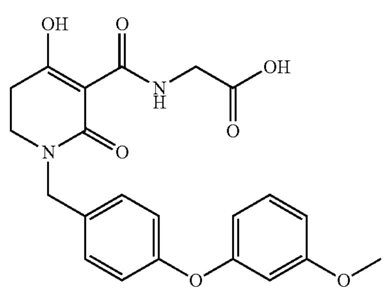 [SMILES: COc1cccc(Oc2ccc(CN3CCC(O)=C(C(=O)NCC(=O)O)C3=O)cc2)c1] | $^1$H NMR (300 MHz, DMSO-$d_6$) δ ppm 2.40-2.50 (m, 2 H) 3.29 (t, J = 7.1 Hz, 2 H) 3.49 (d, J = 4.5 Hz, 2 H) 3.73 (s, 3 H) 4.54 (s, 2 H) 6.44-6.61 (m, 2 H) 6.70 (ddd, J = 8.3, 2.4, 0.9 Hz, 1 H) 6.91-7.05 (m, 2 H) 7.18-7.34 (m, 3 H) 10.10 (br. s., 1 H). MS ESI/APCI Dual posi: 427[M + H]$^+$. MS ESI/APCI Dual nega: 425[M − H]$^-$. | Na |

TABLE 21-41-continued

| Compound No. | Structure | Analytical Data | Salt information |
|---|---|---|---|
| Example 1-287 | 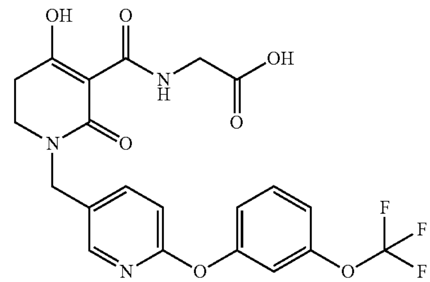 [SMILES: O=C(O)CNC(=O)C1=C(O)CCN(Cc2ccc(Oc3cccc(OC(F)(F)F)c3)nc2)C1=O] | $^1$H NMR (300 MHz, DMSO-d$_6$) δ ppm 2.50-2.57 (m, 2 H) 3.34 (t, J = 7.1 Haz, 2 H) 3.51 (d, J = 4.5 Hz, 2 H) 4.54 (s, 2 H) 7.07 (d, J = 0.6 Hz, 1 H) 7.14-7.28 (m, 3 H) 7.46-7.60 (m, 1 H), 7.81 (dd, J = 8.4, 2.5 Hz, 1 H) 8.12 (d, J = 1.9 Hz, 1 H) 10.07 (br. s., 1 H). <br> MS ESI/APCI Dual posi: 482[M + H]$^+$. <br> MS ESI/APCI Dual nega: 480[M − H]$^−$. | Na |
| Example 1-288 | 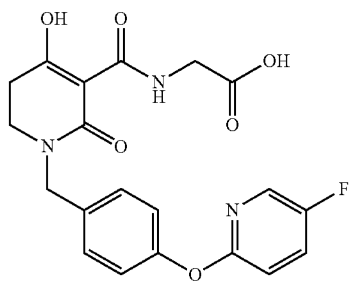 [SMILES: O=C(O)CNC(=O)C1=C(O)CCN(Cc2ccc(Oc3ccc(F)cn3)cc2)C1=O] | $^1$H NMR (300 MHz, DMSO-d$_6$) δ ppm 2.50-2.58 (m, 2 H) 3.33 (t, J = 7.1 Hz, 2 H) 3.49 (d, J = 4.5 Hz, 2 H) 4.56 (s, 2 H) 7.02-7.16 (m, 3 H) 7.27-7.36 (m, 2 H) 7.75-7.88 (m, 1 H) 8.11-8.18 (m, 1 H) 10.09 (br. s., 1 H). <br> MS ESI/APCI Dual posi: 416[M + H]$^+$. <br> MS ESI/APCI Dual nega: 414[M − H]$^−$. | Na |
| Example 1-289 | 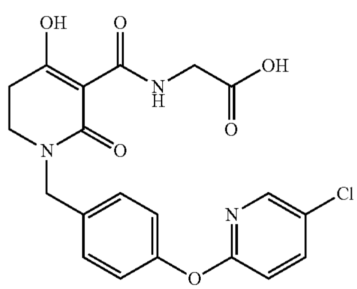 [SMILES: O=C(O)CNC(=O)C1=C(O)CCN(Cc2ccc(Oc3ccc(Cl)cn3)cc2)C1=O] | $^1$H NMR (300 MHz, DMSO-d$_6$) δ ppm 2.60-2.76 (m, 2 H) 3.42 (t, J = 7.1 Hz, 2 H) 4.02 (d, J = 5.8 Hz, 2 H) 4.59 (s, 2 H) 7.03-7.18 (m, 3 H) 7.28-7.38 (m, 2 H) 7.95 (dd, J = 8.8, 2.8 Hz, 1 H) 8.19 (dd, J = 2.8, 0.6 Hz, 1 H) 10.07 (br. s., 1 H). <br> MS ESI/APCI Dual posi: 432[M + H]$^+$. <br> MS ESI/APCI Dual nega: 430[M − H]$^−$. | HCl |
| Example 1-290 | 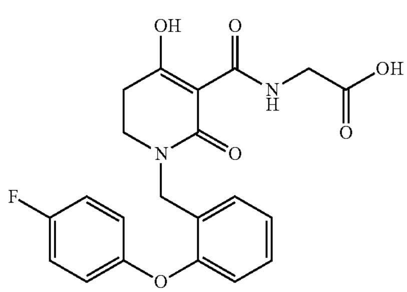 [SMILES: O=C(O)CNC(=O)C1=C(O)CCN(Cc2ccccc2Oc2ccc(F)cc2)C1=O] | $^1$H NMR (300 MHz, DMSO-d$_6$) δ ppm 2.50-2.59 (m, 2 H) 3.36 (t, J = 7.1 Hz, 2 H) 3.50 (d, J = 4.5 Hz, 2 H) 4.57 (s, 2 H) 6.86 (dd, J = 8.1, 1.1 Hz, 1 H) 6.94-7.07 (m, 2 H) 7.10-7.37 (m, 5 H) 10.04 (br. s., 1 H). <br> MS ESI/APCI Dual posi: 415[M + H]$^+$. <br> MS ESI/APCI Dual nega: 413[M − H]$^−$. | Na |

TABLE 21-42

| Compound No. | Structure | Analytical Data | Salt information |
|---|---|---|---|
| Example 1-291 | 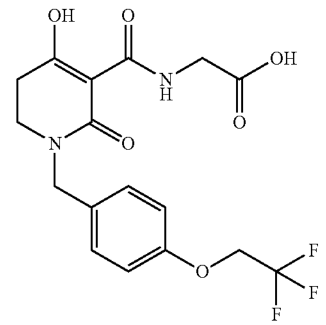 [SMILES: O=C(O)CNC(=O)C1=C(O)CCN(Cc2ccc(OCC(F)(F)F)cc2)C1=O] | ¹H NMR (300 MHz, DMSO-d$_6$) δ ppm 2.44-2.56 (m, 2 H) 3.20-3.31 (m, 2 H) 3.46-3.53 (m, 2 H) 4.51 (s, 2 H) 4.65-4.80 (m, 2 H) 6.96-7.07 (m, 2 H) 7.19-7.30 (m, 2 H) 9.94-10.24 (m, 1 H).<br>MS ESI/APCI Dual posi: 403[M + H]⁺.<br>MS ESI/APCI Dual nega: 401[M − H]⁻. | Na |
| Example 1-292 | 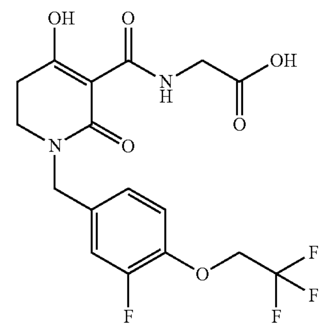 [SMILES: O=C(O)CNC(=O)C1=C(O)CCN(Cc2ccc(OCC(F)(F)F)c(F)c2)C1=O] | ¹H NMR (300 MHz, DMSO-d$_6$) δ ppm 2.50-2.59 (m, 2 H) 3.25-3.35 (m, 2 H) 3.45-3.53 (m, 2 H) 4.50 (s, 2 H) 4.75-4.88 (m, 2 H) 7.04-7.30 (m, 3 H) 9.93-10.19 (m, 1 H).<br>MS ESI/APCI Dual posi: 421[M + H]⁺.<br>MS ESI/APCI Dual nega: 419[M − H]⁻. | Na |
| Example 1-293 | 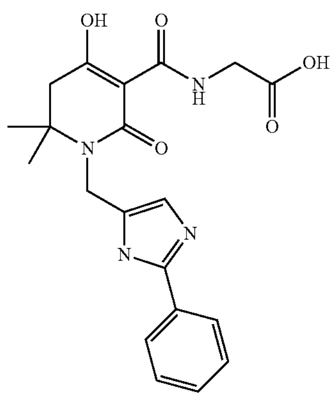 [SMILES: CC1(C)CC(O)=C(C(=O)NCC(=O)O)C(=O)N1Cc1cnc(-c2ccccc2)[nH]1] | ¹H NMR (300 MHz, METHANOL-d$_6$) δ ppm 1.38 (s, 6 H) 2.65 (s, 2 H) 4.06 (s, 2 H) 4.69 (s, 2 H) 7.15 (s, 1 H) 7.38-7.54 (m, 3 H) 7.79-7.89 (m, 2 H).<br>MS ESI/APCI Dual posi: 399[M + H]⁺.<br>MS ESI/APCI Dual nega: 397[M − H]⁻. | Na |
| Example 1-294 | 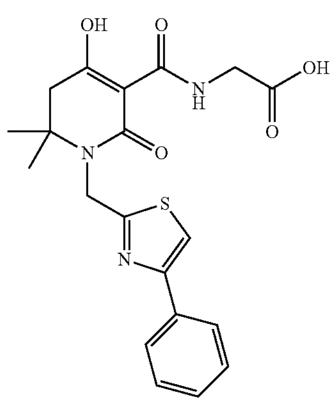 [SMILES: CC1(C)CC(O)=C(C(=O)NCC(=O)O)C(=O)N1Cc1nc(-c2ccccc2)cs1] | ¹H NMR (300 MHz, DMSO-d$_6$) δ ppm 1.29 (s, 6 H) 2.54-2.65 (m, 2 H) 3.49 (d, J = 4.5 Hz, 2 H) 4.90 (s, 2 H) 7.29-7.38 (m, 1 H) 7.39-7.49 (m, 2 H) 7.90-7.98 (m, 2 H) 8.00 (s, 1 H) 9.89-10.12 (m, 1 H).<br>MS ESI/APCI Dual posi: 416[M + H]⁺.<br>MS ESI/APCI Dual nega: 414[M − H]⁻. | Na |

TABLE 21-42-continued

| Compound No. | Structure | Analytical Data | Salt information |
|---|---|---|---|
| Example 1-295 | 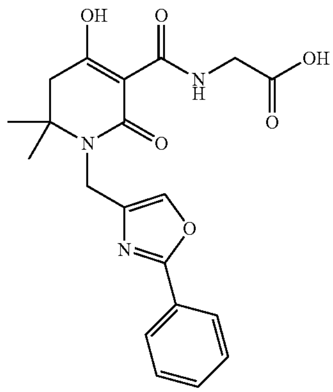 [SMILES: CC1(C)CC(O)=C(C(=O)NCC(=O)O)C(=O)N1Cc1coc(-c2ccccc2)n1] | $^1$H NMR (300 MHz, METHANOL-d$_6$) δ ppm 1.40 (s, 6 H) 2.62 (s, 2 H) 3.89 (s, 2 H) 4.61 (s, 2 H) 7.45-7.52 (m, 3 H) 7.86 (s, 1 H) 7.97-8.04 (m, 2 H).<br>MS ESI/APCI Dual posi: 400[M + H]$^+$.<br>MS ESI/APCI Dual nega: 398[M − H]$^-$. | Na |
| Example 1-296 | 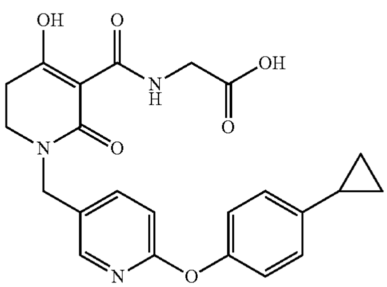 [SMILES: O=C(O)CNC(=O)C1=C(O)CCN(Cc2ccc(Oc3ccc(C4CC4)cc3)nc2)C1=O] | $^1$H NMR (300 MHz, DMSO-d$_6$) δ ppm 0.54-0.73 (m, 2 H) 0.87-1.01 (m, 2 H) 1.82-2.00 (m, 1 H) 2.50-2.58 (m, 2 H) 3.22-3.39 (m, 2 H) 3.47 (d, J = 4.4 Hz, 2 H) 4.51 (s, 2 H) 6.86-7.03 (m, 3 H) 7.04-7.19 (m, 2 H) 7.74 (dd, J = 8.4, 2.6 Hz, 1 H) 8.06 (d, J = 2.6 Hz, 1 H) 9.90-10.20 (m, 1 H).<br>MS ESI/APCI Dual posi: 438[M + H]$^+$.<br>MS ESI/APCI Dual nega: 436[M − H]$^-$. | Na |
| Example 1-297 | 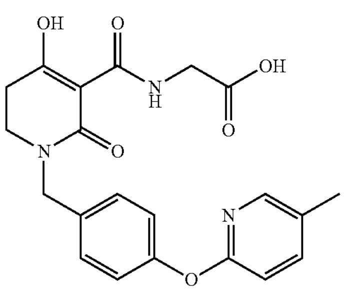 | $^1$H NMR (300 MHz, DMSO-d$_6$) δ ppm 2.24 (s, 3 H) 2.54-2.68 (m, 2 H) 3.37 (t, J = 7.1 Hz, 2 H) 3.72 (d, J = 5.0 Hz, 2 H) 4.57 (s, 2 H) 6.92 (d, J = 8.4 Hz, 1 H) 7.01-7.09 (m, 2 H) 7.25-7.34 (m, 2 H) 7.67 (ddd, J = 8.4, 2.5, 0.6 Hz, 1 H) 7.97 (dt, J = 2.5, 0.6 Hz, 1 H) 10.01-10.19 (m, 1 H).<br>MS ESI/APCI Dual posi: 412[M + H]$^+$.<br>MS ESI/APCI Dual nega: 410[M − H]$^-$. | Na |

TABLE 21-43

| Compound No. | Structure | Analytical Data | Salt information |
|---|---|---|---|
| Example 1-298 | 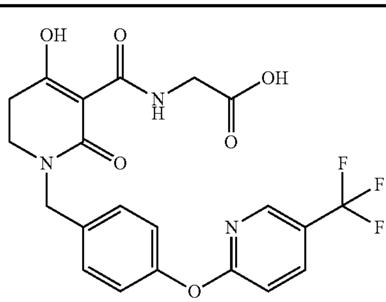 | $^1$H NMR (300 MHz, DMSO-d$_6$) δ ppm 2.59-2.81 (m, 2 H) 3.44 (t, J = 7.3 Hz, 2 H) 4.03 (d, J = 5.8 Hz, 2 H) 4.61 (s, 2 H) 7.15-7.21 (m, 2 H) 7.24 (d, J = 8.7 Hz, 1 H) 7.37 (d, J = 8.7 Hz, 2 H) 8.12-8.28 (m, 1 H) 8.56 (dd, J = 1.8, 0.9 Hz, 1 H) 10.07 (br. s., 1 H).<br>MS ESI/APCI Dual posi: 466[M + H]$^+$.<br>MS ESI/APCI Dual nega: 464[M − H]$^-$. | HCl |

TABLE 21-43-continued

| Compound No. | Structure | Analytical Data | Salt information |
|---|---|---|---|
| Example 1-299 | 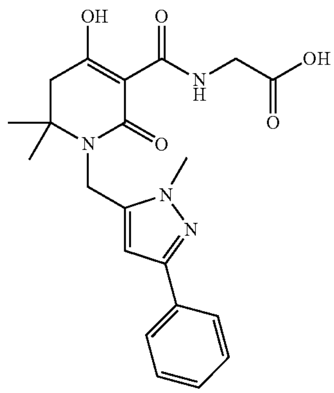 [SMILES: Cn1nc(-c2ccccc2)cc1CN1C(=O)C(C(=O)NCC(=O)O)=C(O)CC1(C)C] | $^1$H NMR (300 MHz, DMSO-d$_6$) δ ppm 1.31 (s, 6 H) 2.78-2.89 (m, 2 H) 3.85 (s, 3 H) 4.01 (d, J = 4.5 Hz, 2 H) 4.65 (br. s., 2 H) 6.60 (br. s., 1 H) 7.20-7.29 (m, 1 H) 7.31-7.39 (m, 2 H) 7.72-7.80 (m, 2 H) 9.93-10.06 (m, 1 H). MS ESI/APCI Dual posi: 413[M + H]$^+$. MS ESI/APCI Dual nega: 411[M − H]$^−$. | HCl |
| Example 1-300 | 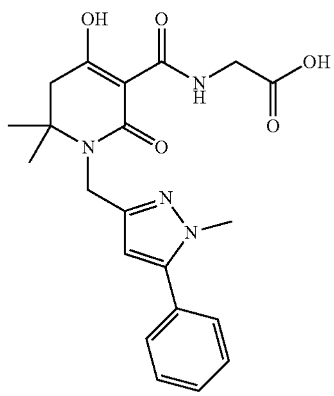 [SMILES: Cn1nc(CN2C(=O)C(C(=O)NCC(=O)O)=C(O)CC2(C)C)cc1-c1ccccc1] | $^1$H NMR (300 MHz, DMSO-d$_6$) δ ppm 1.29 (s, 6 H) 2.64-2.76 (m, 2 H) 3.81 (s, 3 H) 3.96-4.06 (m, 2 H) 4.49-4.65 (m, 2 H) 6.28 (br. s., 1 H) 7.36-7.56 (m, 5 H) 10.02-10.20 (m, 1 H). MS ESI/APCI Dual posi: 413[M + H]$^+$. MS ESI/APCI Dual nega: 411[M − H]$^−$. | HCl |
| Example 1-301 | 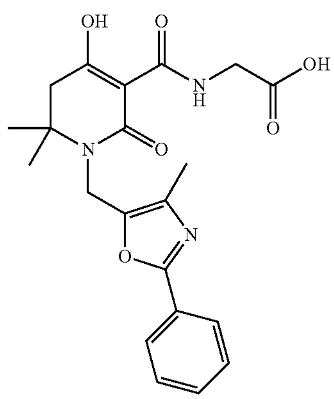 [SMILES: Cc1nc(-c2ccccc2)oc1CN1C(=O)C(C(=O)NCC(=O)O)=C(O)CC1(C)C] | $^1$H NMR (300 MHz, DMSO-d$_6$) δ ppm 1.36 (s, 6 H) 2.22 (s, 3 H) 2.50-2.80 (m, 2 H) 4.04 (d, J = 5.8 Hz, 2 H) 4.70 (br. s., 2 H) 7.44-7.57 (m, 3 H) 7.85-7.94 (m, 2 H) 10.00 (br. s., 1 H). MS ESI/APCI Dual posi: 414[M + H]$^+$. MS ESI/APCI Dual nega: 412[M − H]$^−$. | HCl |
| Example 1-302 | 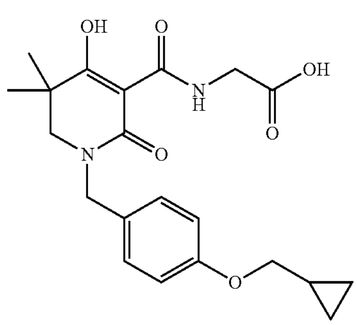 [SMILES: CC1(C)CN(Cc2ccc(OCC3CC3)cc2)C(=O)C(C(=O)NCC(=O)O)=C1O] | $^1$H NMR (300 MHz, DMSO-d$_6$) δ ppm 0.26-0.35 (m, 2 H) 0.51-0.60 (m, 2 H) 0.95 (s, 6 H) 1.12-1.30 (m, 1 H) 2.96-3.07 (m, 2 H) 3.40-3.48 (m, 2 H) 3.78 (d, J = 7.0 Hz, 2 H) 4.48 (s, 2 H) 6.87 (d, J = 8.5 Hz, 2 H) 7.21 (d, J = 8.5 Hz, 2 H). MS ESI/APCI Dual posi: 403[M + H]$^+$. MS ESI/APCI Dual nega: 401[M − H]$^−$. | Na |

TABLE 21-43-continued

| Compound No. | Structure | Analytical Data | Salt information |
|---|---|---|---|
| Example 1-303 | 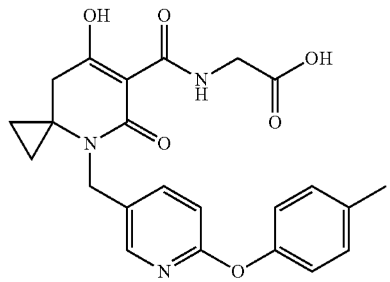 [SMILES: Cc1ccc(Oc2ccc(CN3C(=O)C(C(=O)NCC(=O)O)=C(O)CC34CC4)cn2)cc1] | $^1$H NMR (300 MHz, DMSO-d$_6$) δ ppm 0.64 (s, 2 H) 0.89 (s, 2 H) 2.31 (s, 3 H) 2.45 (s, 2 H) 3.66 (d, J = 4.5 Hz, 2 H) 4.43 (s, 2 H) 6.90-6.96 (m, 1 H) 6.97-7.03 (m, 2 H) 7.15-7.25 (m, 2 H) 7.66-7.77 (m, 1 H) 8.02-8.10 (m, 1 H) 9.93-10.30 (m, 1 H). MS ESI/APCI Dual posi: 438[M + H]$^+$. MS ESI/APCI Dual nega: 436[M − H]$^-$. | Na |
| Example 1-304 | 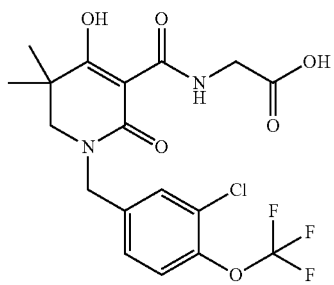 [SMILES: CC1(C)CN(Cc2ccc(OC(F)(F)F)c(Cl)c2)C(=O)C(C(=O)NCC(=O)O)=C1O] | $^1$H NMR (300 MHz, DMSO-d$_6$) δ ppm 1.01 (s, 6 H) 3.15 (s, 2 H) 3.40-3.49 (m, 2 H) 4.59 (s, 2 H) 7.36-7.45 (m, 1 H) 7.51-7.58 (m, 1 H) 7.60-7.64 (m, 1 H) 9.95-10.48 (m, 1 H). MS ESI/APCI Dual posi: 451[M + H]$^+$. MS ESI/APCI Dual nega: 449[M − H]$^-$. | |

TABLE 21-44

| Compound No. | Structure | Analytical Data | Salt information |
|---|---|---|---|
| Example 1-305 | 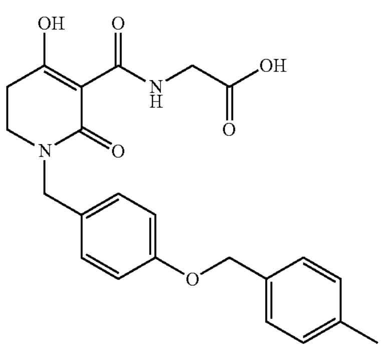 [SMILES: Cc1ccc(COc2ccc(CN3CCC(O)=C(C(=O)NCC(=O)O)C3=O)cc2)cc1] | $^1$H NMR (300 MHz, METHANOL-d$_6$) δ ppm 2.33 (s, 3 H) 2.41-2.63 (m, 2 H) 3.27-3.33 (m, 2 H) 3.88 (s, 2 H) 4.54 (s, 2 H) 5.01 (s, 2 H) 6.94 (d, J = 8.7 Hz, 2 H) 7.13-7.25 (m, 4 H) 7.30 (d, J = 8.1 Hz, 2 H). MS ESI/APCI Dual posi: 425[M + H]$^+$. MS ESI/APCI Dual nega: 423[M − H]$^-$. | |
| Example 1-306 | 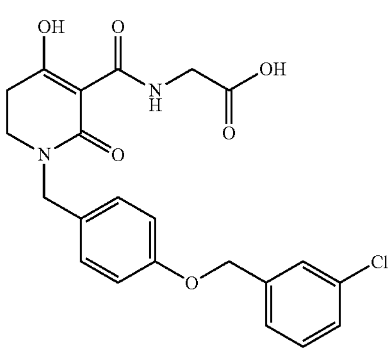 [SMILES: O=C(O)CNC(=O)C1=C(O)CCN(Cc2ccc(OCc3cccc(Cl)c3)cc2)C1=O] | $^1$H NMR (300 MHz, METHANOL-d$_6$) δ ppm 2.44-2.63 (m, 2 H) 3.29-3.33 (m, 2 H) 3.89 (s, 2 H) 4.55 (s, 2 H) 5.07 (s, 2 H) 6.93-6.99 (m, 2 H) 7.24 (d, J = 8.7 Hz, 2 H) 7.27-7.33 (m, 1 H) 7.33-7.38 (m, 2 H) 7.45 (s, 1 H). MS ESI/APCI Dual posi: 445[M + H]$^+$. MS ESI/APCI Dual nega: 443[M − H]$^-$. | |

TABLE 21-44-continued

| Compound No. | Structure | Analytical Data | Salt information |
|---|---|---|---|
| Example 1-307 | 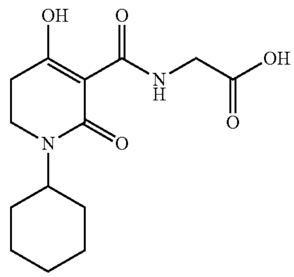 [SMILES: O=C(O)CNC(=O)C1=C(O)CCN(C2CCCCC2)C1=O] | $^1$H NMR (300 MHz, CHLOROFORM-d) δ ppm 1.00-1.20 (m, 1 H) 1.25-1.56 (m, 4 H) 1.61-1.92 (m, 5 H) 2.47-2.67 (m, 2 H) 3.25-3.45 (m, 2 H) 4.12-4.22 (m, 2 H) 4.21-4.53 (m, 1 H) 10.20-10.47 (m, 1 H).<br>MS ESI/APCI Dual posi: 297[M + H]$^+$, 319[M + Na]$^+$.<br>MS ESI/APCI Dual nega: 295[M − H]$^-$. | |

TABLE 21-45

| Compound No. | Structure | Analytical Data | Salt information |
|---|---|---|---|
| Example 1-308 | 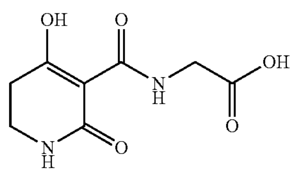 [SMILES: O=C(O)CNC(=O)C1=C(O)CCNC1=O] | $^1$H NMR (300 MHz, DMSO-d$_6$) δ ppm 2.35-2.66 (m, 2 H) 3.18-3.40 (m, 2 H) 3.99 (d, J = 5.8 Hz, 2 H) 9.91-10.02 (m, 1 H).<br>MS ESI/APCI Dual nega: 213[M − H]$^-$. | |
| Example 1-309 | 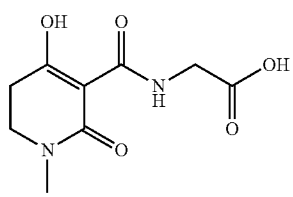 [SMILES: CN1CCC(O)=C(C(=O)NCC(=O)O)C1=O] | $^1$H NMR (300 MHz, DMSO-d$_6$) δ ppm 2.62-2.75 (m, 2 H) 2.84-2.98 (m, 3 H) 3.34-3.48 (m, 2 H) 3.95-4.03 (m, 2 H) 10.02-10.17 (m, 1 H).<br>MS ESI/APCI Dual posi: 251[M + H]$^+$.<br>MS ESI/APCI Dual nega: 227[M − H]$^-$. | |
| Example 1-310 | 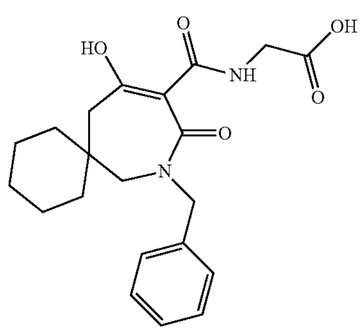 [SMILES: O=C(O)CNC(=O)C1=C(O)CC2(CCCCC2)CN(Cc2ccccc2)C1=O] | $^1$H NMR (300 MHz, DMSO-d$_6$) δ ppm 1.16-1.47 (m, 10 H) 2.31 (s, 2 H) 3.08 (s, 2 H) 3.96 (d, J = 5.7 Hz, 2 H) 4.67 (s, 2 H) 7.22-7.39 (m, 5 H) 8.86 (t, J = 5.7 Hz, 1 H) 12.78 (br. s., 1 H).<br>MS ESI/APCI Dual posi: 387[M + H]$^+$, 409[M + H]$^+$.<br>MS ESI/APCI Dual nega: 385[M − H]$^-$. | |
| Example 1-311 | 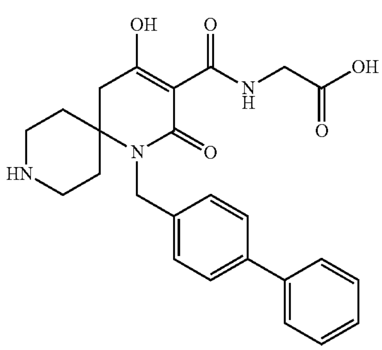 [SMILES: O=C(O)CNC(=O)C1=C(O)CC2(CCNCC2)N(Cc2ccc(-c3ccccc3)cc2)C1=O] | $^1$H NMR (600 MHz, DMSO-d$_6$) δ ppm 1.55-1.68 (m, 2 H) 2.03-2.18 (m, 2 H) 2.83-2.92 (m, 2 H) 2.94-3.07 (m, 4 H) 3.63-3.77 (m, 2 H) 4.56-4.81 (m, 2 H) 7.24-7.35 (m, 3 H) 7.41 (t, J = 7.8 Hz, 2 H) 7.54-7.61 (m, 4 H) 10.03-10.19 (m, 1 H).<br>MS ESI/APCI Dual posi: 450[M + H]$^+$.<br>MS ESI/APCI Dual nega: 448[M − H]$^-$. | |

TABLE 21-45-continued

| Compound No. | Structure | Analytical Data | Salt information |
|---|---|---|---|
| Example 1-312 | 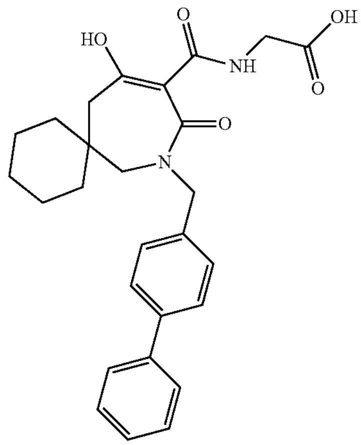 [SMILES: O=C(O)CNC(=O)C1=C(O)CC2(CCCCC2)CN(Cc2ccc(-c3ccccc3)cc2)C1=O] | ¹H NMR (300 MHz, DMSO-d₆) δ ppm 1.11-1.53 (m, 10 H) 2.34 (s, 2 H) 3.11 (s, 2 H) 3.97 (d, J = 5.8 Hz, 2 H) 4.71 (s, 2 H) 7.31-7.41 (m, 3 H) 7.42-7.51 (m, 2 H) 7.60-7.70 (m, 4 H) 8.88 (t, J = 5.5 Hz, 1 H). MS ESI/APCI Dual posi: 463[M + H]⁺, 485[M + Na]⁺. MS ESI/APCI Dual nega: 461[M − H]⁻. | |
| Example 1-313 | 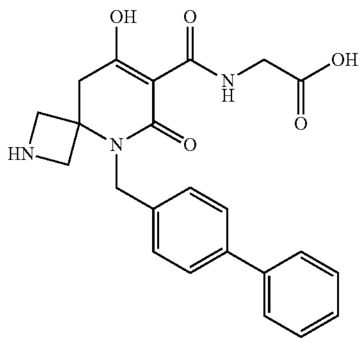 [SMILES: O=C(O)CNC(=O)C1=C(O)CC2(CNC2)N(Cc2ccc(-c3ccccc3)cc2)C1=O] | ¹H NMR (600 MHz, DMSO-d₆) δ ppm 2.42-2.46 (m, 2 H) 3.82-3.93 (m, 2 H) 3.95-4.04 (m, 2 H) 4.22-4.30 (m, 2 H) 4.95-5.07 (m, 2 H) 7.29-7.39 (m, 3 H) 7.40-7.46 (m, 2 H) 7.57-7.66 (m, 4 H) 9.73-9.85 (m, 1 H). | HCL |
| Example 1-314 | 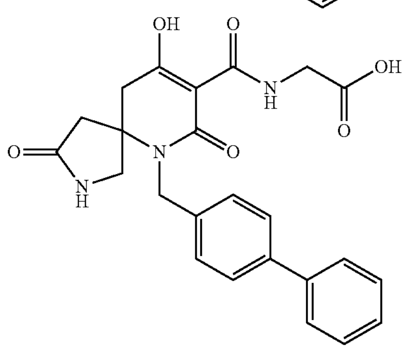 | ¹H NMR (300 MHz, METHANOL-d₆) δ ppm 2.30-2.44 (m, 1 H) 2.79-3.04 (m, 3 H) 3.40-3.47 (m, 1 H) 3.55-3.65 (m, 1 H) 4.03 (s, 2 H) 4.69-4.81 (m, 1 H) 4.94-5.06 (m, 1 H) 7.28-7.45 (m, 5 H) 7.55-7.65 (m, 4 H). MS ESI/APCI Dual posi: 472[M + Na]⁺. MS ESI/APCI Dual nega: 448[M − H]⁻. | |

TABLE 21-46

| Compound No. | Structure | Analytical Data | Salt information |
|---|---|---|---|
| Example 1-315 | 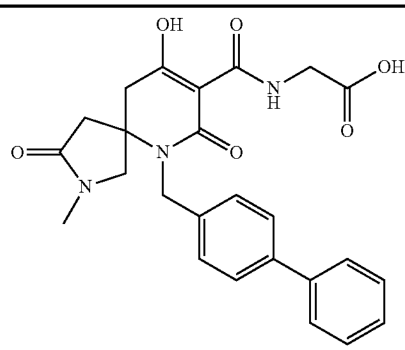 | ¹H NMR (300 MHz, DMSO-d₆) δ ppm 2.34-2.46 (m, 1 H) 2.61-2.75 (m, 4 H) 2.90-3.04 (m, 1 H) 3.04-3.19 (m, 1 H) 3.38-3.57 (m, 2 H) 3.96-4.09 (m, 2 H) 4.57-4.88 (m, 2 H) 7.31-7.40 (m, 3 H) 7.42-7.50 (m, 2 H) 7.58-7.68 (m, 4 H) 9.89-10.30 (m, 1 H). MS ESI/APCI Dual posi: 486[M + Na]⁺. MS ESI/APCI Dual nega: 462[M − H]⁻. | |

TABLE 21-46-continued

| Compound No. | Structure | Analytical Data | Salt information |
|---|---|---|---|
| Example 1-316 | 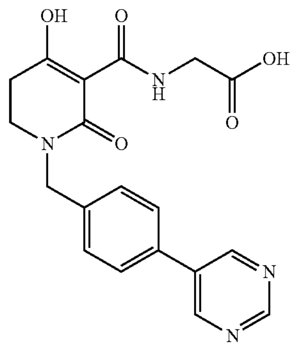 | $^1$H NMR (300 MHz, DMSO-$d_6$) δ ppm 2.66-2.76 (m, 2 H) 3.38-3.46 (m, 2 H) 3.94-4.04 (m, 2 H) 4.64 (s, 2 H) 7.46 (d, J = 8.0 Hz, 2 H) 7.80 (d, J = 8.0 Hz, 2 H) 9.14 (s, 2 H) 9.18 (s, 1 H) 9.99-10.08 (m, 1 H).<br>MS ESI/APCI Dual posi: 383[M + H]$^+$, 405[M + Na]$^+$.<br>MS ESI/APCI Dual nega: 381[M − H]$^-$. | |
| Example 1-317 | 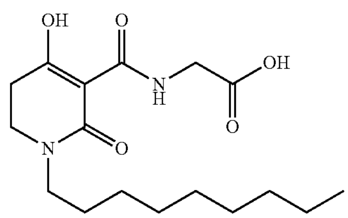 [SMILES: CCCCCCCCCN1CCC(O)=C(C(=O)NCC(=O)O)C1=O] | $^1$H NMR (300 MHz, CHLOROFORM-d) δ ppm 0.73-0.98 (m, 3 H) 1.16-1.38 (m, 12 H) 1.44-1.65 (m, 2 H) 2.52-2.72 (m, 2 H) 3.31-3.48 (m, 4 H) 4.11-4.21 (m, 2 H) 10.16-10.39 (m, 1 H).<br>MS ESI/APCI Dual posi: 341[M + H]$^+$, 363[M + Na]$^+$.<br>MS ESI/APCI Dual nega: 339[M − H]$^-$. | |
| Example 1-318 | 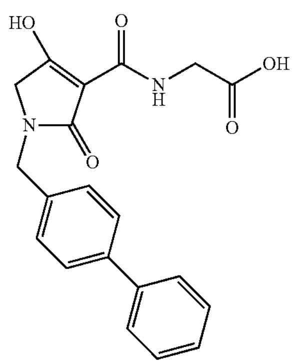 [SMILES: O=C(O)CNC(=O)C1=C(O)CN(Cc2ccc(-c3ccccc3)cc2)C1=O] | $^1$H NMR (500 MHz, METHANOL-$d_6$) δ ppm 3.96 (s, 2 H) 4.11 (s, 2 H) 4.64 (s, 2 H) 7.29-7.36 (m, 3 H) 7.39-7.45 (m, 2 H) 7.57-7.63 (m, 4 H).<br>MS ESI/APCI Dual posi: 367[M + H]$^+$.<br>MS ESI/APCI Dual nega: 365[M − H]$^-$. | |
| Example 1-319 | 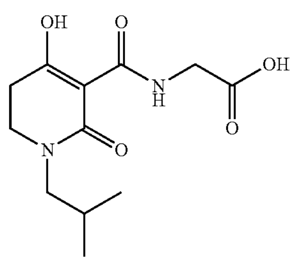 [SMILES: CC(C)CN1CCC(O)=C(C(=O)NCC(=O)O)C1=O] | $^1$H NMR (300 MHz, CHLOROFORM-d) δ ppm 0.88-1.00 (m, 6 H) 1.78-2.16 (m, 1 H) 2.49-2.80 (m, 2 H) 3.10-3.33 (m, 2 H) 3.33-3.60 (m, 2 H) 4.07-4.27 (m, 2 H) 10.04-10.44 (m, 1 H).<br>MS ESI/APCI Dual posi: 271[M + H]$^+$, 293[M + Na]$^+$.<br>MS ESI/APCI Dual nega: 269[M − H]$^-$. | |
| Example 1-320 | 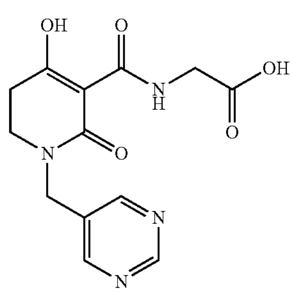 [SMILES: O=C(O)CNC(=O)C1=C(O)CCN(Cc2cncnc2)C1=O] | $^1$H NMR (600 MHz, DMSO-$d_6$) δ ppm 2.68-2.78 (m, 2 H) 3.51 (t, J = 7.2 Hz, 2 H) 3.97-4.04 (m, 2 H) 4.59 (s, 2 H) 8.77 (s, 1 H) 9.11 (s, 1 H).<br>MS ESI/APCI Dual posi: 307[M + H]$^+$, 329[M + Na]$^+$.<br>MS ESI/APCI Dual nega: 305[M − H]$^-$. | HCL |

TABLE 21-46-continued

| Compound No. | Structure | Analytical Data | Salt information |
|---|---|---|---|
| Example 1-321 | 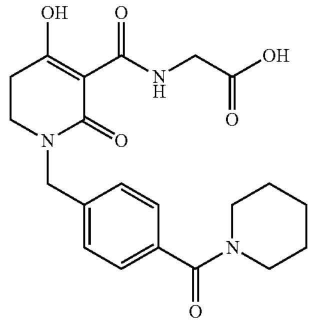 [SMILES: O=C(O)CNC(=O)C1=C(O)CCN(Cc2ccc(C(=O)N3CCCCC3)cc2)C1=O] | ¹H NMR (600 MHz, DMSO-d₆) δ ppm 1.36-1.61 (m, 6 H) 2.63-2.70 (m, 2 H) 3.24-3.27 (m, 2 H) 3.33-3.39 (m, 2 H) 3.45-3.58 (m, m2 H) 3.91-4.03 (m, 2 H) 4.53-4.64 (m, 2 H) 7.24-7.35 (m, 4 H) 9.92-10.02 (m, 1 H). MS ESI/APCI Dual posi: 416[M + H]⁺, 438[M + Na]⁺. MS ESI/APCI Dual nega: 414[M − H]⁻. | |

TABLE 21-47

| Compound No. | Structure | Analytical Data | Salt information |
|---|---|---|---|
| Example 1-322 | 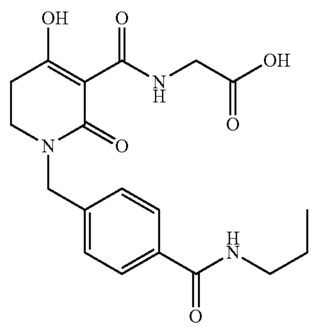 [SMILES: CCCNC(=O)c1ccc(CN2CCC(O)=C(C(=O)NCC(=O)O)C2=O)cc1] | ¹H NMR (600 MHz, DMSO-d₆) δ ppm 0.84 (t, J = 7.4 Hz, 3 H) 1.44-1.563 (m, 2 H) 2.61-2.68 (m, 2 H) 3.13-3.20 (m, 2 H) 3.32-3.41 (m, 2 H) 3.93-4.03 (m, 2 H) 4.55-4.64 (m, 2 H) 7.27-7.35 (m, 2 H) 7.74-7.80 (m, 2 H) 8.33-8.41 (m, 1 H) 9.91-10.22 (m, 1 H). MS ESI/APCI Dual posi: 390[M + H]⁺. MS ESI/APCI Dual nega: 388[M − H]⁻. 412[M + Na]⁺. | |
| Example 1-323 | 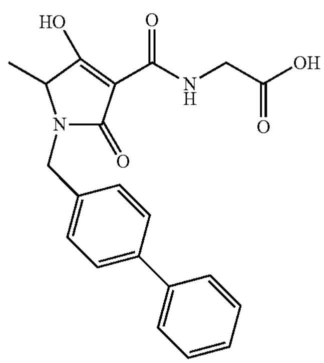 [SMILES: CC1C(O)=C(C(=O)NCC(=O)O)C(=O)N1Cc1ccc(-c2ccccc2)cc1] | ¹H NMR (600 MHz, CHLOROFORM-d) δ ppm 1.40 (d, J = 7.0 Hz, 3 H) 3.96-4.04 (m, 1 H) 4.14 (d, J = 15.7 Hz, 1 H) 4.21 (m, 2 H) 5.13 (d, J = 15.7 Hz, 1 H) 7.30 (m, 2 H) 7.32-7.38 (m, 1 H) 7.40-7.47 (m, 2 H) 7.51-7.61 (m, 4 H) 8.22 (t, J = 5.8 Hz, 1 H). MS ESI/APCI Dual posi: 381[M + H]⁺. MS ESI/APCI Dual nega: 379[M − H]⁻. | |
| Example 1-324 | 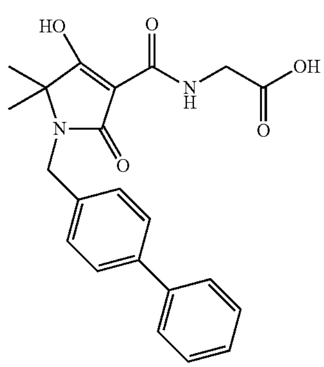 [SMILES: CC1(C)C(O)=C(C(=O)NCC(=O)O)C(=O)N1Cc1ccc(-c2ccccc2)cc1] | ¹H NMR (600 MHz, CHLOROFORM-d) δ ppm 1.32 (s, 6 H) 4.21 (d, J = 6.2 Hz, 2 H) 4.60 (s, 2 H) 7.32-7.39 (m, 3 H) 7.43 (m, 2 H) 7.53-7.60 (m, 4 H) 8.27 (m, 1 H). MS ESI/APCI Dual posi: 395[M + H]⁺. MS ESI/APCI Dual nega: 393[M − H]⁻. | |

TABLE 21-47-continued

| Compound No. | Structure | Analytical Data | Salt information |
|---|---|---|---|
| Example 1-325 | 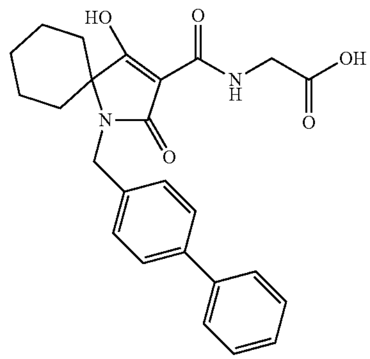 [SMILES: O=C(O)CNC(=O)C1=C(O)C2(CCCCC2)N(Cc2ccc(-c3ccccc3)cc2)C1=O] | ¹H NMR (600 MHz, CHLOROFORM-d) δ ppm 1.06-1.19 (m, 1 H) 1.56-1.81 (m, 7 H) 1.87-2.00 (m, 2 H) 4.16-4.25 (m, 2 H) 4.59 (s, 2 H) 7.29-7.37 (m, 3 H) 7.38-7.47 (m, 2 H) 7.50-7.61 (m, 4 H) 8.28-8.31 (m, 1 H). MS ESI/APCI Dual posi: 435[M + H]⁺. MS ESI/APCI Dual nega: 433[M − H]⁻. | |
| Example 1-326 | 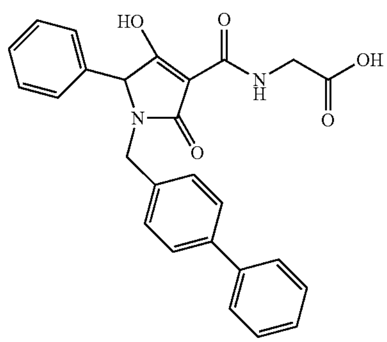 [SMILES: O=C(O)CNC(=O)C1=C(O)C(c2ccccc2)N(Cc2ccc(-c3ccccc3)cc2)C1=O] | ¹H NMR (600 MHz, CHLOROFORM-d) δ ppm 3.68 (d, J = 15.3 Hz, 1 H) 4.21-4.27 (m, 2 H) 4.87 (s, 1 H) 5.23 (d, J = 15.3 Hz, 1 H) 7.14-7.22 (m, 4 H) 7.32-7.39 (m, 1 H) 7.39-7.48 (m, 5 H) 7.50-7.61 (m, 4 H) 8.23-8.32 (m, 1 H). MS ESI/APCI Dual posi: 443[M + H]⁺. MS ESI/APCI Dual nega: 441[M − H]⁻. | |
| Example 1-327 | 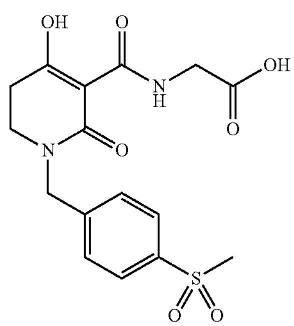 [SMILES: CS(=O)(=O)c1ccc(CN2CCC(O)=C(C(=O)NCC(=O)O)C2=O)cc1] | ¹H NMR (600 MHz, DMSO-d₆) δ ppm 2.64-2.72 (m, 2 H) 3.16 (s, 3 H) 3.37-3.45 (m, 2 H) 3.93-4.04 (m, 2 H) 4.59-4.72 (m, 2 H) 7.47-7.56 (m, 2 H) 7.78-7.92 (m, 2 H) 9.80-10.29 (m, 1 H). MS ESI/APCI Dual posi: 383[M + H]⁺, 405[M + Na]⁺. MS ESI/APCI Dual nega: 381[M − H]⁻. | |
| Example 1-328 | 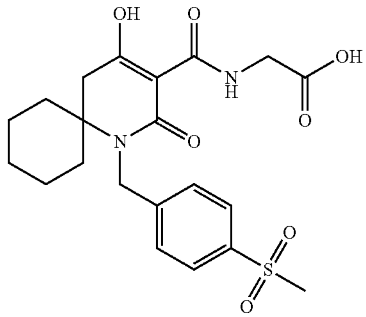 [SMILES: CS(=O)(=O)c1ccc(CN2C(=O)C(C(=O)NCC(=O)O)=C(O)CC23CCCCC3)cc1] | ¹H NMR (300 MHz, DMSO-d₆) δ ppm 1.03-1.79 (m, 10 H) 2.67-3.00 (m, 2 H) 3.14-3.23 (m, 3 H) 3.93-4.10 (m, 2 H) 4.77-4.92 (m, 2 H) 7.48-7.62 (m, 2 H) 7.80-7.94 (m, 2 H) 9.87-10.26 (m, 1 H) 12.84 (br. s., 1 H). MS ESI/APCI Dual posi: 473[M + Na]⁺. MS ESI/APCI Dual nega: 449[M − H]⁻. | |

TABLE 21-48

| Compound No. | Structure | Analytical Data | Salt information |
|---|---|---|---|
| Example 1-329 | 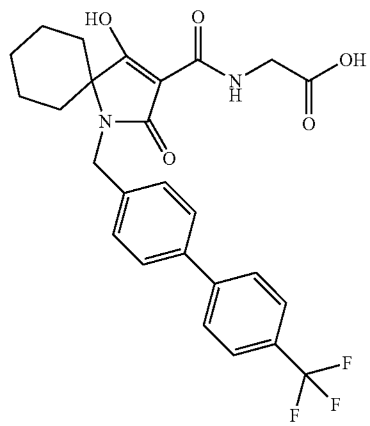 [SMILES: O=C(O)CNC(=O)C1=C(O)C2(CCCCC2)N(Cc2ccc(-c3ccc(C(F)(F)F)cc3)cc2)C1=O] | $^1$H NMR (300 MHz, CHLOROFORM-d) δ ppm 1.01-1.24 (m, 1 H) 1.54-2.07 (m, 9 H) 4.20 (d, J = 5.9 Hz, 2 H) 4.60 (s, 2 H) 7.29-7.41 (m, 2 H) 7.48-7.59 (m, 2 H) 7.59-7.73 (m, 4 H) 8.16-8.33 (m, 1 H). MS ESI/APCI Dual posi: 503[M + H]$^+$, 525[M + Na]$^+$. MS ESI/APCI Dual nega: 501[M − H]$^-$. | |
| Example 1-330 | 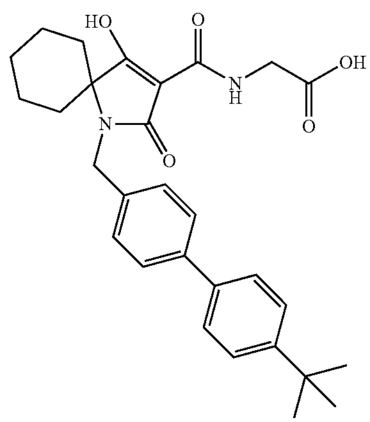 [SMILES: CC(C)(C)c1ccc(-c2ccc(CN3C(=O)C(C(=O)NCC(=O)O)=C(O)C34CCCCC4)cc2)cc1] | $^1$H NMR (300 MHz, CHLOROFORM-d) δ ppm 1.02-1.24 (m, 1 H) 1.29-2.10 (m, 18 H) 4.19 (d, J = 5.8 Hz, 2 H) 4.58 (s, 2 H) 7.20-7.36 (m, 2 H) 7.36-7.58 (m, 6 H) 8.20-8.34 (m, 1 H). MS ESI/APCI Dual posi: 491[M + H]$^+$, 513[M + Na]$^+$. MS ESI/APCI Dual nega: 489M − H]$^-$. | |
| Example 1-331 | 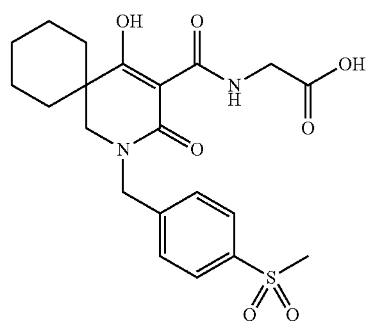 [SMILES: CS(=O)(=O)c1ccc(CN2CC3(CCCCC3)C(O)=C(C(=O)NCC(=O)O)C2=O)cc1] | $^1$H NMR (300 MHz, CHLOROFORM-d) δ ppm 0.93-1.14 (m, 2 H) 1.15-1.63 (m, 6 H) 1.71-1.89 (m, 2 H) 3.02-3.08 (m, 3 H) 3.24 (s, 2 H) 4.14-4.23 (m, 2 H) 4.66-4.75 (m, 2 H) 7.45-7.56 (m, 2 H) 7.85-8.01 (m, 2 H) 10.14-10.69 (m, 1 H). MS ESI/APCI Dual posi: 451[M + H]$^+$, 473[M + Na]$^+$. MS ESI/APCI Dual nega: 449[M − H]$^-$. | |
| Example 1-332 | 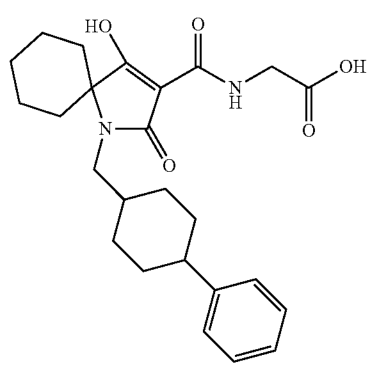 [SMILES: O=C(O)CNC(=O)C1=C(O)C2(CCCCC2)N(CC2CCC(c3ccccc3)CC2)C1=O] | $^1$H NMR (300 MHz, CHLOROFORM-d) δ ppm 0.95-2.16 (m, 19 H) 2.37-2.58 (m, 1 H) 3.00-3.19 (m, 2 H) 4.08-4.26 (m, 2 H) 7.10-7.37 (m, 5 H) 8.18-8.34 (m, 1 H). MS ESI/APCI Dual posi: 441[M + H]$^+$, 463[M + Na]$^+$. MS ESI/APCI Dual nega: 439[M − H]$^-$. | |

TABLE 21-48-continued

| Compound No. | Structure | Analytical Data | Salt information |
|---|---|---|---|
| Example 1-333 | 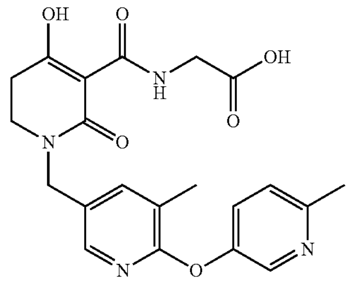 [SMILES: Cc1ccc(Oc2ncc(CN3CCC(O)=C(C(=O)NCC(=O)O)C3=O)cc2C)cn1] | $^1$H NMR (300 MHz, DMSO-$d_6$) δ ppm 2.31 (s, 3 H) 2.47 (s, 3 H) 2.51-2.54 (m, 2 H) 3.30-3.35 (m, 2 H) 3.43 (d, J = 4.4 Hz, 2 H) 4.49 (s, 2 H) 7.26-7.32 (m, 1 H) 7.48 (dd, J = 8.4, 2.8 Hz, 1 H) 7.61-7.65 (m, 1 H) 7.83-7.88 (m, 1 H) 8.27 (dd, J = 2.8, 0.5 Hz, 1 H) 9.89-10.03 (m, 1 H). MS ESI/APCI Dual posi: 427[M + H]$^+$. MS ESI/APCI Dual nega: 425[M − H]$^-$. | Na |
| Example 1-334 | 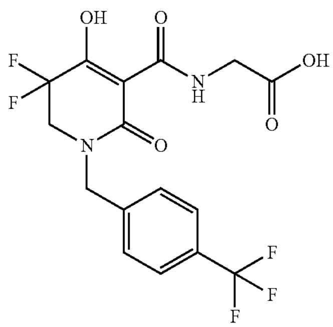 [SMILES: O=C(O)CNC(=O)C1=C(O)C(F)(F)CN(Cc2ccc(C(F)(F)F)cc2)C1=O] | $^1$H NMR (300 MHz, DMSO-$d_6$) δ ppm 3.49-3.74 (m, 2 H) 3.87 (d, J = 5.3 Hz, 2 H) 4.66 (s, 2 H) 7.33-7.54 (m, 2 H) 7.60-7.74 (m, 2 H) 9.99-10.20 (m, 1 H). MS ESI/APCI Dual posi: 409[M + H]$^+$. MS ESI/APCI Dual nega: 407[M − H]$^-$. | Na |
| Example 1-335 | 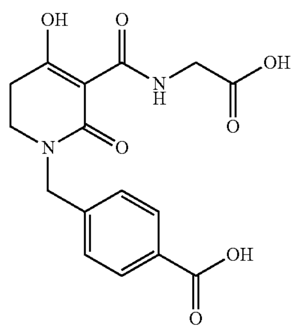 [SMILES: O=C(O)CNC(=O)C1=C(O)CCN(Cc2ccc(C(=O)O)cc2)C1=O] | $^1$H NMR (300 MHz, DMSO-$d_6$) δ ppm 2.64-2.79 (m, 2 H) 3.35-3.49 (m, 2 H) 3.94-4.13 (m, 2 H) 4.57-4.76 (m, 2 H) 7.29-7.49 (m, 2 H) 7.83-8.01 (m, 2 H) 9.93-10.30 (m, 1 H). | |

TABLE 21-49

| Compound No. | Structure | Analytical Data | Salt information |
|---|---|---|---|
| Example 1-336 | 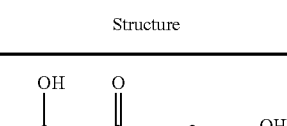 | $^1$H NMR (300 MHz, DMSO-$d_6$) δ ppm 2.73-2.86 (m, 2 H) 3.63 (t, J = 7.1 Hz, 2 H) 4.01 (d, J = 5.7 Hz, 2 H) 4.83 (s, 2 H) 7.68 (d, J = 8.2 Hz, 1 H) 8.11 (dd, J = 8.2, 5.7 Hz, 1 H) 8.45 (d, J = 7.8 Hz, 1 H) 8.83-8.97 (m, 2 H) 9.12 (d, J = 2.0 Hz, 1 H) 9.35 (d, J = 2.0 Hz, 1 H) 9.90 (br. s., 1 H). MS ESI/APCI Dual posi: 383[M + H]$^+$. | HCl |

TABLE 21-49-continued

| Compound No. | Structure | Analytical Data | Salt information |
|---|---|---|---|
| Example 1-337 | (structure) | ¹H NMR (300 MHz, DMSO-d₆) δ ppm 2.62 (br. s., 2 H) 3.37 (t, J = 7.1 Hz, 2 H) 3.80 (s, 3 H) 4.02 (d, J = 5.8 Hz, 2 H) 4.38 (s, 2 H) 7.39 (s, 1 H) 7.66 (s, 1 H) 10.09 (br. s., 1 H). MS ESI/APCI Dual posi: 309[M + H]⁺. | HCl |
| Example 1-338 | (structure) | ¹H NMR (300 MHz, DMSO-d₆) δ ppm 2.76 (t, J = 6.6 Hz, 2 H) 3.52-3.62 (m, 2 H) 4.01 (br. s., 2 H) 4.69 (s, 2 H) 9.02 (s, 2 H) 9.86 (br. s., 1 H). MS ESI/APCI Dual nega: 373[M − H]⁻. | HCl |
| Example 1-339 | (structure) | ¹H NMR (300 MHz, DMSO-d₆) δ ppm 2.53 (s, 3 H) 2.73 (t, J = 7.1 Hz, 2 H) 3.31-3.52 (m, 4 H) 4.00-4.09 (m, 2 H) 4.49-4.66 (m, 2 H) 7.39-7.54 (m, 1 H) 9.82-10.29 (m, 1 H). MS ESI/APCI Dual posi: 309[M + H]⁺. | HCl |
| Example 1-340 | (structure) | ¹H NMR (300 MHz, DMSO-d₆) δ ppm 2.63-2.75 (m, 2 H) 3.33-3.49 (m, 6 H) 3.66-3.76 (m, 4 H) 4.02 (d, J = 5.6 Hz, 2 H) 4.55 (s, 2 H) 7.30 (s, 1 H) 9.91 (br. s., 1 H). MS ESI/APCI Dual posi: 397[M + H]⁺. MS ESI/APCI Dual nega: 395[M − H]⁻. | HCl |

TABLE 21-49-continued

| Compound No. | Structure | Analytical Data | Salt information |
|---|---|---|---|
| Example 1-341 | 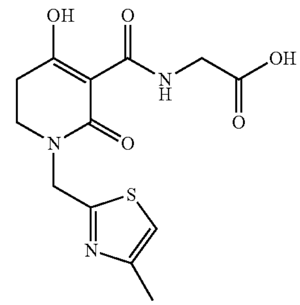 [SMILES: Cc1csc(CN2CCC(O)=C(C(=O)NCC(=O)O)C2=O)n1] | $^1$H NMR (300 MHz, DMSO-d$_6$) δ ppm 2.34 (d, J = 0.9 Hz, 3 H) 2.61-2.79 (m, 2 H) 3.42-3.62 (m, 2 H) 4.02 (d, J = 5.8 Hz, 2 H) 4.81 (s, 2 H) 7.22 (s, 1 H) 8.06-8.39 (m, 1 H) 9.75-10.04 (m, 1 H). MS ESI/APCI Dual posi: 326[M + H]$^+$. | HCl |
| Example 1-342 | 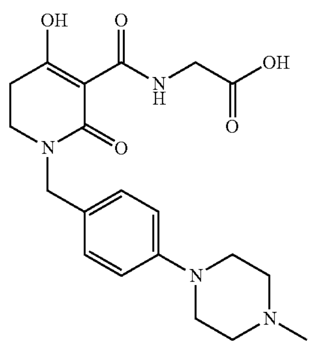 [SMILES: CN1CCN(c2ccc(CN3CCC(O)=C(C(=O)NCC(=O)O)C3=O)cc2)CC1] | $^1$H NMR (300 MHz, DMSO-d$_6$) δ ppm 2.64 (br. s., 2 H) 2.98-3.20 (m, 4 H) 3.27-3.38 (m, 2 H) 3.43-3.52 (m, 2 H) 3.57 (s, 3 H) 3.79 (d, J =11.3 Hz, 2 H) 4.02 (d, J = 5.6 Hz, 2 H) 4.49 (br. s., 2 H) 6.97 (d, J = 8.7 Hz, 2 H) 7.19 (d, JU = 8.7 Hz, 2 H) 9.94-10.84 (m, 1 H). MS ESI/APCI Dual posi: 403[M + H]$^+$. MS ESI/APCI Dual nega: 401[M − H]$^-$. | HCl |

TABLE 21-50

| Compound No. | Structure | Analytical Data | Salt information |
|---|---|---|---|
| Example 1-343 | 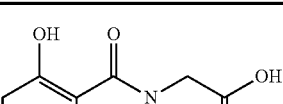 | $^1$H NMR (300 MHz, DMSO-d$_6$) δ ppm 1.95-2.08 (m, 2 H) 2.62 (s, 6 H) 2.97 (br. s., 2 H) 3.29-3.39 (m, 4 H) 3.93-4.05 (m, 4 H) 4.50 (s, 2 H) 8.90 (d, J = 8.4 Hz, 2 H) 7.22 (d, J = 8.4 Hz, 2 H) 10.08 (br. s., 1 H). MS ESI/APCI Dual posi: 406[M + H]$^+$. MS ESI/APCI Dual nega: 404[M − H]$^-$. | Na |

TABLE 21-50-continued

| Compound No. | Structure | Analytical Data | Salt information |
|---|---|---|---|
| Example 1-344 | 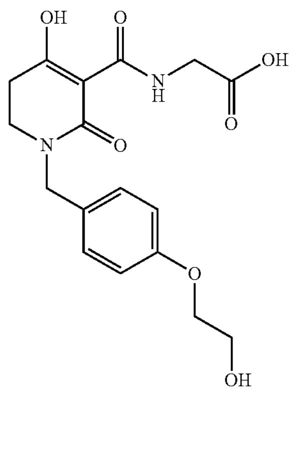 [SMILES: O=C(O)CNC(=O)C1=C(O)CCN(Cc2ccc(OCCO)cc2)C1=O] | $^1$H NMR (300 MHz, DMSO-d$_6$) δ ppm 3.20-3.33 (m, 4 H) 3.51 (d, J = 4.5 Hz, 2 H) 3.69 (t, J = 5.1 Hz, 2 H) 3.91-4.00 (m, 2 H) 4.48 (s, 2 H) 6.85-6.94 (m, 2 H) 7.15-7.24 (m, 2 H) 10.09 (br. s., 1 H).<br>MS ESI/APCI Dual posi: 365[M + H]$^+$. | Na |
| Example 1-345 | 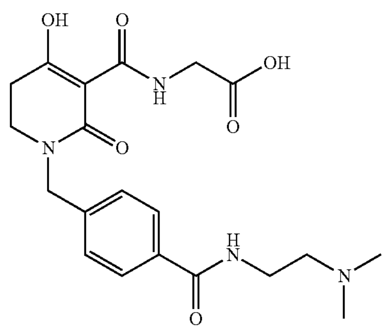 [SMILES: CN(C)CCNC(=O)c1ccc(CN2CCC(O)=C(C(=O)NCC(=O)O)C2=O)cc1] | $^1$H NMR (300 MHz, DMSO-d$_6$) δ ppm 2.69 (t, J = 7.1 Hz, 2 H) 2.82 (d, J = 4.8 Hz, 6 H) 3.18-3.32 (m, 2 H) 3.39 (t, J = 7.1 Hz, 2 H) 3.56-3.68 (m, 2 H) 4.02 (d, J = 5.6 Hz, 2 H) 4.57-4.71 (m, 2 H) 7.38 (d, J = 8.2 Hz, 2 H) 7.89 (d, J = 8.2 Hz, 2 H) 8.72-8.87 (m, 1 H) 9.90-10.28 (m, 1 H).<br>MS ESI/APCI Dual posi: 419[M + H]$^+$.<br>MS ESI/APCI Dual nega: 417[M − H]$^-$. | HCl |
| Example 1-346 | 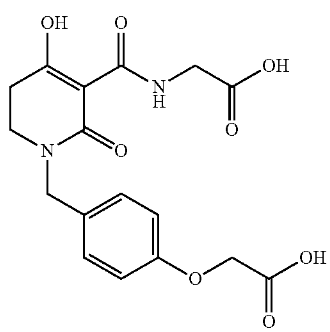 [SMILES: O=C(O)CNC(=O)C1=C(O)CCN(Cc2ccc(OCC(=O)O)cc2)C1=O] | $^1$H NMR (300 MHz, DMSO-d$_6$) δ ppm 2.65 (t, J = 7.1 Hz, 2 H) 3.29-3.39 (m, 2 H) 4.02 (d, J = 5.8 Hz, 2 H) 4.43-4.57 (m, 2 H) 4.64 (s, 2 H) 6.87 (d, J = 8.7 Hz, 2 H) 7.21 (d, J = 8.7 Hz, 2 H) 10.01-10.27 (m, 1 H).<br>MS ESI/APCI Dual posi: 379[M + H]$^+$.<br>MS ESI/APCI Dual nega: 377[M − H]$^-$. | |
| Example 1-347 | 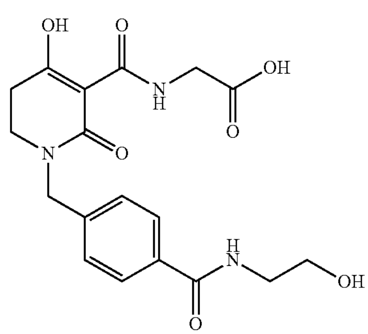 [SMILES: O=C(O)CNC(=O)C1=C(O)CCN(Cc2ccc(C(=O)NCCO)cc2)C1=O] | $^1$H NMR (300 MHz, DMSO-d$_6$) δ ppm 2.52-2.60 (m, 2 H) 3.25-3.39 (m, 4 H) 3.45-3.54 (m, 2 H) 3.58 (d, J = 4.5 Hz, 2 H) 4.60 (s, 2 H) 7.34 (d, J = 8.4 Hz, 2 H) 7.82 (d, J = 8.4 Hz, 2 H) 8.47 (t, J = 5.7 Hz, 1 H) 10.12 (br. s., 1 H).<br>MS ESI/APCI Dual posi: 392[M + H]$^+$.<br>MS ESI/APCI Dual nega: 390[M − H]$^-$. | Na |

TABLE 21-50-continued

| Compound No. | Structure | Analytical Data | Salt information |
|---|---|---|---|
| Example 1-348 | 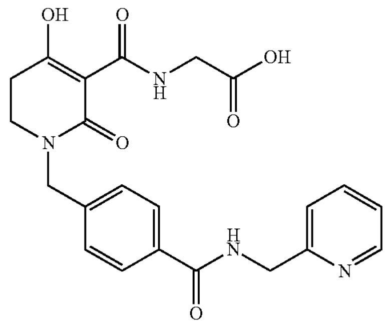 [SMILES: O=C(O)CNC(=O)C1=C(O)CCN(Cc2ccc(C(=O)NCc3ccccn3)cc2)C1=O] | $^1$H NMR (300 MHz, DMSO-d$_6$) δ ppm 2.70 (t, J = 7.0 Hz, 2 H) 3.40 (t, J = 7.0 Hz, 2 H) 4.02 (d, J = 5.6 Hz, 2 H) 4.64 (s, 2 H) 4.78 (d, J = 5.6 Hz, 2 H) 7.41 (d, J = 8.2 Hz, 2 H) 7.73-7.87 (m, 2 H) 7.93 (d, J = 8.2 Hz, 2 H) 8.36 (td, J = 7.8, 1.6 Hz, 1 H) 8.77 (dd, J = 5.5, 0.9 Hz, 1 H) 9.33-9.48 (m, 1 H) 9.95-10.29 (m, 1 H).<br>MS ESI/APCI Dual posi: 439[M + H]$^+$.<br>MS ESI/APCI Dual nega: 437[M − H]$^-$. | HCl |
| Example 1-349 | 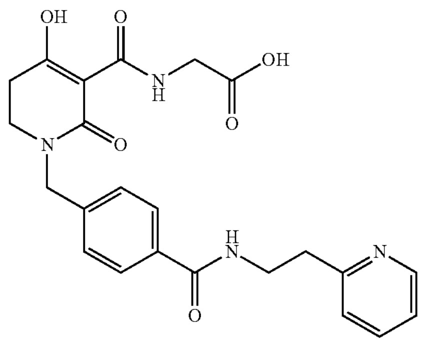 [SMILES: O=C(O)CNC(=O)C1=C(O)CCN(Cc2ccc(C(=O)NCCc3ccccn3)cc2)C1=O] | $^1$H NMR (300 MHz, DMSO-d$_6$) δ ppm 2.69 (t, J = 7.0 Hz, 2 H) 3.29 (t, J = 6.4 Hz, 2 H) 3.38 (t, J = 7.0 Hz, 2 H) 3.72 (q, J = 6.3 Hz, 2 H) 4.02 (d, J = 5.4 Hz, 2 H) 4.53-4.71 (m, 2 H) 7.34 (d, J = 8.2 Hz, 2 H) 7.75 (d, J = 8.2 Hz, 2 H) 7.81-7.93 (m, 2 H) 8.41 (td, J = 7.8, 1.6 Hz, 1 H) 8.68 (t, J = 5.8 Hz, 1 H) 8.79 (d, J = 5.8 Hz, 1 H) 9.92-10.27 (m, 1 H).<br>MS ESI/APCI Dual posi: 453[M + H]$^+$.<br>MS ESI/APCI Dual nega: 451[M − H]$^-$. | HCl |

TABLE 21-51

| Compound No. | Structure | Analytical Data | Salt information |
|---|---|---|---|
| Example 1-350 | 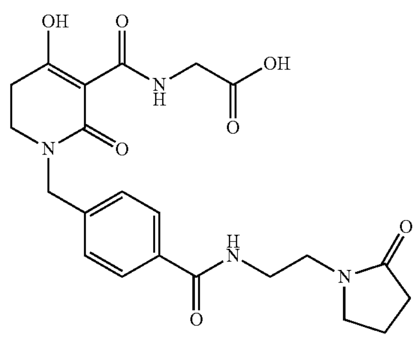 [SMILES: O=C(O)CNC(=O)C1=C(O)CCN(Cc2ccc(C(=O)NCCN3CCCC3=O)cc2)C1=O] | $^1$H NMR (300 MHz, DMSO-d$_6$) δ ppm 1.83-1.97 (m, 2 H) 2.11-2.22 (m, 2 H) 2.61-2.77 (m, 2 H) 3.28-3.46 (m, 8 H) 4.02 (d, J = 5.6 Hz, 2 H) 4.62 (s, 2 H) 7.36 (d, J = 8.2 Hz, 2 H) 7.77 (d, J = 8.2 Hz, 2 H) 8.44-8.58 (m, 1 H) 10.02 (br. s., 1 H).<br>MS ESI/APCI Dual posi: 459[M + H]$^+$.<br>MS ESI/APCI Dual nega: 457[M − H]$^-$. | HCl |
| Example 1-351 | 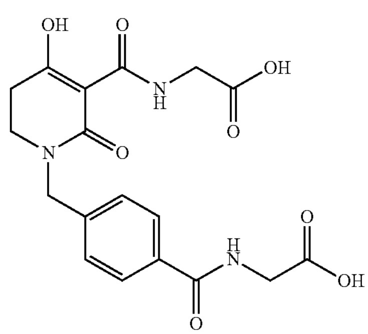 [SMILES: O=C(O)CNC(=O)C1=C(O)CCN(Cc2ccc(C(=O)NCC(=O)O)cc2)C1=O] | $^1$H NMR (300 MHz, DMSO-d$_6$) δ ppm 2.63-2.79 (m, 2 H) 3.31-3.47 (m, 2 H) 3.91 (d, J = 5.9 Hz, 2 H) 3.97-4.10 (m, 2 H) 4.56-4.73 (m, 2 H) 7.38 (d, J = 8.2 Hz, 2 H) 7.84 (d, J = 8.2 Hz, 2 H) 8.80 (t, J = 5.8 Hz, 1 H) 9.92-10.29 (m, 1 H).<br>MS ESI/APCI Dual posi: 406[M + H]$^+$.<br>MS ESI/APCI Dual nega: 404[M − H]$^-$. | |

TABLE 21-51-continued

| Compound No. | Structure | Analytical Data | Salt information |
|---|---|---|---|
| Example 1-352 | 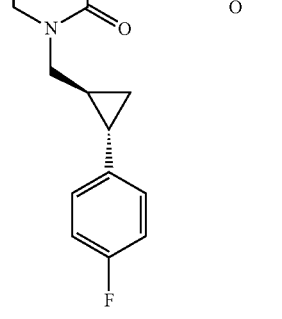 | $^1$H NMR (300 MHz, DMSO-d$_6$) δ ppm 0.79-1.02 (m, 2 H) 1.14-1.35 (m, 1 H) 1.80-1.97 (m, 1 H) 3.04-3.71 (m, 8 H) 6.85-7.26 (m, 4 H) 9.84-10.29 (m, 1 H).<br>MS ESI/APCI Dual posi: 363[M + H]$^+$.<br>MS ESI/APCI Dual nega: 361[M − H]$^−$. | Na |
| Example 1-353 | 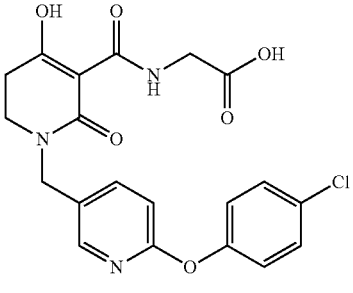 | $^1$H NMR (300 MHz, DMSO-d$_6$) δ ppm 2.52-2.61 (m, 2 H) 3.38-3.53 (m, 4 H) 4.84 (s, 2 H) 7.03-7.14 (m, 2 H) 7.29-7.37 (m, 1 H) 7.40-7.50 (m, 3 H) 8.34 (d, J = 2.8 Hz, 1 H) 9.92-10.23 (m, 1 H).<br>MS ESI/APCI Dual posi: 432[M + H]$^+$.<br>MS ESI/APCI Dual nega: 430[M − H]$^−$. | Na |
| Example 1-354 | 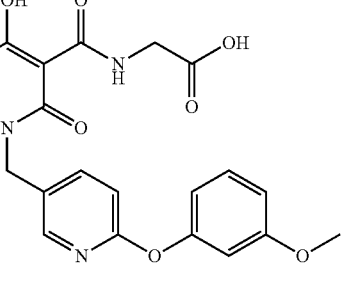 | $^1$H NMR (300 MHz, DMSO-d$_6$) δ ppm 2.66 (br. s., 2 H) 3.42 (t, J = 7.1 Hz, 2 H) 3.74 (s, 3 H) 4.02 (d, J = 5.6 Hz, 2 H) 4.55 (s, 2 H) 6.64-6.74 (m, 2 H) 6.75-6.83 (m, 1 H) 6.99 (d, J = 8.4 Hz, 1 H) 7.30 (t, J = 8.4 Hz, 1 H) 7.78 (dd, J = 8.4, 2.5 Hz, 1 H) 8.13 (d, J = 2.5 Hz, 1 H) 10.02 (br. s., 1 H).<br>MS ESI/APCI Dual posi: 428[M + H]$^+$.<br>MS ESI/APCI Dual nega: 426[M − H]$^−$. | HCl |
| Example 1-355 | 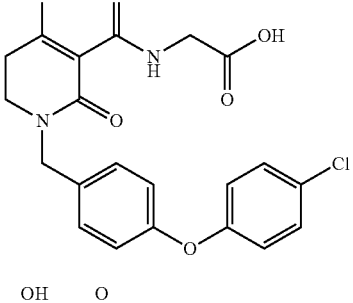 | $^1$H NMR (300 MHz, DMSO-d$_6$) δ ppm 2.43-2.49 (m, 2 H) 3.24-3.32 (m, 2 H) 3.48 (d, J = 4.5 Hz, 2 H) 4.55 (s, 2 H) 7.03-7.11 (m, 2 H) 7.32-7.35 (m, 2 H) 7.51 (d, J = 1.9 Hz, 2 H) 8.20-8.22 (m, 1 H) 10.08 (br. s., 1 H).<br>MS ESI/APCI Dual posi: 432[M + H]$^+$.<br>MS ESI/APCI Dual nega: 430[M − H]$^−$. | Na |
| Example 1-356 | 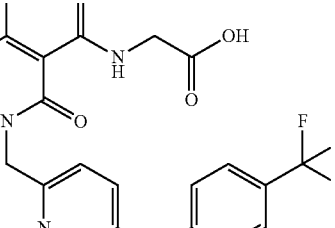 | $^1$H NMR (300 MHz, DMSO-d$_6$) δ ppm 2.51-2.59 (m, 2 H) 3.39-3.52 (m, 4 H) 4.67 (s, 2 H) 7.19 (d, J = 8.5 Hz, 2 H) 7.38 (d, J = 8.5 Hz, 1 H) 7.58 (dd, J = 8.5, 2.8 Hz, 1 H) 7.70-7.81 (m, 2 H) 8.41 (d, J = 2.8 Hz, 1 H) 9.94-10.12 (m, 1 H).<br>MS ESI/APCI Dual posi: 466[M + H]$^+$.<br>MS ESI/APCI Dual nega: 464[M − H]$^−$. | Na |

TABLE 21-52

| Compound No. | Structure | Analytical Data | Salt information |
|---|---|---|---|
| Example 1-357 | 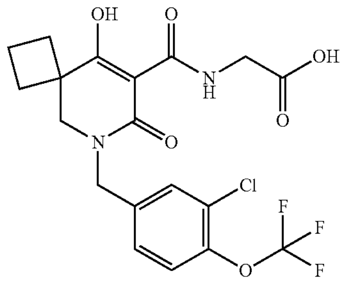 [SMILES: O=C(O)CNC(=O)C1=C(O)C2(CCC2)CN(Cc2ccc(OC(F)(F)F)c(Cl)c2)C1=O] | $^1$H NMR (300 MHz, DMSO-d$_6$) δ ppm 1.54-2.03 (m, 4 H) 2.18-2.37 (m, 2 H) 3.37-3.48 (m, 4 H) 4.61 (s, 2 H) 7.35-7.44 (m, 1 H) 7.51-7.62 (m, 2 H).<br>MS ESI/APCI Dual posi: 463[M + H]$^+$.<br>MS ESI/APCI Dual nega: 461[M − H]$^-$. | Na |
| Example 1-358 | 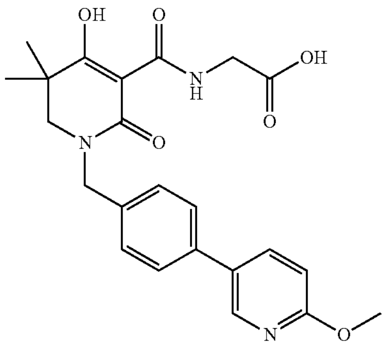 | $^1$H NMR (300 MHz, DMSO-d$_6$) δ ppm 1.00 (s, 6 H) 3.01-3.17 (m, 2 H) 3.39-3.49 (m, 2 H) 3.89 (s, 3 H) 4.61 (s, 2 H) 6.85-6.95 (m, 1 H) 7.34-7.45 (m, 2 H) 7.59-7.69 (m, 2 H) 7.95-8.05 (m, 1 H) 8.43-8.51 (m, 1 H).<br>MS ESI/APCI Dual posi: 440[M + H]$^+$.<br>MS ESI/APCI Dual nega: 438[M − H]$^-$. | Na |
| Example 1-359 | 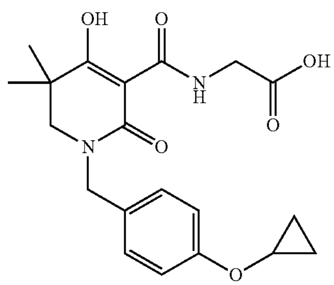 [SMILES: CC1(C)CN(Cc2ccc(OC3CC3)cc2)C(=O)C(C(=O)NCC(=O)O)=C1O] | $^1$H NMR (300 MHz, DMSO-d$_6$) δ ppm 0.57-0.82 (m, 4 H) 0.97 (s, 6 H) 3.05 (s, 2 H) 3.45 (d, J = 4.4 Hz, 2 H) 3.75-3.85 (m, 1 H) 4.50 (s, 2 H) 6.95-7.06 (m, 2 H) 7.18-7.29 (m, 2 H).<br>MS ESI/APCI Dual posi: 389[M + H]$^+$.<br>MS ESI/APCI Dual nega: 387[M − H]$^-$. | Na |
| Example 1-360 | 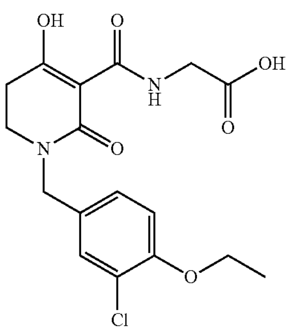 | $^1$H NMR (600 MHz, DMSO-d$_6$) δ ppm 0.31-0.36 (m, 2 H) 0.54-0.80 (m, 2 H) 1.19-1.27 (m, 1 H) 3.22-3.38 (m, 4 H) 3.45-3.52 (m, 2 H) 3.89 (d, J = 7.0 Hz, 2 H) 4.47 (s, 2 H) 7.05-7.10 (m, 1 H) 7.17-7.21 (m, 1 H) 7.31-7.35 (m, 1 H).<br>MS ESI posi: 409[M + H]$^+$.<br>MS ESI nega: 407[M − H]$^-$. | Na |
| Example 1-361 | 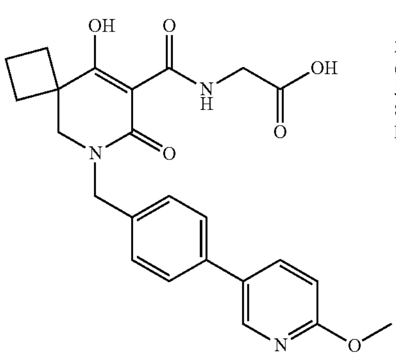 [SMILES: COc1ccc(-c2ccc(CN3CC4(CCC4)C(O)=C(C(=O)NCC(=O)O)C3=O)cc2)cn1] | $^1$H NMR (300 MHz, DMSO-d$_6$) δ ppm 1.59-2.01 (m, 4 H) 2.19-2.38 (m, 2 H) 3.42-3.48 (m, 2 H) 3.70-3.79 (m, 2 H) 3.89 (s, 3 H) 4.64 (s, 2 H) 6.90 (d, J = 8.5 Hz, 1 H) 7.39 (d, J = 8.2 Hz, 2 H) 7.65 (d, J = 8.2 Hz, 2 H) 7.95-8.07 (m, 1 H) 8.42-8.53 (m, 1 H).<br>MS ESI/APCI Dual posi: 452[M + H]$^+$. | Na |

TABLE 21-52-continued

| Compound No. | Structure | Analytical Data | Salt information |
|---|---|---|---|
| Example 1-362 | (structure) | $^1$H NMR (300 MHz, DMSO-$d_6$) δ ppm 0.57-0.69 (m, 2 H) 0.82-1.06 (m, 8 H) 1.81-1.95 (m, 1 H) 2.91-3.09 (m, 2 H) 3.38-3.46 (m, 2 H) 4.51 (s, 2 H) 6.98-7.07 (m, 2 H) 7.12-7.20 (m, 2 H).<br>MS ESI/APCI Dual posi: 373[M + H]$^+$.<br>MS ESI/APCI Dual nega: 371[M − H]$^−$. | Na |
| Example 1-363 | (structure) | $^1$H NMR (300 MHz, DMSO-$d_6$) δ ppm 0.56-0.83 (m, 4 H) 1.47-1.96 (m, 4 H) 2.13-2.34 (m, 2 H) 3.40-3.49 (m, 2 H) 3.75-3.87 (m, 1 H) 4.51 (s, 2 H) 6.96-7.07 (m, 2 H) 7.18-7.29 (m, 2 H). | Na |

TABLE 21-53

| Compound No. | Structure | Analytical Data | Salt information |
|---|---|---|---|
| Example 1-364 | (structure) | $^1$H NMR (300 MHz, METHANOL-$d_4$) δ ppm 2.34 (s, 3 H) 2.46-2.59 (m, 2 H) 3.27-3.34 (m, 2 H) 3.89 (s, 2 H) 4.55 (s, 2 H) 5.02 (s, 2 H) 6.90-6.99 (m, 2 H) 7.07-7.15 (m, 1 H) 7.17-7.27 (m, 5 H).<br>MS ESI/APCI Dual posi: 425[M + H]$^+$.<br>MS ESI/APCI Dual nega: 423[M − H]$^−$. | Na |
| Example 1-365 | (structure) | $^1$H NMR (300 MHz, DMSO-$d_6$) δ ppm 2.51-2.56 (m, 2 H) 3.26-3.35 (m, 2 H) 3.49 (d, J = 4.5 Hz, 2 H) 4.59 (s, 2 H) 7.13-7.22 (m, 2 H) 7.33-7.44 (m, 2 H) 7.48-7.57 (m, 1 H) 7.88 (d, J = 8.5 Hz, 1 H) 8.55 (d, J = 3.0 Hz, 1 H) 10.09 (br. s., 1 H).<br>MS ESI/APCI Dual posi: 466[M + H]$^+$.<br>MS ESI/APCI Dual nega: 464[M − H]$^−$. | Na |

TABLE 21-53-continued

| Compound No. | Structure | Analytical Data | Salt information |
|---|---|---|---|
| Example 1-366 | 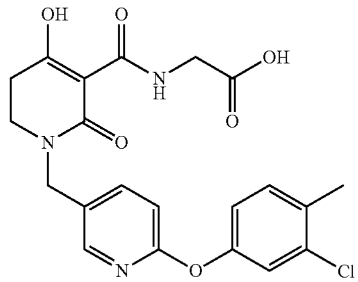 [SMILES: Cc1ccc(Oc2ccc(CN3CCC(O)=C(C(=O)NCC(=O)O)C3=O)cn2)cc1Cl] | $^1$H NMR (300 MHz, DMSO-d$_6$) δ ppm 2.32 (s, 3 H) 2.42-2.48 (m, 2 H) 3.27-3.37 (m, 2 H) 3.48 (d, J = 4.5 Hz, 2 H) 4.52 (s, 2 H) 6.98-7.07 (m, 2 H) 7.24 (d, J = 2.5 Hz, 1 H) 7.37 (d, J = 8.5 Hz, 1 H) 7.77 (dd, J = 8.5, 2.5 Hz, 1 H) 8.09 (d, J = 2.0 Hz, 1 H) 10.06 (d, J = 1.2 Hz, 1 H). MS ESI/APCI Dual posi: 446[M + H]$^+$. MS ESI/APCI Dual nega: 444[M − H]$^−$. | Na |
| Example 1-367 | 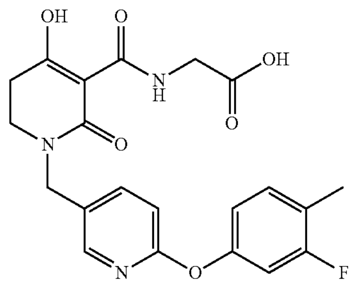 [SMILES: Cc1ccc(Oc2ccc(CN3CCC(O)=C(C(=O)NCC(=O)O)C3=O)cn2)cc1F] | $^1$H NMR (300 MHz, DMSO-d$_6$) δ ppm 2.23 (d, J = 1.9 Hz, 3 H) 2.52-2.57 (m, 2 H) 3.26-3.37 (m, 2 H) 3.47-3.53 (m, 2 H) 4.52 (s, 2 H) 6.88 (dd, J = 8.2, 2.5 Hz, 1 H) 6.96-7.05 (m, 3 H) 7.29 (t, J = 8.7 Hz, 1 H) 7.77 (dd, J = 8.7, 2.5 Hz, 1 H) 8.09 (d, J = 1.9 Hz, 1 H) 10.06 (br. s., 1 H). MS ESI/APCI Dual posi: 430[M + H]$^+$. MS ESI/APCI Dual nega: 428[M − H]$^−$. | Na |
| Example 1-368 | 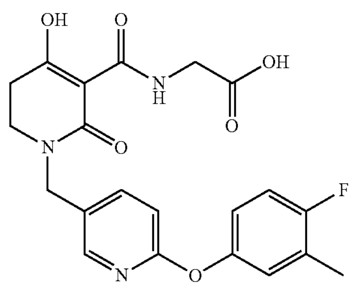 [SMILES: Cc1cc(Oc2ccc(CN3CCC(O)=C(C(=O)NCC(=O)O)C3=O)cn2)ccc1F] | $^1$H NMR (300 MHz, DMSO-d$_6$) δ ppm 2.23 (d, J = 1.9 Hz, 3 H) 2.53-2.59 (m, 2 H) 3.28-3.48 (m, 4 H) 4.51 (s, 2 H) 6.94-7.02 (m, 2 H) 7.04-7.10 (m, 1 H) 7.16 (t, J = 9.2 Hz, 1 H) 7.76 (dd, J = 8.5, 2.5 Hz, 1 H) 8.07 (d, J = 2.0 Hz, 1 H) 10.04 (br. s., 1 H). MS ESI/APCI Dual posi: 430[M + H]$^+$. MS ESI/APCI Dual nega: 428[M − H]$^−$. | Na |
| Example 1-369 | 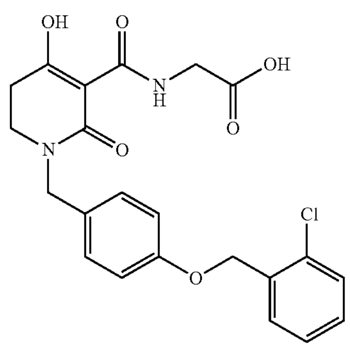 [SMILES: O=C(O)CNC(=O)C1=C(O)CCN(Cc2ccc(OCc3ccccc3Cl)cc2)C1=O] | $^1$H NMR (300 MHz, METHANOL-d$_6$) δ ppm 2.49-2.61 (m, 2 H) 3.33-3.38 (m, 2 H) 3.89 (s, 2 H) 4.56 (s, 2 H) 5.16 (s, 2 J) 6.93-7.01 (m, 2 H) 7.21-7.29 (m, 2 H) 7.29-7.36 (m, 2 H) 7.39-7.48 (m, 1 H) 7.51-7.59 (m, 1 H). MS ESI/APCI Dual posi: 445[M + H]$^+$. MS ESI/APCI Dual nega: 443[M − H]$^−$. | Na |
| Example 1-370 | 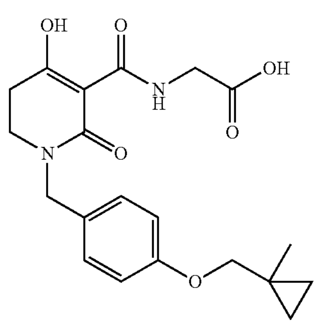 [SMILES: CC1(COc2ccc(CN3CCC(O)=C(C(=O)NCC(=O)O)C3=O)cc2)CC1] | $^1$H NMR (600 MHz, DMSO-d$_6$) δ ppm 0.34-0.39 (m, 2 H) 0.47-0.52 (m, 21 H) 1.16 (s, 3 H) 2.43-2.54 (m, 2 H) 2.99-3.18 (m, 2 H) 3.42 (d, J = 4.1 Hz, 2 H) 3.71 (s, 2 H) 4.45 (s, 2 H) 6.84 (d, J = 8.3 Hz, 2 H) 7.16 (d, J = 8.3 Hz, 2 H). MS ESI/APCI Dual posi: 389[M + H]$^+$, 411[M + Na]$^+$. MS ESI/APCI Dual nega: 387[M − H]$^−$. | Na |

TABLE 21-54

| Compound No. | Structure | Analytical Data | Salt information |
|---|---|---|---|
| Example 1-371 | (structure) | $^1$H NMR (600 MHz, DMSO-$d_6$) δ ppm 2.03-2.21 (m, 4 H) 2.46-2.64 (m, 3 H) 3.28-3.39 (m, 2 H) 3.40-3.50 (m, 2 H) 3.50-3.71 (m, 3 H) 7.04-7.16 (m, 2 H) 7.24-7.36 (m, 2 H) 9.74-10.47 (m, 1 H). MS ESI/APCI Dual posi: 377[M + H]$^+$, 399[M + Na]$^+$. MS ESI/APCI Dual nega: 375[M − H]$^-$. | Na |
| Example 1-372 | (structure) | $^1$H NMR (300 MHz, DMSO-$d_6$) δ ppm 2.43-2.46 (m, 2 H) 3.33-3.35 (m, 2 H) 3.38-3.44 (m, 2 H) 4.46-4.50 (m, 2 H) 5.13 (s, 2 H) 6.97-7.03 (m, 2 H) 7.20-7.25 (m, 2 H) 7.39-7.45 (m, 1 H) 7.84-7.90 (m, 1 H) 8.52-8.56 (m, 1 H) 8.65-8.68 (m, 1 H). MS ESI/APCI Dual posi: 412[M + H]$^+$. MS ESI/APCI Dual nega: 410[M − H]$^-$. | Na |
| Example 1-373 | (structure) | $^1$H NMR (300 MHz, METHANOL-$d_4$) δ ppm 2.46-2.61 (m, 5 H) 3.32-3.34 (m, 2 H) 3.89 (s, 2 H) 4.55 (s, 2 H) 5.12 (s, 2 H) 6.93-7.01 (m, 2 H) 7.18-7.28 (m, 3 H) 7.34-7.40 (m, 1 H) 7.69-7.77 (m, 1 H). MS ESI/APCI Dual posi: 426[M + H]$^+$. MS ESI/APCI Dual nega: 424[M − H]$^-$. | Na |
| Example 1-374 | (structure) | $^1$H NMR (300 MHz, DMSO-$d_6$) δ ppm 2.40-2.49 (m, 2 H) 3.22-3.29 (m, 2 H) 3.45 (d, J = 4.5 Hz, 2 H) 4.47 (s, 2 H) 5.15 (s, 2 H) 6.98-7.08 (m, 1 H) 7.09-7.17 (m, 1 H) 7.17-7.25 (m, 1 H) 7.29-7.50 (m, 5 H). MS ESI/APCI Dual posi: 429[M + H]$^+$. MS ESI/APCI Dual nega: 427[M − H]$^-$. | Na |

TABLE 21-54-continued

| Compound No. | Structure | Analytical Data | Salt information |
|---|---|---|---|
| Example 1-375 | 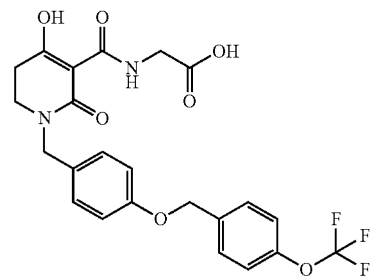 [SMILES: O=C(O)CNC(=O)C1=C(O)CCN(Cc2ccc(OCc3ccc(OC(F)(F)F)cc3)cc2)C1=O] | $^1$H NMR (300 MHz, DMSO-d$_6$) δ ppm 2.41-2.49 (m, 2 H) 3.19-3.28 (m, 2 H) 3.45 (d, J = 4.4 Hz, 2 H) 4.48 (s, 2 H) 5.12 (s, 2 H) 6.94-7.02 (m, 2 H) 7.16-7.26 (m, 2 H) 7.34-7.43 (m, 2 H) 7.54-7.62 (m, 2 H).<br>MS ESI/APCI Dual posi: 495[M + H]$^+$.<br>MS ESI/APCI Dual nega: 493[M − H]$^−$. | Na |
| Example 1-376 | 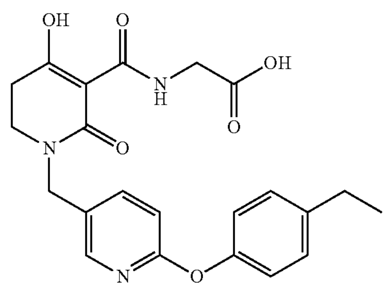 [SMILES: CCc1ccc(Oc2ccc(CN3CCC(O)=C(C(=O)NCC(=O)O)C3=O)cn2)cc1] | $^1$H NMR (300 MHz, DMSO-d$_6$) δ ppm 1.19 (t, J = 7.6 Hz, 3 H) 2.40-2.50 (m, 2 H) 2.54-2.67 (m, 2 H) 3.23-3.35 (m, 2 H) 3.47 (d, J = 4.5 Hz, 2 H) 4.51 (s, 2 H) 6.90-7.07 (m, 3 H) 7.17-7.29 (m, 2 H) 7.75 (dd, J = 8.4, 2.5 Hz, 1 H) 8.07 (s, 1 H). | Na |
| Example 1-377 | 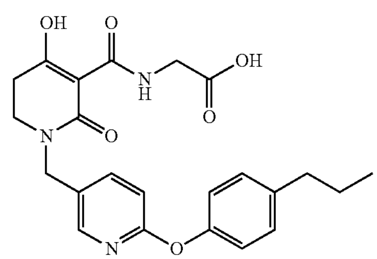 [SMILES: CCCc1ccc(Oc2ccc(CN3CCC(O)=C(C(=O)NCC(=O)O)C3=O)cn2)cc1] | $^1$H NMR (300 MHz, DMSO-d$_6$) δ ppm 0.91 (t, J = 7.3 Hz, 3 H) 1.50-1.69 (m, 2 H) 2.49-2.62 (m, 4 H) 3.21-3.42 (m, 2 H) 3.49 (d, J = 4.4 Hz, 2 H) 4.51 (s, 2 H) 6.89-7.07 (m, 3 H) 7.21 (m, J = 8.5 Hz, 2 H) 7.69-7.79 (m, 1 H) 8.03-8.12 (m, 1 H). | Na |

TABLE 21-55

| Compound No. | Structure | Analytical Data | Salt information |
|---|---|---|---|
| Example 1-378 | 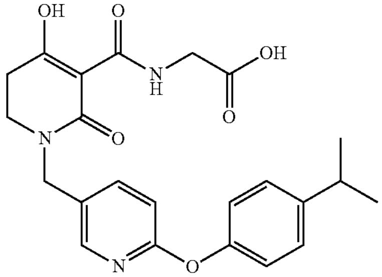 [SMILES: CC(C)c1ccc(Oc2ccc(CN3CCC(O)=C(C(=O)NCC(=O)O)C3=O)cn2)cc1] | $^1$H NMR (300 MHz, DMSO-d$_6$) δ ppm 1.21 (d, J = 7.0 Hz, 6 H) 2.40-2.50 (m, 2 H) 2.82-2.98 (m, 1 H) 3.19-3.41 (m, 2 H) 3.48 (d, J = 4.4 Hz, 2 H) 4.51 (s, 2 H) 6.85-7.16 (m, 3 H) 7.18-7.36 (m, 2 H) 7.63-7.85 (m, 1 H) 7.97-8.19 (m, 1 H). | Na |

TABLE 21-55-continued

| Compound No. | Structure | Analytical Data | Salt information |
|---|---|---|---|
| Example 1-379 | 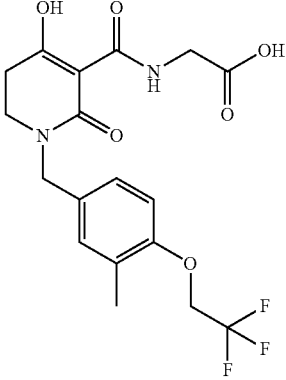 [SMILES: Cc1cc(CN2CCC(O)=C(C(=O)NCC(=O)O)C2=O)ccc1OCC(F)(F)F] | ¹H NMR (300 MHz, DMSO-$d_6$) δ ppm 2.16 (s, 3 H) 2.41-2.55 (m, 2 H) 3.27 (t, J = 7.1 Hz, 2 H) 3.52 (d, J = 4.5 Hz, 2 H) 4.47 (s, 2 H) 4.72 (q, J = 9.0 Hz, 2 H) 6.96-7.04 (m, 1 H) 7.06-7.13 (m, 2 H) 10.10 (br. s., 1 H). MS ESI/APCI Dual posi: 417[M + H]⁺. MS ESI/APCI Dual nega: 415[M − H]⁻. | Na |
| Example 1-380 | 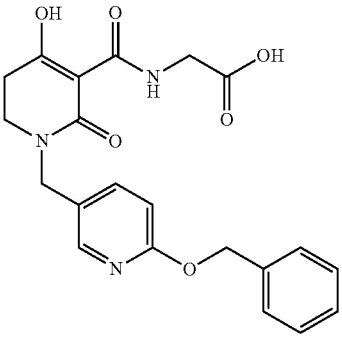 [SMILES: O=C(O)CNC(=O)C1=C(O)CCN(Cc2ccc(OCc3ccccc3)nc2)C1=O] | ¹H NMR (300 MHz, DMSO-$d_6$) δ ppm 2.40-2.50 (m, 2 H) 3.24-3.31 (m, 2 H) 3.43 (d, J = 4.4 Hz, 2 H) 4.49 (s, 2 H) 5.33 (s, 2 H) 6.82-6.89 (m, 1 H) 7.22-7.50 (m, 5 H) 7.62-7.69 (m, 1 H) 8.09-8.15 (m, 1 H). MS ESI/APCI Dual posi: 412[M + H]⁺. MS ESI/APCI Dual nega: 410[M − H]⁻. | Na |
| Example 1-381 | 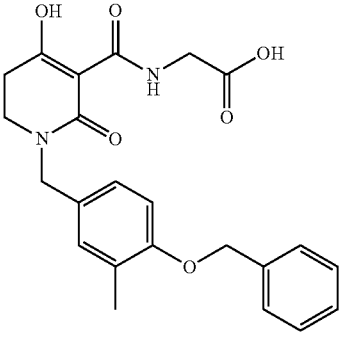 [SMILES: Cc1cc(CN2CCC(O)=C(C(=O)NCC(=O)O)C2=O)ccc1OCc1ccccc1] | ¹H NMR (300 MHz, DMSO-$d_6$) δ ppm 2.18 (s, 3 H) 2.36-2.47 (m, 2 H) 3.15-3.25 (m, 2 H) 3.46 (d, J = 4.5 Hz, 2 H) 4.45 (s, 2 H) 5.09 (s, 2 H) 6.91-7.01 (m, 1 H) 7.01-7.11 (m, 2 H) 7.21-7.53 (m, 5 H) 9.94-10.22 (m, 1 H). MS ESI/APCI Dual posi: 425[M + H]⁺. MS ESI/APCI Dual nega: 423[M − H]⁻. | Na |
| Example 1-382 | 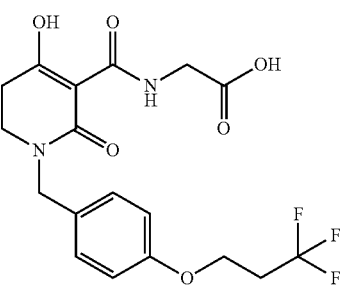 [SMILES: O=C(O)CNC(=O)C1=C(O)CCN(Cc2ccc(OCCC(F)(F)F)cc2)C1=O] | ¹H NMR (300 MHz, DMSO-$d_6$) δ ppm 2.33-2.50 (m, 2 H) 2.66-2.86 (m, 2 H) 3.15-3.31 (m, 2 H) 3.39-3.48 (m, 2 H) 4.18 (t, J = 5.9 Hz, 2 H) 4.48 (s, 2 H) 6.85-6.96 (m, 2 H) 7.22 (m, 2 H) 10.06 (br. s., 1 H). MS ESI/APCI Dual posi: 417[M + H]⁺. MS ESI/APCI Dual nega: 415[M − H]⁻. | Na |

TABLE 21-55-continued

| Compound No. | Structure | Analytical Data | Salt information |
|---|---|---|---|
| Example 1-383 | 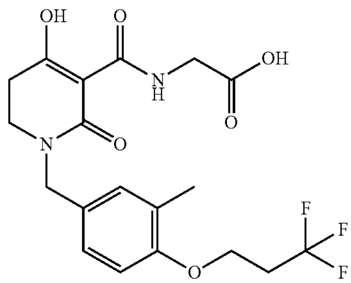 [SMILES: Cc1cc(CN2CCC(O)=C(C(=O)NCC(=O)O)C2=O)ccc1OCCC(F)(F)F] | ¹H NMR (300 MHz, DMSO-d₆) δ ppm 2.12 (s, 3 H) 2.43-2.55 (m, 2 H) 2.78 (qt, J = 11.3, 5.7 Hz, 2 H) 3.19-3.30 (m, 2 H) 3.49 (d, J = 4.5 Hz, 2 H) 4.18 (t, J = 5.7 Hz, 2 H) 4.46 (s, 2 H) 6.86-6.96 (m, 1 H) 7.03-7.11 (m, 2 H) 10.08 (br. s., 1 H). MS ESI/APCI Dual posi: 431[M + H]+. MS ESI/APCI Dual nega: 429[M − H]−. | Na |
| Example 1-384 | 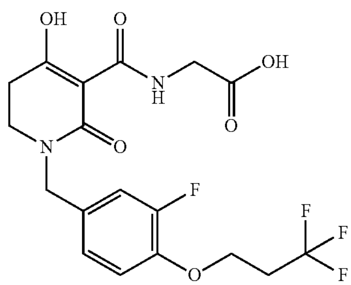 [SMILES: O=C(O)CNC(=O)C1=C(O)CCN(Cc2ccc(OCCC(F)(F)F)c(F)c2)C1=O] | ¹H NMR (300 MHz, DMSO-d₆) δ ppm 2.45-2.54 (m, 2 H) 2.71-2.91 (m, 2 H) 3.23-3.32 (m, 2 H) 3.48 (d, J = 4.5 Hz, 2 H) 4.21-4.29 (m, 2 H) 4.48 (s, 2 H) 7.01-7.24 (m, 3 H) 10.06 (br. s., 1 H). MS ESI/APCI Dual posi: 435[M + H]+. MS ESI/APCI Dual nega: 433[M − H]−. | Na |

TABLE 21-56

| Compound No. | Structure | Analytical Data | Salt information |
|---|---|---|---|
| Example 1-385 | 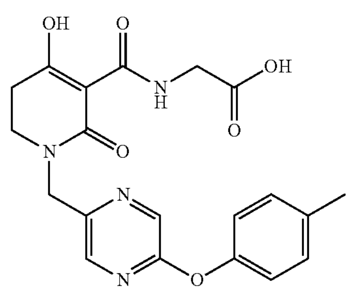 [SMILES: Cc1ccc(Oc2cnc(CN3CCC(O)=C(C(=O)NCC(=O)O)C3=O)cn2)cc1] | ¹H NMR (300 MHz, DMSO-d₆) δ ppm 2.32 (s, 3 H) 2.40-2.50 (m, 2 H) 3.18-3.42 (m, 2 H) 3.42-3.53 (m, 2 H) 4.64 (s, 2 H) 7.02-7.13 (m, 2 H) 7.18-7.27 (m, 2 H) 8.08-8.16 (m, 1 H) 8.39-8.47 (m, 1 H). MS ESI/APCI Dual posi: 413[M + H]+. MS ESI/APCI Dual nega: 411[M − H]−. | Na |
| Example 1-386 | 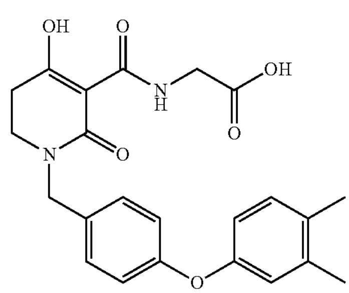 | ¹H NMR (300 MHz, DMSO-d₆) δ ppm 2.19 (s, 6 H) 2.40-2.50 (m, 2 H) 3.23-3.36 (m, 2 H) 3.44 (d, J = 4.4 Hz, 2 H) 4.52 (s, 2 H) 6.68-6.77 (m, 1 H) 6.80-6.86 (m, 1 H) 6.86-6.96 (m, 2 H) 7.07-7.18 (m, 1 H) 7.21-7.32 (m, 2 H). MS ESI/APCI Dual posi: 425[M + H]+. MS ESI/APCI Dual nega: 423[M − H]−. | Na |

TABLE 21-56-continued

| Compound No. | Structure | Analytical Data | Salt information |
|---|---|---|---|
| Example 1-387 | 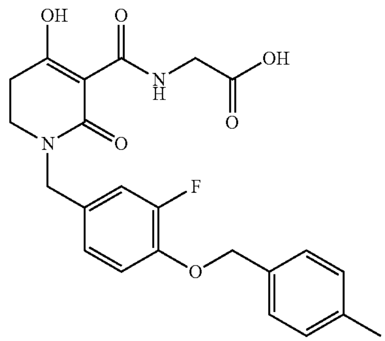 [SMILES: Cc1ccc(COc2ccc(CN3CCC(O)=C(C(=O)NCC(=O)O)C3=O)cc2F)cc1] | $^1$H NMR (300 MHz, DMSO-d$_6$) δ ppm 2.30 (s, 3 H) 2.49-2.54 (m, 2 H) 3.24-3.30 (m, 2 H) 3.46 (d, J = 4.5 Hz, 2 H) 4.47 (s, 2 H) 6.10 (s, 2 H) 6.99-7.07 (m, 1 H) 7.08-7.24 (m, 4 H) 7.28-7.39 (m, 2 H) 9.89-10.17 (m, 1 H). MS ESI/APCI Dual posi: 443[M + H]$^+$. MS ESI/APCI Dual nega: 441[M − H]$^-$. | Na |
| Example 1-388 | 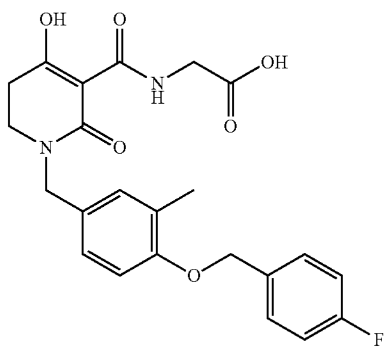 [SMILES: Cc1cc(CN2CCC(O)=C(C(=O)NCC(=O)O)C2=O)ccc1OCc1ccc(F)cc1] | $^1$H NMR (300 MHz, DMSO-d$_6$) δ ppm 2.17 (s, 3 H) 2.43-2.49 (m, 2 H) 3.21-3.28 (m, 2 H) 3.46 (d, J = 4.4 Hz, 2 H) 4.45 (s, 2 H) 5.08 (s, 2 H) 6.91-7.01 (m, 1 H) 7.02-7.11 (m, 2 H) 7.16-7.28 (m, 2 H) 7.45-7.55 (m, 2 H) 9.93-10.17 (m, 1 H). MS ESI/APCI Dual posi: 443[M + H]$^+$. MS ESI/APCI Dual nega: 441[M − H]$^-$. | Na |
| Example 1-389 | 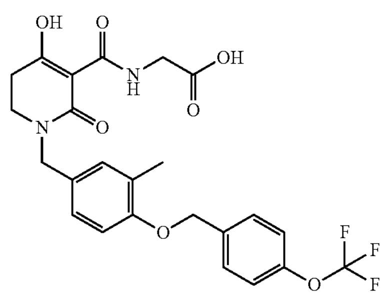 [SMILES: Cc1cc(CN2CCC(O)=C(C(=O)NCC(=O)O)C2=O)ccc1OCc1ccc(OC(F)(F)F)cc1] | $^1$H NMR (300 MHz, DMSO-d$_6$) δ ppm 2.19 (s, 3 H) 2.44-2.49 (m, 2 H) 3.22-3.29 (m, 2 H) 3.46 (d, J = 4.5 Hz, 2 H) 4.46 (s, 2 H) 5.13 (s, 2 H) 6.91-7.01 (m, 1 H) 7.02-7.12 (m, 2 H) 7.34-7.47 (m, 2 H) 7.54-7.55 (m, 2 H) 9.92-10.17 (m, 1 H). MS ESI/APCI Dual posi: 509[M + H]$^+$. MS ESI/APCI Dual nega: 507[M − H]$^-$. | Na |
| Example 1-390 | 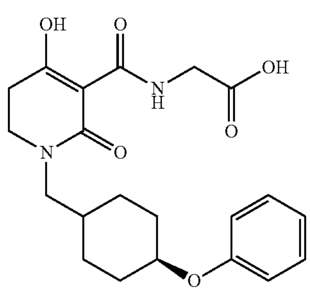 | $^1$H NMR (300 MHz, DMSO-d$_6$) δ ppm 1.03-1.41 (m, 4 H) 1.58-1.79 (m, 3 H) 2.00-2.13 (m, 2 H) 2.46-2.55 (m, 2 H) 3.19-3.51 (m, 6 H) 4.17-4.33 (m, 1 H) 6.83-6.98 (m, 3 H) 7.19-7.32 (m, 2 H) 9.91-10.14 (m, 1 H). MS ESI/APCI Dual posi: 403[M + H]$^+$. MS ESI/APCI Dual nega: 401[M − H]$^-$. | Na |
| Example 1-391 | 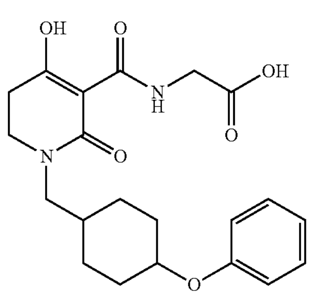 [SMILES: O=C(O)CNC(=O)C1=C(O)CCN(CC2CCC(Oc3ccccc3)CC2)C1=O] | $^1$H NMR (300 MHz, DMSO-d$_6$) δ ppm 1.21-1.64 (m, 6 H) 1.66-1.96 (m, 3 H) 2.47-2.56 (m, 2 H) 3.19-3.45 (m, 6 H) 4.52-4.60 (m, 1 H) 6.85-6.99 (m, 3 H) 7.21-7.31 (m, 2 H) 9.92-10.08 (m, 1 H). MS ESI/APCI Dual posi: 403[M + H]$^+$. MS ESI/APCI Dual nega: 401[M − H]$^-$. | Na |

TABLE 21-57

| Compound No. | Structure | Analytical Data | Salt information |
|---|---|---|---|
| Example 1-392 | 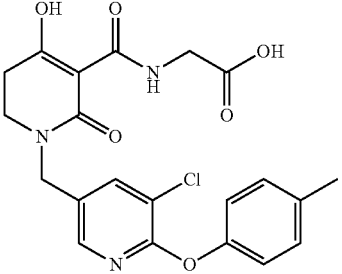 | $^1$H NMR (300 MHz, DMSO-d$_6$) δ ppm 2.31 (s, 3 H) 2.40-2.50 (m, 2 H) 3.16-3.44 (m, 2 H) 3.48 (d, J = 4.5 Hz, 2 H) 4.50 (s, 2 H) 6.94-7.09 (m, 2 H) 7.15-7.29 (s, 2 H) 7.92-7.95 (m, 1 H) 7.98-8.01 (m, 1 H).<br>MS ESI/APCI Dual posi: 446[M + H]$^+$.<br>MS ESI/APCI Dual nega: 444[M − H]$^-$. | Na |
| Example 1-393 | 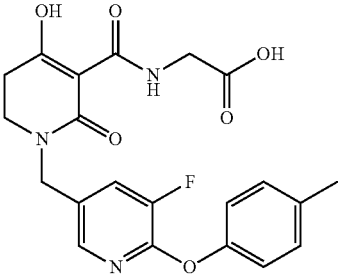 [SMILES: Cc1ccc(Oc2ncc(CN3CCC(O)=C(C(=O)NCC(=O)O)C3=O)cc2F)cc1] | $^1$H NMR (300 MHz, DMSO-d$_6$) δ ppm 2.31 (s, 3 H) 2.40-2.50 (m, 2 H) 3.26-3.42 (m, 2 H) 3.43-3.52 (m, 2 H) 4.52 (s, 2 H) 6.99-7.10 (m, 2 H) 7.16-7.27 (m, 2 H) 7.69-7.79 (m, 1 H) 7.85-7.92 (m, 1 H).<br>MS ESI/APCI Dual posi: 430[M + H]$^+$.<br>MS ESI/APCI Dual nega: 428[M − H]$^-$. | Na |
| Example 1-394 | 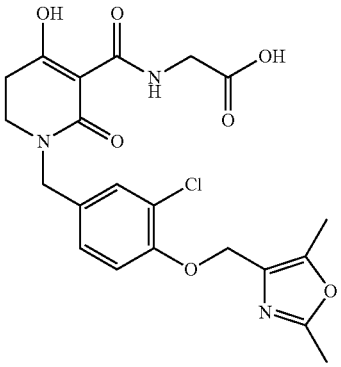 [SMILES: Cc1nc(COc2ccc(CN3CCC(O)=C(C(=O)NCC(=O)O)C3=O)cc2Cl)c(C)o1] | $^1$H NMR (300 MHz, DMSO-d$_6$) δ ppm 2.31 (s, 3 H) 2.35 (s, 3 H) 2.51-2.53 (m, 2 H) 3.26-3.30 (m, 2 H) 3.48 (d, J = 4.5 Hz, 2 H) 4.48 (s, 2 H) 4.95 (s, 2 H) 7.21-7.25 (m, 2 H) 7.32-7.35 (m, 1 H).<br>MS ESI/APCI Dual posi: 464[M + H]$^+$.<br>MS ESI/APCI Dual nega: 462[M − H]$^-$. | Na |
| Example 1-395 | 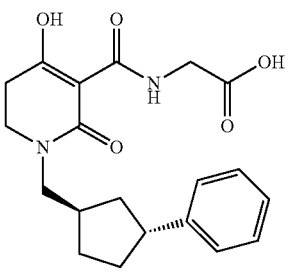 [SMILES: O=C(O)CNC(=O)C1=C(O)CCN(C[C@@H]2CC[C@@H](c3ccccc3)C2)C1=O] | $^1$H NMR (600 MHz, DMSO-d$_6$) δ ppm 1.30-1.40 (m, 1 H) 1.52-1.62 (m, 1 H) 1.65-1.73 (m, 1 H) 1.74-1.82 (m, 1 H) 1.85-1.94 (m, 1 H) 2.03-2.13 (m, 1 H) 2.44-2.57 (m, 3 H) 3.10-3.19 (m, 1 H) 3.26-3.48 (m, 6 H) 7.13-7.18 (m, 1 H) 7.22-7.32 (m, 4 H) 9.93-10.27 (m, 1 H).<br>MS ESI/APCI Dual posi: 373[M + H]$^+$.<br>MS ESI/APCI Dual nega: 371[M − H]$^-$. | Na |
| Example 1-396 | 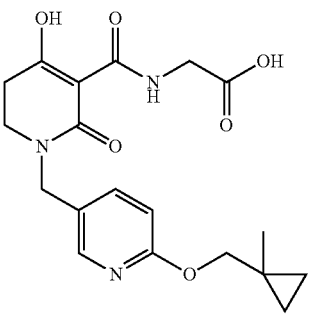 [SMILES: CC1(COc2ccc(CN3CCC(O)=C(C(=O)NCC(=O)O)C3=O)cn2)CC1] | $^1$H NMR (300 MHz, DMSO-d$_6$) δ ppm 0.29-0.41 (m, 2 H) 0.47-0.55 (m, 2 H) 1.15 (s, 3 H) 2.39-2.54 (m, 2 H) 3.19-3.32 (m, 2 H) 3.45 (d, J = 4.4 Hz, 2 H) 4.02 (s, 2 H) 4.47 (s, 2 H) 6.75-6.84 (m, 1 H) 7.56-7.65 (m, 1 H) 8.01-8.08 (m, 1 H) 10.04 (br. s., 1 H).<br>MS ESI/APCI Dual posi: 390[M + H]$^+$.<br>MS ESI/APCI Dual nega: 388[M − H]$^-$. | Na |

TABLE 21-57-continued

| Compound No. | Structure | Analytical Data | Salt information |
|---|---|---|---|
| Example 1-397 | 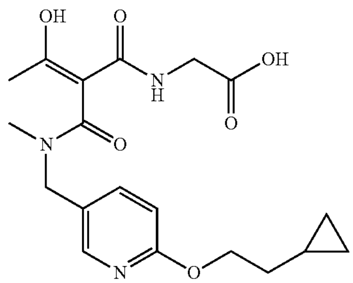 | $^1$H NMR (300 MHz, DMSO-$d_6$) δ ppm 0.04-0.14 (m, 2 H) 0.36-0.47 (m, 2 H) 0.69-0.86 (m, 1 H) 1.53-1.66 (m, 2 H) 2.40-2.50 (m, 2 H) 3.22-3.32 (m, 2 H) 3.48 (d, J = 4.5 Hz, 2 H) 4.21-4.32 (m, 2 H) 4.48 (s, 2 H) 6.72-6.81 (m, 1 H) 7.58-7.65 (m, 1 H) 8.06-8.11 (m, 1 H) 10.07 (br. s., 1 H).<br>MS ESI/APCI Dual posi: 390[M + H]$^+$.<br>MS ESI/APCI Dual nega: 388[M − H]$^-$. | Na |
| Example 1-398 | 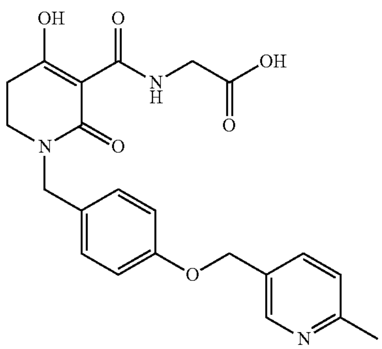 [SMILES: Cc1ccc(COc2ccc(CN3CCC(O)=C(C(=O)NCC(=O)O)C3=O)cc2)cn1] | $^1$H NMR (300 MHz, DMSO-$d_6$) δ ppm 2.47 (s, 3 H) 2.48-2.54 (m, 2 H) 3.23-3.30 (m, 2 H) 3.49 (d, J = 4.4 Hz, 2 H) 4.49 (s, 2 H) 5.07 (s, 2 H) 6.95-7.02 (m, 2 H) 7.17-7.24 (m, 2 H) 7.27 (d, J = 7.8 Hz, 1 H) 7.74 (dd, J = 7.8, 2.2 Hz, 1 H) 8.51 (d, J = 2.2 Hz, 1 H) 9.91-10.17 (m, 1 H).<br>MS ESI/APCI Dual posi: 426[M + H]$^+$.<br>MS ESI/APCI Dual nega: 424[M − H]$^-$. | Na |

TABLE 21-58

| Compound No. | Structure | Analytical Data | Salt information |
|---|---|---|---|
| Example 1-399 | 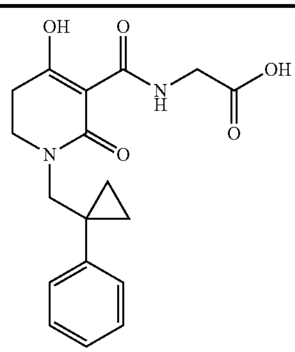 | $^1$H NMR (300 MHz, DMSO-$d_6$) δ ppm 0.74-0.83 (m, 2 H) 0.87-0.96 (m, 2 H) 2.19-2.35 (m, 2 H) 3.04-3.19 (m, 2 H) 3.45-3.64 (m, 4 H) 7.13-7.41 (m, 5 H) 9.78-10.24 (m, 1 H).<br>MS ESI/APCI Dual posi: 345[M + H]$^+$.<br>MS ESI/APCI Dual nega: 343[M − H]$^-$. | Na |
| Example 1-400 | 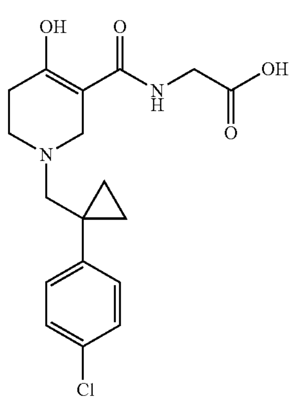 [SMILES: O=C(O)CNC(=O)C1=C(O)CCN(CC2(c3ccc(Cl)cc3)CC2)C1] | $^1$H NMR (300 MHz, DMSO-$d_6$) δ ppm 0.73-0.83 (m, 2 H) 0.88-0.97 (m, 2 H) 2.20-2.41 (m, 2 H) 3.07-3.25 (m, 2 H) 3.41-3.65 (m, 4 H) 7.28-7.41 (m, 4 H) 9.75-10.21 (m, 1 H).<br>MS ESI/APCI Dual posi: 379[M + H]$^+$.<br>MS ESI/APCI Dual nega: 377[M − H]$^-$. | Na |

TABLE 21-58-continued

| Compound No. | Structure | Analytical Data | Salt information |
|---|---|---|---|
| Example 1-401 | 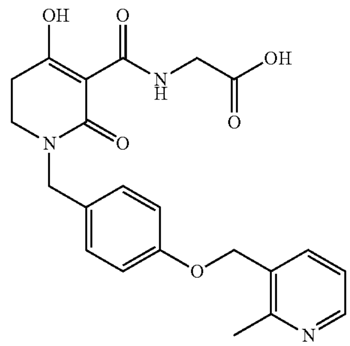 [SMILES: Cc1ncccc1COc1ccc(CN2CCC(O)=C(C(=O)NCC(=O)O)C2=O)cc1] | $^1$H NMR (300 MHz, DMSO-d$_6$) δ ppm 2.40-2.48 (m, 2 H) 2.48-2.51 (m, 3 H) 3.21-3.29 (m, 2 H) 3.46 (d, J = 4.4 Hz, 2 H) 4.49 (s, 2 H) 5.11 (s, 2 H) 6.96-7.05 (m, 2 H) 7.18-7.28 (m, 3 H) 7.78 (dd, J = 7.6, 1.7 Hz, 1 H) 8.40 (dd, J = 4.8, 1.7 Hz, 1 H) 9.98-10.15 (m, 1 H) MS ESI/APCI Dual posi: 426[M + H]$^+$. MS ESI/APCI Dual nega: 424[M − H]$^−$. | Na |
| Example 1-402 | 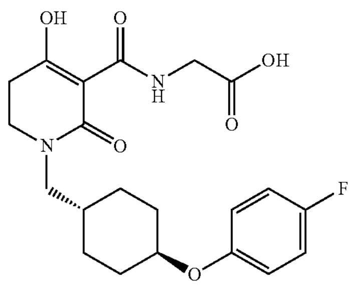 [SMILES: O=C(O)CNC(=O)C1=C(O)CCN(C[C@H]2CC[C@H](Oc3ccc(F)cc3)CC2)C1=O] | $^1$H NMR (300 MHz, DMSO-d$_6$) δ ppm 0.99-1.42 (m, 4 H) 1.54-1.80 (m, 3 H) 1.97-2.14 (m, 2 H) 2.40-2.63 (m, 2 H) 3.16-3.52 (m, 6 H) 4.08-4.30 (m, 1 H) 6.84-7.16 (s, 4 H) 9.90-10.31 (m, 1 H). MS ESI/APCI Dual posi: 421[M + H]$^+$. MS ESI/APCI Dual nega: 419[M − H]$^−$. | Na |
| Example 1-403 | 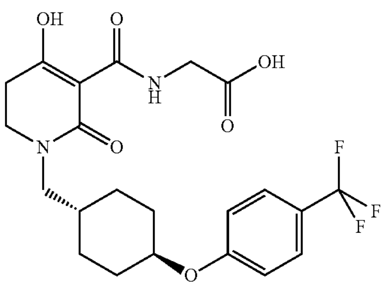 [SMILES: O=C(O)CNC(=O)C1=C(O)CCN(C[C@H]2CC[C@H](Oc3ccc(C(F)(F)F)cc3)CC2)C1=O] | $^1$H NMR (300 MHz, DMSO-d$_6$) δ ppm 1.06-1.44 (m, 4 H) 1.58-1.83 (m, 3 H) 2.00-2.18 (m, 2 H) 2.40-2.63 (m, 2 H) 3.17-3.52 (m, 6 H) 4.30-4.48 (m, 1 H) 7.06-7.20 (m, 2 H) 7.51-7.73 (m, 2 H) 9.91-10.14 (m, 1 H). MS ESI/APCI Dual posi: 471[M + H]$^+$. MS ESI/APCI Dual nega: 469[M − H]$^−$. | Na |
| Example 1-404 | 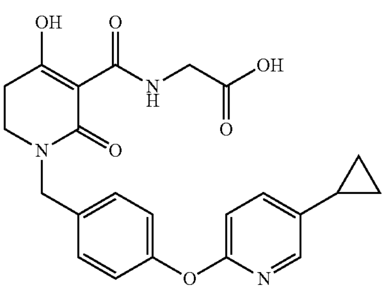 [SMILES: O=C(O)CNC(=O)C1=C(O)CCN(Cc2ccc(Oc3ccc(C4CC4)cn3)cc2)C1=O] | $^1$H NMR (300 MHz, DMSO-d$_6$) δ ppm 0.61-0.73 (m, 2 H) 0.89-1.00 (m, 2 H) 1.83-1.99 (m, 1 H) 2.46-2.61 (m, 2 H) 3.26-3.58 (m, 4 H) 4.55 (s, 2 H) 6.85-6.94 (m, 1 H) 7.00-7.08 (m, 2 H) 7.23-7.35 (m, 2 H) 7.43-7.53 (m, 1 H) 7.93-8.01 (m, 1 H) 10.01-10.19 (m, 1 H). MS ESI/APCI Dual posi: 438[M + H]$^+$. | Na |
| Example 1-405 | 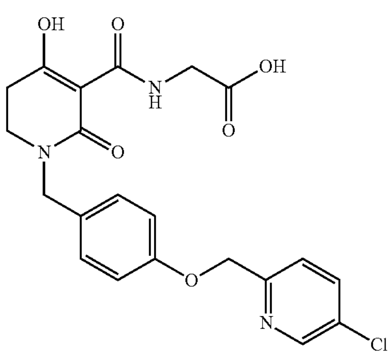 | $^1$H NMR (300 MHz, DMSO-d$_6$) δ ppm 2.49-2.53 (m, 2 H) 3.27 (t, J = 7.1 Hz, 2 H) 3.50 (d, J = 4.4 Hz, 2 H) 4.49 (s, 2 H) 5.16 (s, 2 H) 6.94-7.03 (m, 2 H) 7.17-7.26 (m, 2 H) 7.56 (dd, J = 8.4, 0.6 Hz, 1 H) 7.97 (dd, J = 8.4, 2.5 Hz, 1 H) 8.63 (dd, J = 2.5, 0.6 Hz, 1 H) 9.97-10.17 (m, 1 H). MS ESI/APCI Dual posi: 446[M + H]$^+$. MS ESI/APCI Dual nega: 444[M − H]$^−$. | Na |

TABLE 21-59

| Compound No. | Structure | Analytical Data | Salt information |
|---|---|---|---|
| Example 1-406 | 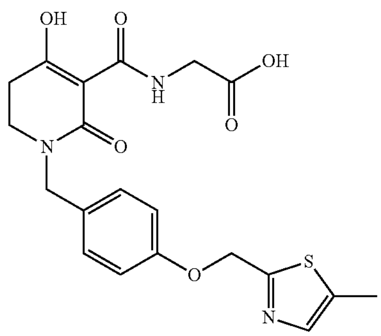 [SMILES: Cc1cnc(COc2ccc(CN3CCC(O)=C(C(=O)NCC(=O)O)C3=O)cc2)s1] | $^1$H NMR (300 MHz, DMSO-d$_6$) δ ppm 2.43 (d, J = 1.1 Hz, 3 H) 2.46-2.52 (m, 2 H) 3.22-3.31 (m, 2 H) 3.48 (d, J = 4.4 Hz, 2 H) 4.49 (s, 2 H) 5.32 (s, 2 H) 6.96-7.06 (m, 2 H) 7.17-7.26 (m, 2 H) 7.49 (q, J = 1.2 Hz, 1 H) 9.96-10.17 (m, 1 H). MS ESI/APCI Dual posi: 432[M + H]$^+$. MS ESI/APCI Dual nega: 430[M − H]$^-$. | Na |
| Example 1-407 | 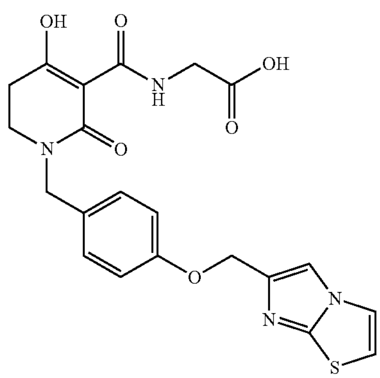 [SMILES: O=C(O)CNC(=O)C1=C(O)CCN(Cc2ccc(OCc3cn4ccsc4n3)cc2)C1=O] | $^1$H NMR (300 MHz, DMSO-d$_6$) δ ppm 2.42-2.49 (m, 2 H) 3.21-3.28 (m, 2 H) 3.44 (d, J = 4.5 Hz, 2 H) 4.48 (s, 2 H) 5.02 (s, 2 H) 6.95-7.03 (m, 2 H) 7.16-7.23 (m, 2 H) 7.24 (d, J = 4.4 Hz, 1 H) 7.84 (s, 1 H) 7.89 (d, J = 4.4 Hz, 1 H) 9.94-10.12 (m, 1 H). MS ESI/APCI Dual posi: 457[M + H]$^+$. MS ESI/APCI Dual nega: 455[M − H]$^-$. | Na |
| Example 1-408 | 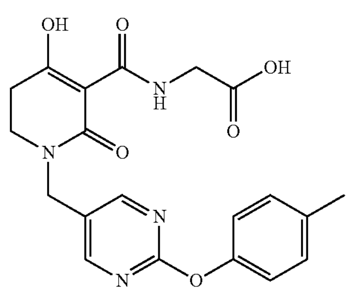 [SMILES: Cc1ccc(Oc2ncc(CN3CCC(O)=C(C(=O)NCC(=O)O)C3=O)cn2)cc1] | $^1$H NMR (600 MHz, DMSO-d$_6$) δ ppm 2.32 (s, 3 H) 2.51-2.62 (m, 2 H) 3.32-3.40 (m, 2 H) 3.46 (d, J = 4.5 Hz, 2 H) 4.50 (s, 2 H) 7.02-7.10 (m, 2 H) 7.18-7.26 (m, 2 H) 8.56 (s, 2 H). | Na |
| Example 1-409 | 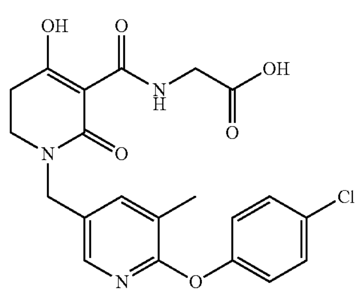 [SMILES: Cc1cc(CN2CCC(O)=C(C(=O)NCC(=O)O)C2=O)cnc1Oc1ccc(Cl)cc1] | $^1$H NMR (600 MHz, DMSO-d$_6$) δ ppm 2.16 (t, J = 6.8 Hz, 2 H) 2.26 (s, 3 H) 2.40-2.50 (m, 2 H) 3.08 (t, J = 6.8 Hz, 2 H) 3.43 (d, J = 4.1 Hz, 2 H) 4.44 (s, 2 H) 7.07-7.15 (m, 2 H) 7.37-7.45 (m, 2 H) 7.62 (d, J = 1.7 Hz, 1 H) 7.87 (d, J = 1.7 Hz, 1 H) 10.08 (t, J = 4.5 Hz, 1 H). MS ESI/APCI Dual posi: 446[M + H]$^+$. MS ESI/APCI Dual nega: 444[M − H]$^-$. | Na |

TABLE 21-59-continued

| Compound No. | Structure | Analytical Data | Salt information |
|---|---|---|---|
| Example 1-410 | 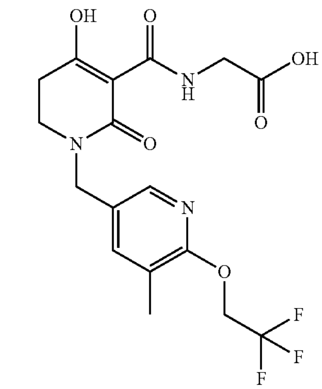 [SMILES: Cc1cc(CN2CCC(O)=C(C(=O)NCC(=O)O)C2=O)cnc1OCC(F)(F)F] | $^1$H NMR (300 MHz, DMSO-d$_6$) δ ppm 2.17 (s, 3 H) 2.45-2.58 (m, 2 H) 3.26-3.36 (m, 2 H) 3.48-3.55 (m, 2 H) 4.49 (s, 2 H) 4.89-5.06 (m, 2 H) 7.52-7.60 (m, 1 H) 7.91-8.01 (m, 1 H) 10.06 (br. s., 1 H).<br>MS ESI/APCI Dual posi: 418[M + H]$^+$.<br>MS ESI/APCI Dual nega: 416[M − H]$^-$. | Na |
| Example 1-411 | 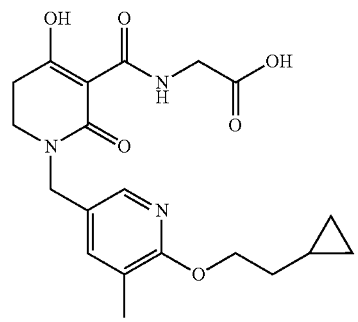 [SMILES: Cc1cc(CN2CCC(O)=C(C(=O)NCC(=O)O)C2=O)cnc1OCCC1CC1] | $^1$H NMR (300 MHz, DMSO-d$_6$) δ ppm 0.05-0.16 (m, 2 H) 0.36-0.48 (m, 2 H) 0.73-0.89 (m, 1 H) 1.55-1.67 (m, 2 H) 2.12 (s, 3 H) 2.42-2.54 (m, 2 H) 3.23-3.34 (m, 2 H) 3.43-3.52 (m, 2 H) 4.23-4.35 (m, 2 H) 4.45 (s, 2 H) 7.41-7.47 (m, 1 H) 7.86-7.94 (m, 1 H) 10.04 (br. s., 1 H).<br>MS ESI/APCI Dual posi: 404[M + H]$^+$.<br>MS ESI/APCI Dual nega: 402[M − H]$^-$. | Na |
| Example 1-412 | 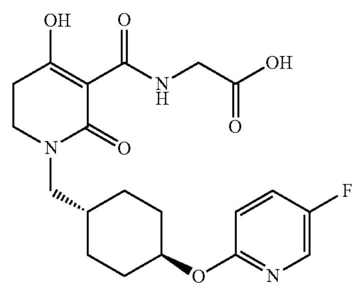 [SMILES: O=C(O)CNC(=O)C1=C(O)CCN(C[C@H]2CC[C@H](Oc3ccc(F)cn3)CC2)C1=O] | $^1$H NMR (300 MHz, DMSO-d$_6$) δ ppm 0.96-1.45 (m, 4 H) 1.55-1.82 (m, 3 H) 1.99-2.17 (m, 2 H) 2.42-2.63 (m, 2 H) 3.11-3.53 (m, 6 H) 4.71-4.93 (m, 1 H) 6.72-6.86 (m, 1 H) 7.56-7.73 (m, 1 H) 8.03-8.20 (m, 1 H) 9.90-10.31 (m, 1H).<br>MS ESI/APCI Dual posi: 422[M + H]$^+$.<br>MS ESI/APCI Dual nega: 420[M − H]$^-$. | Na |

TABLE 21-60

| Compound No. | Structure | Analytical Data | Salt information |
|---|---|---|---|
| Example 1-413 | 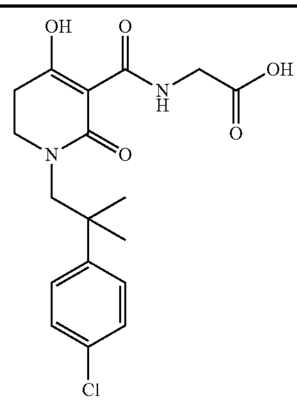 | $^1$H NMR (300 MHz, DMSO-d$_6$) δ ppm 1.29 (s, 6 H) 2.15-2.31 (m, 2 H) 2.75-2.89 (m, 2 H) 3.39-3.52 (m, 4 H) 7.33-7.42 (m, 2 H) 7.44-7.54 (m, 2 H) 9.89-10.14 (m, 1 H).<br>MS ESI/APCI Dual posi: 381[M + H]$^+$.<br>MS ESI/APCI Dual nega: 379[M − H]$^-$. | Na |

TABLE 21-60-continued

| Compound No. | Structure | Analytical Data | Salt information |
|---|---|---|---|
| Example 1-414 | 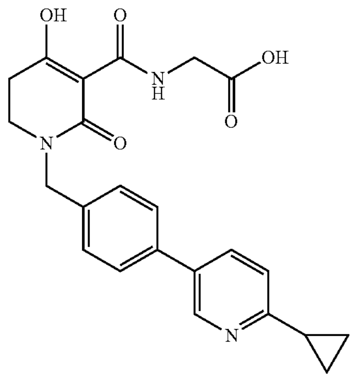 | ¹H NMR (300 MHz, DMSO-d₆) δ ppm 0.89-1.04 (m, 4 H) 2.05-2.21 (m, 1 H) 2.42-2.61 (m, 2 H) 3.20-3.58 (m, 4 H) 4.61 (s, 2 H) 7.32-7.45 (m, 3 H) 7.59-7.71 (m, 2 H) 7.85-7.96 (m, 1 H) 8.64-8.76 (m, 1 H) 10.00-10.23 (m, 1 H). MS ESI/APCI Dual posi: 422[M + H]⁺. | Na |
| Example 1-415 | 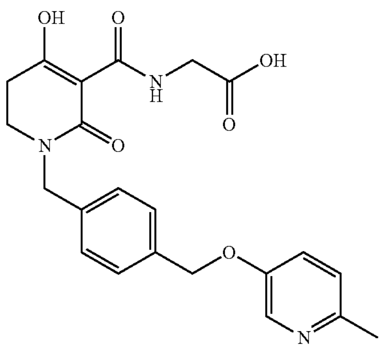 [SMILES: Cc1ccc(OCc2ccc(CN3CCC(O)=C(C(=O)NCC(=O)O)C3=O)cc2)cn1] | ¹H NMR (300 MHz, DMSO-d₆) δ ppm 2.38 (s, 3 H) 2.47-2.53 (m, 2 H) 3.31-3.38 (m, 2 H) 3.76 (d, J = 4.2 Hz, 2 H) 4.58 (s, 2 H) 5.12 (s, 2 H) 7.16 (d, J = 8.5 Hz, 1 H) 7.27-7.37 (m, 3 H) 7.39-7.46 (m, 2 H) 8.20 (d, J = 2.6 Hz, 1 H) 9.95-10.10 (m, 1 H). MS ESI/APCI Dual posi: 426[M + H]⁺. MS ESI/APCI Dual nega: 424[M − H]⁻. | Na |
| Example 1-416 | 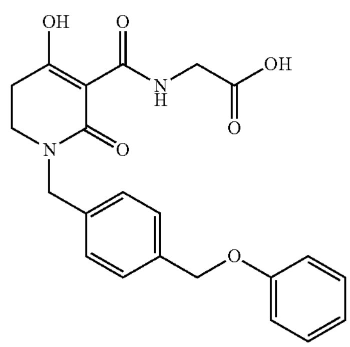 [SMILES: O=C(O)CNC(=O)C1=C(O)CCN(Cc2ccc(COc3ccccc3)cc2)C1=O] | ¹H NMR (300 MHz, DMSO-d₆) δ ppm 2.51-2.56 (m, 2 H) 3.25-3.31 (m, 2 H) 3.43 (d, J = 4.5 Hz, 2 H) 4.56 (s, 2 H) 5.07 (s, 2 H) 6.88-7.05 (m, 3 H) 7.23-7.35 (m, 4 H) 7.42 (d, J = 8.2 Hz, 2 H). MS ESI/APCI Dual posi: 411[M + H]⁺. MS ESI/APCI Dual nega: 409[M − H]⁻. | Na |
| Example 1-417 | 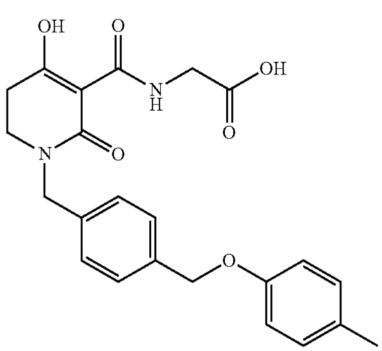 | ¹H NMR (300 MHz, DMSO-d₆) δ ppm 2.22 (s, 3 H) 2.43-2.49 (m, 2 H) 3.25-3.30 (m, 2 H) 3.43 (d, J = 4.4 Hz, 2 H) 4.56 (s, 2 H) 5.03 (s, 2 H) 6.84-6.93 (m, 2 H) 7.03-7.12 (m, 2 H) 7.23-7.32 (m, 2 H) 7.35-7.45 (m, 2 H) 9.87-10.07 (m, 1 H). MS ESI/APCI Dual posi: 425[M + H]⁺. MS ESI/APCI Dual nega: 423[M − H]⁻. | Na |

TABLE 21-60-continued

| Compound No. | Structure | Analytical Data | Salt information |
|---|---|---|---|
| Example 1-418 | 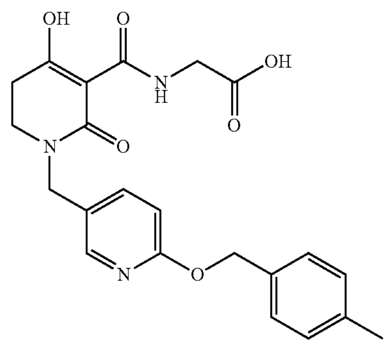 [SMILES: Cc1ccc(COc2ccc(CN3CCC(O)=C(C(=O)NCC(=O)O)C3=O)cn2)cc1] | $^1$H NMR (300 MHz, DMSO-d$_6$) δ ppm 2.30 (s, 3 H) 2.45-2.51 (m, 2 H) 3.26-3.33 (m, 2 H) 3.47 (d, J = 4.5 Hz, 2 H) 4.49 (s, 2 H) 5.27 (s, 2 H) 6.83 (dd, J = 8.5, 0.5 Hz, 1 H) 7.14-7.20 (m, 2 H) 7.29-7.36 (m, 2 H) 7.64 (dd, J = 8.5, 2.4 Hz, 1 H) 8.07-8.14 (m, 1 H) 9.96-10.14 (m, 1 H). MS ESI/APCI Dual posi: 426[M + H]$^+$. MS ESI/APCI Dual nega: 424[M − H]$^−$. | Na |
| Example 1-419 | 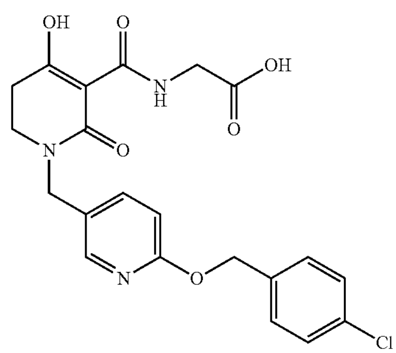 | $^1$H NMR (300 MHz, DMSO-d$_6$) δ ppm 2.45-2.50 (m, 2 H) 3.29-3.38 (m, 2 H) 3.55 (d, J = 4.2 Hz, 2 H) 4.50 (s, 2 H) 5.33 (s, 2 H) 6.78-6.92 (m, 1 H) 7.38-7.51 (m, 4 H) 7.66 (dd, J = 8.5, 2.5 Hz, 1 H) 8.08-8.14 (m, 1 H) 9.88-10.07 (m, 1 H). MS ESI/APCI Dual posi: 446[M + H]$^+$. MS ESI/APCI Dual nega: 444[M − H]$^−$. | Na |

TABLE 21-61

| Compound No. | Structure | Analytical Data | Salt information |
|---|---|---|---|
| Example 1-420 | 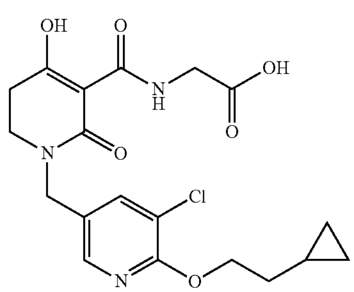 [SMILES: O=C(O)CNC(=O)C1=C(O)CCN(Cc2cnc(OCCC3CC3)c(Cl)c2)C1=O] | $^1$H NMR (300 MHz, DMSO-d$_6$) δ ppm 0.07-0.16 (m, 2 H) 0.34-0.49 (m, 2 H) 0.72-0.91 (m, 1 H) 1.55-1.70 (m, 2 H) 2.43-2.57 (m, 2 H) 3.27-3.39 (m, 2 H) 3.53-3.60 (m, 2 H) 4.32-4.42 (m, 2 H) 4.48 (s, 2 H) 7.77-7.82 (m, 1 H) 8.05-8.09 (m, 1 H) 10.10 (br. s., 1 H). MS ESI/APCI Dual posi: 424[M + H]$^+$. MS ESI/APCI Dual nega: 422[M − H]$^−$. | Na |
| Example 1-421 | 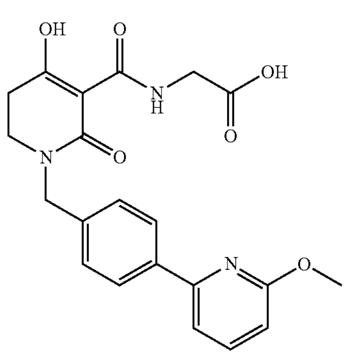 [SMILES: COc1cccc(-c2ccc(CN3CCC(O)=C(C(=O)NCC(=O)O)C3=O)cc2)n1] | $^1$H NMR (300 MHz, DMSO-d$_6$) δ ppm 2.46-2.58 (m, 2 H) 3.33 (t, J = 7.1 Hz, 2 H) 3.50 (d, J = 4.4 Hz, 2 H) 3.95 (s, 3 H) 4.62 (s, 2 H) 6.73-6.81 (m, 1 H) 7.34-7.44 (m, 2 H) 7.50-7.58 (m, 1 H) 7.71-7.83 (m, 1 H) 8.00-8.11 (m, 2 H) 10.02-10.20 (m, 1 H). MS ESI/APCI Dual posi: 412[M + H]$^+$. | Na |

TABLE 21-61-continued

| Compound No. | Structure | Analytical Data | Salt information |
|---|---|---|---|
| Example 1-422 | (structure) | ¹H NMR (300 MHz, DMSO-d₆) δ ppm 2.10-2.31 (m, 2 H) 3.12 (t, J = 6.3 Hz, 2 H) 3.47 (d, J = 4.4 Hz, 2 H) 4.59 (s, 2 H) 7.31-7.43 (m, 2 H) 7.91-8.08 (m, 4 H) 8.62-8.73 (m, 1 H) 10.14-10.25 (m, 1 H). MS ESI/APCI Dual posi: 416[M + H]⁺. | Na |
| Example 1-423 | (structure) | ¹H NMR (300 MHz, DMSO-d₆) δ ppm 2.51-2.59 (m, 2 H) 3.26-3.33 (m, 2 H) 3.46 (d, J = 4.4 Hz, 2 H) 4.58 (s, 2 H) 5.27 (s, 2 H) 7.28-7.36 (m, 2 H) 7.41-7.50 (m, 2 H) 7.68 (dd, J = 8.5, 2.7 Hz, 1 H) 7.80-7.91 (m, 1 H) 8.49-8.54 (m, 1 H) 9.89-10.11 (m, 1 H). MS ESI/APCI Dual posi: 480[M + H]⁺. MS ESI/APCI Dual nega: 478[M − H]⁻. | Na |
| Example 1-424 | (structure) | ¹H NMR (300 MHz, DMSO-d₆) δ ppm 2.41-2.49 (m, 2 H) 3.23-3.30 (m, 2 H) 3.47 (d, J = 4.4 Hz, 2 H) 4.56 (s, 2 H) 5.41 (s, 2 H) 7.03-7.12 (m, 1 H) 7.29 (d, J = 8.1 Hz, 2 H) 7.43 (d, J = 8.1 Hz, 2 H) 8.04-8.14 (m, 1 H) 8.57-8.64 (m, 1 H) 9.98-10.15 (m, 1 H). MS ESI/APCI Dual nega: 478[M − H]⁻. | Na |
| Example 1-425 | (structure) | ¹H NMR (300 MHz, DMSO-d₆) δ ppm 2.46-2.60 (m, 2 H) 3.33 (t, J = 7.0 Hz, 2 H) 3.54 (d, J = 4.5 Hz, 2 H) 3.87 (s, 3 H) 4.61 (s, 2 H) 7.27-7.40 (m, 2 H) 7.42-7.53 (m, 1 H) 7.83-8.04 (m, 3 H) 8.31-8.44 (m, 1 H) 10.03-10.25 (m, 1 H). MS ESI/APCI Dual posi: 412[M + H]⁺. | Na |

TABLE 21-61-continued

| Compound No. | Structure | Analytical Data | Salt information |
|---|---|---|---|
| Example 1-426 | 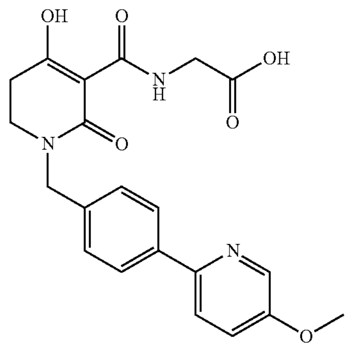 [SMILES: COc1ccc(-c2ccc(CN3CCC(O)=C(C(=O)NCC(=O)O)C3=O)cc2)nc1] | $^1$H NMR (300 MHz, DMSO-d$_6$) δ ppm 2.48-2.62 (m, 2 H) 3.34 (t, J = 7.1 Hz, 2 H) 3.58 (d, J = 4.5 Hz, 2 H) 3.84 (s, 3 H) 4.62 (s, 2 H) 7.29-7.42 (m, 3 H) 7.50-7.61 (m, 1 H) 7.81-7.89 (m, 2 H) 8.21-8.31 (m, 1 H) 10.08-10.23 (m, 1 H). MS ESI/APCI Dual posi: 412[M + H]$^+$. | Na |

TABLE 21-62

| Compound No. | Structure | Analytical Data | Salt information |
|---|---|---|---|
| Example 1-427 | 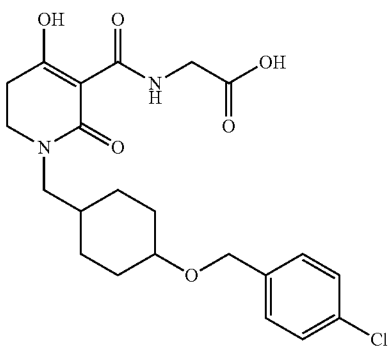 [SMILES: O=C(O)CNC(=O)C1=C(O)CCN(CC2CCC(OCc3ccc(Cl)cc3)CC2)C1=O] | $^1$H NMR (300 MHz, DMSO-d$_6$) δ ppm 1.19-1.62 (m, 6 H) 1.60-1.77 (m, 1 H) 1.78-1.93 (m, 2 H) 2.38-2.51 (m, 2 H) 3.14-3.48 (m, 6 H) 3.53-3.63 (m, 1 H) 4.45 (s, 2 H) 7.31-7.45 (m, 4 H) 9.87-10.22 (m, 1 H). MS ESI/APCI Dual posi: 451[M + H]$^+$. MS ESI/APCI Dual nega: 449[M − H]$^-$. | Na |
| Example 1-428 | 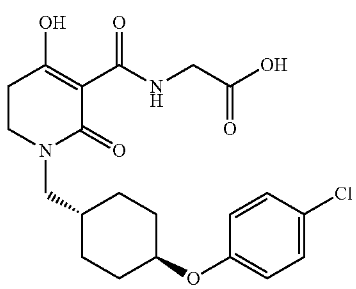 [SMILES: O=C(O)CNC(=O)C1=C(O)CCN(C[C@H]2CC[C@H](Oc3ccc(Cl)cc3)CC2)C1=O] | $^1$H NMR (300 MHz, DMSO-d$_6$) δ ppm 1.01-1.40 (m, 4 H) 1.65-1.79 (m, 3 H) 1.99-2.13 (m, 2 H) 2.43-2.61 (m, 2 H) 3.15-3.50 (m, 6 H) 4.17-4.33 (m, 1 H) 6.91-7.00 (m, 2 H) 7.24-7.33 (m, 2 H) 9.92-10.30 (m, 1 H). MS ESI/APCI Dual posi: 437[M + H]$^+$. MS ESI/APCI Dual nega: 435[M − H]$^-$. | Na |
| Example 1-429 | 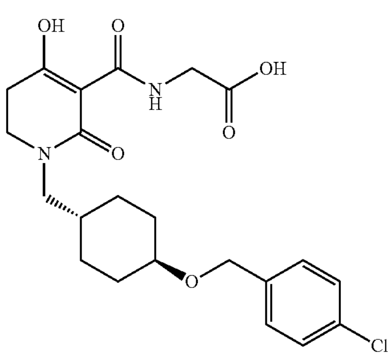 [SMILES: O=C(O)CNC(=O)C1=C(O)CCN(C[C@H]2CC[C@H](OCc3ccc(Cl)cc3)CC2)C1=O] | $^1$H NMR (300 MHz, DMSO-d$_6$) δ ppm 0.85-1.27 (m, 4 H) 1.49-1.74 (m, 3 H) 1.95-2.10 (m, 2 H) 2.42-2.61 (m, 2 H) 3.10-3.48 (m, 7 H) 4.49 (s, 2 H) 7.29-7.43 (m, 4 H) 9.88-10.31 (m, 1 H). MS ESI/APCI Dual posi: 451[M + H]$^+$. MS ESI/APCI Dual nega: 449[M − H]$^-$. | Na |

TABLE 21-62-continued

| Compound No. | Structure | Analytical Data | Salt information |
|---|---|---|---|
| Example 1-430 | 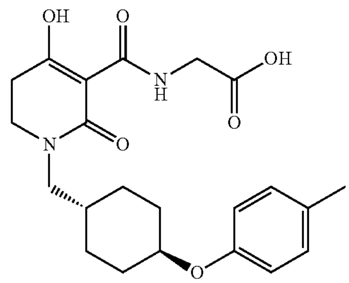 | $^1$H NMR (300 MHz, DMSO-$d_6$) δ ppm 1.00-1.40 (m, 4 H) 1.55-1.79 (m, 3 H) 1.97-2.12 (m, 2 H) 2.21 (s, 3 H) 2.44-2.63 (m, 2 H) 3.15-3.50 (m, 6 H) 4.07-4.27 (m, 1 H) 5.76-6.85 (m, 2 H) 6.99-7.10 (m, 2 H) 9.88-10.28 (m, 1 H). MS ESI/APCI Dual posi: 417[M + H]$^+$. MS ESI/APCI Dual nega: 415[M − H]$^-$. | Na |
| Example 1-431 | 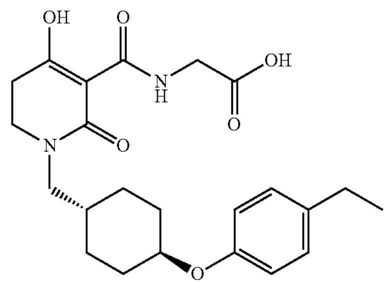 [SMILES: CCc1ccc(O[C@H]2CC[C@H](CN3CCC(O)=C(C(=O)NCC(=O)O)C3=O)CC2)cc1] | $^1$H NMR (300 MHz, DMSO-$d_6$) δ ppm 1.00-1.19 (m, 5 H) 1.20-1.38 (m, 2 H) 1.55-1.79 (m, 3 H) 1.97-2.13 (m, 2 H) 2.44-2.63 (m, 4 H) 3.15-3.50 (m, 6 H) 4.10-4.25 (m, 1 H) 6.76-6.87 (m, 2 H) 7.01-7.15 (m, 2 H) 9.85-10.16 (m, 1 H). MS ESI/APCI Dual posi: 431[M + H]$^+$. MS ESI/APCI Dual nega: 429[M − H]$^-$. | Na |
| Example 1-432 | 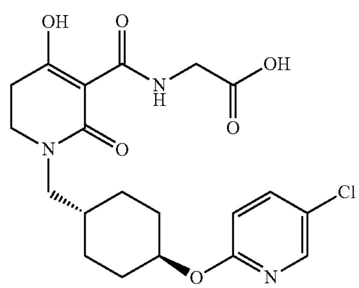 | $^1$H NMR (300 MHz, DMSO-$d_6$) δ ppm 0.98-1.21 (m, 2 H) 1.25-1.47 (m, 2 H) 1.57-1.83 (m, 3 H) 1.98-2-17 (m, 2 H) 2.43-2.62 (m, 2 H) 3.14-3.48 (m, 6 H) 4.75-4.95 (m, 1 H) 6.81 (d, J = 8.9 Hz, 1 H) 7.76 (dd, J = 8.9, 2.6 Hz, 1 H) 8.19 (d, J = 2.6 Hz, 1 H) 9.88-10.27 (m, 1 H). MS ESI/APCI Dual posi: 438[M + H]$^+$. MS ESI/APCI Dual nega: 436[M − H]$^-$. | Na |
| Example 1-433 | 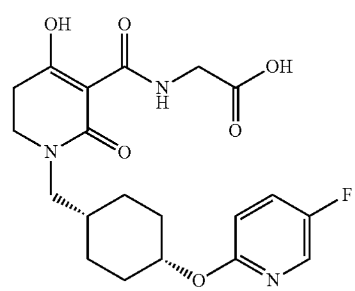 [SMILES: O=C(O)CNC(=O)C1=C(O)CCN(C[C@H]2CC[C@@H](Oc3ccc(F)cn3)CC2)C1=O] | $^1$H NMR (300 MHz, DMSO-$d_6$) δ ppm 1.22-1.97 (m, 9 H) 2.43-2.70 (m, 2 H) 3.18-3.51 (m, 4 H) 3.70-3.86 (m, 2 H) 5.04-5.18 (m, 1 H) 6.81-6.93 (m, 1 H) 7.57-7.72 (m, 1 H) 8.06-8.15 (m, 1 H) 9.98-10.25 (m, 1 H). MS ESI/APCI Dual posi: 422[M + H]$^+$. | Na |

TABLE 21-63

| Compound No. | Structure | Analytical Data | Salt information |
|---|---|---|---|
| Example 1-434 | 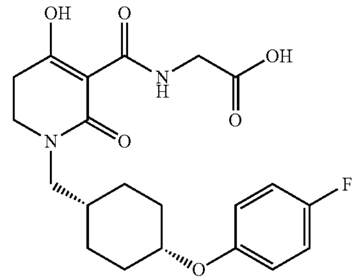 [SMILES: O=C(O)CNC(=O)C1=C(O)CCN(C[C@H]2CC[C@@H](Oc3ccc(F)cc3)CC2)C1=O] | $^1$H NMR (300 MHz, DMSO-$d_6$) δ ppm 1.22-1.62 (m, 6 H) 1.65-1.95 (m, 3 H) 2.25-2.49 (m, 2 H) 3.16-3.47 (m, 6 H) 4.44-4.57 (m, 1 H) 6.90-7.00 (m, 2 H) 7.03-7.15 (m, 2 H) 9.94-10.17 (m, 1 H). MS ESI/APCI Dual posi: 421[M + H]$^+$. | Na |

TABLE 21-63-continued

| Compound No. | Structure | Analytical Data | Salt information |
|---|---|---|---|
| Example 1-435 | 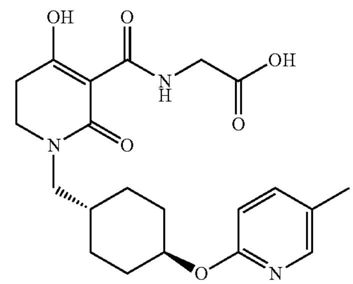 [SMILES: Cc1ccc(O[C@H]2CC[C@H](CN3CCC(O)=C(C(=O)NCC(=O)O)C3=O)CC2)nc1] | $^1$H NMR (300 MHz, DMSO-d$_6$) δ ppm 0.98-1.20 (m, 2 H) 1.23-1.43 (m, 2 H) 1.56-1.80 (m, 3 H) 1.98-2.13 (m, 2 H) 2.18 (s, 3 H) 2.45-2.67 (m, 2 H) 3.15-3.50 (m, 6 H) 4.74-4.96 (m, 1 H) 6.64 (d, J = 8.4 Hz, 1 H) 7.48 (dd, J = 8.4, 2.0 Hz, 1 H) 7.89-7.99 (m, 1 H) 9.86-10.31 (m, 1 H). MS ESI/APCI Dual posi: 418[M + H]$^+$. MS ESI/APCI Dual nega: 416[M − H]$^−$. | Na |
| Example 1-436 | 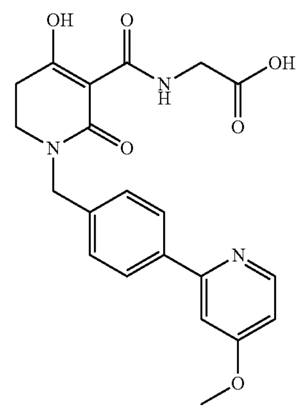 [SMILES: COc1ccnc(-c2ccc(CN3CCC(O)=C(C(=O)NCC(=O)O)C3=O)cc2)c1] | $^1$H NMR (300 MHz, DMSO-d$_6$) δ ppm 2.43-2.62 (m, 2 H) 3.31 (t, J = 6.9 Hz, 2 H) 3.53 (d, J = 4.4 Hz, 2 H) 3.90 (s, 3 H) 4.62 (s, 2 H) 6.89-7.01 (m, 1 H) 7.29-7.54 (m, 3 H) 7.99-8.14 (m, 2 H) 8.41-8.55 (m, 1 H) 10.06-10.24 (m, 1 H). MS ESI/APCI Dual posi: 412[M + H]$^+$. | Na |
| Example 1-437 | 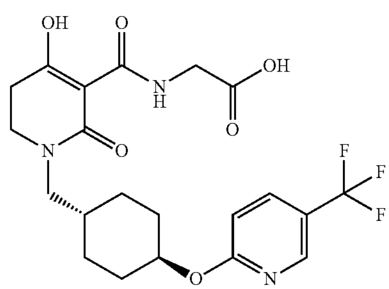 [SMILES: O=C(O)CNC(=O)C1=C(O)CCN(C[C@H]2CC[C@H](Oc3ccc(C(F)(F)F)cn3)CC2)C1=O] | $^1$H NMR (300 MHz, DMSO-d$_6$) δ ppm 1.00-1.24 (m, 2 H) 1.30-1.52 (m, 2 H) 1.58-1.85 (m, 3 H) 2.04-2.18 (m, 2 H) 2.44-2.60 (m, 2 H) 3.16-3.56 (m, 6 H) 4.91-5-12 (m, 1 H) 6.89- 7.00 (m, 1 H) 7.95-8.11 (m, 1 H) 8.50-8.67 (m, 1 H) 9.99-10.21 (m, 1 H). MS ESI/APCI Dual posi: 472[M + H]$^+$. | Na |
| Example 1-438 | 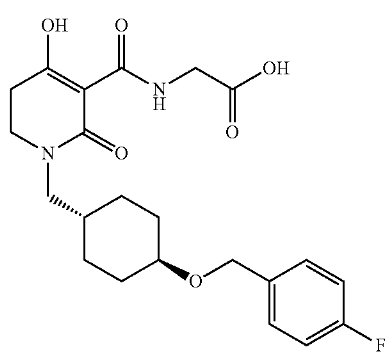 [SMILES: O=C(O)CNC(=O)C1=C(O)CCN(C[C@H]2CC[C@H](OCc3ccc(F)cc3)CC2)C1=O] | $^1$H NMR (300 MHz, DMSO-d$_6$) δ ppm 0.85-1.26 (m, 4 H) 1.49-1.76 (m, 3 H) 1.94-2.11 (m, 2 H) 2.42-2.60 (m, 2 H) 3.12-3.48 (m, 7 H) 4.47 (s, 2 H) 7.08-7.21 (m, 2 H) 7.29-7.41 (m, 2 H) 9.87-10.23 (m, 1 H). MS ESI/APCI Dual posi: 435[M + H]$^+$. MS ESI/APCI Dual nega: 433[M − H]$^−$. | Na |

TABLE 21-63-continued

| Compound No. | Structure | Analytical Data | Salt information |
|---|---|---|---|
| Example 1-439 | 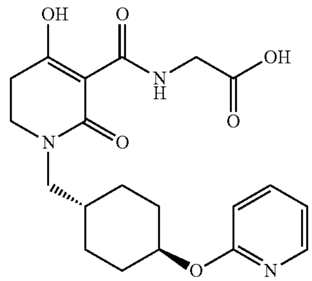 [SMILES: O=C(O)CNC(=O)C1=C(O)CCN(C[C@H]2CC[C@H](Oc3ccccn3)CC2)C1=O] | $^1$H NMR (300 MHz, DMSO-d$_6$) δ ppm 0.98-1.21 (m, 2 H) 1.26-1.45 (m, 2 H) 1.58-1.82 (m, 3 H) 2.03-2.17 (m, 2 H) 2.44-2.66 (m, 2 H) 3.14-3.55 (m, 6 H) 4.83-5.00 (m, 1 H) 6.67-6.79 (m, 1 H) 6.87-7.03 (m, 1 H) 7.59-7.73 (m, 1 H) 8.08-8.20 (m, 1 H) 9.88-10.33 (m, 1 H). MS ESI/APCI Dual posi: 404[M + H]$^+$. | Na |
| Example 1-440 | 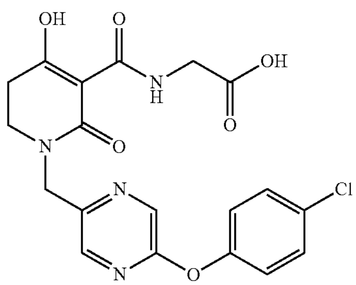 [SMILES: O=C(O)CNC(=O)C1=C(O)CCN(Cc2cnc(Oc3ccc(Cl)cc3)cn2)C1=O] | $^1$H NMR (300 MHz, DMSO-d$_6$) δ ppm 2.51-2.67 (m, 2 H) 3.41-3.59 (m, 4 H) 4.57-4.74 (m, 2 H) 7.18-7.34 (m, 2 H) 7.40-7.57 (m, 2 H) 8.14 (s, 1 H) 8.49 (s, 1 H) 10.00 (br. s., 1 H). MS ESI/APCI Dual posi: 433[M + H]$^+$. MS ESI/APCI Dual nega: 431[M − H]$^-$. | Na |

TABLE 21-64

| Compound No. | Structure | Analytical Data | Salt information |
|---|---|---|---|
| Example 1-441 | 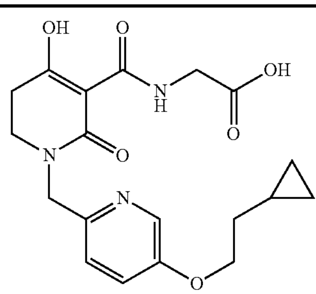 | $^1$H NMR (300 MHz, DMSO-d$_6$) δ ppm 0.06-0.16 (m, 2 H) 0.38-0.50 (m, 2 H) 0.72-0.90 (m, 1 H) 1.62 (q, J = 6.6 Hz, 2 H) 2.51-2.62 (m, 2 H) 3.36-3.43 (m, 2 H) 3.46 (d, J = 4.4 Hz, 2 H) 4.07 (t, J = 6.6 Hz, 2 H) 4.58 (s, 2 H) 7.22 (d, J = 8.5 Hz, 1 H) 7.36 (dd, J = 8.5, 3.0 Hz, 1 H) 8.21 (d, J = 3.0 Hz, 1 H) 9.90-10.10 (m, 1 H). MS ESI/APCI Dual posi: 390[M + H]$^+$. MS ESI/APCI Dual nega: 388[M − H]$^-$. | Na |
| Example 1-442 | 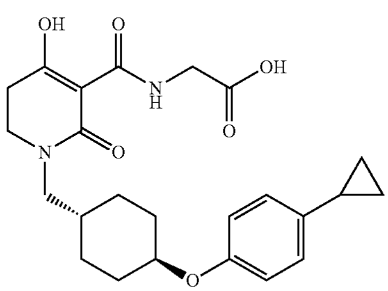 [SMILES: O=C(O)CNC(=O)C1=C(O)CCN(C[C@H]2CC[C@H](Oc3ccc(C4CC4)cc3)CC2)C1=O] | $^1$H NMR(300 MHz, DMSO-d$_6$) δ ppm 0.46-0.63 (m, 2 H) 0.78-0.93 (m, 2 H) 1.00-1.39 (m, 4 H) 1.55-1.76 (m, 3 H) 1.76-1.90 (m, 1 H) 1.96-2.12 (m, 1 H) 2.44-2.60 (m, 2 H) 3.15-3.49 (m, 6 H) 4.08-4.25 (m, 1 H) 6.74-6.85 (m, 2 H) 6.91-7.01 (m, 2 H) 9.89-10.29 (m, 1 H). MS ESI/APCI Dual posi: 443[M + H]$^+$. MS ESI/APCI Dual nega: 441[M − H]$^-$. | Na |
| Example 1-443 | 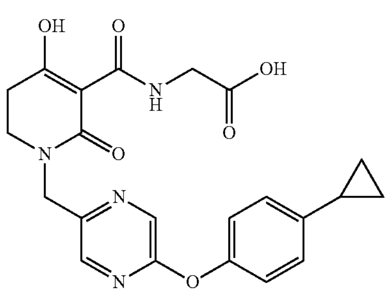 [SMILES: O=C(O)CNC(=O)C1=C(O)CCN(Cc2cnc(Oc3ccc(C4CC4)cc3)cn2)C1=O] | $^1$H NMR (300 MHz, DMSO-d$_6$) δ ppm 0.60-0.73 (m, 2 H) 0.88-1.01 (m, 2 H) 1.85-2.02 (m, 1 H) 2.50-2.66 (m, 2 H) 3.40-3.59 (m, 4 H) 4.64 (s, 2 H) 7.01-7.19 (m, 4 H) 8.12 (d, J = 1.4 Hz, 1 H) 8.44 (d, J = 1.4 Hz, 1 H) 9.84-10.18 (m, 1 H). MS ESI/APCI Dual posi: 439[M + H]$^+$. MS ESI/APCI Dual nega: 437[M − H]$^-$. | Na |

TABLE 21-64-continued

| Compound No. | Structure | Analytical Data | Salt information |
|---|---|---|---|
| Example 1-444 | 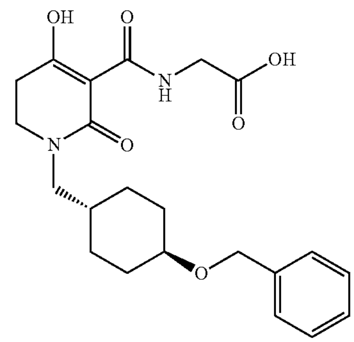 [SMILES: O=C(O)CNC(=O)C1=C(O)CCN(C[C@H]2CC[C@H](OCc3ccccc3)CC2)C1=O] | $^1$H NMR (300 MHz, DMSO-$d_6$) δ ppm 0.86-1.05 (m, 2 H) 1.07-1.26 (m, 2 H) 1.50- l.75 (m, 3 H) 1.97-2.11 (m, 2 H) 2.46-2.54 (m, 2 H) 3.13-3.48 (m, 7 H) 4.49 (s, 2 H) 7.21-7.39 (m, 5 H) 9.90-10.24 (m, 1 H).<br>MS ESI/APCI Dual posi: 417[M + H]$^+$.<br>MS ESI/APCI Dual nega: 415[M − H]$^-$. | Na |
| Example 1-445 | 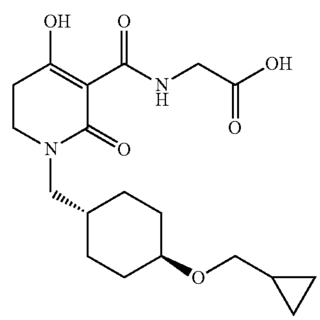 [SMILES: O=C(O)CNC(=O)C1=C(O)CCN(C[C@H]2CC[C@H](OCC3CC3)CC2)C1=O] | $^1$H NMR (300 MHz, DMSO-$d_6$) δ ppm 0.07-0.17 (m, 2 H) 0.37-0.48 (m, 2 H) 0.85-1.16 (m, 5 H) 1.46-1.72 (m, 3 H) 1.88-2.03 (m, 2 H) 2.43-2.59 (m, 2 H) 3.09-3.48 (m, 9 H) 9.84-10.21 (m, 1 H).<br>MS ESI/APCI Dual posi: 381[M + H]$^+$.<br>MS ESI/APCI Dual nega: 379[M − H]$^-$. | Na |
| Example 1-446 | 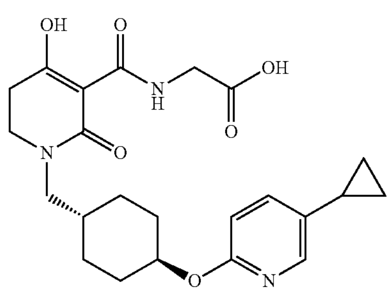 | $^1$H NMR (300 MHz, DMSO-$d_6$) δ ppm 0.51-0.59 (m, 2 H) 0.81-0.96 (m, 2 H) 0.99-1.43 (m, 4 H) 1.55-1.94 (m, 4 H) 1.98-2.15 (m, 2 H) 2.37-2.52 (m, 2 H) 3.15-3.56 (m, 6 H) 4.74-4.95 (m, 1 H) 6.67-6.72 (m, 1 H) 7.26-7.37 (m, 1 H) 7.91-8.00 (m, 1 H) 10.02-10.21 (m, 1 H).<br>MS ESI/APCI Dual posi: 444[M + H]$^+$. | Na |
| Example 1-447 | 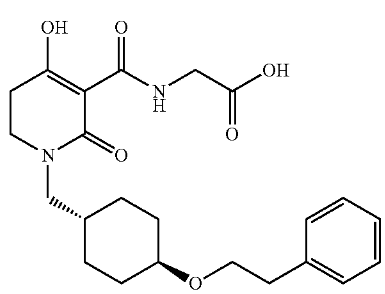 [SMILES: O=C(O)CNC(=O)C1=C(O)CCN(C[C@H]2CC[C@H](OCCc3ccccc3)CC2)C1=O] | $^1$H NMR (600 MHz, DMSO-$d_6$) δ ppm 0.86-0.99 (m, 2 H) 1.01-1.13 (m, 2 H) 1.50-1.69 (m, 3 H) 1.91-2.00 (m, 2 H) 2.45-2.59 (m, 2 H) 2.76 (t, J = 7.2 Hz, 2 H) 3.10-3.22 (m, 3 H) 3.25-3.47 (m, 4 H) 3.60 (t, J = 7.2 Hz, 2 H) 7.14-7.32 (m, 5 H) 9.89-10.26 (m, 1 H).<br>MS ESI/APCI Dual posi: 431[M + H]$^+$.<br>MS ESI/APCI Dual nega: 429[M − H]$^-$. | Na |

TABLE 21-65

| Compound No. | Structure | Analytical Data | Salt information |
|---|---|---|---|
| Example 1-448 | 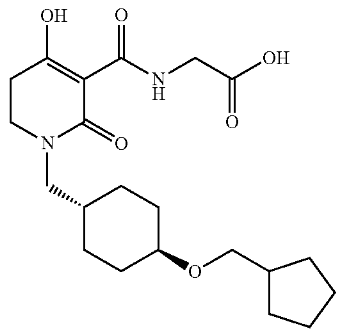 [SMILES: O=C(O)CNC(=O)C1=C(O)CCN(C[C@H]2CC[C@H](OCC3CCCC3)CC2)C1=O] | ¹H NMR (600 MHz, DMSO-d₆) δ ppm 0.87-1.00 (m, 2 H) 1.02-1.12 (m, 2 H) 1.13-1.22 (m, 2 H) 1.41-1.70 (m, 9 H) 1.90-2.06 (m, 3 H) 2.47-2.58 (m, 2 H) 3.07-3.21 (m, 3 H) 3.25 (d, J = 7.0 Hz, 2 H) 3.27-3.48 (m, 4 H) 9.91-10.25 (m, 1 H).<br>MS ESI/APCI Dual posi: 409[M + H]⁺.<br>MS ESI/APCI Dual nega: 407[M − H]⁻. | Na |
| Example 1-449 | 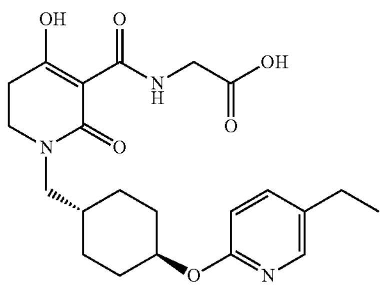 [SMILES: CCc1ccc(O[C@H]2CC[C@H](CN3CCC(O)=C(C(=O)NCC(=O)O)C3=O)CC2)nc1] | ¹H NMR (600 MHz, DMSO-d₆) δ ppm 1.04-1.18 (m, 5 H) 1.27-1.38 (m, 2 H) 1.61-1.77 (m, 3 H) 2.02-2.12 (m, 2 H) 2.45-2.60 (m, 4 H) 3.14-3.49 (m, 5 H) 4.81-4.90 (m, 1 H) 6.66 (d, J = 8.3 Hz, 1 H) 7.52 (dd, J = 8.3, 2.5 Hz, 1 H) 7.96 (d, J = 2.5 Hz, 1 H) 9.91-10.28 (m, 1 H).<br>MS ESI/APCI Dual posi: 432[M + H]⁺.<br>MS ESI/APCI Dual nega: 430[M − H]⁻. | Na |
| Example 1-450 | 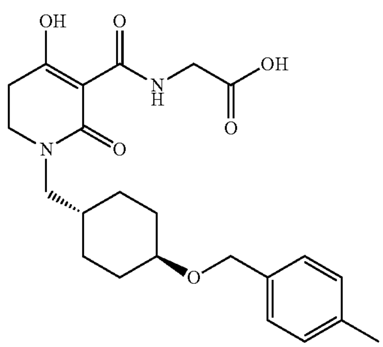 [SMILES: Cc1ccc(CO[C@H]2CC[C@H](CN3CCC(O)=C(C(=O)NCC(=O)O)C3=O)CC2)cc1] | ¹H NMR (600 MHz, DMSO-d₆) δ ppm 0.86-1.01 (m, 2 H) 1.08-1.21 (m, 2 H) 1.53-1.74 (m, 3 H) 1.97-2.06 (m, 2 H) 2.38 (s, 3 H) 2.45-2.59 (m, 2 H) 3.11-3.48 (m, 7 H) 4.44 (s, 2 H) 7.10-7.15 (m, 2 H) 7.17-7.22 (m, 2 H) 9.89-10.29 (m, 1 H).<br>MS ESI/APCI Dual posi: 431[M + H]⁺.<br>MS ESI/APCI Dual nega: 429[M − H]⁻. | Na |
| Example 1-451 | 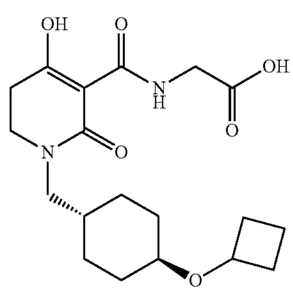 [SMILES: O=C(O)CNC(=O)C1=C(O)CCN(C[C@H]2CC[C@H](OC3CCC3)CC2)C1=O] | ¹H NMR (600 MHz, DMSO-d₆) δ ppm 0.87-0.99 (m, 2 H) 1.03-1.14 (m, 2 H) 1.33-1.47 (m, 1 H) 1.49-1.67 (m, 4 H) 1.74-1.84 (m, 2 H) 1.85-1.93 (m, 2 H) 2.06-2.17 (m, 2 H) 2.46-2.56 (m, 2 H) 3.09-3.21 (m, 3 H) 3.25-3.50 (m, 4 H) 3.93-4.02 (m, 1 H) 9.89-10.27 (m, 1 H).<br>MS ESI/APCI Dual posi: 381[M + H]⁺.<br>MS ESI/APCI Dual nega: 379[M − H]⁻. | Na |

TABLE 21-65-continued

| Compound No. | Structure | Analytical Data | Salt information |
|---|---|---|---|
| Example 1-452 | (structure) | $^1$H NMR (300 MHz, DMSO-d$_6$) δ ppm 1.07 (d, J = 6.7 Hz, 3 H) 2.15-2.30 (m, 2 H) 2.68-2.85 (m, 2 H) 3.10-3.26 (m, 2 H) 3.35-3.46 (m, 2 H) 4.74-4.91 (m, 1 H) 7.19-7.27 (m, 2 H) 7.28-7.36 (m, 2 H) 9.91-10.09 (m, 1 H).<br>MS ESI/APCI Dual posi: 367[M + H]$^+$.<br>MS ESI/APCI Dual nega: 365[M − H]$^-$. | Na |
| Example 1-453 | (structure) | $^1$H NMR (300 MHz, METHANOL-d$_4$) δ ppm 1.24-1.56 (m, 5 H) 1.70-1.91 (m, 5 H) 2.51-2.62 (m, 2 H) 2.76-2.91 (m, 1 H) 3.33-3.40 (m, 2 H) 3.89 (s, 2 H) 4.58 (s, 2 H) 6.92-7.01 (m, 1 H) 7.02-7.09 (m, 1 H) 7.18-7.28 (m, 1 H).<br>MS ESI/APCI Dual posi: 405[M + H]$^+$.<br>MS ESI/APCI Dual nega: 403[M − H]$^-$. | Na |
| Example 1-454 | (structure) | $^1$H NMR (300 MHz, DMSO-d$_6$) δ ppm 2.04-2.19 (m, 2 H) 2.20-2.32 (m, 2 H) 2.40-2.78 (m, 3 H) 3.04-3.67 (m, 6 H) 4.62-5.03 (m, 1 H) 4.84 (quin, J = 6.3 Hz, 1 H) 6.61-7.03 (m, 2 H) 7.16-7.46 (m, 2 H) 9.87-10.27 (m, 1 H).<br>MS ESI/APCI Dual posi: 409[M + H]$^+$.<br>MS ESI/APCI Dual nega: 407[M − H]$^-$. | Na |

TABLE 21-66

| Compound No. | Structure | Analytical Data | Salt information |
|---|---|---|---|
| Example 1-455 | (structure) | $^1$H NMR (300 MHz, DMSO-d$_6$) δ ppm 1.53-1.69 (m, 2 H) 1.95-2.11 (m, 1 H) 2.20-2.37 (m, 2 H) 2.44-2.58 (m, 2 H) 3.25-3.44 (m, 4 H) 3.46-3.56 (m, 2 H) 3.75-3.92 (m, 1 H) 4.34 (s, 2 H) 7.24-7.50 (m, 4 H).<br>MS ESI/APCI Dual posi: 423[M + H]$^+$.<br>MS ESI/APCI Dual nega: 421[M − H]$^-$. | Na |

TABLE 21-66-continued

| Compound No. | Structure | Analytical Data | Salt information |
|---|---|---|---|
| Example 1-456 | 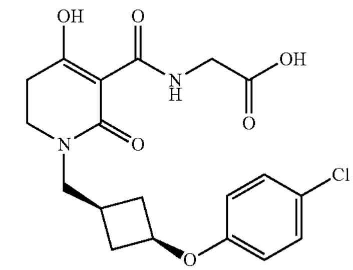 [SMILES: O=C(O)CNC(=O)C1=C(O)CCN(C[C@H]2C[C@@H](Oc3ccc(Cl)cc3)C2)C1=O] | $^1$H NMR (300 MHz, DMSO-d$_6$) δ ppm 1.66-1.88 (m, 2 H) 2.10-2.32 (m, 1 H) 2.47-2.65 (m, 2 H) 3.29-3.52 (m, 8 H) 4.43-4.65 (m, 1 H) 6.76-6.95 (m, 2 H) 7.23-7.37 (m, 2 H).<br>MS ESI/APCI Dual posi: 409[M + H]$^+$.<br>MS ESI/APCI Dual nega: 407[M − H]$^−$. | Na |
| Example 1-457 | 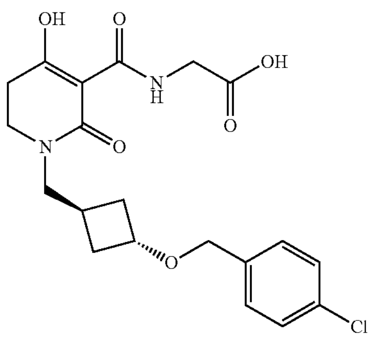 [SMILES: O=C(O)CNC(=O)C1=C(O)CCN(C[C@H]2C[C@H](OCc3ccc(Cl)cc3)C2)C1=O] | $^1$H NMR (300 MHz, DMSO-d$_6$) δ ppm 1.92-2.08 (m, 4 H) 2.44-2.59 (m, 3 H) 3.33-3.51 (m, 6 H) 4.10-4.25 (m, 1 H) 4.35 (s, 2 H) 7.22-7.54 (m, 4 H).<br>MS ESI/APCI Dual posi: 423[M + H]$^+$.<br>MS ESI/APCI Dual nega: 421[M − H]$^−$. | Na |
| Example 1-458 | 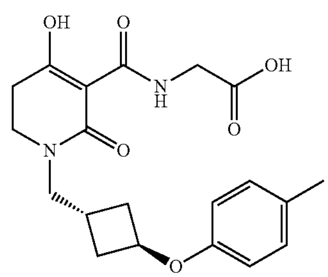 [SMILES: Cc1ccc(O[C@H]2C[C@H](CN3CCC(O)=C(C(=O)NCC(=O)O)C3=O)C2)cc1] | $^1$H NMR (600 MHz, DMSO-d$_6$) δ ppm 2.04-2.16 (m, 2 H) 2.18-2.29 (m, 5 H) 2.47-2.66 (m, 3 H) 3.34-3.57 (m, 6 H) 4.75-4.84 (m, 1 H) 6.65-6.74 (m, 2 H) 7.02-7.09 (m, 2 H).<br>MS ESI/APCI Dual posi: 389[M + H]$^+$.<br>MS ESI/APCI Dual nega: 387[M − H]$^−$. | Na |
| Example 1-459 | 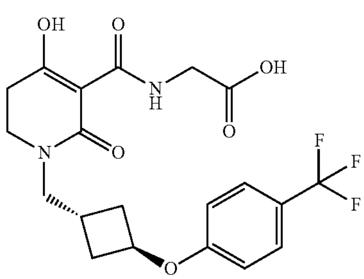 [SMILES: O=C(O)CNC(=O)C1=C(O)CCN(C[C@H]2C[C@H](Oc3ccc(C(F)(F)F)cc3)C2)C1=O] | $^1$H NMR (600 MHz, DMSO-d$_6$) δ ppm 2.10-2.23 (m, 2 H) 2.25-2.37 (m, 2 H) 2.48-2.71 (m, 2 H) 3.33-3.45 (m, 2 H) 3.47-3.61 (m, 4 H) 4.89-5.00 (m, 1 H) 7.00 (d, J = 8.7 Hz, 2 H) 7.63 (d, J = 8.7 Hz, 2 H).<br>MS ESI/APCI Dual posi: 443[M + H]$^+$.<br>MS ESI/APCI Dual nega: 441[M − H]$^−$. | Na |
| Example 1-460 | 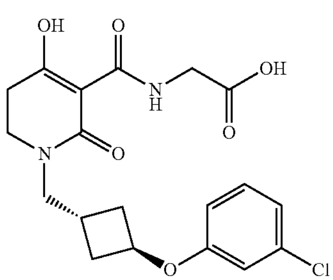 [SMILES: O=C(O)CNC(=O)C1=C(O)CCN(C[C@H]2C[C@H](Oc3cccc(Cl)c3)C2)C1=O] | $^1$H NMR (300 MHz, DMSO-d$_6$) δ ppm 2.06-2.20 (m, 2 H) 2.20-2.35 (m, 2 H) 2.40-2.72 (m, 3 H) 3.33-3.58 (m, 6 H) 4.83-4.97 (m, 1 H) 6.77-6.85 (m, 1 H) 6.86-6.92 (m, 1 H) 6.94-7.03 (m, 1 H) 7.24-7.35 (m, 1 H).<br>MS ESI/APCI Dual posi: 409[M + H]$^+$.<br>MS ESI/APCI Dual nega: 407[M − H]$^−$. | Na |

TABLE 21-66-continued

| Compound No. | Structure | Analytical Data | Salt information |
|---|---|---|---|
| Example 1-461 | (structure) | $^1$H NMR (300 MHz, DMSO-d$_6$) δ ppm 2.42-2.49 (m, 2 H) 3.19-3.27 (m, 2 H) 3.43 (d, J = 4.4 Hz, 2 H) 4.47 (s, 2 H) 6.75 (s, 2 H) 7.04-7.14 (m, 2 H) 7.18-7.27 (m, 2 H) 7.41-7.50 (m, 1 H) 7.57-7.56 (m, 1 H) 7.87-7.96 (m, 1 H) 8.05-8.12 (m, 1 H) 9.91-10.09 (m, 1 H).<br>MS ESI/APCI Dual posi: 452[M + H]$^+$, 474[M + Na]$^+$.<br>MS ESI/APCI Dual nega: 450[M − H]$^-$. | Na |

TABLE 21-67

| Compound No. | Structure | Analytical Data | Salt information |
|---|---|---|---|
| Example 1-462 | (structure) | $^1$H NMR (300 MHz, DMSO-d$_6$) δ ppm 2.10 (s, 3 H) 2.21-2.23 (m, 3 H) 2.48-2.54 (m, 2 H) 3.22-3.29 (m, 2 H) 3.44 (d, J = 4.4 Hz, 2 H) 4.49 (s, 2 H) 5.88 (s, 2 H) 5.90 (s, 1 H) 7.01-7.10 (m, 2 H) 7.17-7.26 (m, 2 H) 9.91-10.09 (m, 1 H).<br>MS ESI/APCI Dual posi: 429[M + H]$^+$.<br>MS ESI/APCI Dual nega: 427[M − H]$^-$. | Na |
| Example 1-463 | (structure) | $^1$H NMR (300 MHz, DMSO-d$_6$) δ ppm 2.41-2.48 (m, 2 H) 3.20-3.28 (m, 2 H) 3.46 (d, J = 4.4 Hz, 2 H) 4.18 (s, 3 H) 4.49 (s, 2 H) 5.57 (s, 2 H) 7.02-7.13 (m, 3 H) 7.18-7.28 (m, 3 H) 7.52-7.63 (m, 1 H) 7.77-7.87 (m, 1 H) 9.96-10.15 (m, 1 H).<br>MS ESI/APCI Dual posi: 465[M + H]$^+$.<br>MS ESI/APCI Dual nega: 463[M − H]$^-$. | Na |
| Example 1-464 | (structure) | $^1$H NMR (300 MHz, DMSO-d$_6$) δ ppm 0.86-1.30 (m, 4 H) 1.49-1.78 (m, 3 H) 1.97-2.13 (m, 2 H) 2.43-2.58 (m, 2 H) 3.13-3.48 (m, 7 H) 4.57 (s, 2 H) 7.40-7.52 (m, 1 H) 7.86-7.97 (m, 1 H) 8.48-8.61 (m, 1 H) 9.88-10.26 (m, 1 H).<br>MS ESI/APCI Dual posi: 452[M + H]$^+$.<br>MS ESI/APCI Dual nega: 460[M − H]$^-$. | Na |

Example 1-465

N-{[1-(4-Biphenylylmethyl)-6-(chloromethyl)-4-hydroxy-6-(hydroxymethyl)-2-oxo-1,2,5,6-tetrahydro-3-pyridinyl]carbonyl}glycine

[Formula 205]

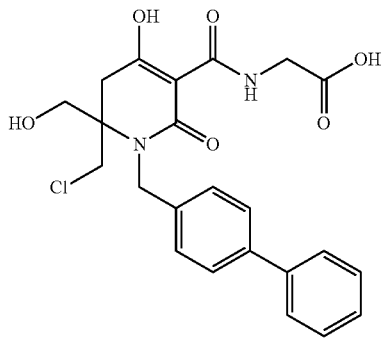

The compound (1.70 g) obtained in Example 1-20) was used and treated by the same technique as in Example 1-1(4) to give the titled compound as a pale brown amorphous mass (363 mg).

$^1$H NMR (300 MHz, DMSO-d$_6$) δ ppm 2.61-3.08 (m, 2 H) 3.45-3.66 (m, 2 H) 3.70-3.93 (m, 2 H) 3.96-4.10 (m, 2 H) 4.69-4.90 (m, 2 H) 5.46 (br. s., 1 H) 7.28-7.51 (m, 5 H) 7.54-7.70 (m, 4 H) 9.89-10.31 (m, 1 H) 12.73-13.04 (m, 1 H).

MS ESI/APCI Dual posi: 459 [M+H]$^+$.

Example 1-466

N-{[1-(3-Chloro-4-hydroxybenzyl)-4-hydroxy-2-oxo-1,2,5,6-tetrahydro-3-pyridinyl]carbonyl}glycine disodium

[Formula 206]

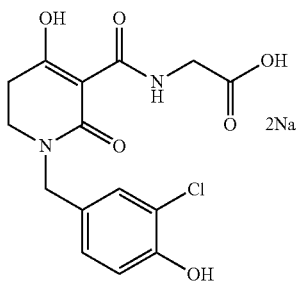

(1) Synthesis of 2-methyl-2-propanyl N-[(1-{3-chloro-4-[(3,5-dimethyl-1,2-oxazol-4-yl)methoxy]benzyl}-4-hydroxy-2-oxo-1,2,5,6-tetrahydro-3-pyridinyl)carbonyl]glycinate

[Formula 207]

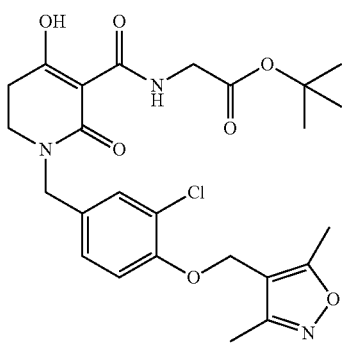

Instead of the compound obtained in Reference Example A-1, the compound (1.36 g) obtained in Reference Example A-301 was used and treated by the same techniques as in Example 1-1(1) to (3) to give 2-methyl-2-propanyl N-[(1-{3-chloro-4-[(3,5-dimethyl-1,2-oxazol-4-yl)methoxy]benzyl}-4-hydroxy-2-oxo-1,2,5,6-tetrahydro-3-pyridinyl)carbonyl]glycinate as a pale yellow gum (1.07 g).

$^1$H NMR (300 MHz, CHLOROFORM-d) δ ppm 1.49 (s, 9 H) 2.32 (s, 3 H) 2.41 (s, 3 H) 2.51-2.66 (m, 2 H) 3.27-3.39 (m, 2 H) 4.01-4.06 (m, 2 H) 4.54 (s, 2 H) 4.84-4.88 (m, 2 H) 6.90-6.97 (m, 1 H) 7.16 (dd, J=8.4, 2.2 Hz, 1 H) 7.29-7.34 (m, 1 H) 10.13-10.51 (m, 1 H).

MS ESI/APCI Dual posi: 520 [M+H]$^+$, 542 [M+Na]$^+$.
MS ESI/APCI Dual nega: 518 [M−H]$^−$.

(2) Synthesis of the Titled Compound

The compound (1.07 g) obtained in step (1) above was used and treated by the same techniques as in Example 1-1(4) and Example 1-3(3) to give the titled compound as a colorless solid (454 mg).

$^1$H NMR (300 MHz, DMSO-d$_6$) δ ppm 2.12-2.22 (m, 2 H) 3.02-3.10 (m, 2 H) 3.46 (d, J=4.2 Hz, 2 H) 4.37 (s, 2 H) 6.85 (d, J=8.4 Hz, 1 H) 6.96 (dd, J=8.4, 2.0 Hz, 1 H) 7.12 (d, J=2.0 Hz, 1 H) 10.04-10.16 (m, 1 H).

MS ESI/APCI Dual posi: 355 [M+H]$^+$.
MS ESI/APCI Dual nega: 353[M−H]$^−$.

Example 1-467

N-({1-[4-(4,4-difluoro-1-cyclohexen-1-yl)benzyl]-4-hydroxy-2-oxo-1,2,5,6-tetrahydro-3-pyridinyl}carbonyl)glycine sodium salt

[Formula 208]

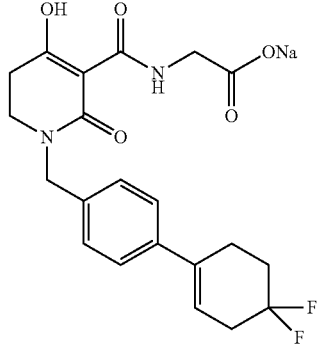

(1) Synthesis of 2-methyl-2-propanyl N-({1-[4-(4,4-difluoro-1-hydroxycyclohexyl)benzyl]-4-hydroxy-2-oxo-1,2,5,6-tetrahydro-3-pyridinyl}carbonyl)glycinate

[Formula 209]

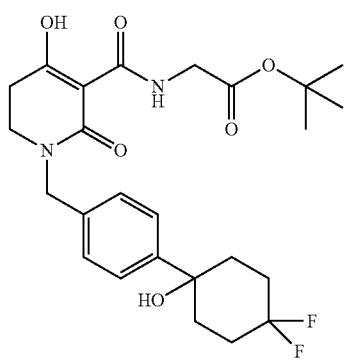

Instead of the compound obtained in Reference Example A-1, the compound (583 mg) obtained in Reference Example B-18 was used and treated by the same techniques as in Examples 1-1(1) to (3) to give 2-methyl-2-propanyl N-({1-[4-(4,4-difluoro-1-hydroxycyclohexyl)benzyl]-4-hydroxy-2-oxo-1,2,5,6-tetrahydro-3-pyridinyl}carbonyl)glycinate as a colorless solid (226 mg).

$^1$H NMR (300 MHz, CHLOROFORM-d) δ ppm 1.49 (s, 9 H) 1.82-1.94 (m, 2 H) 2.07-2.42 (m, 6 H) 2.62 (s, 2 H) 3.30-3.39 (m, 2 H) 4.01-4.06 (m, 2 H) 4.61 (s, 2 H) 7.25-7.30 (m, 2 H) 7.43-7.50 (m, 2 H).

MS ESI/APCI Dual posi: 517 [M+Na]$^+$.

MS ESI/APCI Dual nega: 493 [M–H]$^-$, 529 [M+Cl]$^-$.

(2) Synthesis of the Titled Compound

The compound (226 mg) obtained in step (1) above was used and treated by the same techniques as in Example 1-1(4) and Example 1-3(3) to give the titled compound as a colorless solid (129 mg).

$^1$H NMR (300 MHz, DMSO-d$_6$) δ ppm 2.04-2.30 (m, 4 H) 2.59-2.80 (m, 4 H) 3.24-3.32 (m, 2 H) 3.47 (d, J=4.4 Hz, 2 H) 4.55 (s, 2 H) 5.95-6.04 (m, 1 H) 7.25 (d, J=8.3 Hz, 2 H) 7.41 (d, J=8.3 Hz, 2 H).

MS ESI/APCI Dual posi: 421 [M+H]$^+$.

MS ESI/APCI Dual nega: 419 [M–H]$^-$.

Example 1-468

N-({1-[4-(Cyclopropylmethoxy)-3-methylbenzyl]-4-hydroxy-2-oxo-1,2,5,6-tetrahydro-3-pyridinyl}carbonyl)glycine sodium salt

[Formula 210]

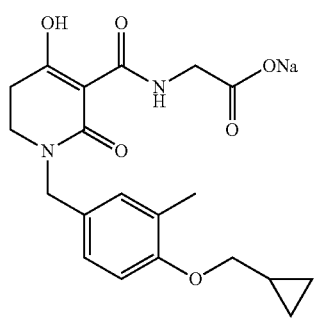

(1) Synthesis of ethyl N-({1-[4-(cyclopropylmethoxy)-3-methylbenzyl]-4-hydroxy-2-oxo-1,2,5,6-tetrahydro-3-pyridinyl}carbonyl)glycinate

[Formula 211]

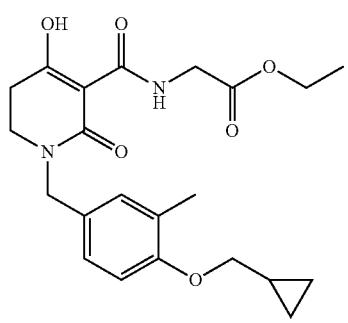

Instead of the compound obtained in Reference Example A-1 and glycine tert-butyl hydrochloride, the compound (2.10 g) obtained in Reference Example A-302 and glycine ethyl hydrochloride (956 mg) were respectively used and treated by the same techniques as in Example 1-1(1) to (3) to give ethyl N-({1-[4-(cyclopropylmethoxy)-3-methylbenzyl]-4-hydroxy-2-oxo-1,2,5,6-tetrahydro-3-pyridinyl}carbonyl)glycinate as a yellow oil (2.01 g).

$^1$H NMR (300 MHz, CHLOROFORM-d) δ ppm 0.29-0.40 (m, 2 H) 0.54-0.68 (m, 2 H) 1.19-1.37 (m, 4 H) 2.16-2.26 (m, 3 H) 2.44-2.64 (m, 2 H) 3.23-3.35 (m, 2 H) 3.75-3.85 (m, 2 H) 4.05-4.17 (m, 2 H) 4.24 (q, J=7.1 Hz, 2 H) 4.47-4.54 (m, 2 H) 6.67-6.79 (m, 1 H) 6.98-7.08 (m, 2 H) 10.11-10.60 (m, 1 H).

MS ESI/APCI Dual posi: 417 [M+H]$^+$.

(2) Synthesis of the Titled Compound

To a solution in ethanol (37.8 mL) of the compound (1.97 g) obtained in step (1) above, 0.5 mol/L sodium hydroxide in aqueous solution (18.9 mL) was added under cooling with ice and the mixture was brought to room temperature at which it was stirred for 15 minutes. After the reaction mixture was concentrated under reduced pressure, the resulting residue was purified by DIAION (registered trademark) HP20 column chromatography (with elution by methanol). The eluted fraction was concentrated under reduced pressure and to a solution of the resulting compound in water (2 mL), acetone (100 mL) was added and the mixture was stirred at room temperature for an hour. The precipitate was recovered by filtration to give the titled compound as a colorless solid (1.60 g).

$^1$H NMR (300 MHz, DMSO-d$_6$) δ ppm 0.25-0.38 (m, 2 H) 0.47-0.61 (m, 2 H) 1.11-1.28 (m, 1 H) 2.13 (s, 3 H) 2.34-2.50 (m, 2 H) 3.15-3.29 (m, 2 H) 3.51 (d, J=4.5 Hz, 2 H) 3.73-3.86 (m, 2 H) 4.44 (s, 2 H) 6.84 (d, J=9.0 Hz, 1 H) 7.00-7.06 (m, 2 H) 10.12 (br. s., 1 H).

MS ESI/APCI Dual posi: 389 [M+H]$^+$.

MS ESI/APCI Dual nega: 387[M–H]$^-$.

Example 2-1

N-({4-Hydroxy-1-[(4'-methylbiphenyl-4-yl)methyl]-2-oxo-1,2,5,6-tetrahydropyridin-3-yl}carbonyl)glycine

[Formula 212]

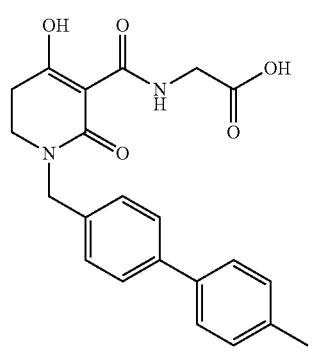

(1) Synthesis of tert-butyl N-{[4-hydroxy-1-(4-iodobenzyl)-2-oxo-1,2,5,6-tetrahydropyridin-3-yl]carbonyl}glycinate

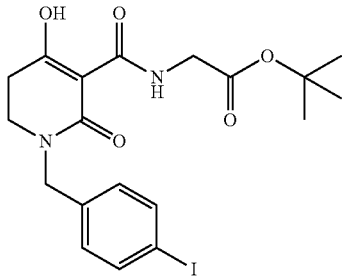

[Formula 213]

Instead of the compound obtained in Reference Example A-1, the compound (6.50 g) obtained in Reference Example A-4 was used and treated by the same techniques as in Example 1-1(1) to (3) to give tert-butyl N-{[4-hydroxy-1-(4-iodobenzyl)-2-oxo-1,2,5,6-tetrahydropyridin-3-yl]carbonyl}glycinate as a colorless solid (7.01 g).

$^1$H NMR (300 MHz, CHLOROFORM-d) δ ppm 1.48 (s, 9 H) 2.49-2.65 (m, 2 H) 3.24-3.42 (m, 2 H) 3.97-4.08 (m, 2 H) 4.56 (s, 2 H) 6.98-7.08 (m, 2 H) 7.57-7.75 (m, 2 H) 10.13-10.51 (m, 1 H).

MS ESI/APCI Dual posi: 487 [M+H]$^+$.
MS ESI/APCI Dual nega: 485 [M−H]$^+$.

(2) Synthesis of tert-butyl N-({4-hydroxy-1-[(4'-methylbiphenyl-4-yl)methyl]-2-oxo-1,2,5,6-tetrahydropyridin-3-yl}carbonyl)glycinate

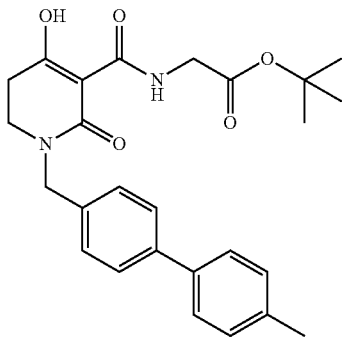

[Formula 214]

A mixture of the compound (300 mg) obtained in step (1) above, 4-methylphenylboronic acid (168 mg), palladium(II) acetate (6.93 mg), tri(2-methylphenyl)phosphine (18.8 mg), tripotassium phosphate (393 mg), ethanol (8.00 mL) and toluene (4.00 mL) was stirred at 90° C. for an hour. After cooling the reaction mixture to room temperature, a saturated aqueous solution of ammonium chloride was added and the resulting mixture was concentrated under reduced pressure. Water was added and three extractions were conducted with chloroform. The combined organic layers were passed through a phase separator and thereafter concentrated under reduced pressure. The resulting residue was purified by silica gel column chromatography (n-hexane:ethyl acetate=100:0-50:50, then chloroform:methanol=100:0-90:10) to give tert-butyl N-({4-hydroxy-1-[(4'-methylbiphenyl-4-yl)methyl]-2-oxo-1,2,5,6-tetrahydropyridin-3-yl}carbonyl)glycinate as a pale yellow solid (485 mg).

$^1$H NMR (600 MHz, CHLOROFORM-d) δ ppm 1.49 (s, 9 H) 2.39 (s, 3 H) 2.53-2.65 (m, 2 H) 3.37 (m, 2 H) 4.00-4.08 (m, 2 H) 4.66 (s, 2 H) 7.25 (d, J=7.8 Hz, 2 H) 7.32 (d, J=7.8 Hz, 2 H) 7.44-7.50 (m, 2 H) 7.51-7.58 (m, 2 H) 10.22-10.49 (m, 1 H).

MS ESI/APCI Dual posi: 473 [M+Na]$^+$.

(3) Synthesis of the Titled Compound

The compound (147 mg) obtained in step (2) above was used and treated by the same technique as in Example 1-1(4) to give the titled compound as a colorless solid (111 mg).

$^1$H NMR (600 MHz, DMSO-d$_6$) δ ppm 2.33 (s, 3 H) 2.46-2.72 (m, 2 H) 3.36-3.46 (m, 2 H) 3.98-4.07 (m, 2 H) 4.57-4.67 (m, 2 H) 7.23-7.29 (m, 2 H) 7.32-7.40 (m, 2 H) 7.50-7.57 (m, 2 H) 7.58-7.65 (m, 2 H) 10.01-10.25 (m, 1 H).

MS ESI/APCI Dual posi: 395 [M+1]$^+$, 417 [M+Na]$^+$.
MS ESI/APCI Dual nega: 393 [M−1]$^−$.

Example 2-2

N-({4-Hydroxy-1-[4-(3-methoxy-4-pyridinyl)benzyl]-2-oxo-1,2,5,6-tetrahydro-3-pyridinyl}carbonyl)glycine sodium salt

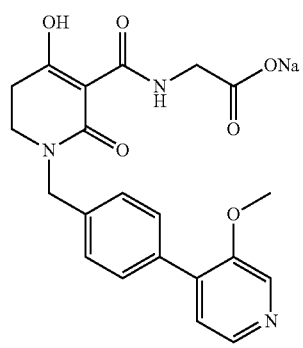

[Formula 215]

(1) Synthesis of 2-methyl-2-propanyl N-({4-hydroxy-1-[4-(3-methoxy-4-pyridinyl)benzyl]-2-oxo-1,2,5,6-tetrahydro-3-pyridinyl}carbonyl)glycinate

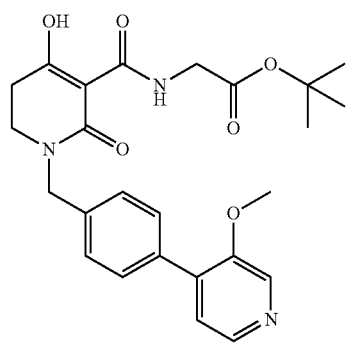

[Formula 216]

A mixture of the compound (1.50 g) obtained in Example 2-1(1), 3-methoxy-4-pyridineboronic acid pinacol ester (870 mg), [1,1'-bis(diphenylphosphino)ferrocene]palladium(II) dichloride dichloromethane complex (1:1) (126 mg), 2 mol/L sodium carbonate in aqueous solution (3.4 mL) and N,N-dimethylformamide (12.3 mL) was stirred at 120° C. for 20 minutes under irradiation with microwaves. After cooling the reaction mixture to room temperature, a saturated aqueous solution of sodium hydrogencarbonate and ethyl acetate were added and the precipitate was recovered by filtration through Celite (registered trademark). Extraction was conducted with ethyl acetate and the combined organic layers were concentrated under reduced pressure. The resulting residue was purified by silica gel column chromatography (n-hexane:ethyl acetate=20:80-0:100, then chloroform:methanol=100:0-80:20) to give 2-methyl-2-propanyl N-({4-hydroxy-1-[4-(3-methoxy-4-pyridinyl)benzyl]-2-oxo-1,2,5,6-tetrahydro-3-pyridinyl}carbonyl)glycinate as a yellow amorphous mass (1.24 g).

$^1$H NMR (300 MHz, CHLOROFORM-d) δ ppm 1.49 (s, 9 H) 2.52-2.69 (m, 2 H) 3.32-3.45 (m, 2 H) 3.92 (s, 3 H) 4.00-4.07 (m, 2 H) 4.67 (s, 2 H) 7.22-7.26 (m, 2 H) 7.32-7.38 (m, 2 H) 7.50-7.60 (m, 2 H) 8.28-8.35 (m, 1 H) 10.18-10.50 (m, 1 H).

MS ESI/APCI Dual posi: 468 [M+H]$^+$.

(2) Synthesis of the Titled Compound

The compound (1.24 g) obtained in step (1) above was used and treated by the same techniques as in Example 1-2(2) and Example 1-3(3) to give the titled compound as a colorless solid (730 mg).

$^1$H NMR (300 MHz, DMSO-d$_6$) δ ppm 2.46-2.61 (m, 2 H) 3.35 (t, J=7.1 Hz, 2 H) 3.56 (d, J=4.5 Hz, 2 H) 3.89 (s, 3 H) 4.61 (s, 2 H) 7.29-7.44 (m, 3 H) 7.50-7.60 (m, 2 H) 8.22-8.33 (m, 1 H) 8.45 (s, 1 H) 10.08-10.21 (m, 1 H).

MS ESI/APCI Dual posi: 412[M+H]$^+$.

Example 2-3

N-({4-Hydroxy-1-[4-(2-methoxy-3-pyridinyl)benzyl]-2-oxo-1,2,5,6-tetrahydro-3-pyridinyl}carbonyl)glycine sodium salt

[Formula 217]

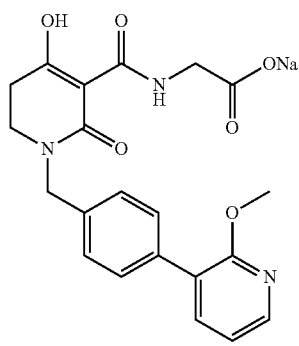

(1) Synthesis of 2-methyl-2-propanyl N-({4-hydroxy-1-[4-(2-methoxy-3-pyridinyl)benzyl]-2-oxo-1,2,5,6-tetrahydro-3-pyridinyl}carbonyl)glycinate

[Formula 218]

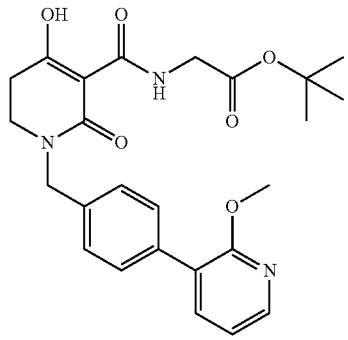

A mixture of the compound (1.00 g) obtained in Example 2-1(1), 2-methoxypyridine-3-boronic acid (426 mg), palladium(II) acetate (25.0 mg), tripotassium phosphate (987 mg) and ethylene glycol (12 mL) was stirred in a sealed tube at 80° C. for 4 hours. After cooling the reaction mixture to room temperature, water and ethyl acetate were added and the precipitate was recovered by filtration through Celite (registered trademark). Extraction was conducted with ethyl acetate and the combined organic layers were concentrated under reduced pressure. The resulting residue was purified by silica gel column chromatography (n-hexane:ethyl acetate=100:0-20:80) to give 2-methyl-2-propanyl N-({4-hydroxy-1-[4-(2-methoxy-3-pyridinyl)benzyl]-2-oxo-1,2,5,6-tetrahydro-3-pyridinyl}carbonyl)glycinate as a yellow oil (1.10 g).

$^1$H NMR (300 MHz, CHLOROFORM-d) δ ppm 1.49 (s, 9 H) 2.52-2.68 (m, 2 H) 3.33-3.42 (m, 2 H) 3.97 (s, 3 H) 4.00-4.08 (m, 2 H) 4.66 (s, 2 H) 6.93-7.01 (m, 1 H) 7.29-7.36 (m, 2 H) 7.46-7.65 (m, 3 H) 8.09-8.21 (m, 1 H) 10.15-10.53 (m, 1 H).

MS ESI/APCI Dual posi: 490 [M+Na]$^+$
MS ESI/APCI Dual nega: 466[M–H]$^-$.

(2) Synthesis of the Titled Compound

The compound (1.10 g) obtained in step (1) above was used and treated by the same techniques as in Example 1-2(2) and Example 1-3(3) to give the titled compound as a colorless solid (461 mg).

$^1$H NMR (300 MHz, DMSO-d$_6$) δ ppm 2.41-2.61 (m, 2 H) 3.40-3.49 (m, 2 H) 3.87 (s, 3 H) 4.60 (s, 2 H) 7.05-7.12 (m, 1 H) 7.29-7.39 (m, 2 H) 7.48-7.57 (m, 2 H) 7.70-7.77 (m, 1 H) 8.13-8.20 (m, 1 H).

MS ESI/APCI Dual posi: 412 [M+H]$^+$.
MS ESI/APCI Dual nega: 410[M–H]$^-$.

Example 2-4

N-({4-Hydroxy-1-[4-(6-methyl-3-pyridinyl)benzyl]-2-oxo-1,2,5,6-tetrahydro-3-pyridinyl}carbonyl)glycine sodium salt

[Formula 219]

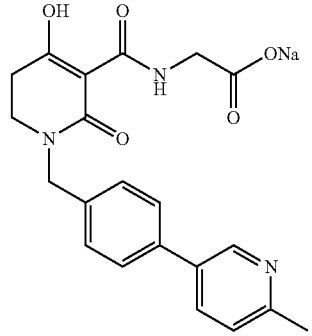

(1) Synthesis of 2-methyl-2-propanyl N-({4-hydroxy-1-[4-(6-methyl-3-pyridinyl)benzyl]-2-oxo-1,2,5,6-tetrahydro-3-pyridinyl}carbonyl)glycinate

[Formula 220]

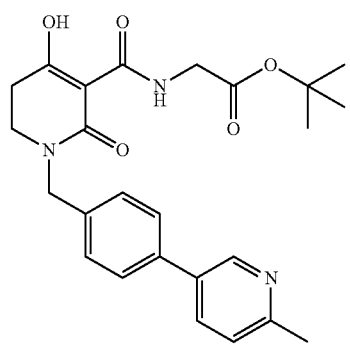

A mixture of the compound (1.00 g) obtained in Example 2-1(1), 2-picoline-5-boronic acid pinacol ester (541 mg), tetrakis(triphenylphosphine)palladium(0) (238 mg), potassium carbonate (569 mg), toluene (10 mL), ethanol (2 mL) and water (2 mL) was stirred at 80° C. for 4 hours. After cooling the reaction mixture to room temperature, the precipitate was removed by passage through Celite (registered trademark) and the filtrate was concentrated under reduced pressure. The resulting residue was purified by silica gel column chromatography (n-hexane:ethyl acetate=100:0-30:70) to give 2-methyl-2-propanyl N-({4-hydroxy-1-[4-(6-methyl-3-pyridinyl)benzyl]-2-oxo-1,2,5,6-tetrahydro-3-pyridinyl}carbonyl)glycinate (560 mg).

$^1$H NMR (300 MHz, CHLOROFORM-d) δ ppm 1.49 (s, 9 H) 2.51-2.69 (m, 5 H) 3.31-3.44 (m, 2 H) 4.00-4.07 (m, 2 H) 4.67 (s, 2 H) 7.17-7.26 (m, 1 H) 7.37 (d, J=8.2 Hz, 2 H) 7.48-7.59 (m, 2 H) 7.72-7.81 (m, 1 H) 8.67-8.77 (m, 1 H) 10.15-10.53 (m, 1 H).

MS ESI/APCI Dual posi: 452 [M+H]$^+$, 474 [M+H]$^+$.

MS ESI/APCI Dual nega: 450 [M−H]$^-$.

(2) Synthesis of the titled compound

The compound (560 mg) obtained in step (1) above was used and treated by the same techniques as in Example 1-2(2) and Example 1-3(3) to give the titled compound as a colorless solid (254 mg).

$^1$H NMR (300 MHz, DMSO-d$_6$) δ ppm 2.36-2.55 (m, 5 H) 3.21-3.34 (m, 2 H) 3.50 (d, J=4.5 Hz, 2 H) 4.60 (s, 2 H) 7.26-7.45 (m, 3 H) 7.59-7.71 (m, 2 H) 7.89-7.99 (m, 1 H) 8.73 (d, J=2.0 Hz, 1 H) 10.01-10.22 (m, 1 H).

MS ESI/APCI Dual posi: 396 [M+H]$^+$.

MS ESI/APCI Dual nega: 394[M−H]$^-$.

Example 2-5

N-({4-Hydroxy-1-[4-(5-methyl-2-pyridinyl)benzyl]-2-oxo-1,2,5,6-tetrahydro-3-pyridinyl}carbonyl)glycine sodium salt

[Formula 221]

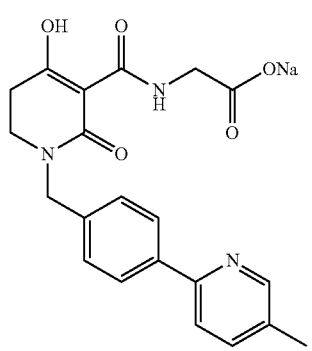

(1) Synthesis of 2-methyl-2-propanyl N-({4-hydroxy-1-[4-(5-methyl-2-pyridinyl)benzyl]-2-oxo-1,2,5,6-tetrahydro-3-pyridinyl}carbonyl)glycinate

[Formula 222]

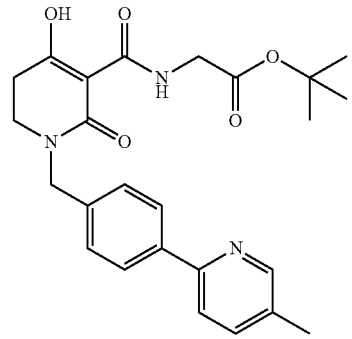

A mixture of the compound (2.00 g) obtained in Example 2-1(1), 5-methylpyridine-2-boronic acid N-phenyldiethanolamine ester (2.32 g), potassium carbonate (1.14 g), copper(I) iodide (313 mg), tri(2-methylphenyl)phosphine (250 mg), palladium(II) acetate (46 mg) and tetrahydrofuran (28.8 mL) was stirred at 95° C. for 4 hours. After cooling the reaction mixture to room temperature, ethyl acetate was added and the precipitate was removed by passage through Celite (registered trademark). The filtrate was concentrated under reduced pressure and the resulting residue was purified by silica gel column chromatography (n-hexane:ethyl acetate=80:20-0:100) to give 2-methyl-2-propanyl N-({4-hydroxy-1-[4-(5-methyl-2-pyridinyl)benzyl]-2-oxo-1,2,5,6-tetrahydro-3-pyridinyl}carbonyl)glycinate as a colorless amorphous mass (1.00 g).

$^1$H NMR (300 MHz, CHLOROFORM-d) δ ppm 1.49 (s, 9 H) 2.37 (s, 3 H) 2.47-2.68 (m, 2 H) 3.25-3.40 (m, 2 H) 4.00-4.07 (m, 2 H) 4.67 (s, 2 H) 7.31-7.42 (m, 2 H) 7.52-7.66 (m, 2 H) 7.87-7.99 (m, 2 H) 8.45-8.59 (m, 1 H) 10.14-10.53 (m, 1 H).

MS ESI/APCI Dual posi: 452 [M+H]$^+$.

(2) Synthesis of the Titled Compound

The compound (1.00 g) obtained in step (1) above was used and treated by the same techniques as in Example 1-2(2) and Example 1-3(3) to give the titled compound as a colorless solid (505 mg).

$^1$H NMR (600 MHz, DMSO-d$_6$) δ ppm 2.29 (s, 3 H) 2.43-2.59 (m, 2 H) 3.22-3.56 (m, 4 H) 4.58 (s, 2 H) 7.28-7.39 (m, 2 H) 7.60-7.69 (m, 1 H) 7.75-7.85 (m, 1 H) 7.94-8.04 (m, 2 H) 8.45 (s, 1 H) 9.87-10.31 (m, 1 H).

MS ESI/APCI Dual posi: 396 [M+H]$^+$.

In the following Examples 2-6 to 2-54, the compound obtained in Reference Examples A-4, A-5, A-303, A-304 or A-305 was used as the starting material which, together with a commercial grade of the corresponding boronic acids or boronic acid esters, was treated by the methods described in Example 2-1(1) and (2) or in step (1) of each of Examples 2-2 to 2-5 or modifications thereof, and the compounds thus obtained were further treated by the method described in Example 1-1(4), 1-2(2) or 1-3(3) or modifications thereof to synthesize the intended compounds. The structures of the synthesized compounds and their NMR and MS data are shown in Tables 22-1 to 22-8. The numerals cited in the column "Example" of each table indicate which of the above-noted Examples 2-1 to 2-5 was repeated or modified to synthesize the compound of interest.

TABLE 22-1

| Compound No. | Structure | Analytical Data | Salt information | Example |
|---|---|---|---|---|
| Example 2-6 | 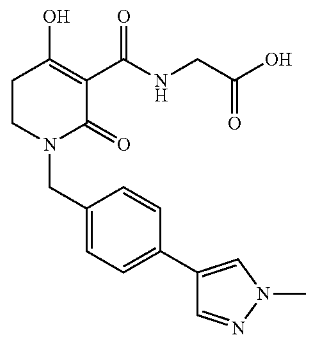 [SMILES: Cn1cc(-c2ccc(CN3CCC(O)=C(C(=O)NCC(=O)O)C3=O)cc2)cn1] | ¹H NMR (300 MHz, DMSO-d₆) δ ppm 2.54-2.77 (m, 2 H) 3.38 (t, J = 7.1 Hz, 2 H) 3.86 (s, 3 H) 4.03 (d, J = 5.6 Hz, 2 H) 4.56 (s, 2 H) 7.27 (d, J = 8.1 Hz, 2 H) 7.53 (d, J = 8.1 Hz, 2 H) 7.83 (s, 1 H) 8.11 (s, 1 H) 10.07 (br. s., 1 H). MS ESI/APCI Dual posi: 385[M + H]⁺, 407[M + Na]⁺. MS ESI/APCI Dual nega: 383[M − H]⁻. | | 2-1 |
| Example 2-7 | 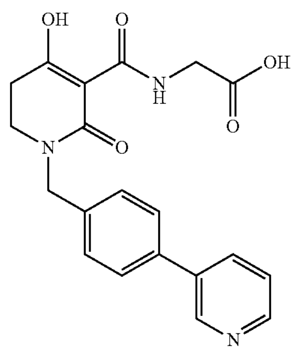 [SMILES: O=C(O)CNC(=O)C1=C(O)CCN(Cc2ccc(-c3cccnc3)cc2)C1=O] | ¹H NMR (300 MHz, DMSO-d₆) δ ppm 2.65-2.76 (m, 2 H) 3.35-3.53 (m, 2 H) 3.98-4.10 (m, 2 H) 4.60-4.75 (m, 2 H) 7.40-7.56 (m, 2 H) 7.76-7.87 (m, 2 H) 7.89-7.97 (m, 1 H) 8.58-8.69 (m, 1 H) 8.75-8.83 (m, 1 H) 9.08-9.18 (m, 1 H) 9.94-10.31 (m, 1 H). MS ESI/APCI Dual posi: 382[M + H]⁺. MS ESI/APCI Dual nega: 380[M − H]⁻. | HCl | 2-1 |
| Example 2-8 | 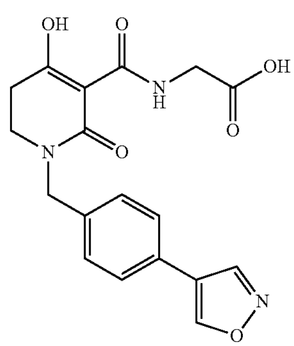 [SMILES: O=C(O)CNC(=O)C1=C(O)CCN(Cc2ccc(-c3cnoc3)cc2)C1=O] | ¹H NMR (300 MHz, CHLOROFORM-d) δ ppm 2.54-2.69 (m, 2 H) 3.37 (t, J = 7.1 Hz, 2 H) 4.16-4.24 (m, 2 H) 4.59-4.68 (m, 2 H) 7.29-7.37 (m, 2 H) 7.41-7.50 (m, 2 H) 8.52-8.57 (m, 1 H) 8.65-8.70 (m, 1 H) 10.15-10.47 (m, 1 H). MS ESI/APCI Dual posi: 372[M + H]⁺, 394[M + Na]⁺. MS ESI/APCI Dual nega: 370[M − H]⁻. | | 2-1 |
| Example 2-9 | 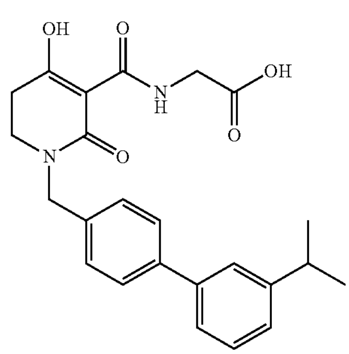 [SMILES: CC(C)c1cccc(-c2ccc(CN3CCC(O)=C(C(=O)NCC(=O)O)C3=O)cc2)c1] | ¹H NMR (600 MHz, DMSO-d₆) δ ppm 1.20-1.29 (m, 6 H) 2.47-2.73 (m, 2 H) 2.90-3.01 (m, 1 H) 3.37-3.47 (m, 2 H) 4.00-4.09 (m, 2 H) 4.57-4.69 (m, 2 H) 7.19-7.27 (m, 1 H) 7.31-7.51 (m, 5 H) 7.58-7.67 (m, 2 H) 10.02-10.27 (m, 1 H) 12.79-12.90 (m, 1 H). MS ESI/APCI Dual posi: 423[M + H]⁺, 445[M + Na]⁺. MS ESI/APCI Dual nega: 421[M − H]⁻. | | 2-1 |

TABLE 22-1-continued

| Compound No. | Structure | Analytical Data | Salt information | Example |
|---|---|---|---|---|
| Example 2-10 | 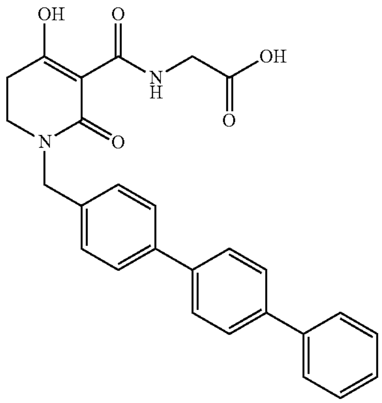 [SMILES: O=C(O)CNC(=O)C1=C(O)CCN(Cc2ccc(-c3ccc(-c4ccccc4)cc3)cc2)C1=O] | $^1$H NMR (600 MHz, DMSO-d$_6$) δ ppm 2.65-2.74 (m, 2 H) 3.39-3.49 (m, 2 H) 4.00-4.10 (m, 2 H) 4.58-4.71 (m, 2 H) 7.35-7.43 (m, 3 H) 7.46-7.51 (m, 2 H) 7.68-7.74 (m, 4 H) 7.76 (s, 4 H) 9.98-10.33 (m, 1 H). MS ESI/APCI Dual posi: 457[M + H]$^+$, 479[M + Na]$^+$. MS ESI/APCI Dual nega: 455[M − H]$^-$. | | 2-1 |
| Example 2-11 | 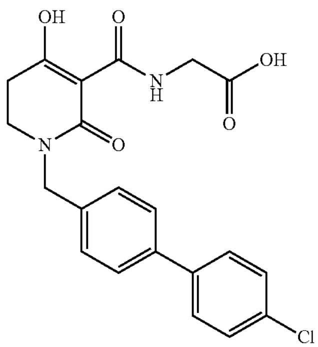 | $^1$H NMR (300 MHz, CHLOROFORM-d) δ ppm 2.54-2.69 (m, 2 H) 3.33-3.44 (m, 2 H) 4.15-4.23 (m, 2 H) 4.61-4.69 (m, 2 H) 7.29-7.44 (m, 4 H) 7.45-7.57 (m, 4 H) 10.15-10.46 (m, 1 H). MS ESI/APCI Dual posi: 415[M + H]$^+$, 437[M + Na]$^+$. MS ESI/APCI Dual nega: 413[M − H]$^-$. | | 2-1 |
| Example 2-12 | 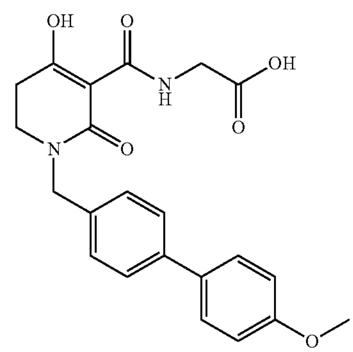 [SMILES: COc1ccc(-c2ccc(CN3CCC(O)=C(C(=O)NCC(=O)O)C3=O)cc2)cc1] | $^1$H NMR (300 MHz, DMSO-d$_6$) δ ppm 2.46-2.76 (m, 2 H) 3.30-3.51 (m, 2 H) 3.74-3.83 (m, 3 H) 3.99-4.08 (m, 2 H) 4.53-4.69 (m, 2 H) 6.96-7.07 (m, 2 H) 7.29-7.40 (m, 2 H) 7.52-7.66 (m, 4 H) 10.00-10.29 (m, 1 H) 12.62-13.06 (m, 1 H). MS ESI/APCI Dual posi: 411[M + H]$^+$, 433[M + Na]$^+$. MS ESI/APCI Dual nega: 409[M − H]$^-$. | | 2-1 |

TABLE 22-2

| Compound No. | Structure | Analytical Data | Salt information | Example |
|---|---|---|---|---|
| Example 2-13 | 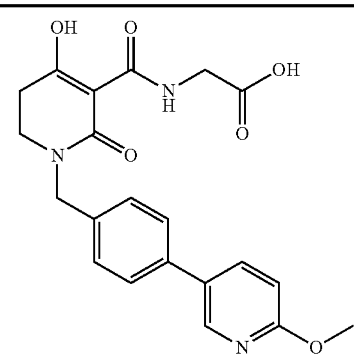 | $^1$H NMR (600 MHz, DMSO-d$_6$) δ ppm 2.47-2.74 (m, 2 H) 3.38-3.45 (m, 2 H) 3.90 (s, 3 H) 4.01-4.06 (m, 2 H) 4.59-4.65 (m, 2 H) 6.90-6.94 (m, 1 H) 7.36-7.40 (m, 2 H) 7.62-7.66 (m, 2 H) 7.99-8.03 (m, 1 H) 8.46-8.49 (m, 1 H) 9.95-10.29 (m, 1 H). MS ESI/APCI Dual posi: 412[M + H]$^+$, 434[M + Na]$^+$. MS ESI/APCI Dual nega: 410[M − H]$^-$. | HCl | 2-1 |

TABLE 22-2-continued

| Compound No. | Structure | Analytical Data | Salt information | Example |
|---|---|---|---|---|
| Example 2-14 | 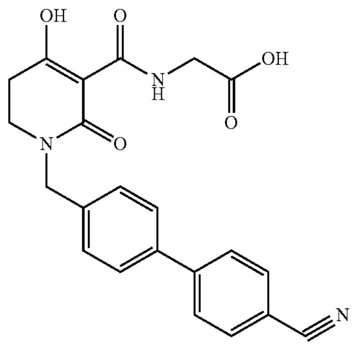 [SMILES: N#Cc1ccc(-c2ccc(CN3CCC(O)=C(C(=O)NCC(=O)O)C3=O)cc2)cc1] | $^1$H NMR (300 MHz, DMSO-d$_6$) δ ppm 2.47-2.76 (m, 2 H) 3.37-3.75 (m, 2 H) 3.98-4.09 (m, 2 H) 4.58-4.72 (m, 2 H) 7.43 (d, J = 8.2 Hz, 2 H) 7.74 (d, J = 8.2 Hz, 2 H) 7.83-7.98 (m, 4 H) 9.96-10.29 (m, 1 H).<br>MS ESI posi: 406[M + H]$^+$.<br>MS ESI nega: 404[M − H]$^-$. | | 2-1 |
| Example 2-15 | 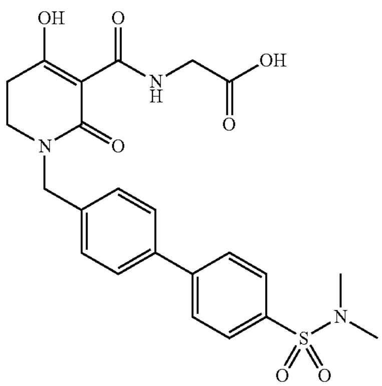 [SMILES: CN(C)S(=O)(=O)c1ccc(-c2ccc(CN3CCC(O)=C(C(=O)NCC(=O)O)C3=O)cc2)cc1] | $^1$H NMR (300 MHz, DMSO-d$_6$) δ ppm 2.44-2.76 (m, 8 H) 3.34-3.49 (m, 2 H) 3.95-4.09 (m, 2 H) 4.58-4.72 (m, 2 H) 7.36-7.48 (m, 2 H) 7.68-7.85 (m, 4 H) 7.87-7.97 (m, 2 H) 9.98-10.27 (m, 1 H).<br>MS ESI posi: 488[M + H]$^+$.<br>MS ESI nega: 486[M − H]$^-$. | | 2-1 |
| Example 2-16 | 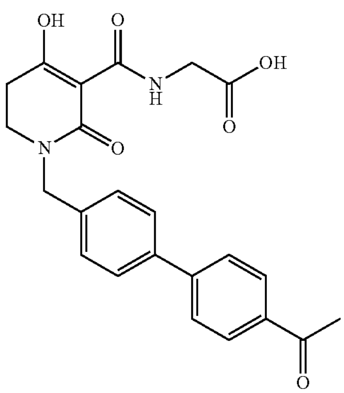 [SMILES: CC(=O)c1ccc(-c2ccc(CN3CCC(O)=C(C(=O)NCC(=O)O)C3=O)cc2)cc1] | $^1$H NMR (300 MHz, DMSO-d$_6$) δ ppm 2.59 (s, 3 H) 2.47-2.77 (m, 2 H) 3.31-3.77 (m, 2 H) 3.93-4.11 (m, 2 H) 4.56-4.73 (m, 2 H) 7.35-7.49 (m, 2 H) 7.65-7.88 (m, 4 H) 7.96-8.09 (m, 2 H) 9.98-10.33 (m, 1 H).<br>MS ESI posi: 423[M + H]$^+$.<br>MS ESI nega: 421[M − H]$^-$. | | 2-1 |
| Example 2-17 | 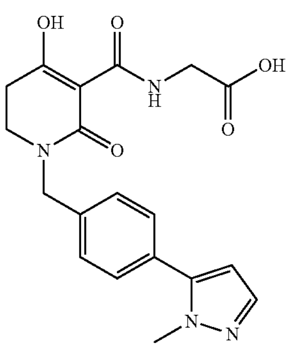 [SMILES: Cn1nccc1-c1ccc(CN2CCC(O)=C(C(=O)NCC(=O)O)C2=O)cc1] | $^1$H NMR (300 MHz, DMSO-d$_6$) δ ppm 2.62-2.79 (m, 2 H) 3.38-3.50 (m, 2 H) 3.85 (s, 3 H) 3.98-4.08 (m, 2 H) 4.56-4.72 (m, 2 H) 6.39 (d, J = 1.9 Hz, 1 H) 7.35-7.57 (m, 5 H) 9.93-10.32 (m, 1 H).<br>MS ESI posi: 385[M + H]$^+$. | | 2-1 |

TABLE 22-2-continued

| Compound No. | Structure | Analytical Data | Salt information | Example |
|---|---|---|---|---|
| Example 2-18 | 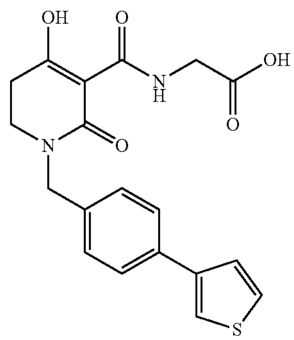 [SMILES: O=C(O)CNC(=O)C1=C(O)CCN(Cc2ccc(-c3ccsc3)cc2)C1=O] | $^1$H NMR (300 MHz, DMSO-d$_6$) δ ppm 2.60-2.76 (m, 2 H) 3.31-3.48 (m, 2 H) 3.95-4.10 (m, 2 H) 4.53-4.69 (m, 2 H) 7.23-7.40 (m, 2 H) 7.49-7.58 (m, 1 H) 7.59-7.75 (m, 3 H) 7.80-7.90 (m, 1 H) 9.99-10.31 (m, 1 H). MS ESI posi: 387[M + H]$^+$. MS ESI nega: 385[M − H]$^-$. | | 2-1 |
| Example 2-19 | 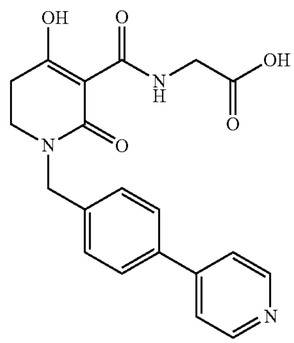 [SMILES: O=C(O)CNC(=O)C1=C(O)CCN(Cc2ccc(-c3ccncc3)cc2)C1=O] | $^1$H NMR (300 MHz, DMSO-d$_6$) δ ppm 2.65-2.79 (m, 2 H) 3.40-3.76 (m, 2 H) 3.97-4.10 (m, 2 H) 4.61-4.77 (m, 2 H) 7.46-7.58 (m, 2 H) 7.91-8.04 (m, 2 H) 8.21-8.32 (m, 2 H) 8.83-8.94 (m, 2 H) 9.96-10.31 (m, 1 H). MS ESI posi: 382[M + H]$^+$. MS ESI nega: 380[M − H]$^-$. | HCl | 2-1 |

TABLE 22-3

| Compound No. | Structure | Analytical Data | Salt information | Example |
|---|---|---|---|---|
| Example 2-20 | 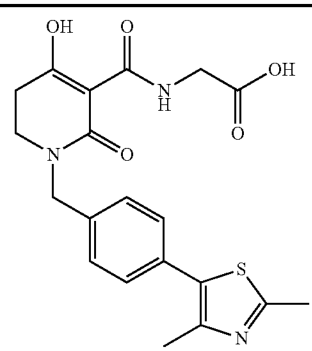 | $^1$H NMR (300 MHz, DMSO-d$_6$) δ ppm 2.37 (s, 3 H) 2.57-2.78 (m, 5 H) 3.36-3.52 (m, 2 H) 3.96-4.09 (m, 2 H) 4.55-4.71 (m, 2 H) 7.30-7.49 (m, 4 H) 9.95-10.11 (m, 1 H). MS ESI posi: 416[M + H]$^+$. MS ESI nega: 414[M − H]$^-$. | | 2-1 |
| Example 2-21 | 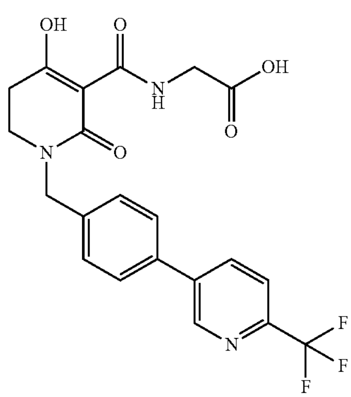 [SMILES: O=C(O)CNC(=O)C1=C(O)CCN(Cc2ccc(-c3ccc(C(F)(F)F)nc3)cc2)C1=O] | $^1$H NMR (300 MHz, DMSO-d$_6$) δ ppm 2.45-2.77 (m, 2 H) 3.34-3.50 (m, 2 H) 3.94-4.11 (m, 2 H) 4.58-4.77 (m, 2 H) 7.38-7.54 (m, 2 H) 7.73-7.87 (m, 2 H) 7.94-8.04 (m, 1 H) 8.28-8.42 (m, 1 H) 9.04-9.13 (m, 1 H) 9.94-10.32 (m, 1 H). MS ESI posi: 450[M + H]$^+$. MS ESI nega: 448[M − H]$^-$. | | 2-1 |

TABLE 22-3-continued

| Compound No. | Structure | Analytical Data | Salt information | Example |
|---|---|---|---|---|
| Example 2-22 | (structure) | $^1$H NMR (300 MHz, DMSO-$d_6$) δ ppm 2.46-2.75 (m, 2 H) 3.36-3.48 (m, 2 H) 3.96-4.09 (m, 2 H) 4.57-4.71 (m, 2 H) 7.32-7.54 (m, 4 H) 7.58-7.74 (m, 4 H) 9.97-10.28 (m, 1 H). MS ESI/APCI Dual posi: 415[M + H]$^+$. MS ESI/APCI Dual nega: 413[M − H]$^-$. | | 2-1 |
| Example 2-23 | (structure) | $^1$H NMR (300 MHz, DMSO-$d_6$) δ ppm 2.49-2.76 (m, 2 H) 3.33-3.51 (m, 2 H) 3.98-4.08 (m, 2 H) 4.58-4.69 (m, 2 H) 7.35-7.44 (m, 2 H) 7.64-7.75 (m, 4 H) 7.90-7.96 (m, 1 H) 9.99-10.27 (m, 1 H). MS ESI/APCI Dual posi: 449[M + H]$^+$. MS ESI/APCI Dual nega: 447[M − H]$^-$. | | 2-1 |
| Example 2-24 | (structure) | $^1$H NMR (300 MHz, DMSO-$d_6$) δ ppm 2.51-2.76 (m, 2 H) 3.37-3.51 (m, 2 H) 3.98-4.09 (m, 2 H) 4.59-4.74 (m, 2 H) 7.38-7.49 (m, 2 H) 7.67-7.95 (m, 6 H) 10.00-10.28 (m, 1 H). MS ESI/APCI Dual posi: 449[M + H]$^+$. MS ESI/APCI Dual nega: 447[M − H]$^-$. | | 2-1 |
| Example 2-25 | (structure) | $^1$H NMR (300 MHz, DMSO-$d_6$) δ ppm 2.37 (s, 3 H) 2.48-2.75 (m, 2 H) 3.34-3.48 (m, 2 H) 3.97-4.10 (m, 2 H) 4.53-4.73 (m, 2 H) 7.10-7.23 (m, 1 H) 7.28-7.50 (m, 5 H) 7.53-7.71 (m, 2 H) 9.95-10.30 (m, 1 H). MS ESI/APCI Dual posi: 395[M + H]$^+$. | | 2-1 |

TABLE 22-3-continued

| Compound No. | Structure | Analytical Data | Salt information | Example |
|---|---|---|---|---|
| Example 2-26 | (structure) | $^1$H NMR (300 MHz, DMSO-$d_6$) δ ppm 2.48-2.76 (m, 2 H) 3.33-3.47 (m, 2 H) 3.82 (s, 3 H) 3.97-4.10 (m, 2 H) 4.56-4.69 (m, 2 H) 6.89-6.97 (m, 1 H) 7.13-7.25 (m, 2 H) 7.31-7.43 (m, 3 H) 7.58-7.70 (m, 2 H) 9.98-10.29 (m, 1 H). MS ESI/APCI Dual posi: 411[M + H]$^+$. MS ESI/APCI Dual nega: 409[M − H]$^−$. | | 2-1 |

TABLE 22-4

| Compound No. | Structure | Analytical Data | Salt information | Example |
|---|---|---|---|---|
| Example 2-27 | (structure) | $^1$H NMR (300 MHz, DMSO-$d_6$) δ ppm 2.65-2.76 (m, 2 H) 3.36-3.53 (m, 2 H) 3.98-4.09 (m, 2 H) 4.61-4.75 (m, 2 H) 7.43-7.53 (m, 2 H) 7.67-7.76 (m, 1 H) 7.80-7.91 (m, 2 H) 8.11-8.25 (m, 2 H) 8.37-8.43 (m, 1 H) 8.60-8.70 (m, 1 H) 8.99-9.07 (m, 1 H) 10.01-10.29 (m, 1 H) MS ESI/APCI Dual posi: 432[M + H]$^+$. | TFA | 2-1 |
| Example 2-28 | (structure) | $^1$H NMR (300 MHz, DMSO-$d_6$) δ ppm 2.62-2.75 (m, 2 H) 3.34-3.52 (m, 2 H) 3.94-4.13 (m, 2 H) 4.53-4.73 (m, 2 H) 7.19-7.46 (m, 4 H) 7.54-7.77 (m, 4 H) 9.99-10.30 (m, 1 H) 12.69-13.01 (m, 1 H). MS ESI/APCI Dual posi: 399[M + H]$^+$, 421[M + Na]$^+$. | | 2-1 |

TABLE 22-4-continued

| Compound No. | Structure | Analytical Data | Salt information | Example |
|---|---|---|---|---|
| Example 2-29 | 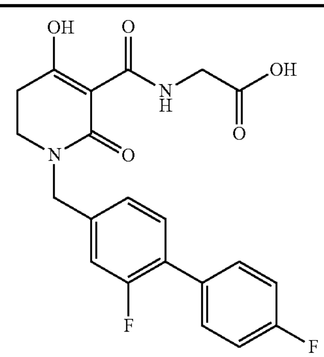 | $^1$H NMR (300 MHz, CHLOROFORM-d) δ ppm 2.56-2.72 (m, 2 H) 3.35-3.47 (m, 2 H) 4.15-4.25 (m, 2 H) 4.60-4.68 (m, 2 H) 7.04-7.17 (m, 4 H) 7.32-7.41 (m, 1 H) 7.45-7.54 (m, 2 H) 10.08-10.50 (m, 1 H). MS ESI/APCI Dual posi: 439[M + Na]$^+$. MS ESI/APCI Dual nega: 415[M − H]$^-$. | | 2-1 |
| Example 2-30 | 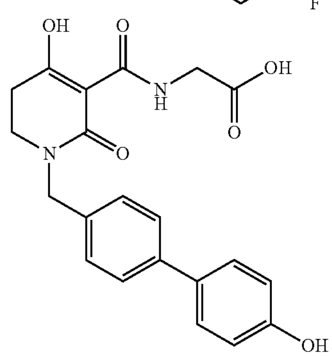 | $^1$H NMR (300 MHz, DMSO-d$_6$) δ ppm 2.68 (t, J = 7.1 Hz, 2 H) 3.32-3.47 (m, 2 H) 3.91-4.14 (m, 2 H) 4.52-4.70 (m, 2 H) 6.84 (d, J = 8.4 Hz, 2 H) 7.32 (d, J = 7.9 Hz, 2 H) 7.39-7.64 (m, 4 H) 9.53 (br. s., 1 H) 9.93-10.33 (m, 1 H). MS ESI posi: 397[M + H]$^+$, 419[M + Na]$^+$. | | 2-1 |

TABLE 22-5

| Compound No. | Structure | Analytical Data | Salt information | Example |
|---|---|---|---|---|
| Example 2-31 | 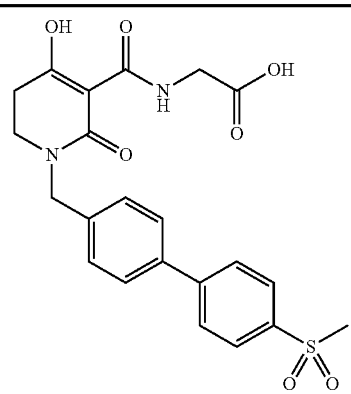 | $^1$H NMR (300 MHz, DMSO-d$_6$) δ ppm 2.56-2.79 (m, 2 H) 3.07-3.29 (m, 3 H) 3.36-3.52 (m, 2 H) 3.81-4.21 (m, 2 H) 4.57-4.73 (m, 2 H) 7.37-7.53 (m, 2 H) 7.65-7.82 (m, 2 H) 7.89-8.05 (m, 4 H) 9.94-10.33 (m, 1 H). MS ESI/APCI Dual posi: 459[M + H]$^+$. MS ESI/APCI Dual nega: 457[M − H]$^-$. | | 2-1 |
| Example 2-32 | 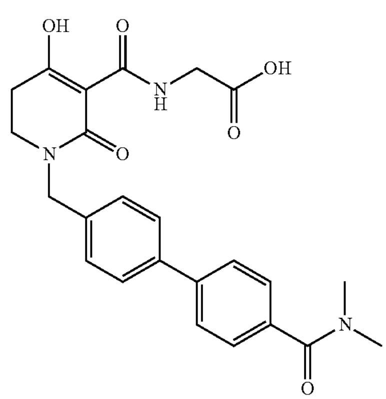 [SMILES: CN(C)C(=O)c1ccc(-c2ccc(CN3CCC(O)=C(C(=O)NCC(=O)O)C3=O)cc2)cc1] | $^1$H NMR (300 MHz, DMSO-d$_6$) δ ppm 2.63-2.76 (m, 2 H) 2.89-3.05 (m, 6 H) 3.36-3.48 (m, 2 H) 3.97-4.08 (m, 2 H) 4.56-4.71 (m, 2 H) 7.36-7.42 (m, 2 H) 7.49 (d, J = 8.1 Hz, 2 H) 7.70 (t, J = 8.1 Hz, 4 H) 9.96-10.31 (m, 1 H). MS ESI/APCI Dual posi: 452[M + H]$^+$. MS ESI/APCI Dual nega: 450[M − H]$^-$. | | 2-1 |

TABLE 22-5-continued

| Compound No. | Structure | Analytical Data | Salt information | Example |
|---|---|---|---|---|
| Example 2-33 | 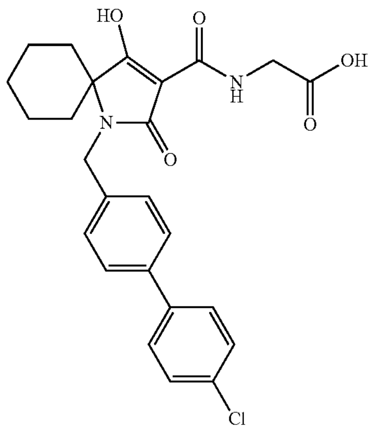 [SMILES: O=C(O)CNC(=O)C1=C(O)C2(CCCCC2)N(Cc2ccc(-c3ccc(Cl)cc3)cc2)C1=O] | ¹H NMR (300 MHz, CHLOROFORM-d) δ ppm 1.00-1.26 (m, 1 H) 1.50-2.08 (m, 9 H) 4.20 (d, J = 5.8 Hz, 2 H) 4.58 (s, 2 H) 7.27-7.57 (m, 8 H) 8.17-8.33 (m, 1 H). MS ESI/APCI Dual posi: 469[M + H]⁺. MS ESI/APCI Dual nega: 467[M − H]⁻. | | 2-2 |
| Example 2-34 | 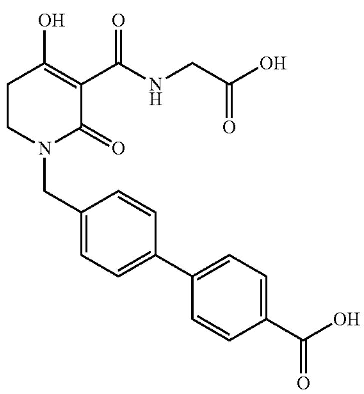 [SMILES: O=C(O)CNC(=O)C1=C(O)CCN(Cc2ccc(-c3ccc(C(=O)O)cc3)cc2)C1=O] | ¹H NMR (300 MHz, DMSO-d₆) δ ppm 2.70 (t, J = 7.2 Hz, 2 H) 3.36-3.55 (m, 2 H) 3.96-4.09 (m, 2 H) 4.54-4.71 (m, 2 H) 7.41 (d, J = 8.4 Hz, 2 H) 7.64-7.86 (m, 4 H) 8.01 (d, J = 8.4 Hz, 2 H) 9.94-10.32 (m, 1 H) 12.91 (br. s., 2 H). MS ESI/APCI Dual posi: 425[M + H]⁺. MS ESI/APCI Dual nega: 423[M − H]⁻. | | 2-2 |
| Example 2-35 | 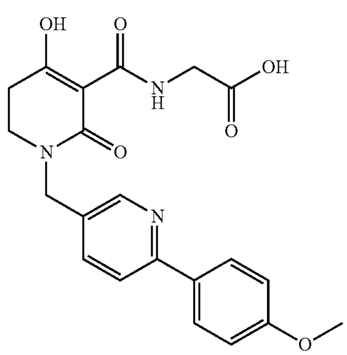 [SMILES: COc1ccc(-c2ccc(CN3CCC(O)=C(C(=O)NCC(=O)O)C3=O)cn2)cc1] | ¹H NMR (300 MHz, DMSO-d₆) δ ppm 2.55-2.73 (m, 2 H) 3.39-3.49 (m, 2 H) 3.75-3.91 (m, 5 H) 4.61 (s, 2 H) 6.96-7.10 (m, 2 H) 7.70-7.79 (m, 1 H) 7.82-7.91 (m, 1 H) 7.98-8.08 (m, 2 H) 8.52-8.60 (m, 1 H). MS ESI/APCI Dual posi: 412[M + H]⁺. MS ESI/APCI Dual nega: 410[M − H]⁻. | Na | 2-3 |
| Example 2-36 | 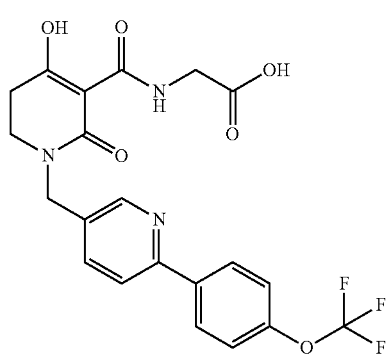 [SMILES: O=C(O)CNC(=O)C1=C(O)CCN(Cc2ccc(-c3ccc(OC(F)(F)F)cc3)nc2)C1=O] | ¹H NMR (300 MHz, DMSO-d₆) δ ppm 2.54-2.71 (m, 2 H) 3.38-3.48 (m, 2 H) 3.58-3.70 (m, 2 H) 4.64 (s, 2 H) 7.42-7.52 (m, 2 H) 7.77-7.85 (m, 1 H) 7.94-8.03 (m, 1 H) 8.15-8.25 (m, 2 H) 8.59-8.65 (m, 1 H). MS ESI/APCI Dual posi: 466[M + H]⁺. MS ESI/APCI Dual nega: 464[M − H]⁻. | Na | 2-3 |

TABLE 22-5-continued

| Compound No. | Structure | Analytical Data | Salt information | Example |
|---|---|---|---|---|
| Example 2-37 | 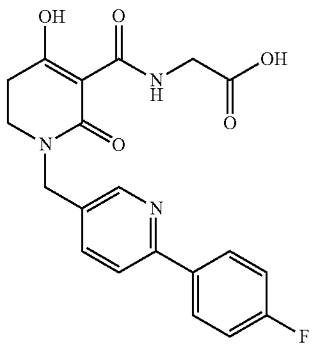 [SMILES: O=C(O)CNC(=O)C1=C(O)CCN(Cc2ccc(-c3ccc(F)cc3)nc2)C1=O] | $^1$H NMR (300 MHz, DMSO-d$_6$) δ ppm 2.38-2.60 (m, 2 H) 3.44 (d, J = 4.2 Hz, 2 H) 4.61 (s, 2 H) 7.23-7.40 (m, 2 H) 7.74-7.83 (m, 1 H) 7.89-7.97 (m, 1 H) 8.07-8.18 (m, 2 H) 8.56-8.63 (m, 1 H). MS ESI/APCI Dual posi: 400[M + H]$^+$. MS ESI/APCI Dual nega: 398[M − H]$^-$. | Na | 2-3 |

TABLE 22-6

| Compound No. | Structure | Analytical Data | Salt information | Example |
|---|---|---|---|---|
| Example 2-38 | 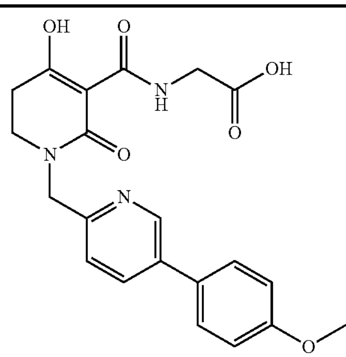 | $^1$H NMR (300 MHz, DMSO-d$_6$) δ ppm 2.41-2.61 (m, 2 H) 3.40-3.50 (m, 2 H) 3.80 (s, 3 H) 4.67 (s, 2 H) 6.98-7.11 (m, 2 H) 7.28-7.38 (m, 1 H) 7.59-7.72 (m, 2 H) 7.94-8.03 (m, 1 H) 8.74-8.81 (m, 1 H). MS ESI/APCI Dual posi: 412[M + H]$^+$. MS ESI/APCI Dual nega: 410[M − H]$^-$. | Na | 2-3 |
| Example 2-39 | 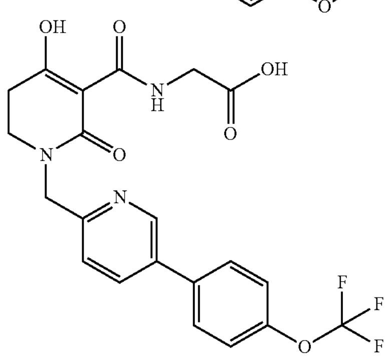 | $^1$H NMR (300 MHz, DMSO-d$_6$) δ ppm 2.56-2.77 (m, 2 H) 3.45-3.71 (m, 4 H) 4.71 (s, 2 H) 7.34-7.55 (m, 3 H) 7.79-7.92 (m, 2 H) 8.02-8.12 (m, 1 H) 8.81-8.89 (m, 1 H). | Na | 2-3 |
| Example 2-40 | 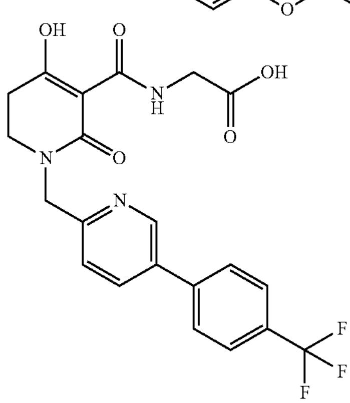 | $^1$H NMR (300 MHz, DMSO-d$_6$) δ ppm 2.48-2.76 (m, 2 H) 3.37-3.61 (m, 4 H) 4.72 (s, 2 H) 7.38-7.47 (m, 1 H) 7.79-7.90 (m, 2 H) 7.91-8.03 (m, 2 H) 8.08-8.18 (m, 1 H) 8.86-8.94 (m, 1 H). | Na | 2-3 |

TABLE 22-6-continued

| Compound No. | Structure | Analytical Data | Salt information | Example |
|---|---|---|---|---|
| Example 2-41 | 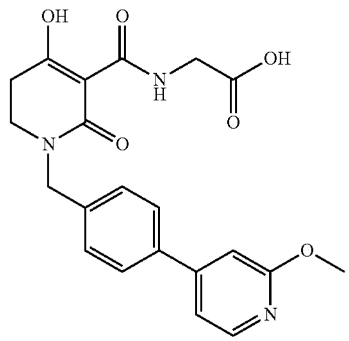 [SMILES: COc1cc(-c2ccc(CN3CCC(O)=C(C(=O)NCC(=O)O)C3=O)cc2)ccn1] | $^1$H NMR (300 MHz, DMSO-d$_6$) δ ppm 2.48-2.65 (m, 2 H) 3.28-3.52 (m, 4 H) 3.89 (s, 3 H) 4.62 (s, 2 H) 7.06-7.12 (m, 1 H) 7.26-7.34 (m, 1 H) 7.37-7.45 (m, 2 H) 7.70-7.81 (m, 2 H) 8.17-8.25 (m, 1 H). | Na | 2-3 |
| Example 2-42 | 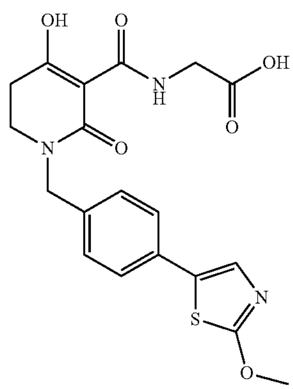 [SMILES: COc1ncc(-c2ccc(CN3CCC(O)=C(C(=O)NCC(=O)O)C3=O)cc2)s1] | $^1$H NMR (600 MHz, DMSO-d$_6$) δ ppm 2.41-2.53 (m, 2 H) 3.22-3.40 (m, 7 H) 4.51 (s, 2 H) 7.24-7.29 (m, 2 H) 7.31-7.36 (m, 2 H) 7.54 (s, 1 H) 9.85-9.99 (m, 1 H). MS ESI/APCI Dual posi: 418[M + H]$^+$. | Na | 2-2 |
| Example 2-43 | 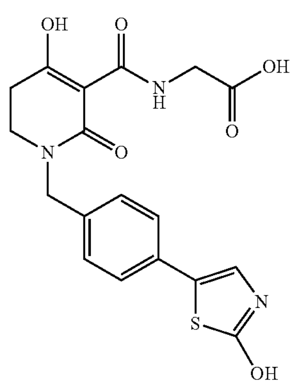 [SMILES: O=C(O)CNC(=O)C1=C(O)CCN(Cc2ccc(-c3cnc(O)s3)cc2)C1=O] | $^1$H NMR (600 MHz, DMSO-d$_6$) δ ppm 2.45-2.56 (m, 2 H) 3.21-3.47 (m, 4 H) 4.52 (s, 2 H) 7.20-7.26 (m, 2 H) 7.28-7.39 (m, 3 H) 8.54 (s, 1 H) 9.81-10.16 (m, 1 H). MS ESI/APCI Dual posi: 404[M + H]$^+$. | Na | 2-2 |
| Example 2-44 | 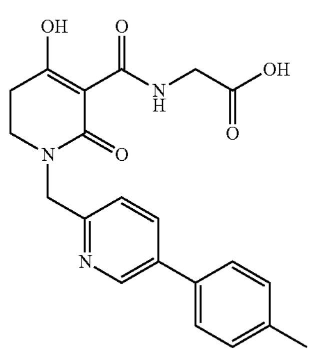 [SMILES: Cc1ccc(-c2ccc(CN3CCC(O)=C(C(=O)NCC(=O)O)C3=O)nc2)cc1] | $^1$H NMR (300 MHz, DMSO-d$_6$) δ ppm 2.28-2.42 (m, 5 H) 3.21-3.54 (m, 4 H) 4.66 (s, 2 H) 7.25-7.36 (m, 3 H) 7.55-7.63 (m, 2 H) 7.93-8.04 (m, 1 H) 8.73-8.80 (m, 1 H) 10.08-10.20 (m, 1 H). MS ESI/APCI Dual posi: 396[M + H]$^+$. | Na | 2-3 |

TABLE 22-7

| Compound No. | Structure | Analytical Data | Salt information | Example |
|---|---|---|---|---|
| Example 2-45 | 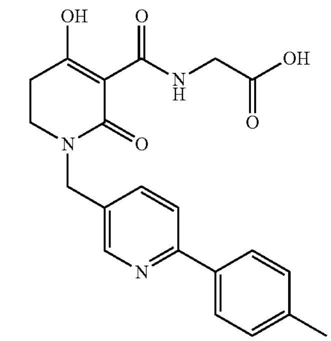 [SMILES: Cc1ccc(-c2ccc(CN3CCC(O)=C(C(=O)NCC(=O)O)C3=O)cn2)cc1] | ¹H NMR (300 MHz, DMSO-d₆) δ ppm 2.36 (s, 3 H) 2.44-2.62 (m, 2 H) 3.26-3.56 (m, 4 H) 4.61 (s, 2 H) 7.24-7.35 (m, 2 H) 7.70-7.80 (m, 1 H) 7.86-8.03 (m, 3 H) 8.55-8.61 (m, 1 H) 9.99-10.16 (m, 1 H).<br>MS ESI/APCI Dual posi: 396[M + H]⁺. | Na | 2-3 |
| Example 2-46 | 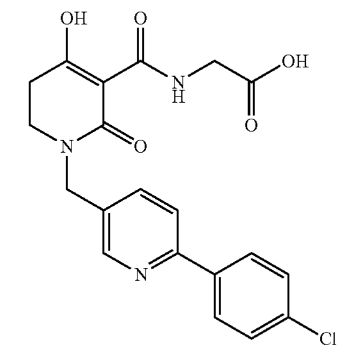 [SMILES: O=C(O)CNC(=O)C1=C(O)CCN(Cc2ccc(-c3ccc(Cl)cc3)nc2)C1=O] | ¹H NMR (300 MHz, DMSO-d₆) δ ppm 2.45-2.61 (m, 2 H) 3.25-3.59 (m, 4 H) 4.62 (s, 2 H) 7.48-7.59 (m, 2 H) 7.74-7.84 (m, 1 H) 7.90-8.01 (m, 1 H) 8.05-8.16 (m, 2 H) 8.61 (s, 1 H) 9.99-10.17 (m, 1 H).<br>MS ESI/APCI Dual posi: 416[M + H]⁺. | Na | 2-3 |
| Example 2-47 | 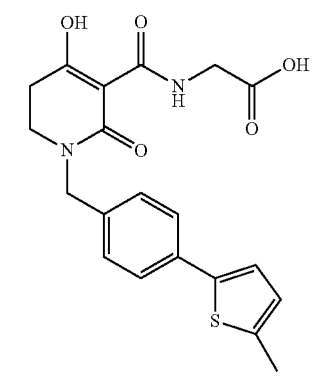 [SMILES: Cc1ccc(-c2ccc(CN3CCC(O)=C(C(=O)NCC(=O)O)C3=O)cc2)s1] | ¹H NMR (300 MHz, DMSO-d₆) δ ppm 2.40-2.58 (m, 5 H) 3.21-3.58 (m, 4 H) 4.56 (s, 2 H) 6.77-6.84 (m, 1 H) 7.22-7.34 (m, 3 H) 7.49-7.59 (m, 2 H) 9.98-10.21 (m, 1 H).<br>MS ESI/APCI Dual posi: 401[M + H]⁺. | Na | 2-2 |
| Example 2-48 | 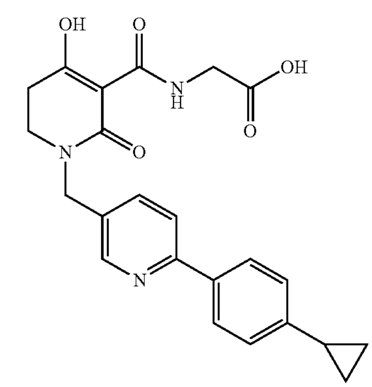 [SMILES: O=C(O)CNC(=O)C1=C(O)CCN(Cc2ccc(-c3ccc(C4CC4)cc3)nc2)C1=O] | ¹H NMR (300 MHz, DMSO-d₆) δ ppm 0.67-0.78 (m, 2 H) 0.94-1.05 (m, 2 H) 1.88-2.04 (m, 1 H) 2.47-2.61 (m, 2 H) 3.37 (t, J = 7.0 Hz, 2 H) 3.51-3.59 (m, 2 H) 4.60 (s, 2 H) 7.13-7.22 (m, 2 H) 7.70-7.79 (m, 1 H) 7.84-8.00 (m, 3 H) 8.54-8.61 (m, 1 H) 10.06-10.18 (m, 1 H).<br>MS ESI/APCI Dual posi: 422[M + H]⁺. | Na | 2-3 |

TABLE 22-7-continued

| Compound No. | Structure | Analytical Data | Salt information | Example |
|---|---|---|---|---|
| Example 2-49 | 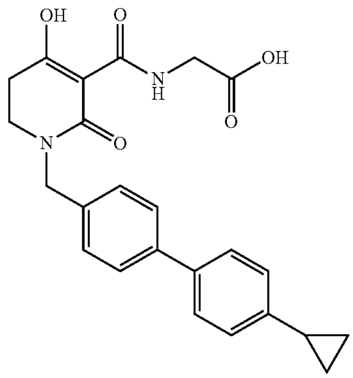 [SMILES: O=C(O)CNC(=O)C1=C(O)CCN(Cc2ccc(-c3ccc(C4CC4)cc3)cc2)C1=O] | $^1$H NMR (300 MHz, DMSO-d$_6$) δ ppm 0.66-0.75 (m, 2 H) 0.91-1.03 (m, 2 H) 1.88-2.03 (m, 1 H) 2.48-2.62 (m, 2 H) 3.34 (t, J = 7.1 Hz, 2 H) 3.60 (d, J = 4.5 Hz, 2 H) 4.60 (s, 2 H) 7.08-7.20 (m, 2 H) 7.30-7.39 (m, 2 H) 7.48-7.65 (m, 4 H) 10.06-10.21 (m, 1 H).<br>MS ESI/APCI Dual posi: 421[M + H]$^+$. | Na | 2-3 |
| Example 2-50 | 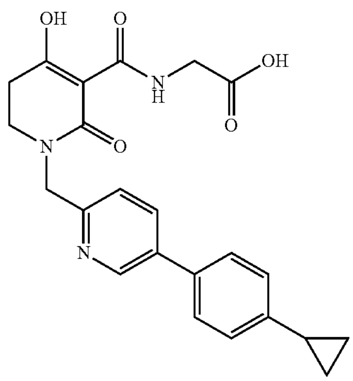 [SMILES: O=C(O)CNC(=O)C1=C(O)CCN(Cc2ccc(-c3ccc(C4CC4)cc3)cn2)C1=O] | $^1$H NMR (300 MHz, DMSO-d$_6$) δ ppm 0.67-0.78 (m, 2 H) 0.88-1.07 (m, 2 H) 1.90-2.05 (m, 1 H) 2.49-2.64 (m, 2 H) 3.38-3.56 (m, 4 H) 4.68 (s, 2 H) 7.13-7.26 (m, 2 H) 7.29-7.39 (m, 1 H) 7.53-7.64 (m, 2 H) 7.92-8.06 (m, 1 H) 8.72-8.84 (m, 1 H) 9.96-10.16 (m, 1 H).<br>MS ESI/APCI Dual posi: 422[M + H]$^+$. | Na | 2-3 |
| Example 2-51 | 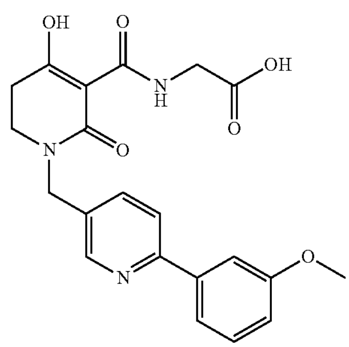 [SMILES: COc1cccc(-c2ccc(CN3CCC(O)=C(C(=O)NCC(=O)O)C3=O)cn2)c1] | $^1$H NMR (300 MHz, DMSO-d$_6$) δ ppm 2.40-2.54 (m, 2 H) 3.34 (t, J = 6.9 Hz, 2 H) 3.53 (d, J = 4.5 Hz, 2 H) 3.83 (s, 3 H) 4.61 (s, 2 H) 6.93-7.06 (m, 1 H) 7.32-7.46 (m, 1 H) 7.58-7.68 (m, 2 H) 7.72-7.82 (m, 1 H) 7.87-7.99 (m, 1 H) 8.55-8.67 (m, 1 H) 10.05-10.21 (m, 1 H).<br>MS ESI/APCI Dual posi: 412[M + H]$^+$. | Na | 2-3 |

TABLE 22-8

| Compound No. | Structure | Analytical Data | Salt information | Example |
|---|---|---|---|---|
| Example 2-52 | 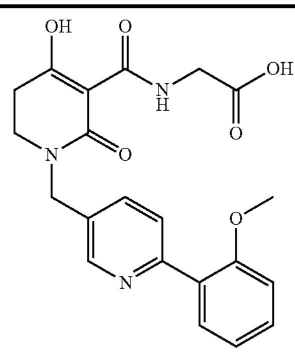 | $^1$H NMR (300 MHz, DMSO-d$_6$) δ ppm 2.53-2.66 (m, 2 H) 3.41 (t, J = 7.1 Hz, 2 H) 3.62 (d, J = 4.7 Hz, 2 H) 3.82 (s, 3 H) 4.62 (s, 2 H) 7.01-7.19 (m, 2 H) 7.32-7.48 (m, 1 H) 7.66-7.85 (m, 3 H) 8.54-8.66 (m, 1 H) 10.02-10.19 (m, 1 H).<br>MS ESI/APCI Dual posi: 412[M + H]$^+$. | Na | 2-3 |

TABLE 22-8-continued

| Compound No. | Structure | Analytical Data | Salt information | Example |
|---|---|---|---|---|
| Example 2-53 | 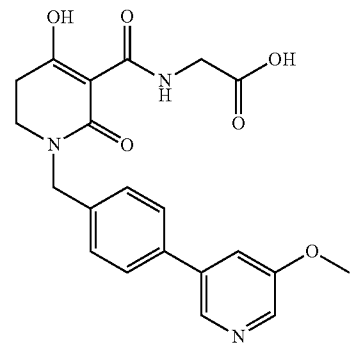 [SMILES: COc1cncc(-c2ccc(CN3CCC(O)=C(C(=O)NCC(=O)O)C3=O)cc2)c1] | ¹H NMR (300 MHz, DMSO-d₆) δ ppm 2.47-2.61 (m, 2 H) 3.34 (t, J = 7.0 Hz, 2 H) 3.57 (d, J = 4.4 Hz, 2 H) 3.90 (s, 3 H) 4.62 (s, 2 H) 7.34-7.47 (m, 2 H) 7.57-7.65 (m, 1 H) 7.69-7.77 (m, 2 H) 8.25-8.31 (m, 1 H) 8.44-8.50 (m, 1 H) 10.07-10.22 (m, 1 H). MS ESI/APCI Dual posi: 412[M + H]⁺. | Na | 2-2 |
| Example 2-54 | 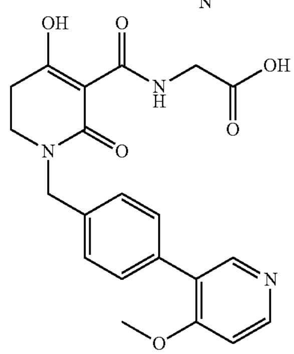 | ¹H NMR (300 MHz, DMSO-d₆) δ ppm 2.45-2.61 (m, 2 H) 3.28-3.41 (m, 2 H) 3.49-3.60 (m, 2 H) 3.85 (s, 3 H) 4.61 (s, 2 H) 7.11-7.23 (m, 1 H) 7.27-7.41 (m, 2 H) 7.43-7.55 (m, 2 H) 8.30-8.52 (m, 2 H) 10.06-10.23 (m, 1 H). MS ESI/APCI Dual posi: 412[M + H]⁺. | Na | 2-2 |

Example 2-55

N-({4-Hydroxy-2-oxo-1-[(4'-sulfamoyl-4-biphenylyl)methyl]-1,2,5,6-tetrahydro-3-pyridinyl}carbonyl)glycine

[Formula 223]

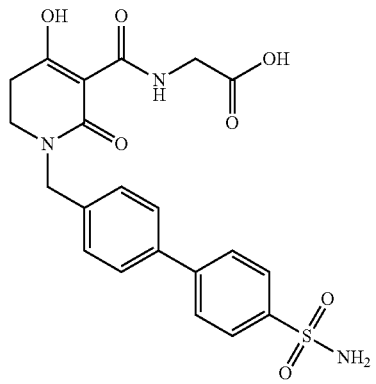

(1) Synthesis of N-{[4-hydroxy-(4-iodobenzyl)-2-oxo-1,2,5,6-tetrahydro-3-pyridinyl]carbonyl}glycine

[Formula 224]

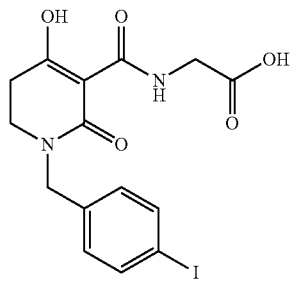

To the compound (5.00 g) obtained in Example 2-1(1), a solution (50 mL) of 4 mol/L, hydrogen chloride in 1,4-dioxane was added and the mixture was stirred at 70° C. for three hours. The reaction mixture was cooled with ice and the resulting precipitate was recovered by filtration to give N-{[4-hydroxy-1-(4-iodobenzyl)-2-oxo-1,2,5,6-tetrahydro-3-pyridinyl]carbonyl}glycine as a colorless solid (3.37 g).

¹H NMR (300 MHz, DMSO-d₆) δ ppm 2.65 (br. s., 2 H) 3.37 (t, J=7.1 Hz, 2 H) 4.02 (d, J=5.8 Hz, 2 H) 4.53 (s, 2 H) 7.11 (d, J=8.4 Hz, 2 H) 7.62-7.81 (m, 2 H) 10.03 (br. s., 1 H).

MS ESI/APCI Dual posi: 453 [M+Na]⁺.

MS ESI/APCI Dual nega: 429 [M−H]⁻.

(2) Synthesis of the Titled Compound

The compound (100 mg) obtained in step (1) above was used and treated by the same technique as in Example 2-2(1) to give the titled compound as a pale yellow solid (45.9 mg).

¹H NMR (300 MHz, DMSO-d₆) δ ppm 2.65-2.75 (m, 2 H) 3.37-3.49 (m, 2 H) 3.96-4.11 (m, 2 H) 4.59-4.71 (m, 2 H) 7.33-7.44 (m, 4 H) 7.68-7.76 (m, 2 H) 7.81-7.93 (m, 4 H) 9.88-10.33 (m, 1 H) 12.85 (br. s., 1 H).

MS ESI/APCI Dual posi: 460 [M+H]⁺.

MS ESI/APCI Dual nega: 458 [M−H]⁻.

The compounds of the following Examples 2-56 to 2-61 were synthesized from commercial grades of the corresponding boronic acid analogs by the method described in Example 2-55 or modifications thereof. The structures of the synthesized compounds and their NMR and MS data are shown in Table 22-9.

TABLE 22-9

| Compound No. | Structure | Analytical Data | Salt information |
|---|---|---|---|
| Example 2-56 | 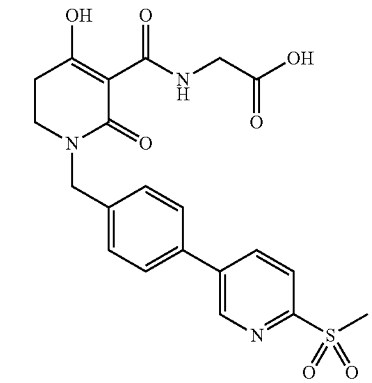 [SMILES: CS(=O)(=O)c1ccc(-c2ccc(CN3CCC(O)=C(C(=O)NCC(=O)O)C3=O)cc2)cn1] | ¹H NMR (300 MHz, DMSO-d₆) δ ppm 2.55-2.69 (m, 2 H) 3.39 (t, J = 7.0 Hz, 2 H) 3.57 (d, J = 4.7 Hz, 2 H) 4.65 (s, 2 H) 7.47 (d, J = 8.2 Hz, 2 H) 7.82 (d, J = 8.2 Hz, 2 H) 8.11 (d, J = 8.4 Hz, 1 H) 8.42 (dd, J = 8.4, 2.2 Hz, 1 H) 9.10 (d, J = 1.6 Hz, 1 H) 10.04 (br. s., 1 H). MS ESI/APCI Dual posi: 460[M + H]⁺. MS ESI/APCI Dual nega: 458[M − H]⁻. | Na |
| Example 2-57 | 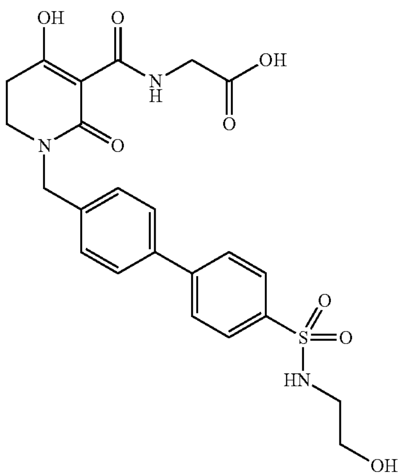 [SMILES: O=C(O)CNC(=O)C1=C(O)CCN(Cc2ccc(-c3ccc(S(=O)(=O)NCCO)cc3)cc2)C1=O] | ¹H NMR (300 MHz, DMSO-d₆) δ ppm 2.60 (br. s., 2 H) 2.82 (q, J = 6.3 Hz, 2 H) 3.28-3.47 (m, 6 H) 3.64 (d, J = 4.7 Hz, 2 H) 4.63 (s, 2 H) 7.42 (d, J = 8.2 Hz, 2 H) 7.64-7.79 (m, 3 H) 7.80-7.96 (m, 4 H) 10.08 (br. s., 1 H). MS ESI/APCI Dual posi: 504[M + H]⁺. MS ESI/APCI Dual nega: 502[M − H]⁻. | Na |
| Example 2-58 | 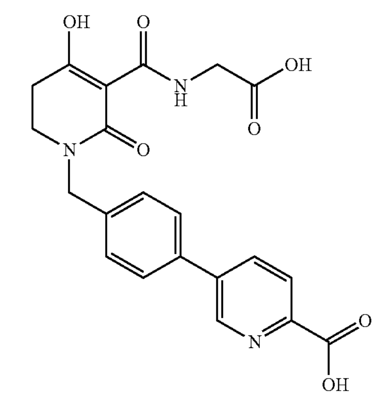 [SMILES: O=C(O)CNC(=O)C1=C(O)CCN(Cc2ccc(-c3ccc(C(=O)O)nc3)cc2)C1=O] | ¹H NMR (300 MHz, DMSO-d₆) δ ppm 2.60-2.78 (m, 2 H) 3.43 (t, J = 7.0 Hz, 2 H) 4.03 (d, J = 5.6 Hz, 2 H) 4.66 (s, 2 H) 7.46 (d, J = 8.2 Hz, 2 H) 7.81 (d, J = 8.2 Hz, 2 H) 8.13 (dd, J = 8.2, 0.7 Hz, 1 H) 8.29 (dd, J = 8.2, 2.3 Hz, 1 H) 9.02 (dd, J = 2.3, 0.7 Hz, 1 H) 10.05 (br. s., 1 H). MS ESI/APCI Dual posi: 426[M + H]⁺. MS ESI/APCI Dual nega: 424[M − H]⁻. | HCl |
| Example 2-59 | 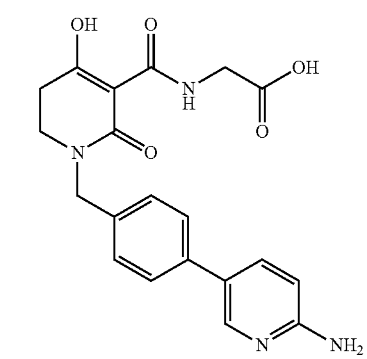 [SMILES: Nc1ccc(-c2ccc(CN3CCC(O)=C(C(=O)NCC(=O)O)C3=O)cc2)cn1] | ¹H NMR (300 MHz, DMSO-d₆) δ ppm 2.69 (br. s., 2 H) 3.33-3.47 (m, 2 H) 4.03 (d, J = 5.6 Hz, 2 H) 4.62 (s, 2 H) 7.12 (d, J = 9.9 Hz, 1 H) 7.40 (d, J = 8.2 Hz, 2 H) 7.65 (d, J = 8.2 Hz, 2 H) 8.15-8.40 (m, 4 H) 10.05 (br. s., 1 H). MS ESI/APCI Dual posi: 397[M + H]⁺. | HCl |

TABLE 22-9-continued

| Compound No. | Structure | Analytical Data | Salt information |
|---|---|---|---|
| Example 2-60 | 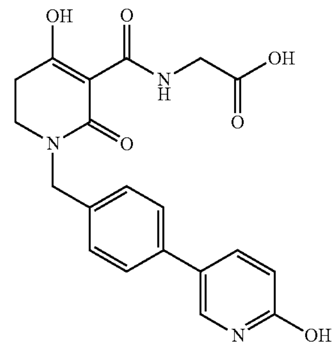 [SMILES: O=C(O)CNC(=O)C1=C(O)CCN(Cc2ccc(-c3ccc(O)nc3)cc2)C1=O] | $^1$H NMR (300 MHz, DMSO-$d_6$) δ ppm 2.58-2.75 (m, 2 H) 3.33-3.45 (m, 2 H) 4.03 (d, J = 5.8 Hz, 2 H) 4.59 (s, 2 H) 6.58 (d, J = 9.5 Hz, 1 H) 7.34 (d, J = 8.2 Hz, 2 H) 7.56 (d, J = 8.2 Hz, 2 H) 7.81 (d, J = 2.6 Hz, 1 H) 7.94 (dd, J = 9.5, 2.6 Hz, 1 H) 10.07 (br. s., 1 H). MS ESI/APCI Dual posi: 398[M + H]$^+$. MS ESI/APCI Dual nega: 396[M − H]$^−$. | HCl |
| Example 2-61 | 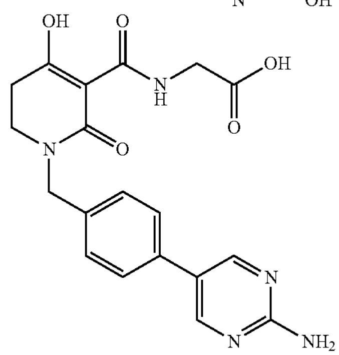 | $^1$H NMR (300 MHz, DMSO-$d_6$) δ ppm 2.68 (br. s., 2 H) 3.36-3.47 (m, 2 H) 4.03 (d, J = 5.6 Hz, 2 H) 4.62 (s, 2 H) 7.41 (d, J = 8.4 Hz, 2 H) 7.70 (d, J = 8.4 Hz, 2 H) 8.93 (s, 2 H) 10.05 (br. s., 1 H). MS ESI/APCI Dual posi: 398[M + H]$^+$. MS ESI/APCI Dual nega: 396[M − H]$^−$. | HCl |

Example 3-1

N-{[1-(4-Cyclopentylbenzyl)-4-hydroxy-2-oxo-1,2,5,6-tetrahydropyridin-3-yl]carbonyl}glycine sodium salt

[Formula 225]

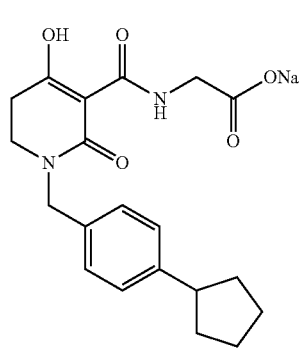

(1) Synthesis of tert-butyl N-[1-(4-cyclopentylbenzyl)-4-hydroxy-2-oxo-1,2,5,6-tetrahydropyridin-3-yl]carbonyl glycinate

[Formula 226]

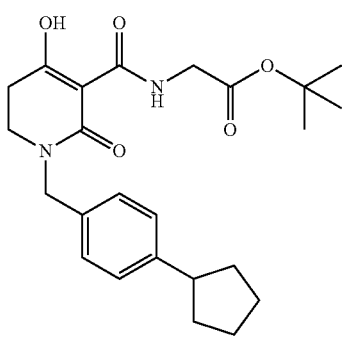

Indium(III) chloride (768 mg) was dried under reduced pressure while it was heated with a thermal gun. After being left to cool to room temperature, the reaction system was internally purged with argon. To the reaction system, dehydrated tetrahydrofuran (20.0 mL) was added and with stirring at −80° C., cyclopentyl magnesium bromide (2.0 mol/L, solution in diethyl ether, 5.23 mL) was added dropwise. After being stirred at that temperature for 30 minutes, the reaction mixture was brought to room temperature and stirred for 45 minutes. The compound (1.50 g) obtained in Example 2-1(1) and bis(tri-tert-butylphosphine)palladium (0) (788 mg) were added and the mixture was stirred at an external temperature of 75° C. for two hours. After standing to cool to room temperature, methanol (5.00 mL) was added and the mixture was stirred for 30 minutes. After concentrating under reduced pressure, chloroform (30.0 mL) was added and the insoluble matter was removed by passage through Celite (registered trademark). The filtrate was concentrated under reduced pressure. The resulting residue was purified by preparative HPLC and further purified twice by silica gel column chromatography (chloroform:ethyl acetate=100:0-85:15) to give tert-butyl N-{[1-(4-cyclopentylbenzyl)-4-hydroxy-2-oxo-1,2,5,6-tetrahydropyridin-3-yl]carbonyl}glycinate as a pale brown oil (600 mg).

$^1$H NMR (600 MHz, CHLOROFORM-d) δ ppm 1.49 (s, 9 H) 1.51-1.61 (m, 2 H) 1.64-1.73 (m, 2 H) 1.75-1.84 (m, 2 H) 2.01-2.10 (m, 2 H) 2.48-2.62 (m, 2 H) 2.93-3.03 (m, 1 H) 3.28-3.38 (m, 2 H) 3.97-4.06 (m, 2 H) 4.58 (s, 2 H) 7.14-7.24 (m, 4 H) 10.19-10.46 (m, 1 H).
MS ESI/APCI Dual posi: 451 [M+Na]$^+$.

(2) Synthesis of the Titled Compound

The compound (590 mg) obtained in step (1) above was used as a starting material and treated by the same techniques as in Example 1-3(2) and (3) to give the titled compound as an orange solid (118 mg).

$^1$H NMR (600 MHz, DMSO-d$_6$) δ ppm 1.46-1.55 (m, 2 H) 1.58-1.68 (m, 2 H) 1.70-1.80 (m, 2 H) 1.93-2.03 (m, 2 H) 2.48-2.60 (m, 2 H) 2.89-2.98 (m, 1 H) 3.27-3.34 (m, 2 H) 3.62-3.68 (m, 2 H) 4.52 (s, 2 H) 7.13-7.25 (m, 4 H) 10.01-10.22 (m, 1 H).

MS ESI posi: 373 [M+H]$^+$.

MS ESI nega: 371[M−H]$^−$.

Example 3-2

N-{[1-(4-Cyclopropylbenzyl)-4-hydroxy-2-oxo-1,2,5,6-tetrahydropyridin-3-yl]carbonyl}glycine sodium salt

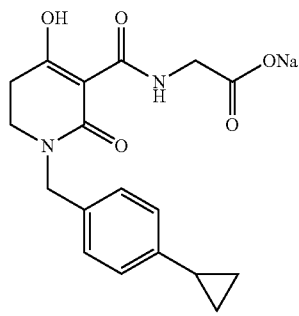

[Formula 227]

Instead of cyclopentyl magnesium bromide (2.0 mol/L, solution in diethyl ether), cyclopropyl magnesium bromide (about 0.7 mol/L, solution in tetrahydrofuran) was used and treated by the same technique as in Example 3-1 to give the titled compound as a pale gray solid (527 mg).

$^1$H NMR (300 MHz, DMSO-d$_6$) δ ppm 0.60-0.67 (m, 2 H) 0.88-0.96 (m, 2 H) 1.81-1.95 (m, 1 H) 2.47-2.54 (m, 2 H) 3.20-3.30 (m, 2 H) 3.47-3.54 (m, 2 H) 4.50 (s, 2 H) 6.97-7.08 (m, 2 H) 7.10-7.19 (m, 2 H) 10.08 (br. s., 1 H).

MS ESI posi: 345 [M+H]$^+$, 367 [M+Na]$^+$.

Example 4-1

N-{[1-(2,4-Dimethoxybenzyl)-4-hydroxy-2-oxo-1,2,5,6-tetrahydropyridin-3-yl]carbonyl}glycine

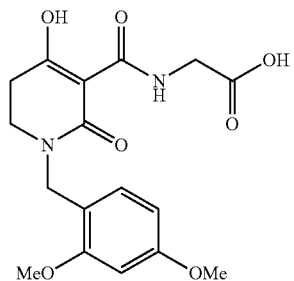

[Formula 228]

(1) Synthesis of ethyl N-(2,4-dimethoxybenzyl)-N-(3-ethoxy-3-oxopropanoyl)-β-alaninate

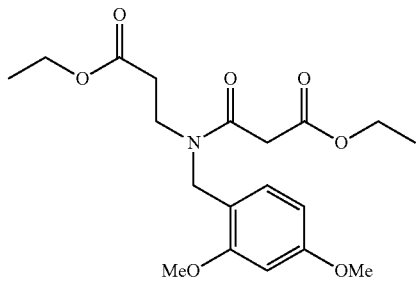

[Formula 229]

Instead of the compound obtained in Reference Example A-1, the compound obtained in Reference Example A-6 (8.05 g) was used as a starting material and treated by the same technique as in Example 1-1(1) to give a mixture (13.0 g) containing ethyl N-(2,4-dimethoxybenzyl)-N-(3-ethoxy-3-oxo-propanoyl)-β-alaninate.

MS ESI/APCI Dual posi: 382 [M+H]$^+$, 404 [M+Na]$^+$.

(2) Synthesis of ethyl 1-(2,4-dimethoxybenzyl)-4-hydroxy-2-oxo-1,2,5,6-tetrahydropyridin-3-carboxylate

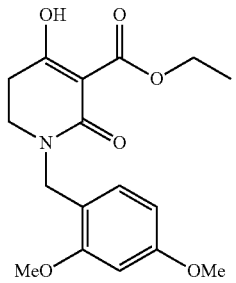

[Formula 230]

To a solution in ethanol (160 mL) of the mixture (13.0 g) obtained in step (1) above, sodium ethoxide (about 20%, solution in ethanol, 20.8 mL) was added and the resulting mixture was stirred at an external temperature of 85° C. for two hours. After cooling to room temperature, ethyl acetate and 2 mol/L hydrochloric acid were added. Extraction was conducted with ethyl acetate and the combined organic layers were washed with saturated brine. After drying over anhydrous magnesium sulfate and removing the desiccant by filtration, the filtrate was concentrated under reduced pressure. The resulting residue was purified by silica gel column chromatography (n-hexane:ethyl acetate=95:5-5:95) to give ethyl 1-(2,4-dimethoxybenzyl)-4-hydroxy-2-oxo-1,2,5,6-tetrahydropyridin-3-carboxylate as a brown oil (8.20 g).

$^1$H NMR (300 MHz, CHLOROFORM-d) δ ppm 1.40 (t, J=7.1 Hz, 3 H) 2.55 (t, J=6.6 Hz, 2 H) 3.33-3.44 (m, 2 H) 3.75-3.85 (m, 6 H) 4.38 (q, J=7.1 Hz, 2 H) 4.57 (s, 2 H) 6.37-6.50 (m, 2 H) 7.20-7.26 (m, 1 H).

MS ESI/APCI Dual posi: 336 [M+H]$^+$.

MS ESI/APCI Dual nega: 334[M−H]$^−$.

(3) Synthesis of 2-(trimethylsilyl)ethyl N-{[1-(2,4-dimethoxybenzyl)-4-hydroxy-2-oxo-1,2,5,6-tetrahydropyridin-3-yl]carbonyl}glycinate

[Formula 231]

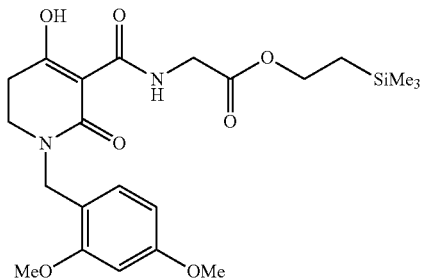

To a solution in 1,2-dimethoxyethane (4.60 mL) of the compound (311 mg) obtained in step (2) above, the compound (195 mg) obtained in Reference Example E-1 was added and the mixture was refluxed for two hours. After being cooled to room temperature, the reaction mixture was concentrated under reduced pressure. Purification by silica gel column chromatography (n-hexane:ethyl acetate=95:5-65:35) gave 2-(trimethylsilyl)ethyl N-{[1-(2,4-dimethoxybenzyl)-4-hydroxy-2-oxo-1,2,5,6-tetrahydropyridin-3-yl]carbonyl}glycinate as a pale yellow oil (283 mg).

$^1$H NMR (300 MHz, CHLOROFORM-d) δ ppm −0.03-0.01 (m, 9 H) 0.97-1.07 (m, 2 H) 2.48-2.62 (m, 2 H) 3.33-3.43 (m, 2 H) 3.76-3.84 (m, 6 H) 4.03-4.13 (m, 2 H) 4.22-4.29 (m, 2 H) 4.52-4.59 (m, 2 H) 6.41-6.50 (m, 2 H) 7.11-7.23 (m, 1 H).

(4) Synthesis of the Titled Compound

To a solution in tetrahydrofuran (3.00 mL) of the compound (283 mg) obtained in step (3) above, tetrabutylammonium fluoride hydrate (1 mol/L, solution in tetrahydrofuran, 0.609 mL) was added and the mixture was stirred at room temperature for 12 hours. More tetrabutylammonium fluoride hydrate (1 mol/L, solution in tetrahydrofuran, 0.609 mL) was added and the mixture was stirred at room temperature for 24.5 hours. The solvent was concentrated under reduced pressure and the resulting residue was purified by silica gel column chromatography (chloroform:methanol=100:0-80:20). To a solution in ethanol of the resulting residue, water was added and the mixture was stirred for 60 hours. After cooling to 0° C., the precipitate was recovered by filtration to give the titled compound as a colorless solid (163 mg).

$^1$H NMR (200 MHz, DMSO-d$_6$) δ ppm 2.36-2.74 (m, 2 H) 3.22-3.43 (m, 2 H) 3.75 (s, 3 H) 3.79 (s, 3 H) 3.99 (d, J=5.7 Hz, 2 H) 4.37-4.52 (m, 2 H) 6.35-6.63 (m, 2 H) 7.07 (d, J=7.5 Hz, 1 H) 9.91-10.22 (m, 1 H).

MS ESI/APCI Dual posi: 365 [M+H]$^+$, 387 [M+Na]$^+$.
MS ESI/APCI Dual nega: 363 [M−H]$^-$.

Example 4-2

N-({4-Hydroxy-2-oxo-1-[4-(prop-2-en-1-yloxy)benzyl]-1,2,5,6-tetrahydropyridin-3-yl}carbonyl)glycine

[Formula 232]

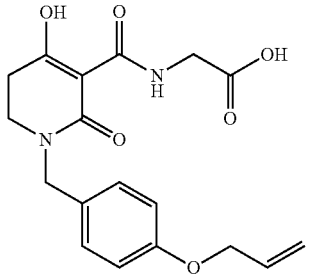

Instead of the compound obtained in Reference Example A-6, the compound obtained in Reference Example A-7 (1.34 g) was used as a starting material and treated by the same technique as in Example 4-1 to give the titled compound as a colorless solid (115 mg).

$^1$H NMR (300 MHz, CHLOROFORM-d) δ ppm 2.48-2.69 (m, 2 H) 3.24-3.40 (m, 2 H) 4.12-4.24 (m, 2 H) 4.47-4.61 (m, 4 H) 5.24-5.34 (m, 1 H) 5.35-5.47 (m, 1 H) 6.05 (ddt, J=17.3, 10.5, 5.2 Hz, 1 H) 6.84-6.93 (m, 2 H) 7.14-7.23 (m, 2 H) 10.06-10.49 (m, 1 H).

MS ESI/APCI Dual posi: 361 [M+H]$^+$, 383 [M+Na]$^+$.
MS ESI/APCI Dual nega: 359 [M−H]$^-$.

Example 4-3

N-{[4-Hydroxy-1-(4-hydroxybenzyl)-2-oxo-1,2,5,6-tetrahydro-3-pyridinyl]carbonyl}glycine

[Formula 233]

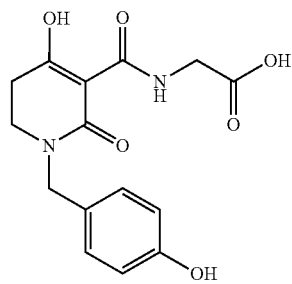

(1) Synthesis of 2-(trimethylsilyl)ethyl N-({1-[4-(allyloxy)benzyl]-4-hydroxy-2-oxo-1,2,5,6-tetrahydro-3-pyridinyl}carbonyl)glycinate

[Formula 234]

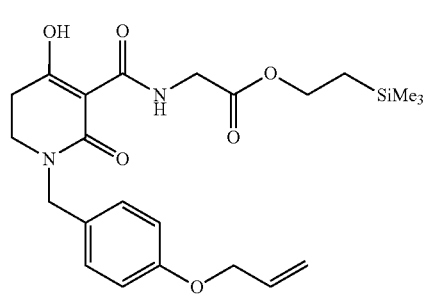

Instead of the compound obtained in Reference Example A-6, the compound (1.34 g) obtained in Reference Example A-7 was used as a starting material and treated by the same techniques as in Example 4-1(1) to (3) to give 2-(trimethylsilyl)ethyl N-({1-[4-(allyloxy)benzyl]-4-hydroxy-2-oxo-1,2,5,6-tetrahydro-3-pyridinyl}carbonyl)glycinate as a pale yellow oil (1.16 g).

$^1$H NMR (300 MHz, CHLOROFORM-d) δ ppm 0.05 (s, 9 H) 0.97-1.09 (m, 2 H) 2.45-2.64 (m, 2 H) 3.25-3.37 (m, 2 H) 4.05-4.16 (m, 2 H) 4.23-4.32 (m, 2 H) 4.50-4.56 (m, 4 H) 5.24-5.34 (m, 1 H) 5.35-5.47 (m, 1 H) 6.05 (ddt, J=17.3, 10.6, 5.3, 5.3 Hz, 1 H) 6.83-6.93 (m, 2 H) 7.14-7.22 (m, 2 H) 10.19-10.53 (m, 1 H).

MS ESI/APCI Dual posi: 461[M+H]$^+$.
MS ESI/APCI Dual nega: 459 [M−H]$^-$.

(2) Synthesis of 2-(trimethylsilyl)ethyl N-{[4-hydroxy-1-(4-hydroxybenzyl)-2-oxo-1,2,5,6-tetrahydro-3-pyridinyl]carbonyl}glycinate

[Formula 235]

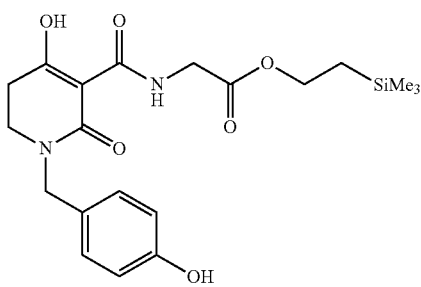

To a solution in tetrahydrofuran (3.8 mL) of the compound (520 mg) obtained in step (1) above, tetrakis(triphenylphosphine)palladium(0) (261 mg) and morpholine (492 μL) were added and the mixture was stirred at room temperature for 22.5 hours. After concentrating under reduced pressure, the resulting residue was purified by silica gel column chromatography (n-hexane:ethyl acetate=85:15-55:45) to give 2-(trimethylsilyl)ethyl N-{[4-hydroxy-1-(4-hydroxybenzyl)-2-oxo-1,2,5,6-tetrahydro-3-pyridinyl]carbonyl}glycinate as a pale yellow oil (362 mg).

$^1$H NMR (300 MHz, CHLOROFORM-d) δ ppm 0.05 (s, 9 H) 0.96-1.12 (m, 2 H) 2.46-2.66 (m, 2 H) 3.24-3.37 (m, 2 H) 4.05-4.16 (m, 2 H) 4.22-4.35 (m, 2 H) 4.54 (s, 2 H) 6.74-6.86 (m, 2 H) 7.10-7.19 (m, 2 H) 10.16-10.49 (m, 1 H).

MS ESI/APCI Dual posi: 421 [M+H]$^+$, 443 [M+Na]$^+$.

MS ESI/APCI Dual nega: 419 [M−H]$^-$, 455 [M+Cl]$^-$.

(3) Synthesis of the Titled Compound

The compound (362 mg) obtained in step (2) above was used and treated by the same technique as in 4-1(4) to give the titled compound as a colorless amorphous mass (138 mg).

$^1$H NMR (300 MHz, DMSO-d$_6$) δ ppm 2.38-2.71 (m, 2 H) 3.25-3.36 (m, 2 H) 3.96-4.09 (m, 2 H) 4.39-4.54 (m, 2 H) 6.65-6.79 (m, 2 H) 7.04-7.15 (m, 2 H) 9.25-9.46 (m, 1 H) 10.01-10.26 (m, 1 H).

MS ESI/APCI Dual posi: 343 [M+Na]$^+$.

MS ESI/APCI Dual nega: 319[M−H]$^-$.

Example 5-1 and Example 5-2

N-{[(5S)-1-(Biphenyl-4-ylmethyl)-4-hydroxy-5-methyl-2-oxo-1,2,5,6-tetrahydropyridin-3-yl]carbonyl}glycine sodium salt Example 5-1

N-{[(5R)-1-(Biphenyl-4-ylmethyl)-4-hydroxy-5-methyl-2-oxo-1,2,5,6-tetrahydropyridin-3-yl]carbonyl}glycine sodium salt Example 5-2

[Formula 236]

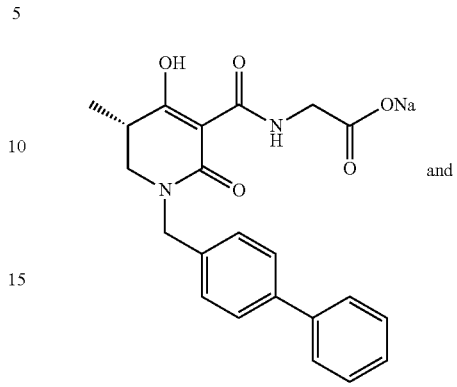

and

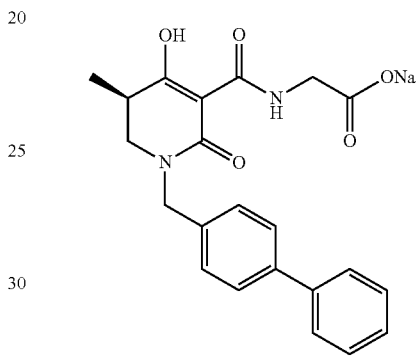

The compound (2.00 g) obtained in Example 1-22 was isolated and purified by optical preparative HPLC to give a less polar isomer (956 mg, 99.9% ee) and a more polar isomer (861 mg, 94.1% ee). To a solution of the resulting less polar isomer (956 mg) in acetone, 1 mol/L sodium hydroxide in aqueous solution (2.42 mL) was added. The resulting precipitate was recovered by filtration to give the titled compound of Example 5-1 as a colorless solid (560 mg, 99.9% ee). The aforementioned more polar isomer (861 mg) was likewise treated using 1 mol/L sodium hydroxide in aqueous solution (2.18 mL) to give the titled compound of Example 5-2 as a colorless solid (393 mg, 98.7% ee). The compounds of Examples 5-1 and 5-2 were respectively converted to the compounds described in Reference Examples X-1 and X-2 cited hereinafter and the absolute configuration at position 5 of the 2-oxo-1,2,5,6-tetrahydropyridine ring of each isomer was determined by X-ray crystallography.

N-{[(5S)-1-(Biphenyl-4-ylmethyl)-4-hydroxy-5-methyl-2-oxo-1,2,5,6-tetrahydropyridin-3-yl]carbonyl}glycine sodium salt Example 5-1

$^1$H NMR (300 MHz, DMSO-d$_6$) δ ppm 1.03 (d, J=6.8 Hz, 3 H) 2.55-2.74 (m, 1 H) 2.96-3.12 (m, 1 H) 3.37-3.47 (m, 1 H) 3.53 (d, J=4.5 Hz, 2 H) 4.45-4.73 (m, 2 H) 7.29-7.40 (m, 3 H) 7.41-7.50 (m, 2 H) 7.59-7.70 (m, 4 H) 10.18 (br. s., 1 H).

MS ESI/APCI Dual posi: 395 [M+H]$^+$.

MS ESI/APCI Dual nega: 393 [M−H]$^-$.

Optical HPLC retention time: 9.136 min.

N-{[(5R)-1-(Biphenyl-4-ylmethyl)-4-hydroxy-5-methyl-2-oxo-1,2,5,6-tetrahydropyridin-3-yl]carbonyl}glycine sodium salt Example 5-2

$^1$H NMR (300 MHz, DMSO-d$_6$) δ ppm 1.03 (d, J=6.8 Hz, 3 H) 2.56-2.74 (m, 1 H) 2.97-3.13 (m, 1 H) 3.37-3.47 (m, 1 H) 3.53 (d, J=4.5 Hz, 2 H) 4.45-4.73 (m, 2 H) 7.29-7.40 (m, 3 H) 7.40-7.50 (m, 2 H) 7.59-7.72 (m, 4 H) 10.18 (br. s., 1 H).
MS ESI/APCI Dual posi: 395 [M+H]$^+$.
MS ESI/APCI Dual nega: 393 [M−H]$^−$.
Optical HPLC retention time: 9.705 min.

Example 6-1

N-{[1-(4-Biphenylylmethyl)-4-hydroxy-2-oxo-1-azaspiro[4.4]non-3-en-3-yl]carbonyl}glycine

[Formula 237]

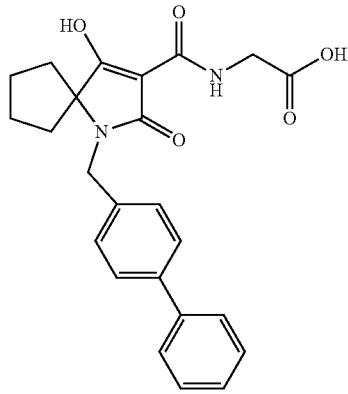

(1) Synthesis of methyl 1-{(4-biphenylylmethyl)[3-({2-[(2-methyl-2-propanyl)oxy]-2-oxoethyl}amino)-3-oxopropanoyl]amino}cyclopentanecarboxylate

[Formula 238]

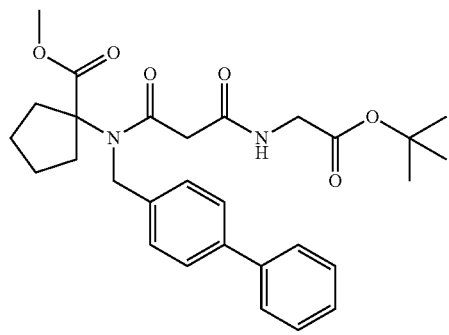

Instead of monobenzyl malonate and glycine tert-butyl hydrochloride, the compound (300 mg) obtained in Reference Example G-1 and the compound (513 mg) obtained in Reference Example A-306 were respectively used and treated by the same technique as in Reference Example G-1(1) to give methyl 1-{(4-biphenylylmethyl)[3-({2-[(2-methyl-2-propanyl)oxy]-2-oxoethyl}amino)-3-oxopropanoyl]amino}cyclopentanecarboxylate as a colorless solid (478 mg).

$^1$H NMR (600 MHz, CHLOROFORM-d) δ ppm 1.47 (s, 9 H) 1.60-1.68 (m, 2 H) 1.71-1.80 (m, 2 H) 1.84-1.92 (m, 2 H) 2.44-2.50 (m, 2 H) 3.32 (s, 2 H) 3.76 (s, 3 H) 3.93 (d, J=5.8 Hz, 2 H) 4.73 (s, 2 H) 7.33-7.47 (m, 5 H) 7.56-7.63 (m, 4 H) 7.81-7.88 (m, 1 H).
MS ESI posi: 531 [M+Na]$^+$.

(2) Synthesis of the titled compound

To a solution in ethanol (5.31 mL) of the compound (270 mg) obtained in step (1) above, cesium carbonate (346 mg) was added and the mixture was stirred at room temperature for an hour. The reaction mixture was concentrated under reduced pressure and 1 mol/L hydrochloric acid was added to the resulting residue. Extraction was conducted with ethyl acetate and the combined organic layers were dried over anhydrous sodium sulfate. After removing the desiccant by filtration, the filtrate was concentrated under reduced pressure. To a solution of the resulting concentrate (253 mg) in chloroform (4.88 mL), trifluoroacetic acid (2.44 mL) was added and the mixture was stirred at room temperature for 15 hours. After concentrating under reduced pressure, the residue was recrystallized with a liquid mixture of n-hexane and ethyl acetate and the precipitate was recovered by filtration to give the titled compound as a colorless solid (335 g).

$^1$H NMR (600 MHz, DMSO-d$_6$) δ ppm 1.67-1.84 (m, 6 H) 1.84-1.92 (m, 2 H) 3.97-4.02 (m, 2 H) 4.58 (s, 2 H) 7.33-7.40 (m, 3 H) 7.43-7.48 (m, 2 H) 7.61-7.67 (m, 4 H) 8.34-8.41 (m, 1 H).
MS ESI/APCI Dual posi: 421 [M+H]$^+$.
MS ESI/APCI Dual nega: 419[M−H]$^+$.

Example 6-2

N-({(6S)-1-[4-(Cyclopropylmethoxy)benzyl]-4-hydroxy-6-methyl-2-oxo-1,2,5,6-tetrahydro-3-pyridinyl}carbonyl)glycine sodium salt

[Formula 239]

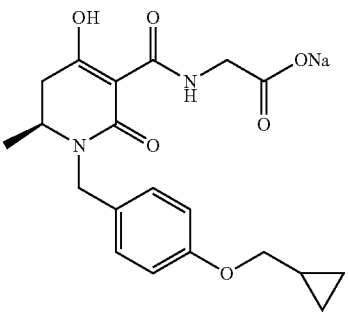

To a solution of the compound (400 mg) of Reference Example G-3 in ethyl acetate (7.07 mL), the compound of Reference Example A-307 (392 mg), triethylamine (428 mg) and propylphosphonic acid anhydride (cyclic trimer) (50%, solution in ethyl acetate, 1.35 g) were added and the mixture was stirred at room temperature for two hours. To the reaction mixture, a saturated aqueous solution of sodium hydrogencarbonate was added and extraction was conducted with ethyl acetate. The combined organic layers were dried over anhydrous sodium sulfate. The desiccant was removed by filtration and the filtrate was concentrated under reduced pressure. To a solution of the resulting residue (708 mg) in ethanol (7.07 mL), cesium carbonate (919 mg) was added and the mixture was stirred at room temperature for two hours. The reaction mixture was concentrated under reduced pressure and 1 mol/L hydrochloric acid was added to the resulting residue. Extraction was conducted with chloroform and the combined organic layers were dried over anhydrous sodium sulfate. After removing the desiccant by filtration, the filtrate was concentrated under reduced pressure. To a solution of the resulting residue (650 mg) in methanol (2.82 mL), 2 mol/L sodium hydroxide in aqueous solution (1.41 mL) was added and the mixture was stirred at room temperature for 15 hours. To the reaction mixture, 2 mol/L hydrochloric acid was added and after the resulting mixture was dissolved in N,N-dimethylformamide, purification was conducted by preparative HPLC. To a solution of the resulting purified product (170 mg) in acetone (4.37 mL), 1 mol/L sodium hydroxide in aqueous solution (437 μL) was added and the mixture was stirred at room temperature for 10 minutes. The reaction mixture was concentrated under reduced pressure and reduced to powder with n-hexane, giving the titled compound as a colorless solid (180 mg).

$^1$H NMR (300 MHz, DMSO-d$_6$) δ ppm 0.26-0.35 (m, 2 H) 0.51-0.61 (m, 2 H) 1.08 (d, J=6.5 Hz, 3 H) 1.13-1.28 (m, 1 H) 2.12-2.26 (m, 1 H) 2.75-2.93 (m, 1 H) 3.51-3.60 (m, 1 H) 3.60-3.66 (m, 2 H) 3.78 (d, J=7.0 Hz, 2 H) 4.05 (d, J=14.9 Hz, 1 H) 4.92 (d, J=14.9 Hz, 1 H) 6.84-6.92 (m, 2 H) 7.17-7.26 (m, 2 H) 10.07 (br. s, 1 H).

MS ESI/APCI Dual posi: 389 [M+H]$^+$.

MS ESI/APCI Dual nega: 387[M−H]$^−$.

The compounds of the following Examples 6-3 to 6-36 were synthesized from the compounds of Reference Examples A-308 to A-340 or A-356 and Reference Example G-1, G-2, or G-3 by the method described in Example 6-1 or 6-2 or modifications thereof. The structures of the synthesized compounds and their NMR and MS data are shown in Tables 23-1 to 23-5.

TABLE 23-1

| Compound No. | Structure | Analytical Data | Salt information |
|---|---|---|---|
| Example 6-3 | 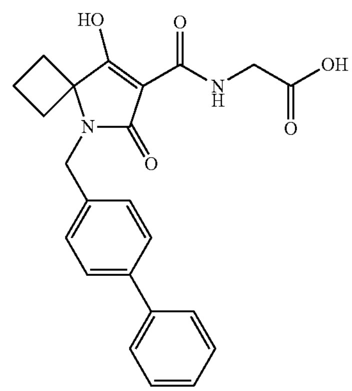 [SMILES: O=C(O)CNC(=O)C1=C(O)C2(CCC2)N(Cc2ccc(-c3ccccc3)cc2)C1=O] | $^1$H NMR (600 MHz, DMSO-d$_6$) δ ppm 1.73-1.82 (m, 1 H) 1.87-1.96 (m, 1 H) 2.20-2.28 (m, 2 H) 2.45-2.56 (m, 2 H) 3.97-4.01 (m, 2 H) 4.75 (s, 2 H) 7.33-7.37 (m, 3 H) 7.43-7.48 (m, 2 H) 7.61-7.67 (m, 4 H).<br>MS ESI/APCI Dual posi: 407[M + H]$^+$.<br>MS ESI/APCI Dual nega: 405[M − H]$^−$. | |
| Example 6-4 | 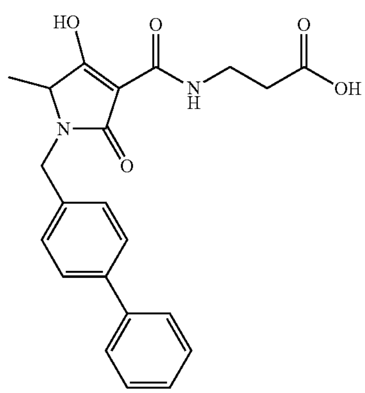 [SMILES: CC1C(O)=C(C(=O)NCCC(=O)O)C(=O)N1Cc1ccc(-c2ccccc2)cc1] | $^1$H NMR (300 MHz, CHLOROFORM-d) δ ppm 1.37 (d, J = 6.8 Hz, 3 H) 2.68 (t, J = 6.1 Hz, 2 H) 3.62-3.74 (m, 2 H) 3.94-3.99 (m, 1 H) 4.08-4.17 (m, 1 H) 5.11 (d, J = 15.2 Hz, 1 H) 7.26-7.47 (m, 4 H) 7.51-7.60 (m, 5 H) 8.18 (br. s., 1 H).<br>MS ESI/APCI Dual posi: 395[M + H]$^+$.<br>MS ESI/APCI Dual nega: 393[M − H]$^−$. | |
| Example 6-5 | 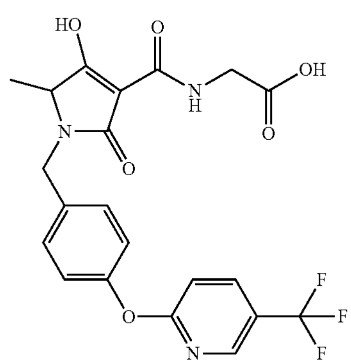 [SMILES: CC1C(O)=C(C(=O)NCC(=O)O)C(=O)N1Cc1ccc(Oc2ccc(C(F)(F)F)cn2)cc1] | $^1$H NMR (300 MHz, DMSO-d$_6$) δ ppm 1.10 (d, J = 6.8 Hz, 3 H) 3.13-3.21 (m, 1 H) 3.51 (d, J = 4.7 Hz, 2 H) 4.08 (d, J = 15.5 Hz, 1 H) 4.85 (d, J = 15.5 Hz, 1 H) 7.09-7.16 (m, 2 H) 7.20 (d, J = 8.7 Hz, 1 H) 7.27 (d, J = 8.7 Hz, 2 H) 8.21 (dd, J = 9.0, 2.3 Hz, 1 H) 8.56 (dt, J = 1.7, 0.9 Hz, 1 H) 8.74 (t, J = 4.6 Hz, 1 H).<br>MS ESI/APCI Dual posi: 466[M + H]$^+$.<br>MS ESI/APCI Dual nega: 464[M − H]$^−$. | Na |

TABLE 23-1-continued

| Compound No. | Structure | Analytical Data | Salt information |
|---|---|---|---|
| Example 6-6 | 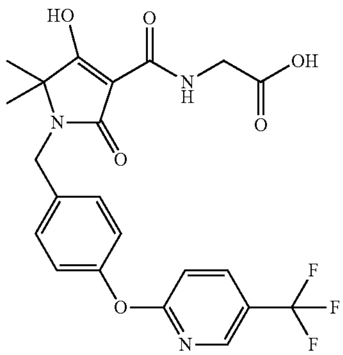 [SMILES: CC1(C)C(O)=C(C(=O)NCC(=O)O)C(=O)N1Cc1ccc(Oc2ccc(C(F)(F)F)cn2)cc1] | $^1$H NMR (300 MHz, DMSO-$d_6$) δ ppm 1.02 (s, 6 H) 3.84 (d, J = 5.4 Hz, 2 H) 4.45 (s, 2 H) 7.04-7.14 (m, 2 H) 7.18 (d, J = 8.7 Hz, 1 H) 7.37 (d, J = 8.7 Hz, 2 H) 8.21 (dd, J = 8.7, 2.3 Hz, 1 H) 8.56 (dd, J = 1.8, 0.9 Hz, 1 H) 8.92 (t, J = 5.6 Hz, 1 H). MS ESI/APCI Dual posi: 480[M + H]$^+$. MS ESI/APCI Dual nega: 478[M − H]$^-$. | Na |
| Example 6-7 | 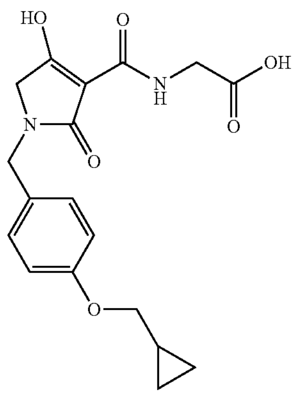 [SMILES: O=C(O)CNC(=O)C1=C(O)CN(Cc2ccc(OCC3CC3)cc2)C1=O] | $^1$H NMR (300 MHz, DMSO-$d_6$) δ ppm 0.30 (dd, J = 4.8, 1.6 Hz, 2 H) 0.48-0.60 (m, 2 H) 1.11-1.26 (m, 1 H) 3.15-3.21 (m, 2 H) 3.65 (d, J = 5.0 Hz, 2 H) 3.77 (d, J = 7.0 Hz, 1 H) 4.31 (d, J = 12.9 Hz, 2 H) 6.68 (d, J = 8.5 Hz, 1 H) 6.84 (d, J = 8.5 Hz, 1 H) 6.97 (d, J = 8.5 Hz, 1 H) 7.08 (d, J = 8.5 Hz, 1 H) 8.72-8.80 (m, 1 H). MS ESI/APCI Dual nega: 359[M − H]$^-$. | Na |
| Example 6-8 | 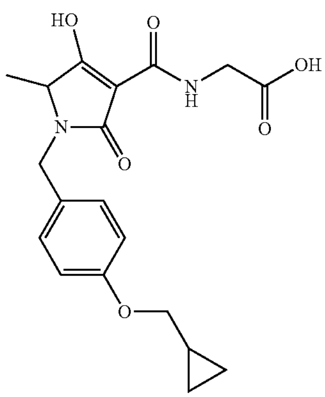 [SMILES: CC1C(O)=C(C(=O)NCC(=O)O)C(=O)N1Cc1ccc(OCC2CC2)cc1] | $^1$H NMR (300 MHz, DMSO-$d_6$) δ ppm 0.25-0.35 (m, 2 H) 0.50-0.60 (m, 2 H) 1.04 (d, J = 6.8 Hz, 3 H) 1.13-1.23 (m, 1 H) 3.02-3.14 (m, 1 H) 3.64-3.94 (m, 4 H) 4.72-4.78 (m, 2 H) 6.67 (d, J = 8.5 Hz, 1 H) 6.72-6.86 (m, 1 H) 6.99 (d, J = 8.5 Hz, 1 H) 7.06-7.13 (m, 1 H) 8.76-8.85 (m, 1 H). MS ESI/APCI Dual posi: 397[M + Na]$^+$. MS ESI/APCI Dual nega: 373[M − H]$^-$. | Na |
| Example 6-9 | 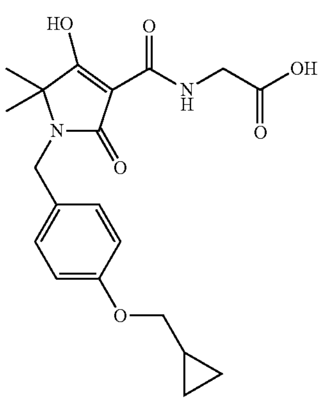 [SMILES: CC1(C)C(O)=C(C(=O)NCC(=O)O)C(=O)N1Cc1ccc(OCC2CC2)cc1] | $^1$H NMR (300 MHz, DMSO-$d_6$) δ ppm 0.21-0.34 (m, 2 H) 0.49-0.61 (m, 2 H) 0.94 (s, 7 H) 2.33-2.49 (m, 2 H) 3.67-3.84 (m, 2 H) 4.26-4.41 (m, 2 H) 6.56-6.67 (m, 1 H) 6.69-6.85 (m, 1 H) 7.04-7.15 (m, 1 H) 7.16-7.25 (m, 1 H) 8.90 (br. s., 1 H). MS ESI/APCI Dual posi: 411[M + Na]$^+$. MS ESI/APCI Dual nega: 387[M − H]$^-$. | Na |

TABLE 23-2

| Compound No. | Structure | Analytical Data | Salt information |
|---|---|---|---|
| Example 6-10 | 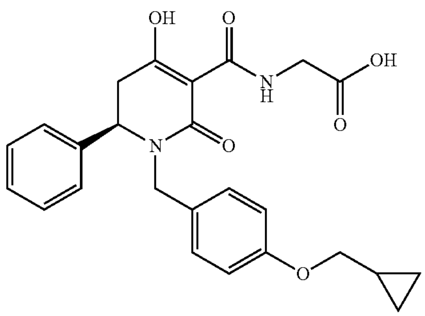 [SMILES: O=C(O)CNC(=O)C1=C(O)C[C@H](c2ccccc2)N(Cc2ccc(OCC3CC3)cc2)C1=O] | $^1$H NMR (300 MHz, DMSO-d$_6$) δ ppm 0.26-0.37 (m, 2 H) 0.49-0.64 (m, 2 H) 1.13-1.28 (m, 1 H) 3.10-3.42 (m, 4 H) 3.46-3.55 (m, 2 H) 3.78 (d, J = 7.0 Hz, 2 H) 4.65 (d, J = 6.4 Hz, 1 H) 5.27 (d, J = 15.5 Hz, 1 H) 6.86 (d, J = 8.7 Hz, 2 H) 7.12-7.22 (m, 4 H) 7.23-7.40 (m, 3 H) 10.09 (br. s., 1 H). MS ESI/APCI Dual posi: 451[M + H]$^+$. MS ESI/APCI Dual nega: 449[M − H]$^-$. | Na |
| Example 6-11 | 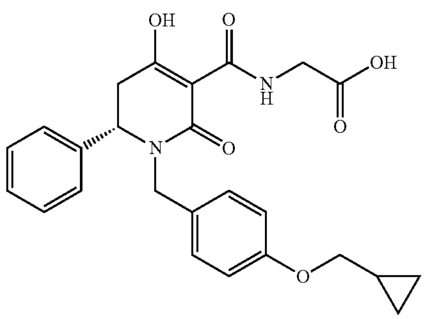 [SMILES: O=C(O)CNC(=O)C1=C(O)C[C@@H](c2ccccc2)N(Cc2ccc(OCC3CC3)cc2)C1=O] | $^1$H NMR (300 MHz, DMSO-d$_6$) δ ppm 0.24-0.37 (m, 2 H) 0.50-0.61 (m, 2 H) 1.13-1.28 (m, 1 H) 3.12-3.34 (m, 4 H) 3.48 (d, J = 4.4 Hz, 2 H) 3.78 (d, J = 6.8 Hz, 2 H) 4.65 (d, J = 7.6 Hz, 1 H) 5.27 (d, J = 15.1 Hz, 1 H) 6.86 (d, J = 8.7 Hz, 2 H) 7.11-7.20 (m, 4 H) 7.32 (d, J = 7.6 Hz, 3 H) 10.08 (br. s., 1 H). MS ESI/APCI Dual posi: 451[M + H]$^+$. MS ESI/APCI Dual nega: 449[M − H]$^-$. | Na |
| Example 6-12 | 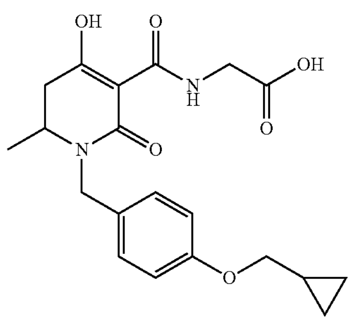 [SMILES: CC1CC(O)=C(C(=O)NCC(=O)O)C(=O)N1Cc1ccc(OCC2CC2)cc1] | $^1$H NMR (300 MHz, DMSO-d$_6$) δ ppm 0.26-0.35 (m, 2 H) 0.51-0.61 (m, 2 H) 1.08 (d, J = 6.5 Hz, 3 H) 1.13-1.28 (m, 1 H) 2.12-2.26 (m, 1 H) 2.75-2.93 (m, 1 H) 3.51-3.60 (m, 1 H) 3.60-3.66 (m, 2 H) 3.78 (d, J = 7.0 Hz, 2 H) 4.05 (d, J = 14.9 Hz, 1 H) 4.92 (d, J = 14.9 Hz, 1 H) 6.84-6.92 (m, 2 H) 7.17-7.26 (m, 2 H) 10.07 (br. s, 1 H). MS ESI/APCI Dual posi: 389[M + H]$^+$. MS ESI/APCI Dual nega: 387[M − H]$^-$. | Na |
| Example 6-13 | 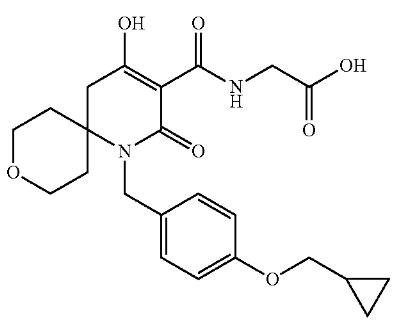 [SMILES: O=C(O)CNC(=O)C1=C(O)CC2(CCOCC2)N(Cc2ccc(OCC3CC3)cc2)C1=O] | $^1$H NMR (300 MHz, DMSO-d$_6$) δ ppm 0.28-0.33 (m, 2 H) 0.53-0.57 (m, 2 H) 1.15-1.24 (m, 1 H) 1.43-1.50 (m, 2 H) 1.85-1.94 (m, 2 H) 2.83-2.95 (m, 2 H) 3.41-3.50 (m, 4 H) 3.64-3.70 (m, 2 H) 3.77 (d, J = 6.6 Hz, 2 H) 4.56-4.75 (m, 2 H) 6.82-6.88 (m, 2 H) 7.17-7.23 (m, 2 H). MS ESI/APCI Dual posi: 445[M + H]$^+$. MS ESI/APCI Dual nega: 443[M − H]$^-$. | Na |
| Example 6-14 | 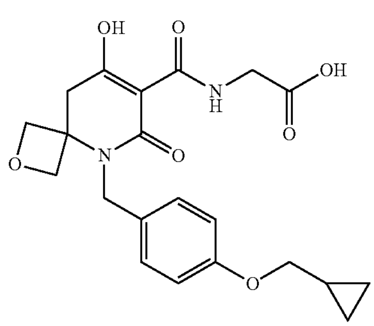 [SMILES: O=C(O)CNC(=O)C1=C(O)CC2(COC2)N(Cc2ccc(OCC3CC3)cc2)C1=O] | $^1$H NMR (300 MHz, DMSO-d$_6$) δ ppm 0.28-0.33 (m, 2 H) 0.53-0.58 (m, 2 H) 1.15-1.25 (m, 1 H) 2.97-3.10 (m, 2 H) 3.45-3.52 (m, 2 H) 3.77 (d, J = 7.0 Hz, 2 H) 4.31 (d, J = 7.0 Hz, 2 H) 4.68 (d, J = 7.0 Hz, 2 H) 4.87-4.96 (m, 2 H) 6.84-6.89 (m, 2 H) 7.16-7.21 (m, 2 H). MS ESI/APCI Dual posi: 417[M + H]$^+$, 439[M + Na]$^+$. MS ESI/APCI Dual nega: 415[M − H]$^-$. | Na |

TABLE 23-2-continued

| Compound No. | Structure | Analytical Data | Salt information |
|---|---|---|---|
| Example 6-15 | 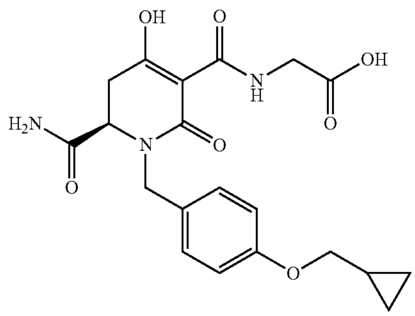 [SMILES: NC(=O)[C@H]1CC(O)=C(C(=O)NCC(=O)O)C(=O)N1Cc1ccc(OCC2CC2)cc1] | $^1$H NMR (300 MHz, DMSO-d$_6$) δ ppm 0.24-0.36 (m, 2 H) 0.49-0.59 (m, 2 H) 1.10-1.27 (m, 1 H) 2.08 (dd, J = 15.1, 8.2 Hz, 1 H) 2.39-2.49 (m, 1 H) 3.46-3.58 (m, 1 H) 3.70 (d, J = 5.1 Hz, 2 H) 3.75 (d, J = 7.0 Hz, 2 H) 3.84 (d, J = 15.1 Hz, 1 H) 4.83 (d, J = 15.1 Hz, 1 H) 6.76-6.83 (m, 2 H) 6.86 (br. s., 1 H) 7.09 (d, J = 8.5 Hz, 2 H) 7.52-7.61 (m, 1 H) 8.71-8.82 (m, 1 H). MS ESI/APCI Dual nega: 416[M − H]$^-$. | Na |
| Example 6-16 | 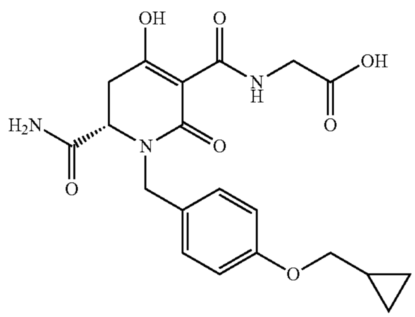 [SMILES: NC(=O)[C@@H]1CC(O)=C(C(=O)NCC(=O)O)C(=O)N1Cc1ccc(OCC2CC2)cc1] | $^1$H NMR (300 MHz, DMSO-d$_6$) δ ppm 0.25-0.39 (m, 2 H) 0.50-0.63 (m, 2 H) 1.14-1.29 (m, 1 H) 2.39-2.70 (m, 2 H) 3.27 (d, J = 15.4 Hz, 1 H) 3.45-3.56 (m, 1 H) 3.73-3.82 (m, 2 H) 4.05-4.22 (m, 1 H) 4.48-4.66 (m, 2 H) 6.80-6.97 (m, 3 H) 7.14 (d, J = 8.9 Hz, 1 H) 7.29-7.37 (m, 2 H) 8.37 (t, J = 5.8 Hz, 1 H) 11.10 (s, 1 H). MS ESI/APCI Dual posi: 440[M + Na]$^+$. MS ESI/APCI Dual nega: 416[M − H]$^-$. | Na |

TABLE 23-3

| Compound No. | Structure | Analytical Data | Salt information |
|---|---|---|---|
| Example 6-17 | 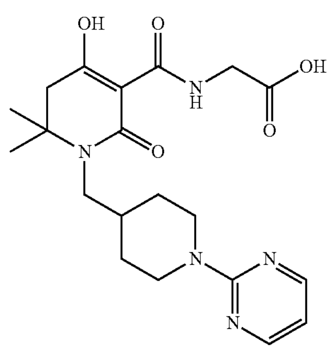 [SMILES: CC1(C)CC(O)=C(C(=O)NCC(=O)O)C(=O)N1CC1CCN(c2ncccn2)CC1] | $^1$H NMR (600 MHz, DMSO-d$_6$) δ ppm 1.04-1.14 (m, 2 H) 1.26 (s, 6 H) 1.66-1.74 (m, 2 H) 1.87-1.97 (m, 1 H) 2.80 (t, J = 11.8 Hz, 2 H) 3.14-3.27 (m, 4 H) 3.45-3.51 (m, 2 H) 4.63-4.70 (m, 2 H) 6.56 (t, J = 4.7 Hz, 1 H) 8.32 (d, J = 4.7 Hz, 2 H). MS ESI/APCI Dual posi: 418[M + H]$^+$. MS ESI/APCI Dual nega: 416[M − H]$^-$. | Na |
| Example 6-18 | 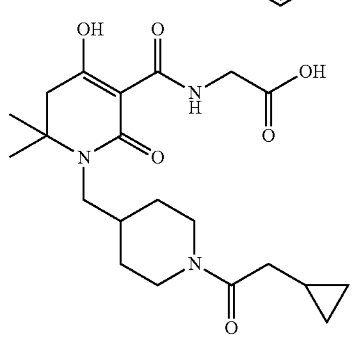 | $^1$H NMR (600 MHz, DMSO-d$_6$) δ ppm 0.06-0.13 (m, 2 H) 0.40-0.47 (m, 2 H) 0.89-1.02 (m, 2 H) 1.03-1.13 (m, 1 H) 1.19-1.30 (m, 6 H) 1.60-1.71 (m, 2 H) 1.77-1.89 (m, 1 H) 2.23 (d, J = 6.6 Hz, 2 H) 2.39-2.49 (m, 1 H) 2.87-2.96 (m, 1 H) 3.09-3.41 (m, 4 H) 3.46-3.53 (m, 3 H) 3.79-3.87 (m, 1 H) 4.35-4.44 (m, 1 H). MS ESI/APCI Dual posi: 422[M + H]$^+$. MS ESI/APCI Dual nega: 420[M − H]$^-$. | Na |

TABLE 23-3-continued

| Compound No. | Structure | Analytical Data | Salt information |
|---|---|---|---|
| Example 6-19 | 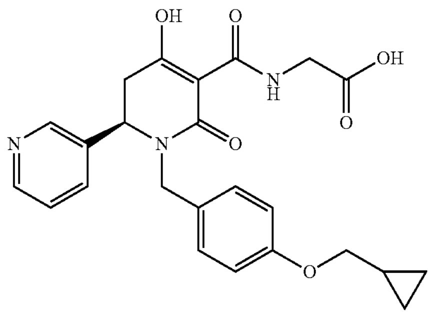 [SMILES: O=C(O)CNC(=O)C1=C(O)C[C@H](c2cccnc2)N(Cc2ccc(OCC3CC3)cc2)C1=O] | $^1$H NMR (300 MHz, DMSO-d$_6$) δ ppm 0.26-0.35 (m, 2 H) 0.51-0.61 (m, 2 H) 1.12-1.27 (m, 1 H) 3.13-3.49 (m, 2 H) 3.72-3.83 (m, 3 H) 3.99-4.08 (m, 2 H) 4.82-4.94 (m, 1 H) 5.13 (d, J = 14.9 Hz, 1 H) 6.84 (d, J = 8.7 Hz, 2 H) 7.14-7.22 (m, 2 H) 7.35-7.43 (m, 1 H) 7.54-7.61 (m, 1 H) 8.37-8.41 (m, 1 H) 8.47-8.52 (m, 1 H) 9.98-10.12 (m, 1 H).<br>MS ESI/APCI Dual posi: 452[M + H]$^+$.<br>MS ESI/APCI Dual nega: 450[M − H]$^−$. | TFA Na |
| Example 6-20 | 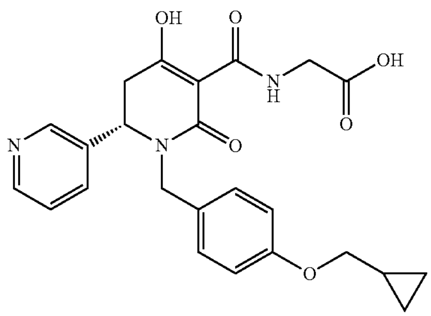 [SMILES: O=C(O)CNC(=O)C1=C(O)C[C@@H](c2cccnc2)N(Cc2ccc(OCC3CC3)cc2)C1=O] | $^1$H NMR (300 MHz, DMSO-d$_6$) δ ppm 0.26-0.34 (m, 2 H) 0.47-0.63 (m, 2 H) 1.13-1.31 (m, 1 H) 3.05-3.49 (m, 2 H) 3.67-3.84 (m, 3 H) 3.96-4.11 (m, 2 H) 4.81-4.96 (m, 1 H) 5.07-5.15 (m, 1 H) 6.77-6.98 (m, 2 H) 7.08-7.27 (m, 2 H) 7.39 (dd, J = 8.2, 5.1 Hz, 1 H) 7.57 (dd, J = 8.2, 2.0 Hz, 1 H) 8.32-8.56 (m, 2 H) 9.88-10.17 (m, 1 H).<br>MS ESI/APCI Dual posi: 452[M + H]$^+$.<br>MS ESI/APCI Dual nega: 450[M − H]$^−$. | TFA Na |
| Example 6-21 | 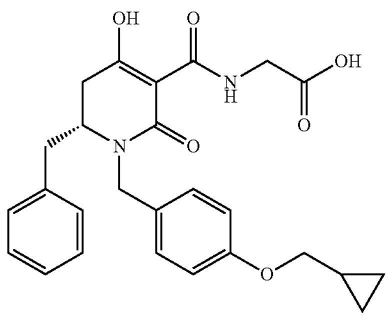 [SMILES: O=C(O)CNC(=O)C1=C(O)C[C@@H](Cc2ccccc2)N(Cc2ccc(OCC3CC3)cc2)C1=O] | $^1$H NMR (600 MHz, DMSO-d$_6$) δ ppm 0.28-0.32 (m, 2 H) 0.52-0.57 (m, 2 H) 1.14-1.23 (m, 1 H) 1.99-2.14 (m, 1 H) 2.41-2.53 (m, 1 H) 2.63-2.71 (m, 1 H) 2.82-2.89 (m, 1 H) 3.44-3.49 (m, 2 H) 3.52-3.62 (m, 1 H) 3.76-3.79 (m, 2 H) 3.81-3.93 (m, 1 H) 4.92-5.01 (m, 1 H) 6.85-6.90 (m, 2 H) 7.10-7.15 (m, 2 H) 7.19-7.25 (m, 3 H) 7.27-7.32 (m, 2 H).<br>MS ESI/APCI Dual posi: 465[M + H]$^+$.<br>MS ESI/APCI Dual nega: 463[M − H]$^−$. | Na |
| Example 6-22 | 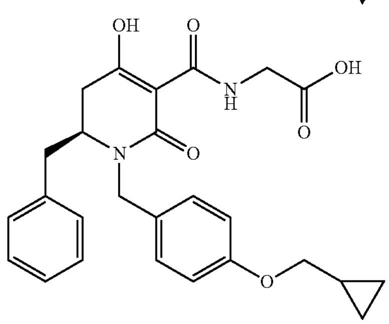 | $^1$H NMR (600 MHz, DMSO-d$_6$) δ ppm 0.28-0.32 (m, 2 H) 0.52-0.57 (m, 2 H) 1.14-1.23 (m, 1 H) 1.99-2.14 (m, 1 H) 2.41-2.53 (m, 1 H) 2.63-2.71 (m, 1 H) 2.82-2.89 (m, 1 H) 3.44-3.49 (m, 2 H) 3.52-3.62 (m, 1 H) 3.76-3.79 (m, 2 H) 3.81-3.93 (m, 1 H) 4.92-5.01 (m, 1 H) 6.85-6.90 (m, 3 H) 7.10-7.15 (m, 2 H) 7.19-7.25 (m, 3 H) 7.27-7.32 (m, 2 H).<br>MS ESI/APCI Dual posi: 465[M + H]$^+$.<br>MS ESI/APCI Dual nega: 463[M − H]$^−$. | Na |
| Example 6-23 | 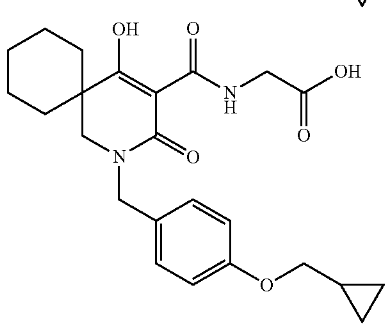 | $^1$H NMR (300 MHz, DMSO-d$_6$) δ ppm 0.24-0.38 (m, 2 H) 0.50-0.61 (m, 2 H) 0.97-1.68 (m, 11 H) 3.20 (s, 2 H) 3.51 (d, J = 4.5 Hz, 2 H) 3.79 (d, J = 7.0 Hz, 2 H) 4.49 (s, 2 H) 6.82-6.95 (m, 2 H) 7.15-7.31 (m, 2 H) 10.24 (br. s., 1 H).<br>MS ESI/APCI Dual posi: 443[M + H]$^+$.<br>MS ESI/APCI Dual nega: 441[M − H]$^−$. | Na |

TABLE 23-4

| Compound No. | Structure | Analytical Data | Salt information |
|---|---|---|---|
| Example 6-24 | 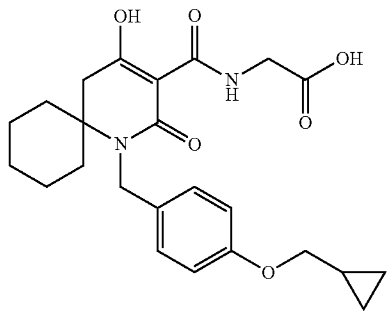 [SMILES: O=C(O)CNC(=O)C1=C(O)CC2(CCCCC2)N(Cc2ccc(OCC3CC3)cc2)C1=O] | ¹H NMR (300 MHz, DMSO-d₆) δ ppm 0.23-0.36 (m, 2 H) 0.49-0.60 (m, 2 H) 0.94-1.71 (m, 11 H) 2.56-2.80 (m, 2 H) 3.45 (d, J = 4.0 Hz, 2 H) 3.77 (d, J = 6.8 Hz, 2 H) 4.63 (br. s., 2 H) 6.83 (d, J = 8.5 Hz, 2 H) 7.18 (d, J = 8.5 Hz, 2 H). MS ESI/APCI Dual posi: 443[M + H]⁺. MS ESI/APCI Dual nega: 441[M − H]⁻. | Na |
| Example 6-25 | 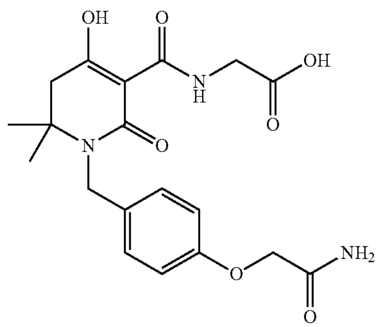 [SMILES: CC1(C)CC(O)=C(C(=O)NCC(=O)O)C(=O)N1Cc1ccc(OCC(N)=O)cc1] | ¹H NMR (300 MHz, DMSO-d₆) δ ppm 1.17 (s, 6 H) 2.54-2.65 (m, 2 H) 3.46 (d, J = 4.2 Hz, 2 H) 4.38 (s, 2 H) 4.49-4.62 (m, 2 H) 6.88 (d, J = 8.7 Hz, 2 H) 7.22 (d, J = 8.7 Hz, 2 H) 7.31-7.41 (m, 1 H) 7.45-7.54 (m, 1 H). MS ESI/APCI Dual posi: 406[M + H]⁺. MS ESI/APCI Dual nega: 404[M − H]⁻. | Na |
| Example 6-26 | 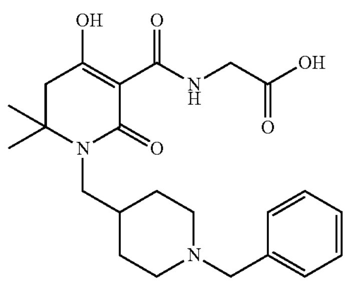 [SMILES: CC1(C)CC(O)=C(C(=O)NCC(=O)O)C(=O)N1CC1CCN(Cc2ccccc2)CC1] | ¹H NMR (600 MHz, DMSO-d₆) δ ppm 1.14-1.27 (m, 8 H) 1.53-1.64 (m, 3 H) 1.81-1.89 (m, 2 H) 2.46-2.58 (m, 2 H) 2.76-2.83 (m, 2 H) 3.12-3.28 (m, 2 H) 3.39-3.48 (m, 4 H) 7.20-7.33 (m, 5 H). MS ESI/APCI Dual posi: 430[M + H]⁺. MS ESI/APCI Dual nega: 428[M − H]⁻. | Na |
| Example 6-27 | 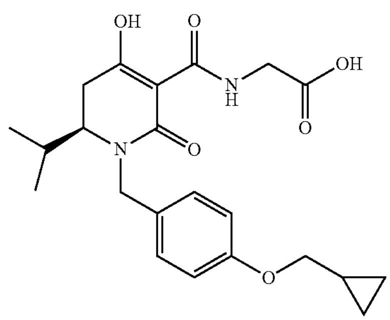 [SMILES: CC(C)[C@H]1CC(O)=C(C(=O)NCC(=O)O)C(=O)N1Cc1ccc(OCC2CC2)cc1] | ¹H NMR (300 MHz, DMSO-d₆) δ ppm 0.24-0.36 (m, 2 H) 0.49-0.61 (m, 2 H) 0.80 (d, J = 6.8 Hz, 3 H) 0.89 (d, J = 6.8 Hz, 3 H) 1.12-1.28 (m, 1 H) 1.96-2.06 (m, 1 H) 2.25-2.41 (m, 1 H) 2.73 (br. s., 1 H) 3.19-3.32 (m, 1 H) 3.55 (d, J = 4.5 Hz, 2 H) 3.78 (d, J = 7.0 Hz, 2 H) 3.95 (d, J = 15.2 Hz, 1 H) 5.12 (d, J = 15.2 Hz, 1 H) 6.76-6.94 (m, 2 H) 7.11-7.28 (m, 2 H) 9.98 (br. s., 1 H). MS ESI/APCI Dual posi: 417[M + H]⁺. MS ESI/APCI Dual nega: 415[M − H]⁻. | Na |
| Example 6-28 | 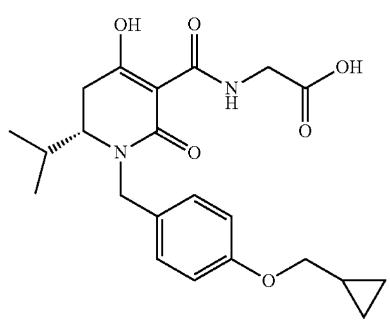 [SMILES: CC(C)[C@@H]1CC(O)=C(C(=O)NCC(=O)O)C(=O)N1Cc1ccc(OCC2CC2)cc1] | ¹H NMR (300 MHz, DMSO-d₆) δ ppm 0.25-0.34 (m, 2 H) 0.49-0.60 (m, 2 H) 0.80 (d, J = 6.8 Hz, 3 H) 0.89 (d, J = 6.8 Hz, 3 H) 1.12-1.28 (m, 1 H) 1.93-2.09 (m, 1 H) 2.21-2.41 (m, 1 H) 2.58-2.86 (m, 1 H) 3.19-3.28 (m, 1 H) 3.50 (d, J = 4.4 Hz, 2 H) 3.78 (d, J = 7.0 Hz, 2 H) 3.86-4.02 (m, 1 H) 5.05-5.24 (m, 1 H) 6.86 (d, J = 8.7 Hz, 2 H) 7.20 (d, J = 8.7 Hz, 2 H) 9.97 (br. s., 1 H). MS ESI/APCI Dual posi: 417[M + H]⁺. MS ESI/APCI Dual nega: 415[M − H]⁻. | Na |

TABLE 23-4-continued

| Compound No. | Structure | Analytical Data | Salt information |
|---|---|---|---|
| Example 6-29 | 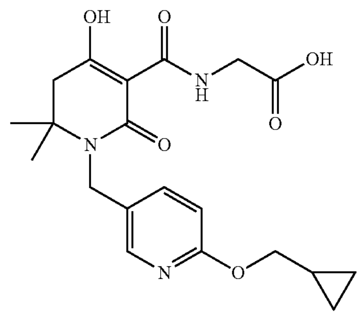 [SMILES: CC1(C)CC(O)=C(C(=O)NCC(=O)O)C(=O)N1Cc1ccc(OCC2CC2)nc1] | ¹H NMR (300 MHz, DMSO-d₆) δ ppm 0.23-0.38 (m, 2 H) 0.46-0.61 (m, 2 H) 1.10-1.28 (m, 7 H) 2.62 (br. s., 2 H) 3.78 (d, J = 5.1 Hz, 2 H) 4.05 (d, J = 7.0 Hz, 2 H) 4.57 (s, 2 H) 6.76 (d, J = 8.5 Hz, 1 H) 7.62 (dd, J = 8.5, 2.5 Hz, 1 H) 8.08 (d, J = 2.5 Hz, 1 H) 10.07 (br. s., 1 H). MS ESI/APCI Dual posi: 404[M + H]⁺. MS ESI/APCI Dual nega: 402[M − H]⁻. | Na |
| Example 6-30 | 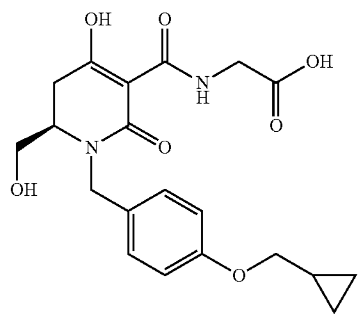 [SMILES: O=C(O)CNC(=O)C1=C(O)C[C@H](CO)N(Cc2ccc(OCC3CC3)cc2)C1=O] | ¹H NMR (300 MHz, DMSO-d₆) δ ppm 0.23-0.38 (m, 2 H) 0.49-0.63 (m, 2 H) 1.11-1.28 (m, 1 H) 3.23-3.40 (m, 2 H) 3.42-3.52 (m, 2 H) 3.78 (d, J = 6.8 Hz, 2 H) 3.95-4.15 (m, 1 H) 5.02 (d, J = 15.1 Hz, 2 H) 6.87 (d, J = 8.7 Hz, 2 H) 7.19 (d, J = 8.7 Hz, 2 H) 9.97 (br. s., 1 H). MS ESI/APCI Dual posi: 405[M + H]⁺. MS ESI/APCI Dual nega: 403[M − H]⁻. | Na |

TABLE 23-5

| Compound No. | Structure | Analytical Data | Salt information |
|---|---|---|---|
| Example 6-31 | 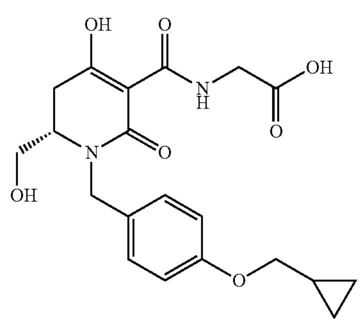 [SMILES: O=C(O)CNC(=O)C1=C(O)C[C@@H](CO)N(Cc2ccc(OCC3CC3)cc2)C1=O] | ¹H NMR (300 MHz, DMSO-d₆) δ ppm 0.24-0.37 (m, 2 H) 0.49-0.61 (m, 2 H) 1.11-1.28 (m, 1 H) 3.25-3.39 (m, 2 H) 3.45 (d, J = 4.4 Hz, 2 H) 3.78 (d, J = 7.0 Hz, 2 H) 3.96-4.13 (m, 1 H) 4.95-5.09 (m, 2 H) 6.82-6.92 (m, 2 H) 7.19 (d, J = 8.5 Hz, 2 H). MS ESI/APCI Dual posi: 405[M + H]⁺. MS ESI/APCI Dual nega: 403[M − H]⁻. | Na |
| Example 6-32 | 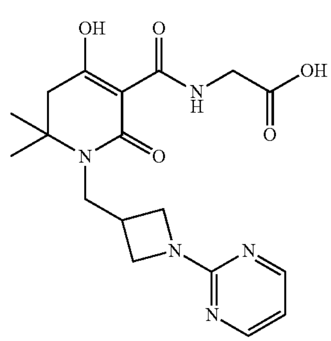 [SMILES: CC1(C)CC(O)=C(C(=O)NCC(=O)O)C(=O)N1CC1CN(c2ncccn2)C1] | ¹H NMR (600 MHz, DMSO-d₆) δ ppm 1.21-1.37 (m, 6 H) 2.43-2.72 (m, 3 H) 3.26-3.35 (m, 2 H) 3.50-3.62 (m, 4 H) 4.05-4.14 (m, 1 H) 4.28-4.37 (m, 1 H) 6.96-7.01 (m, 1 H) 8.38-8.44 (m, 1 H) 8.73-8.78 (m, 1 H). MS ESI/APCI Dual posi: 390[M + H]⁺. MS ESI/APCI Dual nega: 388[M − H]⁻. | TFA Na |

TABLE 23-5-continued

| Compound No. | Structure | Analytical Data | Salt information |
|---|---|---|---|
| Example 6-33 | 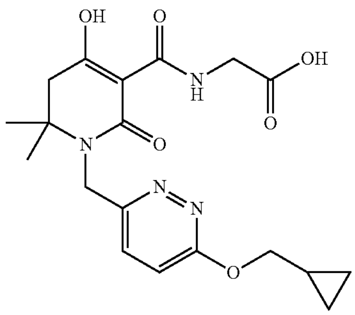 [SMILES: CC1(C)CC(O)=C(C(=O)NCC(=O)O)C(=O)N1Cc1ccc(OCC2CC2)nn1] | $^1$H NMR (600 MHz, DMSO-d$_6$) δ ppm 0.34-0.39 (m, 2 H) 0.54-0.59 (m, 2 H) 1.20 (s, 6 H) 1.25-1.33 (m, 1 H) 2.43-2.55 (m, 2 H) 3.37-3.45 (m, 2 H) 4.24 (d, J = 7.4 Hz, 2 H) 4.73-4.81 (m, 2 H) 7.13-7.19 (m, 1 H) 7.49-7.56 (m, 1 H). MS ESI/APCI Dual posi: 405[M + H]$^+$. MS ESI/APCI Dual nega: 403[M − H]$^-$. | Na |
| Example 6-34 | 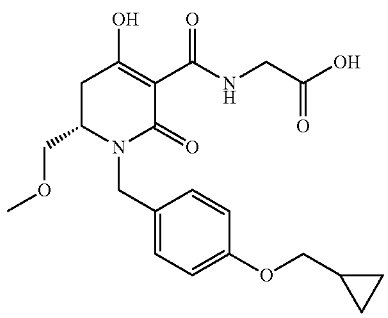 [SMILES: COC[C@@H]1CC(O)=C(C(=O)NCC(=O)O)C(=O)N1Cc1ccc(OCC2CC2)cc1] | $^1$H NMR (300 MHz, DMSO-d$_6$) δ ppm 0.24-0.35 (m, 2 H) 0.49-0.61 (m, 2 H) 1.12-1.27 (m, 1 H) 2.22-2.40 (m, 1 H) 2.64-2.90 (m, 1 H) 3.21 (s, 3 H) 3.26-3.36 (m, 2 H) 3.61 (d, J = 4.5 Hz, 2 H) 3.54-3.63 (m, 1 H) 3.78 (d, J = 7.0 Hz, 2 H) 3.98-4.14 (m, 1 H) 4.86-5.08 (m, 1 H) 6.87 (d, J = 8.7 Hz, 2 H) 7.20 (d, J = 8.7 Hz, 2 H). MS ESI/APCI Dual posi: 419[M + H]$^+$. MS ESI/APCI Dual nega: 417[M − H]$^-$. | Na |
| Example 6-35 | 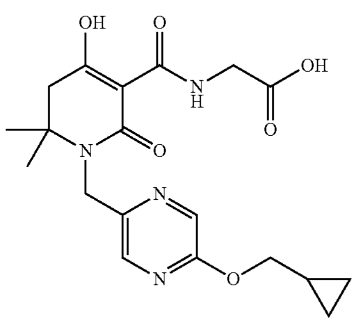 [SMILES: CC1(C)CC(O)=C(C(=O)NCC(=O)O)C(=O)N1Cc1cnc(OCC2CC2)cn1] | $^1$H NMR (600 MHz, DMSO-d$_6$) δ ppm 0.31-0.36 (m, 2 H) 0.51-0.58 (m, 2 H) 1.16-1.29 (m, 7 H) 2.44-2.60 (m, 2 H) 3.46 (d, J = 4.1 Hz, 2 H) 4.11 (d, J = 7.0 Hz, 2 H) 4.62 (br. s., 2 H) 8.15 (s, 1 H) 8.22 (s, 1 H). MS ESI/APCI Dual posi: 405[M + H]$^+$. MS ESI/APCI Dual nega: 403[M − H]$^-$. | Na |
| Example 6-36 | 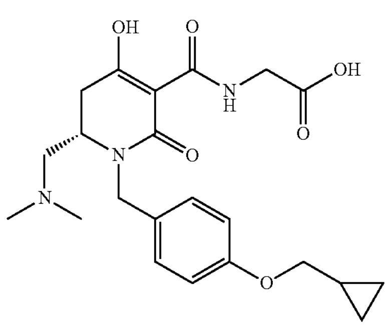 [SMILES: CN(C)C[C@@H]1CC(O)=C(C(=O)NCC(=O)O)C(=O)N1Cc1ccc(OCC2CC2)cc1] | $^1$H NMR (300 MHz, DMSO-d$_6$) δ ppm 0.24-0.36 (m, 2 H) 0.48-0.61 (m, 2 H) 1.07-1.27 (m, 1 H) 2.09 (s, 6 H) 2.13-2.39 (m, 2 H) 2.61-2.90 (m, 2 H) 3.43-3.68 (m, 1 H) 3.70-3.84 (m, 4 H) 3.99-4.16 (m, 1 H) 4.96 (d, J = 14.9 Hz, 1 H) 6.82-6.94 (m, 2 H) 7.17-7.27 (m, 2 H). MS ESI/APCI Dual posi: 432[M + H]$^+$. MS ESI/APCI Dual nega: 430[M − H]$^-$. | TFA Na |

Example 7-1

N-{[9-Benzoyl-1-(4-biphenylylmethyl)-4-hydroxy-2-oxo-1,9-diazaspiro[5.5]undec-3-en-3-yl]carbonyl}glycine

[Formula 240]

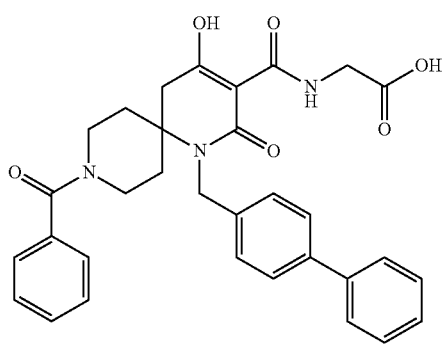

(1) Synthesis of 2-methyl-2-propanyl 4-[(4-biphenylylmethyl)(3-ethoxy-3-oxopropanoyl)amino]-4-(2-methoxy-2-oxoethyl)-1-piperidinecarboxylate

[Formula 241]

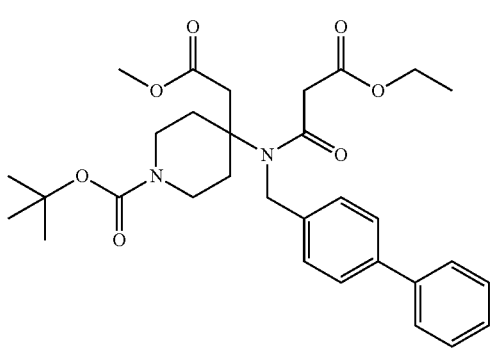

To a solution of the compound of Reference Example A-344 (3.14 g) and triethylamine (1.50 mL) in ethyl acetate (100 mL), ethyl malonyl chloride (1.22 mL) was added at 0° C. and thereafter the mixture was stirred at room temperature for 30 minutes. The insoluble matter was removed by filtration and the filtrate was concentrated under reduced pressure. The resulting residue was purified by silica gel column chromatography (n-hexane:ethyl acetate=90:10-50:50) to give 2-methyl-2-propanyl 4-[(4-biphenylylmethyl)(3-ethoxy-3-oxopropanoyl)amino]-4-(2-methoxy-2-oxoethyl)-1-piperidinecarboxylate as a colorless amorphous mass (3.36 g).

$^1$H NMR (600 MHz, CHLOROFORM-d) δ ppm 1.26 (t, J=7.2 Hz, 3 H) 1.38 (s, 9 H) 1.68-1.79 (m, 2 H) 2.69-2.81 (m, 2 H) 2.82-2.96 (m, 2 H) 3.29-3.37 (m, 2 H) 3.39 (s, 2 H) 3.72 (s, 3 H) 3.80-4.04 (m, 2 H) 4.17 (q, J=7.2 Hz, 2 H) 4.73 (s, 2 H) 7.27-7.31 (m, 2 H) 7.34-7.38 (m, 1 H) 7.43-7.47 (m, 2 H) 7.56-7.63 (m, 4 H).

MS ESI/APCI Dual posi: 575 [M+Na]$^+$.

(2) Synthesis of 3-ethyl 9-(2-methyl-2-propanyl) 1-(4-biphenylylmethyl)-4-hydroxy-2-oxo-1,9-diazaspiro[5.5]undec-3-ene-3,9-dicarboxylate

[Formula 242]

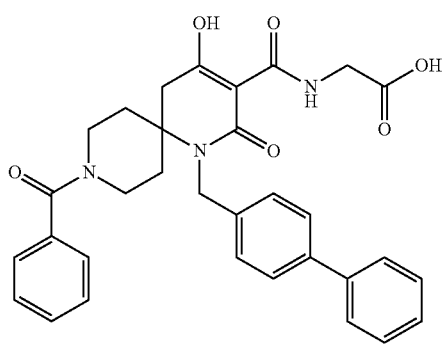

To a solution in tetrahydrofuran (70 mL) of the mixture (3.35 g) obtained in step (1) above, sodium ethoxide (about 20%, solution in ethanol, 2.5 mL) was added and the mixture was stirred with heating under reflux for 4 hours. After cooling to room temperature, 2 mol/L hydrochloric acid was added and extraction was conducted with ethyl acetate. The combined organic layers were dried over anhydrous magnesium sulfate. The desiccant was removed by filtration and the filtrate was concentrated under reduced pressure. The resulting residue was purified by silica gel column chromatography (n-hexane:ethyl acetate=90:10-40:60) to give 3-ethyl 9-(2-methyl-2-propanyl) 1-(4-biphenylylmethyl)-4-hydroxy-2-oxo-1,9-diazaspiro[5.5]undec-3-ene-3,9-dicarboxylate as a colorless amorphous mass (1.87 g).

$^1$H NMR (600 MHz, CHLOROFORM-d) δ ppm 1.41-1.46 (m, 12 H) 1.57 (s, 2 H) 1.64-1.75 (m, 2 H) 1.83-1.99 (m, 2 H) 2.75-2.88 (m, 4 H) 3.91-4.18 (m, 2 H) 4.39-4.45 (m, 2 H) 4.64-4.95 (m, 2 H) 7.30-7.35 (m, 3 H) 7.40-7.44 (m, 2 H) 7.49-7.53 (m, 2 H) 7.55-7.58 (m, 2 H) 14.00-14.18 (m, 1 H).

MS ESI/APCI Dual posi: 521 [M+H]$^+$, 543 [M+Na]$^+$.
MS ESI/APCI Dual nega: 519 [M−H]$^-$.

(3) Synthesis of ethyl 1-(4-biphenylylmethyl)-4-hydroxy-2-oxo-1,9-diazaspiro[5.5]undec-3-ene-3-carboxylate hydrochloride

[Formula 243]

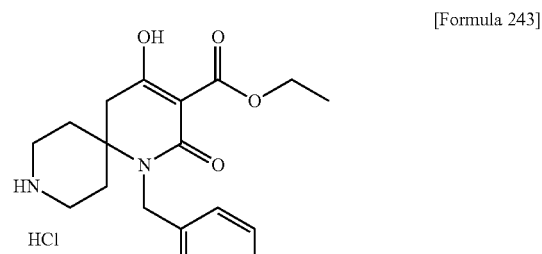

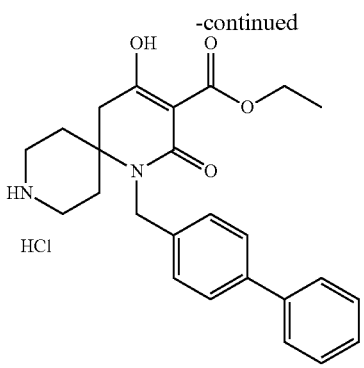

To the compound (1.70 g) obtained in step (2) above, a solution (10 mL) of 4 mol/L hydrogen chloride in 1,4-dioxane was added and the mixture was stirred at room temperature for 68 hours. After concentrating under reduced pressure, the resulting residue was crystallized with a liquid mixture of diethyl ether and ethyl acetate to give ethyl 1-(4-biphenylylmethyl)-4-hydroxy-2-oxo-1,9-diazaspiro[5.5]undec-3-ene-3-carboxylate hydrochloride as a colorless solid (983 mg).

$^1$H NMR (600 MHz, CHLOROFORM-d) δ ppm 1.40 (t, J=7.1 Hz, 3 H) 1.68-1.82 (m, 2 H) 2.55-2.66 (m, 2 H) 2.79-2.87 (m, 2 H) 2.95-3.12 (m, 2 H) 3.36-3.43 (m, 2 H) 4.39 (q, J=7.0 Hz, 2 H) 4.69-5.04 (m, 2 H) 7.28-7.32 (m, 1 H) 7.33-7.37 (m, 2 H) 7.37-7.41 (m, 2 H) 7.46-7.53 (m, 4 H) 9.30-9.44 (m, 1 H) 9.44-9.57 (m, 1 H).

MS ESI/APCI Dual posi: 421 [M+H]$^+$, 443 [M+Na]$^+$.
MS ESI/APCI Dual nega: 419[M−H]$^−$.

(4) Synthesis of ethyl 9-benzoyl-1-(4-biphenylylmethyl)-4-hydroxy-2-oxo-1,9-diazaspiro[5.5]undec-3-ene-3-carboxylate

[Formula 244]

To a solution in tetrahydrofuran (6 mL) of the compound (160 mg) obtained in step (3) above, benzoyl chloride (59 mg) and triethylamine (120 mg) were added and the mixture was stirred at room temperature for 1.5 hours. To the reaction mixture, a saturated aqueous solution of sodium hydrogencarbonate was added and extraction was conducted with ethyl acetate. The combined organic layers were dried over anhydrous magnesium sulfate. The desiccant was removed by filtration and the filtrate was concentrated under reduced pressure. The resulting residue was purified by NH silica gel column chromatography (chloroform:methanol=98:2-80:20) to give ethyl 9-benzoyl-1-(4-biphenylylmethyl)-4-hydroxy-2-oxo-1,9-diazaspiro[5.5]undec-3-ene-3-carboxylate as a colorless solid (56 mg).

MS ESI/APCI Dual posi: 525 [M+H]$^+$.
MS ESI/APCI Dual nega: 523[M−H]$^−$.

(5) Synthesis of 2-methyl-2-propanyl N-{[9-benzoyl-1-(4-biphenylylmethyl)-4-hydroxy-2-oxo-1,9-diazaspiro[5.5]undec-3-en-3-yl]carbonyl}glycinate

[Formula 245]

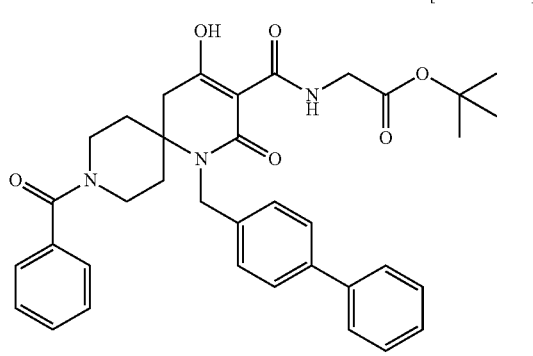

To a solution in N,N-dimethylformamide (4.0 mL) of the compound (52 mg) obtained in step (4) above, glycine tert-butyl hydrochloride (29 mg) was added and the mixture was stirred at 90° C. for two hours. After being cooled to room temperature, the reaction mixture was concentrated under reduced pressure. The resulting residue was purified by silica gel column chromatography to give 2-methyl-2-propanyl N-{[9-benzoyl-1-(4-biphenylylmethyl)-4-hydroxy-2-oxo-1,9-diazaspiro[5.5]undec-3-en-3-yl]carbonyl}glycinate as a colorless oil (14 mg).

$^1$H NMR (600 MHz, CHLOROFORM-d) δ ppm 1.45-1.50 (m, 9 H) 1.61-1.90 (m, 3 H) 2.02-2.17 (m, 1 H) 2.75-2.95 (m, 3 H) 3.02-3.20 (m, 1 H) 3.55-3.75 (m, 1 H) 4.00-4.06 (m, 2 H) 4.68-4.90 (m, 3 H) 7.27-7.46 (m, 10 H) 7.51-7.59 (m, 4 H) 10.14-10.41 (m, 1 H).

MS ESI/APCI Dual posi: 610 [M+H]$^+$, 632 [M+Na]$^+$.
MS ESI/APCI Dual nega: 608 [M−H]$^−$.

(6) Synthesis of the Titled Compound

The compound (14 mg) obtained in step (5) above was used and treated by the same technique as in Example 1-2(2) to give the titled compound as a colorless solid (6 mg).

$^1$H NMR (500 MHz, CHLOROFORM-d) δ ppm 1.62-1.86 (m, 3 H) 2.09 (s, 1 H) 2.79-2.96 (m, 3 H) 3.04-3.17 (m, 1 H) 3.57-3.74 (m, 1 H) 4.14-4.22 (m, 2 H) 4.63-4.95 (m, 3 H) 7.27-7.47 (m, 10 H) 7.50-7.61 (m, 4 H) 10.16-10.37 (m, 1 H).

MS ESI/APCI Dual posi: 554 [M+H]$^+$, 576 [M+Na]$^+$.
MS ESI/APCI Dual nega: 552[M−H]$^−$.

Example 7-2

N-{[9-Benzyl-1-(4-biphenylylmethyl)-4-hydroxy-2-oxo-1,9-diazaspiro[5.5]undec-3-en-3-yl]carbonyl}glycine trifluoroacetate

[Formula 246]

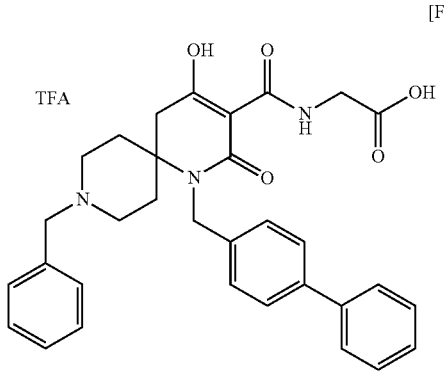

(1) Synthesis of ethyl 9-benzyl-1-(4-biphenylylmethyl)-4-hydroxy-2-oxo-1,9-diazaspiro[5.5]undec-3-ene-3-carboxylate

[Formula 247]

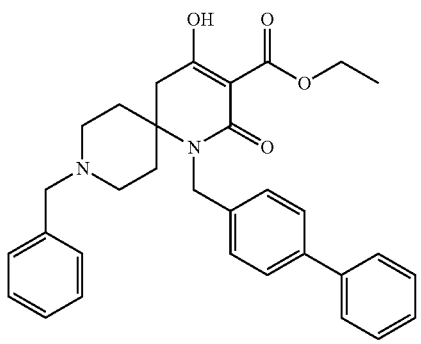

To a solution in chloroform (3 mL) of the compound (128 mg) obtained in Example 7-1(3), triethylamine (77 mg), N,N-dimethylformamide (1 mL) and benzyl bromide (63 mg) were added successively and the mixture was stirred at 50° C. for two hours. After cooling the reaction mixture to room temperature, water was added to it. Extraction was conducted with chloroform and the combined organic layers were concentrated under reduced pressure. The resulting residue was purified by NH silica gel column chromatography (chloroform:methanol=97:3-80:20) to give ethyl 9-benzyl-1-(4-biphenylylmethyl)-4-hydroxy-2-oxo-1,9-diazaspiro[5.5]undec-3-ene-3-carboxylate as a colorless solid (32 mg).

$^1$H NMR (600 MHz, CHLOROFORM-d) δ ppm 1.41 (t, J=7.1 Hz, 3 H) 1.60-1.69 (m, 2 H) 2.02-2.15 (m, 4 H) 2.71-2.85 (m, 4 H) 3.48 (s, 2 H) 4.39 (q, J=7.1 Hz, 2 H) 4.72-4.96 (m, 2 H) 7.23-7.28 (m, 3 H) 7.28-7.34 (m, 5 H) 7.39-7.43 (m, 2 H) 7.46-7.58 (m, 4 H).

MS ESI/APCI Dual posi: 511 [M+H]$^+$.
MS ESI/APCI Dual nega: 509 [M−H]$^-$.

(2) Synthesis of 2-methyl-2-propanyl N-{[9-benzyl-1-(4-biphenylylmethyl)-4-hydroxy-2-oxo-1,9-diazaspiro[5.5]undec-3-en-3-yl]carbonyl}glycinate

[Formula 248]

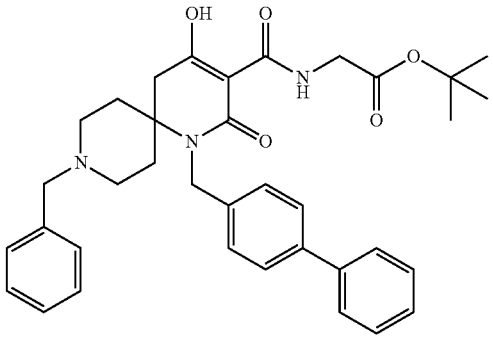

The compound (32 mg) obtained in step (1) above was used and treated by the same technique as in Example 7-1(5) to give 2-methyl-2-propanyl N-{[9-benzyl-1-(4-biphenylylmethyl)-4-hydroxy-2-oxo-1,9-diazaspiro[5.5]undec-3-en-3-yl]carbonyl}glycinate as a colorless oil (32 mg).

$^1$H NMR (600 MHz, CHLOROFORM-d) δ ppm 1.46 (s, 9 H) 1.60-1.67 (m, 2 H) 1.99-2.08 (m, 2 H) 2.09-2.19 (m, 2 H) 2.70-2.82 (m, 4 H) 3.30 (s, 2 H) 3.98-4.06 (m, 2 H) 4.75-4.86 (m, 2 H) 7.22-7.27 (m, 3 H) 7.27-7.35 (m, 5 H) 7.39-7.44 (m, 2 H) 7.48-7.58 (m, 4 H) 10.18-10.40 (m, 1 H).

MS ESI/APCI Dual posi: 596 [M+H]$^+$.
MS ESI/APCI Dual nega: 594 [M−H]$^-$.

(3) Synthesis of the Titled Compound

The compound (27 mg) obtained in step (2) above was used and treated by the same technique as in Example 1-2(2) to give the titled compound as a pale yellow solid (31 mg).

$^1$H NMR (600 MHz, METHANOL-d$_4$) δ ppm 1.95-2.03 (m, 2 H) 2.18-2.28 (m, 2 H) 3.00-3.27 (m, 4 H) 3.33-3.39 (m, 2 H) 3.58 (s, 2 H) 4.07-4.13 (m, 2 H) 4.26 (s, 2 H) 7.27-7.37 (m, 3 H) 7.37-7.41 (m, 2 H) 7.42-7.49 (m, 5 H) 7.53-7.59 (m, 4 H).

MS ESI/APCI Dual posi: 540 [M+H]$^+$.

Example 7-3

N-[(9-Benzoyl-1-benzyl-4-hydroxy-2-oxo-1,9-diazaspiro[5.5]undec-3-en-3-yl)carbonyl]glycine

[Formula 249]

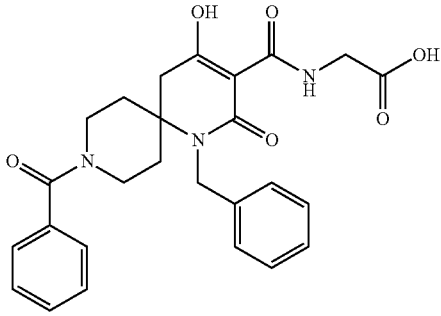

Instead of the compound obtained in Reference Example A-344, the compound (1.08 g) obtained in Reference Example A-341 was used and treated by the same technique as in Example 7-1 to give the titled compound as a colorless solid (25 mg).

$^1$H NMR (600 MHz, DMSO-d$_6$) δ ppm 1.41-1.53 (m, 1 H) 1.57-1.70 (m, 1 H) 1.74-1.93 (m, 2 H) 2.46-2.47 (m, 2 H) 2.79-2.92 (m, 2 H) 2.98-3.09 (m, 2 H) 3.89-4.03 (m, 2 H) 4.70-4.82 (m, 2 H) 7.21-7.35 (m, 7 H) 7.35-7.42 (m, 3 H) 9.92-10.20 (m, 1 H).

MS ESI/APCI Dual posi: 478 [M+H]$^+$, 500 [M+Na]$^+$.

MS ESI/APCI Dual nega: 476[M−H]$^−$.

Example 8-1

4-Hydroxy-N-[2-(hydroxyamino)-2-oxoethyl]-1-(4-methoxybenzyl)-2-oxo-1,2,5,6-tetrahydro-3-pyridinecarboxamide

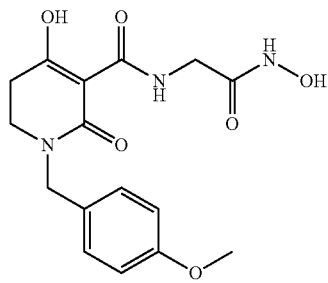

[Formula 250]

Instead of monobenzyl malonate and glycine tert-butyl hydrochloride, the compound (100 mg) obtained in Example 1-48 and hydroxylamine hydrochloride (31 mg) were respectively used and treated by the same technique as in Example G-1(1) to give the titled compound as a colorless amorphous mass (62.2 mg).

$^1$H NMR (300 MHz, CHLOROFORM-d) δ ppm 2.47-2.67 (m, 2 H) 3.26-3.37 (m, 2 H) 3.79 (s, 3 H) 4.00-4.18 (m, 2 H) 4.47-4.59 (m, 2 H) 6.80-6.93 (m, 2 H) 7.14-7.24 (m, 2 H) 10.16-10.28 (m, 1 H).

MS ESI/APCI Dual posi: 350 [M+H]$^+$.

Example 9-1

N-{[4-Hydroxy-1-(4-methoxybenzyl)-2-oxo-1,2,5,6-tetrahydro-3-pyridinyl]carbonyl}-β-alanine

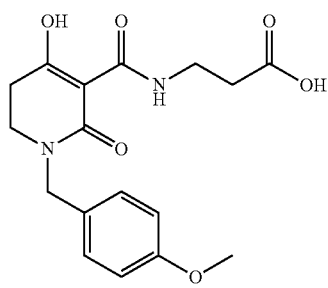

[Formula 251]

(1) Synthesis of sodium 5-(ethoxycarbonyl)-1-(4-methoxybenzyl)-6-oxo-1,2,3,6-tetrahydro-4-pyridinolate

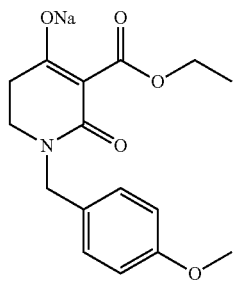

[Formula 252]

Instead of the compound obtained in Reference Example A-1, the compound (12.2 g) obtained in Reference Example A-45 was used and treated by the same techniques as in Example 1-1(1) and (2) to give sodium 5-(ethoxycarbonyl)-1-(4-methoxybenzyl)-6-oxo-1,2,3,6-tetrahydro-4-pyridinolate as a solid (12.5 g).

$^1$H NMR (300 MHz, DMSO-d$_6$) δ ppm 1.10-1.18 (m, 3 H) 2.03 (t, J=6.5 Hz, 2 H) 3.03 (t, J=6.5 Hz, 2 H) 3.72 (s, 3 H) 3.94 (q, J=7.0 Hz, 2 H) 4.40 (s, 2 H) 6.79-6.93 (m, 2 H) 7.04-7.27 (m, 2 H).

MS ESI/APCI Dual posi: 306 [M+H]$^+$, 328 [M+Na]$^+$.

MS ESI/APCI Dual nega: 304 [M−H]$^−$.

(2) Synthesis of 2-methyl-2-propanyl N-{[4-hydroxy-1-(4-methoxybenzyl)-2-oxo-1,2,5,6-tetrahydro-3-pyridinyl]carbonyl}-β-alaninate

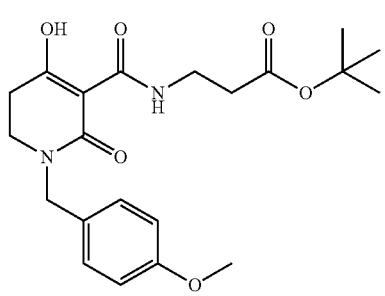

[Formula 253]

The compound obtained in step (1) above and β alanine tert-butyl hydrochloride (334 mg) rather than glycine tert-butyl hydrochloride were used and treated by the same technique as in Example 1-1(3) to give 2-methyl-2-propanyl N-{[4-hydroxy-1-(4-methoxybenzyl)-2-oxo-1,2,5,6-tetrahydro-3-pyridinyl]carbonyl}-β-alaninate as an oil (518 mg).

$^1$H NMR (300 MHz, CHLOROFORM-d) δ ppm 1.48 (s, 9 H) 2.46-2.62 (m, 4 H) 3.22-3.37 (m, 2 H) 3.48-3.72 (m, 2 H) 3.80 (s, 3 H) 4.47-4.61 (m, 2 H) 6.78-6.93 (m, 2 H) 9.95-10.41 (m, 2 H).

MS ESI/APCI Dual posi: 427 [M+Na]$^+$.

MS ESI/APCI Dual nega: 403 [M−H]$^−$.

(3) Synthesis of the Titled Compound

The compound (518 mg) obtained in step (2) above was used and treated by the same technique as in Example 1-1(4) to give the titled compound as a colorless solid (283 mg).

$^1$H NMR (300 MHz, CHLOROFORM-d) δ ppm 2.48-2.77 (m, 4 H) 3.21-3.37 (m, 2 H) 3.58-3.72 (m, 2 H) 3.80 (s, 3 H) 4.46-4.62 (m, 2 H) 6.79-6.94 (m, 2 H) 7.11-7.24 (m, 2 H) 9.95-10.50 (m, 1 H).

MS ESI/APCI Dual posi: 349 [M+H]$^+$, 371 [M+Na]$^+$.

The compounds of the following Examples 9-2 to 9-4 were synthesized using a commercial grade of the corresponding amines by the method described in Example 9-1 or modifications thereof. The structures of the synthesized compounds and their NMR and MS data are shown in Table 24-1.

Example 9-5

N-{[4-Hydroxy-1-(4-methoxybenzyl)-2-oxo-1,2,5,6-tetrahydro-3-pyridinyl]carbonyl}-N-methylglycine

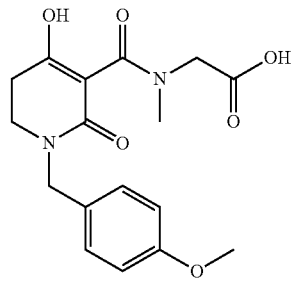

[Formula 254]

TABLE 24-1

| Compound No. | Structure | Analytical Data | Salt information |
|---|---|---|---|
| Example 9-2 | (structure) | $^1$H NMR (300 MHz, CHLOROFORM-d) δ ppm 1.90-2.00 (m, 2 H) 2.45 (t, J = 7.1 Hz, 2 H) 2.54-2.63 (m, 2 H) 3.23-3.36 (m, 2 H) 3.37-3.51 (m, 2 H) 3.75-3.85 (m, 3 H) 4.48-4.60 (m, 2 H) 6.81-6.94 (m, 2 H) 7.14-7.25 (m, 2 H). MS ESI/APCI Dual posi: 363[M + H]$^+$. | |
| Example 9-3 | (structure) | $^1$H NMR (300 MHz, DMSO-d$_6$) δ ppm 1.31 (d, J = 7.1 Hz, 3 H) 2.40-2.50 (m, 2 H) 3.22-3.38 (m, 2 H) 3.73 (s, 3 H) 4.06-4.22 (m, 1 H) 4.49 (s, 3 H) 6.83-6.99 (m, 2 H) 7.15-7.28 (m, 2 H). | Na |
| Example 9-4 | (structure) | $^1$H NMR (300 MHz, DMSO-d$_6$) δ ppm 1.23 (d, J = 6.8 Hz, 3 H) 2.40-2.50 (m, 2 H) 3.17-3.30 (m, 2 H) 3.73 (s, 3 H) 3.78-3.93 (m, 1 H) 4.48 (s, 2 H) 6.80-6.96 (m, 2 H) 7.16-7.27 (m, 2 H). | Na |

(1) Synthesis of 2-methyl-2-propanyl N-{[4-hydroxy-1-(4-methoxybenzyl)-2-oxo-1,2,5,6-tetrahydro-3-pyridinyl]carbonyl}-N-methylglycinate

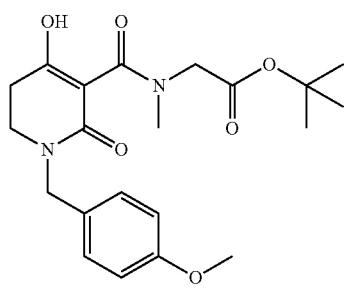

[Formula 255]

To a solution in 1,2-dimethoxyethane (5.0 mL) of the compound (500 mg) obtained in Example 9-1(1), triethylamine (215 mg) and sarcosine tert-butyl hydrochloride (345 mg) were added and the mixture was stirred at 50° C. for 6 hours. After cooling the reaction mixture to room temperature, the insoluble matter was removed by passage through Celite (registered trademark). The filtrate was concentrated under reduced pressure and the resulting residue was purified by silica gel column chromatography (n-hexane:ethyl acetate=100:0-0:100) to give 2-methyl-2-propanyl N-{[4-hydroxy-1-(4-methoxybenzyl)-2-oxo-1,2,5,6-tetrahydro-3-pyridinyl]carbonyl}-N-methylglycinate as a yellow oil (347 mg).

$^1$H NMR (300 MHz, CHLOROFORM-d) δ ppm 1.48 (s, 9 H) 2.49 (t, J=6.7 Hz, 2 H) 3.06 (s, 3 H) 3.31 (t, J=6.7 Hz, 2 H) 3.80 (s, 3 H) 4.00 (s, 2 H) 4.57 (s, 2 H) 6.81-6.91 (m, 2 H) 7.14-7.25 (m, 2 H).

(2) Synthesis of the Titled Compound

The compound (347 mg) obtained in step (1) above was used and treated by the same technique as in Example 1-1(4) to give the titled compound as a colorless solid (116 mg).

$^1$H NMR (300 MHz, DMSO-$d_6$) δ ppm 2.18-2.31 (m, 2 H) 2.80 (br. s., 2 H) 3.14 (t, J=6.9 Hz, 2 H) 3.73 (s, 3 H) 4.39 (s, 2 H) 6.84-6.90 (m, 2 H) 7.12-7.23 (m, 2 H).

Example 10-1

N-[(1-{2-[(4-Biphenylylmethyl)amino]-2-oxoethyl}-4-hydroxy-6,6-dimethyl-2-oxo-1,2,5,6-tetrahydro-3-pyridinyl)carbonyl]glycine sodium salt

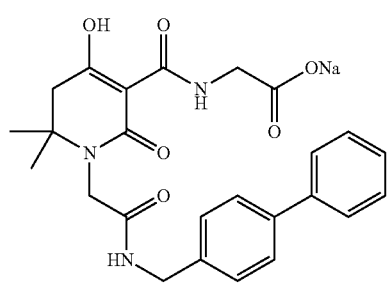

[Formula 256]

(1) Synthesis of 2-methyl-2-propanyl N-{[1-(2-{[dimethyl(2-methyl-2-propanyl)silyl]oxy}ethyl)-4-hydroxy-6,6-dimethyl-2-oxo-1,2,5,6-tetrahydro-3-pyridinyl]carbonyl}glycinate

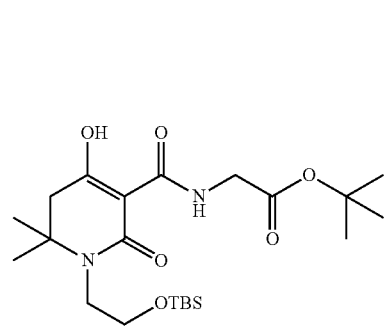

[Formula 257]

Instead of the compound obtained in Reference Example A-1, the compound (19.7 g) obtained in Reference Example A-342 was used and treaded by the same techniques as in Example 1-1(1) to (3) to give 2-methyl-2-propanyl N-{[1-(2-{[dimethyl(2-methyl-2-propanyl)silyl]oxy}ethyl)-4-hydroxy-6,6-dimethyl-2-oxo-1,2,5,6-tetrahydro-3-pyridinyl]carbonyl}glycinate as a pale brown solid (10.9 g).

$^1$H NMR (300 MHz, CHLOROFORM-d) δ ppm 0.04-0.09 (m, 6 H) 0.86-0.93 (m, 9 H) 1.31-1.37 (m, 6 H) 1.48 (s, 9 H) 2.40-2.63 (m, 2 H) 3.40-3.58 (m, 2 H) 3.64-3.84 (m, 2 H) 3.94-4.09 (m, 2 H) 10.14-10.39 (m, 1 H).

MS ESI/APCI Dual posi: 457 [M+H]$^+$.

(2) Synthesis of 2-methyl-2-propanyl N-{[4-hydroxy-1-(2-hydroxyethyl)-6,6-dimethyl-2-oxo-1,2,5,6-tetrahydro-3-pyridinyl]carbonyl}glycinate

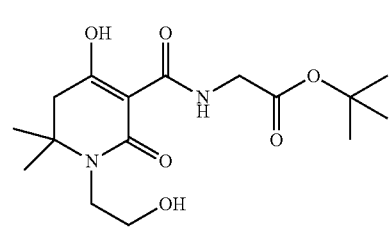

[Formula 258]

The compound (5.25 g) obtained in step (1) above was used and treated by the same technique as in Example 4-1(4) to give 2-methyl-2-propanyl N-{[4-hydroxy-1-(2-hydroxyethyl)-6,6-dimethyl-2-oxo-1,2,5,6-tetrahydro-3-pyridinyl]carbonyl}glycinate as a pale yellow oil (3.90 g).

$^1$H NMR (300 MHz, CHLOROFORM-d) δ ppm 1.34 (s, 6 H) 1.49 (s, 9 H) 2.49-2.64 (m, 2 H) 3.55-3.66 (m, 2 H) 3.71-3.84 (m, 2 H) 3.98-4.06 (m, 2 H) 9.92-10.55 (m, 1 H).

MS ESI/APCI Dual posi: 343 [M+H]$^+$.

MS ESI/APCI Dual nega: 341 [M−H]$^-$.

(3) Synthesis of 2-methyl-2-propanyl N-{[4-hydroxy-6,6-dimethyl-2-oxo-1-(2-oxoethyl)-1,2,5,6-tetrahydro-3-pyridinyl]carbonyl}glycinate

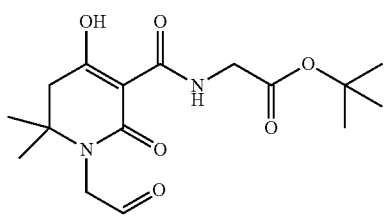

[Formula 259]

The compound (3.90 g) obtained in step (2) above was used and treated by the same technique as in Reference Example 19-1 to give 2-methyl-2-propanyl N-{[4-hydroxy-6,6-dimethyl-2-oxo-1-(2-oxoethyl)-1,2,5,6-tetrahydro-3-pyridinyl]carbonyl}glycinate as a pale yellow solid (2.55 g).

$^1$H NMR (300 MHz, CHLOROFORM-d) δ ppm 1.27-1.33 (m, 6 H) 1.43-1.51 (m, 9 H) 2.54-2.71 (m, 2 H) 3.95-4.18 (m, 4 H) 9.52-9.61 (m, 1 H) 9.90-10.03 (m, 1 H).
MS ESI/APCI Dual posi: 341 [M+H]$^+$.
MS ESI/APCI Dual nega: 339 [M−H]$^-$.

(4) Synthesis of [4-hydroxy-2,2-dimethyl-5-({2-[(2-methyl-2-propanyl)oxy]-2-oxoethyl}carbamoyl)-6-oxo-3,6-dihydro-1(2H)-pyridinyl]acetic acid

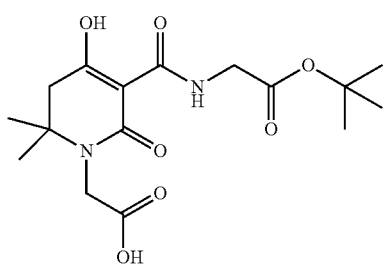

[Formula 260]

To a suspension in ethanol (40 mL) of the compound (1.93 g) obtained in step (3) above and silver nitrate (1.93 g), a solution of sodium hydroxide (907 mg) in water (26 mL) was added dropwise under cooling with ice and the mixture was stirred at the same temperature for 20 minutes. To the reaction mixture, ethyl acetate and 2 mol/L hydrochloric acid were added and the resulting mixture was brought to room temperature. Extraction was conducted with chloroform and the combined organic layers were dried over anhydrous magnesium sulfate. After removing the desiccant by filtration, the filtrate was concentrated under reduced pressure. The resulting residue was purified by silica gel column chromatography (chloroform:methanol=100:0-85:15, then n-hexane:ethyl acetate=98:2-25:75) to give [4-hydroxy-2,2-dimethyl-5-({2-[(2-methyl-2-propanyl)oxy]-2-oxoethyl}carbamoyl)-6-oxo-3,6-dihydro-1(2H)-pyridinyl]acetic acid as a colorless amorphous mass (1.79 g).

$^1$H NMR (300 MHz, CHLOROFORM-d) δ ppm 1.31-1.38 (m, 6 H) 1.45-1.52 (m, 9 H) 2.54-2.70 (m, 2 H) 3.97-4.06 (m, 2 H) 4.11-4.22 (m, 2 H) 9.79-10.54 (m, 1 H).
MS ESI/APCI Dual nega: 355 [M−H]$^-$.

(5) Synthesis of 2-methyl-2-propanyl N-[(1-{2-[(4-biphenylylmethyl)amino]-2-oxoethyl}-4-hydroxy-6,6-dimethyl-2-oxo-1,2,5,6-tetrahydro-3-pyridinyl)carbonyl]glycinate

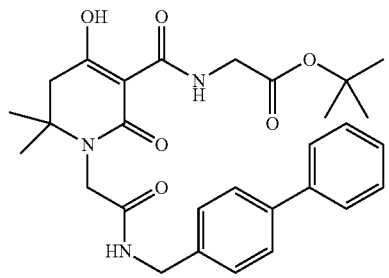

[Formula 261]

Instead of monobenzyl malonate and glycine tert-butyl hydrochloride, the compound (245 mg) obtained in step (4) above and 4-phenylbenzylamine (189 mg) were respectively used and treated by the same technique as in Reference Example G-1(1) to give 2-methyl-2-propanyl N-[(1-{2-[(4-biphenylylmethyl)amino]-2-oxoethyl}-4-hydroxy-6,6-dimethyl-2-oxo-1,2,5,6-tetrahydro-3-pyridinyl)carbonyl]glycinate as a colorless solid (285 mg).

$^1$H NMR (300 MHz, CHLOROFORM-d) δ ppm 1.32-1.37 (m, 6 H) 1.45-1.50 (m, 9 H) 2.51-2.63 (m, 2 H) 3.98-4.06 (m, 2 H) 4.09-4.17 (m, 2 H) 4.44-4.54 (m, 2 H) 6.80-6.90 (m, 1 H) 7.29-7.38 (m, 3 H) 7.39-7.48 (m, 2 H) 7.51-7.62 (m, 4 H) 9.85-10.62 (m, 1 H).
MS ESI/APCI Dual posi: 544 [M+Na]$^+$.
MS ESI/APCI Dual nega: 520 [M−H]$^-$.

(6) Synthesis of the titled compound

The compound (285 mg) obtained in step (5) above was used and treated by the same techniques as in Example 1-3(2) and (3) to give the titled compound as a pale yellow solid (237 mg).

$^1$H NMR (300 MHz, DMSO-d$_6$) δ ppm 1.23 (s, 6 H) 2.54-2.71 (m, 2 H) 3.46 (d, J=4.4 Hz, 2 H) 4.01 (s, 2 H) 4.33 (d, J=6.1 Hz, 2 H) 7.29-7.39 (m, 3 H) 7.40-7.50 (m, 2 H) 7.56-7.70 (m, 4 H) 8.27-8.44 (m, 1 H) 9.86-10.12 (m, 1 H).

The compounds of the following Examples 10-2 and 10-4 were synthesized using a commercial grade of the corresponding amines by the method described in Example 10-1 or a modification thereof. The structures of the synthesized compounds and their NMR and MS data are shown in Table 25-1.

TABLE 25-1

| Compound No. | Structure | Analytical Data | Salt information |
|---|---|---|---|
| Example 10-2 | (structure) | $^1$H NMR (300 MHz, DMSO-$d_6$) δ ppm 1.25 (s, 6 H) 2.67-2.83 (m, 2 H) 3.95-4.05 (m, 4 H) 4.30-4.45 (m, 2 H) 7.40-7.55 (m, 2 H) 7.61-7.74 (m, 2 H) 8.28-8.70 (m, 1 H) 9.84-10.28 (m, 1 H) 12.56-13.06 (m, 1 H). | |
| Example 10-4 | (structure) | $^1$H NMR (300 MHz, DMSO-$d_6$) δ ppm 1.13-1.30 (m, 6 H) 2.40-2.60 (m, 2 H) 2.76-3.04 (m, 3 H) 3.41-3.54 (m, 2 H) 4.18-4.35 (m, 2 H) 4.44-4.68 (m, 2 H) 7.10-7.33 (m, 4 H) 7.33-7.45 (m, 1 H) 9.71-10.24 (m, 1 H). MS ESI/APCI Dual posi: 444[M + Na]$^+$. MS ESI/APCI Dual nega: 420[M − H]$^−$. | Na |

Example 11-1

N-({1-[1-(4'-Fuoro-4-biphenylyl)-2-hydroxyethyl]-4-hydroxy-2-oxo-1,2,5,6-tetrahydro-3-pyridinyl}carbonyl)glycine (1) Synthesis of methyl N-({1-[2-{[dimethyl(2-methyl-2-propanyl)silyl]oxy}-1-(4-iodophenyl)ethyl]-4-hydroxy-2-oxo-1,2,5,6-tetrahydro-3-pyridinyl}carbonyl)glycinate

[Formula 262]

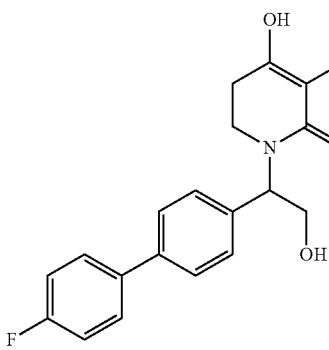

[Formula 263]

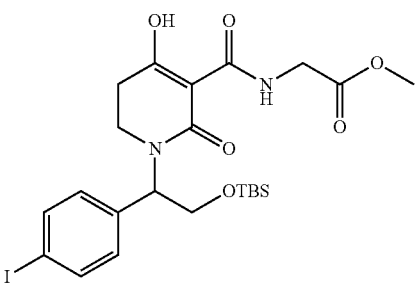

Instead of the compound obtained in Reference Example A-1 and glycine tert-butyl hydrochloride, the compound (1.40 g) obtained in Reference Example B-19 and glycine methyl hydrochloride (442 mg) were respectively used and treated by the same techniques as in Example 1-1(1) to (3) to give methyl N-({1-[2-{[dimethyl(2-methyl-2-propanyl) silyl]oxy}-1-(4-iodophenyl)ethyl]-4-hydroxy-2-oxo-1,2,5, 6-tetrahydro-3-pyridinyl}carbonyl)glycinate as a pale brown solid (1.40 g).

$^1$H NMR (300 MHz, CHLOROFORM-d) δ ppm 0.09 (s, 6 H) 0.87 (s, 9 H) 2.39-2.62 (m, 2 H) 3.05-3.21 (m, 1 H) 3.33-3.50 (m, 1 H) 3.78 (s, 3 H) 3.99-4.21 (m, 4 H) 5.55-5.78 (m, 1 H) 7.04-7.16 (m, 2 H) 7.61-7.74 (m, 2 H).

MS ESI/APCI Dual posi: 589 [M+H]$^+$.

MS ESI/APCI Dual nega: 587 [M−H]$^-$.

(2) Synthesis of methyl N-({4-hydroxy-1-[2-hydroxy-1-(4-iodophenyl)ethyl]-2-oxo-1,2,5,6-tetrahydro-3-pyridinyl}carbonyl)glycinate

[Formula 264]

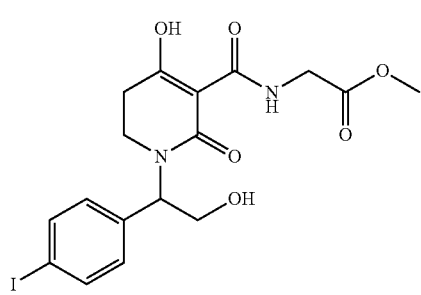

To a solution in ethyl acetate (67 mL) of the compound (1.32 g) obtained in step (1) above, a solution (12.3 mL) of 4 mol/L hydrogen chloride in 1,4-dioxane was added and the mixture was stirred at room temperature for an hour. Water was then added under cooling with ice. Extraction was conducted with ethyl acetate and the organic layer was washed with saturated brine. The washed organic layer was dried over anhydrous magnesium sulfate and after removing the desiccant by filtration, the filtrate was concentrated under reduced pressure. The resulting residue was purified by silica gel column chromatography (n-hexane:ethyl acetate=99:1-0:100) to give methyl N-({4-hydroxy-1-[2-hydroxy-1-(4-iodophenyl)ethyl]-2-oxo-1,2,5,6-tetrahydro-3-pyridinyl}carbonyl)glycinate as a pale yellow amorphous mass (880 mg).

$^1$H NMR (300 MHz, CHLOROFORM-d) δ ppm 2.35-2.62 (m, 2 H) 2.99-3.18 (m, 1 H) 3.26-3.46 (m, 1 H) 3.77 (s, 3 H) 3.94-4.22 (m, 4 H) 5.58-5.80 (m, 1 H) 6.95-7.13 (m, 2 H) 7.57-7.78 (m, 2 H) 9.95-10.56 (m, 1 H).

MS ESI/APCI Dual posi: 475 [M+H]$^+$.

MS ESI/APCI Dual nega: 473 [M−H]$^-$.

(3) Synthesis of methyl N-{[7-hydroxy-3-(4-iodophenyl)-2,3,6,8a-tetrahydro-5H-[1,3]oxazolo[3,2-a] pyridin-8-yl]carbonyl}glycinate

[Formula 265]

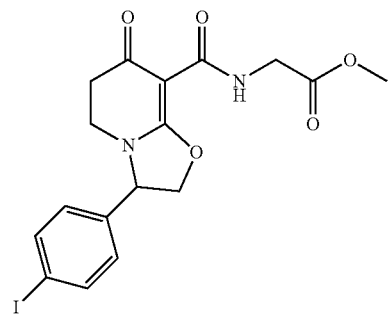

To a solution in acetonitrile (14.8 mL) of the compound (880 mg) obtained in step (2) above, propylphosphonic acid anhydride (cyclic trimer) (50%, solution in ethyl acetate, 5.91 g) was added and the solvent was immediately concentrated under reduced pressure. To the resulting residue, acetonitrile (14.8 mL) was added and the mixture was stirred at 90° C. for three hours. The reaction mixture was concentrated under reduced pressure and chloroform was added to the concentrate. With the solvent being distilled off under reduced pressure, the crude product was adsorbed on diatomaceous earth. The crude product adsorbed on the diatomaceous earth was purified by NH silica gel column chromatography (chlorform:methanol=100:0-95:5) to give methyl N-{[7-hydroxy-3-(4-iodophenyl)-2,3,6,8a-tetrahydro-5H-[1,3]oxazolo[3,2-a]pyridin-8-yl] carbonyl}glycinate as a colorless solid (690 mg).

$^1$H NMR (300 MHz, CHLOROFORM-d) δ ppm 2.51-2.74 (m, 2 H) 3.11-3.37 (m, 2 H) 3.74 (s, 3 H) 4.12 (d, J=5.6 Hz, 2 H) 4.53 (dd, J=9.2, 8.5 Hz, 1 H) 4.75 (t, J=8.5 Hz, 1 H) 4.97-5.22 (m, 1 H) 7.02-7.12 (m, 2 H) 7.73-7.83 (m, 2 H) 9.59 (t, J=5.4 Hz, 1 H).

MS ESI/APCI Dual posi: 457 [M+H]$^+$, 479 [M+Na]$^+$.

(4) Synthesis of methyl N-{[3-(4'-fluoro-4-biphenylyl)-7-hydroxy-2,3,6,8a-tetrahydro-5H-[1,3]oxazolo [3,2-a]pyridin-8-yl]carbonyl}glycinate

[Formula 266]

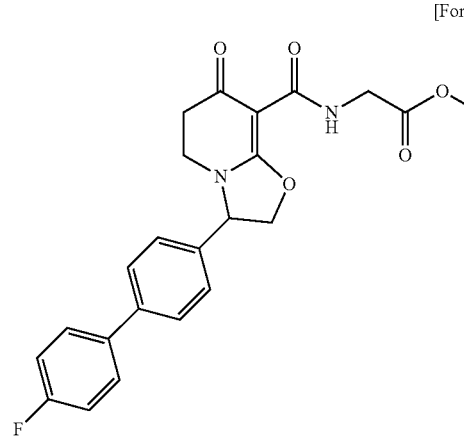

A mixture of the compound (100 mg) obtained in step (3) above, 4-fluorophenylboronic acid (66 mg), palladium(II) acetate (6.6 mg), tri(2-methylphenyl)phosphine (26 mg), potassium carbonate (186 mg), methanol (4.4 mL) and toluene (2.2 mL) was stirred in a sealed tube at 90° C. for 70 minutes. After being cooled to room temperature, the reaction mixture was concentrated under reduced pressure. The resulting residue was purified by silica gel column chromatography (n-hexane:ethyl acetate=99:1-0:100, then chloroform:methanol=100:0-85:15) to give methyl N-{[3-(4'-fluoro-4-biphenylyl)-7-hydroxy-2,3,6,8a-tetrahydro-5H-[1,3]oxazolo[3,2-a]pyridin-8-yl]carbonyl}-glycinate as a pale brown solid (100 mg).

$^1$H NMR (300 MHz, CHLOROFORM-d) δ ppm 2.56-2.76 (m, 2 H) 3.18-3.50 (m, 2 H) 3.74 (s, 3 H) 4.10-4.17 (m, 2 H) 4.54-4.68 (m, 1 H) 4.88 (t, J=8.5 Hz, 1 H) 5.06-5.22 (m, 1 H) 7.09-7.22 (m, 2 H) 7.36-7.47 (m, 2 H) 7.50-7.66 (m, 4 H) 9.69 (t, J=5.5 Hz, 1 H).

MS ESI/APCI Dual posi: 425 [M+H]$^+$, 447 [M+Na]$^+$.

(5) Synthesis of the Titled Compound

To a solution in tetrahydrofuran (2.4 mL) and methanol (2.4 mL) of the compound (100 mg) obtained in step (4) above, 1 mol/L sodium hydroxide in aqueous solution (471 μL) was added and the mixture was stirred at room temperature for 13 hours. The precipitate was recovered by filtration and dissolved in ethyl acetate and 4 mol/L hydrochloric acid. The organic layer was concentrated under reduced pressure and the resulting residue was purified by preparative HPLC. To a solution of the resulting purified product (45.0 mg) in acetone (2 mL), 1 mol/L sodium hydroxide in aqueous solution (105 μL) was added and the mixture was stirred at room temperature. The precipitate was recovered by filtration to give the titled compound as a colorless solid (40 mg).

$^1$H NMR (300 MHz, DMSO-d$_6$) δ ppm 2.40-2.50 (m, 2 H) 3.00-3.22 (m, 1 H) 3.37-3.51 (m, 2 H) 3.83-4.03 (m, 2 H) 5.11 (br. s., 1 H) 5.68 (br. s., 1 H) 7.21-7.35 (m, 2 H) 7.35-7.48 (m, 2 H) 7.55-7.76 (m, 4 H).

MS ESI/APCI Dual posi: 429 [M+H]$^+$.
MS ESI/APCI Dual nega: 427 [M–H]$^-$.

Reference Example X-1

Synthesis of (5S)-1-(biphenyl-4-ylmethyl)-N-{2-[(4-bromophenyl)amino]-2-oxoethyl}-4-hydroxy-5-methyl-2-oxo-1,2,5,6-tetrahydropyridin-3-carboxamide and determination of its absolute configuration by X-ray crystallography

[Formula 267]

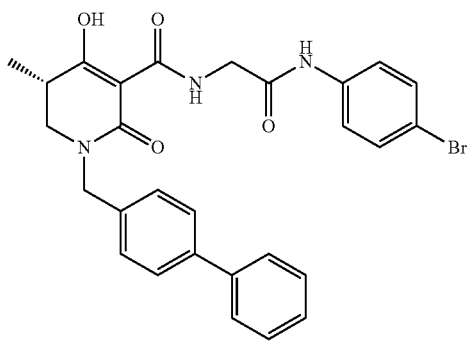

To a solution in N,N-dimethylformamide (1.00 mL) of the compound (60.8 mg) obtained in Example 5-1, 4-bromoaniline (39.0 mg), propylphosphonic acid anhydride (cyclic trimer) (50%, solution in N,N-dimethylformamide, 135 μL) and triethylamine (64.0 μL) were added and the mixture was stirred overnight at room temperature. To the reaction mixture, 4-bromoaniline (39.0 mg), propylphosphonic acid anhydride (cyclic trimer) (50%, solution in N,N-dimethylformamide, 135 μL) and triethylamine (64.0 μL) were further added and the mixture was stirred at room temperature for three hours. The reaction mixture was purified by preparative HPLC to give the residue (43.2 mg). The resulting residue was crystallized with a liquid mixture of n-hexane, diethyl ether, and ethyl acetate to give the titled compound as a colorless solid (25.8 mg, 95.5% ee). Part of the resulting solid was recrystallized with a liquid mixture of chloroform and methanol and the resulting acicular crystal was used in X-ray crystallography. As the result, the 2-oxo-1,2,5,6-tetrahydropyridine ring of the crystal was determined to have an absolute configuration (S) at position 5.

$^1$H NMR (300 MHz, CHLOROFORM-d) δ ppm 1.09-1.24 (m, 3 H) 2.69-2.86 (m, 1 H) 3.10 (dd, J=12.5, 8.2 Hz, 1 H) 3.44 (dd, J=12.5, 5.8 Hz, 1 H) 4.11-4.18 (m, 2 H) 4.60-4.73 (m, 2 H) 7.30-7.39 (m, 3 H) 7.40-7.48 (m, 6 H) 7.53-7.62 (m, 4 H) 8.14-8.24 (m, 1 H) 10.46-10.58 (m, 1 H).

MS ESI/APCI Dual posi: 548 [M+H]$^+$.
MS ESI/APCI Dual nega: 546 [M–H]$^-$.
Optical HPLC retention time: 11.041 min.

Reference Example X-2

Synthesis of (5R)-1-(biphenyl-4-ylmethyl)-N-{2-[(4-bromophenyl)amino]-2-oxoethyl}-4-hydroxy-5-methyl-2-oxo-1,2,5,6-tetrahydropyridin-3-carboxamide and determination of its absolute configuration by X-ray crystallography

[0623]

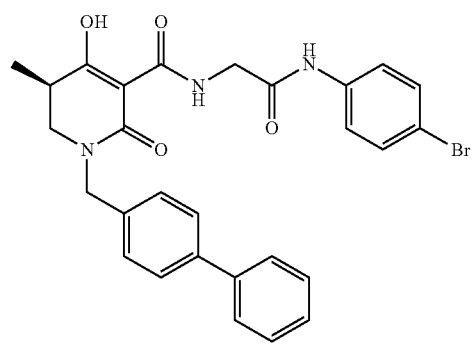

The compound (54.8 mg) obtained in Example 5-2 was used and treated by the same technique as in Reference Example X-1 to give the titled compound as a colorless solid (33.1 mg, 93.8% ee). By subsequent X-ray crystallography, the 2-oxo-1,2,5,6-tetrahydropyridine ring of the crystal was determined to have an absolute configuration (R) at position 5.

$^1$H NMR (300 MHz, CHLOROFORM-d) δ ppm 1.09-1.24 (m, 3 H) 2.55-2.82 (m, 1 H) 3.10 (dd, J=12.5, 8.1 Hz, 1 H) 3.44 (dd, J=12.5, 5.9 Hz, 1 H) 4.12-4.18 (m, 2 H) 4.59-4.73 (m, 2 H) 7.31-7.40 (m, 3 H) 7.40-7.49 (m, 6 H) 7.54-7.62 (m, 4 H) 7.97-8.23 (m, 1 H) 10.46-10.59 (m, 1 H).

MS ESI/APCI Dual posi: 548 [M+H]+.
MS ESI/APCI Dual nega: 546 [M−H]−.
Optical HPLC retention time: 12.096 min.

The PHD2 inhibitory activities of compounds of the present invention were determined in accordance with Tests 1 and 2 described below.

Test 1

(1) Expression and Preparation of Human PHD2

Human PHD2 was expressed in insect cells (HighFive cells). A registered sequence of human PHD2 (NM_022051) was introduced into the pFastBacl vector (Invitrogen), and the sequence was verified. The vector was introduced into Sf9 insect cells (Invitrogen) to acquire human PHD2 baculovirus. HighFive insect cells (Invitrogen) were infected with this recombinant virus and cultured at 27° C. for 72 hours; thereafter, a cell lysis solution containing various protease inhibitors was added and the cells were disrupted to form a suspension. The suspension of disrupted cells was centrifuged at 4° C. and 100,000×g for 30 minutes and the supernatant was recovered as a cell lysate. Analysis by Western blotting confirmed that the human PHD2 protein was expressed only in the lysate of cells infected with the PHD2 baculovirus.

(2) Measurement of Human PHD2 Inhibitory Activity

The activity of human PHD2 enzyme was measured with a substrate which is a 19-residue partial peptide based on the sequence of HIF-1α. Specifically, the conversion of 2-oxoglutarate to succinic acid which would occur simultaneously with the hydroxylation of a proline residue in the peptide with the PHD2 enzyme was utilized. To be more specific, [$^{14}$C]-2-oxogiutarate was added to the reaction system to initiate an enzymatic reaction and the [$^{14}$C]-2-oxoglutarate remaining after the reaction was bound to 2,4-dinitrophenylhydrazine (DNPH), with the resulting precipitate being removed by passage through a filter. Subsequently, radiation counting was conducted on the resulting [$^{14}$C]-succinic acid.

The enzyme and the substrate were each diluted with a 20 mM tris-hydrochloric acid buffer (pH 7.5) containing 6.67 mM KCl, 2 mM $MgCl_2$, 13.3 μM iron sulfate, 2.67 mM ascorbic acid, and 1.33 mM DTT, whereas each test compound was diluted with dimethyl sulfoxide (DMSO).

A test compound, HIF-1αpeptide and [$^{14}$C]-2-oxoglutarate were preliminarily added onto 96-well plates and reaction was initiated by adding a human PHD2 enzyme solution (4 μg/well). After 15-min incubation at 37° C., a DNPH-containing quench solution was added and the mixture was allowed to stand at room temperature for 30 minutes. Thereafter, an excess of non-radiolabelled 2-oxoglutarate was added and the mixture was allowed to stand at room temperature for 60 minutes. The resulting precipitate was removed by passage through a filter and the radiation count on the [$^{14}$C]-succinic acid was quantified (with Micro-Beta). Radiation counting was conducted for each well and the human PHD2 inhibitory activity of each test compound was calculated on the basis of the values for the substrate-free group and the test compound-free group.

(3) Results

The inhibition data of human PHD2 for the test compounds (%, test compound's concentration was 1 μM) are shown in the following Tables 26-1 to 26-3.

TABLE 26-1

| Compound No. | Percent inhibition (% at 1 μM) |
|---|---|
| Ex. 1-1 | 78 |
| Ex. 1-2 | 94 |
| Ex. 1-3 | 74 |
| Ex. 1-4 | 104 |
| Ex. 1-5 | 52 |
| Ex. 1-6 | 50 |
| Ex. 1-7 | 54 |
| Ex. 1-8 | 54 |
| Ex. 1-9 | 88 |
| Ex. 1-10 | 93 |
| Ex. 1-11 | 95 |
| Ex. 1-12 | 88 |
| Ex. 1-13 | 64 |
| Ex. 1-14 | 21 |
| Ex. 1-15 | 72 |
| Ex. 1-16 | 94 |
| Ex. 1-17 | 84 |
| Ex. 1-18 | 88 |
| Ex. 1-19 | 86 |
| Ex. 1-20 | 93 |
| Ex. 1-21 | 72 |
| Ex. 1-22 | 95 |
| Ex. 1-23 | 84 |
| Ex. 1-24 | 74 |
| Ex. 1-25 | 72 |
| Ex. 1-26 | 90 |
| Ex. 1-27 | 75 |
| Ex. 1-28 | 94 |
| Ex. 1-29 | 81 |
| Ex. 1-30 | 77 |
| Ex. 1-31 | 89 |
| Ex. 1-32 | 78 |
| Ex. 1-33 | 72 |
| Ex. 1-34 | 58 |
| Ex. 1-35 | 81 |
| Ex. 1-36 | 83 |
| Ex. 1-37 | 87 |
| Ex. 1-38 | 48 |
| Ex. 1-39 | 76 |
| Ex. 1-40 | 79 |
| Ex. 1-41 | 89 |
| Ex. 1-42 | 90 |
| Ex. 1-43 | 74 |
| Ex. 1-44 | 87 |
| Ex. 1-45 | 82 |
| Ex. 1-46 | 78 |
| Ex. 1-47 | 77 |
| Ex. 1-48 | 67 |
| Ex. 1-49 | 55 |
| Ex. 1-50 | 77 |
| Ex. 1-51 | 58 |
| Ex. 1-52 | 58 |
| Ex. 1-53 | 78 |
| Ex. 1-54 | 60 |
| Ex. 1-55 | 75 |
| Ex. 1-56 | 70 |
| Ex. 1-57 | 58 |
| Ex. 1-58 | 67 |
| Ex. 1-59 | 41 |
| Ex. 1-60 | 66 |
| Ex. 1-61 | 58 |
| Ex. 1-62 | 65 |
| Ex. 1-63 | 43 |
| Ex. 1-64 | 80 |
| Ex. 1-65 | 84 |
| Ex. 1-66 | 80 |
| Ex. 1-67 | 84 |
| Ex. 1-68 | 67 |
| Ex. 1-69 | 85 |
| Ex. 1-70 | 104 |
| Ex. 1-71 | 81 |
| Ex. 1-72 | 98 |
| Ex. 1-73 | 99 |
| Ex. 1-74 | 80 |
| Ex. 1-75 | 54 |
| Ex. 1-76 | 40 |
| Ex. 1-77 | 74 |
| Ex. 1-78 | 70 |
| Ex. 1-79 | 64 |
| Ex. 1-80 | 76 |
| Ex. 1-81 | 72 |

TABLE 26-1-continued

| Compound No. | Percent inhibition (% at 1 μM) |
|---|---|
| Ex. 1-82 | 51 |
| Ex. 1-83 | 54 |
| Ex. 1-84 | 42 |
| Ex. 1-85 | 61 |
| Ex. 1-86 | 48 |
| Ex. 1-87 | 46 |
| Ex. 1-88 | 44 |
| Ex. 1-89 | 69 |
| Ex. 1-90 | 58 |
| Ex. 1-91 | 85 |
| Ex. 1-92 | 69 |
| Ex. 1-93 | 80 |
| Ex. 1-94 | 84 |
| Ex. 1-95 | 85 |
| Ex. 1-96 | 82 |
| Ex. 1-97 | 89 |
| Ex. 1-98 | 88 |
| Ex. 1-99 | 71 |
| Ex. 1-100 | 64 |
| Ex. 1-101 | 60 |
| Ex. 1-102 | 67 |
| Ex. 1-103 | 76 |
| Ex. 1-104 | 87 |
| Ex. 1-105 | 78 |
| Ex. 1-106 | 66 |
| Ex. 1-107 | 67 |
| Ex. 1-108 | 60 |
| Ex. 1-109 | 70 |
| Ex. 1-110 | 82 |
| Ex. 1-111 | 68 |
| Ex. 1-112 | 68 |
| Ex. 1-113 | 79 |
| Ex. 1-114 | 36 |
| Ex. 1-115 | 49 |
| Ex. 1-116 | 82 |
| Ex. 1-117 | 83 |
| Ex. 1-118 | 77 |
| Ex. 1-119 | 85 |
| Ex. 1-120 | 69 |
| Ex. 1-121 | 66 |
| Ex. 1-122 | 65 |
| Ex. 1-123 | 90 |
| Ex. 1-124 | 72 |
| Ex. 1-125 | 98 |
| Ex. 1-126 | 97 |
| Ex. 1-127 | 92 |
| Ex. 1-128 | 88 |
| Ex. 1-129 | 71 |
| Ex. 1-130 | 89 |
| Ex. 1-131 | 93 |
| Ex. 1-132 | 103 |
| Ex. 1-133 | 104 |
| Ex. 1-134 | 86 |
| Ex. 1-135 | 78 |
| Ex. 1-136 | 91 |
| Ex. 1-137 | 78 |
| Ex. 1-138 | 83 |
| Ex. 1-139 | 72 |
| Ex. 1-140 | 79 |
| Ex. 1-141 | 64 |
| Ex. 1-142 | 54 |
| Ex. 1-143 | 41 |
| Ex. 1-144 | 76 |
| Ex. 1-145 | 88 |
| Ex. 1-146 | 69 |
| Ex. 1-147 | 84 |
| Ex. 1-148 | 78 |
| Ex. 1-149 | 74 |
| Ex. 1-150 | 63 |

TABLE 26-2

| Compound No. | Percent inhibition (% at 1 μM) |
|---|---|
| Ex. 1-151 | 57 |
| Ex. 1-152 | 82 |
| Ex. 1-153 | 64 |
| Ex. 1-154 | 77 |
| Ex. 1-155 | 82 |
| Ex. 1-156 | 70 |
| Ex. 1-157 | 67 |
| Ex. 1-158 | 67 |
| Ex. 1-159 | 78 |
| Ex. 1-160 | 74 |
| Ex. 1-161 | 62 |
| Ex. 1-162 | 78 |
| Ex. 1-163 | 84 |
| Ex. 1-164 | 49 |
| Ex. 1-165 | 42 |
| Ex. 1-166 | 82 |
| Ex. 1-167 | 80 |
| Ex. 1-168 | 51 |
| Ex. 1-169 | 28 |
| Ex. 1-170 | 35 |
| Ex. 1-171 | 81 |
| Ex. 1-172 | 77 |
| Ex. 1-173 | 64 |
| Ex. 1-174 | 59 |
| Ex. 1-175 | 32 |
| Ex. 1-176 | 74 |
| Ex. 1-177 | 93 |
| Ex. 1-178 | 81 |
| Ex. 1-179 | 44 |
| Ex. 1-180 | 54 |
| Ex. 1-181 | 73 |
| Ex. 1-182 | 77 |
| Ex. 1-183 | 39 |
| Ex. 1-184 | 59 |
| Ex. 1-185 | 69 |
| Ex. 1-186 | 64 |
| Ex. 1-187 | 47 |
| Ex. 1-188 | 44 |
| Ex. 1-189 | 53 |
| Ex. 1-190 | 84 |
| Ex. 1-191 | 38 |
| Ex. 1-192 | 48 |
| Ex. 1-193 | 67 |
| Ex. 1-194 | 54 |
| Ex. 1-195 | 52 |
| Ex. 1-196 | 41 |
| Ex. 1-197 | 66 |
| Ex. 1-198 | 70 |
| Ex. 1-199 | 65 |
| Ex. 1-200 | 98 |
| Ex. 1-201 | 67 |
| Ex. 1-202 | 58 |
| Ex. 1-203 | 61 |
| Ex. 1-204 | 69 |
| Ex. 1-205 | 104 |
| Ex. 1-206 | 95 |
| Ex. 1-207 | 92 |
| Ex. 1-208 | 90 |
| Ex. 1-209 | 102 |
| Ex. 1-210 | 59 |
| Ex. 1-211 | 76 |
| Ex. 1-212 | 82 |
| Ex. 1-213 | 88 |
| Ex. 1-214 | 89 |
| Ex. 1-215 | 85 |
| Ex. 1-216 | 75 |
| Ex. 1-217 | 52 |
| Ex. 1-218 | 52 |
| Ex. 1-219 | 69 |
| Ex. 1-220 | 72 |
| Ex. 1-221 | 66 |
| Ex. 1-222 | 90 |
| Ex. 1-223 | 90 |
| Ex. 1-224 | 80 |
| Ex. 1-225 | 100 |
| Ex. 1-227 | 76 |
| Ex. 1-228 | 71 |

TABLE 26-2-continued

| Compound No. | Percent inhibition (% at 1 μM) |
|---|---|
| Ex. 1-229 | 74 |
| Ex. 1-230 | 96 |
| Ex. 1-231 | 65 |
| Ex. 1-232 | 89 |
| Ex. 1-233 | 91 |
| Ex. 1-234 | 61 |
| Ex. 1-235 | 91 |
| Ex. 1-236 | 84 |
| Ex. 1-237 | 74 |
| Ex. 1-238 | 92 |
| Ex. 1-239 | 74 |
| Ex. 1-240 | 91 |
| Ex. 1-241 | 97 |
| Ex. 1-242 | 100 |
| Ex. 1-243 | 76 |
| Ex. 1-244 | 47 |
| Ex. 1-245 | 80 |
| Ex. 1-246 | 97 |
| Ex. 1-247 | 81 |
| Ex. 1-249 | 103 |
| Ex. 1-250 | 80 |
| Ex. 1-251 | 90 |
| Ex. 1-252 | 104 |
| Ex. 1-253 | 45 |
| Ex. 1-254 | 103 |
| Ex. 1-255 | 99 |
| Ex. 1-256 | 101 |
| Ex. 1-257 | 95 |
| Ex. 1-258 | 94 |
| Ex. 1-259 | 92 |
| Ex. 1-260 | 95 |
| Ex. 1-261 | 99 |
| Ex. 1-262 | 88 |
| Ex. 1-263 | 81 |
| Ex. 1-264 | 83 |
| Ex. 1-265 | 98 |
| Ex. 1-266 | 83 |
| Ex. 1-267 | 81 |
| Ex. 1-268 | 78 |
| Ex. 1-269 | 85 |
| Ex. 1-270 | 88 |
| Ex. 1-271 | 91 |
| Ex. 1-272 | 65 |
| Ex. 1-273 | 99 |
| Ex. 1-274 | 92 |
| Ex. 1-275 | 85 |
| Ex. 1-276 | 93 |
| Ex. 1-277 | 108 |
| Ex. 1-278 | 93 |
| Ex. 1-279 | 90 |
| Ex. 1-280 | 109 |
| Ex. 1-281 | 70 |
| Ex. 1-282 | 101 |
| Ex. 1-283 | 99 |
| Ex. 1-284 | 107 |
| Ex. 1-285 | 106 |
| Ex. 1-286 | 95 |
| Ex. 1-287 | 94 |
| Ex. 1-288 | 90 |
| Ex. 1-289 | 95 |
| Ex. 1-290 | 63 |
| Ex. 1-291 | 75 |
| Ex. 1-292 | 83 |
| Ex. 1-293 | 35 |
| Ex. 1-294 | 51 |
| Ex. 1-295 | 63 |
| Ex. 1-296 | 100 |
| Ex. 1-297 | 86 |
| Ex. 1-298 | 84 |
| Ex. 1-299 | 47 |
| Ex. 1-300 | 30 |
| Ex. 1-301 | 56 |
| Ex. 1-302 | 61 |

TABLE 26-3

| Compound No. | Percent inhibition (% at 1 μM) |
|---|---|
| Ex. 1-303 | 102 |
| Ex. 1-304 | 35 |
| Ex. 1-305 | 94 |
| Ex. 1-306 | 94 |
| Ex. 1-307 | 51 |
| Ex. 2-1 | 93 |
| Ex. 2-6 | 68 |
| Ex. 2-7 | 88 |
| Ex. 2-8 | 87 |
| Ex. 2-9 | 78 |
| Ex. 2-10 | 84 |
| Ex. 2-11 | 93 |
| Ex. 2-12 | 93 |
| Ex. 2-13 | 92 |
| Ex. 2-14 | 98 |
| Ex. 2-15 | 97 |
| Ex. 2-16 | 102 |
| Ex. 2-17 | 94 |
| Ex. 2-18 | 98 |
| Ex. 2-19 | 96 |
| Ex. 2-20 | 102 |
| Ex. 2-21 | 88 |
| Ex. 2-22 | 95 |
| Ex. 2-23 | 88 |
| Ex. 2-24 | 91 |
| Ex. 2-25 | 92 |
| Ex. 2-26 | 90 |
| Ex. 2-27 | 100 |
| Ex. 2-28 | 90 |
| Ex. 2-29 | 101 |
| Ex. 2-30 | 103 |
| Ex. 3-1 | 102 |
| Ex. 3-2 | 87 |
| Ex. 4-1 | 58 |
| Ex. 4-2 | 77 |
| Ex. 5-1 | 93 |
| Ex. 5-2 | 92 |

Test 2

(1) Expression and Preparation of Human PHD2

Human PHD2 was expressed in human cells (293FT cells). A registered sequence of human PHD2 (NM_022051) was introduced into pcDNA3.1/Hygro(+) vector (Invitrogen), and the sequence was verified. The vector was introduced into 293FT cells (Invitrogen) which were cultured at 37° C. in the presence of 5% $CO_2$ gas for 48 hours; thereafter, a cell lysis solution containing various protease inhibitors was added and the cells were disrupted to form a suspension. The suspension of disrupted cells was centrifuged at 4° C. and 100,000×g for 30 minutes and the supernatant was recovered as a cell lysate. Analysis by Western blotting confirmed that the human PHD2 protein was expressed in the cell lysate.

(2) Measurement of Human PHD2 Inhibitory Activity

The activity of human PHD2 enzyme was measured with a substrate which is a 19-residue partial peptide based on the sequence of HIF-1α; specifically, the hydroxylation of a proline residue in the peptide was measured by FP (Fluorescence Polarization).

The enzyme and the substrate were each diluted with a 50 mM tris-hydrochloric acid buffer (pH 7.5) containing 12.5 mM KCl, 3.75 mM $MgCl_2$, 25 μM iron sulfate, 5 mM ascorbic acid, and 2.5 mM DTT, whereas each test compound was diluted with dimethyl sulfoxide (DMSO).

A test compound and the substrate solution were preliminarily added onto 384-well plates and reaction was initiated by adding a human PHD2 enzyme solution (40 ng/well). After 20-min incubation at 30° C., an EDTA-containing quench solution was added and the amount of the proline residues hydroxylated via binding to an added HIF—OH antibody solution was quantified by fluorescence polarization.

The fluorescence polarization of each well was measured and the human PHD2 inhibitory activity of each test compound was calculated on the basis of the values for the test compound-free group.

(3) Results

The inhibition data of human PHD2 for the test compounds (%, test compound's concentration was 1 μM) are shown in the following Tables 27-1 to 27-4. For representative compounds, their $IC_{50}$ values (nM) are shown in the following Table 28-1.

TABLE 27-1

| Compound No. | Percent inhibition (% at 1 μM) |
| --- | --- |
| Ex. 1-1 | 94 |
| Ex. 1-2 | 92 |
| Ex. 1-3 | 78 |
| Ex. 1-4 | 96 |
| Ex. 1-5 | 76 |
| Ex. 1-6 | 57 |
| Ex. 1-7 | 68 |
| Ex. 1-8 | 87 |
| Ex. 1-9 | 93 |
| Ex. 1-10 | 92 |
| Ex. 1-11 | 93 |
| Ex. 1-12 | 93 |
| Ex. 1-13 | 81 |
| Ex. 1-14 | 36 |
| Ex. 1-15 | 86 |
| Ex. 1-16 | 92 |
| Ex. 1-17 | 85 |
| Ex. 1-18 | 86 |
| Ex. 1-19 | 81 |
| Ex. 1-20 | 93 |
| Ex. 1-21 | 73 |
| Ex. 1-22 | 85 |
| Ex. 1-23 | 82 |
| Ex. 1-24 | 84 |
| Ex. 1-25 | 76 |
| Ex. 1-26 | 94 |
| Ex. 1-27 | 89 |
| Ex. 1-28 | 92 |
| Ex. 1-29 | 86 |
| Ex. 1-30 | 83 |
| Ex. 1-31 | 89 |
| Ex. 1-32 | 82 |
| Ex. 1-33 | 84 |
| Ex. 1-34 | 75 |
| Ex. 1-35 | 90 |
| Ex. 1-36 | 85 |
| Ex. 1-37 | 89 |
| Ex. 1-38 | 66 |
| Ex. 1-39 | 86 |
| Ex. 1-40 | 91 |
| Ex. 1-41 | 90 |
| Ex. 1-42 | 94 |
| Ex. 1-43 | 79 |
| Ex. 1-44 | 91 |
| Ex. 1-45 | 88 |
| Ex. 1-46 | 84 |
| Ex. 1-47 | 81 |
| Ex. 1-48 | 79 |
| Ex. 1-49 | 55 |
| Ex. 1-50 | 83 |
| Ex. 1-51 | 73 |
| Ex. 1-52 | 78 |
| Ex. 1-53 | 78 |
| Ex. 1-54 | 71 |
| Ex. 1-55 | 79 |
| Ex. 1-56 | 69 |
| Ex. 1-57 | 83 |
| Ex. 1-58 | 71 |
| Ex. 1-59 | 54 |

TABLE 27-1-continued

| Compound No. | Percent inhibition (% at 1 μM) |
| --- | --- |
| Ex. 1-60 | 76 |
| Ex. 1-61 | 71 |
| Ex. 1-62 | 68 |
| Ex. 1-63 | 69 |
| Ex. 1-64 | 81 |
| Ex. 1-65 | 85 |
| Ex. 1-66 | 77 |
| Ex. 1-67 | 89 |
| Ex. 1-68 | 66 |
| Ex. 1-69 | 81 |
| Ex. 1-70 | 95 |
| Ex. 1-71 | 85 |
| Ex. 1-72 | 89 |
| Ex. 1-73 | 90 |
| Ex. 1-74 | 86 |
| Ex. 1-75 | 84 |
| Ex. 1-76 | 79 |
| Ex. 1-77 | 85 |
| Ex. 1-78 | 78 |
| Ex. 1-79 | 71 |
| Ex. 1-80 | 88 |
| Ex. 1-81 | 64 |
| Ex. 1-82 | 77 |
| Ex. 1-83 | 73 |
| Ex. 1-84 | 67 |
| Ex. 1-85 | 65 |
| Ex. 1-86 | 71 |
| Ex. 1-87 | 86 |
| Ex. 1-88 | 55 |
| Ex. 1-89 | 72 |
| Ex. 1-90 | 63 |
| Ex. 1-91 | 94 |
| Ex. 1-92 | 66 |
| Ex. 1-93 | 81 |
| Ex. 1-94 | 92 |
| Ex. 1-95 | 91 |
| Ex. 1-96 | 86 |
| Ex. 1-97 | 91 |
| Ex. 1-98 | 88 |
| Ex. 1-99 | 92 |
| Ex. 1-100 | 84 |
| Ex. 1-101 | 86 |
| Ex. 1-102 | 83 |
| Ex. 1-103 | 82 |
| Ex. 1-104 | 94 |
| Ex. 1-105 | 83 |
| Ex. 1-106 | 72 |
| Ex. 1-107 | 90 |
| Ex. 1-108 | 87 |
| Ex. 1-109 | 77 |
| Ex. 1-110 | 84 |
| Ex. 1-111 | 80 |
| Ex. 1-112 | 90 |
| Ex. 1-113 | 84 |
| Ex. 1-114 | 83 |
| Ex. 1-115 | 83 |
| Ex. 1-116 | 84 |
| Ex. 1-117 | 92 |
| Ex. 1-118 | 87 |
| Ex. 1-119 | 84 |
| Ex. 1-120 | 82 |
| Ex. 1-121 | 71 |
| Ex. 1-122 | 76 |
| Ex. 1-123 | 93 |
| Ex. 1-124 | 79 |
| Ex. 1-125 | 97 |
| Ex. 1-126 | 98 |
| Ex. 1-127 | 95 |
| Ex. 1-128 | 84 |
| Ex. 1-129 | 80 |
| Ex. 1-130 | 90 |
| Ex. 1-131 | 96 |
| Ex. 1-132 | 94 |
| Ex. 1-133 | 97 |
| Ex. 1-134 | 85 |
| Ex. 1-135 | 78 |
| Ex. 1-136 | 88 |

TABLE 27-1-continued

| Compound No. | Percent inhibition (% at 1 μM) |
|---|---|
| Ex. 1-137 | 92 |
| Ex. 1-138 | 97 |
| Ex. 1-139 | 78 |
| Ex. 1-140 | 85 |
| Ex. 1-141 | 62 |
| Ex. 1-142 | 52 |
| Ex. 1-143 | 65 |
| Ex. 1-144 | 85 |
| Ex. 1-145 | 83 |
| Ex. 1-146 | 70 |
| Ex. 1-147 | 88 |
| Ex. 1-148 | 82 |
| Ex. 1-149 | 74 |
| Ex. 1-150 | 71 |

TABLE 27-2

| Compound No. | Percent inhibition (% at 1 μM) |
|---|---|
| Ex. 1-151 | 63 |
| Ex. 1-152 | 83 |
| Ex. 1-153 | 63 |
| Ex. 1-154 | 81 |
| Ex. 1-155 | 83 |
| Ex. 1-156 | 80 |
| Ex. 1-157 | 73 |
| Ex. 1-158 | 75 |
| Ex. 1-159 | 90 |
| Ex. 1-160 | 85 |
| Ex. 1-161 | 62 |
| Ex. 1-162 | 77 |
| Ex. 1-163 | 90 |
| Ex. 1-164 | 66 |
| Ex. 1-165 | 55 |
| Ex. 1-166 | 86 |
| Ex. 1-167 | 88 |
| Ex. 1-168 | 69 |
| Ex. 1-169 | 43 |
| Ex. 1-170 | 45 |
| Ex. 1-171 | 82 |
| Ex. 1-172 | 79 |
| Ex. 1-173 | 78 |
| Ex. 1-174 | 74 |
| Ex. 1-175 | 56 |
| Ex. 1-176 | 80 |
| Ex. 1-177 | 92 |
| Ex. 1-178 | 92 |
| Ex. 1-179 | 49 |
| Ex. 1-180 | 65 |
| Ex. 1-181 | 83 |
| Ex. 1-182 | 71 |
| Ex. 1-183 | 50 |
| Ex. 1-184 | 60 |
| Ex. 1-185 | 81 |
| Ex. 1-186 | 77 |
| Ex. 1-187 | 74 |
| Ex. 1-188 | 63 |
| Ex. 1-189 | 60 |
| Ex. 1-190 | 85 |
| Ex. 1-191 | 45 |
| Ex. 1-192 | 49 |
| Ex. 1-193 | 57 |
| Ex. 1-194 | 57 |
| Ex. 1-195 | 57 |
| Ex. 1-196 | 48 |
| Ex. 1-197 | 78 |
| Ex. 1-198 | 79 |
| Ex. 1-199 | 75 |
| Ex. 1-200 | 99 |
| Ex. 1-201 | 73 |
| Ex. 1-202 | 69 |
| Ex. 1-203 | 69 |
| Ex. 1-204 | 79 |

TABLE 27-2-continued

| Compound No. | Percent inhibition (% at 1 μM) |
|---|---|
| Ex. 1-205 | 98 |
| Ex. 1-206 | 93 |
| Ex. 1-207 | 93 |
| Ex. 1-208 | 85 |
| Ex. 1-209 | 95 |
| Ex. 1-210 | 42 |
| Ex. 1-211 | 79 |
| Ex. 1-212 | 85 |
| Ex. 1-213 | 88 |
| Ex. 1-214 | 90 |
| Ex. 1-215 | 86 |
| Ex. 1-216 | 73 |
| Ex. 1-217 | 60 |
| Ex. 1-218 | 62 |
| Ex. 1-219 | 88 |
| Ex. 1-220 | 82 |
| Ex. 1-221 | 73 |
| Ex. 1-222 | 89 |
| Ex. 1-223 | 96 |
| Ex. 1-224 | 90 |
| Ex. 1-225 | 98 |
| Ex. 1-226 | 84 |
| Ex. 1-227 | 75 |
| Ex. 1-228 | 64 |
| Ex. 1-229 | 60 |
| Ex. 1-230 | 95 |
| Ex. 1-231 | 44 |
| Ex. 1-232 | 91 |
| Ex. 1-233 | 93 |
| Ex. 1-234 | 62 |
| Ex. 1-235 | 93 |
| Ex. 1-236 | 87 |
| Ex. 1-237 | 84 |
| Ex. 1-238 | 99 |
| Ex. 1-239 | 87 |
| Ex. 1-240 | 97 |
| Ex. 1-241 | 101 |
| Ex. 1-242 | 101 |
| Ex. 1-243 | 92 |
| Ex. 1-244 | 50 |
| Ex. 1-245 | 78 |
| Ex. 1-246 | 92 |
| Ex. 1-247 | 82 |
| Ex. 1-248 | 94 |
| Ex. 1-249 | 94 |
| Ex. 1-250 | 81 |
| Ex. 1-251 | 83 |
| Ex. 1-252 | 98 |
| Ex. 1-253 | 49 |
| Ex. 1-254 | 96 |
| Ex. 1-255 | 90 |
| Ex. 1-256 | 91 |
| Ex. 1-257 | 89 |
| Ex. 1-258 | 90 |
| Ex. 1-259 | 91 |
| Ex. 1-260 | 92 |
| Ex. 1-261 | 97 |
| Ex. 1-262 | 87 |
| Ex. 1-263 | 83 |
| Ex. 1-264 | 90 |
| Ex. 1-265 | 100 |
| Ex. 1-266 | 89 |
| Ex. 1-267 | 86 |
| Ex. 1-268 | 85 |
| Ex. 1-269 | 89 |
| Ex. 1-270 | 90 |
| Ex. 1-271 | 91 |
| Ex. 1-272 | 82 |
| Ex. 1-273 | 92 |
| Ex. 1-274 | 94 |
| Ex. 1-275 | 94 |
| Ex. 1-276 | 92 |
| Ex. 1-277 | 97 |
| Ex. 1-278 | 94 |
| Ex. 1-279 | 91 |
| Ex. 1-280 | 98 |
| Ex. 1-281 | 77 |

TABLE 27-2-continued

| Compound No. | Percent inhibition (% at 1 μM) |
|---|---|
| Ex. 1-282 | 99 |
| Ex. 1-283 | 97 |
| Ex. 1-284 | 103 |
| Ex. 1-285 | 100 |
| Ex. 1-286 | 96 |
| Ex. 1-287 | 104 |
| Ex. 1-288 | 91 |
| Ex. 1-289 | 98 |
| Ex. 1-290 | 86 |
| Ex. 1-291 | 86 |
| Ex. 1-292 | 86 |
| Ex. 1-293 | 33 |
| Ex. 1-294 | 68 |
| Ex. 1-295 | 74 |
| Ex. 1-296 | 102 |
| Ex. 1-297 | 94 |
| Ex. 1-298 | 94 |
| Ex. 1-299 | 64 |
| Ex. 1-300 | 43 |

TABLE 27-3

| Compound No. | Percent inhibition (% at 1 μM) |
|---|---|
| Ex. 1-301 | 75 |
| Ex. 1-302 | 79 |
| Ex. 1-303 | 100 |
| Ex. 1-304 | 72 |
| Ex. 1-305 | 97 |
| Ex. 1-306 | 99 |
| Ex. 1-307 | 60 |
| Ex. 1-308 | 41 |
| Ex. 1-309 | 58 |
| Ex. 1-310 | 59 |
| Ex. 1-311 | 83 |
| Ex. 1-312 | 86 |
| Ex. 1-313 | 96 |
| Ex. 1-314 | 86 |
| Ex. 1-315 | 81 |
| Ex. 1-316 | 87 |
| Ex. 1-317 | 85 |
| Ex. 1-318 | 96 |
| Ex. 1-319 | 42 |
| Ex. 1-320 | 57 |
| Ex. 1-321 | 84 |
| Ex. 1-322 | 77 |
| Ex. 1-323 | 87 |
| Ex. 1-324 | 91 |
| Ex. 1-325 | 90 |
| Ex. 1-326 | 71 |
| Ex. 1-327 | 81 |
| Ex. 1-328 | 63 |
| Ex. 1-329 | 87 |
| Ex. 1-330 | 69 |
| Ex. 1-331 | 75 |
| Ex. 1-332 | 73 |
| Ex. 1-333 | 91 |
| Ex. 1-334 | 96 |
| Ex. 1-335 | 73 |
| Ex. 1-336 | 82 |
| Ex. 1-337 | 66 |
| Ex. 1-338 | 71 |
| Ex. 1-339 | 40 |
| Ex. 1-340 | 69 |
| Ex. 1-341 | 66 |
| Ex. 1-342 | 57 |
| Ex. 1-343 | 51 |
| Ex. 1-344 | 76 |
| Ex. 1-345 | 55 |
| Ex. 1-346 | 80 |
| Ex. 1-347 | 55 |
| Ex. 1-348 | 76 |
| Ex. 1-349 | 74 |

TABLE 27-3-continued

| Compound No. | Percent inhibition (% at 1 μM) |
|---|---|
| Ex. 1-350 | 61 |
| Ex. 1-351 | 81 |
| Ex. 1-352 | 91 |
| Ex. 1-353 | 100 |
| Ex. 1-354 | 96 |
| Ex. 1-355 | 98 |
| Ex. 1-356 | 96 |
| Ex. 1-357 | 74 |
| Ex. 1-358 | 88 |
| Ex. 1-359 | 69 |
| Ex. 1-360 | 90 |
| Ex. 1-361 | 93 |
| Ex. 1-362 | 83 |
| Ex. 1-363 | 77 |
| Ex. 1-364 | 97 |
| Ex. 1-365 | 97 |
| Ex. 1-366 | 103 |
| Ex. 1-367 | 105 |
| Ex. 1-368 | 101 |
| Ex. 1-369 | 98 |
| Ex. 1-370 | 84 |
| Ex. 1-371 | 90 |
| Ex. 1-372 | 89 |
| Ex. 1-373 | 85 |
| Ex. 1-374 | 96 |
| Ex. 1-375 | 85 |
| Ex. 1-376 | 100 |
| Ex. 1-377 | 96 |
| Ex. 1-378 | 98 |
| Ex. 1-379 | 84 |
| Ex. 1-380 | 92 |
| Ex. 1-381 | 92 |
| Ex. 1-382 | 83 |
| Ex. 1-383 | 83 |
| Ex. 1-384 | 82 |
| Ex. 1-385 | 93 |
| Ex. 1-386 | 92 |
| Ex. 1-387 | 93 |
| Ex. 1-388 | 92 |
| Ex. 1-389 | 69 |
| Ex. 1-390 | 89 |
| Ex. 1-391 | 82 |
| Ex. 1-392 | 98 |
| Ex. 1-393 | 98 |
| Ex. 1-394 | 83 |
| Ex. 1-395 | 90 |
| Ex. 1-396 | 89 |
| Ex. 1-397 | 90 |
| Ex. 1-398 | 91 |
| Ex. 1-399 | 55 |
| Ex. 1-400 | 72 |
| Ex. 1-401 | 90 |
| Ex. 1-402 | 109 |
| Ex. 1-403 | 102 |
| Ex. 1-404 | 96 |
| Ex. 1-405 | 90 |
| Ex. 1-406 | 86 |
| Ex. 1-407 | 85 |
| Ex. 1-408 | 91 |
| Ex. 1-409 | 98 |
| Ex. 1-410 | 82 |
| Ex. 1-411 | 90 |
| Ex. 1-412 | 87 |
| Ex. 1-413 | 75 |
| Ex. 1-414 | 96 |
| Ex. 1-415 | 94 |
| Ex. 1-416 | 95 |
| Ex. 1-417 | 99 |
| Ex. 1-418 | 98 |
| Ex. 1-419 | 98 |
| Ex. 1-420 | 92 |
| Ex. 1-421 | 99 |
| Ex. 1-422 | 100 |
| Ex. 1-423 | 96 |
| Ex. 1-424 | 97 |
| Ex. 1-425 | 90 |
| Ex. 1-426 | 88 |

TABLE 27-3-continued

| Compound No. | Percent inhibition (% at 1 μM) |
|---|---|
| Ex. 1-427 | 95 |
| Ex. 1-428 | 100 |
| Ex. 1-429 | 96 |
| Ex. 1-430 | 95 |
| Ex. 1-431 | 99 |
| Ex. 1-432 | 93 |
| Ex. 1-433 | 76 |
| Ex. 1-434 | 85 |
| Ex. 1-435 | 87 |
| Ex. 1-436 | 85 |
| Ex. 1-437 | 92 |
| Ex. 1-438 | 90 |
| Ex. 1-439 | 81 |
| Ex. 1-440 | 98 |
| Ex. 1-441 | 86 |
| Ex. 1-442 | 98 |
| Ex. 1-443 | 101 |
| Ex. 1-444 | 88 |
| Ex. 1-445 | 75 |
| Ex. 1-446 | 94 |
| Ex. 1-447 | 98 |
| Ex. 1-448 | 92 |
| Ex. 1-449 | 99 |
| Ex. 1-450 | 97 |

TABLE 27-4

| Compound No. | Percent inhibition (% at 1 μM) |
|---|---|
| Ex. 1-451 | 82 |
| Ex. 1-452 | 67 |
| Ex. 1-453 | 94 |
| Ex. 1-454 | 95 |
| Ex. 1-455 | 98 |
| Ex. 1-456 | 98 |
| Ex. 1-457 | 94 |
| Ex. 1-458 | 89 |
| Ex. 1-459 | 96 |
| Ex. 1-460 | 92 |
| Ex. 1-461 | 95 |
| Ex. 1-462 | 87 |
| Ex. 1-463 | 99 |
| Ex. 1-464 | 87 |
| Ex. 1-465 | 80 |
| Ex. 1-466 | 77 |
| Ex. 1-467 | 95 |
| Ex. 1-468 | 85 |
| Ex. 2-1 | 88 |
| Ex. 2-2 | 98 |
| Ex. 2-3 | 92 |
| Ex. 2-4 | 88 |
| Ex. 2-5 | 97 |
| Ex. 2-6 | 80 |
| Ex. 2-7 | 91 |
| Ex. 2-8 | 88 |
| Ex. 2-9 | 82 |
| Ex. 2-10 | 79 |
| Ex. 2-11 | 91 |
| Ex. 2-12 | 91 |
| Ex. 2-13 | 87 |
| Ex. 2-14 | 93 |
| Ex. 2-15 | 90 |
| Ex. 2-16 | 93 |
| Ex. 2-17 | 87 |
| Ex. 2-18 | 91 |
| Ex. 2-19 | 93 |
| Ex. 2-20 | 93 |
| Ex. 2-21 | 93 |
| Ex. 2-22 | 94 |
| Ex. 2-23 | 96 |
| Ex. 2-24 | 93 |
| Ex. 2-25 | 96 |
| Ex. 2-26 | 95 |

TABLE 27-4-continued

| Compound No. | Percent inhibition (% at 1 μM) |
|---|---|
| Ex. 2-27 | 96 |
| Ex. 2-28 | 97 |
| Ex. 2-29 | 95 |
| Ex. 2-30 | 99 |
| Ex. 2-31 | 93 |
| Ex. 2-32 | 85 |
| Ex. 2-33 | 91 |
| Ex. 2-34 | 97 |
| Ex. 2-35 | 96 |
| Ex. 2-36 | 95 |
| Ex. 2-37 | 91 |
| Ex. 2-38 | 92 |
| Ex. 2-39 | 93 |
| Ex. 2-40 | 96 |
| Ex. 2-41 | 93 |
| Ex. 2-42 | 96 |
| Ex. 2-43 | 95 |
| Ex. 2-44 | 96 |
| Ex. 2-45 | 95 |
| Ex. 2-46 | 93 |
| Ex. 2-47 | 100 |
| Ex. 2-48 | 103 |
| Ex. 2-49 | 93 |
| Ex. 2-50 | 99 |
| Ex. 2-51 | 97 |
| Ex. 2-52 | 95 |
| Ex. 2-53 | 97 |
| Ex. 2-54 | 87 |
| Ex. 2-55 | 97 |
| Ex. 2-56 | 92 |
| Ex. 2-57 | 94 |
| Ex. 2-58 | 92 |
| Ex. 2-59 | 97 |
| Ex. 2-60 | 96 |
| Ex. 2-61 | 92 |
| Ex. 3-1 | 95 |
| Ex. 3-2 | 90 |
| Ex. 4-1 | 67 |
| Ex. 4-2 | 81 |
| Ex. 4-3 | 72 |
| Ex. 5-1 | 94 |
| Ex. 5-2 | 90 |
| Ex. 6-1 | 91 |
| Ex. 6-2 | 77 |
| Ex. 6-3 | 96 |
| Ex. 6-4 | 10 |
| Ex. 6-5 | 97 |
| Ex. 6-6 | 87 |
| Ex. 6-7 | 86 |
| Ex. 6-8 | 83 |
| Ex. 6-9 | 85 |
| Ex. 6-10 | 76 |
| Ex. 6-11 | 73 |
| Ex. 6-12 | 67 |
| Ex. 6-13 | 81 |
| Ex. 6-14 | 80 |
| Ex. 6-15 | 55 |
| Ex. 6-16 | 26 |
| Ex. 6-17 | 32 |
| Ex. 6-18 | 24 |
| Ex. 6-19 | 72 |
| Ex. 6-20 | 84 |
| Ex. 6-21 | 85 |
| Ex. 6-22 | 88 |
| Ex. 6-23 | 85 |
| Ex. 6-24 | 78 |
| Ex. 6-25 | 49 |
| Ex. 6-26 | 16 |
| Ex. 6-27 | 51 |
| Ex. 6-28 | 42 |
| Ex. 6-29 | 69 |
| Ex. 6-30 | 45 |
| Ex. 6-31 | 44 |
| Ex. 6-32 | 4 |
| Ex. 6-33 | 68 |
| Ex. 6-34 | 70 |
| Ex. 6-35 | 60 |

TABLE 27-4-continued

| Compound No. | Percent inhibition (% at 1 μM) |
|---|---|
| Ex. 6-36 | 30 |
| Ex. 7-1 | 97 |
| Ex. 7-2 | 88 |
| Ex. 7-3 | 65 |
| Ex. 8-1 | 16 |
| Ex. 9-1 | 29 |
| Ex. 9-2 | 23 |
| Ex. 9-3 | 1 |
| Ex. 9-4 | 42 |
| Ex. 9-5 | 3 |
| Ex. 10-1 | 34 |
| Ex. 10-2 | 6 |
| Ex. 10-4 | 10 |
| Ex. 11-1 | 96 |

TABLE 28-1

| Compound No. | IC$_{50}$ (nM) |
|---|---|
| Ex. 1-4 | 19 |
| Ex. 1-28 | 88 |
| Ex. 1-70 | 39 |
| Ex. 1-72 | 94 |
| Ex. 1-205 | 59 |
| Ex. 1-209 | 49 |
| Ex. 1-225 | 40 |
| Ex. 1-226 | 409 |
| Ex. 1-252 | 87 |
| Ex. 1-254 | 24 |
| Ex. 1-255 | 66 |
| Ex. 1-256 | 66 |
| Ex. 1-257 | 75 |
| Ex. 1-258 | 63 |
| Ex. 1-259 | 96 |
| Ex. 1-260 | 69 |
| Ex. 1-265 | 24 |
| Ex. 1-273 | 112 |
| Ex. 1-274 | 108 |
| Ex. 1-275 | 99 |
| Ex. 1-282 | 77 |
| Ex. 1-283 | 63 |
| Ex. 1-284 | 40 |
| Ex. 1-285 | 43 |
| Ex. 1-286 | 61 |
| Ex. 1-287 | 45 |
| Ex. 1-288 | 146 |
| Ex. 1-289 | 68 |
| Ex. 1-296 | 15 |
| Ex. 1-297 | 89 |
| Ex. 1-298 | 79 |
| Ex. 1-333 | 92 |
| Ex. 1-353 | 43 |
| Ex. 1-354 | 61 |
| Ex. 1-355 | 52 |
| Ex. 1-356 | 60 |
| Ex. 1-365 | 56 |
| Ex. 1-366 | 19 |
| Ex. 1-367 | 26 |
| Ex. 1-368 | 41 |
| Ex. 1-376 | 22 |
| Ex. 1-377 | 15 |
| Ex. 1-378 | 14 |
| Ex. 1-385 | 54 |
| Ex. 1-386 | 48 |
| Ex. 1-392 | 26 |
| Ex. 1-393 | 32 |
| Ex. 1-404 | 56 |
| Ex. 1-408 | 72 |
| Ex. 1-409 | 25 |
| Ex. 1-440 | 39 |
| Ex. 1-443 | 21 |

INDUSTRIAL APPLICABILITY

The compounds of the present invention have a superior PHD2 inhibitory effect and by means of the present invention, it becomes possible to provide pharmaceuticals that are effective for preventing or treating anemia-caused diseases and the like and this is expected to lessen the burden on patients and hence contribute to the development of the pharmaceutical industry.

The invention claimed is:

1. A compound represented by the following general formula (I'):

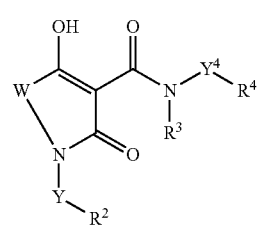

wherein in formula (I'),
W represents the formula —$CR^{11}R^{12}CR^{13}R^{14}$;
$R^{11}$ represents a hydrogen atom, $C_{1-4}$ alkyl, or phenyl;
$R^{12}$ represents a hydrogen atom, a fluoride atom or $C_{1-4}$ alkyl; or
$R^{11}$ and $R^{12}$, together with the adjacent carbon atom, form a $C_{3-8}$ cycloalkane or a 4- to 8-membered saturated heterocycle containing an oxygen atom;
$R^{13}$ represents a hydrogen atom, carbamoyl, $C_{1-4}$ alkyl, wherein the $C_{1-4}$ alkyl is optionally substituted by one group selected from the group consisting of hydroxy, $C_{1-3}$ alkoxy, and di-$C_{1-3}$ alkylamino, halo-$C_{1-4}$ alkyl, phenyl, pyridyl, benzyl, or phenethyl;
$R^{14}$ represents a hydrogen atom, $C_{1-4}$ alkyl, or halo-$C_{1-4}$ alkyl; or
$R^{13}$ and $R^{14}$, together with the adjacent carbon atom, form a $C_{3-8}$ cycloalkane, a 4- to 8-membered saturated heterocycle containing an oxygen atom, or a 4- to 8-membered saturated heterocycle containing a nitrogen atom, wherein the 4- to 8-membered saturated heterocycle containing a nitrogen atom is optionally substituted by one or two groups which are the same or different and are selected from the group consisting of methyl, benzyl, phenylcarbonyl, and oxo; or
$R^{12}$ and $R^{13}$, together with the adjacent carbon atoms, form a $C_{3-8}$ cycloalkane;
Y represents a single bond or $C_{1-6}$ alkanediyl, wherein the $C_{1-6}$ alkanediyl is optonally substituted by one hydroxyl, and one of the carbon atoms in the $C_{1-6}$ alkanediyl is opitinally substituted by $C_{3-6}$ cycloalkane1,1-diyl;
$R^2$ represents:
a hydrogen atom,
$C_{1-6}$ akyl,
$C_{3-8}$ cycloalkyl, wherein the $C_{3-8}$ cycloalkyl is optionally substituted by one or two groups which are the same or different and are selected from the group consisting of $C_{1-6}$ alkyl which is optionally substituted by one phenyl, phenyl which is optionally substituted by one group selected from the group consisting of a halogen atom and halo-$C_{1-6}$ alkyl, C₁₋₆ alkoxy which is optionally substituted by one group selected from the group consisting of $C_{3-8}$ cycloalkyl, phenyl optionally substituted by one group selected from the group consisting of a halogen atom and $C_{1-6}$ alkyl, and pyridyl optionally substituted by one halogen atom, $C_{3-8}$ cycloalkoxy, phenoxy which is optionally substituted by one group selected from the group consisting of a halogen atom, $C_{1-6}$ alkyl, $C_{3-8}$ cycloalkyl, and halo-$C_{1-6}$ alkyl, and pyridyloxy which is optionally substituted by one group selected from the group consisting of a halogen atom, $C_{1-6}$ alkyl, $C_{3-8}$ cycloalkyl, and halo-$C_{1-6}$ alkyl, phenyl, wherein the phenyl is optionally substituted by one to three groups which are the same or different and are selected from group α3 of substituents, naphthyl, indanyl, tetrahydronaphthyl, pyrazolyl, imidazolyl, isoxazolyl, oxazolyl, wherein the pyrazolyl, imidazolyl, isoxazolyl, and oxazolyl are optionally substituted by one or two groups which are the same or different and are selected from the group consisting of $C_{1-6}$ alkyl and phenyl which is optionally substituted by one group selected from the group consisting of a halogen atom and $C_{1-6}$ alkyl, thiazoyl, wherein the thiazoyl is optionally substituted by one or two groups which are the same or different and are selected from the group consisting of $C_{1-6}$ alkyl, phenyl which is optionally substituted by one group selected from the group consisting of a halogen atom and $C_{1-6}$ alkyl, and morpholino, pyridyl, wherein the pyridyl is optionally substituted by one or two groups which are the same or different and are selected from group α5 of substituents, pyridazinyl, pyrimidinyl, pyrazinyl, wherein the pyridazinyl, pyrimidinyl, and pyrazinyl are optionally substituted by one group selected from the group consisting of $C_{1-6}$ alkyl, halo-$C_{1-6}$ alkyl, $C_{3-8}$ cycloalkyl, phenyl, $C_{1-6}$ alkoxy which is optionally substituted by one $C_{3-8}$ cycloalkyl, and phenoxy which is optionally substituted by one group selected from the group consisting of a halogen atom, $C_{1-6}$ alkyl, and $C_{3-8}$ cycloalkyl, benzothiophenyl, quinolyl, methylenedioxyphenyl, wherein the methylenedioxyphenyl is optionally substituted by one or two fluorine atoms, 4- to 8-membered saturated heterocyclyl containing a nitrogen atom, wherein the 4- to 8-membered saturated heterocyclyl containing a nitrogen atom is optionally substituted by one group selected from the group consisting of pyrimidinyl, phenyl-$C_{1-3}$ alkyl, $C_{3-8}$ cycloalkyl-$C_{1-3}$ alkylcarbonyl, and phenyl-$C_{1-3}$ alkoxycarbonyl, or the following formula (I″)

wherein in formula (I″):

$R^5$ represents a hydrogen atom or $C_{1-3}$ alkyl, and $R^6$ represents phenyl which is optionally substituted by one group selected from the group consisting of a halogen atom, $C_{1-6}$ alkyl, halo-$C_{1-6}$ alkyl, and phenyl, group α3 of substituents consists of:

hydroxy, cyano, carboxy, a halogen atom, $C_{1-6}$ alkyl, wherein the $C_{1-6}$ alkyl is optionally substituted by one group selected from the group consisting of $C_{3-8}$ cycloalkyl, phenyl, $C_{1-6}$ alkoxy which is optionally substituted by one $C_{3-8}$ cycloalkyl optionally substituted by one $C_{1-6}$ alkyl, phenoxy which is optionally substituted by one $C_{1-6}$ alkyl, and pyridyloxy which is optionally substituted by one group selected from the group consisting of $C_{1-6}$ alkyl and halo-$C_{1-6}$ alkyl, halo-$C_{1-6}$ alkyl, $C_{3-8}$ cycloalkyl, wherein the $C_{3-8}$ cycloalkyl is optionally substituted by one or two halogen atoms, $C_{3-8}$ cycloalkenyl, wherein the $C_{3-8}$ cycloalkenyl is optionally substituted by one or two halogen atoms, phenyl, wherein the phenyl is optionally substituted by one to three groups which are the same or different and are selected from group α4 of substituents, thienyl, wherein the thienyl is optionally substituted by one $C_{1-6}$ alkyl, pyrazolyl, wherein the pyrazolyl is optionally substituted by one $C_{1-6}$ alkyl, isoxazolyl, thiazoyl, wherein the thiazoyl is optionally substituted by one or two groups which are the same or different and are selected from the group consisting of hydroxy, $C_{1-6}$ alkyl, and $C_{1-6}$ alkoxy, pyridyl, wherein the pyridyl is optionally substituted by one group selected from the group consisting of carboxy, hydroxy, amino, a halogen atom, $C_{1-6}$ alkyl, halo-$C_{1-6}$ alkyl, $C_{3-8}$ cycloalkyl, $C_{1-6}$ alkoxy, halo-$C_{1-6}$ alkoxy, and $C_{1-6}$ alkylsulfonyl, pyrimidinyl, wherein the pyrimidinyl is optionally substituted by one amino, quinolyl, $C_{1-6}$ alkoxy, wherein the $C_{1-6}$ alkoxy is optionally substituted by one group selected from the group consisting of carboxy, hydroxy, carbamoyl, $C_{3-8}$ cycloalkyl which is optionally substituted by one $C_{1-6}$ alkyl, phenyl which is optionally substituted by one group selected from the group consisting of hydroxy, a halogen atom, $C_{1-6}$ alkyl, halo-$C_{1-6}$ alkyl, $C_{1-6}$ alkoxy, halo-$C_{1-6}$ alkoxy, and di-$C_{1-6}$ alkylamino, pyridyl which is optionally substituted by one group selected from the group consisting of a halogen atom and $C_{1-6}$ alkyl, benzotriazolyl, imidazothiazoyl, di-$C_{1-6}$ alkylamino, oxazolyl which is optionally substituted by one or two $C_{1-6}$ alkyls, pyrazolyl, which is optionally substituted by one or two $C_{1-6}$ alkyls, thiazoyl which is optionally substituted by one $C_{1-6}$ alkyl, and indazolyl which is optionally substituted by one $C_{1-6}$ alkyl, halo-$C_{1-6}$ alkoxy, $C_{2-6}$ alkenyloxy, $C_{3-8}$ cycloalkoxy, phenoxy, wherein the phenoxy is optionally substituted by one or two groups which are the same or different and are selected from the group consisting of a halogen atom, $C_{1-6}$ alkyl, halo-$C_{1-6}$ alkyl, $C_{1-6}$ alkoxy, and halo-$C_{1-6}$ alkoxy, pyridyloxy, wherein the pyridyloxy is optionally substituted by one group selected from the group consisting of a halogen atom, $C_{1-6}$ alkyl, halo-$C_{1-6}$ alkyl, and $C_{3-8}$ cycloalkyl,
pyrimidinyloxy,
piperazinyl, wherein the piperazinyl is optionally substituted by one $C_{1-6}$ alkyl,
mono-$C_{1-6}$ alkylaminocarbonyl, wherein the $C_{1-6}$ alkyl in the mono-$C_{1-6}$ alkylaminocarbonyl is optionally substituted by one group selected from the group consisting of carboxy, hydroxy, di-$C_{1-6}$ alkylamino, pyridyl, phenyl, and 2-oxopyrrolidinyl,
di-$C_{1-6}$ alkylaminocarbonyl, wherein the two $C_{1-6}$ alkyls in the di-$C_{1-6}$ alkylaminocarbonyl, together with the adjacent nitrogen atom, optionally form a 4- to 8-membered saturated heterocycle containing a nitrogen atom,
$C_{1-6}$ alkylsulfanyl, and
$C_{1-6}$ alkylsulfonyl;
group α4 of substituents consists of:
carboxy,
cyano,
hydroxy,
sulfamoyl,
a halogen atom,
$C_{1-6}$ alkyl,
halo-$C_{1-6}$ alkyl,
$C_{3-8}$ cycloalkyl,
phenyl,
$C_{1-6}$ alkoxy,
halo-$C_{1-6}$ alkoxy,
$C_{1-6}$ alkylcarbonyl,
di-$C_{1-6}$ alkylaminocarbonyl,
$C_{1-6}$ alkylsulfonyl,
mono-$C_{1-6}$ alkylaminosulfonyl, wherein the $C_{1-6}$ alkyl in the mono-$C_{1-6}$ alkylaminosulfonyl is optionally substituted by one hydroxy, and
di-$C_{1-6}$ alkylaminosulfonyl;
group α5 of substituents consist of:
a halogen atom,
$C_{1-6}$ alkyl,
halo-$C_{1-6}$ alkyl,
$C_{1-6}$ alkoxy, wherein the $C_{1-6}$ alkoxy is optionally substituted by one group selected from the group consisting of $C_{3-8}$ cycloalkyl which is optionally substituted by one $C_{1-6}$ alkyl and phenyl which is optionally substituted by one group selected from the group consisting of a halogen atom and $C_{1-6}$ alkyl,
halo-$C_{1-6}$ alkoxy,
phenyl, wherein the phenyl is optionally substituted by one group selected from group α6 of substituents,
pyridyl,
phenoxy, wherein the phenoxy is optionally substituted by one or two groups which are the same or different and are selected from the group consisting of a halogen atom, cyano, $C_{1-6}$ alkyl, halo-$C_{1-6}$ alkyl, $C_{3-8}$ cycloalkyl, halo-$C_{1-6}$ alkoxy and $C_{1-6}$ alkoxy which is optionally substituted by one phenyl, and,
pyridyloxy, wherein the pyridyloxy is optionally substituted by one $C_{1-6}$ alkyl, and
phenylsulfanyl, wherein the phenylsulfanyl is optionally substituted by one halogen atom;
group α6 of substituents consists of:
a halogen atom,
$C_{1-6}$ alkyl,
halo-$C_{1-6}$ alkyl,
$C_{3-8}$ cycloalkyl,
$C_{1-6}$ alkoxy, and
halo-$C_{1-6}$ alkoxy;
$Y^4$ represents $C_{1-4}$ alkanediyl;
$R^3$ represents a hydrogen atom or methyl;
$R^4$ represents —COOH, —CONHOH, or tetrazolyl;
or a pharmaceutically acceptable salt thereof.

2. The compound according to claim 1 wherein in the aforementioned general formula (I'),
$Y^4$ is methanediyl,
$R^3$ is a hydrogen atom,
$R^4$ is —COOH, or a pharmaceutically acceptable salt thereof.

3. The compound according to claim 2 wherein in the aforementioned general formula (I'),
the compound is represented by general formula (I'-2):

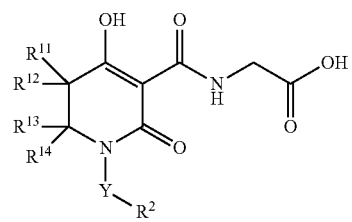

wherein in formula (I'-2):
$R^{11}$ is a hydrogen atom, a fluorine atom, $C_{1-4}$ alkyl, or phenyl,
$R^{12}$ is a hydrogen atom, a fluorine atom, or $C_{1-4}$ alkyl, or
$R^{11}$ and $R^{12}$, together with the adjacent carbon atom, form a $C_{3-8}$ cycloalkane or a 4- to 8-membered saturated heterocycle containing an oxygen atom;
$R^{13}$ is a hydrogen atom, carbamoyl, $C_{1-4}$ alkyl, wherein the $C_{1-4}$ alkyl is optionally substituted by one group selected from the group consisting of hydroxy, $C_{1-3}$ alkoxy, and di-$C_{1-3}$ alkylamino, halo-$C_{1-4}$ alkyl, phenyl, pyridyl, benzyl, or phenethyl;
$R^{14}$ is a hydrogen atom, $C_{1-4}$ alkyl, or halo-$C_{1-4}$ alkyl, or
$R^{13}$ and $R^{14}$, together with the adjacent carbon atom, form a $C_{3-8}$ cycloalkane, a 4- to 8-membered saturated heterocycle containing an oxygen atom, or a 4- to 8-membered saturated heterocycle containing a nitrogen atom, wherein the 4- to 8-membered saturated heterocycle containing a nitrogen atom is optionally substituted by one or two groups which are the same or different and are selected from the group consisting of methyl, benzyl, phenylcarbonyl, and oxo, or
$R^{12}$ and $R^{13}$, together with the adjacent carbon atoms, form a $C_{3-8}$ cycloalkane,
or a pharmaceutically acceptable salt thereof.

4. The compound according to claim 3 wherein in the aforementioned general formula (I'-2),
Y is a single bond or $C_{1-6}$ alkanediyl, wherein one of the carbon atoms in the $C_{1-6}$ alkanediyl is optionally substituted by $C_{3-6}$ cycloalkane-1,1-diyl,
$R^2$ is:
$C_{3-8}$ cycloalkyl, wherein the $C_{3-8}$ cycloalkyl is optionally substituted by one or two groups which are the same or different and are selected from the group consisting of $C_{1-6}$ alkyl which is optionally substituted by one phenyl, phenyl which is optionally substituted by one halo-$C_{1-6}$ alkyl, $C_{1-6}$ alkoxy which is optionally substituted by one group selected from the group consisting of $C_{3-8}$ cycloalkyl, phenyl optionally substituted by one group selected from the group consisting of a halogen atom and $C_{1-6}$ alkyl, and pyridyl optionally substituted by one halogen atom, $C_{3-8}$ cycloalkoxy, phenoxy which is optionally substituted by one group selected from the group consisting of a halogen atom, $C_{1-6}$ alkyl, $C_{3-8}$ cycloalkyl, and halo-$C_{1-6}$ alkyl, and pyridyloxy which is optionally substituted by one group selected from the group consisting of a halogen atom, $C_{1-6}$ alkyl, $C_{3-8}$ cycloalkyl, and halo-$C_{1-6}$ alkyl, phenyl, wherein the phenyl is optionally substituted by one to three groups which are the same or different and are selected from the aforementioned group α3 of substituents, naphthyl, indanyl, tetrahydronaphthyl, pyrazolyl, wherein the pyrazolyl is optionally substituted by one or two groups which are the same or different and are selected from the group consisting of $C_{1-6}$ alkyl and phenyl which is optionally substituted by one $C_{1-6}$ alkyl, imidazolyl, wherein the imidazolyl is optionally substituted by one group selected from the group consisting of $C_{1-6}$ alkyl and phenyl, isoxazolyl, wherein the isoxazolyl is optionally substituted by one phenyl which is optionally substituted by one halogen atom, oxazolyl, wherein the oxazolyl is optionally substituted by one or two groups which are the same or different and are selected from the group consisting of $C_{1-6}$ alkyl and phenyl, thiazoyl, wherein the thiazoyl is optionally substituted by one group selected from the group consisting of $C_{1-6}$ alkyl, phenyl, and morpholino, pyridyl, wherein the pyridyl is optionally substituted by one or two groups which are the same or different and are selected from the aforementioned group α5 of substituents, pyridazinyl, wherein the pyridazinyl is optionally substituted by one $C_{1-6}$ alkoxy which is optionally substituted by one $C_{3-8}$ cycloalkyl, pyrimidinyl, wherein the pyrimidinyl is optionally substituted by one group selected from the group consisting of halo-$C_{1-6}$ alkyl, $C_{3-8}$ cycloalkyl, phenyl, and phenoxy which is optionally substituted by one $C_{1-6}$ alkyl, pyrazinyl, wherein the pyrazinyl is optionally substituted by one group selected from the group consisting of $C_{1-6}$ alkoxy which is optionally substituted by one $C_{3-8}$ cycloalkyl and phenoxy which is optionally substituted by one group selected from the group consisting of a halogen atom, $C_{1-6}$ alkyl, and $C_{3-8}$ cycloalkyl, benzothiophenyl, quinolyl, or methylenedioxyphenyl, wherein the methylenedioxyphenyl is optionally substituted by one or two fluorine atoms, or a pharmaceutically acceptable salt thereof.

5. The compound according to claim 4 wherein in the aforementioned general formula (I'-2):

$R^{11}$ is a hydrogen atom, $R^{12}$ is a hydrogen atom, $R^{13}$ is a hydrogen atom, $R^{14}$ is a hydrogen atom, Y is methanediyl, $R^2$ is:

phenyl, wherein the phenyl is substituted by one group selected from the group consisting of phenyl which is optionally substituted by one or two groups which are the same or different and are selected from the group consisting of carboxy, cyano, hydroxy, sulfamoyl, a halogen atom, $C_{1-6}$ alkyl, halo-$C_{1-6}$ alkyl, $C_{3-8}$ cycloalkyl, phenyl, $C_{1-6}$ alkoxy, halo-$C_{1-6}$ alkoxy, $C_{1-6}$ alkylcarbonyl, di-$C_{1-6}$ alkylaminocarbonyl, $C_{1-6}$ alkylsulfonyl, di-$C_{1-6}$ alkylaminosulfonyl and mono-$C_{1-6}$ alkylaminosulfonyl, wherein the $C_{1-6}$ alkyl in the mono-$C_{1-6}$alkylaminosulfonyl is optionally substituted by one hydroxy, pyridyl which is optionally substituted by one group selected from the group consisting of carboxy, hydroxy, amino, a halogen atom, $C_{1-6}$ alkyl, halo-$C_{1-6}$ alkyl, $C_{3-8}$ cycloalkyl, $C_{1-6}$ alkoxy, and $C_{1-6}$ alkylsulfonyl, phenoxy which is optionally substituted by one or two groups which are the same or different and are selected from the group consisting of a halogen atom, $C_{1-6}$ alkyl, $C_{1-6}$ alkoxy, and halo-$C_{1-6}$ alkoxy, and pyridyloxy which is optionally substituted by one group selected from the group consisting of a halogen atom, $C_{1-6}$ alkyl, halo-$C_{1-6}$ alkyl, and $C_{3-8}$ cycloalkyl, and said substituted phenyl represented by $R^2$ may further be substituted by one halogen atom;

pyridyl, wherein the pyridyl is substituted by one group selected from the group consisting of phenyl which is optionally substituted by one group selected from the group consisting of a halogen atom, $C_{1-6}$ alkyl, halo-$C_{1-6}$ alkyl, $C_{3-8}$ cycloalkyl, $C_{1-6}$ alkoxy, and halo-$C_{1-6}$ alkoxy, pyridyl, phenoxy which is optionally substituted by one or two groups which are the same or different and are selected from the group consisting of a halogen atom, cyano, $C_{1-6}$ alkyl, halo-$C_{1-6}$ alkyl, $C_{3-8}$ cycloalkyl, halo-$C_{1-6}$ alkoxy and $C_{1-6}$ alkoxy optionally substituted by one phenyl, and pyridyloxy which is optionally substituted by one $C_{1-6}$ alkyl, and said substituted pyridyl represented by $R^2$ may further be substituted by one group selected from the group consisting of a halogen atom and $C_{1-6}$ alkyl; or pyrazinyl which is substituted by one phenoxy wherein the phenoxy is optionally substituted by one group selected from the group consisting of a halogen atom, $C_{1-6}$ alkyl, and $C_{3-8}$ cycloalkyl, or a pharmaceutically acceptable salt thereof.

6. The following compound according to claim 1:

N-{[4-hydroxy-2-oxo-1-(4-phenoxybenzyl)-1,2,5,6-tetrahydro-3-pyridinyl]carbonyl}glycine;

N-[(4-hydroxy-1-{1 [6-(4-methylphenoxy)-3-pyridinyl]methyl}-2-oxo-1,2,5,6-tetrahydro-3-pyridinyl)carbonyl]glycine;

N-({4-hydroxy-2-oxo-1-[(6-phenoxy-3-pyridinyl)methyl]-1,2,5,6-tetrahydro-3-pyridinyl}carbonyl)glycine;

N-({1-[4-(4-fluorophenoxy)benzyl]-4-hydroxy-2-oxo-1,2,5,6-tetrahydro-3-pyridinyl}carbonyl)glycine;

N-({4-hydroxy-1-[4-(4-methylphenoxy)benzyl]-2-oxo-1,2,5,6-tetrahydro-3-pyridinyl}carbonyl)glycine;

N-[(1-{[6-(4-cyanophenoxy)-3-pyridinyl]methyl}-4-hydroxy-2-oxo-1,2,5,6-tetrahydro-3-pyridinyl)carbonyl]glycine;

N-({4-hydroxy-2-oxo-1-[4-(2-pyrimidinyloxy)benzyl]-1,2,5,6-tetrahydro-3-pyridinyl}carbonyl)glycine;

N-[(1-{[6-(4-fluorophenoxy)-3-pyridinyl]methyl}-4-hydroxy-2-oxo-1,2,5,6-tetrahydro-3-pyridinyl)carbonyl]glycine;
N-[(1{[-6-(4-chlorophenoxy)-3-pyridinyl]methyl}-4-hydroxy-2-oxo-1,2,5,6-tetrahydro-3-pyridinyl)carbonyl]glycine;
N-{[4-hydroxy-2-oxo-1-({6-[4-(trifluoromethyl)phenoxy]-3-pyridinyl}methyl)-1,2,5,6-tetrahydro-3-pyridinyl]carbonyl}glycine;
N-[(4-hydroxy-1-{[6-(3-methylphenoxy)-3-pyridinyl]methyl}-2-oxo-1,2,5,6-tetrahydro-3-pyridinyl)carbonyl]glycine;
N-[(1-{[6-(3-fluorophenoxy)-3-pyridinyl]methyl}-4-hydroxy-2-oxo-1,2,5,6-tetrahydro-3-pyridinyl)carbonyl]glycine;
N-({4-hydroxy-1-[4-(3-methylphenoxy)benzyl]-2-oxo-1,2,5,6-tetrahydro-3-pyridinyl}carbonyl)glycine;
N-({1-[4-(3-fluorophenoxy)benzyl]-4-hydroxy-2-oxo-1,2,5,6-tetrahydro-3-pyridinyl}carbonyl)glycine;
N-[1-{[5-(4-fluorophenoxy)-2-pyridinyl]methyl}-4-hydroxy-2-oxo-1,2,5,6-tetrahydro-3-pyridinyl)carbonyl]glycine;
N-[(4-hydroxy-1-{[5-(4-methylphenoxy)-2-pyridinyl]methyl}-2-oxo-1,2,5,6-tetrahydro-3-pyridinyl)carbonyl]glycine;
N-({1-[4-(4-chlorophenoxy)benzyl]-4-hydroxy-2-oxo-1,2,5,6-tetrahydro-3-pyridinyl}carbonyl)glycine;
N-[(4-hydroxy-1-{4-[(6-methyl-3-pyridinyl)oxy]benzyl}-2-oxo-1,2,5,6-tetrahydro-3-pyridinyl)carbonyl]glycine;
N-[(1-{[6-(2-fluorophenoxy)-3-pyridinyl]methyl}-4-hydroxy-2-oxo-1,2,5,6-tetrahydro-3-pyridinyl)carbonyl]glycine;
N-[(4-hydroxy-1-{[6-(2-methylphenoxy)-3-pyridinyl]methyl}-2-oxo-1,2,5,6-tetrahydro-3-pyridinyl)carbonyl]glycine;
N-({1-[4-(2-fluorophenoxy)benzyl]-4-hydroxy-2-oxo-1,2,5,6-tetrahydro-3-pyridinyl}carbonyl)glycine;
N-({4-hydroxy-1-[4-(2-methylphenoxy)benzyl]-2-oxo-1,2,5,6-tetrahydro-3-pyridinyl}carbonyl)glycine;
N-[(1-{[6-(3-chlorophenoxy)-3-pyridinyl]methyl}-4-hydroxy-2-oxo-1,2,5,6-tetrahydro-3-pyridinyl)carbonyl]glycine;
N-{[4-hydroxy-2-oxo-1-({6-[3-(trifluoromethyl)phenoxy]-3-pyridinyl}methyl)-1,2,5,6-tetrahydro-3-pyridinyl]carbonyl}glycine;
N-({4-hydroxy-1-[4-(3-methoxyphenoxy)benzyl]-2-oxo-1,2,5,6-tetrahydro-3-pyridinyl}carbonyl)glycine;
N-{[4-hydroxy-2-oxo-1-({6-[3-(trifluoromethoxy)phenoxy]-3-pyridinyl}methyl)-1,2,5,6-tetrahydro-3-pyridinyl]carbonyl}glycine;
N-[(1-{4-[(5-fluoro-2-pyridinyl)oxy]benzyl}-4-hydroxy-2-oxo-1,2,5,6-tetrahydro-3-pyridinyl)carbonyl]glycine;
N-[(1-{4-[(5-chloro-2-pyridinyl)oxy]benzyl}-4-hydroxy-2-oxo-1,2,5,6-tetrahydro-3-pyridinyl)carbonyl]glycine;
N-[1-{[(6-(4-cyclopropylphenoxy)-3-pyridinyl]methyl}-4-hydroxy-2-oxo-1,2,5,6-tetrahydro-3-pyridinyl)carbonyl]glycine;
N-[(4-hydroxy-1-{4-[(5-methyl-2-pyridinyl)oxy]benzyl}-2-oxo-1,2,5,6-tetrahydro-3-pyridinyl)carbonyl]glycine;
N-{[4-hydroxy-2-oxo-1-(4-{[5-(trifluoromethyl)-2-pyridinyl]oxy}benzyl)-1,2,5,6-tetrahydro-3-pyridinyl]carbonyl}glycine;
N-{[4-hydroxy-1-({5-methyl-6-[(6-methyl-3-pyridinyl)oxy]-3-pyridinyl}methyl)-2-oxo-1,2,5,6-tetrahydro-3-pyridinyl]carbonyl}glycine;
N-[(1-{[5-(4-chlorophenoxy)-2-pyridinyl]methyl}-4-hydroxy-2-oxo-1,2,5,6-tetrahydro-3-pyridinyl)carbonyl]glycine;
N-[(4-hydroxy-1-{[6-(3-methoxyphenoxy)-3-pyridinyl]methyl}-2-oxo-1,2,5,6-tetrahydro-3-pyridinyl)carbonyl]glycine;
N-[(1-{4-[(6-chloro-3-pyridinyl)oxy]benzyl}-4-hydroxy-2-oxo-1,2,5,6-tetrahydro-3-pyridinyl)carbonyl]glycine;
N-{[4-hydroxy-2-oxo-1-({5-[4-(trifluoromethyl)phenoxy]-2-pyridinyl}methyl)-1,2,5,6-tetrahydro-3-pyridinyl]carbonyl}glycine;
N-{[4-hydroxy-2-oxo-1-(4-{[6-(trifluoromethyl)-3-pyridinyl]oxy}benzyl)-1,2,5,6-tetrahydro-3-pyridinyl]carbonyl}glycine;
N-[(1-{[6-(3-chloro-4-methylphenoxy)-3-pyridinyl]methyl}-4-hydroxy-2-oxo-1,2,5,6-tetrahydro-3-pyridinyl)carbonyl]glycine;
N-[(1-{[6-(3-fluoro-4-methylphenoxy)-3-pyridinyl]methyl}-4-hydroxy-2-oxo-1,2,5,6-tetrahydro-3-pyridinyl)carbonyl]glycine;
N-[(1-{[6-(4-fluoro-3-methylphenoxy)-3-pyridinyl]methyl}-4-hydroxy-2-oxo-1,2,5,6-tetrahydro-3-pyridinyl)carbonyl]glycine;
N-[(1-{[6-(4-ethylphenoxy)-3-pyridinyl]methyl}-4-hydroxy-2-oxo-1,2,5,6-tetrahydro-3-pyridinyl)carbonyl]glycine;
N-[(4-hydroxy-2-oxo-1-{[6-(4-propylphenoxy)-3-pyridinyl]methyl}-1,2,5,6-tetrahydro-3pyridinyl)carbonyl]glycine;
N-[(4-hydroxy-1-{[6-(4-isopropylphenoxy)-3-pyridinyl]methyl}-2-oxo-1,2,5,6-tetrahydro-3-pyridinyl)carbonyl]glycine;
N-[(4-hydroxy-1-{[5-(4-methylphenoxy)-2-pyrazinyl]methyl}-2-oxo-1,2,5,6-tetrahydro-3-pyridinyl)carbonyl]glycine;
N-({1-[4-(3,4-dimethylphenoxy)benzyl]-4-hydroxy-2-oxo-1,2,5,6-tetrahydro-3-pyridinyl}carbonyl)glycine;
N-[(1-{[5-chloro-6-(4-methylphenoxy)-3-pyridinyl]methyl}-4-hydroxy-2-oxo-1,2,5,6-tetrahydro-3-pyridinyl)carbonyl]glycine;
N-[(1-{[5-fluoro-6-(4-methylphenoxy)-3-pyridinyl]methyl}-4-hydroxy-2-oxo-1,2,5,6-tetrahydro-3-pyridinyl)carbonyl]glycine;
N-[(1-{4-[(5-cyclopropyl-2-pyridinyl)oxy]benzyl}-4-hydroxy-2-oxo-1,2,5,6-tetrahydro-3-pyridinyl)carbonyl]glycine;
N-[(4-hydroxy-1-{[2-(4-methylphenoxy)-5-pyrimidinyl]methyl}-2-oxo-1,2,5,6-tetrahydro-3-pyridinyl)carbonyl]glycine;
N-[(1-{[6-(4-chlorophenoxy)-5-methyl-3-pyridinyl]methyl}-4-hydroxy-2-oxo-1,2,5,6-tetrahydro-3-pyridinyl)carbonyl]glycine;
N-[(1-{[5-(4-chlorophenoxy)-2-pyrazinyl]methyl}-4-hydroxy-2-oxo-1,2,5,6-tetrahydro-3-pyridinyl)carbonyl]glycine; or
N-[(1-{[5-(4-cyclopropylphenoxy)-2-pyrazinyl]methyl}-4-hydroxy-2-oxo-1,2,5,6-tetrahydro-3-pyridinyl)carbonyl]glycine, or a pharmaceutically acceptable salt thereof.

7. The compound according to claim 1, having the aforementioned general formula (I'), wherein
the compound is represented by general formula (I):

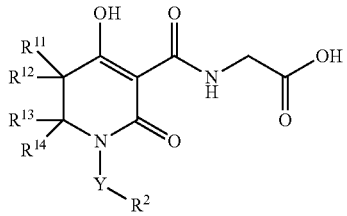

wherein formula (I):
$R^{11}$ is a hydrogen atom, $C_{1-4}$ alkyl, or phenyl,
$R^{12}$ is a hydrogen atom or $C_{1-4}$ alkyl, or
$R^{11}$ and $R^{12}$, together with the adjacent carbon atom, form a $C_{3-8}$ cycloalkane or a 4- to 8-membered saturated heterocycle containing an oxygen atom;
$R^{13}$ is a hydrogen atom, $C_{1-4}$ alkyl, halo-$C_{1-4}$ alkyl, phenyl, benzyl, or phenethyl,
$R^{14}$ is a hydrogen atom or $C_{1-4}$ alkyl, or
$R^{13}$ and $R^{14}$, together with the adjacent carbon atom, form a $C_{3-8}$ cycloalkane or a 4- to 8-membered saturated heterocycle containing an oxygen atom, or
$R^{12}$ and $R^{13}$, together with the adjacent carbon atoms, form a $C_{3-8}$ cycloalkane;
Y is a single bond or $C_{1-6}$ alkanediyl, wherein one of the carbon atoms in the $C_{1-6}$ alkanediyl is optionally substituted by $C_{3-6}$ cycloalkane-1,1-diyl;
$R^2$ is:
$C_{3-8}$ cycloalkyl, wherein the $C_{3-8}$ cycloalkyl is optionally substituted by one group selected from the group consisting of phenyl and benzyl,
phenyl, wherein the phenyl is optionally substituted by one to three groups which are the same or different and are selected from group α1 of substituents,
naphthyl,
indanyl,
tetrahydronaphthyl,
pyrazolyl, wherein the pyrazolyl is substituted by one phenyl, which is optionally substituted by one $C_{1-6}$ alkyl and may further be substituted by one $C_{1-6}$ alkyl,
imidazolyl, wherein the imidazolyl is substituted by one phenyl,
isoxazolyl, wherein the isoxazolyl is substituted by one phenyl which is optionally substituted by one halogen atom,
oxazolyl, wherein the oxazolyl is substituted by one phenyl and may further be substituted by one $C_{1-6}$ alkyl,
thiazoyl, wherein the thiazoyl is substituted by one phenyl,
pyridyl, wherein the pyridyl is substituted by one group selected from the group consisting of phenyl, phenoxy which is optionally substituted by one group selected from the group consisting of a halogen atom, cyano, $C_{1-6}$ alkyl, halo-$C_{1-6}$ alkyl, $C_{3-8}$ cycloalkyl, $C_{1-6}$ alkoxy, and halo-$C_{1-6}$ alkoxy), and phenylsulfanyl which is optionally substituted by one halogen atom,
pyrimidinyl, wherein the pyrimidinyl is substituted by one group selected from the group consisting of cyclohexyl and phenyl,
benzothiophenyl,
quinolyl, or
methylenedioxyphenyl, wherein the methylenedioxyphenyl is optionally substituted by one or two fluorine atoms;
group α1 of substituents consists of:
a halogen atom,
$C_{1-6}$ alkyl, wherein the $C_{1-6}$ alkyl is optionally substituted by one group selected from the group consisting of $C_{3-8}$ cycloalkyl, phenyl, and $C_{1-6}$ alkoxy which is optionally substituted by one $C_{3-8}$ cycloalkyl optionally substituted by one $C_{1-6}$ alkyl,
halo-$C_{1-6}$ alkyl,
$C_{3-8}$ cycloalkyl,
phenyl, wherein the phenyl is optionally substituted by one to three groups which are the same or different and are selected from group α2 of substituents,
thienyl,
pyrazolyl, wherein the pyrazolyl is optionally substituted by one $C_{1-6}$ alkyl,
isoxazolyl,
thiazoyl, wherein the thiazoyl is optionally substituted by one or two $C_{1-6}$ alkyls,
pyridyl, wherein the pyridyl is optionally substituted by one group selected from the group consisting of $C_{1-6}$ alkyl, halo-$C_{1-6}$ alkyl, $C_{1-6}$ alkoxy, and halo-$C_{1-6}$ alkoxy,
quinolyl,
$C_{1-6}$ alkoxy, wherein the $C_{1-6}$ alkoxy is optionally substituted by one group selected from the group consisting of $C_{3-8}$ cycloalkyl and phenyl which is optionally substituted by one group selected from the group consisting of a halogen atom and $C_{1-6}$ alkyl,
halo-$C_{1-6}$ alkoxy,
$C_{2-6}$ alkenyloxy,
$C_{3-8}$ cycloalkoxy,
phenoxy, wherein the phenoxy is optionally substituted by one group selected from the group consisting of a halogen atom, $C_{1-6}$ alkyl, halo-$C_{1-6}$ alkyl, $C_{1-6}$ alkoxy, and halo-$C_{1-6}$ alkoxy,
pyridyloxy, wherein the pyridyloxy is optionally substituted by one group selected from the group consisting of a halogen atom, $C_{1-6}$ alkyl, and halo-$C_{1-6}$ alkyl, and
$C_{1-6}$alkylsulfanyl;
group α2 of substituents consists of a halogen atom, cyano, hydroxy, $C_{1-6}$ alkyl, halo-$C_{1-6}$ alkyl, phenyl, $C_{1-6}$ alkoxy, halo-$C_{1-6}$ alkoxy, $C_{1-6}$ alkylcarbonyl, and di-$C_{1-6}$ alkylaminosulfonyl, or a pharmaceutically acceptable salt thereof.

8. The compound of claim 1 which is N-[(1 {[6-(4-chlorophenoxy)-3-pyridinyl]methyl}-4-hydroxy-2-oxo-1,2,5,6-tetrahydro-3-pyridinyl)carbonyl]glycine, or a pharmaceutically acceptable salt thereof.

9. The compound of claim 1 which is N-[(1-{[6-(4-cyclopropylphenoxy)-3-pyridinyl]methyl}-4-hydroxy-2-oxo-1,2,5,6-tetrahydro-3-pyridinyl)carbonyl]glycine, or a pharmaceutically acceptable salt thereof.

10. The compound of claim 1 which is N-[(4-hydroxy-1-{[6-(3-methylphenoxy)-3-pyridinyl]methyl}-2-oxo-1,2,5,6-tetrahydro-3-pyridinyl)carbonly]glycine, or a pharmaceutically acceptable salt thereof.

11. The compound of claim 1 which is N-[(1-{[6-(3-fluorophenoxy)-3-pyridinyl]methyl}-4-hydroxy-2-oxo-1,2,5,6-tetrahydro-3-pyridinyl)carbonyl]glycine, or a pharmaceutically acceptable salt thereof.

12. The compound of claim 1 which is N-[(4-hydroxy-1-{4-[(6-methyl-3-pyridinyl)oxy]benzyl}-2-oxo-1,2,5,6-tetrahydro-3-pyridinyl)carbonly]glycine, or a pharmaceutically acceptable salt thereof.

13. A medicine comprising the compound according to any one of claims 1, 2, 3 to 7 and 8 to 12 or a pharmaceutically acceptable salt thereof as an active ingredient.

14. A method for inhibiting PHD2 comprising administering to a subject in need thereof an effective amount of the compound according to any one of claims 1, 2, 3 to 7 and 8 to 12 or a pharmaceutically acceptable salt thereof as an active ingredient.

15. A method of promoting production of EPO comprising administering to a subject in need thereof an effective amount of the compound according to any one of claims 1, 2, 3 to 7 and 8 to 12 or a pharmaceutically acceptable salt thereof as an active ingredient.

16. A method for preventing or treating anemia comprising administering to a subject in need thereof an effective amount of the compound according to any one of claims 1, 2, 3 to 7 and 8 to 12 or a pharmaceutically acceptable salt thereof as an active ingredient.

* * * * *